US006528525B1

(12) United States Patent
Yanagisawa et al.

(10) Patent No.: US 6,528,525 B1
(45) Date of Patent: Mar. 4, 2003

(54) AMIDOCARBOXYLIC ACID DERIVATIVES

(75) Inventors: Hiroaki Yanagisawa, Tokyo (JP); Mitsuya Sakurai, Abiko (JP); Makoto Takamura, Kawasaki (JP); Toshihiko Fujiwara, Ebina (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/540,765

(22) Filed: Mar. 30, 2000

Related U.S. Application Data

(63) Continuation-in-part of application No. PCT/JP98/04396, filed on Sep. 30, 1998.

(51) Int. Cl.$^7$ .................. A61K 31/47; A61K 31/44; C07D 215/16; C07D 217/00; C07D 211/72
(52) U.S. Cl. .............. 514/307; 514/311; 514/350; 546/156; 546/146; 546/316; 546/323
(58) Field of Search ............... 546/323, 156, 546/146, 316; 514/354, 311, 307, 350

(56) References Cited

U.S. PATENT DOCUMENTS

| | | | |
|---|---|---|---|
| 4,113,871 A | * | 9/1978 | Stach et al. |
| 4,572,912 A | | 2/1986 | Yoshioka et al. |
| 4,703,052 A | | 10/1987 | Eggler et al. |
| 5,217,994 A | | 6/1993 | Egbertson et al. |
| 5,315,017 A | | 5/1994 | Le Baut et al. |
| 5,330,998 A | | 7/1994 | Clark et al. |

FOREIGN PATENT DOCUMENTS

| | | |
|---|---|---|
| EP | 0008203 A | 2/1980 |
| EP | 0306228 A | 3/1989 |
| EP | 0478328 A | 4/1992 |
| EP | 0512352 A | 11/1992 |
| WO | WO 91/19702 | 12/1991 |
| WO | WO 92/07850 | 5/1992 |
| WO | WO 94/29285 | 12/1994 |
| WO | WO 94/29302 | 12/1994 |
| WO | WO 95/03288 | 2/1995 |
| WO | WO 96/04260 | 2/1996 |
| WO | WO 97/31907 | 9/1997 |

OTHER PUBLICATIONS

T. Fujita et al., "Reduction of Insulin Resistance in Obese and/or Diabetic Animals . . . ", *Diabetes*, vol. 32, No. 9, pp. 804–810 (Sep. 1983).

T. Fujiwara et al., "Characterization of New Oral Antidiabetic Agent CS–045", *Diabetes*, vol. 37, No. 11, pp. 1549–1558 (Nov. 1988).

A. Chang et al, "The Hypoglycemic Effect of Ciglitazone in Obese, Hyperglycemic Animal Models", *Prog. Clin. Biol. Res.*, vol. 265, pp. 177–192 (1988).

J.R. Colca et al, "Ciglitazone, A Hypoglycemic Agent: Early Effects on the Pancreatic Islets of Ob/Ob Mice", *Metabolism*, vol. 37, No. 3, pp. 276–280 (Mar. 1988).

T. Sohda et al, "Studies on Antidiabetic Agents" *Arzneim.–Forsch.*, vol. 40(I), Nr. 1, pp.37–42 (1990).

H. Ikeda et al, "Effects of Pioglitazone on Glucose and Lipid Metabolism in Normal and Insulin Resistant Animals", *Arzneim.–Forsch.*, vol. 40(I), Nr. 2 pp. 156–162 (1990).

Y. Sugiyama et al, "Effects of Pioglitazone on Glucose and Lipid Metabolism in Wistar Fatty Rats", *Arzneim.–Forsch.*, vol. 40(I) Nr. 3, pp. 263–267 (1990).

J.R. Colca et al, "Pioglitazone Hydrochloride Inhibits Cholesterol Absorption and Lowers Plasma Cholesterol Concentrations in Cholesterol–Fed Rats", *Diabetes*, vol. 40, No. 12, pp. 1669–1674 (Dec. 1991).

A.K. Saha et al, "Lipid abnormalities in tissues of the KKA$^y$ mouse: effects of pioglitazone on malonyl–CoA and diacylglycerol", *Am. J. Physiol.*, vol. 267(1, Pt. 1) , pp. E95–E101 (1994).

Nicholas D. Oakes et al, "A New Antidiabetic Agent, BRL 49653, Reduces Lipid Availability and Improves Insulin Action and Glucoregulation in the Rat", *Diabetes*, vol. 43, No. 10, pp. 1203–1210 (Oct. 1994).

L. Bowen et al, "The Effect of CP 68, 722, a Thiozolidinedione Derivative, on Insulin Sensitivity in Lean and Obese Zucker Rats", *Metabolism*, vol. 40, No. 10, pp. 1025–1030 (Oct. 1991).

J.W. Kemnitz et al, "Pioglitazone Increases Insulin Sensitivity, Reduces Blood Glucose . . . ", *Diabetes*, vol. 43, No. 2, pp. 204–211 (Feb. 1994).

H. Keen, "Insulin Resistance And The Prevention of Diabetes Mellitus", *N. Eng. J. Med.*, vol. 331, No. 18, pp. 1226–1227 (Nov. 1994).

(List continued on next page.)

*Primary Examiner*—Alan L. Rotman
*Assistant Examiner*—Benta Robinson
(74) *Attorney, Agent, or Firm*—Frishauf, Holtz, Goodman & Chick, P.C.

(57) ABSTRACT

Amidocarboxylic acid derivatives of the formula:

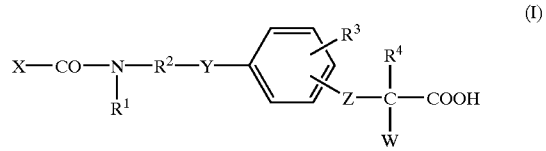

wherein $R^1$ represents a hydrogen atom, etc.; $R^2$ represents an alkylene group; $R^3$ represents a hydrogen atom, etc.; $R^4$ represents a hydrogen atom, etc.; X represents a substituted or unsubstituted aryl group, etc.; Y represents an oxygen atom, etc.; Z represents an alkylene group, etc.; and W represents an alkyl group, etc.; and pharmacologically acceptable salts thereof and pharmacologically acceptable esters thereof are useful as the active ingredient of pharmaceutical compositions. They may be used to treat specified diseases, including diabetes mellitus, hyperlipemia, arteriosclerosis, hypertension, etc.

102 Claims, No Drawings

OTHER PUBLICATIONS

S. Yoshioka et al, "Antihypertensive Effects of CS–045 Treatment in Obese Zucker Rats", *Metabolism,* vol. 42, No. 1, pp. 75–80 (Jan. 1993).

R.K. Dubey et al, "Pioglitazone attenuates hypertension and inhibits growth of renal arteriolar smooth muscle in rats", *Am. J. Physiol.,* vol. 265(4, Pt 2), pp. R726–R732 (1993).

J. Ohsumi et al, "Troglitazone Prevents the Inhibitory Effects of Inflammatory Cytokines . . . ", *Endocrinology,* vol. 135, No. 5, pp. 2279–2282 (1994).

D. Szalkowski et al, "Antidiabetic Thiazolidinediones Block the Inhibitory Effect of Tumor . . . ", *Endocrinology,* vol. 136, No. 4, pp. 1474–1481 (1995).

F. Zhang et al, "Effects of Pioglitazone on Calcium Channels in Vascular Smooth Muscle", *Hypertension,* vol. 24, No. 2, pp. 170–175 (1994).

* cited by examiner

AMIDOCARBOXYLIC ACID DERIVATIVES

This application is a continuation-in-part application of International Application PCT/JP98/04396 filed Sep. 30, 1998.

The present invention relates to amidocarboxylic acid derivatives, or their pharmacologically acceptable salts or their pharmacologically acceptable esters. These compounds have some excellent effects of lowering blood glucose, reducing lipid, ameliorating insulin resistance, alleviating inflammatory diseases, immunoregulation, inhibiting aldose reductase, inhibiting 5-lipoxygenase, suppressing generation of lipid peroxide, activating PPAR (peroxysome proliferator activated receptor) and alleviating osteoporosis.

Furthermore, the present invention relates to a composition containing the above-mentioned amidocarboxylic acid derivatives, pharmacologically acceptable salts thereof or pharmacologically acceptable esters thereof as an active ingredient useful in the treatment and prevention of the following diseases. They include diseases caused mainly by insulin resistance such as diabetes mellitus, hyperlipemia, obesity, impaired glucose tolerance (IGT), insulin resistant non-IGT (NGT), hypertension, fatty liver, diabetic complications (for example, retinopathy, nephropathy, neurosis, cataracts, coronary artery diseases, etc.), arteriosclerosis, gestational diabetes mellitus (GDM), polycystic ovary syndrome (PCOS) and cell injury caused by atherosclerosis (for example cerebral injury induced by apoplexy and the like); inflammatory diseases such as arthrosteitis, pain, pyrexia, rheumatic arthritis, inflammatory enteritis, acne, sunburn, psoriasis, eczema, allergic diseases, asthma, GI ulcers, cancer, cachexia, autoimmune diseases and pancreatitis; osteoporosis; cataracts; etc. The present invention relates to a use of these compounds, their salts and esters for producing a medicament for prevention or treatment of these diseases, or a method of treating or preventing these diseases by the administration of pharmacologically effective amounts of such compounds to warm-blooded animals.

BACKGROUND ART

While insulin and sulfonylurea compounds such as tolbutamide and Glipizide have conventionally been used as therapeutic agents for diabetes mellitus and hyperglycemia, and carboxylic acid derivatives have recently been reported to be useful insulin-nondependent diabetes therapeutic agents. These compounds are described, for example in:

(1-1) International Patent Publication No. WO91/19702 (Japanese PCT Application (Kokai) No. Hei 5-507920);
(1-2) International Patent Publication WO94/29285;
(1-3) International Patent Publication WO94/29302;
(1-4) International Patent Publication WO95/03288; and
(1-5) International Patent Publication WO96/04260.

However, the compounds described above are different from the compounds of the present invention to be described later in that the former compounds do not have the characteristics of the latter compounds which have an amide bond in the side chain of the carboxylic acid derivative.

Compounds having amide bonds in the side chains are described, for example in:

(2-1) Japanese Patent Application (Kokai) No. Hei 6-172339;
(2-2) International Patent Publication WO 92/07850 (=Japanese PCT Application (Kokai) No. Hei 6-502144); and
(2-3) U.S. Pat. No. 5,330,998.

However, these compounds are different from the compounds of the present invention to be described later in that the former compounds have thiazolidyl groups and the like at the terminal of the molecule.

Although carboxylic acid derivatives having amide bonds in the side chains are described, for example, in:

(3-1) Japanese Patent Application (Kokai) No. Hei 5-155828; and
(3-2) Japanese Patent Application (Kokai) No. Hei 5-279353, the compound (3-1) and the compound (3-2) are different from the present invention in pharmacological activity and chemical structure. The compound (3-1) has an effect of inhibiting aggregation and in the molecule of the compound (3-1) there is an amino group or the like at the 2- to 5-positions of the carboxylic acid and a heterocyclic group or the like at the terminal of the side chain. The compound (3-2) has an inhibitory action against damage of ischemic tissue and is an acetic acid derivative.

DISCLOSURE OF THE INVENTION

The present inventors made intensive studies on amidocarboxylic acid derivatives, and pharmacologically acceptable salts and esters thereof, which have strong effects of lowering blood glucose, reducing lipid, ameliorating insulin resistance, alleviating inflammatory diseases, immunoregulation, inhibiting aldose reductase, inhibiting 5-lipoxygenase, suppressing generation of lipid peroxide, activating PPAR (peroxysome proliferator activated receptor) and alleviating osteoporosis, and accomplished the present invention.

To describe it in detail, the present invention provides novel amidocarboxylic acid derivatives, pharmacologically acceptable salts thereof and pharmacologically acceptable esters thereof which are useful as therapeutic or preventive agents for diseases caused mainly by insulin resistance such as diabetes mellitus, hyperlipemia, obesity, impaired glucose tolerance, insulin resistant non-IGT, hypertension, fatty liver, diabetic complications (e.g., retinopathy, nephropathy, neurosis, cataracts, coronary artery diseases, etc.), arteriosclerosis, gestational diabetes mellitus, polycystic ovary syndrome and cell injury caused by atherosclerosis (for example, cerebral injury induced by apoplexy and the like); inflammatory diseases such as arthrosteitis, pain, pyrexia, rheumatic arthritis, inflammatory enteritis, acne, sunburn, psoriasis, eczema, allergic diseases, asthma, GI ulcers, cancer, cachexia, autoimmune diseases (e.g. systemic lupus erythematosus, juvenile rheumatoid arthritis, Sjogren's syndrome, diffuse scleroderma, mixed connective tissue disease, dermatomyositis, Hashimoto's disease, primary myxoma, thyrotoxia, pernicious anemia, ulcerative colitis, autoimmune atrophic gastritis, idiopathic Addison disease, male sterility, Goodpasture's syndrome, acute progressive glomerulonephritis, myasthenia gravis, polymyositis, pemphigus vulgaris, bullous pemphigoid, sympathetic ophthalmitis, multiple sclerosis, autoimmune hemolytic anemia, idiopathic thrombocytopenic purpura, rheumatic fever, lupoid hepatitis, primary biliary cirrhosis, Behcet's disease, CREST syndrome, etc.) and pancreatitis; osteoporosis; and cataracts.

Further, the present invention provides (i) pharmaceutical compositions containing as an active ingredient the novel amidocarboxylic acid derivatives, the pharmacologically acceptable salts thereof or the pharmacologically acceptable esters thereof and (ii) methods of treating by administering said active ingredient to a warm blooded animal, and particularly to a human.

The present invention relates to an amidocarboxylic acid derivative of the formula (I):

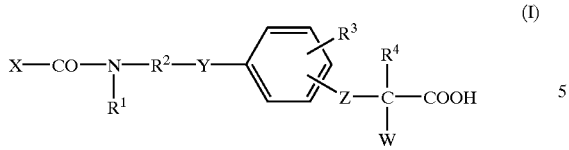

(I)

a pharmacologically acceptable salt thereof or a pharmacologically acceptable ester thereof.

In the formula, $R^1$ represents a hydrogen atom, a straight or branched chain alkyl group having from 1 to 6 carbon atoms or an aralkyl group having from 7 to 12 carbon atoms;

$R^2$ represents a straight or branched chain alkylene group having from 1 to 6 carbon atoms;

$R^3$ represents (i) a hydrogen atom, (ii) a straight or branched chain alkyl group having from 1 to 6 carbon atoms, (iii) a straight or branched chain alkoxy group having from 1 to 4 carbon atoms, (iv) a straight or branched chain alkylthio group having from 1 to 4 carbon atoms, (v) a halogen atom, (vi) a nitro group, (vii) a straight or branched chain dialkylamino group in which each alkyl group may be the same or different and each has from 1 to 4 carbon atoms, (viii) an aryl group having from 6 to 10 carbon atoms which may have from 1 to 5 substituents α described later, (ix) an aralkyl group having from 7 to 12 carbon atoms which may have from 1 to 5 substituents α described later on the aryl moiety, (x) a hydroxyl group or (xi) a straight or branched chain aliphatic acyl group having from 1 to 5 carbon atoms;

$R^4$ represents a hydrogen atom or a straight or branched chain alkyl group having from 1 to 6 carbon atoms;

Z represents a straight or branched chain alkylene group having from 1 to 6 carbon atoms;

W represents (i) a straight or branched chain alkyl group having from 1 to 6 carbon atoms, (ii) a hydroxyl group, (iii) a straight or branched chain alkoxy group having from 1 to 4 carbon atoms, (iv) a straight or branched chain alkylthio group having from 1 to 4 carbon atoms, (v) an aryl group having from 6 to 10 carbon atoms which may have from 1 to 5 substituents α described later, (vi) an aryloxy group having from 6 to 10 carbon atoms which may have from 1 to 5 substituents α described later on the aryl moiety, (vii) an arylthio group having from 6 to 10 carbon atoms which may have from 1 to 5 substituents α described later on the aryl moiety, (viii) an aralkyl group having from 7 to 12 carbon atoms which may have from 1 to 5 substituents α described later on the aryl moiety, (ix) an aralkyloxy group having from 7 to 12 carbon atoms which may have from 1 to 5 substituents α described later on the aryl moiety, (x) an aralkylthio group having from 7 to 12 carbon atoms which may have from 1 to 5 substituents α described later on the aryl moiety, (xi) an aryloxyalkyl group in which the aryl moiety has from 6 to 10 carbon atoms which may have from 1 to 5 substituents α described later and the alkyl moiety is a straight or branched chain alkyl having from 1 to 4 carbon atoms, (xii) a mono- or dicyclic, 5- to 10-membered hetero aryl group containing from 1 to 4 hetero atoms selected from the group consisting of an oxygen atom, a nitrogen atom and a sulfur atom, (xiii) a mono- or dicyclic, 5- to 10-membered hetero aryloxy group containing from 1 to 4 hetero atoms selected from the group consisting of an oxygen atom, a nitrogen atom and a sulfur atom, (xiv) a mono- or dicyclic, 5- to 10-membered hetero arylthio group containing from 1 to 4 hetero atoms selected from the group consisting of an oxygen atom, a nitrogen atom and a sulfur atom, (xv) a mono- or dicyclic, 5- to 10-membered saturated heterocyclic group containing from 1 to 4 hetero atoms selected from the group consisting of an oxygen atom, a nitrogen atom and a sulfur atom, (xvi) an amino group, (xvii) a straight or branched chain monoalkylamino group in which the alkyl moiety has from 1 to 4 carbon atoms, (xviii) a straight or branched chain dialkylamino group in which each alkyl group may be the same or different and each has from 1 to 4 carbon atoms, (xix) an N-alkyl-N-arylamino group having a straight or branched chain alkyl group having from 1 to 4 carbon atoms and an aryl group having from 6 to 10 carbon atoms which may have from 1 to 5 substituents α, (xx) an arylamino group having from 6 to 10 carbon atoms which may have from 1 to 5 substituents α described later on the aryl moiety, (xxi) an aralkylamino group having from 7 to 12 carbon atoms which may have from 1 to 5 substituents α described later on the aryl moiety or (xxii) an aralkyloxycarbonylamino group having an aralkyl group having from 7 to 12 carbon atoms which may have from 1 to 5 substituents α described later on the aryl moiety;

X represents an aryl group having from 6 to 10 carbon atoms which may have from 1 to 3 substituents α described later or a mono- or dicyclic, 5- to 10-membered hetero aryl group having from 1 to 4 hetero atoms selected from the group consisting of an oxygen atom, a nitrogen atom and a sulfur atom which may have from 1 to 3 substituents α described later, when W represents (1) a straight or branched chain alkyl group having from 1 to 6 carbon atoms, (2) a hydroxyl group, (3) a straight or branched chain alkoxy group having from 1 to 4 carbon atoms, (4) a straight or branched chain alkylthio group having from 1 to 4 carbon atoms, (5) an aryl group having from 6 to 10 carbon atoms which may have from 1 to 5 substituents α described later, (6) an aryloxy group having from 6 to 10 carbon atoms which may have from 1 to 5 substituents α described later on the aryl moiety, (7) an arylthio group having from 6 to 10 carbon atoms which may have from 1 to 5 substituents α described on the aryl moiety, (8) an aralkyl group having from 7 to 12 carbon atoms which may have from 1 to 5 substituents α described later on the aryl moiety, (9) an aralkyloxy group having from 7 to 12 carbon atoms which may have from 1 to 5 substituents α described later on the aryl moiety, (10) an aralkylthio group having from 7 to 12 carbon atoms which may have from 1 to 5 substituents α described later on the aryl moiety, (11) an aryloxyalkyl group in which the aryl moiety is an aryl group having from 6 to 10 carbon atoms which may have from 1 to 5 substituents at described later and the alkyl moiety is a straight or branched chain alkyl having from 1 to 4 carbon atoms, (12) a mono- or dicyclic, 5- to 10-membered hetero aryl group containing from 1 to 4 hetero atoms selected from the group consisting of an oxygen atom, a nitrogen atom and a sulfur atom, (13) a mono- or dicyclic, 5- to 10-membered hetero aryloxy group containing from 1 to 4 hetero atoms selected from the group consisting of an oxygen atom, a nitrogen atom and a sulfur atom,

(14) a mono- or dicyclic, 5- to 10-membered hetero arylthio group containing from 1 to 4 hetero atoms selected from the group consisting of an oxygen atom a nitrogen atom and a sulfur atom or (15) a mono- or dicyclic, 5- to 10-membered saturated heterocyclic group containing from 1 to 4 hetero atoms selected from the group consisting of an oxygen atom, a nitrogen atom and a sulfur atom, or X represents an aryl group having from 6 to 10 carbon atoms which may have from 1 to 3 substituents α described later when W represents (1) an amino group, (2) a straight or branched chain monoalkylamino group in which the alkyl moiety has from 1 to 4 carbon atoms, (3) a straight or branched chain dialkylamino group in which each alkyl group may be the same or different and each has from 1 to 4 carbon atoms, (4) an N-alkyl-N-arylamino group having a straight or branched chain alkyl group having from 1 to 4 carbon atoms and an aryl group having from 6 to 10 carbon atoms which may have from 1 to 5 substituents α, (5) an arylamino group having from 6 to 10 carbon atoms which may have from 1 to 5 substituents α described later on the aryl moiety, (6) an aralkylamino group having from 7 to 12 carbon atoms which may have from 1 to 5 substituents α described later on the aryl moiety or (7) an aralkyloxycarbonylamino group having an aralkyl group having from 7 to 12 carbon atoms which may have from 1 to 5 substituents α described later on the aryl moiety.

The above substituent α represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxylgroups, (iv) straight or branched chain aliphatic acyloxy groups having from 1 to 5 carbon atoms, (v) straight or branched chain aliphatic acyl groups having from 1 to 5 carbon atoms, (vi) straight or branched chain alkoxy groups having from 1 to 4 carbon atoms, (vii) straight or branched chain halogenated alkoxy groups having from 1 to 4 carbon atoms, (viii) straight or branched chain alkylenedioxy groups having from 1 to 4 carbon atoms, (ix) aralkyloxy groups having from 7 to 12 carbon atoms which may have from 1 to 3 substituents β described later, (x) straight or branched chain alkylthio groups having from 1 to 4 carbon atoms, (xi) straight or branched chain alkylsulfonyl groups having from 1 to 4 carbon atoms, (xii) halogen atoms, (xiii) nitro groups, (xiv) cyano groups, (xv) amino groups, (xvi) straight or branched chain monoalkylamino groups in which the alkyl moiety has from 1 to 4 carbon atoms. (xvii) straight or branched chain alkoxycarbonylamino groups in which the alkoxy moiety has from 1 to 4 carbon atoms, (xiii) aralkyloxycarbonylamino groups in which the aralkyl moiety has from 7 to 12 carbon atoms, (xix) straight or branched chain dialkylamino groups in which each alkyl group may be the same or different and each has from 1 to 4 carbon atoms, (xx) aralkyl groups having from 7 to 12 carbon atoms which may have from 1 to 3 substituents β described later on the aryl moiety, (xxi) aryl groups having from 6 to 10 carbon atoms and which may have from 1 to 3 substituents β, which may be the same or different, described later, (xxii) aryloxy groups having from 6 to 10 carbon atoms which may have from 1 to 3 substituents β described later on the aryl moiety, (xxiii) arylthio groups having from 6 to 10 carbon atoms which may have from 1 to 3 substituents β described later on the aryl moiety, (xxiv) arylsulfonyl groups having from 6 to 10 carbon atoms which may have from 1 to 3 substituents β described later on the aryl moiety, (xxv) arylsulfonylamino groups having from 6 to 10 carbon atoms which may have from 1 to 3 substituents β described later on the aryl moiety (the nitrogen atom of the amino moiety may be substituted with a straight or branched chain alkyl group having from 1 to 6 carbon atoms), (xxvi) a mono- or dicyclic, 5- to 10-membered hetero aryl group containing from 1 to 4 hetero atoms selected from the group consisting of an oxygen atom, a nitrogen atom and a sulfur atom which may have from 1 to 3 substituents β described later, (xxvii) a mono- or dicyclic, 5- to 10-membered hetero aryloxy group containing from 1 to 4 hetero atoms selected from the group consisting of an oxygen atom, a nitrogen atom and a sulfur atom which may have from 1 to 3 substituents β described later, (xxviii) a mono- or dicyclic, 5- to 10-membered hetero arylthio group containing from 1 to 4 hetero atoms selected from the group consisting of an oxygen atom, a nitrogen atom and a sulfur atom which may have from 1 to 3 substituents β described later, (xxix) a mono- or dicyclic, 5- to 10-membered hetero arylsulfonyl group containing from 1 to 4 hetero atoms selected from the group consisting of an oxygen atom, a nitrogen atom and a sulfur atom which may have from 1 to 3 substituents β described later, (xxx) a mono- or dicyclic, 5- to 10-membered hetero arylsulfonylamino group containing from 1 to 4 hetero atoms selected from the group consisting of an oxygen atom, a nitrogen atom and a sulfur atom which may have from 1 to 3 substituents β described later on the hetero aryl moiety (the nitrogen atom of the amino moiety may be substituted with a straight or branched chain alkyl group having from 1 to 6 carbon atoms) and (xxxi) a mono- or dicyclic, 5- to 10-membered saturated heterocyclic group containing from 1 to 4 hetero atoms selected from the group consisting of an oxygen atom, a nitrogen atom and a sulfur atom;

The above substituent β represents (i) a straight or branched chain alkyl group having from 1 to 6 carbon atoms, (ii) a straight or branched chain halogenated alkyl group having from 1 to 4 carbon atoms, (iii) a hydroxyl group, (iv) a straight or branched chain alkoxy group having from 1 to 4 carbon atoms, (v) a straight or branched chain halogenated alkoxy group having from 1 to 4 carbon atoms, (vi) a straight or branched chain alkylenedioxy group having from 1 to 4 carbon atoms, (vii) a straight or branched chain hydroxyalkyl group having from 1 to 4 carbon atoms, (viii) a straight or branched chain aliphatic acyl group having from 1 to 5 carbon atoms, (ix) a halogen atom, (x) a nitro group, (xi) a cyano group, (xii) a carboxyl group, (xiii) an amino group, (xiv) a straight or branched chain monoalkylamino group in which the alkyl moiety has from 1 to 4 carbon atoms, (xv) a straight or branched chain dialkylamino group in which each alkyl moiety may be the same or different and each has from 1 to 4 carbon atoms, (xvi) a straight or branched chain aminoalkyl group having from 1 to 4 carbon atoms, (xvii) a monoalkylaminoalkyl group in which the monoalkylamino moiety has one straight or branched chain alkyl group having from 1 to 4 carbon atoms and the alkyl moiety is a straight or branched chain alkyl group having from 1 to 4 carbon atoms, (xviii) a dialkylaminoalkyl group in which the dialkylamino moiety has two straight or branched chain alkyl groups which may be the same or different and each has from 1 to 4 carbon atoms and the alkyl moiety is a straight or branched chain alkyl group having from 1 to 4 carbon atoms, (xix) a straight or branched chain alkoxycarbonylamino group in which the alkoxy moiety has from 1 to 4 carbon atoms or (xx) an aralkyloxycarbonylamino group in which the aralkyl moiety has from 7 to 12 carbon atoms; and Y represents a single bond, an oxygen atom, a sulfur atom or a group of the formula: >N—R$^5$ (wherein R$^5$ represents a hydrogen atom, a straight or branched chain alkyl group having from 1 to 6 carbon atoms, a straight or branched chain aliphatic acyl group having from 1 to 8 carbon atoms or an aromatic acyl group having from 7 to 11 carbon atoms).

In the case where R$^1$, R$^3$, R$^4$, R$^5$ or W represent a straight or branched chain alkyl group having from 1 to 6 carbon atoms, the alkyl group includes, for example, a methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl or 1,2,2-trimethylpropyl group; preferably, each of R$^1$, R$^3$, R$^4$ and R$^5$ is a straight or branched chain alkyl group having from 1 to 4 carbon atoms, and W is a straight or branched chain alkyl group having from 2 to 6 carbon atoms; more preferably, each of R$^1$, R$^3$, R$^4$ and R$^5$ is a methyl, ethyl, propyl, isopropyl, butyl or isobutyl group, and W is an ethyl, propyl, isopropyl, butyl, isobutyl or pentyl group. Most preferably, each of R$^1$ and R$^5$ is an alkyl group having one or two carbon atoms (particularly a methyl group), R$^3$ is a methyl, ethyl or isopropyl group (particularly a methyl or isopropyl group), R$^4$ is an alkyl group having one or two carbon atoms (particularly a methyl group), and W is a propyl, butyl or pentyl group (particularly a propyl or butyl group).

In the case where R$^1$ represents an aralkyl group having from 7 to 12 carbon atoms, the aralkyl group is a group in which a straight or branched chain alkyl group having from 1 to 4 carbon atoms is substituted with an aryl group and includes, for example, a benzyl, phenethyl, 3-phenylpropyl, 4-phenylbutyl, 5-phenylpentyl, 6-phenylhexyl, 1-naphthylmethyl or 2-naphthylmethyl group, preferably a benzyl, phenethyl or 3-phenylpropyl-group, more preferably a 3-phenylpropyl group.

In the case where R$^2$ or Z represent a straight or branched chain alkylene group having from 1 to 6 carbon atoms, the alkylene group includes, for example, a methylene, ethylene, methylethylene, ethylethylene, 1,1-dimethylethylene, 1,2-dimethylethylene, trimethylene, 1-methyltrimethylene, 1-ethyltrimethylene, 2-methyltrimethylene, 1,1-dimethyltrimethylene, tetramethylene, pentamethylene or hexamethylene group, preferably R$^2$ is a straight or branched chain alkylene group having from 2 to 5 carbon atoms, more preferably R$^2$ is a straight or branched chain alkylene group having from 2 to 4 carbon atoms, still more preferably R$^2$ is an ethylene, trimethylene or methylethylene group, most preferably R$^2$ is an ethylene group. Preferably, Z is a straight or branched chain alkylene group having from 1 to 4 carbon atoms (for example, a methylene, ethylene, methylethylene, ethylethylene, trimethylene, 1-methyltrimethylene or 2-methyltrimethylene group), more preferably an alkylene group having one or two carbon atoms, most preferably a methylene group.

In the case where R$^3$ or W represents a straight or branched chain alkoxy group having from 1 to 4 carbon atoms, the alkoxy group includes, for example, a methoxy, ethoxy, propoxy, isopropoxy, butoxy, s-butoxy, t-butoxy or isobutoxy group; preferably R$^3$ is an alkoxy group having from 1 to 3 carbon atoms (particularly methoxy, ethoxy or isopropoxy group); more preferably an alkoxy group having one or two carbon atoms (particularly a methoxy group). Preferably, W is an alkoxy group having from 1 to 3 carbon atoms, more preferably an ethoxy group.

In the case where R$^3$ or W represents a straight or branched chain alkylthio group having from 1 to 4 carbon atoms, the alkylthio group includes, for example, methylthio, ethylthio, propylthio, isopropylthio, butylthio, s-butylthio, t-butylthio or isobutylthio group; preferably R$^3$ is an alkylthio group having one or two carbon atoms; more preferably a methylthio group. W is preferably an alkylthio group having from 1 to 3 carbon atoms (for example, a methylthio, ethylthio, propylthio or isopropylthiogroup); more preferably a methylthio group.

In the case where R$^3$ represents a halogen atom, the halogen atom includes a fluorine atom, a chlorine atom, a bromine atom or an iodine atom; preferably a fluorine atom, a chlorine atom or a bromine atom; more preferably a fluorine atom or a chlorine atom.

In the case where R$^3$ or W represents a straight or branched chain dialkylamino group in which each alkyl group may be the same or different and each has from 1 to 4 carbon atoms, the dialkylamino group includes, for example, a dimethylamino, diethylamino, dipropylamino, diisopropylamino, dibutylamino, N-methyl-N-ethylamino or N-ethyl-N-isopropylamino group; preferably a dimethylamino or diethylamino group; more preferably a diethylamino group.

In the case where R$^3$ or W represents an aryl group having from 6 to 10 carbon atoms which may have from 1 to 5 substituents α described later, the unsubstituted aryl group includes, for example, phenyl or naphthyl group, preferably a phenyl group. The substituted aryl group includes, for example, a methylphenyl, ethylphenyl, propylphenyl, isopropylphenyl, trifluoromethylphenyl, hydroxyphenyl, acetylphenyl, methoxyphenyl, methylenedioxyphenyl, benzyloxyphenyl, methylthiophenyl, methanesulfonylphenyl, fluorophenyl, difluorophenyl, chlorophenyl, dichlorophenyl, nitrophenyl, (dimethylamino)phenyl, benzylphenyl, biphenylyl, phenoxyphenyl, phenylthiophenyl, phenylsulfonylphenyl, (phenylsulfonylamino)phenyl, pyridylphenyl, pyridyloxyphenyl, pyridylthiophenyl, (pyridylsulfonylamino)phenyl, methylnaphthyl, trifluoronaphthyl, hydroxynaphthyl, methoxynaphthyl, fluoronaphthyl, chloronaphthyl or pyridylnaphthyl group; preferably an aryl group having from 6 to 10 carbon atoms which may have from 1 to 3 substituents α described later; more preferably a methylphenyl, ethylphenyl, isopropylphenyl, methoxyphenyl, methylthiophenyl or chlorophenyl group.

In the case where R$^3$ or W represents an aralkyl group having from 7 to 12 carbon atoms which may have from 1 to 5 substituents α described later on the aryl moiety, the aralkyl group is a group in which the straight or branched chain alkyl group having from 1 to 4 carbon atoms is substituted with the above aryl group and includes, for example, a benzyl, phenethyl, 3-phenylpropyl, 4-phenylbutyl, 5-phenylpentyl, 6-phenylhexyl, naphthylmethyl, methylbenzyl, trifluoromethylbenzyl, methoxybenzyl, methylenedioxybenzyl, methylthiobenzyl, methanesulfonylbenzyl, fluorobenzyl, chlorobenzyl, 2-(methylphenyl)ethyl, 2-(methoxyphenyl)ethyl, 3-(methylphenyl)propyl, 3-(methoxyphenyl)propyl, 4-(methylphenyl)butyl or 4-(methoxyphenyl)butyl group; preferably R$^3$ is a benzyl or phenethyl group; most preferably a benzyl group. W is preferably an aralkyl group having from 7 to 12 carbon atoms which may have from 1 to 3 substituents α described later on the aryl moiety; more preferably an aralkyl group having from 7 to 10 carbon atoms (for example, a benzyl, phenethyl, 3-phenylpropyl or 4-phenylbutyl group); most preferably a 3-phenylpropyl or 4-phenylbutyl group (particularly the 3-phenylpropyl group).

In the case where $R^3$ represents a straight or branched chain aliphatic acyl group having from 1 to 5 carbon atoms, the aliphatic acyl group includes, for example, a formyl, acetyl, propionyl, butyryl, isobutyryl, pentanoyl or pivaloyl group, preferably a formyl, acetyl or pivaloyl group; most preferably a formyl or acetyl group.

In the case where W represents an aryloxy group having from 6 to 10 carbon atoms which may have from 1 to 5 substituents α described later on the aryl moiety, the unsubstituted aryloxy group includes, for example, a phenoxy or naphthyloxy group; preferably a phenoxy group. The substituted aryloxy group includes, for example, a methylphenoxy, ethylphenoxy, propylphenoxy, isopropylphenoxy, t-butylphenoxy, trifluoromethylphenoxy, methoxyphenoxy, ethoxyphenoxy, isopropoxyphenoxy, trifluoromethoxyphenoxy, methylthiophenoxy, ethylthiophenoxy, cyanophenoxy, formylphenoxy, fluorophenoxy, difluorophenoxy, trifluorophenoxy, pentafluorophenoxy, chlorophenoxy, dichlorophenoxy, trichlorophenoxy, pyridylphenoxy, biphenylyloxy, methanesulfonylphenoxy, methylnaphthyloxy, ethylnaphthyloxy, propylnaphthyloxy, isopropylnaphthyloxy, t-butylnaphthyloxy, trifluoromethylnaphthyloxy, methoxynaphthyloxy, ethoxynaphthyloxy, isopropoxynaphthyloxy, trifluoromethoxynaphthyloxy, methylthionaphthyloxy, ethylthionaphthyloxy, cyanonaphthyloxy, formylnaphthyloxy, fluoronaphthyloxy, difluoronaphthyloxy, trifluoronaphthyloxy, pentafluoronaphthyloxy, chloronaphthyloxy, dichloronaphthyloxy, trichloronaphthyloxy, pyridylnaphthyloxy, biphenylyloxy or methanesulfonylnaphthyloxy group; preferably an aryloxy group having from 6 to 10 carbon atoms which may have from 1 to 3 substituents α described later on the aryl moiety; more preferably a phenoxy group which may have from 1 to 3 substituents α described later on the phenyl moiety (particularly a phenoxy group which may have one substituent α described later on the phenyl moiety); most preferably a methylphenoxy, ethylphenoxy, isopropylphenoxy, t-butylphenoxy, trifluoromethylphenoxy, methoxyphenoxy, ethoxyphenoxy, trifluoromethoxyphenoxy, cyanophenoxy, formylphenoxy, fluorophenoxy, difluorophenoxy, trifluorophenoxy, pentafluorophenoxy, chlorophenoxy, dichlorophenoxy, trichlorophenoxy, pyridylphenoxy or methanesulfonylphenoxy group; still most preferably a methylphenoxy, ethylphenoxy, isopropylphenoxy, t-butylphenoxy, trifluoromethylphenoxy, methoxyphenoxy, ethoxyphenoxy, trifluoromethoxyphenoxy, cyanophenoxy, formylphenoxy, fluorophenoxy, difluorophenoxy, trifluorophenoxy, pentafluorophenoxy, chlorophenoxy, dichlorophenoxy, trichlorophenoxy or methanesulfonylphenoxy group; particularly most preferably a 4-methylphenoxy, 4-isopropylphenoxy, 4-t-butylphenoxy, 4-methoxyphenoxy, 4-trifluoromethoxyphenoxy, 3-fluorophenoxy, 4-fluorophenoxy or 4-chlorophenoxy group.

In the case where W represents an arylthio group having from 6 to 10 carbon atoms which may have from 1 to 5 substituents α described later on the aryl moiety, the unsubstituted arylthio group includes, for example, a phenylthio or naphthylthio group; preferably a phenylthio group. The substituted arylthio group includes, for example, a methylphenylthio, ethylphenylthio, propylphenylthio, isopropylphenylthio, methoxyphenylthio, ethoxyphenylthio, methylthiophenylthio, ethylthiophenylthio, biphenylylthio, 4-methanesulfonylphenylthio, methylnaphthylthio, ethylnaphthylthio, propylnaphthylthio, isopropylnaphthylthio, methoxynaphthylthio, ethoxynaphthylthio, methylthionaphthylthio, ethylthionaphthylthio or 4-methanesulfonylnaphthylthio group; preferably an arylthio group having 6 to 10 carbon atoms which may have from 1 to 3 substituents α described later; more preferably a phenylthio group which may have from 1 to 3 substituents α described later on the phenyl moiety; most preferably a methylphenylthio, isopropylphenylthio or methoxyphenylthio group.

In the case where W represents an aralkyloxy group having from 7 to 12 carbon atoms which may have from 1 to 5 substituents α described later on the aryl moiety, the unsubstituted aralkyloxy group is a group in which the straight or branched chain alkyloxy group having from 1 to 4 carbon atoms is substituted with the above aryl group and includes, for example, a benzyloxy, phenethyloxy, 3-phenylpropyloxy, 4-phenylbutyloxy, 1-naphthylmethyloxy or 2-naphthylmethyloxy group; preferably an aralkyloxy group having from 7 to 10 carbon atoms; more preferably a benzyloxy or phenethyloxy group (particularly a benzyloxy group). The substituted aralkyloxy group includes, for example, a methylbenzyloxy, methoxybenzyloxy, 2-(methylphenyl)ethoxy, 2-(methoxyphenyl)ethoxy, 3-(methylphenyl)propoxy, 3-(methoxyphenyl)propoxy, 4-(methylphenyl)butoxy or 4-(methoxyphenyl)butoxy group; preferably an aralkyloxy group having from 7 to 12 carbon atoms which may have from 1 to 3 substituents α described later on the aryl moiety; more preferably a methylbenzyloxy or 2-(methylphenyl)ethoxy group.

In the case where W represents an aralkylthio group having from 7 to 12 carbon atoms in the aryl moiety which may have from 1 to 5 substituents α described later, the unsubstituted aralkylthio group is a group in which the straight or branched chain alkylthio group having from 1 to 4 carbon atoms is substituted with the above aryl group and includes, for example, a benzylthio, phenethylthio, 3-phenylpropylthio, 4-phenylbutylthio, 1-naphthylmethylthio or 2-naphthylmethylthio group; preferably a benzylthio or phenethylthio group; more preferably a benzylthio group. The substituted aralkylthio group includes, for example, a methylbenzylthio, methoxybenzylthio, 2-(methylphenyl)ethylthio, 2-(methoxyphenyl)ethylthio, 3-(methylphenyl)propylthio, 3-(methoxyphenyl)propylthio, 4-(methylphenyl)butylthio or 4-(methoxyphenyl)butylthio group; preferably an aralkylthio group having from 7 to 12 carbon atoms which may have from 1 to 3 substituents α described later in the aryl moiety; more preferably a methylbenzylthio or 2-(methylphenyl)ethylthio group.

In the case where W represents an aryloxyalkyl group in which the aryl moiety is an aryl group having from 6 to 10 carbon atoms which may have from 1 to 5 substituents α described later and the alkyl moiety is a straight or branched chain alkyl group having from 1 to 4 carbon atoms, the aryloxyalkyl group includes, for example, a phenoxymethyl, 2-phenoxyethyl, 3-phenoxypropyl, 4-phenoxybutyl, naphthyloxymethyl, 2-naphthyloxyethyl, 3-naphthyloxypropyl or 4-naphthyloxybutyl group; preferably an aryloxyalkyl group in which the aryl moiety is an aryl group having from 6 to 10 carbon atoms which may have from 1 to 3 substituents α described later and the alkyl moiety is a straight or branched chain alkyl group having from 1 to 4 carbon atoms; more preferably an aryloxyalkyl group in which the aryl moiety has from 6 to 10 carbon atoms and the alkyl moiety is a straight or branched chain and has from 1 to 4 carbon atoms; still more preferably a phenoxymethyl, 2-phenoxyethyl, 3-phenoxypropyl or 4-phenoxybutyl group; most preferably the 2-phenoxyethyl or 3-phenoxypropyl group particularly a 2-phenoxyethyl group).

In the case where W represents a mono- or dicyclic, 5- to 10-membered hetero aryl group containing 1 to 4 hetero atoms selected from the group consisting of an oxygen atom, a nitrogen atom and a sulfur atom, the hetero aryl group includes, for example, a furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, pyrazinyl, quinolyl or benzoxazolyl group: preferably a pyrrolyl, imidazolyl, furyl, thienyl or pyridyl group; more preferably a pyrrolyl or imidazolyl group.

In the case where W represents a mono- or dicyclic, 5- to 10-membered hetero aryloxy group containing 1 to 4 hetero atoms selected from the group consisting of an oxygen atom, a nitrogen atom and a sulfur atom, the hetero aryloxy group includes, for example, a furyloxy, thienyloxy, pyrrolyloxy, azepinyloxy, pyrazolyloxy, imidazolyloxy, oxazolyloxy, isoxazolyloxy, thiazolyloxy, isothiazolyloxy, 1,2,3-oxadiazolyloxy, triazolyloxy, tetrazolyloxy, thiadiazolyloxy, pyranyloxy, pyridyloxy, pyridazinyloxy, pyrimidinyloxy, pyrazinyloxy or benzoxazolyloxy group; preferably a furyloxy, thienyloxy, pyrrolyloxy, imidazolyloxy, thiazolyloxy or pyridyloxy group; more preferably a pyridyloxy group.

In the case where W represents a mono- or dicyclic, 5- to 10-membered hetero arylthio group containing 1 to 4 hetero atoms selected from the group consisting of an oxygen atom, a nitrogen atom and a sulfur atom, the hetero arylthio group includes, for example, a furylthio, thienylthio, pyrrolylthio, azepinylthio, pyrazolylthio, imidazolylthio, oxazolylthio, isoxazolylthio, thiazolylthio, isothiazolylthio, 1,2,3-oxadiazolylthio, triazolylthio, tetrazolylthio, thiadiazolylthio, pyranylthio, pyridylthio, pyridazinylthio, pyrimidinylthio, pyrazinylthio or benzoxazolylthio group; preferably a furylthio, thienylthio, pyrrolylthio, imidazolylthio, thiazolylthio, pyridylthio or benzoxazolylthio group; more preferably a benzoxazolylthio group.

In the case where W represents a mono- or dicyclic, 5- to 10-membered saturated heterocyclic group containing 1 to 4 hetero atoms selected from the group consisting of an oxygen atom, a nitrogen atom and a sulfur atom, the saturated heterocyclic group includes, for example, morpholinyl, thiomorpholinyl, pyrrolidinyl, pyrrolinyl, imidazolidinyl, imidazolinyl, pyrazolidinyl, pyrazolinyl, piperidyl or piperazinyl group; preferably a morpholinyl, thiomorpholinyl, pyrrolidinyl, imidazolinyl, piperidyl or piperazinyl group.

In the case where W represents a straight or branched chain monoalkylamino group in which the alkyl moiety has from 1 to 4 carbon atoms, the monoalkylamino group includes, for example, a methylamino, ethylamino, propylamino, isopropylamino, butylamino, s-butylamino, t-butylamino or isobutylamino group; preferably a straight or branched chain monoalkylamino group having from 1 to 3 carbon atoms; more preferably a propylamino group.

In the case where W represents a N-alkyl-N-arylamino group having a straight or branched chain alkyl group having from 1 to 4 carbon atoms and an aryl group having from 6 to 10 carbon atoms which may have from 1 to 5 substituents α described later, the alkyl moiety of the unsubstituted N-alkyl-N-arylamino group includes, for example, a methyl, ethyl, propyl, isopropyl, butyl, isobutyl, s-butyl or t-butyl group; preferably a methyl, ethyl, propyl, isopropyl, butyl or isobutyl group; more preferably a methyl or ethyl group. The aryl moiety includes, for example, a phenyl or naphthyl group; preferably a phenyl group. Specific examples of the unsubstituted N-alkyl-N-arylamino group includes, for example, a N-methyl-N-phenylamino, N-ethyl-N-phenylamino, N-propyl-N-phenylamino, N-isopropyl-N-phenylamino, N-butyl-N-phenylamino, N-isobutyl-N-phenylamino or N-methyl-N-naphthylamino group; preferably a N-methyl-N-phenylamino or N-ethyl-N-phenylamino group; more preferably a N-ethyl-N-phenylamino group. The substituted N-alkyl-N-arylamino group includes, for example, a N-methyl-N-(methylphenyl)amino, N-ethyl-N-(methylphenyl)amino, N-methyl-N-(methoxyphenyl)amino or N-ethyl-N-(methoxyphenyl)amino group; preferably a N-methyl-N-(methylphenyl)amino or N-ethyl-N-(methylphenyl)amino group.

In the case where W represents an arylamino group having from 6 to 10 carbon atoms which may have from 1 to 5 substituents α described later on the aryl moiety, the unsubstituted arylamino group includes, for example, a phenylamino or naphthylamino group; preferably a phenylamino group. The substituted arylamino group includes, for example, a (methylphenyl)amino, (ethylphenyl)amino, (propylphenyl)amino, (isopropylphenyl)amino, (methoxyphenyl)amino, (ethoxyphenyl)amino, (methylthiophenyl)amino, (ethylthiophenyl)amino, biphenylylamino or (methanesulfonylphenyl)amino group; preferably a (methylphenyl)amino, (isopropylphenyl)amino or (methoxyphenyl)amino group.

In the case where W represents an aralkylamino group having from 7 to 12 carbon atoms in the aralkyl moiety in which the aryl moiety may have from 1 to 5 substituents α described later, the unsubstituted aralkylamino group is a group in which a straight or branched chain alkylamino group having from 1 to 4 carbon atoms is substituted with the above aryl group and includes, for example, a benzylamino, phenethylamino, (3-phenylpropyl)amino, (4-phenylbutyl)amino, (1-naphthylmethyl)amino or (2-naphthylmethyl)amino group; preferably a benzylamino or phenethylamino group; more preferably a benzylamino group. The substituted aralkylamino group includes, for example, a (methylbenzyl)amino, (methoxybenzyl)-amino, [2-(methylphenyl)ethyl]amino, [2-(methoxyphenyl)ethyl]amino, [3-(methylphenyl)propyl]amino, [3-(methoxyphenyl)propyl]amino, [4-(methylphenyl)-butyl]amino or [4-(methoxyphenyl)butyl]amino group; preferably a (methylbenzyl)-amino or [2-(methylphenyl)ethyl]amino group.

In the case where W represents an aralkyloxycarbonylamino group having an aralkyl moiety having from 7 to 12 carbon which may have from 1 to 5 substituents α described later atoms on the aryl moiety, the group includes, for example, a benzyloxycarbonyl group.

In the case where W represents an amino group, a straight or branched chain monoalkylamino group in which the alkyl moiety has from 1 to 4 carbon atoms, a straight or branched chain dialkylamino group in which each alkyl moiety may be the same or different and each has from 1 to 4 carbon atoms, a N-alkyl-N-arylamino group having a straight or branched chain alkyl moiety having from 1 to 4 carbon atoms and an aryl moiety having from 6 to 10 carbon atoms which may have from 1 to 5 substituents α described later, an arylamino group having from 6 to 10 carbon atoms in the aryl moiety which may have from 1 to 5 substituents α described later, or an aralkylamino group having from 7 to 12 carbon atoms in the aralkyl moiety in which the aryl moiety may have from 1 to 5 substituents α described later, W is preferably: an amino group; a straight or branched chain monoalkylamino group in which the alkyl moiety has from 1 to 4 carbon atoms; a straight or branched chain dialkylamino group in which each alkyl group may be the same or different and each has from 1 to 4 carbon atoms; a N-alkyl-N-arylamino group having a straight or branched chain alkyl moiety having from 1 to 4 carbon atoms and an aryl moeity having from 6 to 10 carbon atoms which may have from 1 to 5 substituents α; or an arylamino group having from 6 to 10 carbon atoms in the aryl moiety which may have from 1 to 5 substituents α described later.

In the case where $R^5$ represents a straight or branched chain aliphatic acyl group having from 1 to 8 carbon atoms or an aromatic acyl group having from 7 to 11 carbon atoms, the acyl group includes, for example, a formyl, acetyl, propionyl, butyryl, pentanoyl, hexanoyl, heptanoyloctanoyl, benzoyl or p-toluoyl group; preferably a straight or branched chain aliphatic acyl group having from 1 to 8 carbon atoms; more preferably a straight or branched chain aliphatic acyl group having from 2 to 5 carbon atoms; most preferably an acetyl group.

In the case where X represents an aryl group having from 6 to 10 carbon atoms which may have from 1 to 3 substituents α described later, the unsubstituted aryl group includes, for example, a phenyl or naphthyl group, preferably a phenyl group. In the case where X represents an aryl group which is substituted with from 1 to 3 substituents α described later, the number of the substituents is preferably one or two, more preferably one.

In the case where X represents a mono- or dicyclic, 5- to 10-membered hetero aryl group containing from 1 to 4 hetero atoms selected from the group consisting of an oxygen atom, a nitrogen atom and a sulfur atom which may have from 1 to 3 substituents α described later, the unsubstituted hetero aryl group comprises a monocyclic system or a dicyclic system. In the case of the dicyclic system, one ring thereof at least is a heterocyclic group. In the case of the dicyclic system, two rings are condensed wherein one ring is a heterocycle and the other is a carbocycle, or both rings are heterocycles. The heterocycle is a 5- or 6-membered ring and contains from 1 to 4 hetero atoms selected from the group consisting of a nitrogen atom, an oxygen atom and a sulfur atom. The carbocycle is an aryl group having from 6 to 10 carbon atoms. The monocyclic system is called a monocyclic hetero aryl group and the dicyclic system is called a condensed hetero aryl group. In the case of the ring having four hetero atoms, all of the four hetero atoms are preferably nitrogen atoms and the number of hetero atoms selected from the group consisting of an oxygen atom and a sulfur atom is zero. In the case of the ring having three hetero atoms, preferably three, two or one of the hetero atoms are nitrogen atoms and one or two of the hetero atoms are those selected from the group consisting of an oxygen and a sulfur atom. In the case of the ring having two hetero atoms, preferably two, one or zero of the hetero atoms are nitrogen atoms and zero, one or two of the hetero atoms are those selected from the group consisting of an oxygen atom and a sulfur atom. In the case where X represents a hetero aryl group substituted with from 1 to 3 substituents α described later, the number of the substituents is preferably one or two, more preferably one.

The unsubstituted monocyclic hetero aryl group includes, for example, a pyrrolyl group such as a 2-pyrrolyl or 3-pyrrolyl group; a furyl group such as a 2-furyl or 3-furyl group; a thienyl group such as a 2-thienyl or 3-thienyl group; a pyridyl group such as a 2-pyridyl, 3-pyridyl or 4-pyridyl group; an imidazolyl group such as a 2-imidazolyl or 4-imidazolyl group; a pyrazolyl group such as a 3-pyrazolyl or 4-pyrazolyl group; an oxazolyl group such as a 2-oxazolyl, 4-oxazolyl or 5-oxazolyl group; an isoxazolyl group such as a 3-isoxazolyl, 4-isoxazolyl or 5-isoxazolyl group; a thiazolyl group such as a 2-thiazolyl, 4-thiazolyl or 5-thiazolyl group; an isothiazolyl group such as a 3-isothiazolyl, 4-isothiazolyl or 5-isothiazolyl group; a triazolyl group such as a 1,2,3-triazol-4-yl, or 1,2,4-triazol-3-yl group; a thiadiazolyl group such as a 1,3,4-thiadiazol-2-yl group; an oxadiazolyl group such as a 1,3,4-oxadiazol-2-yl group; a tetrazolyl group such as a 5-tetrazolyl group; a pyridazinyl group such as a 3-pyridazinyl or 4-pyridazinyl group ; a pyrimidinyl group such as a 2-pyrimidinyl, 4-pyrimidinyl or 5-pyrimidinyl group; a pyrazinyl group; an oxazinyl group such as a 1,4-oxazin-2-yl or 1,4-oxazin-3-yl group; and a thiazinyl group such as a 1,4-thiazin-2-yl or 1,4-thiazin-3-yl group; and the unsubstituted condensed hetero aryl group includes, for example, an indolyl group such as an indol-2-yl, indol-3-yl, indol-4-yl, indol-5-yl, indol-6-yl or indol-7-yl group; an indazolyl group such as an indazol-2-yl, indazol-3-yl, indazol-4-yl, indazol-5-yl, indazol-6-yl or indazol-7-yl group; a benzofuranyl group such as a benzofuran-2-yl, benzofuran-3-yl, benzofuran-4-yl, benzofuran-5-yl, benzofuran-6-yl or benzofuran-7-yl group; a benzothiophenyl group such as a benzothiophen-2-yl, benzothiophen-3-yl, benzothiophen-4-yl, benzothiophen-5-yl, benzothiophen-6-yl or benzothiophen-7-yl group; a benzimidazolyl group such as a benzimidazol-2-yl, benzimidazol-4-yl, benzimidazol-5-yl, benzimidazol-6-yl or benzimidazol-7-yl group; a benzoxazolyl group such as a benzoxazol-2-yl, benzoxazol-4-yl, benzoxazol-5-yl, benzoxazol-6-yl or benzoxazol-7-yl group; a benzothiazolyl group such as a benzothiazol-2-yl, benzothiazol-4-yl, benzothiazol-5-yl, benzothiazol-6-yl or benzothiazol-7-yl group; a quinolyl group such as a 2-quinolyl, 3-quinolyl, 4-quinolyl, 5-quinolyl, 6-quinolyl, 7-quinolyl or 8-quinolyl group; an isoquinolyl group such as a 1-isoquinolyl, 3-isoquinolyl, 4-isoquinolyl or 8-isoquinolyl group; a benzoxazinyl group such as a 1,4-benzoxazin-2-yl or 1,4-benzoxazin-3-yl group; a benzothiazinyl group such as a 1,4-benzothiazin-2-yl or 1,4-benzothiazin-3-yl group; a pyrrolo[2,3-b]pyridyl group such as a pyrrolo[2,3-b]pyrid-2-yl or pyrrolo[2,3-b]pyrid-3-yl; a furo[2,3-b]pyridyl group such as a furo[2,3-b]pyrid-2-yl or furo[2,3-b]pyrid-3-yl group; a thieno[2,3-b]pyridyl group such as a thieno[2,3-b]pyrid-2-yl or thieno[2,3-b]pyrid-3-yl group; a naphthylidinyl group such as a 1,8-naphthylidin-2-yl, 1,8-naphthylidin-3-yl, 1,5-naphthylidin-2-yl and 1,5-naphthylidin-3-yl group; an imidazopyridyl group such as an imidazo[4,5-b]pyrid-2-yl or imidazo[4,5-b]pyrid-5-yl group; an oxazolopyridyl group such as an oxazolo[4,5-b]pyrid-2-yl or oxazolo[5,4-b]pyrid-2-yl group; and a thiazolopyridyl group such as a thiazolo[4,5-b]pyrid-2-yl or thiazolo[4,5-c]pyrid-2-yl group.

The monocyclic hetero aryl group is preferably a 5- or 6-membered ring group having from 1 to 3 hetero atoms selected from the group consisting of a nitrogen atom, an oxygen atom and a sulfur atom and includes the above-exemplified pyrrolyl group, furyl group, thienyl group, pyridyl group, imidazolyl group, pyrazolyl group, oxazolyl group, isoxazolyl group, thiazolyl group, triazolyl group, thiadiazolyl group, oxadiazolyl group, pyridazinyl group, pyrimidinyl group or pyrazinyl group. The condensed hetero aryl group is preferably a condensed ring group of a benzene ring with the 5- or 6-membered monocyclic hetero aryl group having from 1 to 3 hetero atoms selected from the group consisting of a nitrogen atom, oxygen atom and sulfur atom and includes the above-exemplified indolyl group, benzofuranyl group, benzothiophenyl group, benzimidazolyl group, benzoxazolyl group, benzothiazolyl group, quinolyl group or isoquinolyl group; more preferably an imidazolyl group, oxazolyl group, pyridyl group, indolyl group, quinolyl group or isoquinolyl group; still more preferably a pyridyl group, indolyl group, quinolyl group or isoquinolyl group; and most preferably a pyridyl group, quinolyl group or isoquinolyl group; particularly most preferably a pyridyl group.

In the case where the above group X represents an aryl group having from 6 to 10 carbon atoms or a mono- or dicyclic, 5- to 10-membered hetero aryl group containing from 1 to 4 hetero atoms selected from the group consisting of an oxygen atom, nitrogen atom and sulfur atom, the aryl group and the hetero aryl group may have from 1 to 3 substituents α as described above.

In the case where the substituent α represents a straight or branched chain alkyl group having from 1 to 6 carbon atoms, a straight or branched chain alkoxy group having from 1 to 4 carbon atoms, a straight or branched chain alkylthio group having from 1 to 4 carbon atoms, a halogen atom, or a straight or branched chain dialkylamino group in which each alkyl group may be the same or different and each has from 1 to 4 carbon atoms, these groups may include the same groups as described above in the definition of $R^3$. However, in the case where the substituent α represents a straight or branched chain alkyl group having from 1 to 6 carbon atoms, the alkyl group preferably includes a methyl, ethyl, propyl, isopropyl, butyl or t-butyl, more preferably a methyl, isopropyl or t-butyl group.

In the case where the substituent α represents an aralkyloxycarbonylamino group in which the aralkyl moiety has from 7 to 12 carbon atoms, the group includes, for example, a benzyloxycarbonylamino group.

In the case where the substituent α represents a straight or branched chain halogenated alkyl group having from 1 to 4 carbon atoms, the halogenated alkyl group includes, for example, a chloromethyl, bromomethyl, fluoromethyl, iodomethyl, difluoromethyl, trifluoromethyl, pentafluoroethyl, 2,2,2-trifluoroethyl, 2,2,2-trichloroethyl or trichloromethyl group; preferably a fluoromethyl having from 1 to 3 fluorine atoms; more preferably a trifluoromethyl.

In the case where the substituent α represents a straight or branched chain aliphatic acyloxy group having from 1 to 5 carbon atoms, the acyloxy group includes, for example, a formyloxy, acetoxy, propionyloxy, butyryloxy, acroyloxy, methacroyloxy or crotonoyloxy group; preferably an alkanoyloxy group having from 1 to 4 carbon atoms; more preferably an alkanoyloxy group having one or two carbon atoms; most preferably an acetoxy group.

In the case where the substituent α represents a straight or branched chain halogenated alkoxy group having from 1 to 4 carbon atoms, the halogenated alkoxy group includes, for example, a chloromethoxy, bromomethoxy, fluoromethoxy, iodomethoxy, difluoromethoxy, trifluoromethoxy, pentafluoroethoxy, 2,2,2-trifluoroethoxy, 2,2,2-trichloroethoxy, trichloromethoxy or 2,2,3,3-tetrafluoropropoxy group; preferably a straight or branched chain halogenated alkoxy group having from 1 to 3 carbon atoms; more preferably a methoxy group having from 1 to 3 fluorine atoms or a 2,2,3,3-tetrafluoropropoxy group; most preferably a trifluoromethoxy or 2,2,3,3-tetrafluoropropoxy group (particularly a 2,2,3,3-tetrafluoropropoxy group).

In the case where the substituent α represents a straight or branched chain aliphatic acyl group having from 1 to 5 carbon atoms, the acyl group includes, for example, a formyl, acetyl, propionyl, butyryl, acroyl, methacroyl or crotonoyl group; preferably a straight or branched chain aliphatic acyl group having 2 or 3 carbon atoms; more preferably an acetyl group.

In the case where the substituent α represents a straight or branched chain alkylenedioxy group having from 1 to 4 carbon atoms, the alkylenedioxy group includes, for example, a methylenedioxy, ethylenedioxy, trimethylenedioxy, tetramethylenedioxy or propylenedioxy group; preferably a methylenedioxy or ethylenedioxy group; more preferably a methylenedioxy group.

In the case where the substituent α represents an aralkyloxy group having from 7 to 12 carbon atoms which may have from 1 to 3 substituents β described later, the aralkyloxy group includes, for example, a benzyloxy, phenethyloxy, 3-phenylpropoxy, 4-phenylbutoxy, 1-naphthylmethoxy or 2-naphthylmethoxy group; preferably an unsubstituted aralkyloxy having from 7 to 12 carbon atoms (for example, a-benzyloxy, 2-phenethyloxy, 1-naphthylmethoxy or 2-naphthylmethoxy group); more preferably a benzyloxy group.

In the case where the substituent α represents a straight or branched chain alkylsulfonyl group having from 1 to 4 carbon atoms, the alkylsulfonyl group includes, for example, a methanesulfonyl, ethanesulfonyl, propanesulfonyl, isopropanesulfonyl, butanesulfonyl, isobutanesulfonyl, s-butanesulfonyl or t-butanesulfonyl group, preferably a methanesulfonyl, ethanesulfonyl or isopropanesulfonyl group; particularly preferably an alkylsulfonyl group having from one or two carbon atoms (particularly a methanesulfonyl group).

In the case where the substituent α represents a straight or branched chain monoalkylamino group in which the alkyl moiety has from 1 to 4 carbon atoms, the monoalkylamino group includes, for example, a methylamino, ethylamino, propylamino, isopropylamino, butylamino, isobutylamino, s-butylamino or t-butylamino group; preferably a methylamino, ethylamino, isopropylamino or t-butylamino group; more preferably a methylamino group.

In the case where the substituent α represents a straight or branched chain alkoxycarbonylamino group in which the alkoxy moiety has from 1 to 4 carbon atoms, the alkoxycarbonylamino group includes, for example, a methoxycarbonylamino, ethoxycarbonylamino or t-butoxycarbonylamino group; preferably a t-butoxycarbonylamino group.

In the case where the substituent α represents an aralkyl group having from 7 to 12 carbon atoms in the aryl moiety which may have from 1 to 3 substituents β described later, the aralkyl group includes, for example, a benzyl, phenethyl, 3-phenylpropyl, 4-phenylbutyl, 5-phenylpentyl, 6-phenylhexyl, 1-naphthylmethoxy or 2-naphthylmethoxy group; preferably a benzyl group which may have from 1 to 3 substituents β described later on the phenyl moiety; more preferably a benzyl group.

In the case where the substituent α represents an aryl group having from 6 to 10 carbon atoms which may have from 1 to 3 substituents β, which may be the same or different, described later, the aryl group includes, for example, a phenyl, naphthyl, methylphenyl, (trifluoromethyl)phenyl, hydroxyphenyl, methoxyphenyl, ethoxyphenyl, (trifluoromethoxy)phenyl, methylenedioxyphenyl, (hydroxymethyl)phenyl, fluorophenyl, chlorophenyl, bromophenyl, nitrophenyl, formylphenyl, cyanophenyl, carboxyphenyl, aminophenyl, (dimethylamino)phenyl, (aminomethyl)phenyl, (2-aminoethyl)phenyl, [(N,N-dimethylamino)methyl]phenyl, (t-butoxycarbonylamino)phenyl, (benzyloxycarbonylamino)phenyl or 4-hydroxy-3,5-dimethylphenyl group; preferably a phenyl group which may have from 1 to 3 substituents β described later (particularly, a phenyl, methylphenyl, (trifluoromethyl)phenyl, hydroxyphenyl, methoxyphenyl, (trifluoromethoxy)phenyl, methylenedioxyphenyl, (hydroxymethyl)phenyl, fluorophenyl, chlorophenyl, nitrophenyl, formylphenyl, cyanophenyl, carboxyphenyl, dimethylaminophenyl, aminomethylphenyl, (N,N-dimethylaminomethyl)phenyl or 4-hydroxy-3,5-dimethylphenyl group); more preferably a phenyl, methylphenyl, (trifluoromethyl)phenyl, hydroxyphenyl, methoxyphenyl, (trifluoromethoxy)phenyl, methylenedioxyphenyl, (hydroxymethyl)phenyl, fluorophenyl, chlorophenyl, nitrophenyl, formylphenyl, cyanophenyl, carboxyphenyl, (dimethylamino)phenyl, (aminomethyl)phenyl, (N,N-dimethylaminomethyl)phenyl or 4-hydroxy-3,5-dimethoxyphenyl group; most preferably a phenyl, (trifluoromethyl)phenyl, methoxyphenyl, (hydroxymethyl)phenyl, (trifluoromethoxy)phenyl, fluorophenyl, fluorophenyl, chlorophenyl, chlorophenyl, nitrophenyl, formylphenyl, carboxyphenyl, dimethylaminophenyl, (N,N-dimethylaminomethyl)phenyl or 4-hydroxy-3,5-dimethylphenyl group; particularly most preferably a phenyl, (trifluoromethoxy)phenyl, methoxyphenyl, fluorophenyl, chlorophenyl, formylphenyl, carboxyphenyl or (dimethylamino)phenyl group.

In the case where the substituent α represents an aryloxy group having from 6 to 10 carbon atoms in the aryl moiety which may have from 1 to 3 substituents β described later, the aryloxy group includes, for example, a phenoxy, naphthoxy, methylphenoxy, (trifluoromethyl)phenoxy, methoxyphenoxy, ethoxyphenoxy, fluorophenoxy, chlorophenoxy, bromophenoxy or methylenedioxyphenoxy group; preferably a phenoxy group which may have from 1 to 3 substituents β described later (particularly a phenoxy group).

In the case where the substituent α represents an arylthio group having from 6 to 10 carbon atoms in the aryl moiety which may have from 1 to 3 substituents β described later, the arylthio group includes, for example, a phenylthio, methylphenylthio, (trifluoromethyl)phenylthio, methoxyphenylthio, ethoxyphenylthio, chlorophenylthio, bromophenylthio, methylenedioxyphenylthio or naphthylthio group; preferably a phenylthio group which may have from 1 to 3 substituents β described later (particularly a phenylthio group).

In the case where the substituent α represents an arylsulfonyl group having from 6 to 10 carbon atoms in the aryl moiety which may have from 1 to 3 substituents β described later, the arylsulfonyl group includes, for example, a phenylsulfonyl, methylphenylsulfonyl, (trifluoromethyl)phenylsulfonyl, methoxyphenylsulfonyl, ethoxyphenylsulfonyl, chlorophenylsulfonyl, bromophenylsulfonyl, methylenedioxyphenylsulfonyl or naphthylsulfonyl group; preferably a phenylsulfonyl group which may have from 1 to 3 substituents β described later.

In the case where the substituent α represents an arylsulfonylamino group having from 6 to 10 carbon atoms in the aryl moiety which may have from 1 to 3 substituents β described later (the nitrogen atom of the amino moiety may be substituted with a straight or branched chain alkyl group having from 1 to 6 carbon atoms), the alkyl moiety of the substituent on the nitrogen atom has the same meaning as defined above. The arylsulfonylamino group includes, for example, a (phenylsulfonyl)amino, (methylphenylsulfonyl)amino, (trifluoromethylphenylsulfonyl)amino, (methoxyphenylsulfonyl)amino, (ethoxyphenylsulfonyl)amino, chlorophenylsulfonylamino, bromophenylsulfonylamino, methylenedioxyphenylsulfonylamino, N-methyl-phenylsulfonylamino, (naphthylsulfonyl)amino or N-methyl-naphthylsulfonylamino group; preferably a (phenylsulfonyl)amino group which may have from 1 to 3 substituents β described later on the phenyl moiety or a N-methyl-phenylsulfonylamino group (particularly a phenylsulfonylamino or N-methyl-phenylsulfonylamino group).

In the case where the substituent α represents a mono- or dicyclic, 5- to 10-membered hetero aryl group containing from 1 to 4 hetero atoms selected from the group consisting of an oxygen atom, nitrogen atom and sulfur atom which may have from 1 to 3 substituents β described later, the unsubstituted hetero aryl group includes, for example, a furyl, thienyl, oxazolyl, isoxazolyl, thiazolyl, imidazolyl, quinolyl, isoquinolyl, indolyl or pyridyl group; preferably an imidazolyl, quinolyl or pyridyl group; particularly preferably a pyridyl group. The group having a substituent includes methylpyridyl, (trifluoromethyl)pyridyl, hydroxypyridyl, methoxypyridyl, ethoxypyridyl, (trifluoromethoxy)pyridyl, (hydroxymethyl)pyridyl, fluoropyridyl, chloropyridyl, bromopyridyl, nitropyridyl, formylpyridyl, cyanopyridyl, carboxypyridyl, aminopyridyl, (dimethylamino)pyridyl, (aminomethyl)pyridyl, (2-aminoethyl)pyridyl, (N,N-dimethylaminomethyl)pyridyl, (t-butoxycarbonylamino)pyridyl or (benzyloxycarbonylamino)pyridyl group; preferably a pyridyl group which may have from 1 to 3 substituents β described later (for example, a methylpyridyl, (trifluoromethyl)pyridyl, hydroxypyridyl methoxypyridyl, (trifluoromethoxy)pyridyl, fluoropyridyl, chloropyridyl, nitropyridyl, formylpyridyl, cyanopyridyl, carboxypyridyl, aminopyridyl, dimethylaminopyridyl or (N,N-dimethylaminomethyl)pyridyl) group or an imidazolyl group (the nitrogen atom of the ring may be substituted with a straight or branched chain alkyl group having from 1 to 6 carbon atoms, particularly a N-methylimidazolyl group); more preferably a (trifluoromethyl)pyridyl, methoxypyridyl, fluoropyridyl, chloropyridyl, nitropyridyl, cyanopyridyl, aminopyridyl or dimethylaminopyridyl group.

In the case where the substituent α represents a mono- or dicyclic, 5- to 10-membered hetero aryloxy group containing from 1 to 4 hetero atoms selected from the group consisting of an oxygen atom, nitrogen atom and sulfur atom which may have from 1 to 3 substituents β described later, the hetero aryloxy group includes, for example, a furyloxy, thienyloxy, oxazolyloxy, isoxazolyloxy, thiazolyloxy, imidazolyloxy, quinolyloxy, isoquinolyloxy, indolyloxy or pyridyloxy group; preferably a pyridyloxy group which may have from 1 to 3 substituents β described later; particularly preferably a pyridyloxy group.

In the case where the substituent α represents a mono- or dicyclic, 5- to 10-membered hetero arylthio group containing from 1 to 4 hetero atoms selected from the group consisting of an oxygen atom, nitrogen atom and sulfur atom which may have from 1 to 3 substituents β described later, the hetero arylthio group includes, for example, a furylthio, thienylthio, oxazolylthio, isoxazolylthio, thiazolylthio, imidazolylthio, quinolylthio, isoquinolylthio, indolylthio or pyridylthio group; preferably a pyridylthio group which may have from 1 to 3 substituents β described later; particularly preferably a pyridylthiogroup.

In the case where the substituent α represents a mono- or dicyclic, 5- to 10-membered hetero arylsulfonyl group containing from 1 to 4 hetero atoms selected from the group consisting of an oxygen atom, nitrogen atom and sulfur atom which may have from 1 to 3 substituents β described later, the hetero arylsulfonyl group includes, for example, a furylsulfonyl, thienylsulfonyl, oxazolylsulfonyl, isoxazolylsulfonyl, thiazolylsulfonyl, imidazolylsulfonyl, quinolylsulfonyl, isoquinolylsulfonyl, indolylsulfonyl or pyridinesulfonyl group; preferably a pyridylsulfonyl group which may have from 1 to 3 substituents β described later; particularly preferably a pyridylsulfonyl group.

In the case where the substituent α represents a mono- or dicyclic, 5- to 10-membered hetero arylsulfonylamino group containing from 1 to 4 hetero atoms selected from the group consisting of an oxygen atom, nitrogen atom and sulfur atom which may have from 1 to 3 substituents β described later in the hetero aryl moiety (the nitrogen atom of the amino moiety may be substituted with a straight or branched chain alkyl group having from 1 to 6 carbon atoms), the hetero arylsulfonylamino group includes, for example, a furylsulfonylamino, thienylsulfonylamino, oxazolylsulfonylamino, isoxazolylsulfonylamino, thiazolylsulfonylamino, imidazolylsulfonylamino, N-methyl-imidazolylsulfonylamino, quinolylsulfonylamino, isoquinolylsulfonylamino, indolylsulfonylamino, pyridylsulfonylamino or N-methylpyridylsulfonylamino group; preferably a pyridylsulfonylamino group which may have from 1 to 3 substituents β described later on the pyridyl moiety (the nitrogen atom of the amino moiety may be substituted with a straight or branched chain alkyl group having from 1 to 6 carbon atoms); particularly preferably a pyridinesulfonylamino or N-methyl-pyridinesulfonylamino group.

In the case where the substituent α represents a mono- or dicyclic, 5- to 10-membered saturated heterocyclic group containing from 1 to 4 hetero atoms selected from the group consisting of an oxygen atom, nitrogen atom and sulfur atom, the saturated heterocyclic group includes, for example, a morpholinyl, thiomorpholinyl, pyrrolidinyl, pyrrolinyl, imidazolidinyl, imidazolinyl, pyrazolidinyl, pyrazolinyl, piperidyl or piperazinyl group; preferably a morpholinyl, thiomorpholinyl, pyrrolidinyl, piperidyl or piperazinyl group (particularly a piperidyl group).

In the case where the substituent β represents a straight or branched chain alkyl group having from 1 to 6 carbon atoms, a straight or branched chain alkoxy group having from 1 to 4 carbon atoms, a halogen atom, or a straight or branched chain dialkylamino group in which each alkyl group may be the same or different and each has from 1 to 4 carbon atoms, these groups may include the same groups as described above in the definition of $R^3$.

In the case where the substituent β represents a straight or branched chain halogenated alkyl group having from 1 to 4 carbon atoms, a straight or branched chain halogenated alkoxy group having from 1 to 4 carbon atoms, a straight or branched chain alkylenedioxy group having from 1 to 4 carbon atoms, a straight or branched chain aliphatic acyl group having from 1 to 5 carbon atoms, a straight or branched chain monoalkylamino group in which the alkyl moiety has from 1 to 4 carbon atoms, a straight or branched chain alkoxycarbonylamino group in which the alkoxy moiety has from 1 to 4 carbon atoms, or an aralkyloxycarbonylamino group in which the aralkyl moiety has from 7 to 12 carbon atoms, these groups may include the same groups as described above in the definition of α.

In the case where the substituent β represents a straight or branched chain hydroxyalkyl group having from 1 to 4 carbon atoms, the hydroxyalkyl group includes, for example, a hydroxymethyl, 2-hydroxyethyl, 3-hydroxypropyl or 4-hydroxybutyl group, preferably a hydroxymethyl group.

In the case where the substituent β represents a straight or branched chain aminoalkyl group having from 1 to 4 carbon atoms, the aminoalkyl group includes, for example, an aminomethyl, 2-aminoethyl, 3-aminopropyl or 4-aminobutyl group; preferably an aminomethyl or aminoethyl group; more preferably an aminomethyl group.

In the case where the substituent β represents a monoalkylaminoalkyl group in which the monoalkylamino moiety has one straight or branched chain alkyl group having from 1 to 4 carbon atoms and the alkyl moiety is a straight or branched chain alkyl having from 1 to 4 carbon atoms, the monoalkylaminoalkyl group includes, for example, a N-methylaminomethyl, N-ethylaminomethyl, N-methylaminoethyl, N-ethylaminoethyl, N-methylaminopropyl or N-methylaminobutyl group; preferably a N-methylaminomethyl or N-methylaminoethyl group.

In the case where the substituent β represents a dialkylaminoalkyl group in which the dialkylamino moiety has two straight or branched chain alkyl groups having from 1 to 4 carbon atoms which may be the same or different, and the alkyl moiety is a straight or branched chain alkyl group having from 1 to 4 carbon atoms, the dialkylaminoalkyl group includes, for example, a N,N-dimethylaminomethyl, N,N-diethylaminomethyl, N,N-dimethylaminoethyl, N,N-diethylaminoethyl, N,N-dimethylaminopropyl or N,N-dimethylaminobutyl group; preferably a N,N-dimethylaminomethyl or N,N-dimethylaminoethyl group; more preferably a N,N-dimethylaminomethyl group.

Therefore, in the case where X represents a substituted or unsubstituted aryl group having from 6 to 10 carbon atoms or a substituted or unsubstituted mono- or dicyclic, 5- to 10-membered hetero aryl group containing from 1 to 4 hetero atoms selected from the group consisting of an oxygen atom, nitrogen atom and sulfur atom, specific example of these groups preferably includes a phenyl, 1-naphthyl, 2-naphthyl, m-tolyl, p-tolyl, 3-ethylphenyl, 4-ethylphenyl, 3-isopropylphenyl, 4-isopropylphenyl, 3-t-butylphenyl, 4-t-butylphenyl, 4-chloromethylphenyl, 4-bromomethylphenyl, 4-fluoromethylphenyl, 4-iodomethylphenyl, 3-difluoromethylphenyl, 4-trifluoromethylphenyl, 4-pentafluoroethylphenyl, 4-trichloromethylphenyl, 3-hydroxyphenyl, 4-hydroxyphenyl, 3-acetoxyphenyl, 4-acetoxyphenyl, 5-acetoxy-2-hydroxy-3,4,6-trimethylphenyl, 3-methoxyphenyl, 4-methoxyphenyl, 3-ethoxyphenyl, 4-ethoxyphenyl, 3-isopropoxyphenyl, 4-isopropoxyphenyl, 3,4-methylenedioxyphenyl, benzyloxyphenyl, phenethyloxyphenyl, 1-naphthylmethoxyphenyl, 3-methylthiophenyl, 4-methylthiophenyl, 3-ethylthiophenyl, 4-ethylthiophenyl, 3-isopropylthiophenyl, 4-isopropylthiophenyl, 3-methanesulfonylphenyl, 4-methanesulfonylphenyl, 3-ethanesulfonylphenyl, 4-ethanesulfonylphenyl, 3-isopropanesulfonylphenyl, 4-isopropanesulfonylphenyl, 3-fluorophenyl, 4-fluorophenyl, 3-chlorophenyl, 4-chlorophenyl, 3-bromophenyl, 4-bromophenyl, 4-nitrophenyl, 4-aminophenyl, 3-methylaminophenyl, 4-ethylaminophenyl, 3-propylaminophenyl, 4-butylaminophenyl, 3-dimethylaminophenyl, 4-diethylaminophenyl, 3-dipropylaminophenyl, 4-dibutylaminophenyl, 3-benzylphenyl, 4-benzylphenyl, 3-phenethylphenyl, 4-(1-naphthylmethyl)phenyl, 3-biphenylyl, 4-biphenylyl, 3-(4-methylphenyl)phenyl, 4-(4-methylphenyl)phenyl, 3-(4-ethylphenyl)phenyl, 3-(4-trifluoromethylphenyl)phenyl, 4-(4-trifluoromethylphenyl)phenyl, 4-(2-hydroxyphenyl)phenyl, 4-(3-hydroxyphenyl)phenyl, 4-(4-hydroxyphenyl)phenyl, 4-(4-hydroxy-3,5-dimethylphenyl)phenyl, 3-(4-methoxyphenyl)phenyl, 4-(2-methoxyphenyl)phenyl, 4-(3-methoxyphenyl)phenyl, 4-(4-methoxyphenyl)phenyl, 3-(2,4-dimethoxyphenyl)phenyl, 4-(2,4-dimethoxyphenyl)phenyl, 3-(2,5-dimethoxyphenyl)phenyl, 4-(2,5-dimethoxyphenyl)phenyl, 4-(3-hydroxymethylphenyl)phenyl, 4-(4-hydroxymethylphenyl)phenyl, 4-(3-fluorophenyl)phenyl, 4-(4-fluorophenyl)phenyl 4-(3-chlorophenyl)phenyl, 4-(4-chlorophenyl)phenyl, 4-(3-bromophenyl)phenyl 4-(4-bromophenyl)phenyl, 3-(3,4-methylenedioxyphenyl)phenyl, 4-(3,4-methylenedioxyphenyl)phenyl, 4-(2-formylphenyl)phenyl, 4-(3-formylphenyl)phenyl, 4-(4-formylphenyl)phenyl, 4-(3-carboxyphenyl)phenyl, 4-(4-carboxyphenyl)phenyl, 4-(3-N,N-dimethylaminomethylphenyl)phenyl, 4-(4-N,N-dimethylaminomethylphenyl)phenyl, 3-benzylphenyl, 4-benzylphenyl, 3-phenoxyphenyl, 4-phenoxyphenyl, 3-phenylthiophenyl, 4-phenylthiophenyl, 3-phenylsulfonylphenyl, 4-phenylsulfonylphenyl, 3-(phenylsulfonylamino)phenyl, 4-(phenylsulfonylamino)phenyl, 3-(N-methylphenylsulfonylamino)phenyl, 4-(N-methylphenylsulfonylamino)phenyl, 3-(imidazol-1-yl)phenyl, 4-(imidazol-1-yl)phenyl, 3-(1-methylimidazol-4-yl)phenyl, 4-(1-methylimidazol-4-yl)phenyl, 3-(2-furyl)phenyl, 4-(2-furyl)phenyl, 3-(2-thienyl)phenyl, 4-(2-thienyl)phenyl, 3-(3-thienyl)phenyl, 4-(3-thienyl)phenyl, 3-(2-pyridyl)phenyl, 4-(2-pyridyl)phenyl, 4-(2-trifluoromethylpyridin-5-yl)phenyl, 4-(2-methoxypyridin-5-yl)phenyl, 4-(2-nitropyridin-5-yl)phenyl, 4-(2-N,N-dimethylaminopyridin-5-yl)phenyl, 3-(3-pyridyl)phenyl, 4-(3-pyridyl)phenyl, 3-(4-pyridyl)phenyl, 4-(4-pyridyl)phenyl, 4-(imidazol-1-ylthio)phenyl, 4-(2-furylthio)phenyl, 4-(2-thienylthio)phenyl, 4-(2-pyridylthio)phenyl, 4-(4-pyridylthio)phenyl, 3-(2-pyridylsulfonyl)phenyl, 4-(2-pyridylsulfonyl)phenyl, 3-(3-pyridylsulfonyl)phenyl, 4-(3-pyridylsulfonyl)phenyl, 3-(2-pyridylsulfonylamino)phenyl, 3-(N-methyl-2-pyridylsulfonylamino)phenyl, 4-(2-pyridylsulfonylamino)phenyl, 4-(N-methyl-2-pyridylsulfonylamino)phenyl, 3-(3-pyridylsulfonylamino) phenyl, 3-(N-methyl-3-pyridylsulfonylamino)phenyl, 4-(3-pyridylsulIfonylamino)phenyl, 4-(N-methyl-3-pyridylsulfonylamino)phenyl, 3-(oxazol-2-yl)phenyl, 4-(oxazol-2-yl)phenyl, 3-(oxazol-4-yl)phenyl, 4-(oxazol4-yl)phenyl, 3-(oxazol-5-yl)phenyl, 4-(oxazol-5-yl)phenyl, 3-(thiazol-2-yl)phenyl, 4-(thiazol-2-yl)phenyl, 3-(thiazol-4-yl)phenyl, 4-(thiazol-4-yl)phenyl, 3-(thiazol-5-yl)phenyl, 4-(thiazol-5-yl)phenyl, 4-(piperidin-1-yl)phenyl, 1-methyl-2-pyrrolyl, 1-phenyl-2-pyrrolyl, 1-benzyl-2-pyrrolyl, 5-methyl-2-furyl, 5-phenyl-2-furyl, 5-methyl-2-thienyl, 5-phenyl-2-thienyl, 5-methyl-3-thienyl, 5-phenyl-3-thienyl, 1-methyl-3-pyrazolyl, 1-phenyl-3-pyrazolyl, 3-imidazolyl, 1-methyl-2-imidazolyl, 1-phenyl-2-imidazolyl, 1-methyl-4-imidazolyl, 1-phenyl-4-imidazolyl, 1-methyl-2-phenyl-4-imidazolyl, 1,5-dimethyl-2-phenyl-4-imidazolyl, 1,4-dimethyl-2-phenyl-5-imidazolyl, 4-oxazolyl, 5-oxazolyl, 2-methyl-4-oxazolyl, 2-phenyl-4-oxazolyl, 2-methyl-5-oxazolyl, 2-phenyl-5-oxazolyl, 4-methyl-2-phenyl-5-oxazolyl, 5-methyl-2-phenyl-4-oxazolyl, 4-thiazolyl, 5-thiazolyl, 2-methyl-4-thiazolyl, 2-phenyl-4-thiazolyl, 2-methyl-5-thiazolyl, 2-phenyl-5-thiazolyl, 4-methyl-2-phenyl-5-thiazolyl, 5-methyl-2-phenyl-4-thiazolyl, 1-methyl-3-pyrazolyl, 1-phenyl-3-pyrazolyl, 3-methyl-5-isoxazolyl, 3-phenyl-5-isoxazolyl, 2-pyridyl, 3-pyridyl, 4-pyridyl, 3-methyl-5-pyridyl, 3-ethyl-5-pyridyl, 3-phenyl-5-pyridyl, 2-methyl-5-pyridyl, 2-ethyl-5-pyridyl, 2-phenyl-5-pyridyl, 2-(4-methoxyphenyl)-5-pyridyl, 2-(4-fluorophenyl)-5-pyridyl, 2-hydroxy-5-pyridyl, 2-methoxy-5-pyridyl, 2-ethoxy-5-pyridyl, 2-isopropoxy-5-pyridyl, 2-(2,2,3,3-tetrafluoropropoxyphenyl)-5-pyridyl, 2-benzyloxy-5-pyridyl, 2-methylthio-5-pyridyl, 2-ethylthio-5-pyridyl, 2-isopropylthio-5-pyridyl, 2-methanesulfonyl-5-pyridyl, 2-ethanesulfonyl-5-pyridyl, 2-isopropanesulfonyl-5-pyridyl, 2-benzyl-5-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methylphenylsulfonylamino)-5-pyridyl, 3-methyl-6-pyridyl, 3-phenyl-6-pyridyl, 2-methyl-6-pyridyl, 2-phenyl-6-pyridyl, 2-methyl-4-pyrimidinyl, 2-phenyl-4-pyrimidinyl, 2-methoxy-4-pyrimidinyl, 2-ethoxy-4-pyrimidinyl, 2-isopropoxy-4-pyrimidinyl, 2-methylthio-4-pyrimidinyl, 2-ethylthio-4-pyrimidinyl, 2-isopropylthio-4-pyrimidinyl, 2-phenylthio-4-pyrimidinyl, 2-methanesulfonyl-4-pyrimidinyl, 2-ethanesulfonyl-4-pyrimidinyl, 2-isopropylsulfonyl-4-pyrimidinyl, 2-phenylsulfonyl4-pyrimidinyl, 2-methyl-5-pyrimidinyl, 2-phenyl-5-pyrimidinyl, 2-methoxy-5-pyrimidinyl, 2-ethoxy-5-pyrimidinyl, 2-isopropoxy-5-pyrimidinyl, 2-methylthio-5-pyrimidinyl, 2-ethylthio-5-pyrimidinyl, 2-isopropylthio-5-pyrimidinyl, 2-phenylthio-5-pyrimidinyl, 2-methanesulfonyl-5-pyrimidinyl, 2-ethanesulfonyl-5-pyrimidinyl, 2-isopropylsulfonyl-5-pyrimidinyl, 2-phenylsulfonyl-5-pyrimidinyl, 2-indolyl, 3-indolyl, 1-methyl-2-indolyl, 1-methyl-3-indolyl, 2-benzimidazolyl, 1-methyl-2-benzimidazolyl, 2-benzoxazolyl, 2-benzothiazolyl, 2-quinolyl, 3-quinolyl, 4-quinolyl, 1-isoquinolyl, 3-isoquinolyl, 4-isoquinolyl or 8-isoquinolyl group;

preferably a phenyl, 1-naphthyl, 2-naphthyl, m-tolyl, p-tolyl, 3-ethylphenyl, 4-ethylphenyl, 3-isopropylphenyl, 4-isopropylphenyl, 4-trifluoromethylphenyl, 3-hydroxyphenyl, 4-hydroxyphenyl, 4-hydroxy-3,5-dimethylphenyl, 3-acetoxyphenyl, 4-acetoxyphenyl, 5-acetoxy-2-hydroxy-3,4,6-trimethylphenyl, 3-methoxyphenyl, 4-methoxyphenyl, 3-ethoxyphenyl, 4-ethoxyphenyl, 3-isopropoxyphenyl, 4-isopropoxyphenyl, 3,4-methylenedioxyphenyl, benzyloxyphenyl, 3-methylthiophenyl, 4-methylthiophenyl, 3-ethylthiophenyl, 4-ethylthiophenyl, 3-methanesulfonylphenyl, 4-methanesulfonylphenyl, 3-ethanesulfonylphenyl, 4-ethanesulfonylphenyl, 3-fluorophenyl, 4-fluorophenyl, 3-chlorophenyl, 4-chlorophenyl, 4-diethylaminophenyl, 3-benzylphenyl, 4-benzylphenyl, 3-biphenylyl, 4-biphenylyl, 3-(4-methylphenyl)phenyl, 4-(4-methylphenyl)phenyl, 3-(4-ethylphenyl)phenyl, 3-(4-trifluoromethylphenyl)phenyl, 4-(4-trifluoromethylphenyl)phenyl, 4-(2-hydroxyphenyl)phenyl, 4-(3-hydroxyphenyl)phenyl, 4-(4-hydroxyphenyl)phenyl, 4-(4-hydroxy-3,5-dimethylphenyl)phenyl, 3-(4-methoxyphenyl)phenyl, 4-(2-methoxyphenyl)phenyl, 4-(3-methoxyphenyl)phenyl, 4-(4-methoxyphenyl)phenyl, 3-(2,4-dimethoxyphenyl)phenyl, 4-(2,4-dimethoxyphenyl)

phenyl, 3-(2,5-dimethoxyphenyl)phenyl, 4-(2,5-dimethoxyphenyl)phenyl, 4-(3-hydroxymethylphenyl)phenyl, 4-(4-hydroxymethylphenyl)phenyl, 4-(3-fluorophenyl)phenyl, 4-(4-fluorophenyl)phenyl, 4-(3-chlorophenyl)phenyl, 4-(4-chlorophenyl)phenyl, 3-(3,4-methylenedioxyphenyl)phenyl, 4-(3,4-methylenedioxyphenyl)phenyl, 2-formylphenyl, 3-formylphenyl, 4-formylphenyl, 3-carboxyphenyl, 4-carboxyl, 3-N,N-dimethylaminomethylphenyl, 4-N,N-dimethylaminomethylphenyl, 3-phenoxyphenyl, 4-phenoxyphenyl, 3-phenylthiophenyl, 4-phenylthiophenyl, 3-phenylsulfonylphenyl, 4-phenylsulfonylphenyl, 3-(phenylsulfonylamino)phenyl, 4-(phenylsulfonylamino)phenyl, 3-(N-methylphenylsulfonylamino)phenyl, 4-(N-methylphenylsulfonylamino)phenyl, 3-(2-pyridyl)phenyl, 4-(2-pyridyl)phenyl, 4-(2-trifluoromethylpyridin-5-yl)phenyl, 4-(2-methoxypyridin-5-yl)phenyl, 4-(2-nitropyridin-5-yl)phenyl, 4-(2-N,N-dimethylaminopyridin-5-yl)phenyl, 3-(3-pyridyl)phenyl, 4-(3-pyridyl)phenyl, 3-(4-pyridyl)phenyl, 4-(4-pyridyl)phenyl, 4-(2-pyridyloxy)phenyl, 4-(4-pyridyloxy)phenyl, 4-(2-pyridylthio)phenyl, 4-(4-pyridylthio)phenyl, 3-(2-pyridylsulfonyl)phenyl, 4-(2-pyridylsulfonyl)phenyl, 3-(3-pyridylsulfonyl)phenyl, 4-(3-pyridylsulfonyl)phenyl, 3-(2-pyridylsulfonylamino)phenyl, 3-(N-methyl-2-pyridylsulfonylamino)phenyl, 4-(2-pyridylsulfonylamino)phenyl, 4-(N-methyl-2-pyridylsulfonylamino)phenyl 3-(3-pyridylsulfonylamino)phenyl, 3-(N-methyl-3-pyridylsulfonylamino)phenyl, 4-(3-pyridylsulfonylamino)phenyl, 4-(N-methyl-3-pyridylsulfonylamino)phenyl 4-(1-piperidinyl)phenyl, 3-imidazolyl, 2-pyridyl, 3-pyridyl, 4-pyridyl, 3-methyl-5-pyridyl, 3-ethyl-5-pyridyl, 3-phenyl-5-pyridyl, 2-methyl-5-pyridyl, 2-ethyl-5-pyridyl 2-phenyl-5-pyridyl, 2-hydroxy-5-pyridyl, 2-methoxy-5-pyridyl, 2-ethoxy-5-pyridyl, 2-isopropoxy-5-pyridyl, 2-(2,2,3,3-tetrafluoropropoxy)-5-pyridyl, 2-benzyloxy-5-pyridyl, 2-methylthio-5-pyridyl, 2-ethylthio-5-pyridyl, 2-isopropylthio-5-pyridyl, 2-methanesulfonyl-5-pyridyl, 2-ethanesulfonyl-5-pyridyl, 2-isopropanesulfonyl-5-pyridyl, 2-benzyl-5-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methyl-phenylsulfonylamino)-5-pyridyl, 2-(4-methoxyphenyl)-5-pyridyl, 2-(4-fluorophenyl)-5-pyridyl, 3-methyl-6-pyridyl, 3-phenyl-6-pyridyl, 2-methyl-6-pyridyl, 2-phenyl-6-pyridyl, 2-quinolyl, 3-quinolyl, 4-quinolyl, 1-isoquinolyl, 3-isoquinolyl, 4-isoquinolyl or 8-isoquinolyl group;

more preferably a phenyl, m-tolyl, p-tolyl, 3-hydroxyphenyl, 4-hydroxyphenyl, 4-hydroxy-3,5-dimethylphenyl, 3-acetoxyphenyl, 4-acetoxyphenyl, 5-acetoxy-2-hydroxy-3,4,6-trimethylphenyl, 3-chlorophenyl, 4-chlorophenyl, 3-benzylphenyl, 4-benzylphenyl, 3-biphenylyl, 4-biphenylyl, 4-(4-trifluoromethylphenyl)phenyl, 4-(2-hydroxyphenyl)phenyl, 4-(3-hydroxyphenyl)phenyl, 4-(4-hydroxyphenyl)phenyl, 4-(2-methoxyphenyl)phenyl, 4-(3-methoxyphenyl)phenyl, 4-(4-methoxyphenyl)phenyl, 4-(4-hydroxy-3,5-dimethylphenyl)phenyl, 4-(4-fluorophenyl)phenyl, 4-(4-chlorophenyl)phenyl, 4-(2-formylphenyl)phenyl, 4-(3-formylphenyl)phenyl, 4-(4-formylphenyl)phenyl, 4-(3-carboxyphenyl)phenyl, 4-(4-carboxyphenyl)phenyl, 4-(3-hydroxymethylphenyl)phenyl, 4-(4-hydroxymethylphenyl)phenyl, 4-(3-N,N-dimethylaminomethylphenyl)phenyl, 4-(4-N,N-dimethylaminomethylphenyl)phenyl, 3-phenoxyphenyl, 4-phenoxyphenyl, 3-phenylthiophenyl, 4-phenylthiophenyl, 3-phenylsulfonylphenyl, 4-phenylsulfonylphenyl, 3-(phenylsulfonylamino)phenyl, 4-(phenylsulfonylamino)phenyl, 3-(N-methylphenylsulfonylamino)phenyl, 4-(N-methylphenylsulfonylamino)phenyl, 3-(2-pyridyl)phenyl, 4-(2-pyridyl)phenyl, 4-(3-trifluoromethylpyridin-6-yl)phenyl, 4-(3-methoxypyridin-6-yl)phenyl, 4-(3-nitropyridin-6-yl)phenyl, 4-(3-N,N-dimethylaminopyridin-6-yl)phenyl, 3-(3-pyridyl)phenyl, 4-(3-pyridyl)phenyl, 3-(4-pyridyl)phenyl, 4-(4-pyridyl)phenyl, 4-(2-pyridyloxy)phenyl, 4-(4-pyridyloxy)phenyl, 4-(2-pyridylthio)phenyl, 4-(4-pyridylthio)phenyl, 3-(2-pyridylsulfonyl)phenyl, 4-(2-pyridylsulfonyl)phenyl, 3-(3-pyridylsulfonyl)phenyl, 4-(3-pyridylsulfonyl)phenyl, 3-(2-pyridylsulfonylamino)phenyl, 2-pyridyl, 3-pyridyl, 4-pyridyl, 2-methoxy-5-pyridyl, 2-ethoxy-5-pyridyl, 2-isopropoxy-5-pyridyl, 2-(2,2,3,3-tetrafluoropropoxy)-5-pyridyl, 2-benzyloxy-5-pyridyl, 2-methylthio-5-pyridyl, 2-ethylthio-5-pyridyl, 2-methanesulfonyl-5-pyridyl, 2-ethanesulfonyl-5-pyridyl, 2-benzyl-5-pyridyl, 2-phenyl-5-pyridyl, 2-(4-methoxyphenyl)-5-pyridyl, 2-(4-fluorophenyl)-5-pyridyl, 3-phenyl-5-pyridyl, 2-phenyl-6-pyridyl, 3-phenyl-6-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methylphenylsulfonylamino)-5-pyridyl, 2-methyl-5-pyridyl, 3-quinolyl, 3-methyl-5-pyridyl, 3-quinolyl or 3-indolyl group;

most preferably a phenyl, p-tolyl, 4-fluorophenyl, 4-benzylphenyl, 4-biphenylyl, 4-(4-trifluoromethylphenyl)phenyl, 4-(2-hydroxyphenyl)phenyl, 4-(3-hydroxyphenyl)phenyl, 4-(4-hydroxyphenyl)phenyl, 4-(2-methoxyphenyl)phenyl, 4-(3-methoxyphenyl)phenyl, 4-(4-methoxyphenyl)phenyl, 4-(4-hydroxy-3,5-dimethylphenyl)phenyl, 4-(4-fluorophenyl)phenyl, 4-(4-chlorophenyl)phenyl, 4-(2-formylphenyl)phenyl, 4-(3-formylphenyl)phenyl, 4-(4-formylphenyl)phenyl, 4-(3-carboxyphenyl)phenyl, 4-(4-carboxyphenyl)phenyl, 4-(3-hydroxymethylphenyl)phenyl, 4-(4-hydroxymethylphenyl)phenyl, 4-(3-N,N-dimethylaminomethylphenyl)phenyl, 4-(4-N,N-dimethylaminomethylphenyl)phenyl, 4-phenoxyphenyl, 4-phenylthiophenyl, 4-phenylsulfonylphenyl, 4-(phenylsulfonylamino)phenyl, 4-(2-pyridyl)phenyl, 4-(3-trifluoromethylpyridin-6-yl)phenyl, 4-(3-methoxypyridin-6-yl)phenyl, 4-(3-nitropyridin-6-yl)phenyl, 4-(3-N,N-dimethylaminopyridin-6-yl)phenyl, 4-(3-pyridyl)phenyl, 4-(4-pyridyl)phenyl, 2-pyridyl, 3-pyridyl, 4-pyridyl, 2-methoxy-5-pyridyl, 2-ethoxy-5-pyridyl, 2-isopropoxy-5-pyridyl, 2-(2,2,3,3-tetrafluoropropoxy)-5-pyridyl, 2-benzyloxy-5-pyridyl, 2-methylthio-5-pyridyl, 2-ethylthio-5-pyridyl, 2-methanesulfonyl-5-pyridyl, 2-ethanesulfonyl-5-pyridyl, 2-benzyl-5-pyridyl, 2-phenyl-5-pyridyl, 3-phenyl-5-pyridyl, 3-phenyl-6-pyridyl, 2-(4-methoxyphenyl)-5-pyridyl, 2-(4-fluorophenyl)-5-pyridyl, 2-phenyl-6-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methylphenylsulfonylamino)-5-pyridyl, 2-methyl-5-pyridyl or 3-methyl-5-pyridyl group.

In the case where Y represents a group of the formula: >N—$R^5$ (wherein $R^5$ represents a hydrogen atom, a straight or branched chain alkyl group having from 1 to 6 carbon atoms (the alkyl group has the same meaning as described above in the definition of $R^3$) or a straight or branched chain aliphatic acyl group having from 1 to 8 carbon atoms (the aliphatic acyl group includes, for example, an alkanoyl group having from 1 to 8 carbon atoms and an alkenoyl group having from 3 to 8 carbon atoms) or an aromatic acyl group having from 7 to 11 carbon atoms), the group of the formula: >N—$R^5$ includes, for example, an imino, methylimino, ethylimino, propylimino, isopropylimino, butylimino, isobutylimino, s-butylimino, t-butylimino, pentylimino, 1-methylbutylimino, 2-methylbutylimino, 3-methylbutylimino, 1,1-dimethylpropylimino, 1,2-dimethylpropylimino, 2,2-dimethylpropylimino, 1-ethylpropylimino, hexylimino, 1-methylpentylimino, 2-methylpentylimino, 3-methylpentylimino, 4-methylpentylimino, 1,1-dimethylbutylimino, 1,2-dimethylbutylimino, 1,3-dimethylbutylimino, 2,2-dimethylbutylimino, 2,3-dimethylbutylimino, 3,3-dimethylbutylimino, 1-ethylbutylimino, 1,1,2-trimethylpropylimino, 1,2,2-trimethylpropylimino, acetylimino, propionylimino, butyrylimino, pentanoylimino, hexanoylimino, heptanoylimino, octanoylimino, benzoylimino or p-toluoylimino group;

preferably an imino group, a straight or branched chain alkylimino group having from 1 to 4 carbon atoms or an acetylimino group;

most preferably an imino, methylimino, ethylimino or acetylimino group.

The amidocarboxylic acid derivatives of the formula (I) of the present invention can be converted to an acid addition salt according to a conventional method in the case where it has a basic group. Such salts include salts of hydrohalogenic acids such as hydrofluoric acid, hydrochloric acid, hydrobromic acid and hydroiodic acid; inorganic acid salts such as a nitrate, perchlorate, sulfate and phosphate; salts of lower alkanesulfonic acids such as methanesulfonic acid, trifluoromethanesulfonic acid and ethanesulfonic acid; salts of arylsulfonic acid such as benzenesulfonic acid and p-toluenesulfonic acid; salts of amino acids such as glutamic acid and aspartic acid; and salts of carboxylic acids such as acetic acid, fumaric acid, tartaric acid, oxalic acid, maleic acid, malic acid, succinic acid, benzoic acid, mandelic acid, ascorbic acid, lactic acid, gluconic acid and citric acid; preferably salts of hydrohalogenic acids.

Further, the amidocarboxylic acid derivatives of the formula (I) can be converted to a metal salt according to a conventional method since it has a carboxyl group. Such salts include alkali metal salts such as lithium, sodium and potassium; alkaline earth metal salts such as calcium, barium and magnesium; and aluminum salts, preferably alkali metal salts.

The amidocarboxylic acid derivatives of the formula (I) of the present invention can be converted to a pharmacologically acceptable ester according to a conventional method. The pharmacologically acceptable ester of the amidocarboxylic acid derivative of the formula (I) is not particularly limited so long as it can be medically used and pharmacologically accepted in comparison with the amidocarboxylic acid of the formula (I).

The esters of the amidocarboxylic acid derivatives of the formula (I) of the present invention includes a straight or branched chain alkyl group having from 1 to 6 carbon atoms; an aralkyl group having from 7 to 19 carbon atoms; a straight or branched chain alkyl group having from 1 to 5 carbon atoms which is substituted by a straight or branched chain alkanoyloxy group having from 1 to 6 carbon atoms; a straight or branched chain alkyl group having from 1 to 5 carbon atoms which is substituted by a straight or branched chain alkyloxycarbonyloxy group having from 1 to 6 carbon atoms; a straight or branched chain alkyl group having from 1 to 5 carbon atoms which is substituted by a cycloalkylcarbonyloxy group having from 5 to 7 carbon atoms; a straight or branched chain alkyl group having from 1 to 5 carbon atoms which is substituted by a cycloalkyloxycarbonyloxy group having from 5 to 7 carbon atoms; a straight or branched chain alkyl group having from 1 to 5 carbon atoms which is substituted by an arylcarbonyloxy group having from 6 to 10 carbon atoms; a straight or branched chain alkyl group having from 1 to 5 carbon atoms which is substituted by an aryloxycarbonyloxy group having from 6 to 10 carbon atoms; or a 2-oxo-1,3-dioxolen-4-ylmethyl group having a straight or branched chain alkyl group having from 1 to 6 carbon atoms as a substituent at the 5-position.

The straight or branched chain alkyl group having from 1 to 4 carbon atoms and the straight or branched chain alkyl group having from 1 to 6 carbon atoms include a methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl or 1,2,2-trimethylpropyl group; preferably a straight or branched chain alkyl group having from 1 to 4 carbon atoms; more preferably a methyl, ethyl, propyl, isopropyl, butyl or isobutyl group; most preferably a methyl or ethyl group.

The aralkyl group having from 7 to 19 carbon atoms includes a benzyl, phenethyl, 3-phenylpropyl, 4-phenylbutyl, 1-naphthylmethyl, 2-naphthylmethyl or diphenylmethyl group; preferably a benzyl group.

The cycloalkyl group having from 5 to 7 carbon atoms includes a cyclopentyl, cyclohexyl or cycloheptyl group; preferably a cyclohexyl group.

The aryl group having from 6 to 10 carbon atoms includes a phenyl or naphthyl group; preferably the phenyl group.

The specific example of the preferable ester residue a includes a methyl, ethyl, propyl, isopropyl, butyl, isobutyl, t-butyl, benzyl, acetoxymethyl, 1-(acetoxy)ethyl, propionyloxymethyl, 1-(propionyloxy)ethyl, butyryloxymethyl, 1-(butyryloxy)ethyl, isobutyryloxymethyl, 1-(isobutyryloxy)ethyl, valeryloxymethyl, 1-(valeryloxy)ethyl, isovaleryloxymethyl, 1-(isovaleryloxy)ethyl, pivaloyloxymethyl, 1-(pivaloyloxy)ethyl, methoxycarbonyloxymethyl, 1-(methoxycarbonyloxy)ethyl, ethoxycarbonyloxymethyl, 1-(ethoxycarbonyloxy)ethyl, propoxycarbonyloxymethyl, 1-(propoxycarbonyloxy)ethyl, isopropoxycarbonyloxymethyl, 1-(isopropoxycarbonyloxy)ethyl, butoxycarbonyloxymethyl, 1-(butoxycarbonyloxy)ethyl, isobutoxycarbonyloxymethyl, 1-(isobutoxycarbonyloxy)ethyl, t-butoxycarbonyloxymethyl, 1-(t-butoxycarbonyloxy)ethyl, cyclopentanecarbonyloxymethyl, 1-(cyclopentanecarbonyloxy)ethyl, cyclohexanecarbonyloxymethyl, 1-(cyclohexanecarbonyloxy)ethyl, cyclopentyloxycarbonyloxymethyl, 1-(cyclopentyloxycarbonyloxy)ethyl, cyclohexyloxycarbonyloxymethyl, 1-(cyclohexyloxycarbonyloxy)ethyl, benzoyloxymethyl, 1-(benzoyloxy)ethyl, phenoxycarbonyloxymethyl, 1-(phenoxycarbonyloxy)ethyl or 5-methyl-2-oxo-1,3-dioxolen4-ylmethyl group.

Incidentally, the amidocarboxylic acid derivatives of the formula (I), the pharmacologically acceptable salts thereof or the pharmacologically acceptable esters thereof have various isomers. For example, an optical isomer derived from an asymmetric carbon at the α-position of the carboxylic acid exists. In the formula (I), all of the stereoisomers based on these asymmetric carbon atoms and the equivalent and non-equivalent mixtures of these isomers are shown by a single formula. Therefore, the present invention includes all of these isomers and a mixture of these isomers.

Moreover, in the present invention, in the case where the amidocarboxylic acid derivative of the formula (I), the pharmacologically acceptable salts thereof and the pharmacologically acceptable esters thereof form solvates (for example, hydrates), the present invention includes all of these solvates.

Further, the present invention includes all compounds which are metabolized in living bodies and are converted to the amidocarboxylic acid derivatives of the formula (I) or a salt thereof, for example, so-called prodrugs such as amide derivatives.

The amidocarboxylic acid derivatives of the formula (I) preferably include:

(1) amidocarboxylic acid derivatives in which $R^1$ is a hydrogen atom, a straight or branched chain alkyl group having from 1 to 4 carbon atoms or an aralkyl group having from 7 to 9 carbon atoms, pharmacologically acceptable salts thereof or pharmacologically acceptable esters thereof;

(2) amidocarboxylic acid derivatives in which $R^1$ is a hydrogen atom or a straight or branched chain alkyl group having from 1 to 4 carbon atoms, pharmacologically acceptable salts thereof or pharmacologically acceptable esters thereof;

(3) amidocarboxylic acid derivatives in which $R^1$ is a hydrogen atom or an alkyl group having one or two carbon atoms, pharmacologically acceptable salts thereof or pharmacologically acceptable esters thereof;

(4) amidocarboxylic acid derivatives in which $R^1$ is a hydrogen atom, pharmacologically acceptable salts thereof or pharmacologically acceptable esters thereof;

(5) amidocarboxylic acid derivatives in which $R^2$ is a straight or branched chain alkylene group having from 2 to 5 carbon atoms, pharmacologically acceptable salts thereof or pharmacologically acceptable esters thereof.

(6) amidocarboxylic acid derivatives in which $R^2$ is a straight or branched chain alkylene group having from 2 to 4 carbon atoms, pharmacologically acceptable salts thereof or pharmacologically acceptable esters thereof;

(7) amidocarboxylic acid derivatives in which $R^2$ is an ethylene group a trimethylene group or a methylethylene group, pharmacologically acceptable salts thereof or pharmacologically acceptable esters thereof;

(8) amidocarboxylic acid derivatives in which $R^2$ is an ethylene group, pharmacologically acceptable salts thereof or pharmacologically acceptable esters thereof;

(9) amidocarboxylic acid derivatives in which $R^3$ is a hydrogen atom, a straight or branched chain alkyl group having from 1 to 4 carbon atoms, an alkoxy group having one or two carbon atoms, an alkylthio group having one or two carbon atoms, a halogen atom, a nitro group, a hydroxyl group or a straight or branched chain aliphatic acyl group having from 1 to 5 carbon atoms, pharmacologically acceptable salts thereof or pharmacologically acceptable esters thereof;

(10) amidocarboxylic acid derivatives in which $R^3$ is a hydrogen atom, a halogen atom or a nitro group, pharmacologically acceptable salts thereof or pharmacologically acceptable esters thereof;

(11) amidocarboxylic acid derivatives in which $R^3$ is a hydrogen atom, pharmacologically acceptable salts thereof or pharmacologically acceptable esters thereof;

(12) amidocarboxylic acid derivatives in which $R^4$ is a hydrogen atom or a straight or branched chain alkyl group having from 1 to 4 carbon atoms, pharmacologically acceptable salts thereof or pharmacologically acceptable esters thereof;

(13) amidocarboxylic acid derivatives in which $R^4$ is a hydrogen atom or an alkyl group having one or two carbon atoms, pharmacologically acceptable salts thereof or pharmacologically acceptable esters thereof;

(14) amidocarboxylic acid derivatives in which $R^4$ is a hydrogen atom or a methyl group, pharmacologically acceptable salts thereof or pharmacologically acceptable esters thereof;

(15) amidocarboxylic acid derivatives in which $R^4$ is a hydrogen atom, pharmacologically acceptable salts thereof or pharmacologically acceptable esters thereof;

(16) amidocarboxylic acid derivatives in which $R^4$ is a methyl group, pharmacologically acceptable salts thereof or pharmacologically acceptable esters thereof;

(17) amidocarboxylic acid derivatives in which Z is a straight or branched chain alkylene group having from 1 to 4 carbon atoms, pharmacologically acceptable salts thereof or pharmacologically acceptable esters thereof;

(18) amidocarboxylic acid derivatives in which Z is an alkylene group having one or two carbon atoms, pharmacologically acceptable salts thereof or pharmacologically acceptable esters thereof;

(19) amidocarboxylic acid derivatives in which Z is a methylene group, pharmacologically acceptable salts thereof or pharmacologically acceptable esters thereof;

(20) amidocarboxylic acid derivatives in which W represents (i) a straight or branched chain alkyl group having from 1 to 6 carbon atoms, (ii) a hydroxyl group, (iii) a straight or branched chain alkoxy group having from 1 to 4 carbon atoms, (iv) a straight or branched chain alkylthio group having from 1 to 4 carbon atoms, (v) an aryl group having from 6 to 10 carbon atoms which may have from 1 to 3 substituents $\alpha^1$ described later, (vi) an aryloxy group having from 6 to 10 carbon atoms which may have from 1 to 3 substituents al described later on the aryl moiety, (vii) an arylthio group having from 6 to 10 carbon atoms which may have from 1 to 3 substituents $\alpha^1$ described later on the aryl moiety, (viii) an aralkyl group having from 7 to 12 carbon atoms which may have from-1 to 3 substituents $\alpha^1$ described later on the aryl moiety, (ix) an aralkyloxy group having from 7 to 12 carbon atoms which may have from 1 to 3 substituents $\alpha^1$ described later on the aryl moiety, (x) an aralkylthio group having from 7 to 12 carbon atoms which may have from 1 to 3 substituents $\alpha^1$ described later on the aryl moiety, (xi) an aryloxyalkyl group in which the aryl moiety is an aryl group having from 6 to 10 carbon atoms which may have from 1 to 3 substituents $\alpha^1$ described later and the alkyl moiety is a straight or branched chain alkyl group having from 1 to 4 carbon atoms, (xii) a mono- or dicyclic, 5- to 10-membered hetero aryl group containing from 1 to 4 hetero atoms selected from the group consisting of an oxygen atom, nitrogen atom and sulfur atom, (xiii) a mono- or dicyclic, 5- to 10-membered hetero aryloxy group containing from 1 to 4 hetero atoms selected from the group consisting of an oxygen atom, nitrogen atom and sulfur atom, (xiv) a mono- or dicyclic, 5- to 10-membered hetero arylthio group containing from 1 to 4 hetero atoms selected from the group consisting of an oxygen atom, nitrogen atom and sulfur atom or (xv) a mono- or dicyclic, 5- to 10-membered saturated heterocyclic group containing from 1 to 4 hetero atoms selected from the group consisting of an oxygen atom, nitrogen atom and sulfur atom, here, the substituent $\alpha^1$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain aliphatic acyl groups having from 1 to 5 carbon atoms, (vi) straight or branched chain alkoxy groups having from 1 to 4 carbon atoms, (vii) straight or branched chain halogenated alkoxy groups having from 1 to 4 carbon atoms, (viii) straight or branched chain alkylenedioxy groups having from 1 to 4 carbon atoms, (ix) aralkyloxy groups having from 7 to 12 carbon atoms which may have from 1 to 3 substituents $\beta^1$ described later, (x) straight or branched chain alkylthio groups having from 1 to 4 carbon atoms, (xi) straight or branched chain alkylsulfonyl groups having from 1 to 4 carbon atoms, (xii) halogen atoms, (xiii) nitro groups, (xiv) cyano groups, (xv) amino groups, (xvi) straight or branched chain monoalkylamino groups in which the alkyl moiety has from 1 to 4 carbon atoms, (xvii) straight or branched chain alkoxycarbonylamino groups in which the alkoxy moiety has from 1 to 4 carbon atoms, (xviii) aralkyloxycarbonylamino groups in which the aralkyl moiety has from 7 to 12 carbon atoms, (xix) straight or branched chain dialkylamino groups in which each alkyl group may be the same or different and each has from 1 to 4 carbon atoms, (xx) aralkyl groups having from 7 to 12 carbon atoms which may have from 1 to 3 substituents $\beta^1$ described later on the aryl moiety, (xxi) aryl groups having from 6 to 10 carbon atoms which may have from 1 to 3 substituents $\beta^1$, which may be the same or different, described later, (xxii) aryloxy groups having from 6 to 10 carbon atoms which may have from 1 to 3 substituents $\beta^1$ described later on the aryl moiety, (xxiii) arylthio groups having from 6 to 10 carbon atoms which may have from 1 to 3 substituents $\beta^1$ described later on the aryl moiety, (xxiv) arylsulfonyl groups having from 6 to 10 carbon atoms which may have from 1 to 3 substituents $\beta^1$ described later on the aryl moiety, (xxv) arylsulfonylamino groups having from 6 to 10 carbon atoms which may have from 1 to 3 substituents $\beta^1$ described later on the aryl moiety (the nitrogen atom of the amino moiety may be substituted with a straight or branched chain alkyl group having from 1 to 6 carbon atoms), (xxvi) mono- or dicyclic, 5- to 10-membered hetero aryl groups containing from 1 to 4 hetero atoms selected from the group consisting of an oxygen atom, nitrogen atom and sulfur atom which may have from 1 to 3 substituents $\beta^1$ described later, (xxvii) mono- or dicyclic, 5- to 10-membered hetero aryloxy groups containing from 1 to 4 hetero atoms selected from the group consisting of an oxygen atom, nitrogen atom and sulfur atom which may have from 1 to 3 substituents $\beta^1$ described later, (xxviii) mono- or dicyclic, 5- to 10-membered hetero arylthio groups containing from 1 to 4 hetero atoms selected from the group consisting of an oxygen atom, nitrogen atom and sulfur atom which may have from 1 to 3 substituents $\beta^1$ described later, (xxix) mono- or dicyclic, 5- to 10-membered hetero arylsulfonyl groups containing from 1 to 4 hetero atoms selected from the group consisting of an oxygen atom, nitrogen atom and sulfur atom which may have from 1 to 3 substituents $\beta^1$ described later, (xxx) mono- or dicyclic, 5- to 10-membered hetero arylsulfonylamino groups containing from 1 to 4 hetero atoms selected from the group consisting of an oxygen atom, nitrogen atom and sulfur atom which may have from 1 to 3 substituents $\beta^1$ described later on the hetero aryl moiety (the nitrogen atom of the amino moiety may be substituted with a straight or branched chain alkyl having from 1 to 6 carbon atoms) and (xxxi) mono- or dicyclic, 5- to 10-membered saturated heterocyclic groups containing from 1 to 4 hetero atoms selected from the group consisting of an oxygen atom, nitrogen atom and sulfur atom, here, the substituent $\beta^1$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from 1 to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) halogen atoms, (ix) nitro groups, (x) formyl groups, (xi) cyano groups, (xii) carboxyl groups, (xiii) amino groups, (xiv) straight or branched chain monoalkylamino groups in which the alkyl moiety has from 1 to 4 carbon atoms, (xv) straight or branched chain dialkylamino groups in which each alkyl moiety may be the same or different and each has from 1 to 4 carbon atoms, (xvi) straight or branched chain aminoalkyl groups having from 1 to 4 carbon atoms, (xvii) monoalkylaminoalkyl groups in which the monoalkylamino moiety has one straight or branched chain alkyl group having from 1 to 4 carbon atoms and the alkyl moiety is a straight or branched chain alkyl group having from 1 to 4 carbon atoms, (xviii) dialkylaminoalkyl groups in which the dialkylamino moiety has two straight or branched chain alkyl groups having from 1 to 4 carbon atoms which may be the same or different and the alkyl moiety is a straight or branched chain alkyl group having from 1 to 4 carbon atoms, (xix) straight or branched chain alkoxycarbonylamino groups in which the alkoxy moiety has from 1 to 4 carbon atoms or (xx) aralkyloxycarbonylamino groups in which the aryl moiety has from 6 to 10 carbon atoms and the alkyl moiety has from 1 to 4 carbon atoms, pharmacologically acceptable salts thereof and pharmacologically acceptable esters thereof;

(21) amidocarboxylic acid derivatives in which W represents (i) a straight or branched chain alkyl group having from 1 to 6 carbon atoms, (ii) a hydroxyl group, (iii) a straight or branched chain alkoxy group having from 1 to 4 carbon atoms, (iv) a straight or branched chain alkylthio group having from 1 to 4 carbon atoms, (v) an aryl group having from 6 to 10 carbon atoms which may have from 1 to 3 substituents $\alpha^2$ described later, (vi) an aryloxy group having from 6 to 10 carbon atoms which may have from 1 to 3 substituents $\alpha^2$ described later on the aryl moiety, (vii) an arylthio group having from 6 to 10 carbon atoms which may have from 1 to 3 substituents $\alpha^2$ described later on the aryl moiety, (viii) an aralkyl group having from 7 to 12 carbon atoms which may have from 1 to 3 substituents $\alpha^2$ described later on the aryl moiety, (ix) an aralkyloxy group having from 7 to 12 carbon atoms which may have from 1 to 3 substituents $\alpha^2$ described later on the aryl moiety, (x) an aralkylthio group having from 7 to 12 carbon atoms which may have from 1 to 3 substituents $\alpha^2$ described later on the aryl moiety, (xi) an aryloxyalkyl group in which the aryl moiety is an aryl group having from 6 to 10 carbon atoms which may have from 1 to 3 substituents $\alpha^2$ described later and the alkyl moiety is a straight or branched chain alkyl group having from 1 to 4 carbon atoms, (xii) a mono- or dicyclic, 5- to 10-membered hetero aryloxy group containing from 1 to 4 hetero atoms selected from the group consisting of an oxygen atom, nitrogen atom and sulfur atom or (xiii) a mono- or dicyclic, 5- to 10-membered hetero arylthio group containing from 1 to 4 hetero atoms selected from the group consisting of an oxygen atom, nitrogen atom and sulfur atom, here, the substituent $\alpha^2$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain alkoxy groups having from 1 to 4 carbon atoms, (vi) straight or branched chain halogenated alkoxy groups having from 1 to 4 carbon atoms, (vii) straight or branched chain alkylthio groups having from 1 to 4 carbon atoms, (viii) straight or branched chain alkylsulfonyl groups having from 1 to 4 carbon atoms, (ix) halogen atoms, (x) nitro groups, (xi) cyano groups, (xii) straight or branched chain dialkylamino groups in which each alkyl group may be the same or different and each has from 1 to 4 carbon atoms, (xiii) aryl groups having from 6 to 10 carbon atoms which may be the same or different and have from 1 to 3 substituents $\beta^2$ described later, (xiv) aryloxy groups having from 6 to 10 carbon atoms which may have from 1 to 3 substituents $\beta^2$ described later on the aryl moiety, (xv) arylthio groups having from 6 to 10 carbon atoms which may have from 1 to 3 substituents $\beta^2$ described later on the aryl moiety, (xvi) mono- or dicyclic, 5- to 10-membered hetero aryl groups containing from 1 to 4 hetero atoms selected from the group consisting of an oxygen atom, nitrogen atom and sulfur atom which may have from 1 to 3 substituents $\beta^2$ described later, (xvii) mono- or dicyclic, 5- to 10-membered hetero aryloxy groups containing from 1 to 4 hetero atoms selected from the group consisting of an oxygen atom, nitrogen atom and sulfur atom which may have from 1 to 3 substituents $\beta^2$ described later, (xviii) mono- or dicyclic, 5- to 10-membered hetero arylthio groups containing from 1 to 4 hetero atoms selected from the group consisting of an oxygen atom, nitrogen atom and sulfur atom which may have from 1 to 3 substituents $\beta^2$ described later and (xix) mono- or dicyclic, 5- to 10-membered saturated heterocyclic groups containing from 1 to 4 hetero atoms selected from the group consisting of an oxygen atom, nitrogen atom and sulfur atom, here, the substituent $\beta^2$ represents a group selected from the group consisting of (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain hydroxyalkyl groups having from 1 to 4 carbon atoms, (v) halogen atoms, (vi) nitro groups, (vii) formyl groups, (viii) carboxyl groups, (ix) straight or branched chain dialkylamino groups in which each alkyl group may be the same or different and each has from 1 to 4 carbon atoms or (x) dialkylaminoalkyl groups in which the dialkylamino moiety has two straight or branched chain alkyls groups having from 1 to 4 carbon atoms which may be the same or different and the alkyl moiety is a straight or branched chain alkyl group having from 1 to 4 carbon atoms, pharmacologically acceptable salts thereof or pharmacologically acceptable esters thereof;

(22) amidocarboxylic acid derivatives in which W represents (i) a straight or branched chain alkyl group having from 1 to 6 carbon atoms, (ii) a straight or branched chain alkoxy group having from 1 to 4 carbon atoms, (iii) an aryloxy group having from 6 to 10 carbon atoms which may have from 1 to 3 substituents $\alpha^3$ described later on the aryl moiety, (iv) an arylthio group having from 6 to 10 carbon atoms which may have from 1 to 3 substituents $\alpha^3$ described later on the aryl moiety, (v) an aralkyl group having from 7 to 12 carbon atoms which may have from 1 to 3 substituents $\alpha^3$ described later on the aryl moiety, (vi) an aralkyloxy group having from 7 to 12 carbon atoms which may have from 1 to 3 substituents $\alpha^3$ described later on the aryl moiety, (vii) an aryloxyalkyl group in which the aryl moiety is an aryl group having from 6 to 10 carbon atoms which may have from 1 to 3 substituents $\alpha^3$ described later and the alkyl moiety is a straight or branched chain alkyl group having from 1 to 4 carbon atoms, (viii) a mono- or dicyclic, 5- to 10-membered hetero aryloxy group containing from 1 to 4 hetero atoms selected from the group consisting of an oxygen atom, nitrogen atom and sulfur atom or (ix) a mono- or dicyclic, 5- to 10-membered hetero arylthio group containing from 1 to 4 hetero atoms selected from the group consisting of an oxygen atom, nitrogen atom and sulfur atom, here, the substituent $\alpha^3$ represents a group selected from the group consisting of (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain halogenated alkoxy groups having from 1 to 4 carbon atoms, (v) straight or branched chain alkylthio groups having from 1 to 4 carbon atoms, (vi) straight or branched chain alkylsulfonyl groups having from 1 to 4 carbon atoms, (vii) halogen atoms, (viii) cyano groups and (ix) pyridyl groups, pharmacologically acceptable salts thereof or pharmacologically acceptable esters thereof,

(23) amidocarboxylic acid derivatives in which W represents (i) a straight or branched chain alkyl group having from 1 to 6 carbon atoms, (ii) a straight or branched chain alkoxy group having from 1 to 4 carbon atoms, (iii) a phenoxy group which may have from 1 to 3 substituents $\alpha^3$ described later on the phenyl moiety, (iv) a phenylthio group having from 6 to 10 carbon atoms which may have from 1 to 3 substituents $\alpha^4$ described later on the phenyl moiety, (v) an aralkyl group having from 7 to 10 carbon atoms, (vi) an aralkyloxy group having from 7 to 10 carbon atoms, (vii) an aryloxyalkyl group in which the aryl moiety has from 6 to 10 carbon atoms and the alkyl moiety is straight or branched chain and has from 1 to 4 carbon atoms, (viii) a mono- or dicyclic, 5- to 10-membered hetero aryloxy group containing from 1 to 4 hetero atoms selected from the group consisting of an oxygen atom, nitrogen atom and sulfur atom or (ix) a mono- or dicyclic, 5- to 10-membered hetero arylthio group containing from 1 to 4 hetero atoms selected from the group consisting of an oxygen atom, nitrogen atom and sulfur atom, here, the substituent $\alpha^4$ represents a group selected from the group consisting of (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain halogenated alkoxy groups having from 1 to 4 carbon atoms, (v) straight or branched chain alkylthio groups having one or two carbon atoms, (vi) straight or branched chain alkylsulfonyl groups having one or two carbon atoms, (vii) halogen atoms, (viii) cyano groups or (ix) pyridyl groups, pharmacologically acceptable salts thereof or pharmacologically acceptable esters thereof;

(24) amidocarboxylic acid derivatives in which W represents a phenoxy group which may have one substituent $\alpha^5$ described below on the phenyl moiety, here, the substituent $\alpha^5$ represents a group selected from the group consisting of (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain halogenated alkoxy groups having from 1 to 4 carbon atoms, (v) straight or branched chain alkylthio groups having one or two carbon atoms, (vi) straight or branched chain alkylsulfonyl groups having from one or two carbon atoms, (vii) halogen atoms, (viii) cyano groups or (ix) pyridyl groups, pharmacologically acceptable salts thereof or pharmacologically acceptable esters thereof;

(25) amidocarboxylic acid derivatives in which W represents a phenoxy group which may have one substituent $\alpha^6$ described below on the phenyl moiety, here, the substituent $\alpha^6$ represents a group selected from the group consisting of methyl, ethyl, isopropyl, t-butyl, trifluoromethyl, methoxy and trifluoromethoxy groups, and fluorine atoms and chlorine atoms, pharmacologically acceptable salts thereof or pharmacologically acceptable esters thereof;

(26) amidocarboxylic acid derivatives in which W represents a phenoxy, methylphenoxy, ethylphenoxy, isopropylphenoxy, t-butylphenoxy, trifluoromethylphenoxy, methoxyphenoxy, trifluoromethoxyphenoxy, fluorophenoxy or chlorophenoxy group, pharmaceutically acceptable salts thereof or pharmaceutically acceptable esters thereof,

(27) amidocarboxylic acid derivatives in which X represents an aryl group having from 6 to 10 carbon atoms which may have from 1 to 3 substituents $\alpha^7$ described below or a mono- or dicyclic, 5- to 10-membered hetero aryl group containing from 1 to 4 hetero atoms selected from the group consisting of an oxygen atom, nitrogen atom and sulfur atom which may have from 1 to 3 substituents $\alpha^7$ described below, here, the substituent $\alpha^7$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain aliphatic acyl groups having from 1 to 5 carbon atoms, (vi) straight or branched chain alkoxy groups having from 1 to 4 carbon atoms, (vii) straight or branched chain halogenated alkoxy groups having from 1 to 4 carbon atoms, (viii) straight or branched chain alkylenedioxy groups having from 1 to 4 carbon atoms, (ix) aralkyloxy groups having from 7 to 12 carbon atoms which may have from 1 to 3 substituents $\beta^3$ described later, (x) straight or branched chain alkylthio groups having from 1 to 4 carbon atoms, (xi) straight or branched chain alkylsulfonyl groups having from 1 to 4 carbon atoms, (xii) halogen atoms, (xiii) straight or branched chain dialkylamino groups in which each alkyl group may be the same or different and each has from 1 to 4 carbon atoms, (xiv) aralkyl groups having from 7 to 12 carbon atoms which may have from 1 to 3 substituents $\beta^3$ described below, (xv) phenyl groups which may have from 1 to 3 substituents $\beta^3$ described below, (xvi) phenoxy groups which may have from 1 to 3 substituents $\beta^3$ described below, (xvii) phenylthio groups which may have from 1 to 3 substituents $\beta^3$ described below, (xviii) phenylsulfonyl groups which may have from 1 to 3 substituents$\beta^3$ described below, (xix) phenylsulfonylamino groups which may have from 1 to 3 substituents $\beta^3$ described below on the phenyl moiety (the nitrogen atom of the amino moiety may be substituted with a straight or branched chain alkyl group having from 1 to 6 carbon atoms), (xx) furyl groups, (xxi) thienyl groups, (xxii) oxazolyl groups, (xxiii) isoxazolyl groups, (xxiv) thiazolyl groups, (xxv) pyridyl groups which may have from 1 to 3 substituents $\beta^3$ described below, (xxvi) pyridyloxy groups which may have from 1 to 3 substituents $\beta^3$ described below, (xxvii) pyridylthio groups which may have from 1 to 3 substituents $\beta^3$ described below, (xxviii) pyridylsulfonyl groups which may have from 1 to 3 substituents $\beta^3$ described below, (xxix) imidazolyl groups (the nitrogen atom of the ring may be substituted with a straight or branched chain alkyl group having from 1 to 6 carbon atoms), (xxx) pyridylsulfonylamino groups which may have from 1 to 3 substituents $\beta^3$ described below on the pyridyl moiety (the nitrogen atom of the amino moiety may be substituted with a straight or branched chain alkyl group having from 1 to 6 carbon atoms) and (xxxi) mono- or dicyclic, 5- to 10-membered saturated heterocyclic groups containing from 1 to 4 hetero atoms selected from the group consisting of an oxygen atom, nitrogen atom and sulfur atom, here, the substituent $\beta^3$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from 1 to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) halogen atoms, (ix) nitro groups, (x) formyl groups, (xi) cyano groups, (xii) carboxyl groups, (xiii) straight or branched chain dialkylamino groups in which each alkyl group may be the same or different and each has from 1 to 4 carbon atoms and (xiv) dialkylaminoalkyl groups in which the dialkylamino moiety has two straight or branched chain alkyl groups having from 1 to 4 carbon atoms which may be the same or different and the alkyl moiety is a straight or branched chain alkyl group having from 1 to 4 carbon atoms, pharmacologically acceptable salts thereof or pharmacologically acceptable esters thereof;

(28) amidocarboxylic acid derivatives in which X represents an aryl group having from 6 to 10 carbon atoms which may have from 1 to 3 substituents $\alpha^8$ described below or a mono- or dicyclic, 5- to 10-membered hetero aryl group containing from 1 to 4 hetero atoms selected from the group consisting of an oxygen atom, nitrogen atom and sulfur atom which may have from 1 to 3 substituents $\alpha^8$ described below, here, the substituent $\alpha^8$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain alkoxy groups having from 1 to 4 carbon atoms, (vi) straight or branched chain halogenated alkoxy groups having from 1 to 4 carbon atoms, (vii) straight or branched chain alkylthio groups having from 1 to 4 carbon atoms, (viii) halogen atoms, (ix) straight or branched chain dialkylamino groups in which each alkyl group may be the same or different and each has from 1 to 4 carbon atoms, (x) phenyl groups which may have from 1 to 3 substituents $\beta^4$ described below, (xi) phenoxy groups which may have from 1 to 3 substituents $\beta^4$ described below, (xii) phenythio groups which may have from 1 to 3 substituents $\beta^4$ described below, (xiii) furyl groups, (xiv) thienyl groups, (xv) oxazolyl groups, (xvi) isoxazolyl groups, (xvii) thiazolyl groups, (xviii) pyridyl groups which may have from 1 to 3 substituents $\beta^4$ described below, (xix) imidazolyl groups (the nitrogen atom of the ring may be substituted with a straight or branched chain alkyl group having from 1 to 6 carbon atoms) and (xx) mono- or dicyclic, 5- to 10-membered saturated heterocyclic groups containing from 1 to 4 hetero atoms selected from the group consisting of an oxygen atom, nitrogen atom and sulfur atom, here, the substituent $\beta^4$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from 1 to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) halogen atoms, (ix) nitro groups, (x) formyl groups, (xi) cyano groups, (xii) carboxyl groups, (xiii) straight or branched chain dialkylamino groups in which each alkyl group may be the same or different and each has from 1 to 4 carbon atoms and (xiv) dialkylaminoalkyl groups in which the dialkylamino moiety has two straight or branched chain alkyl groups having from 1 to 4 carbon atoms which may be the same or different and the alkyl moiety is a straight or branched chain alkyl group having from 1 to 4 carbon atoms, pharmacologically acceptable salts thereof or pharmacologically acceptable esters thereof;

(29) amidocarboxylic acid derivatives in which X represents an aryl group having from 6 to 10 carbon atoms which may have from 1 to 3 substituents $\alpha^9$ described below or a mono- or dicyclic, 5- to 10-membered hetero aryl group containing from 1 to 4 hetero atoms selected from the group consisting of an oxygen atom, nitrogen atom and sulfur atom which may have from 1 to 3 substituents $\alpha^9$ described below, here, the substituent $\alpha^9$ represents a group selected from the group consisting of (i) hydroxyl groups, (ii) straight or branched chain alkoxy groups having from 1 to 4 carbon atoms, (iii) straight or branched chain halogenated alkoxy groups having from 1 to 4 carbon atoms, (iv) straight or branched chain dialkylamino groups in which each alkyl group may be the same or different and each has from 1 to 4 carbon atoms, (v) phenyl groups which may have from 1 to 3 substituents $\beta^5$ described below, (vi) phenoxy groups which may have from 1 to 3 substituents $\beta^5$ described below, (vii) pyridyl groups which may have from 1 to 3 substituents $\beta^5$ described below and (viii) mono- or dicyclic, 5- to 10-membered saturated heterocyclic groups containing from 1 to 4 hetero atoms selected from the group consisting of an oxygen atom, nitrogen atom and sulfur atom, here, the substituent $\beta^5$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain hydroxyalkyl groups having from 1 to 4 carbon atoms, (vi) halogen atoms, (vii) nitro groups, (viii) formyl groups, (ix) carboxyl groups, (x) straight or branched chain dialkylamino groups in which each alkyl may be the same or different and each has from 1 to 4 carbon atoms and (xi) dialkylaminoalkyl groups in which the dialkylamino moiety has two straight or branched chain alkyl groups having from 1 to 4 carbon atoms which may be the same or different and the alkyl moiety is a straight or branched chain alkyl group having from 1 to 4 carbon atoms, pharmacologically acceptable salts thereof or pharmacologically acceptable esters thereof;

(30) amidocarboxylic acid derivatives in which X represents a phenyl, naphthyl, imidazolyl, oxazolyl, pyridyl, indolyl, quinolyl or isoquinolyl group which may have from 1 to 3 substituents $\alpha^{10}$ described below;

here, the substituent $\alpha^{10}$ represents the group selected from the group consisting of (i) hydroxyl groups, (ii) straight or branched chain alkoxy groups having from 1 to 4 carbon atoms, (iii) straight or branched chain halogenated alkoxy groups having from 1 to 4 carbon atoms, (iv) straight or branched chain dialkylamino groups which may be the same or different and in which each alkyl group has from 1 to 4 carbon atoms, (v) phenyl groups which may have from 1 to 3 substituents $\beta^6$ described below, (vi) phenoxy groups which may have from 1 to 3 substituents $\beta^6$ described below, (vii) pyridyl groups which may have from 1 to 3 substituents $\beta^6$ described below and (viii) 5- to 10-membered saturated heterocyclic groups of one ring or two rings containing from 1 to 4 hetero atoms selected from the group consisting of an oxygen atom, the nitrogen atom and the sulfur atom, here, the substituent $\beta^6$ represents the group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain hydroxyalkyl groups having from 1 to 4 carbon atoms, (vi) halogen atoms, (vii) nitro groups, (viii) formyl groups, (ix) carboxyl groups, (x) straight or branched chain dialkylamino groups which may be the same or different and in which each alkyl groups has from 1 to 4 carbon atoms and (xi) dialkylaminoalkyl groups in which the dialkylamino moiety has two straight or branched chain alkyl groups having from 1 to 4 carbon atoms which may be the same or different and the alkyl moiety is a straight or branched chain alkyl group having from 1 to 4 carbon atoms, pharmaceutically acceptable salts thereof or pharmaceutically acceptable esters thereof;

(31) amidocarboxylic acid derivatives in which X represents a phenyl, indolyl, pyridyl or quinolyl group, which may have from 1 to 3 substituents $\alpha^{11}$ described below.

here, the substituent $\alpha^{11}$ represents a group selected from the group consisting of (i) hydroxyl groups, (ii) straight or branched chain alkoxy groups having from 1 to 4 carbon atoms, (iii) straight or branched chain halogenated alkoxy groups having from 1 to 4 carbon atoms, (iv) straight or branched chain dialkylamino groups in which each alkyl group may be the same or different and each has from 1 to 4 carbon atoms, (v) phenyl groups which may have from 1 to 3 substituents $\beta^7$ described below, (vi) phenoxy groups which may have from 1 to 3 substituents $\beta^7$ described below, (vii) pyridyl groups which may have from 1 to 3 substituents $\beta^7$ described below and (viii) mono- or dicyclic, 5- to 10-membered saturated heterocyclic groups containing from 1 to 4 hetero atoms selected from the group consisting of an oxygen atom, nitrogen atom and sulfur atom, here, the substituent $\beta^7$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain hydroxyalkyl groups having from 1 to 4 carbon atoms, (vi) halogen atoms, (vii) nitro groups, (viii) formyl groups, (ix) carboxyl groups, (x) straight or branched chain dialkylamino groups in which each alkyl group may be the same or different and each has from 1 to 4 carbon atoms and (xi) dialkylaminoalkyl groups in which the dialkylamino moiety has two straight or branched chain alkyl groups having from 1 to 4 carbon atoms which may be the same or different and the alkyl moiety is a straight or branched chain alkyl group having from 1 to 4 carbon atoms, pharmacologically acceptable salts thereof or pharmacologically acceptable esters thereof,

(32) amidocarboxylic acid derivatives in which X represents a phenyl group which may have one substituent $\alpha^{12}$ described below, here, the substituent $\alpha^{12}$ represents a group selected from the group consisting of methyl, isopropyl and hydroxyl groups, fluorine atoms, chlorine atoms, diethylamino and benzyl groups, phenyl groups (the phenyl moiety may be substituted with 1 to 3 substituents, which may be the same or different, including methyl, ethyl, trifluoromethyl, hydroxyl, methoxy, ethoxy, isopropoxy, trifluoromethoxy, methylenedioxy and hydroxymethyl groups, fluorine atoms, chlorine atoms, nitro, formyl, cyano, carboxyl, dimethylamino, diethylamino and N,N-dimethylaminomethyl groups), phenoxy, phenylthio, phenylsufonyl, phenylsulfonylamino, N-methylphenylsulfonylamino and pyridyl groups (the pyridyl moiety may be substituted with a methyl, ethyl, trifluoromethyl, methoxy, ethoxy, isopropoxy or trifluoromethoxy group, a fluorine atom, a chlorine atom, or a nitro, dimethylamino or diethylamino group), pyridyloxy, pyridylthio, pyridylsulfonyl and piperidyl groups, or X represents a pyridyl group which may have one substituent $\alpha^1$ described below, here, the substituent $\alpha^{13}$ represents a group selected from the group consisting of methyl, isopropyl, methoxy, ethoxy, isopropoxy, 2,2,3,3-tetrafluoropropoxy and benzyloxy groups, alkylthio groups having one or two carbon atoms, alkylsulfonyl groups having one or two carbon atoms, benzyl groups, phenyl groups (the phenyl moiety may be substituted with a methyl, ethyl, trifluoromethyl, methoxy, ethoxy or isopropoxy group, a fluorine atom, a chlorine atom, or a nitro, dimethylamino or diethylamino group), phenoxy, phenylthio, phenylsufonyl, phenylsulfonylamino and N-methylphenylsulfonylamino groups, pharmacologically acceptable salts thereof or pharmacologically acceptable esters thereof;

(33) amidocarboxylic acid derivatives in which X represents a phenyl group which may have one substituent $\alpha^{12}$ described below, here, the substituent $\alpha^2$ represents a group selected from the group consisting of methyl, isopropyl and hydroxyl groups, fluorine atoms, chlorine atoms, diethylamino and benzyl groups, phenyl groups (the phenyl moiety may be substituted with 1 to 3 substituents, which may be the same or different, including methyl, ethyl, trifluoromethyl, hydroxyl, methoxy, ethoxy, isopropoxy, trifluoromethoxy, methylenedioxy and hydroxymethyl groups, fluorine atoms, chlorine atoms, nitro, formyl, cyano, carboxyl, dimethylamino, diethylamino and N,N-dimethylaminomethyl groups), phenoxy, phenylthio, phenylsufonyl, phenylsulfonylamino and N-methylphenylsulfonylamino groups, pyridyl groups (the pyridyl moiety may be substituted with a methyl, ethyl, trifluoromethyl, methoxy, ethoxy, isopropoxy, or trifluoromethoxy group, a fluorine atom, a chlorine atom, or a nitro, dimethylamino or diethylamino group), pyridyloxy, pyridylthio, pyridylsulfonyl and piperidyl groups, pharmacologically acceptable salts thereof or pharmacologically acceptable esters thereof;

(34) amidocarboxylic acid derivatives in which X represents a pyridyl group which may have one substituent $\alpha^{13}$ described below, here, the substituent $\alpha^{13}$ represents a group selected from the group consisting of methyl, isopropyl, methoxy, ethoxy, isopropoxy, 2,2,3,3-tetrafluoropropoxy and benzyloxy groups, alkylthio groups having one or two carbon atoms, alkylsulfonyl groups having one or two carbon atoms, benzyl groups, phenyl groups (the phenyl moiety may be substituted with a methyl, ethyl, trifluoromethyl, methoxy, ethoxy or isopropoxy group, a fluorine atom, a chlorine atom, or a nitro, dimethylamino or diethylamino group), phenoxy, phenylthio, phenylsufonyl, phenylsulfonylamino and N-methylphenylsulfonylamino groups, pharmacologically acceptable salts thereof or pharmacologically acceptable esters thereof;

(35) amidocarboxylic acid derivatives in which X represents a 2,2,3,3-tetrafluoropropoxypyridyl group or a phenylpyridyl group (the phenyl moiety may be substituted with a methyl, ethyl, trifluoromethyl, methoxy, ethoxy or isopropoxy group, a fluorine atom, a chlorine atom, or a nitro, dimethylamino or diethylamino group), pharmacologically acceptable salts thereof or pharmacologically acceptable esters thereof;

(36) amidocarboxylic acid derivatives in which X represents a biphenylyl group (each phenyl moiety may be substituted with one substituent, which may be the same or different, including a methyl, trifluoromethyl, hydroxyl, methoxy or hydroxymethyl group, a fluorine atom, a chlorine atom, or a formyl, carboxyl, nitro, dimethylamino or N,N-dimethylaminomethyl group), a pyridylphenyl group (the pyridyl moiety may be substituted with one substituent including a methyl, ethyl, trifluoromethyl, methoxy, ethoxy, isopropoxy or trifluoromethoxy group, a fluorine atom, a chlorine atom, or a nitro, dimethylamino or diethylamino group) or a phenylpyridyl group (the phenyl moiety may be substituted with one substituent including a methyl, ethyl, trifluoromethyl, methoxy, ethoxy or isopropoxy group, a fluorine atom, a chlorine atom, a nitro group or a dimethylamino group), pharmacologically acceptable salts thereof or pharmacologically acceptable esters thereof;

(37) amidocarboxylic acid derivatives in which X represents a biphenylyl, (methylphenyl)phenyl, (trifluoromethylphenyl)phenyl, (hydroxyphenyl)phenyl, (methoxyphenyl)phenyl, (hydroxymethylphenyl)phenyl, (fluorophenyl)phenyl, (chlorophenyl)phenyl, (formylphenyl)phenyl, (carboxyphenyl)phenyl, (nitrophenyl)phenyl, (dimethylaminophenyl)phenyl or (N,N-dimethylaminomethylphenyl)phenyl group, pharmacologically acceptable salts thereof or pharmacologically acceptable esters thereof;

(38) amidocarboxylic acid derivatives in which X represents a biphenylyl, (methylphenyl)phenyl, (trifluoromethylphenyl)phenyl, (methoxyphenyl)phenyl, (fluorophenyl)phenyl or (chlorophenyl)phenyl group, pharmacologically acceptable salts thereof or pharmacologically acceptable esters thereof;

(39) amidocarboxylic acid derivatives in which X represents a biphenylyl, (fluorophenyl)phenyl or (chlorophenyl)phenyl group, pharmacologically acceptable salts thereof or pharmacologically acceptable esters thereof;

(40) amidocarboxylic acid derivatives in which X represents a pyridylphenyl group (the pyridyl moiety may have one methyl, ethyl, trifluoromethyl, methoxy, ethoxy or isopropoxy group, a fluorine atom, a chlorine atom, or a nitro, dimethylamino or diethylamino group), pharmacologically acceptable salts thereof or pharmacologically acceptable esters thereof;

(41) amidocarboxylic acid derivatives in which X represents a pyridylphenyl, (methylpyridyl)phenyl, (methoxypyridyl)phenyl or (dimethylaminopyridyl)phenyl group, pharmacologically acceptable salts thereof or pharmacologically acceptable esters thereof;

(42) amidocarboxylic acid derivatives in which X represents a phenylpyridyl group (the phenyl moiety may have one methyl, ethyl, methoxy, ethoxy or isopropoxy group, a fluorine atom, a chlorine atom or a dimethylamino group), pharmacologically acceptable salts thereof or pharmacologically acceptable esters thereof;

(43) amidocarboxylic acid derivatives in which X represents a phenylpyridyl, (methoxyphenyl)pyridyl or (fluorophenyl)pyridyl group, pharmacologically acceptable salts thereof or pharmacologically acceptable esters thereof,

(44) amidocarboxylic acid derivatives in which Y represents a single bond, an oxygen atom, a sulfur atom or a group of the formula: >N—$R^5$ (wherein $R^5$ represents a hydrogen atom, a straight or branched chain alkyl group having one or two carbon atoms or a straight or branched chain aliphatic acyl group having from 2 to 5 carbon atoms), pharmacologically acceptable salts thereof or pharmacologically acceptable esters thereof;

(45) amidocarboxylic acid derivatives in which Y represents a single bond or an oxygen atom, pharmacologically acceptable salts thereof or pharmacologically acceptable esters thereof,

(46) amidocarboxylic acid derivatives in which Y represents an oxygen atom, pharmacologically acceptable salts thereof or pharmacologically acceptable esters thereof.

Further, compounds in which $R^1$ is selected from (1) to (4), $R^2$ is selected from (5) to (8), $R^3$ is selected from (9) to (11), $R^4$ is selected from (12) to (16), Z is selected from (17) to (19), W is selected from (20) to (26), X is selected from (27) to (43), and Y is selected from (44) to (46) to be combined with one another are preferable.

For example, the phenylalkylcarboxylic acid of the formula (I) includes:

(47) amidocarboxylic acid derivatives in which $R^1$ is a hydrogen atom, a straight or branched chain alkyl group having from 1 to 4 carbon atoms or an aralkyl group having from 7 to 9 carbon atoms;

$R^2$ is a straight or branched chain alkylene group having from 2 to 4 carbon atoms;

$R^3$ is a hydrogen atom, a straight or branched chain alkyl group having from 1 to 4 carbon atoms, an alkoxy group having one or two carbon atoms, an alkylthio group having one or two carbon atoms, a halogen atom, a nitro group, a hydroxyl group or a straight or branched chain aliphatic acyl group having from 1 to 5 carbon atoms;

$R^4$ is a hydrogen atom or a straight or branched chain alkyl group having from 1 to 4 carbon atoms;

Z is a straight or branched chain alkylene group having from 1 to 4 carbon atoms;

W represents (i) a straight or branched chain alkyl group having from 1 to 6 carbon atoms, (ii) a hydroxyl group, (iii) a straight or branched chain alkoxy group having from 1 to 4 carbon atoms, (iv) a straight or branched chain alkylthio group having from 1 to 4 carbon atoms, (v) an aryl group having from 6 to 10 carbon atoms which may have from 1 to 3 substituents $\alpha^1$ described later, (vi) an aryloxy group having from 6 to 10 carbon atoms which may have from 1 to 3 substituents $\alpha^1$ described later on the aryl moiety, (vii) an arylthio group having from 6 to 10 carbon atoms which may have from 1 to 3 substituents $\alpha^1$ described later on the aryl moiety, (viii) an aralkyl group having from 7 to 12 carbon atoms which may have from 1 to 3 substituents $\alpha^1$ described later on the aryl moiety, (ix) an aralkyloxy group having from 7 to 12 carbon atoms which may have from 1 to 3 substituents $\alpha^1$ described later on the aryl moiety, (x) an aralkylthio group having from 7 to 12 carbon atoms which may have from 1 to 3 substituents $\alpha^1$ described later on the aryl moiety, (xi) an aryloxyalkyl group in which the aryl moiety is an aryl group having from 6 to 10 carbon atoms which may have from 1 to 3 substituents $\alpha^1$ described later and the alkyl moiety is a straight or branched chain alkyl group having from 1 to 4 carbon atoms, (xii) a mono- or dicyclic, 5- to 10-membered hetero aryl group containing from 1 to 4 hetero atoms selected from the group consisting of an oxygen atom, nitrogen atom and sulfur atom, (xiii) a mono- or dicyclic, 5- to 10-membered hetero aryloxy group containing from 1 to 4 hetero atoms selected from the group consisting of an oxygen atom, nitrogen atom and sulfur atom, (xiv) a mono- or dicyclic, 5- to 10-membered hetero arylthio group containing from 1 to 4 hetero atoms selected from the group consisting of an oxygen atom, a nitrogen atom and a sulfur atom or (xv) a mono- or dicyclic, 5- to 10-membered saturated heterocyclic group containing from 1 to 4 hetero atoms selected from the group consisting of an oxygen atom, nitrogen atom and sulfur atom, here, the substituent $\alpha^1$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain aliphatic acyl groups having from 1 to 5 carbon atoms, (vi) straight or branched chain alkoxy groups having from 1 to 4 carbon atoms, (vii) straight or branched chain halogenated alkoxy groups having from 1 to 4 carbon atoms, (viii) straight or branched chain alkylenedioxy groups having from 1 to 4 carbon atoms, (ix) aralkyloxy groups having from 7 to 12 carbon atoms which may have 1 to 3 substituents $\beta^1$ described later, (x) straight or branched chain alkylthio groups having from 1 to 4 carbon atoms, (xi) straight or branched chain alkylsulfonyl groups having from 1 to 4 carbon atoms, (xii) halogen atoms, (xiii) nitro groups, (xiv) cyano groups, (xv) amino groups, (xvi) straight or branched chain monoalkylamino groups in which the alkyl moiety has from 1 to 4 carbon atoms, (xvii) straight or branched chain alkoxycarbonylamino groups in which the alkoxy moiety has from 1 to 4 carbon atoms, (xviii) aralkyloxycarbonylamino groups in which the aralkyl moiety has from 7 to 12 carbon atoms, (xix) straight or branched chain dialkylamino groups in which each alkyl group may be the same or different and each has from 1 to 4 carbon atoms, (xx) aralkyl groups having from 7 to 12 carbon atoms which may have from 1 to 3 substituents $\beta^1$ described later on the aryl moiety, (xxi) aryl groups having from 6 to 10 carbon atoms which may have from 1 to 3 substituents $\beta^1$ which may be the same or different, described later, (xxii) aryloxy groups having from 6 to 10 carbon atoms which may have from 1 to 3 substituents $\beta^1$, described later on the aryl moiety, (xxiii) arylthio groups having from 6 to 10 carbon atoms which may have from 1 to 3 substituents $\beta^1$ described later on the aryl moiety, (xxiv) arylsulfonyl groups having from 6 to 10 carbon atoms which may have from 1 to 3 substituents $\beta^1$ described later on the aryl moiety, (xxv) arylsulfonylamino groups having from 6 to 10 carbon atoms which may have from 1 to 3 substituents $\beta^1$ described later on the aryl moiety (the nitrogen atom of the amino moiety may be substituted with a straight or branched chain alkyl group having from 1 to 6 carbon atoms), (xxvi) mono- or dicyclic, 5- to 10-membered hetero aryl groups containing from 1 to 4 hetero atoms selected from the group consisting of an oxygen atom, nitrogen atom and sulfur atom which may have from 1 to 3 substituents $\beta^1$ described later, (xxvii) mono- or dicyclic, 5- to 10-membered hetero aryloxy groups containing from 1 to 4 hetero atoms selected from the group consisting of an oxygen atom, nitrogen atom and sulfur atom which may have from 1 to 3 substituents $\beta^1$ described later, (xxviii) mono- or dicyclic, 5- to 10-membered hetero arylthio groups containing from 1 to 4 hetero atoms selected from the group consisting of an oxygen atom, nitrogen atom and sulfur atom which may have from 1 to 3 substituents $\beta^1$ described later, (xxix) mono- or dicyclic, 5- to 10-membered hetero arylsulfonyl groups containing from 1 to 4 hetero atoms selected from the group consisting of an oxygen atom, nitrogen atom and sulfur atom which may have from 1 to 3 substituents $\beta^1$ described later, (xxx) mono- or dicyclic, 5- to 10-membered hetero arylsulfonylamino groups containing from 1 to 4 hetero atoms selected from the group consisting of an oxygen atom, nitrogen atom and sulfur atom which may have from 1 to 3 substituents described later on the hetero aryl moiety (the nitrogen atom of the amino moiety may be substituted with a straight or branched chain alkyl group having from 1 to 6 carbon atoms) and (xxxi) mono- or dicyclic, 5- to 10-membered saturated heterocyclic groups containing from 1 to 4 hetero atoms selected from the group consisting of an oxygen atom, nitrogen atom and sulfur atom, here, the substituent $\beta^1$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from 1 to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) halogen atoms, (ix) nitro groups, (x) formyl groups, (xi) cyano groups, (xii) carboxyl groups, (xiii) amino groups, (xiv) straight or branched chain monoalkylamino groups in which the alkyl moiety has from 1 to 4 carbon atoms, (xv) straight or branched chain dialkylamino groups in which each alkyl moiety may be the same or different and each has from 1 to 4 carbon atoms, (xvi) straight or branched chain aminoalkyl groups having from 1 to 4 carbon atoms, (xvii) monoalkylaminoalkyl groups in which the monoalkylamino moiety has one straight or branched chain alkyl group having from 1 to 4 carbon atoms and the alkyl moiety is a straight or branched chain alkyl group having from 1 to 4 carbon atoms, (xviii) dialkylaminoalkyl groups in which the dialkylamino moiety has two straight or branched chain alkyl groups having from 1 to 4 carbon atoms which may be the same or different and the alkyl moiety is a straight or branched chain alkyl group having from 1 to 4 carbon atoms, (xix) straight or branched chain alkoxycarbonylamino groups in which the alkoxy moiety is a straight or branched chain alkoxy group having from 1 to 4 carbon atoms and (xx) aralkyloxycarbonylamino groups in which the aryl moiety has from 6 to 10 carbon atoms and the alkyl moiety has from 1 to 4 carbon atoms;

X represents an aryl group having from 6 to 10 carbon atoms which may have from 1 to 3 substituents $\alpha^7$ described later or a mono- or dicyclic, 5- to 10-membered hetero aryl group containing from 1 to 4 hetero atoms selected from the group consisting of an oxygen atom, nitrogen atom and sulfur atom which may have from 1 to 3 substituents $\alpha^7$ described below, here, the substituent $\alpha^7$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain aliphatic acyl groups having from 1 to 5 carbon atoms, (vi) straight or branched chain alkoxy groups having from 1 to 4 carbon atoms, (vii) straight or branched chain halogenated alkoxy groups having from 1 to 4 carbon atoms, (viii) straight or branched chain alkylenedioxy groups having from 1 to 4 carbon atoms, (ix) aralkyloxy groups having from 7 to 12 carbon atoms which may have from 1 to 3 substituents $\beta^3$ described later, (x) straight or branched chain alkylthio groups having from 1 to 4 carbon atoms, (xi) straight or branched chain alkylsulfonyl groups having from 1 to 4 carbon atoms, (xii) halogen atoms, (xiii) straight or branched chain dialkylamino groups in which each alkyl group may be the same or different and each has from 1 to 4 carbon atoms, (xiv) aralkyl groups having from 7 to 12 carbon atoms which may have from 1 to 3 substituents $\beta^3$ described later, (xv) phenyl groups which may have from 1 to 3 substituents $\beta^3$ described later, (xvi) phenoxy groups which may have from 1 to 3 substituents $\beta^3$ described later, (xvii) phenylthio groups which may have from 1 to 3 substituents $\beta^3$ described later, (xviii) phenylsulfonyl groups which may have from 1 to 3 substituents $\beta^3$ described later on the phenyl moiety, (xix) phenylsulfonylamino groups which may have from 1 to 3 substituents $\beta^3$ described later on the phenyl moiety (the nitrogen atom of the amino moiety may be substituted with a straight or branched chain alkyl group having from 1 to 6 carbon atoms), (xx) furyl groups, (xxi) thienyl groups, (xxii) oxazolyl groups, (xxiii) isoxazolyl groups, (xxiv) thiazolyl groups, (xxv) pyridyl groups which may have from 1 to 3 substituents $\beta^3$ described later, (xxvi) pyridyloxy groups which may have from 1 to 3 substituents $\beta^3$ described later, (xxvii) pyridylthio groups which may have from 1 to 3 substituents $\beta^3$ described later, (xxviii) pyridylsulfonyl groups which may have from 1 to 3 substituents $\beta^3$ described later, (xxix) imidazolyl groups (the nitrogen atom of the ring may be substituted with a straight or branched chain alkyl group having from 1 to 6 carbon atoms), (xxx) pyridylsulfonylamino groups which may have from 1 to 3 substituents $\beta^3$ described later on the pyridyl moiety (the nitrogen atom of the amino moiety may be substituted with a straight or branched chain alkyl group having from 1 to 6 carbon atoms) and (xxxi) mono- or dicyclic, 5- to 10-membered saturated heterocyclic groups containing from 1 to 4 hetero atoms selected from the group consisting of an oxygen atom, nitrogen atom and sulfur atom, here, the substituent $\beta^3$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from I to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) halogen atoms, (ix) nitro groups, (x) formyl groups, (xi) cyano groups, (xii) carboxyl groups, (xiii) straight or branched chain dialkylamino group in which each alkyl group may be the same or different and each has from 1 to 4 carbon atoms and (xiv) dialkylaminoalkyl groups in which the dialkylamino moiety has two straight or branched chain alkyl groups having from 1 to 4 carbon atoms which may be the same or different and the alkyl moiety is a straight or branched chain alkyl group having from 1 to 4 carbon atoms; and Y is a single bond or an oxygen atom, pharmacologically acceptable salts thereof or pharmacologically acceptable esters thereof;

(48) amidocarboxylic acid derivatives in which $R^1$ is a hydrogen atom, a straight or branched chain alkyl group having from 1 to 4 carbon atoms or an aralkyl group having from 7 to 9 carbon atoms;

$R^2$ is a straight or branched chain alkylene group having from 2 to 4 carbon atoms;

$R^3$ is a hydrogen atom, a halogen atom or a nitro group;

$R^4$ is a hydrogen atom or a straight or branched chain alkyl group having from 1 to 4 carbon atoms;

Z is a methylene group;

W represents (i) a straight or branched chain alkyl group having from 1 to 6 carbon atoms, (ii) a hydroxyl group, (iii) a straight or branched chain alkoxy group having from 1 to 4 carbon atoms, (iv) a straight or branched chain alkylthio group having from 1 to 4 carbon atoms, (v) an aryl group having from 6 to 10 carbon atoms which may have from 1 to 3 substituents $\alpha^2$ described later, (vi) an aryloxy group having from 6 to 10 carbon atoms which may have from 1 to 3 substituents $\alpha^2$ described later on the aryl moiety, (vii) an arylthio group having from 6 to 10 carbon atoms which may have from 1 to 3 substituents $\alpha^2$ described later on the aryl moiety, (viii) an aralkyl group having from 7 to 12 carbon atoms which may have from 1 to 3 substituents $\alpha^2$ described later on the aryl moiety, (ix) an aralkyloxy group having from 7 to 12 carbon atoms which may have from 1 to 3 substituents $\alpha^2$ described later on the aryl moiety, (x) an aralkylthio group having from 7 to 12 carbon atoms which may have from 1 to 3 substituents $\alpha^2$ described later on the aryl moiety, (xi) an aryloxyalkyl group in which the aryl moiety is an aryl group having from 6 to 10 carbon atoms which may have from 1 to 3 substituents $\alpha^2$ described later and the alkyl moiety is a straight or branched chain alkyl having from 1 to 4 carbon atoms, (xii) a mono- or dicyclic, 5- to 10-membered hetero aryloxy group containing from 1 to 4 hetero atoms selected from the group consisting of an oxygen atom, nitrogen atom and sulfur atom or (xiii) a mono- or dicyclic, 5- to 10-membered hetero arylthio group containing from 1 to 4 hetero atoms selected from the group consisting of an oxygen atom, nitrogen atom and sulfur atom, here, the substituent $\alpha^2$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain alkoxy groups having from 1 to 4 carbon atoms, (vi) straight or branched chain halogenated alkoxy groups having from 1 to 4 carbon atoms, (vii) straight or branched chain alkylthio groups having from 1 to 4 carbon atoms, (viii) straight or branched chain alkylsulfonyl groups having from 1 to 4 carbon atoms, (ix) halogen atoms, (x) nitro groups, (xi) cyano groups, (xii) straight or branched chain dialkylamino groups in which each alkyl group may be the same or different and each has from 1 to 4 carbon atoms, (xiii) aryl groups having from 6 to 10 carbon atoms which may have from 1 to 3 substituents $\beta^2$, which may be the same or different, described later, (xiv) aryloxy groups having from 6 to 10 carbon atoms which may have from 1 to 3 substituents $\beta^2$ described later on the aryl moiety, (xv) arylthio groups having from 6 to 10 carbon atoms which may have from 1 to 3 substituents $\beta^2$ described later on the aryl moiety, (xvi) mono- or dicyclic, 5- to 10-membered hetero aryl groups containing from 1 to 4 hetero atoms selected from the group consisting of an oxygen atom, nitrogen atom and sulfur atom which may have from 1 to 3 substituents $\beta^2$ described later, (xvii) mono- or dicyclic, 5- to 10-membered hetero aryloxy groups containing from 1 to 4 hetero atoms selected from the group consisting of an oxygen atom, nitrogen atom and sulfur atom which may have from 1 to 3 substituents $\beta^2$ described later, (xviii) mono- or dicyclic, 5- to 10-membered hetero arylthio groups containing from 1 to 4 hetero atoms selected from the group consisting of an oxygen atom, nitrogen atom and sulfur atom which may have from 1 to 3 substituents $\beta^2$ described later and (xix) mono- or dicyclic, 5- to 10-membered saturated heterocyclic groups containing from 1 to 4 hetero atoms selected from the group consisting of an oxygen atom, nitrogen atom and sulfur atom, here, the substituent $\beta^2$ represents a group selected from the group consisting of (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain hydroxyalkyl groups having from 1 to 4 carbon atoms, (v) halogen atoms, (vi) nitro groups, (vii) formyl groups, (viii) carboxyl groups, (ix) straight or branched chain dialkylamino groups in which each alkyl group may be the same or different and each has from 1 to 4 carbon atoms and (x) dialkylaminoalkyl groups in which the dialkylamino moiety has two straight or branched chain alkyl groups having from 1 to 4 carbon atoms which may be the same or different and the alkyl moiety is a straight or branched chain alkyl group having from 1 to 4 carbon atoms;

X represents an aryl group having from 6 to 10 carbon atoms which may have from 1 to 3 substituents $\alpha^8$ described below or a mono- or dicyclic, 5- to 10-membered hetero aryl group containing from 1 to 4 hetero atoms selected from the group consisting of an oxygen atom, nitrogen atom and sulfur atom which may have from 1 to 3 substituents $\alpha^8$ described below, here, the substituent $\alpha^8$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain alkoxy groups having from 1 to 4 carbon atoms, (vi) straight or branched chain halogenated alkoxy groups having from 1 to 4 carbon atoms, (vii) straight or branched chain alkylthio groups having from 1 to 4 carbon atoms, (viii) halogen atoms, (ix) straight or branched chain dialkylamino groups in which each alkyl group may be the same or different and each has from 1 to 4 carbon atoms, (x) phenyl groups which may have from 1 to 3 substituents $\beta^4$ described later, (xi) phenoxy groups which may have from 1 to 3 substituents $\beta^4$ described later, (xii) phenylthio groups which may have from 1 to 3 substituents 4 described later, (xiii) furyl groups, (xiv) thienyl groups, (xv) oxazolyl groups, (xvi) isoxazolyl groups, (xvii) thiazolyl groups, (xviii) pyridyl groups which may have from 1 to 3 substituents $\beta^4$ described later, (xix) imidazolyl groups (the nitrogen atom of the ring may be substituted with a straight or branched chain alkyl group having from 1 to 6 carbon atoms) and (xx) mono- or dicyclic, 5- to 10-membered saturated heterocyclic groups containing from 1 to 4 hetero atoms selected from the group consisting of an oxygen atom, nitrogen atom and sulfur atom, here, the substituent $\beta^4$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from 1 to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) halogen atoms, (ix) nitro groups, (x) formyl groups, (xi) cyano groups, (xii) carboxyl groups, (xiii) straight or branched chain dialkylamino groups in which each alkyl group may be the same or different and have from 1 to 4 carbon atoms and (xiv) dialkylamninoalkyl groups in which the dialkylamino moiety has two straight or branched chain alkyl groups having from 1 to 4 carbon atoms which may be the same or different and the alkyl moiety is a straight or branched chain alkyl group having from 1 to 4 carbon atoms; and Y is an oxygen atom, pharmacologically acceptable salts thereof or pharmacologically acceptable esters thereof;

(49) amidocarboxylic acid derivatives in which $R^1$ is a hydrogen atom, a straight or branched chain alkyl group having from 1 to 4 carbon atoms or an aralkyl group having from 7 to 9 carbon atoms;

$R^2$ is a straight or branched chain alkylene group having from 2 to 4 carbon atoms;

$R^3$ is a hydrogen atom, a halogen atom or a nitro group;

$R^4$ is a hydrogen atom or a straight or branched chain alkyl group having from 1 to 4 carbon atoms;

Z is a methylene group;

W represents (i) a straight or branched chain alkyl group having from 1 to 6 carbon atoms, (ii) a straight or branched chain alkoxy group having from 1 to 4 carbon atoms, (iii) an aryloxy group having from 6 to 10 carbon atoms which may have from 1 to 3 substituents $\alpha^3$ described later on the aryl moiety, (iv) an arylthio group having from 6 to 10 carbon atoms which may have from 1 to 3 substituents $\alpha^3$ described later on the aryl moiety, (v) an aralkyl group having from 7 to 12 carbon atoms which may have from 1 to 3 substituents $\alpha^3$ described later on the aryl moiety, (vi) an aralkyloxy group having from 7 to 12 carbon atoms which may have from 1 to 3 substituents $\alpha^3$ described later on the aryl moiety, (vii) an aryloxyalkyl group in which the aryl moiety is an aryl group having from 6 to 10 carbon atoms which may have from 1 to 3 substituents $\alpha^3$ described later and the alkyl moiety is a straight or branched chain alkyl group having from 1 to 4 carbon atoms, (viii) a mono- or dicyclic, 5- to 10-membered hetero aryloxy group containing from 1 to 4 hetero atoms selected from the group consisting of an oxygen atom, nitrogen atom and sulfur atom or (ix) a mono- or dicyclic, 5- to 10-membered hetero arylthio group containing from 1 to 4 hetero atoms selected from the group consisting of an oxygen atom, nitrogen atom and sulfur atom, here, the substituent $\alpha^3$ represents a group selected from the group consisting of (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain halogenated alkoxy groups having from 1 to 4 carbon atoms, (v) straight or branched chain alkylthio groups having from 1 to 4 carbon atoms, (vi) straight or branched chain alkylsulfonyl groups having from 1 to 4 carbon atoms, (vii) halogen atoms, (viii) cyano groups and (ix) pyridyl groups;

X represents an aryl group having from 6 to 10 carbon atoms which may have from 1 to 3 substituents $\alpha^9$ described below or a mono- or dicyclic, 5- to 10-membered hetero aryl group containing from 1 to 4 hetero atoms selected from the group consisting of an oxygen atom, nitrogen atom and sulfur atom which may have from 1 to 3 substituents $\alpha^9$ described below, here, the substituent $\alpha^9$ represents a group selected from the group consisting of (i) hydroxyl groups, (ii) straight or branched chain alkoxy groups having from 1 to 4 carbon atoms, (iii) straight or branched chain halogenated alkoxy groups having from 1 to 4 carbon atoms, (iv) straight or branched chain dialkylamino groups in which each alkyl group may be the same or different and have from 1 to 4 carbon atoms, (v) phenyl groups which may have from 1 to 3 substituents $\beta^5$ described below, (vi) phenoxy groups which may have from 1 to 3 substituents $\beta^5$ described below, (vii) pyridyl groups which may have from 1 to 3 substituents $\beta^5$ described below and (viii) mono- or dicyclic, 5- to 10-membered saturated heterocyclic groups containing from 1 to 4 hetero atoms selected from the group consisting of an oxygen atom, nitrogen atom and sulfur atom, here, the substituent $\beta^5$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain hydroxyalkyl groups having from 1 to 4 carbon atoms, (vi) halogen atoms, (vii) nitro groups, (viii) formyl groups, (ix) carboxyl groups, (x) straight or branched chain dialkylamino groups in which each alkyl group may be the same or different and have from 1 to 4 carbon atoms and (xi) dialkylaminoalkyl groups in which the dialkylamino moiety has two straight or branched chain alkyl groups having from 1 to 4 carbon atoms which may be the same or different and the alkyl moiety is a straight or branched chain alkyl group having from 1 to 4 carbon atoms; and Y is an oxygen atom, pharmacologically acceptable salts thereof or pharmacologically acceptable esters thereof;

(50) amidocarboxylic acid derivatives in which $R^1$ is a hydrogen atom;

$R^2$ is an ethylene group;

$R^3$ is a hydrogen atom;

$R^4$ is a hydrogen atom;

Z is a methylene group;

W is a phenoxy group which may have one substituent $\alpha^5$ described below on the phenyl moiety, here, the substituent $\alpha^5$ represents a group selected from the group consisting of (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain halogenated alkoxy groups having from 1 to 4 carbon atoms, (v) straight or branched chain alkylthio groups having one or two carbon atoms, (vi) straight or branched chain alkylsulfonyl groups having one or two carbon atoms, (vii) halogen atoms, (viii) cyano groups and (ix) pyridyl groups;

X represents a phenyl group which may have one substituent $\alpha^{12}$ described below, here, the substituent $\alpha^{12}$ represents a group selected from the group consisting of methyl, isopropyl and hydroxyl groups, fluorine atoms, chlorine atoms, diethylamino and benzyl groups, phenyl groups (the phenyl moiety may be substituted with 1 to 3 substituents, which may be the same or different, including methyl, ethyl, trifluoromethyl, hydroxyl, methoxy, ethoxy, isopropoxy, trifluoromethoxy, methylenedioxy and hydroxymethyl groups, fluorine atoms, chlorine atoms and nitro, formyl, cyano, carboxyl, dimethylamino, diethylamino and N,N-dimethylaminomethyl groups), phenoxy, phenylthio, phenylsulfonyl, phenylsulfonylamino and N-methylphenylsulfonylamino groups, pyridyl groups (the pyridyl moiety may be substituted with a methyl, ethyl, trifluoromethyl, methoxy, ethoxy, isopropoxy or trifluoromethoxy group, a fluorine atom, a chlorine atom or a nitro, dimethylamino or diethylamino group), pyridyloxy, pyridyithio, pyridylsulfonyl and piperidyl groups, or X represents a pyridyl group which may have one substituent $\alpha^{13}$ described below, here, the substituent $\alpha^{13}$ represents a group selected from the group consisting of methyl, isopropyl, methoxy, ethoxy, isopropoxy, 2,2,3,3-tetrafluoropropoxy and benzyloxy groups, alkylthio groups having one or two carbon atoms, alkylsulfonyl groups having one or two carbon atoms, benzyl groups, phenyl groups (the phenyl moiety may be substituted with a methyl, ethyl, trifluoromethyl, methoxy, ethoxy or isopropoxy group, a fluorine atom, a chlorine atom, or a nitro, dimethylarnino or diethylamino group), phenoxy, phenylthio, phenylsulfonyl, phenylsulfonylamino and N-methylphenylsulfonylamino groups; and Y is an oxygen atom, pharmacologically acceptable salts thereof or pharmacologically acceptable esters thereof; and

(51) amidocarboxylic acid derivatives in which $R^1$ is a hydrogen atom;

$R^2$ is an ethylene group;

$R^3$ is a hydrogen atom;

$R^4$ is a hydrogen atom;

Z is a methylene group;

W is a phenoxy group which may have one substituent $\alpha^6$ described below on the phenyl moiety, here, the substituent $\alpha^6$ represents a group selected from the group consisting of methyl, ethyl, isopropyl, t-butyl, trifluoromethyl, methoxy and trifluoromethoxy groups, and fluorine atoms and chlorine atoms;

X is a biphenylyl group (substituents of each phenyl moiety may be the same or different and one of them may be substituted with a methyl, trifluoromethyl, hydroxyl, methoxy or hydroxymethyl group, a fluorine atom, a chlorine atom, or a formyl, carboxyl, nitro, dimethylamino or N,N-dimethylaminomethyl group), a pyridylphenyl group (the pyridyl moiety may be substituted with one substituent chosen from methyl, ethyl, trifluoromethyl, methoxy, ethoxy, isopropoxy and trifluoromethoxy groups, fluorine atoms, chlorine atoms, and nitro, dimethylamino and diethylamino groups) or a phenylpyridyl group (the phenyl moiety may be substituted with one substituent chosen from methyl, ethyl, trifluoromethyl, methoxy, ethoxy and isopropoxy groups, fluorine atoms, chlorine atoms, and nitro and dimethylamino groups); and Y is an oxygen atom, pharmacologically acceptable salts thereof or pharmacologically acceptable esters thereof.

Further, a compound having the following combination is preferable.

(52) amidocarboxylic acid derivatives in which $R^1$ is a hydrogen atom or a straight or branched chain alkyl group having from 1 to 6 carbon atoms;

$R^2$ is a straight or branched chain alkylene group having from 1 to 6 carbon atoms;

$R^3$ is (i) a hydrogen atom, (ii) a straight or branched chain alkyl group having from 1 to 6 carbon atoms, (iii) a straight or branched chain alkoxy group having from 1 to 4 carbon atoms, (iv) a straight or branched chain alkylthio group having from 1 to 4 carbon atoms, (v) a halogen atom, (vi) a nitro group, (vii) a straight or branched chain dialkylamino group in which each alkyl group may be the same or different and have from 1 to 4 carbon atoms, (viii) an aryl group having from 6 to 10 carbon atoms which may have from 1 to 3 substituents $\alpha$ described later or (ix) an aralkyl group having from 7 to 12 carbon atoms which may have from 1 to 3 substituents $\alpha$ described later on the aryl moiety;

$R^4$ is a hydrogen atom or a straight or branched chain alkyl group having from 1 to 6 carbon atoms;

Z is a straight or branched chain alkylene group having from 1 to 4 carbon atoms;

W is an ethyl, propyl, butyl, pentyl, methoxy, ethoxy, propoxy, isopropoxy, methylthio, ethylthio, propylthio, isopropylthio, phenoxy, 4-methylphenoxy, 4-ethylphenoxy, 4-isopropylphenoxy, 4-methoxyphenoxy, 4-chlorophenoxy, phenylthio, benzyl, phenethyl, 3-phenylpropyl or 4-phenylbutyl group;

X represents an aryl group having from 6 to 10 carbon atoms which may have from 1 to 3 substituents $\alpha$ described later or a mono- or dicyclic, 5- to 10-membered hetero aryl group containing from 1 to 4 hetero atoms selected from the group consisting of an oxygen atom, nitrogen atom and sulfur atom which may have from 1 to 3 substituents $\alpha$ described below, here, the substituent $\alpha$ represents a group selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain alkoxy groups having from 1 to 4 carbon atoms, (vi) straight or branched chain alkylenedioxy groups having from 1 to 4 carbon atoms, (vii) aralkyloxy groups having from 7 to 12 carbon atoms, (viii) straight or branched chain alkylthio groups having from 1 to 4 carbon atoms, (ix) straight or branched chain alkylsulfonyl groups having from 1 to 4 carbon atoms, (x) halogen atoms, (xi) nitro groups, (xii) straight or branched chain dialkylamino groups in which each alkyl group may be the same or different and have from 1 to 4 carbon atoms, (xiii) aralkyl groups having from 7 to 12 carbon atoms, (xiv) aryl groups having from 6 to 10 carbon atoms (the aryl moiety may be substituted with a straight or branched chain alkyl group having from 1 to 6 carbon atoms, a straight or branched chain halogenated alkyl group having from 1 to 4 carbon atoms, a straight or branched chain alkoxy group having from 1 to 4 carbon atoms, a halogen atom or a straight or branched chain alkylenedioxy group having from 1 to 4 carbon atoms), (xv) aryloxy groups having from 6 to 10 carbon atoms (the aryl moiety may be substituted with a straight or branched chain alkyl group having from 1 to 6 carbon atoms, a straight or branched chain halogenated alkyl group having from 1 to 4 carbon atoms, a straight or branched chain alkoxy group having from 1 to 4 carbon atoms, a halogen atom or a straight or branched chain alkylenedioxy group having from 1 to 4 carbon atoms), (xvi) arylthio groups having from 6 to 10 carbon atoms (the aryl moiety may be substituted with a straight or branched chain alkyl having from 1 to 6 carbon atoms, a straight or branched chain halogenated alkyl group having from 1 to 4 carbon atoms, a straight or branched chain alkoxy group having from 1 to 4 carbon atoms, a halogen atom or a straight or branched chain alkylenedioxy group having from 1 to 4 carbon atoms), (xvii) arylsulfonyl groups having from 6 to 10 carbon atoms (the aryl moiety may be substituted with a straight or branched chain alkyl group having from 1 to 6 carbon atoms, a straight or branched chain halogenated alkyl group having from 1 to 4 carbon atoms, a straight or branched chain alkoxy group having from 1 to 4 carbon atoms, a halogen atom or a straight or branched chain alkylenedioxy group having from 1 to 4 carbon atoms), (xviii) arylsulfonylamino groups having from 6 to 10 carbon atoms (the aryl moiety may be substituted with a straight or branched chain alkyl group having from 1 to 6 carbon atoms, a straight or branched chain halogenated alkyl group having from 1 to 4 carbon atoms, a straight or branched chain alkoxy group having from 1 to 4 carbon atoms, a halogen atom or a straight or branched chain alkylenedioxy group having from 1 to 4 carbon atoms and the nitrogen atom of the amino moiety may be substituted with a straight or branched chain alkyl group having from 1 to 6 carbon atoms), (xix) mono- or dicyclic, 5- to 10-membered hetero aryl groups containing from 1 to 4 hetero atoms selected from the group consisting of an oxygen atom, nitrogen atom and sulfur atom, (xx) mono- or dicyclic, 5- to 10-membered hetero aryloxy groups containing from 1 to 4 hetero atoms selected from the group consisting of an oxygen atom, nitrogen atom and sulfur atom, (xxi) mono- or dicyclic, 5- to 10-membered hetero arylthio groups containing from 1 to 4 hetero atoms selected from the group consisting of an oxygen atom, nitrogen atom and sulfur atom, (xxii) mono- or dicyclic, 5- to 10-membered hetero arylsulfonyl groups containing from 1 to 4 hetero atoms selected from the group consisting of an oxygen atom, nitrogen atom and sulfur atom and (xxiii) mono- or dicyclic, 5- to 10-membered hetero arylsulfonylamino groups containing from 1 to 4 hetero atoms selected from the group consisting of an oxygen atom, nitrogen atom and sulfur atom (the nitrogen atom of the amino moiety may be substituted with a straight or branched chain alkyl group having from 1 to 6 carbon atoms); and Y is a single bond, an oxygen atom, a sulfur atom or a group of the formula: >N—$R^5$ (wherein $R^5$ represents a hydrogen atom, a straight or branched chain alkyl group having from 1 to 6 carbon atoms, a straight or branched chain aliphatic acyl group having from 1 to 8 carbon atoms or an aromatic acyl group having from 7 to 11 carbon atoms), pharmacologically acceptable salts thereof or pharmacologically acceptable esters thereof.

Exemplified compounds of the amidocarboxylic acid of formula (I), pharmacologically acceptable salts thereof or pharmacologically acceptable esters thereof of the present invention are illustrated in the following Tables.

Incidentally, the following abbreviation is used in Table 1 to Table 155. Ex.No.Comp: Exemplification Number Compound Ac: acetyl, Bu: butyl, tBu: t-butyl, Bimid: benzimidazolyl Boxa: benzoxazolyl, Bthiz: benzothiazolyl, Bz: benzyl, Dea: diethylamino, Dma: dimethylamino, Dmam: dimethylaminomethyl, Et: ethyl, Fur: furyl, Hex: hexyl, Imid: imidazolyl, Ind: indolyl, Isox: isoxazolyl, MdO: methylenedioxy, Me: methyl, Mor: morpholino, Np: naphthyl, Oxa: oxazolyl, Pen: pentyl, Ph: phenyl, Pip: piperidinyl, PPr: 3-phenylpropyl, Pr: propyl, iPr: isopropyl, Pym: pyrimidinyl, Pyr: pyridyl, Pyrd: pyrrolidinyl, Pyrr: pyrrolyl, Pyza: pyrazolyl, Quin: quinolyl, iQuin: isoquinolyl, Tfp: 2,2,3,3-tetrafluoropropyl, Thi: thienyl, Thiz: thiazolyl.

It should be noted that the compounds of Table 1 to Table 145 have the following formula (Ia) and the compounds of Table 146 to Table 155 have the following formula (Ib).

TABLE 1

(Ia) X—CO—N($R^1$)—$R^2$—Y—[phenyl with $R^3$, $R^4$]—Z—C(W)(COOH)

(Ib) X—CO—N($R^1$)—$R^2$—Y—[phenyl with $R^3$]—[$R^4$]—Z—C(W)(COOH)

| Ex. No. Comp. | $R^1$ | $R^2$ | $R^3$ | $R^4$ | Z | W | X | Y |
|---|---|---|---|---|---|---|---|---|
| 1-1 | H | $(CH_2)_2$ | H | H | $CH_2$ | EtO | Ph | O |
| 1-2 | H | $(CH_2)_2$ | H | H | $CH_2$ | EtO | 1-Np | O |
| 1-3 | H | $(CH_2)_2$ | H | H | $CH_2$ | EtO | 2-Np | O |
| 1-4 | H | $(CH_2)_2$ | H | H | $CH_2$ | EtO | 4-Me-Ph | O |
| 1-5 | H | $(CH_2)_2$ | H | H | $CH_2$ | EtO | 4-Et-Ph | O |
| 1-6 | H | $(CH_2)_2$ | H | H | $CH_2$ | EtO | 3-iPr-Ph | O |
| 1-7 | H | $(CH_2)_2$ | H | H | $CH_2$ | EtO | 4-iPr-Ph | O |
| 1-8 | H | $(CH_2)_2$ | H | H | $CH_2$ | EtO | 3-tBu-Ph | O |
| 1-9 | H | $(CH_2)_2$ | H | H | $CH_2$ | EtO | 4-tBu-Ph | O |
| 1-10 | H | $(CH_2)_2$ | H | H | $CH_2$ | EtO | 3-F-Ph | O |
| 1-11 | H | $(CH_2)_2$ | H | H | $CH_2$ | EtO | 4-F-Ph | O |
| 1-12 | H | $(CH_2)_2$ | H | H | $CH_2$ | EtO | 4-Cl-Ph | O |
| 1-13 | H | $(CH_2)_2$ | H | H | $CH_2$ | EtO | 4-Br-Ph | O |
| 1-14 | H | $(CH_2)_2$ | H | H | $CH_2$ | EtO | 3-Ph-Ph | O |
| 1-15 | H | $(CH_2)_2$ | H | H | $CH_2$ | EtO | 4-Ph-Ph | O |
| 1-16 | H | $(CH_2)_2$ | H | H | $CH_2$ | EtO | 4-BzO-Ph | O |
| 1-17 | H | $(CH_2)_2$ | H | H | $CH_2$ | EtO | 4-Bz-Ph | O |
| 1-18 | H | $(CH_2)_2$ | H | H | $CH_2$ | EtO | 3-PhO-Ph | O |
| 1-19 | H | $(CH_2)_2$ | H | H | $CH_2$ | EtO | 4-PhO-Ph | O |
| 1-20 | H | $(CH_2)_2$ | H | H | $CH_2$ | EtO | 3-PhS-Ph | O |
| 1-21 | H | $(CH_2)_2$ | H | H | $CH_2$ | EtO | 4-PhS-Ph | O |
| 1-22 | H | $(CH_2)_2$ | H | H | $CH_2$ | EtO | 3-$PhSO_2$-Ph | O |
| 1-23 | H | $(CH_2)_2$ | H | H | $CH_2$ | EtO | 4-$PhSO_2$-Ph | O |
| 1-24 | H | $(CH_2)_2$ | H | H | $CH_2$ | EtO | 3-(Imid-1)-Ph | O |
| 1-25 | H | $(CH_2)_2$ | H | H | $CH_2$ | EtO | 4-(Imid-1)-Ph | O |
| 1-26 | H | $(CH_2)_2$ | H | H | $CH_2$ | EtO | 3-(Imid-4)-Ph | O |
| 1-27 | H | $(CH_2)_2$ | H | H | $CH_2$ | EtO | 4-(Imid-4)-Ph | O |
| 1-28 | H | $(CH_2)_2$ | H | H | $CH_2$ | EtO | 3-(Fur-2)-Ph | O |
| 1-29 | H | $(CH_2)_2$ | H | H | $CH_2$ | EtO | 4-(Fur-2)-Ph | O |
| 1-30 | H | $(CH_2)_2$ | H | H | $CH_2$ | EtO | 3-(Thi-2)-Ph | O |
| 1-31 | H | $(CH_2)_2$ | H | H | $CH_2$ | EtO | 4-(Thi-2)-Ph | O |
| 1-32 | H | $(CH_2)_2$ | H | H | $CH_2$ | EtO | 3-(Thi-3)-Ph | O |
| 1-33 | H | $(CH_2)_2$ | H | H | $CH_2$ | EtO | 4-(Thi-3)-Ph | O |
| 1-34 | H | $(CH_2)_2$ | H | H | $CH_2$ | EtO | 3-(Pyr-2)-Ph | O |
| 1-35 | H | $(CH_2)_2$ | H | H | $CH_2$ | EtO | 4-(Pyr-2)-Ph | O |
| 1-36 | H | $(CH_2)_2$ | H | H | $CH_2$ | EtO | 3-(Pyr-3)-Ph | O |
| 1-37 | H | $(CH_2)_2$ | H | H | $CH_2$ | EtO | 4-(Pyr-3)-Ph | O |
| 1-38 | H | $(CH_2)_2$ | H | H | $CH_2$ | EtO | 3-(Pyr-4)-Ph | O |
| 1-39 | H | $(CH_2)_2$ | H | H | $CH_2$ | EtO | 4-(Pyr-4)-Ph | O |
| 1-40 | H | $(CH_2)_2$ | H | H | $CH_2$ | EtO | 3-(Oxa-2)-Ph | O |
| 1-41 | H | $(CH_2)_2$ | H | H | $CH_2$ | EtO | 4-(Oxa-2)-Ph | O |
| 1-42 | H | $(CH_2)_2$ | H | H | $CH_2$ | EtO | 3-(Oxa-4)-Ph | O |
| 1-43 | H | $(CH_2)_2$ | H | H | $CH_2$ | EtO | 4-(Oxa-4)-Ph | O |
| 1-44 | H | $(CH_2)_2$ | H | H | $CH_2$ | EtO | 3-(Oxa-5)-Ph | O |
| 1-45 | H | $(CH_2)_2$ | H | H | $CH_2$ | EtO | 4-(Oxa-5)-Ph | O |
| 1-46 | H | $(CH_2)_2$ | H | H | $CH_2$ | EtO | 3-(Thiz-2)-Ph | O |
| 1-47 | H | $(CH_2)_2$ | H | H | $CH_2$ | EtO | 4-(Thiz-2)-Ph | O |
| 1-48 | H | $(CH_2)_2$ | H | H | $CH_2$ | EtO | 3-(Thiz-4)-Ph | O |
| 1-49 | H | $(CH_2)_2$ | H | H | $CH_2$ | EtO | 4-(Thiz-4)-Ph | O |
| 1-50 | H | $(CH_2)_2$ | H | H | $CH_2$ | EtO | 3-(Thiz-5)-Ph | O |
| 1-51 | H | $(CH_2)_2$ | H | H | $CH_2$ | EtO | 4-(Thiz-5)-Ph | O |
| 1-52 | H | $(CH_2)_2$ | H | H | $CH_2$ | EtO | 1-Me-2-Pyrr | O |
| 1-53 | H | $(CH_2)_2$ | H | H | $CH_2$ | EtO | 1-Ph-2-Pyrr | O |
| 1-54 | H | $(CH_2)_2$ | H | H | $CH_2$ | EtO | 1-Bz-2-Pyrr | O |
| 1-55 | H | $(CH_2)_2$ | H | H | $CH_2$ | EtO | 5-Me-2-Fur | O |
| 1-56 | H | $(CH_2)_2$ | H | H | $CH_2$ | EtO | 5-Ph-2-Fur | O |
| 1-57 | H | $(CH_2)_2$ | H | H | $CH_2$ | EtO | 5-Me-2-Thi | O |

TABLE 1-continued (Ia)
X—CO—N(R¹)—R²—Y—C₆H₃(R³)—Z—C(R⁴)(W)—COOH (Ib)
X—CO—N(R¹)—R²—Y—C₆H₃(R³)—[meta]—Z—C(R⁴)(W)—COOH

| Ex. No. Comp. | R¹ | R² | R³ | R⁴ | Z | W | X | Y |
|---|---|---|---|---|---|---|---|---|
| 1-58 | H | (CH₂)₂ | H | H | CH₂ | EtO | 5-Ph-2-Thi | O |
| 1-59 | H | (CH₂)₂ | H | H | CH₂ | EtO | 5-Me-3-Thi | O |
| 1-60 | H | (CH₂)₂ | H | H | CH₂ | EtO | 5-Ph-3-Thi | O |
| 1-61 | H | (CH₂)₂ | H | H | CH₂ | EtO | 1-Me-3-Pyza | O |
| 1-62 | H | (CH₂)₂ | H | H | CH₂ | EtO | 1-Ph-3-Pyza | O |
| 1-63 | H | (CH₂)₂ | H | H | CH₂ | EtO | 1-Me-2-Imid | O |
| 1-64 | H | (CH₂)₂ | H | H | CH₂ | EtO | 1-Ph-2-Imid | O |
| 1-65 | H | (CH₂)₂ | H | H | CH₂ | EtO | 1-Me-4-Imid | O |
| 1-66 | H | (CH₂)₂ | H | H | CH₂ | EtO | 1-Ph-4-Imid | O |
| 1-67 | H | (CH₂)₂ | H | H | CH₂ | EtO | 4-Oxa | O |
| 1-68 | H | (CH₂)₂ | H | H | CH₂ | EtO | 5-Oxa | O |
| 1-69 | H | (CH₂)₂ | H | H | CH₂ | EtO | 2-Me-4-Oxa | O |
| 1-70 | H | (CH₂)₂ | H | H | CH₂ | EtO | 2-Ph-4-Oxa | O |
| 1-71 | H | (CH₂)₂ | H | H | CH₂ | EtO | 2-Me-5-Oxa | O |
| 1-72 | H | (CH₂)₂ | H | H | CH₂ | EtO | 2-Ph-5-Oxa | O |
| 1-73 | H | (CH₂)₂ | H | H | CH₂ | EtO | 4-Me-2-Ph-5-Oxa | O |
| 1-74 | H | (CH₂)₂ | H | H | CH₂ | EtO | 5-Me-2-Ph-4-Oxa | O |
| 1-75 | H | (CH₂)₂ | H | H | CH₂ | EtO | 4-Thiz | O |
| 1-76 | H | (CH₂)₂ | H | H | CH₂ | EtO | 5-Thiz | O |
| 1-77 | H | (CH₂)₂ | H | H | CH₂ | EtO | 2-Me-4-Thiz | O |
| 1-78 | H | (CH₂)₂ | H | H | CH₂ | EtO | 2-Ph-4-Thiz | O |
| 1-79 | H | (CH₂)₂ | H | H | CH₂ | EtO | 2-Me-5-Thiz | O |
| 1-80 | H | (CH₂)₂ | H | H | CH₂ | EtO | 2-Ph-5-Thiz | O |
| 1-81 | H | (CH₂)₂ | H | H | CH₂ | EtO | 4-Me-2-Ph-5-Thiz | O |
| 1-82 | H | (CH₂)₂ | H | H | CH₂ | Eto | 5-Me-2-Ph-4-Thiz | O |
| 1-83 | H | (CH₂)₂ | H | H | CH₂ | Eto | 1-Me-4-Pyza | O |
| 1-84 | H | (CH₂)₂ | H | H | CH₂ | EtO | 1-Ph-4-Pyza | O |
| 1-85 | H | (CH₂)₂ | H | H | CH₂ | EtO | 2-Me-4-Isox | O |
| 1-86 | H | (CH₂)₂ | H | H | CH₂ | EtO | 2-Ph-4-Isox | O |
| 1-87 | H | (CH₂)₂ | H | H | CH₂ | EtO | 2-Pyr | O |
| 1-88 | H | (CH₂)₂ | H | H | CH₂ | EtO | 3-Pyr | O |
| 1-89 | H | (CH₂)₂ | H | H | CH₂ | EtO | 4-Pyr | O |
| 1-90 | H | (CH₂)₂ | H | H | CH₂ | EtO | 3-Me-5-Pyr | O |
| 1-91 | H | (CH₂)₂ | H | H | CH₂ | EtO | 3-Et-5-Pyr | O |
| 1-92 | H | (CH₂)₂ | H | H | CH₂ | EtO | 3-Ph-5-Pyr | O |
| 1-93 | H | (CH₂)₂ | H | H | CH₂ | EtO | 2-Me-5-Pyr | O |
| 1-94 | H | (CH₂)₂ | H | H | CH₂ | EtO | 2-BzO-5-Pyr | O |
| 1-95 | H | (CH₂)₂ | H | H | CH₂ | EtO | 2-Ph-5-Pyr | O |
| 1-96 | H | (CH₂)₂ | H | H | CH₂ | EtO | 2-MeO-5-Pyr | O |
| 1-97 | H | (CH₂)₂ | H | H | CH₂ | EtO | 2-EtO-5-Pyr | O |
| 1-98 | H | (CH₂)₂ | H | H | CH₂ | EtO | 2-iPrO-5-Pyr | O |
| 1-99 | H | (CH₂)₂ | H | H | CH₂ | EtO | 2-MeS-5-Pyr | O |
| 1-100 | H | (CH₂)₂ | H | H | CH₂ | EtO | 2-EtS-5-Pyr | O |
| 1-101 | H | (CH₂)₂ | H | H | CH₂ | EtO | 2-PhSO₂NH-5-Pyr | O |
| 1-102 | H | (CH₂)₂ | H | H | CH₂ | EtO | 2-MeSO₂-5-Pyr | O |
| 1-103 | H | (CH₂)₂ | H | H | CH₂ | EtO | 2-EtSO₂-5-Pyr | O |
| 1-104 | H | (CH₂)₂ | H | H | CH₂ | EtO | 2-PhSO₂NMe-5-Pyr | O |
| 1-105 | H | (CH₂)₂ | H | H | CH₂ | EtO | 2-Bz-5-Pyr | O |
| 1-106 | H | (CH₂)₂ | H | H | CH₂ | EtO | 2-PhO-5-Pyr | O |
| 1-107 | H | (CH₂)₂ | H | H | CH₂ | EtO | 2-PhS-5-Pyr | O |
| 1-108 | H | (CH₂)₂ | H | H | CH₂ | EtO | 2-PhSO₂-5-Pyr | O |
| 1-109 | H | (CH₂)₂ | H | H | CH₂ | EtO | 3-Me-6-Pyr | O |
| 1-110 | H | (CH₂)₂ | H | H | CH₂ | EtO | 3-Ph-6-Pyr | O |
| 1-111 | H | (CH₂)₂ | H | H | CH₂ | EtO | 2-Me-6-Pyr | O |
| 1-112 | H | (CH₂)₂ | H | H | CH₂ | EtO | 2-Ph-6-Pyr | O |
| 1-113 | H | (CH₂)₂ | H | H | CH₂ | EtO | 2-Me-4-Pym | O |
| 1-114 | H | (CH₂)₂ | H | H | CH₂ | EtO | 2-Ph-4-Pym | O |
| 1-115 | H | (CH₂)₂ | H | H | CH₂ | EtO | 2-MeO-4-Pym | O |
| 1-116 | H | (CH₂)₂ | H | H | CH₂ | EtO | 2-EtO-4-Pym | O |
| 1-117 | H | (CH₂)₂ | H | H | CH₂ | EtO | 2-iPrO-4-Pym | O |
| 1-118 | H | (CH₂)₂ | H | H | CH₂ | EtO | 2-MeS-4-Pym | O |
| 1-119 | H | (CH₂)₂ | H | H | CH₂ | EtO | 2-EtS-4-Pym | O |
| 1-120 | H | (CH₂)₂ | H | H | CH₂ | EtO | 2-iPrS-4-Pym | O |
| 1-121 | H | (CH₂)₂ | H | H | CH₂ | EtO | 6-MeS-4-Pym | O |
| 1-122 | H | (CH₂)₂ | H | H | CH₂ | EtO | 6-EtS-4-Pym | O |
| 1-123 | H | (CH₂)₂ | H | H | CH₂ | EtO | 6-iPrS-4-Pym | O |
| 1-124 | H | (CH₂)₂ | H | H | CH₂ | EtO | 2-PhS-4-Pym | O |
| 1-125 | H | (CH₂)₂ | H | H | CH₂ | EtO | 2-MeSO₂-4-Pym | O |
| 1-126 | H | (CH₂)₂ | H | H | CH₂ | EtO | 2-EtSO₂-4-Pym | O |
| 1-127 | H | (CH₂)₂ | H | H | CH₂ | EtO | 2-iPrSO₂-4-Pym | O |
| 1-128 | H | (CH₂)₂ | H | H | CH₂ | EtO | 2-PhSO₂-4-Pym | O |
| 1-129 | H | (CH₂)₂ | H | H | CH₂ | EtO | 2-Me-5-Pym | O |
| 1-130 | H | (CH₂)₂ | H | H | CH₂ | EtO | 2-Ph-5-Pym | O |
| 1-131 | H | (CH₂)₂ | H | H | CH₂ | EtO | 2-MeO-5-Pym | O |
| 1-132 | H | (CH₂)₂ | H | H | CH₂ | EtO | 2-EtO-5-Pym | O |
| 1-133 | H | (CH₂)₂ | H | H | CH₂ | EtO | 2-iPrO-5-Pym | O |
| 1-134 | H | (CH₂)₂ | H | H | CH₂ | EtO | 2-MeS-5-Pym | O |
| 1-135 | H | (CH₂)₂ | H | H | CH₂ | EtO | 2-EtS-5-Pym | O |
| 1-136 | H | (CH₂)₂ | H | H | CH₂ | EtO | 2-iPrS-5-Pym | O |
| 1-137 | H | (CH₂)₂ | H | H | CH₂ | EtO | 2-PhS-5-Pym | O |
| 1-138 | H | (CH₂)₂ | H | H | CH₂ | EtO | 2-MeSO₂-5-Pym | O |
| 1-139 | H | (CH₂)₂ | H | H | CH₂ | EtO | 2-EtSO₂-5-Pym | O |
| 1-140 | H | (CH₂)₂ | H | H | CH₂ | EtO | 2-iPrSO₂-5-Pym | O |
| 1-141 | H | (CH₂)₂ | H | H | CH₂ | EtO | 2-PhSO₂-5-Pym | O |
| 1-142 | H | (CH₂)₂ | H | H | CH₂ | EtO | 2-Ind | O |
| 1-143 | H | (CH₂)₂ | H | H | CH₂ | EtO | 3-Ind | O |
| 1-144 | H | (CH₂)₂ | H | H | CH₂ | EtO | 1-Me-2-Ind | O |
| 1-145 | H | (CH₂)₂ | H | H | CH₂ | EtO | 1-Me-3-Ind | O |
| 1-146 | H | (CH₂)₂ | H | H | CH₂ | EtO | 2-Bimid | O |
| 1-147 | H | (CH₂)₂ | H | H | CH₂ | EtO | 2-Boxa | O |
| 1-148 | H | (CH₂)₂ | H | H | CH₂ | EtO | 2-Bthiz | O |
| 1-149 | H | (CH₂)₂ | H | H | CH₂ | EtO | 2-Quin | O |
| 1-150 | H | (CH₂)₂ | H | H | CH₂ | EtO | 3-Quin | O |
| 1-151 | H | (CH₂)₂ | H | H | CH₂ | EtO | 4-Quin | O |
| 1-152 | H | (CH₂)₂ | H | H | CH₂ | EtO | 1-iQuin | O |
| 1-153 | H | (CH₂)₂ | H | H | CH₂ | EtO | 3-iQuin | O |
| 1-154 | H | (CH₂)₂ | H | H | CH₂ | EtO | 4-iQuin | O |
| 1-155 | H | (CH₂)₂ | H | H | CH₂ | EtO | 3-MeO-Ph | O |
| 1-156 | H | (CH₂)₂ | H | H | CH₂ | EtO | 4-MeO-Ph | O |
| 1-157 | H | (CH₂)₂ | H | H | CH₂ | EtO | 3-EtO-Ph | O |
| 1-158 | H | (CH₂)₂ | H | H | CH₂ | EtO | 4-EtO-Ph | O |
| 1-159 | H | (CH₂)₂ | H | H | CH₂ | EtO | 3-iPrO-Ph | O |
| 1-160 | H | (CH₂)₂ | H | H | CH₂ | EtO | 4-iPrO-Ph | O |
| 1-161 | H | (CH₂)₂ | H | H | CH₂ | EtO | 3-MeS-Ph | O |
| 1-162 | H | (CH₂)₂ | H | H | CH₂ | EtO | 4-MeS-Ph | O |
| 1-163 | H | (CH₂)₂ | H | H | CH₂ | EtO | 3-EtS-Ph | O |
| 1-164 | H | (CH₂)₂ | H | H | CH₂ | EtO | 4-EtS-Ph | O |
| 1-165 | H | (CH₂)₂ | H | H | CH₂ | EtO | 3-iPrS-Ph | O |
| 1-166 | H | (CH₂)₂ | H | H | CH₂ | EtO | 4-iPrS-Ph | O |
| 1-167 | H | (CH₂)₂ | H | H | CH₂ | EtO | 3-MeSO₂-Ph | O |
| 1-168 | H | (CH₂)₂ | H | H | CH₂ | EtO | 4-MeSO₂-Ph | O |
| 1-169 | H | (CH₂)₂ | H | H | CH₂ | EtO | 3-EtSO₂-Ph | O |
| 1-170 | H | (CH₂)₂ | H | H | CH₂ | EtO | 4-EtSO₂-Ph | O |
| 1-171 | H | (CH₂)₂ | H | H | CH₂ | EtO | 3-iPrSO₂-Ph | O |

TABLE 1-continued

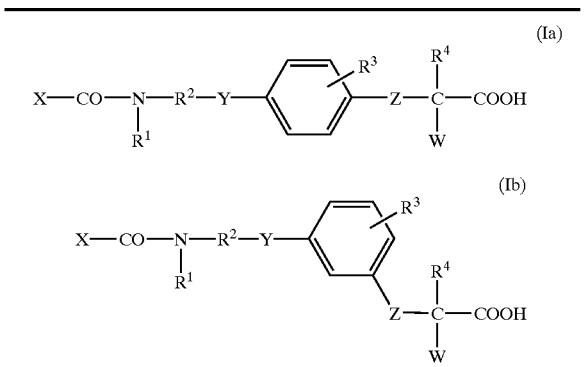

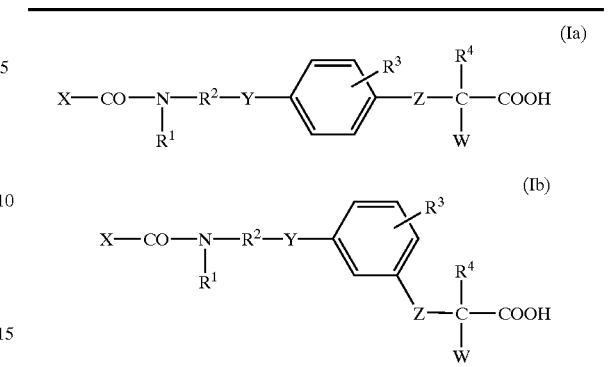

| Ex. No. Comp. | R¹ | R² | R³ | R⁴ | Z | W | X | Y |
|---|---|---|---|---|---|---|---|---|
| 1-172 | H | (CH₂)₂ | H | H | CH₂ | EtO | 4-iPrSO₂-Ph | O |
| 1-173 | H | (CH₂)₂ | H | H | CH₂ | EtO | 3-(1-Me-Imid-4)-Ph | O |
| 1-174 | H | (CH₂)₂ | H | H | CH₂ | EtO | 4-(1-Me-Imid-4)-Ph | O |
| 1-175 | H | (CH₂)₂ | H | H | CH₂ | EtO | 1-Me-2-Ph-4-Imid | O |
| 1-176 | H | (CH₂)₂ | H | H | CH₂ | EtO | 1,4-di-Me-2-Ph-5-Imid | O |
| 1-177 | H | (CH₂)₂ | H | H | CH₂ | EtO | 1,5-di-Me-2-Ph-4-Imid | O |
| 1-178 | H | (CH₂)₂ | H | H | CH₂ | EtO | 3,4-MdO-Ph | O |
| 1-179 | H | (CH₂)₂ | H | H | CH₂ | EtO | 4-(4-MeO-Ph)-Ph | O |
| 1-180 | H | (CH₂)₂ | H | H | CH₂ | EtO | 4-(3,4-MdO-Ph)-Ph | O |
| 1-181 | H | (CH₂)₂ | H | H | CH₂ | EtO | 4-[PhSO₂N(Me)]-Ph | O |
| 1-182 | H | (CH₂)₂ | H | H | CH₂ | EtO | 4-[(Pyr-3)SO₂N(Me)]-Ph | O |
| 1-183 | H | (CH₂)₂ | H | H | CH₂ | EtO | 4-(PhSO₂NH)-Ph | O |
| 1-184 | H | (CH₂)₂ | H | H | CH₂ | EtO | 4-[(Pyr-3)SO₂NH]-Ph | O |
| 1-185 | H | (CH₂)₂ | H | H | CH₂ | EtO | 4-[(Pyr-2)SO₂]-Ph | O |
| 1-186 | H | (CH₂)₂ | H | H | CH₂ | EtO | 4-[(Pyr-3)SO₂]-Ph | O |
| 1-187 | H | (CH₂)₂ | H | H | CH₂ | EtO | 4-[(Pyr-2)SO₂N(Me)]-Ph | O |
| 1-188 | H | (CH₂)₂ | H | H | CH₂ | EtO | 4-[(Pyr-2)SO₂NH]-Ph | O |
| 1-189 | H | (CH₂)₂ | H | H | CH₂ | EtO | 4-(4-Me-Ph)-Ph | O |
| 1-190 | H | (CH₂)₂ | H | H | CH₂ | EtO | 4-(4-F-Ph)-Ph | O |
| 1-191 | H | (CH₂)₂ | H | H | CH₂ | EtO | 4-(4-CF₃-Ph)-Ph | O |
| 1-192 | H | (CH₂)₂ | H | H | CH₂ | EtO | 2-[PhSO₂N(Me)]-5-Pyr | O |
| 1-193 | H | (CH₂)₂ | H | H | CH₂ | EtO | 2-HO-5-Pyr | O |
| 1-194 | H | (CH₂)₂ | H | H | CH₂ | EtO | 2-BzO-5-Pyr | O |
| 1-195 | H | (CH₂)₂ | H | H | CH₂ | EtO | 4-[(Pyr-4)SO₂]-Ph | O |
| 1-196 | H | (CH₂)₂ | H | H | CH₂ | EtO | 4-[(Pyr-4)O]-Ph | O |
| 1-197 | H | (CH₂)₂ | H | H | CH₂ | EtO | 4-[(Pyr-4)S]-Ph | O |
| 1-198 | H | (CH₂)₂ | H | H | CH₂ | EtO | 3-HO-Ph | O |
| 1-199 | H | (CH₂)₂ | H | H | CH₂ | EtO | 4-HO-Ph | O |
| 1-200 | H | (CH₂)₂ | H | H | CH₂ | EtO | 2-HO-3,4,6-tri-Me-Ph | O |
| 1-201 | H | (CH₂)₂ | H | H | CH₂ | EtO | 4-HO-3,5-di-Me-Ph | O |
| 1-202 | H | (CH₂)₂ | H | H | CH₂ | EtO | 3-AcO-Ph | O |
| 1-203 | H | (CH₂)₂ | H | H | CH₂ | EtO | 4-AcO-Ph | O |
| 1-204 | H | (CH₂)₂ | H | H | CH₂ | EtO | 4-(4-Cl-Ph)-Ph | O |
| 1-205 | H | (CH₂)₂ | H | H | CH₂ | EtO | 4-(4-HO-3,5-di-Me-Ph)-Ph | O |
| 1-206 | H | (CH₂)₂ | H | H | CH₂ | EtO | 4-(4-HO-Ph)-Ph | O |
| 1-207 | H | (CH₂)₂ | H | H | CH₂ | EtO | 4-(4-OHC-Ph)-Ph | O |
| 1-208 | H | (CH₂)₂ | H | H | CH₂ | EtO | 4-(4-Dmam-Ph)-Ph | O |
| 1-209 | H | (CH₂)₂ | H | H | CH₂ | EtO | 4-(4-Dma-Ph)-Ph | O |
| 1-210 | H | (CH₂)₂ | H | H | CH₂ | EtO | 4-(4-HOOC-Ph)-Ph | O |
| 1-211 | H | (CH₂)₂ | H | H | CH₂ | EtO | 4-(4-HOH₂C-Ph)-Ph | O |
| 1-212 | H | (CH₂)₂ | H | H | CH₂ | EtO | 4-(3-MeO-Ph)-Ph | O |
| 1-213 | H | (CH₂)₂ | H | H | CH₂ | EtO | 4-(3-HO-Ph)-Ph | O |
| 1-214 | H | (CH₂)₂ | H | H | CH₂ | EtO | 4-(3-OHC-Ph)-Ph | O |
| 1-215 | H | (CH₂)₂ | H | H | CH₂ | EtO | 4-(3-Dmam-Ph)-Ph | O |
| 1-216 | H | (CH₂)₂ | H | H | CH₂ | EtO | 4-(3-Dma-Ph)-Ph | O |
| 1-217 | H | (CH₂)₂ | H | H | CH₂ | EtO | 4-(3-HOOC-Ph)-Ph | O |
| 1-218 | H | (CH₂)₂ | H | H | CH₂ | EtO | 4-(3-HOH₂C-Ph)-Ph | O |
| 1-219 | H | (CH₂)₂ | H | H | CH₂ | EtO | 4-(2-MeO-Ph)-Ph | O |
| 1-220 | H | (CH₂)₂ | H | H | CH₂ | EtO | 4-(2-HO-Ph)-Ph | O |
| 1-221 | H | (CH₂)₂ | H | H | CH₂ | EtO | 4-(2-OHC-Ph)-Ph | O |
| 1-222 | H | (CH₂)₂ | H | H | CH₂ | EtO | 4-(3-MeO-Pyr-6)-Ph | O |
| 1-223 | H | (CH₂)₂ | H | H | CH₂ | EtO | 4-(3-EtO-Pyr-6)-Ph | O |
| 1-224 | H | (CH₂)₂ | H | H | CH₂ | EtO | 4-(3-iPrO-Pyr-6)-Ph | O |
| 1-225 | H | (CH₂)₂ | H | H | CH₂ | EtO | 4-(3-Dma-Pyr-6)-Ph | O |
| 1-226 | H | (CH₂)₂ | H | H | CH₂ | EtO | 4-(3-Dea-Pyr-6)-Ph | O |
| 1-227 | H | (CH₂)₂ | H | H | CH₂ | EtO | 4-(3-F₃C-Pyr-6)-Ph | O |
| 1-228 | H | (CH₂)₂ | H | H | CH₂ | EtO | 4-(3-O₂N-Pyr-6)-Ph | O |
| 1-229 | H | (CH₂)₂ | H | H | CH₂ | EtO | 4-Pip-Ph | O |
| 1-230 | H | (CH₂)₂ | H | H | CH₂ | EtO | 4-Dea-Ph | O |
| 1-231 | H | (CH₂)₂ | H | H | CH₂ | EtO | 2-(4-F-Ph)-5-Pyr | O |
| 1-232 | H | (CH₂)₂ | H | H | CH₂ | EtO | 2-(4-Cl-Ph)-5-Pyr | O |
| 1-233 | H | (CH₂)₂ | H | H | CH₂ | EtO | 2-(4-MeO-Ph)-5-Pyr | O |
| 1-234 | H | (CH₂)₂ | H | H | CH₂ | EtO | 2-(4-EtO-Ph)-5-Pyr | O |
| 1-235 | H | (CH₂)₂ | H | H | CH₂ | EtO | 2-(4-iPrO-Ph)-5-Pyr | O |
| 1-236 | H | (CH₂)₂ | H | H | CH₂ | EtO | 2-TfpO-5-Pyr | O |
| 1-237 | H | (CH₂)₂ | H | H | CH₂ | EtO | 4-(4-AcO-Ph)-Ph | O |
| 1-238 | H | (CH₂)₂ | H | H | CH₂ | EtO | 4-(3-F-Ph)-Ph | G |
| 1-239 | H | (CH₂)₂ | H | H | CH₂ | EtO | 4-(3-Cl-Ph)-Ph | O |
| 1-240 | H | (CH₂)₂ | H | H | CH₂ | EtO | 4-(3-Me-Ph)-Ph | O |
| 1-241 | H | (CH₂)₂ | H | H | CH₂ | EtO | 4-(3-AcO-Ph)-Ph | O |
| 1-242 | H | (CH₂)₂ | H | H | CH₂ | EtO | 4-(3-Me-Pyr-6)-Ph | O |
| 1-243 | H | (CH₂)₂ | H | H | CH₂ | EtO | 4-(3-Et-Pyr-6)-Ph | O |
| 1-244 | H | (CH₂)₂ | H | H | CH₂ | EtO | 2-(4-Me-Ph)-5-Pyr | O |
| 1-245 | H | (CH₂)₂ | H | H | CH₂ | EtO | 2-(4-CF₃-Ph)-5-Pyr | O |
| 1-246 | H | (CH₂)₂ | H | H | CH₂ | EtO | 2-(4-Dma-Ph)-5-Pyr | O |
| 1-247 | H | (CH₂)₂ | H | H | CH₂ | EtO | 2-(3-F-Ph)-5-Pyr | O |
| 1-248 | H | (CH₂)₂ | H | H | CH₂ | EtO | 2-(3-Cl-Ph)-5-Pyr | O |
| 1-249 | H | (CH₂)₂ | H | H | CH₂ | EtO | 2-(3-MeO-Ph)-5-Pyr | O |
| 1-250 | H | (CH₂)₂ | H | H | CH₂ | EtO | 2-(3-EtO-Ph)-5-Pyr | O |
| 1-251 | H | (CH₂)₂ | H | H | CH₂ | EtO | 2-(3-iPrO-Ph)-5-Pyr | O |
| 1-252 | H | (CH₂)₂ | H | H | CH₂ | EtO | 2-(3-Me-Ph)-5-Pyr | O |
| 1-253 | H | (CH₂)₂ | H | H | CH₂ | EtO | 2-(3-CF₃-Ph)-5-Pyr | O |
| 1-254 | H | (CH₂)₂ | H | H | CH₂ | EtO | 2-(3-Dma-Ph)-5-Pyr | O |

TABLE 2

| Ex. No. Comp. | R¹ | R² | R³ | R⁴ | Z | W | X | Y |
|---|---|---|---|---|---|---|---|---|
| 2-1 | H | (CH₂)₂ | H | H | CH₂ | MeO | Ph | O |
| 2-2 | H | (CH₂)₂ | H | H | CH₂ | MeO | 1-Np | O |
| 2-3 | H | (CH₂)₂ | H | H | CH₂ | MeO | 2-Np | O |
| 2-4 | H | (CH₂)₂ | H | H | CH₂ | MeO | 4-Me-Ph | O |
| 2-5 | H | (CH₂)₂ | H | H | CH₂ | MeO | 4-Et-Ph | O |
| 2-6 | H | (CH₂)₂ | H | H | CH₂ | MeO | 3-iPr-Ph | O |
| 2-7 | H | (CH₂)₂ | H | H | CH₂ | MeO | 4-iPr-Ph | O |
| 2-8 | H | (CH₂)₂ | H | H | CH₂ | MeO | 3-tBu-Ph | O |
| 2-9 | H | (CH₂)₂ | H | H | CH₂ | MeO | 4-tBu-Ph | O |
| 2-10 | H | (CH₂)₂ | H | H | CH₂ | MeO | 3-F-Ph | O |
| 2-11 | H | (CH₂)₂ | H | H | CH₂ | MeO | 4-F-Ph | O |

TABLE 2-continued

| Ex. No. Comp. | R¹ | R² | R³ | R⁴ | Z | W | X | Y |
|---|---|---|---|---|---|---|---|---|
| 2-12 | H | (CH₂)₂ | H | H | CH₂ | MeO | 4-Cl-Ph | O |
| 2-13 | H | (CH₂)₂ | H | H | CH₂ | MeO | 4-Br-Ph | O |
| 2-14 | H | (CH₂)₂ | H | H | CH₂ | MeO | 3-Ph-Ph | O |
| 2-15 | H | (CH₂)₂ | H | H | CH₂ | MeO | 4-Ph-Ph | O |
| 2-16 | H | (CH₂)₂ | H | H | CH₂ | MeO | 4-BzO-Ph | O |
| 2-17 | H | (CH₂)₂ | H | H | CH₂ | MeO | 4-Bz-Ph | O |
| 2-18 | H | (CH₂)₂ | H | H | CH₂ | MeO | 3-PhO-Ph | O |
| 2-19 | H | (CH₂)₂ | H | H | CH₂ | MeO | 4-PhO-Ph | O |
| 2-20 | H | (CH₂)₂ | H | H | CH₂ | MeO | 3-PhS-Ph | O |
| 2-21 | H | (CH₂)₂ | H | H | CH₂ | MeO | 4-PhS-Ph | O |
| 2-22 | H | (CH₂)₂ | H | H | CH₂ | MeO | 3-PhSO₂-Ph | O |
| 2-23 | H | (CH₂)₂ | H | H | CH₂ | MeO | 4-PhSO₂-Ph | O |
| 2-24 | H | (CH₂)₂ | H | H | CH₂ | MeO | 3-(Imid-1)-Ph | O |
| 2-25 | H | (CH₂)₂ | H | H | CH₂ | MeO | 4-(Imid-1)-Ph | O |
| 2-26 | H | (CH₂)₂ | H | H | CH₂ | MeO | 3-(Imid-4)-Ph | O |
| 2-27 | H | (CH₂)₂ | H | H | CH₂ | MeO | 4-(Imid-4)-Ph | O |
| 2-28 | H | (CH₂)₂ | H | H | CH₂ | MeO | 3-(Fur-2)-Ph | O |
| 2-29 | H | (CH₂)₂ | H | H | CH₂ | MeO | 4-(Fur-2)-Ph | O |
| 2-30 | H | (CH₂)₂ | H | H | CH₂ | MeO | 3-(Thi-2)-Ph | O |
| 2-31 | H | (CH₂)₂ | H | H | CH₂ | MeO | 4-(Thi-2)-Ph | O |
| 2-32 | H | (CH₂)₂ | H | H | CH₂ | MeO | 3-(Thi-3)-Ph | O |
| 2-33 | H | (CH₂)₂ | H | H | CH₂ | MeO | 4-(Thi-3)-Ph | O |
| 2-34 | H | (CH₂)₂ | H | H | CH₂ | MeO | 3-(Pyr-2)-Ph | O |
| 2-35 | H | (CH₂)₂ | H | H | CH₂ | MeO | 4-(Pyr-2)-Ph | O |
| 2-36 | H | (CH₂)₂ | H | H | CH₂ | MeO | 3-(Pyr-3)-Ph | O |
| 2-37 | H | (CH₂)₂ | H | H | CH₂ | MeO | 4-(Pyr-3)-Ph | O |
| 2-38 | H | (CH₂)₂ | H | H | CH₂ | MeO | 3-(Pyr-4)-Ph | O |
| 2-39 | H | (CH₂)₂ | H | H | CH₂ | MeO | 4-(Pyr-4)-Ph | O |
| 2-40 | H | (CH₂)₂ | H | H | CH₂ | MeO | 3-(Oxa-2)-Ph | O |
| 2-41 | H | (CH₂)₂ | H | H | CH₂ | MeO | 4-(Oxa-2)-Ph | O |
| 2-42 | H | (CH₂)₂ | H | H | CH₂ | MeO | 3-(Oxa-4)-Ph | O |
| 2-43 | H | (CH₂)₂ | H | H | CH₂ | MeO | 4-(Oxa-4)-Ph | O |
| 2-44 | H | (CH₂)₂ | H | H | CH₂ | MeO | 3-(Oxa-5)-Ph | O |
| 2-45 | H | (CH₂)₂ | H | H | CH₂ | MeO | 4-(Oxa-5)-Ph | O |
| 2-46 | H | (CH₂)₂ | H | H | CH₂ | MeO | 3-(Thiz-2)-Ph | O |
| 2-47 | H | (CH₂)₂ | H | H | CH₂ | MeO | 4-(Thiz-2)-Ph | O |
| 2-48 | H | (CH₂)₂ | H | H | CH₂ | MeO | 3-(Thiz-4)-Ph | O |
| 2-49 | H | (CH₂)₂ | H | H | CH₂ | MeO | 4-(Thiz-4)-Ph | O |
| 2-50 | H | (CH₂)₂ | H | H | CH₂ | MeO | 3-(Thiz-5)-Ph | O |
| 2-51 | H | (CH₂)₂ | H | H | CH₂ | MeO | 4-(Thiz-5)-Ph | O |
| 2-52 | H | (CH₂)₂ | H | H | CH₂ | MeO | 1-Me-2-Pyrr | O |
| 2-53 | H | (CH₂)₂ | H | H | CH₂ | MeO | 1-Ph-2-Pyrr | O |
| 2-54 | H | (CH₂)₂ | H | H | CH₂ | MeO | 1-Bz-2-Pyrr | O |
| 2-55 | H | (CH₂)₂ | H | H | CH₂ | MeO | 5-Me-2-Fur | O |
| 2-56 | H | (CH₂)₂ | H | H | CH₂ | MeO | 5-Ph-2-Fur | O |
| 2-57 | H | (CH₂)₂ | H | H | CH₂ | MeO | 5-Me-2-Thi | O |
| 2-58 | H | (CH₂)₂ | H | H | CH₂ | MeO | 5-Ph-2-Thi | O |
| 2-59 | H | (CH₂)₂ | H | H | CH₂ | MeO | 5-Me-3-Thi | O |
| 2-60 | H | (CH₂)₂ | H | H | CH₂ | MeO | 5-Ph-3-Thi | O |
| 2-61 | H | (CH₂)₂ | H | H | CH₂ | MeO | 1-Me-3-Pyza | O |
| 2-62 | H | (CH₂)₂ | H | H | CH₂ | MeO | 1-Ph-3-Pyza | O |
| 2-63 | H | (CH₂)₂ | H | H | CH₂ | MeO | 1-Me-2-Imid | O |
| 2-64 | H | (CH₂)₂ | H | H | CH₂ | MeO | 1-Ph-2-Imid | O |
| 2-65 | H | (CH₂)₂ | H | H | CH₂ | MeO | 1-Me-4-Imid | O |
| 2-66 | H | (CH₂)₂ | H | H | CH₂ | MeO | 1-Ph-4-Imid | O |
| 2-67 | H | (CH₂)₂ | H | H | CH₂ | MeO | 4-Oxa | O |
| 2-68 | H | (CH₂)₂ | H | H | CH₂ | MeO | 5-Oxa | O |
| 2-69 | H | (CH₂)₂ | H | H | CH₂ | MeO | 2-Me-4-Oxa | O |
| 2-70 | H | (CH₂)₂ | H | H | CH₂ | MeO | 2-Ph-4-Oxa | O |
| 2-71 | H | (CH₂)₂ | H | H | CH₂ | MeO | 2-Me-5-Oxa | O |
| 2-72 | H | (CH₂)₂ | H | H | CH₂ | MeO | 2-Ph-5-Oxa | O |
| 2-73 | H | (CH₂)₂ | H | H | CH₂ | MeO | 4-Me-2-Ph-5-Oxa | O |
| 2-74 | H | (CH₂)₂ | H | H | CH₂ | MeO | 5-Me-2-Ph-4-Oxa | O |
| 2-75 | H | (CH₂)₂ | H | H | CH₂ | MeO | 4-Thiz | O |
| 2-76 | H | (CH₂)₂ | H | H | CH₂ | MeO | 5-Thiz | O |
| 2-77 | H | (CH₂)₂ | H | H | CH₂ | MeO | 2-Me-4-Thiz | O |
| 2-78 | H | (CH₂)₂ | H | H | CH₂ | MeO | 2-Ph-4-Thiz | O |
| 2-79 | H | (CH₂)₂ | H | H | CH₂ | MeO | 2-Me-5-Thiz | O |
| 2-80 | H | (CH₂)₂ | H | H | CH₂ | MeO | 2-Ph-5-Thiz | O |
| 2-81 | H | (CH₂)₂ | H | H | CH₂ | MeO | 4-Me-2-Ph-5-Thiz | O |
| 2-82 | H | (CH₂)₂ | H | H | CH₂ | MeO | 5-Me-2-Ph-4-Thiz | O |
| 2-83 | H | (CH₂)₂ | H | H | CH₂ | MeO | 1-Me-4-Pyza | O |
| 2-84 | H | (CH₂)₂ | H | H | CH₂ | MeO | 1-Ph-4-Pyza | O |
| 2-85 | H | (CH₂)₂ | H | H | CH₂ | MeO | 2-Me-4-Isox | O |
| 2-86 | H | (CH₂)₂ | H | H | CH₂ | MeO | 2-Ph-4-Isox | O |
| 2-87 | H | (CH₂)₂ | H | H | CH₂ | MeO | 2-Pyr | O |
| 2-88 | H | (CH₂)₂ | H | H | CH₂ | MeO | 3-Pyr | O |
| 2-89 | H | (CH₂)₂ | H | H | CH₂ | MeO | 4-Pyr | O |
| 2-90 | H | (CH₂)₂ | H | H | CH₂ | MeO | 3-Me-5-Pyr | O |
| 2-91 | H | (CH₂)₂ | H | H | CH₂ | MeO | 3-Et-5-Pyr | O |
| 2-92 | H | (CH₂)₂ | H | H | CH₂ | MeO | 3-Ph-5-Pyr | O |
| 2-93 | H | (CH₂)₂ | H | H | CH₂ | MeO | 2-Me-5-Pyr | O |
| 2-94 | H | (CH₂)₂ | H | H | CH₂ | MeO | 2-BzO-5-Pyr | O |
| 2-95 | H | (CH₂)₂ | H | H | CH₂ | MeO | 2-Ph-5-Pyr | O |
| 2-96 | H | (CH₂)₂ | H | H | CH₂ | MeO | 2-MeO-5-Pyr | O |
| 2-97 | H | (CH₂)₂ | H | H | CH₂ | MeO | 2-EtO-5-Pyr | O |
| 2-98 | H | (CH₂)₂ | H | H | CH₂ | MeO | 2-iPrO-5-Pyr | O |
| 2-99 | H | (CH₂)₂ | H | H | CH₂ | MeO | 2-MeS-5-Pyr | O |
| 2-100 | H | (CH₂)₂ | H | H | CH₂ | MeO | 2-EtS-5-Pyr | O |
| 2-101 | H | (CH₂)₂ | H | H | CH₂ | MeO | 2-PhSO₂NH-5-Pyr | O |
| 2-102 | H | (CH₂)₂ | H | H | CH₂ | MeO | 2-MeSO₂-5-Pyr | O |
| 2-103 | H | (CH₂)₂ | H | H | CH₂ | MeO | 2-EtSO₂-5-Pyr | O |
| 2-104 | H | (CH₂)₂ | H | H | CH₂ | MeO | 2-PhSO₂NMe-5-Pyr | O |
| 2-105 | H | (CH₂)₂ | H | H | CH₂ | MeO | 2-Bz-5-Pyr | O |
| 2-106 | H | (CH₂)₂ | H | H | CH₂ | MeO | 2-PhO-5-Pyr | O |
| 2-107 | H | (CH₂)₂ | H | H | CH₂ | MeO | 2-PhS-5-Pyr | O |
| 2-108 | H | (CH₂)₂ | H | H | CH₂ | MeO | 2-PhSO₂-5-Pyr | O |
| 2-109 | H | (CH₂)₂ | H | H | CH₂ | MeO | 3-Me-6-Pyr | O |
| 2-110 | H | (CH₂)₂ | H | H | CH₂ | MeO | 3-Ph-6-Pyr | O |
| 2-111 | H | (CH₂)₂ | H | H | CH₂ | MeO | 2-Me-6-Pyr | O |
| 2-112 | H | (CH₂)₂ | H | H | CH₂ | MeO | 2-Ph-6-Pyr | O |
| 2-113 | H | (CH₂)₂ | H | H | CH₂ | MeO | 2-Me-4-Pym | O |
| 2-114 | H | (CH₂)₂ | H | H | CH₂ | MeO | 2-Ph-4-Pym | O |
| 2-115 | H | (CH₂)₂ | H | H | CH₂ | MeO | 2-MeO-4-Pym | O |
| 2-116 | H | (CH₂)₂ | H | H | CH₂ | MeO | 2-EtO-4-Pym | O |
| 2-117 | H | (CH₂)₂ | H | H | CH₂ | MeO | 2-iPrO-4-Pym | O |
| 2-118 | H | (CH₂)₂ | H | H | CH₂ | M | 2-MeS-4-Pym | O |
| 2-119 | H | (CH₂)₂ | H | H | CH₂ | MeO | 2-EtS-4-Pym | O |
| 2-120 | H | (CH₂)₂ | H | H | CH₂ | MeO | 2-iPrS-4-Pym | O |
| 2-121 | H | (CH₂)₂ | H | H | CH₂ | MeO | 6-MeS-4-Pym | O |
| 2-122 | H | (CH₂)₂ | H | H | CH₂ | MeO | 6-EtS-4-Pym | O |
| 2-123 | H | (CH₂)₂ | H | H | CH₂ | MeO | 6-iPrS-4-Pym | O |
| 2-124 | H | (CH₂)₂ | H | H | CH₂ | MeO | 2-PhS-4-Pym | O |
| 2-125 | H | (CH₂)₂ | H | H | CH₂ | MeO | 2-MeSO₂-4-Pym | O |
| 2-126 | H | (CH₂)₂ | H | H | CH₂ | MeO | 2-EtSO₂-4-Pym | O |
| 2-127 | H | (CH₂)₂ | H | H | CH₂ | MeO | 2-iPrSO₂-4-Pym | O |
| 2-128 | H | (CH₂)₂ | H | H | CH₂ | MeO | 2-PhSO₂-4-Pym | O |
| 2-129 | H | (CH₂)₂ | H | H | CH₂ | MeO | 2-Me-5-Pym | O |
| 2-130 | H | (CH₂)₂ | H | H | CH₂ | MeO | 2-Ph-5-Pym | O |
| 2-131 | H | (CH₂)₂ | H | H | CH₂ | MeO | 2-MeO-5-Pym | O |
| 2-132 | H | (CH₂)₂ | H | H | CH₂ | MeO | 2-EtO-5-Pym | O |
| 2-133 | H | (CH₂)₂ | H | H | CH₂ | MeO | 2-iPrO-5-Pym | O |
| 2-134 | H | (CH₂)₂ | H | H | CH₂ | MeO | 2-MeS-5-Pym | O |
| 2-135 | H | (CH₂)₂ | H | H | CH₂ | MeO | 2-EtS-5-Pym | O |
| 2-136 | H | (CH₂)₂ | H | H | CH₂ | MeO | 2-iPrS-5-Pym | O |
| 2-137 | H | (CH₂)₂ | H | H | CH₂ | MeO | 2-PhS-5-Pym | O |
| 2-138 | H | (CH₂)₂ | H | H | CH₂ | MeO | 2-MeSO₂-5-Pym | O |
| 2-139 | H | (CH₂)₂ | H | H | CH₂ | MeO | 2-EtSO₂-5-Pym | O |
| 2-140 | H | (CH₂)₂ | H | H | CH₂ | MeO | 2-iPrSO₂-5-Pym | O |
| 2-141 | H | (CH₂)₂ | H | H | CH₂ | MeO | 2-PhSO₂-5-Pym | O |
| 2-142 | H | (CH₂)₂ | H | H | CH₂ | MeO | 2-Ind | O |
| 2-143 | H | (CH₂)₂ | H | H | CH₂ | MeO | 3-Ind | O |
| 2-144 | H | (CH₂)₂ | H | H | CH₂ | MeO | 1-Me-2-Ind | O |
| 2-145 | H | (CH₂)₂ | H | H | CH₂ | MeO | 1-Me-3-Ind | O |
| 2-146 | H | (CH₂)₂ | H | H | CH₂ | MeO | 2-Bimid | O |
| 2-147 | H | (CH₂)₂ | H | H | CH₂ | MeO | 2-Boxa | O |
| 2-148 | H | (CH₂)₂ | H | H | CH₂ | MeO | 2-Bthiz | O |
| 2-149 | H | (CH₂)₂ | H | H | CH₂ | MeO | 2-Quin | O |
| 2-150 | H | (CH₂)₂ | H | H | CH₂ | MeO | 3-Quin | O |
| 2-151 | H | (CH₂)₂ | H | H | CH₂ | MeO | 4-Quin | O |
| 2-152 | H | (CH₂)₂ | H | H | CH₂ | MeO | 1-iQuin | O |
| 2-153 | H | (CH₂)₂ | H | H | CH₂ | MeO | 3-iQuin | O |
| 2-154 | H | (CH₂)₂ | H | H | CH₂ | MeO | 4-iQuin | O |
| 2-155 | H | (CH₂)₂ | H | H | CH₂ | MeO | 3-MeO-Ph | O |
| 2-156 | H | (CH₂)₂ | H | H | CH₂ | MeO | 4-MeO-Ph | O |
| 2-157 | H | (CH₂)₂ | H | H | CH₂ | MeO | 3-EtO-Ph | O |
| 2-158 | H | (CH₂)₂ | H | H | CH₂ | MeO | 4-EtO-Ph | O |
| 2-159 | H | (CH₂)₂ | H | H | CH₂ | MeO | 3-iPrO-Ph | O |
| 2-160 | H | (CH₂)₂ | H | H | CH₂ | MeO | 4-iPrO-Ph | O |
| 2-161 | H | (CH₂)₂ | H | H | CH₂ | MeO | 3-MeS-Ph | O |

TABLE 2-continued

| Ex. No. Comp. | R¹ | R² | R³ | R⁴ | Z | W | X | Y |
|---|---|---|---|---|---|---|---|---|
| 2-162 | H | (CH₂)₂ | H | H | CH₂ | MeO | 4-MeS-Ph | O |
| 2-163 | H | (CH₂)₂ | H | H | CH₂ | MeO | 3-EtS-Ph | O |
| 2-164 | H | (CH₂)₂ | H | H | CH₂ | MeO | 4-EtS-Ph | O |
| 2-165 | H | (CH₂)₂ | H | H | CH₂ | MeO | 3-iPrS-Ph | O |
| 2-166 | H | (CH₂)₂ | H | H | CH₂ | MeO | 4-iPrS-Ph | O |
| 2-167 | H | (CH₂)₂ | H | H | CH₂ | MeO | 3-MeSO₂-Ph | O |
| 2-168 | H | (CH₂)₂ | H | H | CH₂ | MeO | 4-MeSO₂-Ph | O |
| 2-169 | H | (CH₂)₂ | H | H | CH₂ | MeO | 3-EtSO₂-Ph | O |
| 2-170 | H | (CH₂)₂ | H | H | CH₂ | MeO | 4-EtSO₂-Ph | O |
| 2-171 | H | (CH₂)₂ | H | H | CH₂ | MeO | 3-iPrSO₂-Ph | O |
| 2-172 | H | (CH₂)₂ | H | H | CH₂ | MeO | 4-iPrSO₂-Ph | O |
| 2-173 | H | (CH₂)₂ | H | H | CH₂ | MeO | 3-(1-Me-Imid-4)-Ph | O |
| 2-174 | H | (CH₂)₂ | H | H | CH₂ | MeO | 4-(1-Me-Imid-4)-Ph | O |
| 2-175 | H | (CH₂)₂ | H | H | CH₂ | MeO | 1-Me-2-Ph-4-Imid | O |
| 2-176 | H | (CH₂)₂ | H | H | CH₂ | MeO | 1,4-di-Me-2-Ph-5-Imid | O |
| 2-177 | H | (CH₂)₂ | H | H | CH₂ | MeO | 1,5-di-Me-2-Ph-4-Imid | O |
| 2-178 | H | (CH₂)₂ | H | H | CH₂ | MeO | 3,4-MdO-Ph | O |
| 2-179 | H | (CH₂)₂ | H | H | CH₂ | MeO | 4-(4-MeO-Ph)-Ph | O |
| 2-180 | H | (CH₂)₂ | H | H | CH₂ | MeO | 4-(3,4-MdO-Ph)-Ph | O |
| 2-181 | H | (CH₂)₂ | H | H | CH₂ | MeO | 4-[PhSO₂N(Me)]-Ph | O |
| 2-182 | H | (CH₂)₂ | H | H | CH₂ | MeO | 4-[(Pyr-3)SO₂N(Me)]-Ph | O |
| 2-183 | H | (CH₂)₂ | H | H | CH₂ | MeO | 4-(PhSO₂NH)-Ph | O |
| 2-184 | H | (CH₂)₂ | H | H | CH₂ | MeO | 4-[(Pyr-3)SO₂NH]-Ph | O |
| 2-185 | H | (CH₂)₂ | H | H | CH₂ | MeO | 4-[(Pyr-2)SO₂]-Ph | O |
| 2-186 | H | (CH₂)₂ | H | H | CH₂ | MeO | 4-[(Pyr-3)SO₂]-Ph | O |
| 2-187 | H | (CH₂)₂ | H | H | CH₂ | MeO | 4-[(Pyr-2)SO₂N(Me)]-Ph | O |
| 2-188 | H | (CH₂)₂ | H | H | CH₂ | MeO | 4-[(Pyr-2)SO₂NH]-Ph | O |
| 2-189 | H | (CH₂)₂ | H | H | CH₂ | MeO | 4-(4-Me-Ph)-Ph | O |
| 2-190 | H | (CH₂)₂ | H | H | CH₂ | MeO | 4-(4-F-Ph)-Ph | O |
| 2-191 | H | (CH₂)₂ | H | H | CH₂ | MeO | 4-(4-CF₃-Ph)-Ph | O |
| 2-192 | H | (CH₂)₂ | H | H | CH₂ | MeO | 2-[PhSO₂N(Me)]-5-Pyr | O |
| 2-193 | H | (CH₂)₂ | H | H | CH₂ | MeO | 2-HO-5-Pyr | O |
| 2-194 | H | (CH₂)₂ | H | H | CH₂ | MeO | 2-BzO-5-Pyr | O |
| 2-195 | H | (CH₂)₂ | H | H | CH₂ | MeO | 4-[(Pyr-4)SO₂]-Ph | O |
| 2-196 | H | (CH₂)₂ | H | H | CH₂ | MeO | 4-[(Pyr-4)O]-Ph | O |
| 2-197 | H | (CH₂)₂ | H | H | CH₂ | MeO | 4-[(Pyr-4)S]-Ph | O |
| 2-198 | H | (CH₂)₂ | H | H | CH₂ | MeO | 3-HO-Ph | O |
| 2-199 | H | (CH₂)₂ | H | H | CH₂ | MeO | 4-HO-Ph | O |
| 2-200 | H | (CH₂)₂ | H | H | CH₂ | MeO | 2-HO-3,4,6-tri-Me-Ph | O |
| 2-201 | H | (CH₂)₂ | H | H | CH₂ | MeO | 4-HO-3,5-di-Me-Ph | O |
| 2-202 | H | (CH₂)₂ | H | H | CH₂ | MeO | 3-AcO-Ph | O |
| 2-203 | H | (CH₂)₂ | H | H | CH₂ | MeO | 4-AcO-Ph | O |

TABLE 3

| Ex. No. Comp. | R¹ | R² | R³ | R⁴ | Z | W | X | Y |
|---|---|---|---|---|---|---|---|---|
| 3-1 | H | (CH₂)₂ | H | H | CH₂ | Pr | Ph | O |
| 3-2 | H | (CH₂)₂ | H | H | CH₂ | Pr | 1-Np | O |
| 3-3 | H | (CH₂)₂ | H | H | CH₂ | Pr | 2-Np | O |
| 3-4 | H | (CH₂)₂ | H | H | CH₂ | Pr | 4-Me-Ph | O |
| 3-5 | H | (CH₂)₂ | H | H | CH₂ | Pr | 4-Et-Ph | O |
| 3-6 | H | (CH₂)₂ | H | H | CH₂ | Pr | 3-iPr-Ph | O |
| 3-7 | H | (CH₂)₂ | H | H | CH₂ | Pr | 4-iPr-Ph | O |
| 3-8 | H | (CH₂)₂ | H | H | CH₂ | Pr | 3-tBu-Ph | O |
| 3-9 | H | (CH₂)₂ | H | H | CH₂ | Pr | 4-tBu-Ph | O |
| 3-10 | H | (CH₂)₂ | H | H | CH₂ | Pr | 3-F-Ph | O |
| 3-11 | H | (CH₂)₂ | H | H | CH₂ | Pr | 4-F-Ph | O |
| 3-12 | H | (CH₂)₂ | H | H | CH₂ | Pr | 4-Cl-Ph | O |
| 3-13 | H | (CH₂)₂ | H | H | CH₂ | Pr | 4-Br-Ph | O |
| 3-14 | H | (CH₂)₂ | H | H | CH₂ | Pr | 3-Ph-Ph | O |
| 3-15 | H | (CH₂)₂ | H | H | CH₂ | Pr | 4-Ph-Ph | O |
| 3-16 | H | (CH₂)₂ | R | H | CH₂ | Pr | 4-BzO-Ph | O |
| 3-17 | H | (CH₂)₂ | H | H | CH₂ | Pr | 4-Bz-Ph | O |
| 3-18 | H | (CH₂)₂ | H | H | CH₂ | Pr | 3-PhO-Ph | O |
| 3-19 | H | (CH₂)₂ | H | H | CH₂ | Pr | 4-PhO-Ph | O |
| 3-20 | H | (CH₂)₂ | H | H | CH₂ | Pr | 3-PhS-Ph | O |
| 3-21 | H | (CH₂)₂ | H | H | CH₂ | Pr | 4-PhS-Ph | O |
| 3-22 | H | (CH₂)₂ | H | H | CH₂ | Pr | 3-PhSO₂-Ph | O |
| 3-23 | H | (CH₂)₂ | H | H | CH₂ | Pr | 4-PhSO₂-Ph | O |
| 3-24 | H | (CH₂)₂ | H | H | CH₂ | Pr | 3-(Imid-1)-Ph | O |
| 3-25 | H | (CH₂)₂ | H | H | CH₂ | Pr | 4-(Imid-1)-Ph | O |
| 3-26 | H | (CH₂)₂ | H | H | CH₂ | Pr | 3-(Imid-4)-Ph | O |
| 3-27 | H | (CH₂)₂ | H | H | CH₂ | Pr | 4-(Imid-4)-Ph | O |
| 3-28 | H | (CH₂)₂ | H | H | CH₂ | Pr | 3-(Fur-2)-Ph | O |
| 3-29 | H | (CH₂)₂ | H | H | CH₂ | Pr | 4-(Fur-2)-Ph | O |
| 3-30 | H | (CH₂)₂ | H | H | CH₂ | Pr | 3-(Thi-2)-Ph | O |
| 3-31 | H | (CH₂)₂ | H | H | CH₂ | Pr | 4-(Thi-2)-Ph | O |
| 3-32 | H | (CH₂)₂ | H | H | CH₂ | Pr | 3-(Thi-3)-Ph | O |
| 3-33 | H | (CH₂)₂ | R | H | CH₂ | Pr | 4-(Thi-3)-Ph | O |
| 3-34 | H | (CH₂)₂ | H | H | CH₂ | Pr | 3-(Pyr-2)-Ph | O |
| 3-35 | H | (CH₂)₂ | H | H | CH₂ | Pr | 4-(Pyr-2)-Ph | O |
| 3-36 | H | (CH₂)₂ | H | H | CH₂ | Pr | 3-(Pyr-3)-Ph | O |
| 3-37 | H | (CH₂)₂ | H | H | CH₂ | Pr | 4-(Pyr-3)-Ph | O |
| 3-38 | H | (CH₂)₂ | H | H | CH₂ | Pr | 3-(Pyr-4)-Ph | O |
| 3-39 | H | (CH₂)₂ | H | H | CH₂ | Pr | 4-(Pyr-4)-Ph | O |
| 3-40 | H | (CH₂)₂ | H | H | CH₂ | Pr | 3-(Oxa-2)-Ph | O |
| 3-41 | H | (CH₂)₂ | H | H | CH₂ | Pr | 4-(Oxa-2)-Ph | O |
| 3-42 | H | (CH₂)₂ | H | H | CH₂ | Pr | 3-(Oxa-4)-Ph | O |
| 3-43 | H | (CH₂)₂ | H | H | CH₂ | Pr | 4-(Oxa-4)-Ph | O |
| 3-44 | H | (CH₂)₂ | H | H | CH₂ | Pr | 3-(Oxa-5)-Ph | O |
| 3-45 | H | (CH₂)₂ | H | H | CH₂ | Pr | 4-(Oxa-5)-Ph | O |
| 3-46 | H | (CH₂)₂ | H | H | CH₂ | Pr | 3-(Thiz-2)-Ph | O |
| 3-47 | H | (CH₂)₂ | H | H | CH₂ | Pr | 4-(Thiz-2)-Ph | O |
| 3-48 | H | (CH₂)₂ | H | H | CH₂ | Pr | 3-(Thiz-4)-Ph | O |
| 3-49 | H | (CH₂)₂ | H | H | CH₂ | Pr | 4-(Thiz-4)-Ph | O |
| 3-50 | H | (CH₂)₂ | H | H | CH₂ | Pr | 3-(Thiz-5)-Ph | O |
| 3-51 | H | (CH₂)₂ | H | H | CH₂ | Pr | 4-(Thiz-5)-Ph | O |
| 3-52 | H | (CH₂)₂ | H | H | CH₂ | Pr | 1-Me-2-Pyrr | O |
| 3-53 | H | (CH₂)₂ | H | H | CH₂ | Pr | 1-Ph-2-Pyrr | O |
| 3-54 | H | (CH₂)₂ | H | H | CH₂ | Pr | 1-Bz-2-Pyrr | O |
| 3-55 | H | (CH₂)₂ | H | H | CH₂ | Pr | 5-Me-2-Fur | O |
| 3-56 | H | (CH₂)₂ | H | H | CH₂ | Pr | 5-Ph-2-Fur | O |
| 3-57 | H | (CH₂)₂ | H | H | CH₂ | Pr | 5-Me-2-Thi | O |
| 3-58 | H | (CH₂)₂ | H | H | CH₂ | Pr | 5-Ph-2-Thi | O |
| 3-59 | H | (CH₂)₂ | H | H | CH₂ | Pr | 5-Me-3-Thi | O |
| 3-60 | H | (CH₂)₂ | H | H | CH₂ | Pr | 5-Ph-3-Thi | O |
| 3-61 | H | (CH₂)₂ | H | H | CH₂ | Pr | 1-Me-3-Pyza | O |
| 3-62 | H | (CH₂)₂ | H | H | CH₂ | Pr | 1-Ph-3-Pyza | O |
| 3-63 | H | (CH₂)₂ | H | H | CH₂ | Pr | 1-Me-2-Imid | O |
| 3-64 | H | (CH₂)₂ | H | H | CH₂ | Pr | 1-Ph-2-Imid | O |
| 3-65 | H | (CH₂)₂ | H | H | CH₂ | Pr | 1-Me-4-Imid | O |
| 3-66 | H | (CH₂)₂ | H | H | CH₂ | Pr | 1-Ph-4-Imid | O |
| 3-67 | H | (CH₂)₂ | H | H | CH₂ | Pr | 4-Oxa | O |
| 3-68 | H | (CH₂)₂ | H | H | CH₂ | Pr | 5-Oxa | O |
| 3-69 | H | (CH₂)₂ | H | H | CH₂ | Pr | 2-Me-4-Oxa | O |
| 3-70 | H | (CH₂)₂ | H | H | CH₂ | Pr | 2-Ph-4-Oxa | O |
| 3-71 | H | (CH₂)₂ | H | H | CH₂ | Pr | 2-Me-5-Oxa | O |
| 3-72 | H | (CH₂)₂ | H | H | CH₂ | Pr | 2-Ph-5-Oxa | O |
| 3-73 | H | (CH₂)₂ | H | H | CH₂ | Pr | 4-Me-2-Ph-5-Oxa | O |
| 3-74 | H | (CH₂)₂ | H | H | CH₂ | Pr | 5-Me-2-Ph-4-Oxa | O |
| 3-75 | H | (CH₂)₂ | H | H | CH₂ | Pr | 4-Thiz | O |
| 3-76 | H | (CH₂)₂ | H | H | CH₂ | Pr | 5-Thiz | O |
| 3-77 | H | (CH₂)₂ | H | H | CH₂ | Pr | 2-Me-4-Thiz | O |
| 3-78 | H | (CH₂)₂ | H | H | CH₂ | Pr | 2-Ph-4-Thiz | O |
| 3-79 | H | (CH₂)₂ | H | H | CH₂ | Pr | 2-Me-5-Thiz | O |
| 3-80 | H | (CH₂)₂ | H | H | CH₂ | Pr | 2-Ph-5-Thiz | O |
| 3-81 | H | (CH₂)₂ | H | H | CH₂ | Pr | 4-Me-2-Ph-5-Thiz | O |
| 3-82 | H | (CH₂)₂ | H | H | CH₂ | Pr | 5-Me-2-Ph-4-Thiz | O |
| 3-83 | H | (CH₂)₂ | H | H | CH₂ | Pr | 1-Me-4-Pyza | O |
| 3-84 | H | (CH₂)₂ | H | H | CH₂ | Pr | 1-Ph-4-Pyza | O |
| 3-85 | H | (CH₂)₂ | H | H | CH₂ | Pr | 2-Me-4-Isox | O |
| 3-86 | H | (CH₂)₂ | H | H | CH₂ | Pr | 2-Ph-4-Isox | O |
| 3-87 | H | (CH₂)₂ | H | H | CH₂ | Pr | 2-Pyr | O |
| 3-88 | H | (CH₂)₂ | H | H | CH₂ | Pr | 3-Pyr | O |
| 3-89 | H | (CH₂)₂ | H | H | CH₂ | Pr | 4-Pyr | O |
| 3-90 | H | (CH₂)₂ | H | H | CH₂ | Pr | 3-Me-5-Pyr | O |

TABLE 3-continued

| Ex. No. Comp. | R¹ | R² | R³ | R⁴ | Z | W | X | Y |
|---|---|---|---|---|---|---|---|---|
| 3-91 | H | (CH$_2$)$_2$ | H | H | CH$_2$ | Pr | 3-Et-5-Pyr | O |
| 3-92 | H | (CH$_2$)$_2$ | H | H | CH$_2$ | Pr | 3-Ph-5-Pyr | O |
| 3-93 | H | (CH$_2$)$_2$ | H | H | CH$_2$ | Pr | 2-Me-5-Pyr | O |
| 3-94 | H | (CH$_2$)$_2$ | H | H | CH$_2$ | Pr | 2-BzO-5-Pyr | O |
| 3-95 | H | (CH$_2$)$_2$ | H | H | CH$_2$ | Pr | 2-Ph-5-Pyr | O |
| 3-96 | H | (CH$_2$)$_2$ | H | H | CH$_2$ | Pr | 2-MeO-5-Pyr | O |
| 3-97 | H | (CH$_2$)$_2$ | H | H | CH$_2$ | Pr | 2-EtO-5-Pyr | O |
| 3-98 | H | (CH$_2$)$_2$ | H | H | CH$_2$ | Pr | 2-iPrO-5-Pyr | O |
| 3-99 | H | (CH$_2$)$_2$ | H | H | CH$_2$ | Pr | 2-MeS-5-Pyr | O |
| 3-100 | H | (CH$_2$)$_2$ | H | H | CH$_2$ | Pr | 2-EtS-5-Pyr | O |
| 3-101 | H | (CH$_2$)$_2$ | H | H | CH$_2$ | Pr | 2-PhSO$_2$NH-5-Pyr | O |
| 3-102 | H | (CH$_2$)$_2$ | H | H | CH$_2$ | Pr | 2-MeSO$_2$-5-Pyr | O |
| 3-103 | H | (CH$_2$)$_2$ | H | H | CH$_2$ | Pr | 2-EtSO$_2$-5-Pyr | O |
| 3-104 | H | (CH$_2$)$_2$ | H | H | CH$_2$ | Pr | 2-PhSO$_2$NMe-5-Pyr | O |
| 3-105 | H | (CH$_2$)$_2$ | H | H | CH$_2$ | Pr | 2-Bz-5-Pyr | O |
| 3-106 | H | (CH$_2$)$_2$ | H | H | CH$_2$ | Pr | 2-PhO-5-Pyr | O |
| 3-107 | H | (CH$_2$)$_2$ | H | H | CH$_2$ | Pr | 2-PhS-5-Pyr | O |
| 3-108 | H | (CH$_2$)$_2$ | H | H | CH$_2$ | Pr | 2-PhSO$_2$-5-Pyr | O |
| 3-109 | H | (CH$_2$)$_2$ | H | H | CH$_2$ | Pr | 3-Me-6-Pyr | O |
| 3-110 | H | (CH$_2$)$_2$ | H | H | CH$_2$ | Pr | 3-Ph-6-Pyr | O |
| 3-111 | H | (CH$_2$)$_2$ | H | H | CH$_2$ | Pr | 2-Me-6-Pyr | O |
| 3-112 | H | (CH$_2$)$_2$ | H | H | CH$_2$ | Pr | 2-Ph-6-Pyr | O |
| 3-113 | H | (CH$_2$)$_2$ | H | H | CH$_2$ | Pr | 2-Me-4-Pym | O |
| 3-114 | H | (CH$_2$)$_2$ | H | H | CH$_2$ | Pr | 2-Ph-4-Pym | O |
| 3-115 | H | (CH$_2$)$_2$ | H | H | CH$_2$ | Pr | 2-MeO-4-Pym | O |
| 3-116 | H | (CH$_2$)$_2$ | H | H | CH$_2$ | Pr | 2-EtO-4-Pym | O |
| 3-117 | H | (CH$_2$)$_2$ | H | H | CH$_2$ | Pr | 2-iPrO-4-Pym | O |
| 3-118 | H | (CH$_2$)$_2$ | H | H | CH$_2$ | Pr | 2-MeS-4-Pym | O |
| 3-119 | H | (CH$_2$)$_2$ | H | H | CH$_2$ | Pr | 2-EtS-4-Pym | O |
| 3-120 | H | (CH$_2$)$_2$ | H | H | CH$_2$ | Pr | 2-iPrS-4-Pym | O |
| 3-121 | H | (CH$_2$)$_2$ | H | H | CH$_2$ | Pr | 6-MeS-4-Pym | O |
| 3-122 | H | (CH$_2$)$_2$ | H | H | CH$_2$ | Pr | 6-EtS-4-Pym | O |
| 3-123 | H | (CH$_2$)$_2$ | H | H | CH$_2$ | Pr | 6-iPrS-4-Pym | O |
| 3-124 | H | (CH$_2$)$_2$ | H | H | CH$_2$ | Pr | 2-PhS-4-Pym | O |
| 3-125 | H | (CH$_2$)$_2$ | H | H | CH$_2$ | Pr | 2-MeSO$_2$-4-Pym | O |
| 3-126 | H | (CH$_2$)$_2$ | H | H | CH$_2$ | Pr | 2-EtSO$_2$-4-Pym | O |
| 3-127 | H | (CH$_2$)$_2$ | H | H | CH$_2$ | Pr | 2-iPrSO$_2$-4-Pym | O |
| 3-128 | H | (CH$_2$)$_2$ | H | H | CH$_2$ | Pr | 2-PhSO$_2$-4-Pym | O |
| 3-129 | H | (CH$_2$)$_2$ | H | H | CH$_2$ | Pr | 2-Me-5-Pym | O |
| 3-130 | H | (CH$_2$)$_2$ | H | H | CH$_2$ | Pr | 2-Ph-5-Pym | O |
| 3-131 | H | (CH$_2$)$_2$ | H | H | CH$_2$ | Pr | 2-MeO-5-Pym | O |
| 3-132 | H | (CH$_2$)$_2$ | H | H | CH$_2$ | Pr | 2-EtO-5-Pym | O |
| 3-133 | H | (CH$_2$)$_2$ | H | H | CH$_2$ | Pr | 2-iPrO-5-Pym | O |
| 3-134 | H | (CH$_2$)$_2$ | H | H | CH$_2$ | Pr | 2-MeS-5-Pym | O |
| 3-135 | H | (CH$_2$)$_2$ | H | H | CH$_2$ | Pr | 2-EtS-5-Pym | O |
| 3-136 | H | (CH$_2$)$_2$ | H | H | CH$_2$ | Pr | 2-iPrS-5-Pym | O |
| 3-137 | H | (CH$_2$)$_2$ | H | H | CH$_2$ | Pr | 2-PhS-5-Pym | O |
| 3-138 | H | (CH$_2$)$_2$ | H | H | CH$_2$ | Pr | 2-MeSO$_2$-5-Pym | O |
| 3-139 | H | (CH$_2$)$_2$ | H | H | CH$_2$ | Pr | 2-EtSO$_2$-5-Pym | O |
| 3-140 | H | (CH$_2$)$_2$ | H | H | CH$_2$ | Pr | 2-iPrSO$_2$-5-Pym | O |
| 3-141 | H | (CH$_2$)$_2$ | H | H | CH$_2$ | Pr | 2-PhSO$_2$-5-Pym | O |
| 3-142 | H | (CH$_2$)$_2$ | H | H | CH$_2$ | Pr | 2-Ind | O |
| 3-143 | H | (CH$_2$)$_2$ | H | H | CH$_2$ | Pr | 3-Ind | O |
| 3-144 | H | (CH$_2$)$_2$ | H | H | CH$_2$ | Pr | 1-Me-2-Ind | O |
| 3-145 | H | (CH$_2$)$_2$ | H | H | CH$_2$ | Pr | 1-Me-3-Ind | O |
| 3-146 | H | (CH$_2$)$_2$ | H | H | CH$_2$ | Pr | 2-Bimid | O |
| 3-147 | H | (CH$_2$)$_2$ | H | H | CH$_2$ | Pr | 2-Boxa | O |
| 3-148 | H | (CH$_2$)$_2$ | H | H | CH$_2$ | Pr | 2-Bthiz | O |
| 3-149 | H | (CH$_2$)$_2$ | H | H | CH$_2$ | Pr | 2-Quin | O |
| 3-150 | H | (CH$_2$)$_2$ | H | H | CH$_2$ | Pr | 3-Quin | O |
| 3-151 | H | (CH$_2$)$_2$ | H | H | CH$_2$ | Pr | 4-Quin | O |
| 3-152 | H | (CH$_2$)$_2$ | H | H | CH$_2$ | Pr | 1-iQuin | O |
| 3-153 | H | (CH$_2$)$_2$ | H | H | CH$_2$ | Pr | 3-iQuin | O |
| 3-154 | H | (CH$_2$)$_2$ | H | H | CH$_2$ | Pr | 4-iQuin | O |
| 3-155 | H | (CH$_2$)$_2$ | H | H | CH$_2$ | Pr | 3-MeO-Ph | O |
| 3-156 | H | (CH$_2$)$_2$ | H | H | CH$_2$ | Pr | 4-MeO-Ph | O |
| 3-157 | H | (CH$_2$)$_2$ | H | H | CH$_2$ | Pr | 3-EtO-Ph | O |
| 3-158 | H | (CH$_2$)$_2$ | H | H | CH$_2$ | Pr | 4-EtO-Ph | O |
| 3-159 | H | (CH$_2$)$_2$ | H | H | CH$_2$ | Pr | 3-iPrO-Ph | O |
| 3-160 | H | (CH$_2$)$_2$ | H | H | CH$_2$ | Pr | 4-iPro-Ph | O |
| 3-161 | H | (CH$_2$)$_2$ | H | H | CH$_2$ | Pr | 3-MeS-Ph | O |
| 3-162 | H | (CH$_2$)$_2$ | H | H | CH$_2$ | Pr | 4-MeS-Ph | O |
| 3-163 | H | (CH$_2$)$_2$ | H | H | CH$_2$ | Pr | 3-EtS-Ph | O |
| 3-164 | H | (CH$_2$)$_2$ | H | H | CH$_2$ | Pr | 4-EtS-Ph | O |
| 3-165 | H | (CH$_2$)$_2$ | H | H | CH$_2$ | Pr | 3-iPrS-Ph | O |
| 3-166 | H | (CH$_2$)$_2$ | H | H | CH$_2$ | Pr | 4-iPrS-Ph | O |
| 3-167 | H | (CH$_2$)$_2$ | H | H | CH$_2$ | Pr | 3-MeSO$_2$-Ph | O |
| 3-168 | H | (CH$_2$)$_2$ | H | H | CH$_2$ | Pr | 4-MeSO$_2$-Ph | O |
| 3-169 | H | (CH$_2$)$_2$ | H | H | CH$_2$ | Pr | 3-EtSO$_2$-Ph | O |
| 3-170 | H | (CH$_2$)$_2$ | H | H | CH$_2$ | Pr | 4-EtSO$_2$-Ph | O |
| 3-171 | H | (CH$_2$)$_2$ | H | H | CH$_2$ | Pr | 3-iPrSO$_2$-Ph | O |
| 3-172 | H | (CH$_2$)$_2$ | H | H | CH$_2$ | Pr | 4-iPrSO$_2$-Ph | O |
| 3-173 | H | (CH$_2$)$_2$ | H | H | CH$_2$ | Pr | 3-(1-Me-Imid-4)-Ph | O |
| 3-174 | H | (CH$_2$)$_2$ | H | H | CH$_2$ | Pr | 4-(1-Me-Imid-4)-Ph | O |
| 3-175 | H | (CH$_2$)$_2$ | H | H | CH$_2$ | Pr | 1-Me-2-Ph-4-Imid | O |
| 3-176 | H | (CH$_2$)$_2$ | H | H | CH$_2$ | Pr | 1,4-di-Me-2-Ph-5-Imid | O |
| 3-177 | H | (CH$_2$)$_2$ | H | H | CH$_2$ | Pr | 1,5-di-Me-2-Ph-4-Imid | O |
| 3-178 | H | (CH$_2$)$_2$ | H | H | CH$_2$ | Pr | 3,4-MdO-Ph | O |
| 3-179 | H | (CH$_2$)$_2$ | H | H | CH$_2$ | Pr | 4-(4-MeO-Ph)-Ph | O |
| 3-180 | H | (CH$_2$)$_2$ | H | H | CH$_2$ | Pr | 4-(3,4-MdO-Ph)-Ph | O |
| 3-181 | H | (CH$_2$)$_2$ | H | H | CH$_2$ | Pr | 4-[PhSO$_2$N(Me)]-Ph | O |
| 3-182 | H | (CH$_2$)$_2$ | H | H | CH$_2$ | Pr | 4-[(Pyr-3)SO$_2$N(Me)]-Ph | O |
| 3-183 | H | (CH$_2$)$_2$ | H | H | CH$_2$ | Pr | 4-(PhSO$_2$NH)-Ph | O |
| 3-184 | H | (CH$_2$)$_2$ | H | H | CH$_2$ | Pr | 4-[(Pyr-3)SO$_2$NH]-Ph | O |
| 3-185 | H | (CH$_2$)$_2$ | H | H | CH$_2$ | Pr | 4-[(Pyr-2)SO$_2$]-Ph | O |
| 3-186 | H | (CH$_2$)$_2$ | H | H | CH$_2$ | Pr | 4-[(Pyr-3)SO$_2$]-Ph | O |
| 3-187 | H | (CH$_2$)$_2$ | H | H | CH$_2$ | Pr | 4-[(Pyr-2)SO$_2$N(Me)]-Ph | O |
| 3-188 | H | (CH$_2$)$_2$ | H | H | CH$_2$ | Pr | 4-[(Pyr-2)SO$_2$NH]-Ph | O |
| 3-189 | H | (CH$_2$)$_2$ | H | H | CH$_2$ | Pr | 4-(4-Me-Ph)-Ph | O |
| 3-190 | H | (CH$_2$)$_2$ | H | H | CH$_2$ | Pr | 4-(4-F-Ph)-Ph | O |
| 3-191 | H | (CH$_2$)$_2$ | H | H | CH$_2$ | Pr | 4-(4-CF$_3$-Ph)-Ph | O |
| 3-192 | H | (CH$_2$)$_2$ | H | H | CH$_2$ | Pr | 2-[PhSO$_2$N(Me)]-5-Pyr | O |
| 3-193 | H | (CH$_2$)$_2$ | H | H | CH$_2$ | Pr | 2-HO-5-Pyr | O |
| 3-194 | H | (CH$_2$)$_2$ | H | H | CH$_2$ | Pr | 2-BzO-5-Pyr | O |
| 3-195 | H | (CH$_2$)$_2$ | H | H | CH$_2$ | Pr | 4-[(Pyr-4)SO$_2$]-Ph | O |
| 3-196 | H | (CH$_2$)$_2$ | H | H | CH$_2$ | Pr | 4-[(Pyr-4)O]-Ph | O |
| 3-197 | H | (CH$_2$)$_2$ | H | H | CH$_2$ | Pr | 4-[(Pyr-4)S]-Ph | O |
| 3-198 | H | (CH$_2$)$_2$ | H | H | CH$_2$ | Pr | 3-HO-Ph | O |
| 3-199 | H | (CH$_2$)$_2$ | H | H | CH$_2$ | Pr | 4-HO-Ph | O |
| 3-200 | H | (CH$_2$)$_2$ | H | H | CH$_2$ | Pr | 2-HO-3,4,6-tri-Me-Ph | O |
| 3-201 | H | (CH$_2$)$_2$ | H | H | CH$_2$ | Pr | 4-HO-3,5-di-Me-Ph | O |
| 3-202 | H | (CH$_2$)$_2$ | H | H | CH$_2$ | Pr | 3-AcO-Ph | O |
| 3-203 | H | (CH$_2$)$_2$ | H | H | CH$_2$ | Pr | 4-AcO-Ph | O |
| 3-204 | H | (CH$_2$)$_2$ | H | H | CH$_2$ | Pr | 4-(4-Cl-Ph)-Ph | O |
| 3-205 | H | (CH$_2$)$_2$ | H | H | CH$_2$ | Pr | 4-(4-HO-3,5-di-Me-Ph)-Ph | O |
| 3-206 | H | (CH$_2$)$_2$ | H | H | CH$_2$ | Pr | 4-(4-HO-Ph)-Ph | O |
| 3-207 | H | (CH$_2$)$_2$ | H | H | CH$_2$ | Pr | 4-(4-OHC-Ph)-Ph | O |
| 3-208 | H | (CH$_2$)$_2$ | H | H | CH$_2$ | Pr | 4-(4-Dmam-Ph)-Ph | O |
| 3-209 | H | (CH$_2$)$_2$ | H | H | CH$_2$ | Pr | 4-(4-Dma-Ph)-Ph | O |
| 3-210 | H | (CH$_2$)$_2$ | H | H | CH$_2$ | Pr | 4-(4-HOOC-Ph)-Ph | O |
| 3-211 | H | (CH$_2$)$_2$ | H | H | CH$_2$ | Pr | 4-(4-HOH$_2$C-Ph)-Ph | O |
| 3-212 | H | (CH$_2$)$_2$ | H | H | CH$_2$ | Pr | 4-(3-MeO-Ph)-Ph | O |
| 3-213 | H | (CH$_2$)$_2$ | H | H | CH$_2$ | Pr | 4-(3-HO-Ph)-Ph | O |
| 3-214 | H | (CH$_2$)$_2$ | H | H | CH$_2$ | Pr | 4-(3-OHC-Ph)-Ph | O |
| 3-215 | H | (CH$_2$)$_2$ | H | H | CH$_2$ | Pr | 4-(3-Dmam-Ph)-Ph | O |
| 3-216 | H | (CH$_2$)$_2$ | H | H | CH$_2$ | Pr | 4-(3-Dmam-Ph)-Ph | O |
| 3-217 | H | (CH$_2$)$_2$ | H | H | CH$_2$ | Pr | 4-(3-HOOC-Ph)-Ph | O |
| 3-218 | H | (CH$_2$)$_2$ | H | H | CH$_2$ | Pr | 4-(3-HOH$_2$C-Ph)-Ph | O |
| 3-219 | H | (CH$_2$)$_2$ | H | H | CH$_2$ | Pr | 4-(2-MeO-Ph)-Ph | O |
| 3-220 | H | (CH$_2$)$_2$ | H | H | CH$_2$ | Pr | 4-(2-HO-Ph)-Ph | O |
| 3-221 | H | (CH$_2$)$_2$ | H | H | CH$_2$ | Pr | 4-(2-OHC-Ph)-Ph | O |
| 3-222 | H | (CH$_2$)$_2$ | H | H | CH$_2$ | Pr | 4-(3-MeO-Pyr-6)-Ph | O |
| 3-223 | H | (CH$_2$)$_2$ | H | H | CH$_2$ | Pr | 4-(3-EtO-Pyr-6)-Ph | O |
| 3-224 | H | (CH$_2$)$_2$ | H | H | CH$_2$ | Pr | 4-(3-iPrO-Pyr-6)-Ph | O |
| 3-225 | H | (CH$_2$)$_2$ | H | H | CH$_2$ | Pr | 4-(3-Dma-Pyr-6)-Ph | O |
| 3-226 | H | (CH$_2$)$_2$ | H | H | CH$_2$ | Pr | 4-(3-Dea-Pyr-6)-Ph | O |
| 3-227 | H | (CH$_2$)$_2$ | H | H | CH$_2$ | Pr | 4-(3-F$_3$C-Pyr-6)-Ph | O |
| 3-228 | H | (CH$_2$)$_2$ | H | H | CH$_2$ | Pr | 4-(3-O$_2$N-Pyr-6)-Ph | O |
| 3-229 | H | (CH$_2$)$_2$ | H | H | CH$_2$ | Pr | 4-Pip-Ph | O |
| 3-230 | H | (CH$_2$)$_2$ | H | H | CH$_2$ | Pr | 4-Dea-Ph | O |

TABLE 3-continued

| Ex. No. Comp. | R¹ | R² | R³ | R⁴ | Z | W | X | Y |
|---|---|---|---|---|---|---|---|---|
| 3-231 | H | (CH₂)₂ | H | H | CH₂ | Pr | 2-(4-F-Ph)-5-Pyr | O |
| 3-232 | H | (CH₂)₂ | H | H | CH₂ | Pr | 2-(4-Cl-Ph)-5-Pyr | O |
| 3-233 | H | (CH₂)₂ | H | H | CH₂ | Pr | 2-(4-Meo-Ph)-5-Pyr | O |
| 3-234 | H | (CH₂)₂ | H | H | CH₂ | Pr | 2-(4-EtO-Ph)-5-Pyr | O |
| 3-235 | H | (CH₂)₂ | H | H | CH₂ | Pr | 2-(4-iPrO-Ph)-5-Pyr | O |
| 3-236 | H | (CH₂)₂ | H | H | CH₂ | Pr | 2-TfpO-5-Pyr | O |
| 3-237 | H | (CH₂)₂ | H | H | CH₂ | Pr | 4-(4-AcO-Ph)-Ph | O |
| 3-238 | H | (CH₂)₂ | H | H | CH₂ | Pr | 4-(3-F-Ph)-Ph | O |
| 3-239 | H | (CH₂)₂ | H | H | CH₂ | Pr | 4-(3-Cl-Ph)-Ph | O |
| 3-240 | H | (CH₂)₂ | H | H | CH₂ | Pr | 4-(3-Me-Ph)-Ph | O |
| 3-241 | H | (CH₂)₂ | H | H | CH₂ | Pr | 4-(3-AcO-Ph)-Ph | O |
| 3-242 | H | (CH₂)₂ | H | H | CH₂ | Pr | 4-(3-Me-Pyr-6)-Ph | O |
| 3-243 | H | (CH₂)₂ | H | H | CH₂ | Pr | 4-(3-Et-Pyr-6)-Ph | O |
| 3-244 | H | (CH₂)₂ | H | H | CH₂ | Pr | 2-(4-Me-Ph)-5-Pyr | O |
| 3-245 | H | (CH₂)₂ | H | H | CH₂ | Pr | 2-(4-CF₃-Ph)-5-Pyr | O |
| 3-246 | H | (CH₂)₂ | H | H | CH₂ | Pr | 2-(4-Dma-Ph)-5-Pyr | O |
| 3-247 | H | (CH₂)₂ | H | H | CH₂ | Pr | 2-(3-F-Ph)-5-Pyr | O |
| 3-248 | H | (CH₂)₂ | H | H | CH₂ | Pr | 2-(3-Cl-Ph)-5-Pyr | O |
| 3-249 | H | (CH₂)₂ | H | H | CH₂ | Pr | 2-(3-MeO-Ph)-5-Pyr | O |
| 3-250 | H | (CH₂)₂ | H | H | CH₂ | Pr | 2-(3-EtO-Ph)-5-Pyr | O |
| 3-251 | H | (CH₂)₂ | H | H | CH₂ | Pr | 2-(3-iPrO-Ph)-5-Pyr | O |
| 3-252 | H | (CH₂)₂ | H | H | CH₂ | Pr | 2-(3-Me-Ph)-5-Pyr | O |
| 3-253 | H | (CH₂)₂ | H | H | CH₂ | Pr | 2-(3-CF₃-Ph)-5-Pyr | O |
| 3-254 | H | (CH₂)₂ | H | H | CH₂ | Pr | 2-(3-Dma-Ph)-5-Pyr | O |

TABLE 4

| Ex. No. Comp. | R¹ | R² | R³ | R⁴ | Z | W | X | Y |
|---|---|---|---|---|---|---|---|---|
| 4-1 | H | (CH₂)₂ | H | H | CH₂ | Bu | Ph | O |
| 4-2 | H | (CH₂)₂ | H | H | CH₂ | Bu | 1-Np | O |
| 4-3 | H | (CH₂)₂ | H | H | CH₂ | Bu | 2-Np | O |
| 4-4 | H | (CH₂)₂ | H | H | CH₂ | Bu | 4-Me-Ph | O |
| 4-5 | H | (CH₂)₂ | H | H | CH₂ | Bu | 4-Et-Ph | O |
| 4-6 | H | (CH₂)₂ | H | H | CH₂ | Bu | 3-iPr-Ph | O |
| 4-7 | H | (CH₂)₂ | H | H | CH₂ | Bu | 4-iPr-Ph | O |
| 4-8 | H | (CH₂)₂ | H | H | CH₂ | Bu | 3-tBu-Ph | O |
| 4-9 | H | (CH₂)₂ | H | H | CH₂ | Bu | 4-tBu-Ph | O |
| 4-10 | H | (CH₂)₂ | H | H | CH₂ | Bu | 3-F-Ph | O |
| 4-11 | H | (CH₂)₂ | H | H | CH₂ | Bu | 4-F-Ph | O |
| 4-12 | H | (CH₂)₂ | H | H | CH₂ | Bu | 4-Cl-Ph | O |
| 4-13 | H | (CH₂)₂ | H | H | CH₂ | Bu | 4-Br-Ph | O |
| 4-14 | H | (CH₂)₂ | H | H | CH₂ | Bu | 3-Ph-Ph | O |
| 4-15 | H | (CH₂)₂ | H | H | CH₂ | Bu | 4-Ph-Ph | O |
| 4-16 | H | (CH₂)₂ | H | H | CH₂ | Bu | 4-BzO-Ph | O |
| 4-17 | H | (CH₂)₂ | H | H | CH₂ | Bu | 4-Bz-Ph | O |
| 4-18 | H | (CH₂)₂ | H | H | CH₂ | Bu | 3-PhO-Ph | O |
| 4-19 | H | (CH₂)₂ | H | H | CH₂ | Bu | 4-PhO-Ph | O |
| 4-20 | H | (CH₂)₂ | H | H | CH₂ | Bu | 3-PhS-Ph | O |
| 4-21 | H | (CH₂)₂ | H | H | CH₂ | Bu | 4-PhS-Ph | O |
| 4-22 | H | (CH₂)₂ | H | H | CH₂ | Bu | 3-PhSO₂-Ph | O |
| 4-23 | H | (CH₂)₂ | H | H | CH₂ | Bu | 4-PhSO₂-Ph | O |
| 4-24 | H | (CH₂)₂ | H | H | CH₂ | Bu | 3-(Imid-1)-Ph | O |
| 4-25 | H | (CH₂)₂ | H | H | CH₂ | Bu | 4-(Imid-1)-Ph | O |
| 4-26 | H | (CH₂)₂ | H | H | CH₂ | Bu | 3-(Imid-4)-Ph | O |
| 4-27 | H | (CH₂)₂ | H | H | CH₂ | Bu | 4-(Imid-4)-Ph | O |
| 4-28 | H | (CH₂)₂ | H | H | CH₂ | Bu | 3-(Fur-2)-Ph | O |
| 4-29 | H | (CH₂)₂ | H | H | CH₂ | Bu | 4-(Fur-2)-Ph | O |
| 4-30 | H | (CH₂)₂ | H | H | CH₂ | Bu | 3-(Thi-2)-Ph | O |
| 4-31 | H | (CH₂)₂ | H | H | CH₂ | Bu | 4-(Thi-2)-Ph | O |
| 4-32 | H | (CH₂)₂ | H | H | CH₂ | Bu | 3-(Thi-3)-Ph | O |
| 4-33 | H | (CH₂)₂ | H | H | CH₂ | Bu | 4-(Thi-3)-Ph | O |
| 4-34 | H | (CH₂)₂ | H | H | CH₂ | Bu | 3-(Pyr-2)-Ph | O |
| 4-35 | H | (CH₂)₂ | H | H | CH₂ | Bu | 4-(Pyr-2)-Ph | O |
| 4-36 | H | (CH₂)₂ | H | H | CH₂ | Bu | 3-(Pyr-3)-Ph | O |
| 4-37 | H | (CH₂)₂ | H | H | CH₂ | Bu | 4-(Pyr-3)-Ph | O |
| 4-38 | H | (CH₂)₂ | H | H | CH₂ | Bu | 3-(Pyr-4)-Ph | O |
| 4-39 | H | (CH₂)₂ | H | H | CH₂ | Bu | 4-(Pyr-4)-Ph | O |
| 4-40 | H | (CH₂)₂ | H | H | CH₂ | Bu | 3-(Oxa-2)-Ph | O |
| 4-41 | H | (CH₂)₂ | H | H | CH₂ | Bu | 4-(Oxa-2)-Ph | O |
| 4-42 | H | (CH₂)₂ | H | H | CH₂ | Bu | 3-(Oxa-4)-Ph | O |
| 4-43 | H | (CH₂)₂ | H | H | CH₂ | Bu | 4-(Oxa-4)-Ph | O |
| 4-44 | H | (CH₂)₂ | H | H | CH₂ | Bu | 3-(Oxa-5)-Ph | O |
| 4-45 | H | (CH₂)₂ | H | H | CH₂ | Bu | 4-(Oxa-5)-Ph | O |
| 4-46 | H | (CH₂)₂ | H | H | CH₂ | Bu | 3-(Thiz-2)-Ph | O |
| 4-47 | H | (CH₂)₂ | H | H | CH₂ | Bu | 4-(Thiz-2)-Ph | O |
| 4-48 | H | (CH₂)₂ | H | H | CH₂ | Bu | 3-(Thiz-4)-Ph | O |
| 4-49 | H | (CH₂)₂ | H | H | CH₂ | Bu | 4-(Thiz-4)-Ph | O |
| 4-50 | H | (CH₂)₂ | H | H | CH₂ | Bu | 3-(Thiz-5)-Ph | O |
| 4-51 | H | (CH₂)₂ | H | H | CH₂ | Bu | 4-(Thiz-5)-Ph | O |
| 4-52 | H | (CH₂)₂ | H | H | CH₂ | Bu | 1-Me-2-Pyrr | O |
| 4-53 | H | (CH₂)₂ | H | H | CH₂ | Bu | 1-Ph-2-Pyrr | O |
| 4-54 | H | (CH₂)₂ | H | H | CH₂ | Bu | 1-Bz-2-Pyrr | O |
| 4-55 | H | (CH₂)₂ | H | H | CH₂ | Bu | 5-Me-2-Fur | O |
| 4-56 | H | (CH₂)₂ | H | H | CH₂ | Bu | 5-Ph-2-Fur | O |
| 4-57 | H | (CH₂)₂ | H | H | CH₂ | Bu | 5-Me-2-Thi | O |
| 4-58 | H | (CH₂)₂ | H | H | CH₂ | Bu | 5-Ph-2-Thi | O |
| 4-59 | H | (CH₂)₂ | H | H | CH₂ | Bu | 5-Me-3-Thi | O |
| 4-60 | H | (CH₂)₂ | H | H | CH₂ | Bu | 5-Ph-3-Thi | O |
| 4-61 | H | (CH₂)₂ | H | H | CH₂ | Bu | 1-Me-3-Pyza | O |
| 4-62 | H | (CH₂)₂ | H | H | CH₂ | Bu | 1-Ph-3-Pyza | O |
| 4-63 | H | (CH₂)₂ | H | H | CH₂ | Bu | 1-Me-2-Imid | O |
| 4-64 | H | (CH₂)₂ | H | H | CH₂ | Bu | 1-Ph-2-Imid | O |
| 4-65 | H | (CH₂)₂ | H | H | CH₂ | Bu | 1-Me-4-Imid | O |
| 4-66 | H | (CH₂)₂ | H | H | CH₂ | Bu | 1-Ph-4-Imid | O |
| 4-67 | H | (CH₂)₂ | H | H | CH₂ | Bu | 4-Oxa | O |
| 4-68 | H | (CH₂)₂ | H | H | CH₂ | Bu | 5-Oxa | O |
| 4-69 | H | (CH₂)₂ | H | H | CH₂ | Bu | 2-Me-4-Oxa | O |
| 4-70 | H | (CH₂)₂ | H | H | CH₂ | Bu | 2-Ph-4-Oxa | O |
| 4-71 | H | (CH₂)₂ | H | H | CH₂ | Bu | 2-Me-5-Oxa | O |
| 4-72 | H | (CH₂)₂ | H | H | CH₂ | Bu | 2-Ph-5-Oxa | O |
| 4-73 | H | (CH₂)₂ | H | H | CH₂ | Bu | 4-Me-2-Ph-5-Oxa | O |
| 4-74 | H | (CH₂)₂ | H | H | CH₂ | Bu | 5-Me-2-Ph-4-Oxa | O |
| 4-75 | H | (CH₂)₂ | H | H | CH₂ | Bu | 4-Thiz | O |
| 4-76 | H | (CH₂)₂ | H | H | CH₂ | Bu | 5-Thiz | O |
| 4-77 | H | (CH₂)₂ | H | H | CH₂ | Bu | 2-Me-4-Thiz | O |
| 4-78 | H | (CH₂)₂ | H | H | CH₂ | Bu | 2-Ph-4-Thiz | O |
| 4-79 | H | (CH₂)₂ | H | H | CH₂ | Bu | 2-Me-5-Thiz | O |
| 4-80 | H | (CH₂)₂ | H | H | CH₂ | Bu | 2-Ph-5-Thiz | O |
| 4-81 | H | (CH₂)₂ | H | H | CH₂ | Bu | 4-Me-2-Ph-5-Thiz | O |
| 4-82 | H | (CH₂)₂ | H | H | CH₂ | Bu | 5-Me-2-Ph-4-Thiz | O |
| 4-83 | H | (CH₂)₂ | H | H | CH₂ | Bu | 1-Me-4-Pyza | O |
| 4-84 | H | (CH₂)₂ | H | H | CH₂ | Bu | 1-Ph-4-Pyza | O |
| 4-85 | H | (CH₂)₂ | H | H | CH₂ | Bu | 2-Me-4-Isox | O |
| 4-86 | H | (CH₂)₂ | H | H | CH₂ | Bu | 2-Ph-4-Isox | O |
| 4-87 | H | (CH₂)₂ | H | H | CH₂ | Bu | 2-Pyr | O |
| 4-88 | H | (CH₂)₂ | H | H | CH₂ | Bu | 3-Pyr | O |
| 4-89 | H | (CH₂)₂ | H | H | CH₂ | Bu | 4-Pyr | O |
| 4-90 | H | (CH₂)₂ | H | H | CH₂ | Bu | 3-Me-5-Pyr | O |
| 4-91 | H | (CH₂)₂ | H | H | CH₂ | Bu | 3-Et-5-Pyr | O |
| 4-92 | H | (CH₂)₂ | H | H | CH₂ | Bu | 3-Ph-5-Pyr | O |
| 4-93 | H | (CH₂)₂ | H | H | CH₂ | Bu | 2-Me-5-Pyr | O |
| 4-94 | H | (CH₂)₂ | H | H | CH₂ | Bu | 2-BzO-5-Pyr | O |
| 4-95 | H | (CH₂)₂ | H | H | CH₂ | Bu | 2-Ph-5-Pyr | O |
| 4-96 | H | (CH₂)₂ | H | H | CH₂ | Bu | 2-MeO-5-Pyr | O |
| 4-97 | H | (CH₂)₂ | H | H | CH₂ | Bu | 2-EtO-5-Pyr | O |
| 4-98 | H | (CH₂)₂ | H | H | CH₂ | Bu | 2-iPrO-5-Pyr | O |
| 4-99 | H | (CH₂)₂ | H | H | CH₂ | Bu | 2-MeS-5-Pyr | O |
| 4-100 | H | (CH₂)₂ | H | H | CH₂ | Bu | 2-EtS-5-Pyr | O |
| 4-101 | H | (CH₂)₂ | H | H | CH₂ | Bu | 2-PhSO₂NH-5-Pyr | O |
| 4-102 | H | (CH₂)₂ | H | H | CH₂ | Bu | 2-MeSO₂-5-Pyr | O |
| 4-103 | H | (CH₂)₂ | H | H | CH₂ | Bu | 2-EtSO₂-5-Pyr | O |
| 4-104 | H | (CH₂)₂ | H | H | CH₂ | Bu | 2-PhSO₂NMe-5-Pyr | O |
| 4-105 | H | (CH₂)₂ | H | H | CH₂ | Bu | 2-Bz-5-Pyr | O |
| 4-106 | H | (CH₂)₂ | H | H | CH₂ | Bu | 2-PhO-5-Pyr | O |
| 4-107 | H | (CH₂)₂ | H | H | CH₂ | Bu | 2-PhS-5-Pyr | O |
| 4-108 | H | (CH₂)₂ | H | H | CH₂ | Bu | 2-PhSO₂-5-Pyr | O |
| 4-109 | H | (CH₂)₂ | H | H | CH₂ | Bu | 3-Me-6-Pyr | O |
| 4-110 | H | (CH₂)₂ | H | H | CH₂ | Bu | 3-Ph-6-Pyr | O |
| 4-111 | H | (CH₂)₂ | H | H | CH₂ | Bu | 2-Me-6-Pyr | O |
| 4-112 | H | (CH₂)₂ | H | H | CH₂ | Bu | 2-Ph-6-Pyr | O |
| 4-113 | H | (CH₂)₂ | H | H | CH₂ | Bu | 2-Me-4-Pym | O |
| 4-114 | H | (CH₂)₂ | H | H | CH₂ | Bu | 2-Ph-4-Pym | O |
| 4-115 | H | (CH₂)₂ | H | H | CH₂ | Bu | 2-MeO-4-Pym | O |

TABLE 4-continued

| Ex. No. Comp. | R¹ | R² | R³ | R⁴ | Z | W | X | Y |
|---|---|---|---|---|---|---|---|---|
| 4-116 | H | (CH$_2$)$_2$ | H | H | CH$_2$ | Bu | 2-EtO-4-Pym | O |
| 4-117 | H | (CH$_2$)$_2$ | H | H | CH$_2$ | Bu | 2-iPro-4-Pym | O |
| 4-118 | H | (CH$_2$)$_2$ | H | H | CH$_2$ | Bu | 2-MeS-4-Pym | O |
| 4-119 | H | (CH$_2$)$_2$ | H | H | CH$_2$ | Bu | 2-EtS-4-Pym | O |
| 4-120 | H | (CH$_2$)$_2$ | H | H | CH$_2$ | Bu | 2-iPrS-4-Pym | O |
| 4-121 | H | (CH$_2$)$_2$ | H | H | CH$_2$ | Bu | 6-MeS-4-Pym | O |
| 4-122 | H | (CH$_2$)$_2$ | H | H | CH$_2$ | Bu | 6-EtS-4-Pym | O |
| 4-123 | H | (CH$_2$)$_2$ | H | H | CH$_2$ | Bu | 6-iPrS-4-Pym | O |
| 4-124 | H | (CH$_2$)$_2$ | H | H | CH$_2$ | Bu | 2-PhS-4-Pym | O |
| 4-125 | H | (CH$_2$)$_2$ | H | H | CH$_2$ | Bu | 2-MeSO$_2$-4-Pym | O |
| 4-126 | H | (CH$_2$)$_2$ | H | H | CH$_2$ | Bu | 2-EtSO$_2$-4-Pym | O |
| 4-127 | H | (CH$_2$)$_2$ | H | H | CH$_2$ | Bu | 2-iPrSO$_2$-4-Pym | O |
| 4-128 | H | (CH$_2$)$_2$ | H | H | CH$_2$ | Bu | 2-PhSO$_2$-4-Pym | O |
| 4-129 | H | (CH$_2$)$_2$ | H | H | CH$_2$ | Bu | 2-Me-5-Pym | O |
| 4-130 | H | (CH$_2$)$_2$ | H | H | CH$_2$ | Bu | 2-Ph-5-Pym | O |
| 4-131 | H | (CH$_2$)$_2$ | H | H | CH$_2$ | Bu | 2-MeO-5-Pym | O |
| 4-132 | H | (CH$_2$)$_2$ | H | H | CH$_2$ | Bu | 2-EtO-5-Pym | O |
| 4-133 | H | (CH$_2$)$_2$ | H | H | CH$_2$ | Bu | 2-iPrO-5-Pym | O |
| 4-134 | H | (CH$_2$)$_2$ | H | H | CH$_2$ | Bu | 2-MeS-5-Pym | O |
| 4-135 | H | (CH$_2$)$_2$ | H | H | CH$_2$ | Bu | 2-EtS-5-Pym | O |
| 4-136 | H | (CH$_2$)$_2$ | H | H | CH$_2$ | Bu | 2-iPrS-5-Pym | O |
| 4-137 | H | (CH$_2$)$_2$ | H | H | CH$_2$ | Bu | 2-PhS-5-Pym | O |
| 4-138 | H | (CH$_2$)$_2$ | H | H | CH$_2$ | Bu | 2-MeSO$_2$-5-Pym | O |
| 4-139 | H | (CH$_2$)$_2$ | H | H | CH$_2$ | Bu | 2-EtSO$_2$-5-Pym | O |
| 4-140 | H | (CH$_2$)$_2$ | H | H | CH$_2$ | Bu | 2-iPrSO$_2$-5-Pym | O |
| 4-141 | H | (CH$_2$)$_2$ | H | H | CH$_2$ | Bu | 2-PhSO$_2$-5-Pym | O |
| 4-142 | H | (CH$_2$)$_2$ | H | H | CH$_2$ | Bu | 2-Ind | O |
| 4-143 | H | (CH$_2$)$_2$ | H | H | CH$_2$ | Bu | 3-Ind | O |
| 4-144 | H | (CH$_2$)$_2$ | H | H | CH$_2$ | Bu | 1-Me-2-Ind | O |
| 4-145 | H | (CH$_2$)$_2$ | H | H | CH$_2$ | Bu | 1-Me-3-Ind | O |
| 4-146 | H | (CH$_2$)$_2$ | H | H | CH$_2$ | Bu | 2-Bimid | O |
| 4-147 | H | (CH$_2$)$_2$ | H | H | CH$_2$ | Bu | 2-Boxa | O |
| 4-148 | H | (CH$_2$)$_2$ | H | H | CH$_2$ | Bu | 2-Bthiz | O |
| 4-149 | H | (CH$_2$)$_2$ | H | H | CH$_2$ | Bu | 2-Quin | O |
| 4-150 | H | (CH$_2$)$_2$ | H | H | CH$_2$ | Bu | 3-Quin | O |
| 4-151 | H | (CH$_2$)$_2$ | H | H | CH$_2$ | Bu | 4-Quin | O |
| 4-152 | H | (CH$_2$)$_2$ | H | H | CH$_2$ | Bu | 1-iQuin | O |
| 4-153 | H | (CH$_2$)$_2$ | H | H | CH$_2$ | Bu | 3-iQuin | O |
| 4-154 | H | (CH$_2$)$_2$ | H | H | CH$_2$ | Bu | 4-iQuin | O |
| 4-155 | H | (CH$_2$)$_2$ | H | H | CH$_2$ | Bu | 3-MeO-Ph | O |
| 4-156 | H | (CH$_2$)$_2$ | H | H | CH$_2$ | Bu | 4-MeO-Ph | O |
| 4-157 | H | (CH$_2$)$_2$ | H | H | CH$_2$ | Bu | 3-EtO-Ph | O |
| 4-158 | H | (CH$_2$)$_2$ | H | H | CH$_2$ | Bu | 4-EtO-Ph | O |
| 4-159 | H | (CH$_2$)$_2$ | H | H | CH$_2$ | Bu | 3-iPrO-Ph | O |
| 4-160 | H | (CH$_2$)$_2$ | H | H | CH$_2$ | Bu | 4-iPrO-Ph | O |
| 4-161 | H | (CH$_2$)$_2$ | H | H | CH$_2$ | Bu | 3-MeS-Ph | O |
| 4-162 | H | (CH$_2$)$_2$ | H | H | CH$_2$ | Bu | 4-MeS-Ph | O |
| 4-163 | H | (CH$_2$)$_2$ | H | H | CH$_2$ | Bu | 3-EtS-Ph | O |
| 4-164 | H | (CH$_2$)$_2$ | H | H | CH$_2$ | Bu | 4-EtS-Ph | O |
| 4-165 | H | (CH$_2$)$_2$ | H | H | CH$_2$ | Bu | 3-iPrS-Ph | O |
| 4-166 | H | (CH$_2$)$_2$ | H | H | CH$_2$ | Bu | 4-iPrS-Ph | O |
| 4-167 | H | (CH$_2$)$_2$ | H | H | CH$_2$ | Bu | 3-MeSO$_2$-Ph | O |
| 4-168 | H | (CH$_2$)$_2$ | H | H | CH$_2$ | Bu | 4-MeSO$_2$-Ph | O |
| 4-169 | H | (CH$_2$)$_2$ | H | H | CH$_2$ | Bu | 3-EtSO$_2$-Ph | O |
| 4-170 | H | (CH$_2$)$_2$ | H | H | CH$_2$ | Bu | 4-EtSO$_2$-Ph | O |
| 4-171 | H | (CH$_2$)$_2$ | H | H | CH$_2$ | Bu | 3-iPrSO$_2$-Ph | O |
| 4-172 | H | (CH$_2$)$_2$ | H | H | CH$_2$ | Bu | 4-iPrSO$_2$-Ph | O |
| 4-173 | H | (CH$_2$)$_2$ | H | H | CH$_2$ | Bu | 3-(1-Me-Imid-4)-Ph | O |
| 4-174 | H | (CH$_2$)$_2$ | H | H | CH$_2$ | Bu | 4-(1-Me-Imid-4)-Ph | O |
| 4-175 | H | (CH$_2$)$_2$ | H | H | CH$_2$ | Bu | 1-Me-2-Ph-4-Imid | O |
| 4-176 | H | (CH$_2$)$_2$ | H | H | CH$_2$ | Bu | 1,4-di-Me-2-Ph-5-Imid | O |
| 4-177 | H | (CH$_2$)$_2$ | H | H | CH$_2$ | Bu | 1,5-di-Me-2-Ph-4-Imid | O |
| 4-178 | H | (CH$_2$)$_2$ | H | H | CH$_2$ | Bu | 3,4-MdO-Ph | O |
| 4-179 | H | (CH$_2$)$_2$ | H | H | CH$_2$ | Bu | 4-(4-MeO-Ph)-Ph | O |
| 4-180 | H | (CH$_2$)$_2$ | H | H | CH$_2$ | Bu | 4-(3,4-MdO-Ph)-Ph | O |
| 4-181 | H | (CH$_2$)$_2$ | H | H | CH$_2$ | Bu | 4-[PhSO$_2$N(Me)]-Ph | O |
| 4-182 | H | (CH$_2$)$_2$ | H | H | CH$_2$ | Bu | 4-[(Pyr-3)SO$_2$N(Me)]-Ph | O |
| 4-183 | H | (CH$_2$)$_2$ | H | H | CH$_2$ | Bu | 4-(PhSO$_2$NH)-Ph | O |
| 4-184 | H | (CH$_2$)$_2$ | H | H | CH$_2$ | Bu | 4-[(Pyr-3)SO$_2$NH]-Ph | O |
| 4-185 | H | (CH$_2$)$_2$ | H | H | CH$_2$ | Bu | 4-[(Pyr-2)SO$_2$]-Ph | O |
| 4-186 | H | (CH$_2$)$_2$ | H | H | CH$_2$ | Bu | 4-[(Pyr-3)SO$_2$]-Ph | O |
| 4-187 | H | (CH$_2$)$_2$ | H | H | CH$_2$ | Bu | 4-[(Pyr-2)SO$_2$N(Me)]-Ph | O |
| 4-188 | H | (CH$_2$)$_2$ | H | H | CH$_2$ | Bu | 4-[(Pyr-2)SO$_2$NH]-Ph | O |
| 4-189 | H | (CH$_2$)$_2$ | H | H | CH$_2$ | Bu | 4-(4-Me-Ph)-Ph | O |
| 4-190 | H | (CH$_2$)$_2$ | H | H | CH$_2$ | Bu | 4-(4-F-Ph)-Ph | O |
| 4-191 | H | (CH$_2$)$_2$ | H | H | CH$_2$ | Bu | 4-(4-CF$_3$-Ph)-Ph | O |
| 4-192 | H | (CH$_2$)$_2$ | H | H | CH$_2$ | Bu | 2-[PhSO$_2$N(Me)]-5-Pyr | O |
| 4-193 | H | (CH$_2$)$_2$ | H | H | CH$_2$ | Bu | 2-HO-5-Pyr | O |
| 4-194 | H | (CH$_2$)$_2$ | H | H | CH$_2$ | Bu | 2-BzO-5-Pyr | O |
| 4-195 | H | (CH$_2$)$_2$ | H | H | CH$_2$ | Bu | 4-[(Pyr-4)SO$_2$]-Ph | O |
| 4-196 | H | (CH$_2$)$_2$ | H | H | CH$_2$ | Bu | 4-[(Pyr-4)O]-Ph | O |
| 4-197 | H | (CH$_2$)$_2$ | H | H | CH$_2$ | Bu | 4-[(Pyr-4)S]-Ph | O |
| 4-198 | H | (CH$_2$)$_2$ | H | H | CH$_2$ | Bu | 3-HO-Ph | O |
| 4-199 | H | (CH$_2$)$_2$ | H | H | CH$_2$ | Bu | 4-HO-Ph | O |
| 4-200 | H | (CH$_2$)$_2$ | H | H | CH$_2$ | Bu | 2-HO-3,4,6-tri-Me-Ph | O |
| 4-201 | H | (CH$_2$)$_2$ | H | H | CH$_2$ | Bu | 4-HO-3,5-di-Me-Ph | O |
| 4-202 | H | (CH$_2$)$_2$ | H | H | CH$_2$ | Bu | 3-AcO-Ph | O |
| 4-203 | H | (CH$_2$)$_2$ | H | H | CH$_2$ | Bu | 4-AcO-Ph | O |
| 4-204 | H | (CH$_2$)$_2$ | H | H | CH$_2$ | Bu | 4-(4-Cl-Ph)-Ph | O |
| 4-205 | H | (CH$_2$)$_2$ | H | H | CH$_2$ | Bu | 4-(4-HO-3,5-di-Me-Ph)-Ph | O |
| 4-206 | H | (CH$_2$)$_2$ | H | H | CH$_2$ | Bu | 4-(4-HO-Ph)-Ph | O |
| 4-207 | H | (CH$_2$)$_2$ | H | H | CH$_2$ | Bu | 4-(4-OHC-Ph)-Ph | O |
| 4-208 | H | (CH$_2$)$_2$ | H | H | CH$_2$ | Bu | 4-(4-Dmam-Ph)-Ph | O |
| 4-209 | H | (CH$_2$)$_2$ | H | H | CH$_2$ | Bu | 4-(4-Dma-Ph)-Ph | O |
| 4-210 | H | (CH$_2$)$_2$ | H | H | CH$_2$ | Bu | 4-(4-HOOC-Ph)-Ph | O |
| 4-211 | H | (CH$_2$)$_2$ | H | H | CH$_2$ | Bu | 4-(4-HOH$_2$C-Ph)-Ph | O |
| 4-212 | H | (CH$_2$)$_2$ | H | H | CH$_2$ | Bu | 4-(3-MeO-Ph)-Ph | O |
| 4-213 | H | (CH$_2$)$_2$ | H | H | CH$_2$ | Bu | 4-(3-HO-Ph)-Ph | O |
| 4-214 | H | (CH$_2$)$_2$ | H | H | CH$_2$ | Bu | 4-(3-OHC-Ph)-Ph | O |
| 4-215 | H | (CH$_2$)$_2$ | H | H | CH$_2$ | Bu | 4-(3-Dmam-Ph)-Ph | O |
| 4-216 | H | (CH$_2$)$_2$ | H | H | CH$_2$ | Bu | 4-(3-Dma-Ph)-Ph | O |
| 4-217 | H | (CH$_2$)$_2$ | H | H | CH$_2$ | Bu | 4-(3-HOOC-Ph)-Ph | O |
| 4-218 | H | (CH$_2$)$_2$ | H | H | CH$_2$ | Bu | 4-(3-HOH$_2$C-Ph)-Ph | O |
| 4-219 | H | (CH$_2$)$_2$ | H | H | CH$_2$ | Bu | 4-(2-MeO-Ph)-Ph | O |
| 4-220 | H | (CH$_2$)$_2$ | H | H | CH$_2$ | Bu | 4-(2-HO-Ph)-Ph | O |
| 4-221 | H | (CH$_2$)$_2$ | H | H | CH$_2$ | Bu | 4-(2-OHC-Ph)-Ph | O |
| 4-222 | H | (CH$_2$)$_2$ | H | H | CH$_2$ | Bu | 4-(3-MeO-Pyr-6)-Ph | O |
| 4-223 | H | (CH$_2$)$_2$ | H | H | CH$_2$ | Bu | 4-(3-EtO-Pyr-6)-Ph | O |
| 4-224 | H | (CH$_2$)$_2$ | H | H | CH$_2$ | Bu | 4-(3-iPrO-Pyr-6)-Ph | O |
| 4-225 | H | (CH$_2$)$_2$ | H | H | CH$_2$ | Bu | 4-(3-Dma-Pyr-6)-Ph | O |
| 4-226 | H | (CH$_2$)$_2$ | H | H | CH$_2$ | Bu | 4-(3-Dea-Pyr-6)-Ph | O |
| 4-227 | H | (CH$_2$)$_2$ | H | H | CH$_2$ | Bu | 4-(3-F$_3$C-Pyr-6)-Ph | O |
| 4-228 | H | (CH$_2$)$_2$ | H | H | CH$_2$ | Bu | 4-(3-O$_2$-Pyr-6)-Ph | O |
| 4-229 | H | (CH$_2$)$_2$ | H | H | CH$_2$ | Bu | 4-Pip-Ph | O |
| 4-230 | H | (CH$_2$)$_2$ | H | H | CH$_2$ | Bu | 4-Dea-Ph | O |
| 4-231 | H | (CH$_2$)$_2$ | H | H | CH$_2$ | Bu | 2-(4-F-Ph)-5-Pyr | O |
| 4-232 | H | (CH$_2$)$_2$ | H | H | CH$_2$ | Bu | 2-(4-Cl-Ph)-5-Pyr | O |
| 4-233 | H | (CH$_2$)$_2$ | H | H | CH$_2$ | Bu | 2-(4-MeO-Ph)-5-Pyr | O |
| 4-234 | H | (CH$_2$)$_2$ | H | H | CH$_2$ | Bu | 2-(4-EtO-Ph)-5-Pyr | O |
| 4-235 | H | (CH$_2$)$_2$ | H | H | CH$_2$ | Bu | 2-(4-iPrO-Ph)-5-Pyr | O |
| 4-236 | H | (CH$_2$)$_2$ | H | H | CH$_2$ | Bu | 2-TfpO-5-Pyr | O |
| 4-237 | H | (CH$_2$)$_2$ | H | H | CH$_2$ | Bu | 4-(4-AcO-Ph)-Ph | O |
| 4-238 | H | (CH$_2$)$_2$ | H | H | CH$_2$ | Bu | 4-(3-F-Ph)-Ph | O |
| 4-239 | H | (CH$_2$)$_2$ | H | H | CH$_2$ | Bu | 4-(3-Cl-Ph)-Ph | O |
| 4-240 | H | (CH$_2$)$_2$ | H | H | CH$_2$ | Bu | 4-(3-Me-Ph)-Ph | O |
| 4-241 | H | (CH$_2$)$_2$ | H | H | CH$_2$ | Bu | 4-(3-AcO-Ph)-Ph | O |
| 4-242 | H | (CH$_2$)$_2$ | H | H | CH$_2$ | Bu | 4-(3-Me-Pyr-6)-Ph | O |
| 4-243 | H | (CH$_2$)$_2$ | H | H | CH$_2$ | Pr | 4-(3-Et-Pyr-6)-Ph | O |
| 4-244 | H | (CH$_2$)$_2$ | H | H | CH$_2$ | Bu | 2-(4-Me-Ph)-5-Pyr | O |
| 4-245 | H | (CH$_2$)$_2$ | H | H | CH$_2$ | Bu | 2-(4-CF$_3$-Ph)-5-Pyr | O |
| 4-246 | H | (CH$_2$)$_2$ | H | H | CH$_2$ | Bu | 2-(4-Dma-Ph)-5-Pyr | O |
| 4-247 | H | (CH$_2$)$_2$ | H | H | CH$_2$ | Bu | 2-(3-F-Ph)-5-Pyr | O |
| 4-248 | H | (CH$_2$)$_2$ | H | H | CH$_2$ | Bu | 2-(3-Cl-Ph)-5-Pyr | O |
| 4-249 | H | (CH$_2$)$_2$ | H | H | CH$_2$ | Bu | 2-(3-MeO-Ph)-5-Pyr | O |
| 4-250 | H | (CH$_2$)$_2$ | H | H | CH$_2$ | Bu | 2-(3-EtO-Ph)-5-Pyr | O |
| 4-251 | H | (CH$_2$)$_2$ | H | H | CH$_2$ | Bu | 2-(3-iPrO-Ph)-5-Pyr | O |
| 4-252 | H | (CH$_2$)$_2$ | H | H | CH$_2$ | Bu | 2-(3-Me-Ph)-5-Pyr | O |

TABLE 4-continued

| Ex. No. Comp. | R¹ | R² | R³ | R⁴ | Z | W | X | Y |
|---|---|---|---|---|---|---|---|---|
| 4-253 | H | (CH₂)₂ | H | H | CH₂ | Bu | 2-(3-CF₃-Ph)-5-Pyr | O |
| 4-254 | H | (CH₂)₂ | H | H | CH₂ | Bu | 2-(3-Dma-Ph)-5-Pyr | O |

TABLE 5

| Ex. No. Comp. | R¹ | R² | R³ | R⁴ | Z | W | X | Y |
|---|---|---|---|---|---|---|---|---|
| 5-1 | H | (CH₂)₂ | H | H | CH₂ | Pen | Ph | O |
| 5-2 | H | (CH₂)₂ | H | H | CH₂ | Pen | 1-Np | O |
| 5-3 | H | (CH₂)₂ | H | H | CH₂ | Pen | 2-Np | O |
| 5-4 | H | (CH₂)₂ | H | H | CH₂ | Pen | 4-Me—Ph | O |
| 5-5 | H | (CH₂)₂ | H | H | CH₂ | Pen | 4-Et—Ph | O |
| 5-6 | H | (CH₂)₂ | H | H | CH₂ | Pen | 3-iPr—Ph | O |
| 5-7 | H | (CH₂)₂ | H | H | CH₂ | Pen | 4-iPr—Ph | O |
| 5-8 | H | (CH₂)₂ | H | H | CH₂ | Pen | 3-tBu—Ph | O |
| 5-9 | H | (CH₂)₂ | H | H | CH₂ | Pen | 4-tBu—Ph | O |
| 5-10 | H | (CH₂)₂ | H | H | CH₂ | Pen | 3-F—Ph | O |
| 5-11 | H | (CH₂)₂ | H | H | CH₂ | Pen | 4-F—Ph | O |
| 5-12 | H | (CH₂)₂ | H | H | CH₂ | Pen | 4-Cl—Ph | O |
| 5-13 | H | (CH₂)₂ | H | H | CH₂ | Pen | 4-Br—Ph | O |
| 5-14 | H | (CH₂)₂ | H | H | CH₂ | Pen | 3-Ph—Ph | O |
| 5-15 | H | (CH₂)₂ | H | H | CH₂ | Pen | 4-Ph—Ph | O |
| 5-16 | H | (CH₂)₂ | H | H | CH₂ | Pen | 4-BzO—Ph | O |
| 5-17 | H | (CH₂)₂ | H | H | CH₂ | Pen | 4-Bz—Ph | O |
| 5-18 | H | (CH₂)₂ | H | H | CH₂ | Pen | 3-PhO—Ph | O |
| 5-19 | H | (CH₂)₂ | H | H | CH₂ | Pen | 4-PhO—Ph | O |
| 5-20 | H | (CH₂)₂ | H | H | CH₂ | Pen | 3-PhS—Ph | O |
| 5-21 | H | (CH₂)₂ | H | H | CH₂ | Pen | 4-PhS—Ph | O |
| 5-22 | H | (CH₂)₂ | H | H | CH₂ | Pen | 3-PhSO₂—Ph | O |
| 5-23 | H | (CH₂)₂ | H | H | CH₂ | Pen | 4-PhSO₂—Ph | O |
| 5-24 | H | (CH₂)₂ | H | H | CH₂ | Pen | 3-(Imid-1)-Ph | O |
| 5-25 | H | (CH₂)₂ | H | H | CH₂ | Pen | 4-(Imid-1)-Ph | O |
| 5-26 | H | (CH₂)₂ | H | H | CH₂ | Pen | 3-(Imid-4)-Ph | O |
| 5-27 | H | (CH₂)₂ | H | H | CH₂ | Pen | 4-(Imid-4)-Ph | O |
| 5-28 | H | (CH₂)₂ | H | H | CH₂ | Pen | 3-(Fur-2)-Ph | O |
| 5-29 | H | (CH₂)₂ | H | H | CH₂ | Pen | 4-(Fur-2)-Ph | O |
| 5-30 | H | (CH₂)₂ | H | H | CH₂ | Pen | 3-(Thi-2)-Ph | O |
| 5-31 | H | (CH₂)₂ | H | H | CH₂ | Pen | 4-(Thi-2)-Ph | O |
| 5-32 | H | (CH₂)₂ | H | H | CH₂ | Pen | 3-(Thi-3)-Ph | O |
| 5-33 | H | (CH₂)₂ | H | H | CH₂ | Pen | 4-(Thi-3)-Ph | O |
| 5-34 | H | (CH₂)₂ | H | H | CH₂ | Pen | 3-(Pyr-2)-Ph | O |
| 5-35 | H | (CH₂)₂ | H | H | CH₂ | Pen | 4-(Pyr-2)-Ph | O |
| 5-36 | H | (CH₂)₂ | H | H | CH₂ | Pen | 3-(Pyr-3)-Ph | O |
| 5-37 | H | (CH₂)₂ | H | H | CH₂ | Pen | 4-(Pyr-3)-Ph | O |
| 5-38 | H | (CH₂)₂ | H | H | CH₂ | Pen | 3-(Pyr-4)-Ph | O |
| 5-39 | H | (CH₂)₂ | H | H | CH₂ | Pen | 4-(Pyr-4)-Ph | O |
| 5-40 | H | (CH₂)₂ | H | H | CH₂ | Pen | 3-(Oxa-2)-Ph | O |
| 5-41 | H | (CH₂)₂ | H | H | CH₂ | Pen | 4-(Oxa-2)-Ph | O |
| 5-42 | H | (CH₂)₂ | H | H | CH₂ | Pen | 3-(Oxa-4)-Ph | O |
| 5-43 | H | (CH₂)₂ | H | H | CH₂ | Pen | 4-(Oxa-4)-Ph | O |
| 5-44 | H | (CH₂)₂ | H | H | CH₂ | Pen | 3-(Oxa-5)-Ph | O |
| 5-45 | H | (CH₂)₂ | H | H | CH₂ | Pen | 4-(Oxa-5)-Ph | O |
| 5-46 | H | (CH₂)₂ | H | H | CH₂ | Pen | 3-(Tbiz-2)-Ph | O |
| 5-47 | H | (CH₂)₂ | H | H | CH₂ | Pen | 4-(Thiz-2)-Ph | O |
| 5-48 | H | (CH₂)₂ | H | H | CH₂ | Pen | 3-(Thiz-4)-Ph | O |
| 5-49 | H | (CH₂)₂ | H | H | CH₂ | Pen | 4-(Thiz-4)-Ph | O |
| 5-50 | H | (CH₂)₂ | H | H | CH₂ | Pen | 3-(Thiz-5)-Ph | O |
| 5-51 | H | (CH₂)₂ | H | H | CH₂ | Pen | 4-(Thiz-5)-Ph | O |
| 5-52 | H | (CH₂)₂ | H | H | CH₂ | Pen | 1-Me-2-Pyrr | O |
| 5-53 | H | (CH₂)₂ | H | H | CH₂ | Pen | 1-Ph-2-Pyrr | O |
| 5-54 | H | (CH₂)₂ | H | H | CH₂ | Pen | 1-Bz-2-Pyrr | O |
| 5-55 | H | (CH₂)₂ | H | H | CH₂ | Pen | 5-Me-2-Fur | O |
| 5-56 | H | (CH₂)₂ | H | H | CH₂ | Pen | 5-Ph-2-Fur | O |
| 5-57 | H | (CH₂)₂ | H | H | CH₂ | Pen | 5-Me-2-Thi | O |
| 5-58 | H | (CH₂)₂ | H | H | CH₂ | Pen | 5-Ph-2-Thi | O |
| 5-59 | H | (CH₂)₂ | H | H | CH₂ | Pen | 5-Me-3-Thi | O |

TABLE 5-continued

| Ex. No. Comp. | R¹ | R² | R³ | R⁴ | Z | W | X | Y |
|---|---|---|---|---|---|---|---|---|
| 5-60 | H | (CH₂)₂ | H | H | CH₂ | Pen | 5-Ph-3-Thi | O |
| 5-61 | H | (CH₂)₂ | H | H | CH₂ | Pen | 1-Me-3-Pyza | O |
| 5-62 | H | (CH₂)₂ | H | H | CH₂ | Pen | 1-Ph-3-Pyza | O |
| 5-63 | H | (CH₂)₂ | H | H | CH₂ | Pen | 1-Me-2-Imid | O |
| 5-64 | H | (CH₂)₂ | H | H | CH₂ | Pen | 1-Ph-2-Imid | O |
| 5-65 | H | (CH₂)₂ | H | H | CH₂ | Pen | 1-Me-4-Imid | O |
| 5-66 | H | (CH₂)₂ | H | H | CH₂ | Pen | 1-Ph-4-Imid | O |
| 5-67 | H | (CH₂)₂ | H | H | CH₂ | Pen | 4-Oxa | O |
| 5-68 | H | (CH₂)₂ | H | H | CH₂ | Pen | 5-Oxa | O |
| 5-69 | H | (CH₂)₂ | H | H | CH₂ | Pen | 2-Me-4-Oxa | O |
| 5-70 | H | (CH₂)₂ | H | H | CH₂ | Pen | 2-Ph-4-Oxa | O |
| 5-71 | H | (CH₂)₂ | H | H | CH₂ | Pen | 2-Me-5-Oxa | O |
| 5-72 | H | (CH₂)₂ | H | H | CH₂ | Pen | 2-Ph-5-Oxa | O |
| 5-73 | H | (CH₂)₂ | H | H | CH₂ | Pen | 4-Me-2-Ph-5-Oxa | O |
| 5-74 | H | (CH₂)₂ | H | H | CH₂ | Pen | 5-Me-2-Ph-4-Oxa | O |
| 5-75 | H | (CH₂)₂ | H | H | CH₂ | Pen | 4-Thiz | O |
| 5-76 | H | (CH₂)₂ | H | H | CH₂ | Pen | 5-Thiz | O |
| 5-77 | H | (CH₂)₂ | H | H | CH₂ | Pen | 2-Me-4-Thiz | O |
| 5-78 | H | (CH₂)₂ | H | H | CH₂ | Pen | 2-Ph-4-Thiz | O |
| 5-79 | H | (CH₂)₂ | H | H | CH₂ | Pen | 2-Me-5-Thiz | O |
| 5-80 | H | (CH₂)₂ | H | H | CH₂ | Pen | 2-Ph-5-Thiz | O |
| 5-81 | H | (CH₂)₂ | H | H | CH₂ | Pen | 4-Me-2-Ph-5-Thiz | O |
| 5-82 | H | (CH₂)₂ | H | H | CH₂ | Pen | 5-Me-2-Ph-4-Thiz | O |
| 5-83 | H | (CH₂)₂ | H | H | CH₂ | Pen | 1-Me-4-Pyza | O |
| 5-84 | H | (CH₂)₂ | H | H | CH₂ | Pen | 1-Ph-4-Pyza | O |
| 5-85 | H | (CH₂)₂ | H | H | CH₂ | Pen | 2-Me-4-Isox | O |
| 5-86 | H | (CH₂)₂ | H | H | CH₂ | Pen | 2-Ph-4-Isox | O |
| 5-87 | H | (CH₂)₂ | H | H | CH₂ | Pen | 2-Pyr | O |
| 5-88 | H | (CH₂)₂ | H | H | CH₂ | Pen | 3-Pyr | O |
| 5-89 | H | (CH₂)₂ | H | H | CH₂ | Pen | 4-Pyr | O |
| 5-90 | H | (CH₂)₂ | H | H | CH₂ | Pen | 3-Me-5-Pyr | O |
| 5-91 | H | (CH₂)₂ | H | H | CH₂ | Pen | 3-Et-5-Pyr | O |
| 5-92 | H | (CH₂)₂ | H | H | CH₂ | Pen | 3-Ph-5-Pyr | O |
| 5-93 | H | (CH₂)₂ | H | H | CH₂ | Pen | 2-Me-5-Pyr | O |
| 5-94 | H | (CH₂)₂ | H | H | CH₂ | Pen | 2-BzO-5-Pyr | O |
| 5-95 | H | (CH₂)₂ | H | H | CH₂ | Pen | 2-Ph-5-Pyr | O |
| 5-96 | H | (CH₂)₂ | H | H | CH₂ | Pen | 2-MeO-5-Pyr | O |
| 5-97 | H | (CH₂)₂ | H | H | CH₂ | Pen | 2-EtO-5-Pyr | O |
| 5-98 | H | (CH₂)₂ | H | H | CH₂ | Pen | 2-iPrO-5-Pyr | O |
| 5-99 | H | (CH₂)₂ | H | H | CH₂ | Pen | 2-MeS-5-Pyr | O |
| 5-100 | H | (CH₂)₂ | H | H | CH₂ | Pen | 2-EtS-5-Pyr | O |
| 5-101 | H | (CH₂)₂ | H | H | CH₂ | Pen | 2-PhSO₂NH-5-Pyr | O |
| 5-102 | H | (CH₂)₂ | H | H | CH₂ | Pen | 2-MeSO₂-5-Pyr | O |
| 5-103 | H | (CH₂)₂ | H | H | CH₂ | Pen | 2-EtSO₂-5-Pyr | O |
| 5-104 | H | (CH₂)₂ | H | H | CH₂ | Pen | 2-PhSO₂NMe-5-Pyr | O |
| 5-105 | H | (CH₂)₂ | H | H | CH₂ | Pen | 2-Bz-5-Pyr | O |
| 5-106 | H | (CH₂)₂ | H | H | CH₂ | Pen | 2-PhO-5-Pyr | O |
| 5-107 | H | (CH₂)₂ | H | H | CH₂ | Pen | 2-PhS-5-Pyr | O |
| 5-108 | H | (CH₂)₂ | H | H | CH₂ | Pen | 2-PhSO₂-5-Pyr | O |
| 5-109 | H | (CH₂)₂ | H | H | CH₂ | Pen | 3-Me-6-Pyr | O |
| 5-110 | H | (CH₂)₂ | H | H | CH₂ | Pen | 3-Ph-6-Pyr | O |
| 5-111 | H | (CH₂)₂ | H | H | CH₂ | Pen | 2-Me-6-Pyr | O |
| 5-112 | H | (CH₂)₂ | H | H | CH₂ | Pen | 2-Ph-6-Pyr | O |
| 5-113 | H | (CH₂)₂ | H | H | CH₂ | Pen | 2-Me-4-Pym | O |
| 5-114 | H | (CH₂)₂ | H | H | CH₂ | Pen | 2-Ph-4-Pym | O |
| 5-115 | H | (CH₂)₂ | H | H | CH₂ | Pen | 2-MeO-4-Pym | O |
| 5-116 | H | (CH₂)₂ | H | H | CH₂ | Pen | 2-EtO-4-Pym | O |
| 5-117 | H | (CH₂)₂ | H | H | CH₂ | Pen | 2-iPrO-4-Pym | O |
| 5-118 | H | (CH₂)₂ | H | H | CH₂ | Pen | 2-MeS-4-Pym | O |
| 5-119 | H | (CH₂)₂ | H | H | CH₂ | Pen | 2-EtS-4-Pym | O |
| 5-120 | H | (CH₂)₂ | H | H | CH₂ | Pen | 2-iPrS-4-Pym | O |
| 5-121 | H | (CH₂)₂ | H | H | CH₂ | Pen | 6-MeS-4-Pym | O |
| 5-122 | H | (CH₂)₂ | H | H | CH₂ | Pen | 6-EtS-4-Pym | O |
| 5-123 | H | (CH₂)₂ | H | H | CH₂ | Pen | 6-iPrS-4-Pym | O |
| 5-124 | R | (CH₂)₂ | H | H | CH₂ | Pen | 2-PhS-4-Pym | O |
| 5-125 | H | (CH₂)₂ | H | H | CH₂ | Pen | 2-MeSO₂-4-Pym | O |
| 5-126 | H | (CH₂)₂ | H | H | CH₂ | Pen | 2-EtSO₂-4-Pym | O |
| 5-127 | H | (CH₂)₂ | H | H | CH₂ | Pen | 2-iPrSO₂-4-Pyrn | O |
| 5-128 | H | (CH₂)₂ | R | H | CH₂ | Pen | 2-PhSO₂-4-Pym | O |
| 5-129 | H | (CH₂)₂ | H | H | CH₂ | Pen | 2-Me-5-Pym | O |
| 5-130 | H | (CH₂)₂ | H | H | CH₂ | Pen | 2-Ph-5-Pym | O |
| 5-131 | H | (CH₂)₂ | H | H | CH₂ | Pen | 2-MeO-5-Pym | O |
| 5-132 | H | (CH₂)₂ | H | H | CH₂ | Pen | 2-EtO-5-Pym | O |
| 5-133 | H | (CH₂)₂ | H | H | CH₂ | Pen | 2-iPrO-5-Pym | O |
| 5-134 | H | (CH₂)₂ | H | H | CH₂ | Pen | 2-MeS-5-Pym | O |

TABLE 5-continued

| Ex. No. Comp. | R$^1$ | R$^2$ | R$^3$ | R$^4$ | Z | W | X | Y |
|---|---|---|---|---|---|---|---|---|
| 5-135 | H | (CH$_2$)$_2$ | H | H | CH$_2$ | Pen | 2-EtS-5-Pym | O |
| 5-136 | H | (CH$_2$)$_2$ | H | H | CH$_2$ | Pen | 2-iPrS-5-Pym | O |
| 5-137 | H | (CH$_2$)$_2$ | H | H | CH$_2$ | Pen | 2-PhS-5-Pym | O |
| 5-138 | H | (CH$_2$)$_2$ | H | H | CH$_2$ | Pen | 2-MeSO$_2$-5-Pym | O |
| 5-139 | H | (CH$_2$)$_2$ | H | H | CH$_2$ | Pen | 2-EtSO$_2$-5-Pym | O |
| 5-140 | H | (CH$_2$)$_2$ | H | H | CH$_2$ | Pen | 2-iPrSO$_2$-5-Pym | O |
| 5-141 | H | (CH$_2$)$_2$ | H | H | CH$_2$ | Pen | 2-PhSO$_2$-5-Pym | O |
| 5-142 | H | (CH$_2$)$_2$ | H | H | CH$_2$ | Pen | 2-Ind | O |
| 5-143 | H | (CH$_2$)$_2$ | H | H | CH$_2$ | Pen | 3-Ind | O |
| 5-144 | H | (CH$_2$)$_2$ | H | H | CH$_2$ | Pen | 1-Me-2-Ind | O |
| 5-145 | H | (CH$_2$)$_2$ | H | H | CH$_2$ | Pen | 1-Me-3-Ind | O |
| 5-146 | H | (CH$_2$)$_2$ | H | H | CH$_2$ | Pen | 2-Bimid | O |
| 5-147 | H | (CH$_2$)$_2$ | H | H | CH$_2$ | Pen | 2-Boxa | O |
| 5-148 | H | (CH$_2$)$_2$ | H | H | CH$_2$ | Pen | 2-Bthiz | O |
| 5-149 | H | (CH$_2$)$_2$ | H | H | CH$_2$ | Pen | 2-Quin | O |
| 5-150 | H | (CH$_2$)$_2$ | H | H | CH$_2$ | Pen | 3-Quin | O |
| 5-151 | H | (CH$_2$)$_2$ | H | H | CH$_2$ | Pen | 4-Quin | O |
| 5-152 | H | (CH$_2$)$_2$ | H | H | CH$_2$ | Pen | 1-iQuin | O |
| 5-153 | H | (CH$_2$)$_2$ | H | H | CH$_2$ | Pen | 3-iQuin | O |
| 5-154 | H | (CH$_2$)$_2$ | H | H | CH$_2$ | Pen | 4-iQuin | O |
| 5-155 | H | (CH$_2$)$_2$ | H | H | CH$_2$ | Pen | 3-MeO—Ph | O |
| 5-156 | H | (CH$_2$)$_2$ | H | H | CH$_2$ | Pen | 4-MeO—Ph | O |
| 5-157 | H | (CH$_2$)$_2$ | H | H | CH$_2$ | Pen | 3-EtO—Ph | O |
| 5-158 | H | (CH$_2$)$_2$ | H | H | CH$_2$ | Pen | 4-EtO—Ph | O |
| 5-159 | H | (CH$_2$)$_2$ | H | H | CH$_2$ | Pen | 3-iPO—Ph | O |
| 5-160 | H | (CH$_2$)$_2$ | H | H | CH$_2$ | Pen | 4-iPrO—Ph | O |
| 5-161 | H | (CH$_2$)$_2$ | H | H | CH$_2$ | Pen | 3-MeS—Ph | O |
| 5-162 | H | (CH$_2$)$_2$ | H | H | CH$_2$ | Pen | 4-MeS—Ph | O |
| 5-163 | H | (CH$_2$)$_2$ | H | H | CH$_2$ | Pen | 3-EtS—Ph | O |
| 5-164 | H | (CH$_2$)$_2$ | H | H | CH$_2$ | Pen | 4-EtS—Ph | O |
| 5-165 | H | (CH$_2$)$_2$ | H | H | CH$_2$ | Pen | 3-iPrS—Ph | O |
| 5-166 | H | (CH$_2$)$_2$ | H | H | CH$_2$ | Pen | 4-iPrS—Ph | O |
| 5-167 | H | (CH$_2$)$_2$ | H | H | CH$_2$ | Pen | 3-MeSO$_2$—Ph | O |
| 5-168 | H | (CH$_2$)$_2$ | H | H | CH$_2$ | Pen | 4-MeSO$_2$—Ph | O |
| 5-169 | H | (CH$_2$)$_2$ | H | H | CH$_2$ | Pen | 3-EtSO$_2$—Ph | O |
| 5-170 | H | (CH$_2$)$_2$ | H | H | CH$_2$ | Pen | 4-EtSO$_2$—Ph | O |
| 5-171 | H | (CH$_2$)$_2$ | H | H | CH$_2$ | Pen | 3-iPrSO$_2$—Ph | O |
| 5-172 | H | (CH$_2$)$_2$ | R | H | CH$_2$ | Pen | 4-iPrSO$_2$—Ph | O |
| 5-173 | H | (CH$_2$)$_2$ | H | H | CH$_2$ | Pen | 3-(1-Me-Imid-4)-Ph | O |
| 5-174 | H | (CH$_2$)$_2$ | H | H | CH$_2$ | Pen | 4-(1-Me-Imid-4)-Ph | O |
| 5-175 | H | (CH$_2$)$_2$ | H | H | CH$_2$ | Pen | 1-Me-2-Ph-4-Imid | O |
| 5-176 | H | (CH$_2$)$_2$ | H | H | CH$_2$ | Pen | 1,4-di-Me-2-Ph-5-Imid | O |
| 5-177 | H | (CH$_2$)$_2$ | H | H | CH$_2$ | Pen | 1,5-di-Me-2-Ph-4-Imid | O |
| 5-178 | H | (CH$_2$)$_2$ | H | H | CH$_2$ | Pen | 3,4-MdO—Ph | O |
| 5-179 | H | (CH$_2$)$_2$ | H | H | CH$_2$ | Pen | 4-(4-MeO—Ph)—Ph | O |
| 5-180 | H | (CH$_2$)$_2$ | H | H | CH$_2$ | Pen | 4-(3,4-MdO—Ph)—Ph | O |
| 5-181 | H | (CH$_2$)$_2$ | H | H | CH$_2$ | Pen | 4-[PhSO$_2$N(Me)]—Ph | O |
| 5-182 | H | (CH$_2$)$_2$ | H | H | CH$_2$ | Pen | 4-[(Pyr-3)SO$_2$N(Me)]—Ph | O |
| 5-183 | H | (CH$_2$)$_2$ | H | H | CH$_2$ | Pen | 4-(PhSO$_2$NH)—Ph | O |
| 5-184 | H | (CH$_2$)$_2$ | H | H | CH$_2$ | Pen | 4-[(Pyr-3)SO$_2$NH]—Ph | O |
| 5-185 | H | (CH$_2$)$_2$ | H | H | CH$_2$ | Pen | 4-[(Pyr-2)SO$_2$]—Ph | O |
| 5-186 | H | (CH$_2$)$_2$ | H | H | CH$_2$ | Pen | 4-[(Pyr-3)SO$_2$]—Ph | O |
| 5-187 | H | (CH$_2$)$_2$ | H | H | CH$_2$ | Pen | 4-[(Pyr-2)SO$_2$N(Me)]—Ph | O |
| 5-188 | H | (CH$_2$)$_2$ | H | H | CH$_2$ | Pen | 4-[(Pyr-2)SO$_2$NH]—Ph | O |
| 5-189 | H | (CH$_2$)$_2$ | H | H | CH$_2$ | Pen | 4-(4-Me—Ph)—Ph | O |
| 5-190 | H | (CH$_2$)$_2$ | H | H | CH$_2$ | Pen | 4-(4-F—Ph)—Ph | O |
| 5-191 | H | (CH$_2$)$_2$ | H | H | CH$_2$ | Pen | 4-(4-CF$_3$—Ph)—Ph | O |
| 5-192 | H | (CH$_2$)$_2$ | H | H | CH$_2$ | Pen | 2-[PhSO$_2$N(Me)]-5-Pyr | O |
| 5-193 | H | (CH$_2$)$_2$ | H | H | CH$_2$ | Pen | 2-HO-5-Pyr | O |
| 5-194 | H | (CH$_2$)$_2$ | H | H | CH$_2$ | Pen | 2-BzO-5-Pyr | O |
| 5-195 | H | (CH$_2$)$_2$ | H | H | CH$_2$ | Pen | 4-[(Pyr-4)SO$_2$]—Ph | O |
| 5-196 | H | (CH$_2$)$_2$ | H | H | CH$_2$ | Pen | 4-[(Pyr-4)O]—Ph | O |
| 5-197 | H | (CH$_2$)$_2$ | H | H | CH$_2$ | Pen | 4-[(Pyr-4)S]—Ph | O |
| 5-198 | H | (CH$_2$)$_2$ | H | H | CH$_2$ | Pen | 3-HO—Ph | O |
| 5-199 | H | (CH$_2$)$_2$ | H | H | CH$_2$ | Pen | 4-HO—Ph | O |
| 5-200 | H | (CH$_2$)$_2$ | H | H | CH$_2$ | Pen | 2-HO-3,4,6-tri-Me—Ph | O |
| 5-201 | H | (CH$_2$)$_2$ | H | H | CH$_2$ | Pen | 4-HO-3,5-di-Me—Ph | O |

TABLE 5-continued

| Ex. No. Comp. | R¹ | R² | R³ | R⁴ | Z | W | X | Y |
|---|---|---|---|---|---|---|---|---|
| 5-202 | H | (CH₂)₂ | H | H | CH₂ | Pen | 3-AcO—Ph | O |
| 5-203 | H | (CH₂)₂ | H | H | CH₂ | Pen | 4-AcO—Ph | O |

TABLE 6

| Ex. No. Comp. | R¹ | R² | R³ | R⁴ | Z | X | Y | |
|---|---|---|---|---|---|---|---|---|
| 6-1 | H | (CH₂)₂ | H | H | CH₂ | PhO | Ph | O |
| 6-2 | H | (CH₂)₂ | H | H | CH₂ | PhO | 1-Np | O |
| 6-3 | H | (CH₂)₂ | H | H | CH₂ | PhO | 2-Np | O |
| 6-4 | H | (CH₂)₂ | H | H | CH₂ | PhO | 4-Me-Ph | O |
| 6-5 | H | (CH₂)₂ | H | H | CH₂ | PhO | 4-Et-Ph | O |
| 6-6 | H | (CH₂)₂ | H | H | CH₂ | PhO | 3-iPr-Ph | O |
| 6-7 | H | (CH₂)₂ | H | H | CH₂ | PhO | 4-iPr-Ph | O |
| 6-8 | H | (CH₂)₂ | H | H | CH₂ | PhO | 3-tBu-Ph | O |
| 6-9 | H | (CH₂)₂ | H | H | CH₂ | PhO | 4-tBu-Ph | O |
| 6-10 | H | (CH₂)₂ | H | H | CH₂ | PhO | 3-F-Ph | O |
| 6-11 | H | (CH₂)₂ | H | H | CH₂ | PhO | 4-F-Ph | O |
| 6-12 | H | (CH₂)₂ | H | H | CH₂ | PhO | 4-Cl-Ph | O |
| 6-13 | H | (CH₂)₂ | H | H | CH₂ | PhO | 4-Br-Ph | O |
| 6-14 | H | (CH₂)₂ | H | H | CH₂ | PhO | 3-Ph-Ph | O |
| 6-15 | H | (CH₂)₂ | H | H | CH₂ | PhO | 4-Ph-Ph | O |
| 6-16 | H | (CH₂)₂ | H | H | CH₂ | PhO | 4-BzO-Ph | O |
| 6-17 | H | (CH₂)₂ | H | H | CH₂ | PhO | 4-Bz-Ph | O |
| 6-18 | H | (CH₂)₂ | H | H | CH₂ | PhO | 3-PhO-Ph | O |
| 6-19 | H | (CH₂)₂ | H | H | CH₂ | PhO | 4-PhO-Ph | O |
| 6-20 | H | (CH₂)₂ | H | H | CH₂ | PhO | 3-PhS-Ph | O |
| 6-21 | H | (CH₂)₂ | H | H | CH₂ | PhO | 4-PhS-Ph | O |
| 6-22 | H | (CH₂)₂ | H | H | CH₂ | PhO | 3-PhSO₂-Ph | O |
| 6-23 | H | (CH₂)₂ | H | H | CH₂ | PhO | 4-PhSO₂-Ph | O |
| 6-24 | H | (CH₂)₂ | H | H | CH₂ | PhO | 3-(Imid-1)-Ph | O |
| 6-25 | H | (CH₂)₂ | H | H | CH₂ | PhO | 4-(Imid-1)-Ph | O |
| 6-26 | H | (CH₂)₂ | H | H | CH₂ | PhO | 3-(Imid-4)-Ph | O |
| 6-27 | H | (CH₂)₂ | H | H | CH₂ | PhO | 4-(Imid-4)-Ph | O |
| 6-28 | H | (CH₂)₂ | H | H | CH₂ | PhO | 3-(Fur-2)-Ph | O |
| 6-29 | H | (CH₂)₂ | H | H | CH₂ | PhO | 4-(Fur-2)-Ph | O |
| 6-30 | H | (CH₂)₂ | H | H | CH₂ | PhO | 3-(Thi-2)-Ph | O |
| 6-31 | H | (CH₂)₂ | H | H | CH₂ | PhO | 4-(Thi-2)-Ph | O |
| 6-32 | H | (CH₂)₂ | H | H | CH₂ | PhO | 3-(Thi-3)-Ph | O |
| 6-33 | H | (CH₂)₂ | H | H | CH₂ | PhO | 4-(Thi-3)-Ph | O |
| 6-34 | H | (CH₂)₂ | H | H | CH₂ | PhO | 3-(Pyr-2)-Ph | O |
| 6-35 | H | (CH₂)₂ | H | H | CH₂ | PhO | 4-(Pyr-2)-Ph | O |
| 6-36 | H | (CH₂)₂ | H | H | CH₂ | PhO | 3-(Pyr-3)-Ph | O |
| 6-37 | H | (CH₂)₂ | H | H | CH₂ | PhO | 4-(Pyr-3)-Ph | O |
| 6-38 | H | (CH₂)₂ | H | H | CH₂ | PhO | 3-(Pyr-4)-Ph | O |
| 6-39 | H | (CH₂)₂ | H | H | CH₂ | PhO | 4-(Pyr-4)-Ph | O |
| 6-40 | H | (CH₂)₂ | H | H | CH₂ | PhO | 3-(Oxa-2)-Ph | O |
| 6-41 | H | (CH₂)₂ | H | H | CH₂ | PhO | 4-(Oxa-2)-Ph | O |
| 6-42 | H | (CH₂)₂ | H | H | CH₂ | PhO | 3-(Oxa-4)-Ph | O |
| 6-43 | H | (CH₂)₂ | H | H | CH₂ | PhO | 4-(Oxa-4)-Ph | O |
| 6-44 | H | (CH₂)₂ | H | H | CH₂ | PhO | 3-(Oxa-5)-Ph | O |
| 6-45 | H | (CH₂)₂ | H | H | CH₂ | PhO | 4-(Oxa-5)-Ph | O |
| 6-46 | H | (CH₂)₂ | H | H | CH₂ | PhO | 3-(Thiz-2)-Ph | O |
| 6-47 | H | (CH₂)₂ | H | H | CH₂ | PhO | 4-(Thiz-2)-Ph | O |
| 6-48 | H | (CH₂)₂ | H | H | CH₂ | PhO | 3-(Thiz-4)-Ph | O |
| 6-49 | H | (CH₂)₂ | H | H | CH₂ | PhO | 4-(Thiz-4)-Ph | O |
| 6-50 | H | (CH₂)₂ | H | H | CH₂ | PhO | 3-(Thiz-5)-Ph | O |
| 6-51 | H | (CH₂)₂ | H | H | CH₂ | PhO | 4-(Thiz-5)-Ph | O |
| 6-52 | H | (CH₂)₂ | H | H | CH₂ | PhO | 1-Me-2-Pyrr | O |
| 6-53 | H | (CH₂)₂ | H | H | CH₂ | PhO | 1-Ph-2-Pyrr | O |
| 6-54 | H | (CH₂)₂ | H | H | CH₂ | PhO | 1-Bz-2-Pyrr | O |
| 6-55 | H | (CH₂)₂ | H | H | CH₂ | PhO | 5-Me-2-Fur | O |
| 6-56 | H | (CH₂)₂ | H | H | CH₂ | PhO | 5-Ph-2-Fur | O |
| 6-57 | H | (CH₂)₂ | H | H | CH₂ | PhO | 5-Me-2-Thi | O |
| 6-58 | H | (CH₂)₂ | H | H | CH₂ | PhO | 5-Ph-2-Thi | O |
| 6-59 | H | (CH₂)₂ | H | H | CH₂ | PhO | 5-Me-3-Thi | O |
| 6-60 | H | (CH₂)₂ | H | H | CH₂ | PhO | 5-Ph-3-Thi | O |
| 6-61 | H | (CH₂)₂ | H | H | CH₂ | PhO | 1-Me-3-Pyza | O |
| 6-62 | H | (CH₂)₂ | H | H | CH₂ | PhO | 1-Ph-3-Pyza | O |
| 6-63 | H | (CH₂)₂ | H | H | CH₂ | PhO | 1-Me-2-Imid | O |
| 6-64 | H | (CH₂)₂ | H | H | CH₂ | PhO | 1-Ph-2-Imid | O |
| 6-65 | H | (CH₂)₂ | H | H | CH₂ | PhO | 1-Me-4-Imid | O |
| 6-66 | H | (CH₂)₂ | H | H | CH₂ | PhO | 1-Ph-4-Imid | O |
| 6-67 | H | (CH₂)₂ | H | H | CH₂ | PhO | 4-Oxa | O |
| 6-68 | H | (CH₂)₂ | H | H | CH₂ | PhO | 5-Oxa | O |
| 6-69 | H | (CH₂)₂ | H | H | CH₂ | PhO | 2-Me-4-Oxa | O |
| 6-70 | H | (CH₂)₂ | H | H | CH₂ | PhO | 2-Ph-4-Oxa | O |
| 6-71 | H | (CH₂)₂ | H | H | CH₂ | PhO | 2-Me-5-Oxa | O |
| 6-72 | H | (CH₂)₂ | H | H | CH₂ | PhO | 2-Ph-5-Oxa | O |
| 6-73 | H | (CH₂)₂ | H | H | CH₂ | PhO | 4-Me-2-Ph-5-Oxa | O |
| 6-74 | H | (CH₂)₂ | H | H | CH₂ | PhO | 5-Me-2-Ph-4-Oxa | O |
| 6-75 | H | (CH₂)₂ | H | H | CH₂ | PhO | 4-Thiz | O |
| 6-76 | H | (CH₂)₂ | H | H | CH₂ | PhO | 5-Thiz | O |
| 6-77 | H | (CH₂)₂ | H | H | CH₂ | PhO | 2-Me-4-Thiz | O |
| 6-78 | H | (CH₂)₂ | H | H | CH₂ | PhO | 2-Ph-4-Thiz | O |
| 6-79 | H | (CH₂)₂ | H | H | CH₂ | PhO | 2-Me-5-Thiz | O |
| 6-80 | H | (CH₂)₂ | H | H | CH₂ | PhO | 2-Ph-5-Thiz | O |
| 6-81 | H | (CH₂)₂ | H | H | CH₂ | PhO | 4-Me-2-Ph-5-Thiz | O |
| 6-82 | H | (CH₂)₂ | H | H | CH₂ | PhO | 5-Me-2-Ph-4-Thiz | O |
| 6-83 | H | (CH₂)₂ | H | H | CH₂ | PhO | 1-Me-4-Pyza | O |
| 6-84 | H | (CH₂)₂ | H | H | CH₂ | PhO | 1-Ph-4-Pyza | O |
| 6-85 | H | (CH₂)₂ | H | H | CH₂ | PhO | 2-Me4-Isox | O |
| 6-86 | H | (CH₂)₂ | H | H | CH₂ | PhO | 2-Ph-4-Isox | O |
| 6-87 | H | (CH₂)₂ | H | H | CH₂ | PhO | 2-Pyr | O |
| 6-88 | H | (CH₂)₂ | H | H | CH₂ | PhO | 3-Pyr | O |
| 6-89 | H | (CH₂)₂ | H | H | CH₂ | PhO | 4-Pyr | O |
| 6-90 | H | (CH₂)₂ | H | H | CH₂ | PhO | 3-Me-5-Pyr | O |
| 6-91 | H | (CH₂)₂ | H | H | CH₂ | PhO | 3-Et-5-Pyr | O |
| 6-92 | H | (CH₂)₂ | H | H | CH₂ | PhO | 3-Ph-5-Pyr | O |
| 6-93 | H | (CH₂)₂ | H | H | CH₂ | PhO | 2-Me-5-Pyr | O |
| 6-94 | H | (CH₂)₂ | H | H | CH₂ | PhO | 2-BzO-5-Pyr | O |
| 6-95 | H | (CH₂)₂ | H | H | CH₂ | PhO | 2-Ph-5-Pyr | O |
| 6-96 | H | (CH₂)₂ | H | H | CH₂ | PhO | 2-MeO-5-Pyr | O |
| 6-97 | H | (CH₂)₂ | H | H | CH₂ | PhO | 2-EtO-5-Pyr | O |
| 6-98 | H | (CH₂)₂ | H | H | CH₂ | PhO | 2-iPrO-5-Pyr | O |
| 6-99 | H | (CH₂)₂ | H | H | CH₂ | PhO | 2-MeS-5-Pyr | O |
| 6-100 | H | (CH₂)₂ | H | H | CH₂ | PhO | 2-EtS-5-Pyr | O |
| 6-101 | H | (CH₂)₂ | H | H | CH₂ | PhO | 2-PhSO₂NH-5-Pyr | O |
| 6-102 | H | (CH₂)₂ | H | H | CH₂ | PhO | 2-MeSO₂-5-Pyr | O |
| 6-103 | H | (CH₂)₂ | H | H | CH₂ | PhO | 2-EtSO₂-5-Pyr | O |
| 6-104 | H | (CH₂)₂ | H | H | CH₂ | PhO | 2-PhSO₂NMe-5-Pyr | O |
| 6-105 | H | (CH₂)₂ | H | H | CH₂ | PhO | 2-Bz-5-Pyr | O |
| 6-106 | H | (CH₂)₂ | H | H | CH₂ | PhO | 2-PhO-5-Pyr | O |
| 6-107 | H | (CH₂)₂ | H | H | CH₂ | PhO | 2-PhS-5-Pyr | O |
| 6-108 | H | (CH₂)₂ | H | H | CH₂ | PhO | 2-PhSO₂-5-Pyr | O |
| 6-109 | H | (CH₂)₂ | H | H | CH₂ | PhO | 3-Me-6-Pyr | O |
| 6-110 | H | (CH₂)₂ | H | H | CH₂ | PhO | 3-Ph-6-Pyr | O |
| 6-111 | H | (CH₂)₂ | H | H | CH₂ | PhO | 2-Me-6-Pyr | O |
| 6-112 | H | (CH₂)₂ | H | H | CH₂ | PhO | 2-Ph-6-Pyr | O |
| 6-113 | H | (CH₂)₂ | H | H | CH₂ | PhO | 2-Me-4-Pym | O |
| 6-114 | H | (CH₂)₂ | H | H | CH₂ | PhO | 2-Ph-4-Pym | O |
| 6-115 | H | (CH₂)₂ | H | H | CH₂ | PhO | 2-MeO-4-Pym | O |
| 6-116 | H | (CH₂)₂ | H | H | CH₂ | PhO | 2-EtO-4-Pym | O |
| 6-117 | H | (CH₂)₂ | H | H | CH₂ | PhO | 2-iPrO-4-Pym | O |
| 6-118 | H | (CH₂)₂ | H | H | CH₂ | PhO | 2-MeS-4-Pym | O |
| 6-119 | H | (CH₂)₂ | H | H | CH₂ | PhO | 2-EtS-4-Pym | O |
| 6-120 | H | (CH₂)₂ | H | H | CH₂ | PhO | 2-iPrS-4-Pym | O |
| 6-121 | H | (CH₂)₂ | H | H | CH₂ | PhO | 6-MeS-4-Pym | O |
| 6-122 | H | (CH₂)₂ | H | H | CH₂ | PhO | 6-EtS-4-Pym | O |
| 6-123 | H | (CH₂)₂ | H | H | CH₂ | PhO | 6-iPrS-4-Pym | O |
| 6-124 | H | (CH₂)₂ | H | H | CH₂ | PhO | 2-PhS-4-Pym | O |

TABLE 6-continued

| Ex. No. Comp. | R¹ | R² | R³ | R⁴ | Z | X | Y | |
|---|---|---|---|---|---|---|---|---|
| 6-125 | H | (CH₂)₂ | H | H | CH₂ | PhO | 2-MeSO₂-4-Pym | O |
| 6-126 | H | (CH₂)₂ | H | H | CH₂ | PhO | 2-EtSO₂-4-Pym | O |
| 6-127 | H | (CH₂)₂ | H | H | CH₂ | PhO | 2-iPrSO₂-4-Pym | O |
| 6-128 | H | (CH₂)₂ | H | H | CH₂ | PhO | 2-PhSO₂-4-Pym | O |
| 6-129 | H | (CH₂)₂ | H | H | CH₂ | PhO | 2-Me-5-Pym | O |
| 6-130 | H | (CH₂)₂ | H | H | CH₂ | PhO | 2-Ph-5-Pym | O |
| 6-131 | H | (CH₂)₂ | H | H | CH₂ | PhO | 2-MeO-5-Pym | O |
| 6-132 | H | (CH₂)₂ | H | H | CH₂ | PhO | 2-EtO-5-Pym | O |
| 6-133 | H | (CH₂)₂ | H | H | CH₂ | PhO | 2-iPrO-5-Pym | O |
| 6-134 | H | (CH₂)₂ | H | H | CH₂ | PhO | 2-MeS-5-Pym | O |
| 6-135 | H | (CH₂)₂ | H | H | CH₂ | PhO | 2-EtS-5-Pym | O |
| 6-136 | H | (CH₂)₂ | H | H | CH₂ | PhO | 2-iPrS-5-Pym | O |
| 6-137 | H | (CH₂)₂ | H | H | CH₂ | PhO | 2-PhS-5-Pym | O |
| 6-138 | H | (CH₂)₂ | H | H | CH₂ | PhO | 2-MeSO₂-5-Pym | O |
| 6-139 | H | (CH₂)₂ | H | H | CH₂ | PhO | 2-EtSO₂-5-Pym | O |
| 6-140 | H | (CH₂)₂ | H | H | CH₂ | PhO | 2-iPrSO₂-5-Pym | O |
| 6-141 | H | (CH₂)₂ | H | H | CH₂ | PhO | 2-PhSO₂-5-Pym | O |
| 6-142 | H | (CH₂)₂ | H | H | CH₂ | PhO | 2-Ind | O |
| 6-143 | H | (CH₂)₂ | H | H | CH₂ | PhO | 3-Ind | O |
| 6-144 | H | (CH₂)₂ | H | H | CH₂ | PhO | 1-Me-2-Ind | O |
| 6-145 | H | (CH₂)₂ | H | H | CH₂ | PhO | 1-Me-3-Ind | O |
| 6-146 | H | (CH₂)₂ | H | H | CH₂ | PhO | 2-Bimid | O |
| 6-147 | H | (CH₂)₂ | H | H | CH₂ | PhO | 2-Boxa | O |
| 6-148 | H | (CH₂)₂ | H | H | CH₂ | PhO | 2-Bthiz | O |
| 6-149 | H | (CH₂)₂ | H | H | CH₂ | PhO | 2-Quin | O |
| 6-150 | H | (CH₂)₂ | H | H | CH₂ | PhO | 3-Quin | O |
| 6-151 | H | (CH₂)₂ | H | H | CH₂ | PhO | 4-Quin | O |
| 6-152 | H | (CH₂)₂ | H | H | CH₂ | PhO | 1-iQuin | O |
| 6-153 | H | (CH₂)₂ | H | H | CH₂ | PhO | 3-iQuin | O |
| 6-154 | H | (CH₂)₂ | H | H | CH₂ | PhO | 4-iQuin | O |
| 6-155 | H | (CH₂)₂ | H | H | CH₂ | PhO | 3-MeO-Ph | O |
| 6-156 | H | (CH₂)₂ | H | H | CH₂ | PhO | 4-MeO-Ph | O |
| 6-157 | H | (CH₂)₂ | H | H | CH₂ | PhO | 3-EtO-Ph | O |
| 6-158 | H | (CH₂)₂ | H | H | CH₂ | PhO | 4-EtO-Ph | O |
| 6-159 | H | (CH₂)₂ | H | H | CH₂ | PhO | 3-iPrO-Ph | O |
| 6-160 | H | (CH₂)₂ | H | H | CH₂ | PhO | 4-iPrO-Ph | O |
| 6-161 | H | (CH₂)₂ | H | H | CH₂ | PhO | 3-MeS-Ph | O |
| 6-162 | H | (CH₂)₂ | H | H | CH₂ | PhO | 4-MeS-Ph | O |
| 6-163 | H | (CH₂)₂ | H | H | CH₂ | PhO | 3-EtS-Ph | O |
| 6-164 | H | (CH₂)₂ | H | H | CH₂ | PhO | 4-EtS-Ph | O |
| 6-165 | H | (CH₂)₂ | H | H | CH₂ | PhO | 3-iPrS-Ph | O |
| 6-166 | H | (CH₂)₂ | H | H | CH₂ | PhO | 4-iPrS-Ph | O |
| 6-167 | H | (CH₂)₂ | H | H | CH₂ | PhO | 3-MeSO₂-Ph | O |
| 6-168 | H | (CH₂)₂ | H | H | CH₂ | PhO | 4-MeSO₂-Ph | O |
| 6-169 | H | (CH₂)₂ | H | H | CH₂ | PhO | 3-EtSO₂-Ph | O |
| 6-170 | H | (CH₂)₂ | H | H | CH₂ | PhO | 4-EtSO₂-Ph | O |
| 6-171 | H | (CH₂)₂ | H | H | CH₂ | PhO | 3-iPrSO₂-Ph | O |
| 6-172 | H | (CH₂)₂ | H | H | CH₂ | PhO | 4-iPrSO₂-Ph | O |
| 6-173 | H | (CH₂)₂ | H | H | CH₂ | PhO | 3-(1-Me-Imid-4)-Ph | O |
| 6-174 | H | (CH₂)₂ | H | H | CH₂ | PhO | 4-(1-Me-Imid-4)-Ph | O |
| 6-175 | H | (CH₂)₂ | H | H | CH₂ | PhO | 1-Me-2-Ph-4-Imid | O |
| 6-176 | H | (CH₂)₂ | H | H | CH₂ | PhO | 1,4-di-Me-2-Ph-5-Imid | O |
| 6-177 | H | (CH₂)₂ | H | H | CH₂ | PhO | 1,5-di-Me-2-Ph-4-Imid | O |
| 6-178 | H | (CH₂)₂ | H | H | CH₂ | PhO | 3,4-MdO-Ph | O |
| 6-179 | H | (CH₂)₂ | H | H | CH₂ | PhO | 4-(4-MeO-Ph)-Ph | O |
| 6-180 | H | (CH₂)₂ | H | H | CH₂ | PhO | 4-(3,4-MdO-Ph)-Ph | O |
| 6-181 | H | (CH₂)₂ | H | H | CH₂ | PhO | 4-[PhSO₂N(Me)]-Ph | O |
| 6-182 | H | (CH₂)₂ | H | H | CH₂ | PhO | 4-[(Pyr-3)SO₂N(Me)]-Ph | O |
| 6-183 | H | (CH₂)₂ | H | H | CH₂ | PhO | 4-(PhSO₂NH)-Ph | O |
| 6-184 | H | (CH₂)₂ | H | H | CH₂ | PhO | 4-[(Pyr-3)SO₂NH]-Ph | O |
| 6-185 | H | (CH₂)₂ | H | H | CH₂ | PhO | 4-[(Pyr-3)SO₂]-Ph | O |
| 6-186 | H | (CH₂)₂ | H | H | CH₂ | PhO | 4-[(Pyr-2)SO₂]-Ph | O |
| 6-187 | H | (CH₂)₂ | H | H | CH₂ | PhO | 4-[(Pyr-2)SO₂N(Me)]-Ph | O |
| 6-188 | H | (CH₂)₂ | H | H | CH₂ | PhO | 4-[(Pyr-2)SO₂NH]-Ph | O |
| 6-189 | H | (CH₂)₂ | H | H | CH₂ | PhO | 4-(4-Me-Ph)-Ph | O |
| 6-190 | H | (CH₂)₂ | H | H | CH₂ | PhO | 4-(4-F-Ph)-Ph | O |
| 6-191 | H | (CH₂)₂ | H | H | CH₂ | PhO | 4-(4-CF₃-Ph)-Ph | O |
| 6-192 | H | (CH₂)₂ | H | H | CH₂ | PhO | 2-[PhSO₂N(Me)]-5-Pyr | O |
| 6-193 | H | (CH₂)₂ | H | H | CH₂ | PhO | 2-HO-5-Pyr | O |
| 6-194 | H | (CH₂)₂ | H | H | CH₂ | PhO | 2-BzO-5-Pyr | O |
| 6-195 | H | (CH₂)₂ | H | H | CH₂ | PhO | 4-[(Pyr-4)SO₂]-Ph | O |
| 6-196 | H | (CH₂)₂ | H | H | CH₂ | PhO | 4-[(Pyr-4)O]-Ph | O |
| 6-197 | H | (CH₂)₂ | H | H | CH₂ | PhO | 4-[(Pyr-4)S]-Ph | O |
| 6-198 | H | (CH₂)₂ | H | H | CH₂ | PhO | 3-HO-Ph | O |
| 6-199 | H | (CH₂)₂ | H | H | CH₂ | PhO | 4-HO-Ph | O |
| 6-200 | H | (CH₂)₂ | H | H | CH₂ | PhO | 2-HO-3,4,6-tri-Me-Ph | O |
| 6-201 | H | (CH₂)₂ | H | H | CH₂ | PhO | 4-HO-3,5-di-Me-Ph | O |
| 6-202 | H | (CH₂)₂ | H | H | CH₂ | PhO | 3-AcO-Ph | O |
| 6-203 | H | (CH₂)₂ | H | H | CH₂ | PhO | 4-AcO-Ph | O |
| 6-204 | H | (CH₂)₂ | H | H | CH₂ | PhO | 4-(4-Cl-Ph)-Ph | O |
| 6-205 | H | (CH₂)₂ | H | H | CH₂ | PhO | 4-(4-HO-3,5-di-Me-Ph)-Ph | O |
| 6-206 | H | (CH₂)₂ | H | H | CH₂ | PhO | 4-(4-HO-Ph)-Ph | O |
| 6-207 | H | (CH₂)₂ | H | H | CH₂ | PhO | 4-(4-OHC-Ph)-Ph | O |
| 6-208 | H | (CH₂)₂ | H | H | CH₂ | PhO | 4-(4-Dmam-Ph)-Ph | O |
| 6-209 | H | (CH₂)₂ | H | H | CH₂ | PhO | 4-(4-Dma-Ph)-Ph | O |
| 6-210 | H | (CH₂)₂ | H | H | CH₂ | PhO | 4-(4-HOOC-Ph)-Ph | O |
| 6-211 | H | (CH₂)₂ | H | H | CH₂ | PhO | 4-(4-HOH₂C-Ph)-Ph | O |
| 6-212 | H | (CH₂)₂ | H | H | CH₂ | PhO | 4-(3-MeO-Ph)-Ph | O |
| 6-213 | H | (CH₂)₂ | H | H | CH₂ | PhO | 4-(3-HO-Ph)-Ph | O |
| 6-214 | H | (CH₂)₂ | H | H | CH₂ | PhO | 4-(3-OHC-Ph)-Ph | O |
| 6-215 | H | (CH₂)₂ | H | H | CH₂ | PhO | 4-(3-Dmam-Ph)-Ph | O |
| 6-216 | H | (CH₂)₂ | H | H | CH₂ | PhO | 4-(3-Dma-Ph)-Ph | O |
| 6-217 | H | (CH₂)₂ | H | H | CH₂ | PhO | 4-(3-HOOC-Ph)-Ph | O |
| 6-218 | H | (CH₂)₂ | H | H | CH₂ | PhO | 4-(3-HOH₂C-Ph)-Ph | O |
| 6-219 | H | (CH₂)₂ | H | H | CH₂ | PhO | 4-(2-MeO-Ph)-Ph | O |
| 6-220 | H | (CH₂)₂ | H | H | CH₂ | PhO | 4-(2-HO-Ph)-Ph | O |
| 6-221 | H | (CH₂)₂ | H | H | CH₂ | PhO | 4-(2-OHC-Ph)-Ph | O |
| 6-222 | H | (CH₂)₂ | H | H | CH₂ | PhO | 4-(3-MeO-Pyr-6)-Ph | O |
| 6-223 | H | (CH₂)₂ | H | H | CH₂ | PhO | 4-(3-EtO-Pyr-6)-Ph | O |
| 6-224 | H | (CH₂)₂ | H | H | CH₂ | PhO | 4-(3-iPrO-Pyr-6)-Ph | O |
| 6-225 | H | (CH₂)₂ | H | H | CH₂ | PhO | 4-(3-Dma-Pyr-6)-Ph | O |
| 6-226 | H | (CH₂)₂ | H | H | CH₂ | PhO | 4-(3-Dea-Pyr-6)-Ph | O |
| 6-227 | H | (CH₂)₂ | H | H | CH₂ | PhO | 4-(3-F₃C-Pyr-6)-Ph | O |
| 6-228 | H | (CH₂)₂ | H | H | CH₂ | PhO | 4-(3-O₂N-Pyr-6)-Ph | O |
| 6-229 | H | (CH₂)₂ | H | H | CH₂ | PhO | 4-Pip-Ph | O |
| 6-230 | H | (CH₂)₂ | H | H | CH₂ | PhO | 4-Dea-Ph | O |
| 6-231 | H | (CH₂)₂ | H | H | CH₂ | PhO | 2-(4-F-Ph)-5-Pyr | O |
| 6-232 | H | (CH₂)₂ | H | H | CH₂ | PhO | 2-(4-Cl-Ph)-5-Pyr | O |
| 6-233 | H | (CH₂)₂ | H | H | CH₂ | PhO | 2-(4-MeO-Ph)-5-Pyr | O |
| 6-234 | H | (CH₂)₂ | H | H | CH₂ | PhO | 2-(4-EtO-Ph)-5-Pyr | O |
| 6-235 | H | (CH₂)₂ | H | H | CH₂ | PhO | 2-(4-iPrO-Ph)-5-Pyr | O |
| 6-236 | H | (CH₂)₂ | H | H | CH₂ | PhO | 2-TfpO-5-Pyr | O |
| 6-237 | H | (CH₂)₂ | H | H | CH₂ | PhO | 4-(4-AcO-Ph)-Ph | O |
| 6-238 | H | (CH₂)₂ | H | H | CH₂ | PhO | 4-(3-F-Ph)-Ph | O |
| 6-239 | H | (CH₂)₂ | H | H | CH₂ | PhO | 4-(3-Cl-Ph)-Ph | O |
| 6-240 | H | (CH₂)₂ | H | H | CH₂ | PhO | 4-(3-Me-Ph)-Ph | O |
| 6-241 | H | (CH₂)₂ | H | H | CH₂ | PhO | 4-(3-AcO-Ph)-Ph | O |
| 6-242 | H | (CH₂)₂ | H | H | CH₂ | PhO | 4-(3-Me-Pyr-6)-Ph | O |
| 6-243 | H | (CH₂)₂ | H | H | CH₂ | PhO | 4-(3-Et-Pyr-6)-Ph | O |
| 6-244 | H | (CH₂)₂ | H | H | CH₂ | PhO | 2-(4-Me-Ph)-5-Pyr | O |
| 6-245 | H | (CH₂)₂ | H | H | CH₂ | PhO | 2-(4-CF₃-Ph)-5-Pyr | O |
| 6-246 | H | (CH₂)₂ | H | H | CH₂ | PhO | 2-(4-Dma-Ph)-5-Pyr | O |
| 6-247 | H | (CH₂)₂ | H | H | CH₂ | PhO | 2-(3-F-Ph)-5-Pyr | O |
| 6-248 | H | (CH₂)₂ | H | H | CH₂ | PhO | 2-(3-Cl-Ph)-5-Pyr | O |
| 6-249 | H | (CH₂)₂ | H | H | CH₂ | PhO | 2-(3-MeO-Ph)-5-Pyr | O |
| 6-250 | H | (CH₂)₂ | H | H | CH₂ | PhO | 2-(3-EtO-Ph)-5-Pyr | O |
| 6-251 | H | (CH₂)₂ | H | H | CH₂ | PhO | 2-(3-iPrO-Ph)-5-Pyr | O |
| 6-252 | H | (CH₂)₂ | H | H | CH₂ | PhO | 2-(3-Me-Ph)-5-Pyr | O |
| 6-253 | H | (CH₂)₂ | H | H | CH₂ | PhO | 2-(3-CF₃-Ph)-5-Pyr | O |
| 6-254 | H | (CH₂)₂ | H | H | CH₂ | PhO | 2-(3-Dma-Ph)-5-Pyr | O |

TABLE 7

| Ex. No. Comp. | R¹ | R² | R³ | R⁴ | Z | W | X | Y |
|---|---|---|---|---|---|---|---|---|
| 7-1 | H | (CH$_2$)$_2$ | H | H | CH$_2$ | 4-iPr-PhO | Ph | O |
| 7-2 | H | (CH$_2$)$_2$ | H | H | CH$_2$ | 4-iPr-PhO | 1-Np | O |
| 7-3 | H | (CH$_2$)$_2$ | H | H | CH$_2$ | 4-iPr-PhO | 2-Np | O |
| 7-4 | H | (CH$_2$)$_2$ | H | H | CH$_2$ | 4-iPr-PhO | 4-Me-Ph | O |
| 7-5 | H | (CH$_2$)$_2$ | H | H | CH$_2$ | 4-iPr-PhO | 4-Et-Ph | O |
| 7-6 | H | (CH$_2$)$_2$ | H | H | CH$_2$ | 4-iPr-PhO | 3-iPr-Ph | O |
| 7-7 | H | (CH$_2$)$_2$ | H | H | CH$_2$ | 4-iPr-PhO | 4-iPr-Ph | O |
| 7-8 | H | (CH$_2$)$_2$ | H | H | CH$_2$ | 4-iPr-PhO | 3-tBu-Ph | O |
| 7-9 | H | (CH$_2$)$_2$ | H | H | CH$_2$ | 4-iPr-PhO | 4-tBu-Ph | O |
| 7-10 | H | (CH$_2$)$_2$ | H | H | CH$_2$ | 4-iPr-PhO | 3-F-Ph | O |
| 7-11 | H | (CH$_2$)$_2$ | H | H | CH$_2$ | 4-iPr-PhO | 4-F-Ph | O |
| 7-12 | H | (CH$_2$)$_2$ | H | H | CH$_2$ | 4-iPr-PhO | 4-Cl-Ph | O |
| 7-13 | H | (CH$_2$)$_2$ | H | H | CH$_2$ | 4-iPr-PhO | 4-Br-Ph | O |
| 7-14 | H | (CH$_2$)$_2$ | H | H | CH$_2$ | 4-iPr-PhO | 3-Ph-Ph | O |
| 7-15 | H | (CH$_2$)$_2$ | H | H | CH$_2$ | 4-iPr-PhO | 4-Ph-Ph | O |
| 7-16 | H | (CH$_2$)$_2$ | H | H | CH$_2$ | 4-iPr-PhO | 4-BzO-Ph | O |
| 7-17 | H | (CH$_2$)$_2$ | H | H | CH$_2$ | 4-iPr-PhO | 4-Bz-Ph | O |
| 7-18 | H | (CH$_2$)$_2$ | H | H | CH$_2$ | 4-iPr-PhO | 3-PhO-Ph | O |
| 7-19 | H | (CH$_2$)$_2$ | H | H | CH$_2$ | 4-iPr-PhO | 4-PhO-Ph | O |
| 7-20 | H | (CH$_2$)$_2$ | H | H | CH$_2$ | 4-iPr-PhO | 3-PhS-Ph | O |
| 7-21 | H | (CH$_2$)$_2$ | H | H | CH$_2$ | 4-iPr-PhO | 4-PhS-Ph | O |
| 7-22 | H | (CH$_2$)$_2$ | H | H | CH$_2$ | 4-iPr-PhO | 3-PhSO$_2$-Ph | O |
| 7-23 | H | (CH$_2$)$_2$ | H | H | CH$_2$ | 4-iPr-PhO | 4-PhSO$_2$-Ph | O |
| 7-24 | H | (CH$_2$)$_2$ | H | H | CH$_2$ | 4-iPr-PhO | 3-(Imid-1)-Ph | O |
| 7-25 | H | (CH$_2$)$_2$ | H | H | CH$_2$ | 4-iPr-PhO | 4-(Imid-1)-Ph | O |
| 7-26 | H | (CH$_2$)$_2$ | H | H | CH$_2$ | 4-iPr-PhO | 3-(Imid-4)-Ph | O |
| 7-27 | H | (CH$_2$)$_2$ | H | H | CH$_2$ | 4-iPr-PhO | 4-(Imid-4)-Ph | O |
| 7-28 | H | (CH$_2$)$_2$ | H | H | CH$_2$ | 4-iPr-PhO | 3-(Fur-2)-Ph | O |
| 7-29 | H | (CH$_2$)$_2$ | H | H | CH$_2$ | 4-iPr-PhO | 4-(Fur-2)-Ph | O |
| 7-30 | H | (CH$_2$)$_2$ | H | H | CH$_2$ | 4-iPr-PhO | 3-(Thi-2)-Ph | O |
| 7-31 | H | (CH$_2$)$_2$ | H | H | CH$_2$ | 4-iPr-PhO | 4-(Thi-2)-Ph | O |
| 7-32 | H | (CH$_2$)$_2$ | H | H | CH$_2$ | 4-iPr-PhO | 3-(Thi-3)-Ph | O |
| 7-33 | H | (CH$_2$)$_2$ | H | H | CH$_2$ | 4-iPr-PhO | 4-(Thi-3)-Ph | O |
| 7-34 | H | (CH$_2$)$_2$ | H | H | CH$_2$ | 4-iPr-PhO | 3-(Pyr-2)-Ph | O |
| 7-35 | H | (CH$_2$)$_2$ | H | H | CH$_2$ | 4-iPr-PhO | 4-(Pyr-2)-Ph | O |
| 7-36 | H | (CH$_2$)$_2$ | H | H | CH$_2$ | 4-iPr-PhO | 3-(Pyr-3)-Ph | O |
| 7-37 | H | (CH$_2$)$_2$ | H | H | CH$_2$ | 4-iPr-PhO | 4-(Pyr-3)-Ph | O |
| 7-38 | H | (CH$_2$)$_2$ | H | H | CH$_2$ | 4-iPr-PhO | 3-(Pyr-4)-Ph | O |
| 7-39 | H | (CH$_2$)$_2$ | H | H | CH$_2$ | 4-iPr-PhO | 4-(Pyr-4)-Ph | O |
| 7-40 | H | (CH$_2$)$_2$ | H | H | CH$_2$ | 4-iPr-PhO | 3-(Oxa-2)-Ph | O |
| 7-41 | H | (CH$_2$)$_2$ | H | H | CH$_2$ | 4-iPr-PhO | 4-(Oxa-2)-Ph | O |
| 7-42 | H | (CH$_2$)$_2$ | H | H | CH$_2$ | 4-iPr-PhO | 3-(Oxa-4)-Ph | O |
| 7-43 | H | (CH$_2$)$_2$ | H | H | CH$_2$ | 4-iPr-PhO | 4-(Oxa-4)-Ph | O |
| 7-44 | H | (CH$_2$)$_2$ | H | H | CH$_2$ | 4-iPr-PhO | 3-(Oxa-5)-Ph | O |
| 7-45 | H | (CH$_2$)$_2$ | H | H | CH$_2$ | 4-iPr-PhO | 4-(Oxa-5)-Ph | O |
| 7-46 | H | (CH$_2$)$_2$ | H | H | CH$_2$ | 4-iPr-PhO | 3-(Thiz-2)-Ph | O |
| 7-47 | H | (CH$_2$)$_2$ | H | H | CH$_2$ | 4-iPr-PhO | 4-(Thiz-2)-Ph | O |
| 7-48 | H | (CH$_2$)$_2$ | H | H | CH$_2$ | 4-iPr-PhO | 3-(Thiz-4)-Ph | O |
| 7-49 | H | (CH$_2$)$_2$ | H | H | CH$_2$ | 4-iPr-PhO | 4-(Thiz-4)-Ph | O |
| 7-50 | H | (CH$_2$)$_2$ | H | H | CH$_2$ | 4-iPr-PhO | 3-(Thiz-5)-Ph | O |
| 7-51 | H | (CH$_2$)$_2$ | H | H | CH$_2$ | 4-iPr-PhO | 4-(Thiz-5)-Ph | O |
| 7-52 | H | (CH$_2$)$_2$ | H | H | CH$_2$ | 4-iPr-PhO | 1-Me-2-Pyrr | O |
| 7-53 | H | (CH$_2$)$_2$ | H | H | CH$_2$ | 4-iPr-PhO | 1-Ph-2-Pyrr | O |
| 7-54 | H | (CH$_2$)$_2$ | H | H | CH$_2$ | 4-iPr-PhO | 1-Bz-2-Pyrr | O |
| 7-55 | H | (CH$_2$)$_2$ | H | H | CH$_2$ | 4-iPr-PhO | 5-Me-2-Fur | O |
| 7-56 | H | (CH$_2$)$_2$ | H | H | CH$_2$ | 4-iPr-PhO | 5-Ph-2-Fur | O |
| 7-57 | H | (CH$_2$)$_2$ | H | H | CH$_2$ | 4-iPr-PhO | 5-Me-2-Thi | O |
| 7-58 | H | (CH$_2$)$_2$ | H | H | CH$_2$ | 4-iPr-PhO | 5-Ph-2-Thi | O |
| 7-59 | H | (CH$_2$)$_2$ | H | H | CH$_2$ | 4-iPr-PhO | 5-Me-3-Thi | O |
| 7-60 | H | (CH$_2$)$_2$ | H | H | CH$_2$ | 4-iPr-PhO | 5-Ph-3-Thi | O |
| 7-61 | H | (CH$_2$)$_2$ | H | H | CH$_2$ | 4-iPr-PhO | 1-Me-3-Pyza | O |
| 7-62 | H | (CH$_2$)$_2$ | H | H | CH$_2$ | 4-iPr-PhO | 1-Ph-3-Pyza | O |
| 7-63 | H | (CH$_2$)$_2$ | H | H | CH$_2$ | 4-iPr-PhO | 1-Me-2-Imid | O |
| 7-64 | H | (CH$_2$)$_2$ | H | H | CH$_2$ | 4-iPr-PhO | 1-Ph-2-Imid | O |
| 7-65 | H | (CH$_2$)$_2$ | H | H | CH$_2$ | 4-iPr-PhO | 1-Me-4-Imid | O |
| 7-66 | H | (CH$_2$)$_2$ | H | H | CH$_2$ | 4-iPr-PhO | 1-Ph-4-Imid | O |
| 7-67 | H | (CH$_2$)$_2$ | H | H | CH$_2$ | 4-iPr-PhO | 4-Oxa | O |
| 7-68 | H | (CH$_2$)$_2$ | H | H | CH$_2$ | 4-iPr-PhO | 5-Oxa | O |
| 7-69 | H | (CH$_2$)$_2$ | H | H | CH$_2$ | 4-iPr-PhO | 2-Me-4-Oxa | O |
| 7-70 | H | (CH$_2$)$_2$ | H | H | CH$_2$ | 4-iPr-PhO | 2-Ph-4-Oxa | O |
| 7-71 | H | (CH$_2$)$_2$ | H | H | CH$_2$ | 4-iPr-PhO | 2-Me-5-Oxa | O |
| 7-72 | H | (CH$_2$)$_2$ | H | H | CH$_2$ | 4-iPr-PhO | 2-Ph-5-Oxa | O |
| 7-73 | H | (CH$_2$)$_2$ | H | H | CH$_2$ | 4-iPr-PhO | 4-Me-2-Ph-5-Oxa | O |
| 7-74 | H | (CH$_2$)$_2$ | H | H | CH$_2$ | 4-iPr-PhO | 5-Me-2-Ph-4- | O |

TABLE 7-continued

| Ex. No. Comp. | R¹ | R² | R³ | R⁴ | Z | W | X | Y |
|---|---|---|---|---|---|---|---|---|
| | | | | | | | Oxa | |
| 7-75 | H | (CH₂)₂ | H | H | CH₂ | 4-ipr-PhO | 4-Thiz | O |
| 7-76 | H | (CH₂)₂ | H | H | CH₂ | 4-iPr-PhO | 5-Thiz | O |
| 7-77 | H | (CH₂)₂ | H | H | CH₂ | 4-iPr-PhO | 2-Me-4-Thiz | O |
| 7-78 | H | (CH₂)₂ | H | H | CH₂ | 4-iPr-PbO | 2-Ph-4-Thiz | O |
| 7-79 | H | (CH₂)₂ | H | H | CH₂ | 4-iPr-PhO | 2-Me-5-Thiz | O |
| 7-80 | H | (CH₂)₂ | H | H | CH₂ | 4-iPr-PhO | 2-Ph-5-Thiz | O |
| 7-81 | H | (CH₂)₂ | H | H | CH₂ | 4-iPr-PhO | 4-Me-2-Ph-5-Thiz | O |
| 7-82 | H | (CH₂)₂ | H | H | CH₂ | 4-iPr-PhO | 5-Me-2-Ph-4-Thiz | O |
| 7-83 | H | (CH₂)₂ | H | H | CH₂ | 4-iPr-PhO | 1-Me-4-Pyza | O |
| 7-84 | H | (CH₂)₂ | H | H | CH₂ | 4-iPr-PhO | 1-Ph-4-Pyza | O |
| 7-85 | H | (CH₂)₂ | H | H | CH₂ | 4-iPr-PhO | 2-Me-4-Isox | O |
| 7-86 | H | (CH₂)₂ | H | H | CH₂ | 4-iPr-PhO | 2-Ph-4-Isox | O |
| 7-87 | H | (CH₂)₂ | H | H | CH₂ | 4-iPr-PhO | 2-Pyr | O |
| 7-88 | H | (CH₂)₂ | H | H | CH₂ | 4-iPr-PhO | 3-Pyr | O |
| 7-89 | H | (CH₂)₂ | H | H | CH₂ | 4-iPr-PhO | 4-Pyr | O |
| 7-90 | H | (CH₂)₂ | H | H | CH₂ | 4-iPr-PhO | 3-Me-5-Pyr | O |
| 7-91 | H | (CH₂)₂ | H | H | CH₂ | 4-iPr-PhO | 3-Et-5-Pyr | O |
| 7-92 | H | (CH₂)₂ | H | H | CH₂ | 4-iPr-PhO | 3-Ph-5-Pyr | O |
| 7-93 | H | (CH₂)₂ | H | H | CH₂ | 4-iPr-PhO | 2-Me-5-Pyr | O |
| 7-94 | H | (CH₂)₂ | H | H | CH₂ | 4-iPr-PhO | 2-BzO-5-Pyr | O |
| 7-95 | H | (CH₂)₂ | H | H | CH₂ | 4-iPr-PhO | 2-Ph-5-Pyr | O |
| 7-96 | H | (CH₂)₂ | H | H | CH₂ | 4-iPr-PhO | 2-MeO-5-Pyr | O |
| 7-97 | H | (CH₂)₂ | H | H | CH₂ | 4-iPr-PhO | 2-EtO-5-Pyr | O |
| 7-98 | H | (CH₂)₂ | H | H | CH₂ | 4-iPr-PhO | 2-iPrO-5-Pyr | O |
| 7-99 | H | (CH₂)₂ | H | H | CH₂ | 4-iPr-PhO | 2-MeS-5-Pyr | O |
| 7-100 | H | (CH₂)₂ | R | H | CH₂ | 4-iPr-PhO | 2-EtS-5-Pyr | O |
| 7-101 | H | (CH₂)₂ | H | H | CH₂ | 4-iPr-PhO | 2-PhSO₂NH-5-Pyr | O |
| 7-102 | H | (CH₂)₂ | H | H | CH₂ | 4-iPr-PhO | 2-MeSO₂-5-Pyr | O |
| 7-103 | H | (CH₂)₂ | H | H | CH₂ | 4-iPr-PhO | 2-EtSO₂-5-Pyr | O |
| 7-104 | H | (CH₂)₂ | H | H | CH₂ | 4-iPr-PhO | 2-PhSO₂NMe-5-Pyr | O |
| 7-105 | H | (CH₂)₂ | H | H | CH₂ | 4-iPr-PhO | 2-Bz-5-Pyr | O |
| 7-106 | H | (CH₂)₂ | H | H | CH₂ | 4-iPr-PhO | 2-PhO-5-Pyr | O |
| 7-107 | H | (CH₂)₂ | H | H | CH₂ | 4-iPr-PhO | 2-PhS-5-Pyr | O |
| 7-108 | H | (CH₂)₂ | H | H | CH₂ | 4-iPr-PhO | 2-PhSO₂-5-Pyr | O |
| 7-109 | H | (CH₂)₂ | H | H | CH₂ | 4-iPr-PhO | 3-Me-6-Pyr | O |
| 7-110 | H | (CH₂)₂ | H | H | CH₂ | 4-iPr-PhO | 3-Ph-6-Pyr | O |
| 7-111 | H | (CH₂)₂ | H | H | CH₂ | 4-iPr-PhO | 2-Me-6-Pyr | O |
| 7-112 | H | (CH₂)₂ | H | H | CH₂ | 4-iPr-PhO | 2-Ph-6-Pyr | O |
| 7-113 | H | (CH₂)₂ | H | H | CH₂ | 4-iPr-PhO | 2-Me-4-Pym | O |
| 7-114 | H | (CH₂)₂ | H | H | CH₂ | 4-iPr-PhO | 2-Ph-4-Pym | O |
| 7-115 | H | (CH₂)₂ | H | H | CH₂ | 4-iPr-PhO | 2-MeO-4-Pym | O |
| 7-116 | H | (CH₂)₂ | H | H | CH₂ | 4-iPr-PhO | 2-EtO-4-Pym | O |
| 7-117 | H | (CH₂)₂ | H | H | CH₂ | 4-iPr-PhO | 2-iPrO-4-Pym | O |
| 7-118 | H | (CH₂)₂ | H | H | CH₂ | 4-iPr-PhO | 2-MeS-4-Pym | O |
| 7-119 | H | (CH₂)₂ | H | H | CH₂ | 4-iPr-PhO | 2-EtS-4-Pym | O |
| 7-120 | H | (CH₂)₂ | H | H | CH₂ | 4-iPr-PhO | 2-iPrS-4-Pym | O |
| 7-121 | H | (CH₂)₂ | H | H | CH₂ | 4-iPr-PhO | 6-MeS-4-Pym | O |
| 7-122 | H | (CH₂)₂ | H | H | CH₂ | 4-iPr-PhO | 6-EtS-4-Pym | O |
| 7-123 | H | (CH₂)₂ | H | H | CH₂ | 4-iPr-PhO | 6-iPrS-4-Pym | O |
| 7-124 | H | (CH₂)₂ | H | H | CH₂ | 4-iPr-PhO | 2-PhS-4-Pym | O |
| 7-125 | H | (CH₂)₂ | H | H | CH₂ | 4-iPr-PhO | 2-MeSO₂-4-Pym | O |
| 7-126 | H | (CH₂)₂ | H | H | CH₂ | 4-iPr-PhO | 2-EtSO₂-4-Pym | O |
| 7-127 | H | (CH₂)₂ | H | H | CH₂ | 4-iPr-PhO | 2-iPrSO₂-4-Pym | O |
| 7-128 | H | (CH₂)₂ | H | H | CH₂ | 4-iPr-PhO | 2-PhSO₂-4-Pym | O |
| 7-129 | H | (CH₂)₂ | H | H | CH₂ | 4-iPr-PhO | 2-Me-5-Pym | O |
| 7-130 | H | (CH₂)₂ | H | H | CH₂ | 4-iPr-PhO | 2-Ph-5-Pym | O |
| 7-131 | H | (CH₂)₂ | H | H | CH₂ | 4-iPr-PhO | 2-MeO-5-Pym | O |
| 7-132 | H | (CH₂)₂ | H | H | CH₂ | 4-iPr-PhO | 2-EtO-5-Pym | O |
| 7-133 | H | (CH₂)₂ | H | H | CH₂ | 4-iPr-PhO | 2-iPrO-5-Pym | O |
| 7-134 | H | (CH₂)₂ | H | H | CH₂ | 4-iPr-PhO | 2-MeS-5-Pym | O |
| 7-135 | H | (CH₂)₂ | H | H | CH₂ | 4-iPr-PhO | 2-EtS-5-Pym | O |
| 7-136 | H | (CH₂)₂ | H | H | CH₂ | 4-iPr-PhO | 2-iPrS-5-Pym | O |
| 7-137 | H | (CH₂)₂ | H | H | CH₂ | 4-iPr-PhO | 2-PhS-5-Pym | O |
| 7-138 | H | (CH₂)₂ | H | H | CH₂ | 4-iPr-PhO | 2-MeSO₂-5-Pym | O |
| 7-139 | H | (CH₂)₂ | H | H | CH₂ | 4-iPr-PhO | 2-EtSO₂-5-Pym | O |
| 7-140 | H | (CH₂)₂ | H | H | CH₂ | 4-iPr-PhO | 2-iPrSO₂-5-Pym | O |
| 7-141 | H | (CH₂)₂ | H | H | CH₂ | 4-iPr-PhO | 2-PhSO₂-5-Pym | O |
| 7-142 | H | (CH₂)₂ | H | H | CH₂ | 4-iPr-PhO | 2-Ind | O |

TABLE 7-continued

| Ex. No. Comp. | R$^1$ | R$^2$ | R$^3$ | R$^4$ | Z | W | X | Y |
|---|---|---|---|---|---|---|---|---|
| 7-143 | H | (CH$_2$)$_2$ | H | H | CH$_2$ | 4-iPr-PhO | 3-Ind | O |
| 7-144 | H | (CH$_2$)$_2$ | H | H | CH$_2$ | 4-iPr-PhO | 1-Me-2-Ind | O |
| 7-145 | H | (CH$_2$)$_2$ | H | H | CH$_2$ | 4-iPr-PhO | 1-Me-3-Ind | O |
| 7-146 | H | (CH$_2$)$_2$ | H | H | CH$_2$ | 4-iPr-PhO | 2-Bimid | O |
| 7-147 | H | (CH$_2$)$_2$ | H | H | CH$_2$ | 4-iPr-PhO | 2-Boxa | O |
| 7-148 | H | (CH$_2$)$_2$ | H | H | CH$_2$ | 4-iPr-PhO | 2-Bthiz | O |
| 7-149 | H | (CH$_2$)$_2$ | H | H | CH$_2$ | 4-iPr-PhO | 2-Quin | O |
| 7-150 | H | (CH$_2$)$_2$ | H | H | CH$_2$ | 4-iPr-PhO | 3-Quin | O |
| 7-151 | H | (CH$_2$)$_2$ | H | H | CH$_2$ | 4-iPr-PhO | 4-Quin | O |
| 7-152 | H | (CH$_2$)$_2$ | H | H | CH$_2$ | 4-iPr-PhO | 1-iQuin | O |
| 7-153 | H | (CH$_2$)$_2$ | H | H | CH$_2$ | 4-iPr-PhO | 3-iQuin | O |
| 7-154 | H | (CH$_2$)$_2$ | H | H | CH$_2$ | 4-iPr-PhO | 4-iQuin | O |
| 7-155 | H | (CH$_2$)$_2$ | H | H | CH$_2$ | 4-iPr-PhO | 3-MeO-Ph | O |
| 7-156 | H | (CH$_2$)$_2$ | H | H | CH$_2$ | 4-iPr-PhO | 4-MeO-Ph | O |
| 7-157 | H | (CH$_2$)$_2$ | H | H | CH$_2$ | 4-iPr-PhO | 3-EtO-Ph | O |
| 7-158 | H | (CH$_2$)$_2$ | H | H | CH$_2$ | 4-iPr-PhO | 4-EtO-Ph | O |
| 7-159 | H | (CH$_2$)$_2$ | H | H | CH$_2$ | 4-iPr-PhO | 3-iPrO-Ph | O |
| 7-160 | H | (CH$_2$)$_2$ | H | H | CH$_2$ | 4-iPr-PhO | 4-iPrO-Ph | O |
| 7-161 | H | (CH$_2$)$_2$ | H | H | CH$_2$ | 4-iPr-PhO | 3-MeS-Ph | O |
| 7-162 | H | (CH$_2$)$_2$ | H | H | CH$_2$ | 4-iPr-PhO | 4-MeS-Ph | O |
| 7-163 | H | (CH$_2$)$_2$ | H | H | CH$_2$ | 4-iPr-PhO | 3-EtS-Ph | O |
| 7-164 | H | (CH$_2$)$_2$ | H | H | CH$_2$ | 4-iPr-PhO | 4-EtS-Ph | O |
| 7-165 | H | (CH$_2$)$_2$ | H | H | CH$_2$ | 4-iPr-PhO | 3-iPrS-Ph | O |
| 7-166 | H | (CH$_2$)$_2$ | H | H | CH$_2$ | 4-iPr-PhO | 4-iPrS-Ph | O |
| 7-167 | H | (CH$_2$)$_2$ | H | H | CH$_2$ | 4-iPr-PhO | 3-MeSO$_2$-Ph | O |
| 7-168 | H | (CH$_2$)$_2$ | H | H | CH$_2$ | 4-iPr-PhO | 4-MeSO$_2$-Ph | O |
| 7-169 | H | (CH$_2$)$_2$ | H | H | CH$_2$ | 4-iPr-PhO | 3-EtSO$_2$-Ph | O |
| 7-170 | H | (CH$_2$)$_2$ | H | H | CH$_2$ | 4-iPr-PhO | 4-EtSO$_2$-Ph | O |
| 7-171 | H | (CH$_2$)$_2$ | H | H | CH$_2$ | 4-iPr-PhO | 3-iPrSO$_2$-Ph | O |
| 7-172 | H | (CH$_2$)$_2$ | H | H | CH$_2$ | 4-iPr-PhO | 3-iPrSO$_2$-Ph | O |
| 7-173 | H | (CH$_2$)$_2$ | H | H | CH$_2$ | 4-iPr-PhO | 3-(1-Me-Imid-4)-Ph | O |
| 7-174 | H | (CH$_2$)$_2$ | H | H | CH$_2$ | 4-iPr-PhO | 4-(1-Me-Imid-4)-Ph | O |
| 7-175 | H | (CH$_2$)$_2$ | H | H | CH$_2$ | 4-iPr-PhO | Me-2-Ph-4-Imid | O |
| 7-176 | H | (CH$_2$)$_2$ | H | H | CH$_2$ | 4-iPr-PhO | 1,4-di-Me-2-Ph-5-Imid | O |
| 7-177 | H | (CH$_2$)$_2$ | H | H | CH$_2$ | 4-iPr-PhO | 1,5-di-Me-2-Ph-4-Imid | O |
| 7-178 | H | (CH$_2$)$_2$ | H | H | CH$_2$ | 4-iPr-PhO | 3,4-MdO-Ph | O |
| 7-179 | H | (CH$_2$)$_2$ | H | H | CH$_2$ | 4-iPr-PhO | 4-(4-MeO-Ph)-Ph | O |
| 7-180 | H | (CH$_2$)$_2$ | H | H | CH$_2$ | 4-iPr-PhO | 4-(3,4-MdO-Ph)-Ph | O |
| 7-181 | H | (CH$_2$)$_2$ | H | H | CH$_2$ | 4-iPr-PhO | 4-[PhSO$_2$N(Me)]-Ph | O |
| 7-182 | H | (CH$_2$)$_2$ | H | H | CH$_2$ | 4-iPr-PhO | 4-[(Pyr-3)-SO$_2$N(Me)]-Ph | O |
| 7-183 | H | (CH$_2$)$_2$ | H | H | CH$_2$ | 4-iPr-PhO | 4-(PhSO$_2$NH)-Ph | O |
| 7-184 | H | (CH$_2$)$_2$ | H | H | CH$_2$ | 4-iPr-PhO | 4-[(Pyr-3)-SO$_2$NH]-Ph | O |
| 7-185 | H | (CH$_2$)$_2$ | H | H | CH$_2$ | 4-iPr-PhO | 4-[(Pyr-2)SO$_2$]-Ph | O |
| 7-186 | H | (CH$_2$)$_2$ | H | H | CH$_2$ | 4-iPr-PhO | 4-[(Pyr-3)SO$_2$]-Ph | O |
| 7-187 | H | (CH$_2$)$_2$ | H | H | CH$_2$ | 4-iPr-PhO | 4-[(Pyr-2)-SO$_2$N(Me)]-Ph | O |
| 7-188 | H | (CH$_2$)$_2$ | H | H | CH$_2$ | 4-iPr-PhO | 4-[(Pyr-2)-SO$_2$NH]-Ph | O |
| 7-189 | H | (CH$_2$)$_2$ | H | H | CH$_2$ | 4-iPr-PhO | 4-(4-Me-Ph)-Ph | O |
| 7-190 | H | (CH$_2$)$_2$ | H | H | CH$_2$ | 4-iPr-PhO | 4-(4-F-Ph)-Ph | O |
| 7-191 | H | (CH$_2$)$_2$ | H | H | CH$_2$ | 4-iPr-PhO | 4-(4-CF$_3$-Ph)-Ph | O |
| 7-192 | H | (CH$_2$)$_2$ | H | H | CH$_2$ | 4-iPr-PhO | 2-[PhSO$_2$N(Me)]-5-Pyr | O |
| 7-193 | H | (CH$_2$)$_2$ | H | H | CH$_2$ | 4-iPr-PhO | 2-HO-5-Pyr | O |
| 7-194 | H | (CH$_2$)$_2$ | H | H | CH$_2$ | 4-iPr-PhO | 2-BzO-5-Pyr | O |
| 7-195 | H | (CH$_2$)$_2$ | H | H | CH$_2$ | 4-iPr-PhO | 4-[(Pyr4)SO$_2$]-Ph | O |
| 7-196 | H | (CH$_2$)$_2$ | H | H | CH$_2$ | 4-iPr-PhO | 4-[(Pyr-4)O]-Ph | O |
| 7-197 | H | (CH$_2$)$_2$ | H | H | CH$_2$ | 4-iPr-PhO | 4-[(Pyr-4)S]- | O |

TABLE 7-continued

| Ex. No. Comp. | R¹ | R² | R³ | R⁴ | Z | W | X | Y |
|---|---|---|---|---|---|---|---|---|
| 7-198 | H | (CH$_2$)$_2$ | H | H | CH$_2$ | 4-iPr-PhO | 3-HO-Ph | O |
| 7-199 | H | (CH$_2$)$_2$ | H | H | CH$_2$ | 4-iPr-PhO | 4-HO-Ph | O |
| 7-200 | H | (CH$_2$)$_2$ | H | H | CH$_2$ | 4-iPr-PhO | HO-3,4,6-tri-Me-Ph | O |
| 7-201 | H | (CH$_2$)$_2$ | H | H | CH$_2$ | 4-iPr-PhO | 4-HO-3,5-di-Me-Ph | O |
| 7-202 | H | (CH$_2$)$_2$ | H | H | CH$_2$ | 4-iPr-PhO | 3-AcO-Ph | O |
| 7-203 | H | (CH$_2$)$_2$ | H | H | CH$_2$ | 4-iPr-PhO | 4-AcO-Ph | O |
| 7-204 | H | (CH$_2$)$_2$ | H | H | CH$_2$ | 4-iPr-PhO | 4-(4-Cl-Ph)-Ph | O |
| 7-205 | H | (CH$_2$)$_2$ | H | H | CH$_2$ | 4-iPr-PhO | 4-(4-HO-3,5-di-Me-Ph)-Ph | O |
| 7-206 | H | (CH$_2$)$_2$ | H | H | CH$_2$ | 4-iPr-PhO | 4-(4-HO-Ph)-Ph | O |
| 7-207 | H | (CH$_2$)$_2$ | H | H | CH$_2$ | 4-iPr-PhO | 4-(4-OHC-Ph)-Ph | O |
| 7-208 | H | (CH$_2$)$_2$ | H | H | CH$_2$ | 4-iPr-PhO | 4-(4-Dmam-Ph)-Ph | O |
| 7-209 | H | (CH$_2$)$_2$ | H | H | CH$_2$ | 4-iPr-PhO | 4-(4-Dma-Ph)-Ph | O |
| 7-210 | H | (CH$_2$)$_2$ | H | H | CH$_2$ | 4-iPr-PhO | 4-(4-HOOC-Ph)-Ph | O |
| 7-211 | H | (CH$_2$)$_2$ | H | H | CH$_2$ | 4-iPr-PhO | 4-(4-HOH$_2$C-Ph)-Ph | O |
| 7-212 | H | (CH$_2$)$_2$ | H | H | CH$_2$ | 4-iPr-PhO | 4-(3-MeO-Ph)-Ph | O |
| 7-213 | H | (CH$_2$)$_2$ | H | H | CH$_2$ | 4-iPr-PhO | 4-(3-HO-Ph)-Ph | O |
| 7-214 | H | (CH$_2$)$_2$ | H | H | CH$_2$ | 4-iPr-PhO | 4-(3-OHC-Ph)-Ph | O |
| 7-215 | H | (CH$_2$)$_2$ | H | H | CH$_2$ | 4-iPr-PhO | 4-(3-Dmam-Ph)-Ph | O |
| 7-216 | H | (CH$_2$)$_2$ | H | H | CH$_2$ | 4-iPr-PhO | 4-(3-Dma-Ph)-Ph | O |
| 7-217 | H | (CH$_2$)$_2$ | H | H | CH$_2$ | 4-iPr-PhO | 4-(3-HOOC-Ph)-Ph | O |
| 7-218 | H | (CH$_2$)$_2$ | H | H | CH$_2$ | 4-iPr-PhO | 4-(3-HOH$_2$C-Ph-Ph | O |
| 7-219 | H | (CH$_2$)$_2$ | H | H | CH$_2$ | 4-iPr-PhO | 4-(2-MeO-Ph)-Ph | O |
| 7-220 | H | (CH$_2$)$_2$ | H | H | CH$_2$ | 4-iPr-PhO | 4-(2-HO-Ph)-Ph | O |
| 7-221 | H | (CH$_2$)$_2$ | H | H | CH$_2$ | 4-iPr-PhO | 4-(2-OHC-Ph)-Ph | O |
| 7-222 | H | (CH$_2$)$_2$ | H | H | CH$_2$ | 4-iPr-PhO | 4-(3-MeO-Pyr-6)-Ph | O |
| 7-223 | H | (CH$_2$)$_2$ | H | H | CH$_2$ | 4-iPr-PhO | 4-(3-EtO-Pyr-6)-Ph | O |
| 7-224 | H | (CH$_2$)$_2$ | H | H | CH$_2$ | 4-iPr-PhO | 4-(3-iPrO-Pyr-6)-Ph | O |
| 7-225 | H | (CH$_2$)$_2$ | H | H | CH$_2$ | 4-iPr-PhO | 4-(3-Dma-Pyr-6)-Ph | O |
| 7-226 | H | (CH$_2$)$_2$ | H | H | CH$_2$ | 4-iPr-PhO | 4-(3-Dea-Pyr-6)-Ph | O |
| 7-227 | H | (CH$_2$)$_2$ | H | H | CH$_2$ | 4-iPr-PhO | 4-(3-F$_3$C-Pyr-6)-Ph | O |
| 7-228 | H | (CH$_2$)$_2$ | H | H | CH$_2$ | 4-iPr-PhO | 4-(3-O$_2$N-Pyr-6)-Ph | O |
| 7-229 | H | (CH$_2$)$_2$ | H | H | CH$_2$ | 4-iPr-PhO | 4-Pip-Ph | O |
| 7-230 | H | (CH$_2$)$_2$ | H | H | CH$_2$ | 4-iPr-PhO | 4-Dea-Ph | O |
| 7-231 | H | (CH$_2$)$_2$ | H | H | CH$_2$ | 4-iPr-PhO | 2-(4-F-Ph)-5-Pyr | O |
| 7-232 | H | (CH$_2$)$_2$ | H | H | CH$_2$ | 4-iPr-PhO | 2-(4-Cl-Ph)-5-Pyr | O |
| 7-233 | H | (CH$_2$)$_2$ | H | H | CH$_2$ | 4-iPr-PhO | 2-(4-MeO-Ph)-5-Pyr | O |
| 7-234 | H | (CH$_2$)$_2$ | H | H | CH$_2$ | 4-iPr-PhO | 2-(4-EtO-Ph)-5-Pyr | O |
| 7-235 | H | (CH$_2$)$_2$ | H | H | CH$_2$ | 4-iPr-PhO | 2-(4-iPrO-Ph)-5-Pyr | O |
| 7-236 | H | (CH$_2$)$_2$ | H | H | CH$_2$ | 4-iPr-PhO | 2-TfpO-5-Pyr | O |
| 7-237 | H | (CH$_2$)$_2$ | H | H | CH$_2$ | 4-iPr-PhO | 4-(4-AcO-Ph)-Ph | O |
| 7-238 | H | (CH$_2$)$_2$ | H | H | CH$_2$ | 4-iPr-PhO | 4-(3-F-Ph)-Ph | O |

TABLE 7-continued

| Ex. No. Comp. | R¹ | R² | R³ | R⁴ | Z | W | X | Y |
|---|---|---|---|---|---|---|---|---|
| 7-239 | H | (CH₂)₂ | H | H | CH₂ | 4-iPr-PhO | 4-(3-Cl-Ph)-Ph | O |
| 7-240 | H | (CH₂)₂ | H | H | CH₂ | 4-iPr-PhO | 4-(3-Me-Ph)-Ph | O |
| 7-241 | H | (CH₂)₂ | H | H | CH₂ | 4-iPr-PhO | 4-(3-ACO-Ph)-Ph | O |
| 7-242 | H | (CH₂)₂ | H | H | CH₂ | 4-iPr-PhO | 4-(3-Me-Pyr-6)-Ph | O |
| 7-243 | H | (CH₂)₂ | H | H | CH₂ | 4-iPr-PhO | 4-(3-Et-Pyr-6)-Ph | O |
| 7-244 | H | (CH₂)₂ | H | H | CH₂ | 4-iPr-PhO | 2-(4-Me-Ph)-5-Pyr | O |
| 7-245 | H | (CH₂)₂ | H | H | CH₂ | 4-iPr-PhO | 2-(4-CF₃-Ph)-5-Pyr | O |
| 7-246 | H | (CH₂)₂ | H | H | CH₂ | 4-iPr-PhO | 2-(4-Dma-Ph)-5-Pyr | O |
| 7-247 | H | (CH₂)₂ | H | H | CH₂ | 4-iPr-PhO | 2-(3-F-Ph)-5-Pyr | O |
| 7-248 | H | (CH₂)₂ | H | H | CH₂ | 4-iPr-PhO | 2-(3-Cl-Ph)-5-Pyr | O |
| 7-249 | H | (CH₂)₂ | H | H | CH₂ | 4-iPr-PhO | 2-(3-MeO-Ph)-5-Pyr | O |
| 7-250 | H | (CH₂)₂ | H | H | CH₂ | 4-iPr-PhO | 2-(3-EtO-Ph)-5-Pyr | O |
| 7-251 | H | (CH₂)₂ | H | H | CH₂ | 4-iPr-PhO | 2-(3-iPrO-Ph)-5-Pyr | O |
| 7-252 | H | (CH₂)₂ | H | H | CH₂ | 4-iPr-PhO | 2-(3-Me-Ph)-5-Pyr | O |
| 7-253 | H | (CH₂)₂ | H | H | CH₂ | 4-iPr-PhO | 2-(3-CF₃-Ph)-5-Pyr | O |
| 7-254 | H | (CH₂)₂ | H | H | CH₂ | 4-iPr-PhO | 2-(3-Dma-Ph)-5-Pyr | O |

TABLE 8

| Ex. No. Comp. | R¹ | R² | R³ | R⁴ | Z | W | X | Y |
|---|---|---|---|---|---|---|---|---|
| 8-1 | H | (CH₂)₂ | H | H | CH₂ | 4-MeO—PhO | Ph | O |
| 8-2 | H | (CH₂)₂ | H | H | CH₂ | 4-MeO—PhO | 1-Np | O |
| 8-3 | H | (CH₂)₂ | H | H | CH₂ | 4-MeO—PhO | 2-Np | O |
| 8-4 | H | (CH₂)₂ | H | H | CH₂ | 4-MeO—PhO | 4-Me—Ph | O |
| 8-5 | H | (CH₂)₂ | H | H | CH₂ | 4-MeO—PhO | 4-Et—Ph | O |
| 8-6 | H | (CH₂)₂ | H | H | CH₂ | 4-MeO—PhO | 3-iPr—Ph | O |
| 8-7 | H | (CH₂)₂ | H | H | CH₂ | 4-MeO—PhO | 4-iPr—Ph | O |
| 8-8 | H | (CH₂)₂ | H | H | CH₂ | 4-MeO—PhO | 3-tBu—Ph | O |
| 8-9 | H | (CH₂)₂ | H | H | CH₂ | 4-MeO—PhO | 4-tBu—Ph | O |
| 8-10 | H | (CH₂)₂ | H | H | CH₂ | 4-MeO—PhO | 3-F—Ph | O |
| 8-11 | H | (CH₂)₂ | H | H | CH₂ | 4-MeO—PhO | 4-F—Ph | O |
| 8-12 | H | (CH₂)₂ | H | H | CH₂ | 4-MeO—PhO | 4-Cl—Ph | O |
| 8-13 | H | (CH₂)₂ | H | H | CH₂ | 4-MeO—PhO | 4-Br—Ph | O |
| 8-14 | H | (CH₂)₂ | H | H | CH₂ | 4-MeO—PhO | 3-Ph—Ph | O |
| 8-15 | H | (CH₂)₂ | H | H | CH₂ | 4-MeO—PhO | 4-Ph—Ph | O |
| 8-16 | H | (CH₂)₂ | H | H | CH₂ | 4-MeO—PhO | 4-BzO—Ph | O |
| 8-17 | H | (CH₂)₂ | H | H | CH₂ | 4-MeO—PhO | 4-Bz—Ph | O |
| 8-18 | H | (CH₂)₂ | H | H | CH₂ | 4-MeO—PhO | 3-PhO—Ph | O |
| 8-19 | H | (CH₂)₂ | H | H | CH₂ | 4-MeO—PhO | 4-PhO—Ph | O |
| 8-20 | H | (CH₂)₂ | H | H | CH₂ | 4-MeO—PhO | 3-PhS—Ph | O |
| 8-21 | H | (CH₂)₂ | H | H | CH₂ | 4-MeO—PhO | 4-PhS—Ph | O |
| 8-22 | H | (CH₂)₂ | H | H | CH₂ | 4-MeO—PhO | 3-PhSO₂—Ph | O |
| 8-23 | H | (CH₂)₂ | H | H | CH₂ | 4-MeO—PhO | 4-PhSO₂—Ph | O |
| 8-24 | H | (CH₂)₂ | H | H | CH₂ | 4-MeO—PhO | 3-(Imid-1)-Ph | O |
| 8-25 | H | (CH₂)₂ | H | H | CH₂ | 4-MeO—PhO | 4-(Imid-1)-Ph | O |
| 8-26 | H | (CH₂)₂ | H | H | CH₂ | 4-MeO—PhO | 3-(Imid-4)-Ph | O |
| 8-27 | H | (CH₂)₂ | H | H | CH₂ | 4-MeO—PhO | 4-(Imid-4)-Ph | O |
| 8-28 | H | (CH₂)₂ | H | H | CH₂ | 4-MeO—PhO | 3-(Fur-2)-Ph | O |
| 8-29 | H | (CH₂)₂ | H | H | CH₂ | 4-MeO—PhO | 4-(Fur-2)-Ph | O |
| 8-30 | H | (CH₂)₂ | H | H | CH₂ | 4-MeO—PhO | 3-(Thi-2)-Ph | O |
| 8-31 | H | (CH₂)₂ | H | H | CH₂ | 4-MeO—PhO | 4-(Thi-2)-Ph | O |
| 8-32 | H | (CH₂)₂ | H | H | CH₂ | 4-MeO—PhO | 3-(Thi-3)-Ph | O |
| 8-33 | H | (CH₂)₂ | H | H | CH₂ | 4-MeO—PhO | 4-(Thi-3)-Ph | O |

TABLE 8-continued

| Ex. No. Comp. | R¹ | R² | R³ | R⁴ | Z | W | X | Y |
|---|---|---|---|---|---|---|---|---|
| 8-34 | H | (CH$_2$)$_2$ | H | H | CH$_2$ | 4-MeO—PhO | 3-(Pyr-2)-Ph | O |
| 8-35 | H | (CH$_2$)$_2$ | H | H | CH$_2$ | 4-MeO—PhO | 4-(Pyr-2)-Ph | O |
| 8-36 | H | (CH$_2$)$_2$ | H | H | CH$_2$ | 4-MeO—PhO | 3-(Pyr-3)-Ph | O |
| 8-37 | H | (CH$_2$)$_2$ | H | H | CH$_2$ | 4-MeO—PhO | 4-(Pyr-3)-Ph | O |
| 8-38 | H | (CH$_2$)$_2$ | H | H | CH$_2$ | 4-MeO—PhO | 3-(Pyr-4)-Ph | O |
| 8-39 | H | (CH$_2$)$_2$ | H | H | CH$_2$ | 4-MeO—PhO | 4-(Pyr-4)-Ph | O |
| 8-40 | H | (CH$_2$)$_2$ | H | H | CH$_2$ | 4-MeO—PhO | 3-(Oxa-2)-Ph | O |
| 8-41 | H | (CH$_2$)$_2$ | H | H | CH$_2$ | 4-MeO—PhO | 4-(Oxa-2)-Ph | O |
| 8-42 | H | (CH$_2$)$_2$ | H | H | CH$_2$ | 4-MeO—PhO | 3-(Oxa-4)-Ph | O |
| 8-43 | H | (CH$_2$)$_2$ | H | H | CH$_2$ | 4-MeO—PhO | 4-(Oxa-4)-Ph | O |
| 8-44 | H | (CH$_2$)$_2$ | H | H | CH$_2$ | 4-MeO—PhO | 3-(Oxa-5)-Ph | O |
| 8-45 | H | (CH$_2$)$_2$ | H | H | CH$_2$ | 4-MeO—PhO | 4-(Oxa-5)-Ph | O |
| 8-46 | H | (CH$_2$)$_2$ | H | H | CH$_2$ | 4-MeO—PhO | 3-(Thiz-2)-Ph | O |
| 8-47 | H | (CH$_2$)$_2$ | H | H | CH$_2$ | 4-MeO—PhO | 4-(Thiz-2)-Ph | O |
| 8-48 | H | (CH$_2$)$_2$ | H | H | CH$_2$ | 4-MeO—PhO | 3-(Thiz-4)-Ph | O |
| 8-49 | H | (CH$_2$)$_2$ | H | H | CH$_2$ | 4-MeO—PhO | 4-(Thiz-4)-Ph | O |
| 8-50 | H | (CH$_2$)$_2$ | H | H | CH$_2$ | 4-MeO—PhO | 3-(Thiz-5)-Ph | O |
| 8-51 | H | (CH$_2$)$_2$ | H | H | CH$_2$ | 4-MeO—PhO | 4-(Thiz-5)-Ph | O |
| 8-52 | H | (CH$_2$)$_2$ | H | H | CH$_2$ | 4-MeO—PhO | 1-Me-2-Pyrr | O |
| 8-53 | H | (CH$_2$)$_2$ | H | H | CH$_2$ | 4-MeO—PhO | 1-Ph-2-Pyrr | O |
| 8-54 | H | (CH$_2$)$_2$ | H | H | CH$_2$ | 4-MeO—PhO | 1-Bz-2-Pyrr | O |
| 8-55 | H | (CH$_2$)$_2$ | H | H | CH$_2$ | 4-MeO—PhO | 5-Me-2-Fur | O |
| 8-56 | H | (CH$_2$)$_2$ | H | H | CH$_2$ | 4-MeO—PhO | 5-Ph-2-Fur | O |
| 8-57 | H | (CH$_2$)$_2$ | H | H | CH$_2$ | 4-MeO—PhO | 5-Me-2-Thi | O |
| 8-58 | H | (CH$_2$)$_2$ | H | H | CH$_2$ | 4-MeO—PhO | 5-Ph-2-Thi | O |
| 8-59 | H | (CH$_2$)$_2$ | H | H | CH$_2$ | 4-MeO—PhO | 5-Me-3-Thi | O |
| 8-60 | H | (CH$_2$)$_2$ | H | H | CH$_2$ | 4-MeO—PhO | 5-Ph-3-Thi | O |
| 8-61 | H | (CH$_2$)$_2$ | H | H | CH$_2$ | 4-MeO—PhO | 1-Me-3-Pyza | O |
| 8-62 | H | (CH$_2$)$_2$ | H | H | CH$_2$ | 4-MeO—PhO | 1-Ph-3-Pyza | O |
| 8-63 | H | (CH$_2$)$_2$ | H | H | CH$_2$ | 4-MeO—PhO | 1-Me-2-Imid | O |
| 8-64 | H | (CH$_2$)$_2$ | H | H | CH$_2$ | 4-MeO—PhO | 1-Ph-2-Imid | O |
| 8-65 | H | (CH$_2$)$_2$ | H | H | CH$_2$ | 4-MeO—PhO | 1-Me-4-Imid | O |
| 8-66 | H | (CH$_2$)$_2$ | H | H | CH$_2$ | 4-MeO—PhO | 1-Ph-4-Imid | O |
| 8-67 | H | (CH$_2$)$_2$ | H | H | CH$_2$ | 4-MeO—PhO | 4-Oxa | O |
| 8-68 | H | (CH$_2$)$_2$ | H | H | CH$_2$ | 4-MeO—PhO | 5-Oxa | O |
| 8-69 | H | (CH$_2$)$_2$ | H | H | CH$_2$ | 4-MeO—PhO | 2-Me-4-Oxa | O |
| 8-70 | H | (CH$_2$)$_2$ | H | H | CH$_2$ | 4-MeO—PhO | 2-Ph-4-Oxa | O |
| 8-71 | H | (CH$_2$)$_2$ | H | H | CH$_2$ | 4-MeO—PhO | 2-Me-5-Oxa | O |
| 8-72 | H | (CH$_2$)$_2$ | H | H | CH$_2$ | 4-MeO—PhO | 2-Ph-5-Oxa | O |
| 8-73 | H | (CH$_2$)$_2$ | H | H | CH$_2$ | 4-MeO—PhO | 4-Me-2-Ph-5-Oxa | O |
| 8-74 | H | (CH$_2$)$_2$ | H | H | CH$_2$ | 4-MeO—PhO | 5-Me-2-Ph-4-Oxa | O |
| 8-75 | H | (CH$_2$)$_2$ | H | H | CH$_2$ | 4-MeO—PhO | 4-Thiz | O |
| 8-76 | H | (CH$_2$)$_2$ | H | H | CH$_2$ | 4-MeO—PhO | 5-Thiz | O |
| 8-77 | H | (CH$_2$)$_2$ | H | H | CH$_2$ | 4-MeO—PhO | 2-Me-4-Thiz | O |
| 8-78 | H | (CH$_2$)$_2$ | H | H | CH$_2$ | 4-MeO—PhO | 2-Ph-4-Thiz | O |
| 8-79 | H | (CH$_2$)$_2$ | H | H | CH$_2$ | 4-MeO—PhO | 2-Me-5-Thiz | O |
| 8-80 | H | (CH$_2$)$_2$ | H | H | CH$_2$ | 4-MeO—PhO | 2-Ph-5-Thiz | O |
| 8-81 | H | (CH$_2$)$_2$ | H | H | CH$_2$ | 4-MeO—PhO | Me-2-Ph-5-Thiz | O |
| 8-82 | H | (CH$_2$)$_2$ | H | H | CH$_2$ | 4-MeO—PhO | 5-Me-2-Ph-4-Thiz | O |
| 8-83 | H | (CH$_2$)$_2$ | H | H | CH$_2$ | 4-MeO—PhO | 1-Me-4-Pyza | O |
| 8-84 | H | (CH$_2$)$_2$ | H | H | CH$_2$ | 4-MeO—PhO | 1-Ph-4-Pyza | O |
| 8-85 | H | (CH$_2$)$_2$ | H | H | CH$_2$ | 4-MeO—PhO | 2-Me-4-Isox | O |
| 8-86 | H | (CH$_2$)$_2$ | H | H | CH$_2$ | 4-MeO—PhO | 2-Ph-4-Isox | O |
| 8-87 | H | (CH$_2$)$_2$ | H | H | CH$_2$ | 4-MeO—PhO | 2-Pyr | O |
| 8-88 | H | (CH$_2$)$_2$ | H | H | CH$_2$ | 4-MeO—PhO | 3-Pyr | O |
| 8-89 | H | (CH$_2$)$_2$ | H | H | CH$_2$ | 4-MeO—PhO | 4-Pyr | O |
| 8-90 | H | (CH$_2$)$_2$ | H | H | CH$_2$ | 4-MeO—PhO | 3-Me-5-Pyr | O |
| 8-91 | H | (CH$_2$)$_2$ | H | H | CH$_2$ | 4-MeO—PhO | 3-Et-5-Pyr | O |
| 8-92 | H | (CH$_2$)$_2$ | H | H | CH$_2$ | 4-MeO—PhO | 3-Ph-5-Pyr | O |
| 8-93 | H | (CH$_2$)$_2$ | H | H | CH$_2$ | 4-MeO—PhO | 2-Me-5-Pyr | O |
| 8-94 | H | (CH$_2$)$_2$ | H | H | CH$_2$ | 4-MeO—PhO | 2-BzO-5-Pyr | O |
| 8-95 | H | (CH$_2$)$_2$ | H | H | CH$_2$ | 4-MeO—PhO | 2-Ph-5-Pyr | O |
| 8-96 | H | (CH$_2$)$_2$ | H | H | CH$_2$ | 4-MeO—PhO | 2-MeO-5-Pyr | O |
| 8-97 | H | (CH$_2$)$_2$ | H | H | CH$_2$ | 4-MeO—PhO | 2-EtO-5-Pyr | O |
| 8-98 | H | (CH$_2$)$_2$ | H | H | CH$_2$ | 4-MeO—PhO | 2-iPrO-5-Pyr | O |
| 8-99 | H | (CH$_2$)$_2$ | H | H | CH$_2$ | 4-MeO—PhO | 2-MeS-5-Pyr | O |
| 8-100 | H | (CH$_2$)$_2$ | H | H | CH$_2$ | 4-MeO—PhO | 2-EtS-5-Pyr | O |
| 8-101 | H | (CH$_2$)$_2$ | H | H | CH$_2$ | 4-MeO—PhO | 2-PhSO$_2$NH-5-Pyr | O |
| 8-102 | H | (CH$_2$)$_2$ | H | H | CH$_2$ | 4-MeO—PhO | 2-MeSO$_2$-5-Pyr | O |
| 8-103 | H | (CH$_2$)$_2$ | H | H | CH$_2$ | 4-MeO—PhO | 2-EtSO$_2$-5-Pyr | O |
| 8-104 | H | (CH$_2$)$_2$ | H | H | CH$_2$ | 4-MeO—PhO | 2-PhSO$_2$NMe-5-Pyr | O |
| 8-105 | H | (CH$_2$)$_2$ | H | H | CH$_2$ | 4-MeO—PhO | 2-Bz-5-Pyr | O |
| 8-106 | H | (CH$_2$)$_2$ | H | H | CH$_2$ | 4-MeO—PhO | 2-PhO-5-Pyr | O |

TABLE 8-continued

| Ex. No. Comp. | R$^1$ | R$^2$ | R$^3$ | R$^4$ | Z | W | X | Y |
|---|---|---|---|---|---|---|---|---|
| 8-107 | H | (CH$_2$)$_2$ | H | H | CH$_2$ | 4-MeO—PhO | 2-PhS-5-Pyr | O |
| 8-108 | H | (CH$_2$)$_2$ | H | H | CH$_2$ | 4-MeO—PhO | 2-PhSO$_2$-5-Pyr | O |
| 8-109 | H | (CH$_2$)$_2$ | H | H | CH$_2$ | 4-MeO—PhO | 3-Me-6-Pyr | O |
| 8-110 | H | (CH$_2$)$_2$ | H | H | CH$_2$ | 4-MeO—PhO | 3-Ph-6-Pyr | O |
| 8-111 | H | (CH$_2$)$_2$ | H | H | CH$_2$ | 4-MeO—PhO | 2-Me-6-Pyr | O |
| 8-112 | H | (CH$_2$)$_2$ | H | H | CH$_2$ | 4-MeO—PhO | 2-Ph-6-Pyr | O |
| 8-113 | H | (CH$_2$)$_2$ | H | H | CH$_2$ | 4-MeO—PhO | 2-Me-4-Pym | O |
| 8-114 | H | (CH$_2$)$_2$ | H | H | CH$_2$ | 4-MeO—PhO | 2-Ph-4-Pym | O |
| 8-115 | H | (CH$_2$)$_2$ | H | H | CH$_2$ | 4-MeO—PhO | 2-MeO-4-Pym | O |
| 8-116 | H | (CH$_2$)$_2$ | H | H | CH$_2$ | 4-MeO—PhO | 2-EtO-4-Pym | O |
| 8-117 | H | (CH$_2$)$_2$ | H | H | CH$_2$ | 4-MeO—PhO | 2-iPrO-4-Pym | O |
| 8-118 | H | (CH$_2$)$_2$ | H | H | CH$_2$ | 4-MeO—PhO | 2-MeS-4-Pym | O |
| 8-119 | H | (CH$_2$)$_2$ | H | H | CH$_2$ | 4-MeO—PhO | 2-EtS-4-Pym | O |
| 8-120 | H | (CH$_2$)$_2$ | H | H | CH$_2$ | 4-MeO—PhO | 2-iPrS-4-Pym | O |
| 8-121 | H | (CH$_2$)$_2$ | H | H | CH$_2$ | 4-MeO—PhO | 6-MeS-4-Pym | O |
| 8-122 | H | (CH$_2$)$_2$ | H | H | CH$_2$ | 4-MeO—PhO | 6-EtS-4-Pym | O |
| 8-123 | H | (CH$_2$)$_2$ | H | H | CH$_2$ | 4-MeO—PhO | 6-iPrS-4-Pym | O |
| 8-124 | H | (CH$_2$)$_2$ | H | H | CH$_2$ | 4-MeO—PhO | 2-PhS-4-Pym | O |
| 8-125 | H | (CH$_2$)$_2$ | H | H | CH$_2$ | 4-MeO—PhO | 2-MeSO$_2$-4-Pym | O |
| 8-126 | H | (CH$_2$)$_2$ | H | H | CH$_2$ | 4-MeO—PhO | 2-EtSO$_2$-4-Pym | O |
| 8-127 | H | (CH$_2$)$_2$ | H | H | CH$_2$ | 4-MeO—PhO | 2-iPrSO$_2$-4-Pym | O |
| 8-128 | H | (CH$_2$)$_2$ | H | H | CH$_2$ | 4-MeO—PhO | 2-PhSO$_2$-4-Pym | O |
| 8-129 | H | (CH$_2$)$_2$ | H | H | CH$_2$ | 4-MeO—PhO | 2-Me-5-Pym | O |
| 8-130 | H | (CH$_2$)$_2$ | H | H | CH$_2$ | 4-MeO—PhO | 2-Ph-5-Pym | O |
| 8-131 | H | (CH$_2$)$_2$ | H | H | CH$_2$ | 4-MeO—PhO | 2-MeO-5-Pym | O |
| 8-132 | H | (CH$_2$)$_2$ | H | H | CH$_2$ | 4-MeO—PhO | 2-EtO-5-Pym | O |
| 8-133 | H | (CH$_2$)$_2$ | H | H | CH$_2$ | 4-MeO—PhO | 2-iPrO-5-Pym | O |
| 8-134 | H | (CH$_2$)$_2$ | H | H | CH$_2$ | 4-MeO—PhO | 2-MeS-5-Pym | O |
| 8-135 | H | (CH$_2$)$_2$ | H | H | CH$_2$ | 4-MeO—PhO | 2-EtS-5-Pym | O |
| 8-136 | H | (CH$_2$)$_2$ | H | H | CH$_2$ | 4-MeO—PhO | 2-iPrS-5-Pym | O |
| 8-137 | H | (CH$_2$)$_2$ | H | H | CH$_2$ | 4-MeO—PhO | 2-PhS-5-Pym | O |
| 8-138 | H | (CH$_2$)$_2$ | H | H | CH$_2$ | 4-MeO—PhO | 2-MeSO$_2$-5-Pym | O |
| 8-139 | H | (CH$_2$)$_2$ | H | H | CH$_2$ | 4-MeO—PhO | 2-EtSO$_2$-5-Pym | O |
| 8-140 | H | (CH$_2$)$_2$ | H | H | CH$_2$ | 4-MeO—PhO | 2-iPrSO$_2$-5-Pym | O |
| 8-141 | H | (CH$_2$)$_2$ | H | H | CH$_2$ | 4-MeO—PhO | 2-PhSO$_2$-5-Pym | O |
| 8-142 | H | (CH$_2$)$_2$ | H | H | CH$_2$ | 4-MeO—PhO | 2-Ind | O |
| 8-143 | H | (CH$_2$)$_2$ | H | H | CH$_2$ | 4-MeO—PhO | 3-Ind | O |
| 8-144 | H | (CH$_2$)$_2$ | H | H | CH$_2$ | 4-MeO—PhO | 1-Me-2-Ind | O |
| 8-145 | H | (CH$_2$)$_2$ | H | H | CH$_2$ | 4-MeO—PhO | 1-Me-3-Ind | O |
| 8-146 | H | (CH$_2$)$_2$ | H | H | CH$_2$ | 4-MeO—PhO | 2-Bimid | O |
| 8-147 | H | (CH$_2$)$_2$ | H | H | CH$_2$ | 4-MeO—PhO | 2-Boxa | O |
| 8-148 | H | (CH$_2$)$_2$ | H | H | CH$_2$ | 4-MeO—PhO | 2-Bthiz | O |
| 8-149 | H | (CH$_2$)$_2$ | H | H | CH$_2$ | 4-MeO—PhO | 2-Quin | O |
| 8-150 | H | (CH$_2$)$_2$ | H | H | CH$_2$ | 4-MeO—PhO | 3-Quin | O |
| 8-151 | H | (CH$_2$)$_2$ | H | H | CH$_2$ | 4-MeO—PhO | 4-Quin | O |
| 8-152 | H | (CH$_2$)$_2$ | H | H | CH$_2$ | 4-MeO—PhO | 1-iQuin | O |
| 8-153 | H | (CH$_2$)$_2$ | H | H | CH$_2$ | 4-MeO—PhO | 3-iQuin | O |
| 8-154 | H | (CH$_2$)$_2$ | H | H | CH$_2$ | 4-MeO—PhO | 4-iQuin | O |
| 8-155 | H | (CH$_2$)$_2$ | H | H | CH$_2$ | 4-MeO—PhO | 3-MeO—Ph | O |
| 8-156 | H | (CH$_2$)$_2$ | H | H | CH$_2$ | 4-MeO—PhO | 4-MeO—Ph | O |
| 8-157 | H | (CH$_2$)$_2$ | H | H | CH$_2$ | 4-MeO—PhO | 3-EtO—Ph | O |
| 8-158 | H | (CH$_2$)$_2$ | H | H | CH$_2$ | 4-MeO—PhO | 4-EtO—Ph | O |
| 8-159 | H | (CH$_2$)$_2$ | H | H | CH$_2$ | 4-MeO—PhO | 3-iPrO—Ph | O |
| 8-160 | H | (CH$_2$)$_2$ | H | H | CH$_2$ | 4-MeO—PhO | 4-iPrO—Ph | O |
| 8-161 | H | (CH$_2$)$_2$ | H | H | CH$_2$ | 4-MeO—PhO | 3-MeS—Ph | O |
| 8-162 | H | (CH$_2$)$_2$ | H | H | CH$_2$ | 4-MeO—PhO | 4-MeS—Ph | O |
| 8-163 | H | (CH$_2$)$_2$ | H | H | CH$_2$ | 4-MeO—PhO | 3-EtS—Ph | O |
| 8-164 | H | (CH$_2$)$_2$ | H | H | CH$_2$ | 4-MeO—PhO | 4-EtS—Ph | O |
| 8-165 | H | (CH$_2$)$_2$ | H | H | CH$_2$ | 4-MeO—PhO | 3-iPrS—Ph | O |
| 8-166 | H | (CH$_2$)$_2$ | H | H | CH$_2$ | 4-MeO—PhO | 4-iPrS—Ph | O |
| 8-167 | H | (CH$_2$)$_2$ | H | H | CH$_2$ | 4-MeO—PhO | 3-MeSO$_2$—Ph | O |
| 8-168 | H | (CH$_2$)$_2$ | H | H | CH$_2$ | 4-MeO—PhO | 4-MeSO$_2$—Ph | O |
| 8-169 | H | (CH$_2$)$_2$ | H | H | CH$_2$ | 4-MeO—PhO | 3-EtSO$_2$—Ph | O |
| 8-170 | H | (CH$_2$)$_2$ | H | H | CH$_2$ | 4-MeO—PhO | 4-EtSO$_2$—Ph | O |
| 8-171 | H | (CH$_2$)$_2$ | H | H | CH$_2$ | 4-MeO—PhO | 3-iPrSO$_2$—Ph | O |
| 8-172 | H | (CH$_2$)$_2$ | H | H | CH$_2$ | 4-MeO—PhO | 4-iPrSO$_2$—Ph | O |
| 8-173 | H | (CH$_2$)$_2$ | H | H | CH$_2$ | 4-MeO—PhO | 3-(1-Me-Imid-4)-Ph | O |
| 8-174 | H | (CH$_2$)$_2$ | H | H | CH$_2$ | 4-MeO—PhO | 4-(1-Me-Imid-4)-Ph | O |
| 8-175 | H | (CH$_2$)$_2$ | H | H | CH$_2$ | 4-MeO—PhO | Me-2-Ph-4-Imid | O |
| 8-176 | H | (CH$_2$)$_2$ | H | H | CH$_2$ | 4-MeO—PhO | 1,4-di-Me-2-Ph-5-Imid | O |
| 8-177 | H | (CH$_2$)$_2$ | H | H | CH$_2$ | 4-MeO—PhO | 1,5-di-Me-2-Ph-4-Imid | O |

TABLE 8-continued

| Ex. No. Comp. | R¹ | R² | R³ | R⁴ | Z | W | X | Y |
|---|---|---|---|---|---|---|---|---|
| 8-178 | H | (CH$_2$)$_2$ | H | H | CH$_2$ | 4-MeO—PhO | 3,4-MdO—Ph | O |
| 8-179 | H | (CH$_2$)$_2$ | H | H | CH$_2$ | 4-MeO—PhO | 4-(4-MeO—Ph)—Ph | O |
| 8-180 | H | (CH$_2$)$_2$ | H | H | CH$_2$ | 4-MeO—PhO | 4-(3,4-MdO—Ph)—Ph | O |
| 8-181 | H | (CH$_2$)$_2$ | H | H | CH$_2$ | 4-MeO—PhO | 4-[PhSO$_2$N(Me)]—Ph | O |
| 8-182 | H | (CH$_2$)$_2$ | H | H | CH$_2$ | 4-MeO—PhO | 4-[(Pyr-3)-SO$_2$N(Me)]—Ph | O |
| 8-183 | H | (CH$_2$)$_2$ | H | H | CH$_2$ | 4-MeO—PhO | 4-(PhSO$_2$NH)—Ph | O |
| 8-184 | H | (CH$_2$)$_2$ | H | H | CH$_2$ | 4-MeO—PhO | 4-[(Pyr-3)-SO$_2$NH]—Ph | O |
| 8-185 | H | (CH$_2$)$_2$ | H | H | CH$_2$ | 4-MeO—PhO | 4-[(Pyr-2)SO$_2$]—Ph | O |
| 8-186 | H | (CH$_2$)$_2$ | H | H | CH$_2$ | 4-MeO—PhO | 4-[(Pyr-3)SO$_2$]—Ph | O |
| 8-187 | H | (CH$_2$)$_2$ | H | H | CH$_2$ | 4-MeO—PhO | 4-[(Pyr-2)-SO$_2$N(Me)]—Ph | O |
| 8-188 | H | (CH$_2$)$_2$ | H | H | CH$_2$ | 4-MeO—PhO | 4-[(Pyr-2)-SO$_2$NH]—Ph | O |
| 8-189 | H | (CH$_2$)$_2$ | H | H | CH$_2$ | 4-MeO—PhO | 4-(4-Me—Ph)—Ph | O |
| 8-190 | H | (CH$_2$)$_2$ | H | H | CH$_2$ | 4-MeO—PhO | 4-(4-F—Ph)—Ph | O |
| 8-191 | H | (CH$_2$)$_2$ | H | H | CH$_2$ | 4-MeO—PhO | 4-(4-CF$_3$—Ph)—Ph | O |
| 8-192 | H | (CH$_2$)$_2$ | H | H | CH$_2$ | 4-MeO—PhO | 2-[PhSO$_2$N(Me)]-5-Pyr | O |
| 8-193 | H | (CH$_2$)$_2$ | H | H | CH$_2$ | 4-MeO—PhO | 2-HO-5-Pyr | O |
| 8-194 | H | (CH$_2$)$_2$ | H | H | CH$_2$ | 4-MeO—PhO | 2-BzO-5-Pyr | O |
| 8-195 | H | (CH$_2$)$_2$ | H | H | CH$_2$ | 4-MeO—PhO | 4-[(Pyr-4)SO$_2$]—Ph | O |
| 8-196 | H | (CH$_2$)$_2$ | H | H | CH$_2$ | 4-MeO—PhO | 4-[(Pyr-4)O]—Ph | O |
| 8-197 | H | (CH$_2$)$_2$ | H | H | CH$_2$ | 4-MeO—PhO | 4-[(Pyr-4)S]—Ph | O |
| 8-198 | H | (CH$_2$)$_2$ | H | H | CH$_2$ | 4-MeO—PhO | 3-HO—Ph | O |
| 8-199 | H | (CH$_2$)$_2$ | H | H | CH$_2$ | 4-MeO—PhO | 4-HO—Ph | O |
| 8-200 | H | (CH$_2$)$_2$ | H | H | CH$_2$ | 4-MeO—PhO | HO-3,4,6-tri-Me—Ph | O |
| 8-201 | H | (CH$_2$)$_2$ | H | H | CH$_2$ | 4-MeO—PhO | 4-HO-3,5-di-Me—Ph | O |
| 8-202 | H | (CH$_2$)$_2$ | H | H | CH$_2$ | 4-MeO—PhO | 3-AcO—Ph | O |
| 8-203 | H | (CH$_2$)$_2$ | H | H | CH$_2$ | 4-MeO—PhO | 4-AcO—Ph | O |
| 8-204 | H | (CH$_2$)$_2$ | H | H | CH$_2$ | 4-MeO—PhO | 4-(4-Cl—Ph)—Ph | O |
| 8-205 | H | (CH$_2$)$_2$ | H | H | CH$_2$ | 4-MeO—PhO | 4-(4-HO-3,5-di-Me—Ph)—Ph | O |
| 8-206 | H | (CH$_2$)$_2$ | H | H | CH$_2$ | 4-MeO—PhO | 4-(4-HO—Ph)—Ph | O |
| 8-207 | H | (CH$_2$)$_2$ | H | H | CH$_2$ | 4-MeO—PhO | 4-(4-OHC—Ph)—Ph | O |
| 8-208 | H | (CH$_2$)$_2$ | H | H | CH$_2$ | 4-MeO—PhO | 4-(4-Dmam—Ph)—Ph | O |
| 8-209 | H | (CH$_2$)$_2$ | H | H | CH$_2$ | 4-MeO—PhO | 4-(4-Dma—Ph)—Ph | O |
| 8-210 | H | (CH$_2$)$_2$ | H | H | CH$_2$ | 4-MeO—PhO | 4-(4-HOOC—Ph)—Ph | O |
| 8-211 | H | (CH$_2$)$_2$ | H | H | CH$_2$ | 4-MeO—PhO | 4-(4-HOH$_2$C—Ph)—Ph | O |
| 8-212 | H | (CH$_2$)$_2$ | H | H | CH$_2$ | 4-MeO—PhO | 4-(3-MeO—Ph)—Ph | O |
| 8-213 | H | (CH$_2$)$_2$ | H | H | CH$_2$ | 4-MeO—PhO | 4-(3-HO—Ph)—Ph | O |
| 8-214 | H | (CH$_2$)$_2$ | H | H | CH$_2$ | 4-MeO—PhO | 4-(3-OHC—Ph)—Ph | O |
| 8-215 | H | (CH$_2$)$_2$ | H | H | CH$_2$ | 4-MeO—PhO | 4-(3-Dmam—Ph)—Ph | O |
| 8-216 | H | (CH$_2$)$_2$ | H | H | CH$_2$ | 4-MeO—PhO | 4-(3-Dma—Ph)—Ph | O |
| 8-217 | H | (CH$_2$)$_2$ | H | H | CH$_2$ | 4-MeO—PhO | 4-(3-HOOC—Ph)—Ph | O |
| 8-218 | H | (CH$_2$)$_2$ | H | H | CH$_2$ | 4-MeO—PhO | 4-(3-HOH$_2$C—Ph)—Ph | O |
| 8-219 | H | (CH$_2$)$_2$ | H | H | CH$_2$ | 4-MeO—PhO | 4-(2-MeO—Ph)—Ph | O |
| 8-220 | H | (CH$_2$)$_2$ | H | H | CH$_2$ | 4-MeO—PhO | 4-(2-HO—Ph)—Ph | O |
| 8-221 | H | (CH$_2$)$_2$ | H | H | CH$_2$ | 4-MeO—PhO | 4-(2-OHC—Ph)—Ph | O |
| 8-222 | H | (CH$_2$)$_2$ | H | H | CH$_2$ | 4-MeO—PhO | 4-(3-MeO—Pyr-6)-Ph | O |
| 8-223 | H | (CH$_2$)$_2$ | H | H | CH$_2$ | 4-MeO—PhO | 4-(3-EtO—Pyr-6)-Ph | O |
| 8-224 | H | (CH$_2$)$_2$ | H | H | CH$_2$ | 4-MeO—PhO | 4-(3-iPrO—Pyr-6)-Ph | O |
| 8-225 | H | (CH$_2$)$_2$ | H | H | CH$_2$ | 4-MeO—PhO | 4-(3-Dma—Pyr-6)-Ph | O |
| 8-226 | H | (CH$_2$)$_2$ | H | H | CH$_2$ | 4-MeO—PhO | 4-(3-Dea—Pyr-6)-Ph | O |
| 8-227 | H | (CH$_2$)$_2$ | H | H | CH$_2$ | 4-MeO—PhO | 4-(3-F$_3$C—Pyr-6)-Ph | O |

TABLE 8-continued

| Ex. No. Comp. | R¹ | R² | R³ | R⁴ | Z | W | X | Y |
|---|---|---|---|---|---|---|---|---|
| 8-228 | H | (CH₂)₂ | H | H | CH₂ | 4-MeO—PhO | 4-(3-O₂N—Pyr-6)-Ph | O |
| 8-229 | H | (CH₂)₂ | H | H | CH₂ | 4-MeO—PhO | 4-Pip—Ph | O |
| 8-230 | H | (CH₂)₂ | H | H | CH₂ | 4-MeO—PhO | 4-Dea—Ph | O |
| 8-231 | H | (CH₂)₂ | H | H | CH₂ | 4-MeO—PhO | 2-(4-F—Ph)-5-Pyr | O |
| 8-232 | H | (CH₂)₂ | H | H | CH₂ | 4-MeO—PhO | 2-(4-Cl—Ph)-5-Pyr | O |
| 8-233 | H | (CH₂)₂ | H | H | CH₂ | 4-MeO—PhO | 2-(4-MeO—Ph)-5-Pyr | O |
| 8-234 | H | (CH₂)₂ | H | H | CH₂ | 4-MeO—PhO | 2-(4-EtO—Ph)-5-Pyr | O |
| 8-235 | H | (CH₂)₂ | H | H | CH₂ | 4-MeO—PhO | 2-(4-iPrO—Ph)-5-Pyr | O |
| 8-236 | H | (CH₂)₂ | H | H | CH₂ | 4-MeO—PhO | 2-TfpO-5-Pyr | O |
| 8-237 | H | (CH₂)₂ | H | H | CH₂ | 4-MeO—PhO | 4-(4-AcO—Ph)—Ph | O |
| 8-238 | H | (CH₂)₂ | H | H | CH₂ | 4-MeO—PhO | 4-(3-F—Ph)—Ph | O |
| 8-239 | H | (CH₂)₂ | H | H | CH₂ | 4-MeO—PhO | 4-(3-Cl—Ph)—Ph | O |
| 8-240 | H | (CH₂)₂ | H | H | CH₂ | 4-MeO—PhO | 4-(3-Me—Ph)—Ph | O |
| 8-241 | H | (CH₂)₂ | H | H | CH₂ | 4-MeO—PhO | 4-(3-AcO—Ph)—Ph | O |
| 8-242 | H | (CH₂)₂ | H | H | CH₂ | 4-MeO—PhO | 4-(3-Me—Pyr-6)-Ph | O |
| 8-243 | H | (CH₂)₂ | H | H | CH₂ | 4-MeO—PhO | 4-(3-Et—Pyr-6)-Ph | O |
| 8-244 | H | (CH₂)₂ | H | H | CH₂ | 4-MeO—PhO | 2-(4-Me—Ph)-5-Pyr | O |
| 8-245 | H | (CH₂)₂ | H | H | CH₂ | 4-MeO—PhO | 2-(4-CF₃—Ph)-5-Pyr | O |
| 8-246 | H | (CH₂)₂ | H | H | CH₂ | 4-MeO—PhO | 2-(4-Dma—Ph)-5-Pyr | O |
| 8-247 | H | (CH₂)₂ | H | H | CH₂ | 4-MeO—PhO | 2-(3-F—Ph)-5-Pyr | O |
| 8-248 | H | (CH₂)₂ | H | H | CH₂ | 4-MeO—PhO | 2-(3-Cl—Ph)-5-Pyr | O |
| 8-249 | H | (CH₂)₂ | H | H | CH₂ | 4-MeO—PhO | 2-(3-MeO—Ph)-5-Pyr | O |
| 8-250 | H | (CH₂)₂ | H | H | CH₂ | 4-MeO—PhO | 2-(3-EtO—Ph)-5-Pyr | O |
| 8-251 | H | (CH₂)₂ | H | H | CH₂ | 4-MeO—PhO | 2-(3-iPrO—Ph)-5-Pyr | O |
| 8-252 | H | (CH₂)₂ | H | H | CH₂ | 4-MeO—PhO | 2-(3-Me—Ph)-5-Pyr | O |
| 8-253 | H | (CH₂)₂ | H | H | CH₂ | 4-MeO—PhO | 2-(3-CF₃—Ph)-5-Pyr | O |
| 8-254 | H | (CH₂)₂ | H | H | CH₂ | 4-MeO—PhO | 2-(3-Dma—Ph)-5-Pyr | O |

TABLE 9

| Ex. No. Comp. | R¹ | R² | R³ | R⁴ | Z | W | X | Y |
|---|---|---|---|---|---|---|---|---|
| 9-1 | H | (CH₂)₂ | H | H | CH₂ | Ph(CH₂)₃ | Ph | O |
| 9-2 | H | (CH₂)₂ | H | H | CH₂ | Ph(CH₂)₃ | 1-Np | O |
| 9-3 | H | (CH₂)₂ | H | H | CH₂ | Ph(CH₂)₃ | 2-Np | O |
| 9-4 | H | (CH₂)₂ | H | H | CH₂ | Ph(CH₂)₃ | 4-Me—Ph | O |
| 9-5 | H | (CH₂)₂ | H | H | CH₂ | Ph(CH₂)₃ | 4-Et—Ph | O |
| 9-6 | H | (CH₂)₂ | H | H | CH₂ | Ph(CH₂)₃ | 3-iPr—Pb | O |
| 9-7 | H | (CH₂)₂ | H | H | CH₂ | Ph(CH₂)₃ | 4-iPr—Ph | O |
| 9-8 | H | (CH₂)₂ | H | H | CH₂ | Ph(CH₂)₃ | 3-tBu—Ph | O |
| 9-9 | H | (CH₂)₂ | H | H | CH₂ | Ph(CH₂)₃ | 4-tBu—Ph | O |
| 9-10 | H | (CH₂)₂ | H | H | CH₂ | Ph(CH₂)₃ | 3-F—Ph | O |
| 9-11 | H | (CH₂)₂ | H | H | CH₂ | Ph(CH₂)₃ | 4-F—Ph | O |
| 9-12 | H | (CH₂)₂ | H | H | CH₂ | Ph(CH₂)₃ | 4-Cl—Ph | O |
| 9-13 | H | (CH₂)₂ | H | H | CH₂ | Ph(CH₂)₃ | 4-Br—Ph | O |
| 9-14 | H | (CH₂)₂ | H | H | CH₂ | Ph(CH₂)₃ | 3-Ph—Ph | O |
| 9-15 | H | (CH₂)₂ | H | H | CH₂ | Ph(CH₂)₃ | 4-Ph—Ph | O |
| 9-16 | H | (CH₂)₂ | H | H | CH₂ | Ph(CH₂)₃ | 4-BzO—Ph | O |
| 9-17 | H | (CH₂)₂ | H | H | CH₂ | Ph(CH₂)₃ | 4-Bz—Ph | O |
| 9-18 | H | (CH₂)₂ | H | H | CH₂ | Ph(CH₂)₃ | 3-PhO—Ph | O |
| 9-19 | H | (CH₂)₂ | H | H | CH₂ | Ph(CH₂)₃ | 4-PhO—Ph | O |
| 9-20 | H | (CH₂)₂ | H | H | CH₂ | Ph(CH₂)₃ | 3-PhS—Ph | O |
| 9-21 | H | (CH₂)₂ | H | H | CH₂ | Ph(CH₂)₃ | 4-PhS—Ph | O |

TABLE 9-continued

| Ex. No. Comp. | R¹ | R² | R³ | R⁴ | Z | W | X | Y |
|---|---|---|---|---|---|---|---|---|
| 9-22 | H | (CH₂)₂ | H | H | CH₂ | Ph(CH₂)₃ | 3-PhSO₂—Ph | O |
| 9-23 | H | (CH₂)₂ | H | H | CH₂ | Ph(CH₂)₃ | 4-PhSO₂—Ph | O |
| 9-24 | H | (CH₂)₂ | H | H | CH₂ | Ph(CH₂)₃ | 3-(Imid-1)-Ph | O |
| 9-25 | H | (CH₂)₂ | H | H | CH₂ | Ph(CH₂)₃ | 4-(Imid-1)-Ph | O |
| 9-26 | H | (CH₂)₂ | H | H | CH₂ | Ph(CH₂)₃ | 3-(Imid-4)-Ph | O |
| 9-27 | H | (CH₂)₂ | H | H | CH₂ | Ph(CH₂)₃ | 4-(Imid-4)-Ph | O |
| 9-28 | H | (CH₂)₂ | H | H | CH₂ | Ph(CH₂)₃ | 3-(Fur-2)-Ph | O |
| 9-29 | H | (CH₂)₂ | H | H | CH₂ | Ph(CH₂)₃ | 4-(Fur-2)-Ph | O |
| 9-30 | H | (CH₂)₂ | H | H | CH₂ | Ph(CH₂)₃ | 3-(Thi-2)-Ph | O |
| 9-31 | H | (CH₂)₂ | H | H | CH₂ | Ph(CH₂)₃ | 4-(Thi-2)-Ph | O |
| 9-32 | H | (CH₂)₂ | H | H | CH₂ | Ph(CH₂)₃ | 3-(Thi-3)-Ph | O |
| 9-33 | H | (CH₂)₂ | H | H | CH₂ | Ph(CH₂)₃ | 4-(Thi-3)-Ph | O |
| 9-34 | H | (CH₂)₂ | H | H | CH₂ | Ph(CH₂)₃ | 3-(Pyr-2)-Ph | O |
| 9-35 | H | (CH₂)₂ | H | H | CH₂ | Ph(CH₂)₃ | 4-(Pyr-2)-Ph | O |
| 9-36 | H | (CH₂)₂ | H | H | CH₂ | Ph(CH₂)₃ | 3-(Pyr-3)-Ph | O |
| 9-37 | H | (CH₂)₂ | H | H | CH₂ | Ph(CH₂)₃ | 4-(Pyr-3)-Ph | O |
| 9-38 | H | (CH₂)₂ | H | H | CH₂ | Ph(CH₂)₃ | 3-(Pyr-4)-Ph | O |
| 9-39 | H | (CH₂)₂ | H | H | CH₂ | Ph(CH₂)₃ | 4-(Pyr-4)-Ph | O |
| 9-40 | H | (CH₂)₂ | H | H | CH₂ | Ph(CH₂)₃ | 3-(Oxa-2)-Ph | O |
| 9-41 | H | (CH₂)₂ | H | H | CH₂ | Ph(CH₂)₃ | 4-(Oxa-2)-Ph | O |
| 9-42 | H | (CH₂)₂ | H | H | CH₂ | Ph(CH₂)₃ | 3-(Oxa-4)-Ph | O |
| 9-43 | H | (CH₂)₂ | H | H | CH₂ | Ph(CH₂)₃ | 4-(Oxa-4)-Ph | O |
| 9-44 | H | (CH₂)₂ | H | H | CH₂ | Ph(CH₂)₃ | 3-(Oxa-5)-Ph | O |
| 9-45 | H | (CH₂)₂ | H | H | CH₂ | Ph(CH₂)₃ | 4-(Oxa-5)-Ph | O |
| 9-46 | H | (CH₂)₂ | H | H | CH₂ | Ph(CH₂)₃ | 3-(Thiz-2)-Ph | O |
| 9-47 | H | (CH₂)₂ | H | H | CH₂ | Ph(CH₂)₃ | 4-(Thiz-2)-Ph | O |
| 9-48 | H | (CH₂)₂ | H | H | CH₂ | Ph(CH₂)₃ | 3-(Thiz-4)-Ph | O |
| 9-49 | H | (CH₂)₂ | H | H | CH₂ | Ph(CH₂)₃ | 4-(Thiz-4)-Ph | O |
| 9-50 | H | (CH₂)₂ | H | H | CH₂ | Ph(CH₂)₃ | 3-(Thiz-5)-Ph | O |
| 9-51 | H | (CH₂)₂ | H | H | CH₂ | Ph(CH₂)₃ | 4-(Thiz-5)-Ph | O |
| 9-52 | H | (CH₂)₂ | R | H | CH₂ | Ph(CH₂)₃ | 1-Me-2-Pyrr | O |
| 9-53 | H | (CH₂)₂ | H | H | CH₂ | Ph(CH₂)₃ | 1-Ph-2-Pyrr | O |
| 9-54 | H | (CH₂)₂ | H | H | CH₂ | Ph(CH₂)₃ | 1-Bz-2-Pyrr | O |
| 9-55 | H | (CH₂)₂ | H | H | CH₂ | Ph(CH₂)₃ | 5-Me-2-Fur | O |
| 9-56 | H | (CH₂)₂ | H | H | CH₂ | Ph(CH₂)₃ | 5-Ph-2-Fur | O |
| 9-57 | H | (CH₂)₂ | H | H | CH₂ | Ph(CH₂)₃ | 5-Me-2-Thi | O |
| 9-58 | H | (CH₂)₂ | H | H | CH₂ | Ph(CH₂)₃ | 5-Ph-2-Thi | O |
| 9-59 | H | (CH₂)₂ | H | H | CH₂ | Ph(CH₂)₃ | 5-Me-3-Thi | O |
| 9-60 | H | (CH₂)₂ | H | H | CH₂ | Ph(CH₂)₃ | 5-Ph-3-Thi | O |
| 9-61 | H | (CH₂)₂ | H | H | CH₂ | Ph(CH₂)₃ | 1-Me-3-Pyza | O |
| 9-62 | H | (CH₂)₂ | H | H | CH₂ | Ph(CH₂)₃ | 1-Ph-3-Pyza | O |
| 9-63 | H | (CH₂)₂ | H | H | CH₂ | Ph(CH₂)₃ | 1-Me-2-Imid | O |
| 9-64 | H | (CH₂)₂ | H | H | CH₂ | Ph(CH₂)₃ | 1-Ph-2-Imid | O |
| 9-65 | H | (CH₂)₂ | H | H | CH₂ | Ph(CH₂)₃ | 1-Me-4-Imid | O |
| 9-66 | H | (CH₂)₂ | H | H | CH₂ | Ph(CH₂)₃ | 1-Ph-4-Imid | O |
| 9-67 | H | (CH₂)₂ | H | H | CH₂ | Ph(CH₂)₃ | 4-Oxa | O |
| 9-68 | H | (CH₂)₂ | H | H | CH₂ | Ph(CH₂)₃ | 5-Oxa | O |
| 9-69 | H | (CH₂)₂ | H | H | CH₂ | Ph(CH₂)₃ | 2-Me-4-Oxa | O |
| 9-70 | H | (CH₂)₂ | H | H | CH₂ | Ph(CH₂)₃ | 2-Ph-4-Oxa | O |
| 9-71 | H | (CH₂)₂ | H | H | CH₂ | Ph(CH₂)₃ | 2-Me-5-Oxa | O |
| 9-72 | H | (CH₂)₂ | H | H | CH₂ | Ph(CH₂)₃ | 2-Ph-5-Oxa | O |
| 9-73 | H | (CH₂)₂ | H | H | CH₂ | Ph(CH₂)₃ | 4-Me-2-Ph-5-Oxa | O |
| 9-74 | H | (CH₂)₂ | H | H | CH₂ | Ph(CH₂)₃ | 5-Me-2-Ph-4-Oxa | O |
| 9-75 | H | (CH₂)₂ | H | H | CH₂ | Ph(CH₂)₃ | 4-Thiz | O |
| 9-76 | H | (CH₂)₂ | H | H | CH₂ | Ph(CH₂)₃ | 5-Thiz | O |
| 9-77 | H | (CH₂)₂ | H | H | CH₂ | Ph(CH₂)₃ | 2-Me-4-Thiz | O |
| 9-78 | H | (CH₂)₂ | H | H | CH₂ | Ph(CH₂)₃ | 2-Ph-4-Thiz | O |
| 9-79 | H | (CH₂)₂ | H | H | CH₂ | Ph(CH₂)₃ | 2-Me-5-Thiz | O |
| 9-80 | H | (CH₂)₂ | H | H | CH₂ | Ph(CH₂)₃ | 2-Ph-5-Thiz | O |
| 9-81 | H | (CH₂)₂ | H | H | CH₂ | Ph(CH₂)₃ | 4-Me-2-Ph-5-Thiz | O |
| 9-82 | H | (CH₂)₂ | H | H | CH₂ | Ph(CH₂)₃ | 5-Me-2-Ph-4-Thiz | O |
| 9-83 | H | (CH₂)₂ | H | H | CH₂ | Ph(CH₂)₃ | 1-Me-4-Pyza | O |
| 9-84 | H | (CH₂)₂ | H | H | CH₂ | Ph(CH₂)₃ | 1-Ph-4-Pyza | O |
| 9-85 | H | (CH₂)₂ | R | H | CH₂ | Ph(CH₂)₃ | 2-Me-4-Isox | O |
| 9-86 | H | (CH₂)₂ | H | H | CH₂ | Ph(CH₂)₃ | 2-Ph-4-Isox | O |
| 9-87 | H | (CH₂)₂ | H | H | CH₂ | Ph(CH₂)₃ | 2-Pyr | O |
| 9-88 | H | (CH₂)₂ | R | H | CH₂ | Ph(CH₂)₃ | 3-Pyr | O |
| 9-89 | H | (CH₂)₂ | R | H | CH₂ | Ph(CH₂)₃ | 4-Pyr | O |
| 9-90 | H | (CH₂)₂ | H | H | CH₂ | Ph(CH₂)₃ | 3-Me-5-Pyr | O |
| 9-91 | H | (CH₂)₂ | H | H | CH₂ | Ph(CH₂)₃ | 3-Et-5-Pyr | O |
| 9-92 | H | (CH₂)₂ | R | R | CH₂ | Ph(CH₂)₃ | 3-Ph-5-Pyr | O |
| 9-93 | R | (CH₂)₂ | H | H | CH₂ | Ph(CH₂)₃ | 2-Me-5-Pyr | O |
| 9-94 | H | (CH₂)₂ | H | R | CH₂ | Ph(CH₂)₃ | 2-BzO-5-Pyr | O |

TABLE 9-continued

| Ex. No. Comp. | R¹ | R² | R³ | R⁴ | Z | W | X | Y |
|---|---|---|---|---|---|---|---|---|
| 9-95 | H | (CH₂)₂ | H | H | CH₂ | Ph(CH₂)₃ | 2-Ph-5-Pyr | O |
| 9-96 | H | (CH₂)₂ | H | H | CH₂ | Ph(CH₂)₃ | 2-MeO-5-Pyr | O |
| 9-97 | H | (CH₂)₂ | H | H | CH₂ | Ph(CH₂)₃ | 2-EtO-5-Pyr | O |
| 9-98 | R | (CH₂)₂ | R | R | CH₂ | Ph(CH₂)₃ | 2-iPrO-5-Pyr | O |
| 9-99 | R | (CH₂)₂ | H | H | CH₂ | Ph(CH₂)₃ | 2-MeS-5-Pyr | O |
| 9-100 | H | (CH₂)₂ | H | H | CH₂ | Ph(CH₂)₃ | 2-EtS-5-Pyr | O |
| 9-101 | H | (CH₂)₂ | H | H | CH₂ | Ph(CH₂)₃ | 2-PhSO₂NH-5-Pyr | O |
| 9-102 | H | (CH₂)₂ | H | H | CH₂ | Ph(CH₂)₃ | 2-MeSO₂-5-Pyr | O |
| 9-103 | H | (CH₂)₂ | H | H | CH₂ | Ph(CH₂)₃ | 2-EtSO₂-5-Pyr | O |
| 9-104 | H | (CH₂)₂ | H | H | CH₂ | Ph(CH₂)₃ | 2-PhSO₂NMe-5-Pyr | O |
| 9-105 | H | (CH₂)₂ | H | H | CH₂ | Ph(CH₂)₃ | 2-Bz-5-Pyr | O |
| 9-106 | H | (CH₂)₂ | H | H | CH₂ | Ph(CH₂)₃ | 2-PhO-5-Pyr | O |
| 9-107 | H | (CH₂)₂ | H | H | CH₂ | Ph(CH₂)₃ | 2-PhS-5-Pyr | O |
| 9-108 | H | (CH₂)₂ | H | H | CH₂ | Ph(CH₂)₃ | 2-PhSO₂-5-Pyr | O |
| 9-109 | H | (CH₂)₂ | H | H | CH₂ | Ph(CH₂)₃ | 3-Me-6-Pyr | O |
| 9-110 | H | (CH₂)₂ | H | H | CH₂ | Ph(CH₂)₃ | 3-Ph-6-Pyr | O |
| 9-111 | H | (CH₂)₂ | H | H | CH₂ | Ph(CH₂)₃ | 2-Me-6-Pyr | O |
| 9-112 | H | (CH₂)₂ | H | H | CH₂ | Ph(CH₂)₃ | 2-Ph-6-Pyr | O |
| 9-113 | H | (CH₂)₂ | H | H | CH₂ | Ph(CH₂)₃ | 2-Me-4-Pym | O |
| 9-114 | H | (CH₂)₂ | H | H | CH₂ | Ph(CH₂)₃ | 2-Ph-4-Pym | O |
| 9-115 | H | (CH₂)₂ | H | H | CH₂ | Ph(CH₂)₃ | 2-MeO-4-Pym | O |
| 9-116 | H | (CH₂)₂ | H | H | CH₂ | Ph(CH₂)₃ | 2-EtO-4-Pym | O |
| 9-117 | H | (CH₂)₂ | H | H | CH₂ | Ph(CH₂)₃ | 2-iPrO-4-Pym | O |
| 9-118 | H | (CH₂)₂ | H | H | CH₂ | Ph(CH₂)₃ | 2-MeS-4-Pym | O |
| 9-119 | H | (CH₂)₂ | H | H | CH₂ | Ph(CH₂)₃ | 2-EtS-4-Pym | O |
| 9-120 | H | (CH₂)₂ | H | H | CH₂ | Ph(CH₂)₃ | 2-iPrS-4-Pym | O |
| 9-121 | H | (CH₂)₂ | H | H | CH₂ | Ph(CH₂)₃ | 6-MeS-4-Pym | O |
| 9-122 | H | (CH₂)₂ | H | H | CH₂ | Ph(CH₂)₃ | 6-EtS-4-Pym | O |
| 9-123 | H | (CH₂)₂ | H | H | CH₂ | Ph(CH₂)₃ | 6-iPrS-4-Pym | O |
| 9-124 | H | (CH₂)₂ | H | H | CH₂ | Ph(CH₂)₃ | 2-PhS-4-Pym | O |
| 9-125 | H | (CH₂)₂ | H | H | CH₂ | Ph(CH₂)₃ | 2-MeSO₂-4-Pym | O |
| 9-126 | H | (CH₂)₂ | H | H | CH₂ | Ph(CH₂)₃ | 2-EtSO₂-4-Pym | O |
| 9-127 | H | (CH₂)₂ | H | H | CH₂ | Ph(CH₂)₃ | 2-iPrSO₂-4-Pym | O |
| 9-128 | H | (CH₂)₂ | H | H | CH₂ | Ph(CH₂)₃ | 2-PhSO₂-4-Pym | O |
| 9-129 | H | (CH₂)₂ | H | H | CH₂ | Ph(CH₂)₃ | 2-Me-5-Pym | O |
| 9-130 | H | (CH₂)₂ | H | H | CH₂ | Ph(CH₂)₃ | 2-Ph-5-Pym | O |
| 9-131 | H | (CH₂)₂ | H | H | CH₂ | Ph(CH₂)₃ | 2-MeO-5-Pym | O |
| 9-132 | H | (CH₂)₂ | H | H | CH₂ | Ph(CH₂)₃ | 2-EtO-5-Pym | O |
| 9-133 | H | (CH₂)₂ | H | H | CH₂ | Ph(CH₂)₃ | 2-iPrO-5-Pym | O |
| 9-134 | H | (CH₂)₂ | H | H | CH₂ | Ph(CH₂)₃ | 2-MeS-5-Pym | O |
| 9-135 | H | (CH₂)₂ | H | H | CH₂ | Ph(CH₂)₃ | 2-EtS-5-Pym | O |
| 9-136 | H | (CH₂)₂ | H | H | CH₂ | Ph(CH₂)₃ | 2-iPrS-5-Pym | O |
| 9-137 | H | (CH₂)₂ | H | H | CH₂ | Ph(CH₂)₃ | 2-PhS-5-Pym | O |
| 9-138 | H | (CH₂)₂ | H | H | CH₂ | Ph(CH₂)₃ | 2-MeSO₂-5-Pym | O |
| 9-139 | H | (CH₂)₂ | H | H | CH₂ | Ph(CH₂)₃ | 2-EtSO₂-5-Pym | O |
| 9-140 | H | (CH₂)₂ | H | H | CH₂ | Ph(CH₂)₃ | 2-iPrSO₂-5-Pym | O |
| 9-141 | H | (CH₂)₂ | H | H | CH₂ | Ph(CH₂)₃ | 2-PhSO₂-5-Pym | 0 |
| 9-142 | H | (CH₂)₂ | H | H | CH₂ | Ph(CH₂)₃ | 2-Ind | O |
| 9-143 | H | (CH₂)₂ | H | H | CH₂ | Ph(CH₂)₃ | 3-Ind | O |
| 9-144 | H | (CH₂)₂ | H | H | CH₂ | Ph(CH₂)₃ | 1-Me-2-Ind | O |
| 9-145 | H | (CH₂)₂ | H | H | CH₂ | Ph(CH₂)₃ | 1-Me-3-Ind | O |
| 9-146 | H | (CH₂)₂ | H | H | CH₂ | Ph(CH₂)₃ | 2-Bimid | O |
| 9-147 | H | (CH₂)₂ | H | H | CH₂ | Ph(CH₂)₃ | 2-Boxa | O |
| 9-148 | H | (CH₂)₂ | H | H | CH₂ | Ph(CH₂)₃ | 2-Bthiz | O |
| 9-149 | H | (CH₂)₂ | H | H | CH₂ | Ph(CH₂)₃ | 2-Quin | O |
| 9-150 | H | (CH₂)₂ | H | H | CH₂ | Ph(CH₂)₃ | 3-Quin | O |
| 9-151 | H | (CH₂)₂ | H | H | CH₂ | Ph(CH₂)₃ | 4-Quin | O |
| 9-152 | H | (CH₂)₂ | H | H | CH₂ | Ph(CH₂)₃ | 1-iQuin | O |
| 9-153 | H | (CH₂)₂ | H | H | CH₂ | Ph(CH₂)₃ | 3-iQuin | O |
| 9-154 | H | (CH₂)₂ | H | H | CH₂ | Ph(CH₂)₃ | 4-iQuin | O |
| 9-155 | H | (CH₂)₂ | H | H | CH₂ | Ph(CH₂)₃ | 3-MeO—Ph | O |
| 9-156 | H | (CH₂)₂ | H | H | CH₂ | Ph(CH₂)₃ | 4-MeO—Ph | O |
| 9-157 | H | (CH₂)₂ | H | H | CH₂ | Ph(CH₂)₃ | 3-EtO—Ph | O |
| 9-158 | H | (CH₂)₂ | H | H | CH₂ | Ph(CH₂)₃ | 4-EtO—Ph | O |
| 9-159 | H | (CH₂)₂ | H | H | CH₂ | Ph(CH₂)₃ | 3-iPrO—Ph | O |
| 9-160 | H | (CH₂)₂ | H | H | CH₂ | Ph(CH₂)₃ | 4-iPrO—Ph | O |
| 9-161 | H | (CH₂)₂ | H | H | CH₂ | Ph(CH₂)₃ | 3-MeS—Ph | O |
| 9-162 | H | (CH₂)₂ | H | H | CH₂ | Ph(CH₂)₃ | 4-MeS—Ph | O |
| 9-163 | H | (CH₂)₂ | H | H | CH₂ | Ph(CH₂)₃ | 3-EtS—Ph | O |
| 9-164 | H | (CH₂)₂ | H | H | CH₂ | Ph(CH₂)₃ | 4-EtS—Ph | O |
| 9-165 | H | (CH₂)₂ | H | H | CH₂ | Ph(CH₂)₃ | 3-iPrS—Ph | O |
| 9-166 | H | (CH₂)₂ | H | H | CH₂ | Ph(CH₂)₃ | 4-iPrS—Ph | O |
| 9-167 | H | (CH₂)₂ | H | H | CH₂ | Ph(CH₂)₃ | 3-MeSO₂—Ph | O |
| 9-168 | H | (CH₂)₂ | H | H | CH₂ | Ph(CH₂)₃ | 4-MeSO₂—Ph | O |
| 9-169 | H | (CH₂)₂ | H | H | CH₂ | Ph(CH₂)₃ | 3-EtSO₂—Ph | O |

TABLE 9-continued

| Ex. No. Comp. | $R^1$ | $R^2$ | $R^3$ | $R^4$ | Z | W | X | Y |
|---|---|---|---|---|---|---|---|---|
| 9-170 | H | (CH$_2$)$_2$ | H | H | CH$_2$ | Ph(CH$_2$)$_3$ | 4-EtSO$_2$—Ph | O |
| 9-171 | H | (CH$_2$)$_2$ | H | H | CH$_2$ | Ph(CH$_2$)$_3$ | 3-iPrSO$_2$—Ph | O |
| 9-172 | H | (CH$_2$)$_2$ | H | H | CH$_2$ | Ph(CH$_2$)$_3$ | 4-iPrSO$_2$—Ph | O |
| 9-173 | H | (CH$_2$)$_2$ | H | H | CH$_2$ | Ph(CH$_2$)$_3$ | 3-(1-Me-Imid-4)-Ph | O |
| 9-174 | H | (CH$_2$)$_2$ | H | H | CH$_2$ | Ph(CH$_2$)$_3$ | 4-(1-Me-Imid-4)-Ph | O |
| 9-175 | H | (CH$_2$)$_2$ | H | H | CH$_2$ | Ph(CH$_2$)$_3$ | 1-Me-2-Ph-4-Imid | O |
| 9-176 | H | (CH$_2$)$_2$ | H | H | CH$_2$ | Ph(CH$_2$)$_3$ | 1,4-di-Me-2-Ph-5-Imid | O |
| 9-177 | H | (CH$_2$)$_2$ | H | H | CH$_2$ | Ph(CH$_2$)$_3$ | 1,5-di-Me-2-Ph-4-Imid | O |
| 9-178 | H | (CH$_2$)$_2$ | H | H | CH$_2$ | Ph(CH$_2$)$_3$ | 3,4-MdO—Ph | O |
| 9-179 | H | (CH$_2$)$_2$ | H | H | CH$_2$ | Ph(CH$_2$)$_3$ | 4-(4-MeO—Ph)—Ph | O |
| 9-180 | H | (CH$_2$)$_2$ | H | H | CH$_2$ | Ph(CH$_2$)$_3$ | 4-(3,4-MdO—Ph)-Ph | O |
| 9-181 | H | (CH$_2$)$_2$ | H | H | CH$_2$ | Ph(CH$_2$)$_3$ | 4-[PhSO$_2$N(Me)]—Ph | O |
| 9-182 | H | (CH$_2$)$_2$ | H | H | CH$_2$ | Ph(CH$_2$)$_3$ | 4-[(Pyr-3)SO$_2$N(Me)]—Ph | O |
| 9-183 | H | (CH$_2$)$_2$ | H | H | CH$_2$ | Ph(CH$_2$)$_3$ | 4-(PhSO$_2$NH)—Ph | O |
| 9-184 | H | (CH$_2$)$_2$ | H | H | CH$_2$ | Ph(CH$_2$)$_3$ | 4-[(Pyr-3)SO$_2$NH]—Ph | O |
| 9-185 | H | (CH$_2$)$_2$ | H | H | CH$_2$ | Ph(CH$_2$)$_3$ | 4-[(Pyr-2)SO$_2$]—Ph | O |
| 9-186 | H | (CH$_2$)$_2$ | H | H | CH$_2$ | Ph(CH$_2$)$_3$ | 4-[(Pyr-3)SO$_2$]—Ph | O |
| 9-187 | H | (CH$_2$)$_2$ | H | H | CH$_2$ | Ph(CH$_2$)$_3$ | 4-[(Pyr-2)SO$_2$N(Me)]—Ph | O |
| 9-188 | H | (CH$_2$)$_2$ | H | H | CH$_2$ | Ph(CH$_2$)$_3$ | 4-[(Pyr-2)SO$_2$NH]—Ph | O |
| 9-189 | H | (CH$_2$)$_2$ | H | H | CH$_2$ | Ph(CH$_2$)$_3$ | 4-(4-Me—Ph)—Ph | O |
| 9-190 | H | (CH$_2$)$_2$ | H | H | CH$_2$ | Ph(CH$_2$)$_3$ | 4-(4-F—Ph)—Ph | O |
| 9-191 | H | (CH$_2$)$_2$ | H | H | CH$_2$ | Ph(CH$_2$)$_3$ | 4-(4-CF$_3$—Ph)—Ph | O |
| 9-192 | H | (CH$_2$)$_2$ | H | H | CH$_2$ | Ph(CH$_2$)$_3$ | 2-[PhSO$_2$N(Me)]-5-Pyr | O |
| 9-193 | H | (CH$_2$)$_2$ | H | H | CH$_2$ | Ph(CH$_2$)$_3$ | 2-HO-5-Pyr | O |
| 9-194 | H | (CH$_2$)$_2$ | H | H | CH$_2$ | Ph(CH$_2$)$_3$ | 2-BzO-5-Pyr | O |
| 9-195 | H | (CH$_2$)$_2$ | H | H | CH$_2$ | Ph(CH$_2$)$_3$ | 4-[(Pyr-4)SO$_2$]—Ph | O |
| 9-196 | H | (CH$_2$)$_2$ | H | H | CH$_2$ | Ph(CH$_2$)$_3$ | 4-[(Pyr-4)O]—Ph | O |
| 9-197 | H | (CH$_2$)$_2$ | H | H | CH$_2$ | Ph(CH$_2$)$_3$ | 4-[(Pyr-4)S]—Ph | O |
| 9-198 | H | (CH$_2$)$_2$ | H | H | CH$_2$ | Ph(CH$_2$)$_3$ | 3-HO—Ph | O |
| 9-199 | H | (CH$_2$)$_2$ | H | H | CH$_2$ | Ph(CH$_2$)$_3$ | 4-HO—Ph | O |
| 9-200 | H | (CH$_2$)$_2$ | H | H | CH$_2$ | Ph(CH$_2$)$_3$ | 2-HO-3,4,6-tri-Me—Ph | O |
| 9-201 | H | (CH$_2$)$_2$ | H | H | CH$_2$ | Ph(CH$_2$)$_3$ | 3-HO-3,5-di-Me—Ph | O |
| 9-202 | H | (CH$_2$)$_2$ | H | H | CH$_2$ | Ph(CH$_2$)$_3$ | 3-AcO—Ph | O |
| 9-203 | H | (CH$_2$)$_2$ | H | H | CH$_2$ | Ph(CH$_2$)$_3$ | 4-AcO—Ph | O |

TABLE 10

| Ex. No. Comp. | $R^1$ | $R^2$ | $R^3$ | $R^4$ | W | X | Y | |
|---|---|---|---|---|---|---|---|---|
| 10-1 | H | (CH$_2$)$_2$ | H | H | CH$_2$ | Ph(CH$_2$)$_4$ | Ph | O |
| 10-2 | H | (CH$_2$)$_2$ | H | H | CH$_2$ | Ph(CH$_2$)$_4$ | 1-Np | O |
| 10-3 | H | (CH$_2$)$_2$ | H | H | CH$_2$ | Ph(CH$_2$)$_4$ | 2-Np | O |
| 10-4 | H | (CH$_2$)$_2$ | H | H | CH$_2$ | Ph(CH$_2$)$_4$ | 4-Me-Ph | O |
| 10-5 | H | (CH$_2$)$_2$ | H | H | CH$_2$ | Ph(CH$_2$)$_4$ | 4-Et-Ph | O |
| 10-6 | H | (CH$_2$)$_2$ | H | H | CH$_2$ | Ph(CH$_2$)$_4$ | 3-iPr-Ph | O |
| 10-7 | H | (CH$_2$)$_2$ | H | H | CH$_2$ | Ph(CH$_2$)$_4$ | 4-iPr-Ph | O |
| 10-8 | H | (CH$_2$)$_2$ | H | H | CH$_2$ | Ph(CH$_2$)$_4$ | 3-tBu-Ph | O |
| 10-9 | H | (CH$_2$)$_2$ | H | H | CH$_2$ | Ph(CH$_2$)$_4$ | 4-tBu-Ph | O |
| 10-10 | H | (CH$_2$)$_2$ | H | H | CH$_2$ | Ph(CH$_2$)$_4$ | 3-F-Ph | O |
| 10-11 | H | (CH$_2$)$_2$ | H | H | CH$_2$ | Ph(CH$_2$)$_4$ | 4-F-Ph | O |
| 10-12 | H | (CH$_2$)$_2$ | H | H | CH$_2$ | Ph(CH$_2$)$_4$ | 4-Cl-Ph | O |
| 10-13 | H | (CH$_2$)$_2$ | H | H | CH$_2$ | Ph(CH$_2$)$_4$ | 4-Br-Ph | O |
| 10-14 | H | (CH$_2$)$_2$ | H | H | CH$_2$ | Ph(CH$_2$)$_4$ | 3-Ph-Ph | O |
| 10-15 | H | (CH$_2$)$_2$ | H | H | CH$_2$ | Ph(CH$_2$)$_4$ | 4-Ph-Ph | O |

TABLE 10-continued

| Ex. No. Comp. | R¹ | R² | R³ | R⁴ | W | X | Y | |
|---|---|---|---|---|---|---|---|---|
| 10-16 | H | $(CH_2)_2$ | H | H | $CH_2$ | $Ph(CH_2)_4$ | 4-BzO-Ph | O |
| 10-17 | H | $(CH_2)_2$ | H | H | $CH_2$ | $Ph(CH_2)_4$ | 4-Bz-Ph | O |
| 10-18 | H | $(CH_2)_2$ | H | H | $CH_2$ | $Ph(CH_2)_4$ | 3-PhO-Ph | O |
| 10-19 | H | $(CH_2)_2$ | H | H | $CH_2$ | $Ph(CH_2)_4$ | 4-PhO-Ph | O |
| 10-20 | H | $(CH_2)_2$ | H | H | $CH_2$ | $Ph(CH_2)_4$ | 3-PhS-Ph | O |
| 10-21 | H | $(CH_2)_2$ | H | H | $CH_2$ | $Ph(CH_2)_4$ | 4-PhS-Ph | O |
| 10-22 | H | $(CH_2)_2$ | H | H | $CH_2$ | $Ph(CH_2)_4$ | 3-$PhSO_2$-Ph | O |
| 10-23 | H | $(CH_2)_2$ | H | H | $CH_2$ | $Ph(CH_2)_4$ | 4-$PhSO_2$-Ph | O |
| 10-24 | H | $(CH_2)_2$ | H | H | $CH_2$ | $Ph(CH_2)_4$ | 3-(Imid-1)-Ph | O |
| 10-25 | H | $(CH_2)_2$ | H | H | $CH_2$ | $Ph(CH_2)_4$ | 4-(Imid-1)-Ph | O |
| 10-26 | H | $(CH_2)_2$ | H | H | $CH_2$ | $Ph(CH_2)_4$ | 3-(Imid-4)-Ph | O |
| 10-27 | H | $(CH_2)_2$ | H | H | $CH_2$ | $Ph(CH_2)_4$ | 4-(Imid-4)-Ph | O |
| 10-28 | H | $(CH_2)_2$ | H | H | $CH_2$ | $Ph(CH_2)_4$ | 3-(Fur-2)-Ph | O |
| 10-29 | H | $(CH_2)_2$ | H | H | $CH_2$ | $Ph(CH_2)_4$ | 4-(Fur-2)-Ph | O |
| 10-30 | H | $(CH_2)_2$ | H | H | $CH_2$ | $Ph(CH_2)_4$ | 3-(Thi-2)-Ph | O |
| 10-31 | H | $(CH_2)_2$ | H | H | $CH_2$ | $Ph(CH_2)_4$ | 4-(Thi-2)-Ph | O |
| 10-32 | H | $(CH_2)_2$ | H | H | $CH_2$ | $Ph(CH_2)_4$ | 3-(Thi-3)-Ph | O |
| 10-33 | H | $(CH_2)_2$ | H | H | $CH_2$ | $Ph(CH_2)_4$ | 4-(Thi-3)-Ph | O |
| 10-34 | H | $(CH_2)_2$ | H | H | $CH_2$ | $Ph(CH_2)_4$ | 3-(Pyr-2)-Ph | O |
| 10-35 | H | $(CH_2)_2$ | H | H | $CH_2$ | $Ph(CH_2)_4$ | 4-(Pyr-2)-Ph | O |
| 10-36 | H | $(CH_2)_2$ | H | H | $CH_2$ | $Ph(CH_2)_4$ | 3-(Pyr-3)-Ph | O |
| 10-37 | H | $(CH_2)_2$ | H | H | $CH_2$ | $Ph(CH_2)_4$ | 4-(Pyr-3)-Ph | O |
| 10-38 | H | $(CH_2)_2$ | H | H | $CH_2$ | $Ph(CH_2)_4$ | 3-(Pyr-4)-Ph | O |
| 10-39 | H | $(CH_2)_2$ | H | H | $CH_2$ | $Ph(CH_2)_4$ | 4-(Pyr-4)-Ph | O |
| 10-40 | H | $(CH_2)_2$ | H | H | $CH_2$ | $Ph(CH_2)_4$ | 3-(Oxa-2)-Ph | O |
| 10-41 | H | $(CH_2)_2$ | H | H | $CH_2$ | $Ph(CH_2)_4$ | 4-(Oxa-2)-Ph | O |
| 10-42 | H | $(CH_2)_2$ | H | H | $CH_2$ | $Ph(CH_2)_4$ | 3-(Oxa-4)-Ph | O |
| 10-43 | H | $(CH_2)_2$ | H | H | $CH_2$ | $Ph(CH_2)_4$ | 4-(Oxa-4)-Ph | O |
| 10-44 | H | $(CH_2)_2$ | H | H | $CH_2$ | $Ph(CH_2)_4$ | 3-(Oxa-5)-Ph | O |
| 10-45 | H | $(CH_2)_2$ | H | H | $CH_2$ | $Ph(CH_2)_4$ | 4-(Oxa-5)-Ph | O |
| 10-46 | H | $(CH_2)_2$ | H | H | $CH_2$ | $Ph(CH_2)_4$ | 3-(Thiz-2)-Ph | O |
| 10-47 | H | $(CH_2)_2$ | H | H | $CH_2$ | $Ph(CH_2)_4$ | 4-(Thiz-2)-Ph | O |
| 10-48 | H | $(CH_2)_2$ | H | H | $CH_2$ | $Ph(CH_2)_4$ | 3-(Thiz-4)-Ph | O |
| 10-49 | H | $(CH_2)_2$ | H | H | $CH_2$ | $Ph(CH_2)_4$ | 4-(Thiz-4)-Ph | O |
| 10-50 | H | $(CH_2)_2$ | H | H | $CH_2$ | $Ph(CH_2)_4$ | 3-(Thiz-5)-Ph | O |
| 10-51 | H | $(CH_2)_2$ | H | H | $CH_2$ | $Ph(CH_2)_4$ | 4-(Thiz-5)-Ph | O |
| 10-52 | H | $(CH_2)_2$ | H | H | $CH_2$ | $Ph(CH_2)_4$ | 1-Me-2-Pyrr | O |
| 10-53 | H | $(CH_2)_2$ | H | H | $CH_2$ | $Ph(CH_2)_4$ | 1-Ph-2-Pyrr | O |
| 10-54 | H | $(CH_2)_2$ | H | H | $CH_2$ | $Ph(CH_2)_4$ | 1-Bz-2-Pyrr | O |
| 10-55 | H | $(CH_2)_2$ | H | H | $CH_2$ | $Ph(CH_2)_4$ | 5-Me-2-Fur | O |
| 10-56 | H | $(CH_2)_2$ | H | H | $CH_2$ | $Ph(CH_2)_4$ | 5-Ph-2-Fur | O |
| 10-57 | H | $(CH_2)_2$ | H | H | $CH_2$ | $Ph(CH_2)_4$ | 5-Me-2-Thi | O |
| 10-58 | H | $(CH_2)_2$ | H | H | $CH_2$ | $Ph(CH_2)_4$ | 5-Ph-2-Thi | O |
| 10-59 | H | $(CH_2)_2$ | H | H | $CH_2$ | $Ph(CH_2)_4$ | 5-Me-3-Thi | O |
| 10-60 | H | $(CH_2)_2$ | H | H | $CH_2$ | $Ph(CH_2)_4$ | 5-Ph-3-Thi | O |
| 10-61 | H | $(CH_2)_2$ | H | H | $CH_2$ | $Ph(CH_2)_4$ | 1-Me-3-Pyza | O |
| 10-62 | H | $(CH_2)_2$ | H | H | $CH_2$ | $Ph(CH_2)_4$ | 1-Ph-3-Pyza | O |
| 10-63 | H | $(CH_2)_2$ | H | H | $CH_2$ | $Ph(CH_2)_4$ | 1-Me-2-Imid | O |
| 10-64 | H | $(CH_2)_2$ | H | H | $CH_2$ | $Ph(CH_2)_4$ | 1-Ph-2-Imid | O |
| 10-65 | H | $(CH_2)_2$ | H | H | $CH_2$ | $Ph(CH_2)_4$ | 1-Me-4-Imid | O |
| 10-66 | H | $(CH_2)_2$ | R | H | $CH_2$ | $Ph(CH_2)_4$ | 1-Ph-4-Imid | O |
| 10-67 | H | $(CH_2)_2$ | H | H | $CH_2$ | $Ph(CH_2)_4$ | 4-Oxa | O |
| 10-68 | H | $(CH_2)_2$ | H | H | $CH_2$ | $Ph(CH_2)_4$ | 5-Oxa | O |
| 10-69 | H | $(CH_2)_2$ | H | H | $CH_2$ | $Ph(CH_2)_4$ | 2-MeA-Oxa | O |
| 10-70 | H | $(CH_2)_2$ | H | H | $CH_2$ | $Ph(CH_2)_4$ | 2-Ph-4-Oxa | O |
| 10-71 | H | $(CH_2)_2$ | H | H | $CH_2$ | $Ph(CH_2)_4$ | 2-Me-5-Oxa | O |
| 10-72 | H | $(CH_2)_2$ | H | H | $CH_2$ | $Ph(CH_2)_4$ | 2-Ph-5-Oxa | O |
| 10-73 | H | $(CH_2)_2$ | H | H | $CH_2$ | $Ph(CH_2)_4$ | 4-Me-2-Ph-5-Oxa | O |
| 10-74 | H | $(CH_2)_2$ | H | H | $CH_2$ | $Ph(CH_2)_4$ | 5-Me-2-Ph-4-Oxa | O |
| 10-75 | H | $(CH_2)_2$ | H | H | $CH_2$ | $Ph(CH_2)_4$ | 4-Thiz | O |
| 10-76 | H | $(CH_2)_2$ | H | H | $CH_2$ | $Ph(CH_2)_4$ | 5-Thiz | O |
| 10-77 | H | $(CH_2)_2$ | H | H | $CH_2$ | $Ph(CH_2)_4$ | 2-Me-4-Thiz | O |
| 10-78 | H | $(CH_2)_2$ | H | H | $CH_2$ | $Ph(CH_2)_4$ | 2-Ph-4-Thiz | O |
| 10-79 | H | $(CH_2)_2$ | H | H | $CH_2$ | $Ph(CH_2)_4$ | 2-Me-5-Thiz | O |
| 10-80 | H | $(CH_2)_2$ | H | H | $CH_2$ | $Ph(CH_2)_4$ | 2-Ph-5-Thiz | O |
| 10-81 | H | $(CH_2)_2$ | H | H | $CH_2$ | $Ph(CH_2)_4$ | Me-2-Ph-5-Thiz | O |
| 10-82 | H | $(CH_2)_2$ | H | H | $CH_2$ | $Ph(CH_2)_4$ | Me-2-Ph-4-Thiz | O |
| 10-83 | H | $(CH_2)_2$ | H | H | $CH_2$ | $Ph(CH_2)_4$ | 1-Me-4-Pyza | O |
| 10-84 | H | $(CH_2)_2$ | H | H | $CH_2$ | $Ph(CH_2)_4$ | 1-Ph-4-Pyza | O |
| 10-85 | H | $(CH_2)_2$ | H | H | $CH_2$ | $Ph(CH_2)_4$ | 2-Me-4-Isox | O |
| 10-86 | H | $(CH_2)_2$ | H | H | $CH_2$ | $Ph(CH_2)_4$ | 2-Ph-4-Isox | O |
| 10-87 | H | $(CH_2)_2$ | H | H | $CH_2$ | $Ph(CH_2)_4$ | 2-Pyr | O |
| 10-88 | H | $(CH_2)_2$ | H | H | $CH_2$ | $Ph(CH_2)_4$ | 3-Pyr | O |

TABLE 10-continued

| Ex. No. Comp. | R¹ | R² | R³ | R⁴ | W | X | Y | |
|---|---|---|---|---|---|---|---|---|
| 10-89 | H | (CH₂)₂ | H | H | CH₂ | Ph(CH₂)₄ | 4-Pyr | O |
| 10-90 | H | (CH₂)₂ | H | H | CH₂ | Ph(CH₂)₄ | 3-Me-5-Pyr | O |
| 10-91 | H | (CH₂)₂ | H | H | CH₂ | Ph(CH₂)₄ | 3-Et-5-Pyr | O |
| 10-92 | H | (CH₂)₂ | H | H | CH₂ | Ph(CH₂)₄ | 3-Ph-5-Pyr | O |
| 10-93 | H | (CH₂)₂ | H | H | CH₂ | Ph(CH₂)₄ | 2-Me-5-Pyr | O |
| 10-94 | H | (CH₂)₂ | H | H | CH₂ | Ph(CH₂)₄ | 2-BzO-5-Pyr | O |
| 10-95 | H | (CH₂)₂ | H | H | CH₂ | Ph(CH₂)₄ | 2-Ph-5-Pyr | O |
| 10-96 | H | (CH₂)₂ | H | H | CH₂ | Ph(CH₂)₄ | 2-MeO-5-Pyr | O |
| 10-97 | H | (CH₂)₂ | H | H | CH₂ | Ph(CH₂)₄ | 2-EtO-5-Pyr | O |
| 10-98 | H | (CH₂)₂ | H | H | CH₂ | Ph(CH₂)₄ | 2-iPrO-5-Pyr | O |
| 10-99 | H | (CH₂)₂ | H | H | CH₂ | Ph(CH₂)₄ | 2-MeS-5-Pyr | O |
| 10-100 | H | (CH₂)₂ | H | H | CH₂ | Ph(CH₂)₄ | 2-EtS-5-Pyr | O |
| 10-101 | H | (CH₂)₂ | H | H | CH₂ | Ph(CR2)4 | 2-PhSO₂NH-5-Pyr | O |
| 10-102 | H | (CH₂)₂ | H | H | CH₂ | Ph(CH₂)₄ | 2-MeSO₂-5-Pyr | O |
| 10-103 | H | (CH₂)₂ | H | H | CH₂ | Ph(CH₂)₄ | 2-EtSO₂-5-Pyr | O |
| 10-104 | H | (CH₂)₂ | H | H | CH₂ | Ph(CH₂)₄ | 2-PhSO₂NMe-5-Pyr | O |
| 10-105 | H | (CH₂)₂ | H | H | CH₂ | Ph(CH₂)₄ | 2-Bz-5-Pyr | O |
| 10-106 | H | (CH₂)₂ | H | H | CH₂ | Ph(CH₂)₄ | 2-PhO-5-Pyr | O |
| 10-107 | H | (CH₂)₂ | H | H | CH₂ | Ph(CH₂)₄ | 2-PhS-5-Pyr | O |
| 10-108 | H | (CH₂)₂ | H | H | CH₂ | Ph(CH₂)₄ | 2-PhSO₂-5-Pyr | O |
| 10-109 | H | (CH₂)₂ | H | H | CH₂ | Ph(CH₂)₄ | 3-Me-6-Pyr | O |
| 10-110 | H | (CH₂)₂ | H | H | CH₂ | Ph(CH₂)₄ | 3-Ph-6-Pyr | O |
| 10-111 | H | (CH₂)₂ | H | H | CH₂ | Ph(CH₂)₄ | 2-Me-6-Pyr | O |
| 10-112 | H | (CH₂)₂ | H | H | CH₂ | Ph(CH₂)₄ | 2-Ph-6-Pyr | O |
| 10-113 | H | (CH₂)₂ | H | H | CH₂ | Ph(CH₂)₄ | 2-Me-4-Pym | O |
| 10-114 | H | (CH₂)₂ | H | H | CH₂ | Ph(CH₂)₄ | 2-Ph-4-Pym | O |
| 10-115 | H | (CH₂)₂ | H | H | CH₂ | Ph(CH₂)₄ | 2-MeO-4-Pym | O |
| 10-116 | H | (CH₂)₂ | H | H | CH₂ | Ph(CH₂)₄ | 2-EtO-4-Pym | O |
| 10-117 | H | (CH₂)₂ | H | H | CH₂ | Ph(CH₂)₄ | 2-iPrO-4-Pym | O |
| 10-118 | H | (CH₂)₂ | H | H | CH₂ | Ph(CH₂)₄ | 2-MeS-4-Pym | O |
| 10-119 | H | (CH₂)₂ | H | H | CH₂ | Ph(CH₂)₄ | 2-EtS-4-Pym | O |
| 10-120 | H | (CH₂)₂ | H | H | CH₂ | Ph(CH₂)₄ | 2-iPrS-4-Pym | O |
| 10-121 | H | (CH₂)₂ | H | H | CH₂ | Ph(CH₂)₄ | 6-MeS-4-Pym | O |
| 10-122 | H | (CH₂)₂ | H | H | CH₂ | Ph(CH₂)₄ | 6-EtS-4-Pym | O |
| 10-123 | H | (CH₂)₂ | H | H | CH₂ | Ph(CH₂)₄ | 6-iPrS-4-Pym | O |
| 10-124 | H | (CH₂)₂ | H | H | CH₂ | Ph(CH₂)₄ | 2-PhS-4-Pym | O |
| 10-125 | H | (CH₂)₂ | H | H | CH₂ | Ph(CH₂)₄ | 2-MeSO₂-4-Pym | O |
| 10-126 | H | (CH₂)₂ | H | H | CH₂ | Ph(CH₂)₄ | 2-EtSO₂-4-Pym | O |
| 10-127 | H | (CH₂)₂ | H | H | CH₂ | Ph(CH₂)₄ | 2-iPrSO₂-4-Pym | O |
| 10-128 | H | (CH₂)₂ | H | H | CH₂ | Ph(CH₂)₄ | 2-PhSO₂-4-Pym | O |
| 10-129 | H | (CH₂)₂ | H | H | CH₂ | Ph(CH₂)₄ | 2-Me-5-Pym | O |
| 10-130 | H | (CH₂)₂ | H | H | CH₂ | Ph(CH₂)₄ | 2-Ph-5-Pym | O |
| 10-131 | H | (CH₂)₂ | H | H | CH₂ | Ph(CH₂)₄ | 2-MeO-5-Pym | O |
| 10-132 | H | (CH₂)₂ | H | H | CH₂ | Ph(CH₂)₄ | 2-EtO-5-Pym | O |
| 10-133 | H | (CH₂)₂ | H | H | CH₂ | Ph(CH₂)₄ | 2-iPrO-5-Pym | O |
| 10-134 | H | (CH₂)₂ | H | H | CH₂ | Ph(CH₂)₄ | 2-MeS-5-Pym | O |
| 10-135 | H | (CH₂)₂ | H | H | CH₂ | Ph(CH₂)₄ | 2-EtS-5-Pym | O |
| 10-136 | H | (CH₂)₂ | H | H | CH₂ | Ph(CH₂)₄ | 2-iPrS-5-Pym | O |
| 10-137 | H | (CH₂)₂ | H | H | CH₂ | Ph(CH₂)₄ | 2-PhS-5-Pym | O |
| 10-138 | H | (CH₂)₂ | H | H | CH₂ | Ph(CH₂)₄ | 2-MeSO₂-5-Pym | O |
| 10-139 | H | (CH₂)₂ | H | H | CH₂ | Ph(CH₂)₄ | 2-EtSO₂-5-Pym | O |
| 10-140 | H | (CH₂)₂ | H | H | CH₂ | Ph(CH₂)₄ | 2-iPrSO₂-5-Pym | O |
| 10-141 | H | (CH₂)₂ | H | H | CH₂ | Ph(CH₂)₄ | 2-PhSO₂-5-Pym | O |
| 10-142 | H | (CH₂)₂ | H | H | CH₂ | Ph(CH₂)₄ | 2-Ind | O |
| 10-143 | H | (CH₂)₂ | H | H | CH₂ | Ph(CH₂)₄ | 3-Ind | O |
| 10-144 | H | (CH₂)₂ | H | H | CH₂ | Ph(CH₂)₄ | 1-Me-2-Ind | O |
| 10-145 | H | (CH₂)₂ | H | H | CH₂ | Ph(CH₂)₄ | 1-Me-3-Ind | O |
| 10-146 | H | (CH₂)₂ | H | H | CH₂ | Ph(CH₂)₄ | 2-Bimid | O |
| 10-147 | H | (CH₂)₂ | H | H | CH₂ | Ph(CH₂)₄ | 2-Boxa | O |
| 10-148 | H | (CH₂)₂ | H | H | CH₂ | Ph(CH₂)₄ | 2-Bthiz | O |
| 10-149 | H | (CH₂)₂ | H | H | CH₂ | Ph(CH₂)₄ | 2-Quin | O |
| 10-150 | H | (CH₂)₂ | H | H | CH₂ | Ph(CH₂)₄ | 3-Quin | O |
| 10-151 | H | (CH₂)₂ | H | H | CH₂ | Ph(CH₂)₄ | 4-Quin | O |
| 10-152 | H | (CH₂)₂ | H | H | CH₂ | Ph(CH₂)₄ | 1-iQuin | O |
| 10-153 | H | (CH₂)₂ | H | H | CH₂ | Ph(CH₂)₄ | 3-iQuin | O |
| 10-154 | H | (CH₂)₂ | H | H | CH₂ | Ph(CH₂)₄ | 4-iQuin | O |
| 10-155 | H | (CH₂)₂ | H | H | CH₂ | Ph(CH₂)₄ | 3-MeO-Ph | O |
| 10-156 | H | (CH₂)₂ | H | H | CH₂ | Ph(CH₂)₄ | 4-MeO-Ph | O |
| 10-157 | H | (CH₂)₂ | H | H | CH₂ | Ph(CH₂)₄ | 3-EtO-Ph | O |
| 10-158 | H | (CH₂)₂ | H | H | CH₂ | Ph(CH₂)₄ | 4-EtO-Ph | O |
| 10-159 | H | (CH₂)₂ | H | H | CH₂ | Ph(CH₂)₄ | 3-iPrO-Ph | O |
| 10-160 | H | (CH₂)₂ | H | H | CH₂ | Ph(CH₂)₄ | 4-iPrO-Ph | O |
| 10-161 | H | (CH₂)₂ | H | H | CH₂ | Ph(CH₂)₄ | 3-MeS-Ph | O |

TABLE 10-continued

| Ex. No. Comp. | R¹ | R² | R³ | R⁴ | W | X | Y | |
|---|---|---|---|---|---|---|---|---|
| 10-162 | H | (CH₂)₂ | H | H | CH₂ | Ph(CH₂)₄ | 4-MeS-Ph | O |
| 10-163 | H | (CH₂)₂ | H | H | CH₂ | Ph(CH₂)₄ | 3-EtS-Ph | O |
| 10-164 | H | (CH₂)₂ | H | H | CH₂ | Ph(CH₂)₄ | 4-EtS-Ph | O |
| 10-165 | H | (CH₂)₂ | H | H | CH₂ | Ph(CH₂)₄ | 3-iPrS-Ph | O |
| 10-166 | H | (CH₂)₂ | H | H | CH₂ | Ph(CH₂)₄ | 4-iPrS-Ph | O |
| 10-167 | H | (CH₂)₂ | H | H | CH₂ | Ph(CH₂)₄ | 3-MeSO₂-Ph | O |
| 10-168 | H | (CH₂)₂ | H | H | CH₂ | Ph(CH₂)₄ | 4-MeSO₂-Ph | O |
| 10-169 | H | (CH₂)₂ | H | H | CH₂ | Ph(CH₂)₄ | 3-EtSO₂-Ph | O |
| 10-170 | H | (CH₂)₂ | H | H | CH₂ | Ph(CH₂)₄ | 4-EtSO₂-Ph | O |
| 10-171 | H | (CH₂)₂ | H | H | CH₂ | Ph(CH₂)₄ | 3-iPrSO₂-Ph | O |
| 10-172 | H | (CH₂)₂ | H | H | CH₂ | Ph(CH₂)₄ | 4-iPrSO₂-Ph | O |
| 10-173 | H | (CH₂)₂ | H | H | CH₂ | Ph(CH₂)₄ | 3-(1-Me-Imid-4)-Ph | O |
| 10-174 | H | (CH₂)₂ | H | H | CH₂ | Ph(CH₂)₄ | 4-(1-Me-Imid-4)-Ph | O |
| 10-175 | H | (CH₂)₂ | H | H | CH₂ | Ph(CH₂)₄ | 1-Me-2-Ph-4-Imid | O |
| 10-176 | H | (CH₂)₂ | H | H | CH₂ | Ph(CH₂)₄ | 1,4-di-Me-2-Ph-5-Imid | O |
| 10-177 | H | (CH₂)₂ | H | H | CH₂ | Ph(CH₂)₄ | 1,5-di-Me-2-Ph-4-Imid | O |
| 10-178 | H | (CH₂)₂ | H | H | CH₂ | Ph(CH₂)₄ | 3,4-MdO-Ph | O |
| 10-179 | H | (CH₂)₂ | H | H | CH₂ | Ph(CH₂)₄ | 4-(4-MeO-Ph)-Ph | O |
| 10-180 | H | (CH₂)₂ | H | H | CH₂ | Ph(CH₂)₄ | 4-(3,4-MdO-Ph)-Ph | O |
| 10-181 | H | (CH₂)₂ | H | H | CH₂ | Ph(CH₂)₄ | 4-[PhSO₂N(Me)]-Ph | O |
| 10-182 | H | (CH₂)₂ | H | H | CH₂ | Ph(CH₂)₄ | 4-[(Pyr-3)SO₂N(Me)]-Ph | O |
| 10-183 | H | (CH₂)₂ | H | H | CH₂ | Ph(CH₂)₄ | 4-(PhSO₂NH)-Ph | O |
| 10-184 | H | (CH₂)₂ | H | H | CH₂ | Ph(CH₂)₄ | 4-[(Pyr-3)SO₂NH]-Ph | O |
| 10-185 | H | (CH₂)₂ | H | H | CH₂ | Ph(CH₂)₄ | 4-[(Pyr-2)SO₂]-Ph | O |
| 10-186 | H | (CH₂)₂ | H | H | CH₂ | Ph(CH₂)₄ | 4-[(Pyr-3)SO₂]-Ph | O |
| 10-187 | H | (CH₂)₂ | H | H | CH₂ | Ph(CH₂)₄ | 4-[(Pyr-2)SO₂N(Me)]-Ph | O |
| 10-188 | H | (CH₂)₂ | H | H | CH₂ | Ph(CH₂)₄ | 4-[(Pyr-2)SO₂NH]-Ph | O |
| 10-189 | H | (CH₂)₂ | H | H | CH₂ | Ph(CH₂)₄ | 4-(4-Me-Ph)-Ph | O |
| 10-190 | H | (CH₂)₂ | H | H | CH₂ | Ph(CH₂)₄ | 4-(4-F-Ph)-Ph | O |
| 10-191 | H | (CH₂)₂ | H | H | CH₂ | Ph(CH₂)₄ | 4-(4-CF₃-Ph)-Ph | O |
| 10-192 | H | (CH₂)₂ | H | H | CH₂ | Ph(CH₂)₄ | 2-[PhSO₂N(Me)]-5-Pyr | O |
| 10-193 | H | (CH₂)₂ | H | H | CH₂ | Ph(CH₂)₄ | 2-HO-5-Pyr | O |
| 10-194 | H | (CH₂)₂ | H | H | CH₂ | Ph(CH₂)₄ | 2-BzO-5-Pyr | O |
| 10-195 | H | (CH₂)₂ | H | H | CH₂ | Ph(CH₂)₄ | 4-[(Pyr-4)SO₂]-Ph | O |
| 10-196 | H | (CH₂)₂ | H | H | CH₂ | Ph(CH₂)₄ | 4-[(Pyr-4)O]-Ph | O |
| 10-197 | H | (CH₂)₂ | H | H | CH₂ | Ph(CH₂)₄ | 4-[(Pyr-4)S]-Ph | O |
| 10-198 | H | (CH₂)₂ | H | H | CH₂ | Ph(CH₂)₄ | 3-HO-Ph | O |
| 10-199 | H | (CH₂)₂ | H | H | CH₂ | Ph(CH₂)₄ | 4-HO-Ph | O |
| 10-200 | H | (CH₂)₂ | H | H | CH₂ | Ph(CH₂)₄ | 2-HO-3,4,6-tri-Me-Ph | O |
| 10-201 | H | (CH₂)₂ | H | H | CH₂ | Ph(CH₂)₄ | 4-HO-3,5-di-Me-Ph | O |
| 10-202 | H | (CH₂)₂ | H | H | CH₂ | Ph(CH₂)₄ | 3-AcO-Ph | O |
| 10-203 | H | (CH₂)₂ | H | H | CH₂ | Ph(CH₂)₄ | 4-AcO-Ph | O |

TABLE 11

| Ex. No. Comp. | R¹ | R² | R³ | R⁴ | Z | W | X | Y |
|---|---|---|---|---|---|---|---|---|
| 11-1 | H | (CH₂)₂ | H | H | CH₂ | Et | Ph | O |
| 11-2 | H | (CH₂)₂ | H | H | CH₂ | Et | 4-Me-Ph | O |
| 11-3 | H | (CH₂)₂ | H | H | CH₂ | Et | 4-F-Ph | O |
| 11-4 | H | (CH₂)₂ | H | H | CH₂ | Et | 4-Bz-Ph | O |

TABLE 11-continued

| Ex. No. Comp. | R¹ | R² | R³ | R⁴ | Z | W | X | Y |
|---|---|---|---|---|---|---|---|---|
| 11-5 | H | (CH$_2$)$_2$ | H | H | CH$_2$ | Et | 4-Ph-Ph | O |
| I1-6 | H | (CH$_2$)$_2$ | H | H | CH$_2$ | Et | 4-PhO-Ph | O |
| 11-7 | H | (CH$_2$)$_2$ | H | H | CH$_2$ | Et | 4-PhS-Ph | O |
| 11-8 | H | (CH$_2$)$_2$ | H | H | CH$_2$ | Et | 4-PhSO$_2$-Ph | O |
| 11-9 | H | (CH$_2$)$_2$ | H | H | CH$_2$ | Et | 4-PhSO$_2$NH-Ph | O |
| 11-10 | H | (CH$_2$)$_2$ | H | H | CH$_2$ | Et | 4-PhSO$_2$NMe-Ph | O |
| 11-11 | H | (CH$_2$)$_2$ | H | H | CH$_2$ | Et | 4-(Pyr-2)-Ph | O |
| 11-12 | H | (CH$_2$)$_2$ | H | H | CH$_2$ | Et | 4-(Pyr-3)Ph | O |
| 11-13 | H | (CH$_2$)$_2$ | H | H | CH$_2$ | Et | 4-(Pyr-4)-Ph | O |
| 11-14 | H | (CH$_2$)$_2$ | H | H | CH$_2$ | Et | 4-(Pyr-2)O-Ph | O |
| 11-15 | H | (CH$_2$)$_2$ | H | H | CH$_2$ | Et | 4-(Pyr-4)O-Ph | O |
| 11-16 | H | (CH$_2$)$_2$ | H | H | CH$_2$ | Et | 4-(Pyr-2)S-Ph | O |
| 11-17 | H | (CH$_2$)$_2$ | H | H | CH$_2$ | Et | 4-(Pyr-4)S-Ph | O |
| 11-18 | H | (CH$_2$)$_2$ | H | H | CH$_2$ | Et | 4-(Pyr-2)SO$_2$-Ph | O |
| 11-19 | H | (CH$_2$)$_2$ | H | H | CH$_2$ | Et | 4-(Pyr-4)SO$_2$-Ph | O |
| 11-20 | H | (CH$_2$)$_2$ | H | H | CH$_2$ | Et | 4-(Pyr-2)SO$_2$NH-Ph | O |
| 11-21 | H | (CH$_2$)$_2$ | H | H | CH$_2$ | Et | 4-(Pyr-4)SO$_2$NH-Ph | O |
| 11-22 | H | (CH$_2$)$_2$ | H | H | CH$_2$ | Et | 4-(Pyr-2)SO$_2$NMe-Ph | O |
| 11-23 | H | (CH$_2$)$_2$ | H | H | CH$_2$ | Et | 4-(Pyr-4)SO$_2$NMe-Ph | O |
| 11-24 | H | (CH$_2$)$_2$ | H | H | CH$_2$ | Et | 2-Pyr | O |
| 11-25 | H | (CH$_2$)$_2$ | H | H | CH$_2$ | Et | 3-Pyr | O |
| 11-26 | H | (CH$_2$)$_2$ | H | H | CH$_2$ | Et | 4-Pyr | O |
| 11-27 | H | (CH$_2$)$_2$ | H | H | CH$_2$ | Et | 2-Me-5-Pyr | O |
| 11-28 | H | (CH$_2$)$_2$ | H | H | CH$_2$ | Et | 2-Me-3-Pyr | O |
| 11-29 | H | (CH$_2$)$_2$ | H | H | CH$_2$ | Et | 2-MeO-5-Pyr | O |
| 11-30 | H | (CH$_2$)$_2$ | H | H | CH$_2$ | Et | 2-EtO-5-Pyr | O |
| 11-31 | H | (CH$_2$)$_2$ | H | H | CH$_2$ | Et | 2-iPrO-5-Pyr | O |
| 11-32 | H | (CH$_2$)$_2$ | H | H | CH$_2$ | Et | 2-MeS-5-Pyr | O |
| 11-33 | H | (CH$_2$)$_2$ | H | H | CH$_2$ | Et | 2-EtS-5-Pyr | O |
| 11-34 | H | (CH$_2$)$_2$ | H | H | CH$_2$ | Et | 2-MeSO$_2$-5-Pyr | O |
| 11-35 | H | (CH$_2$)$_2$ | H | H | CH$_2$ | Et | 2-EtSO$_2$-5-Pyr | O |
| 11-36 | H | (CH$_2$)$_2$ | H | H | CH$_2$ | Et | 2-Bz-5-Pyr | O |
| 11-37 | H | (CH$_2$)$_2$ | H | H | CH$_2$ | Et | 2-Ph-5-Pyr | O |
| 11-38 | H | (CH$_2$)$_2$ | H | H | CH$_2$ | Et | 3-Ph-6-Pyr | O |
| 11-39 | H | (CH$_2$)$_2$ | H | H | CH$_2$ | Et | 2-PhO-5-Pyr | O |
| 11-40 | H | (CH$_2$)$_2$ | H | H | CH$_2$ | Et | 2-PhS-5-Pyr | O |
| 11-41 | H | (CH$_2$)$_2$ | H | H | CH$_2$ | Et | 2-PhSO$_2$-5-Pyr | O |

TABLE 12

| Ex. No. Comp. | R¹ | R² | R³ | R⁴ | Z | W | X | Y |
|---|---|---|---|---|---|---|---|---|
| 12-1 | H | (CH$_2$)$_2$ | H | H | CH$_2$ | MeS | Ph | O |
| 12-2 | H | (CH$_2$)$_2$ | H | H | CH$_2$ | MeS | 4-Me-Ph | O |
| 12-3 | H | (CH$_2$)$_2$ | H | H | CH$_2$ | MeS | 4-F-Ph | O |
| 12-4 | H | (CH$_2$)$_2$ | H | H | CH$_2$ | MeS | 4-Bz-Ph | O |
| 12-5 | H | (CH$_2$)$_2$ | H | H | CH$_2$ | MeS | 4-Ph-Ph | O |
| 12-6 | H | (CH$_2$)$_2$ | H | H | CH$_2$ | MeS | 4-PhO-Ph | O |
| 12-7 | H | (CH$_2$)$_2$ | H | H | CH$_2$ | MeS | 4-PhS-Ph | O |
| 12-8 | H | (CH$_2$)$_2$ | H | H | CH$_2$ | MeS | 4-PhSO$_2$-Ph | O |
| 12-9 | H | (CH$_2$)$_2$ | H | H | CH$_2$ | MeS | 4-PhSO$_2$NH-Ph | O |
| 12-10 | H | (CH$_2$)$_2$ | H | H | CH$_2$ | MeS | 4-PhSO$_2$NMe-Ph | O |
| 12-11 | H | (CH$_2$)$_2$ | H | H | CH$_2$ | MeS | 4-(Pyr-2)-Ph | O |
| 12-12 | H | (CH$_2$)$_2$ | H | H | CH$_2$ | MeS | 4-(Pyr-3)-Ph | O |
| 12-13 | H | (CH$_2$)$_2$ | H | H | CH$_2$ | MeS | 4-(Pyr-4)-Ph | O |
| 12-14 | H | (CH$_2$)$_2$ | H | H | CH$_2$ | MeS | 4-(Pyr-2)O-Ph | O |
| 12-15 | H | (CH$_2$)$_2$ | H | H | CH$_2$ | MeS | 4-(Pyr-4)O-Ph | O |
| 12-16 | H | (CH$_2$)$_2$ | H | H | CH$_2$ | MeS | 4-(Pyr-2)S-Ph | O |
| 12-17 | H | (CH$_2$)$_2$ | H | H | CH$_2$ | MeS | 4-(Pyr-4)S-Ph | O |
| 12-18 | H | (CH$_2$)$_2$ | H | H | CH$_2$ | MeS | 4-(Pyr-2)SO$_2$-Ph | O |
| 12-19 | H | (CH$_2$)$_2$ | H | H | CH$_2$ | MeS | 4-(Pyr-4)SO$_2$-Ph | O |
| 12-20 | H | (CH$_2$)$_2$ | H | H | CH$_2$ | MeS | 4-(Pyr-2)SO$_2$NH-Ph | O |
| 12-21 | H | (CH$_2$)$_2$ | H | H | CH$_2$ | MeS | 4-(Pyr-4)SO$_2$NH-Ph | O |
| 12-22 | H | (CH$_2$)$_2$ | H | H | CH$_2$ | MeS | 4-(Pyr-2)SO$_2$NMe-Ph | O |
| 12-23 | H | (CH$_2$)$_2$ | H | H | CH$_2$ | MeS | 4-(Pyr-4)SO$_2$NMe-Ph | O |
| 12-24 | H | (CH$_2$)$_2$ | H | H | CH$_2$ | MeS | 2-Pyr | O |
| 12-25 | H | (CH$_2$)$_2$ | H | H | CH$_2$ | MeS | 3-Pyr | O |
| 12-26 | H | (CH$_2$)$_2$ | H | H | CH$_2$ | MeS | 4-Pyr | O |
| 12-27 | H | (CH$_2$)$_2$ | H | H | CH$_2$ | MeS | 2-Me-5-Pyr | O |
| 12-28 | H | (CH$_2$)$_2$ | H | H | CH$_2$ | MeS | 2-Me-3-Pyr | O |
| 12-29 | H | (CH$_2$)$_2$ | H | H | CH$_2$ | MeS | 2-MeO-5-Pyr | O |
| 12-30 | H | (CH$_2$)$_2$ | H | H | CH$_2$ | MeS | 2-EtO-5-Pyr | O |
| 12-31 | H | (CH$_2$)$_2$ | H | H | CH$_2$ | MeS | 2-iPrO-5-Pyr | O |
| 12-32 | H | (CH$_2$)$_2$ | H | H | CH$_2$ | MeS | 2-MeS-5-Pyr | O |
| 12-33 | H | (CH$_2$)$_2$ | H | H | CH$_2$ | MeS | 2-EtS-5-Pyr | O |

TABLE 12-continued

| Ex. No. Comp. | R¹ | R² | R³ | R⁴ | Z | W | X | Y |
|---|---|---|---|---|---|---|---|---|
| 12-34 | H | (CH₂)₂ | H | H | CH₂ | MeS | 2-MeSO₂-5-Pyr | O |
| 12-35 | H | (CH₂)₂ | H | H | CH₂ | MeS | 2-EtSO₂-5-Pyr | O |
| 12-36 | H | (CH₂)₂ | H | H | CH₂ | MeS | 2-Bz-5-Pyr | O |
| 12-37 | H | (CH₂)₂ | H | H | CH₂ | MeS | 2-Ph-5-Pyr | O |
| 12-38 | H | (CH₂)₂ | H | H | CH₂ | MeS | 3-Ph-6-Pyr | O |
| 12-39 | H | (CH₂)₂ | H | H | CH₂ | MeS | 2-PhO-5-Pyr | O |
| 12-40 | H | (CH₂)₂ | H | H | CH₂ | MeS | 2-PhS-5-Pyr | O |
| 12-41 | H | (CH₂)₂ | H | H | CH₂ | MeS | 2-PhSO₂-5-Pyr | O |

TABLE 13

| Ex. No. Comp. | R¹ | R² | R³ | R⁴ | Z | W | X | Y |
|---|---|---|---|---|---|---|---|---|
| 13-1 | H | (CH₂)₂ | H | H | CH₂ | EtS | Ph | O |
| 13-2 | H | (CH₂)₂ | H | H | CH₂ | EtS | 4-Me-Ph | O |
| 13-3 | H | (CH₂)₂ | H | H | CH₂ | EtS | 4-F-Ph | O |
| 13-4 | H | (CH₂)₂ | H | H | CH₂ | EtS | 4-Bz-Ph | O |
| 13-5 | H | (CH₂)₂ | H | H | CH₂ | EtS | 4-Ph-Ph | O |
| 13-6 | H | (CH₂)₂ | H | H | CH₂ | EtS | 4-PhO-Ph | O |
| 13-7 | H | (CH₂)₂ | H | H | CH₂ | EtS | 4-PhS-Ph | O |
| 13-8 | H | (CH₂)₂ | H | H | CH₂ | EtS | 4-PhSO₂-Ph | O |
| 13-9 | H | (CH₂)₂ | H | H | CH₂ | EtS | 4-PhSO₂NH-Ph | O |
| 13-10 | H | (CH₂)₂ | H | H | CH₂ | EtS | 4-PhSO₂NMe-Ph | O |
| 13-11 | H | (CH₂)₂ | H | H | CH₂ | EtS | 4-(Pyr-2)-Ph | O |
| 13-12 | H | (CH₂)₂ | H | H | CH₂ | EtS | 4-(Pyr-3)-Ph | O |
| 13-13 | H | (CH₂)₂ | H | H | CH₂ | EtS | 4-(Pyr-4)-Ph | O |
| 13-14 | H | (CH₂)₂ | H | H | CH₂ | EtS | 4-(Pyr-2)O-Ph | O |
| 13-15 | H | (CH₂)₂ | H | H | CH₂ | EtS | 4-(Pyr-4)O-Ph | O |
| 13-16 | H | (CH₂)₂ | H | H | CH₂ | EtS | 4-(Pyr-2)S-Ph | O |
| 13-17 | H | (CH₂)₂ | H | H | CH₂ | EtS | 4-(Pyr-4)S-Ph | O |
| 13-18 | H | (CH₂)₂ | H | H | CH₂ | EtS | 4-(Pyr-2)SO₂-Ph | O |
| 13-19 | H | (CH₂)₂ | H | H | CH₂ | EtS | 4-(Pyr-4)SO₂-Ph | O |
| 13-20 | H | (CH₂)₂ | H | H | CH₂ | EtS | 4-(Pyr-2)SO₂NH-Ph | O |
| 13-21 | H | (CH₂)₂ | H | H | CH₂ | EtS | 4-(Pyr-4)SO₂NH-Ph | O |
| 13-22 | H | (CH₂)₂ | H | H | CH₂ | EtS | 4-(Pyr-2)SO₂NMe-Ph | O |
| 13-23 | H | (CH₂)₂ | H | H | CH₂ | EtS | 4-(Pyr-4)SO₂NMe-Ph | O |
| 13-24 | H | (CH₂)₂ | H | H | CH₂ | EtS | 2-Pyr | O |
| 13-25 | H | (CH₂)₂ | H | H | CH₂ | EtS | 3-Pyr | O |
| 13-26 | H | (CH₂)₂ | H | H | CH₂ | EtS | 4-Pyr | O |
| 13-27 | H | (CH₂)₂ | H | H | CH₂ | EtS | 2-Me-5-Pyr | O |
| 13-28 | H | (CH₂)₂ | H | H | CH₂ | EtS | 2-Me-3-Pyr | O |
| 13-29 | H | (CH₂)₂ | H | H | CH₂ | EtS | 2-MeO-5-Pyr | O |
| 13-30 | H | (CH₂)₂ | H | H | CH₂ | EtS | 2-EtO-5-Pyr | O |
| 13-31 | H | (CH₂)₂ | H | H | CH₂ | EtS | 2-iPrO-5-Pyr | O |
| 13-32 | H | (CH₂)₂ | H | H | CH₂ | EtS | 2-MeS-5-Pyr | O |
| 13-33 | H | (CH₂)₂ | H | H | CH₂ | EtS | 2-EtS-5-Pyr | O |
| 13-34 | H | (CH₂)₂ | H | H | CH₂ | EtS | 2-MeSO₂-5-Pyr | O |
| 13-35 | H | (CH₂)₂ | H | H | CH₂ | EtS | 2-EtSO₂-5-Pyr | O |
| 13-36 | H | (CH₂)₂ | H | H | CH₂ | EtS | 2-Bz-5-Pyr | O |
| 13-37 | H | (CH₂)₂ | H | H | CH₂ | EtS | 2-Ph-5-Pyr | O |
| 13-38 | H | (CH₂)₂ | H | H | CH₂ | EtS | 3-Ph-6-Pyr | O |
| 13-39 | H | (CH₂)₂ | H | H | CH₂ | EtS | 2-PhO-5-Pyr | O |
| 13-40 | H | (CH₂)₂ | H | H | CH₂ | EtS | 2-PhS-5-Pyr | O |
| 13-41 | H | (CH₂)₂ | H | H | CH₂ | EtS | 2-PhSO₂-5-Pyr | O |

TABLE 14

| Ex. No. Comp. | R¹ | R² | R³ | R⁴ | Z | W | X | Y |
|---|---|---|---|---|---|---|---|---|
| 14-1 | H | (CH₂)₂ | H | H | CH₂ | 4-Me-PhO | Ph | O |
| 14-2 | H | (CH₂)₂ | H | H | CH₂ | 4-Me-PhO | 4-Me-Ph | O |
| 14-3 | H | (CH₂)₂ | H | H | CH₂ | 4-Me-PhO | 4-F-Ph | O |
| 14-4 | H | (CH₂)₂ | H | H | CH₂ | 4-Me-PhO | 4-Bz-Ph | O |
| 14-5 | H | (CH₂)₂ | H | H | CH₂ | 4-Me-PhO | 4-Ph-Ph | O |
| 14-6 | H | (CH₂)₂ | H | H | CH₂ | 4-Me-PhO | 4-PhO-Ph | O |
| 14-7 | H | (CH₂)₂ | H | H | CH₂ | 4-Me-PhO | 4-PhS-Ph | O |

TABLE 14-continued

| Ex. No. Comp. | R¹ | R² | R³ | R⁴ | Z | W | X | Y |
|---|---|---|---|---|---|---|---|---|
| 14-8 | H | (CH₂)₂ | H | H | CH₂ | 4-Me-PhO | 4-PhSO₂-Ph | O |
| 14-9 | H | (CH₂)₂ | H | H | CH₂ | 4-Me-PhO | 4-PhSO₂NH-Ph | O |
| 14-10 | H | (CH₂)₂ | H | H | CH₂ | 4-Me-PhO | 4-PhSO₂NMe-Ph | O |
| 14-11 | H | (CH₂)₂ | H | H | CH₂ | 4-Me-PhO | 4-(Pyr-2)-Ph | O |
| 14-12 | H | (CH₂)₂ | H | H | CH₂ | 4-Me-PhO | 4-(Pyr-3)-Ph | O |
| 14-13 | H | (CH₂)₂ | H | H | CH₂ | 4-Me-PhO | 4-(Pyr-4)-Ph | O |
| 14-14 | H | (CH₂)₂ | H | H | CH₂ | 4-Me-PhO | 4-(Pyr-2)O-Ph | O |
| 14-15 | H | (CH₂)₂ | H | H | CH₂ | 4-Me-PhO | 4-(Pyr-4)O-Ph | O |
| 14-16 | H | (CH₂)₂ | H | H | CH₂ | 4-Me-PhO | 4-(Pyr-2)S-Ph | O |
| 14-17 | H | (CH₂)₂ | H | H | CH₂ | 4-Me-PhO | 4-(Pyr-4)S-Ph | O |
| 14-18 | H | (CH₂)₂ | H | H | CH₂ | 4-Me-PhO | 4-(Pyr-2)SO₂-Ph | O |
| 14-19 | H | (CH₂)₂ | H | H | CH₂ | 4-Me-PhO | 4-(Pyr-4)SO₂-Ph | O |
| 14-20 | H | (CH₂)₂ | H | H | CH₂ | 4-Me-PhO | 4-(Pyr-2)SO₂NH-Ph | O |
| 14-21 | H | (CH₂)₂ | H | H | CH₂ | 4-Me-PhO | 4-(Pyr-4)SO₂NH-Ph | O |
| 14-22 | H | (CH₂)₂ | H | H | CH₂ | 4-Me-PhO | 4-(Pyr-2)SO₂NMe-Ph | O |
| 14-23 | H | (CH₂)₂ | H | H | CH₂ | 4-Me-PhO | 4-(Pyr-4)SO₂NMe-Ph | O |
| 14-24 | H | (CH₂)₂ | H | H | CH₂ | 4-Me-PhO | 2-Pyr | O |
| 14-25 | H | (CH₂)₂ | H | H | CH₂ | 4-Me-PhO | 3-Pyr | O |
| 14-26 | H | (CH₂)₂ | H | H | CH₂ | 4-Me-PhO | 4-Pyr | O |
| 14-27 | H | (CH₂)₂ | H | H | CH₂ | 4-Me-PhO | 2-Me-5-Pyr | O |
| 14-28 | H | (CH₂)₂ | H | H | CH₂ | 4-Me-PhO | 2-Me-3-Pyr | O |
| 14-29 | H | (CH₂)₂ | H | H | CH₂ | 4-Me-PhO | 2-MeO-5-Pyr | O |
| 14-30 | H | (CH₂)₂ | H | H | CH₂ | 4-Me-PhO | 2-EtO-5-Pyr | O |
| 14-31 | H | (CH₂)₂ | H | H | CH₂ | 4-Me-PhO | 2-iPrO-5-Pyr | O |
| 14-32 | H | (CH₂)₂ | H | H | CH₂ | 4-Me-PhO | 2-MeS-5-Pyr | O |
| 14-33 | H | (CH₂)₂ | H | H | CH₂ | 4-Me-PhO | 2-EtS-5-Pyr | O |
| 14-34 | H | (CH₂)₂ | H | H | CH₂ | 4-Me-PhO | 2-MeSO₂-5-Pyr | O |
| 14-35 | H | (CH₂)₂ | H | H | CH₂ | 4-Me-PhO | 2-EtSO₂-5-Pyr | O |
| 14-36 | H | (CH₂)₂ | H | H | CH₂ | 4-Me-PhO | 2-Bz-5-Pyr | O |
| 14-37 | H | (CH₂)₂ | H | H | CH₂ | 4-Me-PhO | 2-Ph-5-Pyr | O |
| 14-38 | H | (CH₂)₂ | H | H | CH₂ | 4-Me-PhO | 3-Ph-6-Pyr | O |
| 14-39 | H | (CH₂)₂ | H | H | CH₂ | 4-Me-PhO | 2-PhO-5-Pyr | O |
| 14-40 | H | (CH₂)₂ | H | H | CH₂ | 4-Me-PhO | 2-PhS-5-Pyr | O |
| 14-41 | H | (CH₂)₂ | H | H | CH₂ | 4-Me-PhO | 2-PhSO₂-5-Pyr | O |
| 14-42 | H | (CH₂)₂ | H | H | CH₂ | 4-Me-PhO | 4-(4-Me-Ph)-Ph | O |
| 14-43 | H | (CH₂)₂ | H | H | CH₂ | 4-Me-PhO | 4-(4-CF₃-Ph)-Ph | O |
| 14-44 | H | (CH₂)₂ | H | H | CH₂ | 4-Me-PhO | 4-(4-F-Ph)-Ph | O |
| 14-45 | H | (CH₂)₂ | H | H | CH₂ | 4-Me-PhO | 4-(4-Cl-Ph)-Ph | O |
| 14-46 | H | (CH₂)₂ | H | H | CH₂ | 4-Me-PhO | 4-(4-HO-3,5-di-Me-Ph)-Ph | O |
| 14-47 | H | (CH₂)₂ | H | H | CH₂ | 4-Me-PhO | 4-(4-MeO-Ph)-Ph | O |
| 14-48 | H | (CH₂)₂ | H | H | CH₂ | 4-Me-PhO | 4-(4-HO-Ph)-Ph | O |
| 14-49 | H | (CH₂)₂ | H | H | CH₂ | 4-Me-PhO | 4-(4-OHC-Ph)-Ph | O |
| 14-50 | H | (CH₂)₂ | H | H | CH₂ | 4-Me-PhO | 4-(4-Dmam-Ph)-Ph | O |
| 14-51 | H | (CH₂)₂ | H | H | CH₂ | 4-Me-PhO | 4-(4-Dma-Ph)-Ph | O |
| 14-52 | H | (CH₂)₂ | H | H | CH₂ | 4-Me-PhO | 4-(4-HOOC-Ph)-Ph | O |
| 14-53 | H | (CH₂)₂ | H | H | CH₂ | 4-Me-PhO | 4-(4-HOH₂C-Ph)-Ph | O |
| 14-54 | H | (CH₂)₂ | H | H | CH₂ | 4-Me-PhO | 4-(3-MeO-Ph)-Ph | O |
| 14-55 | H | (CH₂)₂ | H | H | CH₂ | 4-Me-PhO | 4-(3-HO-Ph)-Ph | O |
| 14-56 | H | (CH₂)₂ | H | H | CH₂ | 4-Me-PhO | 4-(3-OHC-Ph)-Ph | O |
| 14-57 | H | (CH₂)₂ | H | H | CH₂ | 4-Me-PhO | 4-(3-Dmam-Ph)-Ph | O |
| 14-58 | H | (CH₂)₂ | H | H | CH₂ | 4-Me-PhO | 4-(3-Dma-Ph)-Ph | O |
| 14-59 | H | (CH₂)₂ | H | H | CH₂ | 4-Me-PhO | 4-(3-HOOC-Ph)-Ph | O |
| 14-60 | H | (CH₂)₂ | H | H | CH₂ | 4-Me-PhO | 4-(3-HOH₂C-Ph)-Ph | O |
| 14-61 | H | (CH₂)₂ | H | H | CH₂ | 4-Me-PhO | 4-(2-MeO-Ph)-Ph | O |
| 14-62 | H | (CH₂)₂ | H | H | CH₂ | 4-Me-PhO | 4-(2-HO-Ph)-Ph | O |
| 14-63 | H | (CH₂)₂ | H | H | CH₂ | 4-Me-PhO | 4-(2-OHC-Ph)-Ph | O |
| 14-64 | H | (CH₂)₂ | H | H | CH₂ | 4-Me-PhO | 4-(3-MeO-Pyr-6)-Ph | O |
| 14-65 | H | (CH₂)₂ | H | H | CH₂ | 4-Me-PhO | 4-(3-EtO-Pyr-6)-Ph | O |
| 14-66 | H | (CH₂)₂ | H | H | CH₂ | 4-Me-PhO | 4-(3-iPrO-Pyr-6)-Ph | O |
| 14-67 | H | (CH₂)₂ | H | H | CH₂ | 4-Me-PhO | 4-(3-Dma-Pyr-6)-Ph | O |
| 14-68 | H | (CH₂)₂ | H | H | CH₂ | 4-Me-PhO | 4-(3-Dea-Pyr-6)-Ph | O |

TABLE 14-continued

| Ex. No. Comp. | R¹ | R² | R³ | R⁴ | Z | W | X | Y |
|---|---|---|---|---|---|---|---|---|
| 14-69 | H | (CH$_2$)$_2$ | H | H | CH$_2$ | 4-Me-PhO | 4-(3-F$_3$C-Pyr-6)-Ph | O |
| 14-70 | H | (CH$_2$)$_2$ | H | H | CH$_2$ | 4-Me-PhO | 4-(3-O$_2$N-Pyr-3)-Ph | O |
| 14-71 | H | (CH$_2$)$_2$ | H | H | CH$_2$ | 4-Me-PhO | 4-Pip-Ph | O |
| 14-72 | H | (CH$_2$)$_2$ | H | H | CH$_2$ | 4-Me-PhO | 4-Dea-Ph | O |
| 14-73 | H | (CH$_2$)$_2$ | H | H | CH$_2$ | 4-Me-PhO | 2-(4-F-Ph)-5-Pyr | O |
| 14-74 | H | (CH$_2$)$_2$ | H | H | CH$_2$ | 4-Me-PhO | 2-(4-Cl-Ph)-5-Pyr | O |
| 14-75 | H | (CH$_2$)$_2$ | H | H | CH$_2$ | 4-Me-PhO | 2-(4-MeO-Ph)-5-Pyr | O |
| 14-76 | H | (CH$_2$)$_2$ | H | H | CH$_2$ | 4-Me-PhO | 2-(4-EtO-Ph)-5-Pyr | O |
| 14-77 | H | (CH$_2$)$_2$ | H | H | CH$_2$ | 4-Me-PhO | 2-(4-iPrO-Ph)-5-Pyr | O |
| 14-78 | H | (CH$_2$)$_2$ | H | H | CH$_2$ | 4-Me-PhO | 2-TfpO-5-Pyr | O |
| 14-79 | H | (CH$_2$)$_2$ | H | H | CH$_2$ | 4-Me-PhO | 4-(4-AcO-Ph)-Ph | O |
| 14-80 | H | (CH$_2$)$_2$ | H | H | CH$_2$ | 4-Me-PhO | 4-(3-F-Ph)-Ph | O |
| 14-81 | H | (CH$_2$)$_2$ | H | H | CH$_2$ | 4-Me-PhO | 4-(3-Cl-Ph)-Ph | O |
| 14-82 | H | (CH$_2$)$_2$ | H | H | CH$_2$ | 4-Me-PhO | 4-(3-Me-Ph)-Ph | O |
| 14-83 | H | (CH$_2$)$_2$ | H | H | CH$_2$ | 4-Me-PhO | 4-(3-ACO-Ph)-Ph | O |
| 14-84 | H | (CH$_2$)$_2$ | H | H | CH$_2$ | 4-Me-PhO | 4-(3-Me-Pyr-6)-Ph | O |
| 14-85 | H | (CH$_2$)$_2$ | H | H | CH$_2$ | 4-Me-PhO | 4-(3-Et-Pyr-6)-Ph | O |
| 14-86 | H | (CH$_2$)$_2$ | H | H | CH$_2$ | 4-Me-PhO | 2-(4-Me-Ph)-5-Pyr | O |
| 14-87 | H | (CH$_2$)$_2$ | H | H | CH$_2$ | 4-Me-PhO | 2-(4-CF$_3$-Ph)-5-Pyr | O |
| 14-88 | H | (CH$_2$)$_2$ | H | H | CH$_2$ | 4-Me-PhO | 2-(4-Dma-Ph)-5-Pyr | O |
| 14-89 | H | (CH$_2$)$_2$ | H | H | CH$_2$ | 4-Me-PhO | 2-(3-F-Ph)-5-Pyr | O |
| 14-90 | H | (CH$_2$)$_2$ | H | H | CH$_2$ | 4-Me-PhO | 2-(3-Cl-Ph)-5-Pyr | O |
| 14-91 | H | (CH$_2$)$_2$ | H | H | CH$_2$ | 4-Me-PhO | 2-(3-MeO-Ph)-5-Pyr | O |
| 14-92 | H | (CH$_2$)$_2$ | H | H | CH$_2$ | 4-Me-PhO | 2-(3-EtO-Ph)-5-Pyr | O |
| 14-93 | H | (CH$_2$)$_2$ | H | H | CH$_2$ | 4-Me-PhO | 2-(3-iPrO-Ph)-5-Pyr | O |
| 14-94 | H | (CH$_2$)$_2$ | H | H | CH$_2$ | 4-Me-PhO | 2-(3-Me-Ph)-5-Pyr | O |
| 14-95 | H | (CH$_2$)$_2$ | H | H | CH$_2$ | 4-Me-PhO | 2-(3-CF$_3$-Ph)-5-Pyr | O |
| 14-96 | H | (CH$_2$)$_2$ | H | H | CH$_2$ | 4-Me-PhO | 2-(3-Dma-Ph)-5-Pyr | O |

TABLE 15

| Ex. No. Comp. | R¹ | R² | R³ | R⁴ | Z | W | X | Y |
|---|---|---|---|---|---|---|---|---|
| 15-1 | H | (CH$_2$)$_2$ | H | H | CH$_2$ | 4-Et-Ph | Ph | O |
| 15-2 | H | (CH$_2$)$_2$ | H | H | CH$_2$ | 4-Et-Ph | 4-Me-Ph | O |
| 15-3 | H | (CH$_2$)$_2$ | H | H | CH$_2$ | 4-Et-Ph | 4-F-Ph | O |
| 15-4 | H | (CH$_2$)$_2$ | H | H | CH$_2$ | 4-Et-Ph | 4-Bz-Ph | O |
| 15-5 | H | (CH$_2$)$_2$ | H | H | CH$_2$ | 4-Et-Ph | 4-Ph-Ph | O |
| 15-6 | H | (CH$_2$)$_2$ | H | H | CH$_2$ | 4-Et-Ph | 4-PhO-Ph | O |
| 15-7 | H | (CH$_2$)$_2$ | H | H | CH$_2$ | 4-Et-Ph | 4-PhS-Ph | O |
| 15-8 | H | (CH$_2$)$_2$ | H | H | CH$_2$ | 4-Et-Ph | 4-PhSO$_2$-Phh | O |
| 15-9 | H | (CH$_2$)$_2$ | H | H | CH$_2$ | 4-Et-Ph | 4-PhSO$_2$NH-Ph | O |
| 15-10 | H | (CH$_2$)$_2$ | H | H | CH$_2$ | 4-Et-Ph | 4-PhSO$_2$NMe-Ph | O |
| 15-11 | H | (CH$_2$)$_2$ | H | H | CH$_2$ | 4-Et-Ph | 4-(Pyr-2)-Ph | O |
| 15-12 | H | (CH$_2$)$_2$ | H | H | CH$_2$ | 4-Et-Ph | 4-(Pyr-3)-Ph | O |
| 15-13 | H | (CH$_2$)$_2$ | H | H | CH$_2$ | 4-Et-Ph | 4-(Pyr-4)-Ph | O |
| 15-14 | H | (CH$_2$)$_2$ | H | H | CH$_2$ | 4-Et-Ph | 4-(Pyr-2)O-Ph | O |
| 15-15 | H | (CH$_2$)$_2$ | H | H | CH$_2$ | 4-Et-Ph | 4-(Pyr-4)O-Ph | O |
| 15-16 | H | (CH$_2$)$_2$ | H | H | CH$_2$ | 4-Et-Ph | 4-(Pyr-2)S-Ph | O |
| 15-17 | H | (CH$_2$)$_2$ | H | H | CH$_2$ | 4-Et-Ph | 4-(Pyr-4)S-Ph | O |
| 15-18 | H | (CH$_2$)$_2$ | H | H | CH$_2$ | 4-Et-Ph | 4-(Pyr-2)SO$_2$-Ph | O |
| 15-19 | H | (CH$_2$)$_2$ | H | H | CH$_2$ | 4-Et-Ph | 4-(Pyr-4)SO$_2$-Ph | O |

TABLE 15-continued

| Ex. No. Comp. | R$^1$ | R$^2$ | R$^3$ | R$^4$ | Z | W | X | Y |
|---|---|---|---|---|---|---|---|---|
| 15-20 | H | (CH$_2$)$_2$ | H | H | CH$_2$ | 4-Et-Ph | 4-(Pyr-2)SO$_2$NH-Ph | O |
| 15-21 | H | (CH$_2$)$_2$ | H | H | CH$_2$ | 4-Et-Ph | 4-(Pyr-4)SO$_2$NH-Ph | O |
| 15-22 | H | (CH$_2$)$_2$ | H | H | CH$_2$ | 4-Et-Ph | 4-(Pyr-2)SO$_2$NMe-Ph | O |
| 15-23 | H | (CH$_2$)$_2$ | H | H | CH$_2$ | 4-Et-Ph | 4-(Pyr-4)SO$_2$NMe-Ph | O |
| 15-24 | H | (CH$_2$)$_2$ | H | H | CH$_2$ | 4-Et-Ph | 2-Pyr | O |
| 15-25 | H | (CH$_2$)$_2$ | H | H | CH$_2$ | 4-Et-Ph | 3-Pyr | O |
| 15-26 | H | (CH$_2$)$_2$ | H | H | CH$_2$ | 4-Et-Ph | 4-Pyr | O |
| 15-27 | H | (CH$_2$)$_2$ | H | H | CH$_2$ | 4-Et-Ph | 2-Me-5-Pyr | O |
| 15-28 | H | (CH$_2$)$_2$ | H | H | CH$_2$ | 4-Et-Ph | 2-Me-3-Pyr | O |
| 15-29 | H | (CH$_2$)$_2$ | H | H | CH$_2$ | 4-Et-Ph | 2-MeO-5-Pyr | O |
| 15-30 | H | (CH$_2$)$_2$ | H | H | CH$_2$ | 4-Et-Ph | 2-EtO-5-Pyr | O |
| 15-31 | H | (CH$_2$)$_2$ | H | H | CH$_2$ | 4-Et-Ph | 2-iPrO-5-Pyr | O |
| 15-32 | H | (CH$_2$)$_2$ | H | H | CH$_2$ | 4-Et-Ph | 2-MeS-5-Pyr | O |
| 15-33 | H | (CH$_2$)$_2$ | H | H | CH$_2$ | 4-Et-Ph | 2-EtS-5-Pyr | O |
| 15-34 | H | (CH$_2$)$_2$ | H | H | CH$_2$ | 4-Et-Ph | 2-MeSO$_2$-5-Pyr | O |
| 15-35 | H | (CH$_2$)$_2$ | H | H | CH$_2$ | 4-Et-Ph | 2-EtSO$_2$-5-Pyr | O |
| 15-36 | H | (CH$_2$)$_2$ | H | H | CH$_2$ | 4-Et-Ph | 2-Bz-5-Pyr | O |
| 15-37 | H | (CH$_2$)$_2$ | H | H | CH$_2$ | 4-Et-Ph | 2-Ph-5-Pyr | O |
| 15-38 | H | (CH$_2$)$_2$ | H | H | CH$_2$ | 4-Et-Ph | 3-Ph-6-Pyr | O |
| 15-39 | H | (CH$_2$)$_2$ | H | H | CH$_2$ | 4-Et-Ph | 2-PhO-5-Pyr | O |
| 15-40 | H | (CH$_2$)$_2$ | H | H | CH$_2$ | 4-Et-Ph | 2-PhS-5-Pyr | O |
| 15-41 | H | (CH$_2$)$_2$ | H | H | CH$_2$ | 4-Et-Ph | 2-PhSO$_2$-5-Pyr | O |
| 15-42 | H | (CH$_2$)$_2$ | H | H | CH$_2$ | 4-Et-PhO | 4-(4-Me-Ph)-Ph | O |
| 15-43 | H | (CH$_2$)$_2$ | H | H | CH$_2$ | 4-Et-PhO | 4-(4-CF$_3$-Ph)-Ph | O |
| 15-44 | H | (CH$_2$)$_2$ | H | H | CH$_2$ | 4-Et-PhO | 4-(4-F-Ph)-Ph | O |
| 15-45 | H | (CH$_2$)$_2$ | H | H | CH$_2$ | 4-Et-PhO | 4-(4-Cl-Ph)-Ph | O |
| 15-46 | H | (CH$_2$)$_2$ | H | H | CH$_2$ | 4-Et-PhO | 4-(4-HO-3,5-di-Me-Ph)-Ph | O |
| 15-47 | H | (CH$_2$)$_2$ | H | H | CH$_2$ | 4-Et-PhO | 4-(4-MeO-Ph)-Ph | O |
| 15-48 | H | (CH$_2$)$_2$ | H | H | CH$_2$ | 4-Et-PhO | 4-(4-HO-Ph)-Ph | O |
| 15-49 | H | (CH$_2$)$_2$ | H | H | CH$_2$ | 4-Et-PhO | 4-(4-OHC-Ph)-Ph | O |
| 15-50 | H | (CH$_2$)$_2$ | H | H | CH$_2$ | 4-Et-PhO | 4-(4-Dmam-Ph)-Ph | O |
| 15-51 | H | (CH$_2$)$_2$ | H | H | CH$_2$ | 4-Et-PhO | 4-(4-Dma-Ph)-Ph | O |
| 15-52 | H | (CH$_2$)$_2$ | H | H | CH$_2$ | 4-Et-PhO | 4-(4-HOOC-Ph)-Ph | O |
| 15-53 | H | (CH$_2$)$_2$ | H | H | CH$_2$ | 4-Et-PhO | 4-(4-HOH$_2$C-Ph)-Ph | O |
| 15-54 | H | (CH$_2$)$_2$ | H | H | CH$_2$ | 4-Et-PhO | 4-(3-MeO-Ph)-Ph | O |
| 15-55 | H | (CH$_2$)$_2$ | H | H | CH$_2$ | 4-Et-PhO | 4-(3-HO-Ph)-Ph | O |
| 15-56 | H | (CH$_2$)$_2$ | H | H | CH$_2$ | 4-Et-PhO | 4-(3-OHC-Ph)-Ph | O |
| 15-57 | H | (CH$_2$)$_2$ | H | H | CH$_2$ | 4-Et-PhO | 4-(3-Dmam-Ph)-Ph | O |
| 15-58 | H | (CH$_2$)$_2$ | H | H | CH$_2$ | 4-Et-PhO | 4-(3-Dma-Ph)-Ph | O |
| 15-59 | H | (CH$_2$)$_2$ | H | H | CH$_2$ | 4-Et-PhO | 4-(3-HOOC-Ph)-Ph | O |
| 15-60 | H | (CH$_2$)$_2$ | H | H | CH$_2$ | 4-Et-PhO | 4-(3-HOH$_2$C-Ph)-Ph | O |
| 15-61 | H | (CH$_2$)$_2$ | H | H | CH$_2$ | 4-Et-PhO | 4-(2-MeO-Ph)-Ph | O |
| 15-62 | H | (CH$_2$)$_2$ | H | H | CH$_2$ | 4-Et-PhO | 4-(2-HO-Ph)-Ph | O |
| 15-63 | H | (CH$_2$)$_2$ | H | H | CH$_2$ | 4-Et-PhO | 4-(2-OHC-Ph)-Ph | O |
| 15-64 | H | (CH$_2$)$_2$ | H | H | CH$_2$ | 4-Et-PhO | 4-(3-MeO-Pyr-6)-Ph | O |
| 15-65 | H | (CH$_2$)$_2$ | H | H | CH$_2$ | 4-Et-PhO | 4-(3-EtO-Pyr-6)-Ph | O |
| 15-66 | H | (CH$_2$)$_2$ | H | H | CH$_2$ | 4-Et-PhO | 4-(3-iPrO-Pyr-6)-Ph | O |
| 15-67 | H | (CH$_2$)$_2$ | H | H | CH$_2$ | 4-Et-PhO | 4-(3-Dma-Pyr-6)-Ph | O |
| 15-68 | H | (CH$_2$)$_2$ | H | H | CH$_2$ | 4-Et-PhO | 4-(3-Dea-Pyr-6)-Ph | O |
| 15-69 | H | (CH$_2$)$_2$ | H | H | CH$_2$ | 4-Et-PhO | 4-(3-F$_3$C-Pyr-6)-Ph | O |
| 15-70 | H | (CH$_2$)$_2$ | H | H | CH$_2$ | 4-Et-PhO | 4-(3-O$_2$N-Pyr-6)-Ph | O |
| 15-71 | H | (CH$_2$)$_2$ | H | H | CH$_2$ | 4-Et-PhO | 4-Pip-Ph | O |
| 15-72 | H | (CH$_2$)$_2$ | H | H | CH$_2$ | 4-Et-PhO | 4-Dea-Ph | O |
| 15-73 | H | (CH$_2$)$_2$ | H | H | CH$_2$ | 4-Et-PhO | 2-(4-F-Ph)-5-Pyr | O |
| 15-74 | H | (CH$_2$)$_2$ | H | H | CH$_2$ | 4-Et-PhO | 2-(4-Cl-Ph)-5-Pyr | O |
| 15-75 | H | (CH$_2$)$_2$ | H | H | CH$_2$ | 4-Et-PhO | 2-(4-Meo-Ph)-5-Pyr | O |

TABLE 15-continued

| Ex. No. Comp. | R¹ | R² | R³ | R⁴ | Z | W | X | Y |
|---|---|---|---|---|---|---|---|---|
| 15-76 | H | (CH₂)₂ | H | H | CH₂ | 4-Et-PhO | 2-(4-EtO-Ph)-5-Pyr | O |
| 15-77 | H | (CH₂)₂ | H | H | CH₂ | 4-Et-PhO | 2-(4-iPrO-Ph)-5-Pyr | O |
| 15-78 | H | (CH₂)₂ | H | H | CH₂ | 4-Et-PhO | 2-TfpO-5-Pyr | O |
| 15-79 | H | (CH₂)₂ | H | H | CH₂ | 4-Et-PhO | 4-(4-AcO-Ph)-Ph | O |
| 15-80 | H | (CH₂)₂ | H | H | CH₂ | 4-Et-PhO | 4-(3-F-Ph)-Ph | O |
| 15-81 | H | (CH₂)₂ | H | H | CH₂ | 4-Et-PhO | 4-(3-Cl-Ph)-Ph | O |
| 15-82 | H | (CH₂)₂ | H | H | CH₂ | 4-Et-PhO | 4-(3-Me-Ph)-Ph | O |
| 15-83 | H | (CH₂)₂ | H | H | CH₂ | 4-Et-PhO | 4-(3-AcO-Ph)-Ph | O |
| 15-84 | H | (CH₂)₂ | H | H | CH₂ | 4-Et-PhO | 4-(3-Me-Pyr-6)-Ph | O |
| 15-85 | H | (CH₂)₂ | H | H | CH₂ | 4-Et-PhO | 4-(3-Et-Pyr-6)-Ph | O |
| 15-86 | H | (CH₂)₂ | H | H | CH₂ | 4-Et-PhO | 2-(4-Me-Ph)-5-Pyr | O |
| 15-87 | H | (CH₂)₂ | H | H | CH₂ | 4-Et-PhO | 2-(4-CF₃-Ph)-5-Pyr | O |
| 15-88 | H | (CH₂)₂ | H | H | CH₂ | 4-Et-PhO | 2-(4-Dma-Ph)-5-Pyr | O |
| 15-89 | H | (CH₂)₂ | H | H | CH₂ | 4-Et-PhO | 2-(3-F-Ph)-5-Pyr | O |
| 15-90 | H | (CH₂)₂ | H | H | CH₂ | 4-Et-PhO | 2-(3-Cl-Ph)-5-Pyr | O |
| 15-91 | H | (CH₂)₂ | H | H | CH₂ | 4-Et-PhO | 2-(3-MeO-Ph)-5-Pyr | O |
| 15-92 | H | (CH₂)₂ | H | H | CH₂ | 4-Et-PhO | 2-(3-EtO-Ph)-5-Pyr | O |
| 15-93 | H | (CH₂)₂ | H | H | CH₂ | 4-Et-PhO | 2-(3-iPrO)-Ph)-5-Pyr | O |
| 15-94 | H | (CH₂)₂ | H | H | CH₂ | 4-Et-PhO | 2-(3-Me-Ph)-5-Pyr | O |
| 15-95 | H | (CH₂)₂ | H | H | CH₂ | 4-Et-PhO | 2-(3-CF₃-Ph)-5-Pyr | O |
| 15-96 | H | (CH₂)₂ | H | H | CH₂ | 4-Et-PhO | 2-(3-Dma-Ph)-5-Pyr | O |

TABLE 16

| Ex. No. Comp. | R¹ | R² | R³ | R⁴ | Z | W | X | Y |
|---|---|---|---|---|---|---|---|---|
| 16-1 | H | (CH₂)₂ | H | H | CH₂ | Ph(CH₂)₂ | Ph | O |
| 16-2 | H | (CH₂)₂ | H | H | CH₂ | Ph(CH₂)₂ | 4-Me-Ph | O |
| 16-3 | H | (CH₂)₂ | H | H | CH₂ | Ph(CH₂)₂ | 4-F-Ph | O |
| 16-4 | H | (CH₂)₂ | H | H | CH₂ | Ph(CH₂)₂ | 4-Bz-Ph | O |
| 16-5 | H | (CH₂)₂ | H | H | CH₂ | Ph(CH₂)₂ | 4-Ph-Ph | O |
| 16-6 | H | (CH₂)₂ | H | H | CH₂ | Ph(CH₂)₂ | 4-PhO-Ph | O |
| 16-7 | H | (CH₂)₂ | H | H | CH₂ | Ph(CH₂)₂ | 4-PhS-Ph | O |
| 16-8 | H | (CH₂)₂ | H | H | CH₂ | Ph(CH₂)₂ | 4-PhSO₂-Ph | O |
| 16-9 | H | (CH₂)₂ | H | H | CH₂ | Ph(CH₂)₂ | 4-PhSO₂NH-Ph | O |
| 16-10 | H | (CH₂)₂ | H | H | CH₂ | Ph(CH₂)₂ | 4-PhSO₂NMe-Ph | O |
| 16-11 | H | (CH₂)₂ | H | H | CH₂ | Ph(CH₂)₂ | 4-(Pyr-2)-Ph | O |
| 16-12 | H | (CH₂)₂ | H | H | CH₂ | Ph(CH₂)₂ | 4-(Pyr-3)-Ph | O |
| 16-13 | H | (CH₂)₂ | H | H | CH₂ | Ph(CH₂)₂ | 4-(Pyr-4)-Ph | O |
| 16-14 | H | (CH₂)₂ | H | H | CH₂ | Ph(CH₂)₂ | 4-(Pyr-2)O-Ph | O |
| 16-15 | H | (CH₂)₂ | H | H | CH₂ | Ph(CH₂)₂ | 4-(Pyr-4)O-Ph | O |
| 16-16 | H | (CH₂)₂ | H | H | CH₂ | Ph(CH₂)₂ | 4-(Pyr-2)S-Ph | O |
| 16-17 | H | (CH₂)₂ | H | H | CH₂ | Ph(CH₂)₂ | 4-(Pyr-4)S-Ph | O |
| 16-18 | H | (CH₂)₂ | H | H | CH₂ | Ph(CH₂)₂ | 4-(Pyr-2)SO₂-Ph | O |
| 16-19 | H | (CH₂)₂ | H | H | CH₂ | Ph(CH₂)₂ | 4-(Pyr-4)SO₂-Ph | O |
| 16-20 | H | (CH₂)₂ | H | H | CH₂ | Ph(CH₂)₂ | 4-(Pyr-2)SO₂NH-Ph | O |
| 16-21 | H | (CH₂)₂ | H | H | CH₂ | Ph(CH₂)₂ | 4-(Pyr-4)SO₂NH-Ph | O |
| 16-22 | H | (CH₂)₂ | H | H | CH₂ | Ph(CH₂)₂ | 4-(Pyr-2)SO₂NMe-Ph | O |
| 16-23 | H | (CH₂)₂ | H | H | CH₂ | Ph(CH₂)₂ | 4-(Pyr-4)SO₂NMe-Ph | O |
| 16-24 | H | (CH₂)₂ | H | H | CH₂ | Ph(CH₂)₂ | 2-Pyr | O |
| 16-25 | H | (CH₂)₂ | H | H | CH₂ | Ph(CH₂)₂ | 3-Pyr | O |
| 16-26 | H | (CH₂)₂ | H | H | CH₂ | Ph(CH₂)₂ | 4-Pyr | O |

TABLE 16-continued

| Ex. No. Comp. | R¹ | R² | R³ | R⁴ | Z | W | X | Y |
|---|---|---|---|---|---|---|---|---|
| 16-27 | H | (CH$_2$)$_2$ | H | H | CH$_2$ | Ph(CH$_2$)$_2$ | 2-Me-5-Pyr | O |
| 16-28 | H | (CH$_2$)$_2$ | H | H | CH$_2$ | Ph(CH$_2$)$_2$ | 2-Me-3-Pyr | O |
| 16-29 | H | (CH$_2$)$_2$ | H | H | CH$_2$ | Ph(CH$_2$)$_2$ | 2-MeO-5-Pyr | O |
| 16-30 | H | (CH$_2$)$_2$ | H | H | CH$_2$ | Ph(CH$_2$)$_2$ | 2-EtO-5-Pyr | O |
| 16-31 | H | (CH$_2$)$_2$ | H | H | CH$_2$ | Ph(CH$_2$)$_2$ | 2-iPrO-5-Pyr | O |
| 16-32 | H | (CH$_2$)$_2$ | H | H | CH$_2$ | Ph(CH$_2$)$_2$ | 2-MeS-5-Pyr | O |
| 16-33 | H | (CH$_2$)$_2$ | H | H | CH$_2$ | Ph(CH$_2$)$_2$ | 2-EtS-5-Pyr | O |
| 16-34 | H | (CH$_2$)$_2$ | H | H | CH$_2$ | Ph(CH$_2$)$_2$ | 2-MeSO$_2$-5-Pyr | O |
| 16-35 | H | (CH$_2$)$_2$ | H | H | CH$_2$ | Ph(CH$_2$)$_2$ | 2-EtSO$_2$-5-Pyr | O |
| 16-36 | H | (CH$_2$)$_2$ | H | H | CH$_2$ | Ph(CH$_2$)$_2$ | 2-Bz-5-Pyr | O |
| 16-37 | H | (CH$_2$)$_2$ | H | H | CH$_2$ | Ph(CH$_2$)$_2$ | 2-Ph-5-Pyr | O |
| 16-38 | H | (CH$_2$)$_2$ | H | H | CH$_2$ | Ph(CH$_2$)$_2$ | 3-Ph-6-Pyr | O |
| 16-39 | H | (CH$_2$)$_2$ | H | H | CH$_2$ | Ph(CH$_2$)$_2$ | 2-PhO-5-Pyr | O |
| 16-40 | H | (CH$_2$)$_2$ | H | H | CH$_2$ | Ph(CH$_2$)$_2$ | 2-PhS-5-Pyr | O |
| 16-41 | H | (CH$_2$)$_2$ | H | H | CH$_2$ | Ph(CH$_2$)$_2$ | 2-PhSO$_2$-5-Pyr | O |

TABLE 17

| Ex. No. Comp. | R¹ | R² | R³ | R⁴ | Z | W | X | Y |
|---|---|---|---|---|---|---|---|---|
| 17-1 | H | (CH$_2$)$_2$ | H | H | CH$_2$ | PhS | Ph | O |
| 17-2 | H | (CH$_2$)$_2$ | H | H | CH$_2$ | PhS | 4-Me-Ph | O |
| 17-3 | H | (CH$_2$)$_2$ | H | H | CH$_2$ | PhS | 4-F-Ph | O |
| 17-4 | H | (CH$_2$)$_2$ | H | H | CH$_2$ | PhS | 4-Bz-Ph | O |
| 17-5 | H | (CH$_2$)$_2$ | H | H | CH$_2$ | PhS | 4-Ph-Ph | O |
| 17-6 | H | (CH$_2$)$_2$ | H | H | CH$_2$ | PhS | 4-PhO-Ph | O |
| 17-7 | H | (CH$_2$)$_2$ | H | H | CH$_2$ | PhS | 4-PhS-Ph | O |
| 17-8 | H | (CH$_2$)$_2$ | H | H | CH$_2$ | PhS | 4-PhSO$_2$-Ph | O |
| 17-9 | H | (CH$_2$)$_2$ | H | H | CH$_2$ | PhS | 4-PhSO$_2$NH-Ph | O |
| 17-10 | H | (CH$_2$)$_2$ | H | H | CH$_2$ | PhS | 4-PhSO$_2$NMe-Ph | O |
| 17-11 | H | (CH$_2$)$_2$ | H | H | CH$_2$ | PhS | 4-(Pyr-2)-Ph | O |
| 17-12 | H | (CH$_2$)$_2$ | H | H | CH$_2$ | PhS | 4-(Pyr-3)-Ph | O |
| 17-13 | H | (CH$_2$)$_2$ | H | H | CH$_2$ | PhS | 4-Pyr-4)-Ph | O |
| 17-14 | H | (CH$_2$)$_2$ | H | H | CH$_2$ | PhS | 4-(Pyr-2)O-Ph | O |
| 17-15 | H | (CH$_2$)$_2$ | H | H | CH$_2$ | PhS | 4-(Pyr-4)O-Ph | O |
| 17-16 | H | (CH$_2$)$_2$ | H | H | CH$_2$ | PhS | 4-(Pyr-2)S-Ph | O |
| 17-17 | H | (CH$_2$)$_2$ | H | H | CH$_2$ | PhS | 4-(Pyr-4)S-Ph | O |
| 17-18 | H | (CH$_2$)$_2$ | H | H | CH$_2$ | PhS | 4-(Pyr-2)SO$_2$-Ph | O |
| 17-19 | H | (CH$_2$)$_2$ | H | H | CH$_2$ | PhS | 4-(Pyr-4)SO$_2$-Ph | O |
| 17-20 | H | (CH$_2$)$_2$ | H | H | CH$_2$ | PhS | 4-Pyr-2)SO$_2$NH-Ph | O |
| 17-21 | H | (CH$_2$)$_2$ | H | H | CH$_2$ | PhS | 4-(Pyr-4)SO$_2$NH-Ph | O |
| 17-22 | H | (CH$_2$)$_2$ | H | H | CH$_2$ | PhS | 4-(Pyr-2)SO$_2$NMe-Ph | O |
| 17-23 | H | (CH$_2$)$_2$ | H | H | CH$_2$ | PhS | 4-(Pyr-4)SO$_2$NMe-Ph | O |
| 17-24 | H | (CH$_2$)$_2$ | H | H | CH$_2$ | PhS | 2-Pyr | O |
| 17-25 | H | (CH$_2$)$_2$ | H | H | CH$_2$ | PhS | 3-Pyr | O |
| 17-26 | H | (CH$_2$)$_2$ | H | H | CH$_2$ | PhS | 4-Pyr | O |
| 17-27 | H | (CH$_2$)$_2$ | H | H | CH$_2$ | PhS | 2-Me-5-Pyr | O |
| 17-28 | H | (CH$_2$)$_2$ | H | H | CH$_2$ | PhS | 2-Me-3-Pyr | O |
| 17-29 | H | (CH$_2$)$_2$ | H | H | CH$_2$ | PhS | 2-MeO-5-Pyr | O |
| 17-30 | H | (CH$_2$)$_2$ | H | H | CH$_2$ | PhS | 2-EtO-5-Pyr | O |
| 17-31 | H | (CH$_2$)$_2$ | H | H | CH$_2$ | PhS | 2-iPrO-5-Pyr | O |
| 17-32 | H | (CH$_2$)$_2$ | H | H | CH$_2$ | PhS | 2-MeS-5-Pyr | O |
| 17-33 | H | (CH$_2$)$_2$ | H | H | CH$_2$ | PhS | 2-EtS-5-Pyr | O |
| 17-34 | H | (CH$_2$)$_2$ | H | H | CH$_2$ | PhS | 2-MeSO$_2$-5-Pyr | O |
| 17-35 | H | (CH$_2$)$_2$ | H | H | CH$_2$ | PhS | 2-EtSO$_2$-5-Pyr | O |
| 17-36 | H | (CH$_2$)$_2$ | H | H | CH$_2$ | PhS | 2-Bz-5-Pyr | O |
| 17-37 | H | (CH$_2$)$_2$ | H | H | CH$_2$ | PhS | 2-Ph-5-Pyr | O |
| 17-38 | H | (CH$_2$)$_2$ | H | H | CH$_2$ | PhS | 3-Ph-6-Pyr | O |
| 17-39 | H | (CH$_2$)$_2$ | H | H | CH$_2$ | PhS | 2-PhO-5-Pyr | O |
| 17-40 | H | (CH$_2$)$_2$ | H | H | CH$_2$ | PhS | 2-PhS-5-Pyr | O |
| 17-41 | H | (CH$_2$)$_2$ | H | H | CH$_2$ | PhS | 2-PhSO$_2$-5-Pyr | O |

TABLE 17-continued

| Ex. No. Comp. | $R^1$ | $R^2$ | $R^3$ | $R^4$ | Z | W | X | Y |
|---|---|---|---|---|---|---|---|---|
| 17-42 | H | (CH$_2$)$_2$ | H | H | CH$_2$ | PhS | 4-(4-Me-Ph)-Ph | O |
| 17-43 | H | (CH$_2$)$_2$ | H | H | CH$_2$ | PhS | 4-(4-CF$_3$-Ph)-Ph | O |
| 17-44 | H | (CH$_2$)$_2$ | H | H | CH$_2$ | PhS | 4-(4-F-Ph)-Ph | O |
| 17-45 | H | (CH$_2$)$_2$ | H | H | CH$_2$ | PhS | 4-(4-Cl-Ph)-Ph | O |
| 17-46 | H | (CH$_2$)$_2$ | H | H | CH$_2$ | PhS | 4-(4-HO-3,5-di-Me-Ph)-Ph | O |
| 17-47 | H | (CH$_2$)$_2$ | H | H | CH$_2$ | PhS | 4-(4-MeO-Ph)-Ph | O |
| 17-48 | H | (CH$_2$)$_2$ | H | H | CH$_2$ | PhS | 4-(4-HO-Ph)-Ph | O |
| 17-49 | H | (CH$_2$)$_2$ | H | H | CH$_2$ | PhS | 4-(4-OHC-Ph)-Ph | O |
| 17-50 | H | (CH$_2$)$_2$ | H | H | CH$_2$ | PhS | 4-(4-Dmam-Ph)-Ph | O |
| 17-51 | H | (CH$_2$)$_2$ | H | H | CH$_2$ | PhS | 4-(4-Dma-Ph)-Ph | O |
| 17-52 | H | (CH$_2$)$_2$ | H | H | CH$_2$ | PhS | 4-(4-HOOC-Ph)-Ph | O |
| 17-53 | H | (CH$_2$)$_2$ | H | H | CH$_2$ | PhS | 4-(4-HOH$_2$C-Ph)-Ph | O |
| 17-54 | H | (CH$_2$)$_2$ | H | H | CH$_2$ | PhS | 4-(3-MeO-Ph)-Ph | O |
| 17-55 | H | (CH$_2$)$_2$ | H | H | CH$_2$ | PhS | 4-(3-HO-Ph)-Ph | O |
| 17-56 | H | (CH$_2$)$_2$ | H | H | CH$_2$ | PhS | 4-(3-OHC-Ph)-Ph | O |
| 17-57 | H | (CH$_2$)$_2$ | H | H | CH$_2$ | PhS | 4-(3-Dmam-Ph)-Ph | O |
| 17-58 | H | (CH$_2$)$_2$ | H | H | CH$_2$ | PhS | 4-(3-Dma-Ph)-Ph | O |
| 17-59 | H | (CH$_2$)$_2$ | H | H | CH$_2$ | PhS | 4-(3-HOOC-Ph)-Ph | O |
| 17-60 | H | (CH$_2$)$_2$ | H | H | CH$_2$ | PhS | 4-(3-HOH$_2$C-Ph)-Ph | O |
| 17-61 | H | (CH$_2$)$_2$ | H | H | CH$_2$ | PhS | 4-(2-MeO-Ph)-Ph | O |
| 17-62 | H | (CH$_2$)$_2$ | H | H | CH$_2$ | PhS | 4-(2-HO-Ph)-Ph | O |
| 17-63 | H | (CH$_2$)$_2$ | H | H | CH$_2$ | PhS | 4-(2-OHC-Ph)-Ph | O |
| 17-64 | H | (CH$_2$)$_2$ | H | H | CH$_2$ | PhS | 4-(3-MeO-Pyr-6)-Ph | O |
| 17-65 | H | (CH$_2$)$_2$ | H | H | CH$_2$ | PhS | 4-(3-EtO-Pyr-6)-Ph | O |
| 17-66 | H | (CH$_2$)$_2$ | H | H | CH$_2$ | PhS | 4-(3-iPrO-Pyr-6)-Ph | O |
| 17-67 | H | (CH$_2$)$_2$ | H | H | CH$_2$ | PhS | 4-(3-Dma-Pyr-6)-Ph | O |
| 17-68 | H | (CH$_2$)$_2$ | H | H | CH$_2$ | PhS | 4-(3-Dea-Pyr-6)-Ph | O |
| 17-69 | H | (CH$_2$)$_2$ | H | H | CH$_2$ | PhS | 4-(3-F$_3$C-Pyr-6)-Ph | O |
| 17-70 | H | (CH$_2$)$_2$ | H | H | CH$_2$ | PhS | 4-(3-O$_2$N-Pyr-6)-Ph | O |
| 17-71 | H | (CH$_2$)$_2$ | H | H | CH$_2$ | PhS | 4-Pip-Ph | O |
| 17-72 | H | (CH$_2$)$_2$ | H | H | CH$_2$ | PhS | 4-Dea-Ph | O |
| 17-73 | H | (CH$_2$)$_2$ | H | H | CH$_2$ | PhS | 2-(4-F-Ph)-5-Pyr | O |
| 17-74 | H | (CH$_2$)$_2$ | H | H | CH$_2$ | PhS | 2-(4-Cl-Ph)-5-Pyr | O |
| 17-75 | H | (CH$_2$)$_2$ | H | H | CH$_2$ | PhS | 2-(4-MeO-Ph)-5-Pyr | |
| 17-76 | H | (CH$_2$)$_2$ | H | H | CH$_2$ | PhS | 2-(4-Eto-Ph)-5-Pyr | O |
| 17-77 | H | (CH$_2$)$_2$ | H | H | CH$_2$ | PhS | 2-(4-iPrO-Ph)-5-Pyr | O |
| 17-78 | H | (CH$_2$)$_2$ | H | H | CH$_2$ | PhS | 2-TfpO-5-Pyr | O |

TABLE 18

| Ex. No. Comp. | $R^1$ | $R^2$ | $R^3$ | $R^4$ | Z | W | X | Y |
|---|---|---|---|---|---|---|---|---|
| 18-1 | Me | (CH$_2$)$_2$ | H | H | CH$_2$ | EtO | Ph | O |
| 18-2 | Me | (CH$_2$)$_2$ | H | H | CH$_2$ | EtO | 4-Ph-Ph | O |
| 18-3 | Me | (CH$_2$)$_2$ | H | H | CH$_2$ | EtO | 4-(Pyr-2)-Ph | O |
| 18-4 | Me | (CH$_2$)$_2$ | H | H | CH$_2$ | EtO | 4-(Pyr-3)-Ph | O |
| 18-5 | Me | (CH$_2$)$_2$ | H | H | CH$_2$ | EtO | 4-(Pyr-4)-Ph | O |
| 18-6 | Me | (CH$_2$)$_2$ | H | H | CH$_2$ | EtO | 2-Pyr | O |
| 18-7 | Me | (CH$_2$)$_2$ | H | H | CH$_2$ | EtO | 3-Pyr | O |
| 18-8 | Me | (CH$_2$)$_2$ | H | H | CH$_2$ | EtO | 4-Pyr | O |
| 18-9 | Me | (CH$_2$)$_2$ | H | H | CH$_2$ | EtO | 2-Me-5-Pyr | O |
| 18-10 | Me | (CH$_2$)$_2$ | H | H | CH$_2$ | EtO | 2-Me-3-Pyr | O |
| 18-11 | Me | (CH$_2$)$_2$ | H | H | CH$_2$ | EtO | 2-MeO-5-Pyr | O |
| 18-12 | Me | (CH$_2$)$_2$ | H | H | CH$_2$ | EtO | 2-EtO-5-Pyr | O |
| 18-13 | Me | (CH$_2$)$_2$ | H | H | CH$_2$ | EtO | 2-iPrO-5-Pyr | O |
| 18-14 | Me | (CH$_2$)$_2$ | H | H | CH$_2$ | EtO | 2-MeS-5-Pyr | O |
| 18-15 | Me | (CH$_2$)$_2$ | H | H | CH$_2$ | EtO | 2-EtS-5-Pyr | O |
| 18-16 | Me | (CH$_2$)$_2$ | H | H | CH$_2$ | EtO | 2-Ph-5-Pyr | O |
| 18-17 | Me | (CH$_2$)$_2$ | H | H | CH$_2$ | EtO | 3-Ph-6-Pyr | O |

TABLE 19

| Ex. No. Comp. | $R^1$ | $R^2$ | $R^3$ | $R^4$ | Z | W | X | Y |
|---|---|---|---|---|---|---|---|---|
| 19-1 | Me | (CH$_2$)$_2$ | H | H | CH$_2$ | Pr | Ph | O |
| 19-2 | Me | (CH$_2$)$_2$ | H | H | CH$_2$ | Pr | 4-Ph-Ph | O |
| 19-3 | Me | (CH$_2$)$_2$ | H | H | CH$_2$ | Pr | 4-(Pyr-2)-Ph | O |
| 19-4 | Me | (CH$_2$)$_2$ | H | H | CH$_2$ | Pr | 4-(Pyr-3)-Ph | O |
| 19-5 | Me | (CH$_2$)$_2$ | H | H | CH$_2$ | Pr | 4-(Pyr-4)-Ph | O |
| 19-6 | Me | (CH$_2$)$_2$ | H | H | CH$_2$ | Pr | 2-Pyr | O |
| 19-7 | Me | (CH$_2$)$_2$ | H | H | CH$_2$ | Pr | 3-Pyr | O |
| 19-8 | Me | (CH$_2$)$_2$ | H | H | CH$_2$ | Pr | 4-Pyr | O |
| 19-9 | Me | (CH$_2$)$_2$ | H | H | CH$_2$ | Pr | 2-Me-5-Pyr | O |
| 19-10 | Me | (CH$_2$)$_2$ | H | H | CH$_2$ | Pr | 2-Me-3-Pyr | O |
| 19-11 | Me | (CH$_2$)$_2$ | H | H | CH$_2$ | Pr | 2-MeO-5-Pyr | O |
| 19-12 | Me | (CH$_2$)$_2$ | H | H | CH$_2$ | Pr | 2-EtO-5-Pyr | O |
| 19-13 | Me | (CH$_2$)$_2$ | H | H | CH$_2$ | Pr | 2-iPrO-5-Pyr | O |
| 19-14 | Me | (CH$_2$)$_2$ | H | H | CH$_2$ | Pr | 2-MeS-5-Pyr | O |
| 19-15 | Me | (CH$_2$)$_2$ | H | H | CH$_2$ | Pr | 2-EtS-5-Pyr | O |
| 19-16 | Me | (CH$_2$)$_2$ | H | H | CH$_2$ | Pr | 2-Ph-5-Pyr | O |
| 19-17 | Me | (CH$_2$)$_2$ | H | H | CH$_2$ | Pr | 3-Ph-6-Pyr | O |

TABLE 20

| Ex. No. Comp. | R¹ | R² | R³ | R⁴ | Z | W | X | Y |
|---|---|---|---|---|---|---|---|---|
| 20-1 | Me | (CH₂)₂ | H | H | CH₂ | Bu | Ph | O |
| 20-2 | Me | (CH₂)₂ | H | H | CH₂ | Bu | 4-Ph-Ph | O |
| 20-3 | Me | (CH₂)₂ | H | H | CH₂ | Bu | 4-(Pyr-2)-Ph | O |
| 20-4 | Me | (CH₂)₂ | H | H | CH₂ | Bu | 4-(Pyr-3)-Ph | O |
| 20-5 | Me | (CH₂)₂ | H | H | CH₂ | Bu | 4-(Pyr-4)-Ph | O |
| 20-6 | Me | (CH₂)₂ | H | H | CH₂ | Bu | 2-Pyr | O |
| 20-7 | Me | (CH₂)₂ | H | H | CH₂ | Bu | 3-Pyr | O |
| 20-8 | Me | (CH₂)₂ | H | H | CH₂ | Bu | 4-Pyr | O |
| 20-9 | Me | (CH₂)₂ | H | H | CH₂ | Bu | 2-Me-5-Pyr | O |
| 20-10 | Me | (CH₂)₂ | H | H | CH₂ | Bu | 2-Me-3-Pyr | O |
| 20-11 | Me | (CH₂)₂ | H | H | CH₂ | Bu | 2-MeO-5-Pyr | O |
| 20-12 | Me | (CH₂)₂ | H | H | CH₂ | Bu | 2-EtO-5-Pyr | O |
| 20-13 | Me | (CH₂)₂ | H | H | CH₂ | Bu | 2-iPrO-5-Pyr | O |
| 20-14 | Me | (CH₂)₂ | H | H | CH₂ | Bu | 2-MeS-5-Pyr | O |
| 20-15 | Me | (CH₂)₂ | H | H | CH₂ | Bu | 2-EtS-5-Pyr | O |
| 20-16 | Me | (CH₂)₂ | H | H | CH₂ | Bu | 2-Ph-5-Pyr | O |
| 20-17 | Me | (CH₂)₂ | H | H | CH₂ | Bu | 3-Ph-6-Pyr | O |
| 20-18 | Me | (CH₂)₂ | H | H | CH₂ | Bu | 4-(4-Me-Ph)-Ph | O |
| 20-19 | Me | (CH₂)₂ | H | H | CH₂ | Bu | 4-(4-F-Ph)-Ph | O |
| 20-20 | Me | (CH₂)₂ | H | H | CH₂ | Bu | 4-(4-HO-3,5-di-Me-Ph)-Ph | O |
| 20-21 | Me | (CH₂)₂ | H | H | CH₂ | Bu | 4-(4-MeO-Ph)-Ph | O |
| 20-22 | Me | (CH₂)₂ | H | H | CH₂ | Bu | 4-(4-HO-Ph)-Ph | O |
| 20-23 | Me | (CH₂)₂ | H | H | CH₂ | Bu | 4-(4-OHC-Ph)-Ph | O |
| 20-24 | Me | (CH₂)₂ | H | H | CH₂ | Bu | 4-(4-Dma-Ph)-Ph | O |
| 20-25 | Me | (CH₂)₂ | H | H | CH₂ | Bu | 4-(3-MeO-Ph)-Ph | O |
| 20-26 | Me | (CH₂)₂ | H | H | CH₂ | Bu | 4-(3-HO-Ph)-Ph | O |
| 20-27 | Me | (CH₂)₂ | H | H | CH₂ | Bu | 4-(3-Dma-Ph)-Ph | O |
| 20-28 | Me | (CH₂)₂ | H | H | CH₂ | Bu | 4-(2-MeO-Ph)-Ph | O |
| 20-29 | Me | (CH₂)₂ | H | H | CH₂ | Bu | 4-(2-HO-Ph)-Ph | O |
| 20-30 | Me | (CH₂)₂ | H | H | CH₂ | Bu | 4-(3-MeO-Pyr-6)-Ph | O |
| 20-31 | Me | (CH₂)₂ | H | H | CH₂ | Bu | 4-(3-EtO-Pyr-6)-Ph | O |
| 20-32 | Me | (CH₂)₂ | H | H | CH₂ | Bu | 4-(3-iPrO-Pyr-6)-Ph | O |
| 20-33 | Me | (CH₂)₂ | H | H | CH₂ | Bu | 4-(3-Dma-Pyr-6)-Ph | O |
| 20-34 | Me | (CH₂)₂ | H | H | CH₂ | Bu | 4-(3-Dea-Pyr-6)-Ph | O |
| 20-35 | Me | (CH₂)₂ | H | H | CH₂ | Bu | 4-(3-F₃C-Pyr-6)-Ph | O |
| 20-36 | Me | (CH₂)₂ | H | H | CH₂ | Bu | 4-(3-O₂N-Pyr-6)-Ph | O |
| 20-37 | Me | (CH₂)₂ | H | H | CH₂ | Bu | 2-(4-F-Ph)-5-Pyr | O |
| 20-38 | Me | (CH₂)₂ | H | H | CH₂ | Bu | 2-(4-Cl-Ph)-5-Pyr | O |
| 20-39 | Me | (CH₂)₂ | H | H | CH₂ | Bu | 2-(4-MeO-Ph)-5-Pyr | O |
| 20-40 | Me | (CH₂)₂ | H | H | CH₂ | Bu | 2-(4-EtO-Ph)-5-Pyr | O |
| 20-41 | Me | (CH₂)₂ | H | H | CH₂ | Bu | 2-(4-iPrO-Ph)-5-Pyr | O |
| 20-42 | Me | (CH₂)₂ | H | H | CH₂ | Bu | 2-TfpO-5-Pyr | O |
| 20-43 | Et | (CH₂)₂ | H | H | CH₂ | Bu | 4-Ph-Ph | O |
| 20-44 | Et | (CH₂)₂ | H | H | CH₂ | Bu | 4-(Pyr-2)-Ph | O |
| 20-45 | Et | (CH₂)₂ | H | H | CH₂ | Bu | 4-(Pyr-3)-Ph | O |
| 20-46 | Et | (CH₂)₂ | H | H | CH₂ | Bu | 4-(Pyr-4)-Ph | O |
| 20-47 | Et | (CH₂)₂ | H | H | CH₂ | Bu | 4-(3-MeO-Pyr-6)-Ph | O |
| 20-48 | Et | (CH₂)₂ | H | H | CH₂ | Bu | 4-(3-Dma-Pyr-6)-Ph | O |
| 20-49 | Et | (CH₂)₂ | H | H | CH₂ | Bu | 2-(4-F-Ph)-5-Pyr | O |
| 20-50 | Et | (CH₂)₂ | H | H | CH₂ | Bu | 2-(4-MeO-Ph)-5-Pyr | O |
| 20-51 | Et | (CH₂)₂ | H | H | CH₂ | Bu | 2-TfpO-5-Pyr | O |
| 20-52 | Bu | (CH₂)₂ | H | H | CH₂ | Bu | 4-Ph-Ph | O |
| 20-53 | Bu | (CH₂)₂ | H | H | CH₂ | Bu | 4-(Pyr-2)-Ph | O |
| 20-54 | Bu | (CH₂)₂ | H | H | CH₂ | Bu | 4-(Pyr-3)-Ph | O |
| 20-55 | Bu | (CH₂)₂ | H | H | CH₂ | Bu | 4-(Pyr-4)-Ph | O |
| 20-56 | Bu | (CH₂)₂ | H | H | CH₂ | Bu | 4-(3-MeO-Pyr-6)-Ph | O |
| 20-57 | Bu | (CH₂)₂ | H | H | CH₂ | Bu | 4-(3-Dma-Pyr-6)-Ph | O |
| 20-58 | Bu | (CH₂)₂ | H | H | CH₂ | Bu | 2-(4-F-Ph)-5-Pyr | O |
| 20-59 | Bu | (CH₂)₂ | H | H | CH₂ | Bu | 2-(4-MeO-Ph)-5-Pyr | O |
| 20-60 | Bu | (CH₂)₂ | H | H | CH₂ | Bu | 2-TfpO-5-Pyr | O |
| 20-61 | Bz | (CH₂)₂ | H | H | CH₂ | Bu | 4-Ph-Ph | O |
| 20-62 | Bz | (CH₂)₂ | H | H | CH₂ | Bu | 4-(Pyr-2)-Ph | O |
| 20-63 | Bz | (CH₂)₂ | H | H | CH₂ | Bu | 4-(Pyr-3)-Ph | O |
| 20-64 | Bz | (CH₂)₂ | H | H | CH₂ | Bu | 4-(Pyr-4)-Ph | O |
| 20-65 | Bz | (CH₂)₂ | H | H | CH₂ | Bu | 4-(3-MeO-Pyr-6)-Ph | O |
| 20-66 | Bz | (CH₂)₂ | H | H | CH₂ | Bu | 4-(3-Dma-Pyr-6)-Ph | O |
| 20-67 | Bz | (CH₂)₂ | H | H | CH₂ | Bu | 2-(4-F-Ph)-5-Pyr | O |
| 20-68 | Bz | (CH₂)₂ | H | H | CH₂ | Bu | 2-(4-MeO-Ph)-5-Pyr | O |
| 20-69 | Bz | (CH₂)₂ | H | H | CH₂ | Bu | 2-TfpO-5-Pyr | O |
| 20-70 | PPr | (CH₂)₂ | H | H | CH₂ | Bu | 4-Ph-Ph | O |
| 20-71 | PPr | (CH₂)₂ | H | H | CH₂ | Bu | 4-(Pyr-2)-Ph | O |
| 20-72 | PPr | (CH₂)₂ | H | H | CH₂ | Bu | 4-(Pyr-3)-Ph | O |
| 20-73 | PPr | (CH₂)₂ | H | H | CH₂ | Bu | 4-(Pyr-4)-Ph | O |
| 20-74 | PPr | (CH₂)₂ | H | H | CH₂ | Bu | 4-(3-MeO-Pyr-6)-Ph | O |

TABLE 20-continued

| Ex. No. Comp. | R¹ | R² | R³ | R⁴ | Z | W | X | Y |
|---|---|---|---|---|---|---|---|---|
| 20-75 | PPr | (CH₂)₂ | H | H | CH₂ | Bu | 4-(3-Dma-Pyr-6)-Ph | O |
| 20-76 | PPr | (CH₂)₂ | H | H | CH₂ | Bu | 2-(4-F-Ph)-5-Pyr | O |
| 20-77 | PPr | (CH₂)₂ | H | H | CH₂ | Bu | 2-(4-MeO-Ph)-5-Pyr | O |
| 20-78 | PPr | (CH₂)₂ | H | H | CH₂ | Bu | 2-TfpO-5-Pyr | O |
| 20-79 | Me | (CH₂)₃ | H | H | CH₂ | Bu | 4-Ph-Ph | O |
| 20-80 | Me | (CH₂)₃ | H | H | CH₂ | Bu | 4-(Pyr-2)-Ph | O |
| 20-81 | Me | (CH₂)₃ | H | H | CH₂ | Bu | 4-(Pyr-3)-Ph | O |
| 20-82 | Me | (CH₂)₃ | H | H | CH₂ | Bu | 4-(Pyr-4)-Ph | O |
| 20-83 | Me | (CH₂)₃ | H | H | CH₂ | Bu | 4-(3-MeO)-Pyr-6)-Ph | O |
| 20-84 | Me | (CH₂)₃ | H | H | CH₂ | Bu | 4-(3-Dma-Pyr-6)-Ph | O |
| 20-85 | Me | (CH₂)₃ | H | H | CH₂ | Bu | 2-(4-F-Ph)-5-Pyr | O |
| 20-86 | Me | (CH₂)₃ | H | H | CH₂ | Bu | 2-(4-MeO-Ph)-5-Pyr | O |
| 20-87 | Me | (CH₂)₃ | H | H | CH₂ | Bu | 2-TfpO-5-Pyr | O |

TABLE 21

| Ex. No. Comp. | R¹ | R² | R³ | R⁴ | Z | W | X | Y |
|---|---|---|---|---|---|---|---|---|
| 21-1 | Me | (CH₂)₂ | H | H | CH₂ | Pen | Ph | O |
| 21-2 | Me | (CH₂)₂ | H | H | CH₂ | Pen | 4-Ph-Ph | O |
| 21-3 | Me | (CH₂)₂ | H | H | CH₂ | Pen | 4-(Pyr-2)-Ph | O |
| 21-4 | Me | (CH₂)₂ | H | H | CH₂ | Pen | 4-(Pyr-3)-Ph | O |
| 21-5 | Me | (CH₂)₂ | H | H | CH₂ | Pen | 4-(Pyr-4)-Ph | O |
| 21-6 | Me | (CH₂)₂ | H | H | CH₂ | Pen | 2-Pyr | O |
| 21-7 | Me | (CH₂)₂ | H | H | CH₂ | Pen | 3-Pyr | O |
| 21-8 | Me | (CH₂)₂ | H | H | CH₂ | Pen | 4-Pyr | O |
| 21-9 | Me | (CH₂)₂ | H | H | CH₂ | Pen | 2-Me-5-Pyr | O |
| 21-10 | Me | (CH₂)₂ | H | H | CH₂ | Pen | 2-Me-3-Pyr | O |
| 21-11 | Me | (CH₂)₂ | H | H | CH₂ | Pen | 2-MeO-5-Pyr | O |
| 21-12 | Me | (CH₂)₂ | H | H | CH₂ | Pen | 2-EtO-5-Pyr | O |
| 21-13 | Me | (CH₂)₂ | H | H | CH₂ | Pen | 2-iPrO-5-Pyr | O |
| 21-14 | Me | (CH₂)₂ | H | H | CH₂ | Pen | 2-MeS-5-Pyr | O |
| 21-15 | Me | (CH₂)₂ | H | H | CH₂ | Pen | 2-EtS-5-Pyr | O |
| 21-16 | Me | (CH₂)₂ | H | H | CH₂ | Pen | 2-Ph-5-Pyr | O |
| 21-17 | Me | (CH₂)₂ | H | H | CH₂ | Pen | 3-Ph-6-Pyr | O |

TABLE 22

| Ex. No. Comp. | R¹ | R² | R³ | R⁴ | Z | W | X | Y |
|---|---|---|---|---|---|---|---|---|
| 22-1 | Me | (CH₂)₂ | H | H | CH₂ | MeS | Ph | O |
| 22-2 | Me | (CH₂)₂ | H | H | CH₂ | MeS | 4-Ph-Ph | O |
| 22-3 | Me | (CH₂)₂ | H | H | CH₂ | MeS | 4-(Pyr-2)-Ph | O |
| 22-4 | Me | (CH₂)₂ | H | H | CH₂ | MeS | 4-(Pyr-3)-Ph | O |
| 22-5 | Me | (CH₂)₂ | H | H | CH₂ | MeS | 4-(Pyr-4)-Ph | O |
| 22-6 | Me | (CH₂)₂ | H | H | CH₂ | MeS | 2-Pyr | O |
| 22-7 | Me | (CH₂)₂ | H | H | CH₂ | MeS | 3-Pyr | O |
| 22-8 | Me | (CH₂)₂ | H | H | CH₂ | MeS | 4-Pyr | O |
| 22-9 | Me | (CH₂)₂ | H | H | CH₂ | MeS | 2-Me-5-Pyr | O |
| 22-10 | Me | (CH₂)₂ | H | H | CH₂ | MeS | 2-Me-3-Pyr | O |
| 22-11 | Me | (CH₂)₂ | H | H | CH₂ | MeS | 2-MeO-5-Pyr | O |
| 22-12 | Me | (CH₂)₂ | H | H | CH₂ | MeS | 2-EtO-5-Pyr | O |
| 22-13 | Me | (CH₂)₂ | H | H | CH₂ | MeS | 2-iPrO-5-Pyr | O |
| 22-14 | Me | (CH₂)₂ | H | H | CH₂ | MeS | 2-MeS-5-Pyr | O |
| 22-15 | Me | (CH₂)₂ | H | H | CH₂ | MeS | 2-EtS-5-Pyr | O |
| 22-16 | Me | (CH₂)₂ | H | H | CH₂ | MeS | 2-Ph-5-Pyr | O |
| 22-17 | Me | (CH₂)₂ | H | H | CH₂ | MeS | 3-Ph-6-Pyr | O |

TABLE 23

| Ex. No. Comp. | R¹ | R² | R³ | R⁴ | Z | W | X | Y |
|---|---|---|---|---|---|---|---|---|
| 23-1 | Me | (CH₂)₂ | H | H | CH₂ | PhO | Ph | O |
| 23-2 | Me | (CH₂)₂ | H | H | CH₂ | PhO | 4-Ph-Ph | O |
| 23-3 | Me | (CH₂)₂ | H | H | CH₂ | PhO | 4-(Pyr-2)-Ph | O |
| 23-4 | Me | (CH₂)₂ | H | H | CH₂ | PhO | 4-(Pyr-3)-Ph | O |
| 23-5 | Me | (CH₂)₂ | H | H | CH₂ | PhO | 4-(Pyr-4)-Ph | O |
| 23-6 | Me | (CH₂)₂ | H | H | CH₂ | PhO | 2-Pyr | O |
| 23-7 | Me | (CH₂)₂ | H | H | CH₂ | PhO | 3-Pyr | O |
| 23-8 | Me | (CH₂)₂ | H | H | CH₂ | PhO | 4-Pyr | O |
| 23-9 | Me | (CH₂)₂ | H | H | CH₂ | PhO | 2-Me-5-Pyr | O |
| 23-10 | Me | (CH₂)₂ | H | H | CH₂ | PhO | 2-Me-3-Pyr | O |
| 23-11 | Me | (CH₂)₂ | H | H | CH₂ | PhO | 2-MeO-5-Pyr | O |
| 23-12 | Me | (CH₂)₂ | H | H | CH₂ | PhO | 2-EtO-5-Pyr | O |
| 23-13 | Me | (CH₂)₂ | H | H | CH₂ | PhO | 2-iPrO-5-Pyr | O |
| 23-14 | Me | (CH₂)₂ | H | H | CH₂ | PhO | 2-MeS-5-Pyr | O |
| 23-15 | Me | (CH₂)₂ | H | H | CH₂ | PhO | 2-EtS-5-Pyr | O |
| 23-16 | Me | (CH₂)₂ | H | H | CH₂ | PhO | 2-Ph-5-Pyr | O |
| 23-17 | Me | (CH₂)₂ | H | H | CH₂ | PhO | 3-Ph-6-Pyr | O |

TABLE 24

| Ex. No. Comp. | R¹ | R² | R³ | R⁴ | Z | W | X | Y |
|---|---|---|---|---|---|---|---|---|
| 24-1 | Me | (CH₂)₂ | H | H | CH₂ | 4-iPr-PhO | Ph | O |
| 24-2 | Me | (CH₂)₂ | H | H | CH₂ | 4-iPr-PhO | 4-Ph-Ph | O |
| 24-3 | Me | (CH₂)₂ | H | H | CH₂ | 4-iPr-PhO | 4-(Pyr-2)-Ph | O |
| 24-4 | Me | (CH₂)₂ | H | H | CH₂ | 4-iPr-PhO | 4-(Pyr-3)-Ph | O |
| 24-5 | Me | (CH₂)₂ | H | H | CH₂ | 4-iPr-PhO | 4-(Pyr-4)-Ph | O |
| 24-6 | Me | (CH₂)₂ | H | H | CH₂ | 4-iPr-PhO | 2-Pyr | O |
| 24-7 | Me | (CH₂)₂ | H | H | CH₂ | 4-iPr-PhO | 3-Pyr | O |
| 24-8 | Me | (CH₂)₂ | H | H | CH₂ | 4-iPr-PhO | 4-Pyr | O |
| 24-9 | Me | (CH₂)₂ | H | H | CH₂ | 4-iPr-PhO | 2-Me-5-Pyr | O |
| 24-10 | Me | (CH₂)₂ | H | H | CH₂ | 4-iPr-PhO | 2-Me-3-Pvr | O |
| 24-11 | Me | (CH₂)₂ | H | H | CH₂ | 4-iPr-PhO | 2-MeO-5-Pyr | O |
| 24-12 | Me | (CH₂)₂ | H | H | CH₂ | 4-iPr-PhO | 2-EtO-5-Pyr | O |
| 24-13 | Me | (CH₂)₂ | H | H | CH₂ | 4-iPr-PhO | 2-iPrO-5-Pyr | O |
| 24-14 | Me | (CH₂)₂ | H | H | CH₂ | 4-iPr-PhO | 2-MeS-5-Pyr | O |
| 24-15 | Me | (CH₂)₂ | H | H | CH₂ | 4-iPr-PhO | 2-EtS-5-Pyr | O |
| 24-16 | Me | (CH₂)₂ | H | H | CH₂ | 4-iPr-PhO | 2-Ph-5-Pyr | O |
| 24-17 | Me | (CH₂)₂ | H | H | CH₂ | 4-iPr-PhO | 3-Ph-6-Pyr | O |

TABLE 25

| Ex. No. Comp. | R¹ | R² | R³ | R⁴ | Z | W | X | Y |
|---|---|---|---|---|---|---|---|---|
| 25-1 | Me | (CH₂)₂ | H | H | CH₂ | 4-MeO-PhO | Ph | O |
| 25-2 | Me | (CH₂)₂ | H | H | CH₂ | 4-MeO-PhO | 4-Ph-Ph | O |
| 25-3 | Me | (CH₂)₂ | H | H | CH₂ | 4-MeO-PhO | 4-(Pyr-2)-Ph | O |
| 25-4 | Me | (CH₂)₂ | H | H | CH₂ | 4-MeO-PhO | 4-(Pyr-3)-Ph | O |
| 25-5 | Me | (CH₂)₂ | H | H | CH₂ | 4-MeO-PhO | 4-(Pyr-4)-Ph | O |
| 25-6 | Me | (CH₂)₂ | H | H | CH₂ | 4-MeO-PhO | 2-Pyr | O |
| 25-7 | Me | (CH₂)₂ | H | H | CH₂ | 4-MeO-PhO | 3-Pyr | O |
| 25-8 | Me | (CH₂)₂ | H | H | CH₂ | 4-MeO-PhO | 4-Pyr | O |
| 25-9 | Me | (CH₂)₂ | H | H | CH₂ | 4-MeO-PhO | 2-Me-5-Pyr | O |
| 25-10 | Me | (CH₂)₂ | H | H | CH₂ | 4-MeO-PhO | 2-Me-3-Pyr | O |
| 25-11 | Me | (CH₂)₂ | H | H | CH₂ | 4-MeO-PhO | 2-MeO-5-Pyr | O |
| 25-12 | Me | (CH₂)₂ | H | H | CH₂ | 4-MeO-PhO | 2-EtO-5-Pyr | O |
| 25-13 | Me | (CH₂)₂ | H | H | CH₂ | 4-MeO-PhO | 2-iPrO-5-Pyr | O |
| 25-14 | Me | (CH₂)₂ | H | H | CH₂ | 4-MeO-PhO | 2-MeS-5-Pyr | O |
| 25-15 | Me | (CH₂)₂ | H | H | CH₂ | 4-MeO-PhO | 2-EtS-5-Pyr | O |
| 25-16 | Me | (CH₂)₂ | H | H | CH₂ | 4-MeO-PhO | 2-Ph-5-Pyr | O |
| 25-17 | Me | (CH₂)₂ | H | H | CH₂ | 4-MeO-PhO | 3-Ph-6-Pyr | O |

TABLE 26

| Ex. No. Comp. | R¹ | R² | R³ | R⁴ | Z | W | X | Y |
|---|---|---|---|---|---|---|---|---|
| 26-1 | Me | (CH₂)₂ | H | H | CH₂ | PhS | Ph | O |
| 26-2 | Me | (CH₂)₂ | H | H | CH₂ | PhS | 4-Ph-Ph | O |
| 26-3 | Me | (CH₂)₂ | H | H | CH₂ | PhS | 4-(Pyr-2)-Ph | O |
| 26-4 | Me | (CH₂)₂ | H | H | CH₂ | PhS | 4-(Pyr-3)-Ph | O |
| 26-5 | Me | (CH₂)₂ | H | H | CH₂ | PhS | 4-(Pyr-4)-Ph | O |
| 26-6 | Me | (CH₂)₂ | H | H | CH₂ | PhS | 2-Pyr | O |
| 26-7 | Me | (CH₂)₂ | H | H | CH₂ | PhS | 3-Pyr | O |
| 26-8 | Me | (CH₂)₂ | H | H | CH₂ | PhS | 4-Pyr | O |
| 26-9 | Me | (CH₂)₂ | H | H | CH₂ | PhS | 2-Me-5-Pyr | O |
| 26-10 | Me | (CH₂)₂ | H | H | CH₂ | PhS | 2-Me-3-Pyr | O |
| 26-11 | Me | (CH₂)₂ | H | H | CH₂ | PhS | 2-MeO-5-Pyr | O |
| 26-12 | Me | (CH₂)₂ | H | H | CH₂ | PhS | 2-EtO-5-Pyr | O |
| 26-13 | Me | (CH₂)₂ | H | H | CH₂ | PhS | 2-iPrO-5-Pyr | O |
| 26-14 | Me | (CH₂)₂ | H | H | CH₂ | PhS | 2-MeS-5-Pyr | O |
| 26-15 | Me | (CH₂)₂ | H | H | CH₂ | PhS | 2-EtS-5-Pyr | O |
| 26-16 | Me | (CH₂)₂ | H | H | CH₂ | PhS | 2-Ph-5-Pyr | O |
| 26-17 | Me | (CH₂)₂ | H | H | CH₂ | PhS | 3-Ph-6-Pyr | O |

TABLE 27

| Ex. No. Comp. | R¹ | R² | R³ | R⁴ | Z | W | X | Y |
|---|---|---|---|---|---|---|---|---|
| 27-1 | Me | (CH₂)₂ | H | H | CH₂ | Ph(CH₂)₃ | Ph | O |
| 27-2 | Me | (CH₂)₂ | H | H | CH₂ | Ph(CH₂)₃ | 4-Ph-Ph | O |
| 27-3 | Me | (CH₂)₂ | H | H | CH₂ | Ph(CH₂)₃ | 4-(Pyr-2)-Ph | O |
| 27-4 | Me | (CH₂)₂ | H | H | CH₂ | Ph(CH₂)₃ | 4-(Pyr-3)-Ph | O |
| 27-5 | Me | (CH₂)₂ | H | H | CH₂ | Ph(CH₂)₃ | 4-(Pyr-4)-Ph | O |
| 27-6 | Me | (CH₂)₂ | H | H | CH₂ | Ph(CH₂)₃ | 2-Pyr | O |
| 27-7 | Me | (CH₂)₂ | H | H | CH₂ | Ph(CH₂)₃ | 3-Pyr | O |
| 27-8 | Me | (CH₂)₂ | H | H | CH₂ | Ph(CH₂)₃ | 4-Pyr | O |
| 27-9 | Me | (CH₂)₂ | H | H | CH₂ | Ph(CH₂)₃ | 2-Me-5-Pyr | O |
| 27-10 | Me | (CH₂)₂ | H | H | CH₂ | Ph(CH₂)₃ | 2-Me-3-Pyr | O |
| 27-11 | Me | (CH₂)₂ | H | H | CH₂ | Ph(CH₂)₃ | 2-MeO-5-Pyr | O |
| 27-12 | Me | (CH₂)₂ | H | H | CH₂ | Ph(CH₂)₃ | 2-EtO-5-Pyr | O |
| 27-13 | Me | (CH₂)₂ | H | H | CH₂ | Ph(CH₂)₃ | 2-iPrO-5-Pyr | O |
| 27-14 | Me | (CH₂)₂ | H | H | CH₂ | Ph(CH₂)₃ | 2-MeS-5-Pyr | O |
| 27-15 | Me | (CH₂)₂ | H | H | CH₂ | Ph(CH₂)₃ | 2-EtS-5-Pyr | O |
| 27-16 | Me | (CH₂)₂ | H | H | CH₂ | Ph(CH₂)₃ | 2-Ph-5-Pyr | O |
| 27-17 | Me | (CH₂)₂ | H | H | CH₂ | Ph(CH₂)₃ | 3-Ph-6-Pyr | O |

TABLE 28

| Ex. No. Comp. | R¹ | R² | R³ | R⁴ | Z | W | X | Y |
|---|---|---|---|---|---|---|---|---|
| 28-1 | H | (CH₂)₂ | H | Me | CH₂ | EtO | Ph | O |
| 28-2 | H | (CH₂)₂ | H | Me | CH₂ | EtO | 4-Ph—Ph | O |
| 28-3 | H | (CH₂)₂ | H | Me | CH₂ | EtO | 4-(Pyr-2)-Ph | O |
| 28-4 | H | (CH₂)₂ | H | Me | CH₂ | EtO | 4-(Pyr-3)-Ph | O |
| 28-5 | H | (CH₂)₂ | H | Me | CH₂ | EtO | 4-(Pyr-4)-Ph | O |
| 28-6 | H | (CH₂)₂ | H | Me | CH₂ | EtO | 2-Pyr | O |
| 28-7 | H | (CH₂)₂ | H | Me | CH₂ | EtO | 3-Pyr | O |
| 28-8 | H | (CH₂)₂ | H | Me | CH₂ | EtO | 4-Pyr | O |

TABLE 28-continued

| Ex. No. Comp. | R$^1$ | R$^2$ | R$^3$ | R$^4$ | Z | W | X | Y |
|---|---|---|---|---|---|---|---|---|
| 28-9 | H | (CH$_2$)$_2$ | H | Me | CH$_2$ | EtO | 2-Me-5-Pyr | O |
| 28-10 | H | (CH$_2$)$_2$ | H | Me | CH$_2$ | EtO | 2-Me-3-Pyr | O |
| 28-11 | H | (CH$_2$)$_2$ | H | Me | CH$_2$ | EtO | 2-MeO-5-Pyr | O |
| 28-12 | H | (CH$_2$)$_2$ | H | Me | CH$_2$ | EtO | 2-EtO-5-Pyr | O |
| 28-13 | H | (CH$_2$)$_2$ | H | Me | CH$_2$ | EtO | 2-iPrO-5-Pyr | O |
| 28-14 | H | (CH$_2$)$_2$ | H | Me | CH$_2$ | EtO | 2-MeS-5-Pyr | O |
| 28-15 | H | (CH$_2$)$_2$ | H | Me | CH$_2$ | EtO | 2-EtS-5-Pyr | O |
| 28-16 | H | (CH$_2$)$_2$ | H | Me | CH$_2$ | EtO | 2-Ph-5-Pyr | O |
| 28-17 | H | (CH$_2$)$_2$ | H | Me | CH$_2$ | EtO | 3-Ph-6-Pyr | O |
| 28-18 | H | (CH$_2$)$_2$ | H | Me | CH$_2$ | EtO | 4-(4-Me—Ph)—Ph | O |
| 28-19 | H | (CH$_2$)$_2$ | H | Me | CH$_2$ | EtO | 4-(4-F—Ph)—Ph | O |
| 28-20 | H | (CH$_2$)$_2$ | H | Me | CH$_2$ | EtO | 4-(4-Cl—Ph)—Ph | O |
| 28-21 | H | (CH$_2$)$_2$ | H | Me | CH$_2$ | EtO | 4-(4-HO-3,5-di-Me—Ph)—Ph | O |
| 28-22 | H | (CH$_2$)$_2$ | H | Me | CH$_2$ | EtO | 4-(4-MeO—Ph)—Ph | O |
| 28-23 | H | (CH$_2$)$_2$ | H | Me | CH$_2$ | EtO | 4-(4-HO—Ph)—Ph | O |
| 28-24 | H | (CH$_2$)$_2$ | H | Me | CH$_2$ | EtO | 4-(4-OHC—Ph)—Ph | O |
| 28-25 | H | (CH$_2$)$_2$ | H | Me | CH$_2$ | EtO | 4-(4-Dma—Ph)—Ph | O |
| 28-26 | H | (CH$_2$)$_2$ | H | Me | CH$_2$ | EtO | 4-(3-MeO—Ph)—Ph | O |
| 28-27 | H | (CH$_2$)$_2$ | H | Me | CH$_2$ | EtO | 4-(3-HO—Ph)—Ph | O |
| 28-28 | H | (CH$_2$)$_2$ | H | Me | CH$_2$ | EtO | 4-(3-Dma—Ph)—Ph | O |
| 28-29 | H | (CH$_2$)$_2$ | H | Me | CH$_2$ | EtO | 4-(2-MeO—Ph)—Ph | O |
| 28-30 | H | (CH$_2$)$_2$ | H | Me | CH$_2$ | EtO | 4-(2-HO—Ph)—Ph | O |
| 28-31 | H | (CH$_2$)$_2$ | H | Me | CH$_2$ | EtO | 4-(3-MeO—Pyr-6)-Ph | O |
| 28-32 | H | (CH$_2$)$_2$ | H | Me | CH$_2$ | EtO | 4-(3-EtO—Pyr-6)-Ph | O |
| 28-33 | H | (CH$_2$)$_2$ | H | Me | CH$_2$ | EtO | 4-(3-iPrO—Pyr-6)-Ph | O |
| 28-34 | H | (CH$_2$)$_2$ | H | Me | CH$_2$ | EtO | 4-(3-Dma—Pyr-6)-Ph | O |
| 28-35 | H | (CH$_2$)$_2$ | H | Me | CH$_2$ | EtO | 4-(3-Dea—Pyr-6)-Ph | O |
| 28-36 | H | (CH$_2$)$_2$ | H | Me | CH$_2$ | EtO | 4-(3-F$_3$C—Pyr-6)-Ph | O |
| 28-37 | H | (CH$_2$)$_2$ | H | Me | CH$_2$ | EtO | 4-(3-O$_2$N—Pyr-6)-Ph | O |
| 28-38 | H | (CH$_2$)$_2$ | H | Me | CH$_2$ | EtO | 2-(4-F—Ph)-5-Pyr | O |
| 28-39 | H | (CH$_2$)$_2$ | H | Me | CH$_2$ | EtO | 2-(4-Cl—Ph)-5-Pyr | O |
| 28-40 | H | (CH$_2$)$_2$ | H | Me | CH$_2$ | EtO | 2-(4-MeO—Ph)-5-Pyr | O |
| 28-41 | H | (CH$_2$)$_2$ | H | Me | CH$_2$ | EtO | 2-(4-EtO—Ph)-5-Pyr | O |
| 28-42 | H | (CH$_2$)$_2$ | H | Me | CH$_2$ | EtO | 2-(4-iPrO—Ph)-5-Pyr | O |
| 28-43 | H | (CH$_2$)$_2$ | H | Me | CH$_2$ | EtO | 2-TfpO-5-Pyr | O |

TABLE 29

| Ex. No. Comp. | R$^1$ | R$^2$ | R$^3$ | R$^4$ | Z | W | X | Y |
|---|---|---|---|---|---|---|---|---|
| 29-1 | H | (CH$_2$)$_2$ | H | Me | CH$_2$ | Pr | Ph | O |
| 29-2 | H | (CH$_2$)$_2$ | H | Me | CH$_2$ | Pr | 4-Ph—Ph | O |
| 29-3 | H | (CH$_2$)$_2$ | H | Me | CH$_2$ | Pr | 4-(Pyr-2)-Ph | O |
| 29-4 | H | (CH$_2$)$_2$ | H | Me | CH$_2$ | Pr | 4-(Pyr-3)-Ph | O |
| 29-5 | H | (CH$_2$)$_2$ | H | Me | CH$_2$ | Pr | 4-(Pyr-4)-Ph | O |
| 29-6 | H | (CH$_2$)$_2$ | H | Me | CH$_2$ | Pr | 2-Pyr | O |
| 29-7 | H | (CH$_2$)$_2$ | H | Me | CH$_2$ | Pr | 3-Pyr | O |
| 29-8 | H | (CH$_2$)$_2$ | H | Me | CH$_2$ | Pr | 4-Pyr | O |
| 29-9 | H | (CH$_2$)$_2$ | H | Me | CH$_2$ | Pr | 2-Me-5-Pyr | O |
| 29-10 | H | (CH$_2$)$_2$ | H | Me | CH$_2$ | Pr | 2-Me-3-Pyr | O |
| 29-11 | H | (CH$_2$)$_2$ | H | Me | CH$_2$ | Pr | 2-MeO-5-Pyr | O |
| 29-12 | H | (CH$_2$)$_2$ | H | Me | CH$_2$ | Pr | 2-EtO-5-Pyr | O |
| 29-13 | H | (CH$_2$)$_2$ | H | Me | CH$_2$ | Pr | 2-iPrO-5-Pyr | O |
| 29-14 | H | (CH$_2$)$_2$ | H | Me | CH$_2$ | Pr | 2-MeS-5-Pyr | O |
| 29-15 | H | (CH$_2$)$_2$ | H | Me | CH$_2$ | Pr | 2-EtS-5-Pyr | O |
| 29-16 | H | (CH$_2$)$_2$ | H | Me | CH$_2$ | Pr | 2-Ph-5-Pyr | O |
| 29-17 | H | (CH$_2$)$_2$ | H | Me | CH$_2$ | Pr | 3-Ph-6-Pyr | O |
| 29-18 | H | (CH$_2$)$_2$ | H | Me | CH$_2$ | Pr | 4-(4-Me—Ph)—Ph | O |
| 29-19 | H | (CH$_2$)$_2$ | H | Me | CH$_2$ | Pr | 4-(4-F—Ph)—Ph | O |
| 29-20 | H | (CH$_2$)$_2$ | H | Me | CH$_2$ | Pr | 4-(4-Cl—Ph)—Ph | O |
| 29-21 | H | (CH$_2$)$_2$ | H | Me | CH$_2$ | Pr | 4-(4-HO-3,5-di-Me—Ph)—Ph | O |
| 29-22 | H | (CH$_2$)$_2$ | H | Me | CH$_2$ | Pr | 4-(4-MeO—Ph)—Ph | O |
| 29-23 | H | (CH$_2$)$_2$ | H | Me | CH$_2$ | Pr | 4-(4-HO—Ph)—Ph | O |
| 29-24 | H | (CH$_2$)$_2$ | H | Me | CH$_2$ | Pr | 4-(4-OHC—Ph)—Ph | O |
| 29-25 | H | (CH$_2$)$_2$ | H | Me | CH$_2$ | Pr | 4-(4-Dma—Ph)—Ph | O |
| 29-26 | H | (CH$_2$)$_2$ | H | Me | CH$_2$ | Pr | 4-(3-MeO—Ph)—Ph | O |
| 29-27 | H | (CH$_2$)$_2$ | H | Me | CH$_2$ | Pr | 4-(3-HO—Ph)—Ph | O |
| 29-28 | H | (CH$_2$)$_2$ | H | Me | CH$_2$ | Pr | 4-(3-Dma—Ph)—Ph | O |
| 29-29 | H | (CH$_2$)$_2$ | H | Me | CH$_2$ | Pr | 4-(2-MeO—Ph)—Ph | O |
| 29-30 | H | (CH$_2$)$_2$ | H | Me | CH$_2$ | Pr | 4-(2-HO—Ph)—Ph | O |
| 29-31 | H | (CH$_2$)$_2$ | H | Me | CH$_2$ | Pr | 4-(3-MeO—Pyr-6)-Ph | O |
| 29-32 | H | (CH$_2$)$_2$ | H | Me | CH$_2$ | Pr | 4-(3-EtO—Pyr-6)-Ph | O |
| 29-33 | H | (CH$_2$)$_2$ | H | Me | CH$_2$ | Pr | 4-(3-iPrO—Pyr-6)-Ph | O |
| 29-34 | H | (CH$_2$)$_2$ | H | Me | CH$_2$ | Pr | 4-(3-Dma—Pyr-6)-Ph | O |
| 29-35 | H | (CH$_2$)$_2$ | H | Me | CH$_2$ | Pr | 4-(3-Dea—Pyr-6)-Ph | O |
| 29-36 | H | (CH$_2$)$_2$ | H | Me | CH$_2$ | Pr | 4-(3-F$_3$C—Pyr-6)-Ph | O |
| 29-37 | H | (CH$_2$)$_2$ | H | Me | CH$_2$ | Pr | 4-(3-O$_2$N—Pyr-6)-Ph | O |
| 29-38 | H | (CH$_2$)$_2$ | H | Me | CH$_2$ | Pr | 2-(4-F—Ph)-5-Pyr | O |
| 29-39 | H | (CH$_2$)$_2$ | H | Me | CH$_2$ | Pr | 2-(4-Cl—Ph)-5-Pyr | O |
| 29-40 | H | (CH$_2$)$_2$ | H | Me | CH$_2$ | Pr | 2-(4-MeO—Ph)-5-Pyr | O |
| 29-41 | H | (CH$_2$)$_2$ | H | Me | CH$_2$ | Pr | 2-(4-EtO—Ph)-5-Pyr | O |
| 29-42 | H | (CH$_2$)$_2$ | H | Me | CH$_2$ | Pr | 2-(4-iPrO—Ph)-5-Pyr | O |
| 29-43 | H | (CH$_2$)$_2$ | H | Me | CH$_2$ | Pr | 2-TfpO-5-Pyr | O |

TABLE 30

| Ex. No. Comp. | R$^1$ | R$^2$ | R$^3$ | R$^4$ | Z | W | X | Y |
|---|---|---|---|---|---|---|---|---|
| 30-1 | H | (CH$_2$)$_2$ | H | Me | CH$_2$ | Bu | Ph | O |
| 30-2 | H | (CH$_2$)$_2$ | H | Me | CH$_2$ | Bu | 4-Ph—Ph | O |
| 30-3 | H | (CH$_2$)$_2$ | H | Me | CH$_2$ | Bu | 4-(Pyr-2)-Ph | O |

TABLE 30-continued

| Ex. No. Comp. | R¹ | R² | R³ | R⁴ | Z | W | X | Y |
|---|---|---|---|---|---|---|---|---|
| 30-4 | H | (CH₂)₂ | H | Me | CH₂ | Bu | 4-(Pyr-3)-Ph | O |
| 30-5 | H | (CH₂)₂ | H | Me | CH₂ | Bu | 4-(Pyr-4)-Ph | O |
| 30-6 | H | (CH₂)₂ | H | Me | CH₂ | Bu | 2-Pyr | O |
| 30-7 | H | (CH₂)₂ | H | Me | CH₂ | Bu | 3-Pyr | O |
| 30-8 | H | (CH₂)₂ | H | Me | CH₂ | Bu | 4-Pyr | O |
| 30-9 | H | (CH₂)₂ | H | Me | CH₂ | Bu | 2-Me-5-Pyr | O |
| 30-10 | H | (CH₂)₂ | H | Me | CH₂ | Bu | 2-Me-3-Pyr | O |
| 30-11 | H | (CH₂)₂ | H | Me | CH₂ | Bu | 2-MeO-5-Pyr | O |
| 30-12 | H | (CH₂)₂ | H | Me | CH₂ | Bu | 2-EtO-5-Pyr | O |
| 30-13 | H | (CH₂)₂ | H | Me | CH₂ | Bu | 2-iPrO-5-Pyr | O |
| 30-14 | H | (CH₂)₂ | H | Me | CH₂ | Bu | 2-MeS-5-Pyr | O |
| 30-15 | H | (CH₂)₂ | H | Me | CH₂ | Bu | 2-EtS-5-Pyr | O |
| 30-16 | H | (CH₂)₂ | H | Me | CH₂ | Bu | 2-Ph-5-Pyr | O |
| 30-17 | H | (CH₂)₂ | H | Me | CH₂ | Bu | 3-Ph-6-Pyr | O |
| 30-18 | H | (CH₂)₂ | H | Me | CH₂ | Bu | 4-(4-Me—Ph)—Ph | O |
| 30-19 | H | (CH₂)₂ | H | Me | CH₂ | Bu | 4-(4-F—Ph)—Ph | O |
| 30-20 | H | (CH₂)₂ | H | Me | CH₂ | Bu | 4-(4-Cl—Ph)—Ph | O |
| 30-21 | H | (CH₂)₂ | H | Me | CH₂ | Bu | 4-(4-HO-3,5-di-Me—Ph)—Ph | O |
| 30-22 | H | (CH₂)₂ | H | Me | CH₂ | Bu | 4-(4-MeO—Ph)—Ph | O |
| 30-23 | H | (CH₂)₂ | H | Me | CH₂ | Bu | 4-(4-HO—Ph)—Ph | O |
| 30-24 | H | (CH₂)₂ | H | Me | CH₂ | Bu | 4-(4-OHC—Ph)—Ph | O |
| 30-25 | H | (CH₂)₂ | H | Me | CH₂ | Bu | 4-(4-Dma—Ph)—Ph | O |
| 30-26 | H | (CH₂)₂ | H | Me | CH₂ | Bu | 4-(3-MeO—Ph)—Ph | O |
| 30-27 | H | (CH₂)₂ | H | Me | CH₂ | Bu | 4-(3-HO—Ph)—Ph | O |
| 30-28 | H | (CH₂)₂ | H | Me | CH₂ | Bu | 4-(3-Dma—Ph)—Ph | O |
| 30-29 | H | (CH₂)₂ | H | Me | CH₂ | Bu | 4-(2-MeO—Ph)—Ph | O |
| 30-30 | H | (CH₂)₂ | H | Me | CH₂ | Bu | 4-(2-HO—Ph)—Ph | O |
| 30-31 | H | (CH₂)₂ | H | Me | CH₂ | Bu | 4-(3-MeO—Pyr-6)-Ph | O |
| 30-32 | H | (CH₂)₂ | H | Me | CH₂ | Bu | 4-(3-EtO—Pyr-6)-Ph | O |
| 30-33 | H | (CH₂)₂ | H | Me | CH₂ | Bu | 4-(3-iPrO—Pyr-6)-Ph | O |
| 30-34 | H | (CH₂)₂ | H | Me | CH₂ | Bu | 4-(3-Dma—Pyr-6)-Ph | O |
| 30-35 | H | (CH₂)₂ | H | Me | CH₂ | Bu | 4-(3-Dea—Pyr-6)-Ph | O |
| 30-36 | H | (CH₂)₂ | H | Me | CH₂ | Bu | 4-(3-F₃C—Pyr-6)-Ph | O |
| 30-37 | H | (CH₂)₂ | H | Me | CH₂ | Bu | 4-(3-O₂N—Pyr-6)-Ph | O |
| 30-38 | H | (CH₂)₂ | H | Me | CH₂ | Bu | 2-(4-F—Ph)-5-Pyr | O |
| 30-39 | H | (CH₂)₂ | H | Me | CH₂ | Bu | 2-(4-Cl—Ph)-5-Pyr | O |
| 30-40 | H | (CH₂)₂ | H | Me | CH₂ | Bu | 2-(4-MeO—Ph)-5-Pyr | O |
| 30-41 | H | (CH₂)₂ | H | Me | CH₂ | Bu | 2-(4-EtO—Ph)-5-Pyr | O |
| 30-42 | H | (CH₂)₂ | H | Me | CH₂ | Bu | 2-(4-iPrO—Ph)-5-Pyr | O |
| 30-43 | H | (CH₂)₂ | H | Me | CH₂ | Bu | 2-TfpO-5-Pyr | O |

TABLE 31

| Ex. No. Comp. | R¹ | R² | R³ | R⁴ | Z | W | X | Y |
|---|---|---|---|---|---|---|---|---|
| 31-1 | H | (CH₂)₂ | H | Me | CH₂ | Pen | Ph | O |
| 31-2 | H | (CH₂)₂ | H | Me | CH₂ | Pen | 4-Ph—Ph | O |
| 31-3 | H | (CH₂)₂ | H | Me | CH₂ | Pen | 4-(Pyr-2)-Ph | O |
| 31-4 | H | (CH₂)₂ | H | Me | CH₂ | Pen | 4-(Pyr-3)-Ph | O |
| 31-5 | H | (CH₂)₂ | H | Me | CH₂ | Pen | 4-(Pyr-4)-Ph | O |
| 31-6 | H | (CH₂)₂ | H | Me | CH₂ | Pen | 2-Pyr | O |
| 31-7 | H | (CH₂)₂ | H | Me | CH₂ | Pen | 3-Pyr | O |
| 31-8 | H | (CH₂)₂ | H | Me | CH₂ | Pen | 4-Pyr | O |
| 31-9 | H | (CH₂)₂ | H | Me | CH₂ | Pen | 2-Me-5-Pyr | O |
| 31-10 | H | (CH₂)₂ | H | Me | CH₂ | Pen | 2-Me-3-Pyr | O |
| 31-11 | H | (CH₂)₂ | H | Me | CH₂ | Pen | 2-MeO-5-Pyr | O |
| 31-12 | H | (CH₂)₂ | H | Me | CH₂ | Pen | 2-EtO-5-Pyr | O |
| 31-13 | H | (CH₂)₂ | H | Me | CH₂ | Pen | 2-iPrO-5-Pyr | O |
| 31-14 | H | (CH₂)₂ | H | Me | CH₂ | Pen | 2-MeS-5-Pyr | O |
| 31-15 | H | (CH₂)₂ | H | Me | CH₂ | Pen | 2-EtS-5-Pyr | O |
| 31-16 | H | (CH₂)₂ | H | Me | CH₂ | Pen | 2-Ph-5-Pyr | O |
| 31-17 | H | (CH₂)₂ | H | Me | CH₂ | Pen | 3-Ph-6-Pyr | O |

TABLE 32

| Ex. No. Comp. | R¹ | R² | R³ | R⁴ | Z | W | X | Y |
|---|---|---|---|---|---|---|---|---|
| 32-1 | H | (CH₂)₂ | H | Me | CH₂ | MeS | Ph | O |
| 32-2 | H | (CH₂)₂ | H | Me | CH₂ | MeS | 4-Ph—Ph | O |
| 32-3 | H | (CH₂)₂ | H | Me | CH₂ | MeS | 4-(Pyr-2)-Ph | O |
| 32-4 | H | (CH₂)₂ | H | Me | CH₂ | MeS | 4-(Pyr-3)-Ph | O |
| 32-5 | H | (CH₂)₂ | H | Me | CH₂ | MeS | 4-(Pyr-4)-Ph | O |
| 32-6 | H | (CH₂)₂ | H | Me | CH₂ | MeS | 2-Pyr | O |
| 32-7 | H | (CH₂)₂ | H | Me | CH₂ | MeS | 3-Pyr | O |
| 32-8 | H | (CH₂)₂ | H | Me | CH₂ | MeS | 4-Pyr | O |
| 32-9 | H | (CH₂)₂ | H | Me | CH₂ | MeS | 2-Me-5-Pyr | O |
| 32-10 | H | (CH₂)₂ | H | Me | CH₂ | MeS | 2-Me-3-Pyr | O |
| 32-11 | H | (CH₂)₂ | H | Me | CH₂ | MeS | 2-MeO-5-Pyr | O |
| 32-12 | H | (CH₂)₂ | H | Me | CH₂ | MeS | 2-EtO-5-Pyr | O |
| 32-13 | H | (CH₂)₂ | H | Me | CH₂ | MeS | 2-iPrO-5-Pyr | O |
| 32-14 | H | (CH₂)₂ | H | Me | CH₂ | MeS | 2-MeS-5-Pyr | O |
| 32-15 | H | (CH₂)₂ | H | Me | CH₂ | MeS | 2-EtS-5-Pyr | O |
| 32-16 | H | (CH₂)₂ | H | Me | CH₂ | MeS | 2-Ph-5-Pyr | O |
| 32-17 | H | (CH₂)₂ | H | Me | CH₂ | MeS | 3-Ph-6-Pyr | O |

TABLE 33

| Ex. No. Comp. | R¹ | R² | R³ | R⁴ | Z | W | X | Y |
|---|---|---|---|---|---|---|---|---|
| 33-1 | H | (CH₂)₂ | H | Me | CH₂ | PhO | Ph | O |
| 33-2 | H | (CH₂)₂ | H | Me | CH₂ | PhO | 4-Ph-Ph | O |
| 33-3 | H | (CH₂)₂ | H | Me | CH₂ | PhO | 4-(Pyr-2)-Ph | O |
| 33-4 | H | (CH₂)₂ | H | Me | CH₂ | PhO | 4-(Pyr-3)-Ph | O |
| 33-5 | H | (CH₂)₂ | H | Me | CH₂ | PhO | 4-(Pyr-4)-Ph | O |
| 33-6 | H | (CH₂)₂ | H | Me | CH₂ | PhO | 2-Pyr | O |
| 33-7 | H | (CH₂)₂ | H | Me | CH₂ | PhO | 3-Pyr | O |
| 33-8 | H | (CH₂)₂ | H | Me | CH₂ | PhO | 4-Pyr | O |
| 33-9 | H | (CH₂)₂ | H | Me | CH₂ | PhO | 2-Me-5-Pyr | O |

TABLE 33-continued

| Ex. No. Comp. | R¹ | R² | R³ | R⁴ | Z | W | X | Y |
|---|---|---|---|---|---|---|---|---|
| 33-10 | H | (CH₂)₂ | H | Me | CH₂ | PhO | 2-Me-3-Pyr | O |
| 33-11 | H | (CH₂)₂ | H | Me | CH₂ | PhO | 2-MeO-5-Pyr | O |
| 33-12 | H | (CH₂)₂ | H | Me | CH₂ | PhO | 2-EtO-5-Pyr | O |
| 33-13 | H | (CH₂)₂ | H | Me | CH₂ | PhO | 2-iPrO-5-Pyr | O |
| 33-14 | H | (CH₂)₂ | H | Me | CH₂ | PhO | 2-MeS-5-Pyr | O |
| 33-15 | H | (CH₂)₂ | H | Me | CH₂ | PhO | 2-EtS-5-Pyr | O |
| 33-16 | H | (CH₂)₂ | H | Me | CH₂ | PhO | 2-Ph-5-Pyr | O |
| 33-17 | H | (CH₂)₂ | H | Me | CH₂ | PhO | 3-Ph-6-Pyr | O |
| 33-18 | H | (CH₂)₂ | H | Me | CH₂ | PhO | 4-(4-Me-Ph)-Ph | O |
| 33-19 | H | (CH₂)₂ | H | Me | CH₂ | PhO | 4-(4-F-Ph)-Ph | O |
| 33-20 | H | (CH₂)₂ | H | Me | CH₂ | PhO | 4-(4-Cl-Ph)-Ph | O |
| 33-21 | H | (CH₂)₂ | H | Me | CH₂ | PhO | 4-(4-HO-3,5-di-Me-Ph)-Ph | O |
| 33-22 | H | (CH₂)₂ | H | Me | CH₂ | PhO | 4-(4-MeO-Ph)-Ph | O |
| 33-23 | H | (CH₂)₂ | H | Me | CH₂ | PhO | 4-(4-HO-Ph)-Ph | O |
| 33-24 | H | (CH₂)₂ | H | Me | CH₂ | PhO | 4-(4-OHC-Ph)-Ph | O |
| 33-25 | H | (CH₂)₂ | H | Me | CH₂ | PhO | 4-(4-Dma-Ph)-Ph | O |
| 33-26 | H | (CH₂)₂ | H | Me | CH₂ | PhO | 4-(3-MeO-Ph)-Ph | O |
| 33-27 | H | (CH₂)₂ | H | Me | CH₂ | PhO | 4-(3-HO-Ph)-Ph | O |
| 33-28 | H | (CH₂)₂ | H | Me | CH₂ | PhO | 4-(3-Dma-Ph)-Ph | O |
| 33-29 | H | (CH₂)₂ | H | Me | CH₂ | PhO | 4-(2-MeO-Ph)-Ph | O |
| 33-30 | H | (CH₂)₂ | H | Me | CH₂ | PhO | 4-(2-HO-Ph)-Ph | O |
| 33-31 | H | (CH₂)₂ | H | Me | CH₂ | PhO | 4-(3-MeO-Pyr-6)-Ph | O |
| 33-32 | H | (CH₂)₂ | H | Me | CH₂ | PhO | 4-(3-EtO-Pyr-6)-Ph | O |
| 33-33 | H | (CH₂)₂ | H | Me | CH₂ | PhO | 4-(3-iPrO)-Pyr-6)-Ph | O |
| 33-34 | H | (CH₂)₂ | H | Me | CH₂ | PhO | 4-(3-Dma-Pyr-6)-Ph | O |
| 33-35 | H | (CH₂)₂ | H | Me | CH₂ | PhO | 4-(3-Dea-Pyr-6)-Ph | O |
| 33-36 | H | (CH₂)₂ | H | Me | CH₂ | PhO | 4-(3-F₃C-Pyr-6)-Ph | O |
| 33-37 | H | (CH₂)₂ | H | Me | CH₂ | PhO | 4-(3-O₂N-Pyr-6)-Ph | O |
| 33-38 | H | (CH₂)₂ | H | Me | CH₂ | PhO | 2-(4-F-Ph)-5-Pyr | O |
| 33-39 | H | (CH₂)₂ | H | Me | CH₂ | PhO | 2-(4-Cl-Ph)-5-Pyr | O |
| 33-40 | H | (CH₂)₂ | H | Me | CH₂ | PhO | 2-(4-MeO-Ph)-5-Pyr | O |
| 33-41 | H | (CH₂)₂ | H | Me | CH₂ | PhO | 2-(4-EtO-Ph)-5-Pyr | O |
| 33-42 | H | (CH₂)₂ | H | Me | CH₂ | PhO | 2-(4-iPrO-Ph)-5-Pyr | O |
| 33-43 | H | (CH₂)₂ | H | Me | CH₂ | PhO | 2-TfpO-5-Pyr | O |
| 33-44 | H | (CH₂)₂ | H | Me | CH₂ | PhO | 4-(4-AcO-Ph)-Ph | O |
| 33-45 | H | (CH₂)₂ | H | Me | CH₂ | PhO | 4-(3-F-Ph)-Ph | O |
| 33-46 | H | (CH₂)₂ | H | Me | CH₂ | PhO | 4-(3-Cl-Ph)-Ph | O |
| 33-47 | H | (CH₂)₂ | H | Me | CH₂ | PhO | 4-(3-Me-Ph)-Ph | O |
| 33-48 | H | (CH₂)₂ | H | Me | CH₂ | PhO | 4-(3-AcO-Ph)-Ph | O |
| 33-49 | H | (CH₂)₂ | H | Me | CH₂ | PhO | 4-(3-Me-Pyr-6)-Ph | O |
| 33-50 | H | (CH₂)₂ | H | Me | CH₂ | PhO | 4-(3-Et-Pyr-6)-Ph | O |
| 33-51 | H | (CH₂)₂ | H | Me | CH₂ | PhO | 2-(4-Me-Ph)-5-Pyr | O |
| 33-52 | H | (CH₂)₂ | H | Me | CH₂ | PhO | 2-(4-CF₃-Ph)-5-Pyr | O |
| 33-53 | H | (CH₂)₂ | H | Me | CH₂ | PhO | 2-(4-Dma-Ph)-5-Pyr | O |
| 33-54 | H | (CH₂)₂ | H | Me | CH₂ | PhO | 2-(3-F-Ph)-5-Pyr | O |
| 33-55 | H | (CH₂)₂ | H | Me | CH₂ | PhO | 2-(3-Cl-Ph)-5-Pyr | O |
| 33-56 | H | (CH₂)₂ | H | Me | CH₂ | PhO | 2-(3-MeO-Ph)-5-Pyr | O |
| 33-57 | H | (CH₂)₂ | H | Me | CH₂ | PhO | 2-(3-EtO-Ph)-5-Pyr | O |
| 33-58 | H | (CH₂)₂ | H | Me | CH₂ | PhO | 2-(3-iPrO-Ph)-5-Pyr | O |
| 33-59 | H | (CH₂)₂ | H | Me | CH₂ | PhO | 2-(3-Me-Ph)-5-Pyr | O |
| 33-60 | H | (CH₂)₂ | H | Me | CH₂ | PhO | 2-(3-CF₃-Ph)-5-Pyr | O |
| 33-61 | H | (CH₂)₂ | H | Me | CH₂ | PhO | 2-(3-Dma-Ph)-5-Pyr | O |

TABLE 34

| Ex. No. Comp. | R¹ | R² | R³ | R⁴ | Z | W | X | Y |
|---|---|---|---|---|---|---|---|---|
| 34-1 | H | (CH₂)₂ | H | Me | CH₂ | 4-iPr-PhO | Ph | O |
| 34-2 | H | (CH₂)₂ | H | Me | CH₂ | 4-iPr-PhO | 4-Ph-Ph | O |
| 34-3 | H | (CH₂)₂ | H | Me | CH₂ | 4-iPr-PhO | 4-(Pyr-2)-Ph | O |
| 34-4 | H | (CH₂)₂ | H | Me | CH₂ | 4-iPr-PhO | 4-(Pyr-3)-Ph | O |
| 34-5 | H | (CH₂)₂ | H | Me | CH₂ | 4-iPr-PhO | 4-(Pyr-4)-Ph | O |
| 34-6 | H | (CH₂)₂ | H | Me | CH₂ | 4-iPr-PhO | 2-Pyr | O |
| 34-7 | H | (CH₂)₂ | H | Me | CH₂ | 4-iPr-PhO | 3-Pyr | O |
| 34-8 | H | (CH₂)₂ | H | Me | CH₂ | 4-iPr-PhO | 4-Pyr | O |
| 34-9 | H | (CH₂)₂ | H | Me | CH₂ | 4-iPr-PhO | 2-Me-5-Pyr | O |
| 34-10 | H | (CH₂)₂ | H | Me | CH₂ | 4-iPr-PhO | 2-Me-3-Pyr | O |
| 34-11 | H | (CH₂)₂ | H | Me | CH₂ | 4-iPr-PhO | 2-MeO-5-Pyr | O |
| 34-12 | H | (CH₂)₂ | H | Me | CH₂ | 4-iPr-PhO | 2-EtO-5-Pyr | O |

TABLE 34-continued

| Ex. No. Comp. | R¹ | R² | R³ | R⁴ | Z | W | X | Y |
|---|---|---|---|---|---|---|---|---|
| 34-13 | H | (CH$_2$)$_2$ | H | Me | CH$_2$ | 4-iPr-PhO | 2-iPrO-5-Pyr | O |
| 34-14 | H | (CH$_2$)$_2$ | H | Me | CH$_2$ | 4-iPr-PhO | 2-MeS-5-Pyr | O |
| 34-15 | H | (CH$_2$)$_2$ | H | Me | CH$_2$ | 4-iPr-PhO | 2-EtS-5-Pyr | O |
| 34-16 | H | (CH$_2$)$_2$ | H | Me | CH$_2$ | 4-iPr-PhO | 2-Ph-5-Pyr | O |
| 34-17 | H | (CH$_2$)$_2$ | H | Me | CH$_2$ | 4-iPr-PhO | 3-Ph-6-Pyr | O |
| 34-18 | H | (CH$_2$)$_2$ | H | Me | CH$_2$ | 4-iPr-PhO | 4-(4-Me-Ph)-Ph | O |
| 34-19 | H | (CH$_2$)$_2$ | H | Me | CH$_2$ | 4-iPr-PhO | 4-(4-F-Ph)-Ph | O |
| 34-20 | H | (CH$_2$)$_2$ | H | Me | CH$_2$ | 4-iPr-PhO | 4-(4-Cl-Ph)-Ph | O |
| 34-21 | H | (CH$_2$)$_2$ | H | Me | CH$_2$ | 4-iPr-PhO | 4-(4-HO-3,5-di-Me-Ph)-Ph | O |
| 34-22 | H | (CH$_2$)$_2$ | H | Me | CH$_2$ | 4-iPr-PhO | 4-(4-MeO-Ph)-Ph | O |
| 34-23 | H | (CH$_2$)$_2$ | H | Me | CH$_2$ | 4-iPr-PhO | 4-(4-HO-Ph)-Ph | O |
| 34-24 | H | (CH$_2$)$_2$ | H | Me | CH$_2$ | 4-iPr-PhO | 4-(4-OHC-Ph)-Ph | O |
| 34-25 | H | (CH$_2$)$_2$ | H | Me | CH$_2$ | 4-iPr-PhO | 4-(4-Dma-Ph)-Ph | O |
| 34-26 | H | (CH$_2$)$_2$ | H | Me | CH$_2$ | 4-iPr-PhO | 4-(3-MeO-Ph)-Ph | O |
| 34-27 | H | (CH$_2$)$_2$ | H | Me | CH$_2$ | 4-iPr-PhO | 4-(3-HO-Ph)-Ph | O |
| 34-28 | H | (CH$_2$)$_2$ | H | Me | CH$_2$ | 4-iPr-PhO | 4-(3-Dma-Ph)-Ph | O |
| 34-29 | H | (CH$_2$)$_2$ | H | Me | CH$_2$ | 4-iPr-PhO | 4-(2-MeO-Ph)-Ph | O |
| 34-30 | H | (CH$_2$)$_2$ | H | Me | CH$_2$ | 4-iPr-PhO | 4-(2-HO-Ph)-Ph | O |
| 34-31 | H | (CH$_2$)$_2$ | H | Me | CH$_2$ | 4-iPr-PhO | 4-(3-MeO-Pyr-6)-Ph | O |
| 34-32 | H | (CH$_2$)$_2$ | H | Me | CH$_2$ | 4-iPr-PhO | 4-(3-EtO-Pyr-6)-Ph | O |
| 34-33 | H | (CH$_2$)$_2$ | H | Me | CH$_2$ | 4-iPr-PhO | 4-(3-iPrO-Pyr-6)-Ph | |
| 34-34 | H | (CH$_2$)$_2$ | H | Me | CH$_2$ | 4-iPr-PhO | 4-(3-Dma-Pyr-6)-Ph | O |
| 34-35 | H | (CH$_2$)$_2$ | H | Me | CH$_2$ | 4-iPr-PhO | 4-(3-Dea-Pyr-6)-Ph | O |
| 34-36 | H | (CH$_2$)$_2$ | H | Me | CH$_2$ | 4-iPr-PhO | 4-(3-F$_3$C-Pyr-6)-Ph | O |
| 34-37 | H | (CH$_2$)$_2$ | H | Me | CH$_2$ | 4-iPr-PhO | 4-(3-O$_2$N-Pyr-6)-Ph | O |
| 34-38 | H | (CH$_2$)$_2$ | H | Me | CH$_2$ | 4-iPr-PhO | 2-(4-F-Ph)-5-Pyr | O |
| 34-39 | H | (CH$_2$)$_2$ | H | Me | CH$_2$ | 4-iPr-PhO | 2-(4-Cl-Ph)-5-Pyr | O |
| 34-40 | H | (CH$_2$)$_2$ | H | Me | CH$_2$ | 4-iPr-PhO | 2-(4-MeO-Ph)-5-Pyr | O |
| 34-41 | H | (CH$_2$)$_2$ | H | Me | CH$_2$ | 4-iPr-PhO | 2-(4-EtO-Ph)-5-Pyr | O |
| 34-42 | H | (CH$_2$)$_2$ | H | Me | CH$_2$ | 4-iPr-PhO | 2-(4-iPrO-Ph)-5-Pyr | O |
| 34-43 | H | (CH$_2$)$_2$ | H | Me | CH$_2$ | 4-iPr-PhO | 2-TfpO-5-Pyr | O |
| 34-44 | H | (CH$_2$)$_2$ | H | Me | CH$_2$ | 4-iPr-PhO | 4-(4-AcO-Ph)-Ph | O |
| 34-45 | H | (CH$_2$)$_2$ | H | Me | CH$_2$ | 4-iPr-PhO | 4-(3-F-Ph)-Ph | O |
| 34-46 | H | (CH$_2$)$_2$ | H | Me | CH$_2$ | 4-iPr-PhO | 4-(3-Cl-Ph)-Ph | O |
| 34-47 | H | (CH$_2$)$_2$ | H | Me | CH$_2$ | 4-iPr-PhO | 4-(3-Me-Ph)-Ph | O |
| 34-48 | H | (CH$_2$)$_2$ | H | Me | CH$_2$ | 4-iPr-PhO | 4-(3-AcO-Ph)-Ph | O |
| 34-49 | H | (CH$_2$)$_2$ | H | Me | CH$_2$ | 4-iPr-PhO | 4-(3-Me-Pyr-6)-Ph | O |
| 34-50 | H | (CH$_2$)$_2$ | H | Me | CH$_2$ | 4-iPr-PhO | 4-(3-Et-Pyr-6)-Ph | O |
| 34-51 | H | (CH$_2$)$_2$ | H | Me | CH$_2$ | 4-iPr-PhO | 2-(4-Me-Ph)-5-Pyr | O |
| 34-52 | H | (CH$_2$)$_2$ | H | Me | CH$_2$ | 4-iPr-PhO | 2-(4-CF$_3$-Ph)-5-Pyr | O |
| 34-53 | H | (CH$_2$)$_2$ | H | Me | CH$_2$ | 4-iPr-PhO | 2-(4-Dma-Ph)-5-Pyr | O |
| 34-54 | H | (CH$_2$)$_2$ | H | Me | CH$_2$ | 4-iPr-PhO | 2-(3-F-Ph)-5-Pyr | O |
| 34-55 | H | (CH$_2$)$_2$ | H | Me | CH$_2$ | 4-iPr-PhO | 2-(3-Cl-Ph)-5-Pyr | O |
| 34-56 | H | (CH$_2$)$_2$ | H | Me | CH$_2$ | 4-iPr-PhO | 2-(3-MeO-Ph)-5-Pyr | O |
| 34-57 | H | (CH$_2$)$_2$ | H | Me | CH$_2$ | 4-iPr-PhO | 2-(3-EtO-Ph)-5-Pyr | O |

TABLE 34-continued

| Ex. No. Comp. | R$^1$ | R$^2$ | R$^3$ | R$^4$ | Z | W | X | Y |
|---|---|---|---|---|---|---|---|---|
| 34-58 | H | (CH$_2$)$_2$ | H | Me | CH$_2$ | 4-iPr-PhO | 2-(3-iPrO-Ph)-5-Pyr | O |
| 34-59 | H | (CH$_2$)$_2$ | H | Me | CH$_2$ | 4-iPr-PhO | 2-(3-Me-Ph)-5-Pyr | O |
| 34-60 | H | (CH$_2$)$_2$ | H | Me | CH$_2$ | 4-iPr-PhO | 2-(3-CF$_3$-Ph)-5-Pyr | O |
| 34-61 | H | (CH$_2$)$_2$ | H | Me | CH$_2$ | 4-iPr-PhO | 2-(3-Dma-Ph)-5-Pyr | O |

TABLE 35

| Ex. No. Comp. | R$^1$ | R$^2$ | R$^3$ | R$^4$ | Z | W | X | Y |
|---|---|---|---|---|---|---|---|---|
| 35-1 | H | (CH$_2$)$_2$ | H | Me | CH$_2$ | 4-MeO-PhO | Ph | O |
| 35-2 | H | (CH$_2$)$_2$ | H | Me | CH$_2$ | 4-MeO-PhO | 4-Ph-Ph | O |
| 35-3 | H | (CH$_2$)$_2$ | H | Me | CH$_2$ | 4-MeO-PhO | 4-(Pyr-2)-Ph | O |
| 35-4 | H | (CH$_2$)$_2$ | H | Me | CH$_2$ | 4-MeO-PhO | 4-(Pyr-3)-Ph | O |
| 35-5 | H | (CH$_2$)$_2$ | H | Me | CH$_2$ | 4-MeO-PhO | 4-(Pyr-4)-Ph | O |
| 35-6 | H | (CH$_2$)$_2$ | H | Me | CH$_2$ | 4-MeO-PhO | 2-Pyr | O |
| 35-7 | H | (CH$_2$)$_2$ | H | Me | CH$_2$ | 4-MeO-PhO | 3-Pyr | O |
| 35-8 | H | (CH$_2$)$_2$ | H | Me | CH$_2$ | 4-MeO-PhO | 4-Pyr | O |
| 35-9 | H | (CH$_2$)$_2$ | H | Me | CH$_2$ | 4-MeO-PhO | 2-Me-5-Pyr | O |
| 35-10 | H | (CH$_2$)$_2$ | H | Me | CH$_2$ | 4-MeO-PhO | 2-Me-3-Pyr | O |
| 35-11 | H | (CH$_2$)$_2$ | H | Me | CH$_2$ | 4-MeO-PhO | 2-MeO-5-Pyr | O |
| 35-12 | H | (CH$_2$)$_2$ | H | Me | CH$_2$ | 4-MeO-PhO | 2-EtO-5-Pyr | O |
| 35-13 | H | (CH$_2$)$_2$ | H | Me | CH$_2$ | 4-MeO-PhO | 2-iPrO-5-Pyr | O |
| 35-14 | H | (CH$_2$)$_2$ | H | Me | CH$_2$ | 4-MeO-PhO | 2-MeS-5-Pyr | O |
| 35-15 | H | (CH$_2$)$_2$ | H | Me | CH$_2$ | 4-MeO-PhO | 2-EtS-5-Pyr | O |
| 35-16 | H | (CH$_2$)$_2$ | H | Me | CH$_2$ | 4-MeO-PhO | 2-Ph-5-Pyr | O |
| 35-17 | H | (CH$_2$)$_2$ | H | Me | CH$_2$ | 4-MeO-PhO | 3-Ph-6-Pyr | O |
| 35-18 | H | (CH$_2$)$_2$ | H | Me | CH$_2$ | 4-MeO-PhO | 4-(4-Me-Ph)-Ph | O |
| 35-19 | H | (CH$_2$)$_2$ | H | Me | CH$_2$ | 4-MeO-PhO | 4-(4-F-Ph)-Ph | O |
| 35-20 | H | (CH$_2$)$_2$ | H | Me | CH$_2$ | 4-MeO-PhO | 4-(4-Cl-Ph)-Ph | O |
| 35-21 | H | (CH$_2$)$_2$ | H | Me | CH$_2$ | 4-MeO-PhO | 4-(4-HO-3,5-di-Me-Ph)-Ph | O |
| 35-22 | H | (CH$_2$)$_2$ | H | Me | CH$_2$ | 4-MeO-PhO | 4-(4-MeO-Ph)-Ph | O |
| 35-23 | H | (CH$_2$)$_2$ | H | Me | CH$_2$ | 4-MeO-PhO | 4-(4-HO-Ph)-Ph | O |
| 35-24 | H | (CH$_2$)$_2$ | H | Me | CH$_2$ | 4-MeO-PhO | 4-(4-OHC-Ph)-Ph | O |
| 35-25 | H | (CH$_2$)$_2$ | H | Me | CH$_2$ | 4-MeO-PhO | 4-(4-Dma-Ph)-Ph | O |
| 35-26 | H | (CH$_2$)$_2$ | H | Me | CH$_2$ | 4-MeO-PhO | 4-(3-MeO-Ph)-Ph | O |
| 35-27 | H | (CH$_2$)$_2$ | H | Me | CH$_2$ | 4-MeO-PhO | 4-(3-HO-Ph)-Ph | O |
| 35-28 | H | (CH$_2$)$_2$ | H | Me | CH$_2$ | 4-MeO-PhO | 4-(3-Dma-Ph)-Ph | O |
| 35-29 | H | (CH$_2$)$_2$ | H | Me | CH$_2$ | 4-MeO-PhO | 4-(2-MeO-Ph)-Ph | O |
| 35-30 | H | (CH$_2$)$_2$ | H | Me | CH$_2$ | 4-MeO-PhO | 4-(2-HO-Ph)-Ph | O |
| 35-31 | H | (CH$_2$)$_2$ | H | Me | CH$_2$ | 4-MeO-PhO | 4-(3-MeO-Pyr-6)-Ph | O |
| 35-32 | H | (CH$_2$)$_2$ | H | Me | CH$_2$ | 4-MeO-PhO | 4-(3-EtO-Pyr-6)-Ph | O |
| 35-33 | H | (CH$_2$)$_2$ | H | Me | CH$_2$ | 4-MeO-PhO | 4-(3-iPrO-Pyr-6)-Ph | O |
| 35-34 | H | (CH$_2$)$_2$ | H | Me | CH$_2$ | 4-MeO-PhO | 4-(3-Dma-Pyr-6)-Ph | O |
| 35-35 | H | (CH$_2$)$_2$ | H | Me | CH$_2$ | 4-MeO-PhO | 4-(3-Dea-Pyr-6)-Ph | O |
| 35-36 | H | (CH$_2$)$_2$ | H | Me | CH$_2$ | 4-MeO-PhO | 4-(3-F$_3$C-Pyr-6)-Ph | O |
| 35-37 | H | (CH$_2$)$_2$ | H | Me | CH$_2$ | 4-MeO-PhO | 4-(3-O$_2$N-Pyr-6)-Ph | O |
| 35-38 | H | (CH$_2$)$_2$ | H | Me | CH$_2$ | 4-MeO-PhO | 2-(4-F-Ph)-5-Pyr | O |
| 35-39 | H | (CH$_2$)$_2$ | H | Me | CH$_2$ | 4-MeO-PhO | 2-(4-Cl-Ph)-5-Pyr | O |
| 35-40 | H | (CH$_2$)$_2$ | H | Me | CH$_2$ | 4-MeO-PhO | 2-(4-MeO-Ph)-5-Pyr | O |
| 35-41 | H | (CH$_2$)$_2$ | H | Me | CH$_2$ | 4-MeO-PhO | 2-(4-EtO-Ph)-5- | O |

TABLE 35-continued

| Ex. No. Comp. | R¹ | R² | R³ | R⁴ | Z | W | X | Y |
|---|---|---|---|---|---|---|---|---|
| 35-42 | H | (CH₂)₂ | H | Me | CH₂ | 4-MeO-PhO | 2-(4-iPrO-Ph)-5-Pyr | O |
| 35-43 | H | (CH₂)₂ | H | Me | CH₂ | 4-MeO-PhO | 2-TfpO-5-Pyr | O |
| 35-44 | H | (CH₂)₂ | H | Me | CH₂ | 4-MeO-PhO | 4-(4-AcO-Ph)-Ph | O |
| 35-45 | H | (CH₂)₂ | H | Me | CH₂ | 4-MeO-PhO | 4-(3-F-Ph)-Ph | O |
| 35-46 | H | (CH₂)₂ | H | Me | CH₂ | 4-MeO-PhO | 4-(3-Cl-Ph)-Ph | O |
| 35-47 | H | (CH₂)₂ | H | Me | CH₂ | 4-MeO-PhO | 4-(3-Me-Ph)-Ph | O |
| 35-48 | H | (CH₂)₂ | H | Me | CH₂ | 4-MeO-PhO | 4-(3-AcO-Ph)-Ph | O |
| 35-49 | H | (CH₂)₂ | H | Me | CH₂ | 4-MeO-PhO | 4-(3-Me-Pyr-6)-Ph | O |
| 35-50 | H | (CH₂)₂ | H | Me | CH₂ | 4-MeO-PhO | 4-(3-Et-Pyr-6)-Ph | O |
| 35-51 | H | (CH₂)₂ | H | Me | CH₂ | 4-MeO-PhO | 2-(4-Me-Ph)-5-Pyr | O |
| 35-52 | H | (CH₂)₂ | H | Me | CH₂ | 4-MeO-PhO | 2-(4-CF₃-Ph)-5-Pyr | O |
| 35-53 | H | (CH₂)₂ | H | Me | CH₂ | 4-MeO-PhO | 2-(4-Dma-Ph)-5-Pyr | O |
| 35-54 | H | (CH₂)₂ | H | Me | CH₂ | 4-MeO-PhO | 2-(3-F-Ph)-5-Pyr | O |
| 35-55 | H | (CH₂)₂ | H | Me | CH₂ | 4-MeO-PhO | 2-(3-Cl-Ph)-5-Pyr | O |
| 35-56 | H | (CH₂)₂ | H | Me | CH₂ | 4-MeO-PhO | 2-(3-MeO-Ph)-5-Pyr | O |
| 35-57 | H | (CH₂)₂ | H | Me | CH₂ | 4-MeO-PhO | 2-(3-EtO-Ph)-5-Pyr | O |
| 35-58 | H | (CH₂)₂ | H | Me | CH₂ | 4-MeO-PhO | 2-(3-iPrO-Ph)-5-Pyr | O |
| 35-59 | H | (CH₂)₂ | H | Me | CH₂ | 4-MeO-PhO | 2-(3-Me-Ph)-5-Pyr | O |
| 35-60 | H | (CH₂)₂ | H | Me | CH₂ | 4-MeO-PhO | 2-(3-CF₃-Ph)-5-Pyr | O |
| 35-61 | H | (CH₂)₂ | H | Me | CH₂ | 4-MeO-PhO | 2-(3-Dma-Ph)-5-Pyr | O |

TABLE 36

| Ex. No. Comp. | R¹ | R² | R³ | R⁴ | Z | W | X | Y |
|---|---|---|---|---|---|---|---|---|
| 36-1 | H | (CH₂)₂ | H | Me | CH₂ | PhS | Ph | O |
| 36-2 | H | (CH₂)₂ | H | Me | CH₂ | PhS | 4-Ph-Ph | O |
| 36-3 | H | (CH₂)₂ | H | Me | CH₂ | PhS | 4-(Pyr-2)-Ph | O |
| 36-4 | H | (CH₂)₂ | H | Me | CH₂ | PhS | 4-(Pyr-3)-Ph | O |
| 36-5 | H | (CH₂)₂ | H | Me | CH₂ | PhS | 4-(Pyr-4)-Ph | O |
| 36-6 | H | (CH₂)₂ | H | Me | CH₂ | PhS | 2-Pyr | O |
| 36-7 | H | (CH₂)₂ | H | Me | CH₂ | PhS | 3-Pyr | O |
| 36-8 | H | (CH₂)₂ | H | Me | CH₂ | PhS | 4-Pyr | O |
| 36-9 | H | (CH₂)₂ | H | Me | CH₂ | PhS | 2-Me-5-Pyr | O |
| 36-10 | H | (CH₂)₂ | H | Me | CH₂ | PhS | 2-Me-3-Pyr | O |
| 36-11 | H | (CH₂)₂ | H | Me | CH₂ | PhS | 2-MeO-5-Pyr | O |
| 36-12 | H | (CH₂)₂ | H | Me | CH₂ | PhS | 2-EtO-5-Pyr | O |
| 36-13 | H | (CH₂)₂ | H | Me | CH₂ | PhS | 2-iPrO-5-Pyr | O |
| 36-14 | H | (CH₂)₂ | H | Me | CH₂ | PhS | 2-MeS-5-Pyr | O |
| 36-15 | H | (CH₂)₂ | H | Me | CH₂ | PhS | 2-EtS-5-Pyr | O |
| 36-16 | H | (CH₂)₂ | H | Me | CH₂ | PhS | 2-Ph-5-Pyr | O |
| 36-17 | H | (CH₂)₂ | H | Me | CH₂ | PhS | 3-Ph-6-Pyr | O |

TABLE 37

| Ex. No. Comp. | R¹ | R² | R³ | R⁴ | Z | W | X | Y |
|---|---|---|---|---|---|---|---|---|
| 37-1 | H | (CH₂)₂ | H | Me | CH₂ | Ph(CH₂)₃ | Ph | O |
| 37-2 | H | (CH₂)₂ | H | Me | CH₂ | Ph(CH₂)₃ | 4-Ph-Ph | O |
| 37-3 | H | (CH₂)₂ | H | Me | CH₂ | Ph(CH₂)₃ | 4-(Pyr-2)-Ph | O |
| 37-4 | H | (CH₂)₂ | H | Me | CH₂ | Ph(CH₂)₃ | 4-(Pyr-3)-Ph | O |
| 37-5 | H | (CH₂)₂ | H | Me | CH₂ | Ph(CH₂)₃ | 4-(Pyr-4)-Ph | O |
| 37-6 | H | (CH₂)₂ | H | Me | CH₂ | Ph(CH₂)₃ | 2-Pyr | O |
| 37-7 | H | (CH₂)₂ | H | Me | CH₂ | Ph(CH₂)₃ | 3-Pyr | O |
| 37-8 | H | (CH₂)₂ | H | Me | CH₂ | Ph(CH₂)₃ | 4-Pyr | O |
| 37-9 | H | (CH₂)₂ | H | Me | CH₂ | Ph(CH₂)₃ | 2-Me-5-Pyr | O |
| 37-10 | H | (CH₂)₂ | H | Me | CH₂ | Ph(CH₂)₃ | 2-Me-3-Pyr | O |
| 37-11 | H | (CH₂)₂ | H | Me | CH₂ | Ph(CH₂)₃ | 2-MeO-5-Pyr | O |
| 37-12 | H | (CH₂)₂ | H | Me | CH₂ | Ph(CH₂)₃ | 2-EtO-5-Pyr | O |
| 37-13 | H | (CH₂)₂ | H | Me | CH₂ | Ph(CH₂)₃ | 2-iPrO-5-Pyr | O |
| 37-14 | H | (CH₂)₂ | H | Me | CH₂ | Ph(CH₂)₃ | 2-MeS-5-Pyr | O |
| 37-15 | H | (CH₂)₂ | H | Me | CH₂ | Ph(CH₂)₃ | 2-EtS-5-Pyr | O |
| 37-16 | H | (CH₂)₂ | H | Me | CH₂ | Ph(CH₂)₃ | 2-Ph-5-Pyr | O |
| 37-17 | H | (CH₂)₂ | H | Me | CH₂ | Ph(CH₂)₃ | 3-Ph-6-Pyr | O |

TABLE 38

| Ex. No. Comp. | R¹ | R² | R³ | R⁴ | Z | W | X | Y |
|---|---|---|---|---|---|---|---|---|
| 38-1 | H | (CH₂)₃ | H | H | CH₂ | EtO | Ph | O |
| 38-2 | H | (CH₂)₃ | H | H | CH₂ | EtO | 4-Ph-Ph | O |
| 38-3 | H | (CH₂)₃ | H | H | CH₂ | EtO | 4-(Pyr-2)-Ph | O |
| 38-4 | H | (CH₂)₃ | H | H | CH₂ | EtO | 4-(Pyr-3)-Ph | O |

TABLE 38-continued

| Ex. No. Comp. | R¹ | R² | R³ | R⁴ | Z | W | X | Y |
|---|---|---|---|---|---|---|---|---|
| 38-5 | H | (CH₂)₃ | H | H | CH₂ | EtO | 4-(Pyr-4)-Ph | O |
| 38-6 | H | (CH₂)₃ | H | H | CH₂ | EtO | 2-Pyr | O |
| 38-7 | H | (CH₂)₃ | H | H | CH₂ | EtO | 3-Pyr | O |
| 38-8 | H | (CH₂)₃ | H | H | CH₂ | EtO | 4-Pyr | O |
| 38-9 | H | (CH₂)₃ | H | H | CH₂ | EtO | 2-Me-5-Pyr | O |
| 38-10 | H | (CH₂)₃ | H | H | CH₂ | EtO | 2-Me-3-Pyr | O |
| 38-11 | H | (CH₂)₃ | H | H | CH₂ | EtO | 2-MeO-5-Pyr | O |
| 38-12 | H | (CH₂)₃ | H | H | CH₂ | EtO | 2-EtO-5-Pyr | O |
| 38-13 | H | (CH₂)₃ | H | H | CH₂ | EtO | 2-iPrO-5-Pyr | O |
| 38-14 | H | (CH₂)₃ | H | H | CH₂ | EtO | 2-MeS-5-Pyr | O |
| 38-15 | H | (CH₂)₃ | H | H | CH₂ | EtO | 2-EtS-5-Pyr | O |
| 38-16 | H | (CH₂)₃ | H | H | CH₂ | EtO | 2-Ph-5-Pyr | O |
| 38-17 | H | (CH₂)₃ | H | H | CH₂ | EtO | 3-Ph-6-Pyr | O |
| 38-18 | H | (CH₂)₃ | H | H | CH₂ | EtO | 4-(4-Me-Ph)-Ph | O |
| 38-19 | H | (CH₂)₃ | H | H | CH₂ | EtO | 4-(4-F-Ph)-Ph | O |
| 38-20 | H | (CH₂)₃ | H | H | CH₂ | EtO | 4-(4-Cl-Ph)-Ph | O |
| 38-21 | H | (CH₂)₃ | H | H | CH₂ | EtO | 4-(4-HO-3,5-di-Me-Ph)-Ph | O |
| 38-22 | H | (CH₂)₃ | H | H | CH₂ | EtO | 4-(4-MeO-Ph)-Ph | O |
| 38-23 | H | (CH₂)₃ | H | H | CH₂ | EtO | 4-(4-HO-Ph)-Ph | O |
| 38-24 | H | (CH₂)₃ | H | H | CH₂ | EtO | 4-(4-OHC-Ph)-Ph | O |
| 38-25 | H | (CH₂)₃ | H | H | CH₂ | EtO | 4-(4-Dma-Ph)-Ph | O |
| 38-26 | H | (CH₂)₃ | H | H | CH₂ | EtO | 4-(3-MeO-Ph)-Ph | O |
| 38-27 | H | (CH₂)₃ | H | H | CH₂ | EtO | 4-(3-HO-Ph)-Ph | O |
| 38-28 | H | (CH₂)₃ | H | H | CH₂ | EtO | 4-(3-Dma-Ph)-Ph | O |
| 38-29 | H | (CH₂)₃ | H | H | CH₂ | EtO | 4-(2-MeO-Ph)-Ph | O |
| 38-30 | H | (CH₂)₃ | H | H | CH₂ | EtO | 4-(2-HO-Ph)-Ph | O |
| 38-31 | H | (CH₂)₃ | H | H | CH₂ | EtO | 4-(3-MeO-Pyr-6)-Ph | O |
| 38-32 | H | (CH₂)₃ | H | H | CH₂ | EtO | 4-(3-EtO-Pyr-6)-Ph | O |
| 38-33 | H | (CH₂)₃ | H | H | CH₂ | EtO | 4-(3-iPrO-Pyr-6)-Ph | O |
| 38-34 | H | (CH₂)₃ | H | H | CH₂ | EtO | 4-(3-Dma-Pyr-6)-Ph | O |
| 38-35 | H | (CH₂)₃ | H | H | CH₂ | EtO | 4-(3-Dea-Pyr-6)-Ph | O |
| 38-36 | H | (CH₂)₃ | H | H | CH₂ | EtO | 4-(3-F₃C-Pyr-6)-Ph | O |
| 38-37 | H | (CH₂)₃ | H | H | CH₂ | EtO | 4-(3-O₂N-Pyr-6)-Ph | O |
| 38-38 | H | (CH₂)₃ | H | H | CH₂ | EtO | 2-(4-F-Ph)-5-Pyr | O |
| 38-39 | H | (CH₂)₃ | H | H | CH₂ | EtO | 2-(4-Cl-Ph)-5-Pyr | O |
| 38-40 | H | (CH₂)₃ | H | H | CH₂ | EtO | 2-(4-MeO-Ph)-5-Pyr | O |
| 38-41 | H | (CH₂)₃ | H | H | CH₂ | EtO | 2-(4-EtO-Ph)-5-Pyr | O |
| 38-42 | H | (CH₂)₃ | H | H | CH₂ | EtO | 2-(4-iPrO-Ph)-5-Pyr | O |
| 38-43 | H | (CH₂)₃ | H | H | CH₂ | EtO | 2-TfpO-5-Pyr | O |

TABLE 39

| Ex. No. Comp. | R¹ | R² | R³ | R⁴ | Z | W | X | Y |
|---|---|---|---|---|---|---|---|---|
| 39-1 | H | (CH₂)₃ | H | H | CH₂ | Pr | Ph | O |
| 39-2 | H | (CH₂)₃ | H | H | CH₂ | Pr | 4-Ph-Ph | O |
| 39-3 | H | (CH₂)₃ | H | H | CH₂ | Pr | 4-(Pyr-2)-Ph | O |
| 39-4 | H | (CH₂)₃ | H | H | CH₂ | Pr | 4-(Pyr-3)-Ph | O |
| 39-5 | H | (CH₂)₃ | H | H | CH₂ | Pr | 4-(Pyr-4)-Ph | O |
| 39-6 | H | (CH₂)₃ | H | H | CH₂ | Pr | 2-Pyr | O |
| 39-7 | H | (CH₂)₃ | H | H | CH₂ | Pr | 3-Pyr | O |
| 39-8 | H | (CH₂)₃ | H | H | CH₂ | Pr | 4-Pyr | O |
| 39-9 | H | (CH₂)₃ | H | H | CH₂ | Pr | 2-Me-5-Pyr | O |
| 39-10 | H | (CH₂)₃ | H | H | CH₂ | Pr | 2-Me-3-Pyr | O |
| 39-11 | H | (CH₂)₃ | H | H | CH₂ | Pr | 2-MeO-5-Pyr | O |
| 39-12 | H | (CH₂)₃ | H | H | CH₂ | Pr | 2-EtO-5-Pyr | O |
| 39-13 | H | (CH₂)₃ | H | H | CH₂ | Pr | 2-iPrO-5-Pyr | O |
| 39-14 | H | (CH₂)₃ | H | H | CH₂ | Pr | 2-MeS-5-Pyr | O |
| 39-15 | H | (CH₂)₃ | H | H | CH₂ | Pr | 2-EtS-5-Pyr | O |
| 39-16 | H | (CH₂)₃ | H | H | CH₂ | Pr | 2-Ph-5-Pyr | O |
| 39-17 | H | (CH₂)₃ | H | H | CH₂ | Pr | 3-Ph-6-Pyr | O |
| 39-18 | H | (CH₂)₃ | H | H | CH₂ | Pr | 4-(4-Me-Ph)-Ph | O |
| 39-19 | H | (CH₂)₃ | H | H | CH₂ | Pr | 4-(4-F-Ph)-Ph | O |
| 39-20 | H | (CH₂)₃ | H | H | CH₂ | Pr | 4-(4-Cl-Ph)-Ph | O |
| 39-21 | H | (CH₂)₃ | H | H | CH₂ | Pr | 4-(4-HO-3,5-di-Me-Ph)-Ph | O |
| 39-22 | H | (CH₂)₃ | H | H | CH₂ | Pr | 4-(4-MeO-Ph)-Ph | O |
| 39-23 | H | (CH₂)₃ | H | H | CH₂ | Pr | 4-(4-HO-Ph)-Ph | O |
| 39-24 | H | (CH₂)₃ | H | H | CH₂ | Pr | 4-(4-OHC-Ph)-Ph | O |
| 39-25 | H | (CH₂)₃ | H | H | CH₂ | Pr | 4-(4-Dma-Ph)-Ph | O |
| 39-26 | H | (CH₂)₃ | H | H | CH₂ | Pr | 4-(3-MeO-Ph)-Ph | O |
| 39-27 | H | (CH₂)₃ | H | H | CH₂ | Pr | 4-(3-HO-Ph)-Ph | O |
| 39-28 | H | (CH₂)₃ | H | H | CH₂ | Pr | 4-(3-Dma-Ph)-Ph | O |
| 39-29 | H | (CH₂)₃ | H | H | CH₂ | Pr | 4-(2-MeO-Ph)-Ph | O |
| 39-30 | H | (CH₂)₃ | H | H | CH₂ | Pr | 4-(2-HO-Ph)-Ph | O |
| 39-31 | H | (CH₂)₃ | H | H | CH₂ | Pr | 4-(3-MeO-Pyr-6)-Ph | O |
| 39-32 | H | (CH₂)₃ | H | H | CH₂ | Pr | 4-(3-EtO-Pyr-6)-Ph | O |
| 39-33 | H | (CH₂)₃ | H | H | CH₂ | Pr | 4-(3-iPrO-Pyr-6)-Ph | O |
| 39-34 | H | (CH₂)₃ | H | H | CH₂ | Pr | 4-(3-Dma-Pyr-6)-Ph | O |
| 39-35 | H | (CH₂)₃ | H | H | CH₂ | Pr | 4-(3-Dea-Pyr-6)-Ph | O |
| 39-36 | H | (CH₂)₃ | H | H | CH₂ | Pr | 4-(3-F₃C-Pyr-6)-Ph | O |
| 39-37 | H | (CH₂)₃ | H | H | CH₂ | Pr | 4-(3-O₂N-Pyr-6)-Ph | O |
| 39-38 | H | (CH₂)₃ | H | H | CH₂ | Pr | 2-(4-F-Ph)-5-Pyr | O |
| 39-39 | H | (CH₂)₃ | H | H | CH₂ | Pr | 2-(4-Cl-Ph)-5-Pyr | O |
| 39-40 | H | (CH₂)₃ | H | H | CH₂ | Pr | 2-(4-MeO-Ph)-5-Pyr | O |
| 39-41 | H | (CH₂)₃ | H | H | CH₂ | Pr | 2-(4-EtO-Ph)-5-Pyr | O |
| 39-42 | H | (CH₂)₃ | H | H | CH₂ | Pr | 2-(4-iPrO-Ph)-5-Pyr | O |
| 39-43 | H | (CH₂)₃ | H | H | CH₂ | Pr | 2-TfpO-5-Pyr | O |

TABLE 40

| Ex. No. Comp. | R¹ | R² | R³ | R⁴ | Z | W | X | Y |
|---|---|---|---|---|---|---|---|---|
| 40-1 | H | (CH₂)₃ | H | H | CH₂ | Bu | Ph | O |
| 40-2 | H | (CH₂)₃ | H | H | CH₂ | Bu | 4-Ph-Ph | O |
| 40-3 | H | (CH₂)₃ | H | H | CH₂ | Bu | 4-(Pyr-2)-Ph | O |
| 40-4 | H | (CH₂)₃ | H | H | CH₂ | Bu | 4-(Pyr-3)-Ph | O |
| 40-5 | H | (CH₂)₃ | H | H | CH₂ | Bu | 4-(Pyr-4)-Ph | O |
| 40-6 | H | (CH₂)₃ | H | H | CH₂ | Bu | 2-Pyr | O |
| 40-7 | H | (CH₂)₃ | H | H | CH₂ | Bu | 3-Pyr | O |
| 40-8 | H | (CH₂)₃ | H | H | CH₂ | Bu | 4-Pyr | O |
| 40-9 | H | (CH₂)₃ | H | H | CH₂ | Bu | 2-Me-5-Pyr | O |
| 40-10 | H | (CH₂)₃ | H | H | CH₂ | Bu | 2-Me-3-Pyr | O |
| 40-11 | H | (CH₂)₃ | H | H | CH₂ | Bu | 2-MeO-5-Pyr | O |
| 40-12 | H | (CH₂)₃ | H | H | CH₂ | Bu | 2-EtO-5-Pyr | O |
| 40-13 | H | (CH₂)₃ | H | H | CH₂ | Bu | 2-iPrO-5-Pyr | O |
| 40-14 | H | (CH₂)₃ | H | H | CH₂ | Bu | 2-MeS-5-Pyr | O |
| 40-15 | H | (CH₂)₃ | H | H | CH₂ | Bu | 2-EtS-5-Pyr | O |
| 40-16 | H | (CH₂)₃ | H | H | CH₂ | Bu | 2-Ph-5-Pyr | O |
| 40-17 | H | (CH₂)₃ | H | H | CH₂ | Bu | 3-Ph-6-Pyr | O |
| 40-18 | H | (CH₂)₃ | H | H | CH₂ | Bu | 4-(4-Me-Ph)-Ph | O |
| 40-19 | H | (CH₂)₃ | H | H | CH₂ | Bu | 4-(4-F-Ph)-Ph | O |
| 40-20 | H | (CH₂)₃ | H | H | CH₂ | Bu | 4-(4-Cl-Ph)-Ph | O |
| 40-21 | H | (CH₂)₃ | H | H | CH₂ | Bu | 4-(4-HO-3,5-di-Me-Ph)-Ph | O |
| 40-22 | H | (CH₂)₃ | H | H | CH₂ | Bu | 4-(4-MeO-Ph)-Ph | O |
| 40-23 | H | (CH₂)₃ | H | H | CH₂ | Bu | 4-(4-HO-Ph)-Ph | O |
| 40-24 | H | (CH₂)₃ | H | H | CH₂ | Bu | 4-(4-OHC-Ph)-Ph | O |
| 40-25 | H | (CH₂)₃ | H | H | CH₂ | Bu | 4-(4-Dma-Ph)-Ph | O |
| 40-26 | H | (CH₂)₃ | H | H | CH₂ | Bu | 4-(3-MeO-Ph)-Ph | O |
| 40-27 | H | (CH₂)₃ | H | H | CH₂ | Bu | 4-(3-HO-Ph)-Ph | O |
| 40-28 | H | (CH₂)₃ | H | H | CH₂ | Bu | 4-(3-Dma-Ph)-Ph | O |
| 40-29 | H | (CH₂)₃ | H | H | CH₂ | Bu | 4-(2-MeO-Ph)-Ph | O |
| 40-30 | H | (CH₂)₃ | H | H | CH₂ | Bu | 4-(2-HO-Ph)-Ph | O |
| 40-31 | H | (CH₂)₃ | H | H | CH₂ | Bu | 4-(3-MeO-Pyr-6)-Ph | O |
| 40-32 | H | (CH₂)₃ | H | H | CH₂ | Bu | 4-(3-EtO-Pyr-6)-Ph | O |
| 40-33 | H | (CH₂)₃ | H | H | CH₂ | Bu | 4-(3-iPrO-Pyr-6)-Ph | O |
| 40-34 | H | (CH₂)₃ | H | H | CH₂ | Bu | 4-(3-Dma-Pyr-6)-Ph | O |
| 40-35 | H | (CH₂)₃ | H | H | CH₂ | Bu | 4-(3-Dea-Pyr-6)-Ph | O |
| 40-36 | H | (CH₂)₃ | H | H | CH₂ | Bu | 4-(3-F₃C-Pyr-6)-Ph | O |
| 40-37 | H | (CH₂)₃ | H | H | CH₂ | Bu | 4-(3-O₂N-Pyr-6)-Ph | O |
| 40-38 | H | (CH₂)₃ | H | H | CH₂ | Bu | 2-(4-F-Ph)-5-Pyr | O |
| 40-39 | H | (CH₂)₃ | H | H | CH₂ | Bu | 2-(4-Cl-Ph)-5-Pyr | O |
| 40-40 | H | (CH₂)₃ | H | H | CH₂ | Bu | 2-(4-MeO-Ph)-5-Pyr | O |
| 40-41 | H | (CH₂)₃ | H | H | CH₂ | Bu | 2-(4-EtO-Ph)-5-Pyr | O |
| 40-42 | H | (CH₂)₃ | H | H | CH₂ | Bu | 2-(4-iPrO-Ph)-5-Pyr | O |
| 40-43 | H | (CH₂)₃ | H | H | CH₂ | Bu | 2-TfpO-5-Pyr | O |

TABLE 41

| Ex. No. Comp. | R¹ | R² | R³ | R⁴ | Z | W | X | Y |
|---|---|---|---|---|---|---|---|---|
| 41-1 | H | (CH₂)₃ | H | H | CH₂ | Pen | Ph | O |
| 41-2 | H | (CH₂)₃ | H | H | CH₂ | Pen | 4-Ph-Ph | O |
| 41-3 | H | (CH₂)₃ | H | H | CH₂ | Pen | 4-(Pyr-2)-Ph | O |
| 41-4 | H | (CH₂)₃ | H | H | CH₂ | Pen | 4-(Pyr-3)-Ph | O |
| 41-5 | H | (CH₂)₃ | H | H | CH₂ | Pen | 4-(Pyr-4)-Ph | O |
| 41-6 | H | (CH₂)₃ | H | H | CH₂ | Pen | 2-Pyr | O |
| 41-7 | H | (CH₂)₃ | H | H | CH₂ | Pen | 3-Pyr | O |
| 41-8 | H | (CH₂)₃ | H | H | CH₂ | Pen | 4-Pyr | O |
| 41-9 | H | (CH₂)₃ | H | H | CH₂ | Pen | 2-Me-5-Pyr | O |
| 41-10 | H | (CH₂)₃ | H | H | CH₂ | Pen | 2-Me-3-Pyr | O |
| 41-11 | H | (CH₂)₃ | H | H | CH₂ | Pen | 2-MeO-5-Pyr | O |
| 41-12 | H | (CH₂)₃ | H | H | CH₂ | Pen | 2-EtO-5-Pyr | O |
| 41-13 | H | (CH₂)₃ | H | H | CH₂ | Pen | 2-iPrO-5-Pyr | O |
| 41-14 | H | (CH₂)₃ | H | H | CH₂ | Pen | 2-MeS-5-Pyr | O |
| 41-15 | H | (CH₂)₃ | H | H | CH₂ | Pen | 2-EtS-5-Pyr | O |
| 41-16 | H | (CH₂)₃ | H | H | CH₂ | Pen | 2-Ph-5-Pyr | O |
| 41-17 | H | (CH₂)₃ | H | H | CH₂ | Pen | 3-Ph-6-Pyr | O |

TABLE 42

| Ex. No. Comp. | R¹ | R² | R³ | R⁴ | Z | W | X | Y |
|---|---|---|---|---|---|---|---|---|
| 42-1 | H | (CH₂)₃ | H | H | CH₂ | MeS | Ph | O |
| 42-2 | H | (CH₂)₃ | H | H | CH₂ | MeS | 4-Ph-Ph | O |
| 42-3 | H | (CH₂)₃ | H | H | CH₂ | MeS | 4-(Pyr-2)-Ph | O |
| 42-4 | H | (CH₂)₃ | H | H | CH₂ | MeS | 4-(Pyr-3)-Ph | O |
| 42-5 | H | (CH₂)₃ | H | H | CH₂ | MeS | 4-(Pyr-4)-Ph | O |
| 42-6 | H | (CH₂)₃ | H | H | CH₂ | MeS | 2-Pyr | O |
| 42-7 | H | (CH₂)₃ | H | H | CH₂ | MeS | 3-Pyr | O |
| 42-8 | H | (CH₂)₃ | H | H | CH₂ | MeS | 4-Pyr | O |
| 42-9 | H | (CH₂)₃ | H | H | CH₂ | MeS | 2-Me-5-Pyr | O |
| 42-10 | H | (CH₂)₃ | H | H | CH₂ | MeS | 2-Me-3-Pyr | O |
| 42-11 | H | (CH₂)₃ | H | H | CH₂ | MeS | 2-MeO-5-Pyr | O |
| 42-12 | H | (CH₂)₃ | H | H | CH₂ | MeS | 2-EtO-5-Pyr | O |
| 42-13 | H | (CH₂)₃ | H | H | CH₂ | MeS | 2-iPrO-5-Pyr | O |
| 42-14 | H | (CH₂)₃ | H | H | CH₂ | MeS | 2-MeS-5-Pyr | O |
| 42-15 | H | (CH₂)₃ | H | H | CH₂ | MeS | 2-EtS-5-Pyr | O |
| 42-16 | H | (CH₂)₃ | H | H | CH₂ | MeS | 2-Ph-5-Pyr | O |
| 42-17 | H | (CH₂)₃ | H | H | CH₂ | MeS | 3-Ph-6-Pyr | O |

TABLE 43

| Ex. No. Comp. | R¹ | R² | R³ | R⁴ | Z | W | X | Y |
|---|---|---|---|---|---|---|---|---|
| 43-1 | H | (CH₂)₃ | H | H | CH₂ | PhO | Ph | O |
| 43-2 | H | (CH₂)₃ | H | H | CH₂ | PhO | 4-Ph-Ph | O |
| 43-3 | H | (CH₂)₃ | H | H | CH₂ | PhO | 4-(Pyr-2)-Ph | O |
| 43-4 | H | (CH₂)₃ | H | H | CH₂ | PhO | 4-(Pyr-3)-Ph | O |
| 43-5 | H | (CH₂)₃ | H | H | CH₂ | PhO | 4-(Pyr-4)-Ph | O |
| 43-6 | H | (CH₂)₃ | H | H | CH₂ | PhO | 2-Pyr | O |
| 43-7 | H | (CH₂)₃ | H | H | CH₂ | PhO | 3-Pyr | O |
| 43-8 | H | (CH₂)₃ | H | H | CH₂ | PhO | 4-Pyr | O |
| 43-9 | H | (CH₂)₃ | H | H | CH₂ | PhO | 2-Me-5-Pyr | O |
| 43-10 | H | (CH₂)₃ | H | H | CH₂ | PhO | 2-Me-3-Pyr | O |
| 43-11 | H | (CH₂)₃ | H | H | CH₂ | PhO | 2-MeO-5-Pyr | O |
| 43-12 | H | (CH₂)₃ | H | H | CH₂ | PhO | 2-EtO-5-Pyr | O |
| 43-13 | H | (CH₂)₃ | H | H | CH₂ | PhO | 2-iPrO-5-Pyr | O |
| 43-14 | H | (CH₂)₃ | H | H | CH₂ | PhO | 2-MeS-5-Pyr | O |
| 43-15 | H | (CH₂)₃ | H | H | CH₂ | PhO | 2-EtS-5-Pyr | O |
| 43-16 | H | (CH₂)₃ | H | H | CH₂ | PhO | 2-Ph-5-Pyr | O |
| 43-17 | H | (CH₂)₃ | H | H | CH₂ | PhO | 3-Ph-6-Pyr | O |
| 43-18 | H | (CH₂)₃ | H | H | CH₂ | PhO | 4-(4-Me-Ph)-Ph | O |
| 43-19 | H | (CH₂)₃ | H | H | CH₂ | PhO | 4-(4-F-Ph)-Ph | O |
| 43-20 | H | (CH₂)₃ | H | H | CH₂ | PhO | 4-(4-Cl-Ph)-Ph | O |
| 43-21 | H | (CH₂)₃ | H | H | CH₂ | PhO | 4-(4-HO-3,5-di-Me-Ph)-Ph | O |
| 43-22 | H | (CH₂)₃ | H | H | CH₂ | PhO | 4-(4-MeO-Ph)-Ph | O |
| 43-23 | H | (CH₂)₃ | H | H | CH₂ | PhO | 4-(4-HO-Ph)-Ph | O |
| 43-24 | H | (CH₂)₃ | H | H | CH₂ | PhO | 4-(4-OHC-Ph)-Ph | O |
| 43-25 | H | (CH₂)₃ | H | H | CH₂ | PhO | 4-(4-Dma-Ph)-Ph | O |
| 43-26 | H | (CH₂)₃ | H | H | CH₂ | PhO | 4-(3-MeO-Ph)-Ph | O |
| 43-27 | H | (CH₂)₃ | H | H | CH₂ | PhO | 4-(3-HO-Ph)-Ph | O |
| 43-28 | H | (CH₂)₃ | H | H | CH₂ | PhO | 4-(3-Dma-Ph)-Ph | O |
| 43-29 | H | (CH₂)₃ | H | H | CH₂ | PhO | 4-(2-MeO-Ph)-Ph | O |
| 43-30 | H | (CH₂)₃ | H | H | CH₂ | PhO | 4-(2-HO-Ph)-Ph | O |
| 43-31 | H | (CH₂)₃ | H | H | CH₂ | PhO | 4-(3-MeO-Pyr-6)-Ph | O |
| 43-32 | H | (CH₂)₃ | H | H | CH₂ | PhO | 4-(3-EtO-Pyr-6)-Ph | O |
| 43-33 | H | (CH₂)₃ | H | H | CH₂ | PhO | 4-(3-iPrO-Pyr-6)-Ph | O |
| 43-34 | H | (CH₂)₃ | H | H | CH₂ | PhO | 4-(3-Dma-Pyr-6)-Ph | O |
| 43-35 | H | (CH₂)₃ | H | H | CH₂ | PhO | 4-(3-Dea-Pyr-6)-Ph | O |
| 43-36 | H | (CH₂)₃ | H | H | CH₂ | PhO | 4-(3-F₃C-Pyr-6)-Ph | O |
| 43-37 | H | (CH₂)₃ | H | H | CH₂ | PhO | 4-(3-O₂N-Pyr-6)-Ph | O |
| 43-38 | H | (CH₂)₃ | H | H | CH₂ | PhO | 2-(4-F-Ph)-5-Pyr | O |
| 43-39 | H | (CH₂)₃ | H | H | CH₂ | PhO | 2-(4-Cl-Ph)-5-Pyr | O |
| 43-40 | H | (CH₂)₃ | H | H | CH₂ | PhO | 2-(4-MeO-Ph)-5-Pyr | O |
| 43-41 | H | (CH₂)₃ | H | H | CH₂ | PhO | 2-(4-EtO-Ph)-5-Pyr | O |
| 43-42 | H | (CH₂)₃ | H | H | CH₂ | PhO | 2-(4-iPrO-Ph)-5-Pyr | O |
| 43-43 | H | (CH₂)₃ | H | H | CH₂ | PhO | 2-TfpO-5-Pyr | O |

TABLE 44

| Ex. No. Comp. | R¹ | R² | R³ | R⁴ | Z | W | X | Y |
|---|---|---|---|---|---|---|---|---|
| 44-1 | H | (CH₂)₃ | H | H | CH₂ | 4-iPr-PhO | Ph | O |
| 44-2 | H | (CH₂)₃ | H | H | CH₂ | 4-iPr-PhO | 4-Ph-Ph | O |
| 44-3 | H | (CH₂)₃ | H | H | CH₂ | 4-iPr-PhO | 4-(Pyr-2)-Ph | O |
| 44-4 | H | (CH₂)₃ | H | H | CH₂ | 4-iPr-PhO | 4-(Pyr-3)-Ph | O |
| 44-5 | H | (CH₂)₃ | H | H | CH₂ | 4-iPr-PhO | 4-(Pyr-4)-Ph | O |
| 44-6 | H | (CH₂)₃ | H | H | CH₂ | 4-iPr-PhO | 2-Pyr | O |
| 44-7 | H | (CH₂)₃ | H | H | CH₂ | 4-iPr-PhO | 3-Pyr | O |
| 44-8 | H | (CH₂)₃ | H | H | CH₂ | 4-iPr-PhO | 4-Pyr | O |

TABLE 44-continued

| Ex. No. Comp. | R¹ | R² | R³ | R⁴ | Z | W | X | Y |
|---|---|---|---|---|---|---|---|---|
| 44-9 | H | (CH₂)₃ | H | H | CH₂ | 4-iPr-PhO | 2-Me-5-Pyr | O |
| 44-10 | H | (CH₂)₃ | H | H | CH₂ | 4-iPr-PhO | 2-Me-3-Pyr | O |
| 44-11 | H | (CH₂)₃ | H | H | CH₂ | 4-iPr-PhO | 2-MeO-5-Pyr | O |
| 44-12 | H | (CH₂)₃ | H | H | CH₂ | 4-iPr-PhO | 2-EtO-5-Pyr | O |
| 44-13 | H | (CH₂)₃ | H | H | CH₂ | 4-iPr-PhO | 2-iPrO-5-Pyr | O |
| 44-14 | H | (CH₂)₃ | H | H | CH₂ | 4-iPr-PhO | 2-MeS-5-Pyr | O |
| 44-15 | H | (CH₂)₃ | H | H | CH₂ | 4-iPr-PhO | 2-EtS-5-Pyr | O |
| 44-16 | H | (CH₂)₃ | H | H | CH₂ | 4-iPr-PhO | 2-Ph-5-Pyr | O |
| 44-17 | H | (CH₂)₃ | H | H | CH₂ | 4-iPr-PhO | 3-Ph-6-Pyr | O |
| 44-18 | H | (CH₂)₃ | H | H | CH₂ | 4-iPr-PhO | 4-(4-Me-Ph)-Ph | O |
| 44-19 | H | (CH₂)₃ | H | H | CH₂ | 4-iPr-PhO | 4-(4-F-Ph)-Ph | O |
| 44-20 | H | (CH₂)₃ | H | H | CH₂ | 4-iPr-PhO | 4-(4-Cl-Ph)-Ph | O |
| 44-21 | H | (CH₂)₃ | H | H | CH₂ | 4-iPr-PhO | 4-(4-HO-3,5-di-Me-Ph)-Ph | O |
| 44-22 | H | (CH₂)₃ | H | H | CH₂ | 4-iPr-PhO | 4-(4-MeO-Ph)-Ph | O |
| 44-23 | H | (CH₂)₃ | H | H | CH₂ | 4-iPr-PhO | 4-(4-HO-Ph)-Ph | O |
| 44-24 | H | (CH₂)₃ | H | H | CH₂ | 4-iPr-PhO | 4-(4-OHC-Ph)-Ph | O |
| 44-25 | H | (CH₂)₃ | H | H | CH₂ | 4-iPr-PhO | 4-(4-Dma-Ph)-Ph | O |
| 44-26 | H | (CH₂)₃ | H | H | CH₂ | 4-iPr-PhO | 4-(3-MeO-Ph)-Ph | O |
| 44-27 | H | (CH₂)₃ | H | H | CH₂ | 4-iPr-PhO | 4-(3-HO-Ph)-Ph | O |
| 44-28 | H | (CH₂)₃ | H | H | CH₂ | 4-iPr-PhO | 4-(3-Dma-Ph)-Ph | O |
| 44-29 | H | (CH₂)₃ | H | H | CH₂ | 4-iPr-PhO | 4-(2-MeO-Ph)-Ph | O |
| 44-30 | H | (CH₂)₃ | H | H | CH₂ | 4-iPr-PhO | 4-(2-HO-Ph)-Ph | O |
| 44-31 | H | (CH₂)₃ | H | H | CH₂ | 4-iPr-PhO | 4-(3-MeO-Pyr-6)-Ph | O |
| 44-32 | H | (CH₂)₃ | H | H | CH₂ | 4-iPr-PhO | 4-(3-EtO-Pyr-6)-Ph | O |
| 44-33 | H | (CH₂)₃ | H | H | CH₂ | 4-iPr-PhO | 4-(3-iPrO-Pyr-6)-Ph | O |
| 44-34 | H | (CH₂)₃ | H | H | CH₂ | 4-iPr-PhO | 4-(3-Dma-Pyr-6)-Ph | O |
| 44-35 | H | (CH₂)₃ | H | H | CH₂ | 4-iPr-PhO | 4-(3-Dea-Pyr-6)-Ph | O |
| 44-36 | H | (CH₂)₃ | H | H | CH₂ | 4-iPr-PhO | 4-(3-F₃C-Pyr-6)-Ph | O |
| 44-37 | H | (CH₂)₃ | H | H | CH₂ | 4-iPr-PhO | 4-(3-O₂N-Pyr-6)-Ph | O |
| 44-38 | H | (CH₂)₃ | H | H | CH₂ | 4-iPr-PhO | 2-(4-F-Ph)-5-Pyr | O |
| 44-39 | H | (CH₂)₃ | H | H | CH₂ | 4-iPr-PhO | 2-(4-Cl-Ph)-5-Pyr | O |
| 44-40 | H | (CH₂)₃ | H | H | CH₂ | 4-iPr-PhO | 2-(4-MeO-Ph)-5-Pyr | O |
| 44-41 | H | (CH₂)₃ | H | H | CH₂ | 4-iPr-PhO | 2-(4-EtO-Ph)-5-Pyr | O |
| 44-42 | H | (CH₂)₃ | H | H | CH₂ | 4-iPr-PhO | 2-(4-iPrO-Ph)-5-Pyr | O |
| 44-43 | H | (CH₂)₃ | H | H | CH₂ | 4-iPr-PhO | 2-TfpO-5-Pyr | O |

TABLE 45

| Ex. No. Comp. | R¹ | R² | R³ | R⁴ | Z | W | X | Y |
|---|---|---|---|---|---|---|---|---|
| 45-1 | H | (CH₂)₃ | H | H | CH₂ | 4-MeO—PhO | Ph | O |
| 45-2 | H | (CH₂)₃ | H | H | CH₂ | 4-MeO—PhO | 4-Ph—Ph | O |
| 45-3 | H | (CH₂)₃ | H | H | CH₂ | 4-MeO—PhO | 4-(Pyr-2)-Ph | O |
| 45-4 | H | (CH₂)₃ | H | H | CH₂ | 4-MeO—PhO | 4-(Pyr-3)-Ph | O |
| 45-5 | H | (CH₂)₃ | H | H | CH₂ | 4-MeO—PhO | 4-(Pyr-4)-Ph | O |
| 45-6 | H | (CH₂)₃ | H | H | CH₂ | 4-MeO—PhO | 2-Pyr | O |
| 45-7 | H | (CH₂)₃ | H | H | CH₂ | 4-MeO—PhO | 3-Pyr | O |
| 45-8 | H | (CH₂)₃ | H | H | CH₂ | 4-MeO—PhO | 4-Pyr | O |
| 45-9 | H | (CH₂)₃ | H | H | CH₂ | 4-MeO—PhO | 2-Me-5-Pyr | O |
| 45-10 | H | (CH₂)₃ | H | H | CH₂ | 4-MeO—PhO | 2-Me-3-Pyr | O |
| 45-11 | H | (CH₂)₃ | H | H | CH₂ | 4-MeO—PhO | 2-MeO-5-Pyr | O |
| 45-12 | H | (CH₂)₃ | H | H | CH₂ | 4-MeO—PhO | 2-EtO-5-Pyr | O |
| 45-13 | H | (CH₂)₃ | H | H | CH₂ | 4-MeO—PhO | 2-iPrO-5-Pyr | O |
| 45-14 | H | (CH₂)₃ | H | H | CH₂ | 4-MeO—PhO | 2-MeS-5-Pyr | O |
| 45-15 | H | (CH₂)₃ | H | H | CH₂ | 4-MeO—PhO | 2-EtS-5-Pyr | O |
| 45-16 | H | (CH₂)₃ | H | H | CH₂ | 4-MeO—PhO | 2-Ph-5-Pyr | O |
| 45-17 | H | (CH₂)₃ | H | H | CH₂ | 4-MeO—PhO | 3-Ph-6-Pyr | O |
| 45-18 | H | (CH₂)₃ | H | H | CH₂ | 4-MeO—PhO | 4-(4-Me—Ph)—Ph | O |
| 45-19 | H | (CH₂)₃ | H | H | CH₂ | 4-MeO—PhO | 4-(4-F—Ph)—Ph | O |
| 45-20 | H | (CH₂)₃ | H | H | CH₂ | 4-MeO—PhO | 4-(4-Cl—Ph)—Ph | O |
| 45-21 | H | (CH₂)₃ | H | H | CH₂ | 4-MeO—PhO | 4-(4-HO-3,5-di-Me—Ph)—Ph | O |
| 45-22 | H | (CH₂)₃ | H | H | CH₂ | 4-MeO—PhO | 4-(4-MeO—Ph)—Ph | O |
| 45-23 | H | (CH₂)₃ | H | H | CH₂ | 4-MeO—PhO | 4-(4-HO—Ph)—Ph | O |
| 45-24 | H | (CH₂)₃ | H | H | CH₂ | 4-MeO—PhO | 4-(4-OHC—Ph)—Ph | O |
| 45-25 | H | (CH₂)₃ | H | H | CH₂ | 4-MeO—PhO | 4-(4-Dma—Ph)—Ph | O |
| 45-26 | H | (CH₂)₃ | H | H | CH₂ | 4-MeO—PhO | 4-(3-MeO—Ph)—Ph | O |

TABLE 45-continued

| Ex. No. Comp. | R¹ | R² | R³ | R⁴ | Z | W | X | Y |
|---|---|---|---|---|---|---|---|---|
| 45-27 | H | (CH₂)₃ | H | H | CH₂ | 4-MeO—PhO | 4-(3-HO—Ph)—Ph | O |
| 45-28 | H | (CH₂)₃ | H | H | CH₂ | 4-MeO—PhO | 4-(3-Dma—Ph)—Ph | O |
| 45-29 | H | (CH₂)₃ | H | H | CH₂ | 4-MeO—PhO | 4-(2-MeO—Ph)—Ph | O |
| 45-30 | H | (CH₂)₃ | H | H | CH₂ | 4-MeO—PhO | 4-(2-HO—Ph)—Ph | O |
| 45-31 | H | (CH₂)₃ | H | H | CH₂ | 4-MeO—PhO | 4-(3-MeO—Pyr-6)-Ph | O |
| 45-32 | H | (CH₂)₃ | H | H | CH₂ | 4-MeO—PhO | 4-(3-EtO—Pyr-6)-Ph | O |
| 45-33 | H | (CH₂)₃ | H | H | CH₂ | 4-MeO—PhO | 4-(3-iPrO—Pyr-6)-Ph | O |
| 45-34 | H | (CH₂)₃ | H | H | CH₂ | 4-MeO—PhO | 4-(3-Dma—Pyr-6)-Ph | O |
| 45-35 | H | (CH₂)₃ | H | H | CH₂ | 4-MeO—PhO | 4-(3-Dea—Pyr-6)-Ph | O |
| 45-36 | H | (CH₂)₃ | H | H | CH₂ | 4-MeO—PhO | 4-(3-F₃C—Pyr-6)-Ph | O |
| 45-37 | H | (CH₂)₃ | H | H | CH₂ | 4-MeO—PhO | 4-(3-O₂N—Pyr-6)-Ph | O |
| 45-38 | H | (CH₂)₃ | H | H | CH₂ | 4-MeO—PhO | 2-(4-F—Ph)-5-Pyr | O |
| 45-39 | H | (CH₂)₃ | H | H | CH₂ | 4-MeO—PhO | 2-(4-Cl—Ph)-5-Pyr | O |
| 45-40 | H | (CH₂)₃ | H | H | CH₂ | 4-MeO—PhO | 2-(4-MeO—Ph)-5-Pyr | O |
| 45-41 | H | (CH₂)₃ | H | H | CH₂ | 4-MeO—PhO | 2-(4-EtO—Ph)-5-Pyr | O |
| 45-42 | H | (CH₂)₃ | H | H | CH₂ | 4-MeO—PhO | 2-(4-iPrO—Ph)-5-Pyr | O |
| 45-43 | H | (CH₂)₃ | H | H | CH₂ | 4-MeO—PhO | 2-TfpO-5-Pyr | O |

TABLE 46

| Ex. No. Comp. | R¹ | R² | R³ | R⁴ | Z | W | X | Y |
|---|---|---|---|---|---|---|---|---|
| 46-1 | H | (CH₂)₃ | H | H | CH₂ | PhS | Ph | O |
| 46-2 | H | (CH₂)₃ | H | H | CH₂ | PhS | 4-Ph—Ph | O |
| 46-3 | H | (CH₂)₃ | H | H | CH₂ | PhS | 4-(Pyr-2)-Ph | O |
| 46-4 | H | (CH₂)₃ | H | H | CH₂ | PhS | 4-(Pyr-3)-Ph | O |
| 46-5 | H | (CH₂)₃ | H | H | CH₂ | PhS | 4-(Pyr-4)-Ph | O |
| 46-6 | H | (CH₂)₃ | H | H | CH₂ | PhS | 2-Pyr | O |
| 46-7 | H | (CH₂)₃ | H | H | CH₂ | PhS | 3-Pyr | O |
| 46-8 | H | (CH₂)₃ | H | H | CH₂ | PhS | 4-Pyr | O |
| 46-9 | H | (CH₂)₃ | H | H | CH₂ | PhS | 2-Me-5-Pyr | O |
| 46-10 | H | (CH₂)₃ | H | H | CH₂ | PhS | 2-Me-3-Pyr | O |
| 46-11 | H | (CH₂)₃ | H | H | CH₂ | PhS | 2-MeO-5-Pyr | O |
| 46-12 | H | (CH₂)₃ | H | H | CH₂ | PhS | 2-EtO-5-Pyr | O |
| 46-13 | H | (CH₂)₃ | H | H | CH₂ | PhS | 2-iPrO-5-Pyr | O |
| 46-14 | H | (CH₂)₃ | H | H | CH₂ | PhS | 2-MeS-5-Pyr | O |
| 46-15 | H | (CH₂)₃ | H | H | CH₂ | PhS | 2-EtS-5-Pyr | O |
| 46-16 | H | (CH₂)₃ | H | H | CH₂ | PhS | 2-Ph-5-Pyr | O |
| 46-17 | H | (CH₂)₃ | H | H | CH₂ | PhS | 3-Ph-6-Pyr | O |

TABLE 47

| Ex. No. Comp. | R¹ | R² | R³ | R⁴ | Z | W | X | Y |
|---|---|---|---|---|---|---|---|---|
| 47-1 | H | (CH₂)₃ | H | H | CH₂ | Ph(CH₂)₃ | Ph | O |
| 47-2 | H | (CH₂)₃ | H | H | CH₂ | Ph(CH₂)₃ | 4-Ph—Ph | O |
| 47-3 | H | (CH₂)₃ | H | H | CH₂ | Ph(CH₂)₃ | 4-(Pyr-2)-Ph | O |
| 47-4 | H | (CH₂)₃ | H | H | CH₂ | Ph(CH₂)₃ | 4-(Pyr-3)-Ph | O |
| 47-5 | H | (CH₂)₃ | H | H | CH₂ | Ph(CH₂)₃ | 4-(Pyr-4)-Ph | O |
| 47-6 | H | (CH₂)₃ | H | H | CH₂ | Ph(CH₂)₃ | 2-Pyr | O |
| 47-7 | H | (CH₂)₃ | H | H | CH₂ | Ph(CH₂)₃ | 3-Pyr | O |
| 47-8 | H | (CH₂)₃ | H | H | CH₂ | Ph(CH₂)₃ | 4-Pyr | O |
| 47-9 | H | (CH₂)₃ | H | H | CH₂ | Ph(CH₂)₃ | 2-Me-5-Pyr | O |
| 47-10 | H | (CH₂)₃ | H | H | CH₂ | Ph(CH₂)₃ | 2-Me-3-Pyr | O |
| 47-11 | H | (CH₂)₃ | H | H | CH₂ | Ph(CH₂)₃ | 2-MeO-5-Pyr | O |
| 47-12 | H | (CH₂)₃ | H | H | CH₂ | Ph(CH₂)₃ | 2-EtO-5-Pyr | O |
| 47-13 | H | (CH₂)₃ | H | H | CH₂ | Ph(CH₂)₃ | 2-iPrO-5-Pyr | O |
| 47-14 | H | (CH₂)₃ | H | H | CH₂ | Ph(CH₂)₃ | 2-MeS-5-Pyr | O |
| 47-15 | H | (CH₂)₃ | H | H | CH₂ | Ph(CH₂)₃ | 2-EtS-5-Pyr | O |
| 47-16 | H | (CH₂)₃ | H | H | CH₂ | Ph(CH₂)₃ | 2-Ph-5-Pyr | O |
| 47-17 | H | (CH₂)₃ | H | H | CH₂ | Ph(CH₂)₃ | 3-Ph-6-Pyr | O |

TABLE 48

| Ex. No. Comp. | R¹ | R² | R³ | R⁴ | Z | W | X | Y |
|---|---|---|---|---|---|---|---|---|
| 48-1 | H | CHMeCH₂ | H | H | CH₂ | EtO | Ph | O |
| 48-2 | H | CHMeCH₂ | H | H | CH₂ | EtO | 4-Ph—Ph | O |
| 48-3 | H | CHMeCH₂ | H | H | CH₂ | EtO | 4-(Pyr-2)-Ph | O |
| 48-4 | H | CHMeCH₂ | H | H | CH₂ | EtO | 4-(Pyr-3)-Ph | O |
| 48-5 | H | CHMeCH₂ | H | H | CH₂ | EtO | 4-(Pyr-4)-Ph | O |
| 48-6 | H | CHMeCH₂ | H | H | CH₂ | EtO | 2-Pyr | O |
| 48-7 | H | CHMeCH₂ | H | H | CH₂ | EtO | 3-Pyr | O |
| 48-8 | H | CHMeCH₂ | H | H | CH₂ | EtO | 4-Pyr | O |
| 48-9 | H | CHMeCH₂ | H | H | CH₂ | EtO | 2-Me-5-Pyr | O |
| 48-10 | H | CHMeCH₂ | H | H | CH₂ | EtO | 2-Me-3-Pyr | O |
| 48-11 | H | CHMeCH₂ | H | H | CH₂ | EtO | 2-MeO-5-Pyr | O |
| 48-12 | H | CHMeCH₂ | H | H | CH₂ | EtO | 2-EtO-5-Pyr | O |
| 48-13 | H | CHMeCH₂ | H | H | CH₂ | EtO | 2-iPrO-5-Pyr | O |
| 48-14 | H | CHMeCH₂ | H | H | CH₂ | EtO | 2-MeS-5-Pyr | O |
| 48-15 | H | CHMeCH₂ | H | H | CH₂ | EtO | 2-EtS-5-Pyr | O |
| 48-16 | H | CHMeCH₂ | H | H | CH₂ | EtO | 2-Ph-5-Pyr | O |
| 48-17 | H | CHMeCH₂ | H | H | CH₂ | EtO | 3-Ph-6-Pyr | O |

TABLE 49

| Ex. No. Comp. | R¹ | R² | R³ | R⁴ | Z | W | X | Y |
|---|---|---|---|---|---|---|---|---|
| 49-1 | H | CHMeCH₂ | H | H | CH₂ | Pr | Ph | O |
| 49-2 | H | CHMeCH₂ | H | H | CH₂ | Pr | 4-Ph—Ph | O |
| 49-3 | H | CHMeCH₂ | H | H | CH₂ | Pr | 4-(Pyr-2)-Ph | O |
| 49-4 | H | CHMeCH₂ | H | H | CH₂ | Pr | 4-(Pyr-3)-Ph | O |
| 49-5 | H | CHMeCH₂ | H | H | CH₂ | Pr | 4-(Pyr-4)-Ph | O |
| 49-6 | H | CHMeCH₂ | H | H | CH₂ | Pr | 2-Pyr | O |
| 49-7 | H | CHMeCH₂ | H | H | CH₂ | Pr | 3-Pyr | O |
| 49-8 | H | CHMeCH₂ | H | H | CH₂ | Pr | 4-Pyr | O |
| 49-9 | H | CHMeCH₂ | H | H | CH₂ | Pr | 2-Me-5-Pyr | O |
| 49-10 | H | CHMeCH₂ | H | H | CH₂ | Pr | 2-Me-3-Pyr | O |
| 49-11 | H | CHMeCH₂ | H | H | CH₂ | Pr | 2-MeO-5-Pyr | O |
| 49-12 | H | CHMeCH₂ | H | H | CH₂ | Pr | 2-EtO-5-Pyr | O |
| 49-13 | H | CHMeCH₂ | H | H | CH₂ | Pr | 2-iPrO-5-Pyr | O |
| 49-14 | H | CHMeCH₂ | H | H | CH₂ | Pr | 2-MeS-5-Pyr | O |
| 49-15 | H | CHMeCH₂ | H | H | CH₂ | Pr | 2-EtS-5-Pyr | O |
| 49-16 | H | CHMeCH₂ | H | H | CH₂ | Pr | 2-Ph-5-Pyr | O |
| 49-17 | H | CHMeCH₂ | H | H | CH₂ | Pr | 3-Ph-6-Pyr | O |

TABLE 50

| Ex. No. Comp. | R¹ | R² | R³ | R⁴ | Z | W | X | Y |
|---|---|---|---|---|---|---|---|---|
| 50-1 | H | CHMeCH₂ | H | H | CH₂ | Bu | Ph | O |
| 50-2 | H | CHMeCH₂ | H | H | CH₂ | Bu | 4-Ph—Ph | O |
| 50-3 | H | CHMeCH₂ | H | H | CH₂ | Bu | 4-(Pyr-2)-Ph | O |
| 50-4 | H | CHMeCH₂ | H | H | CH₂ | Bu | 4-(Pyr-3)-Ph | O |
| 50-5 | H | CHMeCH₂ | H | H | CH₂ | Bu | 4-(Pyr-4)-Ph | O |
| 50-6 | H | CHMeCH₂ | H | H | CH₂ | Bu | 2-Pyr | O |
| 50-7 | H | CHMeCH₂ | H | H | CH₂ | Bu | 3-Pyr | O |
| 50-8 | H | CHMeCH₂ | H | H | CH₂ | Bu | 4-Pyr | O |
| 50-9 | H | CHMeCH₂ | H | H | CH₂ | Bu | 2-Me-5-Pyr | O |
| 50-10 | H | CHMeCH₂ | H | H | CH₂ | Bu | 2-Me-3-Pyr | O |
| 50-11 | H | CHMeCH₂ | H | H | CH₂ | Bu | 2-MeO-5-Pyr | O |
| 50-12 | H | CHMeCH₂ | H | H | CH₂ | Bu | 2-EtO-5-Pyr | O |
| 50-13 | H | CHMeCH₂ | H | H | CH₂ | Bu | 2-iPrO-5-Pyr | O |
| 50-14 | H | CHMeCH₂ | H | H | CH₂ | Bu | 2-MeS-5-Pyr | O |
| 50-15 | H | CHMeCH₂ | H | H | CH₂ | Bu | 2-EtS-5-Pyr | O |
| 50-16 | H | CHMeCH₂ | H | H | CH₂ | Bu | 2-Ph-5-Pyr | O |
| 50-17 | H | CHMeCH₂ | H | H | CH₂ | Bu | 3-Ph-6-Pyr | O |

TABLE 51

| Ex. No. Comp. | R¹ | R² | R³ | R⁴ | Z | W | X | Y |
|---|---|---|---|---|---|---|---|---|
| 51-1 | H | CHMeCH₂ | H | H | CH₂ | Pen | Ph | O |
| 51-2 | H | CHMeCH₂ | H | H | CH₂ | Pen | 4-Ph-Ph | O |
| 51-3 | H | CHMeCH₂ | H | H | CH₂ | Pen | 4-(Pyr-2)-Ph | O |
| 51-4 | H | CHMeCH₂ | H | H | CH₂ | Pen | 4-(Pyr-3)-Ph | O |
| 51-5 | H | CHMeCH₂ | H | H | CH₂ | Pen | 4-(Pyr-4)-Ph | O |
| 51-6 | H | CHMeCH₂ | H | H | CH₂ | Pen | 2-Pyr | O |
| 51-7 | H | CHMeCH₂ | H | H | CH₂ | Pen | 3-Pyr | O |
| 51-8 | H | CHMeCH₂ | H | H | CH₂ | Pen | 4-Pyr | O |
| 51-9 | H | CHMeCH₂ | H | H | CH₂ | Pen | 2-Me-5-Pyr | O |
| 51-10 | H | CHMeCH₂ | H | H | CH₂ | Pen | 2-Me-3-Pyr | O |
| 51-11 | H | CHMeCH₂ | H | H | CH₂ | Pen | 2-MeO-5-Pyr | O |
| 51-12 | H | CHMeCH₂ | H | H | CH₂ | Pen | 2-EtO-5-Pyr | O |
| 51-13 | H | CHMeCH₂ | H | H | CH₂ | Pen | 2-iPrO-5-Pyr | O |
| 51-14 | H | CHMeCH₂ | H | H | CH₂ | Pen | 2-MeS-5-Pyr | O |
| 51-15 | H | CHMeCH₂ | H | H | CH₂ | Pen | 2-EtS-5-Pyr | O |
| 51-16 | H | CHMeCH₂ | H | H | CH₂ | Pen | 2-Ph-5-Pyr | O |
| 51-17 | H | CHMeCH₂ | H | H | CH₂ | Pen | 3-Ph-6-Pyr | O |

TABLE 52

| Ex. No. Comp. | R¹ | R² | R³ | R⁴ | Z | W | X | Y |
|---|---|---|---|---|---|---|---|---|
| 52-1 | H | CHMeCH₂ | H | H | CH₂ | MeS | Ph | O |
| 52-2 | H | CHMeCH₂ | H | H | CH₂ | MeS | 4-Ph-Ph | O |
| 52-3 | H | CHMeCH₂ | H | H | CH₂ | MeS | 4-(Pyr-2)-Ph | O |
| 52-4 | H | CHMeCH₂ | H | H | CH₂ | MeS | 4-(Pyr-3)-Ph | O |
| 52-5 | H | CHMeCH₂ | H | H | CH₂ | MeS | 4-(Pyr-4)-Ph | O |
| 52-6 | H | CHMeCH₂ | H | H | CH₂ | MeS | 2-Pyr | O |
| 52-7 | H | CHMeCH₂ | H | H | CH₂ | MeS | 3-Pyr | O |
| 52-8 | H | CHMeCH₂ | H | H | CH₂ | MeS | 4-Pyr | O |
| 52-9 | H | CHMeCH₂ | H | H | CH₂ | MeS | 2-Me-5-Pyr | O |
| 52-10 | H | CHMeCH₂ | H | H | CH₂ | MeS | 2-Me-3-Pyr | O |
| 52-11 | H | CHMeCH₂ | H | H | CH₂ | MeS | 2-MeO-5-Pyr | O |
| 52-12 | H | CHMeCH₂ | H | H | CH₂ | MeS | 2-EtO-5-Pyr | O |
| 52-13 | H | CHMeCH₂ | H | H | CH₂ | MeS | 2-iPrO-5-Pyr | O |
| 52-14 | H | CHMeCH₂ | H | H | CH₂ | MeS | 2-MeS-5-Pyr | O |
| 52-15 | H | CHMeCH₂ | H | H | CH₂ | MeS | 2-EtS-5-Pyr | O |
| 52-16 | H | CHMeCH₂ | H | H | CH₂ | MeS | 2-Ph-5-Pyr | O |
| 52-17 | H | CHMeCH₂ | H | H | CH₂ | MeS | 3-Ph-6-Pyr | O |

TABLE 53

| Ex. No. Comp. | R¹ | R² | R³ | R⁴ | Z | W | X | Y |
|---|---|---|---|---|---|---|---|---|
| 53-1 | H | CHMeCH₂ | H | H | CH₂ | PhO | Ph | O |
| 53-2 | H | CHMeCH₂ | H | H | CH₂ | PhO | 4-Ph-Ph | O |
| 53-3 | H | CHMeCH₂ | H | H | CH₂ | PhO | 4-(Pyr-2)-Ph | O |
| 53-4 | H | CHMeCH₂ | H | H | CH₂ | PhO | 4-(Pyr-3)-Ph | O |
| 53-5 | H | CHMeCH₂ | H | H | CH₂ | PhO | 4-(Pyr-4)-Ph | O |
| 53-6 | H | CHMeCH₂ | H | H | CH₂ | PhO | 2-Pyr | O |
| 53-7 | H | CHMeCH₂ | H | H | CH₂ | PhO | 3-Pyr | O |
| 53-8 | H | CHMeCH₂ | H | H | CH₂ | PhO | 4-Pyr | O |
| 53-9 | H | CHMeCH₂ | H | H | CH₂ | PhO | 2-Me-5-Pyr | O |
| 53-10 | H | CHMeCH₂ | H | H | CH₂ | PhO | 2-Me-3-Pyr | O |
| 53-11 | H | CHMeCH₂ | H | H | CH₂ | PhO | 2-MeO-5-Pyr | O |
| 53-12 | H | CHMeCH₂ | H | H | CH₂ | PhO | 2-EtO-5-Pyr | O |
| 53-13 | H | CHMeCH₂ | H | H | CH₂ | PhO | 2-iPrO-5-Pyr | O |
| 53-14 | H | CHMeCH₂ | H | H | CH₂ | PhO | 2-MeS-5-Pyr | O |
| 53-15 | H | CHMeCH₂ | H | H | CH₂ | PhO | 2-EtS-5-Pyr | O |
| 53-16 | H | CHMeCH₂ | H | H | CH₂ | PhO | 2-Ph-5-Pyr | O |
| 53-17 | H | CHMeCH₂ | H | H | CH₂ | PhO | 3-Ph-6-Pyr | O |

TABLE 54

| Ex. No. Comp. | R¹ | R² | R³ | R⁴ | Z | W | X | Y |
|---|---|---|---|---|---|---|---|---|
| 54-1 | H | CHMeCH₂ | H | H | CH₂ | 4-iPr-PhO | Ph | O |
| 54-2 | H | CHMeCH₂ | H | H | CH₂ | 4-iPr-PhO | 4-Ph-Ph | O |
| 54-3 | H | CHMeCH₂ | H | H | CH₂ | 4-iPr-PhO | 4-(Pyr-2)-Ph | O |
| 54-4 | H | CHMeCH₂ | H | H | CH₂ | 4-iPr-PhO | 4-(Pyr-3)-Ph | O |
| 54-5 | H | CHMeCH₂ | H | H | CH₂ | 4-iPr-PhO | 4-(Pyr-4)-Ph | O |
| 54-6 | H | CHMeCH₂ | H | H | CH₂ | 4-iPr-PhO | 2-Pyr | O |
| 54-7 | H | CHMeCH₂ | H | H | CH₂ | 4-iPr-PhO | 3-Pyr | O |
| 54-8 | H | CHMeCH₂ | H | H | CH₂ | 4-iPr-PhO | 4-Pyr | O |
| 54-9 | H | CHMeCH₂ | H | H | CH₂ | 4-iPr-PhO | 2-Me-5-Pyr | O |
| 54-10 | H | CHMeCH₂ | H | H | CH₂ | 4-iPr-PhO | 2-Me-3-Pyr | O |
| 54-11 | H | CHMeCH₂ | H | H | CH₂ | 4-iPr-PhO | 2-MeO-5-Pyr | O |
| 54-12 | H | CHMeCH₂ | H | H | CH₂ | 4-iPr-PhO | 2-EtO-5-Pyr | O |

TABLE 54-continued

| Ex. No. Comp. | R¹ | R² | R³ | R⁴ | Z | W | X | Y |
|---|---|---|---|---|---|---|---|---|
| 54-13 | H | CHMeCH₂ | H | H | CH₂ | 4-iPr-PhO | 2-iPrO-5-Pyr | O |
| 54-14 | H | CHMeCH₂ | H | H | CH₂ | 4-iPr-PhO | 2-MeS-5-Pyr | O |
| 54-15 | H | CHMeCH₂ | H | H | CH₂ | 4-iPr-PhO | 2-EtS-5-Pyr | O |
| 54-16 | H | CHMeCH₂ | H | H | CH₂ | 4-iPr-PhO | 2-Ph-5-Pyr | O |
| 54-17 | H | CHMeCH₂ | H | H | CH₂ | 4-iPr-PhO | 3-Ph-6-Pyr | O |

TABLE 55

| Ex. No. Comp. | R¹ | R² | R³ | R⁴ | Z | W | X | Y |
|---|---|---|---|---|---|---|---|---|
| 55-1 | H | CHMeCH₂ | H | H | CH₂ | 4-MeO-PhO | Ph | O |
| 55-2 | H | CHMeCH₂ | H | H | CH₂ | 4-MeO-PhO | 4-Ph-Ph | O |
| 55-3 | H | CHMeCH₂ | H | H | CH₂ | 4-MeO-PhO | 4-(Pyr-2)-Ph | O |
| 55-4 | H | CHMeCH₂ | H | H | CH₂ | 4-MeO-PhO | 4-(Pyr-3)-Ph | O |
| 55-5 | H | CHMeCH₂ | H | H | CH₂ | 4-MeO-PhO | 4-(Pyr-4)-Ph | O |
| 55-6 | H | CHMeCH₂ | H | H | CH₂ | 4-MeO-PhO | 2-Pyr | O |
| 55-7 | H | CHMeCH₂ | H | H | CH₂ | 4-MeO-PhO | 3-Pyr | O |
| 55-8 | H | CHMeCH₂ | H | H | CH₂ | 4-MeO-PhO | 4-Pyr | O |
| 55-9 | H | CHMeCH₂ | H | H | CH₂ | 4-MeO-PhO | 2-Me-5-Pyr | O |
| 55-10 | H | CHMeCH₂ | H | H | CH₂ | 4-MeO-PhO | 2-Me-3-Pyr | O |
| 55-11 | H | CHMeCH₂ | H | H | CH₂ | 4-MeO-PhO | 2-MeO-5-Pyr | O |
| 55-12 | H | CHMeCH₂ | H | H | CH₂ | 4-MeO-PhO | 2-EtO-5-Pyr | O |
| 55-13 | H | CHMeCH₂ | H | H | CH₂ | 4-MeO-PhO | 2-iPrO-5-Pyr | O |
| 55-14 | H | CHMeCH₂ | H | H | CH₂ | 4-MeO-PhO | 2-MeS-5-Pyr | O |
| 55-15 | H | CHMeCH₂ | H | H | CH₂ | 4-MeO-PhO | 2-EtS-5-Pyr | O |
| 55-16 | H | CHMeCH₂ | H | H | CH₂ | 4-MeO-PhO | 2-Ph-5-Pyr | O |
| 55-17 | H | CHMeCH₂ | H | H | CH₂ | 4-MeO-PhO | 3-Ph-6-Pyr | O |

TABLE 56

| Ex. No. Comp. | R¹ | R² | R³ | R⁴ | Z | W | X | Y |
|---|---|---|---|---|---|---|---|---|
| 56-1 | H | CHMeCH₂ | H | H | CH₂ | PhS | Ph | O |
| 56-2 | H | CHMeCH₂ | H | H | CH₂ | PhS | 4-Ph-Ph | O |
| 56-3 | H | CHMeCH₂ | H | H | CH₂ | PhS | 4-(Pyr-2)-Ph | O |
| 56-4 | H | CHMeCH₂ | H | H | CH₂ | PhS | 4-(Pyr-3)-Ph | O |
| 56-5 | H | CHMeCH₂ | H | H | CH₂ | PhS | 4-(Pyr-4)-Ph | O |
| 56-6 | H | CHMeCH₂ | H | H | CH₂ | PhS | 2-Pyr | O |
| 56-7 | H | CHMeCH₂ | H | H | CH₂ | PhS | 3-Pyr | O |
| 56-8 | H | CHMeCH₂ | H | H | CH₂ | PhS | 4-Pyr | O |
| 56-9 | H | CHMeCH₂ | H | H | CH₂ | PhS | 2-Me-5-Pyr | O |
| 56-10 | H | CHMeCH₂ | H | H | CH₂ | PhS | 2-Me-3-Pyr | O |
| 56-11 | H | CHMeCH₂ | H | H | CH₂ | PhS | 2-MeO-5-Pyr | O |
| 56-12 | H | CHMeCH₂ | H | H | CH₂ | PhS | 2-EtO-5-Pyr | O |
| 56-13 | H | CHMeCH₂ | H | H | CH₂ | PhS | 2-iPrO-5-Pyr | O |
| 56-14 | H | CHMeCH₂ | H | H | CH₂ | PhS | 2-MeS-5-Pyr | O |
| 56-15 | H | CHMeCH₂ | H | H | CH₂ | PhS | 2-EtS-5-Pyr | O |
| 56-16 | H | CHMeCH₂ | H | H | CH₂ | PhS | 2-Ph-5-Pyr | O |
| 56-17 | H | CHMeCH₂ | H | H | CH₂ | PhS | 3-Ph-6-Pyr | O |

TABLE 57

| Ex. No. Comp. | R¹ | R² | R³ | R⁴ | Z | W | X | Y |
|---|---|---|---|---|---|---|---|---|
| 57-1 | H | CHMeCH₂ | H | H | CH₂ | Ph(CH₂)₃ | Ph | O |
| 57-2 | H | CHMeCH₂ | H | H | CH₂ | Ph(CH₂)₃ | 4-Ph-Ph | O |
| 57-3 | H | CHMeCH₂ | H | H | CH₂ | Ph(CH₂)₃ | 4-(Pyr-2)-Ph | O |
| 57-4 | H | CHMeCH₂ | H | H | CH₂ | Ph(CH₂)₃ | 4-(Pyr-3)-Ph | O |
| 57-5 | H | CHMeCH₂ | H | H | CH₂ | Ph(CH₂)₃ | 4-(Pyr-4)-Ph | O |
| 57-6 | H | CHMeCH₂ | H | H | CH₂ | Ph(CH₂)₃ | 2-Pyr | O |
| 57-7 | H | CHMeCH₂ | H | H | CH₂ | Ph(CH₂)₃ | 3-Pyr | O |
| 57-8 | H | CHMeCH₂ | H | H | CH₂ | Ph(CH₂)₃ | 4-Pyr | O |
| 57-9 | H | CHMeCH₂ | H | H | CH₂ | Ph(CH₂)₃ | 2-Me-5-Pyr | O |
| 57-10 | H | CHMeCH₂ | H | H | CH₂ | Ph(CH₂)₃ | 2-Me-3-Pyr | O |
| 57-11 | H | CHMeCH₂ | H | H | CH₂ | Ph(CH₂)₃ | 2-MeO-5-Pyr | O |
| 57-12 | H | CHMeCH₂ | H | H | CH₂ | Ph(CH₂)₃ | 2-EtO-5-Pyr | O |
| 57-13 | H | CHMeCH₂ | H | H | CH₂ | Ph(CH₂)₃ | 2-iPrO-5-Pyr | O |
| 57-14 | H | CHMeCH₂ | H | H | CH₂ | Ph(CH₂)₃ | 2-MeS-5-Pyr | O |

TABLE 57-continued

| Ex. No. Comp. | R¹ | R² | R³ | R⁴ | Z | W | X | Y |
|---|---|---|---|---|---|---|---|---|
| 57-15 | H | CHMeCH₂ | H | H | CH₂ | Ph(CH₂)₃ | 2-EtS-5-Pyr | O |
| 57-16 | H | CHMeCH₂ | H | H | CH₂ | Ph(CH₂)₃ | 2-Ph-5-Pyr | O |
| 57-17 | H | CHMeCH₂ | H | H | CH₂ | Ph(CH₂)₃ | 3-Ph-6-Pyr | O |

TABLE 58

| Ex. No. Comp. | R¹ | R² | R³ | R⁴ | Z | W | X | Y |
|---|---|---|---|---|---|---|---|---|
| 58-1 | H | (CH₂)₂ | H | H | CH₂ | EtO | Ph | — |
| 58-2 | H | (CH₂)₂ | H | H | CH₂ | EtO | 4-Ph-Ph | — |
| 58-3 | H | (CH₂)₂ | H | H | CH₂ | EtO | 4-(Pyr-2)-Ph | — |
| 58-4 | H | (CH₂)₂ | H | H | CH₂ | EtO | 4-(Pyr-3)-Ph | — |
| 58-5 | H | (CH₂)₂ | H | H | CH₂ | EtO | 4-(Pyr-4)-Ph | — |
| 58-6 | H | (CH₂)₂ | H | H | CH₂ | EtO | 2-Pyr | — |
| 58-7 | H | (CH₂)₂ | H | H | CH₂ | EtO | 3-Pyr | — |
| 58-8 | H | (CH₂)₂ | H | H | CH₂ | EtO | 4-Pyr | — |
| 58-9 | H | (CH₂)₂ | H | H | CH₂ | EtO | 2-Me-5-Pyr | — |
| 58-10 | H | (CH₂)₂ | H | H | CH₂ | EtO | 2-Me-3-Pyr | — |
| 58-11 | H | (CH₂)₂ | H | H | CH₂ | EtO | 2-MeO-5-Pyr | — |
| 58-12 | H | (CH₂)₂ | H | H | CH₂ | EtO | 2-EtO-5-Pyr | — |
| 58-13 | H | (CH₂)₂ | H | H | CH₂ | EtO | 2-iPrO-5-Pyr | — |
| 58-14 | H | (CH₂)₂ | H | H | CH₂ | EtO | 2-MeS-5-Pyr | — |
| 58-15 | H | (CH₂)₂ | H | H | CH₂ | EtO | 2-EtS-5-Pyr | — |
| 58-16 | H | (CH₂)₂ | H | H | CH₂ | EtO | 2-Ph-5-Pyr | — |
| 58-17 | H | (CH₂)₂ | H | H | CH₂ | EtO | 3-Ph-6-Pyr | — |

TABLE 59

| Ex. No. Comp. | R¹ | R² | R³ | R⁴ | Z | W | X | Y |
|---|---|---|---|---|---|---|---|---|
| 59-1 | H | (CH₂)₂ | H | H | CH₂ | Pr | Ph | — |
| 59-2 | H | (CH₂)₂ | H | H | CH₂ | Pr | 4-Ph-Ph | — |
| 59-3 | H | (CH₂)₂ | H | H | CH₂ | Pr | 4-(Pyr-2)-Ph | — |
| 59-4 | H | (CH₂)₂ | H | H | CH₂ | Pr | 4-(Pyr-3)-Ph | — |
| 59-5 | H | (CH₂)₂ | H | H | CH₂ | Pr | 4-(Pyr-4)-Ph | — |
| 59-6 | H | (CH₂)₂ | H | H | CH₂ | Pr | 2-Pyr | — |
| 59-7 | H | (CH₂)₂ | H | H | CH₂ | Pr | 3-Pyr | — |
| 59-8 | H | (CH₂)₂ | H | H | CH₂ | Pr | 4-Pyr | — |
| 59-9 | H | (CH₂)₂ | H | H | CH₂ | Pr | 2-Me-5-Pyr | — |
| 59-10 | H | (CH₂)₂ | H | H | CH₂ | Pr | 2-Me-3-Pyr | — |
| 59-11 | H | (CH₂)₂ | H | H | CH₂ | Pr | 2-MeO-5-Pyr | — |
| 59-12 | H | (CH₂)₂ | H | H | CH₂ | Pr | 2-EtO-5-Pyr | — |
| 59-13 | H | (CH₂)₂ | H | H | CH₂ | Pr | 2-iPrO-5-Pyr | — |
| 59-14 | H | (CH₂)₂ | H | H | CH₂ | Pr | 2-MeS-5-Pyr | — |
| 59-15 | H | (CH₂)₂ | H | H | CH₂ | Pr | 2-EtS-5-Pyr | — |
| 59-16 | H | (CH₂)₂ | H | H | CH₂ | Pr | 2-Ph-5-Pyr | — |
| 59-17 | H | (CH₂)₂ | H | H | CH₂ | Pr | 3-Ph-6-Pyr | — |

TABLE 60

| Ex. No. Comp. | R¹ | R² | R³ | R⁴ | Z | W | X | Y |
|---|---|---|---|---|---|---|---|---|
| 60-1 | H | (CH₂)₂ | H | H | CH₂ | Bu | Ph | — |
| 60-2 | H | (CH₂)₂ | H | H | CH₂ | Bu | 4-Ph-Ph | — |
| 60-3 | H | (CH₂)₂ | H | H | CH₂ | Bu | 4-(Pyr-2)-Ph | — |
| 60-4 | H | (CH₂)₂ | H | H | CH₂ | Bu | 4-(Pyr-3)-Ph | — |
| 60-5 | H | (CH₂)₂ | H | H | CH₂ | Bu | 4-(Pyr-4)-Ph | — |
| 60-6 | H | (CH₂)₂ | H | H | CH₂ | Bu | 2-Pyr | — |
| 60-7 | H | (CH₂)₂ | H | H | CH₂ | Bu | 3-Pyr | — |
| 60-8 | H | (CH₂)₂ | H | H | CH₂ | Bu | 4-Pyr | — |
| 60-9 | H | (CH₂)₂ | H | H | CH₂ | Bu | 2-Me-5-Pyr | — |
| 60-10 | H | (CH₂)₂ | H | H | CH₂ | Bu | 2-Me-3-Pyr | — |
| 60-11 | H | (CH₂)₂ | H | H | CH₂ | Bu | 2-MeO-5-Pyr | — |
| 60-12 | H | (CH₂)₂ | H | H | CH₂ | Bu | 2-EtO-5-Pyr | — |
| 60-13 | H | (CH₂)₂ | H | H | CH₂ | Bu | 2-iPrO-5-Pyr | — |
| 60-14 | H | (CH₂)₂ | H | H | CH₂ | Bu | 2-MeS-5-Pyr | — |
| 60-15 | H | (CH₂)₂ | H | H | CH₂ | Bu | 2-EtS-5-Pyr | — |
| 60-16 | H | (CH₂)₂ | H | H | CH₂ | Bu | 2-Ph-5-Pyr | — |
| 60-17 | H | (CH₂)₂ | H | H | CH₂ | Bu | 3-Ph-6-Pyr | — |

TABLE 61

| Ex. No. Comp. | R¹ | R² | R³ | R⁴ | Z | W | X | Y |
|---|---|---|---|---|---|---|---|---|
| 61-1 | H | (CH₂)₂ | H | H | CH₂ | Pen | Ph | — |
| 61-2 | H | (CH₂)₂ | H | H | CH₂ | Pen | 4-Ph-Ph | — |
| 61-3 | H | (CH₂)₂ | H | H | CH₂ | Pen | 4-(Pyr-2)-Ph | — |
| 61-4 | H | (CH₂)₂ | H | H | CH₂ | Pen | 4-(Pyr-3)-Ph | — |
| 61-5 | H | (CH₂)₂ | H | H | CH₂ | Pen | 4-(Pyr-4)-Ph | — |
| 61-6 | H | (CH₂)₂ | H | H | CH₂ | Pen | 2-Pyr | — |
| 61-7 | H | (CH₂)₂ | H | H | CH₂ | Pen | 3-Pyr | — |
| 61-8 | H | (CH₂)₂ | H | H | CH₂ | Pen | 4-Pyr | — |
| 61-9 | H | (CH₂)₂ | H | H | CH₂ | Pen | 2-Me-5-Pyr | — |
| 61-10 | H | (CH₂)₂ | H | H | CH₂ | Pen | 2-Me-3-Pyr | — |
| 61-11 | H | (CH₂)₂ | H | H | CH₂ | Pen | 2-MeO-5-Pyr | — |
| 61-12 | H | (CH₂)₂ | H | H | CH₂ | Pen | 2-EtO-5-Pyr | — |
| 61-13 | H | (CH₂)₂ | H | H | CH₂ | Pen | 2-iPrO-5-Pyr | — |
| 61-14 | H | (CH₂)₂ | H | H | CH₂ | Pen | 2-MeS-5-Pyr | — |
| 61-15 | H | (CH₂)₂ | H | H | CH₂ | Pen | 2-EtS-5-Pyr | — |
| 61-16 | H | (CH₂)₂ | H | H | CH₂ | Pen | 2-Ph-5-Pyr | — |
| 61-17 | H | (CH₂)₂ | H | H | CH₂ | Pen | 3-Ph-6-Pyr | — |

TABLE 62

| Ex. No. Comp. | R¹ | R² | R³ | R⁴ | Z | W | X | Y |
|---|---|---|---|---|---|---|---|---|
| 62-1 | H | (CH₂)₂ | H | H | CH₂ | MeS | Ph | — |
| 62-2 | H | (CH₂)₂ | H | H | CH₂ | MeS | 4-Ph-Ph | — |
| 62-3 | H | (CH₂)₂ | H | H | CH₂ | MeS | 4-(Pyr-2)-Ph | — |
| 62-4 | H | (CH₂)₂ | H | H | CH₂ | MeS | 4-(Pyr-3)-Ph | — |
| 62-5 | H | (CH₂)₂ | H | H | CH₂ | MeS | 4-(Pyr-4)-Ph | — |
| 62-6 | H | (CH₂)₂ | H | H | CH₂ | MeS | 2-Pyr | — |
| 62-7 | H | (CH₂)₂ | H | H | CH₂ | MeS | 3-Pyr | — |
| 62-8 | H | (CH₂)₂ | H | H | CH₂ | MeS | 4-Pyr | — |
| 62-9 | H | (CH₂)₂ | H | H | CH₂ | MeS | 2-Me-5-Pyr | — |
| 62-10 | H | (CH₂)₂ | H | H | CH₂ | MeS | 2-Me-3-Pyr | — |
| 62-11 | H | (CH₂)₂ | H | H | CH₂ | MeS | 2-MeO-5-Pyr | — |
| 62-12 | H | (CH₂)₂ | H | H | CH₂ | MeS | 2-EtO-5-Pyr | — |
| 62-13 | H | (CH₂)₂ | H | H | CH₂ | MeS | 2-iPrO-5-Pyr | — |
| 62-14 | H | (CH₂)₂ | H | H | CH₂ | MeS | 2-MeS-5-Pyr | — |
| 62-15 | H | (CH₂)₂ | H | H | CH₂ | MeS | 2-EtS-5-Pyr | — |
| 62-16 | H | (CH₂)₂ | H | H | CH₂ | MeS | 2-Ph-5-Pyr | — |
| 62-17 | H | (CH₂)₂ | H | H | CH₂ | MeS | 3-Ph-6-Pyr | — |

TABLE 63

| Ex. No. Comp. | R$^1$ | R$^2$ | R$^3$ | R$^4$ | Z | W | X | Y |
|---|---|---|---|---|---|---|---|---|
| 63-1 | H | (CH$_2$)$_2$ | H | H | CH$_2$ | PhO | Ph | — |
| 63-2 | H | (CH$_2$)$_2$ | H | H | CH$_2$ | PhO | 4-Ph—Ph | — |
| 63-3 | H | (CH$_2$)$_2$ | H | H | CH$_2$ | PhO | 4-(Pyr-2)-Ph | — |
| 63-4 | H | (CH$_2$)$_2$ | H | H | CH$_2$ | PhO | 4-(Pyr-3)-Ph | — |
| 63-5 | H | (CH$_2$)$_2$ | H | H | CH$_2$ | PhO | 4-(Pyr-4)-Ph | — |
| 63-6 | H | (CH$_2$)$_2$ | H | H | CH$_2$ | PhO | 2-Pyr | — |
| 63-7 | H | (CH$_2$)$_2$ | H | H | CH$_2$ | PhO | 3-Pyr | — |
| 63-8 | H | (CH$_2$)$_2$ | H | H | CH$_2$ | PhO | 4-Pyr | — |
| 63-9 | H | (CH$_2$)$_2$ | H | H | CH$_2$ | PhO | 2-Me-5-Pyr | — |
| 63-10 | H | (CH$_2$)$_2$ | H | H | CH$_2$ | PhO | 2-Me-3-Pyr | — |
| 63-11 | H | (CH$_2$)$_2$ | H | H | CH$_2$ | PhO | 2-MeO-5-Pyr | — |
| 63-12 | H | (CH$_2$)$_2$ | H | H | CH$_2$ | PhO | 2-EtO-5-Pyr | — |
| 63-13 | H | (CH$_2$)$_2$ | H | H | CH$_2$ | PhO | 2-iPrO-5-Pyr | — |
| 63-14 | H | (CH$_2$)$_2$ | H | H | CH$_2$ | PhO | 2-MeS-5-Pyr | — |
| 63-15 | H | (CH$_2$)$_2$ | H | H | CH$_2$ | PhO | 2-EtS-5-Pyr | — |
| 63-16 | H | (CH$_2$)$_2$ | H | H | CH$_2$ | PhO | 2-Ph-5-Pyr | — |
| 63-17 | H | (CH$_2$)$_2$ | H | H | CH$_2$ | PhO | 3-Ph-6-Pyr | — |

TABLE 64

| Ex. No. Comp. | R$^1$ | R$^2$ | R$^3$ | R$^4$ | Z | W | X | Y |
|---|---|---|---|---|---|---|---|---|
| 64-1 | H | (CH$_2$)$_2$ | H | H | CH$_2$ | 4-iPr—PhO | Ph | — |
| 64-2 | H | (CH$_2$)$_2$ | H | H | CH$_2$ | 4-iPr—PhO | 4-Ph—Ph | — |
| 64-3 | H | (CH$_2$)$_2$ | H | H | CH$_2$ | 4-iPr—PhO | 4-(Pyr-2)-Ph | — |
| 64-4 | H | (CH$_2$)$_2$ | H | H | CH$_2$ | 4-iPr—PhO | 4-(Pyr-3)-Ph | — |
| 64-5 | H | (CH$_2$)$_2$ | H | H | CH$_2$ | 4-iPr—PhO | 4-(Pyr-4)-Ph | — |
| 64-6 | H | (CH$_2$)$_2$ | H | H | CH$_2$ | 4-iPr—PhO | 2-Pyr | — |
| 64-7 | H | (CH$_2$)$_2$ | H | H | CH$_2$ | 4-iPr—PhO | 3-Pyr | — |
| 64-8 | H | (CH$_2$)$_2$ | H | H | CH$_2$ | 4-iPr—PhO | 4-Pyr | — |
| 64-9 | H | (CH$_2$)$_2$ | H | H | CH$_2$ | 4-iPr—PhO | 2-Me-5-Pyr | — |
| 64-10 | H | (CH$_2$)$_2$ | H | H | CH$_2$ | 4-iPr—PhO | 2-Me-3-Pyr | — |
| 64-11 | H | (CH$_2$)$_2$ | H | H | CH$_2$ | 4-iPr—PhO | 2-MeO-5-Pyr | — |
| 64-12 | H | (CH$_2$)$_2$ | H | H | CH$_2$ | 4-iPr—PhO | 2-EtO-5-Pyr | — |
| 64-13 | H | (CH$_2$)$_2$ | H | H | CH$_2$ | 4-iPr—PhO | 2-iPrO-5-Pyr | — |
| 64-14 | H | (CH$_2$)$_2$ | H | H | CH$_2$ | 4-iPr—PhO | 2-MeS-5-Pyr | — |
| 64-15 | H | (CH$_2$)$_2$ | H | H | CH$_2$ | 4-iPr—PhO | 2-EtS-5-Pyr | — |
| 64-16 | H | (CH$_2$)$_2$ | H | H | CH$_2$ | 4-iPr—PhO | 2-Ph-5-Pyr | — |
| 64-17 | H | (CH$_2$)$_2$ | H | H | CH$_2$ | 4-iPr—PhO | 3-Ph-6-Pyr | — |

TABLE 65

| Ex. No. Comp. | R$^1$ | R$^2$ | R$^3$ | R$^4$ | Z | W | X | Y |
|---|---|---|---|---|---|---|---|---|
| 65-1 | H | (CH$_2$)$_2$ | H | H | CH$_2$ | 4-MeO—PhO | Ph | — |
| 65-2 | H | (CH$_2$)$_2$ | H | H | CH$_2$ | 4-MeO—PhO | 4-Ph—Ph | — |
| 65-3 | H | (CH$_2$)$_2$ | H | H | CH$_2$ | 4-MeO—PhO | 4-(Pyr-2)-Ph | — |
| 65-4 | H | (CH$_2$)$_2$ | H | H | CH$_2$ | 4-MeO—PhO | 4-(Pyr-3)-Ph | — |
| 65-5 | H | (CH$_2$)$_2$ | H | H | CH$_2$ | 4-MeO—PhO | 4-(Pyr-4)-Ph | — |
| 65-6 | H | (CH$_2$)$_2$ | H | H | CH$_2$ | 4-MeO—PhO | 2-Pyr | — |
| 65-7 | H | (CH$_2$)$_2$ | H | H | CH$_2$ | 4-MeO—PhO | 3-Pyr | — |
| 65-8 | H | (CH$_2$)$_2$ | H | H | CH$_2$ | 4-MeO—PhO | 4-Pyr | — |
| 65-9 | H | (CH$_2$)$_2$ | H | H | CH$_2$ | 4-MeO—PhO | 2-Me-5-Pyr | — |
| 65-10 | H | (CH$_2$)$_2$ | H | H | CH$_2$ | 4-MeO—PhO | 2-Me-3-Pyr | — |
| 65-11 | H | (CH$_2$)$_2$ | H | H | CH$_2$ | 4-MeO—PhO | 2-MeO-5-Pyr | — |
| 65-12 | H | (CH$_2$)$_2$ | H | H | CH$_2$ | 4-MeO—PhO | 2-EtO-5-Pyr | — |
| 65-13 | H | (CH$_2$)$_2$ | H | H | CH$_2$ | 4-MeO—PhO | 2-iPrO-5-Pyr | — |
| 65-14 | H | (CH$_2$)$_2$ | H | H | CH$_2$ | 4-MeO—PhO | 2-MeS-5-Pyr | — |
| 65-15 | H | (CH$_2$)$_2$ | H | H | CH$_2$ | 4-MeO—PhO | 2-EtS-5-Pyr | — |
| 65-16 | H | (CH$_2$)$_2$ | H | H | CH$_2$ | 4-MeO—PhO | 2-Ph-5-Pyr | — |
| 65-17 | H | (CH$_2$)$_2$ | H | H | CH$_2$ | 4-MeO—PhO | 3-Ph-6-Pyr | — |

TABLE 66

| Ex. No. Comp. | R¹ | R² | R³ | R⁴ | Z | W | X | Y |
|---|---|---|---|---|---|---|---|---|
| 66-1 | H | (CH$_2$)$_2$ | H | H | CH$_2$ | PhS | Ph | — |
| 66-2 | H | (CH$_2$)$_2$ | H | H | CH$_2$ | PhS | 4-Ph—Ph | — |
| 66-3 | H | (CH$_2$)$_2$ | H | H | CH$_2$ | PhS | 4-(Pyr-2)-Ph | — |
| 66-4 | H | (CH$_2$)$_2$ | H | H | CH$_2$ | PhS | 4-(Pyr-3)-Ph | — |
| 66-5 | H | (CH$_2$)$_2$ | H | H | CH$_2$ | PhS | 4-(Pyr-4)-Ph | — |
| 66-6 | H | (CH$_2$)$_2$ | H | H | CH$_2$ | PhS | 2-Pyr | — |
| 66-7 | H | (CH$_2$)$_2$ | H | H | CH$_2$ | PhS | 3-Pyr | — |
| 66-8 | H | (CH$_2$)$_2$ | H | H | CH$_2$ | PhS | 4-Pyr | — |
| 66-9 | H | (CH$_2$)$_2$ | H | H | CH$_2$ | PhS | 2-Me-5-Pyr | — |
| 66-10 | H | (CH$_2$)$_2$ | H | H | CH$_2$ | PhS | 2-Me-3-Pyr | — |
| 66-11 | H | (CH$_2$)$_2$ | H | H | CH$_2$ | PhS | 2-MeO-5-Pyr | — |
| 66-12 | H | (CH$_2$)$_2$ | H | H | CH$_2$ | PhS | 2-EtO-5-Pyr | — |
| 66-13 | H | (CH$_2$)$_2$ | H | H | CH$_2$ | PhS | 2-iPrO-5-Pyr | — |
| 66-14 | H | (CH$_2$)$_2$ | H | H | CH$_2$ | PhS | 2-MeS-5-Pyr | — |
| 66-15 | H | (CH$_2$)$_2$ | H | H | CH$_2$ | PhS | 2-EtS-5-Pyr | — |
| 66-16 | H | (CH$_2$)$_2$ | H | H | CH$_2$ | PhS | 2-Ph-5-Pyr | — |
| 66-17 | H | (CH$_2$)$_2$ | H | H | CH$_2$ | PhS | 3-Ph-6-Pyr | — |

TABLE 67

| Ex. No. Comp. | R¹ | R² | R³ | R⁴ | Z | W | X | Y |
|---|---|---|---|---|---|---|---|---|
| 67-1 | H | (CH$_2$)$_2$ | H | H | CH$_2$ | Ph(CH$_2$)$_3$ | Ph | — |
| 67-2 | H | (CH$_2$)$_2$ | H | H | CH$_2$ | Ph(CH$_2$)$_3$ | 4-Ph—Ph | — |
| 67-3 | H | (CH$_2$)$_2$ | H | H | CH$_2$ | Ph(CH$_2$)$_3$ | 4-(Pyr-2)-Ph | — |
| 67-4 | H | (CH$_2$)$_2$ | H | H | CH$_2$ | Ph(CH$_2$)$_3$ | 4-(Pyr-3)-Ph | — |
| 67-5 | H | (CH$_2$)$_2$ | H | H | CH$_2$ | Ph(CH$_2$)$_3$ | 4-(Pyr-4)-Ph | — |
| 67-6 | H | (CH$_2$)$_2$ | H | H | CH$_2$ | Ph(CH$_2$)$_3$ | 2-Pyr | — |
| 67-7 | H | (CH$_2$)$_2$ | H | H | CH$_2$ | Ph(CH$_2$)$_3$ | 3-Pyr | — |
| 67-8 | H | (CH$_2$)$_2$ | H | H | CH$_2$ | Ph(CH$_2$)$_3$ | 4-Pyr | — |
| 67-9 | H | (CH$_2$)$_2$ | H | H | CH$_2$ | Ph(CH$_2$)$_3$ | 2-Me-5-Pyr | — |
| 67-10 | H | (CH$_2$)$_2$ | H | H | CH$_2$ | Ph(CH$_2$)$_3$ | 2-Me-3-Pyr | — |
| 67-11 | H | (CH$_2$)$_2$ | H | H | CH$_2$ | Ph(CH$_2$)$_3$ | 2-MeO-5-Pyr | — |
| 67-12 | H | (CH$_2$)$_2$ | H | H | CH$_2$ | Ph(CH$_2$)$_3$ | 2-EtO-5-Pyr | — |
| 67-13 | H | (CH$_2$)$_2$ | H | H | CH$_2$ | Ph(CH$_2$)$_3$ | 2-iPrO-5-Pyr | — |
| 67-14 | H | (CH$_2$)$_2$ | H | H | CH$_2$ | Ph(CH$_2$)$_3$ | 2-MeS-5-Pyr | — |
| 67-15 | H | (CH$_2$)$_2$ | H | H | CH$_2$ | Ph(CH$_2$)$_3$ | 2-EtS-5-Pyr | — |
| 67-16 | H | (CH$_2$)$_2$ | H | H | CH$_2$ | Ph(CH$_2$)$_3$ | 2-Ph-5-Pyr | — |
| 67-17 | H | (CH$_2$)$_2$ | H | H | CH$_2$ | Ph(CH$_2$)$_3$ | 3-Ph-6-Pyr | — |

TABLE 68

| Ex. No. Comp. | R¹ | R² | R³ | R⁴ | Z | W | X | Y |
|---|---|---|---|---|---|---|---|---|
| 68-1 | H | (CH$_2$)$_3$ | H | H | CH$_2$ | EtO | Ph | — |
| 68-2 | H | (CH$_2$)$_3$ | H | H | CH$_2$ | EtO | 4-Ph—Ph | — |
| 68-3 | H | (CH$_2$)$_3$ | H | H | CH$_2$ | EtO | 4-(Pyr-2)-Ph | — |
| 68-4 | H | (CH$_2$)$_3$ | H | H | CH$_2$ | EtO | 4-(Pyr-3)-Ph | — |
| 68-5 | H | (CH$_2$)$_3$ | H | H | CH$_2$ | EtO | 4-(Pyr-4)-Ph | — |
| 68-6 | H | (CH$_2$)$_3$ | H | H | CH$_2$ | EtO | 2-Pyr | — |
| 68-7 | H | (CH$_2$)$_3$ | H | H | CH$_2$ | EtO | 3-Pyr | — |
| 68-8 | H | (CH$_2$)$_3$ | H | H | CH$_2$ | EtO | 4-Pyr | — |
| 68-9 | H | (CH$_2$)$_3$ | H | H | CH$_2$ | EtO | 2-Me-5-Pyr | — |
| 68-10 | H | (CH$_2$)$_3$ | H | H | CH$_2$ | EtO | 2-Me-3-Pyr | — |
| 68-11 | H | (CH$_2$)$_3$ | H | H | CH$_2$ | EtO | 2-MeO-5-Pyr | — |
| 68-12 | H | (CH$_2$)$_3$ | H | H | CH$_2$ | EtO | 2-EtO-5-Pyr | — |
| 68-13 | H | (CH$_2$)$_3$ | H | H | CH$_2$ | EtO | 2-iPrO-5-Pyr | — |
| 68-14 | H | (CH$_2$)$_3$ | H | H | CH$_2$ | EtO | 2-MeS-5-Pyr | — |
| 68-15 | H | (CH$_2$)$_3$ | H | H | CH$_2$ | EtO | 2-EtS-5-Pyr | — |
| 68-16 | H | (CH$_2$)$_3$ | H | H | CH$_2$ | EtO | 2-Ph-5-Pyr | — |
| 68-17 | H | (CH$_2$)$_3$ | H | H | CH$_2$ | EtO | 3-Ph-6-Pyr | — |

TABLE 69

| Ex. No. Comp. | R¹ | R² | R³ | R⁴ | Z | W | X | Y |
|---|---|---|---|---|---|---|---|---|
| 69-1 | H | (CH$_2$)$_3$ | H | H | CH$_2$ | Pr | Ph | — |
| 69-2 | H | (CH$_2$)$_3$ | H | H | CH$_2$ | Pr | 4-Ph—Ph | — |
| 69-3 | H | (CH$_2$)$_3$ | H | H | CH$_2$ | Pr | 4-(Pyr-2)-Ph | — |
| 69-4 | H | (CH$_2$)$_3$ | H | H | CH$_2$ | Pr | 4-(Pyr-3)-Ph | — |
| 69-5 | H | (CH$_2$)$_3$ | H | H | CH$_2$ | Pr | 4-(Pyr-4)-Ph | — |
| 69-6 | H | (CH$_2$)$_3$ | H | H | CH$_2$ | Pr | 2-Pyr | — |
| 69-7 | H | (CH$_2$)$_3$ | H | H | CH$_2$ | Pr | 3-Pyr | — |
| 69-8 | H | (CH$_2$)$_3$ | H | H | CH$_2$ | Pr | 4-Pyr | — |
| 69-9 | H | (CH$_2$)$_3$ | H | H | CH$_2$ | Pr | 2-Me-5-Pyr | — |
| 69-10 | H | (CH$_2$)$_3$ | H | H; | CH$_2$ | Pr | 2-Me-3-Pyr | — |
| 69-11 | H | (CH$_2$)$_3$ | H | H | CH$_2$ | Pr | 2-MeO-5-Pyr | — |
| 69-12 | H | (CH$_2$)$_3$ | H | H | CH$_2$ | Pr | 2-EtO-5-Pyr | — |
| 69-13 | H | (CH$_2$)$_3$ | H | H | CH$_2$ | Pr | 2-iPrO-5-Pyr | — |
| 69-14 | H | (CH$_2$)$_3$ | H | H | CH$_2$ | Pr | 2-MeS-5-Pyr | — |
| 69-15 | H | (CH$_2$)$_3$ | H | H | CH$_2$ | Pr | 2-EtS-5-Pyr | — |
| 69-16 | H | (CH$_2$)$_3$ | H | H | CH$_2$ | Pr | 2-Ph-5-Pyr | — |
| 69-17 | H | (CH$_2$)$_3$ | H | H | CH$_2$ | Pr | 3-Ph-6-Pyr | — |

TABLE 70

| Ex. No. Comp. | R¹ | R² | R³ | R⁴ | Z | W | X | Y |
|---|---|---|---|---|---|---|---|---|
| 70-1 | H | (CH$_2$)$_3$ | H | H | CH$_2$ | Bu | Ph | — |
| 70-2 | H | (CH$_2$)$_3$ | H | H | CH$_2$ | Bu | 4-Ph—Ph | — |
| 70-3 | H | (CH$_2$)$_3$ | H | H | CH$_2$ | Bu | 4-(Pyr-2)-Ph | — |
| 70-4 | H | (CH$_2$)$_3$ | H | H | CH$_2$ | Bu | 4-(Pyr-3)-Ph | — |
| 70-5 | H | (CH$_2$)$_3$ | H | H | CH$_2$ | Bu | 4-(Pyr-4)-Ph | — |
| 70-6 | H | (CH$_2$)$_3$ | H | H | CH$_2$ | Bu | 2-Pyr | — |
| 70-7 | H | (CH$_2$)$_3$ | H | H | CH$_2$ | Bu | 3-Pyr | — |
| 70-8 | H | (CH$_2$)$_3$ | H | H | CH$_2$ | Bu | 4-Pyr | — |
| 70-9 | H | (CH$_2$)$_3$ | H | H | CH$_2$ | Bu | 2-Me-5-Pyr | — |
| 70-10 | H | (CH$_2$)$_3$ | H | H | CH$_2$ | Bu | 2-Me-3-Pyr | — |
| 70-11 | H | (CH$_2$)$_3$ | H | H | CH$_2$ | Bu | 2-MeO-5-Pyr | — |
| 70-12 | H | (CH$_2$)$_3$ | H | H | CH$_2$ | Bu | 2-EtO-5-Pyr | — |
| 70-13 | H | (CH$_2$)$_3$ | H | H | CH$_2$ | Bu | 2-iPrO-5-Pyr | — |
| 70-14 | H | (CH$_2$)$_3$ | H | H | CH$_2$ | Bu | 2-MeS-5-Pyr | — |
| 70-15 | H | (CH$_2$)$_3$ | H | H | CH$_2$ | Bu | 2-EtS-5-Pyr | — |
| 70-16 | H | (CH$_2$)$_3$ | H | H | CH$_2$ | Bu | 2-Ph-5-Pyr | — |
| 70-17 | H | (CH$_2$)$_3$ | H | H | CH$_2$ | Bu | 3-Ph-6-Pyr | — |

TABLE 71

| Ex. No. Comp. | R¹ | R² | R³ | R⁴ | Z | W | X | Y |
|---|---|---|---|---|---|---|---|---|
| 71-1 | H | (CH$_2$)$_3$ | H | H | CH$_2$ | Pen | Ph | — |
| 71-2 | H | (CH$_2$)$_3$ | H | H | CH$_2$ | Pen | 4-Ph—Ph | — |
| 71-3 | H | (CH$_2$)$_3$ | H | H | CH$_2$ | Pen | 4-(Pyr-2)-Ph | — |
| 71-4 | H | (CH$_2$)$_3$ | H | H | CH$_2$ | Pen | 4-(Pyr-3)-Ph | — |
| 71-5 | H | (CH$_2$)$_3$ | H | H | CH$_2$ | Pen | 4-(Pyr-4)-Ph | — |
| 71-6 | H | (CH$_2$)$_3$ | H | H | CH$_2$ | Pen | 2-Pyr | — |
| 71-7 | H | (CH$_2$)$_3$ | H | H | CH$_2$ | Pen | 3-Pyr | — |
| 71-8 | H | (CH$_2$)$_3$ | H | H | CH$_2$ | Pen | 4-Pyr | — |
| 71-9 | H | (CH$_2$)$_3$ | H | H | CH$_2$ | Pen | 2-Me-5-Pyr | — |
| 71-10 | H | (CH$_2$)$_3$ | H | H | CH$_2$ | Pen | 2-Me-3-Pyr | — |
| 71-11 | H | (CH$_2$)$_3$ | H | H | CH$_2$ | Pen | 2-MeO-5-Pyr | — |
| 71-12 | H | (CH$_2$)$_3$ | H | H | CH$_2$ | Pen | 2-EtO-5-Pyr | — |
| 71-13 | H | (CH$_2$)$_3$ | H | H | CH$_2$ | Pen | 2-iPrO-5-Pyr | — |
| 71-14 | H | (CH$_2$)$_3$ | H | H | CH$_2$ | Pen | 2-MeS-5-Pyr | — |
| 71-15 | H | (CH$_2$)$_3$ | H | H | CH$_2$ | Pen | 2-EtS-5-Pyr | — |
| 71-16 | H | (CH$_2$)$_3$ | H | H | CH$_2$ | Pen | 2-Ph-5-Pyr | — |
| 71-17 | H | (CH$_2$)$_3$ | H | H | CH$_2$ | Pen | 3-Ph-6-Pyr | — |

TABLE 72

| Ex. No. Comp. | R$^1$ | R$^2$ | R$^3$ | R$^4$ | Z | W | X | Y |
|---|---|---|---|---|---|---|---|---|
| 72-1 | H | (CH$_2$)$_3$ | H | H | CH$_2$ | MeS | Ph | — |
| 72-2 | H | (CH$_2$)$_3$ | H | H | CH$_2$ | MeS | 4-Ph—Ph | — |
| 72-3 | H | (CH$_2$)$_3$ | H | H | CH$_2$ | MeS | 4-(Pyr-2)-Ph | — |
| 72-4 | H | (CH$_2$)$_3$ | H | H | CH$_2$ | MeS | 4-(Pyr-3)-Ph | — |
| 72-5 | H | (CH$_2$)$_3$ | H | H | CH$_2$ | MeS | 4-(Pyr-4)-Ph | — |
| 72-6 | H | (CH$_2$)$_3$ | H | H | CH$_2$ | MeS | 2-Pyr | — |
| 72-7 | H | (CH$_2$)$_3$ | H | H | CH$_2$ | MeS | 3-Pyr | — |
| 72-8 | H | (CH$_2$)$_3$ | H | H | CH$_2$ | MeS | 4-Pyr | — |
| 72-9 | H | (CH$_2$)$_3$ | H | H | CH$_2$ | MeS | 2-Me-5-Pyr | — |
| 72-10 | H | (CH$_2$)$_3$ | H | H | CH$_2$ | MeS | 2-Me-3-Pyr | — |
| 72-11 | H | (CH$_2$)$_3$ | H | H | CH$_2$ | MeS | 2-MeO-5-Pyr | — |
| 72-12 | H | (CH$_2$)$_3$ | H | H | CH$_2$ | MeS | 2-EtO-5-Pyr | — |
| 72-13 | H | (CH$_2$)$_3$ | H | H | CH$_2$ | MeS | 2-iPrO-5-Pyr | — |
| 72-14 | H | (CH$_2$)$_3$ | H | H | CH$_2$ | MeS | 2-MeS-5-Pyr | — |
| 72-15 | H | (CH$_2$)$_3$ | H | H | CH$_2$ | MeS | 2-EtS-5-Pyr | — |
| 72-16 | H | (CH$_2$)$_3$ | H | H | CH$_2$ | MeS | 2-Ph-5-Pyr | — |
| 72-17 | H | (CH$_2$)$_3$ | H | H | CH$_2$ | MeS | 3-Ph-6-Pyr | — |

TABLE 73

| Ex. No. Comp. | R$^1$ | R$^2$ | R$^3$ | R$^4$ | Z | W | X | Y |
|---|---|---|---|---|---|---|---|---|
| 73-1 | H | (CH$_2$)$_3$ | H | H | CH$_2$ | PhO | Ph | — |
| 73-2 | H | (CH$_2$)$_3$ | H | H | CH$_2$ | PhO | 4-Ph—Ph | — |
| 73-3 | H | (CH$_2$)$_3$ | H | H | CH$_2$ | PhO | 4-(Pyr-2)-Ph | — |
| 73-4 | H | (CH$_2$)$_3$ | H | H | CH$_2$ | PhO | 4-(Pyr-3)-Ph | — |
| 73-5 | H | (CH$_2$)$_3$ | H | H | CH$_2$ | PhO | 4-(Pyr-4)-Ph | — |
| 73-6 | H | (CH$_2$)$_3$ | H | H | CH$_2$ | PhO | 2-Pyr | — |
| 73-7 | H | (CH$_2$)$_3$ | H | H | CH$_2$ | PhO | 3-Pyr | — |
| 73-8 | H | (CH$_2$)$_3$ | H | H | CH$_2$ | PbO | 4-Pyr | — |
| 73-9 | H | (CH$_2$)$_3$ | H | H | CH$_2$ | PhO | 2-Me-5-Pyr | — |
| 73-10 | H | (CH$_2$)$_3$ | H | H | CH$_2$ | PhO | 2-Me-3-Pyr | — |
| 73-11 | H | (CH$_2$)$_3$ | H | H | CH$_2$ | PhO | 2-MeO-5-Pyr | — |
| 73-12 | H | (CH$_2$)$_3$ | H | H | CH$_2$ | PhO | 2-EtO-5-Pyr | — |
| 73-13 | H | (CH$_2$)$_3$ | H | H | CH$_2$ | PhO | 2-iPrO-5-Pyr | — |
| 73-14 | H | (CH$_2$)$_3$ | H | H | CH$_2$ | PhO | 2-MeS-5-Pyr | — |
| 73-15 | H | (CH$_2$)$_3$ | H | HJ | CH$_2$ | PhO | 2-EtS-5-Pyr | — |
| 73-16 | H | (CH$_2$)$_3$ | H | HI | CH$_2$ | PhO | 2-Ph-5-Pyr | — |
| 73-17 | H | (CH$_2$)$_3$ | H | HI | CH$_2$ | PhO | 3-Ph-6-Pyr | — |

TABLE 74

| Ex. No. Comp. | R$^1$ | R$^2$ | R$^3$ | R$^4$ | Z | W | X | Y |
|---|---|---|---|---|---|---|---|---|
| 74-1 | H | (CH$_2$)$_3$ | H | H | CH$_2$ | 4-iPr-PhO | Ph | — |
| 74-2 | H | (CH$_2$)$_3$ | H | H | CH$_2$ | 4-iPr-PhO | 4-Ph-Ph | — |
| 74-3 | H | (CH$_2$)$_3$ | H | H | CH$_2$ | 4-iPr-PhO | 4-(Pyr-2)-Ph | — |
| 74-4 | H | (CH$_2$)$_3$ | H | H | CH$_2$ | 4-iPr-PhO | 4-(Pyr-3)-Ph | — |
| 74-5 | H | (CH$_2$)$_3$ | H | H | CH$_2$ | 4-iPr-PhO | 4-(Pyr-4)-Ph | — |
| 74-6 | H | (CH$_2$)$_3$ | H | H | CH$_2$ | 4-iPr-PhO | 2-Pyr | — |
| 74-7 | H | (CH$_2$)$_3$ | H | H | CH$_2$ | 4-iPr-PhO | 3-Pyr | — |
| 74-8 | H | (CH$_2$)$_3$ | H | H | CH$_2$ | 4-iPr-PhO | 4-Pyr | — |
| 74-9 | H | (CH$_2$)$_3$ | H | H | CH$_2$ | 4-iPr-PhO | 2-Me-5-Pyr | — |
| 74-10 | H | (CH$_2$)$_3$ | H | H | CH$_2$ | 4-iPr-PhO | 2-Me-3-Pyr | — |
| 74-11 | H | (CH$_2$)$_3$ | H | H | CH$_2$ | 4-iPr-PhO | 2-MeO-5-Pyr | — |
| 74-12 | H | (CH$_2$)$_3$ | H | H | CH$_2$ | 4-iPr-PhO | 2-EtO-5-Pyr | — |
| 74-13 | H | (CH$_2$)$_3$ | H | H | CH$_2$ | 4-iPr-PhO | 2-iPrO-5-Pyr | — |
| 74-14 | H | (CH$_2$)$_3$ | H | H | CH$_2$ | 4-iPr-PhO | 2-MeS-5-Pyr | — |
| 74-15 | H | (CH$_2$)$_3$ | H | H | CH$_2$ | 4-iPr-PhO | 2-EtS-5-Pyr | — |
| 74-16 | H | (CH$_2$)$_3$ | H | H | CH$_2$ | 4-iPr-PhO | 2-Ph-5-Pyr | — |
| 74-17 | H | (CH$_2$)$_3$ | H | H | CH$_2$ | 4-iPr-PhO | 3-Ph-6-Pyr | — |

TABLE 75

| Ex. No. Comp. | R$^1$ | R$^2$ | R$^3$ | R$^4$ | Z | W | X | Y |
|---|---|---|---|---|---|---|---|---|
| 75-1 | H | (CH$_2$)$_3$ | H | H | CH$_2$ | 4-MeO-PhO | Ph | — |
| 75-2 | H | (CH$_2$)$_3$ | H | H | CH$_2$ | 4-MeO-PhO | 4-Ph-Ph | — |
| 75-3 | H | (CH$_2$)$_3$ | H | H | CH$_2$ | 4-MeO-PhO | 4-(Pyr-2)-Ph | — |
| 75-4 | H | (CH$_2$)$_3$ | H | H | CH$_2$ | 4-MeO-PhO | 4-(Pyr-3)-Ph | — |
| 75-5 | H | (CH$_2$)$_3$ | H | H | CH$_2$ | 4-MeO-PhO | 4-(Pyr-4)-Ph | — |
| 75-6 | H | (CH$_2$)$_3$ | H | H | CH$_2$ | 4-MeO-PhO | 2-Pyr | — |
| 75-7 | H | (CH$_2$)$_3$ | H | H | CH$_2$ | 4-MeO-PhO | 3-Pyr | — |
| 75-8 | H | (CH$_2$)$_3$ | H | H | CH$_2$ | 4-MeO-PhO | 4-Pyr | — |
| 75-9 | H | (CH$_2$)$_3$ | H | H | CH$_2$ | 4-MeO-PhO | 2-Me-5-Pyr | — |
| 75-10 | H | (CH$_2$)$_3$ | H | H | CH$_2$ | 4-MeO-PhO | 2-Me-3-Pyr | — |
| 75-11 | H | (CH$_2$)$_3$ | H | H | CH$_2$ | 4-MeO-PhO | 2-MeO-5-Pyr | — |
| 75-12 | H | (CH$_2$)$_3$ | H | H | CH$_2$ | 4-MeO-PhO | 2-EtO-5-Pyr | — |
| 75-13 | H | (CH$_2$)$_3$ | H | H | CH$_2$ | 4-MeO-PhO | 2-iPrO-5-Pyr | — |
| 75-14 | H | (CH$_2$)$_3$ | H | H | CH$_2$ | 4-MeO-PhO | 2-MeS-5-Pyr | — |
| 75-15 | H | (CH$_2$)$_3$ | H | H | CH$_2$ | 4-MeO-PhO | 2-EtS-5-Pyr | — |
| 75-16 | H | (CH$_2$)$_3$ | H | H | CH$_2$ | 4-MeO-PhO | 2-Ph-5-Pyr | — |
| 75-17 | H | (CH$_2$)$_3$ | H | H | CH$_2$ | 4-MeO-PhO | 3-Ph-6-Pyr | — |

TABLE 76

| Ex. No. Comp. | R$^1$ | R$^2$ | R$^3$ | R$^4$ | Z | W | X | Y |
|---|---|---|---|---|---|---|---|---|
| 76-1 | H | (CH$_2$)$_3$ | H | H | CH$_2$ | PhS | Ph | — |
| 76-2 | H | (CH$_2$)$_3$ | H | H | CH$_2$ | PhS | 4-Ph-Ph | — |
| 76-3 | H | (CH$_2$)$_3$ | H | H | CH$_2$ | PhS | 4-(Pyr-2)-Ph | — |
| 76-4 | H | (CH$_2$)$_3$ | H | H | CH$_2$ | PhS | 4-(Pyr-3)-Ph | — |
| 76-5 | H | (CH$_2$)$_3$ | H | H | CH$_2$ | PhS | 4-(Pyr-4)-Ph | — |
| 76-6 | H | (CH$_2$)$_3$ | H | H | CH$_2$ | PhS | 2-Pyr | — |
| 76-7 | H | (CH$_2$)$_3$ | H | H | CH$_2$ | PhS | 3-Pyr | — |
| 76-8 | H | (CH$_2$)$_3$ | H | H | CH$_2$ | PhS | 4-Pyr | — |
| 76-9 | H | (CH$_2$)$_3$ | H | H | CH$_2$ | PhS | 2-Me-5-Pyr | — |
| 76-10 | H | (CH$_2$)$_3$ | H | H | CH$_2$ | PhS | 2-Me-3-Pyr | — |
| 76-11 | H | (CH$_2$)$_3$ | H | H | CH$_2$ | PhS | 2-MeO-5-Pyr | — |
| 76-12 | H | (CH$_2$)$_3$ | H | H | CH$_2$ | PhS | 2-EtO-5-Pyr | — |

TABLE 76-continued

| Ex. No. Comp. | R¹ | R² | R³ | R⁴ | Z | W | X | Y |
|---|---|---|---|---|---|---|---|---|
| 76-13 | H | (CH₂)₃ | H | H | CH₂ | PhS | 2-iPrO-5-Pyr | — |
| 76-14 | H | (CH₂)₃ | H | H | CH₂ | PhS | 2-MeS-5-Pyr | — |
| 76-15 | H | (CH₂)₃ | H | H | CH₂ | PhS | 2-EtS-5-Pyr | — |
| 76-16 | H | (CH₂)₃ | H | H | CH₂ | PhS | 2-Ph-5-Pyr | — |
| 76-17 | H | (CH₂)₃ | H | H | CH₂ | PhS | 3-Ph-6-Pyr | — |

TABLE 77

| Ex. No. Comp. | R¹ | R² | R³ | R⁴ | Z | W | X | Y |
|---|---|---|---|---|---|---|---|---|
| 77-1 | H | (CH₂)₃ | H | H | CH₂ | Ph(CH₂)₃ | Ph | — |
| 77-2 | H | (CH₂)₃ | H | H | CH₂ | Ph(CH₂)₃ | 4-Ph-Ph | — |
| 77-3 | H | (CH₂)₃ | H | H | CH₂ | Ph(CH₂)₃ | 4-(Pyr-2)-Ph | — |
| 77-4 | H | (CH₂)₃ | H | H | CH₂ | Ph(CH₂)₃ | 4-(Pyr-3)-Ph | — |
| 77-5 | H | (CH₂)₃ | H | H | CH₂ | Ph(CH₂)₃ | 4-(Pyr-4)-Ph | — |
| 77-6 | H | (CH₂)₃ | H | H | CH₂ | Ph(CH₂)₃ | 2-Pyr | — |
| 77-7 | H | (CH₂)₃ | H | H | CH₂ | Ph(CH₂)₃ | 3-Pyr | — |
| 77-8 | H | (CH₂)₃ | H | H | CH₂ | Ph(CH₂)₃ | 4-Pyr | — |
| 77-9 | H | (CH₂)₃ | H | H | CH₂ | Ph(CH₂)₃ | 2-Me-5-Pyr | — |
| 77-10 | H | (CH₂)₃ | H | H | CH₂ | Ph(CH₂)₃ | 2-Me-3-Pyr | — |
| 77-11 | H | (CH₂)₃ | H | H | CH₂ | Ph(CH₂)₃ | 2-MeO-5-Pyr | — |
| 77-12 | H | (CH₂)₃ | H | H | CH₂ | Ph(CH₂)₃ | 2-EtO-5-Pyr | — |
| 77-13 | H | (CH₂)₃ | H | H | CH₂ | Ph(CH₂)₃ | 2-iPrO-5-Pyr | — |
| 77-14 | H | (CH₂)₃ | H | H | CH₂ | Ph(CH₂)₃ | 2-MeS-5-Pyr | — |
| 77-15 | H | (CH₂)₃ | H | H | CH₂ | Ph(CH₂)₃ | 2-EtS-5-Pyr | — |
| 77-16 | H | (CH₂)₃ | H | H | CH₂ | Ph(CH₂)₃ | 2-Ph-5-Pyr | — |
| 77-17 | H | (CH₂)₃ | H | H | CH₂ | Ph(CH₂)₃ | 3-Ph-6-Pyr | — |

TABLE 78

| Ex. No. Comp. | R¹ | R² | R³ | R⁴ | Z | W | X | Y |
|---|---|---|---|---|---|---|---|---|
| 78-1 | H | CH₂ | H | H | CH₂ | EtO | Ph | — |
| 78-2 | H | CH₂ | H | H | CH₂ | EtO | 4-Ph-Ph | — |
| 78-3 | H | CH₂ | H | H | CH₂ | EtO | 4-(Pyr-2)-Ph | — |
| 78-4 | H | CH₂ | H | H | CH₂ | EtO | 4-(Pyr-3)-Ph | — |
| 78-5 | H | CH₂ | H | H | CH₂ | EtO | 4-(Pyr-4)-Ph | — |
| 78-6 | H | CH₂ | H | H | CH₂ | EtO | 2-Pyr | — |
| 78-7 | H | CH₂ | H | H | CH₂ | EtO | 3-Pyr | — |
| 78-8 | H | CH₂ | H | H | CH₂ | EtO | 4-Pyr | — |
| 78-9 | H | CH₂ | H | H | CH₂ | EtO | 2-Me-5-Pyr | — |
| 78-10 | H | CH₂ | H | H | CH₂ | EtO | 2-Me-3-Pyr | — |
| 78-11 | H | CH₂ | H | H | CH₂ | EtO | 2-MeO-5-Pyr | — |
| 78-12 | H | CH₂ | H | H | CH₂ | EtO | 2-EtO-5-Pyr | — |
| 78-13 | H | CH₂ | H | H | CH₂ | EtO | 2-iPrO-5-Pyr | — |
| 78-14 | H | CH₂ | H | H | CH₂ | EtO | 2-MeS-5-Pyr | — |
| 78-15 | H | CH₂ | H | H | CH₂ | EtO | 2-EtS-5-Pyr | — |
| 78-16 | H | CH₂ | H | H | CH₂ | EtO | 2-Ph-5-Pyr | — |
| 78-17 | H | CH₂ | H | H | CH₂ | EtO | 3-Ph-6-Pyr | — |

TABLE 79

| Ex. No. Comp. | R¹ | R² | R³ | R⁴ | Z | W | X | Y |
|---|---|---|---|---|---|---|---|---|
| 79-1 | H | CH₂ | H | H | CH₂ | Pr | Ph | — |
| 79-2 | H | CH₂ | H | H | CH₂ | Pr | 4-Ph-Ph | — |
| 79-3 | H | CH₂ | H | H | CH₂ | Pr | 4-(Pyr-2)-Ph | — |
| 79-4 | H | CH₂ | H | H | CH₂ | Pr | 4-(Pyr-3)-Ph | — |
| 79-5 | H | CH₂ | H | H | CH₂ | Pr | 4-(Pyr-4)-Ph | — |
| 79-6 | H | CH₂ | H | H | CH₂ | Pr | 2-Pyr | — |
| 79-7 | H | CH₂ | H | H | CH₂ | Pr | 3-Pyr | — |
| 79-8 | H | CH₂ | H | H | CH₂ | Pr | 4-Pyr | — |

TABLE 79-continued

| Ex. No. Comp. | R¹ | R² | R³ | R⁴ | Z | W | X | Y |
|---|---|---|---|---|---|---|---|---|
| 79-9 | H | CH₂ | H | H | CH₂ | Pr | 2-Me-5-Pyr | — |
| 79-10 | H | CH₂ | H | H | CH₂ | Pr | 2-Me-3-Pyr | — |
| 79-11 | H | CH₂ | H | H | CH₂ | Pr | 2-MeO-5-Pyr | — |
| 79-12 | H | CH₂ | H | H | CH₂ | Pr | 2-EtO-5-Pyr | — |
| 79-13 | H | CH₂ | H | H | CH₂ | Pr | 2-iPrO-5-Pyr | — |
| 79-14 | H | CH₂ | H | H | CH₂ | Pr | 2-MeS-5-Pyr | — |
| 79-15 | H | CH₂ | H | H | CH₂ | Pr | 2-EtS-5-Pyr | — |
| 79-16 | H | CH₂ | H | H | CH₂ | Pr | 2-Ph-5-Pyr | — |
| 79-17 | H | CH₂ | H | H | CH₂ | Pr | 3-Ph-6-Pyr | — |

TABLE 80

| Ex. No. Comp. | R¹ | R² | R³ | R⁴ | Z | W | X | Y |
|---|---|---|---|---|---|---|---|---|
| 80-1 | H | CH₂ | H | H | CH₂ | Bu | Ph | — |
| 80-2 | H | CH₂ | H | H | CH₂ | Bu | 4-Ph-Ph | — |
| 80-3 | H | CH₂ | H | H | CH₂ | Bu | 4-(Pyr-2)-Ph | — |
| 80-4 | H | CH₂ | H | H | CH₂ | Bu | 4-(Pyr-3)-Ph | — |
| 80-5 | H | CH₂ | H | H | CH₂ | Bu | 4-(Pyr-4)-Ph | — |
| 80-6 | H | CH₂ | H | H | CH₂ | Bu | 2-Pyr | — |
| 80-7 | H | CH₂ | H | H | CH₂ | Bu | 3-Pyr | — |
| 80-8 | H | CH₂ | H | H | CH₂ | Bu | 4-Pyr | — |
| 80-9 | H | CH₂ | H | H | CH₂ | Bu | 2-Me-5-Pyr | — |
| 80-10 | H | CH₂ | H | H | CH₂ | Bu | 2-Me-3-Pyr | — |
| 80-11 | H | CH₂ | H | H | CH₂ | Bu | 2-MeO-5-Pyr | — |
| 80-12 | H | CH₂ | H | H | CH₂ | Bu | 2-EtO-5-Pyr | — |
| 80-13 | H | CH₂ | H | H | CH₂ | Bu | 2-iPrO-5-Pyr | — |
| 80-14 | H | CH₂ | H | H | CH₂ | Bu | 2-MeS-5-Pyr | — |
| 80-15 | H | CH₂ | H | H | CH₂ | Bu | 2-EtS-5-Pyr | — |
| 80-16 | H | CH₂ | H | H | CH₂ | Bu | 2-Ph-5-Pyr | — |
| 80-17 | H | CH₂ | H | H | CH₂ | Bu | 3-Ph-6-Pyr | — |

TABLE 81

| Ex. No. Comp. | R¹ | R² | R³ | R⁴ | Z | W | X | Y |
|---|---|---|---|---|---|---|---|---|
| 81-1 | H | CH₂ | H | H | CH₂ | Pen | Ph | — |
| 81-2 | H | CH₂ | H | H | CH₂ | Pen | 4-Ph-Ph | — |
| 81-3 | H | CH₂ | H | H | CH₂ | Pen | 4-(Pyr-2)-Ph | — |
| 81-4 | H | CH₂ | H | H | CH₂ | Pen | 4-(Pyr-3)-Ph | — |
| 81-5 | H | CH₂ | H | H | CH₂ | Pen | 4-(Pyr-4)-Ph | — |
| 81-6 | H | CH₂ | H | H | CH₂ | Pen | 2-Pyr | — |
| 81-7 | H | CH₂ | H | H | CH₂ | Pen | 3-Pyr | — |
| 81-8 | H | CH₂ | H | H | CH₂ | Pen | 4-Pyr | — |
| 81-9 | H | CH₂ | H | H | CH₂ | Pen | 2-Me-5-Pyr | — |
| 81-10 | H | CH₂ | H | H | CH₂ | Pen | 2-Me-3-Pyr | — |
| 81-11 | H | CH₂ | H | H | CH₂ | Pen | 2-MeO-5-Pyr | — |
| 81-12 | H | CH₂ | H | H | CH₂ | Pen | 2-EtO-5-Pyr | — |
| 81-13 | H | CH₂ | H | H | CH₂ | Pen | 2-iPrO-5-Pyr | — |
| 81-14 | H | CH₂ | H | H | CH₂ | Pen | 2-MeS-5-Pyr | — |
| 81-15 | H | CH₂ | H | H | CH₂ | Pen | 2-EtS-5-Pyr | — |
| 81-16 | H | CH₂ | H | H | CH₂ | Pen | 2-Ph-5-Pyr | — |
| 81-17 | H | CH₂ | H | H | CH₂ | Pen | 3-Ph-6-Pyr | — |

TABLE 82

| Ex. No. Comp. | R¹ | R² | R³ | R⁴ | Z | W | X | Y |
|---|---|---|---|---|---|---|---|---|
| 82-1 | H | CH₂ | H | H | CH₂ | MeS | Ph | — |
| 82-2 | H | CH₂ | H | H | CH₂ | MeS | 4-Ph-Ph | — |
| 82-3 | H | CH₂ | H | H | CH₂ | MeS | 4-(Pyr-2)-Ph | — |
| 82-4 | H | CH₂ | H | H | CH₂ | MeS | 4-(Pyr-3)-Ph | — |

TABLE 82-continued

| Ex. No. Comp. | R¹ | R² | R³ | R⁴ | Z | W | X | Y |
|---|---|---|---|---|---|---|---|---|
| 82-5 | H | CH₂ | H | H | CH₂ | MeS | 4-(Pyr-4)-Ph | — |
| 82-6 | H | CH₂ | H | H | CH₂ | MeS | 2-Pyr | — |
| 82-7 | H | CH₂ | H | H | CH₂ | MeS | 3-Pyr | — |
| 82-8 | H | CH₂ | H | H | CH₂ | MeS | 4-Pyr | — |
| 82-9 | H | CH₂ | H | H | CH₂ | MeS | 2-Me-5-Pyr | — |
| 82-10 | H | CH₂ | H | H | CH₂ | MeS | 2-Me-3-Pyr | — |
| 82-11 | H | CH₂ | H | H | CH₂ | MeS | 2-MeO-5-Pyr | — |
| 82-12 | H | CH₂ | H | H | CH₂ | MeS | 2-EtO-5-Pyr | — |
| 82-13 | H | CH₂ | H | H | CH₂ | MeS | 2-iPrO-5-Pyr | — |
| 82-14 | H | CH₂ | H | H | CH₂ | MeS | 2-MeS-5-Pyr | — |
| 82-15 | H | CH₂ | H | H | CH₂ | MeS | 2-EtS-5-Pyr | — |
| 82-16 | H | CH₂ | H | H | CH₂ | MeS | 2-Ph-5-Pyr | — |
| 82-17 | H | CH₂ | H | H | CH₂ | MeS | 3-Ph-6-Pyr | — |

TABLE 83

| Ex. No. Comp. | R¹ | R² | R³ | R⁴ | Z | W | X | Y |
|---|---|---|---|---|---|---|---|---|
| 83-1 | H | CH₂ | H | H | CH₂ | PhO | Ph | — |
| 83-2 | H | CH₂ | H | H | CH₂ | PhO | 4-Ph-Ph | — |
| 83-3 | H | CH₂ | H | H | CH₂ | PhO | 4-(Pyr-2)-Ph | — |
| 83-4 | H | CH₂ | H | H | CH₂ | PhO | 4-(Pyr-3)-Ph | — |
| 83-5 | H | CH₂ | H | H | CH₂ | PhO | 4-(Pyr-4)-Ph | — |
| 83-6 | H | CH₂ | H | H | CH₂ | PhO | 2-Pyr | — |
| 83-7 | H | CH₂ | H | H | CH₂ | PhO | 3-Pyr | — |
| 83-8 | H | CH₂ | H | H | CH₂ | PhO | 4-Pyr | — |
| 83-9 | H | CH₂ | H | H | CH₂ | PhO | 2-Me-5-Pyr | — |
| 83-10 | H | CH₂ | H | H | CH₂ | PhO | 2-Me-3-Pyr | — |
| 83-11 | H | CH₂ | H | H | CH₂ | PhO | 2-MeO-5-Pyr | — |
| 83-12 | H | CH₂ | H | H | CH₂ | PhO | 2-EtO-5-Pyr | — |
| 83-13 | H | CH₂ | H | H | CH₂ | PhO | 2-iPrO-5-Pyr | — |
| 83-14 | H | CH₂ | H | H | CH₂ | PhO | 2-MeS-5-Pyr | — |
| 83-15 | H | CH₂ | H | H | CH₂ | PhO | 2-EtS-5-Pyr | — |
| 83-16 | H | CH₂ | H | H | CH₂ | PhO | 2-Ph-5-Pyr | — |
| 83-17 | H | CH₂ | H | H | CH₂ | PhO | 3-Ph-6-Pyr | — |

TABLE 84

| Ex. No. Comp. | R¹ | R² | R³ | R⁴ | Z | W | X | Y |
|---|---|---|---|---|---|---|---|---|
| 84-1 | H | CH₂ | H | H | CH₂ | 4-iPr-PhO | Ph | — |
| 84-2 | H | CH₂ | H | H | CH₂ | 4-iPr-PhO | 4-Ph-Ph | — |
| 84-3 | H | CH₂ | H | H | CH₂ | 4-iPr-PhO | 4-(Pyr-2)-Ph | — |
| 84-4 | H | CH₂ | H | H | CH₂ | 4-iPr-PhO | 4-(Pyr-3)-Ph | — |
| 84-5 | H | CH₂ | H | H | CH₂ | 4-iPr-PhO | 4-(Pyr-4)-Ph | — |
| 84-6 | H | CH₂ | H | H | CH₂ | 4-iPr-PhO | 2-Pyr | — |
| 84-7 | H | CH₂ | H | H | CH₂ | 4-iPr-PhO | 3-Pyr | — |
| 84-8 | H | CH₂ | H | H | CH₂ | 4-iPr-PhO | 4-Pyr | — |
| 84-9 | H | CH₂ | H | H | CH₂ | 4-iPr-PhO | 2-Me-5-Pyr | — |
| 84-10 | H | CH₂ | H | H | CH₂ | 4-iPr-PhO | 2-Me-3-Pyr | — |
| 84-11 | H | CH₂ | H | H | CH₂ | 4-iPr-PhO | 2-MeO-5-Pyr | — |
| 84-12 | H | CH₂ | H | H | CH₂ | 4-iPr-PhO | 2-EtO-5-Pyr | — |
| 84-13 | H | CH₂ | H | H | CH₂ | 4-iPr-PhO | 2-iPrO-5-Pyr | — |
| 84-14 | H | CH₂ | H | H | CH₂ | 4-iPr-PhO | 2-MeS-5-Pyr | — |
| 84-15 | H | CH₂ | H | H | CH₂ | 4-iPr-PhO | 2-EtS-5-Pyr | — |
| 84-16 | H | CH₂ | H | H | CH₂ | 4-iPr-PhO | 2-Ph-5-Pyr | — |
| 84-17 | H | CH₂ | H | H | CH₂ | 4-iPr-PhO | 3-Ph-6-Pyr | — |

TABLE 85

| Ex. No. Comp. | R¹ | R² | R³ | R⁴ | Z | W | X | Y |
|---|---|---|---|---|---|---|---|---|
| 85-1 | H | CH₂ | H | H | CH₂ | 4-MeO-PhO | Ph | — |
| 85-2 | H | CH₂ | H | H | CH₂ | 4-MeO-PhO | 4-Ph-Ph | — |
| 85-3 | H | CH₂ | H | H | CH₂ | 4-MeO-PhO | 4-(Pyr-2)-Ph | — |
| 85-4 | H | CH₂ | H | H | CH₂ | 4-MeO-PhO | 4-(Pyr-3)-Ph | — |
| 85-5 | H | CH₂ | H | H | CH₂ | 4-MeO-PhO | 4-(Pyr-4)-Ph | — |
| 85-6 | H | CH₂ | H | H | CH₂ | 4-MeO-PhO | 2-Pyr | — |
| 85-7 | H | CH₂ | H | H | CH₂ | 4-MeO-PhO | 3-Pyr | — |
| 85-8 | H | CH₂ | H | H | CH₂ | 4-MeO-PhO | 4-Pyr | — |
| 85-9 | H | CH₂ | H | H | CH₂ | 4-MeO-PhO | 2-Me-5-Pyr | — |
| 85-10 | H | CH₂ | H | H | CH₂ | 4-MeO-PhO | 2-Me-3-Pyr | — |
| 85-11 | H | CH₂ | H | H | CH₂ | 4-MeO-PhO | 2-MeO-5-Pyr | — |
| 85-12 | H | CH₂ | H | H | CH₂ | 4-MeO-PhO | 2-EtO-5-Pyr | — |
| 85-13 | H | CH₂ | H | H | CH₂ | 4-MeO-PhO | 2-iPrO-5-Pyr | — |
| 85-14 | H | CH₂ | H | H | CH₂ | 4-MeO-PhO | 2-MeS-5-Pyr | — |
| 85-15 | H | CH₂ | H | H | CH₂ | 4-MeO-PhO | 2-EtS-5-Pyr | — |
| 85-16 | H | CH₂ | H | H | CH₂ | 4-MeO-PhO | 2-Ph-5-Pyr | — |
| 85-17 | H | CH₂ | H | H | CH₂ | 4-MeO-PhO | 3-Ph-6-Pyr | — |

TABLE 86

| Ex. No. Comp. | R¹ | R² | R³ | R⁴ | Z | W | X | Y |
|---|---|---|---|---|---|---|---|---|
| 86-1 | H | CH₂ | H | H | CH₂ | PhS | Ph | — |
| 86-2 | H | CH₂ | H | H | CH₂ | PhS | 4-Ph-Ph | — |
| 86-3 | H | CH₂ | H | H | CH₂ | PhS | 4-(Pyr-2)-Ph | — |
| 86-4 | H | CH₂ | H | H | CH₂ | PhS | 4-(Pyr-3)-Ph | — |
| 86-5 | H | CH₂ | H | H | CH₂ | PhS | 4-(Pyr-4)-Ph | — |
| 86-6 | H | CH₂ | H | H | CH₂ | PhS | 2-Pyr | — |
| 86-7 | H | CH₂ | H | H | CH₂ | PhS | 3-Pyr | — |
| 86-8 | H | CH₂ | H | H | CH₂ | PhS | 4-Pyr | — |
| 86-9 | H | CH₂ | H | H | CH₂ | PhS | 2-Me-5-Pyr | — |
| 86-10 | H | CH₂ | H | H | CH₂ | PhS | 2-Me-3-Pyr | — |
| 86-11 | H | CH₂ | H | H | CH₂ | PhS | 2-MeO-5-Pyr | — |
| 86-12 | H | CH₂ | H | H | CH₂ | PhS | 2-EtO-5-Pyr | — |
| 86-13 | H | CH₂ | H | H | CH₂ | PhS | 2-iPrO-5-Pyr | — |
| 86-14 | H | CH₂ | H | H | CH₂ | PhS | 2-MeS-5-Pyr | — |
| 86-15 | H | CH₂ | H | H | CH₂ | PhS | 2-EtS-5-Pyr | — |
| 86-16 | H | CH₂ | H | H | CH₂ | PhS | 2-Ph-5-Pyr | — |
| 86-17 | H | CH₂ | H | H | CH₂ | PhS | 3-Ph-6-Pyr | — |

TABLE 87

| Ex. No. Comp. | R¹ | R² | R³ | R⁴ | Z | W | X | Y |
|---|---|---|---|---|---|---|---|---|
| 87-1 | H | CH₂ | H | H | CH₂ | Ph(CH₂)₃ | Ph | — |
| 87-2 | H | CH₂ | H | H | CH₂ | Ph(CH₂)₃ | 4-Ph-Ph | — |
| 87-3 | H | CH₂ | H | H | CH₂ | Ph(CH₂)₃ | 4-(Pyr-2)-Ph | — |
| 87-4 | H | CH₂ | H | H | CH₂ | Ph(CH₂)₃ | 4-(Pyr-3)-Ph | — |
| 87-5 | H | CH₂ | H | H | CH₂ | Ph(CH₂)₃ | 4-(Pyr-4)-Ph | — |
| 87-6 | H | CH₂ | H | H | CH₂ | Ph(CH₂)₃ | 2-Pyr | — |
| 87-7 | H | CH₂ | H | H | CH₂ | Ph(CH₂)₃ | 3-Pyr | — |
| 87-8 | H | CH₂ | H | H | CH₂ | Ph(CH₂)₃ | 4-Pyr | — |
| 87-9 | H | CH₂ | H | H | CH₂ | Ph(CH₂)₃ | 2-Me-5-Pyr | — |
| 87-10 | H | CH₂ | H | H | CH₂ | Ph(CH₂)₃ | 2-Me-3-Pyr | — |
| 87-11 | H | CH₂ | H | H | CH₂ | Ph(CH₂)₃ | 2-MeO-5-Pyr | — |
| 87-12 | H | CH₂ | H | H | CH₂ | Ph(CH₂)₃ | 2-EtO-5-Pyr | — |
| 87-13 | H | CH₂ | H | H | CH₂ | Ph(CH₂)₃ | 2-iPrO-5-Pyr | — |
| 87-14 | H | CH₂ | H | H | CH₂ | Ph(CH₂)₃ | 2-MeS-5-Pyr | — |
| 87-15 | H | CH₂ | H | H | CH₂ | Ph(CH₂)₃ | 2-EtS-5-Pyr | — |
| 87-16 | H | CH₂ | H | H | CH₂ | Ph(CH₂)₃ | 2-Ph-5-Pyr | — |
| 87-17 | H | CH₂ | H | H | CH₂ | Ph(CH₂)₃ | 3-Ph-6-Pyr | — |

TABLE 88

| Ex. No. Comp. | R¹ | R² | R³ | R⁴ | Z | W | X | Y |
|---|---|---|---|---|---|---|---|---|
| 88-1 | H | CH₂ | H | Me | CH₂ | EtO | 4-Ph-Ph | — |
| 88-2 | H | CH₂ | H | Me | CH₂ | EtO | 4-(Pyr-2)-Ph | — |
| 88-3 | H | CH₂ | H | Me | CH₂ | EtO | 4-(Pyr-3)-Ph | — |
| 88-4 | H | CH₂ | H | Me | CH₂ | EtO | 4-(Pyr-4)-Ph | — |
| 88-5 | H | CH₂ | H | Me | CH₂ | EtO | 2-Ph-5-Pyr | — |
| 88-6 | H | CH₂ | H | Me | CH₂ | EtO | 3-Ph-6-Pyr | — |

TABLE 89

| Ex. No. Comp. | R¹ | R² | R³ | R⁴ | Z | W | X | Y |
|---|---|---|---|---|---|---|---|---|
| 89-1 | H | CH₂ | H | Me | CH₂ | Pr | 4-Ph-Ph | — |
| 89-2 | H | CH₂ | H | Me | CH₂ | Pr | 4-(Pyr-2)-Ph | — |
| 89-3 | H | CH₂ | H | Me | CH₂ | Pr | 4-(Pyr-3)-Ph | — |
| 89-4 | H | CH₂ | H | Me | CH₂ | Pr | 4-(Pyr-4)-Ph | — |
| 89-5 | H | CH₂ | H | Me | CH₂ | Pr | 2-Ph-5-Pyr | — |
| 89-6 | H | CH₂ | H | Me | CH₂ | Pr | 3-Ph-6-Pyr | — |

TABLE 90

| Ex. No. Comp. | R¹ | R² | R³ | R⁴ | Z | W | X | Y |
|---|---|---|---|---|---|---|---|---|
| 90-1 | H | CH₂ | H | Me | CH₂ | Bu | 4-Ph-Ph | — |
| 90-2 | H | CH₂ | H | Me | CH₂ | Bu | 4-(Pyr-2)-Ph | — |
| 90-3 | H | CH₂ | H | Me | CH₂ | Bu | 4-(Pyr-3)-Ph | — |
| 90-4 | H | CH₂ | H | Me | CH₂ | Bu | 4-(Pyr-4)-Ph | — |
| 90-5 | H | CH₂ | H | Me | CH₂ | Bu | 2-Ph-5-Pyr | — |
| 90-6 | H | CH₂ | H | Me | CH₂ | Bu | 3-Ph-6-Pyr | — |

TABLE 91

| Ex. No. Comp. | R¹ | R² | R³ | R⁴ | Z | W | X | Y |
|---|---|---|---|---|---|---|---|---|
| 91-1 | H | CH₂ | H | Me | CH₂ | Pen | 4-Ph-Ph | — |
| 91-2 | H | CH₂ | H | Me | CH₂ | Pen | 4-(Pyr-2)-Ph | — |
| 91-3 | H | CH₂ | H | Me | CH₂ | Pen | 4-(Pyr-3)-Ph | — |
| 91-4 | H | CH₂ | H | Me | CH₂ | Pen | 4-(Pyr-4)-Ph | — |
| 91-5 | H | CH₂ | H | Me | CH₂ | Pen | 2-Ph-5-Pyr | — |
| 91-6 | H | CH₂ | H | Me | CH₂ | Pen | 3-Ph-6-Pyr | — |

TABLE 92

| Ex. No. Comp. | R¹ | R² | R³ | R⁴ | Z | W | X | Y |
|---|---|---|---|---|---|---|---|---|
| 92-1 | H | CH₂ | H | Me | CH₂ | MeS | 4-Ph-Ph | — |
| 92-2 | H | CH₂ | H | Me | CH₂ | MeS | 4-(Pyr-2)-Ph | — |
| 92-3 | H | CH₂ | H | Me | CH₂ | MeS | 4-(Pyr-3)-Ph | — |
| 92-4 | H | CH₂ | H | Me | CH₂ | MeS | 4-(Pyr-4)-Ph | — |
| 92-5 | H | CH₂ | H | Me | CH₂ | MeS | 2-Ph-5-Pyr | — |
| 92-6 | H | CH₂ | H | Me | CH₂ | MeS | 3-Ph-6-Pyr | — |

TABLE 93

| Ex. No. Comp. | R¹ | R² | R³ | R⁴ | Z | W | X | Y |
|---|---|---|---|---|---|---|---|---|
| 93-1 | H | CH₂ | H | Me | CH₂ | PhO | 4-Ph-Ph | — |
| 93-2 | H | CH₂ | H | Me | CH₂ | PhO | 4-(Pyr-2)-Ph | — |
| 93-3 | H | CH₂ | H | Me | CH₂ | PhO | 4-(Pyr-3)-Ph | — |
| 93-4 | H | CH₂ | H | Me | CH₂ | PhO | 4-(Pyr-4)-Ph | — |
| 93-5 | H | CH₂ | H | Me | CH₂ | PhO | 2-Ph-5-Pyr | — |
| 93-6 | H | CH₂ | H | Me | CH₂ | PhO | 3-Ph-6-Pyr | — |

TABLE 94

| Ex. No. Comp. | R¹ | R² | R³ | R⁴ | Z | W | X | Y |
|---|---|---|---|---|---|---|---|---|
| 94-1 | H | CH₂ | H | Me | CH₂ | 4-iPr—PhO | 4-Ph—Ph | — |
| 94-2 | H | CH₂ | H | Me | CH₂ | 4-iPr—PhO | 4-(Pyr-2)-Ph | — |
| 94-3 | H | CH₂ | H | Me | CH₂ | 4-iPr—PhO | 4-(Pyr-3)-Ph | — |
| 94-4 | H | CH₂ | H | Me | CH₂ | 4-iPr—PhO | 4-(Pyr-4)-Ph | — |
| 94-5 | H | CH₂ | H | Me | CH₂ | 4-iPr—PhO | 2-Ph-5-Pyr | — |
| 94-6 | H | CH₂ | H | Me | CH₂ | 4-iPr—PhO | 3-Ph-6-Pyr | — |

TABLE 95

| Ex. No. Comp. | R¹ | R² | R³ | R⁴ | Z | W | X | Y |
|---|---|---|---|---|---|---|---|---|
| 95-1 | H | CH₂ | H | Me | CH₂ | 4-MeO—PhO | 4-Ph—Ph | — |
| 95-2 | H | CH₂ | H | Me | CH₂ | 4-MeO—PhO | 4-(Pyr-2)-Ph | — |
| 95-3 | H | CH₂ | H | Me | CH₂ | 4-MeO—PhO | 4-(Pyr-3)-Ph | — |
| 95-4 | H | CH₂ | H | Me | CH₂ | 4-MeO—PhO | 4-(Pyr-4)-Ph | — |
| 95-5 | H | CH₂ | H | Me | CH₂ | 4-MeO—PhO | 2-Ph-5-Pyr | — |
| 95-6 | H | CH₂ | H | Me | CH₂ | 4-MeO—PhO | 3-Ph-6-Pyr | — |

TABLE 96

| Ex. No. Comp. | R¹ | R² | R³ | R⁴ | Z | W | X | Y |
|---|---|---|---|---|---|---|---|---|
| 96-1 | H | CH₂ | H | Me | CH₂ | PhS | 4-Ph—Ph | — |
| 96-2 | H | CH₂ | H | Me | CH₂ | PhS | 4-(Pyr-2)-Ph | — |
| 96-3 | H | CH₂ | H | Me | CH₂ | PhS | 4-(Pyr-3)-Ph | — |
| 96-4 | H | CH₂ | H | Me | CH₂ | PhS | 4-(Pyr-4)-Ph | — |
| 96-5 | H | CH₂ | H | Me | CH₂ | PhS | 2-Ph-5-Pyr | — |
| 96-6 | H | CH₂ | H | Me | CH₂ | PhS | 3-Ph-6-Pyr | — |

TABLE 97

| Ex. No. Comp. | R¹ | R² | R³ | R⁴ | Z | W | X | Y |
|---|---|---|---|---|---|---|---|---|
| 97-1 | H | CH₂ | H | Me | CH₂ | Ph(CH₂)₃ | 4-Ph—Ph | — |
| 97-2 | H | CH₂ | H | Me | CH₂ | Ph(CH₂)₃ | 4-(Pyr-2)-Ph | — |
| 97-3 | H | CH₂ | H | Me | CH₂ | Ph(CH₂)₃ | 4-(Pyr-3)-Ph | — |
| 97-4 | H | CH₂ | H | Me | CH₂ | Ph(CH₂)₃ | 4-(Pyr-4)-Ph | — |
| 97-5 | H | CH₂ | H | Me | CH₂ | Ph(CH₂)₃ | 2-Ph-5-Pyr | — |
| 97-6 | H | CH₂ | H | Me | CH₂ | Ph(CH₂)₃ | 3-Ph-6-Pyr | — |

TABLE 98

| Ex. No. Comp. | R¹ | R² | R³ | R⁴ | Z | W | X | Y |
|---|---|---|---|---|---|---|---|---|
| 98-1 | H | (CH₂)₂ | H | Me | CH₂ | EtO | 4-Ph—Ph | — |
| 98-2 | H | (CH₂)₂ | H | Me | CH₂ | EtO | 4-(Pyr-2)-Ph | — |
| 98-3 | H | (CH₂)₂ | H | Me | CH₂ | EtO | 4-(Pyr-3)-Ph | — |
| 98-4 | H | (CH₂)₂ | H | Me | CH₂ | EtO | 4-(Pyr-4)-Ph | — |
| 98-5 | H | (CH₂)₂ | H | Me | CH₂ | EtO | 2-Ph-5-Pyr | — |
| 98-6 | H | (CH₂)₂ | H | Me | CH₂ | EtO | 3-Ph-6-Pyr | — |

TABLE 99

| Ex. No. Comp. | R¹ | R² | R³ | R⁴ | Z | W | X | Y |
|---|---|---|---|---|---|---|---|---|
| 99-1 | H | (CH₂)₂ | H | Me | CH₂ | Pr | 4-Ph—Ph | — |
| 99-2 | H | (CH₂)₂ | H | Me | CH₂ | Pr | 4-(Pyr-2)-Ph | — |
| 99-3 | H | (CH₂)₂ | H | Me | CH₂ | Pr | 4-(Pyr-3)-Ph | — |
| 99-4 | H | (CH₂)₂ | H | Me | CH₂ | Pr | 4-(Pyr-4)-Ph | — |
| 99-5 | H | (CH₂)₂ | H | Me | CH₂ | Pr | 2-Ph-5-Pyr | — |
| 99-6 | H | (CH₂)₂ | H | Me | CH₂ | Pr | 3-Ph-6-Pyr | — |

TABLE 100

| Ex. No. Comp. | R¹ | R² | R³ | R⁴ | Z | W | X | Y |
|---|---|---|---|---|---|---|---|---|
| 100-1 | H | (CH₂)₂ | H | Me | CH₂ | Bu | 4-Ph—Ph | — |
| 100-2 | H | (CH₂)₂ | H | Me | CH₂ | Bu | 4-(Pyr-2)-Ph | — |
| 100-3 | H | (CH₂)₂ | H | Me | CH₂ | Bu | 4-(Pyr-3)-Ph | — |
| 100-4 | H | (CH₂)₂ | H | Me | CH₂ | Bu | 4-(Pyr-4)-Ph | — |
| 100-5 | H | (CH₂)₂ | H | Me | CH₂ | Bu | 2-Ph-5-Pyr | — |
| 100-6 | H | (CH₂)₂ | H | Me | CH₂ | Bu | 3-Ph-6-Pyr | — |

TABLE 101

| Ex. No. Comp. | R¹ | R² | R³ | R⁴ | Z | W | X | Y |
|---|---|---|---|---|---|---|---|---|
| 101-1 | H | (CH₂)₂ | H | Me | CH₂ | Pen | 4-Ph—Ph | — |
| 101-2 | H | (CH₂)₂ | H | Me | CH₂ | Pen | 4-(Pyr-2)-Ph | — |
| 101-3 | H | (CH₂)₂ | H | Me | CH₂ | Pen | 4-(Pyr-3)-Ph | — |
| 101-4 | H | (CH₂)₂ | H | Me | CH₂ | Pen | 4-(Pyr-4)-Ph | — |

TABLE 101-continued

| Ex. No. Comp. | R¹ | R² | R³ | R⁴ | Z | W | X | Y |
|---|---|---|---|---|---|---|---|---|
| 101-5 | H | (CH₂)₂ | H | Me | CH₂ | Pen | 2-Ph-5-Pyr | — |
| 101-6 | H | (CH₂)₂ | H | Me | CH₂ | Pen | 3-Ph-6-Pyr | — |

TABLE 102

| Ex. No. Comp. | R¹ | R² | R³ | R⁴ | Z | W | X | Y |
|---|---|---|---|---|---|---|---|---|
| 102-1 | H | (CH₂)₂ | H | Me | CH₂ | MeS | 4-Ph—Ph | — |
| 102-2 | H | (CH₂)₂ | H | Me | CH₂ | MeS | 4-(Pyr-2)-Ph | — |
| 102-3 | H | (CH₂)₂ | H | Me | CH₂ | MeS | 4-(Pyr-3)-Ph | — |
| 102-4 | H | (CH₂)₂ | H | Me | CH₂ | MeS | 4-(Pyr-4)-Ph | — |
| 102-5 | H | (CH₂)₂ | H | Me | CH₂ | MeS | 2-Ph-5-Pyr | — |
| 102-6 | H | (CH₂)₂ | H | Me | CH₂ | MeS | 3-Ph-6-Pyr | — |

TABLE 103

| Ex. No. Comp. | R¹ | R² | R³ | R⁴ | Z | W | X | Y |
|---|---|---|---|---|---|---|---|---|
| 103-1 | H | (CH₂)₂ | H | Me | CH₂ | PhO | 4-Ph—Ph | — |
| 103-2 | H | (CH₂)₂ | H | Me | CH₂ | PhO | 4-(Pyr-2)-Ph | — |
| 103-3 | H | (CH₂)₂ | H | Me | CH₂ | PhO | 4-(Pyr-3)-Ph | — |
| 103-4 | H | (CH₂)₂ | H | Me | CH₂ | PhO | 4-(Pyr-4)-Ph | — |
| 103-5 | H | (CH₂)₂ | H | Me | CH₂ | PhO | 2-Ph-5-Pyr | — |
| 103-6 | H | (CH₂)₂ | H | Me | CH₂ | PhO | 3-Ph-6-Pyr | — |

TABLE 104

| Ex. No. Comp. | R¹ | R² | R³ | R⁴ | Z | W | X | Y |
|---|---|---|---|---|---|---|---|---|
| 104-1 | H | (CH₂)₂ | H | Me | CH₂ | 4-iPr—PhO | 4-Ph—Ph | — |
| 104-2 | H | (CH₂)₂ | H | Me | CH₂ | 4-iPr—PhO | 4-(Pyr-2)-Ph | — |
| 104-3 | H | (CH₂)₂ | H | Me | CH₂ | 4-iPr—PhO | 4-(Pyr-3)-Ph | — |
| 104-4 | H | (CH₂)₂ | H | Me | CH₂ | 4-iPr—PhO | 4-(Pyr-4)-Ph | — |
| 104-5 | H | (CH₂)₂ | H | Me | CH₂ | 4-iPr—PhO | 2-Ph-5-Pyr | — |
| 104-6 | H | (CH₂)₂ | H | Me | CH₂ | 4-iPr—PhO | 3-Ph-6-Pyr | — |

TABLE 105

| Ex. No. Comp. | R¹ | R² | R³ | R⁴ | Z | W | X | Y |
|---|---|---|---|---|---|---|---|---|
| 105-1 | H | (CH₂)₂ | H | Me | CH₂ | 4-MeO—PhO | 4-Ph—Ph | — |
| 105-2 | H | (CH₂)₂ | H | Me | CH₂ | 4-MeO—PhO | 4-(Pyr-2)-Ph | — |
| 105-3 | H | (CH₂)₂ | H | Me | CH₂ | 4-MeO—PhO | 4-(Pyr-3)-Ph | — |
| 105-4 | H | (CH₂)₂ | H | Me | CH₂ | 4-MeO—PhO | 4-(Pyr-4)-Ph | — |
| 105-5 | H | (CH₂)₂ | H | Me | CH₂ | 4-MeO—PhO | 2-Ph-5-Pyr | — |
| 105-6 | H | (CH₂)₂ | H | Me | CH₂ | 4-MeO—PhO | 3-Ph-6-Pyr | — |

TABLE 106

| Ex. No. Comp. | R¹ | R² | R³ | R⁴ | Z | W | X | Y |
|---|---|---|---|---|---|---|---|---|
| 106-1 | H | (CH$_2$)$_2$ | H | Me | CH$_2$ | PhS | 4-Ph—Ph | — |
| 106-2 | H | (CH$_2$)$_2$ | H | Me | CH$_2$ | PhS | 4-(Pyr-2)-Ph | — |
| 106-3 | H | (CH$_2$)$_2$ | H | Me | CH$_2$ | PhS | 4-(Pyr-3)-Ph | — |
| 106-4 | H | (CH$_2$)$_2$ | H | Me | CH$_2$ | PhS | 4-(Pyr-4)-Ph | — |
| 106-5 | H | (CH$_2$)$_2$ | H | Me | CH$_2$ | PhS | 2-Ph-5-Pyr | — |
| 106-6 | H | (CH$_2$)$_2$ | H | Me | CH$_2$ | PhS | 3-Ph-6-Pyr | — |

TABLE 107

| Ex. No. Comp. | R¹ | R² | R³ | R⁴ | Z | W | X | Y |
|---|---|---|---|---|---|---|---|---|
| 107-1 | H | (CH$_2$)$_2$ | H | Me | CH$_2$ | Ph(CH$_2$)$_3$ | 4-Ph—Ph | — |
| 107-2 | H | (CH$_2$)$_2$ | H | Me | CH$_2$ | Ph(CH$_2$)$_3$ | 4-(Pyr-2)-Ph | — |
| 107-3 | H | (CH$_2$)$_2$ | H | Me | CH$_2$ | Ph(CH$_2$)$_3$ | 4-(Pyr-3)-Ph | — |
| 107-4 | H | (CH$_2$)$_2$ | H | Me | CH$_2$ | Ph(CH$_2$)$_3$ | 4-(Pyr-4)-Ph | — |
| 107-5 | H | (CH$_2$)$_2$ | H | Me | CH$_2$ | Ph(CH$_2$)$_3$ | 2-Ph-5-Pyr | — |
| 107-6 | H | (CH$_2$)$_2$ | H | Me | CH$_2$ | Ph(CH$_2$)$_3$ | 3-Ph-6-Pyr | — |

TABLE 108

| Ex. No. Comp. | R¹ | R² | R³ | R⁴ | Z | W | X | Y |
|---|---|---|---|---|---|---|---|---|
| 108-1 | H | (CH$_2$)$_2$ | H | H | CH$_2$ | EtO | 4-Ph—Ph | S |
| 108-2 | H | (CH$_2$)$_2$ | H | H | CH$_2$ | EtO | 4-(Pyr-2)-Ph | S |
| 108-3 | H | (CH$_2$)$_2$ | H | H | CH$_2$ | EtO | 4-(Pyr-3)-Ph | S |
| 108-4 | H | (CH$_2$)$_2$ | H | H | CH$_2$ | EtO | 4-(Pyr-4)-Ph | S |
| 108-5 | H | (CH$_2$)$_2$ | H | H | CH$_2$ | EtO | 2-Ph-5-Pyr | S |
| 108-6 | H | (CH$_2$)$_2$ | H | H | CH$_2$ | EtO | 3-Ph-6-Pyr | S |

TABLE 109

| Ex. No. Comp. | R¹ | R² | R³ | R⁴ | Z | W | X | Y |
|---|---|---|---|---|---|---|---|---|
| 109-1 | H | (CH$_2$)$_2$ | H | H | CH$_2$ | Pr | 4-Ph—Ph | S |
| 109-2 | H | (CH$_2$)$_2$ | H | H | CH$_2$ | Pr | 4-(Pyr-2)-Ph | S |
| 109-3 | H | (CH$_2$)$_2$ | H | H | CH$_2$ | Pr | 4-(Pyr-3)-Ph | S |
| 109-4 | H | (CH$_2$)$_2$ | H | H | CH$_2$ | Pr | 4-(Pyr-4)-Ph | S |
| 109-5 | H | (CH$_2$)$_2$ | H | H | CH$_2$ | Pr | 2-Ph-5-Pyr | S |
| 109-6 | H | (CH$_2$)$_2$ | H | H | CH$_2$ | Pr | 3-Ph-6-Pyr | S |

TABLE 110

| Ex. No. Comp. | R¹ | R² | R³ | R⁴ | Z | W | X | Y |
|---|---|---|---|---|---|---|---|---|
| 110-1 | H | (CH$_2$)$_2$ | H | H | CH$_2$ | Bu | 4-Ph—Ph | S |
| 110-2 | H | (CH$_2$)$_2$ | H | H | CH$_2$ | Bu | 4-(Pyr-2)-Ph | S |
| 110-3 | H | (CH$_2$)$_2$ | H | H | CH$_2$ | Bu | 4-(Pyr-3)-Ph | S |
| 110-4 | H | (CH$_2$)$_2$ | H | H | CH$_2$ | Bu | 4-(Pyr-4)-Ph | S |
| 110-5 | H | (CH$_2$)$_2$ | H | H | CH$_2$ | Bu | 2-Ph-5-Pyr | S |
| 110-6 | H | (CH$_2$)$_2$ | H | H | CH$_2$ | Bu | 3-Ph-6-Pyr | S |

TABLE 111

| Ex. No. Comp. | R¹ | R² | R³ | R⁴ | Z | W | X | Y |
|---|---|---|---|---|---|---|---|---|
| 111-1 | H | (CH$_2$)$_2$ | H | H | CH$_2$ | Pen | 4-Ph—Ph | S |
| 111-2 | H | (CH$_2$)$_2$ | H | H | CH$_2$ | Pen | 4-(Pyr-2)-Ph | S |
| 111-3 | H | (CH$_2$)$_2$ | H | H | CH$_2$ | Pen | 4-(Pyr-3)-Ph | S |
| 111-4 | H | (CH$_2$)$_2$ | H | H | CH$_2$ | Pen | 4-(Pyr-4)-Ph | S |
| 111-5 | H | (CH$_2$)$_2$ | H | H | CH$_2$ | Pen | 2-Ph-5-Pyr | S |
| 111-6 | H | (CH$_2$)$_2$ | H | H | CH$_2$ | Pen | 3-Ph-6-Pyr | S |

TABLE 112

| Ex. No. Comp. | R¹ | R² | R³ | R⁴ | Z | W | X | Y |
|---|---|---|---|---|---|---|---|---|
| 112-1 | H | (CH$_2$)$_2$ | H | H | CH$_2$ | MeS | 4-Ph—Ph | S |
| 112-2 | H | (CH$_2$)$_2$ | H | H | CH$_2$ | MeS | 4-(Pyr-2)-Ph | S |
| 112-3 | H | (CH$_2$)$_2$ | H | H | CH$_2$ | MeS | 4-(Pyr-3)-Ph | S |
| 112-4 | H | (CH$_2$)$_2$ | H | H | CH$_2$ | MeS | 4-(Pyr-4)-Ph | S |
| 112-5 | H | (CH$_2$)$_2$ | H | H | CH$_2$ | MeS | 2-Ph-5-Pyr | S |
| 112-6 | H | (CH$_2$)$_2$ | H | H | CH$_2$ | MeS | 3-Ph-6-Pyr | S |

TABLE 113

| Ex. No. Comp. | R¹ | R² | R³ | R⁴ | Z | W | X | Y |
|---|---|---|---|---|---|---|---|---|
| 113-1 | H | (CH$_2$)$_2$ | H | H | CH$_2$ | PhO | 4-Ph—Ph | S |
| 113-2 | H | (CH$_2$)$_2$ | H | H | CH$_2$ | PhO | 4-(Pyr-2)-Ph | S |
| 113-3 | H | (CH$_2$)$_2$ | H | H | CH$_2$ | PhO | 4-(Pyr-3)-Ph | S |
| 113-4 | H | (CH$_2$)$_2$ | H | H | CH$_2$ | PhO | 4-(Pyr-4)-Ph | S |
| 113-5 | H | (CH$_2$)$_2$ | H | H | CH$_2$ | PhO | 2-Ph-5-Pyr | S |
| 113-6 | H | (CH$_2$)$_2$ | H | H | CH$_2$ | PhO | 3-Ph-6-Pyr | S |

TABLE 114

| Ex. No. Comp. | R¹ | R² | R³ | R⁴ | Z | W | X | Y |
|---|---|---|---|---|---|---|---|---|
| 114-1 | H | (CH$_2$)$_2$ | H | H | CH$_2$ | 4-iPr—PhO | 4-Ph—Ph | S |
| 114-2 | H | (CH$_2$)$_2$ | H | H | CH$_2$ | 4-iPr—PhO | 4-(Pyr-2)-Ph | S |
| 114-3 | H | (CH$_2$)$_2$ | H | H | CH$_2$ | 4-iPr—PhO | 4-(Pyr-3)-Ph | S |
| 114-4 | H | (CH$_2$)$_2$ | H | H | CH$_2$ | 4-iPr—PhO | 4-(Pyr-4)-Ph | S |
| 114-5 | H | (CH$_2$)$_2$ | H | H | CH$_2$ | 4-iPr—PhO | 2-Ph-5-Pyr | S |
| 114-6 | H | (CH$_2$)$_2$ | H | H | CH$_2$ | 4-iPr—PhO | 3-Ph-6-Pyr | S |

TABLE 115

| Ex. No. Comp. | R¹ | R² | R³ | R⁴ | Z | W | X | Y |
|---|---|---|---|---|---|---|---|---|
| 115-1 | H | (CH$_2$)$_2$ | H | H | CH$_2$ | 4-MeO—PhO | 4-Ph—Ph | S |
| 115-2 | H | (CH$_2$)$_2$ | H | H | CH$_2$ | 4-MeO—PhO | 4-(Pyr-2)-Ph | S |
| 115-3 | H | (CH$_2$)$_2$ | H | H | CH$_2$ | 4-MeO—PhO | 4-(Pyr-3)-Ph | S |
| 115-4 | H | (CH$_2$)$_2$ | H | H | CH$_2$ | 4-MeO—PhO | 4-(Pyr-4)-Ph | S |
| 115-5 | H | (CH$_2$)$_2$ | H | H | CH$_2$ | 4-MeO—PhO | 2-Ph-5-Pyr | S |
| 115-6 | H | (CH$_2$)$_2$ | H | H | CH$_2$ | 4-MeO—PhO | 3-Ph-6-Pyr | S |

TABLE 116

| Ex. No. Comp. | R¹ | R² | R³ | R⁴ | Z | W | X | Y |
|---|---|---|---|---|---|---|---|---|
| 116-1 | H | (CH$_2$)$_2$ | H | H | CH$_2$ | PhS | 4-Ph—Ph | S |
| 116-2 | H | (CH$_2$)$_2$ | H | H | CH$_2$ | PhS | 4-(Pyr-2)-Ph | S |
| 116-3 | H | (CH$_2$)$_2$ | H | H | CH$_2$ | PhS | 4-(Pyr-3)-Ph | S |
| 116-4 | H | (CH$_2$)$_2$ | H | H | CH$_2$ | PhS | 4-(Pyr-4)-Ph | S |
| 116-5 | H | (CH$_2$)$_2$ | H | H | CH$_2$ | PhS | 2-Ph-5-Pyr | S |
| 116-6 | H | (CH$_2$)$_2$ | H | H | CH$_2$ | PhS | 3-Ph-6-Pyr | S |

TABLE 117

| Ex. No. Comp. | R¹ | R² | R³ | R⁴ | Z | W | X | Y |
|---|---|---|---|---|---|---|---|---|
| 117-1 | H | (CH$_2$)$_2$ | H | H | CH$_2$ | Ph(CH$_2$)$_3$ | 4-Ph—Ph | S |
| 117-2 | H | (CH$_2$)$_2$ | H | H | CH$_2$ | Ph(CH$_2$)$_3$ | 4-(Pyr-2)-Ph | S |
| 117-3 | H | (CH$_2$)$_2$ | H | H | CH$_2$ | Ph(CH$_2$)$_3$ | 4-(Pyr-3)-Ph | S |
| 117-4 | H | (CH$_2$)$_2$ | H | H | CH$_2$ | Ph(CH$_2$)$_3$ | 4-(Pyr-4)-Ph | S |
| 117-5 | H | (CH$_2$)$_2$ | H | H | CH$_2$ | Ph(CH$_2$)$_3$ | 2-Ph-5-Pyr | S |
| 117-6 | H | (CH$_2$)$_2$ | H | H | CH$_2$ | Ph(CH$_2$)$_3$ | 3-Ph-6-Pyr | S |

TABLE 118

| Ex. No. Comp. | R¹ | R² | R³ | R⁴ | Z | W | X | Y |
|---|---|---|---|---|---|---|---|---|
| 118-1 | H | (CH$_2$)$_2$ | H | H | CH$_2$ | EtO | 4-Ph—Ph | NMe |
| 118-2 | H | (CH$_2$)$_2$ | H | H | CH$_2$ | EtO | 4-(Pyr-2)-Ph | NMe |
| 118-3 | H | (CH$_2$)$_2$ | H | H | CH$_2$ | EtO | 4-(Pyr-3)-Ph | NMe |
| 118-4 | H | (CH$_2$)$_2$ | H | H | CH$_2$ | EtO | 4-(Pyr-4)-Ph | NMe |
| 118-5 | H | (CH$_2$)$_2$ | H | H | CH$_2$ | EtO | 2-Ph-5-Pyr | NMe |
| 118-6 | H | (CH$_2$)$_2$ | H | H | CH$_2$ | EtO | 3-Ph-6-Pyr | NMe |

TABLE 119

| Ex. No. Comp. | R¹ | R² | R³ | R⁴ | Z | W | X | Y |
|---|---|---|---|---|---|---|---|---|
| 119-1 | H | (CH$_2$)$_2$ | H | H | CH$_2$ | Pr | 4-Ph—Ph | NMe |
| 119-2 | H | (CH$_2$)$_2$ | H | H | CH$_2$ | Pr | 4-(Pyr-2)-Ph | NMe |
| 119-3 | H | (CH$_2$)$_2$ | H | H | CH$_2$ | Pr | 4-(Pyr-3)-Ph | NMe |
| 119-4 | H | (CH$_2$)$_2$ | H | H | CH$_2$ | Pr | 4-(Pyr-4)-Ph | NMe |
| 119-5 | H | (CH$_2$)$_2$ | H | H | CH$_2$ | Pr | 2-Ph-5-Pyr | NMe |
| 119-6 | H | (CH$_2$)$_2$ | H | H | CH$_2$ | Pr | 3-Ph-6-Pyr | NMe |

TABLE 120

| Ex. No. Comp. | R¹ | R² | R³ | R⁴ | Z | W | X | Y |
|---|---|---|---|---|---|---|---|---|
| 120-1 | H | (CH$_2$)$_2$ | H | H | CH$_2$ | Bu | 4-Ph—Ph | NMe |
| 120-2 | H | (CH$_2$)$_2$ | H | H | CH$_2$ | Bu | 4-(Pyr-2)-Ph | NMe |
| 120-3 | H | (CH$_2$)$_2$ | H | H | CH$_2$ | Bu | 4-(Pyr-3)-Ph | NMe |
| 120-4 | H | (CH$_2$)$_2$ | H | H | CH$_2$ | Bu | 4-(Pyr-4)-Ph | NMe |
| 120-5 | H | (CH$_2$)$_2$ | H | H | CH$_2$ | Bu | 2-Ph-5-Pyr | NMe |
| 120-6 | H | (CH$_2$)$_2$ | H | H | CH$_2$ | Bu | 3-Ph-6-Pyr | NMe |

TABLE 121

| Ex. No. Comp. | R¹ | R² | R³ | R⁴ | Z | W | X | Y |
|---|---|---|---|---|---|---|---|---|
| 121-1 | H | (CH$_2$)$_2$ | H | H | CH$_2$ | Pen | 4-Ph—Ph | NMe |
| 121-2 | H | (CH$_2$)$_2$ | H | H | CH$_2$ | Pen | 4-(Pyr-2)-Ph | NMe |
| 121-3 | H | (CH$_2$)$_2$ | H | H | CH$_2$ | Pen | 4-(Pyr-3)-Ph | NMe |
| 121-4 | H | (CH$_2$)$_2$ | H | H | CH$_2$ | Pen | 4-(Pyr-4)-Ph | NMe |
| 121-5 | H | (CH$_2$)$_2$ | H | H | CH$_2$ | Pen | 2-Ph-5-Pyr | NMe |
| 121-6 | H | (CH$_2$)$_2$ | H | H | CH$_2$ | Pen | 3-Ph-6-Pyr | NMe |

TABLE 122

| Ex. No. Comp. | R¹ | R² | R³ | R⁴ | Z | W | X | Y |
|---|---|---|---|---|---|---|---|---|
| 122-1 | H | (CH$_2$)$_2$ | H | H | CH$_2$ | MeS | 4-Ph—Ph | NMe |
| 122-2 | H | (CH$_2$)$_2$ | H | H | CH$_2$ | MeS | 4-(Pyr-2)-Ph | NMe |
| 122-3 | H | (CH$_2$)$_2$ | H | H | CH$_2$ | MeS | 4-(Pyr-3)-Ph | NMe |
| 122-4 | H | (CH$_2$)$_2$ | H | H | CH$_2$ | MeS | 4-(Pyr-4)-Ph | NMe |
| 122-5 | H | (CH$_2$)$_2$ | H | H | CH$_2$ | MeS | 2-Ph-5-Pyr | NMe |
| 122-6 | H | (CH$_2$)$_2$ | H | H | CH$_2$ | MeS | 3-Ph-6-Pyr | NMe |

TABLE 123

| Ex. No. Comp. | R¹ | R² | R³ | R⁴ | Z | W | X | Y |
|---|---|---|---|---|---|---|---|---|
| 123-1 | H | (CH$_2$)$_2$ | H | H | CH$_2$ | PhO | 4-Ph—Ph | NMe |
| 123-2 | H | (CH$_2$)$_2$ | H | H | CH$_2$ | PhO | 4-(Pyr-2)-Ph | NMe |
| 123-3 | H | (CH$_2$)$_2$ | H | H | CH$_2$ | PhO | 4-(Pyr-3)-Ph | NMe |
| 123-4 | H | (CH$_2$)$_2$ | H | H | CH$_2$ | PhO | 4-(Pyr-4)-Ph | NMe |
| 123-5 | H | (CH$_2$)$_2$ | H | H | CH$_2$ | PhO | 2-Ph-5-Pyr | NMe |
| 123-6 | H | (CH$_2$)$_2$ | H | H | CH$_2$ | PhO | 3-Ph-6-Pyr | NMe |

TABLE 124

| Ex. No. Comp. | R¹ | R² | R³ | R⁴ | Z | W | X | Y |
|---|---|---|---|---|---|---|---|---|
| 124-1 | H | (CH$_2$)$_2$ | H | H | CH$_2$ | 4-iPr—PhO | 4-Ph—Ph | NMe |
| 124-2 | H | (CH$_2$)$_2$ | H | H | CH$_2$ | 4-iPr—PhO | 4-(Pyr-2)-Ph | NMe |
| 124-3 | H | (CH$_2$)$_2$ | H | H | CH$_2$ | 4-iPr—PhO | 4-(Pyr-3)-Ph | NMe |
| 124-4 | H | (CH$_2$)$_2$ | H | H | CH$_2$ | 4-iPr—PhO | 4-(Pyr-4)-Ph | NMe |
| 124-5 | H | (CH$_2$)$_2$ | H | H | CH$_2$ | 4-iPr—PhO | 2-Ph-5-Pyr | NMe |
| 124-6 | H | (CH$_2$)$_2$ | H | H | CH$_2$ | 4-iPr—PhO | 3-Ph-6-Pyr | NMe |

TABLE 125

| Ex. No. Comp. | R¹ | R² | R³ | R⁴ | Z | W | X | Y |
|---|---|---|---|---|---|---|---|---|
| 125-1 | H | (CH$_2$)$_2$ | H | H | CH$_2$ | 4-MeO—PhO | 4-Ph—Ph | NMe |
| 125-2 | H | (CH$_2$)$_2$ | H | H | CH$_2$ | 4-MeO—PhO | 4-(Pyr-2)-Ph | NMe |
| 125-3 | H | (CH$_2$)$_2$ | H | H | CH$_2$ | 4-MeO—PhO | 4-(Pyr-3)-Ph | NMe |
| 125-4 | H | (CH$_2$)$_2$ | H | H | CH$_2$ | 4-MeO—PhO | 4-(Pyr-4)-Ph | NMe |
| 125-5 | H | (CH$_2$)$_2$ | H | H | CH$_2$ | 4-MeO—PhO | 2-Ph-5-Pyr | NMe |
| 125-6 | H | (CH$_2$)$_2$ | H | H | CH$_2$ | 4-MeO—PhO | 3-Ph-6-Pyr | NMe |

TABLE 126

| Ex. No. Comp. | R¹ | R² | R³ | R⁴ | Z | W | X | Y |
|---|---|---|---|---|---|---|---|---|
| 126-1 | H | (CH$_2$)$_2$ | H | H | CH$_2$ | PhS | 4-Ph-Ph | NMe |
| 126-2 | H | (CH$_2$)$_2$ | H | H | CH$_2$ | PhS | 4-(Pyr-2)-Ph | NMe |
| 126-3 | H | (CH$_2$)$_2$ | H | H | CH$_2$ | PhS | 4-(Pyr-3)-Ph | NMe |
| 126-4 | H | (CH$_2$)$_2$ | H | H | CH$_2$ | PhS | 4-(Pyr-4)-Ph | NMe |
| 126-5 | H | (CH$_2$)$_2$ | H | H | CH$_2$ | PhS | 2-Ph-5-Pyr | NMe |
| 126-6 | H | (CH$_2$)$_2$ | H | H | CH$_2$ | PhS | 3-Ph-6-Pyr | NMe |

TABLE 127

| Ex. No. Comp. | R¹ | R² | R³ | R⁴ | Z | W | X | Y |
|---|---|---|---|---|---|---|---|---|
| 127-1 | H | (CH$_2$)$_2$ | H | H | CH$_2$ | Ph(CH$_2$)$_3$ | 4-Ph-Ph | NMe |
| 127-2 | H | (CH$_2$)$_2$ | H | H | CH$_2$ | Ph(CH$_2$)$_3$ | 4-(Pyr-2)-Ph | NMe |
| 127-3 | H | (CH$_2$)$_2$ | H | H | CH$_2$ | Ph(CH$_2$)$_3$ | 4-(Pyr-3)-Ph | NMe |
| 127-4 | H | (CH$_2$)$_2$ | H | H | CH$_2$ | Ph(CH$_2$)$_3$ | 4-(Pyr-4)-Ph | NMe |
| 127-5 | H | (CH$_2$)$_2$ | H | H | CH$_2$ | Ph(CH$_2$)$_3$ | 2-Ph-5-Pyr | NMe |
| 127-6 | H | (CH$_2$)$_2$ | H | H | CH$_2$ | Ph(CH$_2$)$_3$ | 3-Ph-6-Pyr | NMe |

TABLE 128

| Ex. No. Comp. | R¹ | R² | R³ | R⁴ | Z | W | X | Y |
|---|---|---|---|---|---|---|---|---|
| 128-1 | H | (CH$_2$)$_2$ | H | H | CH$_2$ | EtO | 4-Ph-Ph | NAc |
| 128-2 | H | (CH$_2$)$_2$ | H | H | CH$_2$ | EtO | 4-(Pyr-2)-Ph | NAc |
| 128-3 | H | (CH$_2$)$_2$ | H | H | CH$_2$ | EtO | 4-(Pyr-3)-Ph | NAc |
| 128-4 | H | (CH$_2$)$_2$ | H | H | CH$_2$ | EtO | 4-(Pyr-4)-Ph | NAc |
| 128-5 | H | (CH$_2$)$_2$ | H | H | CH$_2$ | EtO | 2-Ph-5-Pyr | NAc |
| 128-6 | H | (CH$_2$)$_2$ | H | H | CH$_2$ | EtO | 3-Ph-6-Pyr | NAc |

TABLE 129

| Ex. No. Comp. | R¹ | R² | R³ | R⁴ | Z | W | X | Y |
|---|---|---|---|---|---|---|---|---|
| 129-1 | H | (CH$_2$)$_2$ | H | H | CH$_2$ | Pr | 4-Ph-Ph | NAc |
| 129-2 | H | (CH$_2$)$_2$ | H | H | CH$_2$ | Pr | 4-(Pyr-2)-Ph | NAc |
| 129-3 | H | (CH$_2$)$_2$ | H | H | CH$_2$ | Pr | 4-(Pyr-3)-Ph | NAc |
| 129-4 | H | (CH$_2$)$_2$ | H | H | CH$_2$ | Pr | 4-(Pyr-4)-Ph | NAc |
| 129-5 | H | (CH$_2$)$_2$ | H | H | CH$_2$ | Pr | 2-Ph-5-Pyr | NAc |
| 129-6 | H | (CH$_2$)$_2$ | H | H | CH$_2$ | Pr | 3-Ph-6-Pyr | NAc |

TABLE 130

| Ex. No. Comp. | R¹ | R² | R³ | R⁴ | Z | W | X | Y |
|---|---|---|---|---|---|---|---|---|
| 130-1 | H | (CH$_2$)$_2$ | H | H | CH$_2$ | Bu | 4-Ph-Ph | NAc |
| 130-2 | H | (CH$_2$)$_2$ | H | H | CH$_2$ | Bu | 4-(Pyr-2)-Ph | NAc |
| 130-3 | H | (CH$_2$)$_2$ | H | H | CH$_2$ | Bu | 4-(Pyr-3)-Ph | NAc |
| 130-4 | H | (CH$_2$)$_2$ | H | H | CH$_2$ | Bu | 4-(Pyr-4)-Ph | NAc |
| 130-5 | H | (CH$_2$)$_2$ | H | H | CH$_2$ | Bu | 2-Ph-5-Pyr | NAc |
| 130-6 | H | (CH$_2$)$_2$ | H | H | CH$_2$ | Bu | 3-Ph-6-Pyr | NAc |

TABLE 131

| Ex. No. Comp. | R¹ | R² | R³ | R⁴ | Z | W | X | Y |
|---|---|---|---|---|---|---|---|---|
| 131-1 | H | (CH$_2$)$_2$ | H | H | CH$_2$ | Pen | 4-Ph-Ph | NAc |
| 131-2 | H | (CH$_2$)$_2$ | H | H | CH$_2$ | Pen | 4-(Pyr-2)-Ph | NAc |
| 131-3 | H | (CH$_2$)$_2$ | H | H | CH$_2$ | Pen | 4-(Pyr-3)-Ph | NAc |
| 131-4 | H | (CH$_2$)$_2$ | H | H | CH$_2$ | Pen | 4-(Pyr-4)-Ph | NAc |
| 131-5 | H | (CH$_2$)$_2$ | H | H | CH$_2$ | Pen | 2-Ph-5-Pyr | NAc |
| 131-6 | H | (CH$_2$)$_2$ | H | H | CH$_2$ | Pen | 3-Ph-6-Pyr | NAc |

TABLE 132

| Ex. No. Comp. | R¹ | R² | R³ | R⁴ | Z | W | X | Y |
|---|---|---|---|---|---|---|---|---|
| 132-1 | H | (CH$_2$)$_2$ | H | H | CH$_2$ | MeS | 4-Ph-Ph | NAc |
| 132-2 | H | (CH$_2$)$_2$ | H | H | CH$_2$ | MeS | 4-(Pyr-2)-Ph | NAc |
| 132-3 | H | (CH$_2$)$_2$ | H | H | CH$_2$ | MeS | 4-(Pyr-3)-Ph | NAc |
| 132-4 | H | (CH$_2$)$_2$ | H | H | CH$_2$ | MeS | 4-(Pyr-4)-Ph | NAc |
| 132-5 | H | (CH$_2$)$_2$ | H | H | CH$_2$ | MeS | 2-Ph-5-Pyr | NAc |
| 132-6 | H | (CH$_2$)$_2$ | H | H | CH$_2$ | MeS | 3-Ph-6-Pyr | NAc |

TABLE 133

| Ex. No. Comp. | R¹ | R² | R³ | R⁴ | Z | W | X | Y |
|---|---|---|---|---|---|---|---|---|
| 133-1 | H | (CH$_2$)$_2$ | H | H | CH$_2$ | PhO | 4-Ph-Ph | NAc |
| 133-2 | H | (CH$_2$)$_2$ | H | H | CH$_2$ | PhO | 4-(Pyr-2)-Ph | NAc |
| 133-3 | H | (CH$_2$)$_2$ | H | H | CH$_2$ | PhO | 4-(Pyr-3)-Ph | NAc |
| 133-4 | H | (CH$_2$)$_2$ | H | H | CH$_2$ | PhO | 4-(Pyr-4)-Ph | NAc |
| 133-5 | H | (CH$_2$)$_2$ | H | H | CH$_2$ | PhO | 2-Ph-5-Pyr | NAc |
| 133-6 | H | (CH$_2$)$_2$ | H | H | CH$_2$ | PhO | 3-Ph-6-Pyr | NAc |

TABLE 134

| Ex. No. Comp. | R¹ | R² | R³ | R⁴ | Z | W | X | Y |
|---|---|---|---|---|---|---|---|---|
| 134-1 | H | (CH$_2$)$_2$ | H | H | CH$_2$ | 4-iPr-PhO | 4-Ph-Ph | NAc |
| 134-2 | H | (CH$_2$)$_2$ | H | H | CH$_2$ | 4-iPr-PhO | 4-(Pyr-2)-Ph | NAc |
| 134-3 | H | (CH$_2$)$_2$ | H | H | CH$_2$ | 4-iPr-PhO | 4-(Pyr-3)-Ph | NAc |
| 134-4 | H | (CH$_2$)$_2$ | H | H | CH$_2$ | 4-iPr-PhO | 4-(Pyr-4)-Ph | NAc |
| 134-5 | H | (CH$_2$)$_2$ | H | H | CH$_2$ | 4-iPr-PhO | 2-Ph-5-Pyr | NAc |
| 134-6 | H | (CH$_2$)$_2$ | H | H | CH$_2$ | 4-iPr-PhO | 3-Ph-6-Pyr | NAc |

TABLE 135

| Ex. No. Comp. | R¹ | R² | R³ | R⁴ | Z | W | X | Y |
|---|---|---|---|---|---|---|---|---|
| 135-1 | H | (CH$_2$)$_2$ | H | H | CH$_2$ | 4-MeO-PhO | 4-Ph-Ph | NAc |
| 135-2 | H | (CH$_2$)$_2$ | H | H | CH$_2$ | 4-MeO-PhO | 4-(Pyr-2)-Ph | NAc |
| 135-3 | H | (CH$_2$)$_2$ | H | H | CH$_2$ | 4-MeO-PhO | 4-(Pyr-3)-Ph | NAc |
| 135-4 | H | (CH$_2$)$_2$ | H | H | CH$_2$ | 4-MeO-PhO | 4-(Pyr-4)-Ph | NAc |
| 135-5 | H | (CH$_2$)$_2$ | H | H | CH$_2$ | 4-MeO-PhO | 2-Ph-5-Pyr | NAc |
| 135-6 | H | (CH$_2$)$_2$ | H | H | CH$_2$ | 4-MeO-PhO | 3-Ph-6-Pyr | NAc |

TABLE 136

| Ex. No. Comp. | R¹ | R² | R³ | R⁴ | Z | W | X | Y |
|---|---|---|---|---|---|---|---|---|
| 136-1 | H | (CH$_2$)$_2$ | H | H | CH$_2$ | PhS | 4-Ph-Ph | NAc |
| 136-2 | H | (CH$_2$)$_2$ | H | H | CH$_2$ | PhS | 4-(Pyr-2)-Ph | NAc |
| 136-3 | H | (CH$_2$)$_2$ | H | H | CH$_2$ | PhS | 4-(Pyr-3)-Ph | NAc |
| 136-4 | H | (CH$_2$)$_2$ | H | H | CH$_2$ | PhS | 4-(Pyr-4)-Ph | NAc |
| 136-5 | H | (CH$_2$)$_2$ | H | H | CH$_2$ | PhS | 2-Ph-5-Pyr | NAc |
| 136-6 | H | (CH$_2$)$_2$ | H | H | CH$_2$ | PhS | 3-Ph-6-Pyr | NAc |

TABLE 137

| Ex. No. Comp. | R¹ | R² | R³ | R⁴ | Z | W | X | Y |
|---|---|---|---|---|---|---|---|---|
| 137-1 | H | (CH$_2$)$_2$ | H | H | CH$_2$ | Ph(CH$_2$)$_3$ | 4-Ph-Ph | NAc |
| 137-2 | H | (CH$_2$)$_2$ | H | H | CH$_2$ | Ph(CH$_2$)$_3$ | 4-(Pyr-2)-Ph | NAc |
| 137-3 | H | (CH$_2$)$_2$ | H | H | CH$_2$ | Pb(CH$_2$)$_3$ | 4-(Pyr-3)-Ph | NAc |
| 137-4 | H | (CH$_2$)$_2$ | H | H | CH$_2$ | Ph(CH$_2$)$_3$ | 4-(Pyr-4)-Ph | NAc |
| 137-5 | H | (CH$_2$)$_2$ | H | H | CH$_2$ | Ph(CH$_2$)$_3$ | 2-Ph-5-Pyr | NAc |
| 137-6 | H | (CH$_2$)$_2$ | H | H | CH$_2$ | Ph(CH$_2$)$_3$ | 3-Ph-6-Pyr | NAc |

TABLE 138

| Ex. No. Comp. | R¹ | R² | R³ | R⁴ | Z | W | X | Y |
|---|---|---|---|---|---|---|---|---|
| 138-1 | H | (CH$_2$)$_2$ | H | H | CH$_2$ | PhOCH$_2$ | 4-(Pyr-2)-Ph | O |
| 138-2 | H | (CH$_2$)$_2$ | H | H | CH$_2$ | PhO(CH$_2$)$_2$ | 4-(Pyr-2)-Ph | O |
| 138-3 | H | (CH$_2$)$_2$ | H | H | CH$_2$ | 4-tBu-PhO | 4-Ph-Ph | O |
| 138-4 | H | (CH$_2$)$_2$ | H | H | CH$_2$ | 4-tBu-PhO | 4-(4-HO-Ph)-Ph | O |
| 138-5 | H | (CH$_2$)$_2$ | H | H | CH$_2$ | 4-tBu-PhO | 4-(4-MeO-Ph)-Ph | O |
| 138-6 | H | (CH$_2$)$_2$ | H | H | CH$_2$ | 4-tBu-PhO | 4-(4-F-Ph)-Ph | O |
| 138-7 | H | (CH$_2$)$_2$ | H | H | CH$_2$ | 4-tBu-PhO | 4-(4-Cl-Ph)-Ph | O |
| 138-8 | H | (CH$_2$)$_2$ | H | H | CH$_2$ | 4-tBu-PhO | 4-(Pyr-2)-Ph | O |
| 138-9 | H | (CH$_2$)$_2$ | H | H | CH$_2$ | 4-tBu-PhO | 4-(Pyr-3)-Ph | O |
| 138-10 | H | (CH$_2$)$_2$ | H | H | CH$_2$ | 4-tBu-PhO | 4-(Pyr-4)-Ph | O |
| 138-11 | H | (CH$_2$)$_2$ | H | H | CH$_2$ | 4-tBu-PhO | 4-(3-MeO-Pyr-6)-Ph | O |
| 138-12 | H | (CH$_2$)$_2$ | H | H | CH$_2$ | 4-tBu-PhO | 4-(3-Dma-Pyr-6)-Ph | O |
| 138-13 | H | (CH$_2$)$_2$ | H | H | CH$_2$ | 4-tBu-PhO | 4-(3-CF$_3$-Pyr-6)-Ph | O |
| 138-14 | H | (CH$_2$)$_2$ | H | H | CH$_2$ | 4-tBu-PhO | 4-(3-O$_2$N-Pyr-6)-Ph | O |
| 138-15 | H | (CH$_2$)$_2$ | H | H | CH$_2$ | 4-tBu-PhO | 2-Ph-5-Pyr | O |
| 138-16 | H | (CH$_2$)$_2$ | H | H | CH$_2$ | 4-tBu-PhO | 2-(4-F-Ph)-5-Pyr | O |
| 138-17 | H | (CH$_2$)$_2$ | H | H | CH$_2$ | 4-tBu-PhO | 2-(4-MeO-Ph)-5-Pyr | O |

TABLE 138-continued

| Ex. No. Comp. | R$^1$ | R$^2$ | R$^3$ | R$^4$ | Z | W | X | Y |
|---|---|---|---|---|---|---|---|---|
| 138-18 | H | (CH$_2$)$_2$ | H | H | CH$_2$ | 4-tBu-PhO | 2-TfpO-5-Pyr | O |
| 138-19 | H | (CH$_2$)$_2$ | H | H | CH$_2$ | 4-CF$_3$-PhO | 4-Ph-Ph | O |
| 138-20 | H | (CH$_2$)$_2$ | H | H | CH$_2$ | 4-CF$_3$-PhO | 4-(4-HO-Ph)-Ph | O |
| 138-21 | H | (CH$_2$)$_2$ | H | H | CH$_2$ | 4-CF$_3$-PhO | 4-(4-MeO-Ph)-Ph | O |
| 138-22 | H | (CH$_2$)$_2$ | H | H | CH$_2$ | 4-CF$_3$-PhO | 4-(4-F-Ph)-Ph | O |
| 138-23 | H | (CH$_2$)$_2$ | H | H | CH$_2$ | 4-CF$_3$-PhO | 4-(4-Cl-Ph)-Ph | O |
| 138-24 | H | (CH$_2$)$_2$ | H | H | CH$_2$ | 4-CF$_3$-PhO | 4-(Pyr-2)-Ph | O |
| 138-25 | H | (CH$_2$)$_2$ | H | H | CH$_2$ | 4-CF$_3$-PhO | 4-(Pyr-3)-Ph | O |
| 138-26 | H | (CH$_2$)$_2$ | H | H | CH$_2$ | 4-CF$_3$-PhO | 4-(Pyr-4)-Ph | O |
| 138-27 | H | (CH$_2$)$_2$ | H | H | CH$_2$ | 4-CF$_3$-PhO | 4-(3-MeO-Pyr-6)-Ph | O |
| 138-28 | H | (CH$_2$)$_2$ | H | H | CH$_2$ | 4-CF$_3$-PhO | 4-(3-Dma-Pyr-6)-Ph | O |
| 138-29 | H | (CH$_2$)$_2$ | H | H | CH$_2$ | 4-CF$_3$-PhO | 4-(3-CF$_3$-Pyr-6)-Ph | O |
| 138-30 | H | (CH$_2$)$_2$ | H | H | CH$_2$ | 4-CF$_3$-PhO | 4-(3-O$_2$N-Pyr-6)-Ph | O |
| 138-31 | H | (CH$_2$)$_2$ | H | H | CH$_2$ | 4-CF$_3$-PhO | 2-Ph-5-Pyr | O |
| 138-32 | H | (CH$_2$)$_2$ | H | H | CH$_2$ | 4-CF$_3$-PhO | 2-(4-F-Ph)-5-Pyr | O |
| 138-33 | H | (CH$_2$)$_2$ | H | H | CH$_2$ | 4-CF$_3$-PhO | 2-(4-MeO-Ph)-5-Pyr | O |
| 138-34 | H | (CH$_2$)$_2$ | H | H | CH$_2$ | 4-CF$_3$-PhO | 2-TfpO-5-Pyr | O |
| 138-35 | H | (CH$_2$)$_2$ | H | H | CH$_2$ | 4-CF$_3$O-PhO | 4-Ph-Ph | O |
| 138-36 | H | (CH$_2$)$_2$ | H | H | CH$_2$ | 4-CF$_3$O-PhO | 4-(4-HO-Ph)-Ph | O |
| 138-37 | H | (CH$_2$)$_2$ | H | H | CH$_2$ | 4-CF$_3$O-PhO | 4-(4-MeO-Ph)-Ph | O |
| 138-38 | H | (CH$_2$)$_2$ | H | H | CH$_2$ | 4-CF$_3$O-PhO | 4-(4-F-Ph)-Ph | O |
| 138-39 | H | (CH$_2$)$_2$ | H | H | CH$_2$ | 4-CF$_3$O-PhO | 4-(4-Cl-Ph)-Ph | O |
| 138-40 | H | (CH$_2$)$_2$ | H | H | CH$_2$ | 4-CF$_3$O-PhO | 4-(Pyr-2)-Ph | O |
| 138-41 | H | (CH$_2$)$_2$ | H | H | CH$_2$ | 4-CF$_3$O-PhO | 4-(Pyr-3)-Ph | O |
| 138-42 | H | (CH$_2$)$_2$ | H | H | CH$_2$ | 4-CF$_3$O-PhO | 4-(Pyr-4)-Ph | O |
| 138-43 | H | (CH$_2$)$_2$ | H | H | CH$_2$ | 4-CF$_3$O-PhO | 4-(3-MeO-Pyr-6)-Ph | O |
| 138-44 | H | (CH$_2$)$_2$ | H | H | CH$_2$ | 4-CF$_3$O-PhO | 4-(3-Dma-Pyr-6)-Ph | O |
| 138-45 | H | (CH$_2$)$_2$ | H | H | CH$_2$ | 4-CF$_3$O-PhO | 4-(3-CF$_3$-Pyr-6)-Ph | O |
| 138-46 | H | (CH$_2$)$_2$ | H | H | CH$_2$ | 4-CF$_3$O-PhO | 4-(3-O$_2$N-Pyr-6)-Ph | O |
| 138-47 | H | (CH$_2$)$_2$ | H | H | CH$_2$ | 4-CF$_3$O-PhO | 2-Ph-5-Pyr | O |
| 138-48 | H | (CH$_2$)$_2$ | H | H | CH$_2$ | 4-CF$_3$O-PhO | 2-(4-F-Ph)-5-Pyr | O |
| 138-49 | H | (CH$_2$)$_2$ | H | H | CH$_2$ | 4-CF$_3$O-PhO | 2-(4-MeO-Ph)-5-Pyr | O |
| 138-50 | H | (CH$_2$)$_2$ | H | H | CH$_2$ | 4-CF$_3$O-PhO | 2-TfpO-5-Pyr | O |
| 138-51 | H | (CH$_2$)$_2$ | H | H | CH$_2$ | 4-F-PhO | 4-Ph-Ph | O |
| 138-52 | H | (CH$_2$)$_2$ | H | H | CH$_2$ | 4-F-PhO | 4-(4-HO-Ph)-Ph | O |
| 138-53 | H | (CH$_2$)$_2$ | H | H | CH$_2$ | 4-F-PhO | 4-(4-MeO-Ph)-Ph | O |
| 138-54 | H | (CH$_2$)$_2$ | H | H | CH$_2$ | 4-F-PhO | 4-(4-F-Ph)-Ph | O |
| 138-55 | H | (CH$_2$)$_2$ | H | H | CH$_2$ | 4-F-PbO | 4-(4-Cl-Ph)-Ph | O |
| 138-56 | H | (CH$_2$)$_2$ | H | H | CH$_2$ | 4-F-PhO | 4-(Pyr-2-)-Ph | O |
| 138-57 | H | (CH$_2$)$_2$ | H | H | CH$_2$ | 4-F-PhO | 4-(Pyr-3)-Ph | O |
| 138-58 | H | (CH$_2$)$_2$ | H | H | CH$_2$ | 4-F-PhO | 4-(Pyr-4)-Ph | O |
| 138-59 | H | (CH$_2$)$_2$ | H | H | CH$_2$ | 4-F-PhO | 4-(3-MeO-Pyr-6)-Ph | O |
| 138-60 | H | (CH$_2$)$_2$ | H | H | CH$_2$ | 4-F-PhO | 4-(3-Dma-Pyr-6)-Ph | O |
| 138-61 | H | (CH$_2$)$_2$ | H | H | CH$_2$ | 4-F-PhO | 4-(3-CF$_3$-Pyr-6)-Ph | O |
| 138-62 | H | (CH$_2$)$_2$ | H | H | CH$_2$ | 4-F-PhO | 4-(3-O$_2$N-Pyr-6)-Ph | O |
| 138-63 | H | (CH$_2$)$_2$ | H | H | CH$_2$ | 4-F-PhO | 2-Ph-5-Pyr | O |
| 138-64 | H | (CH$_2$)$_2$ | H | H | CH$_2$ | 4-F-PhO | 2-(4-F-Ph)-5-Pyr | O |
| 138-65 | H | (CH$_2$)$_2$ | H | H | CH$_2$ | 4-F-PhO | 2-(4-MeO-Ph)-5-Pyr | O |
| 138-66 | H | (CH$_2$)$_2$ | H | H | CH$_2$ | 4-F-PhO | 2-TfpO-5-Pyr | O |
| 138-67 | H | (CH$_2$)$_2$ | H | H | CH$_2$ | 4-Cl-PhO | 4-Ph-Ph | O |
| 138-68 | H | (CH$_2$)$_2$ | H | H | CH$_2$ | 4-Cl-PhO | 4-(4-HO-Ph)-Ph | O |
| 138-69 | H | (CH$_2$)$_2$ | H | H | CH$_2$ | 4-Cl-PhO | 4-(4-MeO-Ph)-Ph | O |
| 138-70 | H | (CH$_2$)$_2$ | H | H | CH$_2$ | 4-Cl-PhO | 4-(4-F-Ph)-Ph | O |
| 138-71 | H | (CH$_2$)$_2$ | H | H | CH$_2$ | 4-Cl-PhO | 4-(4-Cl-Ph)-Ph | O |
| 138-72 | H | (CH$_2$)$_2$ | H | H | CH$_2$ | 4-Cl-PhO | 4-(Pyr-2)-Ph | O |
| 138-73 | H | (CH$_2$)$_2$ | H | H | CH$_2$ | 4-Cl-PhO | 4-(Pyr-3)-Ph | O |

TABLE 138-continued

| Ex. No. Comp. | R¹ | R² | R³ | R⁴ | Z | W | X | Y |
|---|---|---|---|---|---|---|---|---|
| 138-74 | H | (CH₂)₂ | H | H | CH₂ | 4-Cl-PhO | 4-(Pyr-4)-Ph | O |
| 138-75 | H | (CH₂)₂ | H | H | CH₂ | 4-Cl-PhO | 4-(3-MeO-Pyr-6)-Ph | O |
| 138-76 | H | (CH₂)₂ | H | H | CH₂ | 4-Cl-PhO | 4-(3-Dma-Pyr-6)-Ph | O |
| 138-77 | H | (CH₂)₂ | H | H | CH₂ | 4-Cl-PhO | 4-(3-CF₃-Pyr-6)-Ph | O |
| 138-78 | H | (CH₂)₂ | H | H | CH₂ | 4-Cl-PhO | 4-(3-O₂N-Pyr-6)-Ph | O |
| 138-79 | H | (CH₂)₂ | H | H | CH₂ | 4-Cl-PhO | 2-Ph-5-Pyr | O |
| 138-80 | H | (CH₂)₂ | H | H | CH₂ | 4-Cl-PhO | 2-(4-F-Ph)-5-Pyr | O |
| 138-81 | H | (CH₂)₂ | H | H | CH₂ | 4-Cl-PhO | 2-(4-MeO-Ph)-5-Pyr | O |
| 138-82 | H | (CH₂)₂ | H | H | CH₂ | 4-Cl-PhO | 2-TfpO-5-Pyr | O |
| 138-83 | H | (CH₂)₂ | H | H | CH₂ | 3-F-PhO | 4-Ph-Ph | O |
| 138-84 | H | (CH₂)₂ | H | H | CH₂ | 3-F-PhO | 4-(4-HO-Ph)-Ph | O |
| 138-85 | H | (CH₂)₂ | H | H | CH₂ | 3-F-PhO | 4-(4-MeO-Ph)-Ph | O |
| 138-86 | H | (CH₂)₂ | H | H | CH₂ | 3-F-PhO | 4-(4-F-Ph)-Ph | O |
| 138-87 | H | (CH₂)₂ | H | H | CH₂ | 3-F-PhO | 4-(4-Cl-Ph)-Ph | O |
| 138-88 | H | (CH₂)₂ | H | H | CH₂ | 3-F-PhO | 4-(Pyr-2)-Ph | O |
| 138-89 | H | (CH₂)₂ | H | H | CH₂ | 3-F-PhO | 4-(Pyr-3)-Ph | O |
| 138-90 | H | (CH₂)₂ | H | H | CH₂ | 3-F-PhO | 4-(Pyr-4)-Ph | O |
| 138-91 | H | (CH₂)₂ | H | H | CH₂ | 3-F-PhO | 4-(3-MeO-Pyr-6)-Ph | O |
| 138-92 | H | (CH₂)₂ | H | H | CH₂ | 3-F-PhO | 4-(3-Dma-Pyr-6)-Ph | O |
| 138-93 | H | (CH₂)₂ | H | H | CH₂ | 3-F-PhO | 4-(3-CF₃-Pyr-6)-Ph | O |
| 138-94 | H | (CH₂)₂ | H | H | CH₂ | 3-F-PhO | 4-(3-O₂N-Pyr-6)-Ph | O |
| 138-95 | H | (CH₂)₂ | H | H | CH₂ | 3-F-PhO | 2-Ph-5-Pyr | O |
| 138-96 | H | (CH₂)₂ | H | H | CH₂ | 3-F-PhO | 2-(4-F-Ph)-5-Pyr | O |
| 138-97 | H | (CH₂)₂ | H | H | CH₂ | 3-F-PhO | 2-(4-MeO-Ph)-5-Pyr | O |
| 138-98 | H | (CH₂)₂ | H | H | CH₂ | 3-F-PhO | 2-TfpO-5-Pyr | O |
| 138-99 | H | (CH₂)₂ | H | H | CH₂ | 4-CN-PhO | 4-Ph-Ph | O |
| 138-100 | H | (CH₂)₂ | H | H | CH₂ | 4-CN-PhO | 4-(4-HO-Ph)-Ph | O |
| 138-101 | H | (CH₂)₂ | H | H | CH₂ | 4-CN-PhO | 4-(4-MeO-Ph)-Ph | O |
| 138-102 | H | (CH₂)₂ | H | H | CH₂ | 4-CN-PhO | 4-(4-F-Ph)-Ph | O |
| 138-103 | H | (CH₂)₂ | H | H | CH₂ | 4-CN-PhO | 4-(4-Cl-Ph)-Ph | O |
| 138-104 | H | (CH₂)₂ | H | H | CH₂ | 4-CN-PhO | 4-(Pyr-2)-Ph | O |
| 138-105 | H | (CH₂)₂ | H | H | CH₂ | 4-CN-PhO | 4-(Pyr-3)-Ph | O |
| 138-106 | H | (CH₂)₂ | H | H | CH₂ | 4-CN-PhO | 4-(Pyr-4)-Ph | O |
| 138-107 | H | (CH₂)₂ | H | H | CH₂ | 4-CN-PhO | 4-(3-MeO-Pyr-6)-Ph | O |
| 138-108 | H | (CH₂)₂ | H | H | CH₂ | 4-CN-PhO | 4-(3-Dma-Pyr-6)-Ph | O |
| 138-109 | H | (CH₂)₂ | H | H | CH₂ | 4-CN-PhO | 4-(3-CF₃-Pyr-6)-Ph | O |
| 138-110 | H | (CH₂)₂ | H | H | CH₂ | 4-CN-PhO | 4-(3-O₂N-Pyr-6)-Ph | O |
| 138-111 | H | (CH₂)₂ | H | H | CH₂ | 4-CN-PhO | 2-Ph-5-Pyr | O |
| 138-112 | H | (CH₂)₂ | H | H | CH₂ | 4-CN-PhO | 2-(4-F-Ph)-5-Pyr | O |
| 138-113 | H | (CH₂)₂ | H | H | CH₂ | 4-CN-PhO | 2-(4-MeO-Ph)-5-Pyr | O |
| 138-114 | H | (CH₂)₂ | H | H | CH₂ | 4-CN-PhO | 2-TfpO-5-Pyr | O |
| 138-115 | H | (CH₂)₂ | H | H | CH₂ | 4-MeS-PhO | 4-Ph-Ph | O |
| 138-116 | H | (CH₂)₂ | H | H | CH₂ | 4-MeS-PhO | 4-(4-HO-Ph)-Ph | O |
| 138-117 | H | (CH₂)₂ | H | H | CH₂ | 4-MeS-PhO | 4-(4-MeO-Ph)-Ph | O |
| 138-118 | H | (CH₂)₂ | H | H | CH₂ | 4-MeS-PhO | 4-(4-F-Ph)-Ph | O |
| 138-119 | H | (CH₂)₂ | H | H | CH₂ | 4-MeS-PhO | 4-(4-Cl-Ph)-Ph | O |
| 138-120 | H | (CH₂)₂ | H | H | CH₂ | 4-MeS-PhO | 4-(Pyr-2)-Ph | O |
| 138-121 | H | (CH₂)₂ | H | H | CH₂ | 4-MeS-PhO | 4-(Pyr-3)-Ph | O |
| 138-122 | H | (CH₂)₂ | H | H | CH₂ | 4-MeS-PhO | 4-(Pyr-4)-Ph | O |
| 138-123 | H | (CH₂)₂ | H | H | CH₂ | 4-MeS-PhO | 4-(3-MeO-Pyr-6)-Ph | O |
| 138-124 | H | (CH₂)₂ | H | H | CH₂ | 4-MeS-PhO | 4-(3-Dma-Pyr-6)-Ph | O |
| 138-125 | H | (CH₂)₂ | H | H | CH₂ | 4-MeS-PhO | 4-(3-CF₃-Pyr-6)-Ph | O |
| 138-126 | H | (CH₂)₂ | H | H | CH₂ | 4-MeS-PhO | 4-(3-O₂N-Pyr-6)-Ph | O |
| 138-127 | H | (CH₂)₂ | H | H | CH₂ | 4-MeS-PhO | 2-Ph-5-Pyr | O |
| 138-128 | H | (CH₂)₂ | H | H | CH₂ | 4-MeS-PhO | 2-(4-F-Ph)-5-Pyr | O |
| 138-129 | H | (CH₂)₂ | H | H | CH₂ | 4-MeS-PhO | 2-(4-MeO-Ph)-5-Pyr | O |
| 138-130 | H | (CH₂)₂ | H | H | CH₂ | 4-MeS-PhO | 2-TfpO-5-Pyr | O |
| 138-131 | H | (CH₂)₂ | H | H | CH₂ | 4-MeSO₂-PhO | 4-Ph-Ph | O |
| 138-132 | H | (CH₂)₂ | H | H | CH₂ | 4-MeSO₂-PhO | 4-(4-HO-Ph)-Ph | O |
| 138-133 | H | (CH₂)₂ | H | H | CH₂ | 4-MeSO₂-PhO | 4-(4-MeO-Ph)-Ph | O |
| 138-134 | H | (CH₂)₂ | H | H | CH₂ | 4-MeSO₂-PhO | 4-(4-F-Ph)-Ph | O |
| 138-135 | H | (CH₂)₂ | H | H | CH₂ | 4-MeSO₂-PhO | 4-(4-Cl-Ph)-Ph | O |
| 138-136 | H | (CH₂)₂ | H | H | CH₂ | 4-MeSO₂-PhO | 4-(Pyr-2)-Ph | O |
| 138-137 | H | (CH₂)₂ | H | H | CH₂ | 4-MeSO₂-PhO | 4-(Pyr-3)-Ph | O |
| 138-138 | H | (CH₂)₂ | H | H | CH₂ | 4-MeSO₂- | 4-(Pyr-4)-Ph | O |

TABLE 138-continued

| Ex. No. Comp. | R¹ | R² | R³ | R⁴ | Z | W | X | Y |
|---|---|---|---|---|---|---|---|---|
| 138-139 | H | (CH$_2$)$_2$ | H | H | CH$_2$ | 4-MeSO$_2$-PhO | 4-(3-MeO-Pyr-6)-Ph | O |
| 138-140 | H | (CH$_2$)$_2$ | H | H | CH$_2$ | 4-MeSO$_2$-PhO | 4-(3-Dma-Pyr-6)-Ph | O |
| 138-141 | H | (CH$_2$)$_2$ | H | H | CH$_2$ | 4-MeSO$_2$-PhO | 4-(3-CF$_3$-Pyr-6)-Ph | O |
| 138-142 | H | (CH$_2$)$_2$ | H | H | CH$_2$ | 4-MeSO$_2$-PhO | 4-(3-O$_2$N-Pyr-6)-Ph | O |
| 138-143 | H | (CH$_2$)$_2$ | H | H | CH$_2$ | 4-MeSO$_2$-PhO | 2-Ph-5-Pyr | O |
| 138-144 | H | (CH$_2$)$_2$ | H | H | CH$_2$ | 4-MeSO$_2$-PhO | 2-(4-F-Ph)-5-Pyr | O |
| 138-145 | H | (CH$_2$)$_2$ | H | H | CH$_2$ | 4-MeSO$_2$-PhO | 2-(4-MeO-Ph)-5-Pyr | O |
| 138-146 | H | (CH$_2$)$_2$ | H | H | CH$_2$ | 4-MeSO$_2$-PhO | 2-TfpO-5-Pyr | O |
| 138-147 | H | (CH$_2$)$_2$ | H | H | CH$_2$ | 3,4-di-F-PhO | 4-Ph-Ph | O |
| 138-148 | H | (CH$_2$)$_2$ | H | H | CH$_2$ | 3,4-di-F-PhO | 4-(4-HO-Ph)-Ph | O |
| 138-149 | H | (CH$_2$)$_2$ | H | H | CH$_2$ | 3,4-di-F-PhO | 4-(4-MeO-Ph)-Ph | O |
| 138-150 | H | (CH$_2$)$_2$ | H | H | CH$_2$ | 3,4-di-F-PhO | 4-(4-F-Ph)-Ph | O |
| 138-151 | H | (CH$_2$)$_2$ | H | H | CH$_2$ | 3,4-di-F-PhO | 4-(4-Cl-Ph)-Ph | O |
| 138-152 | H | (CH$_2$)$_2$ | H | H | CH$_2$ | 3,4-di-F-PhO | 4-(Pyr-2)-Ph | O |
| 138-153 | H | (CH$_2$)$_2$ | H | H | CH$_2$ | 3,4-di-F-PhO | 4-(Pyr-3)-Ph | O |
| 138-154 | H | (CH$_2$)$_2$ | H | H | CH$_2$ | 3,4-di-F-PhO | 4-(Pyr-4)-Ph | O |
| 138-155 | H | (CH$_2$)$_2$ | H | H | CH$_2$ | 3,4-di-F-PhO | 4-(3-MeO-Pyr-6)-Ph | O |
| 138-156 | H | (CH$_2$)$_2$ | H | H | CH$_2$ | 3,4-di-F-PhO | 4-(3-Dma-Pyr-6)-Ph | O |
| 138-157 | H | (CH$_2$)$_2$ | H | H | CH$_2$ | 3,4-di-F-PhO | 4-(3-CF$_3$-Pyr-6)-Ph | O |
| 138-158 | H | (CH$_2$)$_2$ | H | H | CH$_2$ | 3,4-di-F-PhO | 4-(3-O$_2$N-Pyr-6)-Ph | O |
| 138-159 | H | (CH$_2$)$_2$ | H | H | CH$_2$ | 3,4-di-F-PhO | 2-Ph-5-Pyr | O |
| 138-160 | H | (CH$_2$)$_2$ | H | H | CH$_2$ | 3,4-di-F-PhO | 2-(4-F-Ph)-5-Pyr | O |
| 138-161 | H | (CH$_2$)$_2$ | H | H | CH$_2$ | 3,4-di-F-PhO | 2-(4-MeO-Ph)-5-Pyr | O |
| 138-162 | H | (CH$_2$)$_2$ | H | H | CH$_2$ | 3,4-di-F-PhO | 2-TfpO-5-Pyr | O |
| 138-163 | H | (CH$_2$)$_2$ | H | H | CH$_2$ | 3,5-di-F-PhO | 4-Ph-Ph | O |
| 138-164 | H | (CH$_2$)$_2$ | H | H | CH$_2$ | 3,5-di-F-PhO | 4-(4-HO-Ph)-Ph | O |
| 138-165 | H | (CH$_2$)$_2$ | H | H | CH$_2$ | 3,5-di-F-PhO | 4-(4-MeO-Ph)-Ph | O |
| 138-166 | H | (CH$_2$)$_2$ | H | H | CH$_2$ | 3,5-di-F-PhO | 4-(4-F-Ph)-Ph | O |
| 138-167 | H | (CH$_2$)$_2$ | H | H | CH$_2$ | 3,5-di-F-PhO | 4-(4-Cl-Ph)-Ph | O |
| 138-168 | H | (CH$_2$)$_2$ | H | H | CH$_2$ | 3,5-di-F-PhO | 4-(Pyr-2)-Ph | O |
| 138-169 | H | (CH$_2$)$_2$ | H | H | CH$_2$ | 3,5-di-F-PhO | 4-(Pyr-3)-Ph | O |
| 138-170 | H | (CH$_2$)$_2$ | H | H | CH$_2$ | 3,5-di-F-PhO | 4-(Pyr-4)-Ph | O |
| 138-171 | H | (CH$_2$)$_2$ | H | H | CH$_2$ | 3,5-di-F-PhO | 4-(3-MeO-Pyr-6)-Ph | O |
| 138-172 | H | (CH$_2$)$_2$ | H | H | CH$_2$ | 3,5-di-F-PhO | 4-(3-Dma-Pyr-6)-Ph | O |
| 138-173 | H | (CH$_2$)$_2$ | H | H | CH$_2$ | 3,5-di-F-PhO | 4-(3-CF$_3$-Pyr-6)-Ph | O |
| 138-174 | H | (CH$_2$)$_2$ | H | H | CH$_2$ | 3,5-di-F-PhO | 4-(3-O$_2$N-Pyr-6)-Ph | O |
| 138-175 | H | (CH$_2$)$_2$ | H | H | CH$_2$ | 3,5-di-F-PhO | 2-Ph-5-Pyr | Q |

TABLE 138-continued

| Ex. No. Comp. | R¹ | R² | R³ | R⁴ | Z | W | X | Y |
|---|---|---|---|---|---|---|---|---|
| 138-176 | H | (CH$_2$)$_2$ | H | H | CH$_2$ | 3,5-di-F-PhO | 2-(4-F-Ph)-5-Pyr | O |
| 138-177 | H | (CH$_2$)$_2$ | H | H | CH$_2$ | 3,5-di-F-PhO | 2-(4-MeO-Ph)-5-Pyr | O |
| 138-178 | H | (CH$_2$)$_2$ | H | H | CH$_2$ | 3,5-di-F-PhO | 2-TfpO-5-Pyr | O |
| 138-179 | H | (CH$_2$)$_2$ | H | H | CH$_2$ | 3,4,5-tri-F-PhO | 4-Ph-Ph | O |
| 138-180 | H | (CH$_2$)$_2$ | H | H | CH$_2$ | 3,4,5-tri-F-PhO | 4-(4-HO-Ph)-Ph | O |
| 138-181 | H | (CH$_2$)$_2$ | H | H | CH$_2$ | 3,4,5-tri-F-PhO | 4-(4-MeO-Ph)-Ph | O |
| 138-182 | H | (CH$_2$)$_2$ | H | H | CH$_2$ | 3,4,5-tri-F-PhO | 4-(4-F-Ph)-Ph | O |
| 138-183 | H | (CH$_2$)$_2$ | H | H | CH$_2$ | 3,4,5-tri-F-PhO | 4-(4-Cl-Ph)-Ph | O |
| 138-184 | H | (CH$_2$)$_2$ | H | H | CH$_2$ | 3,4,5-tri-F-PhO | 4-(Pyr-2)-Ph | O |
| 138-185 | H | (CH$_2$)$_2$ | H | H | CH$_2$ | 3,4,5-tri-F-PhO | 4-(Pyr-3)-Ph | O |
| 138-186 | H | (CH$_2$)$_2$ | H | H | CH$_2$ | 3,4,5-tri-F-PhO | 4-(Pyr-4)-Ph | O |
| 138-187 | H | (CH$_2$)$_2$ | H | H | CH$_2$ | 3,4,5-tri-F-PhO | 4-(3-MeO-Pyr-6)-Ph | O |
| 138-188 | H | (CH$_2$)$_2$ | H | H | CH$_2$ | 3,4,5-tri-F-PhO | 4-(3-Dma-Pyr-6)-Ph | O |
| 138-189 | H | (CH$_2$)$_2$ | H | H | CH$_2$ | 3,4,5-tri-F-PhO | 4-(3-CF$_3$-Pyr-6)-Ph | O |
| 138-190 | H | (CH$_2$)$_2$ | H | H | CH$_2$ | 3,4,5-tri-F-PhO | 4-(3-O$_2$N-Pyr-6)-Ph | O |
| 138-191 | H | (CH$_2$)$_2$ | H | H | CH$_2$ | 3,4,5-tri-F-PhO | 2-Ph-5-Pyr | O |
| 138-192 | H | (CH$_2$)$_2$ | H | H | CH$_2$ | 3,4,5-tri-F-PhO | 2-(4-F-Ph)-5-Pyr | O |
| 138-193 | H | (CH$_2$)$_2$ | H | H | CH$_2$ | 3,4,5-tri-F-PhO | 2-(4-MeO-Ph)-5-Pyr | O |
| 138-194 | H | (CH$_2$)$_2$ | H | H | CH$_2$ | 3,4,5-tri-F-PhO | 2-TfpO-5-Pyr | O |
| 138-195 | H | (CH$_2$)$_2$ | H | H | CH$_2$ | 2,3,4,5,6-penta-F-PhO | 4-Ph-Ph | O |
| 138-196 | H | (CH$_2$)$_2$ | H | H | CH$_2$ | 2,3,4,5,6-penta-F-PhO | 4-(4-HO-Ph)-Ph | O |
| 138-197 | H | (CH$_2$)$_2$ | H | H | CH$_2$ | 2,3,4,5,6-penta-F-PhO | 4-(4-MeO-Ph)-Ph | O |
| 138-198 | H | (CH$_2$)$_2$ | H | H | CH$_2$ | 2,3,4,5,6-penta-F-PhO | 4-(4-F-Ph)-Ph | O |
| 138-199 | H | (CH$_2$)$_2$ | H | H | CH$_2$ | 2,3,4,5,6-penta-F-PhO | 4-(4-Cl-Ph)-Ph | O |
| 138-200 | H | (CH$_2$)$_2$ | H | H | CH$_2$ | 2,3,4,5,6-penta-F-PhO | 4-(Pyr-2)-Ph | O |
| 138-201 | H | (CH$_2$)$_2$ | H | H | CH$_2$ | 2,3,4,5,6-penta-F-PhO | 4-(Pyr-3)-Ph | O |
| 138-202 | H | (CH$_2$)$_2$ | H | H | CH$_2$ | 2,3,4,5,6-penta-F-PhO | 4-(Pyr-4)-Ph | O |
| 138-203 | H | (CH$_2$)$_2$ | H | H | CH$_2$ | 2,3,4,5,6-penta-F-PhO | 4-(3-MeO-Pyr-6)-Ph | O |
| 138-204 | H | (CH$_2$)$_2$ | H | H | CH$_2$ | 2,3,4,5,6-penta-F-PhO | 4-(3-Dma-Pyr-6)-Ph | O |
| 138-205 | H | (CH$_2$)$_2$ | H | H | CH$_2$ | 2,3,4,5,6-penta-F-PhO | 4-(3-CF$_3$-Pyr-6)-Ph | O |
| 138-206 | H | (CH$_2$)$_2$ | H | H | CH$_2$ | 2,3,4,5,6-penta-F-PhO | 4-(3-O$_2$N-Pyr-6)-Ph | O |
| 138-207 | H | (CH$_2$)$_2$ | H | H | CH$_2$ | 2,3,4,5,6- | 2-Ph-5-Pyr | O |

TABLE 138-continued

| Ex. No. Comp. | R¹ | R² | R³ | R⁴ | Z | W | X | Y |
|---|---|---|---|---|---|---|---|---|
| 138-208 | H | (CH$_2$)$_2$ | H | H | CH$_2$ | 2,3,4,5,6-penta-F-PhO | 2-(4-F-Ph)-5-Pyr | O |
| 138-209 | H | (CH$_2$)$_2$ | H | H | CH$_2$ | 2,3,4,5,6-penta-F-PhO | 2-(4-MeO-Ph)-5-Pyr | O |
| 138-210 | H | (CH$_2$)$_2$ | H | H | CH$_2$ | 2,3,4,5,6-penta-F-PhO | 2-TfpO-5-Pyr | O |
| 138-211 | H | (CH$_2$)$_2$ | H | H | CH$_2$ | 3-PYrO | 4-Ph-Ph | O |
| 138-212 | H | (CH$_2$)$_2$ | H | H | CH$_2$ | 3-PYrO | 4-(4-HO-Ph)-Ph | O |
| 138-213 | H | (CH$_2$)$_2$ | H | H | CH$_2$ | 3-PYrO | 4-(4-MeO-Ph)-Ph | O |
| 138-214 | H | (CH$_2$)$_2$ | H | H | CH$_2$ | 3-PYrO | 4-(4-F-Ph)-Ph | O |
| 138-215 | H | (CH$_2$)$_2$ | H | H | CH$_2$ | 3-PYrO | 4-(4-Cl-Ph)-Ph | O |
| 138-216 | H | (CH$_2$)$_2$ | H | H | CH$_2$ | 3-PYrO | 4-(Pyr-2)-Ph | O |
| 138-217 | H | (CH$_2$)$_2$ | H | H | CH$_2$ | 3-PYrO | 4-(Pyr-3)-Ph | O |
| 138-218 | H | (CH$_2$)$_2$ | H | H | CH$_2$ | 3-PYrO | 4-(Pyr-4)-Ph | O |
| 138-219 | H | (CH$_2$)$_2$ | H | H | CH$_2$ | 3-PYrO | 4-(3-MeO-Pyr-6)-Ph | O |
| 138-220 | H | (CH$_2$)$_2$ | H | H | CH$_2$ | 3-PYrO | 4-(3-Dma-Pyr-6)-Ph | O |
| 138-221 | H | (CH$_2$)$_2$ | H | H | CH$_2$ | 3-PyrO | 4-(3-CF$_3$-Pyr-6)-Ph | O |
| 138-222 | H | (CH$_2$)$_2$ | H | H | CH$_2$ | 3-PyrO | 4-(3-O$_2$N-Pyr-6)-Ph | O |
| 138-223 | H | (CH$_2$)$_2$ | H | H | CH$_2$ | 3-PyrO | 2-Ph-5-Pyr | O |
| 138-224 | H | (CH$_2$)$_2$ | H | H | CH$_2$ | 3-PyrO | 2-(4-F-Ph)-5-Pyr | O |
| 138-225 | H | (CH$_2$)$_2$ | H | H | CH$_2$ | 3-PyrO | 2-(4-MeO-Ph)-5-Pyr | O |
| 138-226 | H | (CH$_2$)$_2$ | H | H | CH$_2$ | 3-PyrO | 2-TfpO-5-Pyr | O |
| 138-227 | H | (CH$_2$)$_2$ | H | H | CH$_2$ | BzO | 4-Ph-Ph | O |
| 138-228 | H | (CH$_2$)$_2$ | H | H | CH$_2$ | BzO | 4-(4-HO-Ph)-Ph | O |
| 138-229 | H | (CH$_2$)$_2$ | H | H | CH$_2$ | BzO | 4-(4-MeO-Ph)-Ph | O |
| 138-230 | H | (CH$_2$)$_2$ | H | H | CH$_2$ | BzO | 4-(4-F-Ph)-Ph | O |
| 138-231 | H | (CH$_2$)$_2$ | H | H | CH$_2$ | BzO | 4-(4-Cl-Ph)-Ph | O |
| 138-232 | H | (CH$_2$)$_2$ | H | H | CH$_2$ | BzO | 4-(Pyr-2)-Ph | O |
| 138-233 | H | (CH$_2$)$_2$ | H | H | CH$_2$ | BzO | 4-(Pyr-3)-Ph | O |
| 138-234 | H | (CH$_2$)$_2$ | H | H | CH$_2$ | BzO | 4-(Pyr-4)-Ph | O |
| 138-235 | H | (CH$_2$)$_2$ | H | H | CH$_2$ | BzO | 4-(3-MeO-Pyr-6)-Ph | O |
| 138-236 | H | (CH$_2$)$_2$ | H | H | CH$_2$ | BzO | 4-(3-Dma-Pyr-6)-Ph | O |
| 138-237 | H | (CH$_2$)$_2$ | H | H | CH$_2$ | BzO | 4-(3-CF$_3$-Pyr-6)-Ph | O |
| 138-238 | H | (CH$_2$)$_2$ | H | H | CH$_2$ | BzO | 4-(3-O$_2$N-Pyr-6)-Ph | O |
| 138-239 | H | (CH$_2$)$_2$ | H | H | CH$_2$ | BzO | 2-Ph-5-Pyr | O |
| 138-240 | H | (CH$_2$)$_2$ | H | H | CH$_2$ | BzO | 2-(4-F-Ph)-5-Pyr | O |
| 138-241 | H | (CH$_2$)$_2$ | H | H | CH$_2$ | BzO | 2-(4-MeO-Ph)-5-Pyr | O |
| 138-242 | H | (CH$_2$)$_2$ | H | H | CH$_2$ | BzO | 2-TfpO-5-Pyr | O |
| 138-243 | H | (CH$_2$)$_2$ | H | H | CH$_2$ | 2-BoxaS | 4-Ph-Ph | O |
| 138-244 | H | (CH$_2$)$_2$ | H | H | CH$_2$ | 2-BoxaS | 4-(4-HO-Ph)-Ph | O |
| 138-245 | H | (CH$_2$)$_2$ | H | H | CH$_2$ | 2-BoxaS | 4-(4-MeO-Ph)-Ph | O |
| 138-246 | H | (CH$_2$)$_2$ | H | H | CH$_2$ | 2-BoxaS | 4-(4-F-Ph)-Ph | O |
| 138-247 | H | (CH$_2$)$_2$ | H | H | CH$_2$ | 2-BoxaS | 4-(4-Cl-Ph)-Ph | O |
| 138-248 | H | (CH$_2$)$_2$ | H | H | CH$_2$ | 2-BoxaS | 4-(Pyr-2)-Ph | O |
| 138-249 | H | (CH$_2$)$_2$ | H | H | CH$_2$ | 2-BoxaS | 4-(Pyr-3)-Ph | O |
| 138-250 | H | (CH$_2$)$_2$ | H | H | CH$_2$ | 2-BoxaS | 4-(Pyr-4)-Ph | O |
| 138-251 | H | (CH$_2$)$_2$ | H | H | CH$_2$ | 2-BoxaS | 4-(3-MeO-Pyr-6)-Ph | O |
| 138-252 | H | (CH$_2$)$_2$ | H | H | CH$_2$ | 2-BoxaS | 4-(3-Dma-Pyr-6)-Ph | O |
| 138-253 | H | (CH$_2$)$_2$ | H | H | CH$_2$ | 2-BoxaS | 4-(3-CF$_3$-Pyr-6)-Ph | O |
| 138-254 | H | (CH$_2$)$_2$ | H | H | CH$_2$ | 2-BoxaS | 4-(3-O$_2$N-Pyr-6)-Ph | O |
| 138-255 | H | (CH$_2$)$_2$ | H | H | CH$_2$ | 2-BoxaS | 2-Ph-5-Pyr | O |
| 138-256 | H | (CH$_2$)$_2$ | H | H | CH$_2$ | 2-BoxaS | 2-(4-F-Ph)-5-Pyr | O |
| 138-257 | H | (CH$_2$)$_2$ | H | H | CH$_2$ | 2-BoxaS | 2-(4-MeO-Ph)-5- | O |

TABLE 138-continued

| Ex. No. Comp. | R¹ | R² | R³ | R⁴ | Z | W | X | Y |
|---|---|---|---|---|---|---|---|---|
| 138-258 | H | (CH$_2$)$_2$ | H | H | CH$_2$ | 2-BoxaS | 2-TfpO-5-Pyr | O |
| 138-259 | H | (CH$_2$)$_2$ | H | H | CH$_2$ | 4-(Pyr-2)-PhO | 4-Ph-Ph | O |
| 138-260 | H | (CH$_2$)$_2$ | H | H | CH$_2$ | 4-(Pyr-2)-PhO | 4-(4-HO-Ph)-Ph | O |
| 138-261 | H | (CH$_2$)$_2$ | H | H | CH$_2$ | 4-(Pyr-2)-PhO | 4-(4-MeO-Ph)-Ph | O |
| 138-262 | H | (CH$_2$)$_2$ | H | H | CH$_2$ | 4-(Pyr-2)-PhO | 4-(4-F-Ph)-Ph | O |
| 138-263 | H | (CH$_2$)$_2$ | H | H | CH$_2$ | 4-(Pyr-2)-PhO | 4-(4-Cl-Ph)-Ph | O |
| 138-264 | H | (CH$_2$)$_2$ | H | H | CH$_2$ | 4-(Pyr-2)-PhO | 4-(Pyr-2)-Ph | O |
| 138-265 | H | (CH$_2$)$_2$ | H | H | CH$_2$ | 4-(Pyr-2)-PhO | 4-(Pyr-3)-Ph | O |
| 138-266 | H | (CH$_2$)$_2$ | H | H | CH$_2$ | 4-(Pyr-2)-PhO | 4-(Pyr-4)-Ph | O |
| 138-267 | H | (CH$_2$)$_2$ | H | H | CH$_2$ | 4-(Pyr-2)-PhO | 4-(3-MeO-Pyr-6)-Ph | O |
| 138-268 | H | (CH$_2$)$_2$ | H | H | CH$_2$ | 4-(Pyr-2)-PhO | 4-(3-Dma-Pyr-6)-Ph | O |
| 138-269 | H | (CH$_2$)$_2$ | H | H | CH$_2$ | 4-(Pyr-2)-PhO | 4-(3-CF$_3$-Pyr-6)-Ph | O |
| 138-270 | H | (CH$_2$)$_2$ | H | H | CH$_2$ | 4-(Pyr-2)-PhO | 4-(3-O$_2$N-Pyr-6)-Ph | O |
| 138-271 | H | (CH$_2$)$_2$ | H | H | CH$_2$ | 4-(Pyr-2)-PhO | 2-Ph-5-Pyr | O |
| 138-272 | H | (CH$_2$)$_2$ | H | H | CH$_2$ | 4-(Pyr-2)-PhO | 2-(4-F-Ph)-5-Pyr | O |
| 138-273 | H | (CH$_2$)$_2$ | H | H | CH$_2$ | 4-(Pyr-2)-PhO | 2-(4-MeO-Ph)-5-Pyr | O |
| 138-274 | H | (CH$_2$)$_2$ | H | H | CH$_2$ | 4-(Pyr-2)-PhO | 2-TfpO-5-Pyr | O |
| 138-275 | H | (CH$_2$)$_2$ | H | H | CH$_2$ | 4-tBu-PhO | 4-(4-Me-Ph)-Ph | O |
| 138-276 | H | (CH$_2$)$_2$ | H | H | CH$_2$ | 4-tBu-PhO | 4-(4-Dma-Ph)-Ph | O |
| 138-277 | H | (CH$_2$)$_2$ | H | H | CH$_2$ | 4-tBu-PhO | 4-(4-CF$_3$-Ph)-Ph | O |
| 138-278 | H | (CH$_2$)$_2$ | H | H | CH$_2$ | 4-tBu-PhO | 4-(3-Me-Pyr-6)-Ph | O |
| 138-279 | H | (CH$_2$)$_2$ | H | H | CH$_2$ | 4-tBu-PhO | 4-(3-Et-Pyr-6)-Ph | O |
| 138-280 | H | (CH$_2$)$_2$ | H | H | CH$_2$ | 4-tBu-PhO | 4-(3-EtO-Pyr-6)-Ph | O |
| 138-281 | H | (CH$_2$)$_2$ | H | H | CH$_2$ | 4-tBu-PhO | 2-(4-Me-Ph)-5-Pyr | O |
| 138-282 | H | (CH$_2$)$_2$ | H | H | CH$_2$ | 4-tBu-PhO | 2-(4-CF$_3$-Ph)-5-Pyr | O |
| 138-283 | H | (CH$_2$)$_2$ | H | H | CH$_2$ | 4-tBu-PhO | 2-(4-Cl-Ph)-5-Pyr | O |
| 138-284 | H | (CH$_2$)$_2$ | H | H | CH$_2$ | 4-tBu-PhO | 2-(4-Dma-Ph)-5-Pyr | O |
| 138-285 | H | (CH$_2$)$_2$ | H | H | CH$_2$ | 4-CF$_3$-PhO | 4-(4-Me-Ph)-Ph | O |
| 138-286 | H | (CH$_2$)$_2$ | H | H | CH$_2$ | 4-CF$_3$-PhO | 4-(4-Dma-Ph)-Ph | O |
| 138-287 | H | (CH$_2$)$_2$ | H | H | CH$_2$ | 4-CF$_3$-PhO | 4-(4-CF$_3$-Ph)-Ph | O |
| 138-288 | H | (CH$_2$)$_2$ | H | H | CH$_2$ | 4-CF$_3$-PhO | 4-(3-Me-Pyr-6)-Ph | O |
| 138-289 | H | (CH$_2$)$_2$ | H | H | CH$_2$ | 4-CF$_3$-PhO | 4-(3-Et-Pyr-6)-Ph | O |
| 138-290 | H | (CH$_2$)$_2$ | H | H | CH$_2$ | 4-CF$_3$-PhO | 4-(3-EtO-Pyr-6)-Ph | O |
| 138-291 | H | (CH$_2$)$_2$ | H | H | CH$_2$ | 4-CF$_3$-PhO | 2-(4-Me-Ph)-5-Pyr | O |
| 138-292 | H | (CH$_2$)$_2$ | H | H | CH$_2$ | 4-CF$_3$-PhO | 2-(4-CF$_3$-Ph)-5-Pyr | O |
| 138-293 | H | (CH$_2$)$_2$ | H | H | CH$_2$ | 4-CF$_3$-PhO | 2-(4-Cl-Ph)-5-Pyr | O |
| 138-294 | H | (CH$_2$)$_2$ | H | H | CH$_2$ | 4-CF$_3$-PhO | 2-(4-Dma-Ph)-5-Pyr | O |
| 138-295 | H | (CH$_2$)$_2$ | H | H | CH$_2$ | 4-CF$_3$O-PhO | 4-(4-Me-Ph)-Ph | O |
| 138-296 | H | (CH$_2$)$_2$ | H | H | CH$_2$ | 4-CF$_3$O-PhO | 4-(4-Dma-Ph)-Ph | O |
| 138-297 | H | (CH$_2$)$_2$ | H | H | CH$_2$ | 4-CF$_3$O-PhO | 4-(4-CF$_3$-Ph)-Ph | O |
| 138-298 | H | (CH$_2$)$_2$ | H | H | CH$_2$ | 4-CF$_3$O-PhO | 4-(3-Me-Pyr-6)-Ph | O |
| 138-299 | H | (CH$_2$)$_2$ | H | H | CH$_2$ | 4-CF$_3$O-PhO | 4-(3-Et-Pyr-6)-Ph | O |
| 138-300 | H | (CH$_2$)$_2$ | H | H | CH$_2$ | 4-CF$_3$O-PhO | 4-(3-EtO-Pyr-6)-Ph | O |
| 138-301 | H | (CH$_2$)$_2$ | H | H | CH$_2$ | 4-CF$_3$O-PhO | 2-(4-Me-Ph)-5-Pyr | O |
| 138-302 | H | (CH$_2$)$_2$ | H | H | CH$_2$ | 4-CF$_3$O-PhO | 2-(4-CF$_3$-Ph)-5-Pyr | O |
| 138-303 | H | (CH$_2$)$_2$ | H | H | CH$_2$ | 4-CF$_3$O-PhO | 2-(4-Cl-Ph)-5-Pyr | O |
| 138-304 | H | (CH$_2$)$_2$ | H | H | CH$_2$ | 4-CF$_3$O-PhO | 2-(4-Dma-Ph)-5- | O |

TABLE 138-continued

| Ex. No. Comp. | R¹ | R² | R³ | R⁴ | Z | W | X | Y |
|---|---|---|---|---|---|---|---|---|
| 138-305 | H | (CH₂)₂ | H | H | CH₂ | 4-F-PhO | 4-(4-Me-Ph)-Ph | O |
| 138-306 | H | (CH₂)₂ | H | H | CH₂ | 4-F-PhO | 4-(4-Dma-Ph)-Ph | O |
| 138-307 | H | (CH₂)₂ | H | H | CH₂ | 4-F-PhO | 4-(4-CF₃-Ph)-Ph | O |
| 138-308 | H | (CH₂)₂ | H | H | CH₂ | 4-F-PhO | 4-(3-Me-Pyr-6)-Ph | O |
| 138-309 | H | (CH₂)₂ | H | H | CH₂ | 4-F-PhO | 4-(3-Et-Pyr-6)-Ph | O |
| 138-310 | H | (CH₂)₂ | H | H | CH₂ | 4-F-PhO | 4-(3-EtO-Pyr-6)-Ph | O |
| 138-311 | H | (CH₂)₂ | H | H | CH₂ | 4-F-PhO | 2-(4-Me-Ph)-5-Pyr | O |
| 138-312 | H | (CH₂)₂ | H | H | CH₂ | 4-F-PhO | 2-(4-CF₃-Ph)-5-Pyr | O |
| 138-313 | H | (CH₂)₂ | H | H | CH₂ | 4-F-PhO | 2-(4-Cl-Ph)-5-Pyr | O |
| 138-314 | H | (CH₂)₂ | H | H | CH₂ | 4-F-PhO | 2-(4-Dma-Ph)-5-Pyr | O |
| 138-315 | H | (CH₂)₂ | H | H | CH₂ | 4-Cl-PhO | 4-(4-Me-Ph)-Ph | O |
| 138-316 | H | (CH₂)₂ | H | H | CH₂ | 4-Cl-PhO | 4-(4-Dma-Ph)-Ph | O |
| 138-317 | H | (CH₂)₂ | H | H | CH₂ | 4-Cl-PhO | 4-(4-CF₃-Ph)-Ph | O |
| 138-318 | H | (CH₂)₂ | H | H | CH₂ | 4-Cl-PhO | 4-(3-Me-Pyr-6)-Ph | O |
| 138-319 | H | (CH₂)₂ | H | H | CH₂ | 4-Cl-PhO | 4-(3-Et-Pyr-6)-Ph | O |
| 138-320 | H | (CH₂)₂ | H | H | CH₂ | 4-Cl-PhO | 4-(3-EtO-Pyr-6)-Ph | O |
| 138-321 | H | (CH₂)₂ | H | H | CH₂ | 4-Cl-PhO | 2-(4-Me-Ph)-5-Pyr | O |
| 138-322 | H | (CH₂)₂ | H | H | CH₂ | 4-Cl-PhO | 2-(4-CF₃-Ph)-5-Pyr | O |
| 138-323 | H | (CH₂)₂ | H | H | CH₂ | 4-Cl-PhO | 2-(4-Cl-Ph)-5-Pyr | O |
| 138-324 | H | (CH₂)₂ | H | H | CH₂ | 4-Cl-PhO | 2-(4-Dma-Ph)-5-Pyr | O |
| 138-325 | H | (CH₂)₂ | H | H | CH₂ | 3-F-PhO | 4-(4-Me-Ph)-Ph | O |
| 138-326 | H | (CH₂)₂ | H | H | CH₂ | 3-F-PhO | 4-(4-Dma-Ph)-Ph | O |
| 138-327 | H | (CH₂)₂ | H | H | CH₂ | 3-F-PhO | 4-(4-CF₃-Ph)-Ph | O |
| 138-328 | H | (CH₂)₂ | H | H | CH₂ | 3-F-PhO | 4-(3-Me-Pyr-6)-Ph | O |
| 138-329 | H | (CH₂)₂ | H | H | CH₂ | 3-F-PhO | 4-(3-Et-Pyr-6)-Ph | O |
| 138-330 | H | (CH₂)₂ | H | H | CH₂ | 3-F-PhO | 4-(3-EtO-Pyr-6)-Ph | O |
| 138-331 | H | (CH₂)₂ | H | H | CH₂ | 3-F-PhO | 2-(4-Me-Ph)-5-Pyr | O |
| 138-332 | H | (CH₂)₂ | H | H | CH₂ | 3-F-PhO | 2-(4-CF₃-Ph)-5-Pyr | O |
| 138-333 | H | (CH₂)₂ | H | H | CH₂ | 3-F-PhO | 2-(4-Cl-Ph)-5-Pyr | O |
| 138-334 | H | (CH₂)₂ | H | H | CH₂ | 3-F-PhO | 2-(4-Dma-Ph)-5-Pyr | O |

TABLE 139

| Ex. No. Comp. | R¹ | R² | R³ | R⁴ | Z | W | X | Y |
|---|---|---|---|---|---|---|---|---|
| 139-1 | H | (CH₂)₂ | Cl | H | CH₂ | Ph(OCH₂)₃ | 4-(Pyr-2)-Ph | O |
| 139-2 | H | (CH₂)₂ | Cl | H | CH₂ | EtO | 4-Ph-Ph | O |
| 139-3 | H | (CH₂)₂ | Cl | H | CH₂ | EtO | 4-(Pyr-2)-Ph | O |
| 139-4 | H | (CH₂)₂ | Cl | H | CH₂ | EtO | 4-(3-MeO-Pyr-6)-Ph | O |
| 139-5 | H | (CH₂)₂ | Cl | H | CH₂ | EtO | 4-(3-Dma-Pyr-6)-Ph | O |
| 139-6 | H | (CH₂)₂ | Cl | H | CH₂ | EtO | 2-(4-F-Ph)-5-Pyr | O |
| 139-7 | H | (CH₂)₂ | Cl | H | CH₂ | EtO | 2-(4-MeO-Ph)-5-Pyr | O |
| 139-8 | H | (CH₂)₂ | Cl | H | CH₂ | EtO | 2-TfpO-5-Pyr | O |
| 139-9 | H | (CH₂)₂ | Cl | H | CH₂ | Pr | 4-Ph-Ph | O |
| 139-10 | H | (CH₂)₂ | Cl | H | CH₂ | Pr | 4-(Pyr-2)-Ph | O |
| 139-11 | H | (CH₂)₂ | Cl | H | CH₂ | Pr | 4-(3-MeO-Pyr-6)-Ph | O |
| 139-12 | H | (CH₂)₂ | Cl | H | CH₂ | Pr | 4-(3-Dma-Pyr-6)-Ph | O |
| 139-13 | H | (CH₂)₂ | Cl | H | CH₂ | Pr | 2-(4-F-Ph)-5-Pyr | O |
| 139-14 | H | (CH₂)₂ | Cl | H | CH₂ | Pr | 2-(4-MeO-Ph)-5-Pyr | O |
| 139-15 | H | (CH₂)₂ | Cl | H | CH₂ | Pr | 2-TfpO-5-Pyr | O |
| 139-16 | H | (CH₂)₂ | Cl | H | CH₂ | Bu | 4-Ph-Ph | O |
| 139-17 | H | (CH₂)₂ | Cl | H | CH₂ | Bu | 4-(Pyr-2)-Ph | O |

TABLE 139-continued

| Ex. No. Comp. | R¹ | R² | R³ | R⁴ | Z | W | X | Y |
|---|---|---|---|---|---|---|---|---|
| 139-18 | H | (CH$_2$)$_2$ | Cl | H | CH$_2$ | Bu | 4-(3-MeO-Pyr-6)-Ph | O |
| 139-19 | H | (CH$_2$)$_2$ | Cl | H | CH$_2$ | Bu | 4-(3-Dma-Pyr-6)-Ph | O |
| 139-20 | H | (CH$_2$)$_2$ | Cl | H | CH$_2$ | Bu | 2-(4-F-Ph)-5-Pyr | O |
| 139-21 | H | (CH$_2$)$_2$ | Cl | H | CH$_2$ | Bu | 2-(4-MeO-Ph)-5-Pyr | O |
| 139-22 | H | (CH$_2$)$_2$ | Cl | H | CH$_2$ | Bu | 2-TfpO-5-Pyr | O |
| 139-23 | H | (CH$_2$)$_2$ | Cl | H | CH$_2$ | PhO | 4-Ph-Ph | O |
| 139-24 | H | (CH$_2$)$_2$ | Cl | H | CH$_2$ | PhO | 4-(Pyr-2)-Ph | O |
| 139-25 | H | (CH$_2$)$_2$ | Cl | H | CH$_2$ | PhO | 4-(3-MeO-Pyr-6)-Ph | O |
| 139-26 | H | (CH$_2$)$_2$ | Cl | H | CH$_2$ | PhO | 4-(3-Dma-Pyr-6)-Ph | O |
| 139-27 | H | (CH$_2$)$_2$ | Cl | H | CH$_2$ | PhO | 2-(4-F-Ph)-5-Pyr | O |
| 139-28 | H | (CH$_2$)$_2$ | Cl | H | CH$_2$ | PhO | 2-(4-MeO-Ph)-5-Pyr | O |
| 139-29 | H | (CH$_2$)$_2$ | Cl | H | CH$_2$ | PhO | 2-TfpO-5-Pyr | O |
| 139-30 | H | (CH$_2$)$_2$ | Cl | H | CH$_2$ | 4-iPr-PhO | 4-Ph-Ph | O |
| 139-31 | H | (CH$_2$)$_2$ | Cl | H | CH$_2$ | 4-iPr-PhO | 4-(Pyr-2)-Ph | O |
| 139-32 | H | (CH$_2$)$_2$ | Cl | H | CH$_2$ | 4-iPr-PhO | 4-(3-MeO-Pyr-6)-Ph | O |
| 139-33 | H | (CH$_2$)$_2$ | Cl | H | CH$_2$ | 4-iPr-PhO | 4-(3-Dma-Pyr-6)-Ph | O |
| 139-34 | H | (CH$_2$)$_2$ | Cl | H | CH$_2$ | 4-iPr-PhO | 2-(4-F-Ph)-5-Pyr | O |
| 139-35 | H | (CH$_2$)$_2$ | Cl | H | CH$_2$ | 4-iPr-PhO | 2-(4-MeO-Ph)-5-Pyr | O |
| 139-36 | H | (CH$_2$)$_2$ | Cl | H | CH$_2$ | 4-ipr-PhO | 2-TfpO-5-Pyr | O |
| 139-37 | H | (CH$_2$)$_2$ | Cl | H | CH$_2$ | 4-MeO-PhO | 4-Ph-Ph | O |
| 139-38 | H | (CH$_2$)$_2$ | Cl | H | CH$_2$ | 4-MeO-PhO | 4-(Pyr-2)-Ph | O |
| 139-39 | H | (CH$_2$)$_2$ | Cl | H | CH$_2$ | 4-MeO-PhO | 4-(3-MeO-Pyr-6)-Ph | O |
| 139-40 | H | (CH$_2$)$_2$ | Cl | H | CH$_2$ | 4-MeO-PhO | 4-(3-Dma-Pyr-6)-Ph | O |
| 139-41 | H | (CH$_2$)$_2$ | Cl | H | CH$_2$ | 4-MeO-PhO | 2-(4-F-Ph)-5-Pyr | O |
| 139-42 | H | (CH$_2$)$_2$ | Cl | H | CH$_2$ | 4-MeO-PhO | 2-(4-MeO-Ph)-5-Pyr | O |
| 139-43 | H | (CH$_2$)$_2$ | Cl | H | CH$_2$ | 4-MeO-PhO | 2-TfpO-5-Pyr | O |
| 139-44 | H | (CH$_2$)$_2$ | Cl | H | CH$_2$ | 4-Me-PhO | 4-Ph-Ph | O |
| 139-45 | H | (CH$_2$)$_2$ | Cl | H | CH$_2$ | 4-Me-PhO | 4-(Pyr-2)-Ph | O |
| 139-46 | H | (CH$_2$)$_2$ | Cl | H | CH$_2$ | 4-Me-PhO | 4-(3-MeO-Pyr-6)-Ph | O |
| 139-47 | H | (CH$_2$)$_2$ | Cl | H | CH$_2$ | 4-Me-PhO | 4-(3-Dma-Pyr-6)-Ph | O |
| 139-48 | H | (CH$_2$)$_2$ | Cl | H | CH$_2$ | 4-Me-PhO | 2-(4-F-Ph)-5-Pyr | O |
| 139-49 | H | (CH$_2$)$_2$ | Cl | H | CH$_2$ | 4-Me-PhO | 2-(4-MeO-Ph)-5-Pyr | O |
| 139-50 | H | (CH$_2$)$_2$ | Cl | H | CH$_2$ | 4-Me-PhO | 2-TfpO-5-Pyr | O |
| 139-51 | H | (CH$_2$)$_2$ | Cl | H | CH$_2$ | 4-tBu-PhO | 4-Ph-Ph | O |
| 139-52 | H | (CH$_2$)$_2$ | Cl | H | CH$_2$ | 4-tBu-PhO | 4-(Pyr-2)-Ph | O |
| 139-53 | H | (CH$_2$)$_2$ | Cl | H | CH$_2$ | 4-tBu-PhO | 4-(3-MeO-Pyr-6)-Ph | O |
| 139-54 | H | (CH$_2$)$_2$ | Cl | H | CH$_2$ | 4-tBu-PhO | 4-(3-Dma-Pyr-6)-Ph | O |
| 139-55 | H | (CH$_2$)$_2$ | Cl | H | CH$_2$ | 4-tBu-PhO | 2-(4-F-Ph)-5-Pyr | O |
| 139-56 | H | (CH$_2$)$_2$ | Cl | H | CH$_2$ | 4-tBu-PhO | 2-(4-MeO-Ph)-5-Pyr | O |
| 139-57 | H | (CH$_2$)$_2$ | Cl | H | CH$_2$ | 4-tBu-PhO | 2-TfpO-5-Pyr | O |
| 139-58 | H | (CH$_2$)$_2$ | Cl | H | CH$_2$ | 4-CF$_3$-PhO | 4-Ph-Ph | O |
| 139-59 | H | (CH$_2$)$_2$ | Cl | H | CH$_2$ | 4-CF$_3$-PhO | 4-(Pyr-2)-Ph | O |
| 139-60 | H | (CH$_2$)$_2$ | Cl | H | CH$_2$ | 4-CF$_3$-PhO | 4-(3-MeO-Pyr-6)-Ph | O |
| 139-61 | H | (CH$_2$)$_2$ | Cl | H | CH$_2$ | 4-CF$_3$-PhO | 4-(3-Dma-Pyr-6)-Ph | O |
| 139-62 | H | (CH$_2$)$_2$ | Cl | H | CH$_2$ | 4-CF$_3$-PhO | 2-(4-F-Ph)-5-Pyr | O |
| 139-63 | H | (CH$_2$)$_2$ | Cl | H | CH$_2$ | 4-CF$_3$-PhO | 2-(4-MeO-Ph)-5-Pyr | O |
| 139-64 | H | (CH$_2$)$_2$ | Cl | H | CH$_2$ | 4-CF$_3$-PhO | 2-TfpO-5-Pyr | O |

TABLE 139-continued

| Ex. No. Comp. | R¹ | R² | R³ | R⁴ | Z | W | X | Y |
|---|---|---|---|---|---|---|---|---|
| 139-65 | H | (CH₂)₂ | Cl | H | CH₂ | 4-CF₃O-PhO | 4-Ph-Ph | O |
| 139-66 | H | (CH₂)₂ | Cl | H | CH₂ | 4-CF₃O-PhO | 4-(Pyr-2)-Ph | O |
| 139-67 | H | (CH₂)₂ | Cl | H | CH₂ | 4-CF₃O-PhO | 4-(3-MeO-Pyr-6)-Ph | O |
| 139-68 | H | (CH₂)₂ | Cl | H | CH₂ | 4-CF₃O-PhO | 4-(3-Dma-Pyr-6)-Ph | O |
| 139-69 | H | (CH₂)₂ | Cl | H | CH₂ | 4-CF₃O-PhO | 2-(4-F-Ph)-5-Pyr | O |
| 139-70 | H | (CH₂)₂ | Cl | H | CH₂ | 4-CF₃O-PhO | 2-(4-MeO-Ph)-5-Pyr | O |
| 139-71 | H | (CH₂)₂ | Cl | H | CH₂ | 4-CF₃O-PhO | 2-TfpO-5-Pyr | O |
| 139-72 | H | (CH₂)₂ | Cl | H | CH₂ | 4-F-PhO | 4-Ph-Ph | O |
| 139-73 | H | (CH₂)₂ | Cl | H | CH₂ | 4-F-PhO | 4-(Pyr-2)-Ph | O |
| 139-74 | H | (CH₂)₂ | Cl | H | CH₂ | 4-F-PhO | 4-(3-MeO-Pyr-6)-Ph | O |
| 139-75 | H | (CH₂)₂ | Cl | H | CH₂ | 4-F-PhO | 4-(3-Dma-Pyr-6)-Ph | O |
| 139-76 | H | (CH₂)₂ | Cl | H | CH₂ | 4-F-PhO | 2-(4-F-Ph)-5-Pyr | O |
| 139-77 | H | (CH₂)₂ | Cl | H | CH₂ | 4-F-PhO | 2-(4-MeO-Ph)-5-Pyr | O |
| 139-78 | H | (CH₂)₂ | Cl | H | CH₂ | 4-F-PhO | 2-TfpO-5-Pyr | O |
| 139-79 | H | (CH₂)₂ | Cl | H | CH₂ | 4-Cl-PhO | 4-Ph-Ph | O |
| 139-80 | H | (CH₂)₂ | Cl | H | CH₂ | 4-Cl-PhO | 4-(Pyr-2)-Ph | O |
| 139-81 | H | (CH₂)₂ | Cl | H | CH₂ | 4-Cl-PhO | 4-(3-MeO-Pyr-6)-Ph | O |
| 139-82 | H | (CH₂)₂ | Cl | H | CH₂ | 4-Cl-PhO | 4-(3-Dma-Pyr-6)-Ph | O |
| 139-83 | H | (CH₂)₂ | Cl | H | CH₂ | 4-Cl-PhO | 2-(4-F-Ph)-5-Pyr | O |
| 139-84 | H | (CH₂)₂ | Cl | H | CH₂ | 4-Cl-PhO | 2-(4-MeO-Ph)-5-Pyr | O |
| 139-85 | H | (CH₂)₂ | Cl | H | CH₂ | 4-Cl-PhO | 2-TfpO-5-Pyr | O |
| 139-86 | H | (CH₂)₂ | Cl | H | CH₂ | 3-F-PhO | 4-Ph-Ph | O |
| 139-87 | H | (CH₂)₂ | Cl | H | CH₂ | 3-F-PhO | 4-(Pyr-2)-Ph | O |
| 139-88 | H | (CH₂)₂ | Cl | H | CH₂ | 3-F-PhO | 4-(3-MeO-Pyr-6)-Ph | O |
| 139-89 | H | (CH₂)₂ | Cl | H | CH₂ | 3-F-PhO | 4-(3-Dma-Pyr-6)-Ph | O |
| 139-90 | H | (CH₂)₂ | Cl | H | CH₂ | 3-F-PhO | 2-(4-F-Ph)-5-Pyr | O |
| 139-91 | H | (CH₂)₂ | Cl | H | CH₂ | 3-F-PhO | 2-(4-MeO-Ph)-5-Pyr | O |
| 139-92 | H | (CH₂)₂ | Cl | H | CH₂ | 3-F-PhO | 2-TfpO-5-Pyr | O |

TABLE 140

| Ex. No. Comp. | R¹ | R² | R³ | R⁴ | Z | W | X | Y |
|---|---|---|---|---|---|---|---|---|
| 140-1 | H | (CH₂)₂ | MeO | H | CH₂ | PhO | 4-(Pyr-2)-Ph | O |
| 140-2 | H | (CH₂)₂ | MeO | H | CH₂ | PhO | 4-(Pyr-2)-Ph | O |
| 140-3 | H | (CH₂)₂ | MeO | H | CH₂ | EtO | 4-Ph—Ph | O |
| 140-4 | H | (CH₂)₂ | MeO | H | CH₂ | EtO | 4-(Pyr-2)-Ph | O |
| 140-5 | H | (CH₂)₂ | MeO | H | CH₂ | EtO | 4-(3-MeO—Pyr-6)-Ph | O |
| 140-6 | H | (CH₂)₂ | MeO | H | CH₂ | EtO | 4-(3-Dma—Pyr-6)-Ph | O |
| 140-7 | H | (CH₂)₂ | MeO | H | CH₂ | EtO | 2-(4-F—Ph)-5-Pyr | O |
| 140-8 | H | (CH₂)₂ | MeO | H | CH₂ | EtO | 2-(4-MeO—Ph)-5-Pyr | O |
| 140-9 | H | (CH₂)₂ | MeO | H | CH₂ | EtO | 2-TfpO-5-Pyr | O |
| 140-10 | H | (CH₂)₂ | MeO | H | CH₂ | Pr | 4-Ph—Ph | O |
| 140-11 | H | (CH₂)₂ | MeO | H | CH₂ | Pr | 4-(Pyr-2)-Ph | O |
| 140-12 | H | (CH₂)₂ | MeO | H | CH₂ | Pr | 4-(3-MeO—Pyr-6)-Ph | O |
| 140-13 | H | (CH₂)₂ | MeO | H | CH₂ | Pr | 4-(3-Dma—Pyr-6)-Ph | O |
| 140-14 | H | (CH₂)₂ | MeO | H | CH₂ | Pr | 2-(4-F—Ph)-5-Pyr | O |

TABLE 140-continued

| Ex. No. Comp. | R¹ | R² | R³ | R⁴ | Z | W | X | Y |
|---|---|---|---|---|---|---|---|---|
| 140-15 | H | (CH₂)₂ | MeO | H | CH₂ | Pr | 2-(4-MeO—Ph)-5-Pyr | O |
| 140-16 | H | (CH₂)₂ | MeO | H | CH₂ | Pr | 2-TfpO-5-Pyr | O |
| 140-17 | H | (CH₂)₂ | MeO | H | CH₂ | Bu | 4-Ph—Ph | O |
| 140-18 | H | (CH₂)₂ | MeO | H | CH₂ | Bu | 4-(Pyr-2)-Ph | O |
| 140-19 | H | (CH₂)₂ | MeO | H | CH₂ | Bu | 4-(3-MeO—Pyr-6)-Ph | O |
| 140-20 | H | (CH₂)₂ | MeO | H | CH₂ | Bu | 4-(3-Dma—Pyr-6)-Ph | O |
| 140-21 | H | (CH₂)₂ | MeO | H | CH₂ | Bu | 2-(4-F—Ph)-5-Pyr | O |
| 140-22 | H | (CH₂)₂ | MeO | H | CH₂ | Bu | 2-(4-MeO—Ph)-5-Pyr | O |
| 140-23 | H | (CH₂)₂ | MeO | H | CH₂ | Bu | 2-TfpO-5-Pyr | O |
| 140-24 | H | (CH₂)₂ | MeO | H | CH₂ | PhO | 4-Ph—Ph | O |
| 140-25 | H | (CH₂)₂ | MeO | H | CH₂ | PhO | 4-(3-MeO—Pyr-6)-Ph | O |
| 140-26 | H | (CH₂)₂ | MeO | H | CH₂ | PhO | 4-(3-Dma—Pyr-6)-Ph | O |
| 140-27 | H | (CH₂)₂ | MeO | H | CH₂ | PhO | 2-(4-F—Ph)-5-Pyr | O |
| 140-28 | H | (CH₂)₂ | MeO | H | CH₂ | PhO | 2-(4-MeO—Ph)-5-Pyr | O |
| 140-29 | H | (CH₂)₂ | MeO | H | CH₂ | PhO | 2-TfpO-5-Pyr | O |
| 140-30 | H | (CH₂)₂ | MeO | H | CH₂ | 4-iPr—PhO | 4-Ph—Ph | O |
| 140-31 | H | (CH₂)₂ | MeO | H | CH₂ | 4-iPr—PhO | 4-(Pyr-2)-Ph | O |
| 140-32 | H | (CH₂)₂ | MeO | H | CH₂ | 4-iPr—PhO | 4-(3-MeO—Pyr-6)-Ph | O |
| 140-33 | H | (CH₂)₂ | MeO | H | CH₂ | 4-iPr—PhO | 4-(3-Dma—Pyr-6)-Ph | O |
| 140-34 | H | (CH₂)₂ | MeO | H | CH₂ | 4-iPr—PhO | 2-(4-F—Ph)-5-Pyr | O |
| 140-35 | H | (CH₂)₂ | MeO | H | CH₂ | 4-iPr—PhO | 2-(4-MeO—Ph)-5-Pyr | O |
| 140-36 | H | (CH₂)₂ | MeO | H | CH₂ | 4-iPr—PhO | 2-TfpO-5-Pyr | O |
| 140-37 | H | (CH₂)₂ | MeO | H | CH₂ | 4-MeO—PhO | 4-Ph—Ph | O |
| 140-38 | H | (CH₂)₂ | MeO | H | CH₂ | 4-MeO—PhO | 4-(Pyr-2)-Ph | O |
| 140-39 | H | (CH₂)₂ | MeO | H | CH₂ | 4-MeO—PhO | 4-(3-MeO—Pyr-6)-Ph | O |
| 140-40 | H | (CH₂)₂ | MeO | H | CH₂ | 4-MeO—PhO | 4-(3-Dma—Pyr-6)-Ph | O |
| 140-41 | H | (CH₂)₂ | MeO | H | CH₂ | 4-MeO—PhO | 2-(4-F—Ph)-5-Pyr | O |
| 140-42 | H | (CH₂)₂ | MeO | H | CH₂ | 4-MeO—PhO | 2-(4-MeO—Ph)-5-Pyr | O |
| 140-43 | H | (CH₂)₂ | MeO | H | CH₂ | 4-MeO—PhO | 2-TfpO-5-Pyr | O |
| 140-44 | H | (CH₂)₂ | MeO | H | CH₂ | 4-Me—PhO | 4-Ph—Ph | O |
| 140-45 | H | (CH₂)₂ | MeO | H | CH₂ | 4-Me—PhO | 4-(Pyr-2)-Ph | O |
| 140-46 | H | (CH₂)₂ | MeO | H | CH₂ | 4-Me—PhO | 4-(3-MeO—Pyr-6)-Ph | O |
| 140-47 | H | (CH₂)₂ | MeO | H | CH₂ | 4-Me—PhO | 4-(3-Dma—Pyr-6)-Ph | O |
| 140-48 | H | (CH₂)₂ | MeO | H | CH₂ | 4-Me—PhO | 2-(4-F—Ph)-5-Pyr | O |
| 140-49 | H | (CH₂)₂ | MeO | H | CH₂ | 4-Me—PhO | 2-(4-MeO—Ph)-5-Pyr | O |
| 140-50 | H | (CH₂)₂ | MeO | H | CH₂ | 4-Me—PhO | 2-TfpO-5-Pyr | O |
| 140-51 | H | (CH₂)₂ | MeO | H | CH₂ | 4-tBu—PhO | 4-Ph—Ph | O |
| 140-52 | H | (CH₂)₂ | MeO | H | CH₂ | 4-tBu—PhO | 4-(Pyr-2)-Ph | O |
| 140-53 | H | (CH₂)₂ | MeO | H | CH₂ | 4-tBu—PhO | 4-(3-MeO—Pyr-6)-Ph | O |
| 140-54 | H | (CH₂)₂ | MeO | H | CH₂ | 4-tBu—PhO | 4-(3-Dma—Pyr-6)-Ph | O |
| 140-55 | H | (CH₂)₂ | MeO | H | CH₂ | 4-tBu—PhO | 2-(4-F—Ph)-5-Pyr | O |
| 140-56 | H | (CH₂)₂ | MeO | H | CH₂ | 4-tBu—PhO | 2-(4-MeO—Ph)-5-Pyr | O |
| 140-57 | H | (CH₂)₂ | MeO | H | CH₂ | 4-tBu—PhO | 2-TfpO-5-Pyr | O |
| 140-58 | H | (CH₂)₂ | MeO | H | CH₂ | 4-CF₃—PhO | 4-Ph—Ph | O |
| 140-59 | H | (CH₂)₂ | MeO | H | CH₂ | 4-CF₃—PhO | 4-(Pyr-2)-Ph | O |
| 140-60 | H | (CH₂)₂ | MeO | H | CH₂ | 4-CF₃—PhO | 4-(3-MeO—Pyr-6)-Ph | O |
| 140-61 | H | (CH₂)₂ | MeO | H | CH₂ | 4-CF₃—PhO | 4-(3-Dma—Pyr-6)-Ph | O |
| 140-62 | H | (CH₂)₂ | MeO | H | CH₂ | 4-CF₃—PhO | 2-(4-F—Ph)-5- | O |

TABLE 140-continued

| Ex. No. Comp. | R¹ | R² | R³ | R⁴ | Z | W | X | Y |
|---|---|---|---|---|---|---|---|---|
| 140-63 | H | (CH$_2$)$_2$ | MeO | H | CH$_2$ | 4-CF$_3$—PhO | 2-(4-MeO—Ph)-5-Pyr | O |
| 140-64 | H | (CH$_2$)$_2$ | MeO | H | CH$_2$ | 4-CF$_3$—PhO | 2-TfpO-5-Pyr | O |
| 140-65 | H | (CH$_2$)$_2$ | MeO | H | CH$_2$ | 4-CF$_3$O—PhO | 4-Ph—Ph | O |
| 140-66 | H | (CH$_2$)$_2$ | MeO | H | CH$_2$ | 4-CF$_3$O—PhO | 4-(Pyr-2)-Ph | O |
| 140-67 | H | (CH$_2$)$_2$ | MeO | H | CH$_2$ | 4-CF$_3$O—PhO | 4-(3-MeO—Pyr-6)-Ph | O |
| 140-68 | H | (CH$_2$)$_2$ | MeO | H | CH$_2$ | 4-CF$_3$O—PhO | 4-(3-Dma—Pyr-6)-Ph | O |
| 140-69 | H | (CH$_2$)$_2$ | MeO | H | CH$_2$ | 4-CF$_3$O—PhO | 2-(4-F—Ph)-5-Pyr | O |
| 140-70 | H | (CH$_2$)$_2$ | MeO | H | CH$_2$ | 4-CF$_3$O—PhO | 2-(4-MeO—Ph)-5-Pyr | O |
| 140-71 | H | (CH$_2$)$_2$ | MeO | H | CH$_2$ | 4-CF$_3$O—PhO | 2-TfpO-5-Pyr | O |
| 140-72 | H | (CH$_2$)$_2$ | MeO | H | CH$_2$ | 4-F—PhO | 4-Ph—Ph | O |
| 140-73 | H | (CH$_2$)$_2$ | MeO | H | CH$_2$ | 4-F—PhO | 4-(Pyr-2)-Ph | O |
| 140-74 | H | (CH$_2$)$_2$ | MeO | H | CH$_2$ | 4-F—PhO | 4-(3-MeO—Pyr-6)-Ph | O |
| 140-75 | H | (CH$_2$)$_2$ | MeO | H | CH$_2$ | 4-F—PhO | 4-(3-Dma—Pyr-6)-Ph | O |
| 140-76 | H | (CH$_2$)$_2$ | MeO | H | CH$_2$ | 4-F—PhO | 2-(4-F—Ph)-5-Pyr | O |
| 140-77 | H | (CH$_2$)$_2$ | MeO | H | CH$_2$ | 4-F—PhO | 2-(4-MeO—Ph)-5-Pyr | O |
| 140-78 | H | (CH$_2$)$_2$ | MeO | H | CH$_2$ | 4-F—PhO | 2-TfpO-5-Pyr | O |
| 140-79 | H | (CH$_2$)$_2$ | MeO | H | CH$_2$ | 4-Cl—PhO | 4-Ph—Ph | O |
| 140-80 | H | (CH$_2$)$_2$ | MeO | H | CH$_2$ | 4-Cl—PhO | 4-(Pyr-2)-Ph | O |
| 140-81 | H | (CH$_2$)$_2$ | MeO | H | CH$_2$ | 4-Cl—PhO | 4-(3-MeO—Pyr-6)-Ph | O |
| 140-82 | H | (CH$_2$)$_2$ | MeO | H | CH$_2$ | 4-Cl—PhO | 4-(3-Dma—Pyr-6)-Ph | O |
| 140-83 | H | (CH$_2$)$_2$ | MeO | H | CH$_2$ | 4-Cl—PhO | 2-(4-F—Ph)-5-Pyr | O |
| 140-84 | H | (CH$_2$)$_2$ | MeO | H | CH$_2$ | 4-Cl—PhO | 2-(4-MeO—Ph)-5-Pyr | O |
| 140-85 | H | (CH$_2$)$_2$ | MeO | H | CH$_2$ | 4-Cl—PhO | 2-TfpO-5-Pyr | O |
| 140-86 | H | (CH$_2$)$_2$ | MeO | H | CH$_2$ | 3-F—PhO | 4-Ph—Ph | O |
| 140-87 | H | (CH$_2$)$_2$ | MeO | H | CH$_2$ | 3-F—PhO | 4-(Pyr-2)-Ph | O |
| 140-88 | H | (CH$_2$)$_2$ | MeO | H | CH$_2$ | 3-F—PhO | 4-(3-MeO—Pyr-6)-Ph | O |
| 140-89 | H | (CH$_2$)$_2$ | MeO | H | CH$_2$ | 3-F—PhO | 4-(3-Dma—Pyr-6)-Ph | O |
| 140-90 | H | (CH$_2$)$_2$ | MeO | H | CH$_2$ | 3-F—PhO | 2-(4-F—Ph)-5-Pyr | O |
| 140-91 | H | (CH$_2$)$_2$ | MeO | H | CH$_2$ | 3-F—PhO | 2-(4-MeO—Ph)-5-Pyr | O |
| 140-92 | H | (CH$_2$)$_2$ | MeO | H | CH$_2$ | 3-F—PhO | 2-TfpO-5-Pyr | O |

TABLE 141

| Ex. No. Comp. | R¹ | R² | R³ | R⁴ | Z | W | X | Y |
|---|---|---|---|---|---|---|---|---|
| 140-1 | H | (CH$_2$)$_2$ | Br | H | CH$_2$ | EtO | 4-Ph—Ph | O |
| 141-2 | H | (CH$_2$)$_2$ | Br | H | CH$_2$ | EtO | 4-(Pyr-2)-Ph | O |
| 141-3 | H | (CH$_2$)$_2$ | Br | H | CH$_2$ | EtO | 4-(3-MeO—Pyr-6)-Ph | O |
| 141-4 | H | (CH$_2$)$_2$ | Br | H | CH$_2$ | EtO | 4-(3-Dma—Pyr-6)-Ph | O |
| 141-5 | H | (CH$_2$)$_2$ | Br | H | CH$_2$ | EtO | 2-(4-F—Ph)-5-Pyr | O |
| 141-6 | H | (CH$_2$)$_2$ | Br | H | CH$_2$ | EtO | 2-(4-MeO—Ph)-5-Pyr | O |
| 141-7 | H | (CH$_2$)$_2$ | Br | H | CH$_2$ | EtO | 2-TfpO-5-Pyr | O |
| 141-8 | H | (CH$_2$)$_2$ | Br | H | CH$_2$ | Pr | 4-Ph—Ph | O |
| 141-9 | H | (CH$_2$)$_2$ | Br | H | CH$_2$ | Pr | 4-(Pyr-2)-Ph | O |
| 141-10 | H | (CH$_2$)$_2$ | Br | H | CH$_2$ | Pr | 4-(3-MeO—Pyr-6)-Ph | O |
| 141-11 | H | (CH$_2$)$_2$ | Br | H | CH$_2$ | Pr | 4-(3-Dma—Pyr-6)-Ph | O |

TABLE 141-continued

| Ex. No. Comp. | R$^1$ | R$^2$ | R$^3$ | R$^4$ | Z | W | X | Y |
|---|---|---|---|---|---|---|---|---|
| 141-12 | H | (CH$_2$)$_2$ | Br | H | CH$_2$ | Pr | 2-(4-F—Ph)-5-Pyr | O |
| 141-13 | H | (CH$_2$)$_2$ | Br | H | CH$_2$ | Pr | 2-(4-MeO—Ph)-5-Pyr | O |
| 141-14 | H | (CH$_2$)$_2$ | Br | H | CH$_2$ | Pr | 2-TfpO-5-Pyr | O |
| 141-15 | H | (CH$_2$)$_2$ | Br | H | CH$_2$ | Bu | 4-Ph—Ph | O |
| 141-16 | H | (CH$_2$)$_2$ | Br | H | CH$_2$ | Bu | 4-(Pyr-2)-Ph | O |
| 141-17 | H | (CH$_2$)$_2$ | Br | H | CH$_2$ | Bu | 4-(3-MeO—Pyr-6)-Ph | O |
| 141-18 | H | (CH$_2$)$_2$ | Br | H | CH$_2$ | Bu | 4-(3-Dma—Pyr-6)-Ph | O |
| 141-19 | H | (CH$_2$)$_2$ | Br | H | CH$_2$ | Bu | 2-(4-F—Ph)-5-Pyr | O |
| 141-20 | H | (CH$_2$)$_2$ | Br | H | CH$_2$ | Bu | 2-(4-MeO—Ph)-5-Pyr | O |
| 141-21 | H | (CH$_2$)$_2$ | Br | H | CH$_2$ | Bu | 2-TfpO-5-Pyr | O |
| 141-22 | H | (CH$_2$)$_2$ | Br | H | CH$_2$ | PhO | 4-Ph—Ph | O |
| 141-23 | H | (CH$_2$)$_2$ | Br | H | CH$_2$ | PhO | 4-(Pyr-2)-Ph | O |
| 141-24 | H | (CH$_2$)$_2$ | Br | H | CH$_2$ | PhO | 4-(3-MeO—Pyr-6)-Ph | O |
| 141-25 | H | (CH$_2$)$_2$ | Br | H | CH$_2$ | PhO | 4-(3-Dma—Pyr-6)-Ph | O |
| 141-26 | H | (CH$_2$)$_2$ | Br | H | CH$_2$ | PhO | 2-(4-F—Ph)-5-Pyr | O |
| 141-27 | H | (CH$_2$)$_2$ | Br | H | CH$_2$ | PhO | 2-(4-MeO—Ph)-5-Pyr | O |
| 141-28 | H | (CH$_2$)$_2$ | Br | H | CH$_2$ | PhO | 2-TfpO-5-Pyr | O |
| 141-29 | H | (CH$_2$)$_2$ | Br | H | CH$_2$ | 4-iPr—PhO | 4-Ph—Ph | O |
| 141-30 | H | (CH$_2$)$_2$ | Br | H | CH$_2$ | 4-iPr—PhO | 4-(Pyr-2)-Ph | O |
| 141-31 | H | (CH$_2$)$_2$ | Br | H | CH$_2$ | 4-iPr—PhO | 4-(3-MeO—Pyr-6)-Ph | O |
| 141-32 | H | (CH$_2$)$_2$ | Br | H | CH$_2$ | 4-iPr—PhO | 4-(3-Dma—Pyr-6)-Ph | O |
| 141-33 | H | (CH$_2$)$_2$ | Br | H | CH$_2$ | 4-iPr—PhO | 2-(4-F—Ph)-5-Pyr | O |
| 141-34 | H | (CH$_2$)$_2$ | Br | H | CH$_2$ | 4-iPr—PhO | 2-(4-MeO—Ph)-5-Pyr | O |
| 141-35 | H | (CH$_2$)$_2$ | Br | H | CH$_2$ | 4-iPr—PhO | 2-TfpO-5-Pyr | O |
| 141-36 | H | (CH$_2$)$_2$ | Br | H | CH$_2$ | 4-MeO—PhO | 4-Ph—Ph | O |
| 141-37 | H | (CH$_2$)$_2$ | Br | H | CH$_2$ | 4-MeO—PhO | 4-(Pyr-2)-Ph | O |
| 141-38 | H | (CH$_2$)$_2$ | Br | H | CH$_2$ | 4-MeO—PhO | 4-(3-MeO—Pyr-6)-Ph | O |
| 141-39 | H | (CH$_2$)$_2$ | Br | H | CH$_2$ | 4-MeO—PhO | 4-(3-Dma—Pyr-6)-Ph | O |
| 141-40 | H | (CH$_2$)$_2$ | Br | H | CH$_2$ | 4-MeO—PhO | 2-(4-F—Ph)-5-Pyr | O |
| 141-41 | H | (CH$_2$)$_2$ | Br | H | CH$_2$ | 4-MeO—PhO | 2-(4-MeO—Ph)-5-Pyr | O |
| 141-42 | H | (CH$_2$)$_2$ | Br | H | CH$_2$ | 4-MeO—PhO | 2-TfpO-5-Pyr | O |
| 141-43 | H | (CH$_2$)$_2$ | Br | H | CH$_2$ | 4-Me—PhO | 4-Ph—Ph | O |
| 141-44 | H | (CH$_2$)$_2$ | Br | H | CH$_2$ | 4-Me—PhO | 4-(Pyr-2)-Ph | O |
| 141-45 | H | (CH$_2$)$_2$ | Br | H | CH$_2$ | 4-Me—PhO | 4-(3-MeO—Pyr-6)-Ph | O |
| 141-46 | H | (CH$_2$)$_2$ | Br | H | CH$_2$ | 4-Me—PhO | 4-(3-Dma—Pyr-6)-Ph | O |
| 141-47 | H | (CH$_2$)$_2$ | Br | H | CH$_2$ | 4-Me—PhO | 2-(4-F—Ph)-5-Pyr | O |
| 141-48 | H | (CH$_2$)$_2$ | Br | H | CH$_2$ | 4-Me—PhO | 2-(4-MeO—Ph)-5-Pyr | O |
| 141-49 | H | (CH$_2$)$_2$ | Br | H | CH$_2$ | 4-Me—PhO | 2-TfpO-5-Pyr | O |
| 141-50 | H | (CH$_2$)$_2$ | Br | H | CH$_2$ | 4-tBu—PhO | 4-Ph—Ph | O |
| 141-51 | H | (CH$_2$)$_2$ | Br | H | CH$_2$ | 4-tBu—PhO | 4-(Pyr-2)-Ph | O |
| 141-52 | H | (CH$_2$)$_2$ | Br | H | CH$_2$ | 4-tBu—PhO | 4-(3-MeO—Pyr-6)-Ph | O |
| 141-53 | H | (CH$_2$)$_2$ | Br | H | CH$_2$ | 4-tBu—PhO | 4-(3-Dma—Pyr-6)-Ph | O |
| 141-54 | H | (CH$_2$)$_2$ | Br | H | CH$_2$ | 4-tBu—PhO | 2-(4-F—Ph)-5-Pyr | O |
| 141-55 | H | (CH$_2$)$_2$ | Br | H | CH$_2$ | 4-tBu—PhO | 2-(4-MeO—Ph)-5-Pyr | O |
| 141-56 | H | (CH$_2$)$_2$ | Br | H | CH$_2$ | 4-tBu—PhO | 2-TfpO-5-Pyr | O |
| 141-57 | H | (CH$_2$)$_2$ | Br | H | CH$_2$ | 4-CF$_3$—PhO | 4-Ph—Ph | O |
| 141-58 | H | (CH$_2$)$_2$ | Br | H | CH$_2$ | 4-CF$_3$—PhO | 4-(Pyr-2)-Ph | O |
| 141-59 | H | (CH$_2$)$_2$ | Br | H | CH$_2$ | 4-CF$_3$—PhO | 4-(3-MeO—Pyr-6)-Ph | O |

TABLE 141-continued

| Ex. No. Comp. | R¹ | R² | R³ | R⁴ | Z | W | X | Y |
|---|---|---|---|---|---|---|---|---|
| 141-60 | H | (CH$_2$)$_2$ | Br | H | CH$_2$ | 4-CF$_3$—PhO | 4-(3-Dma—Pyr-6)-Ph | O |
| 141-61 | H | (CH$_2$)$_2$ | Br | H | CH$_2$ | 4-CF$_3$—PhO | 2-(4-F—Ph)-5-Pyr | O |
| 141-62 | H | (CH$_2$)$_2$ | Br | H | CH$_2$ | 4-CF$_3$—PhO | 2-(4-MeO—Ph)-5-Pyr | O |
| 141-63 | H | (CH$_2$)$_2$ | Br | H | CH$_2$ | 4-CF$_3$—PhO | 2-TfpO-5-Pyr | O |
| 141-64 | H | (CH$_2$)$_2$ | Br | H | CH$_2$ | 4-CF$_3$O—PhO | 4-Ph—Ph | O |
| 141-65 | H | (CH$_2$)$_2$ | Br | H | CH$_2$ | 4-CF$_3$O—PhO | 4-(Pyr-2)-Ph | O |
| 141-66 | H | (CH$_2$)$_2$ | Br | H | CH$_2$ | 4-CF$_3$O—PhO | 4-(3-MeO—Pyr-6)-Ph | O |
| 141-67 | H | (CH$_2$)$_2$ | Br | H | CH$_2$ | 4-CF$_3$O—PhO | 4-(3-Dma—Pyr-6)-Ph | O |
| 141-68 | H | (CH$_2$)$_2$ | Br | H | CH$_2$ | 4-CF$_3$O—PhO | 2-(4-F—Ph)-5-Pyr | O |
| 141-69 | H | (CH$_2$)$_2$ | Br | H | CH$_2$ | 4-CF$_3$O—PhO | 2-(4-MeO—Ph)-5-Pyr | O |
| 141-70 | H | (CH$_2$)$_2$ | Br | H | CH$_2$ | 4-CF$_3$O—PhO | 2-TfpO-5-Pyr | O |
| 141-71 | H | (CH$_2$)$_2$ | Br | H | CH$_2$ | 4-F—PhO | 4-Ph—Ph | O |
| 141-72 | H | (CH$_2$)$_2$ | Br | H | CH$_2$ | 4-F—PhO | 4-(Pyr-2)-Ph | O |
| 141-73 | H | (CH$_2$)$_2$ | Br | H | CH$_2$ | 4-F—PhO | 4-(3-MeO—Pyr-6)-Ph | O |
| 141-74 | H | (CH$_2$)$_2$ | Br | H | CH$_2$ | 4-F—PhO | 4-(3-Dma—Pyr-6)-Ph | O |
| 141-75 | H | (CH$_2$)$_2$ | Br | H | CH$_2$ | 4-F—PhO | 2-(4-F—Ph)-5-Pyr | O |
| 141-76 | H | (CH$_2$)$_2$ | Br | H | CH$_2$ | 4-F—PhO | 2-(4-MeO—Ph)-5-Pyr | O |
| 141-77 | H | (CH$_2$)$_2$ | Br | H | CH$_2$ | 4-F—PhO | 2-TfpO-5-Pyr | O |
| 141-78 | H | (CH$_2$)$_2$ | Br | H | CH$_2$ | 4-Cl—PhO | 4-Ph—Ph | O |
| 141-79 | H | (CH$_2$)$_2$ | Br | H | CH$_2$ | 4-Cl—PhO | 4-(Pyr-2)-Ph | O |
| 141-80 | H | (CH$_2$)$_2$ | Br | H | CH$_2$ | 4-Cl—PhO | 4-(3-MeO—Pyr-6)-Ph | O |
| 141-81 | H | (CH$_2$)$_2$ | Br | H | CH$_2$ | 4-Cl—PhO | 4-(3-Dma—Pyr-6)-Ph | O |
| 141-82 | H | (CH$_2$)$_2$ | Br | H | CH$_2$ | 4-Cl—PhO | 2-(4-F—Ph)-5-Pyr | O |
| 141-83 | H | (CH$_2$)$_2$ | Br | H | CH$_2$ | 4-Cl—PhO | 2-(4-MeO—Ph)-5-Pyr | O |
| 141-84 | H | (CH$_2$)$_2$ | Br | H | CH$_2$ | 4-Cl—PhO | 2-TfpO-5-Pyr | O |
| 141-85 | H | (CH$_2$)$_2$ | Br | H | CH$_2$ | 3-F—PhO | 4-Ph—Ph | O |
| 141-86 | H | (CH$_2$)$_2$ | Br | H | CH$_2$ | 3-F—PhO | 4-(Pyr-2)-Ph | O |
| 141-87 | H | (CH$_2$)$_2$ | Br | H | CH$_2$ | 3-F—PhO | 4-(3-MeO—Pyr-6)-Ph | O |
| 141-88 | H | (CH$_2$)$_2$ | Br | H | CH$_2$ | 3-F—PhO | 4-(3-Dma—Pyr-6)-Ph | O |
| 141-89 | H | (CH$_2$)$_2$ | Br | H | CH$_2$ | 3-F—PhO | 2-(4-F—Ph)-5-Pyr | O |
| 141-90 | H | (CH$_2$)$_2$ | Br | H | CH$_2$ | 3-F—PhO | 2-(4-MeO—Ph)-5-Pyr | O |
| 141-91 | H | (CH$_2$)$_2$ | Br | H | CH$_2$ | 3-F—PhO | 2-TfpO-5-Pyr | O |

TABLE 142

| Ex. No. Comp. | R¹ | R² | R³ | R⁴ | Z | W | X | Y |
|---|---|---|---|---|---|---|---|---|
| 142-1 | H | (CH$_2$)$_2$ | NO$_2$ | H | CH$_2$ | EtO | 4-Ph—Ph | O |
| 142-2 | H | (CH$_2$)$_2$ | NO$_2$ | H | CH$_2$ | EtO | 4-(Pyr-2)-Ph | O |
| 142-3 | H | (CH$_2$)$_2$ | NO$_2$ | H | CH$_2$ | EtO | 4-(3-MeO—Pyr-6)-Ph | O |
| 142-4 | H | (CH$_2$)$_2$ | NO$_2$ | H | CH$_2$ | EtO | 4-(3-Dma—Pyr-6)-Ph | O |
| 142-5 | H | (CH$_2$)$_2$ | NO$_2$ | H | CH$_2$ | EtO | 2-(4-F—Ph)-5-Pyr | O |
| 142-6 | H | (CH$_2$)$_2$ | NO$_2$ | H | CH$_2$ | EtO | 2-(4-MeO—Ph)-5-Pyr | O |
| 142-7 | H | (CH$_2$)$_2$ | NO$_2$ | H | CH$_2$ | EtO | 2-TfpO-5-Pyr | O |
| 142-8 | H | (CH$_2$)$_2$ | NO$_2$ | H | CH$_2$ | Pr | 4-Ph—Ph | O |
| 142-9 | H | (CH$_2$)$_2$ | NO$_2$ | H | CH$_2$ | Pr | 4-(Pyr-2)-Ph | O |
| 142-10 | H | (CH$_2$)$_2$ | NO$_2$ | H | CH$_2$ | Pr | 4-(3-MeO—Pyr- |  |

TABLE 142-continued

| Ex. No. Comp. | R¹ | R² | R³ | R⁴ | Z | W | X | Y |
|---|---|---|---|---|---|---|---|---|
| | | | | | | | 6)-Ph | |
| 142-11 | H | (CH₂)₂ | NO₂ | H | CH₂ | Pr | 4-(3-Dma—Pyr-6)-Ph | O |
| 142-12 | H | (CH₂)₂ | NO₂ | H | CH₂ | Pr | 2-(4-F—Ph)-5-Pyr | O |
| 142-13 | H | (CH₂)₂ | NO₂ | H | CH₂ | Pr | 2-(4-MeO—Ph)-5-Pyr | O |
| 142-14 | H | (CH₂)₂ | NO₂ | H | CH₂ | Pr | 2-TfpO-5-Pyr | O |
| 142-15 | H | (CH₂)₂ | NO₂ | H | CH₂ | Bu | 4-Ph—Ph | O |
| 142-16 | H | (CH₂)₂ | NO₂ | H | CH₂ | Bu | 4-(Pyr-2)-Ph | O |
| 142-17 | H | (CH₂)₂ | NO₂ | H | CH₂ | Bu | 4-(3-MeO—Pyr-6)-Ph | O |
| 142-18 | H | (CH₂)₂ | NO₂ | H | CH₂ | Bu | 4-(3-Dma—Pyr-6)-Ph | O |
| 142-19 | H | (CH₂)₂ | NO₂ | H | CH₂ | Bu | 2-(4-F—Ph)-5-Pyr | O |
| 142-20 | H | (CH₂)₂ | NO₂ | H | CH₂ | Bu | 2-(4-MeO—Ph)-5-Pyr | O |
| 142-21 | H | (CH₂)₂ | NO₂ | H | CH₂ | Bu | 2-TfpO-5-Pyr | O |
| 142-22 | H | (CH₂)₂ | NO₂ | H | CH₂ | PhO | 4-Ph—Ph | O |
| 142-23 | H | (CH₂)₂ | NO₂ | H | CH₂ | PhO | 4-(Pyr-2)-Ph | O |
| 142-24 | H | (CH₂)₂ | NO₂ | H | CH₂ | PhO | 4-(3-MeO—Pyr-6)-Ph | O |
| 142-25 | H | (CH₂)₂ | NO₂ | H | CH₂ | PhO | 4-(3-Dma—Pyr-6)-Ph | O |
| 142-26 | H | (CH₂)₂ | NO₂ | H | CH₂ | PhO | 2-(4-F—Ph)-5-Pyr | O |
| 142-27 | H | (CH₂)₂ | NO₂ | H | CH₂ | PhO | 2-(4-MeO—Ph)-5-Pyr | O |
| 142-28 | H | (CH₂)₂ | NO₂ | H | CH₂ | PhO | 2-TfpO-5-Pyr | O |
| 142-29 | H | (CH₂)₂ | NO₂ | H | CH₂ | 4-iPr—PhO | 4-Ph—Ph | O |
| 142-30 | H | (CH₂)₂ | NO₂ | H | CH₂ | 4-iPr—PhO | 4-(Pyr-2)-Ph | O |
| 142-31 | H | (CH₂)₂ | NO₂ | H | CH₂ | 4-iPr—PhO | 4-(3-MeO—Pyr-6)-Ph | O |
| 142-32 | H | (CH₂)₂ | NO₂ | H | CH₂ | 4-iPr—PhO | 4-(3-Dma—Pyr-6)-Ph | O |
| 142-33 | H | (CH₂)₂ | NO₂ | H | CH₂ | 4-iPr—PhO | 2-(4-F—Ph)-5-Pyr | O |
| 142-34 | H | (CH₂)₂ | NO₂ | H | CH₂ | 4-iPr—PhO | 2-(4-MeO—Ph)-5-Pyr | O |
| 142-35 | H | (CH₂)₂ | NO₂ | H | CH₂ | 4-iPr—PhO | 2-TfPo-5-Pyr | O |
| 142-36 | H | (CH₂)₂ | NO₂ | H | CH₂ | 4-MeO—PhO | 4-Ph—Ph | O |
| 142-37 | H | (CH₂)₂ | NO₂ | H | CH₂ | 4-MeO—PhO | 4-(Pyr-2)-Ph | O |
| 142-38 | H | (CH₂)₂ | NO₂ | H | CH₂ | 4-MeO—PhO | 4-(3-MeO—Pyr-6)-Ph | O |
| 142-39 | H | (CH₂)₂ | NO₂ | H | CH₂ | 4-MeO—PhO | 4-(3-Dma—Pyr-6)-Ph | O |
| 142-40 | H | (CH₂)₂ | NO₂ | H | CH₂ | 4-MeO—PhO | 2-(4-F—Ph)-5-Pyr | O |
| 142-41 | H | (CH₂)₂ | NO₂ | H | CH₂ | 4-MeO—PhO | 2-(4-MeO—Ph)-5-Pyr | O |
| 142-42 | H | (CH₂)₂ | NO₂ | H | CH₂ | 4-MeO—PhO | 2-TfpO-5-Pyr | O |
| 142-43 | H | (CH₂)₂ | NO₂ | H | CH₂ | 4-Me—PhO | 4-Ph—Ph | O |
| 142-44 | H | (CH₂)₂ | NO₂ | H | CH₂ | 4-Me—PhO | 4-(Pyr-2)-Ph | O |
| 142-45 | H | (CH₂)₂ | NO₂ | H | CH₂ | 4-Me—PhO | 4-(3-MeO—Pyr-6)-Ph | O |
| 142-46 | H | (CH₂)₂ | NO₂ | H | CH₂ | 4-Me—PhO | 4-(3-Dma—Pyr-6)-Ph | O |
| 142-47 | H | (CH₂)₂ | NO₂ | H | CH₂ | 4-Me—PhO | 2-(4-F—Ph)-5-Pyr | O |
| 142-48 | H | (CH₂)₂ | NO₂ | H | CH₂ | 4-Me—PhO | 2-(4-MeO—Ph)-5-Pyr | O |
| 142-49 | H | (CH₂)₂ | NO₂ | H | CH₂ | 4-Me—PhO | 2-TfpO-5-Pyr | O |
| 142-50 | H | (CH₂)₂ | NO₂ | H | CH₂ | 4-tBu—PhO | 4-Ph—Ph | O |
| 142-51 | H | (CH₂)₂ | NO₂ | H | CH₂ | 4-tBu—PhO | 4-(Pyr-2)-Ph | O |
| 142-52 | H | (CH₂)₂ | NO₂ | H | CH₂ | 4-tBu—PhO | 4-(3-MeO—Pyr-6)-Ph | O |
| 142-53 | H | (CH₂)₂ | NO₂ | H | CH₂ | 4-tBu—PhO | 4-(3-Dma—Pyr-6)-Ph | O |
| 142-54 | H | (CH₂)₂ | NO₂ | H | CH₂ | 4-tBu—PhO | 2-(4-F—Ph)-5-Pyr | O |
| 142-55 | H | (CH₂)₂ | NO₂ | H | CH₂ | 4-tBu—PhO | 2-(4-MeO—Ph)-5-Pyr | O |
| 142-56 | H | (CH₂)₂ | NO₂ | H | CH₂ | 4-tBu—PhO | 2-TfpO-5-Pyr | O |
| 142-57 | H | (CH₂)₂ | NO₂ | H | CH₂ | 4-CF₃—PhO | 4-Ph—Ph | O |

TABLE 142-continued

| Ex. No. Comp. | R¹ | R² | R³ | R⁴ | Z | W | X | Y |
|---|---|---|---|---|---|---|---|---|
| 142-58 | H | (CH₂)₂ | NO₂ | H | CH₂ | 4-CF₃—PhO | 4-(Pyr-2)-Ph | O |
| 142-59 | H | (CH₂)₂ | NO₂ | H | CH₂ | 4-CF₃—PhO | 4-(3-MeO—Pyr-6)-Ph | O |
| 142-60 | H | (CH₂)₂ | NO₂ | H | CH₂ | 4-CF₃—PhO | 4-(3-Dma—Pyr-6)-Ph | O |
| 142-61 | H | (CH₂)₂ | NO₂ | H | CH₂ | 4-CF₃—PhO | 2-(4-F—Ph)-5-Pyr | O |
| 142-62 | H | (CH₂)₂ | NO₂ | H | CH₂ | 4-CF₃—PhO | 2-(4-MeO—Ph)-5-Pyr | O |
| 142-63 | H | (CH₂)₂ | NO₂ | H | CH₂ | 4-CF₃—PhO | 2-TfpO-5-Pyr | O |
| 142-64 | H | (CH₂)₂ | NO₂ | H | CH₂ | 4-CF₃O—PhO | 4-Ph—Ph | O |
| 142-65 | H | (CH₂)₂ | NO₂ | H | CH₂ | 4-CF₃O—PhO | 4-(Pyr-2)-Ph | O |
| 142-66 | H | (CH₂)₂ | NO₂ | H | CH₂ | 4-CF₃O—PhO | 4-(3-MeO—Pyr-6)-Ph | O |
| 142-67 | H | (CH₂)₂ | NO₂ | H | CH₂ | 4-CF₃O—PhO | 4-(3-Dma—Pyr-6)-Ph | O |
| 142-68 | H | (CH₂)₂ | NO₂ | H | CH₂ | 4-CF₃O—PhO | 2-(4-F—Ph)-5-Pyr | O |
| 142-69 | H | (CH₂)₂ | NO₂ | H | CH₂ | 4-CF₃O—PhO | 2-(4-MeO—Ph)-5-Pyr | O |
| 142-70 | H | (CH₂)₂ | NO₂ | H | CH₂ | 4-CF₃O—PhO | 2-TfpO-5-Pyr | O |
| 142-71 | H | (CH₂)₂ | NO₂ | H | CH₂ | 4-F—PhO | 4-Ph—Ph | O |
| 142-72 | H | (CH₂)₂ | NO₂ | H | CH₂ | 4-F—PhO | 4-(Pyr-2)-Ph | O |
| 142-73 | H | (CH₂)₂ | NO₂ | H | CH₂ | 4-F—PhO | 4-(3-MeO—Pyr-6)-Ph | O |
| 142-74 | H | (CH₂)₂ | NO₂ | H | CH₂ | 4-F—PhO | 4-(3-Dma—Pyr-6)-Ph | O |
| 142-75 | H | (CH₂)₂ | NO₂ | H | CH₂ | 4-F—PhO | 2-(4-F—Ph)-5-Pyr | O |
| 142-76 | H | (CH₂)₂ | NO₂ | H | CH₂ | 4-F—PhO | 2-(4-MeO—Ph)-5-Pyr | O |
| 142-77 | H | (CH₂)₂ | NO₂ | H | CH₂ | 4-F—PhO | 2-TfpO-5-Pyr | O |
| 142-78 | H | (CH₂)₂ | NO₂ | H | CH₂ | 4-Cl—PhO | 4-Ph—Ph | O |
| 142-79 | H | (CH₂)₂ | NO₂ | H | CH₂ | 4-Cl—PhO | 4-(Pyr-2)-Ph | O |
| 142-80 | H | (CH₂)₂ | NO₂ | H | CH₂ | 4-Cl—PhO | 4-(3-MeO—Pyr-6)-Ph | O |
| 142-81 | H | (CH₂)₂ | NO₂ | H | CH₂ | 4-Cl—PhO | 4-(3-Dma—Pyr-6)-Ph | O |
| 142-82 | H | (CH₂)₂ | NO₂ | H | CH₂ | 4-Cl—PhO | 2-(4-F—Ph)-5-Pyr | O |
| 142-83 | H | (CH₂)₂ | NO₂ | H | CH₂ | 4-Cl—PhO | 2-(4-MeO—Ph)-5-Pyr | O |
| 142-84 | H | (CH₂)₂ | NO₂ | H | CH₂ | 4-Cl—PhO | 2-TfpO-5-Pyr | O |
| 142-85 | H | (CH₂)₂ | NO₂ | H | CH₂ | 3-F—PhO | 4-Ph—Ph | O |
| 142-86 | H | (CH₂)₂ | NO₂ | H | CH₂ | 3-F—PhO | 4-(Pyr-2)-Ph | O |
| 142-87 | H | (CH₂)₂ | NO₂ | H | CH₂ | 3-F—PhO | 4-(3-MeO—Pyr-6)-Ph | O |
| 142-88 | H | (CH₂)₂ | NO₂ | H | CH₂ | 3-F—PhO | 4-(3-Dma—Pyr-6)-Ph | O |
| 142-89 | H | (CH₂)₂ | NO₂ | H | CH₂ | 3-F—PhO | 2-(4-F—Ph)-5-Pyr | O |
| 142-90 | H | (CH₂)₂ | NO₂ | H | CH₂ | 3-F—PhO | 2-(4-MeO—Ph)-5-Pyr | O |
| 142-91 | H | (CH₂)₂ | NO₂ | H | CH₂ | 3-F—PhO | 2-TfpO-5-Pyr | O |

TABLE 143

| Ex. No. Comp. | R¹ | R² | R³ | R⁴ | Z | W | X | Y |
|---|---|---|---|---|---|---|---|---|
| 143-1 | H | (CH₂)₂ | Ac | H | CH₂ | EtO | 4-Ph—Ph | O |
| 143-2 | H | (CH₂)₂ | Ac | H | CH₂ | EtO | 4-(Pyr-2)-Ph | O |
| 143-3 | H | (CH₂)₂ | Ac | H | CH₂ | EtO | 4-(3-MeO—Pyr-6)-Ph | O |
| 143-4 | H | (CH₂)₂ | Ac | H | CH₂ | EtO | 4-(3-Dma—Pyr-6)-Ph | O |
| 143-5 | H | (CH₂)₂ | Ac | H | CH₂ | EtO | 2-(4-F—Ph)-5-Pyr | O |
| 143-6 | H | (CH₂)₂ | Ac | H | CH₂ | EtO | 2-(4-MeO—Ph)-5-Pyr | O |
| 143-7 | H | (CH₂)₂ | Ac | H | CH₂ | EtO | 2-TfpO-5-Pyr | O |

TABLE 143-continued

| Ex. No. Comp. | R¹ | R² | R³ | R⁴ | Z | W | X | Y |
|---|---|---|---|---|---|---|---|---|
| 143-8 | H | (CH$_2$)$_2$ | Ac | H | CH$_2$ | Pr | 4-Ph—Ph | O |
| 143-9 | H | (CH$_2$)$_2$ | Ac | H | CH$_2$ | Pr | 4-(Pyr-2)-Ph | O |
| 143-10 | H | (CH$_2$)$_2$ | Ac | H | CH$_2$ | Pr | 4-(3-MeO—Pyr-6)-Ph | O |
| 143-11 | H | (CH$_2$)$_2$ | Ac | H | CH$_2$ | Pr | 4-(3-Dma—Pyr-6)-Ph | O |
| 143-12 | H | (CH$_2$)$_2$ | Ac | H | CH$_2$ | Pr | 2-(4-F—Ph)-5-Pyr | O |
| 143-13 | H | (CH$_2$)$_2$ | Ac | H | CH$_2$ | Pr | 2-(4-MeO—Ph)-5-Pyr | O |
| 143-14 | H | (CH$_2$)$_2$ | Ac | H | CH$_2$ | Pr | 2-TfpO-5-Pyr | O |
| 143-15 | H | (CH$_2$)$_2$ | Ac | H | CH$_2$ | Bu | 4-Ph—Ph | O |
| 143-16 | H | (CH$_2$)$_2$ | Ac | H | CH$_2$ | Bu | 4-(Pyr-2)-Ph | O |
| 143-17 | H | (CH$_2$)$_2$ | Ac | H | CH$_2$ | Bu | 4-(3-MeO—Pyr-6)-Ph | O |
| 143-18 | H | (CH$_2$)$_2$ | Ac | H | CH$_2$ | Bu | 4-(3-Dma—Pyr-6)-Ph | O |
| 143-19 | H | (CH$_2$)$_2$ | Ac | H | CH$_2$ | Bu | 2-(4-F—Ph)-5-Pyr | O |
| 143-20 | H | (CH$_2$)$_2$ | Ac | H | CH$_2$ | Bu | 2-(4-MeO—Ph)-5-Pyr | O |
| 143-21 | H | (CH$_2$)$_2$ | Ac | H | CH$_2$ | Bu | 2-TfpO-5-Pyr | O |
| 143-22 | H | (CH$_2$)$_2$ | Ac | H | CH$_2$ | PhO | 4-Ph—Ph | O |
| 143-23 | H | (CH$_2$)$_2$ | Ac | H | CH$_2$ | PhO | 4-(Pyr-2)-Ph | O |
| 143-24 | H | (CH$_2$)$_2$ | Ac | H | CH$_2$ | PhO | 4-(3-MeO—Pyr-6)-Ph | O |
| 143-25 | H | (CH$_2$)$_2$ | Ac | H | CH$_2$ | PhO | 4-(3-Dma—Pyr-6)-Ph | O |
| 143-26 | H | (CH$_2$)$_2$ | Ac | H | CH$_2$ | PhO | 2-(4-F—Ph)-5-Pyr | O |
| 143-27 | H | (CH$_2$)$_2$ | Ac | H | CH$_2$ | PhO | 2-(4-MeO—Ph)-5-Pyr | O |
| 143-28 | H | (CH$_2$)$_2$ | Ac | H | CH$_2$ | PhO | 2-TfpO-5-Pyr | O |
| 143-29 | H | (CH$_2$)$_2$ | Ac | H | CH$_2$ | 4-iPr—PhO | 4-Ph—Ph | O |
| 143-30 | H | (CH$_2$)$_2$ | Ac | H | CH$_2$ | 4-iPr—PhO | 4-(Pyr-2)-Ph | O |
| 143-31 | H | (CH$_2$)$_2$ | Ac | H | CH$_2$ | 4-iPr—PhO | 4-(3-MeO—Pyr-6)-Ph | O |
| 143-32 | H | (CH$_2$)$_2$ | Ac | H | CH$_2$ | 4-iPr—PhO | 4-(3-Dma—Pyr-6)-Ph | O |
| 143-33 | H | (CH$_2$)$_2$ | Ac | H | CH$_2$ | 4-iPr—PhO | 2-(4-F—Ph)-5-Pyr | O |
| 143-34 | H | (CH$_2$)$_2$ | Ac | H | CH$_2$ | 4-iPr—PhO | 2-(4-MeO—Ph)-5-Pyr | O |
| 143-35 | H | (CH$_2$)$_2$ | Ac | H | CH$_2$ | 4-iPr—PhO | 2-TfpO-5-Pyr | O |
| 143-36 | H | (CH$_2$)$_2$ | Ac | H | CH$_2$ | 4-MeO—PhO | 4-Ph—Ph | O |
| 143-37 | H | (CH$_2$)$_2$ | Ac | H | CH$_2$ | 4-MeO—PhO | 4-(Pyr-2)-Ph | O |
| 143-38 | H | (CH$_2$)$_2$ | Ac | H | CH$_2$ | 4-MeO—PhO | 4-(3-MeO—Pyr-6)-Ph | O |
| 143-39 | H | (CH$_2$)$_2$ | Ac | H | CH$_2$ | 4-MeO—PhO | 4-(3-Dma—Pyr-6)-Ph | O |
| 143-40 | H | (CH$_2$)$_2$ | Ac | H | CH$_2$ | 4-MeO—PhO | 2-(4-F—Ph)-5-Pyr | O |
| 143-41 | H | (CH$_2$)$_2$ | Ac | H | CH$_2$ | 4-MeO—PhO | 2-(4-MeO—Ph)-5-Pyr | O |
| 143-42 | H | (CH$_2$)$_2$ | Ac | H | CH$_2$ | 4-MeO—PhO | 2-TfpO-5-Pyr | O |
| 143-43 | H | (CH$_2$)$_2$ | Ac | :H | CH$_2$ | 4-Me—PhO | 4-Ph—Ph | O |
| 143-44 | H | (CH$_2$)$_2$ | Ac | H | CH$_2$ | 4-Me—PhO | 4-(Pyr-2)-Ph | O |
| 143-45 | H | (CH$_2$)$_2$ | Ac | H | CH$_2$ | 4-Me—PhO | 4-(3-MeO—Pyr-6)-Ph | O |
| 143-46 | H | (CH$_2$)$_2$ | Ac | H | CH$_2$ | 4-Me—PhO | 4-(3-Dma—Pyr-6)-Ph | O |
| 143-47 | H | (CH$_2$)$_2$ | Ac | H | CH$_2$ | 4-Me—PhO | 2-(4-F—Ph)-5-Pyr | O |
| 143-48 | H | (CH$_2$)$_2$ | Ac | H | CH$_2$ | 4-Me—PhO | 2-(4-MeO—Ph)-5-Pyr | O |
| 143-49 | H | (CH$_2$)$_2$ | Ac | H | CH$_2$ | 4-Me—PhO | 2-TfpO-5-Pyr | O |
| 143-50 | H | (CH$_2$)$_2$ | Ac | H | CH$_2$ | 4-tBu—PhO | 4-Ph—Ph | O |
| 143-51 | H | (CH$_2$)$_2$ | Ac | H | CH$_2$ | 4-tBu—PhO | 4-(Pyr-2)-Ph | O |
| 143-52 | H | (CH$_2$)$_2$ | Ac | H | CH$_2$ | 4-tBu—PhO | 4-(3-MeO—Pyr-6)-Ph | O |
| 143-53 | H | (CH$_2$)$_2$ | Ac | H | CH$_2$ | 4-tBu—PhO | 4-(3-Dma—Pyr-6)-Ph | O |
| 143-54 | H | (CH$_2$)$_2$ | Ac | H | CH$_2$ | 4-tBu—PhO | 2-(4-F—Ph)-5-Pyr | O |
| 143-55 | H | (CH$_2$)$_2$ | Ac | H | CH$_2$ | 4-tBu—PhO | 2-(4-MeO—Ph)- | O |

TABLE 143-continued

| Ex. No. Comp. | R¹ | R² | R³ | R⁴ | Z | W | X | Y |
|---|---|---|---|---|---|---|---|---|
| | | | | | | | 5-Pyr | |
| 143-56 | H | (CH$_2$)$_2$ | Ac | H | CH$_2$ | 4-tBu—PhO | 2-TfpO-5-Pyr | O |
| 143-57 | H | (CH$_2$)$_2$ | Ac | H | CH$_2$ | 4-CF$_3$—PhO | 4-Ph—Ph | O |
| 143-58 | H | (CH$_2$)$_2$ | Ac | H | CH$_2$ | 4-CF$_3$—PhO | 4-(Pyr-2)-Ph | O |
| 143-59 | H | (CH$_2$)$_2$ | Ac | H | CH$_2$ | 4-CF$_3$—PhO | 4-(3-MeO—Pyr-6)-Ph | O |
| 143-60 | H | (CH$_2$)$_2$ | Ac | H | CH$_2$ | 4-CF$_3$—PhO | 4-(3-Dma—Pyr-6)-Ph | O |
| 143-61 | H | (CH$_2$)$_2$ | Ac | H | CH$_2$ | 4-CF$_3$—PhO | 2-(4-F—Ph)-5-Pyr | O |
| 143-62 | H | (CH$_2$)$_2$ | Ac | H | CH$_2$ | 4-CF$_3$—PhO | 2-(4-MeO—Ph)-5-Pyr | O |
| 143-63 | H | (CH$_2$)$_2$ | Ac | H | CH$_2$ | 4-CF$_3$—PhO | 2-TfpO-5-Pyr | O |
| 143-64 | H | (CH$_2$)$_2$ | Ac | H | CH$_2$ | 4-CF$_3$O—PhO | 4-Ph—Ph | O |
| 143-65 | H | (CH$_2$)$_2$ | Ac | H | CH$_2$ | 4-CF$_3$O—PhO | 4-(Pyr-2)-Ph | O |
| 143-66 | H | (CH$_2$)$_2$ | Ac | H | CH$_2$ | 4-CF$_3$O—PhO | 4-(3-MeO—Pyr-6)-Ph | O |
| 143-67 | H | (CH$_2$)$_2$ | Ac | H | CH$_2$ | 4-CF$_3$O—PhO | 4-(3-Dma—Pyr-6)-Ph | O |
| 143-68 | H | (CH$_2$)$_2$ | Ac | H | CH$_2$ | 4-CF$_3$O—PhO | 2-(4-F—Ph)-5-Pyr | O |
| 143-69 | H | (CH$_2$)$_2$ | Ac | H | CH$_2$ | 4-CF$_3$O—PhO | 2-(4-MeO—Ph)-5-Pyr | O |
| 143-70 | H | (CH$_2$)$_2$ | Ac | H | CH$_2$ | 4-CF$_3$O—PhO | 2-TfpO-5-Pyr | O |
| 143-71 | H | (CH$_2$)$_2$ | Ac | H | CH$_2$ | 4-F—PhO | 4-Ph—Ph | O |
| 143-72 | H | (CH$_2$)$_2$ | Ac | H | CH$_2$ | 4-F—PhO | 4-(Pyr-2)-Ph | O |
| 143-73 | H | (CH$_2$)$_2$ | Ac | H | CH$_2$ | 4-F—PhO | 4-(3-MeO—Pyr-6)-Ph | O |
| 143-74 | H | (CH$_2$)$_2$ | Ac | H | CH$_2$ | 4-F—PhO | 4-(3-Dma—Pyr-6)-Ph | O |
| 143-75 | H | (CH$_2$)$_2$ | Ac | H | CH$_2$ | 4-F—PhO | 2-(4-F—Ph)-5-Pyr | O |
| 143-76 | H | (CH$_2$)$_2$ | Ac | H | CH$_2$ | 4-F—PhO | 2-(4-MeO—Ph)-5-Pyr | O |
| 143-77 | H | (CH$_2$)$_2$ | Ac | H | CH$_2$ | 4-F—PhO | 2-TfpO-5-Pyr | O |
| 143-78 | H | (CH$_2$)$_2$ | Ac | H. | CH$_2$ | 4-Cl—PhO | 4-Ph—Ph | O |
| 143-79 | H | (CH$_2$)$_2$ | Ac | H | CH$_2$ | 4-Cl—PhO | 4-(Pyr-2)-Ph | O |
| 143-80 | H | (CH$_2$)$_2$ | Ac | H | CH$_2$ | 4-Cl—PhO | 4-(3-MeO—Pyr-6)-Ph | O |
| 143-81 | H | (CH$_2$)$_2$ | Ac | H | CH$_2$ | 4-Cl—PhO | 4-(3-Dma—Pyr-6)-Ph | O |
| 143-82 | H | (CH$_2$)$_2$ | Ac | H | CH$_2$ | 4-Cl—PhO | 2-(4-F—Ph)-5-Pyr | O |
| 143-83 | H | (CH$_2$)$_2$ | Ac | H | CH$_2$ | 4-Cl—PhO | 2-(4-MeO—Ph)-5-Pyr | O |
| 143-84 | H | (CH$_2$)$_2$ | Ac | H | CH$_2$ | 4-Cl—PhO | 2-TfpO-5-Pyr | O |
| 143-85 | H | (CH$_2$)$_2$ | Ac | H | CH$_2$ | 3-F—PhO | 4-Ph—Ph | O |
| 143-86 | H | (CH$_2$)$_2$ | Ac | H | CH$_2$ | 3-F—PhO | 4-(Pyr-2)-Ph | O |
| 143-87 | H | (CH$_2$)$_2$ | Ac | H | CH$_2$ | 3-F—PhO | 4-(3-MeO—Pyr-6)-Ph | O |
| 143-88 | H | (CH$_2$)$_2$ | Ac | H | CH$_2$ | 3-F—PhO | 4-(3-Dma—Pyr-6)-Ph | O |
| 143-89 | H | (CH$_2$)$_2$ | Ac | H | CH$_2$ | 3-F—PhO | 2-(4-F—Ph)-5-Pyr | O |
| 143-90 | H | (CH$_2$)$_2$ | Ac | H | CH$_2$ | 3-F—PhO | 2-(4-MeO—Ph)-5-Pyr | O |
| 143-91 | H | (CH$_2$)$_2$ | Ac | H | CH$_2$ | 3-F—PhO | 2-TfpO-5-Pyr | O |

TABLE 144

| Ex. No. Comp. | R¹ | R² | R³ | R⁴ | Z | W | X | Y |
|---|---|---|---|---|---|---|---|---|
| 144-1 | H | (CH$_2$)$_2$ | H | H | CH$_2$ | MeNH | Ph | O |
| 144-2 | H | (CH$_2$)$_2$ | H | H | CH$_2$ | MeNH | 4-Ph—Ph | O |
| 144-3 | H | (CH$_2$)$_2$ | H | H | CH$_2$ | MeNH | 4-(Pyr-2)-Ph | O |
| 144-4 | H | (CH$_2$)$_2$ | H | H | CH$_2$ | MeNH | 4-(Pyr-3)-Ph | O |
| 144-5 | H | (CH$_2$)$_2$ | H | H | CH$_2$ | MeNH | 4-(Pyr-4)-Ph | O |
| 144-6 | H | (CH$_2$)$_2$ | H | H | CH$_2$ | EtNH | Ph | O |
| 144-7 | H | (CH$_2$)$_2$ | H | H | CH$_2$ | EtNH | 4-Ph—Ph | O |
| 144-8 | H | (CH$_2$)$_2$ | H | H | CH$_2$ | EtNH | 4-(Pyr-2)-Ph | O |

TABLE 144-continued

| Ex. No. Comp. | R¹ | R² | R³ | R⁴ | Z | W | X | Y |
|---|---|---|---|---|---|---|---|---|
| 144-9 | H | (CH₂)₂ | H | H | CH₂ | EtNH | 4-(Pyr-3)-Ph | O |
| 144-10 | H | (CH₂)₂ | H | H | CH₂ | EtNH | 4-(Pyr-4)-Ph | O |
| 144-11 | H | (CH₂)₂ | H | H | CH₂ | PrNH | Ph | O |
| 144-12 | H | (CH₂)₂ | H | H | CH₂ | PrNH | 4-Ph—Ph | O |
| 144-13 | H | (CH₂)₂ | H | H | CH₂ | PrNH | 4-(Pyr-2)-Ph | O |
| 144-14 | H | (CH₂)₂ | H | H | CH₂ | PrNH | 4-(Pyr-3)-Ph | O |
| 144-15 | H | (CH₂)₂ | H | H | CH₂ | PrNH | 4-(Pyr-4)-Ph | O |
| 144-16 | H | (CH₂)₂ | H | H | CH₂ | BuNH | Ph | O |
| 144-17 | H | (CH₂)₂ | H | H | CH₂ | BuNH | 4-Ph—Ph | O |
| 144-18 | H | (CH₂)₂ | H | H | CH₂ | BuNH | 4-(Pyr-2)-Ph | O |
| 144-19 | H | (CH₂)₂ | H | H | CH₂ | BuNH | 4-(Pyr-3)-Ph | O |
| 144-20 | H | (CH₂)₂ | H | H | CH₂ | BuNH | 4-(Pyr-4)-Ph | O |
| 144-21 | H | (CH₂)₂ | H | H | CH₂ | Me₂N | Ph | O |
| 144-22 | H | (CH₂)₂ | H | H | CH₂ | Me₂N | 4-Ph—Ph | O |
| 144-23 | H | (CH₂)₂ | H | H | CH₂ | Me₂N | 4-(Pyr-2)-Ph | O |
| 144-24 | H | (CH₂)₂ | H | H | CH₂ | Me₂N | 4-(Pyr-3)-Ph | O |
| 144-25 | H | (CH₂)₂ | H | H | CH₂ | Me₂N | 4-(Pyr-4)-Ph | O |
| 144-26 | H | (CH₂)₂ | H | H | CH₂ | Et₂N | Ph | O |
| 144-27 | H | (CH₂)₂ | H | H | CH₂ | Et₂N | 4-Ph—Ph | O |
| 144-28 | H | (CH₂)₂ | H | H | CH₂ | Et₂N | 4-(Pyr-2)-Ph | O |
| 144-29 | H | (CH₂)₂ | H | H | CH₂ | Et₂N | 4-(Pyr-3)-Ph | O |
| 144-30 | H | (CH₂)₂ | H | H | CH₂ | Et₂N | 4-(Pyr-4)-Ph | O |
| 144-31 | H | (CH₂)₂ | H | H | CH₂ | EtPhN | Ph | O |
| 144-32 | H | (CH₂)₂ | H | H | CH₂ | EtPhN | 4-Ph—Ph | O |
| 144-33 | H | (CH₂)₂ | H | H | CH₂ | EtPhN | 4-(Pyr-2)-Ph | O |
| 144-34 | H | (CH₂)₂ | H | H | CH₂ | EtPhN | 4-(Pyr-3)-Ph | O |
| 144-35 | H | (CH₂)₂ | H | H | CH₂ | EtPhN | 4-(Pyr-4)-Ph | O |
| 144-36 | H | (CH₂)₂ | H | H | CH₂ | 1-Pyrr | Ph | O |
| 144-37 | H | (CH₂)₂ | H | H | CH₂ | 1-Pyrr | 4-Ph—Ph | O |
| 144-38 | H | (CH₂)₂ | H | H | CH₂ | 1-Pyrr | 4-(Pyr-2)-Ph | O |
| 144-39 | H | (CH₂)₂ | H | H | CH₂ | 1-Pyrr | 4-(Pyr-3)-Ph | O |
| 144-40 | H | (CH₂)₂ | H | H | CH₂ | 1-Pyrr | 4-(Pyr-4)-Ph | O |
| 144-41 | H | (CH₂)₂ | H | H | CH₂ | 2-(PhSO₂)—PhNH | Ph | O |
| 144-42 | H | (CH₂)₂ | H | H | CH₂ | 2-(PhSO₂)—PhNH | 4-Ph—Ph | O |
| 144-43 | H | (CH₂)₂ | H | H | CH₂ | 2-(PhSO₂)—PhNH | 4-(Pyr-2)-Ph | O |
| 144-44 | H | (CH₂)₂ | H | H | CH₂ | 2-(PhSO₂)—PhNH | 4-(Pyr-3)-Ph | O |
| 144-45 | H | (CH₂)₂ | H | H | CH₂ | 2-(PhSO₂)—PhNH | 4-(Pyr-4)-Ph | O |
| 144-46 | H | (CH₂)₂ | H | H | CH₂ | 4-(PhSO₂)—PhNH | Ph | O |
| 144-47 | H | (CH₂)₂ | H | H | CH₂ | 4-(PhSO₂)—PhNH | 4-Ph—Ph | O |
| 144-48 | H | (CH₂)₂ | H | H | CH₂ | 4-(PhSO₂)—PhNH | 4-(Pyr-2)-Ph | O |
| 144-49 | H | (CH₂)₂ | H | H | CH₂ | 4-(PhSO₂)—PhNH | 4-(Pyr-3)-Ph | O |
| 144-50 | H | (CH₂)₂ | H | H | CH₂ | 4-(PhSO₂)—PhNH | 4-(Pyr-4)-Ph | O |
| 144-51 | H | (CH₂)₂ | H | H | CH₂ | 2-(PhSO₂NH)—PhNH | Ph | O |
| 144-52 | H | (CH₂)₂ | H | H | CH₂ | 2-(PhSO₂NH)—PhNH | 4-Ph—Ph | O |
| 144-53 | H | (CH₂)₂ | H | H | CH₂ | 2-(PhSO₂NH)—PhNH | 4-(Pyr-2)-Ph | O |
| 144-54 | H | (CH₂)₂ | H | H | CH₂ | 2-(PhSO₂NH)—PhNH | 4-(Pyr-3)-Ph | O |
| 144-55 | H | (CH₂)₂ | H | H | CH₂ | 2-(PhSO₂NH)—PhNH | 4-(Pyr-4)-Ph | O |
| 144-56 | H | (CH₂)₂ | H | H | CH₂ | 4-(PhSO₂NH)—PhNH | Ph | O |
| 144-57 | H | (CH₂)₂ | H | H | CH₂ | 4-(PhSO₂NH)—PhNH | 4-Ph—Ph | O |
| 144-58 | H | (CH₂)₂ | H | H | CH₂ | 4-(PhSO₂NH)—PhNH | 4-(Pyr-2)-Ph | O |
| 144-59 | H | (CH₂)₂ | H | H | CH₂ | 4-(PhSO₂NH)—PhNH | 4-(Pyr-3)-Ph | O |
| 144-60 | H | (CH₂)₂ | H | H | CH₂ | 4-(PhSO₂NH)—PhNH | 4-(Pyr-4)-Ph | O |
| 144-61 | H | (CH₂)₂ | H | H | CH₂ | BzCO₂NH | Ph | O |
| 144-62 | H | (CH₂)₂ | H | H | CH₂ | BzCO₂NH | 4-Ph—Ph | O |
| 144-63 | H | (CH₂)₂ | H | H | CH₂ | BzCO₂NH | 4-(Pyr-2)-Ph | O |

TABLE 144-continued

| Ex. No. Comp. | R¹ | R² | R³ | R⁴ | Z | W | X | Y |
|---|---|---|---|---|---|---|---|---|
| 144-64 | H | (CH₂)₂ | H | H | CH₂ | BzCO₂NH | 4-(Pyr-3)-Ph | O |
| 144-65 | H | (CH₂)₂ | H | H | CH₂ | BzCO₂NH | 4-(Pyr-4)-Ph | O |
| 144-66 | H | (CH₂)₂ | H | H | CH₂ | PhNH | Ph | O |
| 144-67 | H | (CH₂)₂ | H | H | CH₂ | PhNH | 4-Ph—Ph | O |
| 144-68 | H | (CH₂)₂ | H | H | CH₂ | PhNH | 4-(Pyr-2)-Ph | O |
| 144-69 | H | (CH₂)₂ | H | H | CH₂ | PhNH | 4-(Pyr-3)-Ph | O |
| 144-70 | H | (CH₂)₂ | H | H | CH₂ | PhNH | 4-(Pyr-4)-Ph | O |

TABLE 145

| Ex. No. Comp. | R¹ | R² | R³ | R⁴ | Z | W | X | Y |
|---|---|---|---|---|---|---|---|---|
| 145-1 | H | (CH₂)₂ | H | Me | CH₂ | 4-tBu—PhO | 4-Ph—Ph | O |
| 145-2 | H | (CH₂)₂ | H | Me | CH₂ | 4-tBu—PhO | 4-(4-HO—Ph)—Ph | O |
| 145-3 | H | (CH₂)₂ | H | Me | CH₂ | 4-tBu—PhO | 4-(4-MeO—Ph)—Ph | O |
| 145-4 | H | (CH₂)₂ | H | Me | CH₂ | 4-tBu—PhO | 4-(4-F—Ph)—Ph | O |
| 145-5 | H | (CH₂)₂ | H | Me | CH₂ | 4-tBu—PhO | 4-(4-Cl—Ph)—Ph | O |
| 145-6 | H | (CH₂)₂ | H | Me | CH₂ | 4-tBu—PhO | 4-(Pyr-2)-Ph | O |
| 145-7 | H | (CH₂)₂ | H | Me | CH₂ | 4-tBu—PhO | 4-(Pyr-3)-Ph | O |
| 145-8 | H | (CH₂)₂ | H | Me | CH₂ | 4-tBu—PhO | 4-(Pyr-4)-Ph | O |
| 145-9 | H | (CH₂)₂ | H | Me | CH₂ | 4-tBu—PhO | 4-(3-MeO—Pyr-6)-Ph | O |
| 145-10 | H | (CH₂)₂ | H | Me | CH₂ | 4-tBu—PhO | 4-(3-Dma—Pyr-6)-Ph | O |
| 145-11 | H | (CH₂)₂ | H | Me | CH₂ | 4-tBu—PhO | 4-(3-CF₃—Pyr-6)-Ph | O |
| 145-12 | H | (CH₂)₂ | H | Me | CH₂ | 4-tBu—PhO | 4-(3-O₂N—Pyr-6)-Ph | O |
| 145-13 | H | (CH₂)₂ | H | Me | CH₂ | 4-tBu—PhO | 2-Ph-5-Pyr | O |
| 145-14 | H | (CH₂)₂ | H | Me | CH₂ | 4-tBu—PhO | 2-(4-F—Ph)-5-Pyr | O |
| 145-15 | H | (CH₂)₂ | H | Me | CH₂ | 4-tBu—PhO | 2-(4-MeO—Ph)-5-Pyr | O |
| 145-16 | H | (CH₂)₂ | H | Me | CH₂ | 4-tBu—PhO | 2-TfpO-5-Pyr | O |
| 145-17 | H | (CH₂)₂ | H | Me | CH₂ | 4-CF₃—PhO | 4-Ph—Ph | O |
| 145-18 | H | (CH₂)₂ | H | Me | CH₂ | 4-CF₃—PhO | 4-(4-HO—Ph)—Ph | O |
| 145-19 | H | (CH₂)₂ | H | Me | CH₂ | 4-CF₃—PhO | 4-(4-MeO—Ph)—Ph | O |
| 145-20 | H | (CH₂)₂ | H | Me | CH₂ | 4-CF₃—PhO | 4-(4-F—Ph)—Ph | O |
| 145-21 | H | (CH₂)₂ | H | Me | CH₂ | 4-CF₃—PhO | 4-(4-Cl—Ph)—Ph | O |
| 145-22 | H | (CH₂)₂ | H | Me | CH₂ | 4-CF₃—PhO | 4-(Pyr-2)-Ph | O |
| 145-23 | H | (CH₂)₂ | H | Me | CH₂ | 4-CF₃—PhO | 4-(Pyr-3)-Ph | O |
| 145-24 | H | (CH₂)₂ | H | Me | CH₂ | 4-CF₃—PhO | 4-(Pyr-4)-Ph | O |
| 145-25 | H | (CH₂)₂ | H | Me | CH₂ | 4-CF₃—PhO | 4-(3-MeO—Pyr-6)-Ph | O |
| 145-26 | H | (CH₂)₂ | H | Me | CH₂ | 4-CF₃—PhO | 4-(3-Dma—Pyr-6)-Ph | O |
| 145-27 | H | (CH₂)₂ | H | Me | CH₂ | 4-CF₃—PhO | 4-(3-CF₃—Pyr-6)-Ph | O |
| 145-28 | H | (CH₂)₂ | H | Me | CH₂ | 4-CF₃—PhO | 4-(3-O₂N—Pyr-6)-Ph | O |
| 145-29 | H | (CH₂)₂ | H | Me | CH₂ | 4-CF₃—PhO | 2-Ph-5-Pyr | O |
| 145-30 | H | (CH₂)₂ | H | Me | CH₂ | 4-CF₃—PhO | 2-(4-F—Ph)-5-Pyr | O |
| 145-31 | H | (CH₂)₂ | H | Me | CH₂ | 4-CF₃—PhO | 2-(4-MeO—Ph)-5-Pyr | O |

TABLE 145-continued

| Ex. No. Comp. | R¹ | R² | R³ | R⁴ | Z | W | X | Y |
|---|---|---|---|---|---|---|---|---|
| 145-32 | H | (CH₂)₂ | H | Me | CH₂ | 4-CF₃—PhO | 2-TfpO-5-Pyr | O |
| 145-33 | H | (CH₂)₂ | H | Me | CH₂ | 4-CF₃O—PhO | 4-Ph—Ph | O |
| 145-34 | H | (CH₂)₂ | H | Me | CH₂ | 4-CF₃O—PhO | 4-(4-HO—Ph)—Ph | O |
| 145-35 | H | (CH₂)₂ | H | Me | CH₂ | 4-CF₃O—PhO | 4-(4-MeO—Ph)—Ph | O |
| 145-36 | H | (CH₂)₂ | H | Me | CH₂ | 4-CF₃O—PhO | 4-(4-F—Ph)—Ph | O |
| 145-37 | H | (CH₂)₂ | H | Me | CH₂ | 4-CF₃O—PhO | 4-(4-Cl—Ph)—Ph | O |
| 145-38 | H | (CH₂)₂ | H | Me | CH₂ | 4-CF₃O—PhO | 4-(Pyr-2)-Ph | O |
| 145-39 | H | (CH₂)₂ | H | Me | CH₂ | 4-CF₃O—PhO | 4-(Pyr-3)-Ph | O |
| 145-40 | H | (CH₂)₂ | H | Me | CH₂ | 4-CF₃O—PhO | 4-(Pyr-4)-Ph | O |
| 145-41 | H | (CH₂)₂ | H | Me | CH₂ | 4-CF₃O—PhO | 4-(3-MeO—Pyr-6)-Ph | O |
| 145-42 | H | (CH₂)₂ | H | Me | CH₂ | 4-CF₃O—PhO | 4-(3-Dma—Pyr-6)-Ph | O |
| 145-43 | H | (CH₂)₂ | H | Me | CH₂ | 4-CF₃O—PhO | 4-(3-CF₃—Pyr-6)-Ph | O |
| 145-44 | H | (CH₂)₂ | H | Me | CH₂ | 4-CF₃O—PhO | 4-(3-O₂N—Pyr-6)-Ph | O |
| 145-45 | H | (CH₂)₂ | H | Me | CH₂ | 4-CF₃O—PhO | 2-Ph-5-Pyr | O |
| 145-46 | H | (CH₂)₂ | H | Me | CH₂ | 4-CF₃O—PhO | 2-(4-F—Ph)-5-Pyr | O |
| 145-47 | H | (CH₂)₂ | H | Me | CH₂ | 4-CF₃O—PhO | 2-(4-MeO—Ph)-5-Pyr | O |
| 145-48 | H | (CH₂)₂ | H | Me | CH₂ | 4-CF₃O—PhO | 2-TfpO-5-Pyr | O |
| 145-49 | H | (CH₂)₂ | H | Me | CH₂ | 4-F—PhO | 4-Ph—Ph | O |
| 145-50 | H | (CH₂)₂ | H | Me | CH₂ | 4-F—PhO | 4-(4-HO—Ph)—Ph | O |
| 145-51 | H | (CH₂)₂ | H | Me | CH₂ | 4-F—PhO | 4-(4-MeO—Ph)—Ph | O |
| 145-52 | H | (CH₂)₂ | H | Me | CH₂ | 4-F—PhO | 4-(4-F—Ph)—Ph | O |
| 145-53 | H | (CH₂)₂ | H | Me | CH₂ | 4-F—PhO | 4-(4-Cl—Ph)—Ph | O |
| 145-54 | H | (CH₂)₂ | H | Me | CH₂ | 4-F—PhO | 4-(Pyr-2)-Ph | O |
| 145-55 | H | (CH₂)₂ | H | Me | CH₂ | 4-F—PhO | 4-(Pyr-3)-Ph | O |
| 145-56 | H | (CH₂)₂ | H | Me | CH₂ | 4-F—PhO | 4-(Pyr-4)-Ph | O |
| 145-57 | H | (CH₂)₂ | H | Me | CH₂ | 4-F—PhO | 4-(3-MeO—Pyr-6)-Ph | O |
| 145-58 | H | (CH₂)₂ | H | Me | CH₂ | 4-F—PhO | 4-(3-Dma—Pyr-6)-Ph | O |
| 145-59 | H | (CH₂)₂ | H | Me | CH₂ | 4-F—PhO | 4-(3-CF₃—Pyr-6)-Ph | O |
| 145-60 | H | (CH₂)₂ | H | Me | CH₂ | 4-F—PhO | 4-(3-O₂N—Pyr-6)-Ph | O |
| 145-61 | H | (CH₂)₂ | H | Me | CH₂ | 4-F—PhO | 2-Ph-5-Pyr | O |
| 145-62 | H | (CH₂)₂ | H | Me | CH₂ | 4-F—PhO | 2-(4-F—Ph)-5-Pyr | O |
| 145-63 | H | (CH₂)₂ | H | Me | CH₂ | 4-F—PhO | 2-(4-MeO—Ph)-5-Pyr | O |
| 145-64 | H | (CH₂)₂ | H | Me | CH₂ | 4-F—PhO | 2-TfpO-5-Pyr | O |
| 145-65 | H | (CH₂)₂ | H | Me | CH₂ | 4-Cl—PhO | 4-Ph—Ph | O |
| 145-66 | H | (CH₂)₂ | H | Me | CH₂ | 4-Cl—PhO | 4-(4-HO—Ph)—Ph | O |
| 145-67 | H | (CH₂)₂ | H | Me | CH₂ | 4-Cl—PhO | 4-(4-MeO—Ph)—Ph | O |
| 145-68 | H | (CH₂)₂ | H | Me | CH₂ | 4-Cl—PhO | 4-(4-F—Ph)—Ph | O |
| 145-69 | H | (CH₂)₂ | H | Me | CH₂ | 4-Cl—PhO | 4-(4-Cl—Ph)—Ph | O |
| 145-70 | H | (CH₂)₂ | H | Me | CH₂ | 4-Cl—PhO | 4-(Pyr-2)-Ph | O |
| 145-71 | H | (CH₂)₂ | H | Me | CH₂ | 4-Cl—PhO | 4-(Pyr-3)-Ph | O |

TABLE 145-continued

| Ex. No. Comp. | R¹ | R² | R³ | R⁴ | Z | W | X | Y |
|---|---|---|---|---|---|---|---|---|
| 145-72 | H | (CH₂)₂ | H | Me | CH₂ | 4-Cl—PhO | 4-(Pyr-4)-Ph | O |
| 145-73 | H | (CH₂)₂ | H | Me | CH₂ | 4-Cl—PhO | 4-(3-MeO—Pyr-6)-Ph | O |
| 145-74 | H | (CH₂)₂ | H | Me | CH₂ | 4-Cl—PhO | 4-(3-Dma—Pyr-6)-Ph | O |
| 145-75 | H | (CH₂)₂ | H | Me | CH₂ | 4-Cl—PhO | 4-(3-CF₃—Pyr-6)-Ph | O |
| 145-76 | H | (CH₂)₂ | H | Me | CH₂ | 4-Cl—PhO | 4-(3-O₂N—Pyr-6)-Ph | O |
| 145-77 | H | (CH₂)₂ | H | Me | CH₂ | 4-Cl—PhO | 2-Ph-5-Pyr | O |
| 145-78 | H | (CH₂)₂ | H | Me | CH₂ | 4-Cl—PhO | 2-(4-F—Ph)-5-Pyr | O |
| 145-79 | H | (CH₂)₂ | H | Me | CH₂ | 4-Cl—PhO | 2-(4-MeO—Ph)-5-Pyr | O |
| 145-80 | H | (CH₂)₂ | H | Me | CH₂ | 4-Cl—PhO | 2-TfpO-5-Pyr | O |
| 145-81 | H | (CH₂)₂ | H | Me | CH₂ | 3-F—PhO | 4-Ph—Ph | O |
| 145-82 | H | (CH₂)₂ | H | Me | CH₂ | 3-F—PhO | 4-(4-HO—Ph)—Ph | O |
| 145-83 | H | (CH₂)₂ | H | Me | CH₂ | 3-F—PhO | 4-(4-MeO—Ph)—Ph | O |
| 145-84 | H | (CH₂)₂ | H | Me | CH₂ | 3-F—PhO | 4-(4-F—Ph)—Ph | O |
| 145-85 | H | (CH₂)₂ | H | Me | CH₂ | 3-F—PhO | 4-(4-Cl—Ph)—Ph | O |
| 145-86 | H | (CH₂)₂ | H | Me | CH₂ | 3-F—PhO | 4-(Pyr-2)-Ph | O |
| 145-87 | H | (CH₂)₂ | H | Me | CH₂ | 3-F—PhO | 4-(Pyr-3)-Ph | O |
| 145-88 | H | (CH₂)₂ | H | Me | CH₂ | 3-F—PhO | 4-(Pyr-4)-Ph | O |
| 145-89 | H | (CH₂)₂ | H | Me | CH₂ | 3-F—PhO | 4-(3-MeO—Pyr-6)-Ph | O |
| 145-90 | H | (CH₂)₂ | H | Me | CH₂ | 3-F—PhO | 4-(3-Dma—Pyr-6)-Ph | O |
| 145-91 | H | (CH₂)₂ | H | Me | CH₂ | 3-F—PhO | 4-(3-CF₃—Pyr-6)-Ph | O |
| 145-92 | H | (CH₂)₂ | H | Me | CH₂ | 3-F—PhO | 4-(3-O₂N—Pyr-6)-Ph | O |
| 145-93 | H | (CH₂)₂ | H | Me | CH₂ | 3-F—PhO | 2-Ph-5-Pyr | O |
| 145-94 | H | (CH₂)₂ | H | Me | CH₂ | 3-F—PhO | 2-(4-F—Ph)-5-Pyr | O |
| 145-95 | H | (CH₂)₂ | H | Me | CH₂ | 3-F—PhO | 2-(4-MeO—Ph)-5-Pyr | O |
| 145-96 | H | (CH₂)₂ | H | Me | CH₂ | 3-F—PhO | 2-TfpO-5-Pyr | O |
| 145-97 | H | (CH₂)₂ | H | Me | CH₂ | 4-CN—PhO | 4-Ph—Ph | O |
| 145-98 | H | (CH₂)₂ | H | Me | CH₂ | 4-CN—PhO | 4-(4-HO—Ph)—Ph | O |
| 145-99 | H | (CH₂)₂ | H | Me | CH₂ | 4-CN—PhO | 4-(4-MeO—Ph)—Ph | O |
| 145-100 | H | (CH₂)₂ | H | Me | CH₂ | 4-CN—PhO | 4-(4-F—Ph)—Ph | O |
| 145-101 | H | (CH₂)₂ | H | Me | CH₂ | 4-CN—PhO | 4-(4-Cl—Ph)—Ph | O |
| 145-102 | H | (CH₂)₂ | H | Me | CH₂ | 4-CN—PhO | 4-(Pyr-2)-Ph | O |
| 145-103 | H | (CH₂)₂ | H | Me | CH₂ | 4-CN—PhO | 4-(Pyr-3)-Ph | O |
| 145-104 | H | (CH₂)₂ | H | Me | CH₂ | 4-CN—PhO | 4-(Pyr-4)-Ph | O |
| 145-105 | H | (CH₂)₂ | H | Me | CH₂ | 4-CN—PhO | 4-(3-MeO—Pyr-6)-Ph | O |
| 145-106 | H | (CH₂)₂ | H | Me | CH₂ | 4-CN—PhO | 4-(3-Dma—Pyr-6)-Ph | O |
| 145-107 | H | (CH₂)₂ | H | Me | CH₂ | 4-CN—PhO | 4-(3-CF₃—Pyr-6)-Ph | O |
| 145-108 | H | (CH₂)₂ | H | Me | CH₂ | 4-CN—PhO | 4-(3-O₂N—Pyr-6)-Ph | O |
| 145-109 | H | (CH₂)₂ | H | Me | CH₂ | 4-CN—PhO | 2-Ph-5-Pyr | O |
| 145-110 | H | (CH₂)₂ | H | Me | CH₂ | 4-CN—PhO | 2-(4-F—Ph)-5-Pyr | O |
| 145-111 | H | (CH₂)₂ | H | Me | CH₂ | 4-CN—PhO | 2-(4-MeO—Ph)-5-Pyr | O |

TABLE 145-continued

| Ex. No. Comp. | R¹ | R² | R³ | R⁴ | Z | W | X | Y |
|---|---|---|---|---|---|---|---|---|
| 145-112 | H | (CH₂)₂ | H | Me | CH₂ | 4-CN—PhO | 2-TfpO-5-Pyr | O |
| 145-113 | H | (CH₂)₂ | H | Me | CH₂ | 4-MeS—PhO | 4-Ph—Ph | O |
| 145-114 | H | (CH₂)₂ | H | Me | CH₂ | 4-MeS—PhO | 4-(4-HO—Ph)—Ph | O |
| 145-115 | H | (CH₂)₂ | H | Me | CH₂ | 4-MeS—PhO | 4-(4-MeO—Ph)—Ph | O |
| 145-116 | H | (CH₂)₂ | H | Me | CH₂ | 4-MeS—PhO | 4-(4-F—Ph)—Ph | O |
| 145-117 | H | (CH₂)₂ | H | Me | CH₂ | 4-MeS—PhO | 4-(4-Cl—Ph)—Ph | O |
| 145-118 | H | (CH₂)₂ | H | Me | CH₂ | 4-MeS—PhO | 4-(Pyr-2)-Ph | O |
| 145-119 | H | (CH₂)₂ | H | Me | CH₂ | 4-MeS—PhO | 4-(Pyr-3)-Ph | O |
| 145-120 | H | (CH₂)₂ | H | Me | CH₂ | 4-MeS—PhO | 4-(Pyr-4)-Ph | O |
| 145-121 | H | (CH₂)₂ | H | Me | CH₂ | 4-MeS—PhO | 4-(3-MeO—Pyr-6)-Ph | O |
| 145-122 | H | (CH₂)₂ | H | Me | CH₂ | 4-MeS—PhO | 4-(3-Dma—Pyr-6)-Ph | O |
| 145-123 | H | (CH₂)₂ | H | Me | CH₂ | 4-MeS—PhO | 4-(3-CF₃—Pyr-6)-Ph | O |
| 145-124 | H | (CH₂)₂ | H | Me | CH₂ | 4-MeS—PhO | 4-(3-O₂N—Pyr-6)-Ph | O |
| 145-125 | H | (CH₂)₂ | H | Me | CH₂ | 4-MeS—PhO | 2-Ph-5-Pyr | O |
| 145-126 | H | (CH₂)₂ | H | Me | CH₂ | 4-MeS—PhO | 2-(4-F—Ph)-5-Pyr | O |
| 145-127 | H | (CH₂)₂ | H | Me | CH₂ | 4-MeS—PhO | 2-(4-MeO—Ph)-5-Pyr | O |
| 145-128 | H | (CH₂)₂ | H | Me | CH₂ | 4-MeS—PhO | 2-TfpO-5-Pyr | O |
| 145-129 | H | (CH₂)₂ | H | Me | CH₂ | 4-MeSO₂—PhO | 4-Ph—Ph | O |
| 145-130 | H | (CH₂)₂ | H | Me | CH₂ | 4-MeSO₂—PhO | 4-(4-HO—Ph)—Ph | O |
| 145-131 | H | (CH₂)₂ | H | Me | CH₂ | 4-MeSO₂—PhO | 4-(4-MeO—Ph)—Ph | O |
| 145-132 | H | (CH₂)₂ | H | Me | CH₂ | 4-MeSO₂—PhO | 4-(4-F—Ph)—Ph | O |
| 145-133 | H | (CH₂)₂ | H | Me | CH₂ | 4-MeSO₂—PhO | 4-(4-Cl—Ph)—Ph | O |
| 145-134 | H | (CH₂)₂ | H | Me | CH₂ | 4-MeSO₂—PhO | 4-(Pyr-2)-Ph | O |
| 145-135 | H | (CH₂)₂ | H | Me | CH₂ | 4-MeSO₂—PhO | 4-(Pyr-3)-Ph | O |
| 145-136 | H | (CH₂)₂ | H | Me | CH₂ | 4-MeSO₂—PhO | 4-(Pyr-4)-Ph | O |
| 145-137 | H | (CH₂)₂ | H | Me | CH₂ | 4-MeSO₂—PhO | 4-(3-MeO—Pyr-6)-Ph | O |
| 145-138 | H | (CH₂)₂ | H | Me | CH₂ | 4-MeSO₂—PhO | 4-(3-Dma—Pyr-6)-Ph | O |
| 145-139 | H | (CH₂)₂ | H | Me | CH₂ | 4-MeSO₂—PhO | 4-(3-CF₃—Pyr-6)-Ph | O |
| 145-140 | H | (CH₂)₂ | H | Me | CH₂ | 4-MeSO₂—PhO | 4-(3-O₂N—Pyr-6)-Ph | O |
| 145-141 | H | (CH₂)₂ | H | Me | CH₂ | 4-MeSO₂—PhO | 2-Ph-5-Pyr | O |
| 145-142 | H | (CH₂)₂ | H | Me | CH₂ | 4-MeSO₂—PhO | 2-(4-F—Ph)-5-Pyr | O |
| 145-143 | H | (CH₂)₂ | H | Me | CH₂ | 4-MeSO₂—PhO | 2-(4-MeO—Ph)-5-Pyr | O |
| 145-144 | H | (CH₂)₂ | H | Me | CH₂ | 4-MeSO₂—PhO | 2-TfpO-5-Pyr | O |
| 145-145 | H | (CH₂)₂ | H | Me | CH₂ | 3,4-di-F—PhO | 4-Ph—Ph | O |
| 145-146 | H | (CH₂)₂ | H | Me | CH₂ | 3,4-di-F—PhO | 4-(4-HO—Ph)—Ph | O |
| 145-147 | H | (CH₂)₂ | H | Me | CH₂ | 3,4-di-F—PhO | 4-(4-MeO—Ph)—Ph | O |
| 145-145 | H | (CH₂)₂ | H | Me | CH₂ | 3,4-di-F—PhO | 4-(4-F—Ph)—Ph | O |
| 145-149 | H | (CH₂)₂ | H | Me | CH₂ | 3,4-di-F—PhO | 4-(4-Cl—Ph)—Ph | O |
| 145-150 | H | (CH₂)₂ | H | Me | CH₂ | 3,4-di-F—PhO | 4-(Pyr-2)-Ph | O |
| 145-151 | H | (CH₂)₂ | H | Me | CH₂ | 3,4-di-F—PhO | 4-(Pyr-3)-Ph | O |

TABLE 145-continued

| Ex. No. Comp. | R¹ | R² | R³ | R⁴ | Z | W | X | Y |
|---|---|---|---|---|---|---|---|---|
| 145-152 | H | (CH$_2$)$_2$ | H | Me | CH$_2$ | 3,4-di-F—PhO | 4-(Pyr-4)-Ph | O |
| 145-153 | H | (CH$_2$)$_2$ | H | Me | CH$_2$ | 3,4-di-F—PhO | 4-(3-MeO—Pyr-6)-Ph | O |
| 145-154 | H | (CH$_2$)$_2$ | H | Me | CH$_2$ | 3,4-di-F—PhO | 4-(3-Dma—Pyr-6)-Ph | O |
| 145-155 | H | (CH$_2$)$_2$ | H | Me | CH$_2$ | 3,4-di-F—PhO | 4-(3-CF$_3$—Pyr-6)-Ph | O |
| 145-156 | H | (CH$_2$)$_2$ | H | Me | CH$_2$ | 3,4-di-F—PhO | 4-(3-O$_2$N—Pyr-6)-Ph | O |
| 145-157 | H | (CH$_2$)$_2$ | H | Me | CH$_2$ | 3,4-di-F—PhO | 2-Ph-5-Pyr | O |
| 145-158 | H | (CH$_2$)$_2$ | H | Me | CH$_2$ | 3,4-di-F—PhO | 2-(4-F—Ph)-5-Pyr | O |
| 145-159 | H | (CH$_2$)$_2$ | H | Me | CH$_2$ | 3,4-di-F—PhO | 2-(4-MeO—Ph)-5-Pyr | O |
| 145-160 | H | (CH$_2$)$_2$ | H | Me | CH$_2$ | 3,4-di-F—PhO | 2-TfpO-5-Pyr | O |
| 145-161 | H | (CH$_2$)$_2$ | H | Me | CH$_2$ | 3,5-di-F—PhO | 4-Ph—Ph | O |
| 145-162 | H | (CH$_2$)$_2$ | H | Me | CH$_2$ | 3,5-di-F—PhO | 4-(4-HO—Ph)—Ph | O |
| 145-163 | H | (CH$_2$)$_2$ | H | Me | CH$_2$ | 3,5-di-F—PhO | 4-(4-MeO—Ph)—Ph | O |
| 145-164 | H | (CH$_2$)$_2$ | H | Me | CH$_2$ | 3,5-di-F—PhO | 4-(4-F—Ph)—Ph | O |
| 145-165 | H | (CH$_2$)$_2$ | H | Me | CH$_2$ | 3,5-di-F—PhO | 4-(4-Cl—Ph)—Ph | O |
| 145-166 | H | (CH$_2$)$_2$ | H | Me | CH$_2$ | 3,5-di-F—PhO | 4-(Pyr-2)-Ph | O |
| 145-167 | H | (CH$_2$)$_2$ | H | Me | CH$_2$ | 3,5-di-F—PhO | 4-(Pyr-3)-Ph | O |
| 145-168 | H | (CH$_2$)$_2$ | H | Me | CH$_2$ | 3,5-di-F—PhO | 4-(Pyr-4)-Ph | O |
| 145-169 | H | (CH$_2$)$_2$ | H | Me | CH$_2$ | 3,5-di-F—PhO | 4-(3-MeO—Pyr-6)-Ph | O |
| 145-170 | H | (CH$_2$)$_2$ | H | Me | CH$_2$ | 3,5-di-F—PhO | 4-(3-Dma—Pyr-6)-Ph | O |
| 145-171 | H | (CH$_2$)$_2$ | H | Me | CH$_2$ | 3,5-di-F—PhO | 4-(3-CF$_3$—Pyr-6)-Ph | O |
| 145-172 | H | (CH$_2$)$_2$ | H | Me | CH$_2$ | 3,5-di-F—PhO | 4-(3-O$_2$N—Pyr-6)-Ph | O |
| 145-173 | H | (CH$_2$)$_2$ | H | Me | CH$_2$ | 3,5-di-F—PhO | 2-Ph-5-Pyr | O |
| 145-174 | H | (CH$_2$)$_2$ | H | Me | CH$_2$ | 3,5-di-F—PhO | 2-(4-F—Ph)-5-Pyr | O |
| 145-175 | H | (CH$_2$)$_2$ | H | Me | CH$_2$ | 3,5-di-F—PhO | 2-(4-MeO—Ph)-5-Pyr | O |
| 145-176 | H | (CH$_2$)$_2$ | H | Me | CH$_2$ | 3,5-di-F—PhO | 2-TfpO-5-Pyr | O |
| 145-177 | H | (CH$_2$)$_2$ | H | Me | CH$_2$ | 3,4,5-tri-F—PhO | 4-Ph—Ph | O |
| 145-178 | H | (CH$_2$)$_2$ | H | Me | CH$_2$ | 3,4,5-tri-F—PhO | 4-(4-HO—Ph)—Ph | O |
| 145-179 | H | (CH$_2$)$_2$ | H | Me | CH$_2$ | 3,4,5-tri-F—PhO | 4-(4-MeO—Ph)—Ph | O |
| 145-180 | H | (CH$_2$)$_2$ | H | Me | CH$_2$ | 3,4,5-tri-F—PhO | 4-(4-F—Ph)—Ph | O |
| 145-181 | H | (CH$_2$)$_2$ | H | Me | CH$_2$ | 3,4,5-tri-F—PhO | 4-(4-Cl—Ph)—Ph | O |
| 145-182 | H | (CH$_2$)$_2$ | H | Me | CH$_2$ | 3,4,5-tri-F—PhO | 4-(Pyr-2)-Ph | O |
| 145-183 | H | (CH$_2$)$_2$ | H | Me | CH$_2$ | 3,4,5-tri-F—PhO | 4-(Pyr-3)-Ph | O |
| 145-184 | H | (CH$_2$)$_2$ | H | Me | CH$_2$ | 3,4,5-tri-F—PhO | 4-(Pyr-4)-Ph | O |
| 145-185 | H | (CH$_2$)$_2$ | H | Me | CH$_2$ | 3,4,5-tri-F—PhO | 4-(3-MeO—Pyr-6)-Ph | O |
| 145-186 | H | (CH$_2$)$_2$ | H | Me | CH$_2$ | 3,4,5-tri-F—PhO | 4-(3-Dma—Pyr-6)-Ph | O |
| 145-187 | H | (CH$_2$)$_2$ | H | Me | CH$_2$ | 3,4,5-tri-F—PhO | 4-(3-CF$_3$—Pyr-6)-Ph | O |
| 145-188 | H | (CH$_2$)$_2$ | H | Me | CH$_2$ | 3,4,5-tri-F—PhO | 4-(3-O$_2$N—Pyr-6)-Ph | O |
| 145-189 | H | (CH$_2$)$_2$ | H | Me | CH$_2$ | 3,4,5-tri-F—PhO | 2-Ph-5-Pyr | O |
| 145-190 | H | (CH$_2$)$_2$ | H | Me | CH$_2$ | 3,4,5-tri-F—PhO | 2-(4-F—Ph)-5-Pyr | O |

TABLE 145-continued

| Ex. No. Comp. | R¹ | R² | R³ | R⁴ | Z | W | X | Y |
|---|---|---|---|---|---|---|---|---|
| 145-191 | H | (CH₂)₂ | H | Me | CH₂ | 3,4,5-tri-F—PhO | 2-(4-MeO—Ph)-5-Pyr | O |
| 145-192 | H | (CH₂)₂ | H | Me | CH₂ | 3,4,5-tri-F—PhO | 2-TfpO-5-Pyr | O |
| 145-193 | H | (CH₂)₂ | H | Me | CH₂ | 2,3,4,5,6-penta-F—PhO | 4-Ph—Ph | O |
| 145-194 | H | (CH₂)₂ | H | Me | CH₂ | 2,3,4,5,6-penta-F—PhO | 4-(4-HO—Ph)—Ph | O |
| 145-195 | H | (CH₂)₂ | H | Me | CH₂ | 2,3,4,5,6-penta-F—PhO | 4-(4-MeO—Ph)—Ph | O |
| 145-196 | H | (CH₂)₂ | H | Me | CH₂ | 2,3,4,5,6-penta-F—PhO | 4-(4-F—Ph)—Ph | O |
| 145-197 | H | (CH₂)₂ | H | Me | CH₂ | 2,3,4,5,6-penta-F—PhO | 4-(4-Cl—Ph)—Ph | O |
| 145-198 | H | (CH₂)₂ | H | Me | CH₂ | 2,3,4,5,6-penta-F—PhO | 4-(Pyr-2)-Ph | O |
| 145-199 | H | (CH₂)₂ | H | Me | CH₂ | 2,3,4,5,6-penta-F—PhO | 4-(Pyr-3)-Ph | O |
| 145-200 | H | (CH₂)₂ | H | Me | CH₂ | 2,3,4,5,6-penta-F—PhO | 4-(Pyr-4)-Ph | O |
| 145-201 | H | (CH₂)₂ | H | Me | CH₂ | 2,3,4,5,6-penta-F—PhO | 4-(3-MeO—Pyr-6)-Ph | O |
| 145-202 | H | (CH₂)₂ | H | Me | CH₂ | 2,3,4,5,6-penta-F—PhO | 4-(3-Dma—Pyr-6)-Ph | O |
| 145-203 | H | (CH₂)₂ | H | Me | CH₂ | 2,3,4,5,6-penta-F—PhO | 4-(3-CF₃—Pyr-6)-Ph | O |
| 145-204 | H | (CH₂)₂ | H | Me | CH₂ | 2,3,4,5,6-penta-F—PhO | 4-(3-O₂N—Pyr-6)-Ph | O |
| 145-205 | H | (CH₂)₂ | H | Me | CH₂ | 2,3,4,5,6-penta-F—PhO | 2-Ph-5-Pyr | O |
| 145-206 | H | (CH₂)₂ | H | Me | CH₂ | 2,3,4,5,6-penta-F—PhO | 2-(4-F—Ph)-5-Pyr | O |
| 145-207 | H | (CH₂)₂ | H | Me | CH₂ | 2,3,4,5,6-penta-F—PhO | 2-(4-MeO—Ph)-5-Pyr | O |
| 145-208 | H | (CH₂)₂ | H | Me | CH₂ | 2,3,4,5,6-penta-F—PhO | 2-TfpO-5-Pyr | O |
| 145-209 | H | (CH₂)₂ | H | Me | CH₂ | 3-PyrO | 4-Ph—Ph | O |
| 145-210 | H | (CH₂)₂ | H | Me | CH₂ | 3-PyrO | 4-(4-HO—Ph)—Ph | O |
| 145-211 | H | (CH₂)₂ | H | Me | CH₂ | 3-PyrO | 4-(4-MeO—Ph)—Ph | O |
| 145-212 | H | (CH₂)₂ | H | Me | CH₂ | 3-PyrO | 4-(4-F—Ph)—Ph | O |
| 145-213 | H | (CH₂)₂ | H | Me | CH₂ | 3-PyrO | 4-(4-Cl—Ph)—Ph | O |
| 145-214 | H | (CH₂)₂ | H | Me | CH₂ | 3-PyrO | 4-(Pyr-2)-Ph | O |
| 145-215 | H | (CH₂)₂ | H | Me | CH₂ | 3-PyrO | 4-(Pyr-3)-Ph | O |
| 145-216 | H | (CH₂)₂ | H | Me | CH₂ | 3-PyrO | 4-(Pyr-4)-Ph | O |
| 145-217 | H | (CH₂)₂ | H | Me | CH₂ | 3-PyrO | 4-(3-MeO—Pyr-6)-Ph | O |
| 145-218 | H | (CH₂)₂ | H | Me | CH₂ | 3-PyrO | 4-(3-Dma—Pyr-6)-Ph | O |
| 145-219 | H | (CH₂)₂ | H | Me | CH₂ | 3-PyrO | 4-(3-CF₃—Pyr-6)-Ph | O |
| 145-220 | H | (CH₂)₂ | H | Me | CH₂ | 3-PyrO | 4-(3-O₂N—Pyr-6)-Ph | O |
| 145-221 | H | (CH₂)₂ | H | Me | CH₂ | 3-PyrO | 2-Ph-5-Pyr | O |
| 145-222 | H | (CH₂)₂ | H | Me | CH₂ | 3-PyrO | 2-(4-F—Ph)-5-Pyr | O |
| 145-223 | H | (CH₂)₂ | H | Me | CH₂ | 3-PyrO | 2-(4-MeO—Ph)-5-Pyr | O |
| 145-224 | H | (CH₂)₂ | H | Me | CH₂ | 3-PyrO | 2-TfpO-5-Pyr | O |
| 145-225 | H | (CH₂)₂ | H | Me | CH₂ | BzO | 4-Ph—Ph | O |
| 145-226 | H | (CH₂)₂ | H | Me | CH₂ | BzO | 4-(4-HO—Ph)—Ph | O |
| 145-227 | H | (CH₂)₂ | H | Me | CH₂ | BzO | 4-(4-MeO—Ph)—Ph | O |
| 145-228 | H | (CH₂)₂ | H | Me | CH₂ | BzO | 4-(4-F—Ph)—Ph | O |
| 145-229 | H | (CH₂)₂ | H | Me | CH₂ | BzO | 4-(4-Cl—Ph)—Ph | O |

TABLE 145-continued

| Ex. No. Comp. | R¹ | R² | R³ | R⁴ | Z | W | X | Y |
|---|---|---|---|---|---|---|---|---|
| 145-230 | H | (CH₂)₂ | H | Me | CH₂ | BzO | 4-(Pyr-2)-Ph | O |
| 145-231 | H | (CH₂)₂ | H | Me | CH₂ | BzO | 4-(Pyr-3)-Ph | O |
| 145-232 | H | (CH₂)₂ | H | Me | CH₂ | BzO | 4-(Pyr-4)-Ph | O |
| 145-233 | H | (CH₂)₂ | H | Me | CH₂ | BzO | 4-(3-MeO—Pyr-6)-Ph | O |
| 145-234 | H | (CH₂)₂ | H | Me | CH₂ | BzO | 4-(3-Dma—Pyr-6)-Ph | O |
| 145-235 | H | (CH₂)₂ | H | Me | CH₂ | BzO | 4-(3-CF₃—Pyr-6)-Ph | O |
| 145-236 | H | (CH₂)₂ | H | Me | CH₂ | BzO | 4-(3-O₂N—Pyr-6)-Ph | O |
| 145-237 | H | (CH₂)₂ | H | Me | CH₂ | BzO | 2-Ph-5-Pyr | O |
| 145-238 | H | (CH₂)₂ | H | Me | CH₂ | BzO | 2-(4-F—Ph)-5-Pyr | O |
| 145-239 | H | (CH₂)₂ | H | Me | CH₂ | BzO | 2-(4-MeO—Ph)-5-Pyr | O |
| 145-240 | H | (CH₂)₂ | H | Me | CH₂ | BzO | 2-TfpO-5-Pyr | O |
| 145-241 | H | (CH₂)₂ | H | Me | CH₂ | 2-BoxaS | 4-Ph—Ph | O |
| 145-242 | H | (CH₂)₂ | H | Me | CH₂ | 2-BoxaS | 4-(4-HO—Ph)—Ph | O |
| 145-243 | H | (CH₂)₂ | H | Me | CH₂ | 2-BoxaS | 4-(4-MeO—Ph)—Ph | O |
| 145-244 | H | (CH₂)₂ | H | Me | CH₂ | 2-BoxaS | 4-(4-F—Ph)—Ph | O |
| 145-245 | H | (CH₂)₂ | H | Me | CH₂ | 2-BoxaS | 4-(4-Cl—Ph)—Ph | O |
| 145-246 | H | (CH₂)₂ | H | Me | CH₂ | 2-BoxaS | 4-(Pyr-2)-Ph | O |
| 145-247 | H | (CH₂)₂ | H | Me | CH₂ | 2-BoxaS | 4-(Pyr-3)-Ph | O |
| 145-248 | H | (CH₂)₂ | H | Me | CH₂ | 2-BoxaS | 4-(Pyr-4)-Ph | O |
| 145-249 | H | (CH₂)₂ | H | Me | CH₂ | 2-BoxaS | 4-(3-MeO—Pyr-6)-Ph | O |
| 145-250 | H | (CH₂)₂ | H | Me | CH₂ | 2-BoxaS | 4-(3-Dma—Pyr-6)-Ph | O |
| 145-251 | H | (CH₂)₂ | H | Me | CH₂ | 2-BoxaS | 4-(3-CF₃—Pyr-6)-Ph | O |
| 145-252 | H | (CH₂)₂ | H | Me | CH₂ | 2-BoxaS | 4-(3-O₂N—Pyr-6)-Ph | O |
| 145-253 | H | (CH₂)₂ | H | Me | CH₂ | 2-BoxaS | 2-Ph-5-Pyr | O |
| 145-254 | H | (CH₂)₂ | H | Me | CH₂ | 2-BoxaS | 2-(4-F—Ph)-5-Pyr | O |
| 145-255 | H | (CH₂)₂ | H | Me | CH₂ | 2-BoxaS | 2-(4-MeO—Ph)-5-Pyr | O |
| 145-256 | H | (CH₂)₂ | H | Me | CH₂ | 2-BoxaS | 2-TfpO-5-Pyr | O |
| 145-257 | H | (CH₂)₂ | H | Me | CH₂ | 4-(Pyr-2)-PhO | 4-Ph—Ph | O |
| 145-258 | H | (CH₂)₂ | H | Me | CH₂ | 4-(Pyr-2)-PhO | 4-(4-HO—Ph)—Ph | O |
| 145-259 | H | (CH₂)₂ | H | Me | CH₂ | 4-(Pyr-2)-PhO | 4-(4-MeO—Ph)—Ph | O |
| 145-260 | H | (CH₂)₂ | H | Me | CH₂ | 4-(Pyr-2)-PhO | 4-(4-F—Ph)—Ph | O |
| 145-261 | H | (CH₂)₂ | H | Me | CH₂ | 4-(Pyr-2)-PhO | 4-(4-Cl—Ph)—Ph | O |
| 145-262 | H | (CH₂)₂ | H | Me | CH₂ | 4-(Pyr-2)-PhO | 4-(Pyr-2)-Ph | O |
| 145-263 | H | (CH₂)₂ | H | Me | CH₂ | 4-(Pyr-2)-PhO | 4-(Pyr-3)-Ph | O |
| 145-264 | H | (CH₂)₂ | H | Me | CH₂ | 4-(Pyr-2)-PhO | 4-(Pyr-4)-Ph | O |
| 145-265 | H | (CH₂)₂ | H | Me | CH₂ | 4-(Pyr-2)-PhO | 4-(3-MeO—Pyr-6)-Ph | O |
| 145-266 | H | (CH₂)₂ | H | Me | CH₂ | 4-(Pyr-2)-PhO | 4-(3-Dma—Pyr-6)-Ph | O |
| 145-267 | H | (CH₂)₂ | H | Me | CH₂ | 4-(Pyr-2)-PhO | 4-(3-CF₃—Pyr-6)-Ph | O |
| 145-268 | H | (CH₂)₂ | H | Me | CH₂ | 4-(Pyr-2)-PhO | 4-(3-O₂N—Pyr-6)-Ph | O |

TABLE 145-continued

| Ex. No. Comp. | R¹ | R² | R³ | R⁴ | Z | W | X | Y |
|---|---|---|---|---|---|---|---|---|
| 145-269 | H | (CH$_2$)$_2$ | H | Me | CH$_2$ | 4-(Pyr-2)-PhO | 2-Ph-5-Pyr | O |
| 145-270 | H | (CH$_2$)$_2$ | H | Me | CH$_2$ | 4-(Pyr-2)-PhO | 2-(4-F—Ph)-5-Pyr | O |
| 145-271 | H | (CH$_2$)$_2$ | H | Me | CH$_2$ | 4-(Pyr-2)-PhO | 2-(4-MeO—Ph)-5-Pyr | O |
| 145-272 | H | (CH$_2$)$_2$ | H | Me | CH$_2$ | 4-(Pyr-2)-PhO | 2-TfpO-5-Pyr | O |
| 145-273 | H | (CH$_2$)$_2$ | H | Me | CH$_2$ | 4-tBu—PhO | 4-(4-Me—Ph)—Ph | O |
| 145-274 | H | (CH$_2$)$_2$ | H | Me | CH$_2$ | 4-tBu—PhO | 4-(4-Dma—Ph)—Ph | O |
| 145-275 | H | (CH$_2$)$_2$ | H | Me | CH$_2$ | 4-tBu—PhO | 4-(4-CF$_3$—Ph)—Ph | O |
| 145-276 | H | (CH$_2$)$_2$ | H | Me | CH$_2$ | 4-tBu—PhO | 4-(3-Me—Pyr-6)-Ph | O |
| 145-277 | H | (CH$_2$)$_2$ | H | Me | CH$_2$ | 4-tBu—PhO | 4-(3-Et—Pyr-6)-Ph | O |
| 145-278 | H | (CH$_2$)$_2$ | H | Me | CH$_2$ | 4-tBu—PhO | 4-(3-EtO—Pyr-6)-Ph | O |
| 145-279 | H | (CH$_2$)$_2$ | H | Me | CH$_2$ | 4-tBu—PhO | 2-(4-Me—Ph)-5-Pyr | O |
| 145-280 | H | (CH$_2$)$_2$ | H | Me | CH$_2$ | 4-tBu—PhO | 2-(4-CF$_3$—Ph)-5-Pyr | O |
| 145-281 | H | (CH$_2$)$_2$ | H | Me | CH$_2$ | 4-tBu—PhO | 2-(4-Cl—Ph)-5-Pyr | O |
| 145-282 | H | (CH$_2$)$_2$ | H | Me | CH$_2$ | 4-tBu—PhO | 2-(4-Dma—Ph)-5-Pyr | O |
| 145-283 | H | (CH$_2$)$_2$ | H | Me | CH$_2$ | 4-CF$_3$—PhO | 4-(4-Me—Ph)—Ph | O |
| 145-284 | H | (CH$_2$)$_2$ | H | Me | CH$_2$ | 4-CF$_3$—PhO | 4-(4-Dma—Ph)—Ph | O |
| 145-285 | H | (CH$_2$)$_2$ | H | Me | CH$_2$ | 4-CF$_3$—PhO | 4-(4-CF$_3$—Ph)—Ph | O |
| 145-286 | H | (CH$_2$)$_2$ | H | Me | CH$_2$ | 4-CF$_3$—PhO | 4-(3-Me—Pyr-6)-Ph | O |
| 145-287 | H | (CH$_2$)$_2$ | H | Me | CH$_2$ | 4-CF$_3$—PhO | 4-(3-Et—Pyr-6)-Ph | O |
| 145-288 | H | (CH$_2$)$_2$ | H | Me | CH$_2$ | 4-CF$_3$—PhO | 4-(3-EtO—Pyr-6)-Ph | O |
| 145-289 | H | (CH$_2$)$_2$ | H | Me | CH$_2$ | 4-CF$_3$—PhO | 2-(4-Me—Ph)-5-Pyr | O |
| 145-290 | H | (CH$_2$)$_2$ | H | Me | CH$_2$ | 4-CF$_3$—PhO | 2-(4-CF$_3$—Ph)-5-Pyr | O |
| 145-291 | H | (CH$_2$)$_2$ | H | Me | CH$_2$ | 4-CF$_3$—PhO | 2-(4-Cl—Ph)-5-Pyr | O |
| 145-292 | H | (CH$_2$)$_2$ | H | Me | CH$_2$ | 4-CF$_3$—PhO | 2-(4-Dma—Ph)-5-Pyr | O |
| 145-293 | H | (CH$_2$)$_2$ | H | Me | CH$_2$ | 4-CF$_3$O—PhO | 4-(4-Me—Ph)—Ph | O |
| 145-294 | H | (CH$_2$)$_2$ | H | Me | CH$_2$ | 4-CF$_3$O—PhO | 4-(4-Dma—Ph)—Ph | O |
| 145-295 | H | (CH$_2$)$_2$ | H | Me | CH$_2$ | 4-CF$_3$O—PhO | 4-(4-CF$_3$—Ph)—Ph | O |
| 145-296 | H | (CH$_2$)$_2$ | H | Me | CH$_2$ | 4-CF$_3$O—PhO | 4-(3-Me—Pyr-6)-Ph | O |
| 145-297 | H | (CH$_2$)$_2$ | H | Me | CH$_2$ | 4-CF$_3$O—PhO | 4-(3-Et—Pyr-6)-Ph | O |
| 145-298 | H | (CH$_2$)$_2$ | H | Me | CH$_2$ | 4-CF$_3$O—PhO | 4-(3-EtO—Pyr-6)-Ph | O |
| 145-299 | H | (CH$_2$)$_2$ | H | Me | CH$_2$ | 4-CF$_3$O—PhO | 2-(4-Me—Ph)-5-Pyr | O |
| 145-300 | H | (CH$_2$)$_2$ | H | Me | CH$_2$ | 4-CF$_3$O—PhO | 2-(4-CF$_3$—Ph)-5-Pyr | O |
| 145-301 | H | (CH$_2$)$_2$ | H | Me | CH$_2$ | 4-CF$_3$O—PhO | 2-(4-Cl—Ph)-5-Pyr | O |
| 145-302 | H | (CH$_2$)$_2$ | H | Me | CH$_2$ | 4-CF$_3$O—PhO | 2-(4-Dma—Ph)-5-Pyr | O |
| 145-303 | H | (CH$_2$)$_2$ | H | Me | CH$_2$ | 4-F—PhO | 4-(4-Me—Ph)—Ph | O |
| 145-304 | H | (CH$_2$)$_2$ | H | Me | CH$_2$ | 4-F—PhO | 4-(4-Dma—Ph)—Ph | O |
| 145-305 | H | (CH$_2$)$_2$ | H | Me | CH$_2$ | 4-F—PhO | 4-(4-CF$_3$—Ph)—Ph | O |
| 145-306 | H | (CH$_2$)$_2$ | H | Me | CH$_2$ | 4-F—PhO | 4-(3-Me—Pyr- | O |

TABLE 145-continued

| Ex. No. Comp. | R¹ | R² | R³ | R⁴ | Z | W | X | Y |
|---|---|---|---|---|---|---|---|---|
| 145-307 | H | (CH$_2$)$_2$ | H | Me | CH$_2$ | 4-F—PhO | 4-(3-Et—Pyr-6)-Ph | O |
| 145-308 | H | (CH$_2$)$_2$ | H | Me | CH$_2$ | 4-F—PhO | 4-(3-EtO—Pyr-6)-Ph | O |
| 145-309 | H | (CH$_2$)$_2$ | H | Me | CH$_2$ | 4-F—PhO | 2-(4-Me—Ph)-5-Pyr | O |
| 145-310 | H | (CH$_2$)$_2$ | H | Me | CH$_2$ | 4-F—PhO | 2-(4-CF$_3$—Ph)-5-Pyr | O |
| 145-311 | H | (CH$_2$)$_2$ | H | Me | CH$_2$ | 4-F—PhO | 2-(4-Cl—Ph)-5-Pyr | O |
| 145-312 | H | (CH$_2$)$_2$ | H | Me | CH$_2$ | 4-F—PhO | 2-(4-Dma—Ph)-5-Pyr | O |
| 145-313 | H | (CH$_2$)$_2$ | H | Me | CH$_2$ | 4-Cl—PhO | 4-(4-Me—Ph)—Ph | O |
| 145-314 | H | (CH$_2$)$_2$ | H | Me | CH$_2$ | 4-Cl—PhO | 4-(4-Dma—Ph)—Ph | O |
| 145-315 | H | (CH$_2$)$_2$ | H | Me | CH$_2$ | 4-Cl—PhO | 4-(4-CF$_3$—Ph)—Ph | O |
| 145-316 | H | (CH$_2$)$_2$ | H | Me | CH$_2$ | 4-Cl—PhO | 4-(3-Me—Pyr-6)-Ph | O |
| 145-317 | H | (CH$_2$)$_2$ | H | Me | CH$_2$ | 4-Cl—PhO | 4-(3-Et—Pyr-6)-Ph | O |
| 145-318 | H | (CH$_2$)$_2$ | H | Me | CH$_2$ | 4-Cl—PhO | 4-(3-EtO—Pyr-6)-Ph | O |
| 145-319 | H | (CH$_2$)$_2$ | H | Me | CH$_2$ | 4-Cl—PhO | 2-(4-Me—Ph)-5-Pyr | O |
| 145-320 | H | (CH$_2$)$_2$ | H | Me | CH$_2$ | 4-Cl—PhO | 2-(4-CF$_3$—Ph)-5-Pyr | O |
| 145-322 | H | (CH$_2$)$_2$ | H | Me | CH$_2$ | 4-Cl—PhO | 2-(4-Cl—Ph)-5-Pyr | O |
| 145-323 | H | (CH$_2$)$_2$ | H | Me | CH$_2$ | 4-Cl—PhO | 2-(4-Dma—Ph)-5-Pyr | O |

TABLE 146

| Ex. No. Comp. | R¹ | R² | R³ | R⁴ | Z | W | X | Y |
|---|---|---|---|---|---|---|---|---|
| 146-1 | H | (CH$_2$)$_2$ | H | H | CH$_2$ | EtO | 4-Ph—Ph | O |
| 146-2 | H | (CH$_2$)$_2$ | H | H | CH$_2$ | EtO | 4-(Pyr-2)-Ph | O |
| 146-3 | H | (CH$_2$)$_2$ | H | H | CH$_2$ | EtO | 4-(Pyr-3)-Ph | O |
| 146-4 | H | (CH$_2$)$_2$ | H | H | CH$_2$ | EtO | 4-(Pyr-4)-Ph | O |
| 146-5 | H | (CH$_2$)$_2$ | H | H | CH$_2$ | EtO | 2-Ph-5-Pyr | O |
| 146-6 | H | (CH$_2$)$_2$ | H | H | CH$_2$ | EtO | 3-Ph-6-Pyr | O |

TABLE 147

| Ex. No. Comp. | R¹ | R² | R³ | R⁴ | Z | W | X | Y |
|---|---|---|---|---|---|---|---|---|
| 147-1 | H | (CH$_2$)$_2$ | H | H | CH$_2$ | Pr | 4-Ph—Ph | O |
| 147-2 | H | (CH$_2$)$_2$ | H | H | CH$_2$ | Pr | 4-(Pyr-2)-Ph | O |
| 147-3 | H | (CH$_2$)$_2$ | H | H | CH$_2$ | Pr | 4-(Pyr-3)-Ph | O |
| 147-4 | H | (CH$_2$)$_2$ | H | H | CH$_2$ | Pr | 4-(Pyr-4)-Ph | O |
| 147-5 | H | (CH$_2$)$_2$ | H | H | CH$_2$ | Pr | 2-Ph-5-Pyr | O |
| 147-6 | H | (CH$_2$)$_2$ | H | H | CH$_2$ | Pr | 3-Ph-6-Pyr | O |

TABLE 148

| Ex. No. Comp. | R¹ | R² | R³ | R⁴ | Z | W | X | Y |
|---|---|---|---|---|---|---|---|---|
| 148-1 | H | (CH$_2$)$_2$ | H | H | CH$_2$ | Bu | 4-Ph—Ph | O |
| 148-2 | H | (CH$_2$)$_2$ | H | H | CH$_2$ | Bu | 4-(Pyr-2)-Ph | O |
| 148-3 | H | (CH$_2$)$_2$ | H | H | CH$_2$ | Bu | 4-(Pyr-3)-Ph | O |
| 148-4 | H | (CH$_2$)$_2$ | H | H | CH$_2$ | Bu | 4-(Pyr-4)-Ph | O |
| 148-5 | H | (CH$_2$)$_2$ | H | H | CH$_2$ | Bu | 2-Ph-5-Pyr | O |
| 148-6 | H | (CH$_2$)$_2$ | H | H | CH$_2$ | Bu | 3-Ph-6-Pyr | O |

TABLE 149

| Ex. No. Comp. | R¹ | R² | R³ | R⁴ | Z | W | X | Y |
|---|---|---|---|---|---|---|---|---|
| 149-1 | H | (CH$_2$)$_2$ | H | H | CH$_2$ | Pen | 4-Ph—Ph | O |
| 149-2 | H | (CH$_2$)$_2$ | H | H | CH$_2$ | Pen | 4-(Pyr-2)-Ph | O |
| 149-3 | H | (CH$_2$)$_2$ | H | H | CH$_2$ | Pen | 4-(Pyr-3)-Ph | O |
| 149-4 | H | (CH$_2$)$_2$ | H | H | CH$_2$ | Pen | 4-(Pyr-4)-Ph | O |
| 149-5 | H | (CH$_2$)$_2$ | H | H | CH$_2$ | Pen | 2-Ph-5-Pyr | O |
| 149-6 | H | (CH$_2$)$_2$ | H | H | CH$_2$ | Pen | 3-Ph-6-Pyr | O |

TABLE 150

| Ex. No. Comp. | R¹ | R² | R³ | R⁴ | Z | W | X | Y |
|---|---|---|---|---|---|---|---|---|
| 150-1 | H | (CH$_2$)$_2$ | H | H | CH$_2$ | MeS | 4-Ph—Ph | O |
| 150-2 | H | (CH$_2$)$_2$ | H | H | CH$_2$ | MeS | 4-(Pyr-2)-Ph | O |

TABLE 150-continued

| Ex. No. Comp. | $R^1$ | $R^2$ | $R^3$ | $R^4$ | Z | W | X | Y |
|---|---|---|---|---|---|---|---|---|
| 150-3 | H | $(CH_2)_2$ | H | H | $CH_2$ | MeS | 4-(Pyr-3)-Ph | O |
| 150-4 | H | $(CH_2)_2$ | H | H | $CH_2$ | MeS | 4-(Pyr-4)-Ph | O |
| 150-5 | H | $(CH_2)_2$ | H | H | $CH_2$ | MeS | 2-Ph-5-Pyr | O |
| 150-6 | H | $(CH_2)_2$ | H | H | $CH_2$ | MeS | 3-Ph-6-Pyr | O |

TABLE 151

| Ex. No. Comp. | $R^1$ | $R^2$ | $R^3$ | $R^4$ | Z | W | X | Y |
|---|---|---|---|---|---|---|---|---|
| 151-1 | H | $(CH_2)_2$ | H | H | $CH_2$ | PhO | 4-Ph—Ph | O |
| 151-2 | H | $(CH_2)_2$ | H | H | $CH_2$ | PhO | 4-(Pyr-2)-Ph | O |
| 151-3 | H | $(CH_2)_2$ | H | H | $CH_2$ | PhO | 4-(Pyr-3)-Ph | O |
| 151-4 | H | $(CH_2)_2$ | H | H | $CH_2$ | PhO | 4-(Pyr-4)-Ph | O |
| 151-5 | H | $(CH_2)_2$ | H | H | $CH_2$ | PhO | 2-Ph-5-Pyr | O |
| 151-6 | H | $(CH_2)_2$ | H | H | $CH_2$ | PhO | 3-Ph-6-Pyr | O |

TABLE 152

| Ex. No. Comp. | $R^1$ | $R^2$ | $R^3$ | $R^4$ | Z | W | X | Y |
|---|---|---|---|---|---|---|---|---|
| 152-1 | H | $(CH_2)_2$ | H | H | $CH_2$ | 4-iPr—PhO | 4-Ph—Ph | O |
| 152-2 | H | $(CH_2)_2$ | H | H | $CH_2$ | 4-iPr—PhO | 4-(Pyr-2)-Ph | O |
| 152-3 | H | $(CH_2)_2$ | H | H | $CH_2$ | 4-iPr—PhO | 4-(Pyr-3)-Ph | O |
| 152-4 | H | $(CH_2)_2$ | H | H | $CH_2$ | 4-iPr—PhO | 4-(Pyr-4)-Ph | O |
| 152-5 | H | $(CH_2)_2$ | H | H | $CH_2$ | 4-iPr—PhO | 2-Ph-5-Pyr | O |
| 152-6 | H | $(CH_2)_2$ | H | H | $CH_2$ | 4-iPr—PhO | 3-Ph-6-Pyr | O |

TABLE 153

| Ex. No. Comp. | $R^1$ | $R^2$ | $R^3$ | $R^4$ | Z | W | X | Y |
|---|---|---|---|---|---|---|---|---|
| 153-1 | H | $(CH_2)_2$ | H | H | $CH_2$ | 4-MeO—PhO | 4-Ph—Ph | O |
| 153-2 | H | $(CH_2)_2$ | H | H | $CH_2$ | 4-MeO—PhO | 4-(Pyr-2)-Ph | O |
| 153-3 | H | $(CH_2)_2$ | H | H | $CH_2$ | 4-MeO—PhO | 4-(Pyr-3)-Ph | O |
| 153-4 | H | $(CH_2)_2$ | H | H | $CH_2$ | 4-MeO—PhO | 4-(Pyr-4)-Ph | O |
| 153-5 | H | $(CH_2)_2$ | H | H | $CH_2$ | 4-MeO—PhO | 2-Ph-5-Pyr | O |
| 153-6 | H | $(CH_2)_2$ | H | H | $CH_2$ | 4-MeO—PhO | 3-Ph-6-Pyr | O |

TABLE 154

| Ex. No. Comp. | $R^1$ | $R^2$ | $R^3$ | $R^4$ | Z | W | X | Y |
|---|---|---|---|---|---|---|---|---|
| 154-1 | H | $(CH_2)_2$ | H | H | $CH_2$ | PhS | 4-Ph—Ph | O |
| 154-2 | H | $(CH_2)_2$ | H | H | $CH_2$ | PhS | 4-(Pyr-2)-Ph | O |
| 154-3 | H | $(CH_2)_2$ | H | H | $CH_2$ | PhS | 4-(Pyr-3)-Ph | O |
| 154-4 | H | $(CH_2)_2$ | H | H | $CH_2$ | PhS | 4-(Pyr-4)-Ph | O |
| 154-5 | H | $(CH_2)_2$ | H | H | $CH_2$ | PhS | 2-Ph-5-Pyr | O |
| 154-6 | H | $(CH_2)_2$ | H | H | $CH_2$ | PhS | 3-Ph-6-Pyr | O |

TABLE 155

| Ex. No. Comp. | $R^1$ | $R^2$ | $R^3$ | $R^4$ | Z | W | X | Y |
|---|---|---|---|---|---|---|---|---|
| 155-1 | H | $(CH_2)_2$ | H | H | $CH_2$ | $Ph(CH_2)_3$ | 4-Ph—Ph | O |
| 155-2 | H | $(CH_2)_2$ | H | H | $CH_2$ | $Ph(CH_2)_3$ | 4-(Pyr-2)-Ph | O |
| 155-3 | H | $(CH_2)_2$ | H | H | $CH_2$ | $Ph(CH_2)_3$ | 4-(Pyr-3)-Ph | O |
| 155-4 | H | $(CH_2)_2$ | H | H | $CH_2$ | $Ph(CH_2)_3$ | 4-(Pyr-4)-Ph | O |
| 155-5 | H | $(CH_2)_2$ | H | H | $CH_2$ | $Ph(CH_2)_3$ | 2-Ph-5-Pyr | O |
| 155-6 | H | $(CH_2)_2$ | H | H | $CH_2$ | $Ph(CH_2)_3$ | 3-Ph-6-Pyr | O |

In the above tables,
(1) the following compounds are preferred: compounds Nos. 1-15, 1-16, 1-17, 1-19, 1-21, 1-35, 1-37, 1-39, 1-90, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-143, 1-150, 1-179, 1-189, 1-190, 1-191, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-242, 1-243, 1-244, 1-246, 3-15, 3-16, 3-17, 3-19, 3-21, 3-35, 3-37, 3-39, 3-90, 3-92, 3-93, 3-94, 3-95, 3-96, 3-97, 3-98, 3-99, 3-100, 3-101, 3-102, 3-103, 3-104, 3-105, 3-106, 3-107, 3-108, 3-109, 3-110, 3-111, 3-112, 3-143, 3-150, 3-179, 3-189, 3-190, 3-191, 3-204, 3-205, 3-206, 3-207, 3-208, 3-209, 3-210, 3-211, 3-212, 3-213, 3-214, 3-215, 3-216, 3-217, 3-218, 3-219, 3-220, 3-221, 3-222, 3-223, 3-224, 3-225, 3-226, 3-227, 3-228, 3-229, 3-230, 3-231, 3-232, 3-233, 3-234, 3-235, 3-236, 3-242, 3-243, 3-244, 3-246, 4-15, 4-16, 4-17, 4-19, 4-21, 4-35, 4-37, 4-39, 4-90, 4-92, 4-93, 4-94, 4-95, 4-96, 4-97, 4-98, 4-99, 4-100, 4-101, 4-102, 4-103, 4-104, 4-105, 4-106, 4-107, 4-108, 4-109, 4-110, 4-111, 4-112, 4-143, 4-150, 4-179, 4-189, 4-190, 4-191, 4-193, 4-204, 4-205, 4-206, 4-207, 4-208, 4-209, 4-210, 4-211, 4-212, 4-213, 4-214, 4-215, 4-216, 4-217, 4-218, 4-219, 4-220, 4-221, 4-222, 4-223, 4-224, 4-225, 4-226, 4-227, 4-228, 4-229, 4-230, 4-231, 4-232, 4-233, 4-234, 4-235, 4-236, 4-242, 4-243, 4-244, 4-246, 5-15, 5-16, 5-17, 5-19, 5-21, 5-35, 5-37, 5-39, 5-90, 5-92, 5-93, 5-94, 5-95, 5-96, 5-97, 5-98, 5-99, 5-100, 5-101, 5-102, 5-103, 5-104, 5-105, 5-106, 5-107, 5-108, 5-109, 5-110, 5-111, 5-112, 6-15, 6-16, 6-17, 6-19, 6-21, 6-35, 6-37, 6-39, 6-90, 6-92, 6-93, 6-94, 6-95, 6-96, 6-97, 6-98, 6-99, 6-100, 6-101, 6-102, 6-103, 6-104, 6-105, 6-106, 6-107, 6-108, 6-109, 6-110, 6-111, 6-112, 6-143, 6-150, 6-179, 6-189, 6-190, 6-191, 6-204, 6-205, 6-206, 6-207, 6-208, 6-209, 6-210, 6-211, 6-212, 6-213, 6-214, 6-215, 6-216, 6-217, 6-218, 6-219, 6-220, 6-221, 6-222, 6-223, 6-224, 6-225, 6-226, 6-227, 6-228, 6-229, 6-230, 6-231, 6-232, 6-233, 6-234, 6-235, 6-236, 6-242, 6-243, 6-244, 6-246, 7-15, 7-16, 7-17, 7-19, 7-21, 7-35, 7-37, 7-39, 7-90, 7-92, 7-93, 7-94, 7-95, 7-96, 7-97, 7-98, 7-99, 7-100, 7-101, 7-102, 7-103, 7-104, 7-105, 7-106, 7-107, 7-108, 7-109, 7-110, 7-111, 7-112, 7-143, 7-150, 7-179, 7-189, 7-190, 7-191, 7-204, 7-205, 7-206, 7-207, 7-208, 7-209, 7-210, 7-211, 7-212, 7-213, 7-214, 7-215, 7-216, 7-217, 7-218, 7-219, 7-220, 7-221, 7-222, 7-223, 7-224, 7-225, 7-226, 7-227, 7-228, 7-229, 7-230, 7-231, 7-232, 7-233, 7-234, 7-235, 7-236, 7-242, 7-243, 7-244, 7-246, 8-15, 8-16, 8-17, 8-19, 8-21, 8-35, 8-37, 8-39, 8-90, 8-92, 8-93, 8-94, 8-95, 8-96, 8-97, 8-98, 8-99, 8-100, 8-101, 8-102, 8-103, 8-104, 8-105, 8-106, 8-107, 8-1088-109, 8-110, 8-111, 8-112, 8-143, 8-150, 8-179, 8-189, 8-190, 8-191, 8-204, 8-205, 8-206, 8-207, 8-208, 8-209, 8-210, 8-211, 8-212, 8-213, 8-214, 8-215, 8-216, 8-217, 8-218, 8-219, 8-220, 8-221, 8-222, 8-223, 8-224, 8-225, 8-226, 8-227, 8-228, 8-229, 8-230, 8-231, 8-232, 8-233, 8-234, 8-235, 8-236, 8-242, 8-243, 8-244, 8-246, 9-15, 9-16, 9-17, 9-19, 9-21, 9-35, 9-37, 9-39, 9-90, 9-92, 9-93, 9-94, 9-95, 9-96, 9-97, 9-98, 9-99, 9-100, 9-101, 9-102, 9-103, 9-104, 9-105, 9-106, 9-107, 9-108, 9-109, 9-110, 9-111, 9-112, 10-11, 10-15, 10-16, 10-17, 10-19, 10-21, 10-35, 10-37, 10-39, 10-90, 10-92, 10-93, 10-94, 10-95, 10-96, 10-97, 10-98, 10-99, 10-100, 10-101, 10-102, 10-103, 10-104, 10-105, 10-106, 10-107, 10-108, 10-109, 10-110, 10-111, 10-112, 11-5, 11-11, 11-12, 11-13, 11-37, 12-5, 12-11, 12-12, 12-13, 12-37, 13-5, 13-11, 13-12, 13-13, 13-37, 14-5, 14-11, 14-12, 14-13, 14-37, 14-42, 14-43, 14-44, 14-45, 14-46, 14-47, 14-48, 14-49, 14-50, 14-51, 14-52, 14-53, 14-54, 14-55, 14-61, 14-62, 14-64, 14-65, 14-66, 14-67, 14-68, 14-69, 14-70, 14-73, 14-74, 14-75, 14-76, 14-77, 14-78, 14-84, 14-85, 14-86, 14-88, 15-5, 15-11, 15-12, 15-13, 15-37, 15-42, 15-43, 15-44, 15-45, 15-46, 15-47, 15-48, 15-49, 15-50, 15-51, 15-52, 15-53, 15-54, 15-55, 15-61, 15-62, 15-64, 15-65, 15-66, 15-67, 15-68, 15-69, 15-70, 15-73, 15-74, 15-75, 15-76, 15-77, 15-78, 15-84, 15-85, 15-86, 15-88, 16-5, 16-11, 16-12, 16-13, 16-37, 17-5, 17-11, 17-12, 17-13, 17-37, 18-2, 18-3, 18-4, 18-5, 18-16, 19-2, 19-3, 19-4, 19-5, 19-16, 20-2, 20-3, 20-4, 20-5, 20-16, 20-30, 20-33, 20-37, 20-39, 20-42, 20-52, 20-53, 20-70, 20-71, 20-79, 20-80, 23-2, 23-3, 23-4, 23-5, 23-16, 24-2, 24-3, 24-4, 24-5, 25-2, 25-3, 25-4, 25-5, 25-16, 28-2, 28-3, 28-4, 28-5, 28-16, 28-17, 28-18, 28-19, 28-20, 28-21, 28-22, 28-23, 28-24, 28-25, 28-31, 28-32, 28-33, 28-34, 28-35, 28-36, 28-37, 28-38, 28-39, 28-40, 28-41, 28-42, 28-43, 29-2, 29-3, 29-4, 29-5, 29-16, 29-17, 29-18, 29-19, 29-20, 29-21, 29-22, 29-23, 29-24, 29-25, 29-31, 29-32, 29-33, 29-34, 29-35, 29-36, 29-37, 29-38, 29-39, 29-40, 29-41, 29-42, 29-43, 30-2, 30-3, 30-4, 30-5, 30-16, 30-17, 30-18, 30-19, 30-20, 30-21, 30-22, 30-23, 30-24, 30-25, 30-31, 30-32, 30-33, 30-34, 30-35, 30-36, 30-37, 30-38, 30-39, 30-40, 30-41, 30-42, 30-43, 31-2, 31-3, 31-4, 31-5, 31-16, 31-17, 32-2, 32-3, 32-4, 32-5, 32-16, 32-17, 33-2, 33-3, 33-4, 33-5, 33-16, 33-17, 33-18, 33-19, 33-20, 33-21, 33-22, 33-23, 33-24, 33-25, 33-31, 33-32, 33-33, 33-34, 33-35, 33-36, 33-37, 33-38, 33-39, 33-40, 33-41, 33-42, 33-43, 33-49, 33-50, 33-51, 33-53, 34-2, 34-3, 34-4, 34-5, 34-16, 34-17, 34-18, 34-19, 34-20, 34-21, 34-22, 34-23, 34-24, 34-25, 34-31, 34-32, 34-33, 34-34, 34-35, 34-36, 34-37, 34-38, 34-39, 34-40, 34-41, 34-42, 34-43, 34-49, 34-50, 34-51, 34-53, 35-2, 35-3, 35-4, 35-5, 35-16, 35-17, 35-18, 35-19, 35-20, 35-21, 35-22, 35-23, 35-24, 35-25, 35-31, 35-32, 35-33, 35-34, 35-35, 35-36, 35-37, 35-38, 35-39, 35-40, 35-41, 35-42, 35-43, 35-49, 35-50, 35-51, 35-53, 36-2, 36-3, 36-4, 36-5, 36-16, 36-17, 37-2, 37-3, 37-4, 37-5, 37-16, 37-17, 38-2, 38-3, 38-4, 38-5, 38-31, 38-34, 38-38, 38-40, 38-43, 39-2, 39-3, 39-4, 39-5, 39-31, 39-34, 39-38, 39-40, 39-43, 40-2, 40-3, 40-4, 40-5, 40-31, 40-34, 40-38, 40-40, 40-43, 43-2, 43-3, 43-4, 43-5, 43-31, 43-34, 43-38, 43-40, 43-43, 44-2, 44-3, 44-4, 44-5, 44-31, 44-34, 44-38, 44-40, 44-43, 45-2, 45-3, 45-4, 45-5, 45-31, 45-34, 45-38, 45-40, 45-43, 58-2, 58-3, 58-4, 58-5, 58-16, 58-17, 59-2, 59-3, 59-4, 59-5, 59-16, 59-17, 60-2, 60-3, 60-4, 60-5, 60-16, 60-17, 63-2, 63-3, 63-4, 63-5, 63-16, 63-17, 64-2, 64-3, 64-4, 64-5, 64-16, 64-17, 65-2, 65-3, 65-4, 65-5, 65-16, 65-17, 77-2, 77-3, 77-4, 77-5, 78-2, 78-3, 78-4, 78-5, 78-16, 78-17, 79-2, 79-3, 79-4, 79-5, 79-16, 79-17, 80-2, 80-3, 80-4, 80-5, 80-16, 80-17, 83-2, 83-3, 83-4, 83-5, 83-16, 83-17, 84-2, 84-3, 84-4, 84-5, 84-16, 84-17, 85-2, 85-3, 85-4, 85-5, 85-16, 85-17, 88-1, 88-2, 88-3, 88-4, 88-5, 88-6, 89-1, 89-2, 89-3, 89-4, 89-5, 89-6, 90-1, 90-2, 90-3, 90-4, 90-5, 90-6, 93-1, 93-2, 93-3, 93-4, 93-5, 93-6, 94-1, 94-2, 94-3, 94-4, 94-5, 94-6, 95-1, 95-2, 95-3, 95-4, 95-5, 95-6, 98-1, 98-2, 98-3, 98-4, 98-5, 98-6, 103-1, 103-2, 103-3, 103-4, 103-5, 103-6, 104-1, 104-2, 104-3, 104-4, 104-5, 104-6, 105-1, 105-2, 105-3, 105-4, 105-5, 105-6, 138-2, 138-3, 138-4, 138-5, 138-6, 138-7, 138-8, 138-9, 138-10, 138-11, 138-12, 138-13, 138-14, 138-15, 138-16, 138-17, 138-18, 138-19, 138-20, 138-21, 138-22, 138-23, 138-24, 138-25, 138-26, 138-27, 138-28, 138-29, 138-30, 138-31, 138-32, 138-33, 138-34, 138-35, 138-36, 138-37, 138-38, 138-39, 138-40, 138-41, 138-42, 138-43, 138-44, 138-45, 138-46, 138-47, 138-48, 138-49, 138-50, 138-51, 138-52, 138-53, 138-54, 138-55, 138-56, 138-57, 138-58, 138-59, 138-60, 138-61, 138-62, 138-63, 138-64, 138-65, 138-66, 138-67, 138-68, 138-69, 138-70, 138-71, 138-72, 138-73, 138-74, 138-75, 138-76, 138-77, 138-78, 138-79, 138-80, 138-81, 138-82, 138-83, 138-84, 138-85, 138-86, 138-87, 138-88, 138-89, 138-90, 138-91, 138-92, 138-93, 138-94, 138-95, 138-96, 138-97, 138-98, 138-99, 138-104, 138-105, 138-106, 138-107, 138-108, 138-111, 138-112, 138-113, 138-114, 138-115, 138-120, 138-121, 138-122, 138-123, 138-124, 138-127, 138-128, 138-129, 138-130, 138-131, 138-136, 138-137, 138-138, 138-139, 138-140, 138-143, 138-144, 138-145, 138-146, 138-147, 138-152, 138-153, 138-154, 138-155, 138-156, 138-159, 138-160, 138-161, 138-162, 138-163, 138-168, 138-169, 138-170, 138-171, 138-172, 138-175, 138-176, 138-177, 138-178, 138-179, 138-184, 138-185, 138-186, 138-187, 138-188, 138-191, 138-192, 138-193, 138-194, 138-195, 138-200, 138-201, 138-202, 138-203, 138-204, 138-207, 138-208, 138-209, 138-210, 138-211, 138-216, 138-217, 138-218, 138-219, 138-220, 138-223, 138-224, 138-225, 138-226, 138-227, 138-232, 138-233, 138-234, 138-235, 138-236, 138-239, 138-240, 138-241, 138-242, 138-243, 138-248, 138-249, 138-250, 138-251, 138-252, 138-255, 138-256, 138-257, 138-258, 138-259, 138-264, 138-265, 138-266, 138-267, 138-268, 138-271, 138-272, 138-273, 138-274, 138-275, 138-285, 138-295, 138-305, 138-315, 138-325, 139-24, 139-31, 140-2, 140-31, 141-23, 141-30, 142-23, 142-30, 143-23, 143-30, 144-8, 144-13, 144-18, 144-28, 144-33, 144-63, 145-1, 145-6, 145-7, 145-8, 145-9, 145-10, 145-13, 145-14, 145-15, 145-16, 145-17, 145-22, 145-23, 145-24, 145-25, 145-26, 145-29, 145-30, 145-31, 145-32, 145-33, 145-38, 145-39, 145-40, 145-41, 145-42, 145-45, 145-46, 145-47, 145-48, 145-49, 145-54, 145-55, 145-56, 145-57, 145-58, 145-61, 145-62, 145-63, 145-64, 145-65, 145-70, 145-71, 145-72, 145-73, 145-74, 145-77, 145-78, 145-79, 145-80, 145-81, 145-86, 145-87, 145-88, 145-89, 145-90, 145-93, 145-94, 145-95, 145-96, 145-97, 145-102, 145-111, 145-112, 145-118, 145-127, 145-128, 145-134, 145-143, 145-144, 145-150, 145-159, 145-160, 145-166, 145-175, 145-176, 145-182, 145-191, 145-192, 145-198, 145-207, 145-208, 145-214, 145-223, 145-224, 145-

230, 145-239, 145-240, 145-246, 145-255, 145-256, 145-262, 145-271, 145-272, 145-273, 145-283, 145-293, 145-303, and 145-313;

(2) the following compounds are more preferred: compounds Nos. 1-15, 1-35, 1-37, 1-39, 1-95, 1-110, 1-179, 1-189, 1-190, 1-191, 1-204, 1-205, 1-206, 1-207, 1-208, 1-209, 1-210, 1-212, 1-213, 1-219, 1-222, 1-223, 1-224, 1-225, 1-226, 1-227, 1-228, 1-229, 1-230, 1-231, 1-232, 1-233, 1-234, 1-235, 1-236, 1-242, 1-243, 1-244, 3-15, 3-35, 3-37, 3-39, 3-95, 3-110, 3-179, 3-189, 3-190, 3-191, 3-204, 3-205, 3-206, 3-207, 3-208, 3-209, 3-210, 3-212, 3-213, 3-219, 3-222, 3-223, 3-224, 3-225, 3-226, 3-227, 3-228, 3-229, 3-230, 3-231, 3-232, 3-233, 3-234, 3-235, 3-236, 3-242, 3-243, 3-244, 4-15, 4-35, 4-37, 4-39, 4-95, 4-96, 4-98, 4-106, 4-110, 4-143, 4-150, 4-179, 4-189, 4-190, 4-191, 4-193, 4-204, 4-205, 4-206, 4-207, 4-208, 4-209, 4-210, 4-211, 4-212, 4-213, 4-214, 4-215, 4-216, 4-217, 4-218, 4-219, 4-220, 4-221, 4-222, 4-223, 4-224, 4-225, 4-226, 4-227, 4-228, 4-229, 4-230, 4-231, 4-232, 4-233, 4-234, 4-235, 4-236, 4-242, 4-243, 4-244, 5-15, 5-35, 5-37, 5-39, 5-95, 5-110, 6-15, 6-35, 6-37, 6-39, 6-95, 6-96, 6-110, 6-179, 6-189, 6-190, 6-191, 6-204, 6-205, 6-206, 6-207, 6-208, 6-209, 6-210, 6-212, 6-213, 6-219, 6-222, 6-223, 6-224, 6-225, 6-226, 6-227, 6-228, 6-229, 6-230, 6-231, 6-232, 6-233, 6-234, 6-235, 6-236, 6-242, 6-243, 6-244, 7-15, 7-35, 7-37, 7-39, 7-95, 7-110, 7-179, 7-189, 7-190, 7-191, 7-204, 7-205, 7-206, 7-207, 7-208, 7-209, 7-210, 7-212, 7-213, 7-219, 7-222, 7-223, 7-224, 7-225, 7-226, 7-227, 7-228, 7-229, 7-230, 7-231, 7-232, 7-233, 7-234, 7-235, 7-236, 7-242, 7-243, 7-244, 8-15, 8-35, 8-37, 8-39, 8-95, 8-110, 8-179, 8-189, 8-190, 8-191, 8-204, 8-205, 8-206, 8-207, 8-208, 8-209, 8-210, 8-212, 8-213, 8-219, 8-222, 8-223, 8-224, 8-225, 8-226, 8-227, 8-228, 8-229, 8-230, 8-231, 8-232, 8-233, 8-234, 8-235, 8-236, 8-242, 8-243, 8-244, 9-15, 9-35, 9-37, 9-39, 9-95, 9-110, 14-5, 14-11, 14-12, 14-13, 14-37, 14-44, 14-45, 14-47, 14-64, 14-67, 14-73, 14-75, 14-78, 14-84, 14-85, 14-86, 15-5, 15-11, 15-12, 15-13, 15-37, 15-44, 15-45, 15-47, 15-64, 15-67, 15-73, 15-75, 15-78, 15-84, 15-85, 15-86, 17-11, 20-53, 20-71, 20-80, 28-2, 28-3, 28-4, 28-5, 28-16, 28-17, 28-19, 28-22, 28-31, 28-34, 28-38, 28-40, 28-43, 30-3, 33-2, 33-3, 33-4, 33-5, 33-16, 33-17, 33-19, 33-22, 33-31, 33-34, 33-38, 33-40, 33-43, 33-49, 33-50, 33-51, 34-2, 34-3, 34-4, 34-5, 34-16, 34-17, 34-19, 34-22, 34-31, 34-34, 34-38, 34-40, 34-43, 35-49, 35-50, 35-51, 35-2, 35-3, 35-4, 35-5, 35-16, 35-17, 35-19, 35-22, 35-31, 35-34, 35-38, 35-40, 35-43, 35-49, 35-50, 35-51, 37-3, 38-2, 38-3, 38-4, 38-5, 39-2, 39-3, 39-4, 39-5, 40-2, 40-3, 40-4, 40-5, 43-2, 43-3, 43-4, 43-5, 44-2, 44-3, 44-4, 44-5, 45-2, 45-3, 45-4, 45-5, 77-3, 138-2, 138-3, 138-8, 138-9, 138-10, 138-11, 138-12, 138-15, 138-16, 138-17, 138-18, 138-19, 138-24, 138-25, 138-26, 138-27, 138-28, 138-31, 138-32, 138-33, 138-34, 138-35, 138-40, 138-41, 138-42, 138-43, 138-44, 138-47, 138-48, 138-49, 138-50, 138-51, 138-56, 138-57, 138-58, 138-59, 138-60, 138-63, 138-64, 138-65, 138-66, 138-67, 138-72, 138-73, 138-74, 138-75, 138-76, 138-79, 138-80, 138-81, 138-82, 138-83, 138-88, 138-89, 138-90, 138-91, 138-92, 138-95, 138-96, 138-97, 138-98, 138-104, 138-120, 138-136, 138-152, 138-168, 138-184, 138-200, 138-216, 138-232, 138-248, 138-264, 138-275, 138-285, 138-295, 138-305, 138-315, 138-325, 139-24, 139-31, 140-2, 140-31, 141-23, 141-30, 142-23, 142-30, 143-23, 143-30, 144-13, 144-63, 145-6, 145-15, 145-16, 145-22, 145-31, 145-32, 145-47, 145-48, 145-54, 145-63, 145-64, 145-70, 145-79, 145-80, 145-86, 145-95, 145-96, 145-102, 145-118, 145-134, 145-150, 145-166, 145-182, 145-198, 145-214, 145-230, 145-246, 145-262, 145-273, 145-283, 145-293, 145-303 and 145-313;

(3) Much more preferred compounds are selected from the group of the following compounds:

1) 2-ethoxy-3-[4-[2-(4-pyridyl-2-ylbenzoylamino)ethoxy]phenyl]propionic acid
2) 3-[4-[2-(4-pyridyl-2-ylbenzoylamino)ethoxy]phenyl]-2-propylpropionic acid
3) 2-butyl-3-[4-[2-(4-pyridyl-2-ylbenzoylamino)ethoxy]phenyl]propionic acid
4) 3-[4-[2-(biphenyl-4-carbonylamino)ethoxy]phenyl]-2-butylpropionic acid
5) 2-butyl-3-[4-[2-(4'-formylbiphenyl-4-carbonylamino)ethoxy]phenyl]propionic acid
6) 2-butyl-3-[4-[2-(4'-dimethylaminomethylbiphenyl-4-carbonylamino)ethoxy]-phenyl]propionic acid
7) 2-butyl-3-[4-[2-(4'-carboxybiphenyl-4-carbonylamino)ethoxy]phenyl]propionic acid
8) 2-butyl-3-[4-[2-(3'-methoxybiphenyl-4-carbonylamino)ethoxy]phenyl]propionic acid
9) 2-butyl-3-[4-[2-(3'-hydroxybiphenyl-4-carbonylamino)ethoxy]phenyl]propionic acid
10) 2-butyl-3-[4-[2-(2'-methoxybiphenyl-4-carbonylamino)ethoxy]phenyl]propionic acid
11) 2-butyl-3-[4-[2-(4'-hydroxy-3,5-dimethylbiphenyl-4-carbonylamino)ethoxy]-phenyl]propionic acid
12) 2-butyl-3-[4-[2-(2-methoxypyridine-5-carbonylamino)ethoxy]phenyl]propionic acid
13) 2-butyl-3-[4-[2-(4-diethylaminobenzoylamino)ethoxy]phenyl]propionic acid
14) 2-butyl-3-[4-[3-(4-pyridyl-2-ylbenzoylamino)propoxy]phenyl]propionic acid
15) 2-phenoxy-3-[4-[2-(4-pyridyl-2-ylbenzoylamino)ethoxy]phenyl]propionic acid
16) 3-[4-[2-(biphenyl-4-carbonylamino)ethoxy]phenyl]-2-phenoxypropionic acid
17) 3-[4-[2-(4'-fluorobiphenyl-4-carbonylamino)ethoxy]phenyl]-2-phenoxypropionic acid
18) 3-[4-[2-(4'-chlorobiphenyl-4-carbonylamino)ethoxy]phenyl]-2-phenoxypropionic acid
19) 3-[4-[2-(4'-trifluoromethylbiphenyl-4-carbonylamino)ethoxy]phenyl]-2-phenoxypropionic acid
20) 2-(4-isopropylphenoxy)-3-[4-[2-(4-pyridyl-2-ylbenzoylamino)-ethoxy]phenyl]propionic acid
21) 3-[4-[2-(biphenyl-4-carbonylamino)ethoxy]phenyl]-2-(4-isopropylphenoxy)-propionic acid
22) 2-(4-isopropylphenoxy)-3-[4-[2-(2-phenylpyridine-5-carbonylamino)-ethoxy]phenyl]propionic acid
23) 2-(4-isopropylphenoxy)-3-[4-[2-[2-(4-methoxyphenyl)pyridine-5-carbonylamino)ethoxy]phenyl]propionic acid
24) 3-[4-[2-[2-(4-fluorophenyl)pyridine-5-carbonylamino]ethoxy]phenyl]-2-(4-isopropylphenoxy)propionic acid
25) 3-[4-[2-[2-(2,2,3,3-tetrafluoropropoxy)pyridine-5-carbonylamino]ethoxy]phenyl]-2-(4-isopropylphenoxy)propionic acid
26) 2-(4-isopropylphenoxy)-3-[4-[2-[4-(3-trifluoromethylpyridine-6-yl)benzoylamino]ethoxy]phenyl]propionic acid
27) 2-(4-isopropylphenoxy)-3-[4-[2-[4-(3-nitropyridine-6-yl)-benzoylamino]ethoxy]phenyl]propionic acid
28) 2-(4-isopropylphenoxy)-3-[4-[2-[4-(3-methoxypyridine-6-yl)-benzoylamino]ethoxy]phenyl]propionic acid
29) 2-(4-isopropylphenoxy)-3-[4-[2-[4-(3-dimethylaminopyridine-6-yl)benzoylamino]ethoxy]phenyl]propionic acid 30) 2-(4-methoxyphenoxy)-3-[4-[2-(4-pyridyl-2-ylbenzoylamino)ethoxy]-phenyl]propionic acid
31) 2-(3-phenylpropyl)-3-[4-[2-(4-pyridyl-2-ylbenzoylamino)ethoxy]phenyl]propionic acid
32) 2-(4-methylphenoxy)-3-[4-[2-(4-pyridyl-2-ylbenzoylamino)ethoxy]-phenyl]propionic acid
33) 2-(4-t-butylphenoxy)-3-[4-[2-(4-pyridyl-2-ylbenzoylamino)ethoxy]phenyl]-propionic acid
34) 2-(4-fluorophenoxy)-3-[4-[2-(4-pyridyl-2-ylbenzoylamino)ethoxy]phenyl]propionic acid
35) 2-(4-chlorophenoxy)-3-[4-[2-(4-pyridyl-2-ylbenzoylamino)ethoxy]phenyl]propionic acid 36) 2-(4-trifluoromethylphenoxy)-3-[4-[2-(4-pyridyl-2-ylbenzoylamino)ethoxy]phenyl]-propionic acid
37) 2-(4-trifluoromethoxyphenoxy)-3-[4-[2-(4-pyridyl-2-ylbenzoylamino)ethoxy]-phenyl]propionic acid
38) 2-(3-fluorophenoxy)-3-[4-[2-(4-pyridyl-2-ylbenzoylamino)ethoxy]phenyl]propionic acid
39) 2-(3,5-difluorophenoxy)-3-[4-[2-(4-pyridyl-2-ylbenzoylamino)ethoxy]phenyl]-propionic acid
40) 2-(3,4-difluorophenoxy)-3-[4-[2-(4-pyridyl-2-ylbenzoylamino)ethoxy]phenyl]-propionic acid
41) 2-(3,4,5-trifluorophenoxy)-3-[4-[2-(4-pyridyl-2-ylbenzoylamino)ethoxy]phenyl]-propionic acid
42) 2-(2,3,4,5,6-pentafluorophenoxy)-3-[4-[2-(4-pyridyl-2-ylbenzoylamino)ethoxy]-phenyl]propionic acid
43) 2-methyl-2-phenoxy-3-[4-[2-(4-pyridyl-2-ylbenzoylamino)ethoxy]phenyl]-propionic acid
44) 2-(4-isopropylphenoxy)-2-methyl-3-[4-[2-(4-pyridyl-2-ylbenzoylamnino)ethoxy]-phenyl]propionic acid
45) 2-(4-isopropylphenoxy)-3-[4-[2-[2-(4-methoxyphenyl)pyridine-5-carbonylamino]-ethoxy]phenyl]-2-methylpropionic acid and
46) 3-[4-[2-[2-(2,2,3,3-tetrafluoropropoxy)pyridine-5-carbonylamino]ethoxy]phenyl]-2-(4-isopropylphenoxy)-2-methylpropionic acid and pharmaceutically acceptable salts and esters thereof.
(4) Most preferred compounds are selected from the group of the following compounds:

1) 2-ethoxy-3-[4-[2-(4-pyridyl-2-ylbenzoylamino)ethoxy]phenyl]propionic acid
2) 3-[4-[2-(4-pyridyl-2-ylbenzoylamino)ethoxy]phenyl]-2-propylpropionic acid
3) 2-butyl-3-[4-[2-(4-pyridyl-2-ylbenzoylamino)ethoxy]phenyl]propionic acid
4) 2-butyl-3-[4-[2-(4'-formylbiphenyl-4-carbonylamino)ethoxy]phenyl]propionic acid
5) 2-butyl-3-[4-[2-(4'-hydroxy-3,5-dimethybiphenyl-4-carbonylamino)ethoxy]-phenyl]propionic acid
6) 2-phenoxy-3-[4-[2-(4-pyridyl-2-ylbenzoylamino)ethoxy]phenyl]propionic acid
7) 3-[4-[2-(biphenyl-4-carbonylamino)ethoxy]phenyl]-2-phenoxypropionic acid
8) 3-[4-[2-(4'-fluorobiphenyl-4-carbonylamino)ethoxy]phenyl]-2-phenoxypropionic acid
9) 3-[4-[2-(4'-chlorobiphenyl-4-carbonylamino)ethoxy]phenyl]-2-phenoxypropionic acid
10) 2-(4-isopropylphenoxy)-3-[4-[2-(4-pyridyl-2-ylbenzoylamino)ethoxy]phenyl]propionic acid
11) 3-[4-[2-(biphenyl-4-carbonylamino)ethoxy]phenyl]-2-(4-isopropylphenoxy)-propionic acid
12) 2-(4-isopropylphenoxy)-3-[4-[2-(2-phenylpyridine-5-carbonylamino)ethoxy]phenyl]propionic acid
13) 2-(4-isopropylphenoxy)-3-[4-[2-[2-(4-methoxyphenyl)pyridine-5-carbonylamino]ethoxy]phenyl]propionic acid
14) 3-[4-[2-[2-(4-fluorophenyl)pyridine-5-carbonylamino]ethoxy]phenyl]-2-(4-isopropylphenoxy)propionic acid
15) 3-[4-[2-[2-(2,2,3,3-tetrafluoropropoxy)pyridine-5-carbonylamino]ethoxy]phenyl]-2-(4-isopropylphenoxy)propionic acid
16) 2-(4-isopropylphenoxy)-3-[4-[2-[4-(3-methoxypyridine-6-yl)-benzoylamino]ethoxy]phenyl]propionic acid
17) 2-(4-isopropylphenoxy)-3-[4-[2-[4-(3-dimethylaminopyridine-6-yl)benzoylamino]ethoxy]phenyl]propionic acid
18) 2-(4-methoxyphenoxy)-3-[4-[2-(4-pyridyl-2-ylbenzoylamino)ethoxy]phenyl]propionic acid
19) 2-(4-methylphenoxy)-3-[4-[2-(4-pyridyl-2-ylbenzoylamino)ethoxy]phenyl]propionic acid
20) 2-(4-t-butylphenoxy)-3-[4-[2-(4-pyridyl-2-ylbenzoylamino)ethoxy]phenyl]propionic acid
21) 2-(4-fluorophenoxy)-3-[4-[2-(4-pyridyl-2-ylbenzoylamino)ethoxy]phenyl]propionic acid
22) 2-(4-chlorophenoxy)-3-[4-[2-(4-pyridyl-2-ylbenzoylamino)ethoxy]phenyl]propionic acid
23) 2-(4-trifluoromethylphenoxy)-3-[4-[2-(4-pyridyl-2-ylbenzoylamino)ethoxy]phenyl]propionic acid
24) 2-(4-trifluoromethoxyphenoxy)-3-[4-[2-(4-pyridyl-2-ylbenzoylamino)ethoxy]phenyl]propionic acid
25) 2-(3-fluorophenoxy)-3-[4-[2-(4-pyridyl-2-ylbenzoylamino)ethoxy]phenyl]propionic acid
26) 2-(3,4,5-trifluorophenoxy)-3-[4-[2-(4-pyridyl-2-ylbenzoylamino)ethoxy]phenyl]propionic acid
27) 2-methyl-2-phenoxy-3-[4-[2-(4-pyridyl-2-ylbenzoylamino)ethoxy]phenyl]propionic acid
28) 2-(4-isopropylphenoxy)-2-methyl-3-[4-[2-(4-pyridyl-2-yl-benzoylamino)ethoxy]phenyl]propionic acid
29) 2-(4-isopropylphenoxy)-3-[4-[2-[2-(4-methoxyphenyl)pyridine-5-carbonylamino]ethoxy]phenyl]-2-methylpropionic acid and
30) 3-[4-[2-[2-(2,2,3,3-tetrafluoropropoxy)pyridine-5-carbonylamino]ethoxy]phenyl]-2(4-isopropylphenoxy)-2-methylpropionic acid and pharmaceutically acceptable salts and esters thereof.

In the nomenclature herein, reference to a "(4-pyridyl-2-ylbenzoylamino)" group should have correctly named the "(4-pyridine-2-ylbenzoylamino)" group.

The amidocarboxylic acid derivatives of formula (I) of the present invention, pharmacologically acceptable salts thereof or pharmacologically acceptable esters thereof are easily prepared according to the following method A:

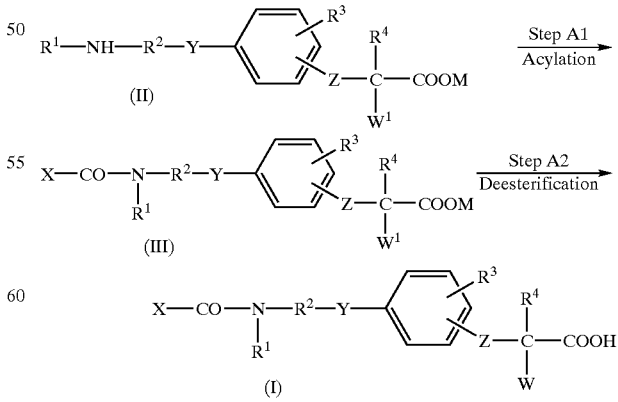

wherein $R^1$, $R^2$, $R^3$, $R^4$, W, X, Y and Z have the same meanings as defined above; $W^1$ represents an amino group protected by a conventional protecting group such as t-butoxycarbonyl in the case where W represents a primary or secondary amino group and $W^1$ has the same meaning as defined for W in the case where $W^1$ represents other groups; and in the case where the amidocarboxylic acid of formula (I) forms an ester, M represents the ester residue.

Step A1

Step A1 is to prepare a compound of formula (III) and the compound is prepared by acylating a compound of formula (II).

The present reaction is a reaction for forming an amide bond well known in organic synthetic chemistry and is preferably usually carried out in the presence of a solvent.

The solvent employed here is not particularly limited so long as it has no adverse effect on the reaction and includes, for example, an inert solvent, preferably halogenated hydrocarbons such as dichloromethane and chloroform; esters such as ethyl acetate; ethers such as tetrahydrofuran and dioxane; and amides such as N,N-dimethylacetamide and N,N-dimethylformamide.

The reaction is carried out by treatment with a condensation agent.

The condensation agent employed here includes carbodiimides such as N,N-dicyclohexylcarbodiimide and 1-(3-dimethylaminopropyl)-3-ethylcarbodiimide hydrochloride; phosphoryl compounds such as diphenylphosphoryl azide and diethylphosphoryl cyanide; carbonyldiimidazole; and triphenylphosphine-diethyl azodicarbonate; preferably carbonyldiimidazole and carbodiimides. In the case where phosphoryl compounds are employed, the reaction is preferably carried out in the presence of a tertiary amine such as triethylamine and N-methylmorpholine.

Alternatively, the present reaction is accomplished by reacting the carboxylic acid used in the present reaction or a salt thereof with a lower alkyl ester of chloroformic acid such as ethyl chloroformate and isobutyl chloroformate in the presence of a tertiary amine such as triethylamine and N-methylmorpholine to form a mixed acid anhydride or by reacting the carboxylic acid used in the present reaction or a salt thereof with N-hydroxysuccinimide, N-hydroxybenzotriazole or p-nitrophenol in the presence of carbodiimides such as N,N-dicyclohexylcarbodiimide to form the corresponding activated ester, and thereafter, by condensing these compounds with amines.

The reaction is preferably usually carried out in the presence of a solvent. The solvent employed here is not particularly limited so long as it has no adverse effect on the reaction and includes, for example, an inert solvent, preferably halogenated hydrocarbons such as dichloromethane and chloroform; ethers such as tetrahydrofuran and dioxane; and aromatic hydrocarbons such as benzene and toluene.

As a further alternative, the compound is obtained by reacting the carboxylic acid used in the present reaction or a salt thereof with a halogenating agent, preferably phosphorus pentachloride, oxalyl chloride or thionyl chloride to afford the corresponding acyl halide and then by reacting the acyl halide with amines in a similar manner to that described above.

The reaction is preferably usually carried out in the presence of a solvent. The solvent employed here is not particularly limited so long as it has no adverse effect on the present reaction and includes, for example, an inert solvent, preferably halogenated hydrocarbons such as dichloromethane; ethers such as tetrahydrofuran and dioxane; and aromatic hydrocarbons such as benzene and toluene.

The reaction is carried out at $-20°$ C. to $100°$ C., preferably at $-5°$ C. to $50°$ C.

While the reaction time varies depending on the reagent, the reaction temperature and the solvent, it is usually 30 minutes to 24 hours, preferably 1 hour to 16 hours.

Step A2

Step A2 is to prepare a phenylalkylcarboxylic acid derivative of formula (I) and is carried out by removal of an ester residue from the compound of formula (III).

The present step is accomplished by hydrolysis with a base in the presence of a solvent.

In the present reaction, the solvent employed here is not particularly limited so long as it has no adverse effect on the reaction and preferably includes, for example, ethers such as diethyl ether, tetrahydrofuran and dioxane; alcohols such as methanol, ethanol and methoxyethanol; water; or a mixture of these solvents.

The base employed in the reaction includes, for example, alkali metal hydroxides such as lithium hydroxide, sodium hydroxide and potassium hydroxide; and alkali metal carbonates such as lithium carbonate, sodium carbonate and potassium carbonate; preferably the alkali metal hydroxides.

The reaction temperature varies depending on the solvent and the base used but is $0°$ C. to $140°$ C., preferably $10°$ C. to $120°$ C.

While the reaction time varies depending on the solvent, the base and the reaction temperature employed, it is usually 10 minutes to 24 hours, preferably 30 minutes to 16 hours.

Alternatively, in the case where the ester residue is a t-butyl group, a diphenylmethyl group or a p-methoxybenzyl group, the present step is carried out by reacting the ester with an organic acid such as formic acid, acetic acid, trifluoroacetic acid, methanesulfonic acid, benzenesulfonic acid, p-toluenesulfonic acid and trifluoromethanesulfonic acid or a mineral acid such as hydrochloric acid and sulfuric acid, preferably trifluoroacetic acid or hydrochloric acid in the presence or absence of a solvent.

In the case where a solvent is used in the present reaction, the solvent is not particularly limited so long as it has no adverse effect on the reaction and includes, for example, hydrocarbons such as benzene, toluene, xylene, hexane and heptane; halogenated hydrocarbons such as chloroform, methylene chloride and carbon tetrachloride; ethers such as diethyl ether, tetrahydrofuran and dioxane; alcohols such as methanol and ethanol; amides such as N,N-dimethylformamide, N,N-dimethylacetamide and hexamethylphosphoric triamide; esters such as methyl acetate and ethyl acetate; water; or a mixture of these solvents; preferably ethers.

While the reaction temperature varies depending on the acid used, it is $-10°$ C. to $120°$ C., preferably $0°$ C. to $100°$ C.

While the reaction time varies depending on the acid used and the reaction temperature, it is usually 10 minutes to 24 hours, preferably 30 minutes to 16 hours.

As a further alternative, the present step is accomplished by carrying out a catalytic hydrogenation reaction on the compound of the formula (III) in the case where the ester residue is an aralkyl group such as a benzyl group or a diphenylmethyl group. The catalyst employed here includes, for example, palladium on carbon, palladium black, platinum oxide and platinum black, preferably palladium on carbon.

The reaction is preferably usually carried out in the presence of a solvent. The solvent employed here is not particularly limited so long as it has no adverse effect on the reaction and includes, for example, hydrocarbons such as benzene, toluene, xylene, hexane and heptane; halogenated hydrocarbons such as chloroform, methylene chloride and carbon tetrachloride; ethers such as diethyl ether, tetrahydrofuran and dioxane; alcohols such as methanol, ethanol and isopropanol; amides such as N,N-dimethylformamide, N,N-dimethylacetamide and hexamethylphosphoric triamide; carboxylic acids such as formic acid and acetic acid; or a mixture of these solvents; preferably alcohols.

The reaction temperature is 10° C. to 140° C., preferably 20° C. to 120° C.

The reaction time varies depending on the reagent, the reaction temperature and the solvent and is usually 30 minutes to 3 days, preferably 1 hour to 24 hours.

As another alternative, in the case where $W^1$ represents a primary or secondary amino group protected by a conventional protecting group such as a t-butoxycarbonyl, after the above reaction, deprotection can be carried out according to a known method, for example, by reacting the protected amino compound with an acid such as hydrochloric acid at room temperature for 30 minutes to 2 hours.

In the formula (II) of Method A, the compound (IIa) in which $R^1$ has the hydrogen atom can be also prepared according to Method B or Method C.

<<Method B>>

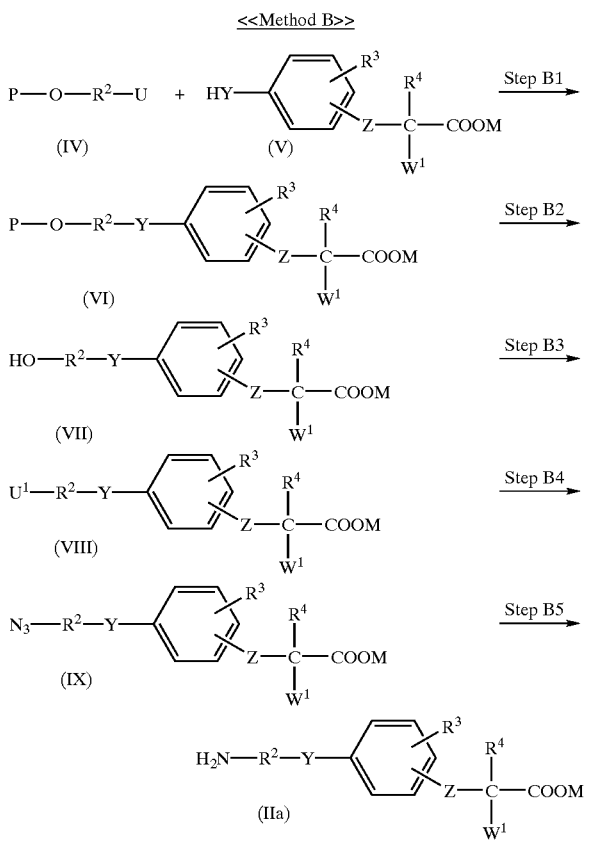

wherein
  $R^2$, $R^3$, $R^4$, Y, Z, $W^1$ and M have the same meanings as defined above.
  P represents a conventional protecting group for a hydroxyl group such as a 2-tetrahydropyranyl group or a methoxymethyl group; U represents a hydroxyl group, a halogen atom (preferably a chlorine atom, a bromine atom or an iodine atom) or a group of the formula: —O—SO$_2$—R$^6$ (wherein R$^6$ represents an alkyl group having from 1 to 6 carbon atoms such as a methyl or ethyl group; a halogenated alkyl group having from 1 to 4 carbon atoms such as a trifluoromethyl group; or an aryl group having from 6 to 10 carbon atoms which may have an alkyl group having from 1 to 4 carbon atoms, a nitro group or halogen atom as a substituent, such as a phenyl, p-tolyl, p-nitrophenyl or p-bromophenyl group). $U^1$ represents a halogen atom or a group of formula: —O—SO$_2$—R$^6$ (wherein R$^6$ has the same meaning as defined above for U).

Step B1

Step B1 in Method B is to prepare a compound of formula (VI) and the compound is prepared by reacting a compound of formula (IV) with a compound of formula (V).

In the case where U is a hydroxyl group, the reaction is carried out according to the conventional Mitsunobu reaction [O. Mitsunobu, Synthesis, page 1, (1981)].

The reaction is usually carried out by contacting azo compounds with phosphines in the presence of a solvent. As the azo compound of the reagent, $C_1$–$C_4$ alkyl azodicarboxylates such as diethyl azodicarboxylate and azodicarboxamides such as 1,1'-(azodicarbonyl)dipiperidine are used. As the phosphines, triarylphosphines such as triphenylphosphine and tri ($C_1$–$C_4$ alkyl)phosphines such as tributylphosphine are used.

The reaction is preferably usually carried out in the presence of a solvent. The solvent employed here is not particularly limited so long as it has no adverse effect on the present reaction and includes, for example, hydrocarbons such as benzene, toluene, xylene, hexane and heptane; halogenated hydrocarbons such as chloroform, methylene chloride, carbon tetrachloride and 1,2-dichloroethane; ethers such as diethyl ether, tetrahydrofuran and dioxane; amides such as N,N-dimethylformamide, N,N-dimethylacetamide and hexamethylphosphoric triamide; or a mixture of these solvents; preferably the hydrocarbons, halogenated hydrocarbons or ethers. The reaction temperature is 10° C. to 100° C., preferably 20° C. to 80° C.

While the reaction time varies depending on the reagent, the reaction temperature and the solvent, it is usually 1 hour to 3 days, preferably 5 hours to 2 days.

In the case where U represents a halogen atom or a group of formula: —O—SO$_2$—R$^6$ (wherein R$^6$ has the same meaning as defined above), the reaction is carried out in an inert solvent in the presence of a base.

The base employed here preferably includes alkali metal carbonates such as sodium carbonate and potassium carbonate; alkali metal hydrides such as sodium hydride, potassium hydride and lithium hydride; alkali metal alkoxides such as sodium methoxide, sodium ethoxide, potassium t-butoxide and lithium methoxide; alkyl lithiums such as butyl lithium and methyl lithium; lithium amides such as lithium diethylamide, lithium diisopropylamide and lithium bis(trimethylsilyl)amide; alkali metal hydrogencarbonates such as sodium hydrogencarbonate and potassium hydrogencarbonate; and tertiary organic amines such as 1,5-diazabicyclo[4.3.0]non-5-ene, 1,8-diazabicyclo[5.4.0]undec-7-ene and N,N-diisopropylethylamine; more preferably alkali metal carbonates, alkali metal hydrides or alkali metal alkoxides.

The inert solvent used in the reaction is not particularly limited so long as it has no adverse effect on the reaction and includes hydrocarbons such as benzene and toluene; ethers such as tetrahydrofuran and dioxane; alcohols such as methanol, ethanol and t-butanol; amides such as N,N-dimethylformamide, N,N-dimethylacetamide and N-methylpyrrolidinone; ketones such as acetone and 2-butanone; nitriles such as acetonitrile; sulfoxides such as dimethyl sulfoxide; or mixtures thereof; preferably ethers, amides, ketones or sulfoxides.

In the case where the present reaction is carried out in the presence of a phase transfer catalyst such as benzyltriethylammonium iodide and tetrabutylammonium iodide, alkali metal hydroxides such as sodium hydroxide and potassium hydroxide are used as the base and the reaction is carried out in a solvent which is a two-layer system of water and a halogenated hydrocarbon such as methylene chloride and chloroform.

The reaction temperature is −10° C. to 120° C., preferably 10° C. to 100° C.

While the reaction time varies depending on the reagent used and the reaction temperature, it is usually 30 minutes to 48 hours, preferably 1 hour to 16 hours.

Step B2

Step B2 is to prepare a compound of formula (VII) and is carried out by removal of the hydroxy protecting group such as a 2-tetrahydropyranyl group from the compound of the formula (VI).

The present reaction is carried out in a similar manner to the method of deprotection using an acid described in Step A2 of Method A.

Step B3

Step B3 is to prepare a compound of formula (VIII) and is carried out by converting the hydroxyl group of the compound of formula (VII) to a halogen atom or a group of formula: —O—SO$_2$—R$^6$ (wherein R$^6$ has the same meaning as defined above).

The halogenation is carried out by reaction of compound (VII) with a hydrohalogenic acid such as hydrochloric acid and hydrobromic acid; halides of inorganic acids such as thionyl chloride, thionyl bromide, phosphorus trichloride, phosphorus tribromide, phosphorus pentachloride and phosphorus oxychloride; Vilsmeier reagents such as N,N-dimethylchloroforminium and N,N-dimethylbromoforminium; or halogenation reagents containing a phosphorus compound such as triphenylphosphine and carbon tetrachloride or carbon tetrabromide, and triethylphosphine dichloride and triethylphosphine dibromide in an inert solvent or without a solvent.

The solvent employed here is not particularly limited so long as it has no adverse effect on the present reaction and includes, for example, hydrocarbons such as benzene, toluene, xylene, hexane and heptane; halogenated hydrocarbons such as chloroform, methylene chloride, carbon tetrachloride and 1,2-dichloroethane; ethers such as diethyl ether, tetrahydrofuran and dioxane; amides such as N,N-dimethylformamide, N,N-dimethylacetamide and hexamethylphosphoric triamide; and mixtures thereof; preferably hydrocarbons, halogenated hydrocarbons or ethers.

The reaction temperature is −50° C. to 150° C., preferably 0° C. to 80° C.

While the reaction time varies depending on the reagent, the reaction temperature and the solvent, it is usually 30 minutes to 3 days, preferably 1 hour to 24 hours.

The sulfonation reaction is carried out by reaction of compound (VII) with a reagent of formula: R$^6$—SO$_2$—U$^2$ or (R$^6$—SO$_2$)$_2$ (wherein R$^6$ has the same meaning as defined above and U$^2$ represents a halogen atom (preferably a chlorine atom)) in an inert solvent in the presence of a base.

The solvent employed here is not particularly limited so long as it has no adverse effect on the present reaction and includes, for example, hydrocarbons such as benzene, toluene, xylene, hexane and heptane; halogenated hydrocarbons such as chloroform, methylene chloride, carbon tetrachloride and 1,2-dichloroethane; ethers such as diethyl ether, tetrahydrofuran and dioxane; amides such as N,N-dimethylformamide, N,N-dimethylacetamide and hexamethylphosphoric triamide; nitrogen-containing aromatic compounds such as pyridine and collidine; or mixtures thereof; preferably halogenated hydrocarbons or nitrogen-containing aromatic compounds.

The base employed here includes alkali metal carbonates such as sodium carbonate and potassium carbaonate; alkali metal hydrogencarbonates such as sodium hydrogencarbonate and potassium hydrogencarbonate; or tertiary organic amines such as triethylamine, N-methylmorpholine, N,N-diisopropylethylamine, 1,5-diazabicyclo[4.3.0]non-5-ene and 1,8-diazabicyclo[5.4.0]undec-7-ene; preferably tertiary organic amines.

The reaction temperature is −70° C. to 100° C., preferably 0° C. to 80° C.

While the reaction time varies depending on the reagent, the reaction temperature and the solvent, it is usually 30 minutes to 48 hours, preferably 1 hour to 16 hours.

Step B4

Step B4 is to prepare a compound of formula (IX) and is carried out by converting the halogen atom or group of formula: —O—SO$_2$—R$^6$ (wherein R$^6$ has the same meaning as defined above) of the compound of formula (VIII) to an azide group.

The present reaction is carried out by reacting a metal azide such as sodium azide or an organic azide such as tetrabutylammonium azide in an inert solvent.

The solvent employed here is not particularly limited so long as it has no adverse effect on the present reaction and includes, for example, hydrocarbons such as benzene, toluene, xylene, hexane and heptane; halogenated hydrocarbons such as chloroform, methylene chloride, carbon tetrachloride and 1,2-dichloroethane; ethers such as diethyl ether, tetrahydrofuran and dioxane; amides such as N,N-dimethylformamide, N,N-dimethylacetamide and hexamethylphosphoric triamide; or mixtures thereof; preferably ethers or amides.

The reaction temperature is 0° C. to 150° C., preferably 20° C. to 100° C.

While the reaction time varies depending on the reagent, the reaction temperature and the solvent, it is usually 1 hour to 3 days, preferably 1 hour to 24 hours.

Step B5

Step B5 is to prepare a compound of formula (IIa) and is carried out by converting the azide group of the compound of formula (IX) to an amino group.

The present reaction is accomplished by carrying out a catalytic reduction using palladium on carbon, Raney nickel, Lindlar catalyst, etc. as a catalyst or a reduction using triphenylphosphine, etc. in an inert solvent.

The solvent employed here is not particularly limited so long as it has no adverse effect on the present reaction and includes, for example, hydrocarbons such as benzene, toluene, xylene, hexane and heptane; alcohols such as methanol and ethanol; ethers such as diethyl ether, tetrahydrofuran and dioxane; amides such as N,N-dimethylformamide, N,N-dimethylacetamide and hexamethylphosphoric triamide; and mixtures thereof; preferably alcohols or ethers.

The reaction temperature is 0° C. to 150° C., preferably 20° C. to 100° C. While the reaction time varies depending on the reagent, the reaction temperature and the solvent, it is usually 1 hour to 3 days, preferably 1 hour to 24 hours.

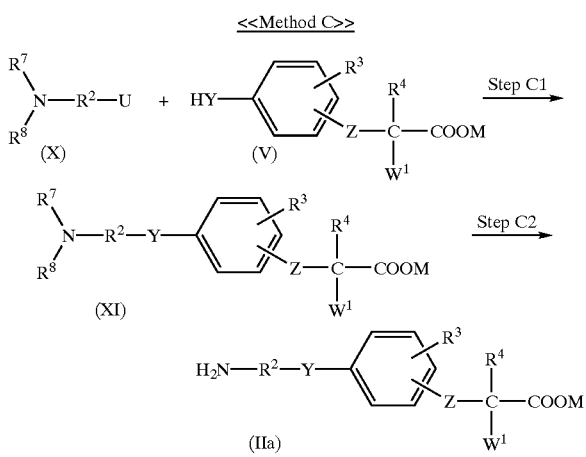

wherein
R$^2$, R$^3$, R$^4$, U, X, Y, W$^1$ and M have the same meanings as defined above;
R$^7$ represents a hydrogen atom; R$^8$ represents an amino protecting group; or R$^7$ and R$^8$ each represent an amino protecting group; or R$^7$, together with R$^8$ represent an amino protecting group.

The amino protecting group of R$^7$ or R$^8$ is a protecting group well-known in organic synthetic chemistry and includes, for example, a C$_7$–C$_{14}$ aralkyl group such as benzyl, diphenylmethyl and trityl; a C$_1$–C$_4$ aliphatic acyl group which may be substituted with fluorine such as formyl and trifluoroacetyl; a C$_1$–C$_4$ alkoxycarbonyl group such as t-butoxycarbonyl; a benzyloxycarbonyl group which may be substituted with methoxy or nitro such as benzyloxycarbonyl, p-methoxybenzyloxycarbonyl or p-nitrobenzyloxycarbonyl. In the case where R$^7$, together with R$^8$ represent an amino protecting group, the protecting group includes, for example, a phthaloyl group, etc.; preferably a t-butoxycarbonyl, benzyloxycarbonyl or phthaloyl group.

Step C1
Step C1 is to prepare a compound of formula (XI) and is carried out by reacting a compound of formula (X) with a compound of formula (V).

The present step is carried out in a similar manner to that described in Step B1 of Method B.

Step C2
Step C2 is to prepare a compound of formula (IIa) and is carried out by removal of the amino protecting group from the compound of formula (XI).

In the case where the protecting group R$^7$ or R$^8$ is a group which can be removed by catalytic reduction such as an aralkyl group and an aralkyloxycarbonyl group or a group which can be removed using an acid such as a trityl group and a t-butoxycarbonyl group, the deprotecting reation is carried out in a similar manner to that described in Step A2 of Process A.

In the case where the protecting group R$^7$ or R$^8$ is an aliphatic acyl group such as formyl and trifluoroacetyl, the protecting group is removed under basic conditions.

The base employed here includes alkali metal hydroxides such as sodium hydroxide, potassium hydroxide and lithium hydroxide; and alkali metal carbonates such as sodium carbonate and potassium carbonate; preferably alkali metal hydroxides.

The present reaction is preferably carried out in an inert solvent, for example, alcohols such as methanol and ethanol; water; ethers such as tetrahydrofuran and dioxane; and mixtures thereof; more preferably alcohols.

The reaction temperature is 0° C. to 100° C., preferably 10° C. to 80° C.

While the reaction time varies depending on the reagent, the reaction temperature and the solvent, it is usually 30 minutes to 24 hours, preferably 1 hour to 16 hours.

In the case where R$^7$, together with R$^8$ represent an amino protecting group and it is a phthaloyl group, the protecting group can be removed by treating it with hydrazines or primary amines.

The hydrazines employed here include, for example, hydrazine, methylhydrazine and phenylhydrazine, preferably hydrazine. The primary amines employed here includes methylamine, ethylamine, propylamine, butylamine, isobutylamine, pentylamine and hexylamine, preferably propylamine or butylamine.

In the present reaction, an inert solvent, for example, alcohols such as methanol and ethanol; ethers such as tetrahydrofuran and dioxane; halogenated hydrocarbons such as methylene chloride and chloroform; and mixtures thereof are preferably used. The alcohols are more preferably employed.

The reaction temperature is 0° C. to 100° C., preferably 10° C. to 80° C.

While the reaction time varies depending on the reagent, the reaction temperature and the solvent, it is usually 30 minutes to 24 hours, preferably 1 hour to 16 hours.

In the formula (II) in Method A, a compound in which R$^1$ is an alkyl group or an aralkyl group can also be prepared according to Method D or Method E.

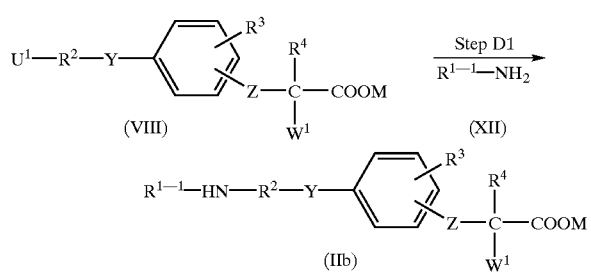

wherein R$^2$, R$^3$, R$^4$, U$^1$, Y, W$^1$ and M have the same meanings as defined above. R$^{1-1}$ represents a straight or branched chain alkyl group having from 1 to 6 carbon atoms or an aralkyl group having from 7 to 12 carbon atoms.

Step D1
Step D1 is to prepare a compound of formula (IIb) and is carried out by reacting a compound of formula (VIII) with an amine of formula (XII).

The present reaction is carried out in an inert solvent in the presence or absence of a base.

The solvent employed here is not particularly limited so long as it has no adverse effect on the present reaction and includes, for example, hydrocarbons such as benzene, toluene, xylene, hexane and heptane; alcohols such as methanol and ethanol; ethers such as diethyl ether, tetrahydrofuran and dioxane; amides such as N,N-dimethylformamide, N,N-dimethylacetamide and hexamethylphosphoric triamide; or mixtures thereof; preferably ethers or amides.

The base employed here includes alkali metal carbonates such as sodium carbonate and potassium carbonate; alkali metal hydrogencarbonates such as sodium hydrogencarbonate and potassium hydrogencarbonate; and tertiary organic amines such as triethylamine, N-methylmorpholine, N,N-diisopropylethylamine, 1,5-diazabicyclo[4.3.0]non-5-ene and 1,8-diazabicyclo[5.4.0]undec-7-ene; preferably alkali metal carbonates or tertiary organic amines.

The reaction temperature is 0° C. to 150° C., preferably 20° C. to 100° C.

While the reaction time varies depending on the reagent, the reaction temperature and the solvent, it is usually 1 hour to 3 days, preferably 1 hour to 24 hours.

<<Method E>>

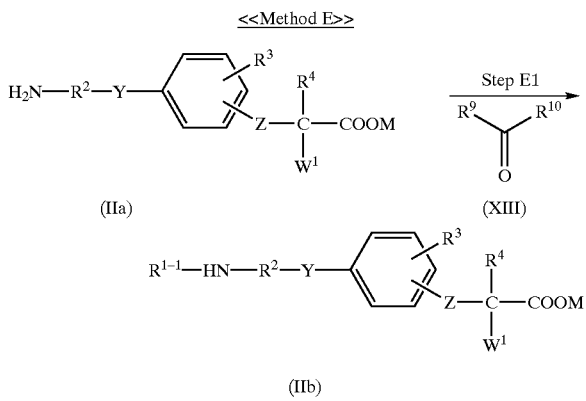

wherein $R^{1-1}$, $R^2$, $R^3$, $R^4$, Y, Z, $W^1$ and M have the same meanings as defined above.

$R^9$ represents a straight or branched chain alkyl group having from 1 to 6 carbon atoms or an aralkyl group having from 7 to 12 carbon atoms and $R^{10}$ represents a straight or branched chain alkyl group having from 1 to 6 carbon atoms, an aralkyl group having from 7 to 12 carbon atoms or a hydrogen atom.

Step E1

Step E1 is to prepare a compound of formula (IIb) and is carried out by reacting a compound of formula (IIa) with a carbonyl compound of formula (XIII).

The present reaction is carried out in an inert solvent under reduction conditions using a metal hydride such as sodium borohydride and sodium cyanoborohydride or under catalytic reduction conditions using palladium on carbon or Raney nickel as a catalyst.

The solvent employed here is not particularly limited so long as it has no adverse effect on the present reaction and includes hydrocarbons such as benzene, toluene, xylene, hexane and heptane; alcohols such as methanol and ethanol; ethers such as diethyl ether, tetrahydrofuran and dioxane; amides such as N,N-dimethylformamide, N,N-dimethylacetamide and hexamethylphosphoric triamide; or mixtures thereof; preferably alcohols or amides.

The reaction temperature is 0° C. to 150° C., preferably 20° C. to 100° C.

While the reaction time varies depending on the reagent, the reaction temperature and the solvent, it is usually 1 hour to 3 days, preferably 1 hour to 24 hours.

In the formula (III) in Method A, the compound (IIIa) in which W is an aryloxy group, a hetero aryloxy group, an arylthio group or a hetero arylthio group can be also prepared according to Method F.

<<Method F>>

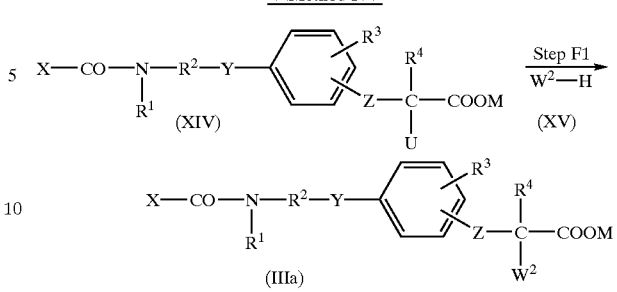

wherein $R^1$, $R^2$, $R^3$, $R^4$, U, X, Y, Z and M have the same meanings as defined above. $W^2$ represents an aryloxy group, an hetero aryl group, an arylthio group or an hetero arylthio group in W described above.

Step F1

Step F1 in Method F is to prepare a compound of formula (IIIa) and the compound is prepared by reacting a compound of formula (XIV) with a compound of formula (XV).

The present step is carried out in a similar manner to that described in Step B1 of Process B.

In the formula (XI) in Method C, the compound (XIa) in which W is an aryloxy group, a hetero aryloxy group, an arylthio group or a hetero arylthio group can be also prepared according to Method G.

<<Method G>>

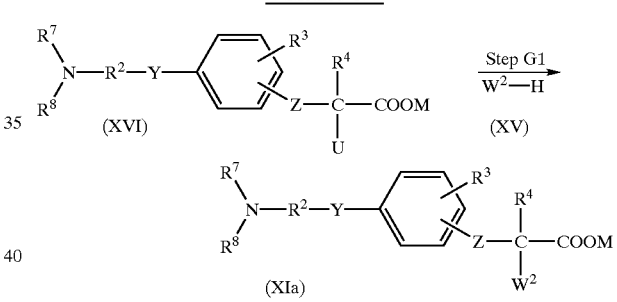

wherein $R^2$, $R^3$, $R^4$, $R^7$, $R^8$, U, $W^2$, Y, Z and M have the same meanings as defined above.

Step G1

Step G1 in Method G is to prepare a compound of formula (XIa) and the compound is prepared by reacting a compound of formula (XVI) with a compound of formula (XV).

The present step is carried out in a similar manner to that described in Step B1 of Process B.

In the formula (I) in Method A, a compound (Ia) in which $R^4$ is a hydrogen atom can be also prepared according to Method H.

<<Method H>>

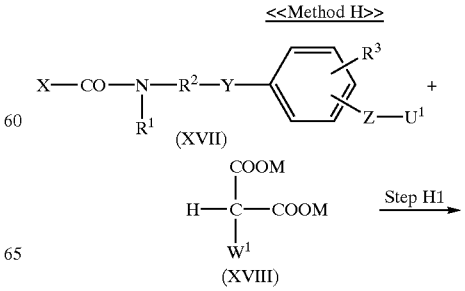

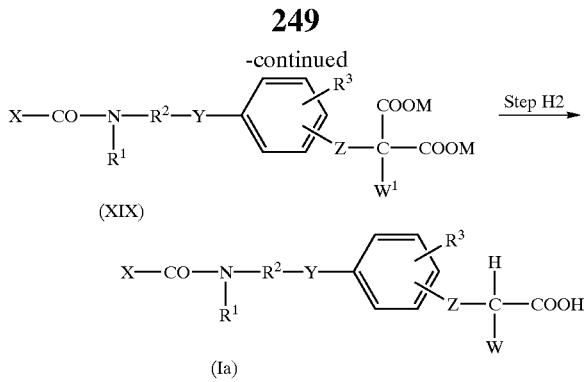

wherein $R^1$, $R^2$, $R^3$, $U^1$, W, $W^1$, Y, Z and M have the same meanings as defined above.

Step H1

Step H1 in Method H is to prepare a compound of formula (XIX) and the compound is prepared by reacting a compound of formula (XVII) with a compound of formula (XVIII).

The present reaction is carried out by reacting the compounds in an inert solvent in the presence of a base.

The base employed here preferably includes alkali metal hydrides such as sodium hydride, potassium hydride and lithium hydride; alkali metal alkoxides such as sodium methoxide, sodium ethoxide, potassium t-butoxide and lithium methoxide; alkyl lithiums such as butyl lithium and methyl lithium; lithium amides such as lithium diethylamide, lithium diisopropylamide and lithium bis(trimethylsilyl)amide; or tertiary organic amines such as 1,5-diazabicyclo[4.3.0]non-5-ene and 1,8-diazabicyclo[5.4.0]undec-7-ene; more preferably alkali metal hydrides, alkali metal alkoxides or lithium amides.

The inert solvent employed in the reaction is not particularly limited so long as it has no adverse effect on the reaction and includes, for example, hydrocarbons such as benzene and toluene; ethers such as tetrahydrofuran and dioxane; alcohols such as methanol, ethanol and t-butanol; amides such as N,N-dimethylformamide, N,N-dimethylacetamide and N-methylpyrrolidinone; ketones such as acetone and 2-butanone; nitriles such as acetonitrile; sulfoxides such as dimethyl sulfoxide; and mixtures thereof; preferably ethers, amides, ketones or sulfoxides.

In the case where the present reaction is carried out in the presence of a phase transfer catalyst such as benzyltriethylammonium iodide and tetrabutylammonium iodide, the present reaction is carried out in a two-layer solvent system of water and a halogenated hydrocarbon such as methylene chloride and chloroform using an alkali metal hydroxide such as sodium hydroxide and potassium hydroxide as the base.

The reaction temperature is −10° C. to 120° C., preferably 10° C. to 100° C.

While the reaction time varies depending on the reagent used and the reaction temperature, it is usually 30 minutes to 48 hours, preferably 1 hour to 16 hours.

Step H2

Step H2 is to prepare a phenylalkylcarboxylic acid derivative of formula (Ia) and is carried out by removal of the ester residues of the malonic acid diester derivative of formula (XIX), and then by decarboxylation.

The removal of the ester residue in the present step is accomplished by carrying out it in a similar manner to that described in Step A2 of Method A.

The step of decarboxylation is accomplished by heating the malonic acid derivative produced by removal of the ester residues of the compound of formula (XIX) in the presence of a solvent.

The solvent employed in the present step is not particularly limited so long as it has no adverse effect on the reaction and includes, for example, hydrocarbons such as benzene, toluene, xylene and heptane; halogenated hydrocarbons such as chloroform and carbon tetrachloride; ethers such as tetrahydrofuran and dioxane; alcohols such as ethanol, propanol, methoxyethanol and ethylene glycol; amides such as N,N-dimethylformamide, N,N-dimethylacetamide and hexamethylphosphoric triamide; and mixtures thereof; preferably hydrocarbons or alcohols.

The reaction temperature is 60° C. to 180° C., preferably 80° C. to 150° C.

While the reaction time varies depending on the reagent, the reaction temperature and the solvent, it is usually 30 minutes to 2 days, preferably 1 hour to 24 hours.

In the formula (I) of Method A, a compound (Ib) in which W is an alkylamino group, a dialkylamino group or an aralkylamino group can be also prepared according to Method I.

<<Method I>>

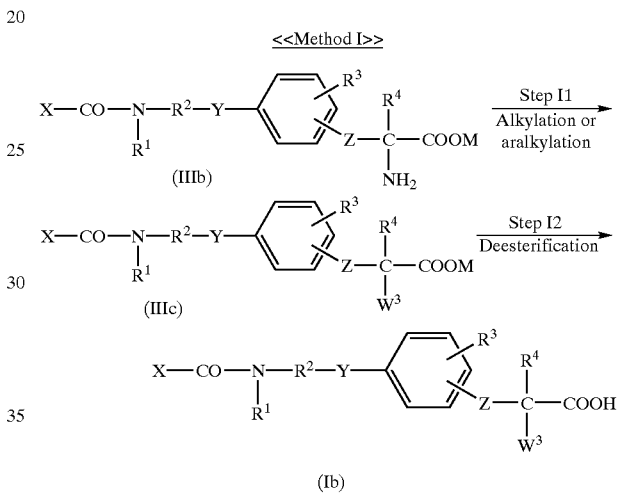

wherein $R^1$, $R^2$, $R^3$, $R^4$, X, Y, Z and M have the same meanings as defined above. $W^3$ represents a straight or branched chain monoalkylamino group having from 1 to 4 carbon atoms, a straight or branched chain dialkylamino group in which each alkyl group may be the same or different and each has from 1 to 4 carbon atoms or an aralkylamino group having from 7 to 12 carbon atoms.

Step I1

Step I1 is to prepare a compound of formula (IIIc) and is carried out by alkylation or aralkylation of a compound of formula (IIIb).

The present reaction is carried out in a similar manner to that described in Step B1 of Method B in the case where an alkyl halide, aralkyl halide, alkyl sulfonate or aralkyl sulfonate is used as an alkylation reagent.

In the case where the alkylation is reductively carried out using a carbonyl compound, it is carried out in a similar manner to that described in Step E1 of Method E.

Step I2

Step I2 is to prepare a compound of formula (Ib) and is carried out by removal of the ester residue of the compound of formula (IIIc).

The present step is carried out in a similar manner to that described in Step A2 of Method A.

The desired compound obtained by each step described above can be purified, if necessary, by conventional methods, for example, column chromatography, recrystallization and reprecipitation after the reaction. For example, the reaction mixture is appropriately neutralized, a solvent is added to the reaction mixture to extract it and the solvent is distilled off from the extract. The residue thus obtained is purified by subjecting it to column chromatography using silica gel to obtain the purified product of the desired compound.

The amidocarboxylic acid derivatives of formula (I), the pharmacologically acceptable salts thereof or the pharmacologically acceptable esters thereof have some excellent effects of lowering glucose, reducing lipid, ameliorating insulin resistance, alleviating inflammatory disease, immunoregulation, inhibiting aldose reductase, inhibiting 5-lipoxygenase, suppressing generation of lipid peroxide, activating PPAR and alleviating osteoporosis and are useful as preventive and/or therapeutic agents (particularly therapeutic agents) for diseases caused by insulin resistance such as diabetes mellitus, hyperlipemia, obesity, impaired glucose torelance, insulin resistant non-impaired glucose torelance, hypertension, fatty liver, diabetic complications (e.g., retinopathy, nephropathy, neurosis, cataracts, coronary artery diseases, etc.), arteriosclerosis, gestational diabetes mellitus and polycystic ovary syndrome, cell injury induced by atherosclerosis and ischemic heart diseases (e.g., brain injury caused by apoplexy); inflammatory diseases such as arthrosteitis, pain, pyrexia, rheumatic arthritis, inflammatory enteritis, acne, sunburn, psoriasis, eczema, allergic diseases, asthma, GI ulcers, cancer, cachexia, autoimmune diseases and panceatitis; osteoporosis; and cataracts, etc.

The amidocarboxylic acid derivatives of formula (I) of the present invention, pharmacologically acceptable salts thereof or esters thereof are administered in various forms. The administration form is not particularly limited and is determined depending on various kinds of pharmaceutical formulation forms, age, sex and other conditions, the degree of disease of the patient, etc. For example, the compound may be orally administered, in the case of tablets, pills, powders, granules, syrups, solutions, suspensions, emulsions, granules and capsules. Meanwhile, in the case of injections, it is intravenously administered singly or in a mixture with a usual adjuvant solution such as glucose, an amino acid, etc. Furthermore, if necessary, it may be singly administered intramuscularly, intracutaneously, subcutaneously or intraperitoneally. In the case of suppositories, it is intrarectally administered. Oral administration is preferable. The various kinds of these pharmaceutical formulations can be prepared using known adjuvants usually used in the known pharmaceutical formulation field such as excipients, binders, disintegrators, lubricants, solubilizers, corrigents, and coating agents for a principal agent according to a conventional method.

When the present component is molded into the form of tablets, carriers known to one of ordinary skill in the art can be widely used, and includes excipients such as lactose, sucrose, sodium chloride, glucose, urea, starch, calcium carbonate, kaolin, crystalline cellulose and silicic acid; binders such as water, ethanol, propanol, single syrup, glucose solution, starch solution, gelatin solution, carboxymethyl cellulose, shellac, methyl cellulose, potassium phosphate, and polyvinylpyrrolidone; disintegrators such as dry starch, sodium alginate, agar powder, laminaran powder, sodium hydrogencarbonate, calcium carbonate, polyoxyethylenesorbitan aliphatic acid ester, sodium lauryl sulfate, stearic acid monoglyceride, starch and lactose; disintegration inhibiting agents such as sucrose, stearic acid, cacao butter and hydrogenated oil; absorption accelerating agents such as a quaternary ammonium base and sodium lauryl sulfate; humectants such as glycerin and starch; adsorbents such as starch, lactose, kaolin, bentonite and colloidal silicic acid; and lubricants such as purified talc, a stearate, boric acid powder and polyethylene glycol. Further, the tablets can be made, if necessary, as tablets to which is applied a coating film, for example, a sugar coating tablet, a gelatin coating tablet, an enteric coated tablet, a film coating tablet, a double layer tablet or a multilayer tablet.

When the present compound is molded into the form of pills, carriers known to one of ordinary skill in the art can be widely used, and include, for example, excipients such as glucose, lactose, starch, cacao butter, hydrogenated vegetable oil, kaolin and talc; binders such as gum Arabic powder, tragacanth powder, gelatin and ethanol; and disintegrants such as laminaran agar. When the present compound is molded into the form of suppositories, carriers known to one of ordinary skill in the art can be widely used, and include, for example, polyethylene glycol, cacao butter, higher alcohols, esters of higher alcohol, gelatin and semi-synthetic glyceride.

In the case where the present compound is formulated as an injection, it is preferable that the solvents and suspending agents are sterilized and are isotonic to blood. When the present compound is formulated into such solutions, emulsions and suspensions, all diluents conventionally used in this field can be used, and include, for example, water, ethyl alcohol, propylene glycol, ethoxylated isostearyl alcohol, polyoxylated isostearyl alcohol and polyoxyethylenesorbitan aliphatic acid ester. Incidentally, in this case, a sufficient amount of NaCl, glucose or glycerin in order to prepare an isotonic solution may be contained in the pharmaceutical formulations. Further, conventional solubility improving agents, buffers and soothing agents may also be added thereto.

Further, colorants, preservatives, flavors, sweeteners and other pharmaceuticals may be contained therein, if necessary.

The amount of the active ingredient contained in the above-mentioned pharmaceutical formulations is not particulaly limited and is appropriately selected from a wide range, and it is preferable that the content is usually from 1 to 70% by weight in all compositions, more preferably from 1 to 30% by weight.

While the does will vary depending on the animal's symptoms, age and body weight, and on the administration methods and form of the pharmaceutical formulations, it is usually administered in an amount of 0.000002 mg/kg (preferably 0.00002 mg/kg, more preferably 0.0002 mg/kg) as a lower limit and 40 mg/kg (preferably 4 mg/kg, more preferably 0.4 mg/kg) as an upper limit. For adult humans, it is usually administered in an amount of 0.0001 mg (preferably 0.001 mg, more preferably 0.01 mg) as a lower limit and 2000 mg (preferably 200 mg, more preferably 20 mg) as an upper limit from once to several times per day to an adult.

The following examples, reference examples, test examples and formulation examples are intended to further illustrate the present invention and are intended in no way to limit the scope of the invention.

All $^1$H-NMR spectra were determined in the solvents indicated and chemical shifts are reported in δ units downfield from the internal standard tetramethylsilane (TMS) and interproton coupling constants are reported in Hertz (Hz).

EXAMPLE 1

Ethyl 2-ethoxy-3-[4-[2-(4-pyridine-2-ylbenzoylamino)ethoxy]phenyl]propionate (ethyl ester of exemplification No. 1-35 compound)

Hydrazine-hydrate (80%, 0.125 ml) was added to a solution of ethyl 2-ethoxy-3-[4-(2-phthaloyliminoethoxy)

phenyl]propionate (760 mg), which is the product of reference example 1, in methanol (5 ml) and the mixture was allowed to stand at room temperature for 1.5 hours. At the end of this time the reaction mixture was concentrated. The residue was partitioned between ethyl acetate and water and the layers were separated. The ethyl acetate layer was dried over anhydrous sodium sulfate and concentrated by evaporation in vacuum to afford an amino derivative.

Separately, carbonyldiimidazole (400 mg) was added to a suspension of 4-pyridine-2-ylbenzoic acid (400 mg) in anhydrous dichloromethane (10 ml) and the mixture was stirred at room temperature for 1.5 hours to give a clear solution. To this clear solution, a solution of the amino derivative produced as described above in dichloromethane (5 ml) was added and the mixture was stirred at room temperature for 30 minutes. To this reaction mixture 4-pyridine-2-ylbenzoic acid (200 mg) and carbonyldiimidazole (170 mg) were added. After the mixture was allowed to stand overnight, the reaction mixture was concentrated by evaporation in vacuum. The residue was partitioned between ethyl acetate and water and the layers were separated. The organic layer was dried over anhydrous magnesium sulfate and evaporated under reduced pressure. The residue was purified via chromatography on a silica gel column using dichloromethane/methanol=20/1 as the eluant to afford the title compound (135 mg) as a gum.

$^1$H-NMR (270 MHz, CDCl$_3$): δ ppm 1.08–1.29 (6H, m), 2.95 (2H, d, J=6.5 Hz), 3.35 (1H, quintuplet, J=7.0 Hz), 3.60 (1H, quintuplet, J=7.0 Hz), 3.83–4.30 (7H, m), 6.72 (1H, t, J=4.5 Hz), 6.86 (1H, t, J=8.5 Hz), 7.17 (2H, d, J=8.5 Hz), 7.25–7.40 (1H, m), 7.72–8.01 (4H, m), 8.07 (2H, d, J=8.5 Hz), 8.70–8.80 (1H,m).

EXAMPLE 2

Sodium 2-ethoxy-3-[4-[2-(4-pyridine-2-ylbenzoylamino)ethoxy]phenyl]propionate
(exemplification No. 1-35 compound)

To a solution of ethyl 2-ethoxy-3-[4-[2-(4-pyridine-2-ylbenzoylamino)ethoxy]phenyl]propionate (135 mg), which is the product of Example 1, in methanol (2 ml) an aqueous solution of sodium hydroxide (1N, 0.55 ml) was added. The mixture was stirred at room temperature for 2 hours. At the end of this time the methanol was evaporated under reduced pressure and an aqueous solution of hydrogen chloride (1N, 0.55 ml) and ethyl acetate were added to the residue. The ethyl acetate layer was separated and dried over anhydrous magnesium sulfate and then concentrated under reduced pressure to afford the desired compound (121 mg) as a gum.

An aqueois 1N sodium hydroxide solution (0.28 ml) was added to a solution of the desired compound in methanol (3 ml) and the mixture was concentrated in vacuum to give the title compound (128 mg) as an amorphous solid.

$^1$H-NMR (270 MHz, deuterated dimethylsulfoxide): δ ppm 1.00 (3H, t, J=7.0 Hz), 2.66 (2H, dd, J=9.0, 14.0 Hz), 2.88 (2H, dd, J=3.5, 14.0 Hz), 3.42–3.70 (5H, m), 4.05–4.13 (1H, m), 6.83 (2H, d, J=8.5 Hz), 7.14 (2H, d, J=8.5 Hz), 7.32–41 (1H, m), 7.85–8.09 (4H, m), 8.17 (2H, d, J=8.5 Hz), 8.69 (1H, d, J=4.0 Hz), 8.80 (1H, t, J=5.5 Hz).

EXAMPLE 3

Ethyl 2-(3-phenylpropyl)-3-[4-[2-(4-pyridine-2-ylbenzoylamino)ethoxy]phenyl]propionate (ethyl ester of exemplification No. 9-35 compound)

In a similar manner to that described in Example 1, a reaction was carried out using ethyl 2-(3-phenylpropyl)-3-[4-(2-phthaloyliminoethoxy)phenyl]propionate (1.50 g), which is the product of Reference example 2, 4-pyridine-2-ylbenzoic acid (285 mg) and carbonyldiimidazole (255 mg) and the reaction mixture was treated, to give the title compound (984 mg) as a gum.

$^1$H-NMR (270 MHz, CDCl$_3$): δ ppm 1.14 (3H, t, J=7.0 Hz), 1.47–1.73 (4H, m), 2.50–2.70 (4H, m), 2.80–2.92 (1H, m), 3.89 (2H, dt, J=5.0, 5.0 Hz), 4.04 (2H, q, J=7.0 Hz), 4.15 (2H, t, J=5.0 Hz), 6.67 (1H, t, J=5.0 Hz), 6.84 (2H, d, J=8.5 Hz), 7.07 (2H, d, J=8.5 Hz), 7.10–7.20 (3H, m), 7.20–7.31 (3H, m), 7.73–7.79 (2H, m), 7.90 (2H, d, J=8.5 Hz), 8.08 (2H, d, J=8.5 Hz), 8.71 (1H, d, J=5.0 Hz).

EXAMPLE 4

2-(3-phenylpropyl)-3-[4-[2-(4-pyridine-2-ylbenzoylamino)ethoxy]phenyl]propionic acid
(exemplification No. 9-35 compound)

In a similar manner to that described in Example 2, ethyl 2-(3-phenylpropyl)-3-[4-[2-(4-pyridine-2-ylbenzoylamino)ethoxy]phenyl]propionate (767 mg), which is the product of Example 3, was reacted with an aqueous sodium hydroxide solution (1N, 2.86 ml) and the reaction mixture was treated. The residue was crystallized from a mixture of diisopropyl ether and ethyl acetate to give the title compound (361 mg) as colorless crystals.

mp 114–116° C.

$^1$H-NMR (270 MHz, CDCl$_3$): δ ppm 1.50–1.79 (4H, m), 2.57–2.75 (4H, m), 2.80–2.94 (1H, m), 3.85 (2H, q, J=5.5 Hz), 4.13–4.20 (2H, m), 6.69 (1H, t, J=5.5 Hz), 6.83 (2H, d, J=8.5 Hz), 7.07 (2H, d, J=8.5 Hz), 7.10–7.20 (3H, m), 7.22–7.32 (3H, m), 7.70–7.84 (4H, m), 7.97 (2H, d, J=8.5 Hz), 8.67–8.71 (1H, m).

EXAMPLE 5

Ethyl 2-(2-phenoxyethyl)-3-[4-[2-(4-pyridine-2-ylbenzoylamino)ethoxy]phenyl]propionate (ethyl ester of exemplification No. 138-2 compound)

Carbonyldiimidazol (272 mg) was added to a suspension of 4-pyridine-2-ylbenzoic acid (279 mg) in dichloromethane (8 ml). The mixture was stirred at ambient temperature for 30 minutes to afford a clear solution. To this solution, a solution of ethyl 3-[4-(2-aminoethoxy)phenyl]-2-(2-phenoxyethyl)propionate (476 mg), which is the product of Reference example 3, in methylene chloride (5 ml) was added and the mixture was stirred at ambient temperature for 30 minutes and allowed to stand overnight. At the end of this time the reaction mixture was concentrated and the residue was partitioned between ethyl acetate and water. The ethyl acetate layer was separated and dried over anhydrous magnesium sulfate and then concentrated under reduced pressure. The residue was purified via chromatography on silica gel column using dichloromethane/ethyl acetate=1/1 as the eluant to give the title compound (374 mg) as a gum.

$^1$H-NMR (270 MHz, CDCl$_3$): δ ppm 1.14 (3H, t, J=7.0 Hz), 1.90–2.21 (2H, m), 2.76–3.10 (3H, m), 3.87–4.19 (8H, m), 6.65–6.69 (1H, m), 6.82–6.89 (4H, m), 6.93 (1H, t, J=7.5 Hz), 7.12 (2H, d, J=8.5 Hz), 7.23–7.32 (3H, m), 7.76–7.83 (2H, m), 7.90 (2H, d, J=8.5 Hz), 8.09 (2H, d, J=8.5 Hz), 8.72–8.75 (1H, m).

EXAMPLE 6

2-(2-Phenoxyethyl)-3-[4-[2-(4-pyridine-2-ylbenzoylamino)ethoxy]phenyl]propionic acid
(exemplification No. 138-2 compound)

An aqueous solution of potassium hydroxide (85%, 0.13 g) was added to a solution of ethyl 2-(2-phenoxyethyl)-3-

[4-[2-(4-pyridine-2-ylbenzoylamino)ethoxy]phenyl]propionate (350 mg) in ethanol (8 ml). The mixture was stirred at 80° C. for 3 hours. At the end of this time the ethanol was evaporated under reduced pressure. An aqueous solution of hydrogen chloride (1N, 2.0 ml) and ethyl acetate was added to the residue. The ethyl acetate layer was separated and dried over anhydrous magnesium sulfate and concentrated under reduced pressure to give the title compound (260 mg) as a mass of foam.

$^1$H-NMR (270 MHz, CDCl$_3$): δ ppm 1.93–2.22 (2H, m), 2.78–3.02 (3H, m), 3.86 (2H, dt, J=5.0, 5.5 Hz), 4.00–4.08 (2H, m), 4.16–4.21 (2H, m), 6.65–6.69 (1H, m), 6.82–6.97 (5H, m), 7.12 (2H, d, J=8.5 Hz), 7.22–7.34 (3H, m), 7.72–7.85 (4H, m), 7.97 (2H, d, J=8.5 Hz), 8.68–8.71 (1H, m).

An aqueous sodium hydroxide solution (1N, 0.51 ml) was added to a solution of the mass of foam in ethanol (3 ml). The mixture was concentrated to give a solid which was washed with diethyl ether to afford the title compound (203 mg) as an amorphous solid.

EXAMPLE 7

Ethyl 2-phenoxy-3-[4-[2-(4-pyridine-2-ylbenzoylarnino)ethoxy]phenyl]propionate (ethyl ester of exemplification No. 6-35 compound)

In a similar manner to that described in Example 5, a reaction was carried out using ethyl 3-[4-(2-aminoethoxy)phenyl]-2-phenoxypropionate (660 mg), which is the product of Reference example 4, 4-pyridine-2 ylbenzoic acid (428 mg) and carbonyldiimidazole (418 mg) and the reaction mixture was treated to give the title compound (367 mg) as a white powder.

mp 118.5–120° C.

$^1$H-NMR (270 MHz, CDCl$_3$): δ ppm 1.19 (3H, t, J=7.0 Hz), 3.17–3.22 (2H, m), 3.89 (2H, dt, J=5.0, 5.5 Hz), 4.13–4.22 (4H, m), 4.74 (1H, dd, J=5.5, 7.0 Hz), 6.63–6.69 (1H, m), 6.84 (2H, d, J=9.0 Hz), 6.87 (2H, d, J=9.0 Hz), 6.94 (1H, t, J=7.5 Hz), 7.20–7.30 (5H, m), 7.75–7.80 (2H, m), 7.90 (2H, d, J=8.5 Hz), 8.07 (2H, d, J=8.5 Hz), 8.72 (1H, d, J=4.5 Hz).

EXAMPLE 8

2-Phenoxy-3-[4-[2-(4-pyridine-2-ylbenzoylamino)ethoxy]phenyl]propioric acid (exemplification No. 6-35 compound)

In a similar manner to that described in Example 6, ethyl 2-phenoxy-3-[4-[2-(4-pyridine-2-ylbenzoylamino)ethoxy]phenyl]propionate (327 mg), which is the product of Example 7, was reacted with aqueous potassium hydroxide solution (85%, 200 mg) and the reaction mixture was treated to give the title compound (280 mg) as colorless crystals.

mp 149–151° C.

$^1$H-NMR (270 MHz, CDCl$_3$): δ ppm 3.21 (2H, d, J=7.0 Hz), 3.87 (2H, dt, J=5.0, 5.5 Hz), 4.14–4.18 (2H, m), 4.73 (1H, t, J=7.0 Hz), 6.84–6.94 (6H, m), 7.19–7.31 (5H, m), 7.75–7.80 (2H, m), 7.88 (2H, d, J=8.5 Hz), 8.05 (2H, d, J=8.5 Hz), 8.71 (1H, d, J=4.5 Hz).

EXAMPLE 9

Ethyl 2-(4-isopropylphenoxy)-3-[4-[2-(4-pyridine-2-ylbenzoylamino)ethoxy]phenyl]propionate (ethyl ester of exemplification No. 7-35 compound)

In a similar manner to that described in Example 5, a reaction was carried out using ethyl 3-[4-(2-aminoethoxy)phenyl]-2-(4-isopropylphenoxy)propionate (13.52 g), which is the product of Reference example 5, 4-pyridine-2-ylbenzoic acid (7.97 g) and carbonyldiimidazole (6.49 g) and the reaction mixture was treated and then the residue was crystallized from diisopropyl ether to give the title compound (8.38 g) as colorless crystals.

mp 77–79° C.

$^1$H-NMR (270 MHz, CDCl$_3$): δ ppm 1.14–1.25 (9H, m), 2.72–2.90 (1H, m), 3.12–3.19 (2H, m), 3.89 (2H, dt, J=5.0, 5.5 Hz), 4.11–4.22 (4H, m), 4.69 (1H, dd, J=5.5, 7.5 Hz), 6.65 (1H, brt), 6.75 (2H, d, J=8.5 Hz), 6.86 (2H, d, J=8.5 Hz), 7.08 (2H, d, J=8.5 Hz), 7.20–7.31 (3H, m), 7.76–7.81 (2H, m), 7.88 (2H, d, J=8.5 Hz), 8.07 (2H, d, J=8.5 Hz), 8.69–8.75 (1H, m).

EXAMPLE 10

2-(4-isopropylphenoxy)-3-[4-[2-(4-pyridine-2-ylbenzoylamino)ethoxy]phenyl]propionic acid (exemplification No. 7-35 compound)

In a similar manner to that described in Example 2, ethyl 2-(4-isopropylphenoxy)-3-[4-[2-(4-pyridine-2-ylbenzoylamino)ethoxy]phenyl]propionate (8.38 g), which is the product of Example 9, was reacted with aqueous sodium hydroxide solution (1N, 30.32 ml) and the reaction mixture was treated to give the title compound (7.95 g) as a white powder.

$^1$H-NMR (270 MHz, CDCl$_3$): δ ppm 1.16 (6H, d, J=7.0 Hz), 2.70–2.88 (1H, m), 3.19 (2H, d, J=6.0 Hz), 3.80–3.89 (2H, m), 4.11–4.18 (2H, m), 4.77 (1H, t, J=6.0 Hz), 6.77–6.88 (5H, m), 7.07 (2H, d, J=8.5 Hz), 7.21 (2H, d, J=8.5 Hz), 7.25–7.35 (1H, m), 7.70 (1H, d, J=8.5 Hz), 7.75–7.86 (3H, m), 7.89 (2H, d, J=8.5 Hz), 8.70–8.77 (1H, m).

EXAMPLE 11

Ethyl 2-butyl-3-[4-[2-(4-pyridine-2-ylbenzoylamino)ethoxy]phenyl]propionate (ethyl ester of exemplification No. 4-35 compound)

In a similar manner to that described in Example 5, a reaction was carried out using ethyl 3-[4-(2-aminoethoxy)phenyl]-2-butylpropionate (1.49 g), which is the product of Reference example 6, 4-pyridine-2-ylbenzoic acid (996 mg) and carbonyldiimidazole (810 mg) and the reaction mixture was treated to give the title compound (1.04 g) as a white powder.

mp 112–115° C.

$^1$H-NMR (270 MHz, CDCl$_3$): δ ppm 0.86 (3H, t, J=6.5 Hz), 1.16 (3H, t, J=7.0 Hz), 1.20–1.37 (4H, m), 1.39–1.68 (2H, m), 2.35–2.63 (1H, m), 2.68 (1H, dd, J=6.5, 13.5 Hz), 2.86 (1H, dd, J=8.5, 13.5 Hz), 3.89 (2H, t, J=5.0 Hz), 4.06 (2H, q, J=7.0 Hz), 4.15 (2H, t, J=5.0 Hz), 6.66 (1H, brs), 6.84 (2H, d, J=8.5 Hz), 7.08 (2H, d, J=8.5 Hz), 7.21–7.31 (1H, m), 7.77–7.79 (2H, m), 7.89 (2H, d, J=8.5 Hz), 8.08 (2H, d, J=8.5 Hz), 8.72 (1H, d, J=4.5 Hz).

EXAMPLE 12

2-butyl-3-[4-[2-(4-pyridine-2-ylbenzoylamino)ethoxy]phenyl]propionic acid (exemplification No. 4-35 compound)

In a similar manner to that described in Example 2, ethyl 2-butyl-3-[4-[2-(4-pyridine-2-ylbenzoylamino)ethoxy]phenyl]propionate (0.92 g), which is the product of Example 11, was reacted with aqueous sodium hydroxide solution (1N, 3.80 ml) and the reaction mixture was treated to give the title compound (1.06 g) as a white powder.

mp 137–139° C.

$^1$H-NMR (270 MHz, CDCl$_3$): δ ppm 0.87 (3H, t, J=7.0 Hz), 1.21–1.42 (4H, m), 1.45–1.70 (2H, m), 2.57–2.80 (1H, m), 2.70 (1H, dd, J=5.0, 13.5 Hz), 2.87 (1H, dd, J=9.0, 13.5 Hz), 3.86 (2H, t, J=5.0 Hz), 4.17 (2H, t, J=5.0 Hz), 6.77 (1H, brs), 6.83 (2H, d, J=8.5 Hz), 7.09 (2H, d, J=8.5 Hz), 7.23–7.38 (1H, m), 7.72–7.75 (2H, m), 7.79 (2H, d, J=8.5 Hz), 7.98 (2H, d, J=8.5 Hz), 8.70 (1H, d, J=4.5 Hz).

EXAMPLE 13

Ethyl 2-methyl-2-(3-phenylpropyl)-3-[4-[2-(4-pyridine-2-yl-benzoylamino)ethoxy]phenyl] propionate (ethyl ester of exemplification No. 37-3 compound)

In a similar manner to that described in Example 5, a reaction was carried out using ethyl 3-[4-(2-aminoethoxy) phenyl]-2-methyl-2-(3-phenylpropyl)propionate (796 mg), which is the product of Reference example 7, 4-pyridine-2-ylbenzoic acid (438 mg) and carbonyldiimidazole (428 mg) and the reaction mixture was treated to give the title compound (285 mg) as a colorless oil.

$^1$H-NMR (270 MHz, CDCl$_3$): δ ppm 1.05 (3H, s), 1.24 (3H, t, J=7.0 Hz), 1.38–1.80 (4H, m), 2.56–2.65 (3H, m), 2.94 (1H, d, J=13.0 Hz), 3.89 (2H, dt, J=5.0, 5.5 Hz), 4.07–4.18 (4H, m), 6.65 (1H, brs), 6.80 (2H, d, J=8.5 Hz), 6.99 (2H, d, J=8.5 Hz), 7.14–7.30 (6H, m), 7.75–7.79 (2H, m), 7.89 (2H, d, J=8.5 Hz), 8.08 (2H, d, J=8.5 Hz), 8.72 (1H, d, J=5.0 Hz).

EXAMPLE 14

Sodium 2-methyl-2-(3-phenylpropyl)-3-[4-[2-(4-pyridine-2-yl-benzoylamino)ethoxy]phenyl] propionate (exemplification No. 37-3 compound)

In a similar manner to that described in Example 6, ethyl 2-methyl-2-(3-phenylpropyl)-3-[4-[2-(4-pyridine-2-ylbenzoylamino)ethoxy]phenyl]propionate (0.131 mg), which is the product of Example 13, was reacted with aqueous potassium hydroxide solution (85%, 0.24 g) and the reaction mixture was treated. The residue was subjected to chromatography on a silica gel column using dichloromethane/methanol=20/1 as the eluant to afford the desired compound. An aqueous solution of sodium hydroxide (1N, 0.37 ml) was added to the desired compound and the mixture was concentrated to afford a solid. The solid was washed with diisopropyl ether to give the title compound (177 mg) as a white powder.

mp 108–111° C.

$^1$H-NMR (270 MHz, deuterated dimethylsulfoxide): δ ppm 1.01 (3H, s), 1.15–1.85 (4H, m), 2.55–2.78 (3H, m), 3.03 (1H, d, J=13.0 Hz), 3.71–3.93 (2H, m), 4.13–4.38 (2H, m), 6.97 (2H, d, J=8.5 Hz), 7.21–7.69 (8H, m), 8.08–8.45 (6H, m), 8.86–8.98 (1H, m), 9.09–9.15 (1H, m).

EXAMPLE 15

Ethyl 2-methyl-2-phenoxy-3-[4-[2-(4-pyridine-2-ylbenzoylamino)ethoxy]phenyl]propionate (ethyl ester of exemplification No. 33-3 compound)

In a similar manner to that described in Example 5, a reaction was carried out using ethyl 3-[4-(2-aminoethoxy) phenyl]-2-methyl-2-phenoxypropionate (760 mg), which is the product of Reference example 8, 4-pyridine-2-ylbenzoic acid (460 mg) and carbonyldiimidazole (440 mg) and the reaction mixture was treated to give the title compound (930 mg) as a syrup.

$^1$H-NMR (270 MHz, CDCl$_3$): δ ppm 1.22 (3H, t, J=7.0 Hz), 1.40 (3H, s), 3.11 (1H, d, J=14.0 Hz), 3.29 (1H, d, J=14.0 Hz), 3.89 (2H, dt, J=5.0, 5.5 Hz), 4.10–4.25 (2H, m), 4.18 (2H, q, J=7.0 Hz), 6.71 (1H, brs), 6.75–6.86 (4H, m), 6.97 (1H, t, J=7.0 Hz), 7.13–7.33 (5H, m), 7.74–7.84 (2H, m), 7.89 (2H, d, J=8.5 Hz), 8.07 (2H, d, J=8.5 Hz), 8.71 (1H, d, J=5.0 Hz).

EXAMPLE 16

2-Methyl-2-phenoxy-3-[4-[2-(4-pyridine-2-ylbenzoylamino)ethoxy]phenyl]propionic acid (exemplification No. 33-3 compound)

In a similar manner to that described in Example 2, ethyl 2-methyl-2-phenoxy-3-[4-[2-(4-pyridine-2-ylbenzoylamino)ethoxy]phenyl]propionate (930 mg), which is the product of Example 15, was reacted with aqueous sodium hydroxide solution (1N, 3.60 ml) at 70° C. and the reaction mixture was treated to give the title compound (545 mg) as a white powder.

mp 76–79° C.

$^1$H-NMR (270 MHz, CDCl$_3$): δ ppm 1.44 (3H, s), 3.15 (1H, d, J=14.0 Hz), 3.28 (1H, d, J=14.0 Hz), 3.87 (2H, t, J=5.0 Hz), 4.16 (2H, t, J=5.0 Hz), 6.75 (1H, brs), 6.84 (2H, d, J=8.5 Hz), 6.92 (2H, d, J=8.5 Hz), 6.97 (1H, t, J=7.0 Hz), 7.15–7.34 (5H, m), 7.70–7.88 (4H, m), 7.97 (2H, d, J=8.5 Hz), 8.73 (1H, d, J=4.0 Hz).

EXAMPLE 17

Ethyl 2-(4-isopropylphenoxy)-2-methyl-3-[4-[2-(4-pyridine-2-ylbenzoylamino)ethoxy]phenyl] propionate (ethyl ester of exemplification No. 34-3 compound)

In a similar manner to that described in Example 5, a reaction was carried out using ethyl 3-[4-(2-aminoethoxy) phenyl]-2-(4-isopropylphenoxy)-2-methylpropionate (510 mg), which is the product of Reference example 9, 4-pyridine-2-ylbenzoic acid (279 mg) and carbonyldiimidazole (272 mg) and the reaction mixture was treated to give the title compound (487 mg) as a colorless oil.

$^1$H-NMR (270 MHz, CDCl$_3$): δ ppm 1.19 (6H, d, J=7.0 Hz), 1.23 (3H, t, J=7.0 Hz), 1.37 (3H, s), 2.83 (1H, septet, J=7.0 Hz), 3.10 (1H, d, J=13.5 Hz), 3.26 (1H, d, J=13.5 Hz), 3.90 (2H, dt, J=5.0, 5.0 Hz), 4.17 (2H, t, J=5.0 Hz), 4.21 (2H, q, J=7.0 Hz), 6.69 (1H, brt, J=5.0 Hz), 6.75 (2H, d, J=8.5 Hz), 6.86 (2H, d, J=8.5 Hz), 7.06 (2H, d, J=8.5 Hz), 7.19 (2H, d, J=8.5 Hz), 7.25–7.32 (1H, m), 7.76–7.79 (2H, m), 7.89 (2H, d, J=8.5 Hz), 8.07 (2H, d, J=8.5 Hz), 8.71–8.73 (1H, m).

EXAMPLE 18

2-(4-Isopropylphenoxy)-2-methyl-3-[4-[2-(4-pyridine-2-ylbenzoylamino)ethoxy]phenyl]propionic acid (exemplification No. 34-3 compound)

In a similar manner to that described in Example 6, ethyl 2-(4-isopropylphenoxy)-2-methyl-3-[4-[2-(4-pyridine-2-ylbenzoylamino)ethoxy]phenyl]propionate (486 mg), which is the product of Example 17, was reacted with aqueous potassium hydroxide solution (85%, 0.17 g) and the reaction mixture was treated. The residue was washed with diisopropyl ether to give the title compound (335 mg) as a white powder.

mp 141–143° C.

$^1$H-NMR (270 MHz, CDCl$_3$): δ ppm 1.20 (6H, d, J=7.0 Hz), 1.43 (3H, s), 2.84 (1H, septet, J=7.0 Hz), 3.15 (1H, d, J=14.0 Hz), 3.25 (1H, d, J=14.0 Hz), 3.83–3.93 (2H, m), 4.17 (2H, t, J=5.0 Hz), 6.70 (1H, brt, J=6.0 Hz), 6.85 (2H, d, J=8.5 Hz), 6.86 (2H, d, J=8.5 Hz), 7.09 (2H, d, J=8.5 Hz), 7.21 (2H, d, J=8.5 Hz), 7.27–7.33 (1H, m), 7.72–7.80 (2H, m), 7.83 (2H, d, J=8.5 Hz), 8.00 (2H, d, J=8.5 Hz), 8.72 (1H, d, J=4.5 Hz).

EXAMPLE 19

Ethyl 2-butyl-2-methyl-3-[4-[2-(4-pyridine-2-ylbenzoylamino)ethoxy]phenyl]propionate (ethyl ester of exemplification No. 30-3 compound)

In a similar manner to that described in Example 5, a reaction was carried out using ethyl 3-[4-(2-aminoethoxy)phenyl]-2-butyl-2-methylpropionate (2.42 g), which is the product of Reference example 10, 4-pyridine-2-ylbenzoic acid (1.72 g) and carbonyldiimidazole (1.69 g) and the reaction mixture was treated to give the title compound (970 mg) as a white powder.

$^1$H-NMR (270 MHz, CDCl$_3$): δ ppm 0.89 (3H, t, J=7.0 Hz), 1.06 (3H, s), 1.12–1.46 (8H, m), 1.60–1.77 (1H, m), 2.63 (1H, d, J=13.5 Hz), 2.97 (1H, d, J=13.5 Hz), 3.86–3.93 (2H, m), 4.07–4.18 (4H, m), 6.68 (1H, brt, J=5.0 Hz), 6.82 (2H, d, J=8.5 Hz), 7.03 (2H, d, J=8.5 Hz), 7.24–7.31 (1H, m), 7.76–7.80 (2H, m), 7.89 (2H, d, J=8.5 Hz), 8.08 (2H, d, J=8.5 Hz), 8.71–8.73 (1H, m).

EXAMPLE 20

2-Butyl-2-methyl-3-[4-[2-(4-pyridine-2-ylbenzoylamino)ethoxy]phenyl]propionic acid (exemplification No. 30-3 compound)

In a similar manner to that described in Example 6, ethyl 2-butyl-2-methyl-3-[4-[2-(4-pyridine-2-ylbenzoylamino)ethoxy]phenyl]propionate (350 mg), which is the product of Example 19, was reacted with aqueous sodium hydroxide solution (1N, 2.00 ml) and aqueous potassium hydroxide solution (85%, 0.1g) and the reaction mixture was treated. The residue was subjected to chromatography on a silica gel column using dichlorometane/methanol=19/1 as the eluant to afford a solid which was washed with a mixture of diisopropyl ether and hexane to give the title compound (133 mg) as a white powder.

mp 105.5–107.5° C.

$^1$H-NMR (270 MHz, CDCl$_3$): δ ppm 0.91 (3H, t, J=7.0 Hz), 1.09 (3H, s), 1.20–1.48 (5H, m), 1.66–1.78 (1H, m), 2.64 (1H, d, J=13.5 Hz), 3.00 (1H, d, J=13.5 Hz), 3.83–3.93 (2H, m), 4.09–4.18 (2H, m), 6.79–6.83 (1H, m), 6.81 (2H, d, J=8.5 Hz), 7.07 (2H, d, J=8.5 Hz), 7.25–7.32 (1H, m), 7.73–7.83 (2H, m), 7.87 (2H, d, J=8.5 Hz), 8.03 (2H, d, J=8.5 Hz), 8.71 (1H, d, J=5.0 Hz).

EXAMPLE 21

Ethyl 3-[4-[2-(biphenyl-4-carbonylamino)ethoxy]phenyl]-2-butylpropionate (ethyl ester of exemplification No. 4-15 compound)

In a similar manner to that described in Example 5, a reaction was carried out using ethyl 3-[4-(2-aminoethoxy)phenyl]-2-butylpropionate (666 mg), which is the product of Reference example 6, biphenyl-4-carboxylic acid (450 mg) and carbonyldiimidazole (442 mg) and the reaction mixture was treated to give the title compound (705 mg) as a yellow powder.

mp 89–90° C.

$^1$H-NMR (270 MHz, CDCl$_3$): δ ppm 0.87 (3H, t, J=7.0 Hz), 1.16 (3H, t, J=7.0 Hz), 1.22–1.32 (4H, m), 1.40–1.69 (2H, m), 2.53–2.63 (1H, m), 2.69 (1H, dd, J=6.5, 13.5 Hz), 2.86 (1H, dd, J=8.5, 13.5 Hz), 3.89 (2H, q, J=5.0 Hz), 4.07 (2H, q, J=7.0 Hz), 4.15 (2H, t, J=5.0 Hz), 6.63 (1H, t, J=5.0 Hz), 6.85 (2H, d, J=8.5 Hz), 7.09 (2H, d, J=8.5 Hz), 7.37–7.50 (3H, m), 7.60–7.68 (4H, m), 7.86 (2H, d, J=8.5 Hz).

EXAMPLE 22

3-[4-[2-(Biphenyl-4-carbonylamino)ethoxy]phenyl]-2-butylpropionic acid (exemplification No. 4-15 compound)

In a similar manner to that described in Example 2, ethyl 3-[4-[2-(biphenyl-4-carbonylamino)ethoxy]phenyl]-2-butylpropionate (450 mg), which is the product of Example 21, was reacted with aqueous sodium hydroxide solution (1N, 3.00 ml) and the reaction mixture was treated to give the title compound (388 mg) as a white powder.

mp 130–131° C.

$^1$H-NMR (270 MHz, CDCl$_3$): δ ppm 0.88 (3H, t, J=7.0 Hz), 1.25–1.43 (4H, m), 1.46–1.73 (2H, m), 2.58–2.66 (1H, m), 2.72 (1H, dd, J=6.5, 13.5 Hz), 2.89 (1H, dd, J=8.5, 13.5 Hz), 3.87 (2H, q, J=5.0 Hz), 4.13 (2H, t, J=5.0 Hz), 6.71 (1H, t, J=5.0 Hz), 6.84 (2H, d, J=8.5 Hz), 7.10 (2H, d, J=8.5 Hz), 7.35–7.49 (3H, m), 7.58–7.70 (4H, m), 7.85 (2H, d, J=8.5 Hz).

EXAMPLE 23

Ethyl 2-butyl-3-[4-[2-(4'-methoxybiphenyl-4-carbonylamino)ethoxy]phenyl]propionate (ethyl ester of exemplification No. 4-179 compound)

In a similar manner to that described in Example 5, a reaction was carried out using ethyl 3-[4-(2-aminoethoxy)phenyl]-2-butylpropionate (540 mg), which is the product of Reference example 6, 4'-methoxybiphenyl-4-carboxylic acid (420 mg) and carbonyldiimidazole (370 mg) and the reaction mixture was treated to give the title compound (486 mg) as a white powder.

mp 121–123° C.

$^1$H-NMR (270 MHz, CDCl$_3$): δ ppm 0.87 (3H, t, J=7.0 Hz), 1.16 (3H, t, J=7.0 Hz), 1.21–1.38 (4H, m), 1.42–1.70 (2H, m), 2.51–2.72 (2H, m), 2.80–2.92 (1H, m), 3.86 (3H, s), 3.87–3.92 (2H, m), 4.07 (2H, q, J=7.0 Hz), 4.14 (2H, t, J=5.0 Hz), 6.62 (1H, t, J=5.5 Hz), 6.84 (2H, d, J=8.5 Hz), 7.00 (2H, d, J=8.5 Hz), 7.09 (2H, d, J=8.5 Hz), 7.55 (2H, d, J=8.5 Hz), 7.62 (2H, d, J=8.5 Hz), 7.83 (2H, d, J=8.5 Hz).

EXAMPLE 24

2-Butyl-3-[4-[2-(4'-methoxybiphenyl-4-carbonylamino)ethoxy]phenyl]propionic acid (exemplification No. 4-179 compound)

In a similar manner to that described in Example 2, ethyl 2-butyl-3-[4-[2-(4'-methoxybiphenyl-4-carbonylamino)ethoxy]phenyl]propionate (400 mg), which is the product of Example 23, was reacted with aqueous sodium hydroxide solution (1N, 4.00 ml) and the reaction mixture was treated to give the title compound (350 mg) as a pale orange powder.

mp 166.5–168° C.

$^1$H-NMR (270 MHz, CDCl$_3$): δ ppm 0.87 (3H, t, J=7.0 Hz), 1.23–1.40 (4H, m), 1.43–1.71 (2H, m), 2.57–2.78 (2H, m), 2.85–2.97 (1H, m), 3.86 (3H, s), 3.82–3.90 (2H, m), 4.13 (2H, t, J=5.0 Hz), 6.69 (1H, t, J=5.5 Hz), 6.83 (2H, d, J=8.5 Hz), 6.98 (2H, d, J=8.5 Hz), 7.10 (2H, d, J=8.5 Hz), 7.55 (2H, d, J=8.5 Hz), 7.60 (2H, d, J=8.5 Hz), 7.81 (2H, d, J=8.5 Hz).

EXAMPLE 25

Ethyl 2-butyl-3-[4-[2-(4'-hydroxybiphenyl-4-carbonylamino)ethoxy]phenyl]propionate (ethyl ester of exemplification No. 4-206 compound)

1-(3-Dimethylaminopropyl)-3-ethylcarbodiimide hydrochloride (359 mg) and 1-hydroxybenzotriazole monohydrate (287 mg) were added to a suspension of 4'-hydroxybiphenyl-4-carboxylic acid (383 mg) in dichloromethane (10 ml) at ambient temperature. The mixture was stirred for 4 hours at ambient temperature. A solution of ethyl 3-[4-(2-aminoethoxy)phenyl]-2-butylpropionate (500 mg), which is the product of Reference example 6, in dichloromethane (10 ml) was then added to the reaction mixture. The mixture was stirred at ambient temperature for 2 hours and then allowed to stand overnight. At the end of this time the reaction mixture was concentrated by evaporation. The residue was partioned between ethyl acetate and water. The layers were separated. The ethyl acetate layer was washed with aqueous hydrogen chloride solution (0.5N), saturated aqueous sodium bicarbonate solution and saturated aqueous sodium chloride solution and dried over anhydrous magnesium sulfate and then concentrated under reduced pressure. The residue was purified via chromatography on a silica gel column using dichloromethane/ethyl acetate=5/1 as the eluant to give the title compound (270 mg) as a colorless oil.

$^1$H-NMR (270 MHz, CDCl$_3$): δ ppm 0.86 (3H, t, J=7.0 Hz), 1.15 (3H, t, J=7.0Hz), 1.21–1.37 (4H, m), 1.40–1.70 (2H, m), 2.55–2.64 (1H, m), 2.68 (1H, dd, J=6.5, 13.5 Hz), 2.86 (1H, dd, J=8.5, 13.5 Hz), 3.88 (2H, q, J=5.0 Hz), 4.05 (2H, q, J=7.0 Hz), 4.14 (2H, t, J=5.0 Hz), 6.36 (1H, brs), 6.65 (1H, t, J=5.0 Hz), 6.83 (2H, d, J=8.5 Hz), 6.93 (2H, d, J=8.5 Hz), 7.08 (2H, d, J=8.5 Hz), 7.49 (2H, d, J=8.5 Hz), 7.60 (2H, d, J=8.5 Hz), 7.82 (2H, d, J=8.5 Hz).

EXAMPLE 26

2-Butyl-3-[4-[2-(4'-hydroxybiphenyl-4-carbonylamino)ethoxy]phenyl]propionic acid (exemplification No. 4-206 compound)

In a similar manner to that described in Example 2, ethyl 2-butyl-3-[4-[2-(4'-hydroxybiphenyl-4-carbonylamino)ethoxy]phenyl]propionate (260 mg), which is the product of Example 25, was reacted with aqueous sodium hydroxide solution (1N, 2.20 ml) and the reaction mixture was treated to give the title compound (230 mg) as a white powder.

mp 182–184° C.

$^1$H-NMR (270 MHz, deuterated dimethyl sulfoxide): δ ppm 0.79 (3H, t, J=6.5 Hz), 1.15–1.30 (4H, m), 1.34–1.53 (2H, m), 2.40–2.50 (1H, m), 2.57 (1H, dd, J=6.0, 13.5 Hz), 2.71 (1H, dd, J=8.5, 13.5 Hz), 3.59 (2H, q, J=5.5 Hz), 4.05 (2H, t, J=5.5 Hz), 6.83 (4H, d, J=8.5 Hz), 7.06 (2H, d, J=8.5 Hz), 7.53 (2H, d, J=8.5 Hz), 7.63 (2H, d, J=8.5 Hz), 7.87 (2H, d, J=8.5 Hz), 8.63 (1H, t, J=5.5 Hz), 9.61 (1H, s).

EXAMPLE 27

2-Butyl-3-[4-[2-(4'-formylbiphenyl-4-carbonylamino)ethoxy]phenyl]propionic acid (exemplification No. 4-207 compound)

In a similar manner to that described in Example 2, ethyl 2-butyl-3-[4-[2-(4'-dimethoxymethylbiphenyl-4-carbonylamino)ethoxy]phenyl]propionate (1.88 g), which is the product of Reference example 11, was reacted with aqueous sodium hydroxide solution (1N, 6.80 ml) and the reaction mixture was treated to give 2-butyl-3-[4-[2-(4'-dimethoxymethylbiphenyl-4-carbonylamino)ethoxy]phenyl]propionic acid (1.78 g) as a pale brown solid.

To a solution of this compound (521 mg) in acetone (15 ml), water (0.17 ml) was added and then amberlyst 15 (100 mg) was added at ambient temperature. The mixture was allowed to stand for 40 minute. The amberlyst 15 was removed by filtration and the filtrate was concentrated. The residue was purified via chromatography on silica gel column using dichloromethane/methanol=20/1 as the eluant to give the title compound (336 mg) as a white solid.

mp 122–124° C.

$^1$H-NMR (270 MHz, CDCl$_3$): δ ppm 0.88 (3H, t, J=7.0 Hz), 1.20–1.37 (4H, m), 1.40–1.59 (1H, m), 1.61–1.71 (1H, m), 2.58–2.69 (1H, m), 2.72 (1H, dd, J=6.5, 13.5 Hz), 2.90 (1H, dd, J=8.5, 13.5 Hz), 3.89 (2H, q, J=5.0 Hz), 4.15 (2H, t, J=5.0 Hz), 6.71 (1H, brt), 6.84 (2H, d, J=8.5 Hz), 7.11 (2H, d, J=8.5 Hz), 7.69 (2H, d, J=8.5 Hz), 7.76 (2H, d, J=8.5 Hz), 7.89 (2H, d, J=8.5 Hz), 7.97 (2H, d, J=8.5 Hz), 10.08 (1H, s).

EXAMPLE 28

2-Butyl-3-[4-[2-(4'-hydroxymethylbiphenyl-4-carbonylamino)ethoxy]phenyl]propionic acid (exemplification No. 4-211 compound)

Sodium borohydride (95%, 34 mg) was added to a solution of 2-butyl-3-[4-[2-(4'-formylbiphenyl-4-carbonylamino)ethoxy]phenyl]propionic acid (366 mg) in ethanol (10 ml) at ambient temperature. The mixture was stirred for 1.5 hours. At the end of this time 50% acetic acid was added to the reaction mixture. The mixture was concentrated under reduced pressure. The residue was partitioned between ethyl acetate and water. The ethyl acetate layer was separated and washed with saturated aqueous sodium chloride solution and dried over anhydrous magnesium sulfate and then concentrated under reduced pressure. Diisopropyl ether was added to the residue to give the title compound (331 mg) as colorless crystals.

mp 111–113° C.

$^1$H-NMR (270 MHz, deuterated methanol): δ ppm 0.88 (3H, t, J=7.0 Hz), 1.22–1.39 (4H, m), 1.40–1.65 (2H, m), 2.52–2.61 (1H, m), 2.67 (1H, dd, J=6.5, 13.5 Hz), 2.86 (1H, dd, J=8.0, 13.5 Hz), 3.80 (2H, t, J=5.5 Hz), 4.16 (2H, t, J=5.5 Hz), 4.68 (2H, s), 6.87 (2H, d, J=8.5 Hz), 7.10 (2H, d, J=8.5 Hz), 7.46 (2H, d, J=8.5 Hz), 7.63 (2H, d, J=8.5 Hz), 7.70 (2H, d, J=8.5 Hz), 7.90 (2H, d, J=8.5 Hz).

EXAMPLE 29

2-Butyl-3-[4-[2-(4'-dimethylaminomethylbiphenyl-4-carbonyl-amino)ethoxy]phenyl]propionic acid (exemplification No. 4-208 compound)

To triethylamine (0.56 ml), dimethylamine hydrochloride (167 mg) and titanium tetraisopropoxide (0.59 ml) was added a suspension of 2-butyl-3-[4-[2-(4'-formylbiphenyl-4-carbonylamino)ethoxy]phenyl]propionic acid (474 mg) in ethanol (20 ml) at ambient temperature to afford a clear solution. Sodium borohydride (60 mg) was added to the solution and the mixture was stirred under nitrogen atmosphere for 18 hours. At the end of this time 50% acetic acid was added to the reaction mixture. This mixture was concentrated under reduced pressure. The residue was partitioned between ethyl acetate and water. The ethyl acetate layer was separated and washed with saturated aqueous sodium chloride solution and dried over anhydrous magnesium sulfate and then concentrated under reduced pressure. Diisopropyl ether was added to the residue to give the title compound (135 mg) as colorless crystals.

mp 125–127° C.

$^1$H-NMR (400 MHz, deuterated methanol): δ ppm 0.87 (3H, t, J=6.5 Hz), 1.22–1.38 (4H, m), 1.41–1.62 (2H, m), 2.50–2.59 (1H, m), 2.66 (1H, dd, J=6.0, 13.5 Hz), 2.82 (1H, dd, J=8.5, 13.5 Hz), 2.86 (6H, s), 3.78 (2H, t, J=5.5 Hz), 4.15 (2H, t, J=5.5 Hz), 4.33 (2H, s), 6.87 (2H, d, J=8.5 Hz), 7.10 (2H, d, J=8.5 Hz), 7.60 (2H, d, J=8.5 Hz), 7.76 (2H, d, J=8.5 Hz), 7.81 (2H, d, J=8.5 Hz), 7.93 (2H, d, J=8.5 Hz).

EXAMPLE 30

2-Butyl-3-[4-[2-(4'-carboxybiphenyl-4-carbonylamino)ethoxy]phenyl]propionic acid (exemplification No. 4-210 compound)

In a similar manner to that described in Example 2, ethyl 2-butyl-3-[4-[2-(4'-methoxycarbonylbiphenyl-4-carbonylamino)ethoxy]phenyl]propionate (243 mg), which is the product of Reference example 12, was reacted with aqueous sodium hydroxide solution (1N, 1.83 ml) and the reaction mixture was treated to give the title compound (163 mg) as a white powder.

mp 199–201° C.

$^1$H-NMR (270 MHz, deuterated dimethyl sulfoxide): δ ppm 0.83 (3H, t, J=6.5 Hz), 1.18–1.31 (4H, m), 1.37–1.52 (2H, m), 2.40–2.50 (1H, m), 2.61 (1H, dd, J=6.0, 13.5 Hz), 2.74 (1H, dd, J=8.5, 13.5 Hz), 3.66 (2H, t, J=5.5 Hz), 4.10 (2H, t, J=5.5 Hz), 6.87 (2H, d, J=8.5 Hz), 7.09 (2H, d, J=8.5 Hz), 7.85 (2H, d, J=8.0 Hz), 7.87 (2H, d, J=8.0 Hz), 7.99 (2H, d, J=8.5 Hz), 8.05 (2H, dd, J=2.5, 8.5 Hz), 8.78 (1H, d, J=5.5 Hz).

EXAMPLE 31

Ethyl 2-butyl-3-[4-[2-(3'-methoxybiphenyl-4-carbonylamino)ethoxy]phenyl]propionate (ethyl ester of exemplification No. 4-212 compound)

In a similar manner to that described in Example 5, a reaction was carried out using ethyl 3-[4-(2-aminoethoxy)phenyl]-2-butylpropionate (620 mg), which is the product of Reference example 6, 3'-methoxybiphenyl-4-carboxylic acid (456 mg) and carbonyldiimidazole (389 mg) and the reaction mixture was treated to give the title compound (740 mg) as a colorless oil.

$^1$H-NMR (270 MHz, CDCl$_3$): δ ppm 0.87 (3H, t, J=7.0 Hz), 1.16 (3H, t, J=7.0 Hz), 1.21–1.31 (4H, m), 1.41–1.68 (2H, m), 2.53–2.64 (1H, m), 2.69 (1H, dd, J=6.5, 13.5 Hz), 2.86 (1H, dd, J=8.5, 13.5 Hz), 3.87 (3H, s), 3.88 (2H, q, J=5.0 Hz), 4.05 (2H, q, J=7.0 Hz), 4.15 (2H, t, J=5.0 Hz), 6.62 (1H, t, J=5.0 Hz), 6.84 (2H, d, J=8.5 Hz), 6.92–6.95 (1H, m), 7.09 (2H, d, J=8.5 Hz), 7.11–7.14 (1H, m), 7.18–7.21 (1H, m), 7.38 (1H, t, J=8.0 Hz), 7.65 (2H, d, J=8.5 Hz), 7.85 (2H, d, J=8.5 Hz).

EXAMPLE 32

2-Butyl-3-[4-[2-(3'-methoxybiphenyl-4-carbonylamino)ethoxy]phenyl]propionic acid (exemplification No. 4-212 compound)

In a similar manner to that described in Example 2, ethyl 2-butyl-3-[4-[2-(3'-methoxybiphenyl-4-carbonylamino)ethoxy]phenyl]propionate (730 mg), which is the product of Example 31, was reacted with aqueous sodium hydroxide solution (1N, 4.50 ml) and the reaction mixture was treated to give the title compound (520 mg) as a white powder.

mp 107–109° C.

$^1$H-NMR (270 MHz, CDCl$_3$): δ ppm 0.87 (3H, t, J=7.0 Hz), 1.21–1.38 (4H, m), 1.45–1.71 (2H, m), 2.58–2.67 (1H, m), 2.71 (1H, dd, J=6.5, 13.5 Hz), 2.90 (1H, dd, J=8.5, 13.5 Hz), 3.83–3.90 (5H, m), 4.13 (2H, t, J=5.0 Hz), 6.71 (1H, t, J=5.0 Hz), 6.83 (2H, d, J=8.5 Hz), 6.93 (1H, dd, J=2.5, 8.0 Hz), 7.10 (2H, d, J=8.5 Hz), 7.12 (1H, d, J=2.5 Hz), 7.18 (2H, d, J=8.0 Hz), 7.37 (1H, t, J=8.0 Hz), 7.64 (2H, d, J=8.5 Hz), 7.85 (2H, d, J=8.5 Hz).

EXAMPLE 33

Ethyl 2-butyl-3-[4-[2-(3'-hydroxybiphenyl-4-carbonylamino)ethoxy]phenyl]propionate (ethyl ester of exemplification No. 4-213 compound)

In a similar manner to that described in Example 25, a reaction was carried out using ethyl 3-[4-(2-aminoethoxy)phenyl]-2-butylpropionate (678 mg), which is the product of Reference example 6, 3'-hydroxybiphenyl-4-carboxylic acid (450 mg). which is the product of Reference example 13, 1-(3-dimethylaminopropyl)-3-ethylcarbodiimide hydrochloride (443 mg) and 1-hydroxybenzotriazole monohydrate (354 mg) and the reaction mixture was treated to give the title compound (291 mg) as a white powder.

mp 76–77.5° C.

$^1$H-NMR (270 MHz, CDCl$_3$): δ ppm 0.86 (3H, t, J=7.0 Hz), 1.16 (3H, t, J=7.0 Hz), 1.21–1.36 (4H, m), 1.40–1.69 (2H, m), 2.52–2.65 (1H, m), 2.68 (1H, dd, J=6.5, 13.5 Hz), 2.86 (1H, dd, J=8.5, 13.5 Hz), 3.89 (2H, q, J=5.0 Hz), 4.06 (2H, q, J=7.0 Hz), 4.14 (2H, t, J=5.0 Hz), 6.10 (1H, s), 6.70 (1H, t, J=5.0 Hz), 6.83 (2H, d, J=8.5 Hz), 6.83–6.91 (1H, m), 7.08 (2H, d, J=8.5 Hz), 7.09–7.16 (2H, m), 7.31 (1H, t, J=8.0 Hz), 7.58 (2H, d, J=8.5 Hz), 7.83 (2H, d, J=8.5 Hz).

EXAMPLE 34

2-Butyl-3-[4-[2-(3'-hydroxybiphenyl-4-carbonylamino)ethoxy]phenyl]propionic acid (exemplification No. 4-213 compound)

In a similar manner to that described in Example 2, ethyl 2-butyl-3-[4-[2-(3'-hydroxybiphenyl-4-carbonylamino)ethoxy]phenyl]propionate (350 mg), which is the product of Example 33, was reacted with aqueous sodium hydroxide solution (1N, 2.85 ml) and the reaction mixture was treated to give the title compound (290 mg) as a white powder.

mp 98–100° C.

$^1$H-NMR (270 MHz, CDCl$_3$): δ ppm 0.84–0.89 (3H, m), 1.21–1.40 (4H, m), 1.45–1.68 (2H, m), 2.51–2.90 (3H, m), 3.80–3.88 (2H, m), 4.12–4.20 (2H, m), 6.82–6.92 (3H, m), 7.04–7.15 (4H, m), 7.27 (1H, t, J=8.0 Hz), 7.55–7.70 (3H, m), 7.90 (2H, d, J=8.0 Hz), 8.91–9.08 (1H, brs).

EXAMPLE 35

2-Butyl-3-[4-[2-(3'-formylbiphenyl-4-carbonylamino)ethoxy]phenyl]propionic acid (exemplification No. 4-214 compound)

In a similar manner to that described in Example 27, ethyl 2-butyl-3-[4-[2-(3'-dimethoxymethylbiphenyl-4-carbonylamino)ethoxy]phenyl]propionate (1.46 g), which is the product of Reference example 14, was reacted with aqueous sodium hydroxide solution (1N, 5.40 ml) and the reaction mixture was treated to give 2-butyl-3-[4-[2-(3'-dimethoxymethylbiphenyl-4-carbonylamino)ethoxy]phenyl]propionic acid (1.39 g) as a syrup. This compound (365 mg) was reacted and the reaction mixture was treated in a similar manner to that described in Example 27 to give the title compound (335 mg) as a yellowish brown solid.

$^1$H-NMR (270 MHz, CDCl$_3$): δ ppm 0.88 (3H, t, J=6.5 Hz), 1.18–1.38 (4H, m), 1.40–1.78 (2H, m), 2.61–2.68 (1H, m), 2.73 (1H, dd, J=6.5, 13.5 Hz), 2.92 (1H, dd, J=8.0, 13.5 Hz), 3.89 (2H, q, J=5.0 Hz), 4.15 (2H, t, J=5.0 Hz), 6.69 (1H, brt), 6.85 (2H, d, J=8.5 Hz), 7.11 (2H, d, J=8.5 Hz), 7.64 (1H, t, J=8.0 Hz), 7.69 (2H, d, J=8.5 Hz), 7.86–7.91 (2H, m), 7.89 (2H, d, J=8.5 Hz), 8.12 (1H, s), 10.10 (1H, s).

EXAMPLE 36

Sodium 2-butyl-3-[4-[2-(3'-hydroxymethylbiphenyl-4-carbonylamino)ethoxy]phenyl]propionic acid (exemplification No. 4-218 compound)

A dioxane solution of hydrogen chloride (4N, 1.2 ml) was added to a suspension of sodium 2-butyl-3-[4-[2-(3'-methoxymethoxymethylbiphenyl-4-carbonylamino)ethoxy]phenyl]propionate (238 mg), which is the product of Reference example 15, in ethanol (20 ml) at ambient temperature. The mixture was allowed to stand overnight. At the end of this time the reaction mixture was concentrated under reduced pressure. The residue was partitioned between ethyl acetate and water. The ethyl acetate layer was separated and washed with saturated aqueous sodium chloride solution and dried over anhydrous magesium sulfate and then concentrated under reduced pressure. The residue was purified via chromatography on a silica gel column using dichloromethane/methanol=20/1–10/1 as the eluant to give the free acid. The title compound (140 mg) was obtained by reaction of the free acid with sodium hydroxide as a yellowish brown solid.

mp 124–126° C.

$^1$H-NMR (270 MHz, deuterated methanol): δ ppm 0.87 (3H, t, J=7.0 Hz), 1.18–1.39 (4H, m), 1.44–1.63 (2H, m), 2.32–2.47 (1H, m), 2.51 (1H, dd, J=7.0, 13.5 Hz), 2.85 (1H, dd, J=6.0, 13.5 Hz), 3.76 (2H, t, J=5.5 Hz), 4.14 (2H, t, J=5.5 Hz), 4.68 (2H, s), 6.84 (2H, d, J=8.5 Hz), 7.12 (2H, d, J=8.5 Hz), 7.36 (1H, d, J=7.5 Hz), 7.44 (1H, t, J=7.5 Hz), 7.56 (1H, d, J=7.5 Hz), 7.66 (1H, s), 7.72 (2H d, J=8.5 Hz), 7.90 (2H, d, J=8.5 Hz).

EXAMPLE 37

Ethyl 2-butyl-3-[4-[2-(3'-formylbiphenyl-4-carbonylamino)ethoxy]phenyl]propionate (ethyl ester of exemplification No. 4-214 compound)

In a similar manner to that described in Example 5, a reaction was carried out using ethyl 3-[4-(2-aminoethoxy)phenyl]-2-butylpropionate (683 mg), which is the product of Reference example 6, 3'-formylbiphenyl-4-carboxylic acid (635 mg) and carbonyldiimidazole (500 mg) and the reaction mixture was treated to give the title compound (506 mg) as a pale brown oil.

$^1$H-NMR (270 MHz, CDCl$_3$): δ ppm 0.86 (3H, t, J=7.0 Hz), 1.16 (3H, t, J=7.0 Hz), 1.21–1.39 (4H, m), 1.41–1.73 (2H, m), 2.53–2.66 (1H, m), 2.69 (1H, dd, J=6.5, 13.5 Hz), 2.86 (1H, dd, J=8.5, 13.5 Hz), 3.90 (2H, q, J=5.0 Hz), 4.06 (2H, q, J=7.0 Hz), 4.16 (2H, t, J=5.0 Hz), 6.64 (1H, brt), 6.84 (2H, d, J=8.5 Hz), 7.09 (2H, d, J=8.5 Hz), 7.64 (1H, t, J=7.5 Hz), 7.70 (2H, d, J=8.5 Hz), 7.86–7.92 (2H, m), 7.90 (2H, d, J=8.5 Hz), 8.12 (1H, s), 10.10 (1H, s).

EXAMPLE 38

Ethyl 2-butyl-3-[4-[2-(3'-dimethylaminomethylbiphenyl-4-carbonylamino)ethoxy]phenyl]propionate (ethyl ester of exemplification No. 4-215 compound)

In a similar manner to that described in Example 29, a reaction was carried out using ethyl 2-butyl-3-[4-[2-(3'-formylbiphenyl-4-carbonylamino)ethoxy]phenyl]propionate (415 mg), which is the product of Example 37, triethylamine (0.23 ml), dimethylamine hydrochloride (139 mg), titanium tetraisopropoxide (0.49 ml) and sodium borohydride (56 mg) and then the reaction mixture was treated to give the title compound (263 mg) as a colorless syrup.

$^1$H-NMR (270 MHz, CDCl$_3$): δ ppm 0.86 (3H, t, J=7.0 Hz), 1.16 (3H, t, J=7.0 Hz), 1.20–1.37 (4H, m), 1.39–1.75 (2H, m), 2.23 (6H, s), 2.55–2.63 (1H, m), 2.68 (1H, dd, J=6.5, 13.5 Hz), 2.86 (1H, dd, J=8.5, 13.5 Hz), 3.52 (2H, s), 3.89 (2H, q, J=5.0 Hz), 4.06 (2H, q, J=7.0 Hz), 4.15 (2H, t, J=5.0 Hz), 6.63 (1H, brt), 6.84 (2H, d, J=8.5 Hz), 7.09 (2H, d, J=8.5 Hz), 7.34 (1H, d, J=7.5 Hz), 7.42 (1H, t, J=7.5 Hz), 7.52 (1H, d, J=7.5 Hz), 7.58 (1H, s), 7.68 (2H, d, J=8.5 Hz), 7.84 (2H, d, J=8.5 Hz).

EXAMPLE 39

2-Butyl-3-[4-[2-(3'-dimethylaminomethylbiphenyl-4-carbonylamino)ethoxy]phenyl]propionic acid (exemplification No. 4-215 compound)

In a similar manner to that described in Example 2, ethyl 2-butyl-3-[4-[2-(3'-dimethylaminomethylbiphenyl-4-carbonylamino)ethoxy]phenyl]propionate (263 mg), which is the product of Example 38, was reacted with aqueous sodium hydroxide solution (1N, 1.00 ml) and the reaction mixture was treated to give the title compound (121 mg) as a white powder.

mp 95–97° C.

$^1$H-NMR (270 MHz, deuterated methanol): δ ppm 0.86 (3H, t, J=7.0 Hz), 1.14–1.34 (4H, m), 1.35–1.61 (2H, m), 2.46–2.57 (1H, m), 2.62 (1H, dd, J=6.5, 13.5 Hz), 2.77 (6H, s), 2.81 (1H, dd, J=8.5, 13.5 Hz), 3.76 (2H, t, J=5.5 Hz), 4.15 (2H, t, J=5.5 Hz), 4.25 (2H, s), 6.86 (2H, d, J=8.5 Hz), 7.08 (2H, d, J=8.5 Hz), 7.49 (1H, d, J=7.5 Hz), 7.57 (1H, t, J=7.5 Hz), 7.74–7.79 (1H, m), 7.75 (2H, d, J=8.5 Hz), 7.82 (1H, s), 7.91 (2H, d, J=8.5 Hz).

EXAMPLE 40

Ethyl 2-butyl-3-[4-[2-(3'-carboxybiphenyl-4-carbonylamino)ethoxy]phenyl]propionate (ethyl ester of exemplification No. 4-217 compound)

Sodium dihydrogenphosphate dihydrate (24 mg) and water (0.3 ml) was added to a solution of ethyl 2-butyl-3-[4-[2-(3'-formylbiphenyl-4-carbonylamino)ethoxy]phenyl]propionate (390 mg), which is the product of Example 37, in acetonitrile (6 ml). Aqueous hydrogen peroxide solution (30%, 0.1.2 ml) and an aqueous solution (0.3 ml) of sodium chlorite (104 mg) was added to the mixture in an ice bath. The mixture was stirred for 1 hour in an ice bath and then stirred for 2.5 hours at ambient temperature. After this, the reaction was quenched with sodium thiosulfate and the reaction mixture was partitioned between ethyl acetate and water. The ethyl acetate layer was separated and washed with saturated aqueous sodium chloride and dried over anhydrous magnesium sulfate and then concentrated under reduced pressure. Diisopropyl ether was added to the residue to give the title compound (217 mg) as a white solid.

¹H-NMR (270 MHz, CDCl₃): δ ppm 0.86 (3H, t, J=6.5 Hz), 1.15 (3H, t, J=7.0 Hz), 1.20–1.39 (4H, m), 1.40–1.51 (1H, m), 1.53–1.68 (1H, m), 2.51–2.63 (1H, m), 2.68 (1H, dd, J=6.5, 13.5 Hz), 2.86 (1H, dd, J=8.5, 13.5 Hz), 3.83–3.95 (2H, m), 4.05 (2H, q, J=7.0 Hz), 4.12–4.20 (2H, m), 6.70 (1H, brt), 6.84 (2H, d, J=8.5 Hz), 7.08 (2H, d, J=8.5 Hz), 7.53–7.61 (1H, m), 7.63–7.77 (2H, m), 7.79–7.94 (3H, m), 8.08–8.19 (1H, m), 8.36 (1H, s).

EXAMPLE 41

2-Butyl-3-[4-[2-(3'-carboxybiphenyl-4-carbonylamino)ethoxy]phenyl]propionic acid (exemplification No. 4-217 compound)

In a similar manner to that described in Example 2, ethyl 2-butyl-3-[4-[2-(3'-carboxybiphenyl-4-carbonylamino)ethoxy]phenyl]propionate (273 mg), which is the product of Example 40, was reacted with aqueous sodium hydroxide solution (1N, 1.10 ml) and the reaction mixture was treated to give the title compound (196 mg) as colorless crystals.

mp 142–143° C.

¹H-NMR (270 MHz, deuterated methanol): δ ppm 0.87 (3H, t, J=7.0 Hz), 1.20–1.44 (4H, m), 1.44–1.65 (2H, m), 2.49–2.60 (1H, m), 2.66 (1H, dd, J=6.0, 13.5 Hz), 2.82 (1H, dd, J=8.5, 13.5 Hz), 3.77 (2H, q, J=5.5 Hz), 4.15 (2H, t, J=5.5 Hz), 6.87 (2H, d, J=8.5 Hz), 7.09 (2H, d, J=8.5 Hz), 7.58 (1H, t, J=7.5 Hz), 7.75 (2H, d, J=8.5 Hz), 7.90 (1H, d, J=7.5 Hz), 7.93 (2H, d, J=8.5 Hz), 8.04 (1H, d, J=7.5 Hz), 8.30 (1H, s), 8.72 (1H, brt).

EXAMPLE 42

Ethyl 2-butyl-3-[4-[2-(2'-methoxybiphenyl-4-carbonylamino)ethoxy]phenyl]propionate (ethyl ester of exemplification No. 4-219 compound)

In a similar manner to that described in Example 5, a reaction was carried out using ethyl 3-[4-(2-aminoethoxy)phenyl]-2-butylpropionate (643 mg), which is the product of Reference example 6, 2'-methoxybiphenyl-4-carboxylic acid (500 mg) and carbonyldiimidazole (426 mg) and the reaction mixture was treated to give the title compound (750 mg) as a pale yellow oil.

¹H-NMR (270 MHz, CDCl₃): δ ppm 0.91 (3H, t, J=6.5 Hz), 1.20 (3H, t, J=7.0 Hz), 1.28–1.40 (4H, m), 1.45–1.73 (2H, m), 2.59–2.79 (2H, m), 2.85–2.97 (1H,), 3.86 (3H, s), 3.93 (2H, q, J=5.0 Hz), 4.10 (2H, q, J=7.0 Hz), 4.18 (2H, t, J=5.0 Hz), 6.67 (1H, t, J=5.0 Hz), 6.86 (2H, d, J=8.5 Hz), 7.06 (2H, t, J=8.0 Hz), 7.13 (2H, d, J=8.5 Hz), 7.35–7.44 (2H, m), 7.65 (2H, d, J=8.0 Hz), 7.86 (2H, d, J=8.0 Hz).

EXAMPLE 43

2-Butyl-3-[4-[2-(2'-methoxybiphenyl-4-carbonylamino)ethoxy]phenyl]propionic acid (exemplification No. 4-219 compound)

In a similar manner to that described in Example 2, ethyl 2-butyl-3-[4-[2-(2'-methoxybiphenyl-4-carbonylamino)ethoxy]phenyl]propionate (750 mg), which is the product of Example 42, was reacted with aqueous sodium hydroxide solution (1N, 5.00 ml) and the reaction mixture was treated to give the title compound (625 mg) as a pale orange powder.

mp 190–192° C.

¹H-NMR (270 MHz, CDCl₃): δ ppm 0.87 (3H, t, J=7.0 Hz), 1.21–1.38 (4H, m), 1.43–1.71 (2H, m), 2.58–2.78 (2H, m), 2.85–2.97 (1H, m), 3.80 (3H, s), 3.87 (2H, q, J=5.0 Hz), 4.13 (2H, t, J=5.0 Hz), 6.67 (1H, t, J=5.0 Hz), 6.83 (2H, d, J=8.5 Hz), 6.98–7.06 (2H, m), 7.10 (2H, d, J=8.5 Hz), 7.28–7.38 (2H, m), 7.59 (2H, d, J=8.5 Hz), 7.81 (2H, d, J=8.5 Hz).

EXAMPLE 44

Ethyl 2-butyl-3-[4-[2-(2'-hydroxybiphenyl-4-carbonylamino)ethoxy]phenyl]propionate (ethyl ester of exemplification No. 4-220 compound)

In a similar manner to that described in Example 25, a reaction was carried out using ethyl 3-[4-(2-aminoethoxy)phenyl]-2-butylpropionate (249 mg), which is the product of Reference example 6, 2'-hydroxybiphenyl-4-carboxylic acid (200 mg), which is the product of Reference example 16, 1-(3-dimethylaminopropyl)-3-ethylcarbodiimide hydrochloride (195 mg) and 1-hydroxybenzotriazole monohydrate (138 mg) and the reaction mixture was treated to give the title compound (386 mg) as a colorless oil.

¹H-NMR (270 MHz, CDCl₃): δ ppm 0.87 (3H, t, J=6.5 Hz), 1.16 (3H, t, J=7.0 Hz), 1.21–1.32 (4H, m), 1.40–1.69 (2H, m), 2.53–2.72 (2H, m), 2.86 (1H, dd, J=8.5, 13.5 Hz), 3.89 (2H, q, J=5.0 Hz), 4.01–4.18 (4H, m), 5.27 (1H, s), 6.61–6.69 (1H, m), 6.83 (2H, d, J=8.5 Hz), 6.95–7.11 (4H, m), 7.21–7.28 (2H, m), 7.58 (2H, d, J=8.0 Hz), 7.88 (2H, d, J=8.0 Hz).

EXAMPLE 45

Sodium 2-butyl-3-[4-[2-(2'-hydroxybiphenyl-4-carbonylamino)ethoxy]phenyl]propionate (exemplification No. 4-220 compound)

In a similar manner to that described in Example 2, ethyl 2-butyl-3-[4-[2-(2'-hydroxybiphenyl-4-carbonylamino)ethoxy]phenyl]propionate (345 mg), which is the product of Example 44, was reacted with aqueous sodium hydroxide solution (1N, 2.82 ml) and the reaction mixture was treated to afford the crude free acid which was subjected to chromatography on a silica gel thin layer plate using dichloromethane/methanol=10/1 as the eluant. The product was converted to the sodium salt to give the title compound (200 mg) as colorless crystals.

mp 153–156° C.

¹H-NMR of the free acid (270 MHz, CDCl₃): δ ppm 0.88 (3H, t, J=7.0 Hz), 1.25–1.37 (4H, m), 1.44–1.71 (2H, m), 2.55–2.78 (2H, m), 2.86 (1H, dd, J=8.5, 13.5 Hz), 3.83 (2H, q, J=5.0 Hz), 4.10 (2H, t, J=5.0 Hz), 6.69–6.79 (1H, m), 6.80 (2H, d, J=8.5 Hz), 6.95–7.10 (4H, m), 7.22–7.30 (2H, m), 7.55 (2H, d, J=8.0 Hz), 7.80 (2H, d, J=8.5 Hz).

EXAMPLE 46

Ethyl 2-butyl-3-[4-[2-(2'-formylbiphenyl-4-carbonylamino)ethoxy]phenyl]propionate (ethyl ester of exemplification No. 4-221 compound)

In a similar manner to that described in Example 5, a reaction was carried out using ethyl 3-[4-(2-aminoethoxy)phenyl]-2-butylpropionate (414 mg), which is the product of Reference example 6, 2'-formylbiphenyl-4-carboxylic acid (350 mg) and carbonyldiimidazole (296 mg) and the reaction mixture was treated to give the title compound (314 mg) as a colorless oil.

¹H-NMR (270 MHz, CDCl₃): δ ppm 0.87 (3H, t, J=7.0 Hz), 1.16 (3H, t, J=7.0 Hz), 1.19–1.33 (4H, m), 1.41–1.68 (2H, m), 2.53–2.72 (2H, m), 2.87 (1H, dd, J=8.5, 13.5 Hz), 3.91 (2H, q, J=5.0 Hz), 4.01–4.20 (4H, m), 6.65–6.72 (1H, m), 6.84 (2H, d, J=8.5 Hz), 7.09 (2H, d, J=8.5 Hz), 7.42–7.59 (4H, m), 7.63–7.70 (1H, m), 7.89 (2H, d, J=8.0 Hz), 8.04 (1H, d, J=7.5 Hz), 9.96 (1H, s).

EXAMPLE 47

2-Butyl-3-[4-[2-(2'-formylbiphenyl-4-carbonylamino)ethoxy]phenyl]propionic acid (exemplification No. 4-221 compound)

In a similar manner to that described in Example 2, ethyl 2-butyl-3-[4-[2-(2'-formylbiphenyl-4-carbonylamino) ethoxy]phenyl]propionate (314 mg), which is the product of Example 46, was reacted with aqueous sodium hydroxide solution (1N, 2.50 ml) and the reaction mixture was treated to afford the crude free acid which was subjected to chromatography on a silica gel thin layer plate using dichloromethane/methanol=10/1 as the eluant to give the title compound (152 mg) as a mass of foam.

$^1$H-NMR (270 MHz, CDCl$_3$): δ ppm 0.86 (3H, t, J=7.0 Hz), 1.22–1.40 (4H, m), 1.42–1.70 (2H, m), 2.55–2.78 (2H, m), 2.88 (1H, dd, J=8.5, 13.5 Hz), 3.83–3.93 (2H,m), 4.07–4.18 (2H, m), 6.81 (2H, d, J=8.0 Hz), 6.95–7.06 (1H, m), 7.09 (2H, d, J=8.5 Hz), 7.38–7.46 (3H, m), 7.48–7.56 (1H, m), 7.61–7.69 (1H, m), 7.89 (2H, d, J=8.0 Hz), 8.02 (1H, d, J=7.5 Hz), 9.92 (1H, s).

EXAMPLE 48

Sodium 2-butyl-3-[4-[2-(4'-hydroxy-3', 5'-dimethylbiphenyl-4-carbonylamino)ethoxy]phenyl] propionate (exemplification No. 4-205 compound)

In a similar manner to that described in Example 36, 2-butyl-3-[4-[2-(4'-methoxymethoxy-3',5'-dimethylbiphenyl-4-carbonylamino)ethoxy]phenyl] propionic acid (1.00 g), which is the product of Reference example 17, was reacted with a dioxane solution of hydrogen chloride (4N, 0.69 ml) and the reaction mixture was treated to give the title compound (528 mg) as a pale brown solid.

mp 137–139° C.

$^1$H-NMR (270 MHz, a mixture of CDCl$_3$ and deuterated methanol (10/3)): δ ppm 0.85 (3H, t, J=7.0 Hz), 1.20–1.40 (5H, m), 1.43–1.60 (1H, m), 2.27 (6H, s), 2.34–2.47 (1H, m), 2.52 (1H, dd, J=7.5, 13.5 Hz), 2.85 (1H, dd, J=7.5, 13.5 Hz), 3.74 (2H, t, J=5.5 Hz), 4.13 (2H, t. J=5.5 Hz), 6.84 (2H, d, J=8.5 Hz), 7.12 (2H, d, J=8.5 Hz), 7.62 (2H, d, J=8.5 Hz), 7.84 (2H, d, J=8.5 Hz).

EXAMPLE 49

Ethyl 2-butyl-3-[4-[2-(2-hydroxypyridine-5-carbonylamino)ethoxy]phenyl]propionate (ethyl ester of exemplification No. 4-193 compound)

In a similar manner to that described in Example 25, a reaction was carried out using ethyl 3-[4-(2-aminoethoxy) phenyl]-2-butylpropionate (843 mg), which is the product of Reference example 6, 6-hydroxynicotinic acid (400 mg), 1-(3-dimethylaminopropyl)-3-ethylcarbodiimide hydrochloride (660 mg) and 1-hydroxybenzotriazole monohydrate (528 mg) and the reaction mixture was treated to give the title compound (636 mg) as a white powder.

mp 102–104° C.

$^1$H-NMR (270 MHz, CDCl$_3$): δ ppm 0.87 (3H, t, J=7.0 Hz), 1.17 (3H, t, J=7.0 Hz), 1.21–1.32 (4H, m), 1.40–1.70 (2H, m), 2.53–2.72 (2H, m), 2.80–2.91 (1H, m), 3.81 (2H, q, J=5.0 Hz), 4.02–4.12 (4H, m), 6.42–6.52 (1H, m), 6.56 (1H, d, J=9.5 Hz), 6.81 (2H, d, J=8.5 Hz), 7.08 (2H, d, J=8.5 Hz), 7.80 (1H, dd, J=2.5, 9.5 Hz), 8.00 (1H, d, J=2.5 Hz).

EXAMPLE 50

2-Butyl-3-[4-[2-(2-hydroxypyridine-5-carbonylamino)ethoxy]phenyl]propionic acid (exemplification No. 4-193 compound)

In a similar manner to that described in Example 2, ethyl 2-butyl-3-[4-[2-(2-hydroxypyridine-5-carbonylamino) ethoxy]phenyl]propionate (300 mg), which is the product of Example 49, was reacted with aqueous sodium hydroxide solution (1N, 3.00 ml) and the reaction mixture was treated to give the title compound (240 mg) as a pale yellow powder.

mp 69–71° C.

$^1$H-NMR (270 MHz, CDCl$_3$): δ ppm 0.90 (3H, t, J=7.0 Hz), 1.30–1.45 (4H, m), 1.50–1.79 (2H, m), 2.57–2.68 (1H, m), 2.77 (1H, d, J=7.5 Hz), 3.68–3.77 (2H, m), 4.00–4.09 (2H, m), 6.42 (1H, d, J=10.0 Hz), 6.71 (2H, d, J=8.5 Hz), 7.05 (2H, d, J=8.5 Hz), 7.10–7.20 (1H, m), 7.75–7.80 (2H, m).

EXAMPLE 51

Ethyl 2-butyl-3-[4-[2-(2-methoxypyridine-5-carbonylamino)ethoxy]phenyl]propionate (ethyl ester of exemplification No. 4-96 compound)

In a similar manner to that described in Example 5, a reaction was carried out using ethyl 3-[4-(2-aminoethoxy) phenyl]-2-butylpropionate (766 mg), which is the product of Reference example 6, 6-methoxynicotinic acid (400 mg) and carbonyldiimidazole (508 mg) and the reaction mixture was treated to give the title compound (783 mg) as colorless crystals.

mp 129–130° C.

$^1$H-NMR (270 MHz, CDCl$_3$): δ ppm 0.87 (3H, t, J=7.0 Hz), 1.16 (3H, t, J=7.0 Hz), 1.22–1.33 (4H, m), 1.40–1.70 (2H, m), 2.52–2.63 (1H, m), 2.68 (1H, dd, J=6.5, 13.5 Hz), 2.86 (1H, dd, J=8.5, 13.5 Hz), 3.85 (2H, q, J=5.0 Hz), 4.00 (3H, s), 4.06 (2H, q, J=7.0 Hz), 4.12 (2H, t, J=5.0 Hz), 6.46–6.55 (1H, m), 6.78 (1H, d, J=8.5 Hz), 6.82 (2H, d, J=8.5 Hz), 7.08 (2H, d, J=8.5 Hz), 7.99 (1H, dd, J=2.5, 8.5 Hz), 8.59 (1H, d, J=2.5 Hz).

EXAMPLE 52

2-Butyl-3-[4-[2-(2-methoxypyridine-5-carbonylamino)ethoxy]phenyl]propionic acid (exemplification No. 4-96 compound)

In a similar manner to that described in Example 2, ethyl 2-butyl-3-[4-[2-(2-methoxypyridine-5-carbonylamino) ethoxy]phenyl]propionate (500 mg), which is the product of Example 51, was reacted with aqueous sodium hydroxide solution (1N, 4.00 ml) and the reaction mixture was treated to give the title compound (293 mg) as a white powder.

mp 144–145° C.

$^1$H-NMR (270 MHz, CDCl$_3$): δ ppm 0.89 (3H, t, J=7.0 Hz), 1.24–1.40 (4H, m), 1.47–1.75 (2H, m), 2.62–2.90 (3H, m), 3.71–3.97 (2H, m), 3.98 (3H, s), 4.11–4.26 (2H, m), 6.48–6.60 (1H, m), 6.78 (1H, d, J=8.5 Hz), 6.85 (2H, d, J=8.5 Hz), 7.11 (2H, d, J=8.5 Hz), 8.03 (1H, dd, J=2.5, 8.5 Hz), 8.31 (1H, d, J=2.5 Hz).

EXAMPLE 53

Ethyl 2-butyl-3-[4-[2-(2-isopropoxypyridine-5-carbonylamino)ethoxy]phenyl]propionate (ethyl ester of exemplification No. 4-98 compound)

In a similar manner to that described in Example 5, a reaction was carried out using ethyl 3-[4-(2-aminoethoxy)

phenyl]-2-butylpropionate (156 mg), which is the product of Reference example 6, 6-isopropoxynicotinic acid (106 mg), which is the product of Reference example 18, and carbonyldiimidazole (112 mg) and the reaction mixture was treated to give the title compound (170 mg) as a colorless oil.

$^1$H-NMR (270 MHz, CDCl$_3$): δ ppm 0.87 (3H, t, J=7.0 Hz), 1.16 (3H, t, J=7.0 Hz), 1.20–1.40 (10H, m), 1.41–1.71 (2H, m), 2.61–2.73 (2H, m), 2.86 (1H, dd, J=8.5, 13.5 Hz), 3.83 (2H, q, J=5.0 Hz), 4.05 (2H, q, J=7.0 Hz), 4.11 (2H, t, J=5.0 Hz), 5.35 (2H, septet, J=6.0 Hz), 6.56–6.62 (1H, m), 6.69 (1H, d, J=8.5 Hz), 6.81 (2H, d, J=8.5 Hz), 7.07 (2H, d, J=8.5 Hz), 7.97 (1H, dd, J=2.5, 8.5 Hz), 8.58 (1H, d, J=2.5 Hz).

EXAMPLE 54

2-Butyl-3-[4-[2-(2-isopropoxypyridine-5-carbonylamino)ethoxy]phenyl]propionic acid (exemplification No. 4-98 compound)

In a similar manner to that described in Example 2, ethyl 2-butyl-3-[4-[2-(2-isopropoxypyridine-5-carbonylamino)ethoxy]phenyl]propionate (170 mg), which is the product of Example 53, was reacted with aqueous sodium hydroxide solution (1N, 0.75 ml) and the reaction mixture was treated to give the title compound (137 mg) as colorless crystals.

mp 117–118° C.

$^1$H-NMR (270 MHz, CDCl$_3$): δ ppm 0.89 (3H, t, J=7.0 Hz), 1.22–1.40 (9H, m), 1.46–1.80 (3H, m), 2.59–2.82 (2H, m), 2.85 (1H, dd, J=9.0, 13.5 Hz), 3.73–3.96 (2H, m), 4.10–4.22 (2H, m), 5.31 (2H, septet, J=6.0 Hz), 6.48–6.57 (1H, m), 6.70 (1H, d, J=8.5 Hz), 6.84 (2H, d, J=8.5 Hz), 7.11 (2H, d, J=8.5 Hz), 8.00 (1H, dd, J=2.5, 8.5 Hz), 8.35 (1H, d, J=2.5 Hz).

EXAMPLE 55

Ethyl 2-butyl-3-[4-[2-(2-phenoxypyridine-5-carbonylamino)ethoxy]phenyl]propionate (ethyl ester of exemplification No. 4-106 compound)

In a similar manner to that described in Example 5, a reaction was carried out using ethyl 3-[4-(2-aminoethoxy)phenyl]-2-butylpropionate (158 mg), which is the product of Reference example 6, 6-phenoxynicotinic acid (125 mg) and carbonyldiimidazole (112 mg) and the reaction mixture was treated to give the title compound (225 mg) as a colorless oil.

$^1$H-NMR (270 MHz, CDCl$_3$): δ ppm 0.86 (3H, t, J=7.0 Hz), 1.15 (3H, t, J=7.0 Hz), 1.20–1.36 (4H, m), 1.41–1.70 (2H, m), 2.52–2.72 (2H, m), 2.85 (1H, dd, J=8.5, 13.5 Hz), 3.78–3.89 (2H, m), 4.01–4.15 (4H, m), 6.65–6.82 (3H, m), 6.92 (1H, d, J=8.5 Hz), 7.06 (2H, d, J=8.5 Hz), 7.13 (2H, d, J=7.5 Hz), 7.20–7.26 (1H, m), 7.38–7.45 (2H, m), 8.12 (1H, dd, J=2.5, 8.5 Hz), 8.58 (1H, d, J=2.5 Hz).

EXAMPLE 56

2-Butyl-3-[4-[2-(2-phenoxypyridine-5-carbonylamino)ethoxy]phenyl]propionic acid (exemplification No. 4-106 compound)

In a similar manner to that described in Example 2, ethyl 2-butyl-3-[4-[2-(2-phenoxypyridine-5-carbonylamino)ethoxy]phenyl]propionate (215 mg), which is the product of Example 55, was reacted with aqueous sodium hydroxide solution (1N, 1.32 ml) and the reaction mixture was treated to afford the crude free acid which was subjected to chromatography on a silica gel thin layer plate using dichloromethane/methanol=10/1 as the eluant to give the title compound (137 mg) as colorless crystals.

mp 124–125° C.

$^1$H-NMR (270 MHz, CDCl$_3$): δ ppm 0.85–0.95 (3H, m), 1.25–1.39 (4H, m), 1.40–1.71 (2H, m), 2.53–2.88 (3H, m), 3.70–3.97 (2H, m), 4.08–4.28 (2H, m), 6.58–6.68 (1H, m), 6.81 (2H, d, J=8.5 Hz), 6.93 (1H, d, J=8.5 Hz), 7.08 (2H, d, J=8.5 Hz), 7.13 (2H, d, J=8.5 Hz), 7.20–7.29 (1H, m), 7.39–7.48 (2H, m), 8.15 (1H, dd, J=8.5 Hz), 8.29 (1H, s).

EXAMPLE 57

Ethyl 2-butyl-3-[4-[2-(quinoline-3-carbonylamino)ethoxy]phenyl]propionate (ethyl ester of exemplification No. 4-150 compound)

In a similar manner to that described in Example 5, a reaction was carried out using ethyl 3-[4-(2-aminoethoxy)phenyl]-2-butylpropionate (529 mg), which is the product of Reference example 6, quinoline-3-carboxylic acid (312 mg) and carbonyldiimidazole (350 mg) and the reaction mixture was treated to give the title compound (760 mg) as a yellow oil.

$^1$H-NMR (270 MHz, CDCl$_3$): δ ppm 0.87 (3H, t, J=6.5 Hz), 1.16 (3H, t, J=7.0 Hz), 1.22–1.37 (4H, m), 1.40–1.70 (2H, m), 2.55–2.63 (1H, m), 2.69 (1H, dd, J=6.5, 13.5 Hz), 2.86 (1H, dd, J=8.5, 13.5 Hz), 3.95 (2H, q, J=5.0 Hz), 4.06 (2H, q, J=7.0 Hz), 4.19 (2H, t, J=5.0 Hz), 6.76–6.82 (1H, m), 6.85 (2H, d, J=8.5 Hz), 7.09 (2H, d, J=8.5 Hz), 7.63 (1H, t, J=8.0 Hz), 7.78–7.85 (1H, m), 7.92 (1H, d, J=8.0 Hz), 8.16 (1H, d, J=8.0 Hz), 8.60 (1H, d, J=2.5 Hz), 9.28 (1H, d, J=2.5 Hz).

EXAMPLE 58

Sodium 2-butyl-3-[4-[2-(quinoline-3-carbonylamino)ethoxy]phenyl]propionic acid (exemplification No. 4-150 compound)

In a similar manner to that described in Example 2, ethyl 2-butyl-3-[4-[2-(quinoline-3-carbonylamino)ethoxy]phenyl]propionate (760 mg), which is the product of Example 57, was reacted with aqueous sodium hydroxide solution (1N, 6.00 ml) and the reaction mixture was treated to give the title compound (386 mg) as a white powder.

mp 245–248° C.

$^1$H-NMR of the free acid (270 MHz, CDCl$_3$): δ ppm 0.90 (3H, t, J=7.0 Hz), 1.28–1.48 (4H, m), 1.50–1.80 (2H, m), 2.58–2.90 (3H, m), 3.80–4.07 (2H, m), 4.20–4.39 (2H, m), 6.68–6.84 (1H, m), 6.87 (2H, d, J=8.5 Hz), 7.12 (2H, d, J=8.5 Hz), 7.62 (1H, t, J=8.0 Hz), 7.81 (1H, t, J=8.0 Hz), 7.91 (1H, d, J=8.0 Hz), 8.13 (1H, d, J=8.0 Hz), 8.70 (1H, s), 8.81 (1H, s).

EXAMPLE 59

Ethyl 2-butyl-3-[4-[2-(indole-3-carbonylamino)ethoxy]phenyl]propionate (ethyl ester of exemplification No. 4-143 compound)

In a similar manner to that described in Example 25, a reaction was carried out using ethyl 3-[4-(2-aminoethoxy)phenyl]-2-butylpropionate (546 mg), which is the product of Reference example 6, indole-3-carboxylic acid (300 mg), 1-(3-dimethylaminopropyl)-3-ethylcarbodiimide hydrochloride (428 mg) and 1-hydroxybenzotriazole monohydrate (342 mg)and the reaction mixture was treated to give the title compound (650 mg) as a yellow oil.

$^1$H-NMR (270 MHz, CDCl$_3$): δ ppm 0.87 (3H, t, J=7.0 Hz), 1.15 (3H, t, J=7.0 Hz), 1.22–1.32 (4H, m), 1.40–1.68 (2H, m), 2.55–2.64 (1H, m), 2.69 (1H, dd, J=6.5, 13.5 Hz), 2.86 (1H, dd, J=8.5, 13.5 Hz), 3.91 (2H, q, J=5.0 Hz), 4.05 (2H, q, J=7.0 Hz), 4.17 (2H, t, J=5.0 Hz), 6.44 (1H, t, J=5.0 Hz), 6.86 (2H, d, J=8.5 Hz), 7.08 (2H, d, J=8.5 Hz), 7.24–7.29 (2H, m), 7.41–7.45 (1H, m), 7.74 (1H, d, J=3.0 Hz), 7.95–7.99 (1H, m), 8.59–8.70 (1H, m).

EXAMPLE 60

2-Butyl-3-[4-[2-(indole-3-carbonylamino)ethoxy]phenyl]propionic acid (exemplification No. 4-143 compound)

In a similar manner to that described in Example 2, ethyl 2-butyl-3-[4-[2-(indole-3-carbonylamino)ethoxy]phenyl]propionate (650 mg), which is the product of Example 59, was reacted with aqueous sodium hydroxide solution (1N, 5.00 ml) and the reaction mixture was treated to give the title compound (500 mg) as a white powder.

mp 171–173° C.

$^1$H-NMR of the free acid (270 MHz, CDCl$_3$): δ ppm 0.86 (3H, t, J=7.0 Hz), 1.22–1.37 (4H, m), 1.40–1.68 (2H, m), 2.40–2.62 (1H, m), 2.68 (1H, dd, J=6.5, 13.5 Hz), 2.90 (1H, dd, J=8.5, 13.5 Hz), 3.88 (2H, q, J=5.0 Hz), 4.17 (2H, t, J=5.0 Hz), 6.73 (1H, t, J=5.0 Hz), 6.85 (2H, d, J=8.5 Hz), 7.11 (2H, d, J=8.5 Hz), 7.17–7.24 (2H, m), 7.42–7.47 (1H, m), 7.78 (1H, d, J=3.0 Hz), 8.00–8.05 (1H, m).

EXAMPLE 61

Ethyl 2-butyl-3-[4-[2-(4-N,N-diethylaminobenzoylamino)ethoxy]phenyl]propionate (ethyl ester of exemplification No. 4-230 compound)

In a similar manner to that described in Example 5, a reaction was carried out using ethyl 3-[4-(2-aminoethoxy)phenyl]-2-butylpropionate (455 mg), which is the product of Reference example 6, 4-N,N-diethylaminobenzoic acid (300 mg) and carbonyldiimidazole (302 mg) and the reaction mixture was treated to give the title compound (346 mg) as a colorless oil.

$^1$H-NMR (270 MHz, CDCl$_3$): δ ppm 0.87 (3H, t, J=7.0 Hz), 1.13–1.20 (9H, m), 1.24–1.37 (4H, m), 1.40–1.70 (2H, m), 2.53–2.63 (1H, m), 2.68 (1H, dd, J=6.5, 13.5 Hz), 2.86 (1H, dd, J=8.5, 13.5 Hz), 3.39 (4H, q, J=7.0 Hz), 3.83 (2H, q, J=5.5 Hz), 4.01–4.14 (4H, m), 6.40 (1H, t, J=5.5 Hz), 6.63 (2H, d, J=8.5 Hz), 6.82 (2H, d, J=8.5 Hz), 7.07 (2H, d, J=8.5 Hz), 7.66 (2H, d, J=8.5 Hz).

EXAMPLE 62

2-Butyl-3-[4-[2-(4-N,N-dietylaminobenzoylamino)ethoxy]phenyl]propionic acid (exemplification No. 4-230 compound)

In a similar manner to that described in Example 2, ethyl 2-butyl-3-[4-[2-(4-N,N-diethylaminobenzoylamino)ethoxy]phenyl]propionate (340 mg), which is the product of Example 61, was reacted with aqueous sodium hydroxide solution (1N, 2.20 ml) and the reaction mixture was treated to give the title compound (257 mg) as a white powder.

mp 76–78° C.

$^1$H-NMR (270 MHz, CDCl$_3$): δ ppm 0.87 (3H, t, J=7.0 Hz), 1.17 (6H, t, J=7.0 Hz), 1.11–1.21 (4H, m), 1.45–1.70 (2H, m), 2.57–2.65 (1H, m), 2.70 (1H, dd, J=6.5, 13.5 Hz), 2.90 (1H, dd, J=8.0, 13.5 Hz), 3.38 (4H, q, J=7.0 Hz), 3.80 (2H, q, J=5.0 Hz), 4.08 (2H, t, J=5.0 Hz), 6.48 (1H, t, J=5.0 Hz), 6.62 (2H, d, J=8.5 Hz), 6.82 (2H, d, J=8.5 Hz), 7.09 (2H, d, J=8.5 Hz), 7.65 (2H, d, J=8.5 Hz).

EXAMPLE 63

Ethyl 2-butyl-3-[4-[2-(4-pipendine-1-ylbenzoylamino)ethoxy]phenyl]propionate (ethyl ester of exemplification No. 4-229 compound)

In a similar manner to that described in Example 5, a reaction was carried out using ethyl 3-[4-(2-aminoethoxy)phenyl]-2-butylpropionate (428 mg), which is the product of Reference example 6, 4-piperidine-1-ylbenzoic acid (300 mg) and carbonyldiimidazole (284 mg) and the reaction mixture was treated to give the title compound (420 mg) as a white powder.

mp 87–89° C.

$^1$H-NMR (270 MHz, CDCl$_3$): δ ppm 0.87 (3H, t, J=7.0 Hz), 1.15 (3H, t, J=7.0 Hz), 1.20–1.37 (4H, m), 1.40–1.73 (8H, m), 2.52–2.61 (1H, m), 2.68 (1H, dd, J=6.5, 13.5 Hz), 2.86 (1H, dd, J=8.5, 13.5 Hz), 3.26–3.33 (4H, m), 3.83 (2H, q, J=5.0 Hz), 4.01–4.16 (4H, m), 6.48 (1H, t, J=5.0 Hz), 6.82 (2H, d, J=8.5 Hz), 6.87 (2H, d, J=9.0 Hz), 7.07 (2H, d, J=8.5 Hz), 7.67 (2H, d, J=9.0 Hz).

EXAMPLE 64

2-Butyl-3-[4-[2-(4-piperidine-1-ylbenzoylamino)ethoxy]phenyl]propionic acid (exemplification No. 4-229 compound)

In a similar manner to that described in Example 2, ethyl 2-butyl-3-[4-[2-(4-piperidine-1-ylbenzoylamino)ethoxy]phenyl]propionate (370 mg), which is the product of Example 63, was reacted with aqueous sodium hydroxide solution (1N, 2.30 ml) and the reaction mixture was treated to give the title compound (324 mg) as a white powder.

mp 112.5–114° C.

$^1$H-NMR (270 MHz, CDCl$_3$): δ ppm 0.90 (3H, t, J=6.5 Hz), 1.28–1.44 (4H, m), 1.48–1.77 (8H, m), 2.61–2.69 (1H, m), 2.73 (1H, dd, J=6.5, 13.5 Hz), 2.92 (1H, dd, J=8.0, 13.5 Hz), 3.27–3.33 (4H, m), 3.84 (2H, q, J=5.0 Hz), 4.11 (2H, t, J=5.0 Hz), 6.54 (1H, t, J=5.0 Hz), 6.84 (2H, d, J=8.5 Hz), 6.89 (2H, d, J=9.0 Hz), 7.12 (2H, d, J=8.5 Hz), 7.70 (2H, d, J=9.0 Hz).

EXAMPLE 65

Ethyl 2-butyl-3-[4-[2-(N-(3-phenylpropyl)-(4-pyridine-2-ylbenzoyl)amino)ethoxy]phenyl]propionate (ethyl ester of exemplification No. 20-71 compound)

Triethylamine (0.37 ml) was added to a solution of ethyl 2-butyl-3-[4-[2-(3-phenylpropylamino)ethoxy]phenyl]propionate (460 mg), which is the product of Reference example 19, and 4-pyridine-2-ylbenzoylchloride hydrochloride (341 mg) in dichloromethane (10 ml) at ambient temperature. After the mixture was stirred for 5 hours at ambient temperature, the solvent was distilled off under reduced pressure. The residue was partitioned between ethyl acetate and water and the ethyl acetate layer was separated and dried over anhydrous magnesium sulfate and then concentrated under reduced pressure. The residue was purified via chromatography on a silica gel column using dichloromethane/methanol=19/1 as the eluant to give the title compound (275 mg) as a colorless oil.

¹H-NMR (270 MHz, CDCl₃): δ ppm 0.87 (3H, t, J=7.0 Hz), 1.12–2.05 (1H, m), 2.42–2.91 (5H, m), 3.35–4.30 (8H, m), 6.70–6.88 (2H, m), 7.00–7.60 (10H, m), 7.73–7.85 (2H, m), 7.99–8.06 (2H, m), 8.72 (1H, d, J=5.0 Hz).

EXAMPLE 66

2-Butyl-3-[4-[2-(N-(3-phenylpropyl)-(4-pyridine-2-ylbenzoyl)amino)ethoxy]phenyl]propionic acid hydrochloride (exemplification No. 20-71 compound)

In a similar manner to that described in Example 2, ethyl 2-butyl-3-[4-[2-(N-(3-phenylpropyl)-(4-pyridine-2-ylbenzoyl)amino)ethoxy]phenyl]propionate (275 mg), which is the product of Example 65, was reacted with aqueous sodium hydroxide solution (1N, 1.00 ml) and the reaction mixture was treated. The title compound (230 mg) was obtained as a mass of foam by treating the product with a dioxane solution of hydrogen chloride (4N).

¹H-NMR of free acid (270 MHz, CDCl₃): δ ppm 0.92 (3H, t, J=7.0 Hz), 1.30–1.45 (4H, m), 1.50–2.10 (4H, m), 2.55–2.82 (5H, m), 3.48–3.83 (4H, m), 4.00–4.36 (2H, m), 6.57–6.86 (2H, m), 7.02–7.39 (10H, m), 7.68–7.89 (4H, m), 8.69 (1H, d, J=5.0 Hz).

EXAMPLE 67

Ethyl 2-butyl-3-[4-[2-[N-butyl-(4-pyridine-2-ylbenzoyl)amino]ethoxy]phenyl]propionate (ethyl ester of exemplification No. 20-53 compound)

In a similar manner to that described in Example 65, a reaction was carried out using ethyl 2-butyl-3-[4-[2-(butylamino)ethoxy]phenyl]propionate (390 mg), which is the product of Reference example 20, 4-pyridine-2-ylbenzoylchloride hydrochloride (340 mg) and triethylamine (0.37 ml) and the reaction mixture was treated to give the title compound (165 mg) as a colorless oil.

¹H-NMR (270 MHz, CDCl₃): δ ppm 0.78–1.71 (19H, m), 2.55–2.77 (2H, m), 2.82–2.91 (1H, m), 3.34–3.47 (1H, m), 3.65–3.80 (3H, m), 3.83–3.94 (1H, m), 4.06 (2H, q, J=7.0 Hz), 4.23–4.32 (1H, m), 6.68–6.91 (2H, m), 7.01–7.15 (2H, m), 7.23–7.30 (1H, m), 7.43–7.81 (4H, m), 8.02 (2H, d, J=8.5 Hz), 8.70 (0.6H, d, J=5.0 Hz), 8.90 (0.4H, d, J=5.0 Hz).

EXAMPLE 68

2-Butyl-3-[4-[2-[N-butyl-(4-pyridine-2-ylbenzoyl)amino]ethoxy]phenyl]propionic acid hydrochloride (exemplification No. 20-53 compound)

In a similar manner to that described in Example 2, ethyl 2-butyl-3-[4-[2-[N-butyl-(4-pyridine-2-ylbenzoyl)amino]ethoxy]phenyl]propionate (165 mg), which is the product of Example 67, was reacted with aqueous sodium hydroxide solution (1N, 1.00 ml) and the reaction mixture was treated. The title compound (110 mg) was obtained as a mass of foam by treating the product with a dioxane solution of hydrogen chloride (4N).

¹H-NMR of free acid (270 MHz, CDCl₃): δ ppm 0.80–1.01 (6H, m), 1.10–1.85 (10H, m), 2.60–2.85 (3H, m), 3.30–3.90 (4H, m), 4.11–4.38 (2H, m), 6.58–6.90 (2H, m), 7.02–7.14 (2H, m), 7.28–7.40 (3H, m), 7.68–7.90 (4H, m), 8.69 (1H, d, J=5.0 Hz).

EXAMPLE 69

Ethyl 2-butyl-3-[4-[3-(4-pyridine-2-ylbenzoylamino)propoxy]phenyl]propionate (ethyl ester of exemplification No. 40-3 compound)

In a similar manner to that described in Example 5, a reaction was carried out using ethyl 3-[4-(3-aminopropoxy)phenyl]-2-butylpropionate (500 mg), which is the product of Reference example 21, 4-pyridine-2-ylbenzoic acid (340 mg) and carbonyldiimidazole (333 mg) and the reaction mixture was treated to give the title compound (178 mg) as a white powder.

mp 110–112° C.

¹H-NMR (270 MHz, CDCl₃): δ ppm 0.87 (3H, t, J=7.0 Hz), 1.16 (3H, t, J=7.0 Hz), 1.21–1.33 (4H, m), 1.42–1.70 (2H, m), 2.14 (2H, quintuplet, J=6.0 Hz), 2.53–2.73 (2H, m), 2.80–2.91 (1H, m), 3.71 (2H, q, J=6.0 Hz), 4.06 (2H, q, J=7.0 Hz), 4.13 (2H, t, J=6.0 Hz), 6.76–6.80 (1H, m), 6.83 (2H, d, J=8.5 Hz), 7.10 (2H, d, J=8.5 Hz), 7.25–7.32 (1H, m), 7.76–7.81 (2H, m), 7.89 (2H, d, J=8.5 Hz), 8.08 (2H, d, J=8.5 Hz), 8.73 (1H, d, J=5.0 Hz).

EXAMPLE 70

2-Butyl-3-[4-[3-(4-pyridine-2-ylbenzoylamino)propoxy]phenyl]propionic acid (exemplification No. 40-3 compound)

In a similar manner to that described in Example 2, ethyl 2-butyl-3-[4-[3-(4-pyridine-2-ylbenzoylamino)propoxy]phenyl]propionate (161 mg), which is the product of Example 69, was reacted with aqueous sodium hydroxide solution (1N, 1.20 ml) and the reaction mixture was treated to give the title compound (117 mg) as a white powder.

mp 151–152° C.

¹H-NMR (270 MHz, CDCl₃): δ ppm 0.90 (3H, t, J=7.0 Hz), 1.28–1.44 (4H, m), 1.51–1.64 (1H, m), 1.65–1.78 (1H, m), 2.15 (2H, quintuplet, J=6.0 Hz), 2.58–2.92 (3H, m), 3.60–3.80 (2H, m), 4.15–4.21 (2H, m), 6.84 (2H, d, J=8.5 Hz), 6.87–6.95 (1H, m), 7.16 (2H, d, J=8.5 Hz), 7.30–7.35 (1H, m), 7.74–7.90 (6H, m), 8.69 (1H, d, J=5.5 Hz).

EXAMPLE 71

Ethyl 2-butyl-3-[4-[3-[N-methyl-(4-pyridine-2-ylbenzoyl)amino]propoxy]phenyl]propionate (ethyl ester of exemplification No. 20-80 compound)

In a similar manner to that described in Example 65, a reaction was carried out using ethyl 2-butyl-3-[4-(3-methylaminopropoxy)phenyl]propionate (380 mg), which is the product of Reference example 22, 4-pyridine-2-ylbenzoylchloride hydrochloride (360 mg) and triethylamine (0.40 ml) and the reaction mixture was treated to give the title compound (259 mg) as a white powder.

mp 58–60° C.

¹H-NMR (270 MHz, CDCl₃): δ ppm 0.86 (3H, t, J=7.0 Hz), 1.15 (3H, t, J=7.0 Hz), 1.20–1.38 (4H, m), 1.40–1.70 (2H, m), 1.96–2.23 (2H, m), 2.52–2.72 (2H, m), 2.80–2.91 (1H, m), 3.00–3.19 (3H,m), 3.49–3.60 (1H, m), 3.71–3.89 (2H, m), 4.00–4.12 (3H,m), 6.61–6.70 (1H, m), 6.79–6.89 (1H, m), 6.99–7.10 (2H, m), 7.23–7.28 (1H, m), 7.41–7.55 (2H, m), 7.70–7.81 (2H, m), 7.91–8.06 (2H, m), 8.71 (1H, d, J=5.0 Hz).

EXAMPLE 72

2-Butyl-3-[4-[3-[N-methyl-(4-pyridine-2-ylbenzoyl)amino]propoxy]phenyl]propionic acid (exemplification No. 20-80 compound)

In a similar manner to that described in Example 2, ethyl 2-butyl-3-[4-[3-[N-methyl-(4-pyridine-2-ylbenzoyl)amino]propoxy]phenyl]propionate (200 mg). which is the product of Example 71, was reacted with aqueous sodium hydroxide solution (1N, 1.20 ml) and the reaction mixture was treated to give the title compound (127 mg) as a white powder.

mp 110–112° C.

$^1$H-NMR (270 MHz, CDCl$_3$): δ ppm 0.91 (3H, t, J=7.0 Hz), 1.21–1.41 (4H, m), 1.48–1.61 (1H, m), 1.64–1.83 (1H, m), 1.93–2.23 (2H, m), 2.58–2.83 (3H, m), 3.00–3.17 (3H, m), 3.37–3.60 (1H, m), 3.68–4.26 (3H, m), 6.66–7.01 (2H, m), 7.10–7.30 (2H, m), 7.33–7.60 (3H, m), 7.70–8.20 (4H, m), 8.76–9.05 (1H, m).

EXAMPLE 73

Ethyl 2-propyl-3-[4-[2-(4-pyridine-2-ylbenzoylamino)ethoxy]phenyl]propionate (ethyl ester of exemplification No. 3-35 compound)

A solution of ethyl 3-[4-(2-t-butoxycarbonylaminoethoxy)phenyl]-2-propylpropionate (2.20 g) in dioxane containing hydrogen chloride (4N, 30 ml) was allowed to stand at ambient temperature for 40 minutes. At the end of this time the reaction mixture was concentrated under reduced pressure and the hydrogen chloride was azeotropically distilled off with toluene to give a residue. A solution of diethyl cyanophosphonate (0.97 ml) in N,N-dimethylformamide (4.0 ml) was added to a solution of the residue obtained above (ethyl 3-[4-(2-aminoethoxy)phenyl]-2-propylpropionate hydrochloride), 4-pyridine-2-ylbenzoic acid (1.21 g) and triethylamine (1.80 ml) in N,N-dimethylformamide (8.0 ml) in an ice bath. The mixture was stirred for 1 hour in an ice bath and for 3 hours at ambient temperature. The reaction mixture was partitioned between ethyl acetate and water and the ethyl acetate was separated and washed with saturated aqueous sodium hydrogencarbonate and dried over anhydrous magnesium sulfate and concentrated under reduced pressure. The residue was purified via chromatography on a silica gel column using dichloroethane/ethyl acetate=7/3 as the eluant to give the title compound (2.20 g) as a pale yellow powder.

mp 90.5–92° C.

$^1$H-NMR (270 MHz, CDCl$_3$): δ ppm 0.88 (3H, t, J=7.0 Hz), 1.16 (3H, t, J=7.0 Hz), 1.21–1.71 (4H, m), 2.50–2.72 (2H, m), 2.80–2.92 (1H, m), 3.81–3.95 (2H, m), 4.00–421 (4H, m), 6.60–6.71 (1H, m), 6.84 (2H, d, J=8.5 Hz), 7.09 (2H, d, J=8.5 Hz), 7.20–7.31 (1H, m), 7.70–7.80 (2H, m), 7.88 (2H, d, J=8.5 Hz), 8.07 (2H, d, J=8.5 Hz), 8.72 (1H, d, J=5.0 Hz).

EXAMPLE 74

2-Propyl-3-[4-[2-(4-pyridine-2-ylbenzoylamino)ethoxy]phenyl]propionic acid (exemplification No. 3-53 compound)

In a similar manner to that described in Example 2, ethyl 2-propyl-3-[4-[2-(4-pyridine-2-ylbenzoylamino)ethoxy]phenyl]propionate (2.10 g), which is the product of Example 73, was reacted with aqueous sodium hydroxide solution (1N, 15.0 ml) and the reaction mixture was treated to give the title compound (1.96 g) as a white powder.

mp 81–82.5° C.

$^1$H-NMR (270 MHz, CDCl$_3$): δ ppm 0.90 (3H, t, J=7.0 Hz), 1.20–1.71 (4H, m), 2.55–2.75 (2H, m), 2.75–2.92 (1H, m), 3.74–3.90 (2H, m), 4.03–421 (2H, m), 6.71–6.89 (3H, m), 7.09 (2H, d, J=8.5 Hz), 7.21–7.31 (1H, m), 7.66–7.83 (4H, m), 7.97 (2H, d, J=8.5 Hz), 8.71 (1H, d, J=4.5 Hz).

EXAMPLE 75

Ethyl 3-[4-[2-(biphenyl-4-carbonylamino)ethoxy]phenyl]-2-phenoxypropionate (ethyl ester of exemplification No. 6-15 compound)

In a similar manner to that described in Example 5, a reaction was carried out using ethyl 3-[4-(2-aminoethoxy)phenyl]-2-phenoxypropionate (666 mg), which is the product of Reference example 4, biphenyl-4-carboxylic acid (400 mg) and carbonyldiimidazole (393 mg) and the reaction mixture was treated to give the title compound (280 mg) as a white powder.

mp 103–104.5° C.

$^1$H-NMR (270 MHz, CDCl$_3$): δ ppm 1.19 (3H, t, J=7.0 Hz), 3.15–3.22 (2H, m), 3.89 (2H, q, J=5.0 Hz), 4.13–4.22 (4H, m), 4.74 (1H, dd, J=6.0, 7.5 Hz), 6.62 (1H, t, J=5.0 Hz), 6.84 (2H, d, J=9.0 Hz), 6.87 (2H, d, J=9.0 Hz), 6.94 (1H, t, J=7.5 Hz), 7.19–7.25 (4H, m), 7.35–7.50 (3H, m), 7.57–7.63 (2H, m), 7.65 (2H, d, J=8.5 Hz), 7.85 (2H, d, J=8.5 Hz).

EXAMPLE 76

3-[4-[2-(Biphenyl-4-carbonylamino)ethoxy]phenyl]-2-phenoxypropionic acid (exemplification No. 6-15 compound)

In a similar manner to that described in Example 2, ethyl 3-[4-[2-(biphenyl-4-carbonylamino)ethoxy]phenyl]-2-phenoxypropionate (270 mg), which is the product of Example 75, was reacted with aqueous sodium hydroxide solution (1N, 2.00 ml) and the reaction mixture was treated to give the title compound (250 mg) as a white powder.

mp 171–173° C.

$^1$H-NMR (270 MHz, CDCl$_3$): δ ppm 3.20 (2H, d, J=6.5 Hz), 3.82–3.90 (2H, m), 4.15 (2H, t, J=5.0 Hz), 4.71 (1H, t, J=6.5 Hz), 6.86 (4H, d, J=8.0 Hz), 6.91 (1H, t, J=7.5 Hz), 7.01–7.12 (1H, m), 7.18–7.27 (4H, m), 7.35–7.50 (3H, m), 7.61 (2H, d, J=8.5 Hz), 7.65 (2H, d, J=8.5 Hz), 7.88 (2H, d, J=8.0 Hz).

EXAMPLE 77

Ethyl 3-[4-[2-(4'-fluorobiphenyl-4-carbonylamino)ethoxy]phenyl]-2-phenoxypropionate (ethyl ester of exemplification No. 6-190 compound)

In a similar manner to that described in Example 5, a reaction was carried out using ethyl 3-[4-(2-aminoethoxy)phenyl]-2-phenoxypropionate (1.63 g), which is the product of Reference example 4, 4'-fluorobiphenyl-4-carboxylic acid (1.20 g) and carbonyldiimidazole (1.08 g) and the reaction mixture was treated to give the title compound (915 mg) as a white powder.

mp 99–101° C.

$^1$H-NMR (270 MHz, CDCl$_3$): δ ppm 1.25 (3H, t, J=7.0 Hz), 3.22–3.26 (2H, m), 3.94 (2H, q, J=5.0 Hz), 4.20 (2H, t, J=5.0 Hz), 4.22 (2H, q, J=7.0 Hz), 4.79 (1H, dd, J=5.5, 7.5 Hz), 6.67 (1H, t, J=5.0 Hz), 6.86–6.93 (4H, m), 6.96–7.01 (1H, m), 7.19 (2H, t, J=8.5 Hz), 7.28 (2H, d, J=8.5 Hz), 7.59–7.68 (4H, m), 7.89 (2H, d, J=8.5 Hz).

EXAMPLE 78

3-[4-[2-(4'-Fluorobiphenyl-4-carbonylamino)ethoxy]phenyl]-2-phenoxypropionic acid (exemplification No. 6-190 compound)

In a similar manner to that described in Example 2, ethyl 3-[4-[2-(4'-fluorobiphenyl-4-carbonylamino)ethoxy]phenyl]-2-phenoxypropionate (915 mg), which is the product of Example 77, was reacted with aqueous sodium hydroxide solution (1N, 5.00 ml) and the reaction mixture was treated to give the title compound (866 mg) as a white powder.

mp 195–196° C.

$^1$H-NMR (270 MHz, deuterated dimethyl sulfoxide): δ ppm 3.08–3.17 (2H, m), 3.63 (2H, q, J=5.5 Hz), 4.10 (2H, t, J=5.5 Hz), 4.83–4.89 (1H, m), 6.83 (2H, d, J=8.5 Hz), 6.88–6.95 (3H, m), 7.23–7.39 (6H, m), 7.73–7.84 (4H, m), 7.95 (2H, d, J=8.0 Hz), 8.75 (1H, t, J=5.5 Hz).

EXAMPLE 79

Ethyl 3-[4-[2-(4'-chlorobiphenyl-4-carbonylamino) ethoxy]phenyl]-2-phenoxypropionate (ethyl ester of exemplification No. 6-204 compound)

A solution of diethyl cyanophosphonate (0.76 ml) in tetrahydrofuran (10 ml) was added to a solution of ethyl 3-[4-(2-aminoethoxy)phenyl]-2-phenoxypropionate (1.50 g), 4'-chlorobiphenyl-4-carboxylic acid (1.17 g) and triethylamine (0.70 ml) in tetrahydrofuran (20 ml) in an ice bath. The mixture was stirred for 1 hour in an ice bath and for 4 hours at ambient temperature. At the end of this time the solvent was distilled off under reduced pressure. The residue was partitioned between ethyl acetate and water and the ethyl acetate layer was separated and washed with saturated aqueous sodium hydrogencarbonate solution and dried over anhydrous magnesium sulfate and concentrated under reduced pressure. The residue was purified via chromatography on a silica gel column using dichloroethane/ethyl acetate=19/1 as the eluant to give the title compound (0.90 g) as a pale yellow oil.

$^1$H-NMR (270 MHz, CDCl$_3$): δ ppm 1.19 (3H, t, J=7.0 Hz), 3.12–3.21 (2H, m), 3.79–3.90 (2H, m), 4.05–4.21 (4H, m), 4.69–4.79 (1H, m), 6.68–6.78 (1H, m), 6.80–6.89 (4H, m), 6.90–6.96 (1H, m), 7.16–7.27 (4H, m), 7.41 (2H, d, J=8.5 Hz), 7.51 (2H, d, J=8.5 Hz), 7.58 (2H, d, J=8.5 Hz), 7.84 (2H, d, J=8.5 Hz).

EXAMPLE 80

3-[4-[2-(4'-Chlorobiphenyl-4-carbonylamino) ethoxy]phenyl]-2-phenoxypropionic acid (exemplification No. 6-204 compound)

In a similar manner to that described in Example 2, ethyl 3-[4-[2-(4'-chlorobiphenyl-4-carbonylamino)ethoxy] phenyl]-2-phenoxypropionate (900 mg), which is the product of Example 79, was reacted with aqueous sodium hydroxide solution (1N, 5.00 ml) and the reaction mixture was treated to give the title compound (638 mg) as a white powder.

mp 194.5–197° C.

$^1$H-NMR (270 MHz, deuterated dimethyl sulfoxide): δ ppm 3.05–3.15 (2H, m), 3.58–3.67 (2H, m), 4.01–4.12 (2H, m), 4.80–4.89 (1H, m), 6.78–6.95 (5H, m), 7.18–7.28 (4H, m), 7.55 (2H, d, J=8.5 Hz), 7.71–7.81 (4H, m), 7.96 (2H, d, J=8.0 Hz), 8.71–8.79 (1H, m).

EXAMPLE 81

Ethyl 3-[4-[2-(4'-trifluoromethylbiphenyl-4-carbonylamino)ethoxy]phenyl]-2-phenoxypropionate (ethyl ester of exemplification No. 6-191 compound)

In a similar manner to that described in Example 5, a reaction was carried out using ethyl 3-[4-(2-aminoethoxy) phenyl]-2-phenoxypropionate (1.60 g), which is the product of Reference example 4, 4'-trifluoromethylbiphenyl-4-carboxylic acid (1.30 g) and carbonyldiimidazole (0.95 g) and the reaction mixture was treated to give the title compound (1.10 g) as a pale yellow oil.

$^1$H-NMR (270 MHz, CDCl$_3$): δ ppm 1.25 (3H, t, J=7.0 Hz), 3.18–3.25 (2H, m), 3.95 (2H, q, J=5.0 Hz), 4.20 (2H, t, J=5.0 Hz), 4.22 (2H, q, J=7.0 Hz), 4.79 (1H, dd, J=5.5, 7.5 Hz), 6.70 (1H, t, J=5.0 Hz), 6.82–6.98 (5H, m), 7.20–7.32 (4H, m), 7.65–7.76 (6H, m), 7.93 (2H, d, J=8.5 Hz).

EXAMPLE 82

3-[4-[2-(4'-Trifluoromethylbiphenyl-4-carbonylamino)ethoxy]phenyl]-2-phenoxypropionic acid (exemplification No. 6-191 compound)

In a similar manner to that described in Example 2, ethyl 3-[4-[2-(4'-trifluoromethylbiphenyl-4-carbonylamino) ethoxy]phenyl]-2-phenoxypropionate (1.10 g), which is the product of Example 81, was reacted with aqueous sodium hydroxide solution (1N, 5.00 ml) and the reaction mixture was treated to give the title compound (850 mg) as a white powder.

mp 217–218.5° C.

$^1$H-NMR (270 MHz, deuterated dimethyl sulfoxide): δ ppm 3.06–3.16 (2H, m), 3.66 (2H, q, J=5.5 Hz), 4.11 (2H, t, J=5.5 Hz), 4.85 (1H, dd, J=5.0, 7.5 Hz), 6.80–6.96 (5H, m), 7.20–7.28 (4H, m), 7.85 (4H, d, J=8.5 Hz), 7.94–8.02 (4H, m), 8.80 (1H, t, J=5.5 Hz).

EXAMPLE 83

Sodium 3-[4-[2-(4'-hydroxy-3',5'-dimethylbiphenyl-4-carbonylamino)ethoxy]phenyl]-2-phenoxypropionate (exemplification No. 6-205 compound)

In a similar manner to that described in Example 36, 3-[4-[2-(4'-methoxymethoxy-3',5'-dimethylbiphenyl-4-carbonylamino)ethoxy]phenyl]-2-phenoxypropionic acid (330 mg), which is the product of Reference example 24, was reacted with a dioxane solution of hydrogen chloride (4N, 3.30 ml) and the reaction mixture was treated to give the title compound (257 mg) as a white powder.

mp 134–135° C.

$^1$H-NMR (270 MHz, deuterated dimethyl sulfoxide): δ ppm 2.23 (6H, s), 2.90 (1H, dd, J=9.5, 14.5 Hz), 3.05 (1H, dd, J=1.5, 14.5 Hz), 3.61 (2H, q, J=5.5 Hz), 4.07 (2H, t, J=5.5 Hz), 4.32 (1H, dd, J=1.5, 9.5 Hz), 6.74 (2H, d, J=7.5 Hz), 6.78 (1H, d, J=7.5 Hz), 6.85 (2H, d, J=8.5 Hz), 7.13 (2H, d, J=7.5 Hz), 7.19 (2H, d, J=8.5 Hz), 7.31 (2H, s), 7.66 (2H, d, J=8.5 Hz), 7.89 (2H, d, J=8.5 Hz), 8.54 (1H, brs), 8.68 (1H, brt).

EXAMPLE 84

Ethyl 3-[4-[2-(2-methoxypyridine-5-carbonylamino) ethoxy]phenyl]-2-phenoxypropionate (ethyl ester of exemplification No. 6-96 compound)

In a similar manner to that described in Example 5, a reaction was carried out using ethyl 3-[4-(2-aminoethoxy) phenyl]-2-phenoxypropionate (753 mg), which is the product of Reference example 4, 6-methoxynicotinic acid (350 mg) and carbonyldiimidazole (445 mg) and the reaction mixture was treated to give the title compound (355 mg) as a white powder.

mp 114–116° C.

$^1$H-NMR (270 MHz, CDCl$_3$): δ ppm 1.20 (3H, t, J=7.0 Hz), 3.17–3.20 (2H, m), 3.85 (2H, q, J=5.0 Hz), 3.98 (3H, s), 4.12 (2H, t, J=5.0 Hz), 4.18 (2H, q, J=7.0 Hz), 4.73 (1H, dd, J=6.0, 7.0 Hz), 6.48 (1H, t, J=5.0 Hz), 6.77 (1H, d, J=8.5

Hz), 6.82–6.86 (4H, m), 6.94 (1H, t, J=7.5 Hz), 7.20–7.28 (4H, m), 7.98 (1H, dd, J=2.5, 8.5 Hz), 8.59 (1H, d, J=2.5 Hz).

EXAMPLE 85

3-[4-[2-(2-Methoxypyridine-5-carbonylamino) ethoxy]phenyl]-2-phenoxypropionic acid (exemplification No. 6-96 compound)

In a similar manner to that described in Example 2, ethyl 3-[4-[2-(2-methoxypyridine-5-carbonylamino)ethoxy] phenyl]-2-phenoxypropionate (330 mg), which is the product of Example 84, was reacted with aqueous sodium hydroxide solution (1N, 2.50 ml) and the reaction mixture was treated to give the title compound (260 mg) as colorless crystals.

mp 145–146.5° C.

$^1$H-NMR (270 MHz, CD$_3$Cl): δ ppm 3.18–3.23 (2H, m), 3.81 (2H, q, J=5.0 Hz), 3.97 (3H, s), 4.14 (2H, t, J=5.0 Hz), 4.71 (1H, dd, J=5.5, 7.0 Hz), 6.76 (1H, d, J=8.5 Hz), 6.85 (2H, d, J=8.5 Hz), 6.86 (2H, d, J=8.5 Hz), 6.93 (1H, t, J=8.0 Hz), 7.02–7.11 (1H, m), 7.17–7.27 (4H, m), 8.02 (1H, dd, J=2.5, 8.5 Hz), 8.60 (1H, d, J=2.5 Hz).

EXAMPLE 86

Ethyl 3-[4-[2-(biphenyl-4-carbonylamino)ethoxy] phenyl]-2-(4-isopropylphenoxy)propionate (ethyl ester of exemplification No. 7-15 compound)

In a similar manner to that described in Example 73, a reaction was carried out using ethyl 3-[4-(2-t-butoxycarbonylaminoethoxy)phenyl]-2-(4-isopropylphenoxy)propionate (723 mg), which is the product of Reference example 25, biphenyl-4-carboxylic acid (303 mg), diethyl cyanophosphonate (0.25 ml) and triethylamine (0.47 ml) and the reaction mixture was treated to give the title compound (630 mg) as a yellow oil.

$^1$H-NMR (270 MHz, CDCl$_3$): δ ppm 1.18 (6H, d, J=7.0 Hz), 1.21 (3H, t, J=7.0 Hz), 2.82 (1H, septet, J=7.0 Hz), 3.15–3.20 (2H, m), 3.89 (2H, q, J=5.0 Hz), 4.15 (2H, t, J=5.0 Hz), 4.20 (2H, q, J=7.0 Hz), 4.69 (1H, dd, J=5.5, 7.5 Hz), 6.64 (1H, t, J=5.0 Hz), 6.76 (2H, d, J=8.5 Hz), 6.86 (2H, d, J=8.5 Hz), 7.08 (2H, d, J=8.5 Hz), 7.24 (2H, d, J=8.5 Hz), 7.35–7.51 (3H, m), 7.59–7.63 (2H, m), 7.66 (2H, d, J=8.5 Hz), 7.86 (2H, d, J=8.5 Hz).

EXAMPLE 87

3-[4-[2-(Biphenyl-4-carbonylamino)ethoxy]phenyl]-2-(4-isopropylphenoxy)propionic acid (exemplification No. 7-15 compound)

In a similar manner to that described in Example 2, ethyl 3-[4-[2-(biphenyl-4-carbonylamino)ethoxy]phenyl]-2-(4-isopropylphenoxy)propionate (630 mg), which is the product of Example 86, was reacted with aqueous sodium hydroxide solution (1N, 2.00 ml) and the reaction mixture was treated to give the title compound (510 mg) as a white powder.

mp 172–173° C.

$^1$H-NMR (270 MHz, CD$_3$Cl): δ ppm 1.18 (6H, d, J=7.0 Hz), 2.82 (1H, septet, J=7.0 Hz), 3.21 (2H, d, J=6.0 Hz), 3.86 (2H, q, J=5.0 Hz), 4.12 (2H, t, J=5.0 Hz), 4.78 (1H, t, J=6.0 Hz), 6.68 (1H, t, J=5.0 Hz), 6.79 (2H, d, J=8.5 Hz), 6.85 (2H, d, J=8.5 Hz), 7.10 (2H, d, J=8.5 Hz), 7.23 (2H, d, J=8.5 Hz), 7.35–7.49 (3H, m), 7.57–7.62 (2H, m), 7.65 (2H, d, J=8.5 Hz), 7.85 (2H, d, J=8.5 Hz).

EXAMPLE 88

Ethyl 2-(4-isopropylphenoxy)-3-[4-[2-(4'-methoxybiphenyl-4-carbonylamino)ethoxy]phenyl] propionate (ethyl ester of exemplification No. 7-179 compound)

In a similar manner to that described in Example 73, a reaction was carried out using ethyl 3-[4-(2-t-butoxycarbonylaminoethoxy)phenyl]-2-(4-isopropylphenoxy)propionate (723 mg), which is the product of Reference example 25, 4'-methoxybiphenyl-4-carboxylic acid (350 mg), diethyl cyanophosphonate (0.25 ml) and triethylamine (0.47 ml) and the reaction mixture was treated to give the title compound (600 mg) as a white powder.

mp 116–117° C.

$^1$H-NMR (270 MHz, CDCl$_3$): δ ppm 1.18 (6H, d, J=7.0 Hz), 1.20 (3H, t, J=7.0 Hz), 2.82 (1H, septet, J=7.0 Hz), 3.15–3.21 (2H, m), 3.86 (3H, s), 3.86–3.91 (2H, m), 4.14 (2H, t, J=5.0 Hz), 4.18 (2H, q, J=7.0 Hz), 4.69 (1H, dd, J=6.0, 7.0 Hz), 6.62 (1H, t, J=5.0 Hz), 6.76 (2H, d, J=8.5 Hz), 6.86 (2H, d, J=8.5 Hz), 6.99 (2H, d, J=8.5 Hz), 7.08 (2H, d, J=8.5 Hz), 7.23 (2H, d, J=8.5 Hz), 7.55 (2H, d, J=8.5 Hz), 7.61 (2H, d, J=8.0 Hz), 7.83 (2H, d, J=8.0 Hz).

EXAMPLE 89

2-(4-Isopropylphenoxy)-3-[4-[2-(4'-methoxybiphenyl-4-carbonylamino)ethoxy]phenyl] propionic acid (exemplification No. 7-179 compound)

In a similar manner to that described in Example 2, ethyl 2-(4-isopropylphenoxy)-3-[4-[2-(4'-methoxybiphenyl-4-carbonylamino)ethoxy]phenyl]propionate (580 mg), which is the product of Example 88, was reacted with aqueous sodium hydroxide solution (1N, 2.00 ml) and the reaction mixture was treated to give the title compound (450 mg) as a white powder.

mp 159–160° C.

$^1$H-NMR (270 MHz, CD$_3$Cl): δ ppm 1.18 (6H, d, J=6.5 Hz), 2.77–2.80 (1H, m), 3.18–3.27 (2H, m), 3.80–3.90 (5H, m), 4.10–4.18 (2H, m), 4.76–4.82 (1H, m), 6.67–6.70 (1H, m), 6.78 (2H, d, J=8.0 Hz), 6.84 (2H, d, J=8.0 Hz), 6.98 (2H, d, J=8.0 Hz), 7.09 (2H, d, J=8.0 Hz), 7.22 (2H, d, J=8.0 Hz), 7.54 (2H, d, J=8.0 Hz), 7.59 (2H, d, J=8.0 Hz), 7.81 (2H, d, J=8.0 Hz).

EXAMPLE 90

Ethyl 3-[4-[2-(4'-fluorobiphenyl-4-carbonylamino) ethoxy]phenyl]-2-(4-isopropylphenoxy)propionate (ethyl ester of exemplification No. 7-190 compound)

In a similar manner to that described in Example 73, a reaction was carried out using ethyl 3-[4-(2-t-butoxycarbonylaminoethoxy)phenyl]-2-(4-isopropylphenoxy)propionate (723 mg), which is the product of Reference example 25, 4'-fluorobiphenyl-4-carboxylic acid (331 mg), diethyl cyanophosphonate (0.25 ml) and triethylamine (0.47 ml) and the reaction mixture was treated to give the title compound (460 mg) as a colorless oil.

$^1$H-NMR (270 MHz, CDCl$_3$): δ ppm 1.18 (6H, d, J=7.0 Hz), 1.20 (3H, t, J=7.0 Hz), 2.82 (1H, septet, J=7.0 Hz), 3.12–3.18 (2H, m), 3.88 (2H, q, J=5.0 Hz), 4.13 (2H, t, J=5.0 Hz), 4.18 (2H, q, J=7.0 Hz), 4.69 (1H, dd, J=6.0, 7.0 Hz), 6.63 (1H, t, J=5.0 Hz), 6.75 (2H, d, J=8.5 Hz), 6.86 (2H, d, J=8.5 Hz), 7.00–7.29 (6H, m), 7.53–7.60 (2H, m), 7.60 (2H, d, J=8.5 Hz), 7.84 (2H, d, J=8.5 Hz).

EXAMPLE 91

3-[4-[2-(4'-Fluorobiphenyl-4-carbonylamino)ethoxy]phenyl]-2-(4-isopropylphenoxy)propionic acid (exemplification No. 7-190 compound)

In a similar manner to that described in Example 2, ethyl 3-[4-[2-(4'-fluorobiphenyl-4-carbonylamino)ethoxy]phenyl]-2-(4-isopropylphenoxy)propionate (450 mg), which is the product of Example 90, was reacted with aqueous sodium hydroxide solution (1N, 2.00 ml) and the reaction mixture was treated to give the title compound (380 mg) as a white powder.

mp 192–193° C.

$^1$H-NMR (270 MHz, CD$_3$Cl): δ ppm 1.17 (6H, d, J=7.0 Hz), 2.84 (1H, septet, J=7.0 Hz), 3.18 (2H, d, J=6.0 Hz), 3.84 (2H, q, J=5.0 Hz), 4.16 (2H, t, J=5.0 Hz), 4.66 (1H, t, J=6.0 Hz), 6.77 (2H, d, J=8.5 Hz), 6.86 (2H, d, J=8.5 Hz), 7.07 (2H, d, J=8.5 Hz), 7.10–7.19 (2H, m), 7.22–7.33 (3H, m), 7.55–7.62 (4H, m), 7.90 (2H, d, J=8.5 Hz).

EXAMPLE 92

Ethyl 2-(4-isopropylphenoxy)-3-[4-[2-(3'-methoxybiphenyl-4-carbonylamino)ethoxy]phenyl]propionate (ethyl ester of exemplification No. 7-212 compound)

In a similar manner to that described in Example 73, a reaction was carried out using ethyl 3-[4-(2-t-butoxycarbonylaminoethoxy)phenyl]-2-(4-isopropylphenoxy)propionate (723 mg), which is the product of Reference example 25, 3'-methoxybiphenyl-4-carboxylic acid (350 mg), diethyl cyanophosphonate (0.25 ml) and triethylamine (0.47 ml) and the reaction mixture was treated to give the title compound (700 mg) as a pale yellow oil.

$^1$H-NMR (270 MHz, CDCl$_3$): δ ppm 1.22 (6H, d, J=7.0 Hz), 1.24 (3H, t, J=7.0 Hz), 2.85 (1H, septet, J=7.0 Hz), 3.18–3.25 (2H, m), 3.91 (3H, s), 3.92–3.99 (2H, m), 4.12–4.28 (4H, m), 4.73 (1H, dd, J=6.0, 7.0 Hz), 6.62–6.70 (1H, m), 6.79 (2H, d, J=8.5 Hz), 6.90 (2H, d, J=8.5 Hz), 6.97 (1H, dd, J=2.5, 8.0 Hz), 7.12 (2H, d, J=8.5 Hz), 7.17 (1H, d, J=2.5 Hz), 7.20–7.30 (3H, m), 7.41 (1H, t, J=8.0 Hz), 7.69 (2H, d, J=8.5 Hz), 7.88 (2H, d, J=8.5 Hz).

EXAMPLE 93

2-(4-Isopropylphenoxy)-3-[4-[2-(3'-methoxybiphenyl-4-carbonylamino)ethoxy]phenyl]propionic acid (exemplification No. 7-212 compound)

In a similar manner to that described in Example 2, ethyl 2-(4-isopropylphenoxy)-3-[4-[2-(3'-methoxybiphenyl-4-carbonylamino)ethoxy]phenyl]propionate (700 mg), which is the product of Example 92, was reacted with aqueous sodium hydroxide solution (1N, 3.00 ml) and the reaction mixture was treated to give the title compound (310 mg) as a white powder.

mp 138–139° C.

$^1$H-NMR (270 MHz, CD$_3$Cl): δ ppm 1.24 (6H, d, J=7.0 Hz), 2.89 (1H, septet, J=7.0 Hz), 3.27 (2H, d, J=6.0 Hz), 3.93 (3H, s), 3.84–3.96 (2H, m), 4.18 (2H, t, J=5.0 Hz), 4.85 (1H, t, J=6.0 Hz), 6.74 (1H, t, J=5.0 Hz), 6.85 (2H, d, J=8.5 Hz), 6.91 (2H, d, J=8.5 Hz), 6.99 (1H, dd, J=2.5, 8.0 Hz), 7.16 (2H, d, J=8.5 Hz), 7.20–7.27 (2H, m), 7.29 (2H, d, J=8.5 Hz), 7.44 (1H, t, J=8.0 Hz), 7.70 (2H, d, J=8.0 Hz), 7.90 (2H, d, J=8.0 Hz).

EXAMPLE 94

Ethyl 2-(4-isopropylphenoxy)-3-[4-[2-(2'-methoxybiphenyl-4-carbonylamino)ethoxy]phenyl]propionate (ethyl ester of exemplification No. 7-219 compound)

In a similar manner to that described in Example 73, a reaction was carried out using ethyl 3-[4-(2-t-butoxycarbonylaminoethoxy)phenyl]-2-(4-isopropylphenoxy)propionate (723 mg), which is the product of Reference example 25, 2'-methoxybiphenyl-4-carboxylic acid (350 mg), diethyl cyanophosphonate (0.25 ml) and triethylamine (0.47 ml) and the reaction mixture was treated to give the title compound (710 mg) as a colorless oil.

$^1$H-NMR (270 MHz, CDCl$_3$): δ ppm 1.18 (6H, d, J=7.0 Hz), 1.20 (3H, t, J=7.0 Hz), 2.82 (1H, septet, J=7.0 Hz), 3.15–3.20 (2H, m), 3.81 (3H, s), 3.88 (2H, q, J=5.0 Hz), 4.14 (2H, t, J=5.0 Hz), 4.18 (2H, q, J=7.0 Hz), 4.66–4.72 (1H, m), 6.62 (1H, t, J=5.0 Hz), 6.76 (2H, d, J=8.5 Hz), 6.86 (2H, d, J=8.5 Hz), 6.98–7.10 (4H, m), 7.21–7.38 (4H, m), 7.60 (2H, d, J=8.0 Hz), 7.81 (2H, d, J=8.0 Hz).

EXAMPLE 95

Sodium 2-(4-isopropylphenoxy)-3-[4-[2-(2'-methoxybiphenyl-4-carbonylamino)ethoxy]phenyl]propionate (exemplification No. 7-219 compound)

In a similar manner to that described in Example 2, ethyl 2-(4-isopropylphenoxy)-3-[4-[2-(2'-methoxybiphenyl-4-carbonylamino)ethoxy]phenyl]propionate (700 mg), which is the product of Example 94, was reacted with aqueous sodium hydroxide solution (1N, 3.60 ml) and the reaction mixture was treated to give the title compound (528 mg) as a white powder.

mp 205–208° C.

$^1$H-NMR of free acid (270 MHz, CD$_3$Cl): δ ppm 1.18 (6H, d, J=7.0 Hz), 2.82 (1H, septet, J=7.0 Hz), 3.21 (2H, d, J=6.5 Hz), 3.80 (3H, s), 3.86 (2H, q, J=5.0 Hz), 4.12 (2H, t, J=5.0 Hz), 4.78 (1H, t, J=6.5 Hz), 6.66 (1H, t, J=5.0 Hz), 6.78 (2H, d, J=8.5 Hz), 6.84 (2H, d, J=8.5 Hz), 6.97–7.07 (2H, m), 7.10 (2H, d, J=8.5 Hz), 7.22 (2H, d, J=8.5 Hz), 7.28–7.37 (2H, m), 7.59 (2H, d, J=8.5 Hz), 7.80 (2H, d, J=8.5 Hz).

EXAMPLE 96

Ethyl 2-(4-isopropylphenoxy)-3-[4-[2-(2-phenylpyridine-5-carbonylamino)ethoxy]phenyl]propionate (ethyl ester of exemplification No. 7-95 compound)

In a similar manner to that described in Example 5, a reaction was carried out using ethyl 3-[4-(2-aminoethoxy)phenyl]-2-(4-isopropylphenoxy)propionate (743 mg), which is the product of Reference example 5, 6-phenylnicotinic acid (438 mg) and carbonyldiimidazole (357 mg) and the reaction mixture was treated to give the title compound (196 mg) as colorless crystals.

mp 113–114° C.

$^1$H-NMR (270 MHz, CDCl$_3$): δ ppm 1.10–1.23 (9H, m), 2.72–2.88 (1H, m), 3.12–3.19 (2H, m), 3.82–3.93 (2H, m), 4.10–4.23 (4H, m), 4.69 (1H, dd, J=5.5, 7.5 Hz), 6.61–6.69 (1H, m), 6.75 (2H, d, J=8.5 Hz), 6.86 (2H, d, J=8.5 Hz), 7.08 (2H, d, J=8.5 Hz), 7.24 (2H, d, J=8.5 Hz), 7.41–7.53 (3H, m), 7.81 (1H, d, J=8.5 Hz), 8.00–8.08 (2H, m), 8.12–8.20 (1H,m), 9.01–9.39 (1H, m).

EXAMPLE 97

2-(4-Isopropylphenoxy)-3-[4-[2-(2-phenylpyridine-5-carbonylamino)ethoxy]phenyl]propionic acid (exemplification No. 7-95 compound)

In a similar manner to that described in Example 2, ethyl 2-(4-isopropylphenoxy)-3-[4-[2-(2-phenylpyridine-5-carbonylamino)ethoxy]phenyl]propionate (169 mg), which is the product of Example 96, was reacted with aqueous sodium hydroxide solution (1N, 0.60 ml) and the reaction mixture was treated to give the title compound (126 mg) as colorless crystals.

mp 174–176° C.

$^1$H-NMR (270 MHz, CD$_3$Cl): δ ppm 1.19 (6H, d, J=7.0 Hz), 2.79–2.90 (1H, m), 3.27 (2H, d, J=5.5 Hz), 3.71–3.88 (1H, m), 3.88–4.01 (1H, m), 4.28–4.40 (2H, m), 4.94 (1H, t, J=5.5 Hz), 6.50–6.59 (1H, m), 6.84 (2H, d, J=8.5 Hz), 6.95 (2H, d, J=8.5 Hz), 7.11 (2H, d, J=8.5 Hz), 7.30 (2H, d, J=8.5 Hz), 7.42–7.49 (3H, m), 7.75–7.81 (1H, m), 7.85–7.92 (2H,m), 8.25–8.31 (2H, m).

EXAMPLE 98

Ethyl 2-(4-isopropylphenoxy)-3-[4-[2-(2-(4-methoxyphenyl)-pyridine-5-carbonylamino)ethoxy] phenyl]propionate (ethyl ester of exemplification No. 7-233 compound)

In a similar manner to that described in Example 5, a reaction was carried out using ethyl 3-[4-(2-aminoethoxy) phenyl]-2-(4-isopropylphenoxy)propionate (743 mg), which is the product of Reference example 5, 6-(4-methoxyphenyl) nicotinic acid (504 mg) which is the product of Rreference example 26, and carbonyldiimidazole (357 mg) and the reaction mixture was treated to give the title compound (182 mg) as colorless crystals.

mp 100–101° C.

$^1$H-NMR (270 MHz, CDCl$_3$): δ ppm 1.13–1.23 (9H, m), 2.74–2.89 (1H, m), 3.12–3.19 (2H, m), 3.88 (3H, s), 3.86–3.93 (2H, m), 4.11–4.23 (4H, m), 4.69 (1H, dd, J=5.5, 7.5 Hz), 6.59–6.65 (1H, m), 6.75 (2H, d, J=8.5 Hz), 6.85 (2H, d, J=8.5 Hz), 7.01 (2H, d, J=8.5 Hz), 7.08 (2H, d, J=8.5 Hz), 7.24 (2H, d, J=8.5 Hz), 7.74 (1H, d, J=8.5 Hz), 8.00 (2H, d, J=8.5 Hz), 8.13 (1H, dd, J=2.0, 8.5 Hz), 9.01 (1H, d, J=2.0 Hz).

EXAMPLE 99

2-(4-Isopropylphenoxy)-3-[4-[2-[2-(4-methoxyphenyl)pyridine-5-carbonylamino]ethoxy] phenyl]propionic acid (exemplification No. 7-233 compound)

In a similar manner to that described in Example 2, ethyl 2-(4-isopropylphenoxy)-3-[4-[2-[2-(4-methoxyphenyl) pyridine-5-carbonylamino]ethoxy]phenyl]propionate (170 mg), which is the product of Example 98, was reacted with aqueous sodium hydroxide solution (1N, 0.58 ml) and the reaction mixture was treated to give the title compound (153 mg) as colorless crystals.

mp 166–167° C.

$^1$H-NMR (270 MHz, CD$_3$Cl): δ ppm 1.20 (6H, d, J=7.0 Hz), 2.78–2.90 (1H, m), 3.27 (2H, d, J=5.5 Hz), 3.86 (3H, s), 3.70–4.01 (2H, m), 4.29–4.39 (2H, m), 4.95 (1H, t, J=5.5 Hz), 6.43–6.51 (1H, m), 6.84 (2H, d, J=8.5 Hz), 6.90–7.00 (4H, m), 7.12 (2H, d, J=8.5 Hz), 7.30 (2H, d, J=8.5 Hz), 7.73 (1H, d, J=8.5 Hz), 7.80–7.88 (2H, m), 8.19 (1H, d, J=2.5 Hz), 8.27 (1H, dd, J=2.5, 8.5 Hz).

EXAMPLE 100

Ethyl 3-[4-[2-[2-(4-fluorophenyl)pyridine-5-carbonylamino]ethoxy]phenyl]-2-(4-isopropylphenoxy)propionate (ethyl ester of exemplification No. 7-231 compound)

In a similar manner to that described in Example 73, a reaction was carried out using ethyl 3-[4-(2-t-butoxycarbonylaminoethoxy)phenyl]-2-(4-isopropylphenoxy)propionate (718 mg), which is the product of Reference example 25, 6-(4-fluorophenyl)nicotinic acid (330 mg), which is the product of Reference example 27, diethyl cyanophosphonate (0.25 ml) and triethylamine (0.47 ml) and the reaction mixture was treated to give the title compound (560 mg) as a white powder.

mp 117–118° C.

$^1$H-NMR (270 MHz, CDCl$_3$): δ ppm 1.18 (6H, d, J=7.0 Hz), 1.21 (3H, t, J=7.0 Hz), 2.82 (1H, septet, J=7.0 Hz), 3.15–3.20 (2H, m), 3.90 (2H, q, J=5.0 Hz), 4.13–422 (4H, m), 4.69 (1H, dd, J=5.5, 7.0 Hz), 6.66 (1H, t, J=5.0 Hz), 6.75 (2H, d, J=8.5 Hz), 6.86 (2H, d, J=8.5 Hz), 7.08 (2H, d, J=8.5 Hz), 7.14–7.25 (4H, m), 7.76 (1H, d, J=8.5 Hz), 8.00–8.07 (2H, m), 8.16 (1H, dd, J=2.0, 8.5 Hz), 9.03 (1H, d, J=2.0 Hz).

EXAMPLE 101

3-[4-[2-[2-(4-Fluorophenyl)pyridine-5-carbonylamino]ethoxy]phenyl]-2-(4-isopropylphenoxy)propionic acid (exemplification No.7-231 compound)

In a similar manner to that described in Example 2, ethyl 3-[4-[2-[2-(4-fluorophenyl)pyridine-5-carbonylamino] ethoxy]-phenyl]-2-(4-isopropylphenoxy)propionate (540 mg), which is the product of Example 100, was reacted with aqueous sodium hydroxide solution (1N, 3.00 ml) and the reaction mixture was treated to give the title compound (495 mg) as a white powder.

mp 199–200° C.

$^1$H-NMR (270 MHz, CD$_3$Cl): δ ppm 1.20 (6H, d, J=7.0 Hz), 2.84 (1H, septet, J=7.0 Hz), 3.20–3.23 (2H, m), 3.86 (2H, q, J=5.5 Hz), 4.21 (2H, t, J=5.5 Hz), 4.70 (1H, dd, J=5.5, 7.0 Hz), 6.80 (2H, d, J=8.5 Hz), 6.89 (2H, d, J=8.5 Hz), 7.10 (2H, d, J=8.5 Hz), 7.13–7.30 (4H, m), 7.79 (1H, d, J=8.5 Hz), 7.92 (1H, t, J=5.5 Hz), 8.03–8.09 (2H, m), 8.25 (1H, dd, J=2.0, 8.5 Hz), 9.12 (1H, d, J=2.0 Hz).

EXAMPLE 102

Ethyl 3-[4-[2-[2-(2,2,3,3,-tetrafluoropropoxy) pyridine-5-carbonylamino]ethoxy]phenyl]-2-(4-isopropylphenoxy)propionate (ethyl ester of exemplification No. 7-236 compound)

In a similar manner to that described in Example 5, a reaction was carried out using ethyl 3-[4-(2-aminoethoxy) phenyl]-2-(4-isopropylphenoxy)propionate (500 mg), which is the product of Reference example 5, 6-(2,2,3,3- tetrafluoropropoxy)nicotinic acid (375 mg), which is the product of Reference example 28, and carbonyldiimidazole (240 mg) and the reaction mixture was treated to give the title compound (137 mg) as a colorless oil.

$^1$H-NMR (270 MHz, CDCl$_3$): δ ppm 1.11–1.28 (9H, m), 2.82 (1H, septet, J=7.0 Hz), 3.10–3.20 (2H, m), 3.83 (2H, q, J=7.0 Hz), 4.08–4.25 (4H, m), 4.68–4.87 (3H, m), 5.99 (1H, tt, J=4.5, 53 Hz), 6.63–6.89 (6H, m), 7.08 (2H, d, J=8.5 Hz), 7.22 (2H, d, J=8.5 Hz), 8.05 (1H, dd, J=2.5, 8.5 Hz), 8.58 (1H, d, J=2.5 Hz).

EXAMPLE 103

Sodium 3-[4-[2-[2-(2,2,3,3-tetrafluoropropoxy)pyridine-5-carbonylamino]ethoxy]phenyl]-2-(4-isopropylphenoxy)propionate (exemplification No. 7-236 compound)

In a similar manner to that described in Example 2, ethyl 3-[4-[2-[2-(2,2,3,3-tetrafluoropropoxy)pyridine-5-carbonylamino]ethoxy]phenyl]-2-(4-isopropylphenoxy)propionate (73 mg), which is the product of Example 102, was reacted with aqueous sodium hydroxide solution (1N, 0.13 ml) and the reaction mixture was treated to give the title compound (51 mg) as colorless crystals.

mp 204–207° C.

$^1$H-NMR (270 MHz, deuterated methanol): δ ppm 1.11–1.21 (6H, m), 2.77 (1H, septet, J=7.0 Hz), 2.99–3.17 (2H, m), 3.73 (2H, t, J=5.5 Hz), 4.12 (2H, t, J=5.5 Hz), 4.78–4.90 (3H, m), 6.30 (1H, tt, J=5.0, 53 Hz), 6.74 (2H, d, J=8.5 Hz), 6.85 (2H, d, J=8.5 Hz), 6.93 (1H, d, J=8.5 Hz), 7.01 (2H, d, J=8.5 Hz), 7.25 (2H, d, J=8.5 Hz), 8.13 (1H, dd, J=2.5, 8.5 Hz), 8.64 (1H, d, J=2.5 Hz).

EXAMPLE 104

(S)-2-(4-Isopropylphenoxy)-3-[4-[2-(4-pyridine-2-ylbenzoylamino)ethoxy]phenyl]propionic acid (an optically active compound of exemplification No. 7-35 compound)

A tetrahydrofuran solution of tetrabutylammonium fluoride (1M, 2.25 ml) was added to a solution of 2-trimethylsilylethyl (S)-2-(4-isopropylphenoxy)-3-[4-[2-(4-pyridine-2-ylbenzoylamino)ethoxy]phenyl]propionate (562 mg), which is the product of Reference example 29, in tetrahydrofuran (4.0 ml) at ambient temperature. After the mixture was stirred for 1 hour, the reaction mixture was concentrated under reduced pressure. The residue was partitioned between ethyl acetate and water. The ethyl acetate layer was washed with aqueous hydrochloric acid solution (0.5 N) and saturated aqueous sodium chloride solution and dried over anhydrous magnesium sulfate and then concentrated under reduced pressure.

The residue was purified via chromatography on a thin layer plate using dichloromethane/methanol=5/1 as the eluant. The product was crystallized from diisopropyl ether to give the title compound (278 mg) as colorless crystals.

mp 100–101° C.

[α]$_D^{25}$+13.9° (c=0.9, chloroform)

$^1$H-NMR (400 MHz, CDCl$_3$): δ ppm 1.11 (6H, d, J=7.0 Hz), 2.74 (1H, septet, J=7.0 Hz), 3.02–3.16 (2H, m), 3.73–3.82 (2H, m), 3.98–4.07 (2H, m), 4.63–4.74 (1H, m), 6.69–6.80 (4H, m), 6.95–7.01 (3H, m), 7.11 (2H, d, J=8.0 Hz), 7.25–7.31(1H, m), 7.68 (1H, d, J=8.0 Hz), 7.72–7.85 (3H, m), 7.93 (2H, d, J=8.0 Hz), 8.69 (1H, d, J=4.5 Hz).

EXAMPLE 105

(R)-2-(4-Isopropylphenoxy)-3-[4-[2-(4-pyridine-2-ylbenzoylmino)ethoxy]phenyl]propionic acid (an optical active compound of exemplification No. 7-35 compound)

In a similar manner to that described in Example 104, a reaction was carried out using 2-trimethylsilylethyl (R)-2-(4-isopropylphenoxy)-3-[4-[2-(4-pyridine-2-ylbenzoylamino)ethoxy]phenyl]propionate (270 mg), which is the product of Reference example 30 and tetrabutylammonium fluoride in tetrahydrofuran (1M, 1.08 ml) and the reaction mixture was treated to give the title compound (117 mg) as colorless crystals.

mp 95–96° C.

[α]$_D^{25}$–10.5° (c=1.5, chloroform)

$^1$H-NMR (400 MHz, CDCl$_3$): δ ppm 1.11 (6H, d, J=7.0 Hz), 2.73 (1H, septet, J=7.0 Hz), 3.02–3.16 (2H, m), 3.73–3.82 (2H, m), 3.98–4.07 (2H, m), 4.63–4.74 (1H, m), 6.69–6.80 (4H, m), 6.95–7.02 (3H, m), 7.12 (2H, d, J=8.0 Hz), 7.25–7.31(1H, m), 7.65 (1H, d, J=8.0 Hz), 7.72–7.83 (3H, m), 7.88 (2H, d, J=8.0 Hz), 8.70 (1H, d, J=4.5 Hz).

EXAMPLE 106

Ethyl 2-(4-isopropylphenoxy)-3-[4-[2-[4-(3-trifluoromethylpyridine-6-yl)benzoylamino]ethoxy]phenyl]propionate (ethyl ester of exemplification No. 7-227 compound)

One drop of N,N-dimethylformamide and thionyl chloride (0.75 ml) were added to a solution of 3-trifluoromethylpyridine-6-ylbenzoic acid (546 mg) in toluene (28.0 ml) at ambient temperature. After the mixture was stirred for 4 hours at 85° C., the solvent was distilled off and the thionyl chloride was azeotropically evaporated with toluene to dryness under reduced pressure. Triethylamine (1.23 ml) was added to a solution of the residue obtained above and ethyl 3-[4-(2-aminoethoxy)phenyl]-2-(4-isopropylphenoxy)propionate (201 mg), which is the product of Reference example 5, in dichloromethane (10 ml) in an ice bath. After the mixture was stirred for 30 minutes, the reaction mixture was concentrated. The residue was partitioned between ethyl acetate and water. The ethyl acetate layer was separated and washed with saturated aqueous sodium chloride and dried over anhydrous magnesium sulfate and then evaporated under reduced pressure. The residue was purified via chromatography on a silica gel column using hexane/ethyl acetate=3/2-1/1 as the eluant to give the title compound (570 mg) as a mass of yellow foam.

$^1$H-NMR (270 MHz, CDCl$_3$): δ ppm 1.18 (6H, d, J=7.0 Hz), 1.21 (3H, t, J=7.0 Hz), 2.81 (1H, septet, J=7.0 Hz), 3.17 (2H, d, J=6.5 Hz), 3.90 (2H, q, J=5.0 Hz), 4.14 (2H, t, J=5.0 Hz), 4.18 (2H, t, J=7.0 Hz), 4.70 (1H, t, J=6.5 Hz), 6.67 (1H, brt), 6.75 (2H, d, J=8.5 Hz), 6.86 (2H, d, J=8.5 Hz), 7.07 (2H, d, J=8.5 Hz), 7.24 (2H, d, J=8.5 Hz), 7.88 (1H, d, J=8.5 Hz), 7.91 (2H, d, J=8.5 Hz), 8.01 (1H, d, J=8.5 Hz), 8.12 (2H, d, J=8.5 Hz), 8.99 (1H, s).

EXAMPLE 107

2-(4-isopropylphenoxy)-3-[4-[2-[4-(3-trifluoromethylpyridine-6-yl)benzoylamino]ethoxy]phenyl]propionic acid (exemplification No. 7-227 compound)

In a similar manner to that described in Example 2, ethyl 2-(4-isopropylphenoxy)-3-[4-[2-[4-(3-tuoromethylpyridine-6-yl)benzoylamino]ethoxy]phenyl]propionate (500 mg), which is the product of Example 106, was reacted with aqueous sodium hydroxide solution (1N, 1.60 ml) and the reaction mixture was treated to give the title compound (383 mg) as a white powder.

mp 212–214° C.

$^1$H-NMR (270 MHz, deuterated dimethyl sulfoxide): δ ppm 1.13 (6H, d, J=7.0 Hz), 2.78 (1H, septet, J=7.0 Hz), 3.07 (1H, d, J=7.0 Hz), 3.09 (1H, d, J=5.0 Hz), 3.64 (2H, q, J=5.5 Hz), 4.11 (2H, t, J=5.5 Hz), 4.77 (1H, dd, J=5.0, 7.0 Hz), 6.74 (2H, d, J=8.5 Hz), 6.90 (2H, d, J=8.5 Hz), 7.09 (2H, d, J=8.5 Hz), 7.23 (2H, d, J=8.5 Hz), 8.02 (2H, d, J=8.5 Hz), 8.27 (2H, d, J=8.5 Hz), 8.30–8.36 (2H, m), 8.84 (1H, brt), 9.08 (1H, s).

EXAMPLE 108

Ethyl 2-(4-isopropylphenoxy)-3-[4-[2-[4-(3-nitropyridine-6-yl)benzoylamino]ethoxy]phenyl] propionic acid (ethyl ester of exemplification No. 7-228 compound)

In a similar manner to that described in Example 79, a reaction was carried out using ethyl 3-[4-(2-aminoethoxy) phenyl]-2-(4-isopropylphenoxy)propionate (290 mg), which is the product of Reference example 5, 3-nitropyridine-6-ylbenzoic acid (277 mg), which is the product of Reference example 32, diethyl cyanophosphonate (0.18 ml) and triethylamine (0.29 ml) and the reaction mixture was treated to give the title compound (379 mg) as a syrup.

$^1$H-NMR (270 MHz, CDCl$_3$): δ ppm 1.18 (6H, d, J=7.0 Hz), 1.21 (3H, t, J=7.0 Hz), 2.82 (1H, septet, J=7.0 Hz), 3.17 (1H, d, J=5.0 Hz), 3.18 (1H, d, J=7.5 Hz), 3.90 (2H, q, J=5.0 Hz), 4.06–4.39 (4H, m), 4.69 (1H, dd, J=5.0, 7.5 Hz), 6.68 (1H, brt), 6.75 (2H, d, J=8.5 Hz), 6.86 (2H, d, J=8.5 Hz), 7.13 (2H, d, J=8.5 Hz), 7.24 (2H, d, J=8.5 Hz), 7.93 (2H, d, J=8.5 Hz), 7.95 (1H, d, J=8.5 Hz), 8.17 (2H, d, J=8.5 Hz), 8.56 (1H, dd, J=2.0, 8.5 Hz), 9.51 (1H, d, J=2.0 Hz).

EXAMPLE 109

2-(4-Isopropylphenoxy)-3-[4-[2-[4-(3-nitropyridine-6-yl)benzoylamino]ethoxy]phenyl]propionic acid (exemplification No. 7-228 compound)

In a similar manner to that described in Example 2, ethyl 2-(4-isopropylphenoxy)-3-[4-[2-[4-(3-nitropyridine-6-yl) benzoylamino]ethoxy]phenyl]propionate (397 mg), which is the product of Example 108, was reacted with aqueous sodium hydroxide solution (1N, 1.30 ml) and the reaction mixture was treated to give the title compound (216 mg) as a white powder.

mp 198–199° C.

$^1$H-NMR (270 MHz, deuterated dimethyl sulfoxide): δ ppm 1.13 (6H, d, J=7.0 Hz), 2.79 (1H, septet, J=7.0 Hz), 3.07 (1H, d, J=7.5 Hz), 3.09 (1H, d, J=5.5 Hz), 3.65 (2H, q, J=5.5 Hz), 4.11 (2H, t, J=5.5 Hz), 4.78 (1H, dd, J=5.5, 7.5 Hz), 6.74 (2H, d, J=8.5 Hz), 6.90 (2H, d, J=8.5 Hz), 7.10 (2H, d, J=8.5 Hz), 7.23 (2H, d, J=8.5 Hz), 8.04 (2H, d, J=8.5 Hz), 8.31 (2H, d, J=8.5 Hz), 8.36 (1H, d, J=8.5 Hz), 8.70 (1H, dd, J=2.0, 8.5 Hz), 8.86 (1H, brt), 9.47 (1H, d, J=2.0 Hz).

EXAMPLE 110

Ethyl 2-(4-isopropylphenoxy)-3-[4-[2-[4-(3-methoxypyridine-6-yl)benzoylamino]ethoxy]phenyl] propionate (ethyl ester of exemplification No. 7-222 compound)

In a similar manner to that described in Example 106, a reaction was carried out using ethyl 3-[4-(2-aminoethoxy) phenyl]-2-(4-isopropylphenoxy)propionate (301 mg), which is the product of Reference example 5, 3-methoxypyridine-6-ylbenzoic acid (195 mg) which is the product of Reference example 33, thionyl cloride (0.31 ml) and triethylamine (0.36 ml) and the reaction mixture was treated to give the title compound (199 mg) as a white powder.

mp 118–119° C.

$^1$H-NMR (270 MHz, CDCl$_3$): δ ppm 1.18 (6H, d, J=7.0 Hz), 1.23 (3H, t, J=7.0 Hz), 2.82 (1H, septet, J=7.0 Hz), 3.16 (1H, d, J=5.0 Hz), 3.18 (1H, d, J=7.5 Hz), 3.89 (2H, q, J=5.0 Hz), 3.92 (3H, s), 4.15 (2H, t, J=5.0 Hz), 4.18 (2H, q, J=7.0 Hz), 4.69 (1H, dd, J=5.0, 7.5 Hz), 6.63 (1H, brt), 6.76 (2H, d, J=8.5 Hz), 6.86 (2H, d, J=8.5 Hz), 7.08 (2H, d, J=8.5 Hz), 7.23 (2H, d, J=8.5 Hz), 7.28 (1H, dd, J=3.0, 8.5 Hz), 7.71 (1H, d, J=8.5 Hz), 7.86 (2H, d, J=8.5 Hz), 8.01 (2H, d, J=8.5 Hz), 8.41 (1H, d, J=3.0 Hz).

EXAMPLE 111

2-(4-Isopropylphenoxy)-3-[4-[2-[4-(3-methoxypyridine-6-yl)-benzoylamino]ethoxy] phenyl]propionic acid (exemplification No. 7-222 compound)

In a similar manner to that described in Example 2, ethyl 2-(4-isopropylphenoxy)-3-[4-[2-[4-(3-methoxypyridine-6-yl)benzoylamino]ethoxy]phenyl]propionate (210 mg), which is the product of Example 110, was reacted with aqueous sodium hydroxide solution (1N, 0.72 ml) and the reaction mixture was treated to give the title compound (185 mg) as a white powder.

mp 145–146° C.

$^1$H-NMR (270 MHz, CDCl$_3$): δ ppm 1.19 (6H, d, J=7.0 Hz), 2.83 (1H, septet, J=7.0 Hz), 3.22 (2H, d, J=6.0 Hz), 3.88 (2H, q, J=5.0 Hz), 3.91 (3H, s), 4.20 (2H, t, J=5.0 Hz), 4.82 (1H, t, J=6.0 Hz), 6.65 (1H, brt), 6.83 (2H, d, J=8.5 Hz), 6.86 (2H, d, J=8.5 Hz), 7.11 (2H, d, J=8.5 Hz), 7.21 (2H, d, J=8.5 Hz), 7.32 (1H, dd, J=3.0, 9.0 Hz), 7.67 (1H, d, J=9.0 Hz), 7.75 (2H, d, J=8.5 Hz), 7.88 (2H, d, J=8.5 Hz), 8.41 (1H, d, J=3.0 Hz).

EXAMPLE 112

Ethyl 3-[4-[2-[4-(3-dimethylaminopyridine-6-yl) benzoylamino]ethoxy]phenyl]-2-(4-isopropylphenoxy)propionate (ethyl ester of exemplification No. 7-225 compound)

In a similar manner to that described in Example 106, a reaction was carried out using ethyl 3-[4-(2-aminoethoxy) phenyl]-2-(4-isopropylphenoxy)propionate (370 mg), which is the product of Reference example 5, 3-dimethylaminopyridine-6-ylbenzoic acid (221 mg) which is the product of Reference example 34, thionyl cloride (0.34 ml) and triethylamine (0.51 ml) and the reaction mixture was treated to give the title compound (456 mg) as a mass of foam.

$^1$H-NMR (270 MHz, CDCl$_3$): δ ppm 1.18 (6H, d, J=7.0 Hz), 1.20 (3H, t, J=7.0 Hz), 2.82 (1H, septet, J=7.0 Hz), 3.04 (6H, s), 3.16 (1H, d, J=5.0 Hz), 3.17 (1H, d, J=7.5 Hz), 3.88 (2H, q, J=5.0 Hz), 4.14 (2H, t, J=5.0 Hz), 4.18 (2H, q, J=7.0 Hz), 4.69 (1H, dd, J=5.0, 7.5 Hz), 6.76 (2H, d, J=8.5 Hz), 6.86 (2H, d, J=8.5 Hz), 7.06 (1H, dd, J=2.5, 9.0 Hz), 7.08 (2H, d, J=8.5 Hz), 7.23 (2H, d, J=8.5 Hz), 7.45 (1H, brt), 7.64 (1H, d, J=9.0 Hz), 7.83 (2H, d, J=8.5 Hz), 8.00 (2H, d, J=8.5 Hz), 8.23 (1H, d, J=2.5 Hz).

EXAMPLE 113

3-[4-[2-[4-(3-Dimethylaminopyridine-6-yl) benzoylamino]ethoxy]-phenyl]-2-(4-isopropylphenoxy)propionic acid (exemplification No. 7-225 compound)

In a similar manner to that described in Example 2, ethyl 3-[4-[2-[4-(3-dimethylaminopyridine-6-yl)benzoylamino]

ethoxy]-phenyl]-2-(4-isopropylphenoxy)propionate (429 mg), which is the product of Example 112, was reacted with aqueous sodium hydroxide solution (1N, 1.44 ml) and the reaction mixture was treated to give the title compound (219 mg) as a white powder.

mp 150–151° C.

$^1$H-NMR (270 MHz, CDCl$_3$/deuterated methanol=1/5): δ ppm 1.15 (6H, d, J=7.0 Hz), 2.77 (1H, septet, J=7.0 Hz), 3.04 (6H, s), 3.10 (1H, dd, J=8.5, 14.5 Hz), 3.15 (1H, dd, J=4.5, 14.5 Hz), 3.76 (2H, t, J=5.5 Hz), 4.14 (2H, t, J=5.5 Hz), 4.58 (1H, dd, J=4.5, 8.5 Hz), 6.74 (2H, d, J=8.5 Hz), 6.87 (2H, d, J=8.5 Hz), 7.02 (2H, d, J=8.5 Hz), 7.22 (1H, dd, J=3.0, 9.0 Hz), 7.23 (2H, d, J=8.5 Hz), 7.72 (1H, d, J=9.0 Hz), 7.85–7.95 (4H, m), 8.11 (1H, d, J=3.0 Hz).

EXAMPLE 114

Ethyl 2-(4-methylphenoxy)-3-[4-[2-(4-pyridine-2-ylbenzoylamino)ethoxy]phenyl]propionate (ethyl ester of exemplification No. 14-11 compound)

In a similar manner to that described in Example 73, a reaction was carried out using ethyl 3-[4-(2-t-butoxycarbonylaminoethoxy)phenyl]-2-(4-methylphenoxy)propionate (798 mg), which is the product of Reference example 35, 4-pyridine-2-ylbenzoic acid (365 mg), diethyl cyanophosphonate (0.28 ml) and triethylamine (0.46 ml) and the reaction mixture was treated to give the title compound (680 mg) as a colorless oil.

$^1$H-NMR (270 MHz, CDCl$_3$): δ ppm 1.23 (3H, t, J=7.0 Hz), 2.28 (3H, s), 3.14–3.22 (2H, m), 3.88–3.96 (2H, m), 4.11–4.27 (4H, m), 4.73 (1H, t, J=6.0 Hz), 6.62–6.71 (1H, m), 6.76 (2H, d, J=8.5 Hz), 6.90 (2H, d, J=8.5 Hz), 7.05 (2H, d, J=8.5 Hz), 7.22–7.33 (3H, m), 7.78–7.83 (2H, m), 7.92 (2H, d, J=8.5 Hz), 8.11 (2H, d, J=8.5 Hz), 8.71–8.78 (1H, m).

EXAMPLE 115

2-(4-Methylphenoxy)-3-[4-[2-(4-pyridine-2-ylbenzoylamino)ethoxy]phenyl]propionic acid (exemplification No. 14-11 compound)

In a similar manner to that described in Example 2, ethyl 2-(4-methylphenoxy)-3-[4-[2-(4-pyridine-2-ylbenzoylamino)ethoxy]phenyl]propionate (680 mg), which is the product of Example 114, was reacted with aqueous sodium hydroxide solution (1N, 2.60 ml) and the reaction mixture was treated to give the title compound (570 mg) as a white powder.

mp 129–131° C.

$^1$H-NMR (270 MHz, CDCl$_3$): δ ppm 2.25 (3H, s), 3.21 (2H, d, J=6.0 Hz), 3.81–3.90 (2H, m), 4.15–4.21 (2H, m), 4.80 (1H, t, J=6.0 Hz), 6.68–6.75 (1H, m), 6.79 (2H, d, J=8.5 Hz), 6.85 (2H, d, J=8.5 Hz), 7.03 (2H, d, J=8.5 Hz), 7.21 (2H, d, J=8.5 Hz), 7.29–7.36 (1H, m), 7.70–7.88 (4H, m), 7.92 (2H, d, J=8.5 Hz), 8.69–8.73 (1H, m).

EXAMPLE 116

Ethyl 2-(4-t-butylphenoxy)-3-[4-[2-(4-pyridine-2-ylbenzoylamino)ethoxy]phenyl]propionate (ethyl ester of exemplification No. 138-8 compound)

In a similar manner to that described in Example 73, a reaction was carried out using ethyl 3-[4-(2-t-butoxycarbonylaminoethoxy)phenyl]-2-(4-t-butylphenoxy)propionate (530 mg), which is the product of Reference example 36, 4-pyridine-2-ylbenzoic acid (227 mg), diethyl cyanophosphonate (0.18 ml) and triethylamine (0.33 ml) and the reaction mixture was treated to give the title compound (370 mg) as a mass of foam.

$^1$H-NMR (270 MHz, CDCl$_3$): δ ppm 1.21 (3H, t, J=7.0 Hz), 1.25 (9H, s), 3.15–3.20 (2H, m), 3.89 (2H, q, J=5.0 Hz), 4.10–422 (4H, m), 4.69 (1H, dd, J=5.5, 7.5 Hz), 6.66 (1H, t, J=5.0 Hz), 6.76 (2H, d, J=8.5 Hz), 6.86 (2H, d, J=8.5 Hz), 7.23–7.30 (5H, m), 7.74–7.80 (2H, m), 7.89 (2H, d, J=8.5 Hz), 8.07 (2H, d, J=8.5 Hz), 8.72 (1H, d, J=4.5 Hz).

EXAMPLE 117

2-(4-t-Butylphenoxy)-3-[4-[2-(4-pyridine-2-ylbenzoylamino)ethoxy]phenyl]propionic acid (exemplification No. 138-8 compound)

In a similar manner to that described in Example 2, ethyl 2-(4-t-butylphenoxy)-3-[4-[2-(4-pyridine-2-ylbenzoylamino)ethoxy]phenyl]propionate (360 mg), which is the product of Example 116, was reacted with aqueous sodium hydroxide solution (1N, 2.00 ml) and the reaction mixture was treated to give the title compound (315 mg) as a white powder.

mp 94–96° C.

$^1$H-NMR (270 MHz, CDCl$_3$): δ ppm 1.24 (9H, s), 3.20 (2H, d, J=6.0 Hz), 3.80–3.90 (2H, m), 4.13–420 (2H, m), 4.79 (1H, t, J=6.0 Hz), 6.76 (1H, t, J=5.0 Hz), 6.82 (2H, d, J=8.0 Hz), 6.85 (2H, d, J=8.0 Hz), 7.22 (2H, d, J=8.0 Hz), 7.25 (2H, d, J=8.0 Hz), 7.28–7.35 (1H, m), 7.70–7.90 (4H, m), 7.91 (2H, d, J=8.5 Hz), 8.73 (1H, d, J=4.5 Hz).

EXAMPLE 118

Ethyl 2-(4-fluorophenoxy)-3-[4-[2-(4-pyridine-2-ylbenzoylamino)ethoxy]phenyl]propionate (ethyl ester of exemplification No. 138-56 compound)

In a similar manner to that described in Example 65, a reaction was carried out using ethyl 3-[4-(2-aminoethoxy)phenyl]-2-(4-fluorophenoxy)propionate (2.10 g), which is the product of Reference example 37, 4-pyridine-2-ylbenzoylchloride hydrochloride (1.90 g) and triethylamine (2.20 ml) and the reaction mixture was treated to give the title compound (2.50 g) as a white powder.

mp 116–118° C.

$^1$H-NMR (270 MHz, CDCl$_3$): δ ppm 1.20 (3H, t, J=7.0 Hz), 3.17 (2H, d, J=6.5 Hz), 3.80–3.91 (2H, m), 4.08–4.21 (4H, m), 4.66 (1H, t, J=6.5 Hz), 6.62–6.70 (1H, m), 6.70–6.80 (2H, m), 6.80–6.92 (4H, m), 7.20–7.30 (3H, m), 7.71–7.80 (2H, m), 7.88 (2H, d, J=8.5 Hz), 8.07 (2H, d, J=8.5 Hz), 8.71 (1H, d, J=5.0 Hz).

EXAMPLE 119

2-(4-Fluorophenoxy)-3-[4-[2-(4-pyridine-2-ylbenzoylamino)ethoxy]phenyl]propionic acid (exemplification No. 138-56 compound)

In a similar manner to that described in Example 2, ethyl 2-(4-fluorophenoxy)-3-[4-[2-(4-pyridine-2-ylbenzoylamino)ethoxy]phenyl]propionate (2.45 g), which is the product of Example 118, was reacted with aqueous sodium hydroxide solution (1N, 15.0 ml) and the reaction mixture was treated to give the title compound (2.30 g) as a white powder.

mp 139–140.5° C.

$^1$H-NMR (270 MHz, CDCl$_3$): δ ppm 3.20 (2H, d, J=6.5 Hz), 3.80–3.91 (2H, m), 4.16–4.22 (2H, m), 4.74 (1H, t, J=6.5 Hz), 6.69–6.77 (1H, m), 6.77–6.92 (6H, m), 7.19 (2H, d, J=8.5 Hz), 7.30–7.37 (1H, m), 7.69–7.80 (3H, m), 7.80–7.90 (3H, m), 8.71 (1H, d, J=4.0 Hz).

EXAMPLE 120

Ethyl 2-(4-chlorophenoxy)-3-[4-[2-(4-pyridine-2-ylbenzoylaminoethoxy]phenyl]propionate (ethyl ester of exemplification No. 138-72 compound)

In a similar manner to that described in Example 73, a reaction was carried out using ethyl 3-[4-(2-t-butoxycarbonylaminoethoxy)phenyl]-2-(4-chlorophenoxy) propionate (1.23 g), which is the product of Reference example 38, 4-pyridine-2-ylbenzoic acid (539 mg), diethyl cyanophosphonate (0.41 ml) and triethylamine (0.68 ml) and the reaction mixture was treated to give the title compound (977 mg) as colorless crystals.

mp 134–135° C.

$^1$H-NMR (270 MHz, CDCl$_3$): δ ppm 1.20 (3H, t, J=7.0 Hz), 3.17 (2H, d, J=6.5 Hz), 3.83–3.92 (2H, m), 4.08–4.21 (4H, m), 4.69 (1H, t, J=6.5 Hz), 6.60–6.68 (1H, m), 6.75 (2H, d, J=8.5 Hz), 6.87 (2H, d, J=8.5 Hz), 7.13–7.30 (5H, m), 7.72–7.79 (2H, m), 7.89 (2H, d, J=8.5 Hz), 8.08 (2H, d, J=8.5 Hz), 8.70–8.73 (1H, m).

EXAMPLE 121

2-(4-Chlorophenoxy)-3-[4-[2-(4-pyridine-2-ylbenzoylamino)ethoxy]phenyl]propionic acid (exemplification No. 138-72 compound)

In a similar manner to that described in Example 2, ethyl 2-(4-chlorophenoxy)-3-[4-[2-(4-pyridine-2-ylbenzoylamino)ethoxy]phenyl]propionate (950 mg), which is the product of Example 120, was reacted with aqueous sodium hydroxide solution (1N, 3.49 ml) and the reaction mixture was treated to give the title compound (834 mg) as colorless crystals.

mp 155–156° C.

$^1$H-NMR (270 MHz, CDCl$_3$): δ ppm 3.21 (2H, d, J=6.0 Hz), 3.80–3.90 (2H, m), 4.12–4.22 (2H, m), 4.76 (1H, t, J=6.0 Hz), 6.70–6.88 (5H, m), 7.15 (2H, d, J=8.5 Hz), 7.20 (2H, d, J=8.5 Hz), 7.30–7.38 (1H, m), 7.79–7.90 (6H, m), 8.70–8.74 (1H, m).

EXAMPLE 122

Ethyl 3-[4-[2-(4-pyridine-2-ylbenzoylamino)ethoxy] phenyl]-2-(4-trifluoromethylphenoxy)propionate (ethyl ester of exemplification No. 138-24 compound)

A solution of diethyl azodicarboxylate (40% toluene solution, 0.52 ml) in toluene (3.0 ml) was added dropwise to a solution of ethyl 2-hydroxy-3-[4-[2-(4-pyridine-2-ylbenzoylamino)ethoxy]phenyl]propionate (332 mg), which is the product of Reference example 39, 4-trifluoromethylphenol (186 mg) and triphenylphosphine (300 mg) in toluene (10 ml) at ambient temperature. After the mixture was stirred for 2 hours at ambient temperature, triphenylphosphine (100 mg) and diethyl azodicarboxylate (40% toluene solution, 0.19 ml) were added to the reaction mixture. The mixture was stirred for 18 hours. The reaction mixture was concentrated under reduced pressure. The residue was purified via chromatography on a silica gel column using dichloromethane/ethyl acetate=3/2 as the eluant to give the title compound (283 mg, containing some contaminants) as a white powder.

$^1$H-NMR (270 MHz, CDCl$_3$): δ ppm 1.20 (3H, t, J=7.0 Hz), 3.21 (2H, d, J=6.5 Hz), 3.89 (2H, q, J=5.0 Hz), 4.16 (2H, t, J=5.0 Hz), 4.21 (2H, q, J=7.0 Hz), 4.77 (1H, t, J=6.5 Hz), 6.66 (1H, brt), 6.88 (2H, d, J=8.5 Hz), 6.90 (2H, d, J=8.5 Hz), 7.23 (2H, d, J=8.5 Hz), 7.26–7.34 (1H, m), 7.49 (2H, d, J=8.5 Hz), 7.75–7.83 (2H, m), 7.89 (2H, d, J=8.5 Hz), 8.07 (2H, d, J=8.5 Hz), 8.72 (1H, d, J=5.0 Hz).

EXAMPLE 123

3-[4-[2-(4-Pyridine-2-ylbenzoylamino)ethoxy] phenyl]-2-(4-trifluoromethylphenoxy)propionic acid (exemplification No. 138-24 compound)

In a similar manner to that described in Example 2, ethyl 3-[4-[2-(4-pyridine-2-ylbenzoylamino)ethoxy]phenyl]-2-(4-trifluoromethylphenoxy)propionate (269 mg), which is the product of Example 122, was reacted with aqueous sodium hydroxide solution (1N, 0.55 ml) and the reaction mixture was treated to give the title compound (138 mg) as a white powder.

mp 154–155° C.

$^1$H-NMR (270 MHz, deuterated dimethyl sulfoxide): δ ppm 3.02 (1H, dd, J=5.0, 13.5 Hz), 3.16 (1H, dd, J=2.0, 13.5 Hz), 3.63 (2H, q, J=5.5 Hz), 4.10 (2H, t, J=5.5 Hz), 4.64 (1H, dd, J=2.0, 5.0 Hz), 6.88 (2H, d, J=8.5 Hz), 6.95 (2H, d, J=8.5 Hz), 7.23 (2H, d, J=8.0 Hz), 7.41 (1H, dd, J=6.0, 7.5 Hz), 7.54 (2H, d, J=8.5 Hz), 7.88–7.97 (1H, m), 7.98 (2H, d, J=8.5 Hz), 8.05 (1H, d, J=7.5 Hz), 8.18 (2H, d, J=8.0 Hz), 8.70 (1H, d, J=3.5 Hz), 8.78 (1H, brt).

EXAMPLE 124

Ethyl 2-(4-methoxyphenoxy)-3-[4-[2-(4-pyridine-2-ylbenzoylamino)ethoxy]phenyl]propionate (ethyl ester of exemplification No. 8-35 compound)

In a similar manner to that described in Example 122, a reaction was carried out using ethyl 2-hydroxy-3-[4-[2-(4-pyridine-2-ylbenzoylamino)ethoxy]phenyl]propionate (433 mg), which is the product of Reference example 39, 4-methoxyphenol (247 mg), triphenylphosphine (523 mg) and diethyl azodicarboxylate (40% toluene solution, 0.65 ml) and the reaction mixture was treated to give the title compound (320 mg) as a yellow oil.

$^1$H-NMR (270 MHz, CDCl$_3$): δ ppm 1.20 (3H, t, J=7.0 Hz), 3.17 (2H, d, J=6.5 Hz), 3.72 (3H, s), 3.89 (2H, q, J=5.5 Hz), 4.10–4.21 (4H, m), 4.63 (1H, t, J=6.5 Hz), 6.66 (1H, t, J=5.5 Hz), 6.87 (2H, d, J=8.5 Hz), 7.23 (2H, d, J=8.5 Hz), 7.23–7.30 (1H, m), 7.40–7.70 (4H, m), 7.75–7.80 (2H, m), 7.88 (2H, d, J=8.5 Hz), 8.08 (2H, d, J=8.5 Hz), 8.72 (1H, d, J=4.5 Hz).

EXAMPLE 125

2-(4-Methoxyphenoxy)-3-[4-[2-(4-pyridine-2-ylbenzoylamino)ethoxy]phenyl]propionic acid (exemplification.No. 8-35 compound)

In a similar manner to that described in Example 2, ethyl 2-(4-methoxyphenoxy)-3-[4-[2-(4-pyridine-2-ylbenzoylamino)ethoxy]phenyl]propionate (310 mg), which is the product of Example 124, was reacted with aqueous sodium hydroxide solution (1N, 2.00 ml) and the reaction mixture was treated to give the title compound (150 mg) as a white powder.

mp 67.5–70° C.

$^1$H-NMR (270 MHz, CDCl$_3$): δ ppm 3.20 (2H, d, J=6.0 Hz), 3.73 (3H, s), 3.82–3.92 (2H, m), 4.16–4.25 (2H, m), 4.74 (1H, t, J=6.5 Hz), 6.65–6.90 (7H, m), 7.21 (2H, d, J=8.5 Hz), 7.27–7.37 (1H, m), 7.70–7.89 (4H, m), 7.93 (2H, d, J=8.5 Hz), 8.72 (1H, d, J=5.0 Hz).

EXAMPLE 126

Ethyl 3-[4-[2-(4-pyridine-2-ylbenzoylamino)ethoxy]phenyl]-2-(4-trifluoromethoxy-phenoxy)propionate (ethyl ester of exemplification No. 138-40 compound)

Ethyl 3-[4-(2-t-butoxycarbonylaminoethoxy)phenyl]-2-(4-trifluoromethoxyphenoxy)propionate (2.11 g), which is the product of Reference Example 40, was dissolved in a dioxane solution of hydrogen chloride (4N, 30 ml). The mixture was allowed to stand for 40 minutes at ambient temperature. After, the reaction mixture was concentrated under reduced pressure and the hydrogen chloride was azeotropically evaporated with toluene. The residue, which is ethyl 3-[4-(2-aminoethoxy)phenyl]-2-(4-trifluoromethoxyphenoxy)propionate hydrogen chloride, and 4-pyridine-2-ylbenzoylchloride hydrochloride (1.25 g) were suspended in dichloromethane (70 ml). To this suspension, triethylamine (2.28 ml) was added in an ice bath and the mixture was stirred for 1 hour at the same temperature. The reaction mixture was concentrated under reduced pressure. The residue was partitioned between ethyl acetate and water and the ethyl acetate layer was separated and washed with saturated aqueous sodium chloride solution and dried over anhydrous magnesium sulfate and concentrated under reduced pressure. The residue was purified via chromatograpy on silica gel column using hexane/ethyl acetate=2/3 as the eluant to give the title compound (1.75 g) as colorless crystals.

mp 87–88° C.

$^1$H-NMR (270 MHz, CDCl$_3$): δ ppm 1.17 (3H, t, J=7.0 Hz), 3.18 (2H, d, J=6.5 Hz), 3.89 (2H, q, J=5.0 Hz), 4.10–4.25 (4H, m), 4.70 (1H, t, J=6.5 Hz), 6.65 (1H, brt), 6.81 (2H, d, J=8.5 Hz), 6.88 (2H, d, J=8.5 Hz), 7.08 (2H, d, J=8.5 Hz), 7.14–7.31 (1H, m), 7.23 (2H, d, J=8.5 Hz), 7.72–7.82 (2H, m), 7.89 (2H, d, J=8.5 Hz), 8.07 (2H, d, J=8.5 Hz), 8.72 (1H, d, J=4.5 Hz).

EXAMPLE 127

3-[4-[2-(4-Pyridine-2-ylbenzoylamino)ethoxy]phenyl]-2-(4-trifluoromethoxyphenoxy)propionic acid (exemplification No.138-40 compound)

In a similar manner to that described in Example 2, ethyl 3-[4-[2-(4-pyridine-2-ylbenzoylamino)ethoxy]phenyl]-2-(4-trifluoromethoxyphenoxy)propionate (1.65 g), which is the product of Example 126, was reacted with aqueous sodium hydroxide solution (1N, 5.54 ml) and the reaction mixture was treated to give the title compound (1.33 g) as colorless crystals.

mp 180–181° C.

$^1$H-NMR (270 MHz, deuterated methanol): δ ppm 3.16 (1H, dd, J=8.0, 14.5 Hz), 3.22 (1H, dd, J=4.5, 14.5 Hz), 3.78 (2H, q, J=5.5 Hz), 4.16 (2H, t, J=5.5 Hz), 4.83 (1H, dd, J=4.5, 8.0 Hz), 6.89 (2H, d, J=8.5 Hz), 6.91 (2H, d, J=8.5 Hz), 7.13 (2H, d, J=8.5 Hz), 7.24 (1H, d, J=8.5 Hz), 7.36–7.45 (1H, m), 7.88–7.99 (2H, m), 7.94 (2H, d, J=8.5 Hz), 8.05 (2H, d, J=8.5 Hz), 8.64 (1H, d, J=5.0 Hz), 8.77 (1H, brt).

EXAMPLE 128

Ethyl 2-(4-cyanophenoxy)-3-[4-[2-(4-pyridine-2-ylbenzoylamino)ethoxy]phenyl]propionate (ethyl ester of exemplification No. 138-104 compound)

In a similar manner to that described in Example 126, a reaction was carried out using ethyl 3-[4-(2-t-butoxycarbonylaminoethoxy)phenyl]-2-(4-cyanophenoxy)propionate (237 mg), which is the product of Reference Example 41, 4-pyridine-2-ylbenzoylchloride hydrochloride (131 mg) and triethylamine (0.29 ml) and the reaction mixture was treated to give the title compound (244 mg) as a syrup.

$^1$H-NMR (270 MHz, CDCl$_3$): δ ppm 1.20 (3H, t, J=7.0 Hz), 3.21 (2H, d, J=6.5 Hz), 3.89 (2H, q, J=5.0 Hz), 4.16 (2H, t, J=5.0 Hz), 4.19 (2H, q, J=7.0 Hz), 4.79 (1H, t, J=6.5 Hz), 6.65 (1H, brt), 6.88 (2H, d, J=8.5 Hz), 7.21 (2H, d, J=8.5 Hz), 7.24–7.31 (1H, m), 7.54 (2H, d, J=8.5 Hz), 7.70–7.84 (2H, m), 7.88 (2H, d, J=8.5 Hz), 8.07 (2H, d, J=8.5 Hz), 8.72 (1H, d, J=5.0 Hz).

EXAMPLE 129

2-(4-Cyanophenoxy)-3-[4-[2-(4-pyridine-2-ylbenzoylamino)ethoxy]phenyl]propionic acid (exemplification No. 138-104 compound)

In a similar manner to that described in Example 2, ethyl 2-(4-cyanophenoxy)-3-[4-[2-(4-pyridine-2-ylbenzoylamino)ethoxy]phenyl]propionate (244 mg), which is the product of Example 128, was reacted with aqueous sodium hydroxide solution (1N, 0.92 ml) and the reaction mixture was treated to give the title compound (184 mg) as colorless crystals.

mp 92–93° C.

$^1$H-NMR (270 MHz, deuterated methanol): δ ppm 3.24 (2H, d, J=6.0 Hz), 3.86 (2H, q, J=5.5 Hz), 4.15–4.25 (2H, m), 4.85 (1H, t, J=6.0 Hz), 6.76 (1H, brt), 6.85 (2H, d, J=8.0 Hz), 6.91 (2H, d, J=8.5 Hz), 7.20 (2H, d, J=8.5 Hz), 7.37 (1H, dd, J=5.0, 6.0 Hz), 7.48 (2H, d, J=7.5 Hz), 7.73 (3H, d, J=8.0 Hz), 7.84 (2H, d, J=7.5 Hz), 7.87 (1H, dd, J=6.0, 8.0 Hz), 8.71 (1H, d, J=5.0 Hz).

EXAMPLE 130

Methyl 2-(4-methylthiophenoxy)-3-[4-[2-(4-pyridine-2-ylbenzoylamino)ethoxy]phenyl]propionate (methyl ester of exemplification No. 138-120 compound)

In a similar manner to that described in Example 126, a reaction was carried out using methyl 3-[4-(2-t-butoxycarbonylaminoethoxy)phenyl]-2-(4-methylthiophenoxy)propionate (265 mg), which is the product of Reference Example 42, 4-pyridine-2-ylbenzoylchloride hydrochloride (175 mg) and triethylamine (0.32 ml) and the reaction mixture was treated to give the title compound (164 mg) as colorless crystals.

mp 94–95° C.

$^1$H-NMR (270 MHz, CDCl$_3$): δ ppm 2.41 (3H, s), 3.17 (2H, d, J=6.5 Hz), 3.71 (3H, s), 3.89 (2H, q, J=5.0 Hz), 4.16 (2H, t, J=5.0 Hz), 4.72 (1H, t, J=6.5 Hz), 6.66 (1H, brt), 6.77 (2H, d, J=8.5 Hz), 6.87 (2H, d, J=8.5 Hz), 7.18 (2H, d, J=8.5 Hz), 7.21 (2H, d, J=8.0 Hz), 7.23–7.30 (1H, m), 7.73–7.84 (2H, m), 7.88 (2H, d, J=8.0 Hz), 8.07 (2H, d, J=8.5 Hz), 8.72 (1H, d, J=4.5 Hz).

EXAMPLE 131

2-(4-Methylthiophenoxy)-3-[4-[2-(4-pyridine-2-ylbenzoylamino)ethoxy]phenyl]propionic acid (exemplification No. 138-120 compound)

In a similar manner to that described in Example 2, methyl 2-(4-methylthiophenoxy)-3-[4-[2-(4-pyridine-2- ylbenzoylamino)ethoxy]phenyl]propionate (203 mg), which is the product of Example 130, was reacted with aqueous sodium hydroxide solution (1N, 0.74 ml) and the reaction mixture was treated to give the title compound (153 mg) as colorless crystals.

mp 168–169° C.

$^1$H-NMR (270 MHz, CDCl$_3$): δ ppm 2.40 (3H, s), 3.22 (2H, d, J=6.0 Hz), 3.87 (2H, q, J=5.0 Hz), 4.21 (2H, t, J=5.0 Hz), 4.80 (1H, t, J=6.0 Hz), 6.72 (1H, brt), 6.84 (2H, d, J=8.5 Hz), 6.86 (2H, d, J=8.5 Hz), 7.20 (2H, d, J=8.5 Hz), 7.21 (2H, d, J=8.5 Hz), 7.34 (1H, dd, J=5.0, 7.0 Hz), 7.74 (1H, dd, J=7.0, 7.5 Hz), 7.75 (2H, d, J=8.5 Hz), 7.83 (1H, d, J=7.5 Hz), 7.90 (2H, d, J=8.5 Hz), 8.72 (1H, d, J=5.0 Hz).

EXAMPLE 132

Methyl 2-(4-methanesulfonylphenoxy)-3-[4-[2-(4-pyridine-2-ylbenzoylamino)ethoxy]phenyl] propionate (methyl ester of exemplification No. 138-136 compound)

In a similar manner to that described in Example 126, a reaction was carried out using methyl 3-[4-(2-t-butoxycarbonylaminoethoxy)phenyl]-2-(4-methanesulfonylphenoxy)propionate (387 mg), which is the product of Reference example 43, 4-pyridine-2-ylbenzoylchloride hydrochloride (219 mg) and triethylamine (0.44 ml) and the reaction mixture was treated to give the title compound (278 mg) as colorless crystals.

mp 80–81° C.

$^1$H-NMR (270 MHz, CDCl$_3$): δ ppm 2.99 (3H, s), 3.23 (2H, d, J=6.5 Hz), 3.74 (3H, s), 3.89 (2H, q, J=5.0 Hz), 4.16 (2H, t, J=5.0 Hz), 4.85 (1H, t, J=6.5 Hz), 6.65 (1H, brt), 6.88 (2H, d, J=8.5 Hz), 6.94 (2H, d, J=9.0 Hz), 7.21 (2H, d, J=8.5 Hz), 7.23–7.38 (1H, m), 7.74–7.82 (2H, m), 7.82 (2H, d, J=9.0 Hz), 7.89 (2H, d, J=8.5 Hz), 8.08 (2H, d, J=8.5 Hz), 8.73 (1H, d, J=4.5 Hz).

EXAMPLE 133

2-(4-Methanesulfonylphenoxy)-3-[4-[2-(4-pyridine-2-ylbenzoylamino)ethoxy]phenyl]propionic acid (exemplification No. 138-136 compound)

In a similar manner to that described in Example 2, methyl 2-(4-metaesulfonylphenoxy)-3-[4-[2-(4-pyridine-2-ylbenzoylamino)ethoxy]phenyl]propionate (263 mg), which is the product of Example 132, was reacted with aqueous sodium hydroxide solution (1N, 0.94 ml) and the reaction mixture was treated to give the title compound (195 mg) as colorless crystals.

mp 231–233° C.

$^1$H-NMR (270 MHz, deuterated dimethyl sulfoxide): δ ppm 3.03–3.24 (2H, m), 313 (3H, s), 3.64 (2H, q, J=5.5 Hz), 4.10 (2H, t, J=5.5 Hz), 5.10 (1H, dd, J=4.5, 7.5 Hz), 6.90 (2H, d, J=8.5 Hz), 7.07 (2H, d, J=9.0 Hz), 7.25 (2H, d, J=8.5 Hz), 7.40 (1H, dd, J=5.0, 7.5 Hz), 7.78 (2H, d, J=9.0 Hz), 7.92 (1H, dd, J=7.5, 8.0 Hz), 7.98 (2H, d, J=8.5 Hz), 8.05 (1H, d, J=8.0 Hz), 8.18 (2H, d, J=8.5 Hz), 8.70 (1H, d, J=5.0 Hz), 8.78 (1H, t, J=5.5 Hz).

EXAMPLE 134

Ethyl 2-(4-pyridine-2-ylphenoxy)-3-[4-[2-(4-pyridine-2-ylbenzoylamino)ethoxy]phenyl] propionate (ethyl ester of exemplification No. 138-264 compound)

In a similar manner to that described in Example 122, a reaction was carried out using ethyl 2-hydroxy-3-[4-[2-(4-pyridine-2-ylbenzoylamino)ethoxy]phenyl]propionate (370 mg), which is the product of Reference example 39, 4-(pyridine-2-yl)phenol (292 mg), triphenylphosphine (447 mg) and diethyl azodicarboxylate (40% toluene solution, 0.56 ml) and the reaction mixture was treated to give the title compound (500 mg) as a colorless oil.

$^1$H-NMR (270 MHz, CDCl$_3$): δ ppm 1.20 (3H, t, J=7.0 Hz), 3.22 (2H, d, J=6.0 Hz), 3.89 (2H, q, J=5.0 Hz), 4.16 (2H, t, J=5.0 Hz), 4.18 (2H, q, J=7.0 Hz), 4.82 (1H, t, J=6.0 Hz), 6.66 (1H, t, J=5.0 Hz), 6.88 (2H, d, J=8.5 Hz), 7.93 (2H, d, J=8.5 Hz), 7.10–7.30 (3H, m), 7.45–7.80 (5H, m), 7.89 (4H, d, J=8.5 Hz), 8.07 (2H, d, J=8.5 Hz), 8.63 (1H, d, J=4.5 Hz), 8.71 (1H, d, J=4.5 Hz).

EXAMPLE 135

2-(4-Pyridine-2-ylphenoxy)-3-[4-[2-(4-pyridine-2-ylbenzoylamino)ethoxy]phenyl]propionic acid (exemplification No. 138-264 compound)

In a similar manner to that described in Example 2, ethyl 2-(4-pyridine-2-ylphenoxy)-3-[4-[2-(4-pyridine-2-ylbenzoylamino)ethoxy]phenyl]propionate (500 mg), which is the product of Example 134, was reacted with aqueous sodium hydroxide solution (1N, 2.00 ml) and the reaction mixture was treated to give the title compound (390 mg) as a white powder.

mp 98–101° C.

$^1$H-NMR (270 MHz, deuterated dimethyl sulfoxide): δ ppm 3.08–3.22 (2H, m), 3.60–3.70 (2H, m), 4.05–4.15 (2H, m), 4.90–5.00 (1H, m), 6.92 (2H, d, J=7.5 Hz), 6.95 (2H, d, J=8.5 Hz), 7.27 (3H, d, J=7.5 Hz), 7.40 (1H, t, J=6.0 Hz), 7.50–7.70 (1H, m), 7.77–8.10 (7H, m), 8.18 (2H, d, J=7.5 Hz), 8.60 (1H, d, J=4.0 Hz), 8.70 (1H, d, J=5.0 Hz), 8.75–8.82 (1H, m).

EXAMPLE 136

Ethyl 2-(3-fluorophenoxy)-3-[4-[2-(4-pyridine-2-ylbenzoylamino)ethoxy]phenyl]propionate (ethyl ester of exemplification No. 138-88 compound)

In a similar manner to that described in Example 122, a reaction was carried out using ethyl 2-hydroxy-3-[4-[2-(4-pyridine-2-ylbenzoylamino)ethoxy]phenyl]propionate (500 mg), which is the product of Reference example 39, 3-fluorophenol (258 mg), triphenylphosphine (604 mg) and diethyl azodicarboxylate (40% toluene solution, 0.75 ml) and the reaction mixture was treated to give the title compound (524 mg) as a white powder.

mp 133–134.5° C.

$^1$H-NMR (270 MHz, CDCl$_3$): δ ppm 1.20 (3H, t, J=7.0 Hz), 3.18 (2H, d, J=6.5 Hz), 3.81–3.92 (2H, m), 4.10–422 (4H, m), 4.72 (1H, t, J=6.5 Hz), 6.51–6.70 (4H, m), 6.88 (2H, d, J=8.5 Hz), 7.11–7.30 (4H, m), 7.71–7.82 (2H, m), 7.89 (2H, d, J=8.5 Hz), 8.07 (2H, d, J=8.5 Hz), 8.72 (1H, d, J=5.0 Hz).

EXAMPLE 137

2-(3-Fluorophenoxy)-3-[4-[2-(4-pyridine-2-ylbenzoylamino)ethoxy]phenyl]propionic acid (exemplification No. 138-88 compound)

In a similar manner to that described in Example 2, ethyl 2-(3-fluorophenoxy)-3-[4-[2-(4-pyridine-2-ylbenzoylamino)ethoxy]phenyl]propionate (500 mg), which is the product of Example 136, was reacted with aqueous sodium hydroxide solution (1N, 2.00 ml) and the reaction mixture was treated to give the title compound (410 mg) as a white powder.

mp 136.5–138° C.

$^1$H-NMR (270 MHz, deuterated dimethyl sulfoxide): δ ppm 3.00–3.20 (2H, m), 3.56–3.70 (2H, m), 4.01–4.12 (2H, m), 4.90–5.00 (1H, m), 6.62–6.80 (3H, m), 6.91 (2H, d, J=8.5 Hz), 7.16–7.31 (3H, m), 7.37–7.43 (1H, m), 7.85–8.08 (4H, m), 8.19 (2H, d, J=8.5 Hz), 8.70 (1H, d, J=5.0 Hz), 8.71–8.82 (1H, m).

EXAMPLE 138

Ethyl 2-(3,5-difluorophenoxy)-3-[4-[2-(4-pyridine-2-ylbenzoylamino)ethoxy]phenyl]propionate (ethyl ester of exemplification No. 138-168 compound)

In a similar manner to that described in Example 122, a reaction was carried out using ethyl 2-hydroxy-3-[4-[2-(4-pyridine-2-ylbenzoylamino)ethoxy]phenyl]propionate (400 mg), which is the product of Reference example 39, 3,5-difluorophenol (240 mg), triphenylphosphine (483 mg) and diethyl azodicarboxylate (40% toluene solution, 0.60 ml) and the reaction mixture was treated to give the title compound (460 mg) as a white powder.

mp 146–147° C.

$^1$H-NMR (270 MHz, CDCl$_3$): δ ppm 1.21 (3H, t, J=7.0 Hz), 3.18 (2H, d, J=6.5 Hz), 3.89 (2H, d, J=5.0 Hz), 4.16 (2H, t, J=5.0 Hz), 4.19 (2H, q, J=7.0 Hz), 4.68 (1H, t, J=6.5 Hz), 6.31–6.45 (3H, m), 6.66 (1H, t, J=5.0 Hz), 6.86 (2H, d, J=8.5 Hz), 7.21 (2H, d, J=8.5 Hz), 7.26–7.31 (1H, m), 7.75–7.80 (2H, m), 7.89 (2H, d, J=8.5 Hz), 8.07 (2H, d, J=8.5 Hz), 8.72 (1H, d, J=5.0 Hz).

EXAMPLE 139

2-(3,5-Difluorophenoxy)-3-[4-[2-(4-pyridine-2-ylbenzoylamino)ethoxy]phenyl]propionic acid (exemplification No. 138-168 compound)

In a similar manner to that described in Example 2, ethyl 2-(3,5-difluorophenoxy)-3-[4-[2-(4-pyridine-2-ylbenzoylamino)ethoxy]phenyl]propionate (410 mg), which is the product of Example 138, was reacted with aqueous sodium hydroxide solution (1N, 2.00 ml) and the reaction mixture was treated to give the title compound (350 mg) as a white powder.

mp 149.5–151° C.

$^1$H-NMR (270 MHz, deuterated dimethyl sulfoxide): δ ppm 3.05–3.25 (2H, m), 3.65 (2H, d, J=5.5 Hz), 4.11 (2H, t, J=5.5 Hz), 5.08 (1H, t, J=5.5 Hz), 6.65 (2H, d, J=9.0 Hz), 6.70–6.83 (1H, m), 6.91 (2H, d, J=7.5 Hz), 7.23 (2H, d, J=7.5 Hz), 7.38–7.45 (1H, m), 7.90–8.10 (4H, m), 8.18 (2H, d, J=8.5 Hz), 8.70 (1H, d, J=4.5 Hz), 8.79 (1H, t, J=5.0 Hz).

EXAMPLE 140

Ethyl 2-(3,4-difluorophenoxy)-3-[4-[2-(4-pyridine-2-ylbenzoylamino)ethoxy]phenyl]propionate (ethyl ester of exemplification No. 138-152 compound)

In a similar manner to that described in Example 122, a reaction was carried out using ethyl 2-hydroxy-3-[4-[2-(4-pyridine-2-ylbenzoylamino)ethoxy]phenyl]propionate (312 mg), which is the product of Reference example 39, 3,4-difluorophenol (187 mg), triphenylphosphine (377 mg) and diethyl azodicarboxylate (40% toluene solution, 0.65 ml) and the reaction mixture was treated to give the title compound (213 mg) as a white powder.

mp 133–134° C.

$^1$H-NMR (270 MHz, CDCl$_3$): δ ppm 1.21 (3H, t, J=7.0 Hz), 3.17 (2H, d, J=6.5 Hz), 3.90 (2H, q, J=5.0 Hz), 4.16 (2H, t, J=5.0 Hz), 4.18 (2H, q, J=7.0 Hz), 4.64 (1H, t, J=6.5 Hz), 6.48–6.60 (1H, m), 6.62–6.84 (2H, m), 6.88 (2H, d, J=8.5 Hz), 7.00 (1H, q, J=9.5 Hz), 7.21 (2H, d, J=8.5 Hz), 7.26–7.31 (1H, m), 7.72–7.82 (2H, m), 7.89 (2H, d, J=8.5 Hz), 8.07 (2H, d, J=8.5 Hz), 8.72 (1H, d, J=5.0 Hz).

EXAMPLE 141

2-(3,4-Difluorophenoxy)-3-[4-[2-(4-pyridine-2-ylbenzoylamino)ethoxy]phenyl]propionic acid (exemplification No. 138-152 compound)

In a similar manner to that described in Example 2, ethyl 2-(3,4-difluorophenoxy)-3-[4-[2-(4-pyridine-2-ylbenzoylamino)ethoxy]phenyl]propionate (281 mg), which is the product of Example 140, was reacted with aqueous sodium hydroxide solution (1N, 1.02 ml) and the reaction mixture was treated to give the title compound (246 mg) as a white powder.

mp 135–136° C.

$^1$H-NMR (270 MHz, CDCl$_3$): δ ppm 3.20 (2H, d, J=6.5 Hz), 3.80 (2H, q, J=5.5 Hz), 4.23 (2H, t, J=5.5 Hz), 4.73 (1H, t, J=6.5 Hz), 6.56–6.66 (1H, m), 6.68–6.77 (2H, m), 6.86 (2H, d, J=8.5 Hz), 7.00 (1H, q, J=9.5 Hz), 7.19 (2H, d, J=8.5 Hz), 7.36 (1H, dd, J=5.5, 7.5 Hz), 7.74 (1H, d, J=7.5 Hz), 7.74 (2H, d, J=8.5 Hz), 7.84–7.87 (1H, m), 7.88 (2H, d, J=8.5 Hz), 8.71 (1H, d, J=4.5 Hz).

EXAMPLE 142

Ethyl 2-(3,4,5-trifluorophenoxy)-3-[4-[2-(4-pyridine-2-yl-benzoylamino)ethoxy]phenyl] propionate (ethyl ester of exemplification No. 138-184 compound)

In a similar manner to that described in Example 122, a reaction was carried out using ethyl 2-hydroxy-3-[4-[2-(4-pyridine-2-ylbenzoylamino)ethoxy]phenyl]propionate (385 mg), which is the product of Reference example 39, 3,4,5-trifluorophenol (262 mg), triphenylphosphine (465 mg) and diethyl azodicarboxylate (40% toluene solution, 0.58 ml) and the reaction mixture was treated to give the title compound (415 mg) as a white powder.

mp 150–152° C.

$^1$H-NMR (270 MHz, CDCl$_3$): δ ppm 1.22 (3H, t, J=7.0 Hz), 3.16 (2H, d, J=6.5 Hz), 3.90 (2H, q, J=5.0 Hz), 4.16 (2H, t, J=5.0 Hz), 4.19 (2H, q, J=7.0 Hz), 4.62 (1H, t, J=6.5 Hz), 6.41–6.50 (2H, m), 6.66 (1H, t, J=5.0 Hz), 6.88 (2H, d, J=8.5 Hz), 7.20 (2H, d, J=8.5 Hz), 7.25–7.30 (1H, m), 7.73–7.81 (2H, m), 7.89 (2H, d, J=8.5 Hz), 8.08 (2H, d, J=8.5 Hz), 8.72 (1H, d, J=5.0 Hz).

EXAMPLE 143

2-(3,4,5-Trifluorophenoxy)-3-[4-[2-(4-pyridine-2-ylbenzoylamino)ethoxy]phenyl]propionic acid (exemplification No. 138-184 compound)

In a similar manner to that described in Example 2, ethyl 2-(3,4,5-trifluorophenoxy)-3-[4-[2-(4-pyridine-2-ylbenzoylamino)ethoxy]phenyl]propionate (380 mg), which is the product of Example 142, was reacted with aqueous sodium hydroxide solution (1N, 2.00 ml) and the reaction mixture was treated to give the title compound (320 mg) as a white powder.

mp 144–146° C.

¹H-NMR (270 MHz, CDCl₃): δ ppm 3.16–3.23 (2H, m), 3.80–3.90 (2H, m), 4.17–4.25 (2H, m), 4.66 (1H, t, J=6.0 Hz), 6.41–6.58 (2H, m), 6.75–6.82 (1H, m), 6.84 (2H, d, J=8.5 Hz), 7.17 (2H, d, J=8.5 Hz), 7.38 (1H, t, J=6.0 Hz), 7.70–7.90 (6H, m), 8.72 (1H, d, J=5.0 Hz).

EXAMPLE 144

Ethyl 2-pentafluorophenoxy-3-[4-[2-(4-pyridine-2-ylbenzoylamino)ethoxy]phenyl]propionate (ethyl ester of exemplification No. 138-200 compound)

In a similar manner to that described in Example 122, a reaction was carried out using ethyl 2-hydroxy-3-[4-[2-(4-pyridine-2-ylbenzoylamino)ethoxy]phenyl]propionate (500 mg), which is the product of Reference example 39, pentafluorophenol (424 mg), triphenylphosphine (604 mg) and diethyl azodicarboxylate (40% toluene solution, 1.10 ml) and the reaction mixture was treated to give the title compound (918 mg, containing some concomitant) as a white powder.

¹H-NMR (270 MHz, CDCl₃): δ ppm 1.22 (3H, t, J=7.0 Hz), 3.12–3.33 (2H, m), 3.82–3.94 (2H, m), 4.10–427 (4H, m), 4.91 (1H, dd, J=5.0, 7.5 Hz), 6.62–6.72 (1H, m), 6.88 (2H, d, J=8.5 Hz), 7.18–7.30 (3H, m), 7.70–7.80 (2H, m), 7.90 (2H, d, J=8.5 Hz), 8.08 (2H, d, J=8.5 Hz), 8.72 (1H, d, J=5.0 Hz).

EXAMPLE 145

2-Pentafluorophenoxy-3-[4-[2-(4-pyridine-2-ylbenzoylamino)ethoxy]phenyl]propionic acid (exemplification No. 138-200 compound)

In a similar manner to that described in Example 2, ethyl 2-pentafluorophenoxy-3-[4-[2-(4-pyridine-2-ylbenzoylamino)ethoxy]phenyl]propionate (910 mg), which is the product of Example 144, was reacted with aqueous sodium hydroxide solution (1N, 2.00 ml) and the reaction mixture was treated to give the title compound (240 mg) as a white powder.

mp 145–146° C.

¹H-NMR (270 MHz, CDCl₃): δ ppm 3.19–3.41 (2H, m), 3.75–4.10 (2H, m), 4.21–432 (2H, m), 5.04 (1H, t, J=6.0 Hz), 6.70–6.85 (1H, m), 6.90 (2H, d, J=8.5 Hz), 7.26 (2H, d, J=8.5 Hz), 7.38–7.46 (1H, m), 7.68–7.81 (3H, m), 7.81–7.98 (3H, m), 8.77 (1H, d, J=4.5 Hz).

EXAMPLE 146

Methyl 3-[4-[2-(biphenyl-4-carbonylamino)ethoxy]phenyl]-2-(4-fluorophenoxy)propionate (methyl ester of exemplification No. 138-51 compound)

In a similar manner to that described in Example 73, a reaction was carried out using methyl 3-[4-(2-t-butoxycarbonylaminoethoxy)phenyl]-2-(4-fluorophenoxy)propionate (314 mg), which is the product of Reference example 44, biphenyl-4-carboxylic acid (158 mg), diethyl cyanophosphonate (0.12 ml) and triethylamine (0.30 ml) and the reaction mixture was treated to give the title compound (276 mg) as a white powder.

mp 105–106° C.

¹H-NMR (270 MHz, CDCl₃): δ ppm 3.17 (2H, d, J=6.5 Hz), 3.72 (3H, s), 3.89 (2H, q, J=5.0 Hz), 4.16 (2H, t, J=5.0 Hz), 4.68 (1H, t, J=6.5 Hz), 6.63 (1H, brt), 6.76 (2H, dd, J=4.0, 9.0 Hz), 6.88 (2H, d, J=8.5 Hz), 6.91 (2H, d, J=9.0 Hz), 7.22 (2H, d, J=8.5 Hz), 7.41 (1H, t, J=7.0 Hz), 7.44 (1H, t, J=7.0 Hz), 7.47 (1H, t, J=7.0 Hz), 7.61 (2H, d, J=7.0 Hz), 7.66 (2H, d, J=8.5 Hz), 7.85 (2H, d, J=8.5 Hz).

EXAMPLE 147

3-[4-[2-(biphenyl-4-carbonylamino)ethoxy]phenyl]-2-(4-fluorophenoxy)propionic acid (exemplification No. 138-51 compound)

In a similar manner to that described in Example 2, methyl 3-[4-[2-(biphenyl-4-carbonylamino)ethoxy]phenyl]-2-(4-fluorophenoxy)propionate (266 mg), which is the product of Example 146, was reacted with aqueous sodium hydroxide solution (1N, 1.04 ml) and the reaction mixture was treated to give the title compound (241 mg) as colorless crystals.

mp 162–163° C.

¹H-NMR (270 MHz, CDCl₃/deuterated methanol=10/1): δ ppm 3.19 (1H, d, J=7.5 Hz), 3.20 (1H, d, J=5.0 Hz), 3.87 (2H, q, J=5.0 Hz), 4.14 (2H, t, J=5.0 Hz), 4.66 (1H, dd, J=5.0, 7.5 Hz), 6.78 (2H, dd, J=4.5, 9.0 Hz), 6.87 (2H, d, J=8.5 Hz), 6.91 (2H, t, J=9.0 Hz), 7.24 (2H, d, J=8.5 Hz), 7.38 (1H, t, J=7.0 Hz), 7.43 (1H, t, J=7.0 Hz), 7.46 (1H, t, J=7.0 Hz), 7.60 (2H, d, J=7.0 Hz), 7.65 (2H, d, J=7.0 Hz), 7.85 (2H, d, J=8.5 Hz).

EXAMPLE 148

Ethyl 2-(4-isopropylphenoxy)-3-[4-[2-[6-(4-methoxyphenyl)pyridine-3-carbonylamino]ethoxy]phenyl]-2-methylpropionate (ethyl ester of exemplification No. 34-40 compound)

In a similar manner to that described in Example 73, a reaction was carried out using ethyl 3-[4-(2-t-butoxycarbonylaminoethoxy)phenyl]-2-(4-isopropylphenoxy)-2-methylpropionate (400 mg), which is the product of Reference example 45, 6-(4-methoxyphenyl) nicotinic acid (208 mg), which is the product of Reference example 26, diethyl cyanophosphonate (0.14 ml) and triethylamine (0.23 ml) and the reaction mixture was treated to give the title compound (355 mg) as colorless crystals.

mp 92–94° C.

¹H-NMR (270 MHz, CDCl₃): δ ppm 1.01–1.28 (9H, m), 1.36 (3H, s), 2.76–2.91 (1H, m), 3.10 (1H, d, J=14.0 Hz), 3.26 (1H, d, J=14.0 Hz), 3.87 (3H, s), 3.81–3.94 (2H, m), 4.10–4.27 (4H, m), 6.60–6.68 (1H, m), 6.75 (2H, d, J=8.5 Hz), 6.85 (2H, d, J=8.5 Hz), 7.01 (2H, d, J=9.0 Hz), 7.06 (2H, d, J=8.5 Hz), 7.19 (2H, d, J=8.5 Hz), 7.74 (1H, d, J=8.5 Hz), 8.01 (2H, d, J=8.5 Hz), 8.13 (1H, dd, J=2.0, 8.5 Hz), 9.01 (1H, d, J=2.0 Hz).

EXAMPLE 149

2-(4-Isopropylphenoxy)-3-[4-[2-(2-(4-methoxyphenyl)pyridine-5-carbonylamino]ethoxy]phenyl]-2-methylpropionic acid (exemplification No. 34-40 compound)

In a similar manner to that described in Example 2, ethyl 2-(4-isopropylphenoxy)-3-[4-[2-[2-(4-methoxyphenyl)pyridine-5-carbonylamino]ethoxy]phenyl]-2-methylpropionate (341 mg), which is the product of Example 148, was reacted with aqueous sodium hydroxide solution (1N, 1.14 ml) and the reaction mixture was treated to give the title compound (144 mg) as colorless crystals.

mp 194–196° C.

¹H-NMR (270 MHz, deuterated dimethyl sulfoxide): δ ppm 1.15 (6H, d, J=7.0 Hz), 1.27 (3H, s), 2.72–2.89 (1H, m), 3.06 (1H, d, J=13.5 Hz), 3.17 (1H, d, J=13.5 Hz), 3.61–3.70 (2H, m), 3.83 (3H, s), 4.08–4.16 (2H, m), 6.74 (2H, d, J=8.5 Hz), 6.91 (2H, d, J=8.5 Hz), 7.07 (2H, d, J=8.5 Hz), 7.12 (2H, d, J=8.5 Hz), 7.17 (2H, d, J=8.5 Hz), 8.01 (1H, d, J=8.5 Hz), 8.12 (2H, d, J=8.5 Hz), 8.24 (1H, dd, J=2.0, 8.5 Hz), 8.86–8.94 (1H, m), 9.05 (1H, d, J=2.0 Hz).

EXAMPLE 150

Ethyl 3-[4-[2-[2-(2,2,3,3-tetrafluoropropoxy) pyridine-5-carbonylamino]ethoxy]phenyl]-2-(4-isopropylphenoxy)-2-methylpropionate (ethyl ester of exemplification No. 34-43 compound)

In a similar manner to that described in Example 73, a reaction was carried out using ethyl 3-[4-(2-t-butoxycarbonylaminoethoxy)phenyl]-2-(4-isopropylphenoxy)-2-methylpropionate (600 mg), which is the product of Reference example 45, 6-(2,2,3,3-tetrafluoropropoxy)nicotinic acid (344 mg), which is the product of Reference example 28, diethyl cyanophosphonate (0.21 ml) and triethylamine (0.38 ml) and the reaction mixture was treated to give the title compound (260 mg) as a colorless oil.

¹H-NMR (400 MHz, CDCl₃): δ ppm 1.16–1.28 (9H, m), 1.37 (3H, s), 2.83 (1H, septet, J=7.0 Hz), 3.11 (1H, d, J=13.5 Hz), 3.26 (1H, d, J=13.5 Hz), 3.83–3.89 (2H, m), 4.10–4.18 (2H, m), 4.21 (2H, q, J=7.0 Hz), 4.75 (2H, t, J=12.5 Hz), 6.00 (1H, tt, J=4.5, 53 Hz), 6.53–6.60 (1H, m), 6.75 (2H, d, J=8.5 Hz), 6.81–6.90 (3H, m), 7.06 (2H, d, J=8.5 Hz), 7.19 (2H, d, J=8.5 Hz), 8.07 (1H, d, J=8.5 Hz), 8.59 (1H, s).

EXAMPLE 151

3-[4-[2-[2-(2,2,3,3-Tetrafluoropropoxy)pyridine-5-carbonylamino]ethoxy]phenyl]-2-(4-isopropylphenoxy)-2-methylpropionic acid (exemplification No. 34-43 compound)

In a similar manner to that described in Example 2, ethyl 3-[4-[2-[2-(2,2,3,3-tetrafluoropropoxy)pyridine-5-carbonylamino]ethoxy]phenyl]-2-(4-isopropylphenoxy)-2-methylpropionate (210 mg), which is the product of Example 150, was reacted with aqueous sodium hydroxide solution (1N, 0.51 ml) and the reaction mixture was treated to give the title compound (140 mg) as colorless crystals.

mp 173–175° C.

¹H-NMR (400 MHz, CDCl₃/deuterated methanol=20/1): δ ppm 1.20 (6H, d, J=7.0 Hz), 1.40 (3H, s), 2.84 (1H, septet, J=7.0 Hz), 3.13 (1H, d, J=14.0 Hz), 3.26 (1H, d, J=14.0 Hz), 3.80–3.89 (2H, m), 4.14–4.20 (2H, m), 4.78 (2H, t, J=12.5 Hz), 6.00 (1H, tt, J=4.5, 53 Hz), 6.80–6.92 (5H, m), 7.09 (2H, d, J=8.5 Hz), 7.22 (2H, d, J=8.5 Hz), 8.09 (1H, d, J=8.5 Hz), 8.55 (1H, s).

EXAMPLE 152

Methyl 2-phenylthio-3-[4-[2-(4-pyridine-2-ylbenzoylamino)ethoxy]phenyl]propionate (methyl ester of exemplification No. 17-11 compound)

In a similar manner to that described in Example 126, a reaction was carried out using methyl 3-[4-(2-t-butoxycarbonylaminoethoxy)phenyl]-2-phenylthiopropionate (209 mg), which is the product of Reference example 46, 4-pyridine-2-ylbenzoylchloride hydrochloride (135 mg) and triethylamine (0.27 ml) and the reaction mixture was treated to give the title compound (146 mg) as colorless crystals.

mp 102–104° C.

¹H-NMR (270 MHz, CDCl₃): δ ppm 3.00 (1H, dd, J=6.0, 13.5 Hz), 3.14 (1H, dd, J=9.0, 13.5 Hz), 3.58 (3H, s), 3.86 (1H, dd, J=6.0, 9.0 Hz), 3.90 (2H, q, J=5.0 Hz), 4.15 (2H, t, J=5.0 Hz), 6.65 (1H, brt), 6.85 (2H, d, J=8.5 Hz), 7.12 (2H, d, J=8.5 Hz), 7.16–7.37 (4H, m), 7.38–7.48 (2H, m), 7.71–7.81 (2H, m), 7.89 (2H, d, J=8.5 Hz), 8.05 (2H, d, J=8.5 Hz), 8.72 (1H, d, J=5.0 Hz).

EXAMPLE 153

2-Phenylthio-3-[4-[2-(4-pyridine-2-ylbenzoylamino) ethoxy]phenyl]propionic acid (exemplification No. 17-11 compound)

In a similar manner to that described in Example 2, methyl 2-phenylthio-3-[4-[2-(4-pyridine-2-ylbenzoylamino)ethoxy]phenyl]propionate (150 mg), which is the product of Example 152, was reacted with aqueous sodium hydroxide solution (1N, 0.58 ml) and the reaction mixture was treated to give the title compound (138 mg) as colorless crystals.

mp 75–77° C.

¹H-NMR (270 MHz, CDCl₃): δ ppm 3.00 (1H, dd, J=5.0, 13.5 Hz), 3.11 (1H, dd, J=10.5, 13.5 Hz), 3.82 (2H, t, J=5.0 Hz), 3.87 (1H, dd, J=5.0, 10.5 Hz), 4.24 (1H, dd, J=5.0, 9.5 Hz), 4.33 (1H, dd, J=5.0, 9.5 Hz), 6.53 (1H, brt), 6.84 (2H, d, J=8.5 Hz), 7.09 (2H, d, J=8.5 Hz), 7.27–7.38 (4H, m), 7.51–7.54 (2H, m), 7.61 (2H, d, J=8.5 Hz), 7.71 (1H, d, J=8.0 Hz), 7.82–7.89 (1H, m), 7.87 (2H, d, J=8.5 Hz), 8.63 (1H, d, J=5.0 Hz).

EXAMPLE 154

Methyl 3-[4-[2-(4-pyridine-2-ylbenzoylamino) ethoxy]phenyl]-2-(pyridine-3-yloxy)propionate (methyl ester of exemplification No. 138-216 compound)

In a similar manner to that described in Example 126, a reaction was carried out using methyl 3-[4-(2-t-butoxycarbonylaminoethoxy)phenyl]-2-(pyridine-3-yloxy) propionate (345 mg), which is the product of Reference example 47, 4-pyridine-2-ylbenzoylchloride hydrochloride (261 mg) and triethylamine (0.60 ml) and the reaction mixture was treated to give the title compound (271 mg) as colorless crystals.

mp 101–103° C.

¹H-NMR (270 MHz, CDCl₃): δ ppm 3.22 (2H, d, J=6.5 Hz), 3.73 (3H, s), 3.90 (2H, q, J=5.0 Hz), 4.16 (2H, t, J=5.0 Hz), 4.78 (1H, t, J=6.5 Hz), 6.66 (1H, brt), 6.88 (2H, d, J=8.5 Hz), 7.09–7.18 (2H, m), 7.22 (2H, d, J=8.5 Hz), 7.26–7.33 (1H, m), 7.73–7.82 (2H, m), 7.89 (2H, d, J=8.5 Hz), 8.07 (2H, d, J=8.5 Hz), 8.16–8.26 (2H, m), 8.72 (1H, d, J=5.0 Hz).

EXAMPLE 155

3-[4-[2-(4-Pyridine-2-ylbenzoylamino)ethoxy] phenyl]-2-(pyridine-3-yloxy)propionic acid (exemplification No. 138-216 compound)

In a similar manner to that described in Example 2, methyl 3-[4-[2-(4-pyridine-2-ylbenzoylamino)ethoxy] phenyl]-2-(pyridine-3-yloxy)propionate (248 mg), which is the product of Example 154, was reacted with aqueous sodium hydroxide solution (1N, 1.00 ml) and the reaction mixture was treated to give the title compound (212 mg) as colorless crystals.

mp 194–196° C.

$^1$H-NMR (270 MHz, deuterated dimethyl sulfoxide): δ ppm 3.10 (1H, dd, J=8.5, 14.5 Hz), 3.18 (1H, dd, J=4.0, 14.5 Hz), 3.64 (2H, q, J=5.5 Hz), 4.10 (2H, t, J=5.5 Hz), 5.04 (1H, dd, J=4.0, 8.5 Hz), 6.91 (2H, d, J=8.5 Hz), 7.25 (2H, d, J=8.5 Hz), 7.26 (1H, dd, J=6.5, 8.0 Hz), 7.27 (1H, d, J=6.5 Hz), 7.40 (1H, dd, J=4.5, 8.0 Hz), 7.92 (1 H, t, J=8.0 Hz), 7.98 (2H, d, J=8.5 Hz), 8.05 (1H, d, J=8.0 Hz), 8.14 (1H, s), 8.18 (2H, d, J=8.5 Hz), 8.18 (1H, d, J=8.0 Hz), 8.70 (1H, d, J=4.5 Hz), 8.79 (1H, brt).

EXAMPLE 156

Methyl 2-(Benzoxazole-2-ylthio)-3-[4-[2-(4-pyridine-2-ylbenzoylamino)ethoxy]phenyl]propionate (methyl ester of exemplification No. 138-248 compound)

In a similar manner to that described in Example 126, a reaction was carried out using methyl 2-(benzoxazole-2-ylthio)-3-[4-(2-t-butoxycarbonylaminoethoxy)phenyl]propionate (665 mg), which is the product of Reference example 48, 4-pyridine-2-ylbenzoylchloride hydrochloride (444 mg) and triethylamine (0.81 ml) and the reaction mixture was treated to give the title compound (582 mg) as a mass of foam.

$^1$H-NMR (270 MHz, CDCl$_3$): δ ppm 3.30 (1H, dd, J=7.5, 15.0 Hz), 3.35 (1H, dd, J=7.5, 15.0 Hz), 3.71 (3H, s), 3.88 (2H, q, J=5.0 Hz), 4.13 (2H, t, J=5.0 Hz), 4.77 (1H, t, J=7.5 Hz), 6.68 (1H, brt), 6.86 (2H, d, J=8.5 Hz), 7.18 (2H, d, J=8.5 Hz), 7.24–7.38 (3H, m), 7.42 (1H, d, J=7.5 Hz), 7.60 (1H, d, J=6.0 Hz), 7.75–7.82 (2H, m), 7.89 (2H, d, J=8.5 Hz), 8.08 (2H, d, J=8.5 Hz), 8.72 (1H, d, J=5.0 Hz).

EXAMPLE 157

2-(Benzoxazole-2-ylthio)-3-[4-[2-(4-pyridine-2-ylbenzoylamino)ethoxy]phenyl]propionic acid (exemplification No. 138-248 compound)

In a similar manner to that described in Example 2, methyl 2-(benzoxazole-2-ylthio)-3-[4-[2-(4-pyridine-2-ylbenzoylamino)ethoxy]phenyl]propionate (361 mg), which is the product of Example 156, was reacted with aqueous sodium hydroxide solution (1N, 1.30 ml) and the reaction mixture was treated to give the title compound (248 mg) as colorless crystals.

mp 66–67° C.

$^1$H-NMR (270 MHz, deuterated methanol): δ ppm 3.20–3.36 (2H, m), 3.75 (2H, t, J=5.5 Hz), 4.10 (1H, t, J=5.5 Hz), 4.19 (1H, t, J=5.5 Hz), 6.85 (1H, d, J=8.5 Hz), 6.89 (1H, d, J=8.5 Hz), 7.15 (1H, d, J=8.5 Hz), 7.21 (2H, d, J=8.5 Hz), 7.28 (1H, t, J=4.5 Hz), 7.40 (1H, dd, J=4.5, 8.5 Hz), 7.48 (1H, dd, J=4.0, 5.0 Hz), 7.54 (1H, dd, J=4.0, 5.0 Hz), 7.92 (2H, d, J=4.0 Hz), 7.95 (2H, d, J=8.5 Hz), 8.06 (2H, d, J=8.5 Hz), 8.64 (1H, d, J=4.5 Hz).

EXAMPLE 158

Methyl 2-benzyloxy-3-[4-[2-(4-pyridine-2-ylbenzoylamino)ethoxy]phenyl]propionate (methyl ester of exemplification No. 138-232 compound)

In a similar manner to that described in Example 126, a reaction was carried out using methyl 2-benzyloxy-3-[4-(2-t-butoxycarbonylaminoethoxy)phenyl]propionate (195 mg), which is the product of Reference example 49, 4-pyridine-2-ylbenzoylchloride hydrochloride (127 mg) and triethylamine (0.25 ml) and the reaction mixture was treate d to give the title compound (106 mg) as colorless crystals.

mp 122–123° C.

$^1$H-NMR (270 MHz, CDCl$_3$): δ ppm 3.00 (1H, d, J=7.5 Hz), 3.01 (1H, d, J=5.5 Hz), 3.71 (3H, s), 3.91 (2H, q, J=5.0 Hz), 410 (1H, dd, J=5.5, 7.5 Hz), 4.17 (2H, t, J=5.0 Hz), 4.37 (1H, d, J=12.0 Hz), 4.66 (1H, d, J=12.0 Hz), 6.68 (1H, brt), 6.86 (2H, d, J=8.5 Hz), 7.15 (2H, d, J=8.5 Hz), 7.19 (2H, d, J=8.0 Hz), 7.22–7.37 (4H, m), 7.76–7.83 (2H, m), 7.90 (2H, d, J=8.5, Hz), 8.08 (2H, d, J=8.5 Hz), 8.72 (1H, d, J=5.0 Hz).

EXAMPLE 159

2-Benzyloxy-3-[4-[2-(4-pyridine-2-ylbenzoylamino)ethoxy]phenyl]propionic acid (exemplification No. 138-232 compound)

In a similar manner to that described in Example 2, methyl 2-benzyloxy-3-[4-[2-(4-pyridine-2-ylbenzoylamino)ethoxy]phenyl]propionate (94 mg), which is the product of Example 158, was reacted with aqueous sodium hydroxide solution (1N, 0.36 ml) and the reaction mixture was treated to give the title compound (86 mg) as colorless crystals.

mp 138–139° C.

$^1$H-NMR (270 MHz, CDCl$_3$): δ ppm 3.01 (1H, dd, J=7.0, 14.5 Hz), 3.12 (1H, dd, J=5.0, 14.5 Hz), 3.90 (2H, q, J=5.5 Hz), 4.18 (1H, dd, J=5.0, 7.0 Hz), 4.20 (2H, t, J=5.5 Hz), 4.48 (1H, d, J=11.5 Hz), 4.67 (1H, d, J=11.5 Hz), 6.69(1H, brt), 6.85 (2H, d, J=8.5 Hz), 7.16 (2H, d, J=8.5 Hz), 7.22–7.43 (6H, m), 7.75 (1H, d, J=8.0 Hz), 7.79 (1H, dd, J=8.0, 9.0 Hz), 7.81 (2H, d, J=8.5 Hz), 8.00 (2H, d, J=8.5 Hz), 8.72 (1H, d, J=4.5 Hz).

EXAMPLE 160

2-(3-Phenylpropyl)-2-[4-[3-(4-pyridine-2-ylbenzoylamino)propyl]phenyl]propionic acid (exemplification No. 77-3 compound)

Palladium on carbon (5%, 0.12 g) was added to a solution of dibenzyl 2-(3-phenylpropyl)-2-[4-[3-(4-pyridine-2-ylbenzoylamino)propyl]benzyl]malonate (0.65 g), which is the product of Reference example 50, in ethanol (20 ml). The mixture was stirred under an atmosphere of hydrogen at 60° C. for 5 hours. After the catalyst was removed by filtration, the filtrate was concentrated. The residue was dissolved in 2-methoxyethanol (10 ml). The solution was stirred at 150° C. for 4 hours and then was concentrated. The residue was purified via chromatography on a silica gel column using dichloromethane/methanol=9/1 as the eluant to give the title compound (330 mg) as crystals.

mp 118–119° C.

$^1$H-NMR (270 MHz, CDCl$_3$): δ ppm 1.75–1.82 (4H, m), 1.99 (2H, quintuplet, J=7.5 Hz), 2.58–2.77 (6H, m), 2.96 (1H, dd, J=11.0, 15.0 Hz), 3.51 (2H, dt, J=5.5, 7.5 Hz), 6.16 (1H, brt, J=5.5 Hz), 7.12–7.18 (6H, m), 7.23–7.33 (4H, m), 7.60 (2H, d, J=8.0 Hz), 7.71 (1H, dd, J=1.0, 8.0 Hz), 7.80 (1H, dd, J=2.0, 8.0 Hz), 7.93 (2H, d, J=8.5 Hz), 8.65–8.67 (1H, m).

EXAMPLE 161

Ethyl 3-[3-chloro-4-[2-(4-pyridine-2-ylbenzoylamino)ethoxy]phenyl]-2-phenoxypropionate (ethyl ester of exemplification No. 139-24 compound)

In a similar manner to that described in Example 126, a reaction was carried out using methyl 3-[4-(2-t- butoxycarbonylaminoethoxy)-3-chlorophenyl]-2-phenoxypropionate (738 mg), which is the product of Reference example 51, 4-pyridine-2-ylbenzoylchloride hydrochloride (445 mg) and triethylamine (0.89 ml) and the reaction mixture was treated to give the title compound (677 mg) as a mass of foam.

$^1$H-NMR (270 MHz, CDCl$_3$): δ ppm 1.20 (3H, t, J=7.0 Hz), 3.16 (1H, d, J=5.5 Hz), 3.17 (1H, d, J=7.0 Hz), 3.93 (2H, q, J=5.0 Hz), 4.19 (2H, q, J=7.0 Hz), 4.22 (2H, t, J=5.0 Hz), 4.73 (1H, dd, J=5.5, 7.0 Hz), 6.83 (2H, d, J=8.5 Hz), 6.91 (1H, d, J=8.5 Hz), 6.95 (1H, t, J=8.0 Hz), 7.18 (1H, dd, J=2.0, 8.5 Hz), 7.24 (2H, t, J=8.0 Hz), 7.26–7.33 (1H, m), 7.35 (1H, d, J=2.0 Hz), 7.77–7.85 (2H, m), 7.85 (2H, d, J=8.5 Hz), 8.08 (2H, d, J=8.5 Hz), 8.72 (1H, d, J=4.5 Hz).

EXAMPLE 162

3-[3-chloro-4-[2-(4-pyridine-2-ylbenzoylamino) ethoxy]phenyl]-2-phenoxypropionic acid (exemplification No. 139-24 compound)

In a similar manner to that described in Example 2, ethyl 3-[3-chloro-4-[2-(4-pyridine-2-ylbenzoylamino)ethoxy] phenyl]-2-phenoxypropionate (540 mg), which is the product of Example 161, was reacted with aqueous sodium hydroxide solution (1N, 1.98 ml) and the reaction mixture was treated to give the title compound (404 mg) as colorless crystals.

mp 59–61° C.

$^1$H-NMR (270 MHz, CDCl$_3$): δ ppm 3.19 (2H, d, J=6.0 Hz), 3.83–3.98 (2H, m), 4.23 (2H, brt), 4.79 (1H, t, J=6.0 Hz), 6.86 (2H, d, J=8.0 Hz), 6.87 (1H, d, J=8.5 Hz), 6.93 (1H, t, J=8.0 Hz), 7.12 (1H, dd, J=2.0, 8.5 Hz), 7.23 (2H, t, J=8.0 Hz), 7.33 (1H, dd, J=4.5, 7.5 Hz), 7.36 (1H, d, J=2.0 Hz), 7.72 (1H, d, J=8.0 Hz), 7.80 (2H, d, J=8.5 Hz), 7.84 (1H, dd, J=7.5, 8.0 Hz), 7.91 (2H, d, J=8.5 Hz), 8.72 (1H, d, J=4.5 Hz).

EXAMPLE 163

Ethyl 3-[3-bromo-4-[2-(4-pyridine-2-ylbenzoylamino)ethoxy]phenyl]-2-phenoxypropionate (ethyl ester of exemplification No. 141-23 compound)

In a similar manner to that described in Example 126, a reaction was carried out using methyl 3-[3-bromo-4-(2-t-butoxycarbonylaminoethoxy)phenyl]-2-phenoxypropionate (466 mg), which is the product of Reference example 52, 4-pyridine-2-ylbenzoylchloride hydrochloride (254 mg) and triethylamine (0.51 ml) and the reaction mixture was treated to give the title compound (498 mg) as a mass of foam.

$^1$H-NMR (270 MHz, CDCl$_3$): δ ppm 1.21 (3H, t, J=7.0 Hz), 3.16 (1H, d, J=5.5 Hz), 3.17 (1H, d, J=7.0 Hz), 3.94 (2H, q, J=5.0 Hz), 4.19 (2H, q, J=7.0 Hz), 4.22 (2H, t, J=5.0 Hz), 4.73 (1H, dd, J=5.5, 7.0 Hz), 6.82–6.98 (1H, m), 6.83 (2H, d, J=8.5 Hz), 6.88 (1H, d, J=8.5 Hz), 6.95 (1H, t, J=7.5 Hz), 7.21–7.32 (1H, m), 7.24 (2H, dd, J=7.5, 8.0 Hz), 7.25 (1H, dd, J=2.0, 8.5 Hz), 7.52 (1H, d, J=2.0 Hz), 7.76–7.80 (2H, m), 7.95 (2H, d, J=8.5 Hz), 8.08 (2H, d, J=8.5 Hz), 8.72 (1H, d, J=4.5 Hz).

EXAMPLE 164

3-[3-Bromo4-[2-(4-pyridine-2-ylbenzoylamino) ethoxy]phenyl]-2-phenoxypropionic acid (exemplification No. 141-23 compound)

In a similar manner to that described in Example 2, ethyl 3-[3-bromo-4-[2-(4-pyridine-2-ylbenzoylamino)ethoxy] phenyl]-2-phenoxypropionate (237 mg), which is the product of Example 163, was reacted with aqueous sodium hydroxide solution (1N, 0.80 ml) and the reaction mixture was treated to give the title compound (174 mg) as colorless crystals.

mp 83–84° C.

$^1$H-NMR (270 MHz, deuterated methanol): δ ppm 3.12 (1H, dd, J=7.5, 14.0 Hz), 3.20 (1H, dd, J=5.0, 14.0 Hz), 3.81 (2H, t, J=5.5 Hz), 4.24 (2H, t, J=5.5 Hz), 4.86 (1H, dd, J=5.0, 7.5 Hz), 6.84 (2H, d, J=8.0 Hz), 6.91 (1H, t, J=7.5 Hz), 7.02 (1H, d, J=8.5 Hz), 7.17 (1H, d, J=8.0 Hz), 7.22 (2H, dd, J=7.5, 8.0 Hz), 7.26 (1H, dd, J=2.0, 8.5 Hz), 7.40 (1H, dd, J=4.5, 8.0 Hz), 7.52 (1H, d, J=2.0 Hz), 7.93 (1H, t, J=4.5 Hz), 7.95 (2H, d, J=8.5 Hz), 8.05 (2H, d, J=8.5 Hz), 8.64 (1H, d, J=4.5 Hz).

EXAMPLE 165

Ethyl 3-[3-nitro-4-[2-(4-pyridine-2-ylbenzoylamino) ethoxy]phenyl]-2-phenoxypropionate (ethyl ester of exemplification No. 142-23 compound)

In a similar manner to that described in Example 126, a reaction was carried out using methyl 3-[3-nitro-4-(2-t-butoxycarbonylaminoethoxy)phenyl]-2-phenoxypropionate (723 mg), which is the product of Reference example 53, 4-pyridine-2-ylbenzoylchloride hydrochloride (465 mg) and triethylamine (0.85 ml) and the reaction mixture was treated to give the title compound (843 mg) as a mass of foam.

$^1$H-NMR (270 MHz, CDCl$_3$): δ ppm 1.22 (3H, t, J=7.0 Hz), 3.24 (2H, d, J=6.0 Hz), 3.96 (2H, q, J=5.0 Hz), 4.21 (2H, q, J=7.0 Hz), 4.31 (2H, t, J=5.0 Hz), 4.76 (1H, t, J=6.0 Hz), 6.83 (2H, d, J=8.5 Hz), 6.96 (1H, t, J=7.5 Hz), 7.05 (1H, d, J=8.5 Hz), 7.09 (1H, brt), 7.22–7.30 (1H, m), 7.24 (2H, dd, J=7.5, 8.0 Hz), 7.53 (1H, dd, J=2.5, 8.5 Hz), 7.75–7.80 (2H, m), 7.88 (1H, d, J=2.5 Hz), 7.97 (2H, d, J=8.5 Hz), 8.09 (2H, d, J=8.5 Hz), 8.72 (1H, d, J=4.5 Hz).

EXAMPLE 166

3-[3-Nitro-4-[2-(4-pyridine-2-ylbenzoylamino) ethoxy]phenyl]-2-phenoxypropionic acid (exemplification No. 142-23 compound)

In a similar manner to that described in Example 2, ethyl 3-[3-nitro-4-[2-(4-pyridine-2-ylbenzoylamino)ethoxy] phenyl]-2-phenoxypropionate (223 mg), which is the product of Example 165, was reacted with aqueous sodium hydroxide solution (1N, 0.80 ml) and the reaction mixture was treated to give the title compound (137 mg) as colorless crystals.

mp 178–179° C.

$^1$H-NMR (270 MHz, CDCl$_3$/deuterated methanol=1/9): δ ppm 3.22 (1H, dd, J=8.0, 14.5 Hz), 3.26 (1H, dd, J=5.0, 14.5 Hz), 3.84 (2H, q, J=5.0 Hz), 4.36 (2H, t, J=5.0 Hz), 4.83 (1H, dd, J=5.0, 8.0 Hz), 6.85 (2H, d, J=8.0 Hz), 6.92 (1H, t, J=7.5 Hz), 7.23 (2H, dd, J=7.5, 8.0 Hz), 7.24 (1H, d, J=6.5 Hz), 7.40 (1H, dd, J=4.5, 6.5 Hz), 7.58 (1H, dd, J=2.0, 8.5 Hz), 7.84 (1H, d, J=2.0 Hz), 7.91 (1H, t, J=8.5 Hz), 7.92(1H, t, J=4.5 Hz), 7.96 (2H, d, J=8.5 Hz), 8.03 (2H, d, J=8.5 Hz), 8.65 (1H, d, J=4.5 Hz).

EXAMPLE 167

Methyl (S)-2-benzyloxycarbonylamino-3-[4-[2-(4-pyridine-2-ylbenzoylamino)ethoxy]phenyl] propionate (methyl ester of exemplification No. 144-63 compound)

In a similar manner to that described in Example 73, a reaction was carried out using methyl (S)-2- benzyloxycarbonylamino-3-[4-(2-t-butoxycarbonylaminoethoxy)phenyl]propionate (368 mg), which is the product of Reference example 54, 4-pyridine-2-ylbenzoic acid (175 mg), diethyl cyanophosphonate (0.13 ml) and triethylamine (0.22 ml) and the reaction mixture was treated to give the title compound (300 mg) as colorless crystals.

mp 150–151° C.

$^1$H-NMR (270 MHz, CDCl$_3$): δ ppm 2.90–3.12 (2H, m), 3.72 (3H, s), 3.82–3.94 (2H, m), 0.15 (2H, t, J=5.0 Hz), 4.55–4.69 (1H, m), 5.09 (2H, ABq, J=12.5 Hz, δ=0.03 ppm), 5.21 (1H, d, J=8.0 Hz), 6.61–6.72 (1H, m), 6.83 (2H, d, J=8.5 Hz), 7.01 (2H, d, J=8.5 Hz), 7.22–7.41 (6H, m), 7.72–7.82 (2H, m), 7.89 (2H, d, J=8.5 Hz), 8.08 (2H, d, J=8.5 Hz), 8.72 (1H, d, J=5.0 Hz).

EXAMPLE 168

(S)-2-benzyloxycarbonylamino-3-[4-[2-(4-pyridine-2-ylbenzoylamino)ethoxy]phenyl]propionic acid (exemplification No. 144-63 compound)

In a similar manner to that described in Example 2, methyl (S)-2-benzyloxycarbonylamino-3-[4-[2-(4-pyridine-2-ylbenzoylamino)ethoxy]phenyl]propionate (200 mg), which is the product of Example 167, was reacted with aqueous sodium hydroxide solution (1N, 0.72 ml) and the reaction mixture was treated to give the title compound (144 mg) as a mass of foam.

$^1$H-NMR (270 MHz, CDCl$_3$): δ ppm 3.08 (2H, d, J=5.0 Hz), 3.68–4.00 (2H, m), 4.08–4.30 (2H, m), 4.55–4.69 (1H, m), 5.11 (2H, s), 5.37 (1H, d, J=8.0 Hz), 6.70–6.90 (3H, m), 6.99 (2H, d, J=8.5 Hz), 7.20–7.41 (6H, m), 7.70–7.93 (6H, m), 8.70 (1H, d, J=4.5 Hz).

EXAMPLE 169

Methyl (S)-2-propylamino-3-[4-[2-(4-pyridine-2-ylbenzoylamino)ethoxy]phenyl]propionate (methyl ester of exemplification No. 144-13 compound)

In a similar manner to that described in Reference example 1(d), a reaction was carried out using methyl (S)-2-benzyloxycarbonylamino-3-[4-[2-(4-pyridine-2-ylbenzoylamino)ethoxy]phenyl]propionate (1.53 g) and palladium on carbon (5%, 150 mg) and the reaction mixture was treated to give methyl (S)-2-amino-3-[4-[2-(4-pyridine-2-ylbenzoylamino)ethoxy]phenyl]propionate (1.14 g). Propyl bromide (0.24 ml) and potassium carbonate (387 mg) were added to a solution of the amine derivative (1.12 g) obtained above in N,N-dimethylformamide (10 ml). The mixture was stirred at 70° C. for 16 hours. The reaction mixture was partitioned between ethyl acetate and water and the ethyl acetate layer was separated and dried over anhydrous magnesium sulfate and concentrated under reduced pressure. The residue was purified via chromatography on a silica gel column using dichloromethane/methanol=19/1 to give the title compound (196 mg) as colorless crystals.

mp 86–87° C.

$^1$H-NMR (270 MHz, CDCl$_3$): δ ppm 0.86 (3H, t, J=7.5 Hz), 1.39–1.59 (2H, m), 2.39–2.60 (2H, m), 2.90 (2H, d, J=7.0 Hz), 3.48 (1H, t, J=7.0 Hz), 3.64 (3H, s), 3.87–3.95 (2H, m), 4.10–4.20 (2H, m), 6.60–6.71 (1H, m), 6.86 (2H, d, J=8.5 Hz), 7.11 (2H, d, J=8.5 Hz), 7.25–7.30 (1H, m), 7.78–7.80 (2H, m), 7.89 (2H, d, J=8.5 Hz), 8.09 (2H, d, J=8.5 Hz), 8.72 (1H, d, J=5.0 Hz).

EXAMPLE 170

(S)-2-propylamino-3-[4-[2-(4-pyridine-2-ylbenzoylamino)ethoxy]phenyl]propionic acid (exemplification No. 144-13 compound)

In a similar manner to that described in Example 2, methyl (S)-2-propylamino-3-[4-[2-(4-pyridine-2-ylbenzoylamino)ethoxy]phenyl]propionate (169 mg), which is the product of Example 169, was reacted with aqueous sodium hydroxide solution (1N, 0.73 ml) and the reaction mixture was treated to give the title compound (144 mg) as colorless crystals.

mp 242–244° C.

$^1$H-NMR of sodium salt (270 MHz, deuterated dimethyl sulfoxide): δ ppm 0.76 (3H, t, J=7.5 Hz), 1.15–1.35 (2H, m), 1.60–1.72 (1H, m), 2.04–2.21 (1H, m), 2.31–2.50 (1H, m), 2.70–2.81 (2H, m), 3.30–3.41 (1H, m), 3.58–3.72 (2H, m), 4.00–4.12 (2H, m), 6.80 (2H, d, J=8.5 Hz), 7.12 (2H, d, J=8.5 Hz), 7.37–7.45 (1H, m), 7.88–8.11 (4H, m), 8.19 (2H, d, J=8.5 Hz), 8.70 (1H, d, J=4.5 Hz), 8.80–8.88 (1H, m).

EXAMPLE 171

Ethyl 2-phenylamino-3-[4-[2-(4-pyridine-2-ylbenzoylamino)ethoxy]phenyl]propionate (ethyl ester of exemplification No. 144-68 compound)

In a similar manner to that described in Example 122, a reaction is carried out using 2-(4-pyridine-2-ylbenzoylamino)ethanol, which is the product of Reference example 61, ethyl 3-(4-hydroxyphenyl)-2-(phenylamino) propionate, which is the product of Reference example 55(b), triphenylphosphine and diethyl azodicarboxylate to give the title compound.

EXAMPLE 172

2-Phenylamino-3-[4-[2-(4-pyridine-2-ylbenzoylamino)ethoxy]phenyl]propionic acid (exemplification No. 144-68 compound)

Ethyl 2-phenylamino-3-[4-[2-(4-pyridine-2-ylbenzoylamino)ethoxy]phenyl]propionate is hydrolyzed by sodium hydroxide in methanol to give the title compound.

EXAMPLE 173

Ethyl 3-[4-[2-(biphenyl-4-carbonylamino)ethoxy] phenyl]-2-phenylaminopropionate (ethyl ester of exemplification No. 144-67 compound)

In a similar manner to that described in Example 122, a reaction is carried out using 2-(biphenyl-4-carbonylamino) ethanol, ethyl 3-(4-hydroxyphenyl)-2-(phenylamino) propionate, which is the product of Reference example 55(b) triphenylphosphine and diethyl azodicarboxylate to give the title compound.

EXAMPLE 174

3-[4-[2-(biphenyl-4-carbonylamino)ethoxy]phenyl]-2-phenylaminopropionate (exemplification No. 144-67 compound)

Ethyl 3-[4-[2-(biphenyl-4-carbonylamino)ethoxy] phenyl]-2-phenylaminopropionate, which is the product of Example 173, is hydrolyzed by sodium hydroxide in methanol to give the title compound.

EXAMPLE 175

Ethyl 2-ethylamino-3-[4-[2-(4-pyridine-2-ylbenzoylamino)ethoxy]phenyl]propionate hydrochloride (ethyl ester of exemplification No. 144-8 compound)

(a) Ethyl 2-(N-t-butoxycarbonyl)ethylamino-3-[4-[2-(4-pyridine-2-ylbenzoylamino)ethoxy]phenyl] propionate In a similar manner to that described in Example 122, a reaction is carried out using 2-(4-pyridine-2- ylbenzoylamino)ethanol, which is the product of Reference example 61, ethyl 2-(N-t-butoxycarbonyl)ethylamino-3-(4-hydroxyphenyl)propionate, which is the product of Reference example 59(b) triphenylphosphine and diethyl azodicarboxylate to give the title compound.

(b) Ethyl 2-ethylamino-3-[4-[2-(4-pyridine-2-ylbenzoylamino)ethoxy]phenyl]propionate hydrochloride (ethyl ester of exemplification No. 144-8 compound)

Ethyl 2-(N-t-butoxycarbonyl)ethylamino-3-[4-[2-(4-pyridine-2-ylbenzoylamino)-ethoxy]phenyl]propionate is treated with a solution of hydrogen chloride in dioxane (4N) to give the title compound.

EXAMPLE 176

2-Ethylamino-3-[4-[2-(4-pyridine-2-ylbenzoylamino)ethoxy]phenyl]propionate (exemplification No. 144-8 compound)

Ethyl 2-ethylamino-3-[4-[2-(4-pyridine-2-ylbenzoylamino)ethoxy]phenyl]propionate hydrochloride, which is the product of Example 175(b), is hydrolyzed by sodium hydroxide in methanol to give the title compound.

EXAMPLE 177

Ethyl 3-[4-[2-(biphenyl-4-carbonylamino)ethoxy]phenyl]-2-ethylaminopropionate hydrochloride (ethyl ester of exemplification No. 144-7 compound)

(a) Ethyl 3-[4-[2-(biphenyl-4-carbonylamino)ethoxy]phenyl]-2-(N-t-butoxycarbonyl)ethylaminopropionate In a similar manner to that described in Example 122, a reaction is carried out using 2-(biphenyl-4-carbonylamino)ethanol, ethyl 2-(N-t-butoxycarbonyl)ethylamino-3-(4-hydroxyphenyl)propionate, which is the product of Reference example 59(b), triphenylphosphine and diethyl azodicarboxylate to give the title compound.

(b) Ethyl 3-[4-[2-(biphenyl-4-carbonylamino)ethoxy]phenyl]-2-ethylaminopropionate hydrochloride (ethyl ester of exemplification No. 144-7 compound)

Ethyl 3-[4-[2-(biphenyl-4-carbonylamino)ethoxy]phenyl]-2-(N-t-butoxycarbonyl)ethylaminopropionate, which is the product of Example 177(a), is treated with a solution of hydrogen chloride in dioxane (4N) to give the title compound.

EXAMPLE 178

3-[4-[2-(Biphenyl-4-carbonylamino)ethoxy]phenyl]-2-ethylaminopropionic acid (exemplification No. 144-7 compound)

Ethyl 3-[4-[2-(biphenyl-4-carbonylamino)ethoxy]phenyl]-2-ethylaminopropionate hydrochloride, which is the product of Example 177(b), is hydrolyzed by sodium hydroxide in methanol to give the title compound.

EXAMPLE 179

Ethyl 2-(N-ethyl-N-phenylamino)-3-[4-[2-(4-pyridine-2-ylbenzoylamino)ethoxy]phenyl] propionate (ethyl ester of exemplification No. 144-33 compound)

In a similar manner to that described in Example 122, a reaction is carried out using 2-(4-pyridine-2-ylbenzoylamino)ethanol, which is the product of Reference example 61, ethyl 2-(N-ethyl-N-phenylamino)-3-(4-hydroxyphenyl)propionate, which is the product of Reference example 56(b), triphenylphosphine and diethyl azodicarboxylate to give the title compound.

EXAMPLE 180

2-(N-ethyl-N-phenylamino)-3-[4-[2-(4-pyridine-2-ylbenzoylamino)ethoxy]phenyl]propionic acid (exemplification No. 144-33 compound)

Ethyl 2-(N-ethyl-N-phenylamino)-3-[4-[2-(4-pyridine-2-ylbenzoylamino)-ethoxy]phenyl]propionate, which is the product in Example 179, is hydrolyzed by sodium hydroxide in methanol to give the title compound.

EXAMPLE 181

Ethyl 3-[4-[2-(biphenyl-4-carbonylamino)ethoxy]phenyl]-2-(N-ethyl-N-phenylamino)propionate (ethyl ester of exemplification No. 144-32 compound)

In a similar manner to that described in Example 122, a reaction is carried out using 2-(biphenyl-4-carbonylamino)ethanol, ethyl 2-(N-ethyl-N-phenylamino)-3-(4-hydroxyphenyl)propionate, which is the product of Reference example 56(b), triphenylphosphine and diethyl azodicarboxylate to give the title compound.

EXAMPLE 182

3-[4-[2-(biphenyl-4-carbonylamino)ethoxy]phenyl]-2-(N-ethyl-N-phenylamino)propionic acid (exemplification No. 144-32 compound)

Ethyl 3-[4-[2-(biphenyl-4-carbonylamino)ethoxy]phenyl]-2-(N-ethyl-N-phenylamino)propionate, which is the product of Example 181, is hydrolyzed by sodium hydroxide in methanol to give the title compound.

EXAMPLE 183

Ethyl 2-propylamino-3-[4-[2-(4-pyridine-2-ylbenzoylamino)ethoxy]phenyl]propionate hydrochloride (ethyl ester of exemplification No. 144-13 compound)

(a) Ethyl 2-(N-t-butoxycarbonyl)propylamino-3-[4-[2-(4-pyridine-)-ylbenzoylamino)ethoxy]phenyl] propionate In a similar manner to that described in Example 122, a reaction is carried out using 2-(4-pyridine-2-ylbenzoylamino)ethanol, which is the product of Reference example 61, ethyl 2-(N-t-butoxycarbonyl)propylamino-3-(4-hydroxyphenyl)propionate, which is the product of Reference example 60(b) triphenylphosphine and diethyl azodicarboxylate to give the title compound.

(b) Ethyl 2-propylamino-3-[4-[2-(4-pyridine-2-ylbenzoylamino)ethoxy]phenyl]propionate hydrochloride (ethyl ester of exemplification No. 144-13 compound)

Ethyl 2-(N-t-butoxycarbonyl)propylamino-3-[4-[2-(4-pyridine-2-ylbenzoylamino)ethoxy]-phenyl]propionate, which is the product of Example 183(a), is treated with a solution of hydrogen chloride in dioxane (4N) to give the title compound.

EXAMPLE 184

2-Propylamino-3-[4-[2-(4-pyridine-2-ylbenzoylamino)ethoxy]phenyl]propionic acid (exemplification No. 144-13 compound)

Ethyl 2-propylamino-3-[4-[2-(4-pyridine-2-ylbenzoylamino)ethoxy]phenyl]propionate hydrochloride, which is the product of Example 183(b) is hydrolyzed by sodium hydroxide in methanol to give the title compound.

EXAMPLE 185

Ethyl 3-[4-[2-(biphenyl-4-carbonylamino)ethoxy]phenyl]-2-propylaminopropionate hydrochloride (ethyl ester of exemplification No. 144-12 compound)

(a) Ethyl 3-[4-[2-(biphenyl-4-carbonylamino)ethoxy]phenyl]-2-(N-t-butoxycarbonyl)propylaminopropionate In a similar manner to that described in Example 122, a reaction is carried out using 2-(biphenyl-4-carbonylamino)ethanol, ethyl 2-(N-t-butoxycarbonyl)propylamino-3-(4-hydroxyphenyl)propionate, which is the product of Reference example 60(b), triphenylphosphine and diethyl azodicarboxylate to give the title compound.

(b) Ethyl 3-[4-[2-(biphenyl-4-carbonylamino)ethoxy]phenyl]-2-propylaminopropionate hydrochloride (ethyl ester of exemplification No. 144-12 compound)

Ethyl 2-(N-t-butoxycarbonyl)propylamino-3-[4-[2-(4-phenylbenzoylamino)ethoxy]phenyl]propionate, which is the product of Example 185(a), is treated with a solution of hydrogen chloride in dioxane (4N) to give the title compound.

EXAMPLE 186

3-[4-[2-(Biphenyl-4-carbonylamino)ethoxy]phenyl]-2-propylaminopropionic acid (exemplification No. 144-12 compound)

Ethyl 3-[4-[2-(biphenyl-4-carbonylamino)ethoxy]phenyl]-2-propylaminopropionate hydrochloride, which is the product of Example 185(b), is hydrolyzed by sodium hydroxide in methanol to give the title compound.

EXAMPLE 187

Ethyl 2-(N,N-diethylamino)-3-[4-[2-(4-pyridine-2-benzoylamino)ethoxy]phenyl]propionate (ethyl ester of exemplification No. 144-28 compound)

In a similar manner to that described in Example 122, a reaction is carried out using 2-(4-pyridine-2-ylbenzoylamino)ethanol, which is the product of Reference example 61, ethyl 2-(N,N-diethylamino)-3-(4-hydroxyphenyl)propionate, which is the product of Reference example 58, triphenylphosphine and diethyl azodicarboxylate to give the title compound.

EXAMPLE 188

2-(N,N-Diethylamino)-3-[4-[2-(4-pyridine-2-ylbenzoylamino)ethoxy]phenyl]propionic acid (exemplification No. 144-28 compound)

Ethyl 2-(N,N-diethylamino)-3-[4-[2-(4-pyridine-2-benzoylamino)ethoxy]-phenyl]propionate, which is the product Example 187, is hydrolyzed by sodium hydroxide in methanol to give the title compound.

EXAMPLE 189

Ethyl 3-[4-[2-(biphenyl-4-carbonylamino)ethoxy]phenyl]-2-(N,N-diethylamino)propionate (ethyl ester of exemplification No. 144-27 compound)

In a similar manner to that described in Example 122, a reaction is carried out using 2-(biphenyl-4-carbonylamino)ethanol, ethyl 2-(N,N-diethylamino)-3-(4-hydroxyphenyl)propionate, which is the product of Reference example 58, triphenylphosphine and diethyl azodicarboxylate to give the title compound.

EXAMPLE 190

3-[4-[2-(Biphenyl-4-carbonylamino)ethoxy]phenyl]-2-(N,N-diethylamino)propionic acid (exemplification No. 144-27 compound)

Ethyl 2-(N,N-diethylamino)-3-[4-[2-(4-phenylbenzoylamino)ethoxy]phenyl]-propionate, which is the product of Example 189, is hydrolyzed by sodium hydroxide in methanol to give the title compound.

EXAMPLE 191

Ethyl 3-[4-[2-(4-pyridine-2-ylbenzoylamino)ethoxy]phenyl]-2-(pyrrole-1-yl)propionate (ethyl ester of exemplification No. 144-38 compound)

In a similar manner to that described in Example 122, a reaction is carried out using 2-(4-pyridine-2-ylbenzoylamino)ethanol, which is the product of Reference example 61, ethyl 3-(4-hydroxyphenyl)-2-(pyrrole-1-yl)propionate, which is the product of Reference example 57(b), triphenylphosphine and diethyl azodicarboxylate to give the title compound.

EXAMPLE 192

3-[4-[2-(4-pyridine-2-ylbenzoylamino)ethoxy]phenyl]-2-(pyrrole-1-yl)propionic acid (exemplification No. 144-38 compound)

Ethyl 3-[4-[2-(4-pyridine-2-ylbenzoylamino)ethoxy]phenyl]-2-(pyrrole-1-yl)propionate, which is the product of Example 191, is hydrolyzed by sodium hydroxide in methanol to give the title compound.

EXAMPLE 193

Ethyl 3-[4-[2-(biphenyl-4-carbonylamino)ethoxy]phenyl]-2-(pyrrole-1-yl)propionate (ethyl ester of exemplification No. 144-37 compound)

In a similar manner to that described in Example 122, a reaction is carried out using 2-(biphenyl-4-carbonylamino)ethanol, ethyl 3-(4-hydroxyphenyl)-2-(pyrrole-1-yl)propionate, which is the product of Reference example 57(b), triphenylphosphine and diethyl azodicarboxylate to give the title compound.

EXAMPLE 194

3-[4-[2-(Biphenyl-4-carbonylamino)ethoxy]phenyl]-2-(pyrrole-1-yl)propionic acid (exemplification No. 144-37 compound)

Ethyl 3-[4-[2-(4-phenylbenzoylamino)ethoxy]phenyl]-2-(pyrrole-1-yl)propionate, which is the product of Example 193, is hydrolyzed by sodium hydroxide in methanol to give the title compound.

Reference Example 1

Ethyl 2-ethoxy-3-[4-(2-phthaliminoethoxy)phenyl]propionate (a) N-[2-(methanesulfonyloxy)ethyl]phthalimide After methanesulfonyl chloride (12.7 g) was added to a solution of N-(2-hydroxyethyl)phthalimide (19.1 g) in anhydrous dichloromethane (200 ml), triethylamine (20 ml) was added dropwise to the mixture in an ice bath. The mixture was stirred at ambient temperature for 4 hours. At the end of this time the reaction mixture was concentrated under reduced pressure. The residual solid was washed with ethyl acetate and water and then recrystallized from ethyl acetate to afford the desired compound (18.2 g).

mp 138–139° C.

$^1$H-NMR (270 MHz, CDCl$_3$): δ ppm 3.02 (3H, s), 4.05 (2H, t, J=5.5 Hz), 4.49 (2H, t, J=5.5 Hz), 7.70–7.80 (2H, m), 7.83–7.93 (2H, m).

(b) Ethyl 3-(4-benzyloxyphenyl)lactate

Benzyl bromide (21.9 g) and potassium carbonate (35.3 g) were added to a solution of ethyl 3-(4-hydroxyphenyl)lactate (22.4 g) in dimethylformnamide (220 ml). The mixture was stirred at 50° C. for 2 hours. The reaction mixture was partitioned between ethyl acetate and water. The ethyl acetate layer was separated and dried over magnesium sulfate and then concentrated under reduced pressure. The residue was purified via chromatography silica gel column using hexane/ethyl acetate=7/3 as the eluant to give the desired compound (31.0 g) as a pale yellow oil.

(c) Ethyl 3-(4-benzyloxyphenyl)-2-ethoxypropionate

Sodium hydride (55% suspension in oil, 1.65 g) was added to a solution ethyl 3-(4-benzyloxyphenyl)lactate (10.30 g), which is the product of Reference example 1(b), in a mixture of N,N-dimethylacetamide (50 ml) and toluene (50 ml). The mixture was stirred at 40° C. for 30 minutes. To the reaction mixture were added ethyl iodide (3.3 ml) and toluene (5 ml). This mixture was stirred at 40° C. for 2 hours. At the end of this time the reaction mixture was partitioned between ethyl acetate and water. The ethyl acetate layer was separated and dried over anhydrous magnesium sulfate and evaporated under reduced pressure. The residue was purified via chromatography on a silica gel column using hexane/ethyl acetate=5/1 as the eluant to give the desired compound (5.50 g) as a syrup.

$^1$H-NMR (270 MHz, CDCl$_3$): δ ppm 1.11–1.26 (6H, m), 2.95 (2H, d, J=6.5 Hz), 3.36 (1H, quintuplet, J=7.0 Hz), 3.60 (1H, quintuplet, J=7.0 Hz), 3.97 (1H, t, J=6.5 Hz), 4.15 (2H, q, J=7.0 Hz), 5.05 (2H, s), 6.89 (2H, d, J=8.5 Hz), 7.16 (2H, d, J=8.5 Hz) 7.30–7.48 (5H, m).

(d) Ethyl 2-ethoxy-3-hydroxyphenylpropionate

Palladium on carbon (5%, 0.70 g) was added to a solution of ethyl 3-(4-benzyloxyphenyl)-2-ethoxypropionate (5.50 g), which is the product of Reference example 1(c), in ethanol (60 ml). The mixture was stirred under an atmosphere of hydrogen at 40° C. for 2 hours. At the end of this time the catalyst was removed by filtration and the filtrate was concentrated under reduced pressure. The residue was partitioned between ethyl acetate and water and the the layers were separated. The ethyl acetate layer was dried over anhydrous magnesium sulfate and then concentrated under reduced pressure to afford the desired product (3.80 g) as a syrup.

$^1$H-NMR (270 MHz, CDCl$_3$): δ ppm 1.12–1.28 (6H, m), 2.95 (2H, d, J=6.5 Hz), 3.37 (1H, quintuplet, J=7.0 Hz), 3.60 (1H, quintuplet, J=7.0 Hz),-3.99 (1H, t, J=6.5 Hz), 4.19 (2H, q, J=7.0 Hz), 5.38 (1H, s), 6.73 (2H, d, J=8.5 Hz), 7.10 (2H, d, J=8.5 Hz).

(e) Ethyl 2-ethoxy-3-[4-(2-phthaloiminoethoxy)phenyl]propionate

Sodium hydride (55% suspension in oil, 200 mg) was added to a solution of ethyl 2-ethoxy-3-hydroxyphenylpropionate (1.00 g), which is the product of Reference example 1(d), in a mixture of dimethylacetamide (10 ml) and toluene (10 ml). The mixture was stirred at ambient temperature for 20 minutes. To the reaction mixture N-[2-(methanesulfonyloxy)ethyl]phthalimide (1.50 g), which is the product of Reference example 1(a), was added and the mixture was stirred at 70° C. for 2.5 hours and then at 60° C. for 24 hours. At the end of this time the reaction mixture was partitioned between ethyl acetate and water. The ethyl acetate was separated and dried over anhydrous magnesium sulfate and evaporated under reduced pressure. The residue was purified via chromatography on a silica gel column using benzene/ethyl acetate=8/1 as the eluant to afford the title compound (0.31 g) as a syrup.

$^1$H-NMR (270 MHz, CDCl$_3$): δ ppm 1.09–1.28 (6H, m), 2.92 (2H, d, J=6.5 Hz), 3.37 (1H, quintuplet, J=7.0 Hz), 3.58 (1H, quintuplet, J=7.0 Hz), 3.93 (1H, t, J=6.5 Hz), 4.06–4.25 (6H, m), 6.79 (2H, d, J=8.5 Hz), 7.11 (2H, d, J=8.5 Hz), 7.68–7.91 (4H, m).

Reference Example 2

Ethyl 2-(3-phenylpropyl)-3-[4-(2-phthaliminoethoxy)phenyl]propionate (a) Diethyl 2-(4-benzyloxybenzyl)-2-(3-phenylpropyl)malonate Sodium hydride (55% suspension in oil, 0.48 g) was added to a solution of diethyl 2-(3-phenylpropyl)malonate (2.78 g) in a mixture of N,N-dimethylacetamide (10 ml) and toluene (20 ml). The mixture was stirred at ambient temperature for 30 minutes. To the reaction mixture 4-benzyloxybenzyl chloride (2.45 g) was added and the mixture was stirred at ambient temperature for 30 minutes and then at 60° C. for 30 minutes. At the end of this time the reaction mixture was partitioned between ethyl acetate and water. The ethyl acetate layer was separated and dried over anhydrous magnesium sulfate and concentrated. The residue was purified via chromatography on a silica gel column using hexane/ethyl acetate=9/1 as the eluant to afford the desired compound (3.91 g) as a syrup.

$^1$H-NMR (270 MHz, CDCl$_3$): δ ppm 1.21 (6H, t, J=7.0 Hz), 1.57–1.66 (2H, m), 1.76–1.85 (2H, m), 2.61 (2H, t, J=6.5 Hz), 3.14 (2H, s), 4.15 (4H, dq, J=1.5, 7.0 Hz), 5.01 (2H, s), 6.79 (2H, d, J=8.5 Hz), 6.89 (2H, d, J=8.5 Hz), 7.15–7.44 (10H, m).

(b) Ethyl 2-(4-benzyloxybenzyl)-5-phenylvalerate

Potassium hydroxide (2.00 g) was added to a solution of diethyl 2-(4-benzyloxybenzyl)-2-(3-phenylpropyl)malonate (3.91 g) in a mixture of 2-methoxyethanol (30 ml) and water (3 ml). The mixture was stirred at 130° C. in an oil bath for 1.5 hours. At the end of this time the reaction mixture was partitioned between ethyl acetate and water and the mixture was acidified with aqueous hydrogen chloride solution (6N). The ethyl acetate layer was separated and washed with aqueous sodium chloride solution and dried over anhydrous magnesium sulfate and concentrated. A solution of the residual syrup in xylene (20 ml) was stirred for 1 hour and then concentrated. Concentrated sulfuric acid (1 ml) was added to a solution of the syrup residue of 2-(4-benzyloxybenzyl)-5-phenylvaleric acid in ethanol (40 ml). The mixture was stirred at 80° C. for 3 hours and allowed to stand at ambient temperature for 16 hours. At the end of this time the reaction mixture was concentrated and the residue was partitioned between ethyl acetate and water. The ethyl acetate layer was separated and dried over anhydrous magnesium sulfate and concentrated to dryness to afford the desired compound (3.32 g) as a syrup.

$^1$H-NMR (270 MHz, CDCl$_3$): δ ppm 1.13 (3H, t, J=7.0 Hz), 1.50–1.80 (4H, m), 2.53–2.71 (4H, m), 2.82–2.90 (1H, m), 4.04 (2H, q, J=7.0 Hz), 5.04 (2H, s), 6.87 (2H, d, J=8.5 Hz), 7.05 (2H, d, J=8.5 Hz), 7.10–7.44 (10H, m).

(c) Ethyl 2-(4-hydroxybenzyl)-5-phenylvalerate

In a similar manner to that described in Reference example 1(d), a reaction was carried out using ethyl 2-(4-benzyloxybenzyl)-5-phenylvalerate (3.32 g) and palladium on carbon (5%, 0.40 g) and the reaction mixture was treated to afford the desired compound (2.56 g) as a syrup.

$^1$H-NMR (270 MHz, CDCl$_3$): δ ppm 1.14 (3H, t, J=7.0 Hz), 1.50–1.75 (4H, m), 2.53–2.71 (4H, m), 2.78–2.87 (1H, m), 4.05 (2H, q, J=7.0 Hz), 6.70 (2H, d, J=8.5 Hz), 6.98 (2H, d, J=8.5 Hz), 7.12–7.29 (5H, m).

(d) Ethyl 2-(3-phenylpropyl)-3-[4-(2-phthaliminoethoxy)phenyl]propionate

In a similar manner to that described in Reference example 1(e), a reaction was carried out using ethyl 2-(4-hydroxybenzyl)-5-phenylvalerate (1.42 g), which is the product of Reference example 2(c), sodium hydride (55% suspension in oil, 228 mg) and N-[2-(methanesulfonyloxy)ethyl]phthalimide (1.25 g), which is the product of Reference example 1(a) and the reaction mixture was treated to afford the desired compound (1.34 g) as a syrup.

$^1$H-NMR (270 MHz, CDCl$_3$): δ ppm 1.12 (3H, t, J=7.0 Hz), 1.46–1.70 (4H, m), 2.50–2.70 (4H, m), 2.76–2.89 (1H, m), 4.02 (2H, q, J=7.0 Hz), 4.10 (2H, t, J=5.5 Hz), 4.19 (2H, t, J=5.5 Hz), 6.77 (2H, d, J=8.5 Hz), 7.00 (2H, d, J=8.5 Hz), 7.10–7.20 (3H, m), 7.21–7.29 (2H, m), 7.69–7.76 (2H, m), 7.82–7.89 (2H, m).

Reference Example 3

Ethyl 3-[4-(2-aminoethoxy)phenyl]-2-(2-phenoxyethyl)propionate (a) Diethyl 2-(4-methoxybenzylidene)malonate Piperidine (1.5 ml) and diethyl malonate (14.9 ml) were added to a solution of 4-methoxymethoxybenzaldehyde (16.2 g) in ethanol (160 ml). The mixture was heated at reflux for 7 hours. At the end of this time ethyl acetate was added to the reaction mixture and the ethyl acetate was washed with aqueous hydrogen chloride solution (0.8N) and saturated aqueous sodium hydrogencarbonate solution and saturated aqueous sodium chloride and dried over anhydrous magnesium sulfate and then concentrated. The residue was purified via chromatography on a silica gel column using hexane/ethyl acetate=9/1-3/1 as the eluant to afford the desired compound (5.00 g) as a syrup.

$^1$H-NMR (270 MHz, CDCl$_3$): δ ppm 1.33 (6H, t, J=7.0 Hz), 3.48 (3H, s), 4.29 (2H, q, J=7.0 Hz), 4.36 (2H, q, J=7.0 Hz), 5.20 (2H, s), 7.03 (2H, d, J=9.0 Hz), 7.42 (2H, d, J=9.0 Hz), 7.67 (1H, s).

(b) Diethyl 2-(4-methoxymethoxybenzyl)malonate

In a similar manner to that described in Reference example 1(d), a reaction was carried out using diethyl 2-(4-methoxymethoxybenzylidene)malonate (4.98 g) and palladium on carbon (5%, 0.50 g) and the reaction mixture was treated to afford the desired compound (5.00 g) as a syrup.

$^1$H-NMR (270 MHz, CDCl$_3$): δ ppm 1.24 (6H, t, J=7.0 Hz), 3.18 (2H, d, J=8.0 Hz), 3.49 (3H, s), 3.62 (1H, t, J=8.0 Hz), 4.18 (4H, q, J=7.0 Hz), 5.17 (2H, s), 6.97 (2H, d, J=8.5 Hz), 7.15 (2H, d, J=8.5 Hz).

(c) Diethyl 2-(4-methoxymethoxybenzyl)-2-(2-phenoxyethyl)malonate

In a similar manner to that described in Reference example 2(a), a reaction was carried out using diethyl 2-(4-methoxymethoxybenzyl)malonate (1.58 g), which is the product of Reference example 3(b), sodium hydride (55% suspension in oil, 0.24 g) and 2-phenoxyethyl bromide (1.23 g) and the reaction mixture was treated to afford the desired compound (1.72 g) as a syrup.

$^1$H-NMR (270 MHz, CDCl$_3$): δ ppm 1.22 (6H, t, J=7.5 Hz), 2.30 (2H, t, J=6.5 Hz), 3.30 (2H, s), 3.47 (3H, s), 4.08 (2H, t, J=6.5 Hz), 4.19 (4H, q, J=7.5 Hz), 5.14 (2H, s), 6.84–6.96 (5H, m), 7.05 (2H, d, J=9.0 Hz), 7.16–7.30 (2H, m).

(d) Ethyl 2-(4-hydroxybenzyl)-4-phenoxybutyrate

In a similar manner to that described in Reference example 2(b), a reaction was carried out using diethyl 2-(4-methoxymethoxybenzyl)-2-(2-phenoxyethyl)malonate (1.71 g) and potassium hydroxide and the reaction mixture was treated to afford the desired compound (1.25 g) as a syrup.

$^1$H-NMR (270 MHz, CDCl$_3$): δ ppm 1.13 (3H, t, J=7.0 Hz), 1.90–2.20 (2H, m), 2.74–2.98 (3H, m), 3.90–4.14 (4H, m), 4.71 (1H, s), 6.74 (2H, d, J=8.5 Hz), 6.85 (2H, d, J=8.5 Hz), 6.93 (1H, t, J=7.5 Hz), 7.05 (2H, d, J=8.5 Hz), 7.22–7.30 (2H, m).

(e) Ethyl 2-(2-phenoxyethyl)-3-[4-[2-(tetrahydropyran-2-yl-oxy)ethoxy]phenyl]propionate 2-(2-bromoethoxy)tetrahydropyran (1.24 g) and potassium carbonate (1.09 g) were added to a solution of ethyl 2-(4-hydroxybenzyl)-4-phenoxybutyrate (620 mg), which is the product of Reference example 3(d), in 2-butanone (8 ml). The mixture was stirred at 100° C. for 5 hours. To the reaction mixture dimethylacetamide (10 ml) was added and the mixture was stirred at 100° C. for 1.5 hours. At the end of this time the reaction mixture was partitioned between ethyl acetate and water. The ethyl acetate layer was separated and washed with saturated aqueous sodium chloride solution and dried over anhydrous magnesium sulfate and then concentrated. The residue was purified via chromatography on a silica gel column using hexane/ethyl acetate=4/1 as the eluant to afford the desired compound (738 mg) as a syrup.

$^1$H-NMR (270 MHz, CDCl$_3$): δ ppm 1.13 (3H, t, J=7.0 Hz), 1.50–2.10 (8H, m), 2.73–2.98 (3H, m), 3.48–3.58 (1H, m), 3.77-4.17 (9H, m), 4.71 (1H, t, J=3.5 Hz), 6.82–6.87 (4H, m), 6.93 (1H, t, J=7.5 Hz), 7.09 (2H, d, J=8.5 Hz), 7.23–7.29 (2H, m).

(f) Ethyl 3-[4-(2-hydroxyethoxy)phenyl]-2-(2-phenoxyethyl)propionate p-Toluenesulfonic acid monohydrate (0.40) was added to a solution of ethyl 2-(2-phenoxyethyl)-3-[4-[2-(tetrahydropyran-2-yloxy)ethoxy]phenyl]propionate (738 mg), which is the product of Reference example 3(e), in ethanol (10 ml). The mixture was stirred at ambient temperature for 2 hours. At the end of this time the reaction mixture was concentrated. The residue was partitioned between ethyl acetate and saturated aqueous sodium hydrogencarbonate solution. The ethyl acetate layer was separated and dried over anhydrous magnesium sulfate and then concentrated. The residue was purified via chromatography on a silica gel column using hexane/ethyl acetate=7/3-3/2 as the eluant to afford the desired compound (503 mg) as a syrup.

$^1$H-NMR (270 MHz, CDCl$_3$): δ ppm 1.13 (3H, t, J=7.0 Hz), 1.90–2.10 (3H, m), 2.75–3.00 (3H, m), 3.92–4.11 (8H, m), 6.82–6.87 (4H, m), 6.93 (1H, t, J=7.5 Hz), 7.10 (2H, d, J=8.5 Hz), 7.23–7.29 (2H, m).

(g) Ethyl 3-[4-(2-methanesulfonyloxyethoxy)phenyl]-2-(2-phenoxyethyl)propionate

Triethylamine (0.29 ml) and methanesulfonyl chloride (0.12 ml) were added to a solution of ethyl 3-[4-(2-hydroxyethoxy)phenyl]-2-(2-phenoxyethyl)propionate (503 mg), which is the product of Reference example 3(f), in anhydrous dichloromethane (10 ml). The reaction mixture was stirred at ambient temperature for 2 hours. At the end of this time the reaction mixture was concentrated. The residue was partitioned between ethyl acetate and water. The ethyl acetate layer was separated and dried over anhydrous magnesium sulfate and then concentrated. The residue was purified via chromatography on silica gel column using hexane/ethyl acetate=2/1-3/2 as the eluant to afford the desired compound (632 mg) as a syrup.

$^1$H-NMR (270 MHz, CDCl$_3$): δ ppm 1.13 (3H, t, J=7.0 Hz), 1.90–2.20 (2H, m), 2.75–3.00 (3H, m), 3.09 (3H, s), 3.89–4.02 (2H, m), 4.07 (2H, q, J=7.0 Hz), 4.20–4.23 (2H, m), 4.54–4.58 (2H, m), 6.80–6.87 (4H, m), 6.93 (1H, t, J=7.5 Hz), 7.11 (2H, d, J=8.5 Hz), 7.23–7.30 (2H, m).

(h) Ethyl 3-[4-(2-azidoethoxy)phenyl]-2-(2-phenoxyethyl)propionate

Sodium azide (0.29 g) was added to a solution of ethyl 3-[4-(2-methanesulfonyloxyethoxy)phenyl]-2-(2-phenoxyethyl)propionate, which is the product of Reference example 3(g), in dimethylformamide (8 ml). The mixture was stirred at 70° C. for 2 hours. At the end of this time the reaction mixture was partitioned between ethyl acetate and water. The ethyl acetate layer was separated and dried over anhydrous magnesium sulfate and then concentrated to afford the desired compound (546 mg) as a syrup.

$^1$H-NMR (270 MHz, CDCl$_3$): δ ppm 1.13 (3H, t, J=7.0 Hz), 1.90–2.20 (2H, m), 2.75–3.00 (3H, m), 3.58 (2H, t, J=5.0 Hz), 3.89–4.14 (6H, m), 6.81–6.87 (4H, m), 6.93 (1H, t, J=7.5 Hz), 7.11 (2H, d, J=8.5 Hz), 7.22–7.30 (2H, m).

(i) Ethyl 3-[4-(2-aminoethoxy)phenyl]-2-(phenoxyethyl)propionate

In a similar manner to that described in Reference example 1(d), a reaction was carried out using ethyl 3-[4-(2-azidoethoxy)phenyl]-2-(2-phenoxyethyl)propionate (538 mg) and palladium on carbon (5%, 500 mg) and the reaction mixture was treated to afford the title compound (476 mg) as a syrup.

$^1$H-NMR (270 MHz, CDCl$_3$): δ ppm 1.13 (3H, t, J=7.0 Hz), 1.66 (2H, brs), 1.90–2.21 (2H, m), 2.75–3.07 (3H, m), 3.08 (2H, t, J=5.0 Hz), 3.90–4.12 (6H, m), 6.82–6.88 (4H, m), 6.93 (1H, t, J=7.5 Hz), 7.10 (2H, d, J=8.5 Hz), 7.23–7.30 (2H, m).

Reference Example 4

Ethyl 3-[4-(2-aminoethoxy)phenyl]-2-phenoxypropionate (a) Diethyl 2-(4-benzyloxybenzyl)-2-phenoxymalonate In a similar manner to that described in Reference example 2(a), a reaction was carried out using diethyl 2-phenoxymalonate (2.81 g), 4-benzyloxybenzyl chloride (2.59 g) and sodium hydride (55% suspension in oil, 530 mg) and the reaction mixture was treated to afford the desired compound (3.10 g) as a syrup.

$^1$H-NMR (270 MHz, CDCl$_3$): δ ppm 1.12 (6H, t, J=7.0 Hz), 3.57 (2H, s), 4.15 (4H, q, J=7.0 Hz), 5.02 (2H, s), 6.84–7.14 (6H, m), 7.22–7.41 (8H, m).

(b) Ethyl 3-(4-benzyloxyphenyl)-2-phenoxypropionate

In a similar manner to that described in Reference example 2(b), a reaction was carried out using diethyl 2-(4-benzyloxbenzyl)-2-phenoxymalonate (3.10 g) and potassium hydroxide (2.10 g) and the reaction mixture was treated to afford, via a syrup of 3-(4-benzyloxyphenyl)-2-phenoxypropionic acid, the desired compound (2.10 g) as a syrup.

$^1$H-NMR (270 MHz, CDCl$_3$): δ ppm 1.18 (3H, t, J=7.0 Hz), 3.11–3.20 (2H, m), 4.16 (2H, q, J=7.0 Hz), 4.74 (1H, dd, J=5.5, 6.5 Hz), 5.04 (2H, s), 6.84 (2H, d, J=8.0 Hz), 6.91 (2H, d, J=8.5 Hz), 6.92–6.97 (1H, m), 7.05–7.09 (1H, m), 7.22 (2H, d, J=8.5 Hz), 7.20–7.43 (6H, m).

(c) Ethyl 3-(4-hydroxyphenyl)-2-phenoxypropionate

In a similar manner to that described in Reference example 1(d), a reaction was carried out using ethyl 3-(4-benzyloxyphenyl)-2-phenoxypropionate (2.10 g), which is the product of Reference example 4(b) and palladium on carbon (5%, 0.32 g) and the reaction mixture was treated to afford the desired compound (1.01 g) as a syrup.

$^1$H-NMR (270 MHz, CDCl$_3$): δ ppm 1.19 (3H, t, J=7.0 Hz), 3.10–3.24 (2H, m), 4.17 (2H, q, J=7.0 Hz), 4.74 (1H, dd, J=6.0, 7.0 Hz), 5.00 (1H, s), 6.74 (2H, d, J=8.5 Hz), 6.84 (2H, d, J=8.0 Hz), 6.95 (1H, t, J=7.5 Hz), 7.16 (2H, d, J=8.5 Hz), 7.21–7.26 (2H, m).

(d) Ethyl 2-phenoxy-3-[4-[2-(tetrahydropyran-2-yloxy)ethoxy]phenyl]propionate

In a similar manner to that described in Reference example 3(e), a reaction was carried out using ethyl 3-(4-hydroxyphenyl)-2-phenoxypropionate (3.33 g), which is the product of Reference example 4(c), 2-(2-bromoethoxy)tetrahydropyran (7.27 g) and potassium carbonate (6.41 g) in dimethylacetamide and the reaction mixture was treated to afford the desired compound (4.53 g) as a syrup.

$^1$H-NMR (270 MHz, CDCl$_3$): δ ppm 1.19 (3H, t, J=7.0 Hz), 1.50–1.88 (6H, m), 3.16–3.20 (2H, m), 3.48–3.56 (1H, m), 3.76–3.93 (2H, m), 4.00–4.21 (5H, m), 4.69–4.76 (2H, m), 6.83 (2H, d, J=8.5 Hz), 6.86 (2H, d, J=8.5 Hz), 6.94 (1H, t, J=7.0 Hz), 7.18–7.26 (4H, m).

(e) Ethyl 3-[4-(2-hydroxyethoxy)phenyl]-2-phenoxypropionate

In a similar manner to that described in Reference example 3(f), a reaction was carried out using ethyl 2-phenoxy-3-[4-[2-(tetrahydropyran-2-yloxy)ethoxy]phenyl]propionate (4.53 g), which is the product of Reference example 4(d), and p-toluenesulfonic acid monohydrate (2.70 g) and the reaction mixture was treated to afford the desired compound (3.28 g) as a syrup.

$^1$H-NMR (270 MHz, CDCl$_3$): δ ppm 1.19 (3H, t, J=7.0 Hz), 1.98–2.02 (1H, brs), 3.14–3.20 (2H, m), 3;904.00 (2H, m), 4.06 (2H, t, J=4.5 Hz), 4.17 (2H, q, J=7.0 Hz), 4.74 (1H, dd, J=6.0, 7.5 Hz), 6.82–6.88 (4H, m), 6.95 (1H, t, J=7.0 Hz), 7.21–7.26 (4H, m).

(f) Ethyl 3-[4-(2-methanesulfonyloxyethoxy)phenyl]-2-phenoxypropionate

In a similar manner to that described in Reference example 3(g), a reaction was carried out using ethyl 3-[4-(2-hydroxyethoxy)phenyl]-2-phenoxypropionate (3.27 g), which is the product of Reference example 4(e), triethylamine (2.07 ml) and methanesulfonyl chloride (0.84 ml) and the reaction mixture was treated to afford the desired compound (4.20 g) as a syrup.

$^1$H-NMR (270 MHz, CDCl$_3$): δ ppm 1.20 (3H, t, J=7.0 Hz), 3.07 (3H, s), 3.19 (2H, d, J=7.0 Hz), 4.14–4.25 (4H, m), 4.56 (2H, t, J=4.5 Hz), 4.74 (1H, t, J=7.0 Hz), 6.84 (4H, d, J=8.5 Hz), 6.95 (1H, t, J=7.0 Hz), 7.20–7.29 (4H, m).

(g) Ethyl 3-[4-(2-azidoethoxy)phenyl]-2-phenoxypropionate

In a similar manner to that described in Reference example 3(h), a reaction was carried out using ethyl 3-[4-(2-methanesulfonyloxyethoxy)phenyl]-2-phenoxypropionate (4.00 g), which is the product of Reference example 4(f), and sodium azide (1.93 g) and the reaction mixture was treated to afford the desired compound (3.40 g) as a syrup.

$^1$H-NMR (270 MHz, CDCl$_3$): δ ppm 1.19 (3H, t, J=7.0 Hz), 3.14–3.22 (2H, m), 3.58 (2H, t, J=5.0 Hz), 4.13 (2H, t, J=5.0 Hz), 4.18 (2H, q, J=7.0 Hz), 4.74 (1H, dd, J=6.0, 7.5 Hz), 6.82–6.97 (5H, m), 7.21–7.29 (4H, m).

(h) Ethyl 3-[4-(2-aminoethoxy)phenyl]-2-phenoxypropionate

In a similar manner to that described in Reference example 1(d), a reaction was carried out using ethyl 3-[4-(2-azidoethoxy)phenyl]-2-phenoxypropionate (3.40 g), which is the product of Reference example 4(g), and palladium on carbon (5%, 350 mg) and the reaction mixture was treated to afford the title compound (3.10 g) as a syrup.

$^1$H-NMR (270 MHz, CDCl$_3$): δ ppm 1.19 (3H, t, J=7.0 Hz), 3.07 (2H, t, J=5.0 Hz), 3.14–3.20 (2H, m), 3.90–4.15 (2H, m), 4.17 (2H, q, J=7.0 Hz), 4.74 (1H, dd, J=6.0, 7.0 Hz), 6.84 (4H, d, J=8.5 Hz), 6.94 (1H, t, J=7.5 Hz), 7.19–7.30 (4H, m).

Reference Example 5

Ethyl 3-[4-(2-aminoethoxy)phenyl]-2-(4-isopropylphenoxy)propionate

(a) Diethyl 2-(4-isopropylphenoxy)malonate

Sodium hydride (55% suspension in oil, 5.22 g) was added to a solution of 4-isopropylphenol (15.0 g) in a mixture of dimethylformamide (63 ml) and toluene (75 ml). The mixture was stirred at ambient temperature for 1 hour. To the reaction mixture, diethyl 2-chloromalonate (18.5 g) was added. The mixture was stirred at 60° C. for 2.5 hours. At the end of this time ethyl acetate was added to the reaction mixture. The ethyl acetate layer was separated and washed with saturated aqueous sodium chloride solution and dried over anhydrous magnesium sulfate and then concentrated. The residue was purified via chromatography on a silica gel column using hexane/ethyl acetate=4/1 as the eluant to afford the desired compound (21.5 g) as a syrup.

$^1$H-NMR (270 MHz, CDCl$_3$): δ ppm 1.21 (6H, d, J=7.0 Hz), 2.81–2.95 (1H, m), 3.85 (6H, s), 5.21 (1H, s), 6.88 (2H, d, J=8.5 Hz), 7.15 (2H, d, J=8.5 Hz).

(b) Diethyl 2-(4-benzyloxybenzyl)-2-(4-isopropylphenoxy)malonate

In a similar manner to that described in Reference example 2(a), a reaction was carried out using diethyl 2-(4-isopropylphenoxy)malonate (21.5 g), which is the product of Reference example 5(a), 4-benzyloxybenzyl chloride (19.7 g) and sodium hydride (55% suspension in oil, 3.53 g) and the reaction mixture was treated to afford the desired compound (32.3 g) as a syrup.

$^1$H-NMR (270 MHz, CDCl$_3$): δ ppm 1.21 (6H, d, J=6.5 Hz), 2.79–2.92 (1H, m), 3.55 (2H, s), 3.68 (6H, s), 5.02 (2H, s), 6.86 (4H, d, J=8.5 Hz), 7.09 (4H, d, J=8.5 Hz), 7.30–7.43 (5H, m).

(c) Diethyl 2-(4-hydroxyphenyl)-2-(4-isopropylphenoxy)malonate

In a similar manner to that described in Reference example 1(d), a reaction was carried out using diethyl 2-(4-benzyloxybenzyl)-2-(4-isopropylphenoxy)malonate (32.3 g), which is the product of Reference example 5(b), and palladium on carbon (5%, 2.00 g) and the reaction mixture was treated to afford the desired compound (25.2 g) as a syrup.

$^1$H-NMR (270 MHz, CDCl$_3$): δ ppm 1.21 (6H, d, J=7.0 Hz), 2.75–2.95 (1H, m), 3.54 (2H, s), 3.68 (6H, s), 4.93 (1H, brs), 6.69 (2H, d, J=8.5 Hz), 6.87 (2H, d, J=8.5 Hz), 7.04 (2H, d, J=8.5 Hz), 7.09 (2H, d, J=8.5 Hz).

(d) Ethyl 3-(4-hydroxyphenyl)-2-(4-isopropylphenoxy)propionate

In a similar manner to that described in Reference example 2(b), a reaction was carried out using diethyl 2-(4-hydroxyphenyl)-2-(4-isopropylphenoxy)malonate (25.2 g), which is the product of Reference example 5(c), and potassium hydroxide (20.0 g) and the reaction mixture was treated to afford, via crystals of 3-(4-hydroxyphenyl)-2-(4-isopropylphenoxy)propionic acid, the desired compound (19.8 g) as a syrup.

$^1$H-NMR (270 MHz, CDCl$_3$): δ ppm 1.13–1.22 (9H, m), 2.75–2.88 (1H, m), 3.11–3.18 (2H, m), 4.17 (2H, q, J=7.5 Hz), 4.69 (1H, dd, J=5.5, 7.5 Hz), 4.77 (1H, brs), 6.76 (4H, d, J=8.5 Hz), 7.08 (2H, d, J=8.5 Hz), 7.17 (2H, d, J=8.5 Hz).

(e) Ethyl 2-(4-isopropylphenoxy)-3-[4-[2-(tetrahydropyran-2-yloxy)ethoxy]phenyl]propionate In a similar manner to that described in Reference example 3(e), a reaction was carried out using ethyl 3-(4-hydroxyphenyl)-2-(4-isopropylphenoxy)propionate (14.8 g), which is the product of Reference example 5(d), 2-(2-bromoethoxy)tetrahydropyran (28.2 g) and potassium carbonate (24.9 g) in dimethylformamide and the reaction mixture was treated to afford the desired compound (20.6 g) as a syrup.

(f) Ethyl 3-[4-(2-hydroxyethoxy)phenyl]-2-(4-isopropylphenoxy)propionate In a similar manner to that described in Reference example 3(f), a reaction was carried out using ethyl 2-(4-isopropylphenoxy)-3-[4-[2-(tetrahydropyran-2-yloxy)ethoxy]phenyl]propionate (20.6 g), which is the product of Reference example 5(e), and p-toluenesulfonic acid monohydrate (7.85 g) and the reaction mixture was treated to afford the desired compound (16.2 g) as a syrup.

$^1$H-NMR (270 MHz, CDCl$_3$): δ ppm 1.15–1.22 (9H, m), 2.75–3.00 (1H, m), 3.12–3.20 (2H, m), 3.90–3.99 (2H, m), 4.06 (2H, t, J=4.5 Hz), 4.17 (2H, q, J=7.5 Hz), 4.69 (1H, dd, J=5.5, 7.5 Hz), 6.76 (2H, d, J=8.5 Hz), 6.84 (2H, d, J=8.5 Hz), 7.08 (2H, d, J=8.5 Hz), 7.22 (2H, d, J=8.5 Hz).

(g) Ethyl 2-(4-isopropylphenoxy)-3-[4-(2-methanesulfonyloxyethoxy)phenyl]-propionate In a similar manner to that described in Reference example 3 (g), a reaction was carried out using ethyl 3-[4-(2-hydroxyethoxy)phenyl]-2-(4-isopropylphenoxy)propionate (16.2 g), which is the product of Reference example 5(f), triethylamine (12.1 ml) and methanesulfonyl chloride (5.05 ml) and the reaction mixture was treated to afford the desired compound (19.6 g) as a syrup.

$^1$H-NMR (270 MHz, CDCl$_3$): δ ppm 1.16–1.23 (9H, m), 2.72–2.90 (1H, m), 3.07 (314, s), 3.12–3.19 (2H, m), 4.10–4.23 (4H, m), 4.51–4.58 (2H, m), 4.69 (1H, dd, J=5.5, 7.5 Hz), 6.76 (2H, d, J=8.5 Hz), 6.83 (2H, d, J=8.5 Hz), 7.09 (2H, d, J=8.5 Hz), 7.23 (2H, d, J=8.5 Hz).

(h) Ethyl 3-[4-(2-azidoethoxy)phenyl]-2-(4-isopropylphenoxy)propionate

In a similar manner to that described in Reference example 3 (h), a reaction was carried out using ethyl 2-(4-isopropylphenoxy)-3-[4-(2-methanesulfonyloxyethoxy)phenyl]propionate (19.6 g), which is the product of Reference example 5(g), and sodium azide (7.06 g), and the reaction mixture was treated to afford the desired compound (15.8 g) as a syrup.

(i) Ethyl 3-[4-(2-aminoethoxy)phenyl]-2-(4-isopropylphenoxy)propionate

In a similar manner to that described in Reference example 1(d), a reaction was carried out using ethyl 3-[4-(2-azidoethoxy)phenyl]-2-(4-isopropylphenoxy)propionate (15.8 g), which is the product of Reference example 5(h), and palladium on carbon (5%, 1.60 g) and the reaction mixture was treated to afford the title compound (13.5 g) as a syrup.

Reference Example 6

Ethyl 3-[4-(2-aminoethoxy)phenyl]-2-butylpropionate (a) Diethyl 2-(4-benzyloxybenzyl)-2-butylmalonate In a similar manner to that described in Reference example 2(a), a reaction was carried out using diethyl 2-butylmalonate (2.16 g), 4-benzyloxybenzyl chloride (2.44 g) and sodium hydride (55% suspension in oil, 480 mg) and the reaction mixture was treated to afford the desired compound (3.67 g) as crystals.

mp 73° C.

$^1$H-NMR (270 MHz, CDCl$_3$): δ ppm 0.91 (3H, t, J=7.0 Hz), 1.24 (6H, t, J=7.0 Hz), 1.20–1.38 (4H, m), 1.74–1.80 (2H, m), 3.18 (2H, s), 4.11–4.23 (4H, m), 5.02 (2H, s), 6.86 (2H, d, J=8.5 Hz), 6.99 (2H, d, J=8.5 Hz), 7.31–7.44 (5H, m).

(b) Ethyl 2-(4-benzyloxybenzyl)caproate

In a similar manner to that described in Reference example 2(b), a reaction was carried out using diethyl 2-(4-benzyloxybenzyl)-2-butylmalonate (3.60 g), which is the product of Reference example 6(a), and potassium hydroxide (2.00 g) and the reaction mixture was treated to afford, via crystals of 2-(4-benzyloxybenzyl)-2-caproic acid, the desired compound (2.71 g) as a syrup.

$^1$H-NMR (270 MHz, CDCl$_3$): δ ppm 0.87 (3H, t, J=7.0 Hz), 1.14 (3H, t, J=7.0 Hz), 1.20–1.70 (6H, m), 2.51–2.72 (2H, m), 2.85 (1H, dd, J=8.5, 13.5 Hz), 4.05 (2H, q, J=7.0 Hz), 5.03 (2H, s), 6.88 (2H, d, J=8. 5 Hz), 7.07 (2H, d, J=8.5 Hz), 7.31–7.45 (5H, m). (c) Ethyl 2-(4-hydroxybenzyl)caproate In a similar manner to that described in Reference example 1(d), a reaction was carried out using ethyl 2-(4-benzyloxybenzyl)caproate (2.71 g), which is the product of Reference example 6(b), and palladium on carbon (5%, 0.40 g) and the reaction mixture was treated to afford the desired compound (1.90 g) as a syrup.

$^1$H-NMR (270 MHz, CDCl$_3$): δ ppm 0.87 (3H, t, J=7.0 Hz), 1.16 (3H, t, J=7.0 Hz), 1.20–1.35 (4H, m), 1.40–1.70 (2H, m), 2.53–2.72 (2H, m), 2.84 (1H, dd, J=8.5, 13.5 Hz), 4.06 (2H, q, J=7 Hz), 4.93 (1H, s), 6.72 (2H, d, J=8.5 Hz), 7.02 (2H, d, J=8.5 Hz).

(d) Ethyl 2-butyl-3-[4-[2-(tetrahydropyran-2-yloxy)ethoxy]phenyl]propionate

In a similar manner to that described in Reference example 3(e), a reaction was carried out using ethyl 2-(4-hydroxybenzyl)caproate (2.40 g), which is the product of Reference example 6(c), 2-(2-bromoethoxy)tetrahydropyran (1.63 g) and potassium carbonate (3.23 g) in dimethylacetamide and the reaction mixture was treated to afford the desired compound (2.47 g) as a syrup.

$^1$H-NMR (270 MHz, CDCl$_3$): δ ppm 0.87 (3H, t, J=7.0 Hz), 1.16 (3H, t, J=7.0 Hz), 1.21–1.36 (4H, m), 1.38–1.90 (8H, m), 2.51–2.63 (1H, m), 2.67 (1H, dd, J=6.5, 13.5 Hz), 2.85 (1H, dd, J=8.5, 13.5 Hz), 3.48–3.56 (1H, m), 3.72–3.94 (3H, m), 3.96 4.16 (4H, m), 4.70 (1H, t, J=3.5 Hz), 6.83 (2H, d, J=8.5 Hz), 7.06 (2H, d, J=8.5 Hz).

(e) Ethyl 2-butyl-3-[4-(2-hydroxyethoxy)phenyl]propionate

In a similar manner to that described in Reference example 3(f), a reaction was carried out using ethyl 2-butyl-3-[4-[2-(tetrahydropyran-2-yloxy)ethoxy]phenyl]propionate (2.47 g), which is the product of Reference example 6(d), and p-toluenesulfonic acid monohydrate (1.24 g) and the reaction mixture was treated to afford the desired compound (1.44 g) as a syrup.

$^1$H-NMR (270 MHz, CDCl$_3$): δ ppm 0.87 (3H, t, J=7.0 Hz), 1.16 (3H, t, J=7.0 Hz), 1.20–1.37 (3H, m), 1.39–1.70 (3H, m), 2.08 (1H, brs), 2.51–2.63 (1H, m), 2.68 (1H, dd, J=6.5, 13.5 Hz), 2.86 (1H, dd, J=8.5, 13.5 Hz), 3.89–4.00 (2H, m), 4.02–4.11 (4H, m), 6.82 (2H, d, J=8.5 Hz), 7.08 (2H, d, J=8.5 Hz).

(f) Ethyl 2-butyl-3-[4-(2-methanesulfonyloxyethoxy)phenyl]propionate

In a similar manner to that described in Reference example 3(g), a reaction was carried out using ethyl 2-butyl- 3-[4-(2-hydroxyethoxy)phenyl]propionate (1.44 g), which is the product of Reference example 6(e), triethylamine (2.04 ml) and methanesulfonyl chloride (0.76 ml) and the reaction mixture was treated to afford the desired compound (1.65 g) as a syrup.

$^1$H-NMR (270 MHz, CDCl$_3$): δ ppm 0.87 (3H, t, J=7.0 Hz), 1.16 (3H, t, J=7.0 Hz), 1.22–1.39 (4H, m), 1.40–1.70 (2H, m), 2.52–2.61 (1H, m), 2.69 (1H, dd, J=6.5, 13.5 Hz), 2.86 (1H, dd, J=8.5, 13.5 Hz), 3.09 (3H, s), 4.06 (2H, q, J=7.0 Hz), 4.21 (2H, t, J=4.5 Hz), 4.55 (2H, t, J=4.5 Hz), 6.81 (2H, d, J=8.5 Hz), 7.09 (2H, d, J=8.5 Hz).

(g) Ethyl 3-[4-(2-azidoethoxy)phenyl]-2-butylpropionate

In a similar manner to that described in Reference example 3(h), a reaction was carried out using ethyl 2-butyl-3-[4-(2-methanesulfonyloxyethoxy)phenyl]propionate (1.65 g), which is the product of Reference example 6(f), and sodium azide (0.95 g) and the reaction mixture was treated to afford the desired compound (1.62 g) as a syrup.

$^1$H-NMR (270 MHz, CDCl$_3$): δ ppm 0.87 (3H, t, J=7.0 Hz), 1.16 (3H, t, J=7.0 Hz), 1.20–1.39 (3H, m), 1.40–1.70 (3H, m), 2.53–2.64 (1H, m), 2.68 (1H, dd, J=6.5, 13.5 Hz), 2.86 (1H, dd, J=8.5, 13.5 Hz), 3.58 (2H, t, J=5.0 Hz), 4.06 (2H, q, J=7.0 Hz), 4.12 (2H, t, J=5.0 Hz), 6.82 (2H, d, J=8.5 Hz), 7.08 (2H, d, J=8.5 Hz).

(h) Ethyl 3-[4-(2-aminoethoxy)phenyl]-2-butylpropionate

In a similar manner to that described in Reference example 1(d), a reaction was carried out using ethyl 3-[4-(2-azidoethoxy)phenyl]-2-butylpropionate (1.62 g), which is the product of Reference example 6(g), and palladium on carbon (5%, 243 mg) and the reaction mixture was treated to afford the title compound (1.49 g) as a syrup.

Reference Example 7

Ethyl 3-[4-(2-aminoethoxy)phenyl]-2-methyl-2-(3-phenylpropyl)propionate (a) Diethyl 2-methyl-2-(3-phenylpropyl)malonate In a similar manner to that described in Reference example 2(a), a reaction was carried out using diethyl 2-methylmalonate (3.48 g), 3-phenylpropyl bromide (3.98 g) and sodium hydride (55% suspension in oil, 0.96 g) and the reaction mixture was treated to afford the desired compound (4.63 g) as a syrup.

$^1$H-NMR (270 MHz, CDCl$_3$): δ ppm 1.22 (6H, t, J=7.0 Hz), 1.34 (3H, s), 1.50–1.63 (2H, m), 1.88–1.94 (2H, m), 2.62 (2H, t, J=7.5 Hz), 4.16 (4H, q, J=7.0 Hz), 7.15–7.30 (5H, m).

(b) Ethyl 2-methyl-5-phenylvalerate

In a similar manner to that described in Reference example 2(b), a reaction was carried out using diethyl 2-methyl-2-(3-phenylpropyl)malonate (4.63 g) and potassium hydroxide (3.55 g) and the reaction mixture was treated to afford the desired compound (3.18 g) as a syrup.

$^1$H-NMR (270 MHz, CDCl$_3$): δ ppm 1.14 (3H, d, J=7.0 Hz), 1.24 (3H, t, J=7.0 Hz), 1.37–1.54 (1H, m), 1.55–1.87 (3H, m), 2.37–2.44 (1H, m), 2.61 (2H, t, J=7.5 Hz), 4.12 (2H, q, J=7.0 Hz), 7.10–7.35 (5H, m).

(c) Ethyl 2-(4-benzyloxybenzyl)-2-methyl-5-phenylvalerate

A solution of n-butyllithium in hexane (1.65M, 19.4 ml) was added dropwise over a period of 20 minutes at −60° C. to a solution of diisopropylamine (3.23 g) in anhydrous tetrahydrofuran (60 ml). The mixture was stirred at 0° C. for 30 minutes. To this mixture a solution of 2-methyl-5-phenylvalerate (7.05 g) in anhydrous tetrahydrofuran (30 ml) was added dropwise over a period of 20 minutes at −70° C. and the mixture was stirred at −70° C. for 40 minutes. To this reaction mixture a solution of 4-benzyloxybenzyl chloride (9.68 g) in anhydrous tetrahydrofuran (80 ml) was added dropwise at −70° C. The mixture was stirred at −70° C. for 3 hours. At the end of this time the reaction mixture was partitioned between ethyl acetate and water. The ethyl acetate layer was separated and washed with saturated aqueous sodium chloride solution and dried over anhydrous magnesium sulfate and then concentrated under reduced pressure. The residue was purified via chromatography on a silica gel column using hexane/ethyl acetate=15/1 as the eluant to afford the desired compound (1.88 g) as a syrup.

$^1$H-NMR (270 MHz, CDCl$_3$): δ ppm 1.06 (3H, s), 1.19 (3H, t, J=7.0 Hz), 1.38–1.87 (4H, m), 2.51–2.61 (2H, m), 2.62 (1H, d, J=13.5 Hz), 2.93 (1H, d, J=13.5 Hz), 4.08 (2H, q, J=7.0 Hz), 5.01 (2H, s), 6.84 (2H, d, J=8.5 Hz), 6.97 (2H, d, J=8.5 Hz), 7.14–7.49 (10H, m).

(d) Ethyl 2-(4-hydroxybenzyl)-2-methyl-5-phenylvalerate

In a similar manner to that described in Reference example 1(d), a reaction was carried out using ethyl 2-(4-benzyloxybenzyl)-2-methyl-5-phenylvalerate (1.88 g), which is the product of Reference example 7(c), and palladium on carbon (5%, 0.28 g) and the reaction mixture was treated to afford the desired compound (1.58 g) as a syrup.

$^1$H-NMR (270 MHz, CDCl$_3$): δ ppm 1.06 (3H, s), 1.20 (3H, t, J=7.0 Hz), 1.35–1.85 (4H, m), 2.56–2.68 (2H, m), 2.60 (1H, d, J=13.5 Hz), 2.92 (1H, d, J=13.5 Hz), 4.09 (2H, q, J=7.0 Hz), 5.18 (1H, brs), 6.68 (2H, d, J=8.5 Hz), 6.91 (2H, d, J=8.5 Hz), 7.05–7.36 (5H, m).

(e) Ethyl 2-methyl-2-(3-phenylpropyl)-3-[4-[2-(tetrahydropyran-2-yloxy)ethoxy]phenyl]propionate In a similar manner to that described in Reference example 3(e), a reaction was carried out using ethyl 2-(4-hydroxybenzyl)-2-methyl-5-phenylvalerate (1.58 g), which is the product of Reference example 7(d), 2-(2-bromoethoxy)tetrahydropyran (0.94 g) and potassium carbonate (1.86 g) in dimethylacetamide and the reaction mixture was treated to afford the desired compound (1.64 g) as a syrup.

$^1$H-NMR (270 MHz, CDCl$_3$): δ ppm 1.05 (3H, s), 1.21 (3H, t, J=7.10 Hz), 1.35–1.90 (10H, m), 2.50–2.64 (2H, m), 2.62 (1H, d, J=13.5 Hz), 2.93 (1H, d, J=13.5 Hz), 3.45–3.56 (1H, m), 3.67–4.15 (7H, m), 4.71 (1H, t, J=3.5 Hz), 6.80 (2H, d, J=8.5 Hz), 6.96 (2H, d, J=8.5 Hz), 7.11–7.31 (5H, m).

(f) Ethyl 3-[4-(2-hydroxyethoxy)phenyl]-2-methyl-2-(3-phenylpropyl)propionate

In a similar manner to that described in Reference example 3(f), a reaction was carried out using ethyl 2-methyl-2-(3-phenylpropyl)-3-[4-[2-(tetrahydropyran-2-yloxy)ethoxy]phenyl]propionate (1.64 g), which is the product of Reference example 7(e), and p-toluenesulfonic acid monohydrate (0.68 g) and the reaction mixture was treated to afford the desired compound (0.95 g) as a syrup.

$^1$H-NMR (270 MHz, CDCl$_3$): δ ppm 1.06 (3H, s), 1.21 (3H, t, J=7.0 Hz), 1.38–1.82 (4H, m), 2.04 (1H, brs), 2.56–2.65 (3H, m), 2.94 (1H, d, J=13.5 Hz), 3.87–3.97 (2H, m), 3.99–4.14 (4H, m), 6.79 (2H, d, J=8.5 Hz), 6.98 (2H, d, J=8.5 Hz), 7.10–7.31 (5H, m).

(g) Ethyl 3-[4-(2-methanesulfonyloxyethoxy) phenyl]-2-methyl-2-(3-phenylpropyl)propionate In a similar manner to that described in Reference example 3(g), a reaction was carried out using ethyl 3-[4-(2-hydroxyethoxy)phenyl]-2-methyl-2-(3-phenylpropyl) propionate (0.95 g), which is the product of Reference example 7(f), triethylamine (1.07 ml) and methanesulfonyl chloride (0.40 ml) and the reaction mixture was treated to afford the desired compound (1.16 g) as a syrup.

$^1$H-NMR (270 MHz, CDCl$_3$): δ ppm 1.05 (3H, s), 1.21 (3H, t, J=7.0 Hz), 1.38–1.82 (4H, m), 2.59 (2H, t, J=7.0 Hz), 2.62 (1H, d, J=13.5 Hz), 2.94 (1H, d, J=13.5 Hz), 3.08 (3H, s), 4.09 (2H, q, J=7.0 Hz), 4.21 (2H, t, J=4.5 Hz), 4.56 (2H, t, J=4.5 Hz), 6.77 (2H, d, J=8.5 Hz), 6.99 (2H, d, J=8.5 Hz), 7.15–7.31 (5H, m).

(h) Ethyl 3-[4-(2-azidoethoxy)phenyl]-2-methyl-2-(3-phenylpropyl)propionate

In a similar manner to that described in Reference example 3(h), a reaction was carried out using ethyl 3-[4-(2-methanesulfonyloxyethoxy)phenyl]-2-methyl-2-(3-phenylpropyl)propionate (1.16 g), which is the product of Reference example 7(g), and sodium azide (0.50 g) and the reaction mixture was treated to afford the desired compound (0.86 g) as a syrup.

$^1$H-NMR (270 MHz, CDCl$_3$): δ ppm 1.06 (3H, s), 1.21 (3H, t, J=7.0 Hz), 1.38–1.82 (4H, m), 2.56–2.65 (3H, m), 2.94 (1H, d, J=13.5 Hz), 3.58 (2H, t, J=5.0 Hz), 4.05–4.14 (4H, m), 6.78 (2H, d, J=8.5 Hz), 6.99 (2H, d, J=8.5 Hz), 7.15–7.31 (5H, m).

(i) Ethyl 3-[4-(2-aminoethoxy)phenyl]-2-methyl-2-(3-phenylpropyl)propionate

In a similar manner to that described in Reference example 1(d), a reaction was carried out using ethyl 3-[4-(2-azidoethoxy)phenyl]-2-methyl-2-(3-phenylpropyl) propionate (0.86 g), which is the product of Reference example 7(h), and palladium on carbon (5%, 129 mg) and the reaction mixture was treated to afford the title compound (0.80 g) as a syrup.

Reference Example 8

Ethyl 3-[4-(2-aminoethoxy)phenyl]-2-methyl-2-phenoxypropionate (a) Ethyl 3-(4-benzyloxyphenyl)-2-methyl-2-phenoxypropionate In a similar manner to that described in Reference example 7(c), a reaction was carried out using ethyl 2-phenoxypropionate (6.15 g), 4-benzyloxybenzyl chloride (9.62 g) and dicyclohexylamine (5.78 g) instead of diisopropylamine and the reaction mixture was treated to afford the desired compound (4.97 g) as a syrup.

$^1$H-NMR (270 MHz, CDCl$_3$): δ ppm 1.20 (3H, t, J=7.0 Hz), 1.40 (3H, s), 3.11 (1H, d, J=14.0 Hz), 3.28 (1H, d, J=14.0 Hz), 4.19 (2H, q, J=7.0 Hz), 5.04 (2H, s), 6.75–7.02 (5H, m), 7.11–7.47 (9H, m).

(b) Ethyl 3-(4-hydroxyphenyl)-2-methyl-2-phenoxypropionate

In a similar manner to that described in Reference example 1(d), a reaction was carried out using ethyl 3-(4-benzyloxyphenyl)-2-methyl-2-phenoxypropionate (4.97 g), which is the product of Reference example 8(a), and palladium on carbon (5%, 0.75 g) and the reaction mixture was treated to afford the desired compound (3.85 g) as a syrup.

1.20 (3H, t, J=7.0 Hz), 1.40 (3H, s), 3.10 (1H, d, J=14.0 Hz), 3.24 (1H, d, J=14.0 Hz), 4.20 (2H, q, J=7.0 Hz), 6.13 (1H, brs), 6.74 (2H, d, J=8.5 Hz), 6.83 (2H, d, J=8.5 Hz), 6.96 (1H, t, J=7.5 Hz), 7.09 (2H, d, J=8.5 Hz), 7.20 (2H, dd, J=7.5, 8.5 Hz).

(c) Ethyl 2-methyl-2-phenoxy-3-[4-[2-(tetrahydropyran-2-yloxy)ethoxy]phenyl]propionate In a similar manner to that described in Reference example 3(e), a reaction was carried out using ethyl 3-(4-hydroxyphenyl)-2-methyl-2-phenoxypropionate (1.55 g), which is the product of Reference example 8(b), 2-(2-bromoethoxy)tetrahydropyran (1.08 g) and potassium carbonate (2.14 g) in dimethylacetamide and the reaction mixture was treated to afford the desired compound (1.60 g) as a syrup.

$^1$H-NMR (270 MHz, CDCl$_3$): δ ppm 1.21 (3H, t, J=7.0 Hz), 1.39 (3H, s), 1.45–1.90 (6H, m), 3.11 (1H, d, J=13.5 Hz), 3.27 (1H, d, J=13.5 Hz), 3.49–3.56 (1H, m), 3.75–4.15 (5H, m), 4.20 (2H, q, J=7.0 Hz), 4.71 (1H, t, J=3.5 Hz), 6.78–6.90 (4H, m), 6.97 (1H, t, J=7.5 Hz), 7.11–7.25 (4H, m).

(d) Ethyl 3-[4-(2-hydroxyethoxy)phenyl]-2-methyl-2-phenoxypropionate

In a similar manner to that described in Reference example 3(f), a reaction was carried out using ethyl 2-methyl-2-phenoxy-3-[4-[2-(tetrahydropyran-2-yloxy) ethoxy]phenyl]propionate (1.60 g), which is the product of Reference example 8(c), and p-toluenesulfonic acid monohydrate (0.70 g) and the reaction mixture was treated to afford the desired compound (1.10 g) as a syrup.

$^1$H-NMR (270 MHz, CDCl$_3$): δ ppm 1.22 (3H, t, J=7.0 Hz), 1.40 (3H, s), 2.09 (1H, brs), 3.11 (1H, d, J=13.5 Hz), 3.28 (1H, d, J=13.5 Hz), 3.91–4.00 (2H, m), 4.07 (2H, t, J=4.5 Hz), 4.21 (2H, q, J=7.0 Hz), 6.81–6.90 (4H, m), 6.97 (1H, t, J=7.5 Hz), 7.13–7.28 (4H, m).

(e) Ethyl 3-[4-(2-methanesulfonyloxyethoxy) phenyl]-2-methyl-2-phenoxypropionate In a similar manner to that described in Reference example 3(g), a reaction was carried out using ethyl 3-[4-(2-hydroxyethoxy)phenyl]-2-methyl-2-phenoxypropionate (1.10 g), which is the product of Reference example 8(d), triethylamine (0.49 ml) and methanesulfonyl chloride (0.25 ml) and the reaction mixture was treated to afford the desired compound (1.42 g) as a syrup.

$^1$H-NMR (270 MHz, CDCl$_3$): δ ppm 1.22 (3H, t, J=7.0 Hz), 1.40 (3H, s), 3.07 (3H, s), 3.11 (1H, d, J=14.0 Hz), 3.29 (1H, d, J=14.0 Hz), 4.17–4.25 (4H, m), 4.56 (2H, t, J=4.5 Hz), 6.81–6.93 (4H, m), 6.98 (1H, t, J=7.5 Hz), 7.17–7.26 (4H, m).

(f) Ethyl 3-[4-(2-azidoethoxy)phenyl]-2-methyl-2-phenoxypropionate

In a similar manner to that described in Reference example 3(h), a reaction was carried out using ethyl 3-[4-(2-methanesulfonyloxyethoxy)phenyl]-2-methyl-2-phenoxypropionate (i1.42 g), which is the product of Reference example 8(e), and sodium azide (0.66 g) and the reaction mixture was treated to afford the desired compound (0.82 g) as a syrup.

¹H-NMR (270 MHz, CDCl₃): δ ppm 1.22 (3H, t, J=7.0 Hz), 1.40 (3H, s), 3.12 (1H, d, J=14.0 Hz), 3.29 (1H, d, J=14.0 Hz), 3.58 (2H, t, J=5.0 Hz), 4.13 (2H, t, J=5.0 Hz), 4.20 (2H, q, J=7.0 Hz), 6.82–6.89 (4H, m), 6.97 (1H, t, J=7.5 Hz), 7.17–7.27 (4H, m).

(g) Ethyl 3-[4-(2-aminoethoxy)phenyl]-2-methyl-2-phenoxypropionate

In a similar manner to that described in Reference example 1(d), a reaction was carried out using ethyl 3-[4-(2-azidoethoxy)phenyl]-2-methyl-2-phenoxypropionate (0.82 g), which is the product of Reference example 8(f), and palladium on carbon (5%, 123 mg) and the reaction mixture was treated to afford the title compound (0.76 g) as a syrup.

Reference Example 9

3-[4-(2-aminoethoxy)phenyl]-2-(4-isopropylphenoxy)-2-methylpropionate

(a) Ethyl 3-(4-benzyloxyphenyl)-2-(4-isopropylphenoxy)-2-methylpropionate

In a similar manner to that described in Reference example 7(c), a reaction was carried out using ethyl 2-(4-isopropylphenoxy)propionate (4.72 g) and 4-benzyloxybenzyl chloride (6.00 g) and dicyclohexylamine (3.62 g) instead of diisopropylamine and the reaction mixture was treated to afford the desired compound (6.16 g) as a syrup.

¹H-NMR (270 MHz, CDCl₃): δ ppm 1.20 (6H, d, J=7.0 Hz), 1.21 (3H, t, J=7.5 Hz), 1.38 (3H, s), 2.83 (1H, septet, J=7.0 Hz), 3.11 (1H, d, J=13.5 Hz), 3.25 (1H, d, J=13.5 Hz), 4.20 (2H, q, J=7.5 Hz), 5.05 (2H, s), 6.75 (2H, d, J=8.5 Hz), 6.91 (2H, d, J=8.5 Hz), 7.06 (2H, d, J=8.5 Hz), 7.18 (2H, d, J=8.5 Hz), 7.30–7.45 (5H, m).

(b) Ethyl 3-(4-hydroxyphenyl)-2-(4-isopropylphenoxy)-2-methylpropionate

In a similar manner to that described in Reference example 1(d), a reaction was carried out using ethyl 3-(4-benzyloxyphenyl)-2-(4-isopropylphenoxy)-2-methylpropionate (6.16 g), which is the product of Reference example 9(a), and palladium on carbon (5%, 1.00 g) and the reaction mixture was treated to afford the title compound (4.18 g) as a syrup.

¹H-NMR (270 MHz, CDCl₃): δ ppm 1.20 (6H, d, J=7.0 Hz), 1.22 (3H, t, J=7.5 Hz), 1.38 (3H, s), 2.83 (1H, septet, J=7.0 Hz), 3.10 (1H, d, J=13.5 Hz), 3.24 (1H, d, J=13.5 Hz), 4.20 (2H, q, J=7.5 Hz), 4.81 (1H, s), 6.75 (4H, d, J=8.5 Hz), 7.06 (2H, d, J=8.5 Hz), 7.13 (2H, d, J=8.5 Hz).

(c) Ethyl 2-(4-isopropylphenoxy)-2-methyl-3-[4-[2-(tetrahydropyran-2-yloxy)ethoxy]phenyl]propionate In a similar manner to that described in Reference example 3(e), a reaction was carried out using ethyl 3-(4-hydroxyphenyl)-2-(4-isopropylphenoxy)-2-methylpropionate (1.00 g), which is the product of Reference example 9(b), 2-(2-bromoethoxy)tetrahydropyran (1.84 g) and potassium carbonate (1.62 g) in dimethylacetamide and the reaction mixture was treated to afford the desired compound (1.06 g) as a syrup.

¹H-NMR (270 MHz, CDCl₃): δ ppm 1.20 (6H, d, J=7.0 Hz), 1.23 (3H, t, J=7.0 Hz), 1.36 (3H, s), 1.48–1.90 (6H, m), 2.83 (1H, septet, J=7.0 Hz), 3.10 (1H, d, J=13.5 Hz), 3.25 (1H, d, J=13.5 Hz), 3.48–3.57 (1H, m), 3.78–3.96 (2H, m), 4.01–4.25 (5H, m), 4.70–4.73 (1H, m), 6.75 (2H, d, J=8.5 Hz), 6.86 (2H, d, J=8.5 Hz), 7.06 (2H, d, J=8.5 Hz), 7.17 (2H, d, J=8.5 Hz).

(d) Ethyl 2-(4-isopropylphenoxy)-3-[4-(2-hydroxyethoxy)phenyl]-2-methylpropionate In a similar manner to that described in Reference example 3(t), a reaction was carried out using ethyl 2-(4-isopropylphenoxy)-2-methyl-3-[4-[2-(tetrahydropyran-2-yloxy)ethoxy]phenyl]propionate (1.06 g), which is the product of Reference example 9(c), and p-toluenesulfonic acid monohydrate (0.60 g) and the reaction mixture was treated to afford the desired compound (0.66 g) as a syrup.

¹H-NMR (270 MHz, CDCl₃): δ ppm 1.20 (6H, d, J=7.0 Hz), 1.23 (3H, t, J=7.0 Hz), 1.37 (3H, s), 2.01 (1H, t, J=6.0 Hz), 2.83 (1H, septet, J=7.0 Hz), 3.11 (1H, d, J=13.5 Hz), 3.26 (1H, d, J=13.5 Hz), 3.93–4.00 (2H, m), 4.05–4.10 (2H, m), 4.21 (2H, q, J=7.0 Hz), 6.75 (2H, d, J=8.5 Hz), 6.85 (2H, d, J=8.5 Hz), 7.06 (2H, d, J=8.5 Hz), 7.19 (2H, d, J=8.5 Hz).

(e) Ethyl 2-(4-isopropylphenoxy)-3-[4-(2-methanesulfonyloxyethoxy)phenyl]-2-methylpropionate In a similar manner to that described in Reference example 3(g), a reaction was carried out using ethyl 2-(4-isopropylphenoxy)-3-[4-(2-hydroxyethoxy)phenyl]-2-methylpropionate (0.66 g), which is the product of Reference example 9(d), triethylamine (0.36 ml) and methanesulfonyl chloride (0.15 ml) and the reaction mixture was treated to afford the desired compound (0.64 g) as a syrup.

¹H-NMR (270 MHz, CDCl₃): δ ppm 1.20 (6H, d, J=7.0 Hz), 1.23 (3H, t, J=7.0 Hz), 1.37 (3H, s), 2.83 (1H, septet, J=7.0 Hz), 3.09 (3H, s), 3.11 (1H, d, J=13.5 Hz), 3.26 (1H, d, J=13.5 Hz), 4.21 (2H, q, J=7.0 Hz), 4.22–4.26 (2H, m), 4.55–4.59 (2H, m), 6.75 (2H, d, J=8.5 Hz), 6.83 (2H, d, J=8.5 Hz), 7.06 (2H, d, J=8.5 Hz), 7.20 (2H, d, J=8.5 Hz).

(f) Ethyl 3-[4-(2-azidoethoxy)phenyl]-2-(4-isopropylphenoxy)-2-methylpropionate In a similar manner to that described in Reference example 3(h), a reaction was carried out using ethyl 2-(4-isopropylphenoxy)-3-[4-(2-methanesulfonyloxyethoxy)phenyl]-2-methylpropionate (0.64 g), which is the product of Reference example 9(e), and sodium azide (0.27 g) and the reaction mixture was treated to afford the desired compound (0.56 g) as a syrup.

¹H-NMR (270 MHz, CDCl₃): δ ppm 1.20 (6H, d, J=7.0 Hz), 1.23 (3H, t, J=7.0 Hz), 1.37 (3H, s), 2.83 (1H, septet, J=7.0 Hz), 3.11 (1H, d, J=13.5 Hz), 3.26 (1H, d, J=13.5 Hz), 3.59 (2H, t, J=5.0 Hz), 4.14 (2H, t, J=5.0 Hz), 4.21 (2H, q, J=7.0 Hz), 6.75 (2H, d, J=8.5 Hz), 6.85 (2H, d, J=8.5 Hz), 7.06 (2H, d, J=8.5 Hz), 7.19 (2H, d, J=8.5 Hz).

(g) Ethyl 3-[4-(2-aminoethoxy)phenyl]-2-(4-isopropylphenoxy)-2-methylpropionate In a similar manner to that described in Reference example 1(d), a reaction was carried out using ethyl 3-[4-(2-azidoethoxy)phenyl]-2-(4-isopropylphenoxy)-2-methylpropionate (0.56 g), which is the product of Reference example 9(f), and palladium on carbon (5%, 60 mg) and the reaction mixture was treated to afford the title compound (0.51 g) as a syrup.

¹H-NMR (270 MHz, CDCl₃): δ ppm 1.20 (6H, d, J=7.0 Hz), 1.23 (3H, t, J=7.0 Hz), 1.37 (3H, s), 1.63 (2H, brs), 2.83

(1H, septet, J=7.0 Hz), 3.08 (2H, t, J=5.0 Hz), 3.10 (1H, d, J=13.5 Hz), 3.25 (1H, d, J=13.5 Hz), 3.92–4.13 (2H, m), 4.21 (2H, q, J=7.0 Hz), 6.75 (2H, d, J=8.5 Hz), 6.84 (2H, d, J=8.5 Hz), 7.06 (2H, d, J=8.5 Hz), 7.18 (2H, d, J=8.5 Hz).

Reference Example 10

Ethyl 3-[4-(2-aminoethoxy)phenyl]-2-butyl-2-methylpropionate (a) Ethyl 2-(4-benzyloxybenzyl)-2-methylcaproate In a similar manner to that described in Reference example 7(c), a reaction was carried out using ethyl 2-(4-benzyloxybenzyl)caproate (2.04 g) and methyl iodide (1.12 ml) instead of 4-benzyloxybenzyl chloride and cyclohexylisopropylamine (1.48 ml) instead of diisopropylamine and the reaction mixture was treated to afford the desired compound (1.80 g) as a syrup.

$^1$H-NMR (270 MHz, CDCl$_3$): δ ppm 0.89 (3H, t, J=7.0 Hz), 1.06 (3H, s), 1.10–1.45 (8H, m), 1.63–1.79 (1H, m), 2.63 (1H, d, J=13.5 Hz), 2.96 (1H, d, J=13.5 Hz), 4.10 (2H, q, J=7.0 Hz), 5.03 (2H, s), 6.86 (2H, d, J=8.5 Hz), 7.02 (2H, d, J=8.5 Hz), 7.25–7.46 (5H, m).

(b) Ethyl 2-butyl-3-(4-hydroxyphenyl)-2-methylpropionate

In a similar manner to that described in Reference example 1(d), a reaction was carried out using ethyl 2-(4-benzyloxybenzyl)-2-methylcaproate (3.95 g), which is the product of Reference example 10(a), and palladium on carbon (5%, 0.40 g) and the reaction mixture was treated to afford the desired compound (2.95 g) as a syrup.

$^1$H-NMR (270 MHz, CDCl$_3$): δ ppm 0.89 (3H, t, J=7.0 Hz), 1.06 (3H, s), 1.10–1.45 (8H, m), 1.62–1.79 (1H, m), 2.61 (1H, d, J=13.5 Hz), 2.95 (1H, d, J=13.5 Hz), 4.10 (2H, q, J=7.0 Hz), 4.80 (1H, brs), 6.71 (2H, d, J=8.5 Hz), 6.96 (2H, d, J=8.5 Hz).

(c) Ethyl 2-butyl-2-methyl-3-[4-[2-(tetrahydropyran-2-yloxy)ethoxy]phenyl]propionate In a similar manner to that described in Reference example 3(e), a reaction was carried out using ethyl 2-butyl-3-(4-hydroxyphenyl)-2-methylpropionate (2.95 g), which is the product of Reference example 10(b), 2-(2-bromoethoxy)tetrahydropyran (4.66 g) and potassium carbonate (4.62 g) in dimethylacetamide and the reaction mixture was treated to afford the desired compound (4.18 g) as a syrup.

$^1$H-NMR (270 MHz, CDCl$_3$): δ ppm 0.89 (3H, t, J=7.0 Hz), 1.05 (3H, s), 1.11–1.43 (8H, m), 1.47–1.90 (7H, m), 2.62 (1H, d, J=13.5 Hz), 2.95 (1H, d, J=13.5 Hz), 3.48–3.57 (1H, m), 3.64–4.18 (7H, m), 4.67–4.72 (1H, m), 6.81 (2H, d, J=8.5 Hz), 7.00 (2H, d, J=8.5 Hz).

(d) Ethyl 2-butyl-3-[4-(2-hydroxyethoxy)phenyl]-2-methylpropionate

In a similar manner to that described in Reference example 3(f), a reaction was carried out using ethyl 2-butyl-2-methyl-3-[4-[2-(tetrahydropyran-2-yloxy)ethoxy]phenyl]propionate (4.18 g), which is the product of Reference example 10(c), and p-toluenesulfonic acid monohydrate (2.61 g) and the reaction mixture was treated to afford the desired compound (2.73 g) as a syrup.

$^1$H-NMR (270 MHz, CDCl$_3$): δ ppm 0.90 (3H, t, J=7.0 Hz), 1.06 (3H, s), 1.10–1.47 (8H, m), 1.65–1.78 (1H, m), 2.04 (1H, brs), 2.63 (1H, d, J=13.5 Hz), 2.96 (1H, d, J=13.5 Hz), 3.91–3.98 (2H, m), 4.04–4.17 (4H, m), 6.81 (2H, d, J=8.5 Hz), 7.02 (2H, d, J=8.5 Hz).

(e) Ethyl 2-butyl-3-[4-(2-methanesulfonyloxyethoxy)phenyl]-2-methylpropionate

In a similar manner to that described in Reference example 3(g), a reaction was carried out using ethyl 2-butyl-3-[4-(2-hydroxyethoxy)phenyl]-2-methylpropionate (2.73 g), which is the product of Reference example 10(d), triethylamine (1.85 ml) and methanesulfonyl chloride (0.75 ml) and the reaction mixture was treated to afford the desired compound (3.17 g) as a syrup.

$^1$H-NMR (270 MHz, CDCl$_3$): δ ppm 0.89 (3H, t, J=7.0 Hz), 1.06 (3H, s), 1.10–1.44 (8H, m), 1.66–1.80 (1H, m), 2.62 (1H, d, J=13.5 Hz), 2.97 (1H, d, J=13.5 Hz), 3.08 (3H, s), 4.11 (2H, q, J=7.5 Hz), 4.20–4.23 (2H, m), 4.54–4.58 (2H, m), 6.79 (2H, d, J=8.5 Hz), 7.03 (2H, d, J=8.5 Hz).

(f) Ethyl 3-[4-(2-azidoethoxy)phenyl]-2-butyl-2-methylpropionate

In a similar manner to that described in Reference example 3(h), a reaction was carried out using ethyl 2-butyl-3-[4-(2-methanesulfonyloxyethoxy)phenyl]-2-methylpropionate (3.17 g), which is the product of Reference example 10(e), and sodium azide (1.60 g) and the reaction mixture was treated to afford the desired compound (2.80 g) as a syrup.

$^1$H-NMR (270 MHz, CDCl$_3$): δ ppm 0.90 (3H, t, J=7.0 Hz), 1.06 (3H, s), 1.10–1.44 (8H, m), 1.66–1.78 (1H, m), 2.63 (1H, d, J=13.5 Hz), 2.96 (1H, d, J=13.5 Hz), 3.58 (2H, t, J=5.0 Hz), 4.11 (2H, q, J=7.5 Hz), 4.12 (2H, t, J=5.0 Hz), 6.81 (2H, d, J=8.5 Hz), 7.03 (2H, d, J=8.5 Hz).

(g) Ethyl 3-[4-(2-aminoethoxy)phenyl]-2-butyl-2-methylpropionate

In a similar manner to that described in Reference example 1(d), a reaction was carried out using ethyl 3-[4-(2-azidoethoxy)phenyl]-2-butyl-2-methylpropionate (2.73 g), which is the product of Reference example 10(f), and palladium on carbon (5%, 270 mg) and the reaction mixture was treated to afford the title compound (2.42 g) as a syrup.

$^1$H-NMR (270 MHz, CDCl$_3$): δ ppm 0.89 (3H, t, J=7.0 Hz), 1.06 (3H, s), 1.10–1.43 (9H, m), 1.71 (2H, brs), 2.62 (1H, d, J=13.5 Hz), 2.96 (1H, d, J=13.5 Hz), 3.07 (2H, t, J=5.0 Hz), 3.91–4.10 (2H, m), 4.11 (2H, q, J=7.0 Hz), 6.80 (2H, d, J=8.5 Hz), 7.01 (2H, d, J=8.5 Hz).

Reference Example 11

Ethyl 2-butyl-3-[4-[2-(4'-dimethoxymethylbiphenyl-4-carbonylamino)ethoxy]phenyl]propionate (a) Methyl 4'-dimethoxymethylbiphenyl-4-carboxylate Methyl orthoformate (4.55 ml) and amberlyst 15 (200 mg) were added to a solution of methyl 4'-formylbiphenyl-4-carboxylate (2.00 g) in methanol (20 ml). The mixture was allowed to stand at ambient temperature for 14 hours. The amberlyst was removed by filtration and the filtrate was concentrated under reduced pressure. Excess methyl orthoformate was azeotropicaly evaporated off with toluene.

The residue was crystallized from diisopropyl ether to afford the desired compound (2.23 g) as colorless crystals.

mp 76–77° C.

¹H-NMR (270 MHz, CDCl₃): δ ppm 3.37 (6H, s), 3.94 (3H, s), 5.45 (1H, s), 7.55 (2H, d, J=8.5 Hz), 7.64 (2H, d, J=8.5 Hz), 7.67 (2H, d, J=8.5 Hz), 8.11 (2H, d, J=8.5 Hz).

(b) 4'-Dimethoxymethylbiphenyl-4-carboxylic acid

In a similar manner to that described in Example 2, a reaction was carried out using methyl 4'-dimethoxymethylbiphenyl-4-carboxylate (1.89 g), which is the product of Reference example 11(a), and aqueous sodium hydroxide (1N, 9.90 ml) and the reaction mixture was treated to afford the desired compound (1.80 g) as colorless crystals.

mp 164° C.

¹H-NMR (270 MHz, deuterated dimethyl sulfoxide): δ ppm 3.28 (6H, s), 5.45 (1H, s), 7.51 (2H, d, J=8.5 Hz), 7.76 (2H, d, J=8.5 Hz), 7.81 (2H, d, J=8.5 Hz), 8.02 (2H, d, J=8.5 Hz).

(c) Ethyl 2-butyl-3-[4-[2-(4'-dimethoxymethylbiphenyl-4-carbonylamino)ethoxy]phenyl]propionate In a similar manner to that described in Example 5, a reaction was carried out using ethyl 3-[4-(2-aminoethoxy)phenyl]-2-butylpropionate (1.81 g), which is the product of Reference example 6, 4'-dimethoxymethylbiphenyl-4-carboxylic acid (1.68 g), which is the product of reference example 11(b), and carbonyldiimidazole (1.20 g) and the reaction mixture was treated to afford the desired compound (2.77 g) as a pale brown solid.

¹H-NMR (270 MHz, CDCl₃): δ ppm 0.86 (3H, t, J=7.0 Hz), 1.16 (3H, t, J=7.0 Hz), 1.22–1.36 (4H, m), 1.38–1.49 (1H, m), 1.51–1.71 (1H, m), 2.52–2.63 (1H, m), 2.68 (1H, dd, J=6.5, 13.5 Hz), 2.86 (1H, dd, J=8.5, 13.5 Hz), 3.36 (6H, s), 3.88 (2H, q, J=5.0 Hz), 4.05 (2H, q, J=7.0 Hz), 4.14 (2H, t, J=5.0 Hz), 5.45 (1H, s), 6.65 (1H, brt), 6.83 (2H, d, J=8.5 Hz), 7.08 (2H, d, J=8.5 Hz), 7.54 (2H, d, J=8.5 Hz), 7.62 (2H, d, J=8.5 Hz), 7.66 (2H, d, J=8.5 Hz), 7.85 (2H, d, J=8.5 Hz).

Reference Example 12

Ethyl 2-butyl-3-[4-[2-(4'-methoxycarbonylbiphenyl-4-carbonylamino)ethoxy]phenyl]propionate In a similar manner to that described in Example 5, a reaction was carried out using ethyl 3-[4-(2-aminoethoxy)phenyl]-2-butylpropionate (375 mg), which is the product of Reference example 6, 4'-methoxycarbonylbiphenyl-4-carboxylic acid (328 mg) and carbonyldiimidazole (225 mg) and the reaction mixture was treated to afford the title compound (257 mg) as colorless crystals.

mp 93–95° C.

¹H-NMR (270 MHz, CDCl₃): δ ppm 0.86 (3H, t, J=6.5 Hz), 1.16 (3H, t, J=7.0 Hz), 1.21–1.36 (4H, m), 1.40–1.67 (2H, m), 2.52–2.63 (1H, m), 2.68 (1H, dd, J=6.5, 13.5 Hz), 2.88 (1H, dd, J=8.5, 13.5 Hz), 3.89 (2H, t, J=5.0 Hz), 3.95 (3H, s), 4.05 (2H, q, J=7.0 Hz), 4.15 (2H, t, J=5.0 Hz), 6.63 (1H, brs), 6.84 (2H, d, J=8.5 Hz), 7.09 (2H, d, J=8.5 Hz), 7.68 (2H, d, J=8.5 Hz), 7.69 (2H, d, J=8.5 Hz), 7.88 (2H, d, J=8.5 Hz), 8.12 (2H, d, J=8.5 Hz).

Reference Example 13

3'-Hydroxybiphenyl-4-carboxylic acid

A solution of boron tribromide in dichloromethane (1N, 24.8 ml) was added to a solution of methyl 3'-methoxybiphenyl-4-carboxylate (2.00 g) in anhydrous dichloromethane (10 ml) at −70° C. The mixture was stirred at ambient temperature for 4 hours and a mixture of ice and water was added to the reaction mixture in an ice bath and then the mixture was stirred for 30 minutes. The reaction mixture was concentrated under reduced pressure. The residue was partitioned between ethyl acetate and water and the layers were separated. The ethyl acetate layer was dried over anhydrous magnesium sulfate and concentrated under reduced pressure. The residue was crystallized from a mixture of hexane and diisopropyl ether to afford the title compound (1.82 g) as pale yellow crystals.

mp 250–253° C.

¹H-NMR (270 MHz, CDCl₃): δ ppm 6.89 (1H, d, J=8.0 Hz), 7.11 (1H, d, J=8.0 Hz), 7.13 (1H, s), 7.28 (1H, t, J=8.0 Hz), 7.64 (2H, d, J=8.5 Hz), 8.12 (2H, d, J=8.5 Hz).

Reference Example 14

Ethyl 2-butyl-3-[4-[2-(3'-dimethoxymethylbiphenyl-4-carbonylamino)ethoxy]phenyl]propionate (a) Methyl 3'-formylbiphenyl-4-carboxylate A solution of tetrakis(triphenylphosphine)palladium (297 mg) was added to a solution of 3-formylphenylboric acid (3.00 g) and methyl 4-bromobenzoic acid (4.30 g) in a mixture of toluene (30 ml), ethanol (50 ml) and saturated aqueous sodium hydrogencarbonate solution (30 ml) at ambient temperature. The mixture was heated at reflux for 2 hours at 100° C. The reaction mixture was partitioned between ethyl acetate and water and the layers were separated. The ethyl acetate layer was washed with saturated aqueous sodium chloride solution and dried over anhydrous magnesium sulfate and concentrated under reduced pressure. The residue was crystallized from diisopropyl ether to afford the title compound (3.37 g) as colorless crystals.

mp 95–97° C.

¹H-NMR (270 MHz, CDCl₃): δ ppm 3.96 (3H, s), 7.65 (1H, d, J=7.5 Hz), 7.70 (2H, d, J=8.5 Hz), 7.88–7.93 (2H, m), 8.14 (1H, s), 8.15 (2H, d, J=8.5 Hz), 10.11 (1H, s).

(b) Methyl 3'-dimethoxymethylbiphenyl-4-carboxylate

In a similar manner to that described in Example 11(a), a reaction was carried out using methyl 3'-formylbiphenyl-4-carboxylate (1.60 g), which is the product of Reference example 14(a), methyl orthoformate (3.64 ml) and amberlyst 15 (160 mg) and the reaction mixture was treated to afford the desired compound (1.91 g) as a syrup.

¹H-NMR (270 MHz, CDCl₃): δ ppm 3.37 (6H, s), 3.94 (3H, s), 5.46 (1H, s), 7.47 (1H, d, J=4.5 Hz), 7.49 (1H, d, J=2.5 Hz), 7.57–7.64 (1H, m), 7.68 (2H, d, J=8.5 Hz), 7.72 (1H, s), 8.11 (2H, d, J=8.5 Hz).

(c) 3'-Dimethoxymethylbiphenyl-4-carboxylic acid

In a similar manner to that described in Example 2, a reaction was carried out using methyl 3'-dimethoxymethylbiphenyl-4-carboxylate (1.91 g), which is the product of Reference example 14(b), and aqueous sodium hydroxide (1N, 10.0 ml) and the reaction mixture was treated to afford the desired compound (1.55 g) as colorless crystals.

mp 130–131° C.

¹H-NMR (270 MHz, CDCl₃): δ ppm 3.38 (6H, s), 5.48 (1H, s), 7.49 (1H, d, J=5.0 Hz), 7.49 (1H, d, J=3.5 Hz), 7.59–7.66 (1H, m), 7.73 (2H, d, J=8.5 Hz), 7.75 (1H, s), 8.19 (2H, d, J=8.5 Hz).

(d) Ethyl 2-butyl-3-[4-[2-(3'-dimethoxymethylbiphenyl-4-carbonylamino)ethoxy]phenyl]propionate In a similar manner to that described in Example 5, a reaction was carried out using ethyl 3-[4-(2-aminoethoxy)phenyl]-2-butylpropionate (1.55 g), which is the product of Reference example 6, 3'-dimethoxymethylbiphenyl-4-carboxylic acid (1.44 g), which is the product of reference example 14(c), and carbonyldiimidazole (1.03 g) and the reaction mixture was treated to afford the desired compound (2.72 g) as a syrup.

$^1$H-NMR (270 MHz, CDCl$_3$): δ ppm 0.87 (3H, t, J=7.0 Hz), 1.16 (3H, t, J=7.0 Hz), 1.21–1.35 (4H, m), 1.39–1.56 (1H, m), 1.58–1.67 (1H, m), 2.53–2.65 (1H, m), 2.69 (1H, dd, J=6.5, 13.5 Hz), 2.86 (1H, dd, J=8.5, 13.5 Hz), 3.37 (6H, s), 3.89 (2H, q, J=5.0 Hz), 4.06 (2H, q, J=7.0 Hz), 4.15 (2H, t, J=5.0 Hz), 5.45 (1H, s), 6.64(1H, brt), 6.84 (2H, d, J=8.5 Hz), 7.08 (2H, d, J=8.5 Hz), 7.46 (1H, d, J=5.0 Hz), 7.47 (1H, d, J=3.0 Hz), 7.54–7.61 (1H, m), 7.68 (2H, d, J=8.5 Hz), 7.71 (1H, s), 7.85 (2H, d, J=8.5 Hz).

Reference Example 15

Sodium 2-butyl-3-[4-[2-(3'-ethoxymethoxymethylbiphenyl-4-carbonylamino)ethoxy]phenyl]propionate (a) Methyl 3'-hydroxymethylbiphenyl-4-carboxylate Sodium borohydride (132 mg) was added to a solution of methyl 3'-formylbiphenyl-4-carboxylate (720 mg), which is the product of Reference example 14(a), in ethanol (50 ml) at ambient temperature. The mixture was stirred under an atmosphere of nitrogen for 50 minutes. The reaction mixture was quenched with 50% acetic acid and concentrated under reduced pressure. The residue was partitioned between ethyl acetate and water and the layers were separated. The ethyl acetate layer was washed with saturated aqueous sodium chloride solution and dried over anhydrous magnesium sulfate and concentrated under reduced pressure. The residue was crystallized from diisopropyl ether to afford the desired compound (522 mg) as colorless crystals.

mp 88–89° C.

$^1$H-NMR (270 MHz, CDCl$_3$): δ ppm 3.95 (3H, s), 4.79 (2H, s), 7.40 (1H, d, J=7.5 Hz), 7.47 (1H, t, J=7.5 Hz), 7.56 (1H, d, J=7.5 Hz), 7.64 (1H,s), 7.67 (2H, d, J=8.5 Hz), 8.11 (2H, d, J=8.5 Hz).

(b) Methyl 3'-methoxymethoxymethylbiphenyl-4-carboxylate

Chloromethylmethyl ether (0.24 ml) and diisopropylethylamine (0.74 ml) was added to a solution of methyl 3'-hydroxymethylbiphenyl-4-carboxylate (504 mg), which is the product of Reference example 15(a), in anhydrous dichloromethane (10 ml) at 0° C. The mixture was stirred at 0° C. for 1 hour and then allowed to stand at ambient temperature for 14 hours. The reaction mixture was concentrated under reduced pressure. The residue was partitioned between ethyl acetate and water and the layers were separated. The ethyl acetate layer was washed with saturated aqueous sodium chloride solution and dried over anhydrous magnesium sulfate and concentrated under reduced pressure. The residue was purified via chromatography on a silica gel column using hexane/ethyl acetate=2/1 as the eluant to afford the desired compound (467 mg) as colorless crystals.

mp 54–55° C.

$^1$H-NMR (270 MHz, CDCl$_3$): δ ppm 3.44 (3H, s), 3.94 (3H, s), 4.67 (2H, s), 4.75 (2H, s), 7.39 (1H, d, J=7.5 Hz), 7.46 (1H, t, J=7.5 Hz), 7.56 (1H, d, J=7.5 Hz), 7.63 (1H, s), 7.67 (2H, d, J=8.5 Hz), 8.11 (2H, d, J=8.5 Hz).

(c) 3'-Methoxymethoxylmethylbiphenyl-4-carboxylic acid

In a similar manner to that described in Example 2, a reaction was carried out using methyl 3'-methoxymethoxymethylbiphenyl-4-carboxylate (445 mg), which is the product of Reference example 15(b), and aqueous sodium hydroxide (1N, 3.10 ml) and the reaction mixture was treated to afford the desired compound (342 mg) as colorless crystals.

mp 126–127° C.

$^1$H-NMR (270 MHz, CDCl$_3$): δ ppm 3.45 (3H, s), 4.68 (2H, s), 4.76 (2H, s), 7.41 (1H, d, J=7.5 Hz), 7.47 (1H, t, J=7.5 Hz), 7.58 (1H, d, J=7.5 Hz), 7.64 (1H, s), 7.71 (2H, d, J=8.5 Hz), 8.17 (2H, d, J=8.5 Hz).

(d) Ethyl 2-butyl-3-[4-[2-(3'-methoxymethoxymethylbiphenyl-4-carbonylamino)ethoxy]phenyl]propionate In a similar manner to that described in Example 5, a reaction was carried out using ethyl 3-[4-(2-aminoethoxy)phenyl]-2-butylpropionate (358 mg), which is the product of Reference example 6, 3'-methoxymethoxymethylbiphenyl-4-carboxylic acid (333 mg), which is the product of reference example 15(c), and carbonyldiimidazole (238 mg) and the reaction mixture was treated to afford the desired compound (573 mg) as a brown syrup.

$^1$H-NMR (270 MHz, CDCl$_3$): δ ppm 0.87 (3H, t, J=7.0 Hz), 1.16 (3H, t, J=7.0 Hz), 1.22–1.39 (4H, m), 1.40–1.51 (1H, m), 1.54–1.67 (1H, m), 2.53–2.63 (1H, m), 2.68 (1H, dd, J=6.5, 13.5 Hz), 2.86 (1H, dd, J=8.5, 13.5 Hz), 3.44 (3H, s), 3.88 (2H, q, J=5.0 Hz), 4.05 (2H, q, J=7.0 Hz), 4.14 (2H, t, J=5.0 Hz), 4.67 (2H, s), 4.74 (2H, s), 6.69 (1H, brt), 6.84 (2H, d, J=8.5 Hz), 7.08 (2H, d, J=8.5 Hz), 7.38 (1H, d, J=7.5 Hz), 7.45 (1H, t, J=7.5 Hz), 7.54 (2H, d, J=7.5 Hz), 7.60 (1H, s), 7.66 (2H, d, J=8.5 Hz), 7.86 (2H, d, J=8.5 Hz).

(e) Sodium 2-butyl-3-[4-[2-(3'-methoxymethoxymethylbiphenyl-4-carbonylamino)ethoxy]phenyl]propionate In a similar manner to that described in Example 2, a reaction was carried out using ethyl 2-butyl-3-[4-[2-(3'-methoxymethoxymethylbiphenyl-4-carbonylamino)ethoxy]phenyl]propionate (573 mg), which is the product of Reference example 15(d), and aqueous sodium hydroxide (1N, 2.00 ml) and the reaction mixture was treated to afford the desired compound (472 mg) as a white powder.

mp 216–218° C.

$^1$H-NMR (270 MHz, deuterated methanol): δ ppm 0.85 (3H, t, J=7.0 Hz), 1.17–1.40 (4H, m), 1.46–1.60 (2H, m), 2.36–2.46 (1H, m), 2.52 (1H, dd, J=7.0, 13.5 Hz), 2.86 (1H, dd, J=7.5, 13.5 Hz), 3.41 (3H, s), 3.77 (2H, t, J=5.5 Hz), 4.14 (2H, t, J=5.5 Hz), 4.66 (2H, s), 4.73 (2H, s), 6.84 (2H, d, J=8.5 Hz), 7.13 (2H, d, J=8.5 Hz), 7.38 (1H, d, J=7.5 Hz), 7.45 (1H, t, J=7.5 Hz), 7.60 (1H, d, J=7.5 Hz), 7.66 (1H, s), 7.72 (2H, d, J=8.5 Hz), 7.91 (2H, d, J=8.5 Hz).

Reference Example 16

2'-Hydroxybiphenyl-4-carboxylic acid

In a similar manner to that described in Example 2, a reaction was carried out using methyl 2'-hydroxybiphenyl- 4-carboxylate (498 mg) and aqueous sodium hydroxide (1N, 4.81 ml) and the reaction mixture was treated to afford the title compound (434 mg) as colorless crystals.

mp 176–178° C.

$^1$H-NMR (270 MHz, CDCl$_3$/deuterated methanol=20/1): δ ppm 6.92–7.05 (2H, m), 7.21–7.32 (2H, m), 7.64 (2H, d, J=8.5 Hz), 8.15 (2H, d, J=8.5 Hz).

Reference Example 17

2-Butyl-3-[4-[2-(4'-methoxymethoxy-3',5'-dimethylbiphenyl-4-carbonylamino)ethoxy]phenyl] propionic acid (a) Methyl 4'-methoxymethoxy-3',5'-dimethylbiphenyl-4-carboxylate A solution of 5-bromo-2-methoxymethoxy-1,3-dimethylbenzene (3.35 g) in tetrahydrofliran (7.0 ml) was added dropwise a period of 15 minutes to a suspension of magnesium (327 mg) in tetrahydrofuran (45 ml) at 65° C. The mixture was stirred at 80° C. for 1 hour to prepare a Grignard reagent. This solution was added dropwise to a solution of trimethyl borate (2.00 ml) in anhydrous diethyl ether (20 ml) over a period of 30 minutes at −50° C. The mixture was stirred at room temperature for 2 hours. At the end of this time the reaction was quenched with potassium hydrogensulfate and partitioned between ethyl acetate and water. The ethyl acetate layer was separated and washed with saturated aqueous sodium chloride solution and dried over anhydrous magnesium sulfate and then concentrated under reduced pressure. The residue was crystallized from diisopropyl ether to afford 4'-methoxymethoxy-3',5'-dimethylphenyl borate (1.04 g) as colorless crystals.

In a similar manner to that described in Reference example 14(a), a reaction was carried out using 4'-methoxymethoxy-3',5'-dimethylphenyl borate obtained above (1.04 g), methyl 4-bromobenzoic acid (1 06 g) and tetrakis(triphenylphosphine)palladium (96 mg) and the reaction mixture was treated to afford the desired compound (1.36 g) as colorless crystals.

mp 100–101° C.

$^1$H-NMR (270 MHz, CDCl$_3$): δ ppm 2.37 (6H, s), 3.64 (3H, s), 3.93 (3H, s), 5.01 (2H, s), 7.28 (2H, s), 7.61 (2H, d, J=8.5 Hz), 8.07 (2H, d, J=8.5 Hz).

(b) 4'-Methoxymethoxy-3',5'-dimethylbiphenyl-4-carboxylic acid

In a similar manner to that described in Example 2, a reaction was carried out using methyl 4'-methoxymethoxy-3',5'-dimethylbiphenyl-4-carboxylate (1.24 g) and aqueous sodium hydroxide (1N, 8.20 ml) and the reaction mixture was treated to afford the desired compound (0.99 g) as colorless crystals.

mp 153–154° C.

$^1$H-NMR (270 MHz, CDCl$_3$): δ ppm 2.38 (6H, s), 3.64 (3H, s), 5.02 (2H, s), 7.30 (2H, s), 7.65 (2H, d, J=8.5 Hz), 8.14 (2H, d, J=8.5 Hz).

(c) Ethyl 2-butyl-3-[4-[2-(4'-methoxymethoxy-3',5'-dimethylbiphenyl-4-carbonylamino)ethoxy]phenyl] propionate In a similar manner to that described in Example 5, a reaction was carried out using ethyl 3-[4-(2-aminoethoxy) phenyl]-2-butylpropionate (880 mg), which is the product of Reference example 6, 4'-methoxymethoxy-3',5'-dimethylbiphenyl-4-carboxylic acid (859 mg), which is the product of reference example 17(b), and carbonyldiimidazole (577 mg) and the reaction mixture was treated to afford the desired compound (1 18 g) as colorless crystals.

mp 70–71° C.

$^1$H-NMR (270 MHz, CDCl$_3$): δ ppm 0.87 (3H, t, J=7.0 Hz), 1.16 (3H, t, J=7.0 Hz), 1.22–1.40 (4H, m), 1.41–1.77 (2H, m), 2.36 (6H, s), 2.52–2.63 (1H, m), 2.68 (1H, dd, J=6.5, 13.5 Hz), 2.86 (1H, dd, J=8.0, 13.5 Hz), 3.63 (3H, s), 3.88 (2H, q, J=5.0 Hz), 4.05 (2H, q, J=7.0 Hz), 4.14 (2H, t, J=5.0 Hz), 5.00 (2H, s), 6.62 (1H, brt), 6.83 (2H, d, J=8.5 Hz), 7.08 (2H, d, J=8.5 Hz), 7.60 (2H, d, J=8.5 Hz), 7.82 (2H, d, J=8.5 Hz).

(d) 2-Butyl-3-[4-[2-(4'-methoxymethoxy-3',5'-dimethylbiphenyl-4-carbonylamino)ethoxy]phenyl] propionic acid In a similar manner to that described in Example 2, a reaction was carried out using ethyl 2-butyl-3-[4-[2-(4'-methoxymethoxy-3',5'-dimethylbiphenyl-4-carbonylamino) ethoxy]phenyl]propionate (1.01 g), which is the product of Reference example 17(c) and aqueous sodium hydroxide solution (1N, 3.60 ml) and the reaction mixture was treated to afford the title compound (1.00 g) as a foam powder.

$^1$H-NMR (270 MHz, CDCl$_3$): δ ppm 0.87 (3H, t, J=7.0 Hz), 1.21–1.39 (4H, m), 1.40–1.70 (2H, m), 2.35 (6H, s), 2.56–2.65 (1H, m), 2.71 (1H, dd, J=6.5, 13.5 Hz), 2.89 (1H, dd, J=8.5, 13.5 Hz), 3.63 (3H, s), 3.86 (2H, q, J=5.0 Hz), 4.12 (2H, t, J=5.0 Hz), 5.00 (2H, s), 6.73. (1H, brt), 6.82 (2H, d, J=8.5 Hz), 7.09 (2H, d, J=8.5 Hz), 7.58 (2H, d, J=8.5 Hz), 7.81 (2H, d, J=8.5 Hz).

Reference Example 18

6-Isopropoxynicotinic acid (a) Isopropyl 6-isopropoxynicotinate

Cesium carbonate (7.94 g) was added to a solution of 6-chloronicotinyl chloride (1.56 g) in isopropanol (20 ml). The mixture was heated at reflux for 3 hours. The reaction mixture was concentrated under reduced pressure. The residue was partitioned between ethyl acetate and water and the layers were separated. The ethyl acetate was dried over anhydrous magnesium sulfate and concentrated under reduced pressure. The residue was purified via chromatography on a silica gel column using hexane/ethyl acetate=4/1 as the eluant to afford the desired compound (143 mg) as colorless liquid.

H-NMR (270 MHz, CDCl$_3$): δ ppm 1.36 (12H, d, J=6.5 Hz), 5.24 (1H, septet, J=6.5 Hz), 5.39 (1H, septet, J=6.5 Hz), 6.68 (1H, d, J=8.5 Hz), 8.12 (1H, dd, J=2.5, 8.5 Hz), 8.81 (1H, d, J=2.5 Hz).

(b) 6-Isopropoxynicotinic acid

In a similar manner to that described in Example 2, a reaction was carried out using isopropyl 6-isopropoxynicotinate (130 mg), which is the product of Reference example 18(a) and aqueous sodium hydroxide solution (1N, 0.87 ml) and the reaction mixture was treated to afford the title compound (106 mg) as crystals.

H-NMR (270 MHz, CDCl$_3$): δ ppm 1.38 (6H, d, J=6.0 Hz), 5.42 (1H, septet, J=6.0 Hz), 6.73 (1H, d, J=8.5 Hz), 8.18 (1H, dd, J=2.5, 8.5 Hz), 8.92 (1H, d, J=2.5 Hz).

Reference Example 19

Ethyl 2-butyl-3-[4-[2-(3-phenylpropylamino)ethoxy] phenyl]propionate 3-phenylpropionaldehyde (0.23 ml), sodium cyanoborohydride (117 mg) and acetic acid (one drop) were added to a solution of ethyl 3-[4-(2-aminoethoxy)phenyl]-2-butylpropionate (500 mg), which is the product of Reference example 6, in ethanol (10 ml). The mixture was stirred at ambient temperature for 18 hours. The reaction mixture was concentrated under reduced pressure. The residue was partitioned between ethyl acetate and water and the layers were separated. The ethyl acetate solution was dried over anhydrous magnesium sulfate and concentrated under reduced pressure. The residue was purified via chromatography on silica gel column using dichloromethane/methanol=19/1 as the eluant to afford the desired compound (460 mg) as a pale yellow oil.

$^1$H-NMR (270 MHz, CDCl$_3$): δ ppm 0.87 (3H, t, J=7.0 Hz), 1.15 (3H, t, J=7.0 Hz), 1.23–1.32 (4H, m), 1.40–1.95 (4H, m), 2.52–3.00 (9H, m), 3.99–4.09 (4H, m), 6.80 (2H, d, J=8.5 Hz), 7.06 (2H, d, J=8.5 Hz), 7.15–7.31 (5H, m).

Reference Example 20

Ethyl 2-butyl-3-[4-[2-(butylamino)ethoxy]phenyl]propionate

In a similar manner to that described in Reference example 19, a reaction was carried out using ethyl 3-[4-(2-aminoethoxy)phenyl]-2-butylpropionate (500 mg), which is the product of Reference example 6, butylaldehyde (0.15 ml), sodium cyanoborohydride (107 mg) and acetic acid (one drop) and the reaction mixture was treated to afford the title compound (390 mg) as a yellow oil.

$^1$H-NMR (270 MHz, CDCl$_3$): δ ppm 0.87 (3H, t, J=7.0 Hz), 0.94 (3H, t, J=7.5 Hz), 1.17 (3H, t, J=7.0 Hz), 1.22–1.73 (10H, m), 2.52–3.00 (5H, m), 3.20–3.28 (2H, m), 3.99–4.20 (4H, m), 6.84 (2H, d, J=8.5 Hz), 7.07 (2H, d, J=8.5 Hz).

Reference Example 21

Ethyl 3-[4-(3-aminopropoxy)phenyl]-2-butylpropionate (a) 2-butyl-3-[4-[3-(tetrahydropyran-2-yloxy)propoxy]phenyl]propionate In a similar manner to that described in Reference example 3(e), a reaction was carried out using ethyl 2-(4-hydroxybenzyl)caproate (3.02 g), 2-(3-bromopropoxy)tetrahydropyran (3.23 g) and potassium carbonate (5.00 g) and the reaction mixture was treated to afford the desired compound (4.42 g) as a colorless oil.

$^1$H-NMR (270 MHz, CDCl$_3$): δ ppm 0.87 (3H, t, J=7.0 Hz), 1.15 (3H, t, J=7.0 Hz), 1.22–1.35 (4H, m), 1.47–1.88 (8H, m), 2.06 (2H, quintuplet, J=6.0 Hz), 2.52–2.63 (1H, m), 2.67 (1H, dd, J=6.5, 13.5 Hz), 2.85 (1H, dd, J=8.5, 13.5 Hz), 3.46–3.61 (2H, m), 3.80–3.97 (2H, m), 4.01–4.10 (4H, m), 4.60 (1H, t, J=3.5 Hz), 6.80 (2H, d, J=8.5 Hz), 7.06 (2H, d, J=8.5 Hz).

(b) Ethyl 2-butyl-3-[4-(3-hydroxypropoxy)phenyl]propionate

In a similar manner to that described in Reference example 3(f), a reaction was carried out using ethyl 2-butyl-3-[4-[3-(tetrahydropyran-2-yloxy)propoxy]phenyl]propionate (4.42 g) and p-toluensulfonic acid monohydrate (2.57 g) and the reaction mixture was treated to afford the desired compound (3.02 g) as a colorless oil.

$^1$H-NMR (270 MHz, CDCl$_3$): δ ppm 0.87 (3H, t, J=7.0 Hz), 1.16 (3H, t, J=7.0 Hz), 1.22–1.35 (4H, m), 1.40–1.70 (2H, m), 1.77 (1H, t, J=5.5 Hz), 2.03 (2H, quintuplet, J=5.5 Hz), 2.53–2.65 (1H, m), 2.68 (1H, dd, J=6.5, 13.5 Hz), 2.86 (1H, dd, J=8.5, 13.5 Hz), 3.86 (2H, q, J=5.5 Hz), 4.02–4.17 (4H, m), 6.81 (2H, d, J=8.5 Hz), 7.07 (2H, d, J=8.5 Hz).

(c) Ethyl 2-butyl-3-[4-(3-methansulfonyloxypropoxy)phenyl]propionate

In a similar manner to that described in Reference example 3(g), a reaction was carried out using ethyl 2-butyl-3-[4-(3-hydroxypropoxy)phenyl]propionate (3.02 g), triethylamine (2.05 ml) and methanesulfonyl chloride (0.83 ml) and the reaction mixture was treated to afford the desired compound (3.49 g) as a colorless oil.

$^1$H-NMR (270 MHz, CDCl$_3$): δ ppm 0.87 (3H, t, J=7.0 Hz), 1.16 (3H, t, J=7.0 Hz), 1.22–1.34 (4H, m), 1.40–1.70 (2H, m), 2.21 (2H, quintuplet, J=6.0 Hz), 2.52–2.64 (1H, m), 2.68 (1H, dd, J=6.5, 13.5 Hz), 2.86 (1H, dd, J=8.5, 13.5 Hz), 2.98 (3H, s), 4.02–4.11 (4H, m), 4.44 (2H, t, J=6.0 Hz), 6.80 (2H, d, J=8.5 Hz), 7.07 (2H, d, J=8.5 Hz).

(d) Ethyl 3-[4-(3-azidopropoxy)phenyl]-2-butylpropionate

In a similar manner to that described in Reference example 3(h), a reaction was carried out using ethyl 2-butyl-3-[4-(3-methanesulfonyloxypropoxy)phenyl]propionate (2.98 g) and sodium azide (1.50 g) and the reaction mixture was treated to afford the desired compound (2.45 g) as a colorless oil.

$^1$H-NMR (270 MHz, CDCl$_3$): δ ppm 0.87 (3H, t, J=7.0 Hz), 1.16 (3H, t, J=7.0 Hz), 1.20–1.34 (4H, m), 1.40–1.70 (2H, m), 2.03 (2H, quintuplet, J=6.5 Hz), 2.51–2.63 (1H, m), 2.67 (1H, dd, J=6.5, 13.5 Hz), 2.85 (1H, dd, J=8.5, 13.5 Hz), 3.51 (2H, t, J=6.5 Hz), 4.02 (2H, t, J=6.5 Hz), 4.05 (2H, q, J=7.0 Hz), 6.80 (2H, d, J=8.5 Hz), 7.06 (2H, d, J=8.5 Hz).

(e) Ethyl 3-[4-(3-aminopropoxy)phenyl]-2-butylpropionate

In a similar manner to that described in Reference example 1(d), a reaction was carried out using ethyl 3-[4-(3-azidopropoxy)phenyl]-2-butylpropionate (2.45 g) and palladium on carbon (5%, 250 mg) and the reaction mixture was treated to afford the desired compound (1.62 g) as a colorless oil.

$^1$H-NMR (270 MHz, CDCl$_3$): δ ppm 0.87 (3H, t, J=6.5 Hz), 1.16 (3H, t, J=7.0 Hz), 1.22–1.34 (4H, in), 1.40–1.70 (2H, m), 1.80–2.10 (2H, m), 2.52–2.94 (6H, m), 4.00–4.11 (4H, m), 6.80 (2H, d, J=8.5 Hz), 7.06 (2H, d, J=8.5 Hz).

Reference Example 22

Ethyl 2-butyl-3-[4-(3-methylaminopropoxy)phenyl]propionate

A solution of methylamine in methanol (40%, 5.0 ml) was added to a solution of ethyl 2-butyl-3-[4-(3-methansulfonyloxypropoxy)phenyl]propionate (500 mg), which is the product of Reference example 21 (c) in toluene (10 ml). The mixture was stirred at 90° C. for 2 days. The reaction mixture was concentrated under reduced pressure. The residue was partitioned between ethyl acetate and water and the layers were separated. The ethyl acetate solution was dried over anhydrous magnesium sulfate and concentrated under reduced pressure. The residue was purified via chromatography on a silica gel column using dichloromethane/methanol=5/1 as the eluant to afford the title compound (389 mg) as a pale yellow oil.

$^1$H-NMR (270 MHz, CDCl$_3$): δ ppm 0.87 (3H, t, J=6.5 Hz), 1.15 (1.5H, t, J=7.0 Hz), 1.16 (1.5H, t, J=7.0 Hz), 1.22–1.35 (4H, m), 1.42–1.70 (2H, m), 1.92–2.02 (1H, m), 2.17–2.27 (1H, m), 2.52–3.09 (8H, m), 3.92–4.10 (4H, m), 6.73–6.81 (2H, m), 7.00–7.09 (2H, m).

Reference Example 23

Ethyl 3-[4-(2-t-butoxycarbonylaminoethoxy) phenyl]-2-propylpropionate (a) Diethyl 2-(4-benzyloxybenzyl)-2-propylmalonate In a similar manner to that described in Reference example 2(a), a reaction was carried out using diethyl 2-propylmalonate (5.00 g), 4-benzyloxybenzyl chloride (6.32 g) and sodium hydride (55% suspension in oil, 1.13 g) and the reaction mixture was treated to afford the desired compound (9.80 g) as a colorless oil.

$^1$H-NMR (270 MHz, CDCl$_3$): δ ppm 0.92 (3H, t, J=7.0 Hz), 1.23 (6H, t, J=7.0 Hz), 1.23–1.38 (2H, m), 1.71–1.80 (2H, m), 3.18 (2H, s), 4.08–4.21 (4H, m), 5.02 (2H, s), 6.86 (2H, d, J=8.5 Hz), 6.99 (2H, d, J=8.5 Hz), 7.30–7.48 (5H, m).

(b) 3-(4-benzyloxyphenyl)-2-propylpropionic acid

In a similar manner to that described in Reference example 2(b), a reaction was carried out using diethyl 2-(4-benzyloxybenzyl)-2-propylmalonate (9.85 g), which is the product of Reference example 23(a), and potassium hydroxide (5.25 g) and the reaction mixture was treated to afford the desired compound (3.96 g) as brown crystals.

mp 83–85° C.

$^1$H-NMR (270 MHz, CDCl$_3$): δ ppm 0.90 (3H, t, J=7.0 Hz), 1.24–1.70 (4H, m), 2.59–3.00 (3H, m), 5.03 (2H, s), 6.90 (2H, d, J=8.5 Hz), 7.10 (2H, d, J=8.5 Hz), 7.21–7.48 (5H, m).

(c) Ethyl 3-(4-benzyloxyphenyl)-2-propylpropionate (c)

1,8-Diazabicyclo[5.4.0]undec-7-ene (2.34 ml) and ethyl iodide (1.57 ml) were added to a solution of 3-(4-benzyloxyphenyl)-2-propylpropionic acid (3.90 g), which is the product of Reference example 23(b), in N,N-dimethylformamide (40 ml). The reaction mixture was stirred at 60° C. for 4 hours. The reaction mixture was partitioned between ethyl acetate and water and the layers were separated. The ethyl acetate layer was dried over anhydrous magnesium sulfate and concentrated under reduced pressure. The residue was purified via chromatography on a silica gel column using hexane/ethyl acetate=5/1-4/1 as the eluant to afford the desired compound (4.00 g) as a colorless oil.

$^1$H-NMR (270 MHz, CDCl$_3$): δ ppm 0.89 (3H, t, J=7.0 Hz), 1.14 (3H, t, J=7.0 Hz), 1.20–1.70 (4H, m), 2.56–2.62 (1H, m), 2.68 (1H, dd, J=6.0, 13.0 Hz), 2.86 (1H, dd, J=8.0, 13.0 Hz), 4.05 (2H, q, J=7.0 Hz), 5.03 (2H, s), 6.88 (2H, d, J=8.5 Hz), 7.07 (2H, d, J=8.5 Hz), 7.28–7.47 (5H, m).

(d) Ethyl 3-(4-hydroxyphenyl)-2-propylpropionate

In a similar manner to that described in Reference example 1(d), a reaction was carried out using ethyl 3-(4-benzyloxyphenyl)-2-propylpropionate (4.00 g) and palladium on carbon (5%, 0.40 g) and the reaction mixture was treated to afford the desired compound (3.10 g) as a syrup.

$^1$H-NMR (270 MHz, CDCl$_3$): δ ppm 0.89 (3H, t, J=7.0 Hz), 1.15 (3H, t, J=7.0 Hz), 1.21–1.70 (4H, m), 2.53–2.72 (2H, m), 2.84 (1H, dd, J=8.5, 13.0 Hz), 4.05 (2H, q, J=7.0 Hz), 4.75–4.82 (1H, m), 6.72 (2H, d? J=8.5 Hz), 7.02 (2H, d, J=8.5 Hz).

(e) Ethyl 3-[4-(2-t-butoxycarbonylaminoeyhoxy) phenyl]-2-propylpropionate

In a similar manner to that described in Example 122, a reaction was carried out using ethyl 3-(4-hydroxyphenyl)-2-propylpropionate (1.65 g), which is the product of Reference example 23(d), t-butyl 2-hydroxyethylcarbamate (5.63 g) triphenylphophine (9.16 g) and diethyl azodicarboxylate (6.14 ml) and the reaction mixture was treated to afford the desired compound (2.22 g) as a colorless oil.

$^1$H-NMR (270 MHz, CDCl$_3$): δ ppm 0.88 (3H, t, J=7.0 Hz), 1.16 (3H, t, J=7.0 Hz), 1.20–1.70 (4H, m), 1.45 (9H, s), 2.55–2.71 (2H, m), 2.86 (1H, dd, J=8.0, 13.0 Hz), 3.51 (2H, q, J=5.0 Hz), 3.90–4.15 (4H, m), 4.93–5.03 (1H, m), 6.79 (2H, d, J=8.5 Hz), 7.07 (2H, d, J=8.5 Hz).

Reference Example 24

3-[4-[2-(4'-Methoxymethoxy-3',5'-dimethylbiphenyl-4-carbonylamino)ethoxy]phenyl]-2-phenoxypropionic acid (a) Ethyl 3-[4-[2-(4'-methoxymethoxy-3',5'-dimethylbiphenyl-4-carbonylamino)ethoxy]phenyl]-2-phenoxypropionate In a similar manner to that described in Example 5, a reaction was carried out using ethyl 3-[4-(2-aminoethoxy) phenyl]-2-phenoxypropionate (2.07 g), which is the product of Reference example 4, 4'-methoxymethoxy-3',5'-dimethylbiphenyl-4-carboxylic acid (1.50 g), which is the product of reference example 17(b), and carbonyldiimidazole (1.10 g) and the reaction mixture was treated to afford the desired compound (720 mg) as a colorless oil.

$^1$H-NMR (270 MHz, CDCl$_3$): δ ppm 1.20 (3H, t, J=7.0 Hz), 2.36 (6H, s), 3.18 (1H, d, J=5.5 Hz), 3.19 (1H, d, J=7.5 Hz), 3.64 (3H, s), 3.88 (2H, q, J=5.0 Hz), 4.15 (2H, t, J=5.0 Hz), 4.18 (2H, q, J=7.0 Hz), 4.74 (1H, dd, J=5.5, 7.5 Hz), 5.00 (2H, s), 6.61 (1H, brt), 6.83 (2H, d, J=8.5 Hz), 6.87 (2H, d, J=8.5 Hz), 6.94 (1H, t, J=7.5 Hz), 7.20–7.30 (6H, m), 7.60 (2H, d, J=8.5 Hz), 7.82 (2H, d, J=8.5 Hz).

(b) 3-[4-[2-(4'-Methoxymethoxy-3',5'-dimethylbiphenyl-4-carbonylamino)ethoxy]phenyl]-2-phenoxypropionic acid In a similar manner to that described in Example 2, a reaction was carried out using ethyl 3-[4-[2-(4'-methoxymethoxy-3',5'-dimethylbiphenyl-4-carbonylamino) ethoxy]phenyl]-2-phenoxypropionate (720 mg), which is the product of Reference example 24(a) and aqueous sodium hydroxide (1N, 2.40 ml) and the reaction mixture was treated to afford the title compound (520 mg) as a white powder.

mp 142–143° C.

H-NMR (270 MHz, deuterated methanol): δ ppm 2.35 (6H, s), 3.14 (1H, d, J=7.5 Hz), 3.16 (1H, d, J=4.5 Hz), 3.60 (3H, s), 3.77 (2H, q, J=5.5 Hz), 4.16 (2H, t, J=5.5 Hz), 4.86 (1H, dd, J=4.5, 7.5 Hz), 5.00 (2H, s), 6.83 (2H, d, J=7.5 Hz), 6.86–6.93 (1H, m), 6.90 (2H, d, J=8.5 Hz), 7.19 (2H, d, J=7.5 Hz), 7.24 (2H, d, J=8.5 Hz), 7.33 (2H, s), 7.65 (2H, d, J=8.5 Hz), 7.86 (2H, d, J=8.5 Hz), 8.68 (1H, brt).

Reference Example 25

Ethyl 3-[4-(2-t-butoxycarbonylaminoethoxy) phenyl]-2-(4-isopropylphenoxy)propionate Potassium carbonate (23.5 g) was added to a solution of ethyl 3-(4-hydroxyphenyl)-2-(4-iospropylphenoxy)

propionate (18.2 g), which is the product of Reference example 5(d), in a mixture of N,N-dimethylformamide (200 ml) and toluene (100 ml) at ambient temperature. To this suspension a solution of t-butyl 2-methanesulfonyloxyethylcarbamate (12.2 g) in toluene (40 ml) was added dropwise at 70° C. and the mixture was stirred at the same temperature for 2 hours. Further, to this reaction mixture a solution of t-butyl 2-methanesulfonyloxyethylcarbamate (12.2 g) in a mixture of N,N-dimethylformamide (10 ml) and toluene (40 ml) was added and the the mixture was stirred at 70° C. overnight. The reaction mixture was partitioned between ethyl acetate and water. The ethyl acetate layer was washed with saturated aqueous sodium chloride solution and dried over anhydrous magnesium sulfate and concentrated under reduced pressure. The residue was purified via chromatography on a silica gel column using toluene/ethyl acetate=20/1-hexane/ethyl acetate=3/1 as the eluant to afford the desired compound (18.7 g) as a colorless oil.

$^1$H-NMR (270 MHz, CDCl$_3$): δ ppm 1.19 (6H, d, J=7.0 Hz), 1.45 (9H, s), 2.82 (1H, septet, J=7.0 Hz), 3.16 (1H, d, J=5.0 Hz), 3.18 (1H, d, J=7.5 Hz), 3.52 (2H, q, J=5.0 Hz), 3.99 (2H, t, J=5.0 Hz), 4.18 (2H, q, J=7.0 Hz), 4.69 (1H, dd, J=5.0, 7.5 Hz), 4.97 (1H, brt), 6.76 (2H, d, J=8.5 Hz), 6.81 (2H, d, J=8.5 Hz), 7.08 (2H, d, J=8.5 Hz), 7.21 (2H, d, J=8.5 Hz).

Reference Example 26

6-(4-Methoxyphenyl)nicotinic acid

In a similar manner to that described in Example 2, a reaction was carried out using methyl 6-(4-methoxyphenyl)nicotinate (3.95 g) and aqueous sodium hydroxide solution (1N, 32.5 ml) and the reaction mixture was treated to afford the title compound (2.63 g) as colorless crystals.

mp 252–253° C.

$^1$H-NMR (270 MHz, CDCl$_3$): δ ppm 3.84 (3H, s), 7.08 (2H, d, J=9.0 Hz), 8.04 (1H, d, J=8.5 Hz), 8.14 (2H, d, J=9.0 Hz), 8.27 (1H, dd, J=2.5, 8.5 Hz), 9.09 (1H, d, J=2.5 Hz).

Reference Example 27

6-(4-Fluorophenyl)nicotinic acid

In a similar manner to that described in Example 2, a reaction was carried out using methyl 6-(4-fluorophenyl)nicotinate (390 mg) and aqueous sodium hydroxide solution (1N, 5.00 ml) and the reaction mixture was treated to afford the title compound (345 mg) as a pale yellow solid.

$^1$H-NMR (270 MHz, CDCl$_3$): δ ppm 7.35 (2H, t, J=8.5 Hz), 8.11 (1H, d, J=8.5 Hz), 8.15–8.29 (2H, m), 8.32 (1H, dd, J=2.0, 8.5 Hz), 9.13 (1H, d, J=2.0Hz).

Reference Example 28

6-(2,2,3,3-tetrafluoropropoxy)nicotinic acid

In a similar manner to that described in Reference example 1(c), a reaction was carried out using 2,2,3,3-tetrafluoropropanol (5.23 ml), sodium hydride (55% suspension in oil, 1.91 g) and methyl 6-chloronicotinate (5.00 g) and treated to afford crude methyl 6-(2,2,3,3-tetrafluoropropoxy)nicotinate (5.42 g) as a colorless oil. In a similar manner to that described in Example 2, a reaction was carried out using the crude product described above (2.70 g) and aqueous sodium hydroxide solution (2N, 15 ml) and the reaction mixture was treated to afford crude title compound (1.60 g). This product was used in Example 102 and Example 150 without further purification.

Reference Example 29

2-Trimethylsilylethyl (S)-2-(4-isopropylphenoxy)-3-[4-[2-(4-pyridine-2-yl-benzoylamino)ethoxy]phenyl]propionate (a) (S)-4-benzyl-3-[(4-isopropylphenoxy)acetyl]oxazolidine-2-one Oxalyl chloride (16.8 ml) and N,N-dimethylformamide (three drops) were added to a solution of 4-isopropylphenoxyacetic acid (15.0 g) in dichloromethane (75 ml) at ambient temperature. The reaction mixture was stirred for 1.5 hours. The reaction mixture was concentrated at reduced pressure and residual reagents were azeotropically evaporated off with toluene. The residue was dried under reduced pressure.

A solution of n-butyl lithium in hexane (1.61N, 48.0 ml) was added dropwise to a solution of (S)-4-benzyloxazolidine-2-one (12.4 g) in tetrahydrofuran (150 ml) at −78° C. and the mixture was stirred at the same temperature for 30 minutes. To this solution a solution of 4-isopropylphenoxyacetyl chloride, which had been obtained above, in tetrahydrofuran (100 ml) was added at −78° C. The mixture was stirred at 0° C. for 1 hour. The reaction mixture was partitioned between ethyl acetate and water. The ethyl acetate layer was washed with aqueous hydrogen chloride solution (1N), saturated aqueous sodium hydrogencarbonate solution and saturated aqueous sodium chloride solution. The ethyl acetate solution was dried over anhydrous magnesium sulfate and concentrated under reduced pressure. The residue was crystallized from a mixture of hexane/ethyl acetate=6/1 to afford the desired compound (20.9 g) as colorless crystals.

mp 104.5–105° C.

$^1$H-NMR (270 MHz, CDCl$_3$): δ ppm 1.23 (6H, d, J=7.0 Hz), 2.79–2.92 (2H, m), 3.36 (1H, dd, J=3.0, 13.5 Hz), 4.24–4.37 (2H, m), 4.68–4.78 (1H, m), 5.22 (2H, s), 6.91 (2H, d, J=8.5 Hz), 7.13–7.38 (7H, m).

(b) (S)-4-benzyl-3-[(2S,3R)-3-(4-benzyloxyphenyl)-3-hydroxy-2-(4-isopropylphenoxy)propionyl]oxazolidine-2-one A solution of dibutylboron triflate in dichloromethane (1M, 67.9 ml) and triethylamine (10.2 ml) was added to a solution of (S)-4-benzyl-3-[(4-isopropylphenoxy)acetyl]oxazolidine-2-one (20.0 g) in dichloromethane (150 ml) at 0° C. The mixture was stirred at the same temperature for 1 hour. To the reaction mixture a solution of 4-benzyloxybenzaldehyde (13.2 g) in dichloromethane (20 ml) was added dropwise at −78° C. and then stirred at the same temperature for 40 minutes. The reaction mixture was further stirred at 0° C. for 1 hour. At the end of this time a mixture of saturated aqueous sodium chloride solution/methanol=1/1 (50 ml) and aqueous hydrogen peroxide solution (31%)/methanol=2/1 (150 ml) was added to the reaction mixture and stirred for 1 hour. The mixture was concentrated under reduced pressure. The residue was partitioned between ethyl acetate and water and the layers were separated. The ethyl acetate layer was washed with aqueous hydrogen chloride solution (1N), saturated aqueous sodium hydrogencarbonate solution and saturated aqueous sodium chloride solution and dried over anhydrous magnesium sulfate and concentrated under reduced pressure. The residue was purified via chromatography on a silica gel column using hexane/ethyl acetate=3/1-1/1 as the eluant to afford the desired compound (25.7 g) as a mass of foam.

$^1$H-NMR (270 MHz, CDCl$_3$): δ ppm 1.20 (6H, d, J=7.0 Hz), 2.73 (1H, dd, J=9.5, 13.5 Hz), 2.85 (1H, septet, J=7.0 Hz), 3.07 (1H, dd, J=3.0, 13.5 Hz), 3.58 (1H, t, J=8.5 Hz), 3.97 (1H, d, J=9.0 Hz), 4.23–4.29 (1H, m), 5.04 (2H, s), 5.09 (1H, d, J=5.5 Hz), 6.18 (1H, d, J=5.5 Hz), 6.91 (2H, d, J=8.5 Hz), 6.94 (2H, d, J=8.5 Hz), 7.05–7.10 (2H, m), 7.14 (2H, d, J=8.5 Hz), 7.23–7.44 (10H, m).

(c) (S)-4-benzyl-3-[(2S,3R)-3-hydroxy-3-(4-hydroxyphenyl)-2-(4-isopropylphenoxy)propionyl] oxazolidine-2-one In a similar manner to that described in Reference example 1(d), a reaction was carried out using (S)-4-benzyl-3-[(2S,3R)-3-(4-benzyloxyphenyl)-3-hydroxy-2-(4-isopropylphenoxy)propionyl]oxazolidine-2-one (25.0 g), which is the product of Reference example 29(b) and palladium on carbon (5%, 2.50 g) and the reaction mixture was treated to afford the desired compound (19.1 g) as a mass of foam.

$^1$H-NMR (270 MHz, CDCl$_3$): δ ppm 1.21 (6H, d, J=7.0 Hz), 2.76 (1H, dd, J=9.0, 13.5 Hz), 2.85 (1H, septet, J=7.0 Hz), 3.07 (1H, dd, J=3.0, 13.5 Hz), 3.17 (1H, d, J=4.5 Hz), 3.73 (1H, t, J=8.5 Hz), 4.04 (1H, d, J=8.5 Hz), 4.25–4.35 (1H, m), 5.07 (1H, t, J=5.0 Hz), 5.52 (1H, s), 6.18 (1H, d, J=5.5 Hz), 6.78 (2H, d, J=8.5 Hz), 6.92 (2H, d, J=8.5 Hz), 7.02–7.12 (2H, m), 7.14 (2H, d, J=8.5 Hz), 7.22–7.29 (3H, m), 7.32 (2H, d, J=8.5 Hz).

(d) (S)-4-benzyl-3-[(S)-3-(4-hydroxyphenyl)-2-(4-isopropylphenoxy)propionyl]oxazolidine-2-one Triethylsilane (30.2 ml) was added to a solution of (S)-4-benzyl-3-[(2S,3R)-3-hydroxy-3-(4-hydroxyphenyl)-2-(4-isopropylphenoxy)propionyl]oxazolidine-2-one (18.0 g), which is the product of Reference example 29(c), in trifluoroacetic acid (150 ml) at ambient temperature. The mixture was stirred for 18 hours. The reaction mixture was concentrated under reduced pressure. The residue was partitioned between ethyl acetate and water and the layers were separated. The ethyl acetate layer was washed with saturated aqueous sodium hydrogencarbonate solution, aqueous hydrogen chloride solution (1N) and saturated aqueous sodium chloride solution and dried over anhydrous magnesium sulfate and concentrated under reduced pressure. The residue was purified via chromatography on a silica gel column using hexane/ethyl acetate=3/1 as the eluant to afford the desired compound (10.7 g) as colorless crystals.

mp 142–143° C.

$^1$H-NMR (400 MHz, CDCl$_3$): δ ppm 1.19 (6H, d, J=7.0 Hz), 2.75–2.88 (2H, m), 3.10–3.21 (3H, m), 4.03 (1H, t, J=8.0 Hz), 4.17 (1H, d, J=9.0 Hz), 4.48–4.55 (1H, m), 4.89 (1H, s), 6.08 (1H, dd, J=5.5, 8.0 Hz), 6.74 (2H, d, J=8.5 Hz), 6.83 (2H, d, J=8.5 Hz), 7.05–7.16 (4H, m), 7.21–7.36 (5H, m).

(e) 2-Trimethylsilylethyl (S)-3-(4-hydroxyphenyl)-2-(4-isopropylphenoxy)propionate A mixture of aqueous lithium hydroxide solution (1N, 57.0 ml) and aqueous hydrogen peroxide solution (31%, 6.34 ml) was added dropwise to a suspension of (S)-4-benzyl-3-[(S)-3-(4-hydroxyphenyl)-2-(4-isopropylphenoxy) propionyl]oxazolidine-2-one (10.6 g), which is the product of Reference example 29(d), in a mixture of methanol (140 ml) and tetrahydrofuran (15 ml). After the mixture was stirred at ambient temperature for 6 hours, a solution of sodium dithionite (10.1 g) in water (50 ml) was added to the reaction mixture and the mixture was stirred for 1 hour. The reaction mixture was concentrated under reduced pressure. Aqueous sodium hydroxide solution (1N) was added to the residue to make it basic. The solution was washed with dichloromethane and partitioned between aqueous hydrogen chloride solution and ethyl acetate. The ethyl acetate layer was separated and dried over anhydrous magnesium sulfate and then concentrated under reduced pressure. The residue was crystallized from hexane to afford (S)-3-(4-hydroxyphenyl)-2-(4-isopropylphenoxy)propionic acid (6.00 g) as a white powder. Oxalyl chloride (5.50 ml) and N,N-dimethylformamide (5 drops) were added to a suspension of this carboxylic acid (4.43 g) in dichloromethane (100 ml) at ambient temperature. The mixture was stirred for 1 hour. At the end of this time the reaction mixture was concentrated under reduced pressure. The residue was azeotropically distilled off using toluene to remove excess reagent. 2-Trimethylsilylethanol (9.06 ml) was added to a solution of the residue in dichloromethane (50 ml). This mixture was stirred at ambient temperature for 15 hours. Triethylamine (4.40 ml) and 4-N,N-dimethylaminopyridine (155 mg) were added to the mixture. This mixture was stirred at ambient temperature for 2 hours. The reaction mixture was concentrated under reduced pressure. The residue was partitioned between ethyl acetate and water and the layers were separated. The ethyl acetate layer was washed with saturated aqueous sodium chloride solution and dried over anhydrous magnesium sulfate and concentrated under reduced pressure. The residue was purified via chromatography on a silica gel column using hexane/ethyl acetate=5/1-4/1 as the eluant to afford the desired compound (5.30 g) as a pale yellow oil.

$^1$H-NMR (270 MHz, CDCl$_3$): δ ppm 0.00 (9H, s), 0.92 (2H, t, J=8.5 Hz), 1.18 (6H, d, J=7.0 Hz), 2.81 (1H, septet, J=7.0 Hz), 3.10–3.17 (2H, m), 4.19 (2H, t, J=8.5 Hz), 4.66 (1H, dd, J=6.0, 7.0 Hz), 6.73 (2H, d, J=8.5 Hz), 6.74 (2H, d, J=8.5 Hz), 7.07 (2H, d, J=8.5 Hz), 7.15 (2H, d, J=8.5 Hz).

(f) 2-Trimethylsilylethyl (S)-3-[4-(2-t-butoxycarbonylaminoethoxy)phenyl]-2-(4-isopropylphenoxy)propionate In a similar manner to that described in Reference example 25, a reaction was carried out using 2-trimethylsilylethyl (S)-3-(4-hydroxyphenyl)-2-(4-isopropylphenoxy)propionate (4.80 g), which is the product of Reference example 29(e), t-butyl 2-methanesulfonyloxyethylcarbamate (7.17 g) and potassium carbonate (8.28 g) and the reaction mixture was treated to afford the desired compound (5.94 g) as a colorless oil.

$[\alpha]_D^{25}$ −6.0° (c=0.9, chloroform)

$^1$H-NMR (400 MHz, CDCl$_3$): δ ppm 0.00 (9H, s), 0.91 (2H, t, J=8.5 Hz), 1.17 (6H, d, J=7.0 Hz), 1.45 (9H, s), 2.81 (1H, septet, J=7.0 Hz), 3.08–3.18 (2H, m), 3.45–3.54 (2H, m), 3.93–4.00 (2H, m), 4.10–4.25 (2H, m), 4.65 (1H, dd, J=5.5, 7.5 Hz), 4.93–5.00 (1H, m), 6.74 (2H, d, J=8.5 Hz), 6.80 (2H, d, J=8.5 Hz), 7.06 (2H, d, J=8.5 Hz), 7.20 (2H, d, J=8.5 Hz).

(g) 2-Trimethylsilylethyl (S)-2-(4-isopropylphenoxy)-3-[4-[2-(4-pyridine-2-yl-benzoylamino)ethoxy]phenyl]propionate In a similar manner to that described in Example 73, a reaction was carried out using 2-trimethylsilylethyl (S)-3-

[4-(2-t-butoxycarbonylaminoethoxy)phenyl]-2-(4-isopropylphenoxy)propionate (0.95 g), 4-pyridine-2-ylbenzoic acid (382 mg), diethyl cyanophosphonate (0.29 ml) and triethylamine (0.53 ml) and the reaction mixture was treated to afford the title compound (0.62 g) as a colorless oil.

$[\alpha]_D^{25}$ −3.0° (c=0.7, chloroform)

$^1$H-NMR (400 MHz, CDCl$_3$): δ ppm 0.05 (9H, s), 0.97 (2H, t, J=8.5 Hz), 1.15–1.23 (6H, m), 2.86 (1H, septet, J=7.0 Hz), 3.14–3.23 (2H, m), 3.85–3.95 (2H, m), 4.15–4.27 (4H, m), 4.70 (1H, dd, J=5.5, 7.5 Hz), 6.64–6.74 (1H, m), 6.79 (2H, d, J=8.5 Hz), 6.90 (2H, d, J=8.5 Hz), 7.12 (2H, d, J=8.5 Hz), 7.24–7.34 (3H, m), 7.76–7.84 (2H, m), 7.93 (2H, d, J=8.5 Hz), 8.11 (2H, d, J=8.5 Hz), 8.76 (1H, d, J=5.0 Hz).

Reference Example 30

2-Trimethylsilylethyl (R)-2-(4-isopropylphenoxy)-3-[4-[2-(4-pyridine-2-yl-benzoylamino)ethoxy]phenyl]propionate (a) (R)-4-benzyl-3-[(4-isopropylphenoxy)acetyl]oxazolidine-2-one In a similar manner to that described in Refernce example 29(a), a reaction was carried out using 4-isopropylphenoxyacetic acid (14.1 g), oxalyl chloride (15.8 ml), (R)-4-benzyloxazolidine-2-one (11.7 g) and a solution of n-butyl lithium in hexane (1.61N, 45.0 ml) and the reaction mixture was treated to afford the desired compound (18.6 g) as colorless crystals.

mp 104.5–105°.5C.

$^1$H-NMR (400 MHz, CDCl$_3$): δ ppm 1.23 (6H, d, J=7.0 Hz), 2.80–2.91 (2H, m), 3.36 (1H, dd, J=3.0, 13.5 Hz), 4.28 (1H, dd, J=3.0, 9.0 Hz), 4.33 (1H, dd, J=8.0, 9.0 Hz), 4.68–4.78 (1H, m), 5.22 (2H, s), 6.91 (2H, d, J=8.5 Hz), 7.14–7.38 (7H, m).

(b) (R)-4-benzyl-3-[(2R,3R)-3-(4-benzyloxyphenyl)-3-hydroxy-2-(4-isopropylphenoxy)propionyl]oxazolidine-2-one In a similar manner to that described in Reference example 29(b), a reaction was carried out using (R)-4-benzyl-3-[(4isopropylphenoxy)acetyl]oxazolidine-2-one (10.0 g), which is the product of Reference example 30(a), solution of dibutylboron triflate in dichloromethane (1M, 34.0 ml), triethylamine (5.11 ml) and 4-benzyloxybenzaldehyde (6.60 g) and the reaction mixture was treated to afford the desired compound (12.1 g) as a mass of foam.

$^1$H-NMR (270 MHz, CDCl$_3$): δ ppm 1.21 (6H, d, J=7.0 Hz), 2.73 (1H, dd, J=9.0, 13.5 Hz), 2.85 (1H, septet, J=7.0 Hz), 3.02–3.12 (1H, m), 3.53–3.63 (1H, m), 3.93–4.01 (1H, m), 4.21–4.32 (1H, m), 5.02–5.12 (3H, m), 6.18 (1H, d, J=6.0 Hz), 6.88–7.46 (18H, m).

(c) (R)-4-benzyl-3-[(2R,3S)-3-hydroxy-3-(4-hydroxyphenyl)-2-(4-isopropyl-phenoxy)propionyl]oxazolidine-2-one In a similar manner to that described in Reference example 1(d), a reaction was carried out using (R)-4-benzyl-3-[(2R,3S)-3-(4-benzyloxyphenyl)-3-hydroxy-2-(4-isopropylphenoxy)propionyl]oxazolidine-2-one (9.00 g), which is the product of Reference example 30(b) and palladium on carbon (5%, 1.80 g) and the reaction mixture was treated to afford the desired compound (7.48 g) as a mass of foam.

$^1$H-NMR (270 MHz, CDCl$_3$): δ ppm 1.21 (6H, d, J=7.0 Hz), 2.75 (1H, dd, J=9.0, 13.5 Hz), 2.85 (1H, septet, J=7.0 Hz), 3.05–3.14 (2H, m), 3.70–3.79 (1H, m), 4.01–4.09 (1H, m), 4.26–4.35 (1H, m), 5.04–5.12 (1H, m), 5.34 (1H, brs), 6.18 (1H, d, J=6.0 Hz), 6.80 (2H, d, J=8.5 Hz), 6.92 (2H, d, J=8.5 Hz), 7.04–7.37 (9H, m).

(d) (R)-4-benzyl-3-[(R)-3-(4-hydroxyphenyl)-2-(4-isopropylphenoxy)propionyl]oxazolidine-2-one In a similar manner to that described in Reference example 29(d), a reaction was carried out using (R)-4-benzyl-3-[(2R,3S)-3-hydroxy-3-(4-hydroxyxyphenyl)-2-(4-isopropylphenoxy)propionyl]oxazolidine-2-one (7.00 g), which is the product of Reference example 30(c), and triethylsilane (18.8 ml) and the reaction mixture was treated to afford the desired compound (4.89 g) as colorless crystals.

mp 147–148° C.

$^1$H-NMR (270 MHz, CDCl$_3$): δ ppm 1.19 (6H, d, J=7.0 Hz), 2.71–2.88 (2H, m), 3.09–3.22 (3H, m), 3.97–4.07 (1H, m), 4.15 (1H, dd, J=2.5, 7.0 Hz), 4.47–4.57 (1H, m), 4.88 (1H, s), 6.08 (1H, d, J=5.5, 8.0 Hz), 6.75 (2H, d, J=8.5 Hz), 6.83 (2H, d, J=8.5 Hz), 7.05–7.30 (9H, m).

(e) 2-Trimethylsilylethyl (R)-3-(4-hydroxyphenyl)-2-(4-isopropylphenoxy)propionate In a similar manner to that described in Reference example 29(e), a reaction was carried out using (R)-4-benzyl-3-[(R)-3-(4-hydroxyphenyl)-2-(4-isopropylphenoxy)propionyl]oxazolidine-2-one (3.78 g), which is the product of Reference example 30(d), aqueous lithium hydroxide solution (1N, 20.6 ml) and aqueous hydrogen peroxide solution (31%, 2.26 ml) and the reaction mixture was treated to afford (R)-3-(4-hydroxyphenyl)-2-(4-isopropylphenoxy)propionic acid (2.18 g) as a white powder. This acid (1.95 g) was reacted with oxalyl chloride (2.73 ml) and 2-trimethylsilylethanol (4.66 ml) and the reaction mixture was treated in a similar manner to that described Reference example 29(e) to afford the desired compound (2.26 g) as a colorless oil.

$^1$H-NMR (270 MHz, CDCl$_3$): δ ppm 0.00 (9H, s), 0.92 (2H, t, J=8.5 Hz), 1.18 (6H, d, J=7.0 Hz), 2.81 (1H, septet, J=7.0 Hz), 3.07–3.18 (2H, m), 4.11–4.25 (2H, m), 4.70 (1H, dd, J=5.5, 7.0 Hz), 5.75 (1H, s), 6.72 (2H, d, J=8.5 Hz), 6.75 (2H, d, J=8.5 Hz), 7.07 (2H, d, J=8.5 Hz), 7.12 (2H, d, J=8.5 Hz).

(f) 2-Trimethylsilylethyl (R)-3-[4-(2-t-butoxycarbonylaminoethoxy)phenyl]-2-(4-isopropylphenoxy)propionate In a similar manner to that described in Reference example 25, a reaction was carried out using 2-trimethylsilylethyl (R)-3-(4-hydroxyphenyl)-2-(4-isopropylphenoxy)propionate (221 mg), which is the product of Reference example 30(e), t-butyl 2-methanesulfonyloxyethylcarbamate (330 mg) and potassium carbonate (381 mg) and the reaction mixture was treated to afford the desired compound (264 mg) as a colorless oil.

$[\alpha]_D^{25}$ +6.8° (c=0.9, chloroform)

$^1$H-NMR (270 MHz, CDCl$_3$): δ ppm 0.00 (9H, s), 0.93 (2H, t, J=8.5 Hz), 1.19 (6H, d, J=7.0 Hz), 1.45 (9H, s), 2.82 (1H, septet, J=7.0 Hz), 3.10–3.20 (2H, m), 3.43–3.54 (2H, m), 3.98 (2H, t, J=5.0 Hz), 4.11–4.25 (2H, m), 4.66 (1H, dd, J=5.5, 7.0 Hz), 4.91–5.01 (1H, m), 6.75 (2H, d, J=8.5 Hz), 6.81 (2H, d, J=8.5 Hz), 7.08 (2H, d, J=8.5 Hz), 7.22 (2H, d, J=8.5 Hz).

(g) 2-Trimethylsilylethyl (R)-2-(4-isopropylphenoxy)-3-[4-[2-(4-pyridine-2-yl-benzoylamino)ethoxy]phenyl]propionate In a similar manner to that described in Example 73, a reaction was carried out using 2-trimethylsilylethyl (R)-3-[4-(2-t-butoxycarbonylaminoethoxy)phenyl]-2-(4-isopropylphenoxy)propionate (356 mg), 4-pyridine-2-ylbenzoic acid (143 mg), diethyl cyanophosphonate (0.11 ml) and triethylamine (0.10 ml) and the reaction mixture was treated to afford the title compound (307 mg) as a colorless oil.

$[\alpha]_D^{25}$ +2.8° (c=2.1, chloroform)

$^1$H-NMR (400 MHz, CDCl$_3$): δ ppm 0.05 (9H, s), 0.97 (2H, t, J=8.5 Hz), 1.18–1.22 (6H, m), 2.85 (1H, septet, J=7.0 Hz), 3.15–3.23 (2H, m), 3.92 (2H, q, J=5.0 Hz), 4.15–4.30 (4H, m), 4.71 (1H, dd, J=5.5, 7.5 Hz), 6.64–6.74 (1H, m), 6.79 (2H, d, J=8.5 Hz), 6.89 (2H, d, J=8.5 Hz), 7.11 (2H, d, J=8.5 Hz), 7.26–7.34 (3H, m), 7.78–7.83 (2H, m), 7.93 (2H, d, J=8.5 Hz), 8.10 (2H, d, J=8.5 Hz), 8.75 (1H, d, J=5.0 Hz).

Reference Example 31

3-Trifluoromethylpyridine-6-ylbenzoic acid

(a) Methyl 3-trifluoromethylpyridine-6-ylbenzoate 4-methoxycarbonylphenyl boronic acid (541 mg) and 2-chloro-5-trifluoromethylpyridine (718 mg) were added to a suspension of bisbenzonitriledichloropalladium (119 mg) and 1,4-bisdiphenylphosphinobutane (131 mg) in toluene (10 ml) at ambient temperature and then ethanol (5 ml) and saturated aqueous sodium hydrogencarbonate solution (5 ml) were added to the mixture. This mixture was heated at reflux for 5 hours at 100° C. The reaction mixture was partitioned between ethyl acetate and water. The ethyl acetate layer was separated and washed with saturated aqueous sodium chloride solution and dried over anhydrous magnesium sulfate and concentrated under reduced pressure. To the residue diisopropyl ether was added to afford the desired compound (841 mg) as a white powder which include some impurity.

$^1$H-NMR (270 MHz, CDCl$_3$): δ ppm 3.96 (3H, s), 7.91 (1H, d, J=8.5 Hz), 8.04 (1H, d, J=8.5 Hz), 8.12 (2H, d, J=8.5 Hz), 8.18 (2H, d, J=8.5 Hz), 8.98 (1H, s).

(b) 3-Trifluoromethylpyridine-6-ylbenzoic acid

In a similar manner to that described in Example 2, a reaction was carried out using methyl 3-trifluoromethylpyridine-6-ylbenzoate (791 mg) and aqueous sodium hydroxide solution (1N, 5.60 ml) and the reaction mixture was treated to afford the title compound (546 mg) which includes some impurity and was used in example 106 without further purification.

$^1$H-NMR (270 MHz, deuterated dimethyl sulfoxide): δ ppm 8.05 (1H, d, J=8.5 Hz), 8.10 (2H, d, J=8.5 Hz), 8.29 (2H, d, J=8.5 Hz), 8.35 (1H, d, J=8.5 Hz), 9.10 (1H, s).

Reference Example 32

3-Nitropyridine-6-ylbenzoic acid

(a) Methyl 3-nitropyridine-6-ylbenzoate

In a similar manner to that described in Reference example 14(a), a reaction was carried out using 4-methoxycarbonylphenyl boronic acid (3.24 g), 2-bromo-5-nitropyridine (4.75 g) and tetrakis(triphenylphosphine) palladium (1.04 g) and treated to afford the desired compound (3.67 g) as colorless crystals.

mp 197–199° C.

$^1$H-NMR (270 MHz, CDCl$_3$): δ ppm 3.97 (3H, s), 7.98 (1H, d, J=8.5 Hz), 8.19 (4H, s), 8.58 (1H, dd, J=2.5, 8.5 Hz), 9.53 (1H, d, J=2.5 Hz).

(b) 3-Nitropyridine-6-ylbenzoic acid

In a similar manner to that described in Example 2, a reaction was carried out using methyl 3-nitropyridine-6-ylbenzoate (545 mg), which is the product of Reference example 32(a), and aqueous sodium hydroxide solution (1N, 3.16 ml) at 90° C. and the reaction mixture was treated to afford the title compound (370 mg) as colorless crystals.

mp 262–264° C.

$^1$H-NMR (270 MHz, deuterated dimethyl sulfoxide): δ ppm 8.11 (2H, d, J=8.0 Hz), 8.33 (2H, d, J=8.0 Hz), 8.36 (1H, d, J=8.0 Hz), 8.71 (1H, dd, J=2.0, 8.0 Hz), 9.48 (1H, d, J=2.0 Hz).

Reference Example 33

3-Methoxypyridine-6-ylbenzoic acid

(a) Methyl 3-aminopyridine-2-ylbenzoate

In a similar manner to that described in Reference example 1(d), a reaction was carried out using methyl 3-nitropyridine-6-ylbenzoate (1.13 g), which is the product of Reference example 32(a) and palladium on carbon (221 mg) and treated to afford the desired compound (738 mg) as colorless crystals.

mp 188–189° C.

$^1$H-NMR (270 MHz, CDCl$_3$): δ ppm 3.83 (2H, brs), 3.93 (3H, s), 7.06 (1H, dd, J=3.0, 8.5 Hz), 7.61 (1H, d, J=8.5 Hz), 7.98 (2H, d, J=8.5 Hz), 8.09 (2H, d, J=8.5 Hz), 8.20 (1H, d, J=3.0 Hz).

(b) Methyl 3-methoxypyridine-6-ylbenzoate

Concentrated sulfuric acid (0.14 ml) were added to a suspension of methyl 3-aminopyridine-6-ylbenzoate (425 mg) and sodium bromide (383 mg) in water at 0° C. (10 ml) and then a solution of sodium nitrite (295 mg) in water (1.5 ml) was added dropwise to the mixture at 80° C. The mixture was stirred at the same temperature for 15 minutes. At the end of this time a solution of amidosulfuric acid and concentrated sulfuric acid (0.21 ml) in water (1.60 ml) was added to the reaction mixture and this mixture was stirred for 1.5 hours at 80° C. and at ambient tmperature for 1 hour and then allowed to stand for 14 hours. The pH of the reaction mixture was adjusted to pH 8 with aqueous sodium hydroxide solution (1N). After addition of acetic anhydride (2.00 ml) to the solution, the mixture was stirred at ambient temperature for 30 minutes. The reaction mixture was partitioned between ethyl acetate and water and the ethyl acetate layer was separated and washed with saturated aqueous sodium chloride solution and dried over anhydrous magnesium sulfate. The ethyl acetate was distilled off under reduced pressure to afford a mixture (457 mg) of methyl 5-acetoxypyridine-2-ylbenzoate and methyl 5-hydroxypyridine-2-ylbenzoate. In a similar manner to that described in Example 2, a reaction was carried out using the mixture obtained above and aqueous sodium hydroxide solution (1N, 2.10 ml) and the reaction mixture was treated to afford 5-hydroxypyridine-2-ylbenzoic acid as a white powder. In a similar manner that described in Reference example 1(c) a reaction was carried out using 5-hydroxypyridine-2-ylbenzoic acid obtained above, sodium hydride (55% suspension in oil, 174 mg) and methyl iodide (0.35 ml) and the reaction mixture was treated to afford the desired compound (429 mg) as colorless crystals mp 130–132° C.

$^1$H-NMR (270 MHz, CDCl$_3$): δ ppm 3.93 (3H, s), 3.94 (3H, s), 7.30 (1H, dd, J=3.0, 9.0 Hz), 7.74 (1H, d, J=9.0 Hz), 8.02 (2H, d, J=8.5 Hz), 8.12 (2H, d, J=8.5 Hz), 8.43 (1H, d, J=3.0 Hz).

(c) 3-Methoxypyridine-6-ylbenzoic acid

In a similar manner to that described in Example 2, a reaction was carried out using methyl 3-methoxypyridine-6-ylbenzoate (249 mg), which is the product of Reference example 33(b), and aqueous sodium hydroxide solution (1N, 1.20 ml) and the reaction mixture was treated to afford the title compound (206 mg) as colorless crystals.

mp 221–223° C.

$^1$H-NMR (270 MHz, CDCl$_3$/deuterated methanol=3/1): δ ppm 3.94 (3H, s), 7.35 (1H, dd, J=3.0, 8.5 Hz), 7.75 (1H, d, J=8.5 Hz), 7.96 (2H, d, J=8.5 Hz), 8.13 (2H, d, J=8.5 Hz), 8.38 (1H, d, J=3.0 Hz).

Reference Example 34

3-Dimethylaminopyridine-6-ylbenzoic acid (a) Methyl 3-dimethylaminopyridine-6-ylbenzoate An aqueous solution of formaldehyde (35%, 3.20 ml) and palladium on carbon (5%, 640 mg) was added to a suspension of methyl 3-nitropyridine-6-ylbenzoate (519 mg) in a mixture of methanol (25 ml) and 2-methoxyethanol (5 ml). The mixture was stirred under an atmosphere of hydrogen at 50° C. for 3 days. The catalyst was removed by filtration and the filtrate was concentrated under reduced pressure. The residue was partitioned between ethyl acetate and water. The ethyl acetate layer was separated and washed with saturated aqueous sodium hydrogencarbonate solution and saturated aqueous sodium chloride solution and dried over anhydrous magnesium sulfate and concentrated under reduced pressure. The residue was crystallized from diisopropyl ether to afford the desired product (288 mg) as colorless crystals.

mp 161–163° C.

$^1$H-NMR (270 MHz, CDCl$_3$): δ ppm 3.05 (6H, s), 3.93 (3H, s), 7.05 (1H, dd, J=3.0, 8.5 Hz), 7.66 (1H, d, J=8.5 Hz), 8.00 (2H, d, J=8.5 Hz), 8.09 (2H, d, J=8.5 Hz), 8.24 (1H, d, J=3.0 Hz).

(b) 3-Dimethylaminopyridine-6-ylbenzoic acid

In a similar manner to that described in Example 2, a reaction was carried out using methyl 3-dimethylaminopyridine-6-ylbenzoate (277 mg), which is the product of Reference example 34(a), and aqueous sodium hydroxide solution (1N, 2.20 ml) and the reaction mixture was treated to afford the title compound (237 mg)as colorless crystals.

mp 234–236° C.

$^1$H-NMR (270 MHz, deuterated dimethyl sulfoxide): δ ppm 3.01 (6H, s), 7.18 (1H, dd, J=3.0, 9.0 Hz), 7.87 (1H, d, J=9.0 Hz), 7.97 (2H, d, J=8.5 Hz), 8.10 (2H, d, J=8.5 Hz), 8.23 (1H, d, J=3.0 Hz).

Reference Example 35

Ethyl 3-[4-(2-t-butoxycarbonylaminoethoxy) phenyl]-2-(4-methylphenoxy)propionate (a) Ethyl 3-(4-benzyloxyphenyl)-2-methanesulfonyloxypropionate Methanesulfonyl chloride (0.94 ml) was added to a solution of ethyl 3-(4-benzyloxyphenyl)lactate (3.32 g), which is the product of Reference example 1(b), in anhydrous dichloromethane (30 ml). To this mixture triethylamine (2.47 ml) was added dropwise in an ice bath. The mixture was stirred at ambient temperature for 3 hours. The reaction mixture was concentrated under reduced pressure. The residue was partitioned between ethyl acetate and water. The ethyl acetate layer was separated and dried over anhydrous magnesium sulfate and concentrated under reduced pressure. The residue was crystallized from hexane to afford the desired product (3.60 g) as colorless crystals.

mp 81–83° C.

$^1$H-NMR (270 MHz, CDCl$_3$): δ ppm 1.27 (3H, t, J=7.0 Hz), 2.80 (3H, s), 3.02–3.29 (2H, m), 4.24 (2H, q, J=7.0 Hz), 5.05 (2H, s), 5.05–5.14 (1H, m), 6.93 (2H, d, J=8.5 Hz), 7.17 (2H, d, J=8.5 Hz), 7.28–7.45 (5H, m).

(b) Ethyl 3-(4-benzyloxyphenyl)-2-(4-methylphenoxy)propionate

Potassium carbonate (8.09 g) was added to a solution of ethyl 3-(4-benzyloxyphenyl)-2-methanesulfonyloxypropionate (11.1 g), which is the product of Reference example 35(a), and p-cresol (2.85 g) in N,N-dimethylformamide (110 ml). This mixture was stirred at 70° C. for 16 hours. The reaction mixture was partitioned between ethyl acetate and water and the layers were separated. The ethyl acetate layer was dried over anhydrous magnesium sulfate and concentrated under reduced pressure. The residue was purified via chromatography on silica gel column using hexane/ethyl acetate=9/1 as the eluant to afford the desired compound (2.84 g) as a colorless oil.

$^1$H-NMR (270 MHz, CDCl$_3$): δ ppm 1.23 (3H, t, J=7.0 Hz), 2.30 (3H, s), 3.15–3.28 (2H, m), 4.15–4.25 (2H, m), 4.70–4.79 (1H, m), 5.08 (2H, s), 6.78 (2H, d, J=8.5 Hz), 6.95 (2H, d, J=8.5 Hz), 7.07 (2H, d, J=8.5 Hz), 7.26 (2H, d, J=8.5 Hz), 7.32–7.60 (5H, m).

(c) Ethyl 3-(4-hydroxyphenyl)-2-(4-methylphenoxy) propionate

In a similar manner to that described in Reference example 1(d), a reaction was carried out using ethyl 3-(4-benzyloxyphenyl)-2-(4-methylphenoxy)propionate (2.84 g), which is the product of Reference example 35(b), and palladium on carbon (284 mg) and the reaction mixture was treated to afford the desired compound (2.27 g) as a syrup.

NMR (270 MHz, CDCl$_3$): δ ppm 1.19 (3H, t, J=7.0 Hz), 2.25 (3H, s), 3.09–3.18 (2H, m), 4.16 (2H, q, J=7.0 Hz), 4.64–4.72 (1H, m), 4.76 (1H, brs), 6.65–6.79 (4H, m), 7.02 (2H, d, J=8.5 Hz), 7.16 (2H, d, J=8.5 Hz).

(d) Ethyl 3-[4-(2-t-butoxycarbonylaminoethoxy) phenyl]-2-(4-methylphenoxy)propionate In a similar manner to that described in Reference example 25, a reaction was carried out using ethyl 3-(4-hydroxyphenyl)-2-(4-methylphenoxy)propionate (300 mg), which is the-product of Reference example 35(c), t-butyl 2-methanesulfonyloxy-ethylcarbamate (598 mg) and potassium carbonate (691 mg) and the reaction mixture was treated to afford the title compound (261 mg) as a colorless oil.

$^1$H-NMR (270 MHz, CDCl$_3$): δ ppm 1.20 (3H, t, J=7.0 Hz), 1.45 (9H, s), 2.25 (3H, s), 3.12–3.18 (2H, m), 3.45–3.55 (2H, m), 3.99 (2H, t, J=5.0 Hz), 4.17 (2H, q, J=7.0 Hz), 4.69 (1H, dd, J=5.5, 7.5 Hz), 4.96 (1H, brs), 6.72 (2H, d, J=8.5 Hz), 6.82 (2H, d, J=8.5 Hz), 7.02 (2H, d, J=8.5 Hz), 7.21 (2H, d, J=8.5 Hz).

Reference Example 36

Ethyl 3-[4-(2-t-butoxycarbonylaminoethoxy)phenyl]-2-(4-t-butylphenoxy)propionate (a) Ethyl 3-(4-benzyloxyphenyl)-2-(4-t-butylphenoxy)propionate In a similar manner to that described in Example 122, a reaction was carried out using ethyl 3-(4-benzyloxyphenyl) lactate (5.00 g), which is the product of Reference example 1(b), 4-t-butylphenol (2.50 g), triphenylphosphine (5.24 g) and a solution of diethylazodicarboxylate in toluene (40%, 8.80 ml) and the reaction mixture was treated to afford the desired compound (3.00 g) as a colorless oil.

$^1$H-NMR (270 MHz, CDCl$_3$): δ ppm 1.19 (3H, t, J=7.0 Hz), 1.26 (9H, s), 3.12–3.21 (2H, m), 4.17 (2H, q, J=7.0 Hz), 4.70 (1H, dd, J=5.5, 7.5 Hz), 5.04 (2H, s), 6.76 (2H, d, J=8.5 Hz), 6.90 (2H, d, J=8.5 Hz), 7.20–7.26 (4H, m), 7.31–7.45 (5H, m).

(b) Ethyl 2-(4-t-butylphenoxy)-3-(4-hydroxyphenyl)propionate

In a similar manner to that described in Reference example 1(d), a reaction was carried out using ethyl 3-(4-benzyloxyphenyl)-2-(4-t-butylphenoxy)propionate (3.00 g), which is the product of Reference example 36(a) and palladium on carbon (5%, 300 mg) and the reaction mixture was treated to afford the desired compound (2.37 g) as a colorless oil.

NMR (270 MHz, CDCl$_3$): δ ppm 1.20 (3H, t, J=7.0 Hz), 1.26 (9H, s), 3.13–3.20 (2H, m), 4.18 (2H, q, J=7.0 Hz), 4.69 (1H, dd, J=5.5, 7.5 Hz), 4.81 (1H, brs), 6.75 (2H, d, J=8.5 Hz), 6.76 (2H, d, J=8.5 Hz), 7.17 (2H, d, J=8.5 Hz), 7.24 (2H, d, J=8.5 Hz).

(c) Ethyl 3-[4-(2-t-butoxycarbonylaminoethoxy)phenyl]-2-(4-t-butylphenoxy)propionate In a similar manner to that described in Reference example 25, a reaction was carried out using ethyl 2-(4-t-butylphenoxy)-3-(4-hydroxyphenyl)propionate (2.37 g), which is the product of Reference example 36(b), t-butyl 2-methanesulfonyloxyethylcarbamate (3.60 g) and potassium carbonate (4.78 g) and the reaction mixture was treated to afford the title compound (3.13 g) as a colorless oil.

$^1$H-NMR (270 MHz, CDCl$_3$): δ ppm 1.21 (3H, t, J=7.0 Hz), 1.26 (9H, s), 1.45 (9H, s), 3.13–3.19 (2H, m), 3.51 (2H, q, J=5.0 Hz), 3.99 (2H, t, J=5.0 Hz), 4.18 (2H, q, J=7.0 Hz), 4.66–4.72 (1H, m), 4.90–5.02 (1H, m), 6.76 (2H, d, J=8.5 Hz), 6.82 (2H, d, J=8.5 Hz), 7.22 (2H, d, J=8.5 Hz), 7.24 (2H, d, J=8.5 Hz).

Reference Example 37

Ethyl 3-[4-(2-aminoethoxy)phenyl]-2-(4-fluorophenoxy)propionate (a) Ethyl 3-(4-benzyloxyphenyl)-2-(4-fluorophenoxy)propionate In a similar manner to that described in Example 122, a reaction was carried out using ethyl 3-(4-benzyloxyphenyl) lactate (10.0 g), which is the product of Reference example 1(b), 4-fluorophenol (4.15 g), triphenylphosphine (10.6 g) and diethylazodicarboxylate (6.40 ml) and the reaction mixture was treated to afford the desired compound (7.00 g) as a colorless oil.

$^1$H-NMR (270 MHz, CDCl$_3$): δ ppm 1.18 (3H, t, J=7.0 Hz), 3.16 (2H, d, J=6.5 Hz), 4.16 (2H, q, J=7.0 Hz), 4.66 (1H, t, J=6.5 Hz), 5.04 (2H, s), 6.72–6.80 (2H, m), 6.89–6.97 (4H, m), 7.21 (2H, d, J=8.5 Hz), 7.31–7.48 (5H, m).

(b) Ethyl 2-(4-fluorophenoxy)-3-(4-hydroxyphenyl)propionate

A solution of ethyl 3-(4-benzyloxyphenyl)-2-(4-fluorophenoxy)propionate (7.00 g), which is the product of Reference example 37(a) in a solution of hydrogen bromide in acetic acid (25%, 70 ml) was stirred at ambient temperature for 3 hours. The reaction mixture was concentrated under reduced pressure. Potassium carbonate (6.90 g) was added to a solution of the residue in ethanol (70 ml). This mixture was stirred at ambient temperature for 4 hours. The reaction mixture was concentrated under reduced pressure. The residue was partitioned between ethyl acetate and water and the layers were separated. The ethyl acetate layer was dried over anhydrous magnesium sulfate and concentrated under reduced pressure. The residue was purified via chromatography on a silica gel column using hexane/ethyl acetate=9/1-4/1 as the eluant to afford the desired compound (2.75 g) as a white powder.

mp 80–81° C.

$^1$H-NMR (270 MHz, CDCl$_3$): δ ppm 1.19 (3H, t, J=7.0 Hz), 3.15 (2H, d, J=6.5 Hz), 4.17 (2H, q, J=7.0 Hz), 4.65 (1H, t, J=6.5 Hz), 4.76 (1H, s), 6.71–6.80 (4H, m), 6.87–6.95 (2H, m), 7.16 (2H, d, J=8.5 Hz).

(c) Ethyl 2-(4-fluorophenoxy)-3-[4-[2-(tetrahydropyran-2-yloxy)ethoxy]phenyl]-propionate In a similar manner to that described in Reference example 3(e), a reaction was carried out using ethyl 2-(4-fluorophenoxy)-3-(4-hydroxyphenyl)propionate (2.75 g), which is the product of Reference example 37(b), 2-(2-bromoethyoxy)tetrahydropyran (2.08 g)and potassium carbonate (3.75 g) and the reaction mixture was treated to afford the desired compound (3.75 g) as a colorless oil.

$^1$H-NMR (270 MHz, CDCl$_3$): δ ppm 1.20 (3H, t, J=7.0 Hz), 1.48–1.90 (6H, m), 3.16 (2H, d, J=6.5 Hz), 3.49–3.57 (1H, m), 3.77–3.95 (2H, m), 4.00–4.21 (5H, m), 4.60–4.73 (2H, m), 6.74–6.79 (2H, m), 6.84–6.95 (4H, m), 7.20 (2H, d, J=8.5 Hz).

(d) Ethyl 2-(4-fluorophenoxy)-3-[4-(2-hydroxyethoxy)phenyl]propionate

In a similar manner to that described in Reference example 3(f), a reaction was carried out using ethyl 2-(4-fluorophenoxy)-3-[4-[2-(tetrahydropyran-2-yloxy)ethoxy]-phenyl]propionate (3.75 g), which is the product of Reference example 37(c), and p-toluensulfonic acid monohydrate (2.15 g) and the reaction mixture was treated to afford the desired compound (2.68 g) as a colorless oil.

$^1$H-NMR (270 MHz, CDCl$_3$): δ ppm 1.25 (3H, t, J=7.0 Hz), 2.06 (1H, t, J=6.5 Hz), 3.20–3.23 (2H, m), 3.98–4.02 (2H, m), 4.10–4.13 (2H, m), 4.22 (2H, q, J=7.0 Hz), 4.71 (1H, dd, J=6.0, 7.0 Hz), 6.80–7.00 (6H, m), 7.25–7.28 (2H, m).

(e) Ethyl 2-(4-fluorophenoxy)-3-[4-(2-methanesulfonyloxyethoxy)phenyl]propionate In a similar manner to that described in Reference example 3(g), a reaction was carried out using ethyl 2-(4-fluorophenoxy)-3-[4-(2-hydroxyethoxy)phenyl]propionate (2.68 g), which is the product of Reference example 37(d), triethylamine (1.61 ml) and methanesulfonyl chloride (0.65 ml) and the reaction mixture was treated to afford the desired compound (3.17 g) as a pale yellow oil.

$^1$H-NMR (270 MHz, CDCl$_3$): δ ppm 1.20 (3H, t, J=7.0 Hz), 3.08 (3H, s), 3.17 (2H, d, J=6.5 Hz), 4.18 (2H, q, J=7.0 Hz), 4.20–4.24 (2H, m), 4.54–4.58 (2H, m), 4.66 (1H, t, J=6.5 Hz), 6.74–6.96 (6H, m), 7.23 (2H, d, J=8.5 Hz).

(f) Ethyl 3-[4-(2-azidoethoxy)phenyl]-2-(4-fluorophenoxy)propionate

In a similar manner to that described in Reference example 3(h), a reaction was carried out using ethyl 2-(4-fluorophenoxy)-3-[4-(2-methanesulfonyloxyethoxy)phenyl]propionate (3.16 g), which is the product of Reference example 37(e), and sodium azide (1.45 g) and the reaction mixture was treated to afford the desired compound (2.67 g) as a colorless oil.

$^1$H-NMR (270 MHz, CDCl$_3$): δ ppm 1.20 (3H, t, J=7.0 Hz), 3.17 (2H, d, J=6.5 Hz), 3.58 (2H, t, J=5.0 Hz), 4.08–4.23 (4H, m), 4.66 (1H, t, J=6.5 Hz), 6.74–6.96 (6H, m), 7.20–7.25 (2H, m).

(g) Ethyl 3-[4-(2-aminoethoxy)phenyl]-2-(4-fluorophenoxy)propionate

In a similar manner to that described in Reference example 1(d), a reaction was carried out using ethyl 3-[4-(2-azidoethoxy)phenyl]-2-(4-fluorophenoxy)propionate (2.60 g), which is the product of Reference example 37(f), and palladium on carbon (5%, 250 mg) and the reaction mixture was treated to afford the title compound (2.30 g) as a colorless oil.

$^1$H-NMR (270 MHz, CDCl$_3$): δ ppm 1.20 (3H, t, J=7.0 Hz), 2.99–3.15 (2H, m), 3.16 (2H, d, J=6.5 Hz), 3.97 (2H, t, J=5.0 Hz), 4.17 (2H, q, J=7.0 Hz), 4.66 (1H, t, J=6.5 Hz), 6.72–6.96 (6H, m), 7.1–7.27 (2H, m).

Reference Example 38

Ethyl 3-[4-(2-t-butoxycarbonylaminoethoxy)phenyl]-2-(4-chlorophenoxy)propionate (a) Ethyl 3-(4-benzyloxyphenyl)-2-(4-chlorophenoxy)propionate In a similar manner to that described in Reference example 35(b), a reaction was carried out using ethyl 3-(4-benzyloxyphenyl)-2-methanesulfonyloxypropionate (8.82 g), which is the product of Reference example 35(a), 4-chlorophenol (3.00 g) and potassium carbonate (6.44 g) and the reaction mixture was treated to afford the desired compound (5.99 g) as colorless crystals.

mp 63–64° C.

$^1$H-NMR (270 MHz, CDCl$_3$): δ ppm 1.18 (3H, t, J=7.0 Hz), 3.17 (2H, d, J=6.5 Hz), 4.16 (2H, q, J=7.0 Hz), 4.69 (1H, t, J=6.5 Hz), 5.04 (2H, s), 6.75 (2H, d, J=9.0 Hz), 6.91 (2H, d, J=8.5 Hz), 7.13–7.23 (4H, m), 7.25–7.55 (5H, m).

(b) Ethyl 2-(4-chlorophenoxy)-3-(4-hydroxyphenyl)propionate

In a similar manner to that described in Reference example 37(b), a reaction was carried out using ethyl 3-(4-benzyloxyphenyl)-2-(4-chlorophenoxy)propionate (5.99 g), which is the product of Reference example 38(a), a solution of hydrogen bromide in acetic acid (25%, 60 ml) and potassium carbonate (4.68 g) and the reaction mixture was treated to afford the desired compound (3.85 g) as colorless crystals.

mp 90–93° C.

$^1$H-NMR (270 MHz, CDCl$_3$): δ ppm 1.19 (3H, t, J=7.0 Hz), 3.16 (2H, d, J=6.5 Hz), 4.17 (2H, q, J=7.0 Hz), 4.69 (1H, t, J=6.5 Hz), 4.95 (1H, brs), 6.76 (4H, d, J=8.5 Hz), 7.15 (2H, d, J=8.5 Hz), 7.18 (2H, d, J=8.5 Hz).

(c) Ethyl 3-[4-(2-t-butoxycarbonylaminoethoxy)phenyl]-2-(4-chlorophenoxy)propionate In a similar manner to that described in Example 122, a reaction was carried out using ethyl 2-(4-chlorophenoxy)-3-(4-hydroxyphenyl)propionate (1.01 g), which is the product of Reference example 38(b), t-butyl 2-hydroxyethylcarbamate (1.27 g), triphenylphosphine (2.06 g) and diethylazodicarboxylate (1.37 g) and the reaction mixture was treated to afford the title compound (1.14 g) as a colorless oil.

$^1$H-NMR (270 MHz, CDCl$_3$): δ ppm 1.20 (3H, t, J=7.0 Hz), 1.45 (9H, s), 3.17 (2H, t, J=6.5 Hz), 3.43–3.57 (2H, m), 3.99 (2H, t, J=5.0 Hz), 4.17 (2H, q, J=7.0 Hz), 4.69 (1H, t, J=6.5 Hz), 4.96 (1H, brs), 6.76 (2H, d, J=8.5 Hz), 6.82 (2H, d, J=8.5 Hz), 7.10–7.20 (4H, m).

Reference Example 39

Ethyl 2-hydroxy-3-[4-[2-(4-pyridine-2-ylbenzoylamino)ethoxy]phenyl]propionate (a) Ethyl 3-[4-(2-t-butoxycarbonylaminoethoxy)phenyl]-2-hydroxypropionate In a similar manner to that described in Reference example 25, a reaction was carried out using ethyl 4-hydroxyphenylactate (224 mg), t-butyl 2-methanesulfonyloxy-ethylcarbamate (638 mg) and potassium carbonate (737 mg) and the reaction mixture was treated to afford the title compound (205 mg) as a colorless oil.

$^1$H-NMR (270 MHz, CDCl$_3$): δ ppm 1.29 (3H, t, J=7.0 Hz), 1.45 (9H, s), 2.72 (1H, d, J=6.0 Hz), 2.91 (1H, dd, J=6.5, 14.0 Hz), 3.07 (1H, dd, J=4.5, 14.0 Hz), 3.52 (2H, q, J=5.0 Hz), 3.99 (2H, t, J=5.0 Hz), 4.22 (2H, q, J=7.0 Hz), 4.39 (1H, ddd, J=4.5, 6.0, 6.5 Hz), 4.98 (1H, brt), 6.82 (2H, d, J=8.5 Hz), 7.13 (2H, d, J=8.5 Hz).

(b) Ethyl 2-hydroxy-3-[4-[2-(4-pyridine-2-ylbenzoylamino)ethoxy]phenyl]propionate In a similar manner to that described in Example 126, a reaction was carried out using ethyl 3-[4-(2-t-butoxycarbonylaminoethoxy)phenyl]-2-hydroxypropionate (168 mg), 4-pyridine-2-ylbenzoylchloride hydrochloride (126 mg) and triethylamine (0.28 ml) and the reaction mixture was treated to afford the title compound (188 mg) as colorless crystals.

mp 97–99° C.

$^1$H-NMR (270 MHz, CDCl$_3$): δ ppm 1.29 (3H, t, J=7.0 Hz), 2.92 (1H, d, J=6.5, 14.0 Hz), 3.07 (1H, dd, J=4.5, 14.0 Hz), 3.90 (2H, q, J=5.0 Hz), 4.16 (2H, t, J=5.0 Hz), 4.22 (2H, q, J=7.0 Hz), 4.39 (1H, dd, J=4.5, 6.5 Hz), 6.66 (1H, brt), 6.87 (2H, d, J=8.5 Hz), 7.15 (2H, d, J=8.5 Hz), 7.27–7.32 (1H, m), 7.73–7.84 (2H, m), 7.89 (2H, d, J=8.5 Hz), 8.07 (2H, d, J=8.5 Hz), 8.73 (1H, d, J=5.0 Hz).

Reference Example 40

Ethyl 3-[4-(2-t-butoxycarbonylaminoethoxy)phenyl]-2-(4-trifluoromethoxyphenoxy)propionate (a) Ethyl 3-(4-benzyloxyphenyl)-2-(4-trifluoromethoxyphenoxy)propionate In a similar manner to that described in Example 122, a reaction was carried out using ethyl 3-(4-benzyloxyphenyl)

lactate (4.50 g), which is the product of Reference example 1(b), 4-trifluoromethoxyphenol (2.33 ml), triphenylphosphine (4.71 g) and solution of diethylazodicarboxylate in toluene (40%, 8.15 ml) and the reaction mixture was treated to afford the desired compound (4.19 g) as colorless crystals. mp 34–36° C.

$^1$H-NMR (270 MHz, CDCl$_3$): δ ppm 1.19 (3H, t, J=7.0 Hz), 3.18 (2H, d, J=6.5 Hz), 4.18 (2H, q, J=7.0 Hz), 4.70 (1H, t, J=6.5 Hz), 5.04 (2H, s), 6.82 (2H, d, J=8.5 Hz), 6.91 (2H, d, J=8.5 Hz), 7.09 (2H, d, J=8.5 Hz), 7.21 (2H, d, J=8.5 Hz), 7.29–7.46 (5H, m).

(b) Ethyl 3-(4-hydroxyphenyl)-2-(4-trifluoromethoxyphenoxy)propionate

In a similar manner to that described in Reference example 37(b), a reaction was carried out using ethyl 3-(4-benzyloxyphenyl)-2-(4-trifluoromethoxyphenoxy)propionate (4.08 g), which is the product of Reference example 40(a), a solution of hydrogen bromide in acetic acid (25%, 40 ml) and potassium carbonate (1.68 g) and the reaction mixture was treated to afford the desired compound (2.98 g) as a colorless oil.

$^1$H-NMR (270 MHz, CDCl$_3$): δ ppm 1.20 (3H, t, J=7.0 Hz), 3.17 (2H, d, J=6.5 Hz), 3.50 (1H, brs), 4.18 (2H, q, J=7.0 Hz), 4.70 (1H, t, J=6.5 Hz), 6.76 (2H, d, J=8.5 Hz), 6.82 (2H, d, J=8.5 Hz), 7.09 (2H, d, J=8.5 Hz), 7.15 (2H, d, J=8.5 Hz).

(c) Ethyl 3-[4-(2-t-butoxycarbonylaminoethoxy)phenyl]-2-(4-trifluoromethoxyphenoxy)propionate In a similar manner to that described in Reference example 25, a reaction was carried out using ethyl 3-(4-hydroxyphenyl)-2-(4-trifluoromethoxyphenoxy)propionate (2.93 g), t-butyl 2-methanesulfonyloxyethylcarbamate (4.73 g) and potassium carbonate (5.46 g) and the reaction mixture was treated to afford the title compound (2.28 g) as a colorless oil.

$^1$H-NMR (270 MHz, CDCl$_3$): δ ppm 1.20 (3H, t, J=7.0 Hz), 1.44 (9H, s), 3.18 (2H, d, J=6.5 Hz), 3.51 (2H, q, J=5.0 Hz), 3.99 (2H, t, J=5.0 Hz), 4.19 (2H, q, J=7.0 Hz), 4.70 (1H, t, J=6.5 Hz), 4.97 (1H, brt), 6.81 (2H, d, J=8.5 Hz), 6.83 (2H, d, J=8.5 Hz), 7.08 (2H, d, J=8.5 Hz), 7.21 (2H, d, J=8.5 Hz).

Reference Example 41

Ethyl 3-[4-(2-t-butoxycarbonylaminoethoxy)phenyl]-2-(4-cyanophenoxy)propionate (a) Ethyl 3-(4-benzyloxyphenyl)-2-(4-cyanophenoxy)propionate In a similar manner to that described in Example 122, a reaction was carried out using ethyl 3-(4-benzyloxyphenyl) lactate (1.01 g), which is the product of Reference example 1(b), 4-cyanophenol (481 mg), triphenylphosphine (1.06 g) and solution of diethylazodicarboxylate in toluene (40%, 0.73 ml) and the reaction mixture was treated to afford the desired compound (619 mg) as a colorless oil.

$^1$H-NMR (270 MHz, CDCl$_3$): δ ppm 1.20 (3H, t, J=7.0 Hz), 3.21 (2H, d, J=6.5 Hz), 4.17 (2H, q, J=7.0 Hz), 4.79 (1H, t, J=6.5 Hz), 5.04 (2H, s), 6.88 (2H, d, J=8.5 Hz), 6.91 (2H, d, J=8.5 Hz), 7.19 (2H, d, J=8.5 Hz), 7.28–7.48 (5H, m), 7.54 (2H, d, J=8.5 Hz).

(b) Ethyl 2-(4-cyanophenoxy)-3-(4-hydroxyphenyl)propionate

In a similar manner to that described in Reference example 1(d), a reaction was carried out using ethyl 3-(4-benzyloxyphenyl)-2-(4-cyanophenoxy)propionate (376 mg), which is the product of Reference example 41(a), and palladium on carbon (5%, 65 mg) and the reaction mixture was treated to afford the title compound (293 mg) as a colorless oil.

$^1$H-NMR (270 MHz, CDCl$_3$): δ ppm 1.19 (3H, t, J=7.0 Hz), 3.19 (2H, d, J=6.5 Hz), 4.18 (2H, q, J=7.0 Hz), 4.78 (1H, t, J=6.5 Hz), 6.76 (2H, d, J=8.5 Hz), 6.88 (2H, d, J=9.0 Hz), 7.14 (2H, d, J=8.5 Hz), 7.62 (2H, d, J=9.0 Hz).

(c) Ethyl 3-[4-(2-t-butoxycarbonylaminoethoxy)phenyl]-2-(4-cyanophenoxy)propionate In a similar manner to that described in Reference example 25, a reaction was carried out using ethyl 2-(4-cyanophenoxy)-3-(4-hydroxyphenyl)propionate (293 mg), t-butyl 2-methanesulfonyloxyethylcarbamate (560 mg) and potassium carbonate (520 mg) and the reaction mixture was treated to afford the title compound (245 mg) as a colorless oil.

$^1$H-NMR (270 MHz, CDCl$_3$): δ ppm 1.20 (3H, t, J=7.0 Hz), 1.45 (9H, s), 3.21 (2H, d, J=6.5 Hz), 3.52 (2H, q, J=5.0 Hz), 3.99 (2H, t, J=5.0 Hz), 4.19 (2H, q, J=7.0 Hz), 4.79 (1H, t, J=6.5 Hz), 4.97 (1H, brt), 6.83 (2H, d, J=8.5 Hz), 6.88 (2H, d, J=8.5 Hz), 7.20 (2H, d, J=8.5 Hz), 7.55 (2H, d, J=8.5 Hz).

Reference Example 42

Methyl 3-[4-(2-t-butoxycarbonylaminoethoxy)phenyl]-2-(4-methylthiophenoxy)propionate In a similar manner to that described in Example 122, a reaction was carried out using methyl 3-[4-(2-t-butoxycarbonylaminoethoxy)phenyl]-2-hydroxypropionate (389 mg), which is obtained in a similar manner to that described in Reference example 39(a), 4-methylthiophenol (241 mg), triphenylphosphine (463 mg) and solution of diethylazodicarboxylate in toluene (40%, 0.31 ml) and the reaction mixture was treated to afford the desired compound (265 mg) as a colorless oil which contained some impurities.

$^1$H-NMR (270 MHz, CDCl$_3$): δ ppm 1.45 (9H, s), 2.43 (3H, s), 3.17 (2H, d, J=6.5 Hz), 3.52 (2H, q, J=5.0 Hz), 3.72 (3H, s), 3.99 (2H, t, J=5.0 Hz), 4.72 (1H, t, J=6.5 Hz), 4.98 (1H, brt), 6.78 (2H, d, J=8.5 Hz), 6.82 (2H, d, J=8.5 Hz), 7.20 (4H, d, J=8.5 Hz).

Reference Example 43

Methyl 3-[4-(2-t-butoxycarbonylaminoethoxy)phenyl]-2-(4-methanesulfonylphenoxy)propionate In a similar manner to that described in Example 122, a reaction was carried out using methyl 3-[4-(2-t-butoxycarbonylaminoethoxy)phenyl]-2-hydroxypropionate (518 mg), which is obtained in a similar manner to that described in Reference example 39(a), 4-methanesulfonylphenol (394 mg), tributylphosphine (0.57 ml) instead of triphenylphosphine and 1,1'-(azodicarbonyl)dipiperidine (578 mg) instead of diethylazodicarboxylate and the reaction mixture was treated to afford the desired compound (441 mg) as a mass of foam.

$^1$H-NMR (270 MHz, CDCl$_3$): δ ppm 1.44 (9H, s), 3.00 (3H, s), 3.22 (2H, d, J=6.5 Hz), 3.51 (2H, q, J=5.0 Hz), 3.74 (3H, s), 3.99 (2H, t, J=5.0 Hz), 4.84 (1H, t, J=6.5 Hz), 4.97 (1H, brt), 6.83 (2H, d, J=8.5 Hz), 6.94 (2H, d, J=9.0 Hz), 7.19 (2H, d, J=8.5 Hz), 7.82 (2H, d, J=9.0 Hz).

Reference Example 44

Methyl 3-[4-(2-t-butoxycarbonylaminoethoxy)phenyl]-2-(4-fluorophenoxy)propionate In a similar manner to that described in Example 122, a reaction was carried out using methyl 3-[4-(2-t- butoxycarbonylaminoethoxy)phenyl]-2-hydroxypropionate (420 mg), which is obtained in a similar manner to that described in Reference example 39(a), 4-fluorophenol (284 mg), triphenylphosphine (666 mg) and solution of diethylazodicarboxylate in toluene (40%, 1.10 ml) and the reaction mixture was treated to afford the desired compound (314 mg) as a colorless oil.

$^1$H-NMR (270 MHz, CDCl$_3$): δ ppm 1.45 (9H, s), 3.16 (2H, d, J=6.5 Hz), 3.52 (2H, q, J=5.0 Hz), 3.72 (3H, s), 3.99 (2H, t, J=5.0 Hz), 4.67 (1H, t, J=6.5 Hz), 4.96 (1H, brt), 6.76 (2H, dd, J=4.0, 9.0 Hz), 6.83 (2H, d, J=8.5 Hz), 6.92 (2H, dd, J=8.0, 9.0 Hz), 7.20 (2H, d, J=8.5 Hz).

Reference Example 45

Ethyl 3-[4-(2-t-butoxycarbonylaminoethoxy) phenyl]-2-(4-isopropylphenoxy)-2-methylpropionate In a similar manner to that described in Reference example 25, a reaction was carried out using ethyl 3-(4-hydroxyphenyl)-2-(4-isopropylphenoxy)-2-methylpropionate (4.85 g), which is the product of Reference example 9(b), t-butyl 2-methanesulfonyloxyethylcarbamate (8.47 g) and potassium carbonate (9.78 g) and the reaction mixture was treated to afford the title compound (6.23 g) as a colorless oil.

$^1$H-NMR (270 MHz, CDCl$_3$): δ ppm 1.15–1.28 (9H, m), 1.37 (3H, s), 1.45 (9H, s), 2.83 (1H, septet, J=7.0 Hz), 3.10 (1H, d, J=13.5 Hz), 3.25 (1H, d, J=13.5 Hz), 3.46–3.58 (2H, m), 4.00 (2H, t, J=5.0 Hz), 4.21 (2H, q, J=7.0 Hz), 4.95–5.05 (1H, m), 6.75 (2H, d, J=8.5 Hz), 6.81 (2H, d, J=8.5 Hz), 7.06 (2H, d, J=8.5 Hz), 7.17 (2H, d, J=8.5 Hz).

Reference Example 46

Methyl 3-[4-(2-t-butoxycarbonylaminoethoxy) phenyl]-2-phenylthiopropionate

In a similar manner to that described in Example 122, a reaction was carried out using methyl 3-[4-(2-t-butoxycarbonylaminoethoxy)phenyl]-2-hydroxypropionate (366 mg), which is obtained in a similar manner to that described in Reference example 39(a), thiophenol (0.17 ml), triphenylphosphine (438 mg) and solution of diethylazodicarboxylate in toluene (40%, 0.29 ml) and the reaction mixture was treated to afford the desired compound (209 mg) as a colorless oil.

$^1$H-NMR (270 MHz, CDCl$_3$): δ ppm 1.45 (9H, s), 3.00 (1H, dd, J=6.5, 13.5 Hz), 3.13 (1H, dd, J=9.5, 13.5 Hz), 3.52 (2H, t, J=5.0 Hz), 3.58 (3H, s), 3.86 (1H, dd, J=6.5, 9.5 Hz), 3.98 (2H, t, J=5.0 Hz), 5.00 (1H, brt), 6.80 (2H, d, J=8.5 Hz), 7.10 (2H, d, J=8.5 Hz), 7.30–7.40 (3H, m), 7.41–7.56 (2H, m).

Reference Example 47

Methyl 3-[4-(2-t-butoxycarbonylaminoethoxy) phenyl]-2-(pyridine-3-yloxy)propionate In a similar manner to that described in Example 122, a reaction was carried out using methyl 3-[4-(2-t-butoxycarbonylaminoethoxy)phenyl]-2-hydroxypropionate (404 mg), which is obtained in a similar manner to that described in Reference example 39(a), 3-hydroxypyridine (227 mg), triphenylphosphine (938 mg) and solution of diethylazodicarboxylate in toluene (40%, 0.65 ml) and the reaction mixture was treated to afford the desired compound (345 mg) as a colorless oil.

$^1$H-NMR (270 MHz, CDCl$_3$): δ ppm 1.44 (9H, s), 3.21 (2H, d, J=6.5 Hz), 3.52 (2H, q, J=5.0 Hz), 3.74 (3H, s), 3.99 (2H, t, J=5.0 Hz), 4.78 (1H, t, J=6.5 Hz), 4.96 (1H, brt), 6.84 (2H, d, J=8.5 Hz), 7.11 (1H, d, J=8.5 Hz), 7.18 (1H, dd, J=5.0, 8.5 Hz), 7.20 (2H, d, J=8.5 Hz), 8.23 (1H, d, J=5.0 Hz), 8.24 (1H, s).

Reference Example 48

Methyl 2-(benzoxazole-2-ylthio)-3-[4-(2-t-butoxycarbonylaminoethoxy)phenyl]-propionate In a similar manner to that described in Example 122, a reaction was carried out using methyl 3-[4-(2-t-butoxycarbonylaminoethoxy)phenyl]-2-hydroxypropionate (415 mg), which is obtained in a similar manner to that described in Reference example 39(a), 2-mercaptobenzoxazole (277 mg), tributylphosphine (0.46 ml) instead of triphenylphosphine and 1,1'-(azodicarbonyl) dipiperidine (460 mg) instead of diethylazodicarboxylate and the reaction mixture was treated to afford the desired compound (665 mg) as a colorless oil which contained some impurities.

$^1$H-NMR (270 MHz,. CDCl$_3$): δ ppm 1.46 (9H, s), 3.26 (1H, dd, J=7.0, 14.0 Hz), 3.35 (1H, dd, J=7.5, 14.0 Hz), 3.51 (2H, q, J=5.0 Hz), 3.71 (3H, s), 3.96 (2H, t, J=5.0 Hz), 4.76 (1H, dd, J=7.0, 7.5 Hz), 4.89 (1H, brt), 6.81 (2H, d, J=8.0 Hz), 7.17 (2H, d, J=8.0 Hz), 7.22–7.29 (2H, m), 7.43 (1H, d, J=7.5 Hz), 7.60 (1H, d, J=6.0 Hz).

Reference Example 49

Methyl 2-benzyloxy-3-[4-(2-t-butoxycarbonylaminoethoxy)phenyl]propionate

In a similar manner to that described in Reference example 1(c), a reaction was carried out using methyl 3-[4-(2-t-butoxycarbonylaminoethoxy)phenyl]-2-hydroxypropionate (398 mg), which is obtained in a similar manner to that described in Reference example 39(a), benzylbromide (0.28 ml), hydride (55% suspension in oil, 168 mg) and tetrabutylammonium iodide (43 mg) and the reaction mixture was treated to afford the desired compound (133 mg) as a colorless oil.

$^1$H-NMR (270 MHz, CDCl$_3$): δ ppm 1.46 (9H, s), 2.99 (1H, d, J=7.5 Hz), 3.00 (1H, d, J=5.5 Hz), 3.53 (2H, q, J=5.0 Hz), 3.71 (3H, s), 4.00 (2H, t, J=5.0 Hz), 4.09 (1H, dd, J=5.5, 7.5 Hz), 4.37 (1H, d, J=12.0 Hz), 4.65 (1H, d, J=12.0 Hz), 5.00 (1H, brt), 6.81 (2H, d, J=8.5 Hz), 7.13 (2H, d, J=8.5 Hz), 7.17–7.22 (2H, m), 7.25–7.31 (3H, m).

Reference Example 50

Dibenzyl 2-(3-phenylpropyl)-2-[4-[3-(4-pyridine-2-ylbenzoylamino)propyl]benzyl]malonate (a) 4-(3-Benzyloxycarbonylaminopropyl) benzylalcohol A solution of methyl 4-(2-cyanoethyl)benzoate (10.0 g) in tetrahydrofuran (80 ml) was added dropwise to a suspension of lithium aluminum hydride (4.00 g) in tetrahydrofuran (1 80 ml) in an ice bath. The mixture was stirred at ambient temperature for 1 hour and at 60° C. for 3 hours. To the reaction mixture, water (4 ml), aqueous sodium hydroxide solution (15%, 4 ml) and water (12 ml) were added successively and the mixture was stirred for 1 hour. The insoluble material in the reaction mixture was removed by filtration and washed with tetrahydrofuran. N-Benzyloxycarbonyl-5-norbornene-2,3-dicarboxyimide (16.5 g) was added to the mixture of the filtrate and the tetrahydrofuran solution and this mixture was stirred at ambient temperature for 3 hours. The reaction mixture was concentrated. The residue was partitioned between ethyl acetate and water. The ethyl acetate layer was separated and washed with saturated aqueous sodium chloride solution and saturated aqueous sodium hydrogencarbonate solution and dried over anhydrous magnesium sulfate and concentrated. The residue was purified via chromatography on a silica gel column using hexane/ethyl acetate=1/1 as the eluant to afford the desired compound (5.67 g) as crystals.

$^1$H-NMR (270 MHz, CDCl$_3$): δ ppm 1.82 (2H, quintuplet, J=7.5 Hz), 2.64 (2H, t, J=7.5 Hz), 3.22 (2H, dt, J=6.5, 7.5 Hz), 4.65 (2H, s), 4.75 (1H, brs), 5.09 (2H, s), 7.16 (2H, d, J=8.0 Hz), 7.26–7.36 (7H, m).

(b) 4-[3-(4-Pyridine-2-ylbenzoylamino)propyl] benzylalcohol

Palladium on carbon (5%, 0.15 g) was added to a solution of 4-(3-benzyloxycarbonylaminopropyl)benzylalcohol (1.00 g), which is the product of Reference example 50(a) in ethanol (20 ml). The mixture was stirred under an atmosphere of hydrogen at ambient temperature for 2 hours. The catalyst was removed by filtration and the filtrate was concentrated to afford 4-(3-aminopropyl)benzylalcohol as a gum. In a similar manner to that described in Example 5, a reaction was carried out using 4-(3-aminopropyl) benzylalcohol, 4-pyridine-2-ylbenzoic acid (668 mg) and carbonyidiimidazole (650 mg) and the reaction mixture was treated to afford the desired compound (0.74 g) as colorless crystals.

mp 118–120° C.

$^1$H-NMR (270 MHz, CDCl$_3$): δ ppm 2.00 (2H, quintuplet, J=7.5 Hz), 2.75 (2H, t, J=7.5 Hz), 3.53 (2H, dt, J=6.5, 7.5 Hz), 4.65 (2H, s), 6.10 (1H brs), 7.20–7.31 (5H, m), 7.72–7.80 (4H, m), 8.02 (2H, d, J=8.5 Hz), 8.71 (1H, d, J=5.0 Hz).

(c) 4-[3-(4-pyridine-2-ylbenzoylamino)propyl] benzylchloride

Methanesulfonyl chloride (294 mg) and triethylamine (0.37 ml) were successively added to a solution of 4-[3-(4-pyridine-2-ylbenzoylamino)propyl]benzylalcohol (0.74 g) in dichloromethane (20 ml). The mixture was allowed to stand at ambient temperature for 16 hours. The reaction mixture was concentrated. The residue was partitioned between ethyl acetate and water. The ethyl acetate layer was separated and washed with saturated aqueous sodium chloride solution and dried over anhydrous magnesium sulfate and concentrated to afford crystals. The crystals were washed with a small amount of diisopropyl ether to afford the desired compound (0.68 g).

mp 115–117° C.

$^1$H-NMR (270 MHz, CDCl$_3$): δ ppm 1.99 (2H, quintuplet, J=7.5 Hz), 2.75 (2H, t, J=7.5 Hz), 3.53 (2H, dt, J=6.5, 7.5 Hz), 6.15 (1H, brs), 7.21–7.34 (5H, m), 7.76–7.82 (4H, m), 8.06 (2H, d, J=8.5 Hz) 8.70–8.73 (1H m).

(d) Dibenzyl 2-(3-phenylpropyl)-2-[4-[3-(4-pyridine-2-ylbenzoylamino)propyl]benzyl]malonate In a similar manner to that described in Reference example 2(a), a reaction was carried out using 4-[3-(4-pyridine-2-ylbenzoylamino)propyl]benzylchloride (488 mg), which is the product of Reference example 50(c), sodium hydride (55% suspension in oil, 64 mg) and benzyl (3-phenylpropyl)malonate (540 mg) and the reaction mixture was treated to afford the title compound (0.65 g) as a syrup.

$^1$H-NMR (270 MHz, CDCl$_3$): δ ppm 1.44–1.58 (2H, m), 1.78–1.87 (2H, m), 1.92 (2H, t, J=7.5 Hz), 2.52 (2H, t, J=7.5 Hz), 2.65 (2H, t, J=7.5 Hz), 3.19 (2H, s), 3.49 (2H, dt, J=6.0, 7.5 Hz), 5.05 (1H, d, J=12.0 Hz), 5.09 (1H, d, J=12.0 Hz), 6.16 (1H, brt, J=6.0 Hz), 6.78 (2H, d, J=8.0 Hz), 6.96 (2H, d, J=8.0 Hz), 7.05 (2H, d, J=8.0 Hz), 7.17–7.35 (14H, m), 7.76–7.82 (4H, m), 8.06 (2H, d, J=8.5 Hz), 8.71 (1H, d, J=5.0 Hz).

Reference Example 51

Ethyl 3-[4-(2-t-butoxycarbonylaminoethoxy)-3-chlorophenyl]-2-phenoxypropionate (a) Ethyl 3-(3-chloro-4-hydroxyphenyl)-2-phenoxypropionate A solution of sulfuryl chloride (0.71 ml) in diethyl ether (5 ml) was added dropwise to a solution of ethyl 3-(4-hydroxyphenyl)-2-phenoxypropionate (1.43 g) in diethyl ether (20 ml) at ambient temperature. The mixture was stirred for 8 hour and allowed to stand overnight. The reaction mixture was partitioned between ethyl acetate and water. The ethyl acetate layer was separated and washed with saturated aqueous sodium hydrogencarbonate solution and saturated aqueous sodium chloride solution and dried over anhydrous magnesium sulfate and concentrated under reduced pressure. The residue was purified via chromatography on a silica gel column using hexane/ethyl acetate= 10/3 as the eluant to afford the desired compound (1.09 g) as a colorless oil.

$^1$H-NMR (270 MHz, CDCl$_3$): δ ppm 1.20 (3H, t, J=7.0 Hz), 3.15 (1H, d, J=5.0 Hz), 3.16 (1H, d, J=7.5 Hz), 4.19 (2H, q, J=7.0 Hz), 4.73 (1H, dd, J=5.0, 7.5 Hz), 5.49 (1H, s), 6.84 (2H, d, J=8.0 Hz), 6.94 (1H, d, J=8.5 Hz), 6.96 (1H, t, J=8.0 Hz), 7.12 (1H, dd, J=2.0, 8.5 Hz), 7.25 (2H, t, J=8.0 Hz), 7.28 (1H, d, J=2.0 Hz).

(b) Ethyl 3-[4-(2-t-butoxycarbonylaminoethoxy)-3-chlorophenyl]-2-phenoxypropionate In a similar manner to that described in Example 122, a reaction was carried out using ethyl 3-(3-chloro-4-hydroxyphenyl)-2-phenoxypropionate (761 mg), which is the product of Reference example 51(a), t-butyl 2-hydroxyethylcarbamate (0.96 g), triphenylphosphine (1.55 g) and solution of diethylazodicarboxylate in toluene (40%, 2.69 ml) and the reaction mixture was treated to afford the desired compound (1.03 g) as a colorless oil.

$^1$H-NMR (270 MHz, CDCl$_3$): δ ppm 1.21 (3H, t, J=7.0 Hz), 1.45 (9H, s), 3.15 (1H, d, J=5.5 Hz), 3.16 (1H, d, J=7.5 Hz), 3.56 (2H, q, J=5.0 Hz), 4.05 (2H, t, J=5.0 Hz), 4.19 (2H, q, J=7.0 Hz), 4.73 (1H, dd, J=5.5, 7.5 Hz), 5.06 (1H, brt), 6.84 (2H, d, J=8.0 Hz), 6.85 (1H, d, J=8.5 Hz), 6.96 (1H, t, J=8.0 Hz), 7.15 (1H, dd, J=2.0, 8.5 Hz), 7.25 (2H, t, J=8.0 Hz), 7.33 (1H, d, J=2.0 Hz).

Reference Example 52

Ethyl 3-[3-bromo-4-(2-t-butoxycarbonylaminoethoxy)phenyl]-2-phenoxypropionate (a) Ethyl 3-(3-bromo4-hydroxyphenyl)-2-phenoxypropionate N-bromosuccinimide (1.12 g) was added to a solution of ethyl 3-(4-hydroxyphenyl)-2-phenoxypropionate (1.43 g), which is the product of reference example 4(c) in chloroform (20 ml) at ambient temperature. The mixture was stirred at 70° C. for 4 hour and concentrated under reduced pressure. The residue was partitioned between ethyl acetate and water. The ethyl acetate layer was separated and washed with saturated aqueous sodium chloride solution and dried over anhydrous magnesium sulfate and concentrated under reduced pressure. The residue was purified via chromatography on silica gel column using hexane/ethyl acetate=4/1 as the eluant to afford the desired compound (1.41 g) as a colorless oil.

$^1$H-NMR (270 MHz, CDCl$_3$): δ ppm 1.20 (3H, t, J=7.0 Hz), 3.148 (1H, d, J=5.5 Hz), 3.153 (1H, d, J=7.0 Hz), 4.18 (2H, q, J=7.0 Hz), 4.72 (1H, dd, J=5.5, 7.0 Hz), 5.45 (1H, brs), 6.84 (2H, d, J=8.0 Hz), 6.94 (1H, d, J=8.5 Hz), 6.96 (1H, t, J=8.0 Hz), 7.16 (1H, dd, J=2.0, 8.5 Hz), 7.25 (2H, t, J=8.0 Hz), 7.42 (1H, d, J=2.0 Hz).

(b) Ethyl 3-[3-bromo-4-(2-t-butoxycarbonylaminoethoxy)phenyl]-2-phenoxypropionate In a similar manner to that described in Example 122, a reaction was carried out using ethyl 3-(3-bromo-4-hydroxyphenyl)-2-phenoxypropionate (374 mg), which is the product of Reference example 52(a), t-butyl 2-hydroxyethylcarbamate (403 mg), triphenylphosphine (672 mg) and a solution of diethylazodicarboxylate in toluene (40%, 1.16 ml) and the reaction mixture was treated to afford the desired compound (466 mg) as a colorless oil.

$^1$H-NMR (270 MHz, CDCl$_3$): δ ppm 1.21 (3H, t, J=7.0 Hz), 1.45 (9H, s), 3.15 (1H, d, J=5.5 Hz), 3.16 (1H, d, J=7.0 Hz), 3.56 (2H, q, J=5.0 Hz), 4.04 (2H, t, J=5.0 Hz), 4.19 (2H, q, J=7.0 Hz), 4.72 (1H, dd, J=5.5, 7.0 Hz), 5.08 (1H, brt), 6.82 (1H, d, J=8.5 Hz), 6.85 (2H, d, J=8.0 Hz), 6.96 (1H, t, J=7.5 Hz), 7.20 (1H, dd, J=2.0, 8.5 Hz), 7.25 (2H, dd, J=7.5, 8.0 Hz), 7.50 (1H, d, J=2.0 Hz).

Reference Example 53

Ethyl 3-[4-(2-t-butoxycarbonylaminoethoxy)-3-nitrophenyl]-2-phenoxypropionate (a) Ethyl 3-(4-hydroxy-3-nitrophenyl)-2-phenoxypropionate Water (2.5 ml), concentrated aqueous hydrogen chloride solution (1.17 ml) and sodium nitrate (297 mg) were added to a solution of ethyl 3-(4-hydroxyphenyl)-2-phenoxypropionate (1.00 g), which is the product of Reference example 4(c), in a mixture of dichloromethane (4.0 ml) and diethyl ether (8.0 ml) at ambient temperature. The mixture was stirred for 2.5 hours at the same temperature and allowed to stand for 14 hours. The reaction mixture was partitioned between ethyl acetate and water. The ethyl acetate layer was separated and washed with saturated aqueous sodium hydrogencarbonate solution and saturated aqueous sodium chloride solution and dried over anhydrous magnesium sulfate and concentrated under reduced pressure. The residue was purified via chromatography on a silica gel column using hexane/ethyl acetate=4/1 as the eluant to afford the desired compound (935 mg) as a colorless oil.

$^1$H-NMR (270 MHz, CDCl$_3$): δ ppm 1.23 (3H, t, J=7.0 Hz), 3.23 (2H, d, J=6.0 Hz), 4.21 (2H, q, J=7.0 Hz), 4.76 (1H, t, J=6.0 Hz), 6.83 (2H, d, J=8.0 Hz), 6.97 (1H, t, J=7.5 Hz), 7.11 (1H, d, J=8.5 Hz), 7.25 (2H, dd, J=7.5, 8.0 Hz), 7.56 (1H, dd, J=2.0, 8.5 Hz), 8.08 (1H, d, J=2.0 Hz).

(b) Ethyl 3-[4-(2-t-butoxycarbonylaminoethoxy)-3-nitrophenyl]-2-phenoxypropionate In a similar manner to that described in Example 122, a reaction was carried out using ethyl 3-(4-hydroxy-3-nitrophenyl)-2-phenoxypropionate (270 mg), which is the product of Reference example 53(a), t-butyl 2-hydroxyethylcarbamate (322 mg), triphenylphosphine (535 mg) and a solution of diethylazodicarboxylate in toluene (40%, 0.93 ml) and the reaction mixture was treated to afford the desired compound (349 mg) as a colorless oil.

$^1$H-NMR (270 MHz, CDCl$_3$): δ ppm 1.23 (3H, t, J=7.0 Hz), 1.44 (9H, s), 3.23 (2H, d, J=6.0 Hz), 3.57 (2H, q, J=5.0 Hz), 4.14 (2H, t, J=5.0 Hz), 4.21 (2H, q, J=7.0 Hz), 4.76 (1H, t, J=6.0 Hz), 5.14 (1H, brt), 6.83 (2H, d, J=8.0 Hz), 6.97 (1H, t, J=7.5 Hz), 7.00 (1H, d, J=8.5 Hz), 7.25 (2H, dd, J=7.5, 8.0 Hz), 7.50 (1H, dd, J=2.0, 8.5 Hz), 7.85 (1H, d, J=2.0 Hz).

Reference Example 54

Methyl (S)-2-benzyloxycarbonylamino-3-[4-(2-t-butoxycarbonylaminoethoxy)phenyl]-propionate In a similar manner to that described in Reference example 25, a reaction was carried out using N-benzyloxycarbonyl-L-tyrosine methyl ester (4.94 g), t-butyl 2-methanesulfonyloxyethylcarbamate (8.97 g) and potassium carbonate (10.4 g) and the reaction mixture was treated to afford the title compound (3.32 g) as colorless crystals.

mp 89–91° C.

$^1$H-NMR (270 MHz, CDCl$_3$): δ ppm 1.62 (9H, s), 3.00–3.10 (2H, m), 3.48–3.56 (2H, m), 3.72 (3H, s), 3.98 (2H, t, J=5.0 Hz), 4.56–4.68 (1H, m), 4.99 (1H, brs), 5.10 (2H, ABq, J=12.5 Hz, δ=0.03 ppm), 5.15–5.24 (1H, m), 6.79 (2H, d, J=8.5 Hz), 7.00 (2H, d, J=8.5 Hz), 7.23–7.41 (5H, m).

Reference Example 55

Ethyl 3-(4-hydroxyphenyl)-2-(phenylamino)propionate (a) Ethyl 3-(4-benzyloxyphenyl)-2-(phenylamino)propionate A mixture of ethyl 3-(4-benzyloxyphenyl)-2-methanesulfonyloxypropionate (4.00 g) and aniline (5 ml) was stirred at 110° C. for 24 hours. The reaction mixture was purified via chromatography on silica gel column using ethyl acetate/hexane=1/4 as the eluant to afford the desired compound (3.94 g) as a syrup.

$^1$H-NMR (270 MHz, CDCl$_3$): δ ppm 1.17 (3H, t, J=7 Hz), 3.00–3.14 (2H, m), 4.12 (2H, dq, J=1.5, 7 Hz), 4.30 (1H, t, J=6 Hz), 5.04 (2H, s), 6.60 (2H, d, J=8.5 Hz), 6.73 (1H, t, J=7.5 Hz), 6.89 (2H, d, J=8.5 Hz), 7.09 (2H, d, J=8.5 Hz), 7.16 (2H, d, J=8.5 Hz), 7.31–7.44 (5H, m).

(b) Ethyl 3-(4-hydroxyphenyl)-2-(phenylamino)propionate

Palladium on carbon (5%, 0.80 g) was added to a solution of ethyl 3-(4-benzyloxyphenyl)-2-(phenylamino)propionate (3.94 g), which is the product of Reference example 55(a), in a mixture of ethanol (40 ml) and tetrahydrofuran (20 ml). The mixture was stirred under an atmosphere of hydrogen at 50° C. for 6 hours. The catalyst was removed by filtration and the filtrate was concentrated. The residue was purified via chromatography on a silica gel column using ethyl acetate/hexane=1/2 as the eluant to afford the title compound (2.95 g) as a syrup.

$^1$H-NMR (270 MHz, CDCl$_3$): δ ppm 1.19 (3H, t, J=7 Hz), 3.00–3.13 (2H, m), 4.13 (2H, dq, J=1, 7 Hz), 4.30 (1H, brt, J=6 Hz), 4.88 (1H, brs), 6.60 (2H, d, J=8 Hz), 6.71–6.76 (3H, m), 7.03 (2H, d, J=8 Hz), 7.14–7.20 (2H, m).

Reference Example 56

Ethyl 3-(4-hydroxyphenyl)-2-(N-ethyl-N-phenylamino)propionate (a) Ethyl 3-(4-benzyloxyphenyl)-2-(N-ethyl-N-phenylamino)propionate In a similar manner to that described in Reference example 55(a), a reaction was carried out using ethyl 3-(4-benzyloxyphenyl)-2-methanesulfonyloxypropionate (4.50 g) and N-ethylaniline (5.6 ml) and the reaction mixture was treated to afford a mixture of the desired compound and N-ethylaniline (6.30 g) as a syrup.

$^1$H-NMR (270 MHz, CDCl$_3$): δ ppm 1.07 (3H, t, 3H, J=7 Hz), 1.14 (3H, t, J=7 Hz), 3.01–3.45 (4H, m), 4.09 (2H, q, J=7 Hz), 4.39 (1H, t, J=7.5 Hz), 5.02 (2H, s), 6.66–6.75 (3H, m), 6.87(2H, d, J=8 Hz), 7.10 (2H, d, J=8.5 Hz), 7.15–7.25 (2H, m), 7.31–7.44 (5H, m).

(b) Ethyl 2-(N-ethyl-N-phenylamino)-3-(4-hydroxyphenyl)propionate

In a similar manner to that described in Reference example 55(b), a reaction was carried out using the mixture (6.30 g), which is the product of Reference example 56(a) and the reaction mixture was treated to afford the title compound (2.37 g) as a syrup.

$^1$H-NMR (270 MHz, CDCl$_3$): δ ppm 1.07 (3H, t, J=7 Hz), 1.15 (3H, t, J=7 Hz), 3.05 (1H, dd, J=8, 14 Hz), 3.26 (1H, d, d, J=7.5, 14 Hz), 3.30–3.46 (2H, m), 4.10 (2H, q, J=7 Hz), 4.38 (1H, t, J=8 Hz), 4.75 (1H, br.s), 6.67–6.79 (5H, m), 7.05 (2H, d, J=8.5 Hz), 7.18–7.26 (2H, m).

Reference Example 57

Ethyl 3-(4-hydroxyphenyl)-2-(pyrrole-1-yl)propionate (a) Ethyl 3-(4-benzyloxyphenyl)-2-(pyrrole-1-yl)propionate 1,4-dichloro-1,4-dimethoxybutane (3.30 g) was added to a solution of ethyl 3-(4-benzyloxyphenyl)-2-aminopropionate (3.30 g) in dichloromethane (80 ml) and then amberlyst A-21 (20 g) was added to the mixture. The mixture was stirred at ambient temperature for 18 hours and the reaction mixture was filtered. The filtrate was concentrated and the residue was purified via chromatography on a silica gel column using ethyl acetate/hexane=1/5 as the eluant to afford the desired compound (1.00 g) as a syrup.

$^1$H-NMR (270 MHz, CDCl$_3$): δ ppm 1.19(3H, t, J=7 Hz), 3.19(1H, dd, J=8.5, 14 Hz), 3.34 (1H, dd, J=7, 14 Hz), 4.14 (2H, q, J=7 Hz), 4.68 (1H, dd, J=7, 8.5 Hz), 5.01 (2H, s), 6.15 (2H, t, J=2 Hz), 6.73 (2H, t, J=2 Hz), 6.84 (2H, d, J=8.5 Hz), 6.94 (2H, d, J=8.5 Hz), 7.28–7.43 (5H, m).

(b) Ethyl 3-(4-hydroxyphenyl)-2-(pyrrole-1-yl)propionate

In a similar manner to that described in Reference example 55(b), a reaction was carried out using ethyl 3-(4-benzyloxyphenyl)-2-(pyrrole-1-yl)propionate (1.00 g) obtained in Reference example 57(a) and palladium on carbon (5%, 0.12 g) and the reaction mixture was treated to afford the title compound (0.71 g) as a syrup.

$^1$H-NMR (270 MHz, CDCl$_3$): δ ppm 1.20 (3H, t, J=7 Hz), 3.18 (1H, dd, J=8.5, 14 Hz), 3.33 (1H, dd, J=7, 14 Hz), 4.15 (2H, q, J=7 Hz), 4.67 (1H, dd, J=7, 8.5 Hz), 4.80 (1H, s), 6.14 (2H, t, J=2 Hz), 6.71 (2H, d, J=8.5 Hz), 6.72 (2H, d, J=2 Hz), 6.88 (2H, d, J=8.5 Hz).

Reference Example 58

Ethyl 2-(N,N-diethylamino)-3-(4-hydroxyphenyl)propionate

Acetic acid (0.3 ml) and acetaldehyde (0.5 ml) were added to a solution of DL-tyrosine ethyl ester hydrochloride (491 mg) in methanol (5 ml). To the mixture sodium cyanoborohydride (126 mg) was added and the mixture was stirred at ambient temperature for 2 hours. At the end of this time the reaction mixture was concentrated. The residue was partitioned between ethyl acetate and water. The ethyl acetate layer was separated and washed with aqueous sodium hydrogencarbonate solution and dried over anhydrous magnesium sulfate and concentrated under reduced pressure. The residue was purified via chromatography on a silica gel column using methanol/dichloromethane=1/20 as the eluant to afford the desired compound (420 mg) as a syrup.

$^1$H-NMR (270 MHz, CDCl$_3$): δ ppm 1.02 (6H, t, J=7 Hz), 1.16 (3H, t, J=7 Hz), 2.53 (2H, sextet, J=7 Hz), 2.79 (2H, sextet, J=7 Hz), 2.81 (1H, dd, J=6, 13.5 Hz), 2.99 (1H, dd, J=9, 13.5 Hz), 3.55 (1H, dd, J=6, 9 Hz), 4.02–4.11 (2H, m), 6.72 (2H, d, J=8.5 Hz), 7.02 (2H, d, J=8.5 Hz).

Reference Example 59

Ethyl 2-N-(t-butoxycarbonyl)ethylamino-3-(4-hydroxyphenyl)propionate (a) Ethyl 2-ethylamino-3-(4-hydroxyphenyl)propionate In a similar manner to that described in Reference example 9, a reaction was carried out using DL-tyrosine ethyl ester hydrochloride (983 mg), acetaldehyde (0.26 ml) and sodium cyanoborohydride (100 mg) and the reaction mixture was treated to afford the desired compound (515 mg) as a syrup which was allowed to stand to give crystals.

mp 87–89° C.

$^1$H-NMR (270 MHz, CDCl$_3$): δ ppm 1.08 (3H, t, J=7 Hz), 1.18 (3H, t, J=7 Hz), 2.48–2.72 (2H, m), 2.82–2.96 (2H, m), 3.50 (1H, t, J=7 Hz), 4.11 (2H, q, J=7 Hz), 6.68 (2H, d, J=8.5 Hz), 7.01 (2H, d, J=8.5 Hz).

(b) Ethyl 2-N-(t-butoxycarbonyl)ethylamino-3-(4-hydroxyphenyl)propionate

Triethylamine (1 ml) was added dropwise to a solution of ethyl 2-ethylamino-3-(4-hydroxyphenyl)propionate (569 mg), which is the product of Reference example 59(a), and di-t-butylcarbonate (785 mg) in dichloromethane (10 ml) in an ice bath. The mixture was stirred at ambient temperature for 4 hours. At the end of this time the reaction mixture was concentrated. The residue was partitioned between ethyl acetate and water. The ethyl acetate layer was separated and dried over anhydrous magnesium sulfate and concentrated under reduced pressure. The residue was purified via chromatography on a silica gel column using ethyl acetate/hexane=1/2 as the eluant to afford the title compound (663 mg) as a syrup.

$^1$H-NMR (270 MHz, CDCl$_3$): δ ppm 0.90 (3H, br t, J=7 Hz), 1.21–1.31 (3H, m), 1.45 (9H, s), 3.15–3.37 (1H, m), 3.08 (1H, dd, J=10, 14 Hz), 3.15–3.37 (1H, m), 3.24 (1H, dd, J=5, 14 Hz), 3.85–4.30 (3H, m), 6.76 (2H, br d, J=8.5 Hz), 7.00–7.11 (2H, m).

Reference Example 60

Ethyl 2-N-(t-butoxycarbonyl)propylamino-3-(4-hydroxyphenyl)propionate (a) Ethyl 3-(4-hydroxyphenyl)-2-propylaminopropionate In a similar manner to that described in Reference example 59(a), a reaction is carried out using DL-tyrosine ethyl ester hydrochloride, propionaldehyde and sodium cyanoborohydride and the reaction mixture is treated to afford the desired compound.

(b) Ethyl 2-N-(t-butoxycarbonyl)propylamino-3-(4-hydroxyphenyl)propionate

In a similar manner to that described in Reference example 59(b), a reaction is carried out using ethyl 3-(4-hydroxyphenyl)-2-propylaminopropionate, which is the product of reference example 60(a), and t-butyldicarbonate and the reaction mixture is treated to afford the title compound.

Reference Example 61

2-(4-pyridine-2-ylbenzoylamino)ethanol

Triethylamine (0.14 ml) was added to a suspension of 4-pyridine-2-ylbenzoylchloride hydrochloride (254 mg) in dichloromethane (2 ml). To the mixture a solution of ethanolamine (0.060 ml) in dichloromethane (3 ml) was added. This mixture was stirred for 30 minutes. At the end of this time the reaction mixture was concentrated and the residue was partitioned between ethyl acetate and water. The ethyl acetate layer was separated and washed with aqueous sodium chloride and dried over anhydrous magnesium sulfate and concentrated to afford crystals. The crystals were washed with isopropyl ether to afford the title compound (111 mg).

mp 86–88° C.

$^{1}$H-NMR (270 MHz, CDCl$_{3}$): δ ppm 2.52 (1H, t, J=4.5 Hz), 3.68 (2H, dt, J=5.0, 5.5 Hz), 3.88(2H, dt, J=4.5, 5.5 Hz), 6.68 (1H, br s), 7.24–7.33 (1H, m), 7.77–7.82 (1H, m), 7.90 (2H, d, J=8.5 Hz), 8.09 (2H, d, J=8.5 Hz), 8.72 (1H, d, J=5 Hz).

Test Example
Action in Depressing Blood Glucose (Method 1)

Each compound, admixed with powder feed F-2 (Funabashi Farm) was administered to hyperglycemic male KK mice each having a body weight of 40 g or more at a rate of 0.01% (ca. 10 mg/kg/day) for three days. Meanwhile, mice of a control group were fed with the powder feed only. Then, a blood sample was collected from the caudal vein of each mouse under no anesthesia and centrifuged. The blood glucose in the plasma thus obtained was determined using Glucoloader F (Product of A & T Co., Ltd.).

The blood glucose depression rate were estimated from the following equation:

Blood glucose depression rate (%)=[(Blood glucose in Control group−Blood glucose in administered group)/Blood glucose in Control group]×100

The results are summarized in Table 156.

TABLE 156

| Test Compound | Rate of hypoglycemic activity (%) |
|---|---|
| Compound of Example 2 | 43 |
| Compound of Example 4 | 15 |
| Compound of Example 8 | 22 |
| Compound of Example 10 | 64 |
| Compound of Example 12 | 42 |
| Compound of Example 16 | 64 |
| Compound of Example 18 | 68 |
| Compound of Example 22 | 17 |
| Compound of Example 27 | 35 |
| Compound of Example 29 | 20 |
| Compound of Example 30 | 18 |
| Compound of Example 32 | 21 |
| Compound of Example 34 | 22 |
| Compound of Example 43 | 20 |
| Compound of Example 48 | 37 |
| Compound of Example 52 | 20 |
| Compound of Example 62 | 16 |
| Compound of Example 70 | 23 |
| Compound of Example 74 | 60 |
| Compound of Example 76 | 50 |
| Compound of Example 78 | 53 |
| Compound of Example 80 | 50 |
| Compound of Example 82 | 32 |
| Compound of Example 97 | 66 |
| Compound of Example 99 | 57 |
| Compound of Example 101 | 51 |
| Compound of Example 103 | 48 |
| Compound of Example 104 | 73 |
| Compound of Example 107 | 38 |
| Compound of Example 109 | 38 |
| Compound of Example 111 | 70 |
| Compound of Example 113 | 64 |
| Compound of Example 115 | 66 |
| Compound of Example 117 | 70 |
| Compound of Example 119 | 49 |
| Compound of Example 121 | 60 |
| Compound of Example 123 | 43 |
| Compound of Example 125 | 54 |
| Compound of Example 127 | 56 |
| Compound of Example 137 | 49 |
| Compound of Example 139 | 23 |
| Compound of Example 141 | 27 |
| Compound of Example 143 | 43 |
| Compound of Example 145 | 28 |
| Compound of Example 152 | 58 |

These data show that the compounds of the present invention exhibit excellent hypoglycemic activity.

Formulation example

| (1) Capsule | |
|---|---|
| Compound of Example 2 | 10 mg |
| Lactose | 110 mg |
| Corn starch | 58 mg |
| Magnesium stearate | 2 mg |
| | 180 mg |

Powders of each component mentioned above were mixed and passed through a sieve of 60 mesh (the standard of mesh was based on Tyler). The mixed powder (180 mg) was used to fill a gelatin capsule (No. 3) to give a capsule.

| (2) Tablet | |
|---|---|
| Compound of example 2 | 10 mg |
| Lactose | 85 mg |
| Corn starch | 34 mg |
| Finely crystallized cellulose | 20 mg |
| Magnesium stearate | 1 mg |
| | 150 mg |

Powders of each component shown above were mixed and compression-molded to prepare a tablet (150 mg). If necessary the tablet may be coated with sugar or film.

| (3) Granule | |
|---|---|
| Compound of Example 2 | 10 mg |
| Lactose | 839 mg |
| Corn starch | 150 mg |
| Hydroxypropyl cellulose | 1 mg |
| | 1000 mg |

Powders of each component shown above were mixed and wetted with pure water, granulated using a basket type granulator and dried to give a granule.

[Industrial Applicability]

The amidocarboxylic acid derivatives, the pharmacologically acceptable salts thereof and the pharmacologically acceptable esters thereof of the present invention are useful as a preventive agent and/or therapeutic agent for diabetes mellitus, hyperlipemia, obesity, impaired glucose tolerance, insuline resistant non-impaired glucose tolerance, hypertension, diabetic complications, arteriosclerosis, gestational diabetes mellitus, polycystic ovary syndrome, cell injury caused by atherosclerosis, arthrosteitis, rheumatic arthritis, allergic diseases, asthma, cancer, autoimmune diseases, pancreatitis, osteoporosis, cataracts, etc.

What is claimed is:

1. An amidocarboxylic acid compound of formula (1):

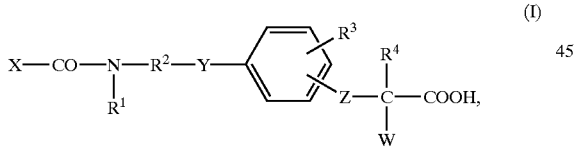

(I)

wherein:

$R^1$ is selected from the group consisting of hydrogen atoms, straight or branched chain alkyl groups having from 1 to 6 carbon atoms and aralkyl groups having from 7 to 12 carbon atoms which include a straight or branched chain alkyl group having I to 4 carbon atoms substituted with an aryl moiety;

$R^2$ is selected from the group consisting of straight or branched chain alkylene groups having from 1 to 6 carbon atoms;

$R^3$ is selected from the group consisting of (i) hydrogen atoms, (ii) straight or branched chain alkyl groups having from 1 to 6 carbon atoms, (iii) straight or branched chain alkoxy groups having from 1 to 4 carbon atoms, (iv) straight or branched chain alkylthio groups having from 1 to 4 carbon atoms, (v) halogen atoms, (vi) nitro groups, (vii) straight or branched chain dialkylamino groups in which each of said alkyl groups are the same or different and each has from 1 to 4 carbon atoms, (viii) aryl groups having from 6 to 10 carbon atoms which are unsubstituted or have from 1 to 5 substituents selected from substituents a defined below, (ix) aralkyl groups having from 7 to 12 carbon atoms which are unsubstituted or have from 1 to 5 substituents selected from substituents a defined below on said aryl moiety, (x) hydroxyl groups and (xi) straight or branched chain aliphatic acyl groups having from 1 to 5 carbon atoms;

$R^4$ is selected from the group consisting of hydrogen atoms and straight or branched chain alkyl groups having from 1 to 6 carbon atoms;

Z is selected from the group consisting of straight or branched chain alkylene group having from 1 to 6 carbon atoms;

W is selected from the group consisting of (i) straight or branched chain alkyl groups having from 1 to 6 carbon atoms, (ii) hydroxyl groups, (iii) straight or branched chain alkoxy groups having from 1 to 4 carbon atoms, (iv) straight or branched chain alkylthio groups having from 1 to 4 carbon atoms, (v) aryl groups having from 6 to 10 carbon atoms which are unsubstituted or have from 1 to 5 substituents selected from substituents a defined below, (vi) aryloxy groups having from 6 to 10 carbon atoms which are unsubstituted or have from 1 to 5 substituents selected from substituents a defined below on said aryl moiety, (vii) arylthio groups having from 6 to 10 carbon atoms which are unsubstituted or have from 1 to 5 substituents selected from substituents α defined below on said aryl moiety, (viii) aralkyl groups having from 7 to 12 carbon atoms which include a straight or branched chain alkyl group having 1 to 4 carbon atoms substituted with an aryl moiety which are unsubstituted or have from 1 to 5 substituents selected from substituents α defined below on said aryl moiety, (ix) aralkyloxy groups having from 7 to 12 carbon atoms which are unsubstituted or have from 1 to 5 substituents selected from substituents α defined below on said aryl moiety, (x) aralkylthio groups having from 7 to 12 carbon atoms which are unsubstituted or have from 1 to 5 substituents selected from substituents α defined below on said aryl moiety, (xi) aryloxyalkyl groups in which said aryl moiety is an aryl group having from 6 to 10 carbon atoms which are unsubstituted or have from 1 to 5 substituents selected from substituents α defined below and said alkyl moiety is a straight or branched chain alkyl group having from 1 to 4 carbon atoms, (xii) pyridyl, (xiii) quinolyl, (xiv) amino groups, (xv) straight or branched chain monoalkylamino groups in which said alkyl moiety has from 1 to 4 carbon atoms, and (xvi) straight or branched chain dialkylamino groups in which each of said alkyl moieties may be the same or different and each has from 1 to 4 carbon atoms, X is a phenyl group which is unsubstituted or has 1 to 3 substituents a defined below or a hetero aryl group selected from the group consisting of pyridyl, quinolyl and isoquinolyl, said hetero aryl group being unsubstituted or having from 1 to 3 substituents selected from substituents α defined below;

said substituents α are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain aliphatic acyl groups having from 1 to 5 carbon atoms, (vi) straight or branched chain alkoxy groups having from 1 to 4 carbon atoms, (vii) straight or branched chain halogenated alkoxy groups having from 1 to 4 carbon atoms, (viii) straight or branched chain alkylenedioxy groups having from 1 to 4 carbon atoms, (ix) aralkyloxy groups having from 7 to 12 carbon atoms which are unsubstituted or have from 1 to 3 substituents selected from substituents β defined below, (x) straight or branched chain alkylthio groups having from 1 to 4 carbon atoms, (xi) straight or branched chain alkylsulfonyl groups having from 1 to 4 carbon atoms, (xii) halogen atoms, (xiii) nitro groups, (xiv) cyano groups, (xv) amino groups, (xvi) straight or branched chain monoalkylamino groups in which said alkyl moiety has from 1 to 4 carbon atoms, (xvii) straight or branched chain alkoxycarbonylamino groups in which said alkoxy moiety has from 1 to 4 carbon atoms, (xviii) straight or branched chain dialkylamino groups in which said alkyl moieties are the same or different and each has from 1 to 4 carbon atoms, (xix) a phenyl group which is unsubstituted or has 1 to 3 substituents β defined below and (xx) a hetero aryl group selected from the group consisting of pyridyl, quinolyl and isoquinolyl, said hetero aryl group being unsubstituted or having from 1 to 3 substituents β defined below;

said substituents β are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from 1 to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) straight or branched chain aliphatic acyl groups having from 1 to 5 carbon atoms, (ix) halogen atoms, (x) nitro groups, (xi) cyano groups, (xii) carboxyl groups, (xiii) amino groups, (xiv) straight or branched chain monoalkylamino groups in which said alkyl moiety has from 1 to 4 carbon atoms, (xv) straight or branched chain dialkylamino groups in which said alkyl moieties may be the same or different and each has from 1 to 4 carbon atoms, (xvi) straight or branched chain aminoalkyl groups having from 1 to 4 carbon atoms, (xvii) monoalkylaminoalkyl groups in which said monoalkylamino moiety has one straight or branched chain alkyl group having from 1 to 4 carbon atoms and said alkyl moiety is a straight or branched chain alkyl group having from 1 to 4 carbon atoms, (xviii) dialkylaminoalkyl groups in which said dialkylamino moiety has two straight or branched chain alkyl groups which are the same or different and each has from 1 to 4 carbon atoms and said alkyl moiety is a straight or branched chain alkyl group having from 1 to 4 carbon atoms, and (xix) straight or branched chain alkoxycarbonylamino groups in which said alkoxy moiety has from 1 to 4 carbon atoms; and Y is selected from the group consisting of a single bond, an oxygen atom, a sulfur atom and a group of formula: >N—$R^5$ wherein $R^5$ is selected from the group consisting of hydrogen atoms, straight or branched chain alkyl groups having from 1 to 6 carbon atoms, and straight or branched chain aliphatic acyl groups having from 1 to 8 carbon atoms; or a pharmacologically acceptable salt thereof or a pharmacologically acceptable ester thereof.

2. An amidocarboxylic acid compound according to claim 1, a pharmacologically acceptable salt thereof or a pharmacologically acceptable ester thereof, wherein $R^1$ is selected from the group consisting of hydrogen atoms, straight or branched chain alkyl groups having from 1 to 4 carbon atoms and said aralkyl groups having from 7 to 9 carbon atoms.

3. An amidocarboxylic acid compound according to claim 1, a pharmacologically acceptable salt thereof or a pharmacologically acceptable ester thereof, wherein:

$R^1$ is selected from the group consisting of hydrogen atoms and straight or branched chain alkyl groups having from 1 to 4 carbon atoms.

4. An amidocarboxylic acid compound according to claim 1, a pharmacologically acceptable salt thereof or a pharmacologically acceptable ester thereof, wherein:

$R^1$ is a hydrogen atom.

5. An amidocarboxylic acid compound according to claim 1, a pharmacologically acceptable salt thereof or a pharmacologically acceptable ester thereof, wherein:

$R^2$ is a straight or branched chain alkylene group having from 2 to 4 carbon atoms.

6. An amidocarboxylic acid compound according to claim 1, a pharmacologically acceptable salt thereof or a pharmacologically acceptable ester thereof, wherein:

$R^2$ is an ethylene group.

7. An amidocarboxylic acid compound according to claim 1, a pharmacologically acceptable salt thereof or a pharmacologically acceptable ester thereof, wherein:

$R^3$ is selected from the group consisting of hydrogen atoms, straight or branched chain alkyl groups having from 1 to 4 carbon atoms, alkoxy groups having one or two carbon atoms, alkylthio groups having one or two carbon atoms, halogen atoms, nitro groups, hydroxyl groups and straight or branched chain aliphatic acyl groups having from 1 to 5 carbon atoms.

8. An amidocarboxylic acid compound according to claim 1, a pharmacologically acceptable salt thereof or a pharmacologically acceptable ester thereof, wherein:

$R^3$ is selected from the group consisting of hydrogen atoms, halogen atoms and nitro groups.

9. An amidocarboxylic acid compound according to claim 1, a pharmacologically acceptable salt thereof or a pharmacologically acceptable ester thereof, wherein:

$R^3$ is a hydrogen atom.

10. An amidocarboxylic acid compound according to claim 1, a pharmacologically acceptable salt thereof or a pharmacologically acceptable ester thereof, wherein:

$R^4$ is selected from the group consisting of hydrogen atoms and straight or branched chain alkyl groups having from 1 to 4 carbon atoms.

11. An amidocarboxylic acid compound according to claim 1, a pharmacologically acceptable salt thereof or a pharmacologically acceptable ester thereof, wherein:

$R^4$ is selected from the group consisting of hydrogen atoms and methyl groups.

12. An amidocarboxylic acid compound according to claim 1, a pharmacologically acceptable salt thereof or a pharmacologically acceptable ester thereof, wherein:

R⁴ is a hydrogen atom.

13. An amidocarboxylic acid compound according to claim 1, a pharmacologically acceptable salt thereof or a pharmacologically acceptable ester thereof, wherein:
Z is a straight or branched chain alkylene group having from 1 to 4 carbon atoms.

14. An amidocarboxylic acid compound according to claim 1, a pharmacologically acceptable salt thereof or a pharmacologically acceptable ester thereof, wherein:
Z is a methylene group.

15. An amidocarboxylic acid compound according to claim 1, a pharmacologically acceptable salt thereof or a pharmacologically acceptable ester thereof, wherein:
W is selected from the group consisting of (i) straight or branched chain alkyl groups having from 1 to 6 carbon atoms, (ii) hydroxyl groups, (iii) straight or branched chain alkoxy groups having from 1 to 4 carbon atoms, (iv) straight or branched chain alkylthio groups having from 1 to 4 carbon atoms, (v) aryl groups having from 6 to 10 carbon atoms which are unsubstituted or have from 1 to 3 substituents selected from substituents $\alpha^1$ defined below, (vi) aryloxy groups having from 6 to 10 carbon atoms which are unsubstituted or have from 1 to 3 substituents selected from substituents $\alpha^1$ defined below on said aryl moiety, (vii) arylthio groups having from 6 to 10 carbon atoms which are unsubstituted or have from 1 to 3 substituents selected from substituents $\alpha^1$ defined below on said aryl moiety, (viii) said aralkyl groups having from 7 to 12 carbon atoms which are unsubstituted or have from 1 to 3 substituents selected from substituents $\alpha^1$ defined below on said aryl moiety, (ix) aralkyloxy groups having from 7 to 12 carbon atoms which are unsubstituted or have from 1 to 3 substituents selected from substituents $\alpha^1$ defined below on said aryl moiety, (x) aralkylthio groups having from 7 to 12 carbon atoms which are unsubstituted or have from 1 to 3 substituents selected from substituents $\alpha^1$ defined below on said aryl moiety, (xi) aryloxyalkyl groups in which said aryl moiety is an aryl group having from 6 to 10 carbon atoms which are unsubstituted or have from 1 to 3 substituents selected from substituents $\alpha^1$ defined below and said alkyl moiety is a straight or branched chain alkyl group having from 1 to 4 carbon atoms, (xii) pyridyl and (xiii) quinolyl;

said substituents $\alpha^1$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain aliphatic acyl groups having from 1 to 5 carbon atoms, (vi) straight or branched chain alkoxy groups having from 1 to 4 carbon atoms, (vii) straight or branched chain halogenated alkoxy groups having from 1 to 4 carbon atoms, (viii) straight or branched chain alkylenedioxy groups having from 1 to 4 carbon atoms, (ix) aralkyloxy groups having from 7 to 12 carbon atoms which are unsubstituted or have from 1 to 3 substituents selected from substituents $\beta^1$ defined below, (x) straight or branched chain alkylthio groups having from 1 to 4 carbon atoms, (xi) straight or branched chain alkylsulfonyl groups having from 1 to 4 carbon atoms, (xii) halogen atoms, (xiii) nitro groups, (xiv) cyano groups, (xv) amino groups, (xvi) straight or branched chain monoalkylamino groups in which said alkyl moiety has from 1 to 4 carbon atoms, (xvii) straight or branched chain dialkylamino groups in which each of said alkyl groups are the same or different and each has from 1 to 4 carbon atoms, (xix) a hetero aryl group selected from the group consisting of pyridyl, quinolyl and isoquinolyl, said hetero aryl group being unsubstituted or having from 1 to 3 substituents $\beta^1$ defined below and (xx) a phenyl group which is unsubstituted or has 1 to 3 substituents $\beta^1$ defined below;

said substituents $\beta^1$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from 1 to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) halogen atoms, (ix) nitro groups, (x) formyl groups, (xi) cyano groups, (xii) carboxyl groups, (xiii) amino groups, (xiv) straight or branched chain monoalkylamino groups in which said alkyl moiety has from 1 to 4 carbon atoms, (xv) straight or branched chain dialkylamino groups in which each of said alkyl moieties may be the same or different and each has from 1 to 4 carbon atoms, (xvi) straight or branched chain aminoalkyl groups having from 1 to 4 carbon atoms, (xvii) monoalkylaminoalkyl groups in which said monoalkylamino moiety has one straight or branched chain alkyl group having from 1 to 4 carbon atoms and said alkyl moiety is a straight or branched chain alkyl group having from 1 to 4 carbon atoms, (xviii) dialkylaminoalkyl groups in which said dialkylamino moiety has two straight or branched chain alkyl groups having from 1 to 4 carbon atoms which may be the same or different and said alkyl moiety is a straight or branched chain alkyl group having from 1 to 4 carbon atoms, and (xix) straight or branched chain alkoxycarbonylamino groups in which said alkoxy moiety has from 1 to 4 carbon atoms.

16. An aminocarboxylic acid compound according to claim 1, a pharmacologically acceptable salt thereof or a pharmacologically acceptable ester thereof, wherein:
W is selected from the group consisting of (i) straight or branched chain alkyl groups having from 1 to 6 carbon atoms, (ii) hydroxyl groups, (iii) straight or branched chain alkoxy groups having from 1 to 4 carbon atoms, (iv) straight or branched chain alkylthio groups having from 1 to 4 carbon atoms, (v) aryl groups having from 6 to 10 carbon atoms which are unsubstituted or have from 1 to 3 substituents selected from substituents $\alpha^2$ defined below, (vi) aryloxy groups having from 6 to 10 carbon atoms which are unsubstituted or have from 1 to 3 substituents selected from substituents $\alpha^2$ defined below on said aryl moiety, (vii) arylthio groups having from 6 to 10 carbon atoms which are unsubstituted or have from 1 to 3 substituents selected from substituents $\alpha^2$ defined below on said aryl moiety, (viii) said aralkyl groups having from 7 to 12 carbon atoms which are unsubstituted or have from 1 to 3 substituents selected from substituents $\alpha^2$ defined below on said aryl moiety, (ix) aralkyloxy groups having from 7 to 12 carbon atoms which are unsubstituted or have from 1 to 3 substituents selected from substituents $\alpha^2$ defined below on said aryl moiety, (x) aralkylthio groups having from 7 to 12 carbon atoms which are unsubstituted or have from 1 to 3 substituents selected from substituents $\alpha^2$ defined below on said aryl moiety, (xi) aryloxyalkyl group in which said aryl moiety is an aryl group having from 6 to 10 carbon atoms which are unsubstituted or have from 1 to 3 substituents selected from substituents $\alpha^2$ defined below and said alkyl moiety is a straight or branched chain alkyl group having from 1 to 4 carbon atoms, (xii) pyridyl and (xiii) quinolyl;

said substituents $\alpha^2$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain alkoxy groups having from 1 to 4 carbon atoms, (vi) straight or branched chain halogenated alkoxy groups having from 1 to 4 carbon atoms, (vii) straight or branched chain alkylthio groups having from 1 to 4 carbon atoms, (viii) straight or branched chain alkylsulfonyl groups having from 1 to 4 carbon atoms, (ix) halogen atoms, (x) nitro groups, (xi) cyano groups, (xii) straight or branched chain dialkylamino groups in which each of said alkyl moieties may be the same or different and each has from 1 to 4 carbon atoms, (xiii) a phenyl group which has from 1 to 3 substituents selected from substituents $\beta^2$ defined below, (xiv) aryloxy groups having from 6 to 10 carbon atoms which are unsubstituted or have from 1 to 3 substituents selected from substituents $\beta^2$ defined below on said aryl moiety, and (xv) a hetero aryl group selected from the group consisting of pyridyl, quinolyl and isoquinolyl, said hetero aryl group being unsubstituted or having 1 to 3 substituents $\beta^2$ defined below;

said substituents $\beta^2$ are selected from the group consisting of (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain hydroxyalkyl groups having from 1 to 4 carbon atoms, (v) halogen atoms, (vi) nitro groups, (vii) formyl groups, (viii) carboxyl groups, (ix) straight or branched chain dialkylamino groups in which each of said alkyl moieties are the same or different and each has from 1 to 4 carbon atoms and (x) dialkylaminoalkyl groups in which said dialkylamino moiety has two straight or branched chain alkyl groups having from 1 to 4 carbon atoms which may be the same or different and said alkyl moiety is a straight or branched chain alkyl group having from 1 to 4 carbon atoms.

17. An amidocarboxylic acid compound according to claim 1, a pharmacologically acceptable salt thereof or a pharmacologically acceptable ester thereof, wherein:

W is selected from the group consisting of (i) straight or branched chain alkyl groups having from 1 to 6 carbon atoms, (ii) straight or branched chain alkoxy groups having from 1 to 4 carbon atoms, (iii) aryloxy groups having from 6 to 10 carbon atoms which are unsubstituted or have from 1 to 3 substituents selected from substituents $\alpha^3$ defined below on said aryl moiety, (iv) arylthio groups having from 6 to 10 carbon atoms which are unsubstituted or have from 1 to 3 substituents selected from substituents $\alpha^3$ defined below on said aryl moiety, (v) said aralkyl groups having from 7 to 12 carbon atoms which are unsubstituted or have from 1 to 3 substituents selected from substituents $\alpha^3$ defined below on said aryl moiety, (vi) aralkyloxy groups having from 7 to 12 carbon atoms which are unsubstituted or have from 1 to 3 substituents selected from substituents $\alpha^3$ defined below on said aryl moiety, (vii) aralkyloxy groups having from 7 to 12 carbon atoms which may have from 1 to 3 substituents selected from substituents $\alpha^3$ defined below on said aryl moiety, (vii) aryloxyalkyl groups in which said aryl moiety is an aryl group having from 6 to 10 carbon atoms which are unsubstituted or have from 1 to 3 substituents selected from substituents $\alpha^3$ defined below and said alkyl moiety is a straight or branched chain alkyl group having from 1 to 4 carbon atoms, (viii) pyridyl and (ix) quinolyl;

said substituents $\alpha^3$ are selected from the group consisting of (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain halogenated alkoxy groups having from 1 to 4 carbon atoms, (v) straight or branched chain alkylthio groups having from 1 to 4 carbon atoms, (vi) straight or branched chain alkylsulfonyl groups having from 1 to 4 carbon atoms, (vii) halogen atoms, (viii) cyano groups and (ix) pyridyl groups.

18. An amidocarboxylic acid compound according to claim 1, a pharmacologically acceptable salt thereof or a pharmacologically acceptable ester thereof, wherein:

W is selected from the group consisting of (i) straight or branched chain alkyl groups having from 1 to 6 carbon atoms, (ii) straight or branched chain alkoxy groups having from 1 to 4 carbon atoms, (iii) phenoxy groups which are unsubstituted or have from 1 to 3 substituents selected from substituents $\alpha^4$ defined below on said phenyl moiety, (iv) phenylthio groups having from 6 to 10 carbon atoms which are unsubstituted or have from 1 to 3 substituents selected from substituents $\alpha^4$ defined below on said phenyl moiety, (v) said aralkyl groups having from 7 to 10 carbon atoms, (vi) aralkyloxy groups having from 7 to 10 carbon atoms, (vii) aryloxyalkyl groups in which said aryl moiety has from 6 to 10 carbon atoms and said alkyl moiety is straight or branched chain and has from 1 to 4 carbon atoms, (viii) pyridyl and (ix) quinolyl;

said substituents $\alpha^4$ are selected from the group consisting (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain halogenated alkoxy groups having from 1 to 4 carbon atoms, (v) straight or branched chain alkylthio groups having one or two carbon atoms, (vi) straight or branched chain alkylsulfonyl groups having one or two carbon atoms, (vii) halogen atoms, (viii) cyano groups and (ix) pyridyl groups.

19. An amidocarboxylic acid compound according to claim 1, a pharmacologically acceptable salt thereof or a pharmacologically acceptable ester thereof, wherein:

W is selected from the group consisting of phenoxy groups which are unsubstituted or have one substituent selected from substituents $\alpha^5$ defined below on said phenyl moiety;

said substituents $\alpha^5$ are selected from the group consisting of (i) straight or branched chain all groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain halogenated alkoxy groups having from 1 to 4 carbon atoms, (v) straight or branched chain alkylthio groups having one or two carbon atoms, (vi) straight or branched chain alkylsulfonyl groups having from one or two carbon atoms, (vii) halogen atoms, (viii) cyano groups and (ix) pyridyl groups.

20. An amidocarboxylic acid compound according to claim 1, a pharmacologically acceptable salt thereof or a pharmacologically acceptable ester thereof, wherein:

W is selected from the group consisting of phenoxy groups which are unsubstituted or have one substituent selected from substituents $\alpha^6$ defined below on said phenyl moiety;

said substituents $\alpha^6$ are selected from the group consisting of methyl, ethyl, isopropyl, t-butyl, trifluoromethyl, methoxy, trifluoromethoxy, fluorine atoms and chlorine atoms.

21. An amidocarboxylic acid compound according to claim 1, a pharmacologically acceptable salt thereof or a pharmacologically acceptable ester thereof, wherein:

X is a hetero aryl group selected from the group consisting of pyridyl, quinolyl and isoquinolyl, said hetero aryl group being unsubstituted or having from 1 to 3 substituents selected from substituents $\alpha^7$ defined below;

said substituents $\alpha^7$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain aliphatic acyl groups having from 1 to 5 carbon atoms, (vi) straight or branched chain alkoxy groups having from 1 to 4 carbon atoms, (vii) straight or branched chain halogenated alkoxy groups having from 1 to 4 carbon atoms, (viii) straight or branched chain alkylenedioxy groups having from 1 to 4 carbon atoms, (ix) aralkyloxy groups having from 7 to 12 carbon atoms which are unsubstituted or have from 1 to 3 substituents selected from substituents $\beta^3$ defined below, (x) straight or branched chain alkylthio groups having from 1 to 4 carbon atoms, (xi) straight or branched chain alkylsulfonyl groups having from 1 to 4 carbon atoms, (xii) halogen atoms, (xiii) straight or branched chain dialkylamino groups in which each alkyl group are the same or different and each has from 1 to 4 carbon atoms, a phenyl group which is unsubstituted or has 1 to 3 substituents $\beta^3$ defined below and (xiv) pyridyl groups which are unsubstituted or have from 1 to 3 substituents selected from substituents $\beta^3$ defined below;

said substituents $\beta^3$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from 1 to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) halogen atoms, (ix) nitro groups, (x) formyl groups, (xi) cyano groups, (xii) carboxyl groups, (xiii) straight or branched chain dialkylamino groups in which each alkyl group may be the same or different and each has from 1 to 4 carbon atoms and (xiv) dialkylaminoalkyl groups in which said dialkylamino moiety has two straight or branched chain alkyl groups having from 1 to 4 carbon atoms which may be the same or different and said alkyl moiety is a straight or branched chain alkyl group having from 1 to 4 carbon atoms.

22. An amidocarboxylic acid compound according to claim 1, a pharmacologically acceptable salt thereof or a pharmacologically acceptable ester thereof, wherein:

X is a hetero aryl group selected from the group consisting of pyridyl, quinolyl and isoquinolyl, said hetero aryl group being unsubstituted or having from 1 to 3 substituents selected from substituents $\alpha^8$ defined below or a phenyl group which is unsubstituted or having 1 to 3 substituents $\alpha^8$ defined below;

said substituents $\alpha^8$ are selected from the group consisting of (i) straight or branched chain alkyl groups having from 1 to 6 carbon atoms, (ii) straight or branched chain halogenated allyl groups having from 1 to 4 carbon atoms, (iii) hydroxyl groups, (iv) straight or branched chain aliphatic acyloxy groups having from 1 to 5 carbon atoms, (v) straight or branched chain alkoxy groups having from 1 to 4 carbon atoms, (vi) straight or branched chain halogenated alkoxy groups having from 1 to 4 carbon atoms, (vii) straight or branched chain alkylthio groups having from 1 to 4 carbon atoms, (viii) halogen atoms, (ix) straight or branched chain dialkylamino groups in which each alkyl group is the same or different and each has from 1 to 4 carbon atoms, (x) a phenyl group which is unsubstituted or has 1 to 3 substituents $\beta^4$ defined below and (xi) pyridyl groups which are unsubstituted or have from 1 to 3 substituents selected from substituents $\beta^4$ defined below;

said substituents $\beta^4$ are selected from the group consisting (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from 1 to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) halogen atoms, (ix) nitro groups, (x) formyl groups, (xi) cyano groups, (xii) carboxyl groups, (xiii) straight or branched chain dialkylamino groups in which each alkyl group may be the same or different and each has from 1 to 4 carbon atoms and (xiv) dialkylaminoalkyl groups in which said dialkylamnino moiety has two straight or branched chain alkyl groups having from 1 to 4 carbon atoms which may be the same or different and said alkyl moiety is a straight or branched chain alkyl group having from 1 to 4 carbon atoms.

23. An amidocarboxylic acid compound according to claim 1, a pharmacologically acceptable salt thereof or a pharmacologically acceptable ester thereof, wherein:

X is a hetero aryl group selected from the group consisting of pyridyl, quinolyl and isoquinolyl, which are unsubstituted or having from 1 to 3 substituents $\alpha^9$ defined below, or a phenyl group which is unsubstituted or has 1 to 3 substituents $\alpha^9$ defined below;

said substituents $\alpha^9$ are selected from the group consisting of (i) hydroxyl groups, (ii) straight or branched chain alkoxy groups having from 1 to 4 carbon atoms, (iii) straight or branched chain halogenated alkoxy groups having from 1 to 4 carbon atoms, (iv) straight or branched chain dialkylamino groups in which each alkyl group may be the same or different and each has from 1 to 4 carbon atoms, (v) phenyl groups which are unsubstituted or have from 1 to 3 substituents selected from substituents $\beta^5$ defined below, (vi) phenoxy groups which are unsubstituted or have from 1 to 3 substituents selected from substituents $\beta^5$ defined below, and (vii) pyridyl groups which are unsubstituted or have from 1 to 3 substituents selected from substituents $\beta^5$ defined below;

said substituents $\beta^5$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain hydroxyalkyl groups having from 1 to 4 carbon atoms, (vi) halogen atoms, (vii) nitro groups, (viii) formyl groups, (ix) carboxyl groups, (x) straight or branched chain dialkylamino groups in which each alkyl group may be the same or different and each has from 1 to 4 carbon atoms and (xi) dialkylaminoalkyl groups in which said dialkylamino moiety has two straight or branched chain alkyl groups having from 1 to 4 carbon atoms which are the same or different and said alkyl moiety is a straight or branched chain alkyl group having from 1 to 4 carbon atoms.

24. An amidocarboxylic acid compound according to claim 1, a pharmacologically acceptable salt thereof or a pharmacologically acceptable ester thereof, wherein:

X is a hetero aryl group selected from the group consisting of pyridyl, quinolyl and isoquinolyl groups, said hetero aryl group being unsubstituted or having from 1 to 3 substituents selected from substituents $\alpha^{11}$ defined below; or a phenyl group $\alpha$ which is unsubstituted or has 1 to 3 substituents $\alpha^{11}$ defined below;

said substituents $\alpha^{11}$ are selected from the group consisting of (i) hydroxyl groups, (ii) straight or branched chain alkoxy groups having from 1 to 4 carbon atoms, (iii) straight or branched chain halogenated alkoxy groups having from 1 to 4 carbon atoms, (iv) straight or branched chain dialkylamino groups in which each alkyl group may be the same or different and each has from 1 to 4 carbon atoms, a phenyl group which is unsubstituted or has 1 to 3 substituents $\beta^3$ defined below and (vi) pyridyl groups which are unsubstituted or have from 1 to 3 substituents selected from substituents $\beta^7$ defined below;

said substituents $\beta^7$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain hydroxyalkyl groups having from 1 to 4 carbon atoms, (vi) halogen atoms, (vii) nitro groups, (viii) formyl groups, (ix) carboxyl groups, (x) straight or branched chain dialkylamino groups in which each all group may be the same or different and each has from 1 to 4 carbon atoms and (xi) dialkylaminoalkyl groups in which said dialkylamino moiety has two straight or branched chain alkyl groups having from 1 to 4 carbon atoms which may be the same or different and said alkyl moiety is a straight or branched chain alkyl group having from 1 to 4 carbon atoms.

25. An amidocarboxylic acid compound according to claim 1, a pharmacologically acceptable salt thereof or a pharmacologically acceptable ester thereof, wherein:

X is selected from the group consisting of phenyl groups which may have one substituent selected from substituents $\alpha^{12}$ defined below;

said substituents $\alpha^{12}$ are selected from the group consisting of methyl, isopropyl and hydroxyl groups, fluorine atoms, chlorine atoms, diethylamino and benzyl groups, phenyl groups, said phenyl groups may be substituted with 1 to 3 substituents, which may be the same or different, selected from the group consisting of methyl, ethyl, trifluoromethyl, hydroxyl, methoxy, ethoxy, isopropoxy, trifluoromethoxy, methylenedioxy and hydroxymethyl groups, fluorine atoms, chlorine atoms, and nitro, formyl, cyano, carboxyl, dimethylamino, diethylamino and N,N-dimethylaminomethyl groups; phenoxy, phenylthio, phenylsufonyl, phenylsulfonylamino, N-methylphenylsulfonylamino and pyridyl groups, said pyridyl groups may be substituted with a substituent selected from the group consisting of methyl, ethyl, trifluoromethyl, methoxy, ethoxy, isopropoxy and trifluoromethoxy groups, fluorine atoms, chlorine atoms, and nitro, dimethylamino and diethylamino groups; pyridyloxy, pyridylthio, pyridylsulfonyl and piperidyl groups; or X is selected from the group consisting of pyridyl groups which may have one substituent selected from substituents $\alpha^{13}$ defined below;

said substituents $\alpha^{13}$ are selected from the group consisting of methyl, isopropyl, methoxy, ethoxy, isopropoxy, 2,2,3,3-tetrafluoropropoxy and benzyloxy groups, alkylthio groups having one or two carbon atoms, alkylsulfonyl groups having one or two carbon atoms, benzyl groups, phenyl groups, said phenyl groups may be substituted with a substituent selected from the group consisting of methyl, ethyl, trifluoromethyl, methoxy, ethoxy and isopropoxy groups, fluorine atoms, chlorine atoms and nitro, dimethylamino and diethylamino groups; phenoxy, phenylthio, phenylsufonyl, phenylsulfonylamino and N-methylphenylsulfonylamino groups.

26. An amidocarboxylic acid compound according to claim 1, a pharmacologically acceptable salt thereof or a pharmacologically acceptable ester thereof, wherein:

Y is selected from the group consisting of a single bond and an oxygen atom.

27. An amidocarboxylic acid compound according to claim 1, a pharmacologically acceptable salt thereof or a pharmacologically acceptable ester thereof, wherein:

Y is an oxygen atom.

28. An amidocarboxylic acid compound according to claim 1, a pharmacologically acceptable salt thereof or a pharmacologically acceptable ester thereof, wherein:

$R^1$ is selected from the group consisting of hydrogen atoms, straight or branched chain alkyl groups having from 1 to 4 carbon atoms and said aralkyl groups having from 7 to 9 carbon atoms;

$R^2$ is a straight or branched chain alkylene group having from 2 to 4 carbon atoms;

$R^3$ is selected from the group consisting of hydrogen atoms, straight or branched chain alkyl groups having from 1 to 4 carbon atoms, alkoxy groups having one or two carbon atoms, alkylthio groups having one or two carbon atoms, halogen atoms, nitro groups, hydroxyl groups and straight or branched chain aliphatic acyl groups having from 1 to 5 carbon atoms;

$R^4$ is selected from the group consisting of hydrogen atoms and straight or branched chain alkyl groups having from 1 to 4 carbon atoms;

Z is a straight or branched chain alkylene group having from 1 to 4 carbon atoms;

W is selected from the group consisting of (i) straight or branched chain alkyl groups having from 1 to 6 carbon atoms, (ii) hydroxyl groups, (iii) straight or branched chain alkoxy groups having from 1 to 4 carbon atoms, (iv) straight or branched chain alkylthio groups having from 1 to 4 carbon atoms, (v) aryl groups having from 6 to 10 carbon atoms which may have from 1 to 3 substituents selected from substituents $\alpha^1$ defined below, (vi) aryloxy groups having from 6 to 10 carbon atoms which may have from 1 to 3 substituents selected from substituents $\alpha^1$ defined below on said aryl moiety, (vii) arylthio groups having from 6 to 10 carbon atoms which are unsubstituted or have from 1 to 3 substituents selected from substituents $\alpha^1$ defined below on said aryl moiety, (viii) said aralkyl groups having from 7 to 12 carbon atoms which are unsubstituted or have from 1 to 3 substituents selected from substituents $\alpha^1$ defined below on said aryl moiety, (ix) aralkyloxy groups having from 7 to 12 carbon atoms which are unsubstituted or have from 1 to 3 substituents selected from substituents $\alpha^1$ defined below on said aryl moiety, (x) aralkylthio groups having from 7 to 12 carbon atoms which are unsubstituted or have from 1 to 3 substituents selected from substituents $\alpha^1$ defined below on said aryl moiety, (xi) aryloxyalkyl groups in which said aryl moiety is an aryl group having from 6 to 10 carbon atoms which are unsubstituted or have from 1 to 3 substituents selected from substituents $\alpha^1$ defined below and said alkyl moiety is a straight or branched chain alkyl group having from 1 to 4 carbon atoms, (xii) pyridyl and (xiii) quinolyl;

said substituents $\alpha^1$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain aliphatic acyl groups having from 1 to 5 carbon atoms, (vi) straight or branched chain alkoxy groups having from 1 to 4 carbon atoms, (vii) straight or branched chain halogenated alkoxy groups having from 1 to 4 carbon atoms, (viii) straight or branched chain alkylenedioxy groups having from 1 to 4 carbon atoms, (ix) aralkyloxy groups having from 7 to 12 carbon atoms which are unsubstituted or have from 1 to 3 substituents selected from substituents $\beta^1$ defined below, (x) straight or branched chain alkylthio groups having from 1 to 4 carbon atoms, (xi) straight or branched chain alkylsulfonyl groups having from 1 to 4 carbon atoms, (xii) halogen atoms, (xiii) nitro groups, (xiv) cyano groups, (xv) amino groups, (xvi) straight or branched chain monoalkylamino groups in which said alkyl moiety has from 1 to 4 carbon atoms, (xvii) straight or branched chain alkoxycarbonylamino groups in which said alkoxy moiety has from 1 to 4 carbon atoms, (xviii) straight or branched chain dialkylamino groups in which each of said alkyl groups are the same or different and each has from 1 to 4 carbon atoms, (xix) a hetero aryl group selected from the group consisting of pyridyl, quinolyl and isoquinolyl, said hetero aryl group being unsubstituted or having from 1 to 3 substituents selected from substituents $\beta^1$ defined below and (xx) a phenyl group which is unsubstiuted or has 1 to 3 substituents $\beta^1$ defined below;

said substituents $\beta^1$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from 1 to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) halogen atoms, (ix) nitro groups, (x) formyl groups, (xi) cyano groups, (xii) carboxyl groups, (xiii) amino groups, (xiv) straight or branched chain monoalkylamino groups in which said alkyl moiety has from 1 to 4 carbon atoms, (xv) straight or branched chain dialkylamino groups in which each of said alkyl moieties are the same or different and each has from 1 to 4 carbon atoms, (xvi) straight or branched chain aminoalkyl groups having from 1 to 4 carbon atoms, (xvii) monoalkylaminoalkyl groups in which said monoalkylamino moiety has one straight or branched chain alkyl group having from 1 to 4 carbon atoms and said alkyl moiety is a straight or branched chain alkyl group having from 1 to 4 carbon atoms, (xviii) dialkylaminoalkyl groups in which said dialkylamino moiety has two straight or branched chain alkyl groups having from 1 to 4 carbon atoms which may be the same or different and said alkyl moiety is a straight or branched chain alkyl group having from 1 to 4 carbon atoms, and (xix) straight or branched chain alkoxycarbonylamino groups in which said alkoxy moiety has from 1 to 4 carbon atoms;

X is a hetero aryl group selected from the group consisting of pyridyl, quinolyl and isoquinolyl, said hetero aryl group being unsubstituted or having from 1 to 3 substituents selected from substituents $\alpha^7$ defined below or a phenyl group which is unsubstituted or has 1 to 3 substituents $\alpha^7$ defind below;

said substituents $\alpha^7$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain aliphatic acyl groups having from 1 to 5 carbon atoms, (vi) straight or branched chain alkoxy groups having from 1 to 4 carbon atoms, (vii) straight or branched chain halogenated alkoxy groups having from 1 to 4 carbon atoms, (viii) straight or branched chain alkylenedioxy groups having from 1 to 4 carbon atoms, (ix) aralkyloxy groups having from 7 to 12 carbon atoms which are unsubstituted or have from 1 to 3 substituents selected from substituents $\beta^3$ defined below, (x) straight or branched chain alkylthio groups having from 1 to 4 carbon atoms, (xi) straight or branched chain alkylsulfonyl groups having from 1 to 4 carbon atoms, (xii) halogen atoms, (xiii) straight or branched chain dialkylamino groups in which each alkyl group are the same or different and each has from 1 to 4 carbon atoms, (xiv) a phenyl group which is unsubstituted or has 1 to 3 substituents $\beta^3$ defined below and (xv) pyridyl groups which are unsubstituted or have from 1 to 3 substituents selected from substituents $\beta^3$ defined below;

said substituents $\beta^3$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from 1 to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) halogen atoms, (ix) nitro groups, (x) formyl groups, (xi) cyano groups, (xii) carboxyl groups, (xiii) straight or branched chain dialkylamino groups in which each alkyl group are the same or different and each has from 1 to 4 carbon atoms and (xiv) dialkylaminoalkyl groups in which said dialkylamino moiety has two straight or branched chain alkyl groups having from 1 to 4 carbon atoms which are the same or different and said alkyl moiety is a straight or branched chain alkyl group having from 1 to 4 carbon atoms; and Y is selected from the group consisting of a single bond and an oxygen atom.

29. An amidocarboxylic acid compound according to claim 1, a pharmacologically acceptable salt thereof or a pharmacologically acceptable ester thereof, wherein:

$R^1$ is selected from the group consisting of hydrogen atoms, straight or branched chain alkyl groups having from 1 to 4 carbon atoms and said aralkyl groups having from 7 to 9 carbon atoms;

$R^2$ is a straight or branched chain alkylene group having from 2 to 4 carbon atoms;

$R^3$ is selected from the group consisting of hydrogen atoms, halogen atoms and nitro groups;

$R^4$ is selected from the group consisting of hydrogen atoms and straight or branched chain alkyl groups having from 1 to 4 carbon atoms;

Z is a methylene group;

W is selected from the group consisting of (i) straight or branched chain alkyl groups having from 1 to 6 carbon atoms, (ii) hydroxyl groups, (iii) straight or branched chain alkoxy groups having from 1 to 4 carbon atoms, (iv) straight or branched chain alkylthio groups having from 1 to 4 carbon atoms, (v) aryl groups having from 6 to 10 carbon atoms which may have from 1 to 3 substituents selected from substituents $\alpha^2$ defined below, (vi) aryloxy groups having from 6 to 10 carbon atoms which are unsubstituted or have from 1 to 3 substituents selected from substituents $\alpha^2$ defined below on said aryl moiety, (vii) arylthio groups having from 6 to 10 carbon atoms which are unsubstituted or have from 1 to 3 substituents selected from substituents $\alpha^2$ defined below on said aryl moiety, (viii) said aralkyl groups having from 7 to 12 carbon atoms which are unsubstituted or have from 1 to 3 substituents selected from substituents $\alpha^2$ defined below on said aryl moiety, (ix) aralkyloxy groups having from 7 to 12 carbon atoms which are unsubstituted or have from 1 to 3 substituents selected from substituents $\alpha^2$ defined below on said aryl moiety, (x) aralkylthio groups having from 7 to 12 carbon atoms which are unsubstituted or have from 1 to 3 substituents selected from substituents $\alpha^2$ defined below on said aryl moiety, (xi) aryloxyalkyl groups in which said aryl moiety is an aryl group having from 6 to 10 carbon atoms which are unsubstituted or have from 1 to 3 substituents selected from substituents $\alpha^2$ defined below and said alkyl moiety is a straight or branched chain alkyl group having from 1 to 4 carbon atoms, (xii) pyridyl and (xiii) quinolyl;

said substituents $\alpha^2$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain alkoxy groups having from 1 to 4 carbon atoms, (vi) straight or branched chain halogenated alkoxy groups having from 1 to 4 carbon atoms, (vii) straight or branched chain alkylthio groups having from 1 to 4 carbon atoms, (viii) straight or branched chain alkylsulfonyl groups having from 1 to 4 carbon atoms, (ix) halogen atoms, (x) nitro groups, (xi) cyano groups, (xii) straight or branched chain dialkylamino groups in which each of said alkyl moieties are the same or different and each has from 1 to 4 carbon atoms, (xiii) a hetero aryl group selected from the group consisting of pyridyl, quinolyl and isoquinolyl, said hetero aryl group being unsubstituted or having from 1 to 3 substituents selected from substituents $\beta^2$ defined below and (xiv) a phenyl group which is unsubstituted or has 1 to 3 substituents $\beta^2$ defined below;

said substituents $\beta^2$ are selected from the group consisting of (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain hydroxyalkyl groups having from 1 to 4 carbon atoms, (v) halogen atoms, (vi) nitro groups, (vii) formyl groups, (viii) carboxyl groups, (ix) straight or branched chain dialkylamino groups in which each of said alkyl moieties are the same or different and each has from 1 to 4 carbon atoms and (x) dialkylaminoalkyl groups in which said dialkylamino moiety has two straight or branched chain alkyl groups having from 1 to 4 carbon atoms which may be the same or different and said alkyl moiety is a straight or branched chain alkyl group having from 1 to 4 carbon atoms;

X is a hetero aryl group selected from the group consisting of pyridyl, quinolyl and isoquinolyl, said hetero aryl group being unsubstituted or having from 1 to 3 substituents selected from substituents $\alpha^8$ defined below, or a phenyl group which is unsubstituted or has 1 to 3 substituents $\alpha^8$ defined below;

said substituents $\alpha^8$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain alkoxy groups having from 1 to 4 carbon atoms, (vi) straight or branched chain halogenated alkoxy groups having from 1 to 4 carbon atoms, (vii) straight or branched chain alkylthio groups having from 1 to 4 carbon atoms, (viii)

halogen atoms, (ix) straight or branched chain dialkylamino groups in which each alkyl group are the same or different and each has from 1 to 4 carbon atoms, (x) a phenyl group which is unsubstituted or has 1 to 3 substituents $\beta^4$ defined below and (xi) pyridyl groups which are unsubstituted or have from 1 to 3 substituents selected from substituents $\beta^4$ defined below;

said substituents $\beta^4$ are selected from the group consisting (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain halogenated alkoxy groups having from 1 to 4 carbon atoms, (vi) straight or branched chain alkylenedioxy groups having from 1 to 4 carbon atoms, (vii) straight or branched chain hydroxyalkyl groups having from 1 to 4 carbon atoms, (viii) halogen atoms, (ix) nitro groups, (x) formyl groups, (xi) cyano groups, (xii) carboxyl groups, (xiii) straight or branched chain dialkylamino groups in which each alkyl group are the same or different and each has from 1 to 4 carbon atoms and (xiv) dialkylaminoalkyl groups in which said dialkylamino moiety has two straight or branched chain alkyl groups having from 1 to 4 carbon atoms which are the same or different and said alkyl moiety is a straight or branched chain alkyl group having from 1 to 4 carbon atoms; and Y is an oxygen atom.

30. An amidocarboxylic acid compound according to claim 1, a pharmacologically acceptable salt thereof or a pharmacologically acceptable ester thereof, wherein:

$R^1$ is selected from the group consisting of hydrogen atoms, straight or branched chain alkyl groups having from 1 to 4 carbon atoms and aralkyl groups having from 7 to 9 carbon atoms;

$R^1$ is a straight or branched chain alkylene group having from 2 to 4 carbon atoms;

$R^3$ is selected from the group consisting of hydrogen atoms, halogen atoms and nitro groups;

$R^4$ is selected from the group consisting of hydrogen atoms and straight or branched chain alkyl groups having from 1 to 4 carbon atoms;

Z is a methylene group;

W is selected from the group consisting of (i) straight or branched chain alkyl groups having from 1 to 6 carbon atoms, (ii) straight or branched chain alkoxy groups having from 1 to 4 carbon atoms, (iii) aryloxy groups having from 6 to 10 carbon atoms which are unsubstituted or have from 1 to 3 substituents selected from substituents $\alpha^3$ described below on the aryl moiety, (iv) arylthio groups having from 6 to 10 carbon atoms which are unsubstituted or have from 1 to 3 substituents selected from substituents $\alpha^3$ defined below on said aryl moiety, (v) said aralkyl groups having from 7 to 12 carbon atoms which are unsubstituted or have from 1 to 3 substituents selected from substituents $\alpha^3$ defined below on said aryl moiety, (vi) aralkyloxy groups having from 7 to 12 carbon atoms which are unsubstituted or have from 1 to 3 substituents selected from substituents $\alpha^3$ defined below on said aryl moiety, (vii) aryloxyalkyl groups in which said aryl moiety is an aryl group having from 6 to 10 carbon atoms which are unsubstituted or have from 1 to 3 substituents selected from substituents $\alpha^3$ defined below and said alkyl moiety is a straight or branched chain alkyl group having from 1 to 4 carbon atoms, (viii) pyridyl and (ix) quinolyl;

said substituents $\alpha^3$ are selected from the group consisting of (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain halogenated alkoxy groups having from 1 to 4 carbon atoms, (v) straight or branched chain alkylthio groups having from 1 to 4 carbon atoms, (vi) straight or branched chain alkylsulfonyl groups having from 1 to 4 carbon atoms, (vii) halogen atoms, (viii) cyano groups and (ix) pyridyl groups;

X is a hetero aryl group selected from the group consisting of pyridyl, quinolyl and isoquinolyl, said hetero aryl group being unsubstituted or having from 1 to 3 substituents selected from substituents $\alpha^9$ defined below, or a phenyl group which is unsubstituted or substituted with 1 to 3 substituents $\alpha^9$ defined below;

said substituents $\alpha^9$ are selected from the group consisting of (i) hydroxyl groups, (ii) straight or branched chain alkoxy groups having from 1 to 4 carbon atoms, (iii) straight or branched chain halogenated alkoxy groups having from 1 to 4 carbon atoms, (iv) straight or branched chain dialkylamino groups in which each alkyl group is the same or different and each has from 1 to 4 carbon atoms, (v) a phenyl group which is unsubstituted or has 1 to 3 substituents $\beta^5$ defined below and (vi) pyridyl groups which are unsubstituted or have from 1 to 3 substituents selected from substituents $\beta^5$ defined below;

said substituents $\beta^5$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain alkoxy groups having from 1 to 4 carbon atoms, (v) straight or branched chain hydroxyalkyl groups having from 1 to 4 carbon atoms, (vi) halogen atoms, (vii) nitro groups, (viii) formyl groups, (ix) carboxyl groups, (x) straight or branched chain dialkylamino groups in which each alkyl group are the same or different and each has from 1 to 4 carbon atoms and (xi) dialkylaminoalkyl groups in which said dialkylamino moiety has two straight or branched chain alkyl groups having from 1 to 4 carbon atoms which are the same or different and said alkyl moiety is a straight or branched chain alkyl group having from 1 to 4 carbon atoms; and Y is an oxygen atom.

31. An amidocarboxylic acid compound according to claim 1, a pharmacologically acceptable salt thereof or a pharmacologically acceptable ester thereof, wherein:

$R^1$ is a hydrogen atom;

$R^2$ is an ethylene group;

$R^3$ is a hydrogen atom;

$R^4$ is a hydrogen atom;

Z is a methylene group;

W is a phenoxy group which may have one substituent selected from substituents $\alpha^5$ defined below on said phenyl moiety;

said substituents $\alpha^5$ are selected from the group consisting of (i) straight or branched chain alkyl groups having from 1 to 6 carbon atoms, (ii) straight or branched chain halogenated alkyl groups having from 1 to 4 carbon atoms, (iii) straight or branched chain alkoxy groups having from 1 to 4 carbon atoms, (iv) straight or branched chain halogenated alkoxy groups having from 1 to 4 carbon atoms, (v) straight or branched chain alkylthio groups having one or two carbon atoms, (vi) straight or branched chain alkylsulfonyl groups having from one or two carbon atoms, (vii) halogen atoms, (viii) cyano groups and (ix) pyridyl groups;

X is a phenyl group which is unsubstituted or has one substituent selected from substituents $\alpha^{12}$ defined below;

said substituents $\alpha^{12}$ are selected from the group consisting of methyl, isopropyl and hydroxyl groups, fluorine atoms, chlorine atoms, diethylamino and benzyl groups, phenyl groups, said phenyl groups are unsubstituted or substituted with 1 to 3 substituents, which are the same or different, selected from the group consisting of methyl, ethyl, trifluoromethyl, hydroxyl, methoxy, ethoxy, isopropoxy, trifluoromethoxy, methylenedioxy and hydroxymethyl groups, fluorine atoms, chlorine atoms, and nitro, formyl, cyano, carboxyl, dimethylamino, diethylamino and N,N-dimethylaminomethyl groups; phenoxy, phenylthio, phenylsulfonyl, phenylsulfonylamino, N-methylphenylsulfonylamino and pyridyl groups, said pyridyl groups are unsubstituted or substituted with a substituent selected from the group consisting of methyl, ethyl, trifluoromethyl, methoxy, ethoxy, isopropoxy and trifluoromethoxy groups, fluorine atoms, chlorine atoms, and nitro, dimethylamino and diethylamino groups; or X is a pyridyl group which is unsubstituted or has one substituent selected from substituents $\alpha^{13}$ defined below;

said substituents $\alpha^{13}$ are selected from the group consisting of methyl, isopropyl, methoxy, ethoxy, isopropoxy, 2,2,3,3-tetrafluoropropoxy and benzyloxy groups, alkylthio groups having one or two carbon atoms, alkylsulfonyl groups having one or two carbon atoms, benzyl groups, phenyl groups, said phenyl groups are unsubstituted or substituted with a substituent selected from the group consisting of methyl, ethyl, trifluoromethyl, methoxy, ethoxy and isopropoxy groups, fluorine atoms, chlorine atoms and nitro, dimethylamino and diethylamino groups; and Y is an oxygen atom.

32. An amidocarboxylic acid compound according to claim 1, a pharmacologically acceptable salt thereof or a pharmacologically acceptable ester thereof, wherein:

$R^1$ is a hydrogen atom;
$R^2$ is an ethylene group;
$R^3$ is a hydrogen atom;
$R^4$ is a hydrogen atom;
Z is a methylene group;
W is a phenoxy group which is unsubstituted or has one substituent selected from substituents $\alpha^6$ defined below on said phenyl moiety;

said substituents $\alpha^6$ are selected from the group consisting of methyl, ethyl, isopropyl, t-butyl, trifluoromethyl, methoxy, trifluoromethoxy and fluorine a toms and chlorine atoms; and Y is an oxygen atom.

33. An amidocarboxylic acid compound according to claim 1, a pharmacologically acceptable salt thereof or a pharmacologically acceptable ester thereof, wherein:

$R^1$ is selected from the group consisting of hydrogen atoms and straight or branched chain alkyl groups having from 1 to 6 carbon atoms;

$R^2$ is a straight or branched chain alkylene group having from 1 to 6 carbon atoms;

$R^3$ is selected from the group consisting of (i) hydrogen atoms, (ii) straight or branched chain alkyl groups having from 1 to 6 carbon atoms, (iii) straight or branched chain alkoxy groups having from 1 to 4 carbon atoms, (iv) straight or branched chain alkylthio groups having from 1 to 4 carbon atoms, (v) halogen atoms, (vi) nitro groups, (vii) straight or branched chain dialkylamino groups in which each alkyl group are the same or different and have from 1 to 4 carbon atoms, (viii) aryl groups having from 6 to 10 carbon atoms which are unsubstituted or have from 1 to 3 substituents $\alpha$ defined below and (ix) aralkyl groups having from 7 to 12 carbon atoms which are unsubstituted or have from 1 to 3 substituents a defined below on said aryl moiety;

$R^4$ is selected from the group consisting of hydrogen atoms and straight or branched chain alkyl groups having from 1 to 6 carbon atoms;

Z is a straight or branched chain alkylene group having from 1 to 4 carbon atoms;

W is selected from the group consisting of ethyl, propyl, butyl, pentyl, methoxy, ethoxy, propoxy, isopropoxy, methylthio, ethylthio, propylthio, isopropylthio, phenoxy, 4-methylphenoxy, 4-ethylphenoxy, 4-isopropylphenoxy, 4-methoxyphenoxy, 4-chlorophenoxy, phenylthio, benzyl, phenethyl, 3-phenylpropyl and 4-phenylbutyl groups;

X is a hetero aryl group selected from the group consisting of pyridyl, quinolyl and isoquinolyl, said hetero aryl group being unsubstituted or having from 1 to 3 substituents selected from substituents $\alpha$ defined below, or a phenyl group which is unsubstituted or has 1 to 3 substituents $\alpha$ defined below;

said substituents $\alpha$ are selected from the group consisting of (i) straight or branched chain alkyl groups having from 1 to 6 carbon atoms, (ii) straight or branched chain halogenated alkyl groups having from 1 to 4 carbon atoms, (iii) hydroxyl groups, (iv) straight or branched chain aliphatic acyloxy groups having from 1 to 5 carbon atoms, (v) straight or branched chain alkoxy groups having from 1 to 4 carbon atoms, (vi) straight or branched chain alkylenedioxy groups having from 1 to 4 carbon atoms, (vii) aralkyloxy groups having from 7 to 12 carbon atoms, (viii) straight or branched chain alkylthio groups having from 1 to 4 carbon atoms, (ix) straight or branched chain alkylsulfonyl groups having from 1 to 4 carbon atoms, (x) halogen atoms, (xi) nitro groups, (xii) straight or branched chain dialkylamino groups in which each alkyl group may be the same or different and have from 1 to 4 carbon atoms, (xiii) a hetero aryl group selected from the group consisting of pyridyl, quinolyl and isoquinolyl and (xiv) a phenyl group which is unsubstituted or substituted with a substituent selected from the group consisting of straight or branched chain alkyl groups having from 1 to 4 carbon atoms, straight or branched chain halogenated alkyl groups having from 1 to 4 carbon atoms, straight or branched halogen chain alkoxy groups having from 1 to 4 carbon atoms, halogen atoms and straight or branched chain alkylenedioxy groups having from 1 to 4 carbon atoms; and Y is selected from the group consisting of a single bond, an oxygen atom, a sulfur atom and groups of formula: >N—$R^5$ wherein $R^5$ is selected from the group consisting of hydrogen atoms, straight or branched chain alkyl groups having from 1 to 6 carbon atoms, straight or branched chain aliphatic acyl groups having from 1 to 8 carbon atoms and aromatic acyl groups having from 7 to 11 carbon atoms.

34. An amidocarboxylic acid compound according to claim 1, a pharmacologically acceptable salt thereof or a pharmacologically acceptable ester thereof, selected from the group consisting of:

2-ethoxy-3-[4-[2-(4-pyridine-2-ylbenzoylamino)ethoxy]phenyl]propionic acid,
3-[4-[2-(4-pyridine-2-ylbenzoylamino)ethoxy]phenyl]-2-propylpropionic acid,
2-butyl-3-[4-[2-(4-pyridine-2-ylbenzoylamino)ethoxy]phenyl]propionic acid,
3-[4-[2-(biphenyl-4-carbonylamino)ethoxy]phenyl]-2-butylpropionic acid,
2-butyl-3-[4-[2-(4'-formylbiphenyl-4-carbonylamino)ethoxy]phenyl]propionic acid,
2-butyl-3-[4-[2-(4'-dimethylaminomethylbiphenyl-4-carbonylamino)ethoxy]phenyl]-propionic acid,
2-butyl-3-[4-[2-(4'-carboxybiphenyl-4-carbonylamino)ethoxy]phenyl]propionic acid,
2-butyl-3-[4-[2-(3'-methoxybiphenyl-4-carbonylamino)ethoxy]phenyl]propionic acid,
2-butyl-3-[4-[2-(3'-hydroxybiphenyl-4-carbonylamino)ethoxy]phenyl]propionic acid,
2-butyl-3-[4-[2-(2'-methoxybiphenyl-4-carbonylamino)ethoxy]phenyl]propionic acid,
2-butyl-3-[4-[2-(4'-hydroxy-3,5-dimethylbiphenyl-4-carbonylamino)ethoxy]phenyl]-propionic acid,
2-butyl-3-[4-[2-(2-methoxypyridine-5-carbonylamino)ethoxy]phenyl]propionic acid,
2-butyl-3-[4-[2-(4-diethylaminobenzoylamino)ethoxy]phenyl]propionic acid,
2-butyl-3-[4-[3-(4-pyridine-2-ylbenzoylamino)propoxy]phenyl]propionic acid,
2-phenoxy-3-[4-[2-(4-pyridine-2-ylbenzoylamino)ethoxy]phenyl]propionic acid,
3-[4-[2-(biphenyl-4-carbonylamino)ethoxy]phenyl]-2-phenoxypropionic acid,
3-[4-[2-(4'-fluorobiphenyl-4-carbonylamino)ethoxy]phenyl]-2-phenoxypropionic acid,
3-[4-[2-(4'-chlorobiphenyl-4-carbonylamino)ethoxy]phenyl]-2-phenoxypropionic acid,
3-[4-[2-(4'-trifluoromethylbiphenyl-4-carbonylamino)ethoxy]phenyl]-2-phenoxy-propionic acid,
2-(4-isopropylphenoxy)-3-[4-[2-(4-pyridine-2-ylbenzoylamino)ethoxy]phenyl]-propionic acid,
3-[4-[2-(biphenyl-4-carbonylamino)ethoxy]phenyl]-2-(4-isopropylphenoxy)propionic acid,
2-(4-isopropylphenoxy)-3-[4-[2-(2-phenylpyridine-5-carbonylamino)ethoxy]phenyl]-propionic acid,
2-(4-isopropylphenoxy)-3-[4-[2-[2-(4-methoxyphenyl)pyridine-5-carbonylamino]-ethoxy]phenyl]propionic acid,
3-[4-[2-[2-(4-fluorophenyl)pyridine-5-carbonylamino]ethoxy]phenyl]-2-(4-isopropylphenoxy)propionic acid,
3-[4-[2-[2-(2,2,3,3-tetrafluoropropoxy)pyridine-5-carbonylamino]methoxy]phenyl]-2-(4-isopropylphenoxy)propionic acid,
2-(4-isopropylphenoxy)-3-[4-[2-[4-(3-trifluoromethylpyridine-6-yl)benzoylamino]ethoxy]phenyl]propionic acid,
2-(4-isopropylphenoxy)-3-[4-[2-[4(3-nitropyridine-6-yl)benzoylamino]ethoxy]phenyl]-propionic acid,
2-(4-isopropylphenoxy)-3-[4-[2-[4-(3-methoxypyridine-6-yl)benzoylamino]ethoxy]-phenyl]propionic acid,
2-(4-isopropylphenoxy)-3-[4-[2-[4-(3-dimethylaminopyridine-6-yl)benxoylamino]-ethoxy]phenyl]propionic acid,
2-(4-methoxyphenoxy)-3-[4-[2-(4-pyridine-2-ulbenzoylamino)ethoxy]phenyl]propionic acid,
2-(3-phenylpropyl)-3-[4-[2-(4-pyridine-2-ylbenzoylamino)ethoxy]phenyl]propionic acid,
2-(4-methylphenoxy(-3-[4-[2-(4-pyridine-2-ylbenzoylamino)ethoxy]phenyl]propionic acid,
2-(4-t-butylphenoxy)-3-[4-[2-(4-pyridine-2-ylbenzoylamino)ethoxy]phenyl]propionic acid,
2-(4-fluorophenoxy)-3-[4-[2-(4-pyridine-2-ylbenzoylamino)ethoxy]phenyl]propionic acid,
2-(4-chlorophenoxy)-3-[4-[2-(4-pyridine-2-ylbenzoylamino)ethoxy]phenyl]propionic acid,
2-(4-trifluoromethylphenoxy)-3-[4-[2-(4-pyridine-2-ylbenzoylamino)ethoxy]phenyl]-propionic acid,
2-(4-trifluromethoxyphenoxy)-3-[4-[2-(4-pyridine-2-ylbenzoylamino)ethoxy]phenyl]-propionic acid,
2-(3-fluorophenoxy)-3-[4-[2-(4-pyridine-2-ylbenzoylamino)ethoxy]phenyl]propionic acid,
2-(3,5-difluorophenoxy)-3-[4-[2-(4-pyridine-2-ylbenzoylamino)ethoxy]phenyl]-propionic acid,
2-(3,4-difluorophenoxy)-3-[4-[2-(4-pyridine-2-ylbenzoylamino)ethoxy]phenyl]-propionic acid,
2-(3,4,5-trifluorophenoxy)-3-[4-[2-(4-pyridine-2-ylbenzoylamino)ethoxy]phenyl]-propionic acid
2-(2,3,4,5,6-pentafluorophenoxy)-3-[4-[2-(4-pyridine-2-ylbenzoylamino)ethoxy]-phenyl]propionic acid,
2-methyl-2-phenoxy-3-[4-[2-(4-pyridine-2-ylbenzoylamino)ethoxy]phenyl]propionic acid,
2-(4-isopropylphenoxy)-2-methyl-3-[4-[2-(4-pyridine-2-ylbenzoylamino)ethoxy]-phenyl]propionic acid,
2-(4-isopropylphenoxy)-3-[4-[2-[2-(4-methoxyphenyl)pyridine-5-carbonylamino]-ethoxy]phenyl]
-2-methylpropionic acid, and
3-[4-[2-[2-(2,2,3,3-tetrafluoropropoxy)pyridine-5-carbonylamino]ethoxy]phenyl]-2-(4-isopropylphenoxy)-2-methylpropionic acid.

35. An amidocarboxylic acid compound according to claim 1, a pharmacologically acceptable salt thereof or a pharmacologically ester thereof, selected from the group consisting of:

2-ethoxy-3-[4-[2-(4-pyridine-2-ylbenzoylamino)ethoxy]phenyl]propionic acid,
3-[4-[2-(4-pyridine-2-ylbenzoylamino)ethoxy]phenyl]-2-propylpropionic acid,
2-butyl-3-[4-[2-(4-pyridine-2-ylbenzoylamino)ethoxy]phenyl]propionic acid,
2-butyl-3-[4-[2-(4'-formylbiphenyl-4-carbonylamino)ethoxy]phenyl]propionic acid,
2-butyl-3-[4-[2-(4'-hydroxy-3,5-dimethylbiphenyl-4-carbonylamino)ethoxy]phenyl]-propionic acid,
2-phenoxy-3-[4-[2-(4-pyridine-2-ylbenzoylamino)ethoxy]phenyl]propionic acid,
3-[4-[2-(biphenyl-4-carbonylamino)ethoxy]phenyl]-2-phenoxypropionic acid,
3-[4-[2-(4'-fluorobiphenyl-4-carbonylamino)ethoxy]phenyl]-2-phenoxypropionic acid,
3-[4-[2-(4'-chlorobiphenyl-4-carbonylamino)ethoxy]phenyl]-2-phenoxypropionic acid,
2-(4-isopropylphenoxy)-3-[4-[2-(4-pyridine-2-ylbenzoylamino)ethoxy]phenyl]-propionic acid,
3-[4-[2-(biphenyl-4-carbonylamino)ethoxy]phenyl]-2-(4-isopropylphenoxy)propionic acid, 2-(4-isopropylphenoxy)-3-[4-[2-(2-phenylpyridine-5-carbonylamino)ethoxy]phenyl]-propionic acid,
2-(4-isopropylphenoxy)-3-[4-[2-[2-(4-methoxyphenyl)pyridine-5-carbonylamino]-ethoxy]phenyl]propionic acid,
3-[4-[2-[2-(4-fluorophenyl)pyridine-5-carbonylamino]ethoxy]phenyl]-2-(4-isopropylphenoxy)propionic acid,
3-[4-[2-[2-(2,2,3,3-tetrafluoropropoxy)pyridine-5-carbonylamino]ethoxy]phenyl]-2-(4-isopropylphenoxy)propionic acid,
2-(4-isopropylphenoxy)-3-[4-[2-[4-(3-methoxypyridine-6-yl)benzoylamino]ethoxy]-phenyl]propionic acid,
2-(4-isopropylphenoxy)-3-[4-[2-[4-(3-dimethylaminopyridine-6-yl)benzoylamino]-ethoxy]phenyl]propionic acid,
2-(4-methoxyphenoxy)-3-[4-[2-(4-pyridine-2-ylbenzoylamino)ethoxy]phenyl]propionic acid,
2-(4-methylphenoxy)-3-[4-[2-(4-pyridine-2-ylbenzoylamino)ethoxy]phenyl]propionic acid,
2-(4-t-butylphenoxy)-3-[4-[2-(4-pyridine-2-ylbenzoylamino)ethoxy]phenyl]propionic acid,
2-(4-fluorophenoxy)-3-[4-[2-(4-pyridine-2-ylbenzoylamino)ethoxy]phenyl]propionic acid,
2-(4-chlorophenoxy)-3-[4-[2-(4-pyridine-2-ylbenzoylamino)ethoxy]phenyl]propionic acid,
2-(4-trifluoromethylphenoxy)-3-[4-[2-(4-pyridine-2-ylbenzoylamino)ethoxy]phenyl]-propionic acid,
2-(4-trifluoromethoxyphenoxy)-3-[4-[2-(4-pyridine-2-ylbenzoylamino)ethoxy]phenyl]-propionic acid,
2-(3-fluorophenoxy)-3-[4-[2-(4-pyridine-2-ylbenzoylamino)ethoxy]phenyl]propionic acid,
2-(3,4,5-trifluorophenoxy)-3-[4-[2-(4-pyridine-2-ylbenzoylamino)ethoxy]phenyl]-propionic acid,
2-methyl-2-phenoxy-3-[4-[2-(4-pyridine-2-ylbenzoylamino)ethoxy]phenyl]propionic acid,
2-(4-isopropylphenoxy)-2-methyl-3-[4-[2-(4-pyridine-2-ylbenzoylamino)ethoxy]-phenyl]propionic acid,
2-(4-isopropylphenoxy)-3-[4-[2-[2-(4-methoxyphenyl)pyridine-5-carbonylamino]-ethoxy]phenyl]-2-methylpropionic acid, and
3-[4-[2-[2-(2,2,3,3-tetrafluoropropoxy)pyridine-5-carbonylamino]ethoxy]phenyl]-2-(4-isopropylphenoxy)-2-methylpropionic acid.

36. An amidocarboxylic acid compound according to claim 32, wherein X is selected from the group consisting of an unsubstituted biphenyl group, an unsubstituted pyridylphenyl group and an unsubstituted phenylpyridyl group.

37. An amidocarboxylic acid compound according to claim 35, wherein said compound is the compound 3-[4-[2-(biphenyl-4-carbonylamino)ethoxy]phenyl]-2-(4-isopropylphenoxy)propionic acid.

38. An amidocarboxylic acid compound according to claim 35, wherein said compound is the compound 2-(4-isopropylphenoxy)-3-[4-[2-(2-phenylpyridine-5-carbonylamino)-ethoxy]phenyl]propionic acid.

39. An amidocarboxylic acid compound according to claim 35, wherein said compound is the compound 2-(4-methylphenoxy)-3-[4-[2-(4-pyridine-2-ylbenzoylamino)ethoxy]phenyl]propionic acid.

40. An amidocarboxylic acid compound according to claim 35, wherein said compound is the compound 2-(4-t-butylphenoxy)-3-[4-[2-(4-pyridine-2-ylbenzoylamino)ethoxy]phenyl]propionic acid.

41. An amidocarboxylic acid compound according to claim 35, wherein said compound is the compound 2-(4-chlorophenoxy)-3-[4-[2-(4-pyridine-2-ylbenzoylamino)ethoxy]phenyl]propionic acid.

42. An amidocarboxylic acid compound according to claim 34, which is 2-(4-isopropylphenoxy)-3-[4-[2-(4-pyridine-2-ylbenzoylamino)ethoxyl]phenyl]propionic acid, a pharmacologically acceptable salt thereof or pharmacologically acceptable ester thereof.

43. An amidocarboxylic acid compound according to claim 42, which is ethyl 2-(4-isopropylphenoxy)-3-[4-[2-(4-pyridine-2-ylbenzoylamino)ethoxy]-phenyl]propionate.

44. An amidocarboxylic acid compound according to claim 42, which is 2-(4-isopropylphenoxy)-3-[4-[2-(4-pyridine-2-ylbenzoylamino)ethoxy]phenyl]propionic acid.

45. An amidocarboxylic acid compound according to claim 42, which is (S)-2-(4-isopropylphenoxy)-3-[4-[2-(4-pyridine-2-ylbenzoylamino)ethoxy]phenyl]propionic acid.

46. An amidocarboxylic acid compound according to claim 42, which is (R)-2-(4-isopropylphenoxy)-3-[4-[2-(4-pyridine-2-ylbenzoylamino)ethoxy]phenyl]propionic acid.

47. An amidocarboxylic acid compound according to claim 1, which is ethyl 3-[4-[2-biphenyl-4-carbonylamino)ethoxy]phenyl]-2-(4-isopropylphenoxy)propionate.

48. An amidocarboxylic acid compound according to claim 1, which is ethyl 2-(4-isopropylphenoxy)-3-[4-[2-(2-phenylpyridine-5-carbonylamino)ethoxy]-phenyl]propionate.

49. An amidocarboxylic acid compound according to claim 1, which is ethyl 2-(4-methylphenoxy)-3[4-[2-(4-pyridine-2-ylbenzoylamino)ethoxy]phenyl]-propionate.

50. An amidocarboxylic acid compound according to claim 1, which is ethyl 2-(4-t-butylphenoxy)-3-[4-[2-pyridine-2-ylbenzoylamino)ethoxy]phenyl]-propionate.

51. An amidocarboxylic acid compound according to claim 1, which is ethyl 2-[4-chlorophenoxy)-3-[4-[2-(4-pyridine-2 ylbenzoylaminoethoxy]phenyl]-propionate.

52. A pharmaceutical composition comprising a pharmacologically effective amount of a pharmacologically effective compound together with a pharmacologically acceptable carrier, wherein said pharmacologically effective compound is an amidocarboxylic acid compound according to claim 1 or a pharmacologically acceptable salt or ester thereof.

53. A pharmaceutical composition comprising a pharmacologically effective amount of a pharmacologically effective compound together with a pharmacologically acceptable carrier, wherein said pharmacologically effective compound is an amidocarboxylic acid compound according to claim 2 or a pharmacologically acceptable salt or ester thereof.

54. A pharmaceutical composition comprising a pharmacologically effective amount of a pharmacologically effective compound together with a pharmacologically acceptable carrier, wherein said pharmacologically effective compound is an amidocarboxylic acid compound according to claim 3 or a pharmacologically acceptable salt or ester thereof.

55. A pharmaceutical composition comprising a pharmacologically effective amount of a pharmacologically effective compound together with a pharmacologically acceptable carrier, wherein said pharmacologically effective compound is an amidocarboxylic acid compound according to claim 4 or a pharmacologically acceptable salt or ester thereof.

56. A pharmaceutical composition comprising a pharmacologically effective amount of a pharmacologically effective compound together with a pharmacologically acceptable carrier, wherein said pharmacologically effective compound is an amidocarboxylic acid compound according to claim 5 or a pharmacologically acceptable salt or ester thereof.

57. A pharmaceutical composition comprising a pharmacologically effective amount of a pharmacologically effective compound together with a pharmacologically acceptable carrier, wherein said pharmacologically effective compound is an amidocarboxylic acid compound according to claim 6 or a pharmacologically acceptable salt or ester thereof.

58. A pharmaceutical composition comprising a pharmacologically effective amount, of a pharmacologically effective compound together with a pharmacologically acceptable carrier, wherein said pharmacologically effective compound is an amidocarboxylic acid compound according to claim 7 or a pharmacologically acceptable salt or ester thereof.

59. A pharmaceutical composition comprising a pharmacologically effective amount of a pharmacologically effective compound together with a pharmacologically acceptable carrier, wherein said pharmacologically effective compound is an amidocarboxylic acid compound according to claim 8 or a pharmacologically acceptable salt or ester thereof.

60. A pharmaceutical composition comprising a pharmacologically effective amount of a pharmacologically effective compound together with a pharmacologically acceptable carrier, wherein said pharmacologically effective compound is an amidocarboxylic acid compound according to claim 9 or a pharmacologically acceptable salt or ester thereof.

61. A pharmaceutical composition comprising a pharmacologically effective amount of a pharmacologically effective compound together with a pharmacologically acceptable carrier, wherein said pharmacologically effective compound is an amidocarboxylic acid compound according to claim 10 or a pharmacologically acceptable salt or ester thereof.

62. A pharmaceutical composition comprising a pharmacologically effective amount of a pharmacologically effective compound together with a pharmacologically acceptable carrier, wherein said pharmacologically effective compound is an amidocarboxylic acid compound according to claim 11 or a pharmacologically acceptable salt or ester thereof.

63. A pharmaceutical composition comprising a pharmacologically effective amount of a pharmacologically effective compound together with a pharmacologically acceptable carrier, wherein said pharmacologically effective compound is an amidocarboxylic acid compound according to claim 12 or a pharmacologically acceptable salt or ester thereof.

64. A pharmaceutical composition comprising a pharmacologically effective amount of a pharmacologically effective compound together with a pharmacologically acceptable carrier, wherein said pharmacologically effective compound is an amidocarboxylic acid compound according to claim 13 or a pharmacologically acceptable salt or ester thereof.

65. A pharmaceutical composition comprising a pharmacologically effective amount of a pharmacologically effective compound together with a pharmacologically acceptable carrier, wherein said pharmacologically effective compound is an amidocarboxylic acid compound according to claim 14 or a pharmacologically acceptable salt or ester thereof.

66. A pharmaceutical composition comprising a pharmacologically effective amount of a pharmacologically effective compound together with a pharmacologically acceptable carrier, wherein said pharmacologically effective compound is an amidocarboxylic acid compound according to claim 15 or a pharmacologically acceptable salt or ester thereof.

67. A pharmaceutical composition comprising a pharmacologically effective amount of a pharmacologically effective compound together with a pharmacologically acceptable carrier, wherein said pharmacologically effective compound is an amidocarboxylic acid compound according to claim 16 or a pharmacologically acceptable salt or ester thereof.

68. A pharmaceutical composition comprising a pharmacologically effective amount of a pharmacologically effective compound together with a pharmacologically acceptable carrier, wherein said pharmacologically effective compound is an amidocarboxylic acid compound according to claim 17 or a pharmacologically acceptable salt or ester thereof.

69. A pharmaceutical composition comprising a pharmacologically effective amount of a pharmacologically effective compound together with a pharmacologically acceptable carrier, wherein said pharmacologically effective compound is an amidocarboxylic acid compound according to claim 18 or a pharmacologically acceptable salt or ester thereof.

70. A pharmaceutical composition comprising a pharmacologically effective amount of a pharmacologically effective compound together with a pharmacologically acceptable carrier, wherein said pharmacologically effective compound is an amidocarboxylic acid compound according to claim 19 or a pharmacologically acceptable salt or ester thereof.

71. A pharmaceutical composition comprising a pharmacologically effective amount of a pharmacologically effective compound together with a pharmacologically acceptable carrier, wherein said pharmacologically effective compound is an amidocarboxylic acid compound according to claim 20 or a pharmacologically acceptable salt or ester thereof.

72. A pharmaceutical composition comprising a pharmacologically effective amount of a pharmacologically effective compound together with a pharmacologically acceptable carrier, wherein said pharmacologically effective compound is an amidocarboxylic acid compound according to claim 21 or a pharmacologically acceptable salt or ester thereof.

73. A pharmaceutical composition comprising a pharmacologically effective amount of a pharmacologically effective compound together with a pharmacologically acceptable carrier, wherein said pharmacologically effective compound is an amidocarboxylic acid compound according to claim 22 or a pharmacologically acceptable salt or ester thereof.

74. A pharmaceutical composition comprising a pharmacologically effective amount of a pharmacologically effective compound together with a pharmacologically acceptable carrier, wherein said pharmacologically effective compound is an amidocarboxylic acid compound according to claim 23 or a pharmacologically acceptable salt or ester thereof.

75. A pharmaceutical composition comprising a pharmacologically effective amount of a pharmacologically effective compound together with a pharmacologically acceptable carrier, wherein said pharmacologically effective compound is an amidocarboxylic acid compound according to claim 24 or a pharmacologically acceptable salt or ester thereof.

76. A pharmaceutical composition comprising a pharmacologically effective amount of a pharmacologically effec- 76. (continued) ...pharmacologically effective compound together with a pharmacologically acceptable carrier, wherein said pharmacologically effective compound is an amidocarboxylic acid compound according to claim 25 or a pharmacologically acceptable salt or ester thereof.

77. A pharmaceutical composition comprising a pharmacologically effective amount of a pharmacologically effective compound together with a pharmacologically acceptable carrier, wherein said pharmacologically effective compound is an amidocarboxylic acid compound according to claim 26 or a pharmacologically acceptable salt or ester thereof.

78. A pharmaceutical composition comprising a pharmacologically effective amount of a pharmacologically effective compound together with a pharmacologically acceptable carrier, wherein said pharmacologically effective compound is an amidocarboxylic acid compound according to claim 27 or a pharmacologically acceptable salt or ester thereof.

79. A pharmaceutical composition comprising a pharmacologically effective amount of a pharmacologically effective compound together with a pharmacologically acceptable carrier, wherein said pharmacologically effective compound is an amidocarboxylic acid compound according to claim 28 or a pharmacologically acceptable salt or ester thereof.

80. A pharmaceutical composition comprising a pharmacologically effective amount of a pharmacologically effective compound together with a pharmacologically acceptable carrier, wherein said pharmacologically effective compound is an amidocarboxylic acid compound according to claim 29 or a pharmacologically acceptable salt or ester thereof.

81. A pharmaceutical composition comprising a pharmacologically effective amount of a pharmacologically effective compound together with a pharmacologically acceptable carrier, wherein said pharmacologically effective compound is an amidocarboxylic acid compound according to claim 32 or a pharmacologically acceptable salt or ester thereof.

82. A pharmaceutical composition comprising a pharmacologically effective amount of a pharmacologically effective compound together with a pharmacologically acceptable carrier, wherein said pharmacologically effective compound is an amidocarboxylic acid compound according to claim 31 or a pharmacologically acceptable salt or ester thereof.

83. A pharmaceutical composition comprising a pharmacologically effective amount of a pharmacologically effective compound together with a pharmacologically acceptable carrier, wherein said pharmacologically effective compound is an amidocarboxylic acid compound according to claim 32 or a pharmacologically acceptable salt or ester thereof.

84. A pharmaceutical composition comprising a pharmacologically effective amount of a pharmacologically effective compound together with a pharmacologically acceptable carrier, wherein said pharmacologically effective compound is an amidocarboxylic acid compound according to claim 33 or a pharmacologically acceptable salt or ester thereof.

85. A pharmaceutical composition comprising a pharmacologically effective amount of a pharmacologically effective compound together with a pharmacologically acceptable carrier, wherein said pharmacologically effective compound is an amidocarboxylic acid compound according to claim 34 or a pharmacologically acceptable salt or ester thereof.

86. A pharmaceutical composition comprising a pharmacologically effective amount of a pharmacologically effective compound together with a pharmacologically acceptable carrier, wherein said pharmacologically effective compound is an amidocarboxylic acid compound according to claim 35 or a pharmacologically acceptable salt or ester thereof.

87. A pharmaceutical composition comprising a pharmacologically effective amount of a pharmacologically effective compound together with a pharmacologically acceptable carrier, wherein said pharmacologically effective compound is an amidocarboxylic acid compound according to claim 36 or a pharmacologically acceptable salt or ester thereof.

88. A pharmaceutical composition comprising a pharmacologically effective amount of a pharmacologically effective compound together with a pharmacologically acceptable carrier, wherein said pharmacologically effective compound is an amidocarboxylic acid compound according to claim 37 or a pharmacologically acceptable salt or ester thereof.

89. A pharmaceutical composition comprising a pharmacologically effective amount of a pharmacologically effective compound together with a pharmacologically acceptable carrier, wherein said pharmacologically effective compound is an amidocarboxylic acid compound according to claim 38 or a pharmacologically acceptable salt or ester thereof.

90. A pharmaceutical composition comprising a pharmacologically effective amount of a pharmacologically effective compound together with a pharmacologically acceptable carrier, wherein said pharmacologically effective compound is an amidocarboxylic acid compound according to claim 39 or a pharmacologically acceptable salt or ester thereof.

91. A pharmaceutical composition comprising a pharmacologically effective amount of a pharmacologically effective compound together with a pharmacologically acceptable carrier, wherein said pharmacologically effective compound is an amidocarboxylic acid compound according to claim 40 or a pharmacologically acceptable salt or ester thereof.

92. A pharmaceutical composition comprising a pharmacologically effective amount of a pharmacologically effective compound together with a pharmacologically acceptable carrier, wherein said pharmacologically effective compound is an amidocarboxylic acid compound according to claim 41 or a pharmacologically acceptable salt or ester thereof.

93. A pharmaceutical composition comprising a pharmacologically effective amount of a pharmacologically effective compound together with a pharmacologically acceptable carrier, wherein said pharmacologically effective compound is an amidocarboxylic acid compound according to claim 42 or a pharmacologically acceptable salt or ester thereof.

94. A pharmaceutical composition comprising a pharmacologically effective amount of a pharmacologically effective compound together with a pharmacologically acceptable carrier, wherein said pharmacologically effective compound is an amidocarboxylic acid compound according to claim 43 or a pharmacologically acceptable salt or ester thereof.

95. A pharmaceutical composition comprising a pharmacologically effective amount of a pharmacologically effective compound together with a pharmacologically acceptable carrier, wherein said pharmacologically effective compound is an amidocarboxylic acid compound according to claim 44 or a pharmacologically acceptable salt or ester thereof.

96. A pharmaceutical composition comprising a pharmacologically effective amount of a pharmacologically effective compound together with a pharmacologically acceptable carrier, wherein said pharmacologically effective compound is an amidocarboxylic acid compound according to claim 45 or a pharmacologically acceptable salt or ester thereof.

97. A pharmaceutical composition comprising a pharmacologically effective amount of a pharmacologically effective compound together with a pharmacologically acceptable carrier, wherein said pharmacologically effective compound is an amidocarboxylic acid compound according to claim 46 or a pharmacologically acceptable salt or ester thereof.

98. A pharmaceutical composition comprising a pharmacologically effective amount of a pharmacologically effective compound together with a pharmacologically acceptable carrier, wherein said pharmacologically effective compound is an amidocarboxylic acid compound according to claim 47 or a pharmacologically acceptable salt or ester thereof.

99. A pharmaceutical composition comprising a pharmacologically effective amount of a pharmacologically effective compound together with a pharmacologically acceptable carrier, wherein said pharmacologically effective compound is an amidocarboxylic acid compound according to claim 48 or a pharmacologically acceptable salt or ester thereof.

100. A pharmaceutical composition comprising a pharmacologically effective amount of a pharmacologically effective compound together with a pharmacologically acceptable carrier, wherein said pharmacologically effective compound is an amidocarboxylic acid compound according to claim 49 or a pharmacologically acceptable salt or ester thereof.

101. A pharmaceutical composition comprising a pharmacologically effective amount of a pharmacologically effective compound together with a pharmacologically acceptable carrier, wherein said pharmacologically effective compound is an amidocarboxylic acid compound according to claim 50 or a pharmacologically acceptable salt or ester thereof.

102. A pharmaceutical composition comprising a pharmacologically effective amount of a pharmacologically effective compound together with a pharmacologically acceptable carrier, wherein said pharmacologically effective compound is an amidocarboxylic acid compound according to claim 51 or a pharmacologically acceptable salt or ester thereof.

* * * * *

UNITED STATES PATENT AND TRADEMARK OFFICE
CERTIFICATE OF CORRECTION

PATENT NO. : 6,528,525 B1　　　　　　　　　　　　　　　　　　　　　Page 1 of 1
DATED     : March 4, 2003
INVENTOR(S) : Hiroaki Yanagisawa et al.

It is certified that error appears in the above-identified patent and that said Letters Patent is hereby corrected as shown below:

<u>Title page,</u>
Following Item [63], insert the following:
-- [30]　Foreign Application Priority Data
October 2, 1997　　　　(JP) .........Hei 9-269923 --.

Signed and Sealed this

Ninth Day of September, 2003

JAMES E. ROGAN
*Director of the United States Patent and Trademark Office*